US011156615B2

(12) United States Patent
Hellinga et al.

(10) Patent No.: US 11,156,615 B2
(45) Date of Patent: Oct. 26, 2021

(54) GLUCOSE BIOSENSORS AND USES THEREOF

(71) Applicant: Duke University, Durham, NC (US)

(72) Inventors: Homme W. Hellinga, Durham, NC (US); Malin J. Allert, Raleigh, NC (US)

(73) Assignee: Duke University, Durham, NC (US)

(*) Notice: Subject to any disclaimer, the term of this patent is extended or adjusted under 35 U.S.C. 154(b) by 281 days.

(21) Appl. No.: 15/776,725

(22) PCT Filed: Sep. 2, 2016

(86) PCT No.: PCT/US2016/050297
§ 371 (c)(1),
(2) Date: May 16, 2018

(87) PCT Pub. No.: WO2017/087051
PCT Pub. Date: May 26, 2017

(65) Prior Publication Data

US 2018/0328935 A1 Nov. 15, 2018

Related U.S. Application Data

(60) Provisional application No. 62/257,784, filed on Nov. 20, 2015, provisional application No. 62/257,796, filed on Nov. 20, 2015.

(51) Int. Cl.

| | |
|---|---|
| ***G01N 33/66*** | (2006.01) |
| ***C12Q 1/54*** | (2006.01) |
| ***C07K 14/245*** | (2006.01) |

(52) U.S. Cl.
CPC ........... *G01N 33/66* (2013.01); *C07K 14/245* (2013.01); *C12Q 1/54* (2013.01); *C07K 2319/20* (2013.01); *G01N 2333/195* (2013.01); *G01N 2333/245* (2013.01)

(58) Field of Classification Search
CPC ......... G01N 33/66; C07K 14/245; C12Q 1/54
USPC ........................................ 424/9.6; 436/94–95
See application file for complete search history.

(56) References Cited

U.S. PATENT DOCUMENTS

| | | | | |
|---|---|---|---|---|
| 5,342,789 A * | 8/1994 | Chick | A61K 49/0004 424/9.6 |
| 6,197,534 B1 * | 3/2001 | Lakowicz | C12Q 1/485 435/14 |
| 6,256,522 B1 * | 7/2001 | Schultz | A61B 5/14532 600/310 |
| 6,277,627 B1 * | 8/2001 | Hellinga | G01N 33/582 204/400 |
| 8,608,310 B2 | 12/2013 | Otis et al. | |
| 2002/0004217 A1 | 1/2002 | Hellinga | |

(Continued)

FOREIGN PATENT DOCUMENTS

WO 2017/087051 A1 5/2017

OTHER PUBLICATIONS

Zukin, R. S. et al, Biochemistry 1977, 16, 381-386.*

(Continued)

*Primary Examiner* — Arlen Soderquist
(74) *Attorney, Agent, or Firm* — Mintz Levin Cohn Ferris Glovsky and Popeo, P.C.; Ingrid A. Beattie

(57) ABSTRACT

The present subject matter provides glucose biosensors as well as compositions, devices, and methods comprising such biosensors.

25 Claims, 173 Drawing Sheets

Specification includes a Sequence Listing.

(56) References Cited

U.S. PATENT DOCUMENTS

2003/0129622 A1* 7/2003 Hellinga ................ B82Y 15/00 435/6.19
2003/0130167 A1* 7/2003 Pitner .............. G01N 33/54373 435/14
2003/0134346 A1* 7/2003 Amiss .................. C07K 14/245 435/14
2003/0153026 A1* 8/2003 Alarcon ................. C07K 17/04 435/14
2003/0232370 A1* 12/2003 Trifiro ............ C12Y 207/01001 435/6.13
2003/0232383 A1* 12/2003 Daunert ............... G01N 33/542 435/7.1
2004/0118681 A1 6/2004 Hellinga et al.
2004/0229290 A1* 11/2004 Hellinga ................ G16B 15/00 435/7.1
2004/0234962 A1* 11/2004 Alarcon ................. G01N 33/68 435/6.11
2005/0014290 A1* 1/2005 Hsieh ................... G01N 33/543 436/518
2005/0074845 A1* 4/2005 Mueller ................. C07K 14/62 435/69.1
2005/0112685 A1* 5/2005 Amiss .................. G01N 33/542 435/7.1
2005/0118726 A1* 6/2005 Schultz ................ G01N 33/582 436/518
2005/0239155 A1* 10/2005 Alarcon ............. G01N 33/5436 435/14
2006/0040327 A1* 2/2006 Amiss ................ C12N 15/1037 435/7.1
2006/0078908 A1* 4/2006 Pitner .............. G01N 33/54366 435/6.12
2006/0100493 A1* 5/2006 Strassler .............. A61B 5/0031 600/365
2006/0280652 A1* 12/2006 Pitner ..................... C09B 23/10 422/68.1
2007/0136825 A1* 6/2007 Frommer ............. G01N 33/542 800/3
2007/0191702 A1* 8/2007 Yodfat ..................... A61B 5/15 600/365
2007/0219346 A1* 9/2007 Trifiro .................. C12N 9/1205 530/308
2008/0044856 A1* 2/2008 Amiss .................... G01N 33/66 435/69.1
2008/0200788 A1* 8/2008 Brister ................. A61B 5/1495 600/345
2008/0261255 A1* 10/2008 Tolosa ................. G01N 33/542 435/15
2008/0311675 A1* 12/2008 Thomas .................. C09B 57/02 436/501
2009/0286873 A1* 11/2009 Miller .................. C07K 14/255 514/473
2010/0037329 A1* 2/2010 Frommer ............. C07K 14/245 800/13
2010/0138944 A1* 6/2010 Frommer ............. G01N 33/542 800/13
2011/0091919 A1* 4/2011 Ye .......................... G01N 33/84 435/14
2011/0117661 A1* 5/2011 Daunert ............... A61B 5/1459 436/95
2011/0171737 A1 7/2011 Hellinga et al.
2012/0076736 A1* 3/2012 Borkholder ............ G01N 33/66 424/9.6
2012/0083048 A1* 4/2012 Lee ...................... G01N 33/582 436/501
2012/0232251 A1* 9/2012 Pickup ................... C07K 17/06 530/350
2013/0211212 A1* 8/2013 Stumber .............. A61B 5/1455 600/316
2014/0256060 A1 9/2014 Ye et al.
2014/0350370 A1* 11/2014 Cummins .......... A61B 5/14735 600/365
2015/0056634 A1* 2/2015 Ferriter .................. A61K 38/17 435/7.9
2015/0111222 A1* 4/2015 Marvin ................ C07K 14/245 435/7.2
2016/0220686 A1 8/2016 Brudno et al.
2016/0258964 A1* 9/2016 Zhang .................... G01N 33/66
2018/0037928 A1* 2/2018 Hellinga ............ G01N 33/5438

OTHER PUBLICATIONS

Mahoney, W. C. et al, Journal of Biological Chemistry 1981, 256, 4350-4356.*
Becker, P. S. et al, Infection and Immunity 1994, 62, 1381-1391.*
Careaga, C. L. et al, Biochemistry 1995, 34, 3048-3055.*
Tolosa, L. et al, Analytical Biochemistry 1999, 267, 114-120.*
Looger, L. L. et al, Nature 2003, 423, 185-190.*
Fehr, M. et al, Journal of Biological Chemistry 2003, 278, 19127-19133.*
Ye, K. et al, Analytical Chemistry 2003, 75, 3451-3459.*
Tolosa, L. et al, SPIE 2003, 4967, 19-25.*
Ge, X. et al, Biotechnology and Bioengineering 2003, 84, 723-731.*
Ge, X. et al, Analytical Chemistry 2004, 76, 1403-1410.*
Piszczek, G. et al, Biochemical Journal 2004, 381, 97-103.*
Dwyer, M. A. et al, Current Opinion in Structural Biology 2004, 14, 495-504.*
Moschou, E. A. et al, Journal of Fluorescence 2004, 14, 535-547.*
Hsieh, H. V. et al, Biosensors and Bioelectronics 2004, 19, 653-680.*
Carmon, K. S. et al, Biochemistry 2004, 43, 14249-14256.*
De Champdore, M. et al, International Symposium on Electrophiles and Their Applications 2005, 302-309.*
Herman, P. et al, Proteins 2005, 61, 184-195.*
Fehr, M. et al, Molecular and Cellular Biology 2005, 25, 11102-11112.*
D'Auria, S. et al, Journal of Biochemistry 2006, 139, 213-221.*
Thomas, K. J. et al, Diabetes Technology & Therapeutics 2006, 8, 261-268.*
Tolosa, L.. et al, "The Glucose Binding Protein as Glucose Sensor". In Glucose Sensing. Topics in Fluorescence Spectroscopy : Geddes C.D. et al, eds, Springer, Boston, MA, 2006, 11, 323-331.*
Cuneo, M. J. et al, Journal of Molecular Biology 2006, 362, 259-270.*
Deuschle, K. et al, Plant Cell 2006, 18, 2314-2325.*
Marabotti, A. et al, Biochemistry 2006, 45, 11885-11894.*
Tripathi, A. et al, Analytical Chemistry 2007, 79, 1266-1270.*
Messina, T. C. et al, Biophysical Journal 2007, 93, 579-585.*
Tian, Y. et al, Protein Science 2007, 16, 2240-2250.*
Amiss, T. J. et al, Protein Science 2007, 16, 2350-2359.*
Dweik, M. et al, SPIE 2007, 6759, paper 67590I, 8 pages.*
Scognamiglio, V. et al, Journal of Proteome Research 2007, 6, 4119-4126.*
Khan, F. et al, Biochemical and Biophysical Research Communications 2008, 365, 102-106.*
Der, B. S. et al, Analytical Biochemistry 2008, 375, 132-140.*
Hamorsky, K. T. et al, Angewandte Chemie International Edition 2008, 47, 3718-3721.*
Ge, X. et al, Biotechnology Progress 2008, 24, 691-697.*
Sakaguchi-Mikami, A. et al, Biotechnology Letters 2008, 30, 1453-1460.*
Saxl, T. et al, Biosensors and Bioelectronics 24, 3229-3234.*
Taneoka, A. et al, Biosensors and Bioelectronics 25, 76-81.*
Khan, F. et al, Analytical Biochemistry 2010, 399, 39-43.*
Siegrist, J. et al, Sensors and Actuators B 2010, 149, 51-58.*
Jin, S. et al, Biosensors and Bioelectronics 2011, 26, 3427-3431.*
Stepanenko, O. V. et al, Journal of Physical CHemistry B 2011, 115, 9022-9032.*
Galban, J. et al, Analytical and Bioanalytical Chemistry 2012, 402, 3039-3054.*
Kaminski, M. T. et al, Biochimica et Biophysica Acta 2012, 1823, 1697-1707.*
Hsieh, H. V. et al, Journal of Diabetes Science and Technology 2012, 6, 1286-1295.*

(56) References Cited

OTHER PUBLICATIONS

Ortega, G. et al, Journal of the American Chemical Society 2012, 134, 19869-19876.*
Pickup, J. C. et al, Journal of Diabetes Science and Technology 2013, 7, 62-71.*
Khan, F. et al, Biochemical and Biophysical Research Communications 2013, 438, 488-492.*
Grunewald, F. S., BIOREV 2014, 1,205-236.*
Kanjananimmanont, S. et al, Journal of Diabetes Science and Technology 2014, 8, 291-298.*
Modak, A. et al, FEBS Journal 2014, 281, 365-375.*
Fonin, A. V. et al, PeerJ 2014, 2, paper e275, 15 pages.*
Joel, S. et al, ACS Chemical Biology 2014, 9, 1595-1602.*
Stepanenko, O. V. et al, Journal of Fluorescence 2015, 25, 87-94.*
Albers, S.-V. et al, Journal of Bacteriology 1999, 181, 4285-4291.*
Ha, J.-H. et al, Biochemistry 2013, 52, 600-612.*
Verbeke, T. J. et al, PLOS one 2013, 8, paper e59363, 18 pages.*
Abouhamad et al. (Jun. 1991) "Peptide Transport and Chemotaxis in *Escherichia coli* and *Salmonella typhimurium*: Characterization of the Dipeptide Permease (Dpp) and the Dipeptide-Binding Protein", Molecular Microbiology, 5(5):1035-1047.
Adams et al. (Feb. 2010) "Phenix: A Comprehensive Python-Based System for Macromolecular Structure Solution", Acta Crystallographica Section D, 66(Part 2):213-221.
Adey et al. (Apr. 14, 1995) "Characterization of Phage that Bind Plastic from Phage-Displayed Random Peptide Libraries", Gene, 156(1):27-31.
Adhikari et al. (Oct. 20, 1995) "Biochemical Characterization of a Haemophilus influenzae Periplasmic Iron Transport Operon", The Journal of Biological Chemistry, 270(42):25142-25149.
Adhikary et al. (Aug. 13, 2009) "Solvation Dynamics of the Fluorescent Probe PRODAN in Heterogeneous Environments: Contributions from the Locally Excited and Charge-Transferred States", Journal of Physical Chemistry, 113(35):11999-12004.
Allert et al. (Oct. 8, 2010) "Multifactorial Determinants of Protein Expression in Prokaryotic Open Reading Frames", Journal of Molecular Biology, 402(5):905-918.
Altschul et al. (Oct. 1990) "Basic Local Alignment Search Tool", Journal of Molecular Biology, 215(3):403-410.
Anraku (Jun. 10, 1968) "Transport of Sugars and Amino Acids in Bacteria", Journal of Biological Chemistry, 243(11):3116-3122.
Artimo et al. (May 2012) "ExPASy: SIB Bioinformatics Resource Portal", Nucleic Acids Research, 40:W597-W603.
Avvkumova et al. (Jan. 2014) "Biotechnological Approaches Toward Nanoparticle Biofunctionalization", Trends in Biotechnology, 32(1):11-20.
Balter et al. (Feb. 5, 1988) "Some Remarks on the Interpretation of the Spectral Properties of Prodan", Chemical Physics Letters, 143(6):565-570.
Baneyx et al. (Jul. 5, 2007) "Selection and Analysis of Solid-Binding Peptides", Current Opinion in Biotechnology, 18(4):312-317.
Barash et al. (Mar. 28, 1975) "Purification and Properties of Glutamate Binding Protein from the Periplasmic Space of *Escherichia coli* K-12", Biochimica et Biophysica Acta (BBA)—Protein Structure, 386(1):168-180.
Barucha-Kraszewska et al. (Sep. 2010) "Numerical Studies of the Membrane Fluorescent Dyes Dynamics in Ground and Excited States", Biochimica et Biophysica Acta (BBA)—Biomembranes, 1798(9):1724-1734.
Baskin et al. (Oct. 23, 2007) "Copper-Free Click Chemistry for Dynamic in Vivo Imaging", PNAS, 104 (43):16793-16797.
Benedetti et al. (Jul. 13, 2012) "Synthesis and Photophysical Properties of a Series of Cyclopenta[b]naphthalene Solvatochromic Fluorophores", Journal of the American Chemical Society, 134(30):12418-12421.
Berman et al. (2000) "The Protein Data Bank", Nucleic Acids Research, 28(1):235-242.
Biju et al. (Feb. 7, 2014) "Chemical Modifications and Bioconjugate Reactions of Nanomaterials for Sensing, Imaging, Drug Delivery and Therapy", Chemical Society Reviews, 43(3):744-764.
Bjorkman et al. (Jun. 12, 1998) "Multiple Open Forms of Ribose-Binding Protein Trace the Path of its Conformational Change", Journal of Molecular Biology, 279(3):651-664.
Bruns et al. (2001) "Crystallographic and Biochemical Analyses of the Metal-Free Haemophilus influenzae Fe3+-Binding Protein", Biochemistry, 40(51):15631-15637.
Bruns et al. (Nov. 1997) "Structure of Haemophilus Influenzae Fe+3-Binding Protein Reveals Convergent Evolution within a Superfamily", Nature Structural Biology, 4(11):919-924.
Care et al. (May 2015) "Solid-Binding Peptides: Smart Tools for Nanobiotechnology", Trends in Biotechnology, 33(5):259-268.
Catalan et al. (Dec. 1991) "Analysis of the Solvent Effect on the Photophysics Properties of 6-Propionyl-2-(dimethylamino)Naphthalene (PRODAN)", Journal of Fluorescence, 1(4):215-223.
Chen et al. (Feb. 2011) "Binding Analysis of Peptides That Recognize Preferentially Cis-Azobenzene Groups of Synthetic Polymers", Journal of Peptide Science, 17(2):163-168.
Chenna et al. (Jul. 2003) "Multiple Sequence Alignment with the Clustal Series of Programs", Nucleic Acids Research, 31(13):3497-3500.
Chothia et al. (1986) "The Relation Between the Divergence of Sequence and Structure in Proteins", The EMBO Journal, 5(4):823-826.
Clark et al. (Apr. 27, 1982) "Thermodynamics of the Binding of L-Arabinose the L-Arabinose-Binding Protein of *Escherichia* and of D-Galactose to *coli*", Biochemistry, 21(9):2227-2233.
Cox et al. (Mar. 2007) "Protein Fabrication Automation", Protein Science, 16(3):379-390.
Cwiklik et al. (Sep. 12, 2011) "Absorption and Fluorescence of PRODAN in Phospholipid Bilayers: A Combined Quantum Mechanics and Classical Molecular Dynamics Study", The Journal of Physical Chemistry A, 115(41):11428-11437.
Daneri et al. (Sep. 1, 2015) "A Higher-Order Preferential Solvation Model for the Fluorescence of Two PRODAN Derivatives in Toluene-Alcohol Mixtures", Journal of Photochemistry and Photobiology A: Chemistry, 310:106-112.
Date et al. (Feb. 2, 2011) "Polymer-Binding Peptides for the Noncovalent Modification of Polymer Surfaces: Effects of Peptide Density on the Subsequent Immobilization of Functional Proteins", ACS Applied Materials & Interfaces, 3(2):351-359.
Dattelbaum et al. (2001) "Optical Determination of Glutamine Using a Genetically Engineered Protein", Analytical Biochemistry, 291(1):89-95.
Davis et al. (Jan. 29, 2005) "Synthesis and Photophysical Properties of Models for Twisted PRODAN and Dimethylaminonaphthonitrile", The Journal of Physical Chemistry A, 109(7):1295-1298.
De Lorimier et al. (Aug. 1, 2006) "Binding and Signaling of Surface-Immobilized Reagentless Fluorescent Biosensors Derived from Periplasmic Binding Proteins", Protein Science, 15(8):1936-1944.
De Lorimier et al. (2002) "Construction of a Fluorescent Biosensor Family", Protein Science, 11:2655-2575.
Demchenko (Dec. 5, 2014) "Practical Aspects of Wavelength Ratiometry in the Studies of Intermolecular Interactions", Journal of Molecular Structure, 1077:51-67.
Demchenko (Sep. 2010) "The Concept of λ-Ratiometry in Fluorescence Sensing and Imaging", Journal of Fluorescence, 20(5):1099-1128.
Dunten (Nov. 1995) "Crystal Structure of the Dipeptide Binding Protein From *Escherichia coli* Involved in Active Transport and Chemotaxis", Protein Science, 4(11): 2327-2334.
Duplay et al. (Aug. 25, 1984) "Sequences of the malE Gene and of its Product, the Maltose-binding Protein of *Escherichia coli* K12", The Journal of Biological Chemistry, 259(16):10606-10613.
Ejima et al. (Oct. 15, 2010) "Biological Identification of Peptides that Specifically Bind to Poly(phenylene vinylene) Surfaces: Recognition of the Branched or Linear Structure of the Conjugated Polymer", Langmuir, 2(22):17278-17285.

(56) References Cited

OTHER PUBLICATIONS

Everett et al. (Apr. 1, 2010) "Does PRODAN Possess an O-TICT Excited State? Synthesis and Properties of Two Constrained Derivatives", Journal of Physical Chemistry, 114(14):4946-4950.
fukuda et al. (Nov. 12, 2012) "Optical Absorption and Fluorescence of PRODAN in Aolution: Quantum Chemical Study Based on the Symmetry-Adapted Cluster-Configuration Interaction Method", Chemical Physics Letters, 552:53-57.
Gilardi et al. (Dec. 1994) "Engineering the Maltose Binding Protein for Reagentless Fluorescence Sensing", Analytical Chemistry, 66(21):3840-3847.
Gilardi et al. (1997) "Spectroscopic Properties of an Engineered Maltose Binding Protein", Protein Engineering, 10(5):479-486.
Gill et al. (Nov. 1, 1989) "Calculation of Protein Extinction Coefficients from Amino Acid Sequence Data", Analytical Biochemistry, 182(2):319-326.
Gough et al. (Sep. 1995) "Development of the Implantable Glucose Sensor: What Are the Prospects and Why Is It Taking So Long?", Diabetes, 44(9):1005-1009.
Grabowski et al. (Sep. 17, 2003) "Structural Changes Accompanying Intramolecular Electron Transfer: Focus on Twisted Intramolecular Charge-Transfer States and Structures", Chemical Reviews, 103(10):3899-4032.
Green et al. (Aug. 15, 2012) "Carbonyl-Twisted 6-Acyl-2-dialkylaminonaphthalenes as Solvent Acidity Sensors",The Journal of Organic Chemistry, 78(5):1784-1789.
Grimley et al. (Oct. 9, 2013) "Visualization of Synaptic Inhibition with an Optogenetic Sensor Developed by Cell-Free Protein Engineering Automation", The Journal of Neuroscience, 33(41):16297-16309.
Weber et al. (Jul. 10, 1979) "Synthesis and Spectral Properties of a Hydrophobic Fluorescent Probe: 6-propionyl-2-(dimethylamino)naphthalene", Biochemistry, 18(14):3075-3078.
Weidemaier et al. (Jun. 15, 2011) "Multi-Day Pre-Clinical Demonstration of Glucose/Galactose Binding Protein-Based Fiber Optic Sensor", Biosensors and Bioelectronics, 26(10):4117-4123.
Weiner et al. (1971) "A Binding Protein for L-Glutamine and its Relation to Active Transport in *E. coli*", Archives of Biochemistry and Biophysics, 124:715-717.
Wenner et al. (2001) "Genetically Designed Biosensing Systems for High-Throughput Screening of Pharmaceuticals, Clinical Diagnostics, and Environmental Monitoring", Visual Communications and Image Processing, 4252:59-70.
Wilkins et al. (Jun. 1996) "Glucose Monitoring: State of Art and Future Possibilities", Medical Engineering & Physics, 18:273-288.
Willis et al. (Apr. 10, 1975) "Purification and Properties of a Periplasmic Glutamate- Aspartate Binding Protein from *Escherichkz coli* K12 Strain W3092", The Journal of Biological Chemistry, 250(7):2574-2580.
Willis et al. (Nov. 10, 1974) "Purification and Properties of a Ribose-binding Protein from *Escherichia coli*", Journal of Biological Chemistry, 249(21):6926-6929.
Willner et al. (Oct. 23, 1996) "Electrical Wiring of Glucose Oxidase by Reconstitution of FAD-Modified Monolayers Assembled onto Au-Electrodes", Journal of the American Chemical Society, 118(42):10321-10322.
Yao et al. (Apr. 26, 1994) "Refined 1.89-A Structure of the Histidine-Binding Protein Complexed with Histidine and its Relationship with Many Other Active Transport/Chemosensory Proteins", Biochemistry, 33(16):4769-4779.
Zeng, et al. (2014) "Nanomaterials Enhanced Surface Plasmon Resonance for Biological and Chemical Sensing Applications", Chemical Society Reviews, 43(10):3426-3452.
Borrok et al., Conformational Changes of Glucose/Galactose-binding Protein Illuminated by Open, Unliganded, and Ulta-High-Resolution Ligand-Bound Structures, Protein Sci (Jun. 2007), vol. 16, No. 6, pp. 1032-1041.
Scognamiglio et al., D-Galactose/D-Glucose-Binding Protein Form *Escherichia coli* as Probe for a Non-Consuming Implantable Fluorescence Biosensor, Sensors (Oct. 24, 2007), vol. 7, No. 10, pp. 2484-2494.
UniProtKB—D9TSJ1 D-galactose ABC Transporter Substrate Binding Protein, Oct. 5, 2010.
Nikitina et al. (Sep. 3, 2013) "Preferential Solvation in Carbonyl-Twisted PRODAN Derivatives", The Journal of Physical Chemistry A, 117(38):9189-9195.
Niko et al. (Jul. 22, 2013) "Solvatochromic Pyrene Analogues of Prodan Exhibiting Extremely High Fluorescence Quantum Yields in Apolar and Polar Solvents", Chemistry, 19(30):9760-9765.
Nitschke et al. (Feb. 13, 2012) "Molecular Dynamics Investigations of PRODAN in a DLPC Bilayer", The Journal of Physical Chemistry B, 116(9):2713-2721.
Nohno et al. (1986) "Cloning and Complete Nucleotide Sequence of the *Escherichia coli* Glutamine Permease Operon (Glnhpq)", Molecular Genetics and Genomics, 205:260-269.
Nowak et al. (Aug. 1986) "On the Possibility of Fluorescence from Twisted Intramolecular Charge Transfer States of 2-dimethylamino-6-acylnaphthalenes. A Quantum-Chemical Study", Journal of Molecular Structure: THEOCHEM, 139(1-2):13-23.
Nwe et al. (2009) "Growing Applications of "Click Chemistry" for Bioconjugation in Contemporary Biomedical Research", Cancer Biotherapy and Radiopharmaceuticals, 24(3):289-302.
Oliveira et al. (May-Aug. 2015) "Recombinant CBM-Fusion Technology—Applications Overview", Biotechnology Advances, 33(3-4):358-369.
Oneto et al. (2014) "Implantable Biomaterial Based on Click Chemistry for Targeting Small Molecules", Acta Biomaterilia, 10:5099-5105.
Parusel et al. (Jun. 30, 1997) "An Ab Initio Study on Excited and Ground State Properties of the Organic Fluorescence Probe PRODAN", Journal of Molecular Structure: THEOCHEM, 398-399:341-346.
Parusel et al. (Aug. 15, 1998) "Comparative Theoretical Study on Charge-Transfer Fluorescence Probes: 6-Propanoyl-2-(N,N-dimethylamino)naphthalene and Derivatives", The Journal of Physical Chemistry A, 102 (36):7149-7156.
Parusel et al. (1998) "Semiempirical Studies of Solvent Effects on the Intramolecular Charge Transfer of the Fluorescence Probe PRODAN", Journal of the Chemical Society, Faraday Transactions, 94(19):2923-2927.
Pasquel et al. (Nov. 2014) "Hyperosmolar Hyperglycemic State: A Historic Review of the Clinical Presentation, Diagnosis, and Treatment", Diabetes Care, 37(11):3124-3131.
Pederzoli et al. (Mar. 28, 2014) "Fluorescence of PRODAN in Water: A Computational QM/MM MD Study", Chemical Physics Letters, 597:57-62.
Pflugrath et al. (Mar. 21, 1985) "Sulphate Sequestered in the Sulphate-Binding Protein of *Salmonella typhimurium* is Bound Solely by Hydrogen Bonds", Nature, 314:257-260.
Pickup (1993) "Developing Glucose Sensors for in Vivo Use", Tibtech, 11:285-291.
Quiocho et al. (Apr. 1996) "Atomic Structure and Specificity of Bacterial Periplasmic Receptors for Active Transport and Chemotaxis: Variation of Common Themes", Molecular Microbiology, 20(1):17-25.
Quiocho et al. (Aug. 15, 1997) "Extensive Features of Tight Oligosaccharide Binding Revealed in High-Resolution Structures of the Maltodextrin Transport/Chemosensory Receptor", Structure, 5(8):997-1015.
Quiocho et al. (Aug. 2, 1984) "Novel Stereospecificity of the L-Arabinose-Binding Protein", Nature, 310:381-386.
Resch-Genger et al. (Oct. 2008) "Quantum Dots Versus Organic Dyes as Fluorescent Labels", Nature Methods, 5(9):763-775.
Rettig (Nov. 1986) "Charge Separation in Excited States of Decoupled Systems—TICT Compounds and Implications Regarding the Development of New Laser Dyes and the Primary Process of Vision and Photosynthesis", Angewandte Chemie, 25(11):971-988.
Riklin et al. (Aug. 24, 1995) "Improving Enzyme—Electrode Contacts by Redox Modification of Cofactors", Nature, 376:672-675.

(56) References Cited

OTHER PUBLICATIONS

Rossin et al. (Apr. 10, 2010) "In Vivo Chemistry for Pretargeted Tumor Imaging in Live Mice", Angewandte Chemie, 49(19):3375-3378.
Salins et al. (2001) "A Novel Reagentless Sensing System for Measuring Glucose Based on the Galactose/Glucose-Binding Protein", Analytical Biochemistry, 294:19-26.
Samanta et al. (Sep. 1, 2000) "Excited State Dipole Moment of PRODAN as Determined from Transient Dielectric Loss Measurements", The Journal of Physical Chemistry A, 104(39):8972-7975.
Sanders et al. (Oct. 1994) "Identification of a Locus Involved in the Utilization of Iron by Haemophilus Influenzae", Infection and Immunity, 62(10):4515-4525.
Sapsford et al. (Jul. 10, 2006) "Materials for Fluorescence Resonance Energy Transfer Analysis: Beyond Traditional Donor—Acceptor Combinations", Angew Chern Int Ed Engl, 45(28):4562-4589.
Scheller et al. (Feb. 2001) "Research and Development in Biosensors", Current Opinion in Biotechnology, 12(1):35-40.
Scholle et al. (Jun. 1987) "Sequence of the Mglb Gene from *Escherichia coli* K12: Comparison of Wild-Type and Mutant Galactose Chemoreceptors", Molecular and General Genetics MGG, 208(1-2):247-253.
Schwartz et al. (1976) "Further Studies on the Binding of Maltose to the Maltose-Binding Protein of *Escherichia coli*", European Journal of Biochemistry, 71:167-170.
Scripture et al. (Sep. 5, 1987) "High-Affinity L-Arabinose Transport Operon. Nucleotide Sequence and Analysis of Gene Products", Journal of Molecular Biology, 197(1):37-46.
Serizawa et al. (Sep. 15, 2005) "A Peptide Motif Recognizing a Polymer Stereoregularity", Journal of the American Chemical Society, 127(40):13780-13781.
Serizawa et al. (Oct. 23, 2007) "Highly Specific Affinities of Short Peptides Against Synthetic Polymers", Langmuir, 23(22):11127-11133.
Serizawa et al. (Jun. 18, 2007) "Isolation of Peptides that Can Recognize Syndiotactic Polystyrene", Chembiochem, 8(9):989-993.
Serizawa et al. (2007) "Peptide Motifs that Recognize Differences in Polymer-Film Surfaces", Angew Chem Int Ed Engl, 46(5):723-726.
Sharff et al. (Nov. 10, 1992) "Crystallographic Evidence of a Large Ligand-Induced Hinge-Twist Motion between the two Domains of the Maltodextrin Binding Protein Involved in Active Transport and Chemotaxis", Biochemistry, 31(44):10657-10663.
Shen et al. (Dec. 21, 2015) "Fluorescence Enhancement on Silver Nanoplates at the Single- and Sub-Nanoparticle Level", Nanoscale, 7(47):20132-20141.
Shin et al. (2005) "Chemical structure and physical properties of cyclic olefin copolymers (IUPAC Technical Report)", Pure and Applied Chemistry, 77(5):801-814.
Shoseyov et al. (Jun. 2006) "Carbohydrate Binding Modules: Biochemical Properties and Novel Applications", Microbiology and Molecular Biology Reviews, 70(2):283-295.
Smith et al. (2005) "Orthogonal Site-Specific Protein Modification by Engineering Reversible Thiol Protection Mechanisms", Protein Science, 14:64-73.
Smith et al. (1999) "Substrate Specificity of the Periplasmic Dipeptide-Binding Protein from *Escherichia coli*: Experimental Basis for the Design of Peptide Prodrugs", Microbiology, 145:2891-2901.
Spurlino et al. (Mar. 15, 1991) "The 2.3-A Resolution Structure of the Maltose- or Maltodextrinbinding Protein, A Primary Receptor of Bacterial Active Transport and Chemotaxis", Journal of Biological Chemistry, 266(8):5202-5219.
Sun et al. (Apr. 24, 1998) "The Structure of Glutamine-Binding Protein Complexed With Glutamine at 1.94 A Resolution: Comparisons with other Amino Acid Binding Proteins", Journal of Molecular Biology, 278(1):219-229.
Tam et al. (Jun. 1993) "Structural, Functional, and Evolutionary Relationships among Extracellular Solute-Binding Receptors of Bacteria", Microbiological Reviews, 57(2):320-346.
Tian et al. (Oct. 1, 2003) "How Well is Enzyme Function Conserved as a Function of Pairwise Sequence Identity?", Journal of Molecular Biology, 333(4):863-882.
Todd (Apr. 1, 2001) "Evolution of Function in Protein Superfamilies, from a Structural Perspective", Journal of Molecular Biology, 307(4):1113-1143.
Vodnik et al. (May 15, 2012) "HWGMWSY, an Unanticipated Polystyrene Binding Peptide from Random Phage Display Libraries", Analytical Biochemistry, 424(2):83-86.
Vyas et al. (Apr. 26, 1994) "Crystallographic Analysis of the Epimeric and Anomeric Specificity of the Periplasmic Transport/Chemosensory Protein Receptor for D-Glucose and D-Galactose", Biochemistry, 33(16):4762-4768.
Vyas et al. (Dec. 2, 1988) "Sugar and Signal-Transducer Binding Sites of the *Escherichia coli* Galactose Chemoreceptor Protein", Science, 242(4883):1290-1295.
Groarke et al. (Nov. 1983) "The Amino Acid Sequence of D-Ribose-binding Protein from *Escherichia coli* K12", Journal of Biological Chemistry, 258(21):12952-12956.
Group (Sep. 30, 1993) "The Effect of Intensive Treatment of Diabetes on the Development and Progression of Long-Term Complications in Insulin-Dependent Diabetes Mellitus", The New England Journal of Medicine, 329:977-986.
Gunay et al. (Oct. 21, 2015) "Identification of Soft Matter Binding Peptide Ligands Using Phage Display", Bioconjugate Chemistry, 26(10):2002-2015.
Guo et al. (Jun. 10, 2013) "Identification and Characterization of a Cellulose Binding Heptapeptide Revealed by Phage Display", Biomacromolecules, 14(6):1795-1805.
Guyer et al. (Nov. 1986) "Binding Specificity of the Periplasmic Oligopeptide-Binding Protein from *Escherichia coli*", Journal of Bacteriology, 168(2):775-779.
He et al. (1993) "Dominant Role of Local Dipoles in Stabilizing Uncompensated Charges on a Sulfate Sequestered in a Periplasmic Active Transport Protein", Protein Science, 2:1643-1647.
Heisel et al. (Jul. 24, 1987) "Experimental Evidence of an Intramolecular Reaction in Excited PRODAN Solution", Chemical Physics Letters, 138(4):321-326.
Hellinga et al. (Jul. 1985) "Nucleotide Sequence and High-Level Expression of the Major *Escherichia coli* Phosphofructokinase", European Journal of Biochemistry, 149(2)363-373.
Hellinga et al. (Apr. 1998) "Protein Engineering and the Development of Generic Biosensors", Trends in Biotechnology, 16:183-189.
Henry et al. (1992) "Singular Value Decomposition: Application to Analysis of Experimental Data", Methods in Enzymology, 210:129-192.
Hnilova et al. (2012) "Peptide-Directed Co-Assembly of Nanoprobes on Multimaterial Patterned Solid Surfaces", Soft Matter, 8(16):4327-4334.
Hsiao et al. (Sep. 20, 1996) "The Crystal Structure of Glutamine-binding Protein from *Escherichia coli*", Journal of Molecular Biology, 262(2):225-242.
Jacobson et al. (Dec. 5, 1998) "Sulfate-Binding Protein Dislikes Protonated Oxyacids. a Molecular Explanation", Journal of Molecular Biology, 204(3):783-787.
Joshi et al. (Jan. 29, 1998) "*Escherichia coli* Lysine-Arginine-Omithine(LAO)-Binding Periplasmic Protein Argt (Argt) Gene, Partial Cds, Histidine-Binding Periplasmic Protein Hisj (Hisj) And Histidine Transport System Permease Protein Hisq (Hisq) Genes, Complete Cds, and Histidine Tran", GenBank: U47027.1, 2 pages.
Judge et al. (Feb. 27, 2011) "Continuous Glucose Monitoring Using a Novel Glucose/Galactose Binding Protein: Results of a 12-Hour Feasibility Study with the Becton Dickinson Glucose/Galactose Binding Protein Sensor", Diabetes Technology & Therapeutics, 13(3):309-317.
Kabsch (2010) "XDS", Acta Crystallographica Section D Biological Crystallography, D66:125-132.
Kawski et al. (May 2001) "Ground and Excited State Dipole Moments of BADAN and ACRYLODAN Determined from

(56) References Cited

OTHER PUBLICATIONS

Solvatochromic Shifts of Absorption and Fluorescence Spectra", Zeitschrift für Naturforschung A, 56(5):407-411.
Kawski et al. (Aug. 2002) "Thermochromic Absorption, Fluorescence Band Shifts and Dipole Moments of BADAN and ACRYLODAN", Zeitschrift für Naturforschung A, 57(8):716-722.
Kleywegt et al. (Aug. 15, 1996) "Checking Your Imagination: Applications of the Free R Value", Structure, 4(8):897-904.
Klymchenko et al. (Jan. 1, 2013) "Fluorescent Environment-Sensitive Dyes as Reporters of Biomolecular Interactions", Progress in Molecular Biology and Translational Science, 113:35-58.
Kolb et al. (Jun. 1, 2001) "Click Chemistry: Diverse Chemical Function from a Few Good Reactions", Angewandte Chemie International Edition, 40(11):2004-2021.
Koo et al. (Nov. 19, 2012) "Bioorthogonal Copper-Free Click Chemistry In Vivo for Tumor-Targeted Delivery of Nanoparticles", Angewandte Chemie, 51(47):11836-11840.
Kucherak et al. (Jan. 12, 2010) "Fluorene Analogues of Prodan with Superior Fluorescence Brightness and Solvatochromism", The Journal of Physical Chemistry Letters, 1(3):616-620.
Kumada et al. (Dec. 14, 2009) "Characterization of Polystyrene-Binding Peptides (PS-tags) for Site-Specific Immobilization of Proteins", Journal of Bioscience and Bioengineering, 109(6):583-587.
Kumada et al. (Aug. 31, 2012) "Screening of PC and PMMA-Binding Peptides for Site-Specific Immobilization of Proteins", Journal of Biotechnology, 160(3-4):222-228.
Kumada (Nov. 2014) "Site-Specific Immobilization of Recombinant Antibody Fragments Through Material-Binding Peptides for the Sensitive Detection of Antigens in Enzyme Immunoassays", Biochimica et Biophysica Acta (BBA)—Proteins and Proteomics, 1844(11):1960-1969.
Layton et al. (Nov. 4, 2010) "Thermodynamic Analysis of Ligand-Induced Changes in Protein Thermal Unfolding Applied to High-Throughput Determination of Ligand Affinities with Extrinsic Fluorescent Dyes", Biochemistry, 49(51):10831-10841.
Ledvina et al. (Jun. 1996) "Negative Electrostatic Surface Potential of Protein Sites Specific for Anionic Ligands", Proceedings of the National Academy of Sciences, 93:6786-6791.
Lee et al. (Jun. 2002) "Ordering of Quantum Dots Using Genetically Engineered Viruses", Science, 296(5569):892-895.
Lobo et al. (Nov. 20, 2003) "Does PRODAN Possess a Planar or Twisted Charge-Transfer Excited State? Photophysical Properties of Two PRODAN Derivatives", The Journal of Physical Chemistry A, 107(50):10938-10943.
Lu et al. (Nov. 23, 2006) "Long-Wavelength Analogue of PRODAN: Synthesis and Properties of Anthradan, a Fluorophore with a 2,6-Donor-Acceptor Anthracene Structure", The Journal of Organic Chemistry, 71(26):9651-9657.
Luecke et al. (Sep. 27, 1990) "High Specificity of a Phosphate Transport Protein Determined by Hydrogen Bonds", Nature, 347:402-406.
Magota et al. (Mar. 1984) "Nucleotide Sequence of the phoS Gene, the Structural Gene for the Phosphate-Binding Protein of *Escherichia coli*", Journal of Bacteriology, 157(3):909-917.
Marini et al. (Dec. 3, 2010) "What is Solvatochromism?", The Journal of Physical Chemistry B, 114(51):17128-17135.
Marvin et al. (Apr. 24, 2001) "Conversion of A Maltose Receptor into a Zinc Biosensor by Computational Design", Proceedings of the National Academy of Sciences, 98(9):4955-4960.
Marvin et al. (1998) "Engineering Biosensors by Introducing Fluorescent Allosteric Signal Transducers: Construction of a Novel Glucose Sensor", Journal of the American Chemical Society, 120:7-11.
Marvin et al. (Apr. 1997) "The Rational Design of Allosteric Interactions in a Monomeric Protein and its Applications to the Construction of Biosensors", Proceedings of the National Academy of Sciences, 94:4366-4371.
MATSUNO et al. (May 24, 2008) "Biological Selection of Peptides for Poly(l-lactide) Substrates", Langmuir, 24(13):6399-6403.
Mcdonagh et al. (Jan. 30, 2008) "Optical Chemical Sensors", Chemical Reviews, 108(2):400-422.
Meadows et al. (Oct. 1996) "Recent Developments with Biosensing Technology and Applications in the Pharmaceutical Industry", Advanced Drug Delivery Reviews, 21(3):179-189.
Medintz et al. (Jun. 1, 2005) "Quantum Dot Bioconjugates for Imaging, Labelling and Sensing", Nature Materials, 4:435-446.
Medveczky et al. (Nov. 18, 1969) "The Binding and Release of Phosphate by a Protein Isolated from *Escherichia coli*", Biochimica et Biophysica Acta (BBA)—General Subjects, 192(2):369-371.
Mennucci et al. (Nov. 16, 2007) "How the Environment Controls Absorption and Fluorescence Spectra of PRODAN: A Quantum-Mechanical Study in Homogeneous and Heterogeneous Media", The Journal of Physical Chemistry B, 112(2):414-423.
Meyerhoff et al. (1966) "Current Status of the Glucose Sensor", Endricon, 6(1):51-58.
Miller et al. (Nov. 25, 1983) "Rates of Ligand Binding to Periplasmic Proteins Involved in Bacterial Transport and Chemotaxis", The Journal of Biological Chemistry, 258(22)13665-13672.
Mowbray et al. (May 5, 1992) "1.7 A X-Ray Structure of the Periplasmic Ribose Receptor from *Escherichia coli*", Journal of Molecular Biology, 225(1)155-175.
Naughton et al. (Mar. 11, 2013) "Local Solvent Acidities in β-Cyclodextrin Complexes with PRODAN Derivatives", The Journal of Physical Chemistry B, 117(12):3323-3327.
Nemkovich et al. (Jan. 1, 2007) "Molecular Stark-Effect Spectroscopy of Prodan and Laurdan in Different Solvents and Electric Dipole Moments in their Equilibrated Ground and Franck-Condon Excited State", Journal of Photochemistry and Photobiology A: Chemistry, 185(1):26-31.
Neves et al. (Jun. 19, 2013) "Imaging Cell Surface Glycosylation in Vivo Using "Double Click" Chemistry", Bioconjugate chemistry, 24(6):934-941.
Nickitenko (Dec. 1995) "2 A Resolution Structure of DppA, a Periplasmic Dipeptide Transport/Chemosensory Receptor", Biochemistry, 34(51):16585-16595.
Brune et al. (Jul. 1994) "Direct, Real-Time Measurement of Rapid Inorganic Phosphate Release Using a Novel Flourescent Probe and its Application to Actomyosin Subfragment 1 ATPase", Biochemistry, 33(27):8262-8271.

* cited by examiner

| Position | Allowed residues |
|---|---|
| 14 | D, N |
| 16 | F, Y, W |
| 91 | N, D |
| 152 | H, N, Q |
| 154 | D, N |
| 158 | R |
| 183 | W, F, Y |
| 211 | N, D |
| 236 | D, N |
| 256 | N, D |

FIG. 3 (cont.)

```
        β6         α6                β7          α7               β8        α8                         β9
EF     ------    ==============      -------    ============      ------    ==========================     -----
  140        150       160       170        180       190       200       210       220                         230
DLNKDGQIQFVLLKGEPGHPDAEARTTYVIKELNDKG-IKTEQLQ-LDTAMWDTAQAKDKMDAWLSGPNAN-KIEVVIANNDAMAMGAVEALK-------A----HNKSS---IPVFGVD  ecGGBP
DKNHDGVMQYVMLMGQPGHQDAILRTQYSIQTVKDAG-IKVQELA-KDYANWDRVTAHDKMAAWLSSFG--DKIEAVFCNNDDMALGAIEALKSAGYFT-G----N--KY---IPVVGVD  ttGGBP
DKNHDGIMQYVMITGEPGHQDAILRTEYSIKAVEAAG-IRVKCLA-QDTAMWDRVKGQEKMQAFLASFG-D-KIEAVFCNNDDMALGAIEALK-------AAGYFKDGKY---VPVVGVD  cobGGBP
DKNHNGIMEYVMITGEPGHQDAILRTEYSIKAVEAAG-IKTKALA-QDTAMWDRVKGQEKMQAFLAS-FGD-RIEAVFCNNDDMALGAIEALKAAG---YF----KNGKY---IPVVGVD  chyGGBP
DKNGDGKLQYVLLQGEPGHQDAELRTKFSVQAIQDAG-IEVEALA-VDTAMWDRVKGQEKMQTFLAS-HGD-KIEAVLANNDDMALGAIEALKAAG---YF----SGDKY---MPVVGVD  pspGGBP
DKNGDGRIQYVILEGEMGHQDAIVRTESVTESMKNNG-LQIEKLS-CQIANWNRAQAQNRMTQLIGQ-YKN-SIELVIANNDAMALGAIDAYEKLG----V----TESNV---PAFFGVD  ereGGBP
D----GTIRYIMLKGEMRNQDAEKRTQYSIKALEDSG-FKVQKVA-EDTAMWDRTKAQEKMTSFISS-YGP-NFDCVIANNDDMALGAVDALKAAG--Y-F----NGGKY---VPVVGVD  cauGGBP
DIDGDGSVSYITLMGDPANVDAKQRTEYSVKGLEEKGVKTNALAQ-PYQANWDTAKGQEFTANALEQF-GN-KLEVVFANNDGMAVGAVTAIE-------A----AGRKVGEDIFVVGVD  erhGGBP
DKNGDGIFQYVVLEGEAGHQDAIVRTEYSVSTMIDSG-VEVEKLG-YAIANWNRAQAQTKMAQLMSQ-FGD-SIELVIANNDDMALGAIDALKASG----L----TKDEW---PAVIGID  rinGGPB_B
D----GTIRYIMLKGETRNQDAEKRTQYSIKALKDSG-FKVQKVA-EDTAMWDRTKAQEKMTSFISSYG--PNFDCVIANNDDMALGAVDALKAAGYFN-G----G--KY---VPVVGVD  cljGGBP
DINGDGKITYIMCKGDPENIDAQYRTEYSIKALTDAG-KEVECLYE-YLDNWDQTTAQQDVANALSQYGEK--IEVVFCNNDAMALGALQSIQQAG----R----TVGKD---VYLVGVD  fprGGBP
DLNGNGKIDYVMVEGDPENVDAQYRTEYSVKALEDAG-LEVNCLS-DQVGNWQQDQAQQIVANALGQ-YGN-DVEVVFCNNDAMALGALQAIQSAG----R----TVGTD---IYLVGVD  rinGGBP_A
DHNGDGKIQYFMIEGAPENIDAGYRTLYSVSALQNSE-MEMDCLLD-EVGNWDETTASLLVSKGI-QNGLK--PEVIICNNDAMALGAIKAAEKSG----L----VPGED---VYIVGVD  bprGGBP
DFNGDGVVSYVMLMGEKGHEDSQYRTEYSIKALEEGGMKTEELFS--GNGNWNKDEGKKLAKQALASW-GN-RIEVFFCNNDSMANGALEAVE-------E----AGRIPGKDIYLVGVD  csaGGBP

    α9       β10 h2     α10                                  h3    β11
 ========    ------===============                           ------------
240       250       260       270        280           290       300
ALPEALALVKSGALAGTVLNDANNQAKATFDLAKNQA--DGK---G-AADG-TNWKIDN------KVVRVPYVGVDKDNLAEFSKK  ecGGBP
ATAPGIQAIKDGTLLGTVLNDAKNQAKATFNIAYELA-----QGIT-PTKD-NIGYDITDG----KYVWIPYKKITKDNISDAEQ  ttGGBP
ATTPGLQALEEGTLLGTVLNDAKAQGKATFNLAYVLA--KGE---K-P-----TKENVGFEITDGKYIWVPYQKVTKDNLEEMKKYVNEQ  cobGGBP
ATTPGLQALEEGTLLGTVLNDAKAQGKATFNLAYVLA--KGE---K-PTKE-NVGFDITDG----KYIWVPYQKVTKDNLEEMKKYVNEQ  chyGGBP
ATAPAVQALEDGTLLGTVLNDAKSQGKASVAIAAALS--KGE---A-PNKE-NTGFDITDG----KYVWIAYKKITKDNIADAK  pspGGBP
GTDDGLEAVQQSKLAATVYNDKEGQAMAMAQLAYLAA--TGG---S--MKN-IK-FEDKK------YVYLPYEKVTPDNVNEFVKDEQ  ereGGBP
ATAPAVKAVEDGTLFGTVLNDAAKQGDAAFDLSYILS--KGK---IPDESN-FKYKITDG-----KYIWIDYKMITKENVQDAK  cauGGBP
AIPDAIELLKGGKLTGTVLNDHFNQSHTAVDVALELLQ----------GKDVSAYYWHDYV----GVTKPEEAELKRAEARKETVEEAVKRYAERDAQ  erhGGBP
GTDVGLEAVKNKEMIGTVYNDKEGQADAMLNLAYELS--TGS---D--LSD-LN-LIDGK------YIRLPYARVTCDDVDSYMEGDTE  rinGGPB_B
ATAPAVKAVEDGTLFGTVLNDAAKQGDAAFDLSYILS-----KGKI-PDES-NFKYKVTDG----KYIWIDYKMITKENVQDAK  cljGGBP
ALVEAVQNVVDGNMTGTVLNDDVGQATKAAEATKLFV--EGK-------DV-EKYYWVDYV----KVTKDNASQYLKED  fprGGBP
ALSEALEDVLAGTMTGTVFNDHFSQSHSAADAAINYITG------------------AGND----HYIGCDYVKVTKDNAQDVLDMVK  rinGGBP_A
ALPEAIEMIKAGKLAGTVYNDYVLQSHKSADAVINYL--KGI-------DN-EHYIGCDYV----KVDIDNAESIAGLTNTDEEDID  bprGGBP
ALQDTVTYIKEGRMTGTVLNDHEGQSQMAADTLKKMID----------GESVETRYQVDYI----KVTAISTFQTLKGED  csaGGBP
```

$CH_3SO_3^-$

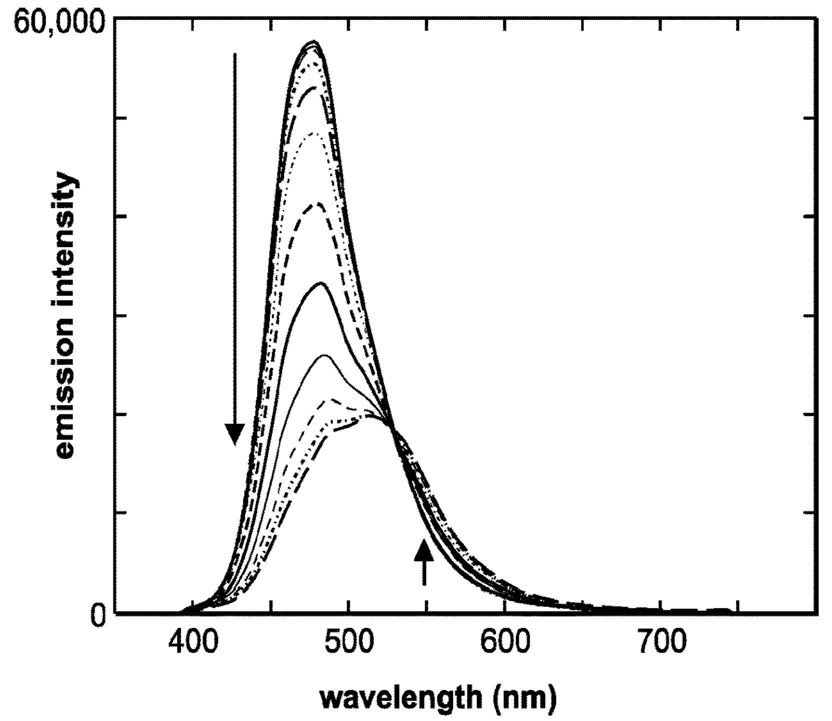
FIG. 11A
FIG. 11B
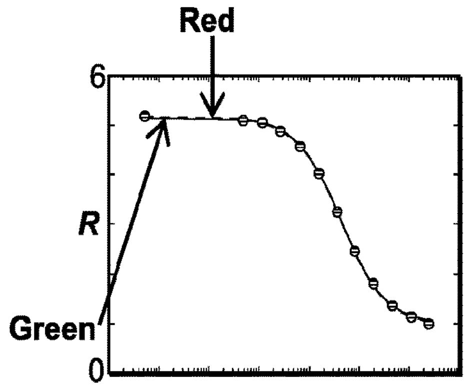
FIG. 11C
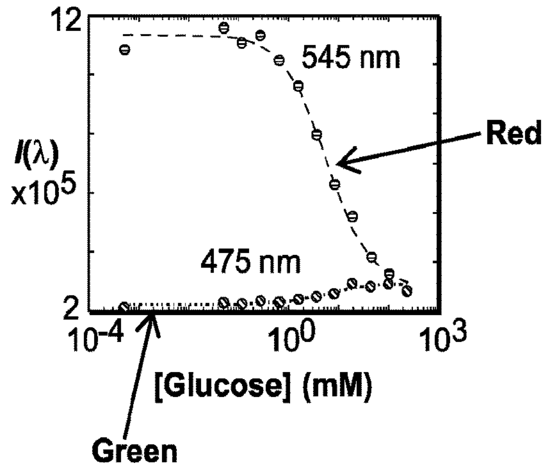

FIG. 20

```
>Exemplary csaGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                              10
                                                                              M  E  T  G  P  K  I  G  V  S  I
CACTATAGGGAGACCACAACGGTTTCCCTCTAGAAATAATTTTGTTTAACTTTAAGAAGGAGATATACCATGGAAACAGGTCCAAAAATTGGTGTAAGTA
GTGATATCCCTCTGGTGTTGCCAAAGGGAGATCTTTATTAAAACAAATTGAAATTCTTCCTCTATATGGTACCTTTGTCCAGGTTTTTAACCACATTCAT
       110       120       130       140       150       160       170       180       190       200

                      20                            30                            40
 Y  R  Y  D  D  T  F  M  K  L  Y  R  Q  E  L  K  Q  Y  L  E  E  T  Y  H  A  E  V  I  M  R  N  A  G
TATACAGGTACGACGACACCTTCATGAAGCTGTATCGCCAGGAACTGAAGCAGTACCTGGAAGAAACCTACCATGCGGAAGTGATCATGCGCAATGCTGG
ATATGTCCATGCTGCTGTGGAAGTACTTCGACATAGCGGTCCTTGACTTCGTCATGGACCTTCTTTGGATGGTACGCCTTCACTAGTACGCGTTACGACC
       210       220       230       240       250       260       270       280       290       300

            50                            60                            70
 G  D  Q  K  E  Q  D  K  Q  V  N  Q  F  I  S  D  G  C  D  G  I  I  V  N  P  V  E  I  P  A  A  Q  E
TGGTGACCAGAAAGAGCAGGACAAACAGGTGAACCAGTTCATCTCAGACGGATGTGACGGGATCATAGTGAATCCGGTGGAAATTCCGGCAGCTCAGGAG
ACCACTGGTCTTTCTCGTCCTGTTTGTCCACTTGGTCAAGTAGAGTCTGCCTACACTGCCCTAGTATCACTTAGGCCACCTTTAAGGCCGTCGAGTCCTC
       310       320       330       340       350       360       370       380       390       400

    80                            90                           100                           110
L  A  D  A  C  S  R  A  G  I  P  L  V  F  I  N  R  E  P  K  E  E  E  Q  K  R  W  R  E  K  Q  M  A  V
CTTGCGGATGCGTGCAGTCGTGCGGGAATCCCCCTTGTGTTCATAAACCGTGAACCCAAGGAAGAAGAACAGAAACGTTGGCGCGAAAAGCAGATGGCAG
GAACGCCTACGCACGTCAGCACGCCCTTAGGGGGAACACAAGTATTTGGCACTTGGGTTCCTTCTTCTTGTCTTTGCAACCGCGCTTTTCGTCTACCGTC
       410       420       430       440       450       460       470       480       490       500

                      120                           130                           140
 S  C  V  G  T  D  S  R  Q  A  G  T  Y  Q  G  E  I  I  L  E  T  L  N  K  G  D  F  N  G  D  G  V  V
TTTCGTGTGTAGGCACCGATAGCCGTCAGGCGGGTACCTATCAGGGCGAAATCATCCTGGAAACCCTGAACAAAGGCGACTTCAACGGTGATGGTGTCGT
AAAGCACACATCCGTGGCTATCGGCAGTCCGCCCATGGATAGTCCCGCTTTAGTAGGACCTTTGGGACTTGTTTCCGCTGAAGTTGCCACTACCACAGCA
       510       520       530       540       550       560       570       580       590       600

            150                           160                           170
 S  Y  V  M  L  M  G  E  K  G  N  E  D  S  Q  Y  R  T  E  Y  S  I  K  A  L  E  E  G  G  M  K  T  E
GTCCTACGTGATGCTCATGGGTGAGAAGGGCAATGAGGACTCGCAATACCGGACGGAATACAGCATCAAAGCGCTGGAAGAAGGCGGCATGAAAACCGAA
CAGGATGCACTACGAGTACCCACTCTTCCCGTTACTCCTGAGCGTTATGGCCTGCCTTATGTCGTAGTTTCGCGACCTTCTTCCGCCGTACTTTTGGCTT
       610       620       630       640       650       660       670       680       690       700
```

FIG. 20 (cont.)

```
 180                           190                           200                           210
E  L  F  S  G  N  G  N  W  N  K  D  E  G  K  K  L  A  K  Q  A  L  A  S  W  G  N  R  I  E  V  F  F  C
GAGCTGTTTTCGGGCAACGGCAACTGGAACAAAGACGAAGGCAAGAAACTGGCGAAACAGGCGCTTGCCTCTTGGGGTAACCGCATAGAGGTGTTCTTCT
CTCGACAAAAGCCCGTTGCCGTTGACCTTGTTTCTGCTTCCGTTCTTTGACCGCTTTGTCCGCGAACGGAGAACCCCATTGGCGTATCTCCACAAGAAGA
       710       720       730       740       750       760       770       780       790       800

                    220                           230                           240
 N  N  D  S  M  A  N  G  A  L  E  A  V  E  E  A  G  R  I  P  G  K  D  I  Y  L  V  G  V  D  A  L  Q
GCAACAACGATTCGATGGCGAATGGTGCGTTGGAAGCAGTGGAGGAGGCAGGTAGGATCCCAGGCAAAGACATCTACCTGGTTGGTGTGGATGCGTTGCA
CGTTGTTGCTAAGCTACCGCTTACCACGCAACCTTCGTCACCTCCTCCGTCCATCCTAGGGTCCGTTTCTGTAGATGGACCAACCACACCTACGCAACGT
       810       820       830       840       850       860       870       880       890       900

          250                           260                           270
 D  T  V  T  Y  I  K  E  G  R  M  T  G  T  V  L  N  D  H  E  G  Q  S  Q  M  A  A  D  T  L  K  K  M
GGATACGGTGACCTACATCAAAGAAGGCCGTATGACCGGAACAGTCCTGAACGACCACGAAGGTCAGAGCCAGATGGCAGCTGATACGCTGAAGAAAATG
CCTATGCCACTGGATGTAGTTTCTTCCGGCATACTGGCCTTGTCAGGACTTGCTGGTGCTTCCAGTCTCGGTCTACCGTCGACTATGCGACTTCTTTTAC
       910       920       930       940       950       960       970       980       990      1000

 280                           290                          300                            310
I  D  G  E  S  V  E  T  R  Y  Q  V  D  Y  I  K  V  T  A  I  S  T  F  Q  T  L  K  G  E  D  G  G  S  H
ATCGATGGAGAGTCAGTGGAGACTCGGTATCAGGTGGACTACATCAAAGTGACTGCCATCTCTACGTTTCAAACTTTAAAAGGTGAAGATGGAGGAAGCC
TAGCTACCTCTCAGTCACCTCTGAGCCATAGTCCACCTGATGTAGTTTCACTGACGGTAGAGATGCAAAGTTTGAAATTTTCCACTTCTACCTCCTTCGG
      1010      1020      1030      1040      1050      1060      1070      1080      1090      1100

 H  H  H  H  H  *  *  *
ATCATCATCATCATCATTAATAATGAAAGGGCGATATCCAGCACACTGGCGGCCGTTACTAGTGGATCCGGCTGCTAACAAAGCCCGAAAGGAAGCTGAG
TAGTAGTAGTAGTAGTAATTATTACTTTCCCGCTATAGGTCGTGTGACCGCCGGCAATGATCACCTAGGCCGACGATTGTTTCGGGCTTTCCTTCGACTC
      1110      1120      1130      1140      1150      1160      1170      1180      1190      1200

TTGGCTGCTGCCACCGCTGAGCAATAACTAGCATAACCCCTTGGGGCCTCTAAACGGGTCTTGAGGGGTTTTTTGCTGAAAGGAGGAACTATATCCGGAG
AACCGACGACGGTGGCGACTCGTTATTGATCGTATTGGGGAACCCCGGAGATTTGCCCAGAACTCCCCAAAAAACGACTTTCCTCCTTGATATAGGCCTC
      1210      1220      1230      1240      1250      1260      1270      1280      1290      1300

CGACTCCCACGGCACGTTGGCAAGCTCG
GCTGAGGGTGCCGTGCAACCGTTCGAGC
      1310      1320
```

FIG. 21

```
>Exemplary bprGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                  10
                                                                                     M  D  A  K  V  G  V  C  I  Y  Q
CACTATAGGGAGACCACAACGGTTTCCCTCTAGAAATAATTTTGTTTAACTTTAAGAAGGAGATATACCATGGATGCAAAAGTTGGTGTATGTATATATC
GTGATATCCCTCTGGTGTTGCCAAAGGGAGATCTTTATTAAAACAAATTGAAATTCTTCCTCTATATGGTACCTACGTTTTCAACCACATACATATATAG
       110       120       130       140       150       160       170       180       190       200

                                       20                             30                             40
 K  S  D  N  F  M  S  L  F  S  S  E  L  V  K  Y  L  V  S  R  G  F  S  K  D  N  I  I  L  Y  D  S  N
AAAAATCGGACAACTTCATGTCGCTCTTCTCCAGCGAACTGGTGAAGTACCTGGTGAGTCGTGGGTTCAGCAAGGACAACATCATCCTGTACGACTCCAA
TTTTTAGCCTGTTGAAGTACAGCGAGAAGAGGTCGCTTGACCACTTCATGGACCACTCAGCACCCAAGTCGTTCCTGTTGTAGTAGGACATGCTGAGGTT
       210       220       230       240       250       260       270       280       290       300

                            50                             60                             70
 N  D  E  N  V  Q  L  S  Q  V  E  E  L  I  A  S  G  I  N  A  L  I  I  N  P  V  N  S  S  V  A  H  S
CAACGACGAGAACGTGCAGTTGTCGCAGGTGGAAGAGCTCATTGCGTCTGGGATCAATGCGCTCATCATCAACCCAGTGAACTCGAGTGTTGCTCACTCG
GTTGCTGCTCTTGCACGTCAACAGCGTCCACCTTCTCGAGTAACGCAGACCCTAGTTACGCGAGTAGTAGTTGGGTCACTTGAGCTCACAACGAGTGAGC
       310       320       330       340       350       360       370       380       390       400

      80                             90                            100                            110
I  T  D  M  A  S  A  S  N  I  P  L  V  Y  I  N  R  E  P  S  G  D  E  E  N  R  W  E  M  Y  Q  L  N  V
ATCACGGACATGGCATCTGCCTCGAACATCCCGTTAGTCTACATCAACCGTGAACCGTCTGGTGACGAAGAGAACCGTTGGGAGATGTATCAGCTGAACG
TAGTGCCTGTACCGTAGACGGAGCTTGTAGGGCAATCAGATGTAGTTGGCACTTGGCAGACCACTGCTTCTCTTGGCAACCCTCTACATAGTCGACTTGC
       410       420       430       440       450       460       470       480       490       500

                                      120                            130                            140
 C  Y  V  G  C  D  A  R  Q  S  G  I  Y  Q  G  E  I  L  L  S  L  G  K  N  K  L  D  H  N  G  D  G  K
TGTGCTATGTCGGCTGTGATGCACGCCAATCTGGCATCTACCAGGGGGAAATCCTCCTGTCTCTGGGCAAAAACAAGCTGGATCACAACGGAGATGGCAA
ACACGATACAGCCGACACTACGTGCGGTTAGACCGTAGATGGTCCCCCTTTAGGAGGACAGAGACCCGTTTTTGTTCGACCTAGTGTTGCCTCTACCGTT
       510       520       530       540       550       560       570       580       590       600

                            150                            160                            170
 I  Q  Y  F  M  I  E  G  A  P  E  N  I  D  A  G  Y  R  T  L  Y  S  V  S  A  L  Q  N  S  E  M  E  M
GATCCAGTACTTCATGATCGAAGGTGCACCGGAGAACATCGATGCAGGCTATCGTACGCTGTACTCCGTTTCTGCTCTGCAGAACAGCGAAATGGAGATG
CTAGGTCATGAAGTACTAGCTTCCACGTGGCCTCTTGTAGCTACGTCCGATAGCATGCGACATGAGGCAAAGACGAGACGTCTTGTCGCTTTACCTCTAC
       610       620       630       640       650       660       670       680       690       700
```

FIG. 21 (cont.)

```
  180                                     190                                     200                                     210
D  C  L  L  D  E  V  G  N  W  D  E  T  T  A  S  L  L  V  S  K  G  I  Q  N  G  L  K  P  E  V  I  I  C
GATTGCCTGCTGGATGAAGTGGGCAACTGGGATGAAACCACTGCCAGTCTGCTGGTCTCCAAGGGCATCCAGAATGGGCTCAAACCGGAGGTCATCATCT
CTAACGGACGACCTACTTCACCCGTTGACCCTACTTTGGTGACGGTCAGACGACCAGAGGTTCCCGTAGGTCTTACCCGAGTTTGGCCTCCAGTAGTAGA
        710       720       730       740       750       760       770       780       790       800

                                    220                                     230                                     240
  N  N  D  A  M  A  L  G  A  I  K  A  A  E  K  S  G  L  V  P  G  E  D  V  Y  I  V  G  V  D  A  L  P
GCAACAACGACGCGATGGCACTGGGTGCCATCAAAGCGGCGGAAAAATCGGGTCTGGTTCCGGGTGAAGACGTCTACATCGTGGGTGTTGACGCCTTGCC
CGTTGTTGCTGCGCTACCGTGACCCACGGTAGTTTCGCCGCCTTTTTAGCCCAGACCAAGGCCCACTTCTGCAGATGTAGCACCCACAACTGCGGAACGG
        810       820       830       840       850       860       870       880       890       900

                        250                                     260                                     270
 E  A  I  E  M  I  K  A  G  K  L  A  G  T  V  Y  N  D  Y  V  L  Q  S  H  K  S  A  D  A  V  I  N  Y
TGAAGCGATCGAAATGATCAAAGCAGGGAAGCTCGCAGGTACCGTGTACAACGACTACGTGCTGCAGTCCCACAAAAGCGCAGATGCGGTCATCAACTAC
ACTTCGCTAGCTTTACTAGTTTCGTCCCTTCGAGCGTCCATGGCACATGTTGCTGATGCACGACGTCAGGGTGTTTTCGCGTCTACGCCAGTAGTTGATG
        910       920       930       940       950       960       970       980       990      1000

  280                                     290                                     300                                     310
L  K  G  I  D  N  E  H  Y  I  G  C  D  Y  V  K  V  D  I  D  N  A  E  S  I  A  G  L  T  N  T  D  E  E
CTGAAAGGGATCGACAACGAGCACTACATCGGTTGCGATTACGTGAAAGTGGATATCGACAACGCGGAAAGCATTGCGGGGTTGACAAATACAGATGAAG
GACTTTCCCTAGCTGTTGCTCGTGATGTAGCCAACGCTAATGCACTTTCACCTATAGCTGTTGCGCCTTTCGTAACGCCCCAACTGTTTATGTCTACTTC
       1010      1020      1030      1040      1050      1060      1070      1080      1090      1100

                                    320
  D  I  D  G  G  S  H  H  H  H  H  H  *  *  *
AAGATATTGATGGAGGAAGCCATCATCATCATCATCATTAGTAATAAAAGGGCGATATCCAGCACACTGGCGGCCGTTACTAGTGGATCCGGCTGCTAAC
TTCTATAACTACCTCCTTCGGTAGTAGTAGTAGTAGTAATCATTATTTTCCCGCTATAGGTCGTGTGACCGCCGGCAATGATCACCTAGGCCGACGATTG
       1110      1120      1130      1140      1150      1160      1170      1180      1190      1200

AAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGA
TTTCGGGCTTTCCTTCGACTCAACCGACGACGGTGGCGACTCGTTATTGATCGTATTGGGGAACCCCGGAGATTTGCCCAGAACTCCCCAAAAAACGACT
       1210      1220      1230      1240      1250      1260      1270      1280      1290      1300

AAGGAGGAACTATATCCGGAGCGACTCCCACGGCACGTTGGCAAGCTCG
TTCCTCCTTGATATAGGCCTCGCTGAGGGTGCCGTGCAACCGTTCGAGC
       1310      1320      1330      1340
```

FIG. 22

```
>Exemplary rinGGBP_A (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                  10
                                                                                M  K  V  G  V  C  I  Y  Q  F  S
CACTATAGGGAGACCACAACGGTTTCCCTCTAGAAATAATTTTGTTTAACTTTAAGAAGGAGATATACCATGAAAGTTGGTGTATGTATTTACCAATTTA
GTGATATCCCTCTGGTGTTGCCAAAGGGAGATCTTTATTAAAACAAATTGAAATTCTTCCTCTATATGGTACTTTCAACCACATACATAAATGGTTAAAT
       110       120       130       140       150       160       170       180       190       200

                         20                             30                             40
 D  N  F  M  T  L  F  R  T  E  L  E  N  Y  L  V  E  K  G  F  S  K  D  N  I  T  I  V  D  G  A  N  D
GTGACAACTTCATGACGCTCTTCCGTACCGAACTGGAAAACTACCTGGTGGAAAAAGGCTTTAGCAAGGACAACATCACCATCGTTGATGGCGCTAACGA
CACTGTTGAAGTACTGCGAGAAGGCATGGCTTGACCTTTTGATGGACCACCTTTTTCCGAAATCGTTCCTGTTGTAGTGGTAGCAACTACCGCGATTGCT
       210       220       230       240       250       260       270       280       290       300

               50                             60                             70
Q  A  T  Q  T  G  Q  I  D  N  F  I  T  E  G  V  D  V  L  I  I  N  P  V  N  S  S  S  A  A  T  I  T
TCAGGCTACGCAGACTGGCCAGATCGACAACTTCATCACCGAAGGGGTGGATGTCCTCATCATCAATCCGGTCAACAGCAGCAGTGCAGCGACGATTACC
AGTCCGATGCGTCTGACCGGTCTAGCTGTTGAAGTAGTGGCTTCCCCACCTACAGGAGTAGTAGTTAGGCCAGTTGTCGTCGTCACGTCGCTGCTAATGG
       310       320       330       340       350       360       370       380       390       400

   80                             90                             100                            110
D  K  V  V  A  A  G  I  P  L  V  Y  I  N  R  E  P  D  E  E  E  Q  K  R  W  S  D  N  N  W  D  V  T  Y
GATAAAGTGGTGGCAGCAGGCATTCCGCTGGTCTACATCAACCGAGAACCGGATGAAGAAGAGCAGAAACGCTGGAGTGACAACAACTGGGACGTGACGT
CTATTTCACCACCGTCGTCCGTAAGGCGACCAGATGTAGTTGGCTCTTGGCCTACTTCTTCTCGTCTTTGCGACCTCACTGTTGTTGACCCTGCACTGCA
       410       420       430       440       450       460       470       480       490       500

                        120                            130                            140
 V  G  C  D  A  R  Q  S  G  T  F  Q  G  E  M  I  S  D  L  G  L  D  T  V  D  L  N  G  N  G  K  I  D
ACGTGGGTTGCGATGCGCGTCAGTCTGGGACATTCCAGGGTGAGATGATCAGCGATCTTGGCCTGGATACGGTCGATCTGAACGGAAACGGGAAAATCGA
TGCACCCAACGCTACGCGCAGTCAGACCCTGTAAGGTCCCACTCTACTAGTCGCTAGAACCGGACCTATGCCAGCTAGACTTGCCTTTGCCCTTTTAGCT
       510       520       530       540       550       560       570       580       590       600

              150                            160                            170
Y  V  M  V  E  G  D  P  E  N  V  D  A  Q  Y  R  T  E  Y  S  V  K  A  L  E  D  A  G  L  E  V  N  C
CTACGTCATGGTGGAAGGTGATCCAGAGAACGTGGATGCCCAGTATCGCACGGAATACTCCGTGAAAGCACTGGAAGATGCGGGTCTCGAAGTGAACTGC
GATGCAGTACCACCTTCCACTAGGTCTCTTGCACCTACGGGTCATAGCGTGCCTTATGAGGCACTTTCGTGACCTTCTACGCCCAGAGCTTCACTTGACG
       610       620       630       640       650       660       670       680       690       700
```

FIG. 22 (cont.)

```
180                                190                                200                                210
L  S  D  Q  V  G  N  W  Q  Q  D  Q  A  Q  Q  I  V  A  N  A  L  G  Q  Y  G  N  D  V  E  V  V  F  C  N
TTGAGCGATCAGGTTGGGAACTGGCAGCAGGATCAGGCACAGCAGATTGTGGCGAATGCTCTCGGTCAGTATGGCAACGACGTAGAGGTTGTGTTCTGCA
AACTCGCTAGTCCAACCCTTGACCGTCGTCCTAGTCCGTGTCGTCTAACACCGCTTACGAGAGCCAGTCATACCGTTGCTGCATCTCCAACACAAGACGT
       710       720       730       740       750       760       770       780       790       800

                   220                                230                                240
 N  D  A  M  A  L  G  A  L  Q  A  I  Q  S  A  G  R  T  V  G  T  D  I  Y  L  V  G  V  D  A  L  S  E
ACAACGACGCTATGGCGTTAGGTGCCTTACAGGCGATTCAGAGCGCAGGTCGTACCGTTGGTACTGACATCTACCTGGTTGGTGTGGATGCGTTGAGCGA
TGTTGCTGCGATACCGCAATCCACGGAATGTCCGCTAAGTCTCGCGTCCAGCATGGCAACCATGACTGTAGATGGACCAACCACACCTACGCAACTCGCT
       810       820       830       840       850       860       870       880       890       900

          250                                260                                270
A  L  E  D  V  L  A  G  T  M  T  G  T  V  F  N  D  H  F  S  Q  S  H  S  A  A  D  A  A  I  N  Y  I
AGCACTGGAGGATGTGCTGGCTGGTACCATGACCGGAACTGTGTTCAACGACCACTTCAGTCAGTCCCATAGTGCGGCAGATGCGGCTATCAACTACATC
TCGTGACCTCCTACACGACCGACCATGGTACTGGCCTTGACACAAGTTGCTGGTGAAGTCAGTCAGGGTATCACGCCGTCTACGCCGATAGTTGATGTAG
       910       920       930       940       950       960       970       980       990      1000

280                                290                                300                                310
T  G  A  G  N  D  H  Y  I  G  C  D  Y  V  K  V  T  K  D  N  A  Q  D  V  L  D  M  V  K  G  G  S  H  H
ACAGGAGCTGGAAACGACCACTACATCGGCTGCGATTACGTGAAAGTGACCAAAGACAACGCACAAGATGTGTTAGATATGGTTAAAGGAGGAAGCCATC
TGTCCTCGACCTTTGCTGGTGATGTAGCCGACGCTAATGCACTTTCACTGGTTTCTGTTGCGTGTTCTACACAATCTATACCAATTTCCTCCTTCGGTAG
      1010      1020      1030      1040      1050      1060      1070      1080      1090      1100

 H  H  H  H  *  *  *
ATCATCATCATCATTAATGATAAAAGGGCGATATCCAGCACACTGGCGGCCGTTACTAGTGGATCCGGCTGCTAACAAAGCCCGAAAGGAAGCTGAGTTG
TAGTAGTAGTAGTAATTACTATTTTCCCGCTATAGGTCGTGTGACCGCCGGCAATGATCACCTAGGCCGACGATTGTTTCGGGCTTTCCTTCGACTCAAC
      1110      1120      1130      1140      1150      1160      1170      1180      1190      1200

GCTGCTGCCACCGCTGAGCAATAACTAGCATAACCCCTTGGGGCCTCTAAACGGGTCTTGAGGGGTTTTTTGCTGAAAGGAGGAACTATATCCGGAGCGA
CGACGACGGTGGCGACTCGTTATTGATCGTATTGGGGAACCCCGGAGATTTGCCCAGAACTCCCCAAAAAACGACTTTCCTCCTTGATATAGGCCTCGCT
      1210      1220      1230      1240      1250      1260      1270      1280      1290      1300

CTCCCACGGCACGTTGGCAAGCTCG
GAGGGTGCCGTGCAACCGTTCGAGC
      1310      1320
```

FIG. 23

```
>Exemplary fprGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                   10
                                                                                M S A N I G V C I Y Q
CACTATAGGGAGACCACAACGGTTTCCCTCTAGAAATAATTTTGTTTAACTTTAAGAAGGAGATATACCATGTCTGCTAATATTGGAGTTTGTATTTATC
GTGATATCCCTCTGGTGTTGCCAAAGGGAGATCTTTATTAAAACAAATTGAAATTCTTCCTCTATATGGTACAGACGATTATAACCTCAAACATAAATAG
       110       120       130       140       150       160       170       180       190       200

                         20                            30                            40
  F  A  D  N  F  M  T  L  Y  R  A  D  L  E  G  Y  L  K  D  M  G  Y  S  V  T  I  M  D  G  K  N  D  Q
AATTTGCCGACAACTTCATGACCCTCTATCGTGCTGACCTGGAAGGCTACCTGAAGGACATGGGCTATTCCGTCACCATCATGGACGGAAAAACGACCA
TTAAACGGCTGTTGAAGTACTGGGAGATAGCACGACTGGACCTTCCGATGGACTTCCTGTACCCGATAAGGCAGTGGTAGTACCTGCCCTTTTTGCTGGT
       210       220       230       240       250       260       270       280       290       300

               50                            60                            70
 N  T  Q  T  E  Q  I  N  T  F  L  Q  Q  G  V  D  V  L  V  I  N  P  V  Q  T  T  S  A  Q  T  I  V  D
GAACACCCAAACCGAGCAGATCAACACCTTCCTGCAGCAAGGCGTTGACGTGCTGGTCATCAACCCAGTTCAGACCACTAGTGCACAGACCATCGTAGAC
CTTGTGGGTTTGGCTCGTCTAGTTGTGGAAGGACGTCGTTCCGCAACTGCACGACCAGTAGTTGGGTCAAGTCTGGTGATCACGTGTCTGGTAGCATCTG
       310       320       330       340       350       360       370       380       390       400

    80                            90                           100                           110
T  V  S  P  S  G  T  P  I  V  F  I  N  R  E  P  E  E  S  V  L  D  S  Y  K  G  K  C  C  Y  V  G  A  D
ACCGTTTCTCCGTCTGGTACCCCAATCGTGTTCATCAACCGTGAACCTGAGGAAAGCGTCCTGGATAGCTACAAGGGCAAGTGCTGCTACGTGGGAGCTG
TGGCAAAGAGGCAGACCATGGGGTTAGCACAAGTAGTTGGCACTTGGACTCCTTTCGCAGGACCTATCGATGTTCCCGTTCACGACGATGCACCCTCGAC
       410       420       430       440       450       460       470       480       490       500

                        120                           130                           140
  A  R  Q  S  G  T  Y  Q  G  E  L  I  L  A  T  D  T  Q  G  D  I  N  G  D  G  K  I  T  Y  I  M  C  K
ATGCTCGGCAGAGTGGTACGTACCAGGGTGAGCTGATCCTGGCAACCGATACGCAAGGCGACATCAACGGTGATGGCAAGATCACCTACATCATGTGCAA
TACGAGCCGTCTCACCATGCATGGTCCCACTCGACTAGGACCGTTGGCTATGCGTTCCGCTGTAGTTGCCACTACCGTTCTAGTGGATGTAGTACACGTT
       510       520       530       540       550       560       570       580       590       600

             150                           160                           170
 G  D  P  E  N  I  D  A  Q  Y  R  T  E  Y  S  I  K  A  L  T  D  A  G  K  E  V  E  C  L  Y  E  Y  L
AGGCGATCCGGAGAACATCGACGCACAGTACCGTACCGAGTACAGCATCAAGGCACTGACCGATGCAGGCAAGGAAGTGGAGTGCCTGTACGAGTACCTG
TCCGCTAGGCCTCTTGTAGCTGCGTGTCATGGCATGGCTCATGTCGTAGTTCCGTGACTGGCTACGTCCGTTCCTTCACCTCACGGACATGCTCATGGAC
       610       620       630       640       650       660       670       680       690       700
```

FIG. 23 (cont.)

```
    180                                                     190                                                     200                                                     210
D  N  W  D  Q  T  T  A  Q  Q  D  V  A  N  A  L  S  Q  Y  G  E  K  I  E  V  V  F  C  N  N  D  A  M  A
GACAACTGGGATCAGACCACTGCACAGCAAGACGTGGCTAACGCACTGTCCCAGTATGGCGAGAAGATCGAAGTCGTCTTCTGCAACAACGACGCTATGG
CTGTTGACCCTAGTCTGGTGACGTGTCGTTCTGCACCGATTGCGTGACAGGGTCATACCGCTCTTCTAGCTTCAGCAGAAGACGTTGTTGCTGCGATACC
         710       720       730       740       750       760       770       780       790       800

                                     220                                                     230                                                     240
 L  G  A  L  Q  S  I  Q  Q  A  G  R  T  V  G  K  D  V  Y  L  V  G  V  D  A  L  V  E  A  V  Q  N  V
CACTGGGCGCATTGCAGAGCATCCAGCAAGCTGGTCGTACCGTTGGCAAAGACGTCTACCTGGTTGGAGTCGATGCGCTGGTAGAGGCTGTCCAGAACGT
GTGACCCGCGTAACGTCTCGTAGGTCGTTCGACCAGCATGGCAACCGTTTCTGCAGATGGACCAACCTCAGCTACGCGACCATCTCCGACAGGTCTTGCA
         810       820       830       840       850       860       870       880       890       900

                         250                                                     260                                                     270
 V  D  G  N  M  T  G  T  V  L  N  D  D  V  G  Q  A  T  K  A  A  E  A  T  K  L  F  V  E  G  K  D  V
TGTCGACGGTAACATGACCGGAACCGTGCTCAACGACGACGTTGGTCAGGCAACGAAAGCTGCAGAAGCGACCAAGCTGTTCGTGGAGGGCAAAGACGTG
ACAGCTGCCATTGTACTGGCCTTGGCACGAGTTGCTGCTGCAACCAGTCCGTTGCTTTCGACGTCTTCGCTGGTTCGACAAGCACCTCCCGTTTCTGCAC
         910       920       930       940       950       960       970       980       990      1000

    280                                                     290                                                     300                                                     310
E  K  Y  Y  W  V  D  Y  V  K  V  T  K  D  N  A  S  Q  Y  L  K  E  D  G  G  S  H  H  H  H  H  H  *  *
GAGAAGTACTACTGGGTGGACTACGTCAAAGTCACCAAGGATAATGCAAGTCAATATCTGAAAGAAGATGGAGGAAGCCATCATCATCATCATCATTAGT
CTCTTCATGATGACCCACCTGATGCAGTTTCAGTGGTTCCTATTACGTTCAGTTATAGACTTTCTTCTACCTCCTTCGGTAGTAGTAGTAGTAGTAATCA
        1010      1020      1030      1040      1050      1060      1070      1080      1090      1100

  *
AATAAAAGGGCGATATCCAGCACACTGGCGGCCGTTACTAGTGGATCCGGCTGCTAACAAAGCCCGAAAGGAAGCTGAGTTGGCTGCTGCCACCGCTGAG
TTATTTTCCCGCTATAGGTCGTGTGACCGCCGGCAATGATCACCTAGGCCGACGATTGTTTCGGGCTTTCCTTCGACTCAACCGACGACGGTGGCGACTC
        1110      1120      1130      1140      1150      1160      1170      1180      119 0     1200

CAATAACTAGCATAACCCCTTGGGGCCTCTAAACGGGTCTTGAGGGGTTTTTTGCTGAAAGGAGGAACTATATCCGGAGCGACTCCCACGGCACGTTGGC
GTTATTGATCGTATTGGGGAACCCCGGAGATTTGCCCAGAACTCCCCAAAAAACGACTTTCCTCCTTGATATAGGCCTCGCTGAGGGTGCCGTGCAACCG
        1210      1220      1230      124 0     1250      1260      1270      1280      1290      1300

AAGCTCG
TTCGAGC
```

FIG. 24

```
>Exemplary cljGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                  10
                                                                                 M  P  V  I  G  F  V  A  Y  E  F
CACTATAGGGAGACCACAACGGTTTCCCTCTAGAAATAATTTTGTTTAACTTTAAGAAGGAGATATACCATGCCAGTTATTGGATTTGTTGCTTATGAAT
GTGATATCCCTCTGGTGTTGCCAAAGGGAGATCTTTATTAAAACAAATTGAAATTCTTCCTCTATATGGTACGGTCAATAACCTAAACAACGAATACTTA
       110       120       130       140       150       160       170       180       190       200

                                      20                             30                             40
 N  N  T  W  I  T  E  L  K  N  E  I  Y  K  V  S  S  G  K  A  R  V  D  I  W  N  G  D  N  I  Q  T  V
TTAACAACACGTGGATCACCGAACTGAAGAACGAGATCTACAAGGTGTCTAGCGGCAAAGCGCGTGTGGACATCTGGAACGGCGATAACATCCAGACCGT
AATTGTTGTGCACCTAGTGGCTTGACTTCTTGCTCTAGATGTTCCACAGATCGCCGTTTCGCGCACACCTGTAGACCTTGCCGCTATTGTAGGTCTGGCA
       210       220       230       240       250       260       270       280       290       300

                            50                             60                             70
 E  N  D  K  I  N  L  F  I  N  R  K  V  N  V  L  D  I  N  P  V  D  V  N  A  A  G  Q  I  I  E  K  C
TGAGAACGACAAGATCAACCTCTTCATCAACCGCAAAGTGAACGTGCTCGACATCAACCCGGTTGATGTCAACGCAGCTGGACAGATCATCGAAAAGTGC
ACTCTTGCTGTTCTAGTTGGAGAAGTAGTTGGCGTTTCACTTGCACGAGCTGTAGTTGGGCCAACTACAGTTGCGTCGACCTGTCTAGTAGCTTTTCACG
       310       320       330       340       350       360       370       380       390       400

      80                             90                            100                            110
K  K  A  N  I  P  T  V  F  V  N  R  Q  P  K  K  E  D  M  E  K  W  N  K  V  Y  Y  V  G  A  K  A  E  Q
AAAAAAGCGAACATTCCGACCGTGTTCGTGAATCGCCAACCGAAAAAAGAGGATATGGAGAAATGGAACAAAGTGTACTACGTTGGTGCCAAAGCCGAAC
TTTTTTCGCTTGTAAGGCTGGCACAAGCACTTAGCGGTTGGCTTTTTTCTCCTATACCTCTTTACCTTGTTTCACATGATGCAACCACGGTTTCGGCTTG
       410       420       430       440       450       460       470       480       490       500

                                     120                            130                            140
 S  G  T  I  Q  G  Q  M  L  V  N  Y  F  K  G  H  P  T  Q  D  G  T  I  R  Y  I  M  L  K  G  E  T  R
AGTCGGGTACCATCCAAGGGCAGATGCTCGTGAACTACTTCAAAGGCCATCCGACTCAGGATGGCACTATCCGCTACATCATGCTCAAGGGTGAAACGCG
TCAGCCCATGGTAGGTTCCCGTCTACGAGCACTTGATGAAGTTTCCGGTAGGCTGAGTCCTACCGTGATAGGCGATGTAGTACGAGTTCCCACTTTGCGC
       510       520       530       540       550       560       570       580       590       600

                   150                            160                            170
 N  Q  D  A  E  K  R  T  Q  Y  S  I  K  A  L  K  D  S  G  F  K  V  Q  K  V  A  E  D  T  A  M  W  D
AAACCAGGATGCGGAGAAACGCACCCAGTACAGCATCAAAGCGCTGAAAGACAGCGGTTTCAAGGTGCAGAAGGTTGCGGAAGACACCGCAATGTGGGAT
TTTGGTCCTACGCCTCTTTGCGTGGGTCATGTCGTAGTTTCGCGACTTTCTGTCGCCAAAGTTCCACGTCTTCCAACGCCTTCTGTGGCGTTACACCCTA
       610       620       630       640       650       660       670       680       690       700
```

FIG. 24 (cont.)

```
    180                                     190                                     200                                     210
R  T  K  A  Q  E  K  M  T  S  F  I  S  S  Y  G  P  N  F  D  C  V  I  A  N  N  D  D  M  A  L  G  A  V
CGTACGAAGGCACAGGAGAAGATGACTTCGTTCATATCCTCCTACGGACCCAACTTCGACTGTGTGATAGCGAACAACGACGACATGGCCTTAGGAGCCG
GCATGCTTCCGTGTCCTCTTCTACTGAAGCAAGTATAGGAGGATGCCTGGGTTGAAGCTGACACACTATCGCTTGTTGCTGCTGTACCGGAATCCTCGGC
       710       720       730       740       750       760       770       780       790       800

                        220                                     230                                     240
  D  A  L  K  A  A  G  Y  F  N  G  G  K  Y  V  P  V  V  G  V  D  A  T  A  P  A  V  K  A  V  E  D  G
TTGATGCCCTCAAAGCGGCAGGCTACTTCAACGGCGGCAAATATGTGCCGGTGGTTGGTGTGGATGCCACTGCTCCGGCTGTCAAAGCAGTGGAAGACGG
AACTACGGGAGTTTCGCCGTCCGATGAAGTTGCCGCCGTTTATACACGGCCACCAACCACACCTACGGTGACGAGGCCGACAGTTTCGTCACCTTCTGCC
       810       820       830       840       850       860       870       880       890       900

             250                                     260                                     270
 T  L  F  G  T  V  L  N  D  A  A  K  Q  G  D  A  A  F  D  L  S  Y  I  L  S  K  G  K  I  P  D  E  S
AACGTTGTTCGGAACTGTGCTGAACGATGCTGCGAAACAGGGTGATGCGGCCTTTGATCTGTCGTACATCCTTTCCAAAGGGAAGATCCCGGATGAAAGC
TTGCAACAAGCCTTGACACGACTTGCTACGACGCTTTGTCCCACTACGCCGGAAACTAGACAGCATGTAGGAAAGGTTTCCCTTCTAGGGCCTACTTTCG
       910       920       930       940       950       960       970       980       990      1000

    280                                     290                                     300                                     310
N  F  K  Y  K  V  T  D  G  K  Y  I  W  I  D  Y  K  M  I  T  K  E  N  V  Q  D  A  K  G  G  S  H  H  H
AACTTCAAGTACAAGGTGACGGATGGCAAGTACATTTGGATCGACTACAAGATGATCACTAAAGAAAATGTTCAAGATGCAAAAGGAGGAAGCCATCATC
TTGAAGTTCATGTTCCACTGCCTACCGTTCATGTAAACCTAGCTGATGTTCTACTAGTGATTTCTTTTACAAGTTCTACGTTTTCCTCCTTCGGTAGTAG
      1010      1020      1030      1040      1050      1060      1070      1080      1090      1100

  H  H  H  *  *  *
ATCATCATCATTAGTGATAAAAGGGCGATATCCAGCACACTGGCGGCCGTTACTAGTGGATCCGGCTGCTAACAAAGCCCGAAAGGAAGCTGAGTTGGCT
TAGTAGTAGTAATCACTATTTTCCCGCTATAGGTCGTGTGACCGCCGGCAATGATCACCTAGGCCGACGATTGTTTCGGGCTTTCCTTCGACTCAACCGA
      1110      1120      1130      1140      1150      1160      1170      1180      1190      1200

GCTGCCACCGCTGAGCAATAACTAGCATAACCCCTTGGGGCCTCTAAACGGGTCTTGAGGGGTTTTTTGCTGAAAGGAGGAACTATATCCGGAGCGACTC
CGACGGTGGCGACTCGTTATTGATCGTATTGGGGAACCCCGGAGATTTGCCCAGAACTCCCCAAAAAACGACTTTCCTCCTTGATATAGGCCTCGCTGAG
      1210      1220      1230      1240      1250      1260      1270      1280      1290      1300

CCACGGCACGTTGGCAAGCTCG
GGTGCCGTGCAACCGTTCGAGC
      1310      1320
```

FIG. 25

```
>Exemplary cauGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                  10
                                                                                    M  E  P  V  I  G  F  V  A  Y  E
CACTATAGGGAGACCACAACGGTTTCCCTCTAGAAATAATTTTGTTTAACTTTAAGAAGGAGATATACCATGGAACCAGTAATTGGTTTTGTTGCTTATG
GTGATATCCCTCTGGTGTTGCCAAAGGGAGATCTTTATTAAAACAAATTGAAATTCTTCCTCTATATGGTACCTTGGTCATTAACCAAAACAACGAATAC
       110       120       130       140       150       160       170       180       190       200

                     20                             30                             40
  F  N  N  T  W  I  T  E  L  K  N  E  M  Y  K  V  S  N  G  K  A  R  V  D  I  W  N  G  N  N  I  Q  T
AGTTCAACAACACGTGGATTACCGAACTGAAGAACGAGATGTACAAGGTGTCTAACGGCAAAGCGCGTGTGGACATCTGGAACGGCAACAACATCCAGAC
TCAAGTTGTTGTGCACCTAATGGCTTGACTTCTTGCTCTACATGTTCCACAGATTGCCGTTTCGCGCACACCTGTAGACCTTGCCGTTGTTGTAGGTCTG
       210       220       230       240       250       260       270       280       290       300

           50                             60                             70
 V  E  N  D  K  I  S  L  F  I  N  R  K  V  D  V  L  D  I  N  P  V  D  V  N  A  A  G  Q  I  I  E  K
GGTCGAGAACGACAAGATCTCCCTGTTCATCAACCGCAAAGTCGACGTTCTGGACATCAACCCGGTTGACGTGAACGCAGCTGGACAGATCATCGAGAAA
CCAGCTCTTGCTGTTCTAGAGGGACAAGTAGTTGGCGTTTCAGCTGCAAGACCTGTAGTTGGGCCAACTGCACTTGCGTCGACCTGTCTAGTAGCTCTTT
       310       320       330       340       350       360       370       380       390       400

   80                             90                             100                            110
C  K  K  A  N  I  P  T  V  F  V  N  R  Q  P  K  K  E  D  V  E  K  W  N  K  V  Y  Y  V  G  A  K  A  E
TGCAAAAAAGCGAACATTCCGACGGTGTTCGTGAACCGTCAACCGAAAAAGGAAGATGTGGAAAAGTGGAACAAAGTCTACTACGTTGGTGCGAAAGCCG
ACGTTTTTTCGCTTGTAAGGCTGCCACAAGCACTTGGCAGTTGGCTTTTTCCTTCTACACCTTTTCACCTTGTTTCAGATGATGCAACCACGCTTTCGGC
       410       420       430       440       450       460       470       480       490       500

                    120                            130                            140
  Q  S  G  T  I  Q  G  Q  M  L  V  N  Y  F  K  G  H  P  T  Q  D  G  T  I  R  Y  I  M  L  K  G  E  M
AACAGTCTGGCACCATACAGGGACAGATGCTGGTGAACTACTTCAAAGGGCATCCGACCCAGGATGGAACCATCCGCTACATCATGCTCAAAGGGGAAAT
TTGTCAGACCGTGGTATGTCCCTGTCTACGACCACTTGATGAAGTTTCCCGTAGGCTGGGTCCTACCTTGGTAGGCGATGTAGTACGAGTTTCCCCTTTA
       510       520       530       540       550       560       570       580       590       600

          150                            160                            170
 R  N  Q  D  A  E  K  R  T  Q  Y  S  I  K  A  L  E  D  S  G  F  K  V  Q  K  V  A  E  D  T  A  M  W
GCGCAACCAGGATGCGGAGAAACGCACCCAGTACAGCATCAAAGCCCTGGAAGATTCTGGGTTCAAGGTCCAGAAGGTGGCAGAAGACACCGCTATGTGG
CGCGTTGGTCCTACGCCTCTTTGCGTGGGTCATGTCGTAGTTTCGGGACCTTCTAAGACCCAAGTTCCAGGTCTTCCACCGTCTTCTGTGGCGATACACC
       610       620       630       640       650       660       670       680       690       700
```

FIG. 25 (cont.)

```
 180                       190                       200                       210
D  R  T  K  A  Q  E  K  M  T  S  F  I  S  S  Y  G  P  N  F  D  C  V  I  A  N  N  D  D  M  A  L  G  A
GATCGTACCAAGGCTCAGGAGAAGATGACTTCGTTCATCTCCTCATACGGACCGAACTTCGACTGTGTGATCGCCAACAACGACGACATGGCCTTAGGAG
CTAGCATGGTTCCGAGTCCTCTTCTACTGAAGCAAGTAGAGGAGTATGCCTGGCTTGAAGCTGACACACTAGCGGTTGTTGCTGCTGTACCGGAATCCTC
       710       720       730       740       750       760       77 0      780       790       800

                     220                       230                       240
 V  D  A  L  K  A  A  G  Y  F  N  G  G  K  Y  V  P  V  V  G  V  D  A  T  A  P  A  V  K  A  V  E  D
CTGTTGATGCCCTGAAAGCTGCAGGCTACTTCAACGGCGGCAAATATGTGCCGGTGGTTGGTGTGGATGCTACTGCTCCGGCAGTGAAAGCTGTCGAGGA
GACAACTACGGGACTTTCGACGTCCGATGAAGTTGCCGCCGTTTATACACGGCCACCAACCACACCTACGATGACGAGGCCGTCACTTTCGACAGCTCCT
       810       820       830       840       850       860       870       880       890       900

           250                       260                       270
 G  T  L  F  G  T  V  L  N  D  A  A  K  Q  G  D  A  A  F  D  L  S  Y  I  L  S  K  G  K  I  P  D  E
TGGGACACTGTTCGGAACTGTCCTGAACGATGCAGCGAAACAGGGTGATGCGGCCTTTGATCTGTCGTACATCCTTTCCAAGGGGAAGATTCCGGATGAA
ACCCTGTGACAAGCCTTGACAGGACTTGCTACGTCGCTTTGTCCCACTACGCCGGAAACTAGACAGCATGTAGGAAAGGTTCCCCTTCTAAGGCCTACTT
       910       920       930       940       950       960       970       980       990      1000

 280                       290                       300                       310
S  N  F  K  Y  K  I  T  D  G  K  Y  I  W  I  D  Y  K  M  I  T  K  E  N  V  Q  D  A  K  G  G  S  H  H
AGCAACTTCAAGTACAAGATCACGGATGGCAAGTACATTTGGATCGACTACAAGATGATTACTAAAGAAAATGTTCAAGATGCTAAAGGAGGAAGCCATC
TCGTTGAAGTTCATGTTCTAGTGCCTACCGTTCATGTAAACCTAGCTGATGTTCTACTAATGATTTCTTTTACAAGTTCTACGATTTCCTCCTTCGGTAG
      1010      1020      1030      1040      1050      1060      1070      1080      1090      1100

 H  H  H  H  *  *  *
ATCATCATCATCATTAGTAATAAAAGGGCGATATCCAGCACACTGGCGGCCGTTACTAGTGGATCCGGCTGCTAACAAAGCCCGAAAGGAAGCTGAGTTG
TAGTAGTAGTAGTAATCATTATTTTCCCGCTATAGGTCGTGTGACCGCCGGCAATGATCACCTAGGCCGACGATTGTTTCGGGCTTTCCTTCGACTCAAC
      1110      1120      1130      1140      1150      1160      1170      1180      1190      1200

GCTGCTGCCACCGCTGAGCAATAACTAGCATAACCCCTTGGGGCCTCTAAACGGGTCTTGAGGGGTTTTTTGCTGAAAGGAGGAACTATATCCGGAGCGA
CGACGACGGTGGCGACTCGTTATTGATCGTATTGGGGAACCCCGGAGATTTGCCCAGAACTCCCCAAAAAACGACTTTCCTCCTTGATATAGGCCTCGCT
      1210      1220      1230      1240      1250      1260      1270      1280      1290      1300

CTCCCACGGCACGTTGGCAAGCTCG
GAGGGTGCCGTGCAACCGTTCGAGC
      1310      1320
```

FIG. 26

```
>Exemplary rinGGBP_B (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                  10
                                                                                  M  K  S  I  K  I  G  I  S  V  Y
CACTATAGGGAGACCACAACGGTTTCCCTCTAGAAATAATTTTGTTTAACTTTAAGAAGGAGATATACCATGAAATCAATAAAAATTGGTATAAGTGTTT
GTGATATCCCTCTGGTGTTGCCAAAGGGAGATCTTTATTAAAACAAATTGAAATTCTTCCTCTATATGGTACTTTAGTTATTTTTAACCATATTCACAAA
       110       120       130       140       150       160       170       180       190       200

                                       20                             30                             40
 D  Q  Y  D  T  F  V  S  E  M  M  K  D  F  N  D  Y  A  T  K  K  E  E  E  T  G  V  A  I  N  I  D  T
ATGATCAGTATGACACCTTTGTGAGCGAAATGATGAAAGACTTCAACGATTATGCGACCAAGAAAGAAGAAGAGACTGGTGTTGCCATCAACATCGACAC
TACTAGTCATACTGTGGAAACACTCGCTTTACTACTTTCTGAAGTTGCTAATACGCTGGTTCTTTCTTCTTCTCTGACCACAACGGTAGTTGTAGCTGTG
       210       220       230       240       250       260       270       280       290       300

                            50                             60                             70
 Y  N  A  S  A  S  Q  S  T  Q  N  S  Q  V  E  N  M  I  T  E  G  C  D  V  I  C  V  N  L  V  D  R  T
ATACAACGCTAGTGCAAGCCAGTCTACGCAGAACAGTCAGGTCGAGAACATGATCACGGAAGGCTGCGATGTGATCTGTGTCAACCTGGTTGACAGGACG
TATGTTGCGATCACGTTCGGTCAGATGCGTCTTGTCAGTCCAGCTCTTGTACTAGTGCCTTCCGACGCTACACTAGACACAGTTGGACCAACTGTCCTGC
       310       320       330       340       350       360       370       380       390       400

      80                             90                             100                            110
D  P  T  A  I  I  D  L  A  E  K  N  N  I  P  V  I  F  F  N  R  E  L  V  E  E  D  L  E  R  W  T  R  L
GATCCAACTGCGATCATCGATCTTGCGGAGAAAAACAACATCCCCGTGATTTTTTTCAACCGTGAACTGGTGGAGGAAGACCTGGAACGTTGGACAAGGC
CTAGGTTGACGCTAGTAGCTAGAACGCCTCTTTTTGTTGTAGGGGCACTAAAAAAAGTTGGCACTTGACCACCTCCTTCTGGACCTTGCAACCTGTTCCG
       410       420       430       440       450       460       470       480       490       500

                                      120                            130                            140
 Y  Y  V  G  A  Q  A  F  E  S  G  I  M  Q  G  E  L  A  A  E  A  F  L  T  D  Q  S  L  D  K  N  G  D
TGTACTACGTTGGTGCACAGGCGTTCGAAAGCGGCATCATGCAGGGTGAACTGGCTGCAGAAGCCTTTCTGACCGATCAGAGCCTGGACAAGAACGGAGA
ACATGATGCAACCACGTGTCCGCAAGCTTTCGCCGTAGTACGTCCCACTTGACCGACGTCTTCGGAAAGACTGGCTAGTCTCGGACCTGTTCTTGCCTCT
       510       520       530       540       550       560       570       580       590       600

                           150                            160                            170
 G  I  F  Q  Y  V  V  L  E  G  E  A  G  H  Q  D  A  I  V  R  T  E  Y  S  V  S  T  M  I  D  S  G  V
TGGGATCTTCCAGTACGTGGTGCTTGAAGGTGAGGCTGGACACCAGGATGCCATCGTGCGTACGGAGTACTCGGTTAGCACCATGATCGATAGCGGAGTG
ACCCTAGAAGGTCATGCACCACGAACTTCCACTCCGACCTGTGGTCCTACGGTAGCACGCATGCCTCATGAGCCAATCGTGGTACTAGCTATCGCCTCAC
       610       620       630       640       650       660       670       680       690       700
```

FIG. 26 (cont.)

```
   180                                190                                 200                                 210
E  V  E  K  L  G  Y  A  I  A  N  W  N  R  A  Q  A  Q  T  K  M  A  Q  L  M  S  Q  F  G  D  S  I  E  L
GAAGTGGAGAAACTGGGCTACGCAATCGCCAACTGGAATCGTGCACAGGCTCAGACGAAAATGGCGCAGCTGATGTCCCAGTTTGGTGACAGCATAGAGC
CTTCACCTCTTTGACCCGATGCGTTAGCGGTTGACCTTAGCACGTGTCCGAGTCTGCTTTTACCGCGTCGACTACAGGGTCAAACCACTGTCGTATCTCG
        710       720       730       740       750       760       77 0      780       790       800

                                 220                                 230                                 240
  V  I  A  N  N  D  D  M  A  L  G  A  I  D  A  L  K  A  S  G  L  T  K  D  E  W  P  A  V  I  G  I  D
TGGTCATCGCCAACAACGACGACATGGCTCTAGGAGCCATAGATGCGCTCAAGGCGTCTGGTCTGACCAAGGACGAATGGCCGGCAGTCATTGGGATCGA
ACCAGTAGCGGTTGTTGCTGCTGTACCGAGATCCTCGGTATCTACGCGAGTTCCGCAGACCAGACTGGTTCCTGCTTACCGGCCGTCAGTAACCCTAGCT
        810       820       830       840       850       860       870       880       890       900

                  250                                260                                 270
 G  T  D  V  G  L  E  A  V  K  N  K  E  M  I  G  T  V  Y  N  D  K  E  G  Q  A  D  A  M  L  N  L  A
TGGAACGGATGTGGGCTTAGAGGCGGTCAAGAACAAAGAGATGATCGGTACCGTGTACAACGATAAGGAAGGCCAAGCGGATGCGATGCTGAACCTGGCG
ACCTTGCCTACACCCGAATCTCCGCCAGTTCTTGTTTCTCTACTAGCCATGGCACATGTTGCTATTCCTTCCGGTTCGCCTACGCTACGACTTGGACCGC
        910       920       930       940       950       960       970       980       990       1000

   280                                290                                 300                                 310
Y  E  L  S  T  G  S  D  L  S  D  L  N  L  I  D  G  K  Y  I  R  L  P  Y  A  R  V  T  C  D  D  V  D  S
TACGAACTGAGTACCGGTAGCGATCTGTCGGATCTGAACCTGATCGATGGCAAATACATCCGTCTGCCTTATGCGCGAGTGACGTGTGATGATGTGGATA
ATGCTTGACTCATGGCCATCGCTAGACAGCCTAGACTTGGACTAGCTACCGTTTATGTAGGCAGACGGAATACGCGCTCACTGCACACTACTACACCTAT
       1010      1020      1030      1040      1050      1060      1070      1080      1090      1100

                                 320                                 330
  Y  M  E  G  D  T  E  G  G  S  H  H  H  H  H  H  *  *  *
GTTATATGGAAGGTGATACCGAAGGAGGAAGCCATCATCATCATCATCATTAATAATGAAAGGGCGATATCCAGCACACTGGCGGCCGTTACTAGTGGAT
CAATATACCTTCCACTATGGCTTCCTCCTTCGGTAGTAGTAGTAGTAGTAATTATTACTTTCCCGCTATAGGTCGTGTGACCGCCGGCAATGATCACCTA
       1110      1120      1130      1140      1150      1160      1170      1180      1190      1200

CCGGCTGCTAACAAAGCCCGAAAGGAAGCTGAGTTGGCTGCTGCCACCGCTGAGCAATAACTAGCATAACCCCTTGGGGCCTCTAAACGGGTCTTGAGGG
GGCCGACGATTGTTTCGGGCTTTCCTTCGACTCAACCGACGACGGTGGCGACTCGTTATTGATCGTATTGGGGAACCCCGGAGATTTGCCCAGAACTCCC
       1210      1220      1230      1240      1250      1260      1270      1280      1290      1300

GTTTTTTGCTGAAAGGAGGAACTATATCCGGAGCGACTCCCACGGCACGTTGGCAAGCTCG
CAAAAAACGACTTTCCTCCTTGATATAGGCCTCGCTGAGGGTGCCGTGCAACCGTTCGAGC
       1310      1320      1330      1340      1350      1360
```

FIG. 27

```
>Exemplary erhGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                 10
                                                                                     M  K  T  Y  N  I  G  V  A  I  Y
CACTATAGGGAGACCACAACGGTTTCCCTCTAGAAATAATTTTGTTTAACTTTAAGAAGGAGATATACCATGAAAACTTATAATATTGGTGTTGCAATTT
GTGATATCCCTCTGGTGTTGCCAAAGGGAGATCTTTATTAAAACAAATTGAAATTCTTCCTCTATATGGTACTTTTGAATATTATAACCACAACGTTAAA
       110       120       130       140       150       160       170       180       190       200

                             20                             30                             40
 K  F  D  D  N  F  M  T  L  Y  R  E  E  L  A  S  Y  F  K  E  V  G  E  K  D  G  N  T  Y  K  L  D  I
ATAAGTTCGATGACAACTTCATGACGCTGTATCGTGAAGAACTGGCGAGCTACTTCAAAGAAGTGGGTGAGAAAGACGGCAACACGTACAAACTGGACAT
TATTCAAGCTACTGTTGAAGTACTGCGACATAGCACTTCTTGACCGCTCGATGAAGTTTCTTCACCCACTCTTTCTGCCGTTGTGCATGTTTGACCTGTA
       210       220       230       240       250       260       270       280       290       300

                  50                             60                             70
 Q  D  G  K  Q  D  Q  A  N  Q  T  E  Q  I  N  N  F  I  A  Q  G  K  D  L  I  I  A  N  M  V  D  P  T
CCAGGATGGCAAGCAGGACCAAGCTAACCAGACCGAACAGATCAACAACTTTATCGCACAGGGTAAAGACCTGATCATCGCGAACATGGTCGATCCGACC
GGTCCTACCGTTCGTCCTGGTTCGATTGGTCTGGCTTGTCTAGTTGTTGAAATAGCGTGTCCCATTTCTGGACTAGTAGCGCTTGTACCAGCTAGGCTGG
       310       320       330       340       350       360       370       380       390       400

   80                            90                            100                            110
A  A  G  S  I  I  N  S  A  K  A  K  E  I  P  V  V  F  I  N  R  E  P  E  T  Q  E  L  E  I  W  P  G  K
GCAGCGGGTAGCATCATCAACAGCGCGAAAGCGAAAGAAATCCCGGTGGTCTTCATCAACCGAGAACCGGAAACCCAGGAACTGGAAATCTGGCCGGGCA
CGTCGCCCATCGTAGTAGTTGTCGCGCTTTCGCTTTCTTTAGGGCCACCAGAAGTAGTTGGCTCTTGGCCTTTGGGTCCTTGACCTTTAGACCGGCCCGT
       410       420       430       440       450       460       470       480       490       500

                           120                            130                            140
 T  T  Y  V  G  A  D  A  T  Q  S  G  T  I  Q  G  Y  M  I  A  N  L  E  N  K  G  D  I  D  G  D  G  S
AAACCACCTACGTTGGTGCGGATGCGACCCAGTCAGGCACCATTCAGGGCTACATGATCGCGAACTTGGAGAACAAAGGCGACATCGACGGTGATGGGAG
TTTGGTGGATGCAACCACGCCTACGCTGGGTCAGTCCGTGGTAAGTCCCGATGTACTAGCGCTTGAACCTCTTGTTTCCGCTGTAGCTGCCACTACCCTC
       510       520       530       540       550       560       570       580       590       600

                 150                            160                            170
 V  S  Y  I  T  L  M  G  D  P  A  N  V  D  A  K  Q  R  T  E  Y  S  V  K  G  L  E  E  K  G  V  K  T
TGTCAGCTACATCACGCTGATGGGAGATCCTGCGAACGTGGATGCGAAACAGCGTACCGAATACAGCGTGAAAGGCCTGGAAGAGAAAGGCGTGAAAACC
ACAGTCGATGTAGTGCGACTACCCTCTAGGACGCTTGCACCTACGCTTTGTCGCATGGCTTATGTCGCACTTTCCGGACCTTCTCTTTCCGCACTTTTGG
       610       620       630       640       650       660       670       680       690       700
```

FIG. 27 (cont.)

```
180                                     190                                     200                                     210
N  A  L  A  Q  P  Y  Q  A  N  W  D  T  A  K  G  Q  E  F  T  A  N  A  L  E  Q  F  G  N  K  L  E  V  V
AACGCGCTTGCGCAGCCGTACCAAGCGAACTGGGATACCGCGAAAGGCCAGGAATTCACCGCAAACGCGCTGGAACAGTTTGGCAACAAACTGGAAGTGG
TTGCGCGAACGCGTCGGCATGGTTCGCTTGACCCTATGGCGCTTTCCGGTCCTTAAGTGGCGTTTGCGCGACCTTGTCAAACCGTTGTTTGACCTTCACC
        710       720       730       740       750       760       77 0      780       790       800

                         220                                     230                                     240
 F  A  N  N  D  G  M  A  V  G  A  V  T  A  I  E  A  A  G  R  K  V  G  E  D  I  F  V  V  G  V  D  A
TGTTCGCGAACAACGATGGCATGGCGGTTGGTGCGGTGACCGCGATTGAAGCTGCGGGACGCAAAGTCGGAGAGGACATCTTCGTGGTTGGTGTCGATGC
ACAAGCGCTTGTTGCTACCGTACCGCCAACCACGCCACTGGCGCTAACTTCGACGCCCTGCGTTTCAGCCTCTCCTGTAGAAGCACCAACCACAGCTACG
        810       820       830       840       850       860       870       880       890       900

              250                                     260                                     270
 I  P  D  A  I  E  L  L  K  G  G  K  L  T  G  T  V  L  N  D  H  F  N  Q  S  H  T  A  V  D  V  A  L
CATTCCGGATGCCATCGAGCTCCTGAAAGGCGGTAAACTGACCGGTACTGTCCTCAACGACCACTTCAACCAGAGCCATACCGCGGTGGATGTGGCACTG
GTAAGGCCTACGGTAGCTCGAGGACTTTCCGCCATTTGACTGGCCATGACAGGAGTTGCTGGTGAAGTTGGTCTCGGTATGGCGCCACCTACACCGTGAC
        910       920       930       940       950       960       970       980       990      1000

    280                                     290                                     300                                     310
E  L  L  Q  G  K  D  V  S  A  Y  Y  W  H  D  Y  V  G  V  T  K  P  E  E  A  E  L  K  R  A  E  A  R  K
GAACTGCTGCAGGGCAAAGATGTGAGCGCCTACTACTGGCATGACTACGTTGGCGTGACCAAACCGGAAGAAGCGGAACTGAAACGTGCAGAAGCACGCA
CTTGACGACGTCCCGTTTCTACACTCGCGGATGATGACCGTACTGATGCAACCGCACTGGTTTGGCCTTCTTCGCCTTGACTTTGCACGTCTTCGTGCGT
       1010      1020      1030      1040      1050      1060      1070      1080      1090      1100

                         320                                     330
 E  T  V  E  E  A  V  K  R  Y  A  E  R  D  A  Q  G  G  S  H  H  H  H  H  H  *  *  *
AAGAGACCGTGGAAGAAGCGGTTAAACGTTATGCAGAACGTGATGCTCAAGGAGGAAGCCATCATCATCATCATCATTAATAATGAAAGGGCGATATCCA
TTCTCTGGCACCTTCTTCGCCAATTTGCAATACGTCTTGCACTACGAGTTCCTCCTTCGGTAGTAGTAGTAGTAGTAATTATTACTTTCCCGCTATAGGT
       1110      1120      1130      1140      1150      1160      1170      1180      1190      1200

GCACACTGGCGGCCGTTACTAGTGGATCCGGCTGCTAACAAAGCCCGAAAGGAAGCTGAGTTGGCTGCTGCCACCGCTGAGCAATAACTAGCATAACCCC
CGTGTGACCGCCGGCAATGATCACCTAGGCCGACGATTGTTTCGGGCTTTCCTTCGACTCAACCGACGACGGTGGCGACTCGTTATTGATCGTATTGGGG
       1210      1220      1230      1240      1250      1260      1270      1280      1290      1300

TTGGGGCCTCTAAACGGGTCTTGAGGGGTTTTTTGCTGAAAGGAGGAACTATATCCGGAGCGACTCCCACGGCACGTTGGCAAGCTCG
AACCCCGGAGATTTGCCCAGAACTCCCCAAAAAACGACTTTCCTCCTTGATATAGGCCTCGCTGAGGGTGCCGTGCAACCGTTCGAGC
       1310      1320      1330      1340      1350      1360      1370      13 80
```

FIG. 28

```
>Exemplary ereGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                   10
                                                                                    M  K  Q  I  Y  I  G  V  T  C  Y
CACTATAGGGAGACCACAACGGTTTCCCTCTAGAAATAATTTTGTTTAACTTTAAGAAGGAGATATACCATGAAACAGATTTATATTGGTGTAACTTGTT
GTGATATCCCTCTGGTGTTGCCAAAGGGAGATCTTTATTAAAACAAATTGAAATTCTTCCTCTATATGGTACTTTGTCTAAATATAACCACATTGAACAA
       110       120       130       140       150       160       170       180       190       200

                        20                             30                             40
 D  Q  K  D  T  F  I  G  E  L  I  E  T  F  K  K  E  C  A  S  L  D  T  D  K  Y  D  I  S  M  T  I  M
ATGATCAGAAGGATACCTTCATTGGAGAGCTGATCGAGACCTTCAAGAAGGAATGCGCGTCTCTGGATACCGACAAGTACGACATCAGCATGACCATCAT
TACTAGTCTTCCTATGGAAGTAACCTCTCGACTAGCTCTGGAAGTTCTTCCTTACGCGCAGAGACCTATGGCTGTTCATGCTGTAGTCGTACTGGTAGTA
       210       220       230       240       250       260       270       280       290       300

              50                             60                             70
D  A  A  G  S  Q  R  A  Q  D  D  Q  V  Q  E  M  I  E  D  G  C  N  V  L  C  I  N  L  A  D  R  T  D
GGATGCTGCAGGTAGCCAGCGTGCACAGGATGATCAGGTGCAGGAGATGATCGAAGACGGTTGCAACGTACTGTGCATCAACCTGGCAGATCGTACCGAC
CCTACGACGTCCATCGGTCGCACGTGTCCTACTAGTCCACGTCCTCTACTAGCTTCTGCCAACGTTGCATGACACGTAGTTGGACCGTCTAGCATGGCTG
       310       320       330       340       350       360       370       380       390       400

     80                             90                             100                            110
L  S  H  I  I  N  A  A  M  E  K  D  I  P  I  I  F  F  N  R  E  P  V  D  E  D  L  N  R  W  D  K  L  Y
TTGTCGCACATCATCAACGCGGCGATGGAGAAGGATATCCCGATCATCTTCTTCAACCGAGAACCGGTGGATGAGGATCTCAACCGTTGGGACAAGCTGT
AACAGCGTGTAGTAGTTGCGCCGCTACCTCTTCCTATAGGGCTAGTAGAAGAAGTTGGCTCTTGGCCACCTACTCCTAGAGTTGGCAACCCTGTTCGACA
       410       420       430       440       450       460       470       480       490       500

                       120                            130                            140
 Y  V  G  A  K  A  K  Q  S  G  Q  M  Q  G  E  L  I  A  D  Y  I  K  N  N  P  G  V  D  K  N  G  D  G
ACTACGTAGGAGCAAAGGCGAAACAGAGCGGTCAGATGCAAGGAGAGCTCATTGCGGACTACATCAAAAACAACCCGGGTGTGGACAAGAACGGTGATGG
TGATGCATCCTCGTTTCCGCTTTGTCTCGCCAGTCTACGTTCCTCTCGAGTAACGCCTGATGTAGTTTTTGTTGGGCCCACACCTGTTCTTGCCACTACC
       510       520       530       540       550       560       570       580       590       600

             150                            160                            170
R  I  Q  Y  V  I  L  E  G  E  M  G  H  Q  D  A  I  V  R  T  E  S  V  T  E  S  M  K  N  N  G  L  Q
GAGGATCCAGTACGTCATCCTGGAAGGGGAAATGGGTCATCAGGATGCCATCGTACGGACTGAAAGCGTGACCGAATCGATGAAGAACAACGGTCTGCAG
CTCCTAGGTCATGCAGTAGGACCTTCCCCTTTACCCAGTAGTCCTACGGTAGCATGCCTGACTTTCGCACTGGCTTAGCTACTTCTTGTTGCCAGACGTC
       610       620       630       640       650       660       670       680       690       700
```

FIG. 28 (cont.)

```
    180                                       190                                       200                                       210
I  E  K  L  S  C  Q  I  A  N  W  N  R  A  Q  A  Q  N  R  M  T  Q  L  I  G  Q  Y  K  N  S  I  E  L  V
ATCGAGAAGCTGAGCTGCCAGATCGCGAACTGGAATCGAGCTCAAGCTCAGAACCGGATGACGCAGCTGATTGGCCAGTACAAGAACTCGATCGAGCTGG
TAGCTCTTCGACTCGACGGTCTAGCGCTTGACCTTAGCTCGAGTTCGAGTCTTGGCCTACTGCGTCGACTAACCGGTCATGTTCTTGAGCTAGCTCGACC
        710       720       730       740       750       760       770       780       790       800

                                 220                                       230                                       240
  I  A  N  N  D  A  M  A  L  G  A  I  D  A  Y  E  K  L  G  V  T  E  S  N  V  P  A  F  F  G  V  D  G
TGATCGCCAACAACGATGCCATGGCTCTAGGTGCGATCGATGCCTACGAGAAACTCGGTGTAACGGAAAGCAACGTTCCAGCGTTTTTCGGTGTGGATGG
ACTAGCGGTTGTTGCTACGGTACCGAGATCCACGCTAGCTACGGATGCTCTTTGAGCCACATTGCCTTTCGTTGCAAGGTCGCAAAAAGCCACACCTACC
        810       820       830       840       850       860       870       880       890       900

                   250                                       260                                       270
 T  D  D  G  L  E  A  V  Q  Q  S  K  L  A  A  T  V  Y  N  D  K  E  G  Q  A  M  A  M  A  Q  L  A  Y
TACAGACGATGGACTGGAAGCAGTGCAGCAGAGCAAGCTTGCGGCAACGGTGTACAACGACAAGGAAGGTCAGGCGATGGCGATGGCTCAGTTGGCCTAT
ATGTCTGCTACCTGACCTTCGTCACGTCGTCTCGTTCGAACGCCGTTGCCACATGTTGCTGTTCCTTCCAGTCCGCTACCGCTACCGAGTCAACCGGATA
        910       920       930       940       950       960       970       980       990      1000

    280                                       290                                       300                                       310
L  A  A  T  G  G  S  M  K  N  I  K  F  E  D  K  K  Y  V  Y  L  P  Y  E  K  V  T  P  D  N  V  N  E  F
CTCGCTGCAACTGGTGGAAGCATGAAGAACATCAAATTCGAAGACAAAAAGTATGTGTATCTGCCGTATGAGAAGGTGACACCGGATAACGTTAATGAAT
GAGCGACGTTGACCACCTTCGTACTTCTTGTAGTTTAAGCTTCTGTTTTTCATACACATAGACGGCATACTCTTCCACTGTGGCCTATTGCAATTACTTA
       1010      1020      1030      1040      1050      1060      1070      1080      1090      1100

                                 320
  V  K  D  E  Q  G  G  S  H  H  H  H  H  H  *  *  *
TTGTTAAAGATGAACAAGGAGGAAGCCATCATCATCATCATCATTGATAATAAAAGGGCGATATCCAGCACACTGGCGGCCGTTACTAGTGGATCCGGCT
AACAATTTCTACTTGTTCCTCCTTCGGTAGTAGTAGTAGTAGTAACTATTATTTTCCCGCTATAGGTCGTGTGACCGCCGGCAATGATCACCTAGGCCGA
       1110      1120      1130      1140      1150      1160      1170      1180      1190      1200

GCTAACAAAGCCCGAAAGGAAGCTGAGTTGGCTGCTGCCACCGCTGAGCAATAACTAGCATAACCCCTTGGGGCCTCTAAACGGGTCTTGAGGGGTTTTT
CGATTGTTTCGGGCTTTCCTTCGACTCAACCGACGACGGTGGCGACTCGTTATTGATCGTATTGGGGAACCCCGGAGATTTGCCCAGAACTCCCCAAAAA
       1210      1220      1230      1240      1250      1260      1270      1280      1290      1300

TGCTGAAAGGAGGAACTATATCCGGAGCGACTCCCACGGCACGTTGGCAAGCTCG
ACGACTTTCCTCCTTGATATAGGCCTCGCTGAGGGTGCCGTGCAACCGTTCGAGC
       1310      1320      1330      1340      1350
```

FIG. 29

```
>Exemplary ttGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                   10
                                                                                  M  K  Q  L  N  I  G  V  A  I  Y
CACTATAGGGAGACCACAACGGTTTCCCTCTAGAAATAATTTTGTTTAACTTTAAGAAGGAGATATACCATGAAACAATTAAATATTGGTGTTGCGATTT
GTGATATCCCTCTGGTGTTGCCAAAGGGAGATCTTTATTAAAACAAATTGAAATTCTTCCTCTATATGGTACTTTGTTAATTTATAACCACAACGCTAAA
       110       120       130       140       150       160       170       180       190       200

                        20                             30                             40
 K  F  D  D  T  F  M  T  G  V  R  N  A  M  T  A  E  A  Q  G  K  A  K  L  N  M  V  D  S  Q  N  S  Q
ATAAATTCGATGACACCTTCATGACCGGTGTTCGGAATGCGATGACTGCGGAAGCGCAAGGCAAGGCGAAGCTCAACATGGTTGACAGCCAGAACAGCCA
TATTTAAGCTACTGTGGAAGTACTGGCCACAAGCCTTACGCTACTGACGCCTTCGCGTTCCGTTCCGCTTCGAGTTGTACCAACTGTCGGTCTTGTCGGT
       210       220       230       240       250       260       270       280       290       300

              50                             60                             70
 P  T  Q  N  D  Q  V  D  L  F  I  T  K  K  M  N  A  L  A  I  N  P  V  D  R  T  A  A  G  T  I  I  D
ACCAACCCAGAACGATCAGGTTGACCTGTTCATCACGAAGAAGATGAACGCACTTGCGATCAACCCGGTGGATCGCACTGCAGCAGGCACCATCATCGAC
TGGTTGGGTCTTGCTAGTCCAACTGGACAAGTAGTGCTTCTTCTACTTGCGTGAACGCTAGTTGGGCCACCTAGCGTGACGTCGTCCGTGGTAGTAGCTG
       310       320       330       340       350       360       370       380       390       400

  80                             90                             100                            110
K  A  K  Q  A  N  I  P  V  V  F  F  N  R  E  P  L  P  E  D  M  K  K  W  D  K  V  Y  Y  V  G  A  K  A
AAAGCCAAACAGGCCAACATTCCGGTGGTCTTCTTCAACCGTGAACCGCTGCCGGAAGACATGAAGAAATGGGATAAAGTGTACTATGTGGGTGCGAAAG
TTTCGGTTTGTCCGGTTGTAAGGCCACCAGAAGAAGTTGGCACTTGGCGACGGCCTTCTGTACTTCTTTACCCTATTTCACATGATACACCCACGCTTTC
       410       420       430       440       450       460       470       480       490       500

                       120                            130                            140
 E  Q  S  G  I  L  Q  G  Q  I  M  A  D  Y  W  K  A  H  P  E  A  D  K  N  H  D  G  V  M  Q  Y  V  M
CGGAACAGAGTGGCATTTTGCAGGGTCAGATCATGGCTGACTACTGGAAAGCCCATCCTGAAGCGGACAAGAACCATGATGGCGTGATGCAGTACGTCAT
GCCTTGTCTCACCGTAAAACGTCCCAGTCTAGTACCGACTGATGACCTTTCGGGTAGGACTTCGCCTGTTCTTGGTACTACCGCACTACGTCATGCAGTA
       510       520       530       540       550       560       570       580       590       600

             150                            160                            170
 L  M  G  Q  P  G  H  Q  D  A  I  L  R  T  Q  Y  S  I  Q  T  V  K  D  A  G  I  K  V  Q  E  L  A  K
GCTGATGGGTCAGCCAGGTCATCAGGATGCGATACTGCGTACACAGTACAGCATCCAAACGGTGAAAGATGCAGGCATCAAAGTGCAGGAACTGGCCAAA
CGACTACCCAGTCGGTCCAGTAGTCCTACGCTATGACGCATGTGTCATGTCGTAGGTTTGCCACTTTCTACGTCCGTAGTTTCACGTCCTTGACCGGTTT
       610       620       630       640       650       660       670       680       690       700
```

FIG. 29 (cont.)

```
180                                             190                                             200                                             210
D  Y  A  N  W  D  R  V  T  A  H  D  K  M  A  A  W  L  S  S  F  G  D  K  I  E  A  V  F  C  N  N  D  D
GACTACGCAAACTGGGATCGCGTTACCGCGCATGACAAAATGGCAGCGTGGTTGTCGAGCTTTGGCGACAAGATCGAAGCCGTCTTCTGCAACAACGACG
CTGATGCGTTTGACCCTAGCGCAATGGCGCGTACTGTTTTACCGTCGCACCAACAGCTCGAAACCGCTGTTCTAGCTTCGGCAGAAGACGTTGTTGCTGC
       710       720       730       740       750       760       770       780       790       800

                    220                                             230                                             240
 M  A  L  G  A  I  E  A  L  K  S  A  G  Y  F  T  G  N  K  Y  I  P  V  V  G  V  D  A  T  A  P  G  I
ACATGGCGTTGGGTGCCATCGAAGCGCTGAAGTCTGCAGGCTACTTCACCGGCAACAAATACATCCCGGTTGTGGGCGTGGATGCGACCGCACCGGGCAT
TGTACCGCAACCCACGGTAGCTTCGCGACTTCAGACGTCCGATGAAGTGGCCGTTGTTTATGTAGGGCCAACACCCGCACCTACGCTGGCGTGGCCCGTA
       810       820       830       840       850       860       870       880       890       900

          250                                             260                                             270
 Q  A  I  K  D  G  T  L  L  G  T  V  L  N  D  A  K  N  Q  A  K  A  T  F  N  I  A  Y  E  L  A  Q  G
TCAGGCGATCAAGGATGGTACCCTGTTGGGAACCGTGTTGAACGATGCGAAGAACCAGGCGAAAGCCACCTTCAACATCGCCTACGAACTGGCTCAGGGC
AGTCCGCTAGTTCCTACCATGGGACAACCCTTGGCACAACTTGCTACGCTTCTTGGTCCGCTTTCGGTGGAAGTTGTAGCGGATGCTTGACCGAGTCCCG
       910       920       930       940       950       960       970       980       990      1000

280                                             290                                             300                                             310
I  T  P  T  K  D  N  I  G  Y  D  I  T  D  G  K  Y  V  W  I  P  Y  K  K  I  T  K  D  N  I  S  D  A  E
ATTACCCCGACGAAGGACAACATAGGGTACGACATCACAGACGGGAAGTACGTGTGGATTCCGTACAAAAAGATCACGAAAGACAATATATCAGATGCTG
TAATGGGGCTGCTTCCTGTTGTATCCCATGCTGTAGTGTCTGCCCTTCATGCACACCTAAGGCATGTTTTTCTAGTGCTTTCTGTTATATAGTCTACGAC
      1010      1020      1030      1040      1050      1060      1070      1080      1090      1100

                    320
 Q  G  G  S  H  H  H  H  H  H  *  *  *
AACAAGGAGGAAGCCATCATCATCATCATCATTAGTAATAAAAGGGCGATATCCAGCACACTGGCGGCCGTTACTAGTGGATCCGGCTGCTAACAAAGCC
TTGTTCCTCCTTCGGTAGTAGTAGTAGTAGTAATCATTATTTTCCCGCTATAGGTCGTGTGACCGCCGGCAATGATCACCTAGGCCGACGATTGTTTCGG
      1110      1120      1130      1140      1150      1160      1170      1180      1190      1200

CGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAG
GCTTTCCTTCGACTCAACCGACGACGGTGGCGACTCGTTATTGATCGTATTGGGGAACCCCGGAGATTTGCCCAGAACTCCCCAAAAAACGACTTTCCTC
      1210      1220      1230      1240      1250      1260      1270      1280      1290      1300

GAACTATATCCGGAGCGACTCCCACGGCACGTTGGCAAGCTCG
CTTGATATAGGCCTCGCTGAGGGTGCCGTGCAACCGTTCGAGC
      1310      1320      1330      1340
```

FIG. 30

```
>Exemplary cobGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                 10
                                                                                M  K  P  Y  I  G  V  A  I  Y  K
CACTATAGGGAGACCACAACGGTTTCCCTCTAGAAATAATTTTGTTTAACTTTAAGAAGGAGATATACCATGAAACCTTATATAGGTGTTGCTATATATA
GTGATATCCCTCTGGTGTTGCCAAAGGGAGATCTTTATTAAAACAAATTGAAATTCTTCCTCTATATGGTACTTTGGAATATATCCACAACGATATATAT
       110       120       130       140       150       160       170       180       190       200

                    20                            30                            40
 F  D  D  T  F  M  T  G  V  R  N  A  I  A  K  E  G  E  G  K  A  K  L  D  F  V  D  C  Q  N  S  Q  S
AGTTTGACGACACCTTCATGACCGGTGTGCGTAACGCGATTGCGAAAGAAGGCGAAGGCAAAGCGAAACTGGATTTCGTCGATTGCCAGAACAGCCAGTC
TCAAACTGCTGTGGAAGTACTGGCCACACGCATTGCGCTAACGCTTTCTTCCGCTTCCGTTTCGCTTTGACCTAAAGCAGCTAACGGTCTTGTCGGTCAG
       210       220       230       240       250       260       270       280       290       300

          50                            60                            70
 T  Q  N  D  K  I  D  L  F  I  T  K  K  V  D  A  L  A  I  N  P  V  D  R  T  A  A  G  V  L  I  D  K
GACCCAGAACGACAAGATCGACCTGTTCATCACCAAGAAGGTCGATGCACTGGCGATCAACCCAGTTGATCGCACAGCAGCAGGTGTGCTCATCGACAAG
CTGGGTCTTGCTGTTCTAGCTGGACAAGTAGTGGTTCTTCCAGCTACGTGACCGCTAGTTGGGTCAACTAGCGTGTCGTCGTCCACACGAGTAGCTGTTC
       310       320       330       340       350       360       370       380       390       400

   80                            90                            100                           110
A  K  Q  A  N  I  P  V  V  F  F  N  R  E  P  L  P  E  D  M  K  K  W  D  K  V  Y  Y  V  G  A  K  A  E
GCGAAACAGGCGAACATCCCTGTTGTCTTCTTCAACCGTGAACCGCTTCCGGAAGACATGAAGAAATGGGATAAGGTGTACTACGTGGGTGCGAAAGCGG
CGCTTTGTCCGCTTGTAGGGACAACAGAAGAAGTTGGCACTTGGCGAAGGCCTTCTGTACTTCTTTACCCTATTCCACATGATGCACCCACGCTTTCGCC
       410       420       430       440       450       460       470       480       490       500

                    120                           130                           140
 Q  S  G  T  L  Q  G  E  I  M  A  E  Y  W  K  S  H  P  E  A  D  K  N  H  D  G  I  M  Q  Y  V  M  I
AACAGAGTGGCACTCTGCAAGGCGAAATCATGGCGGAGTACTGGAAAAGCCATCCGGAAGCGGACAAAAACCATGATGGCATTATGCAGTATGTCATGAT
TTGTCTCACCGTGAGACGTTCCGCTTTAGTACCGCCTCATGACCTTTTCGGTAGGCCTTCGCCTGTTTTTGGTACTACCGTAATACGTCATACAGTACTA
       510       520       530       540       550       560       570       580       590       600

          150                           160                           170
 T  G  E  P  G  H  Q  D  A  I  L  R  T  E  Y  S  I  K  A  V  E  A  A  G  I  R  V  K  C  L  A  Q  D
CACTGGTGAACCTGGACACCAGGATGCCATACTCCGGACTGAGTACTCCATAAAGGCGGTGGAAGCGGCTGGTATCCGCGTGAAATGCCTGGCGCAGGAT
GTGACCACTTGGACCTGTGGTCCTACGGTATGAGGCCTGACTCATGAGGTATTTCCGCCACCTTCGCCGACCATAGGCGCACTTTACGGACCGCGTCCTA
       610       620       630       640       650       660       670       680       690       700
```

FIG. 30 (cont.)

```
  180                                       190                                       200                                       210
T  A  M  W  D  R  V  K  G  Q  E  K  M  Q  A  F  L  A  S  F  G  D  K  I  E  A  V  F  C  N  N  D  D  M
ACCGCGATGTGGGATCGAGTGAAAGGCCAGGAAAAGATGCAGGCATTCCTTGCGAGCTTTGGCGACAAAATCGAAGCCGTGTTCTGCAACAACGACGACA
TGGCGCTACACCCTAGCTCACTTTCCGGTCCTTTTCTACGTCCGTAAGGAACGCTCGAAACCGCTGTTTTAGCTTCGGCACAAGACGTTGTTGCTGCTGT
         710        720        730        740        750        760        770        780        790        800

                       220                                       230                                       240
 A  L  G  A  I  E  A  L  K  A  A  G  Y  F  K  D  G  K  Y  V  P  V  V  G  V  D  A  T  T  P  G  L  Q
TGGCACTGGGTGCGATTGAAGCGCTGAAAGCGGCTGGCTACTTCAAGGATGGCAAGTATGTGCCGGTTGTGGGCGTGGATGCGACCACCCCGGGTCTGCA
ACCGTGACCCACGCTAACTTCGCGACTTTCGCCGACCGATGAAGTTCCTACCGTTCATACACGGCCAACACCCGCACCTACGCTGGTGGGGCCCAGACGT
         810        820        830        840        850        860        870        880        890        900

             250                                       260                                       270
 A  L  E  E  G  T  L  L  G  T  V  L  N  D  A  K  A  Q  G  K  A  T  F  N  L  A  Y  V  L  A  K  G  E
GGCGCTGGAAGAAGGTACCCTGCTTGGTACCGTGTTGAACGATGCGAAAGCGCAAGGTAAGGCTACTTTCAACCTCGCTTACGTGCTGGCGAAAGGCGAA
CCGCGACCTTCTTCCATGGGACGAACCATGGCACAACTTGCTACGCTTTCGCGTTCCATTCCGATGAAAGTTGGAGCGAATGCACGACCGCTTTCCGCTT
         910        920        930        940        950        960        970        980        990       1000

  280                                       290                                       300                                       310
K  P  T  K  E  N  V  G  F  E  I  T  D  G  K  Y  I  W  V  P  Y  Q  K  V  T  K  D  N  L  E  E  M  K  K
AAACCGACCAAAGAAAACGTGGGTTTCGAAATCACCGATGGCAAATACATCTGGGTTCCGTACCAGAAAGTGACCAAAGACAACCTGGAAGAAATGAAAA
TTTGGCTGGTTTCTTTTGCACCCAAAGCTTTAGTGGCTACCGTTTATGTAGACCCAAGGCATGGTCTTTCACTGGTTTCTGTTGGACCTTCTTTACTTTT
        1010       1020       1030       1040       1050       1060       1070       1080       1090       1100

                       320
 Y  V  N  E  Q  G  G  S  H  H  H  H  H  H  *  *  *
AATATGTGAATGAACAGGGAGGAAGCCATCATCATCATCATCATTAATAATGAAAGGGCGATATCCAGCACACTGGCGGCCGTTACTAGTGGATCCGGCT
TTATACACTTACTTGTCCCTCCTTCGGTAGTAGTAGTAGTAGTAATTATTACTTTCCCGCTATAGGTCGTGTGACCGCCGGCAATGATCACCTAGGCCGA
        1110       1120       1130       1140       1150       1160       1170       1180       1190       1200

GCTAACAAAGCCCGAAAGGAAGCTGAGTTGGCTGCTGCCACCGCTGAGCAATAACTAGCATAACCCCTTGGGGCCTCTAAACGGGTCTTGAGGGGTTTTT
CGATTGTTTCGGGCTTTCCTTCGACTCAACCGACGACGGTGGCGACTCGTTATTGATCGTATTGGGGAACCCCGGAGATTTGCCCAGAACTCCCCAAAAA
        1210       1220       1230       1240       1250       1260       1270       1280       1290       1300

TGCTGAAAGGAGGAACTATATCCGGAGCGACTCCCACGGCACGTTGGCAAGCTCG
ACGACTTTCCTCCTTGATATAGGCCTCGCTGAGGGTGCCGTGCAACCGTTCGAGC
        1310       1320       1330       1340       1350
```

FIG. 31

```
>Exemplary chyGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                  10
                                                                          M  K  P  Y  I  G  V  A  I  Y  K
CACTATAGGGAGACCACAACGGTTTCCCTCTAGAAATAATTTTGTTTAACTTTAAGAAGGAGATATACCATGAAACCTTATATTGGTGTTGCAATATATA
GTGATATCCCTCTGGTGTTGCCAAAGGGAGATCTTTATTAAAACAAATTGAAATTCTTCCTCTATATGGTACTTTGGAATATAACCACAACGTTATATAT
       110       120       130       140       150       160       170       180       190       200

                                  20                            30                            40
 F  D  D  T  F  M  T  G  V  R  N  A  I  A  K  E  G  E  G  K  A  K  L  D  F  V  D  C  Q  N  S  Q  S
AGTTTGACGACACATTCATGACCGGTGTTCGCAACGCGATTGCGAAAGAAGGCGAAGGCAAAGCGAAACTGGACTTTGTCGATTGCCAGAACAGCCAGTC
TCAAACTGCTGTGTAAGTACTGGCCACAAGCGTTGCGCTAACGCTTTCTTCCGCTTCCGTTTCGCTTTGACCTGAAACAGCTAACGGTCTTGTCGGTCAG
       210       220       230       240       250       260       270       280       290       300

                         50                            60                            70
 T  Q  N  D  K  I  D  L  F  I  T  K  K  V  D  A  L  A  I  N  P  V  D  R  T  A  A  G  V  L  I  D  K
GACCCAGAACGACAAGATCGACCTCTTCATAACCAAGAAAGTGGACGCTTTGGCGATCAATCCGGTTGATCGTACCGCGGCAGGTGTGTTGATCGACAAG
CTGGGTCTTGCTGTTCTAGCTGGAGAAGTATTGGTTCTTTCACCTGCGAAACCGCTAGTTAGGCCAACTAGCATGGCGCCGTCCACACAACTAGCTGTTC
       310       320       330       340       350       360       370       380       390       400

    80                            90                            100                           110
A  K  Q  A  N  I  P  V  V  F  F  N  R  E  P  L  P  E  D  M  K  K  W  D  K  V  Y  Y  V  G  A  K  A  E
GCGAAACAGGCGAACATCCCAGTCGTCTTCTTCAACCGAGAGCCGTTACCGGAAGATATGAAGAAATGGGATAAGGTGTACTACGTTGGTGCCAAAGCTG
CGCTTTGTCCGCTTGTAGGGTCAGCAGAAGAAGTTGGCTCTCGGCAATGGCCTTCTATACTTCTTTACCCTATTCCACATGATGCAACCACGGTTTCGAC
       410       420       430       440       450       460       470       480       490       500

                                 120                           130                           140
 Q  S  G  T  L  Q  G  E  I  M  A  E  Y  W  K  S  H  P  E  A  D  K  N  H  N  G  I  M  E  Y  V  M  I
AACAGTCAGGCACTCTGCAGGGGGAAATCATGGCAGAGTACTGGAAAAGCCATCCGGAAGCCGACAAGAACCACAACGGCATCATGGAATACGTGATGAT
TTGTCAGTCCGTGAGACGTCCCCCTTTAGTACCGTCTCATGACCTTTTCGGTAGGCCTTCGGCTGTTCTTGGTGTTGCCGTAGTACCTTATGCACTACTA
       510       520       530       540       550       560       570       580       590       600

                      150                           160                           170
 T  G  E  P  G  H  Q  D  A  I  L  R  T  E  Y  S  I  K  A  V  E  A  A  G  I  K  T  K  A  L  A  Q  D
CACCGGTGAACCGGGTCATCAGGATGCGATCTTGCGTACCGAGTACTCGATCAAAGCGGTTGAGGCTGCGGGTATCAAGACCAAAGCGCTTGCTCAGGAT
GTGGCCACTTGGCCCAGTAGTCCTACGCTAGAACGCATGGCTCATGAGCTAGTTTCGCCAACTCCGACGCCCATAGTTCTGGTTTCGCGAACGAGTCCTA
       610       620       630       640       650       660       670       680       690       700
```

FIG. 31 (cont.)

```
   180                                     190                                     200                                     210
T  A  M  W  D  R  V  K  G  Q  E  K  M  Q  A  F  L  A  S  F  G  D  R  I  E  A  V  F  C  N  N  D  D  M
ACAGCCATGTGGGATAGGGTGAAAGGTCAGGAGAAGATGCAGGCGTTCCTTGCGAGCTTTGGCGATCGGATTGAGGCTGTATTCTGCAACAACGACGATA
TGTCGGTACACCCTATCCCACTTTCCAGTCCTCTTCTACGTCCGCAAGGAACGCTCGAAACCGCTAGCCTAACTCCGACATAAGACGTTGTTGCTGCTAT
        710        720        730        740        750        760        770        780        790        800

                                220                                     230                                     240
  A  L  G  A  I  E  A  L  K  A  A  G  Y  F  K  N  G  K  Y  I  P  V  V  G  V  D  A  T  T  P  G  L  Q
TGGCACTGGGTGCCATTGAAGCGCTCAAAGCAGCAGGGTACTTCAAGAACGGCAAATACATCCCTGTTGTGGGTGTGGATGCGACCACTCCGGGTCTGCA
ACCGTGACCCACGGTAACTTCGCGAGTTTCGTCGTCCCATGAAGTTCTTGCCGTTTATGTAGGGACAACACCCACACCTACGCTGGTGAGGCCCAGACGT
        810        820        830        840        850        860        870        880        890        900

                      250                                     260                                     270
 A  L  E  E  G  T  L  L  G  T  V  L  N  D  A  K  A  Q  G  K  A  T  F  N  L  A  Y  V  L  A  K  G  E
GGCGCTGGAAGAAGGTACCCTGCTGGGTACCGTCTTGAACGACGCCAAAGCTCAGGGTAAGGCTACGTTCAACTTGGCGTATGTGCTGGCGAAAGGCGAA
CCGCGACCTTCTTCCATGGGACGACCCATGGCAGAACTTGCTGCGGTTTCGAGTCCCATTCCGATGCAAGTTGAACCGCATACACGACCGCTTTCCGCTT
        910        920        930        940        950        960        970        980        990       1000

   280                                     290                                     300                                     310
K  P  T  K  E  N  V  G  F  D  I  T  D  G  K  Y  I  W  V  P  Y  Q  K  V  T  K  D  N  L  E  E  M  K  K
AAACCGACCAAAGAGAATGTCGGCTTCGACATCACGGATGGCAAGTACATTTGGGTGCCGTACCAGAAAGTGACCAAGGACAACTTGGAAGAGATGAAAA
TTTGGCTGGTTTCTCTTACAGCCGAAGCTGTAGTGCCTACCGTTCATGTAAACCCACGGCATGGTCTTTCACTGGTTCCTGTTGAACCTTCTCTACTTTT
       1010       1020       1030       1040       1050       1060       1070       1080       1090       1100

                                320
  Y  V  N  E  Q  G  G  S  H  H  H  H  H  H  *  *  *
AATACGTAAATGAACAAGGAGGAAGCCATCATCATCATCATCATTAATAATGAAAGGGCGATATCCAGCACACTGGCGGCCGTTACTAGTGGATCCGGCT
TTATGCATTTACTTGTTCCTCCTTCGGTAGTAGTAGTAGTAGTAATTATTACTTTCCCGCTATAGGTCGTGTGACCGCCGGCAATGATCACCTAGGCCGA
       1110       1120       1130       1140       1150       1160       1170       1180       1190       1200


GCTAACAAAGCCCGAAAGGAAGCTGAGTTGGCTGCTGCCACCGCTGAGCAATAACTAGCATAACCCCTTGGGGCCTCTAAACGGGTCTTGAGGGGTTTTT
CGATTGTTTCGGGCTTTCCTTCGACTCAACCGACGACGGTGGCGACTCGTTATTGATCGTATTGGGGAACCCCGGAGATTTGCCCAGAACTCCCCAAAAA
       1210       1220       1230       1240       1250       1260       1270       1280       1290       1300


TGCTGAAAGGAGGAACTATATCCGGAGCGACTCCCACGGCACGTTGGCAAGCTCG
ACGACTTTCCTCCTTGATATAGGCCTCGCTGAGGGTGCCGTGCAACCGTTCGAGC
       1310       1320       1330       1340       1350
```

FIG. 32

```
>Exemplary pspGGBP (Table 2) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACT
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGA
        10        20        30        40        50        60        70        80        90       100

                                                                                                  10
                                                                                   M  V  G  V  A  I  Y  K  F  D  D
CACTATAGGGAGACCACAACGGTTTCCCTCTAGAAATAATTTTGTTTAACTTTAAGAAGGAGATATACCATGGTTGGTGTAGCAATTTATAAGTTTGATG
GTGATATCCCTCTGGTGTTGCCAAAGGGAGATCTTTATTAAAACAAATTGAAATTCTTCCTCTATATGGTACCAACCACATCGTTAAATATTCAAACTAC
       110       120       130       140       150       160       170       180       190       200

                      20                              30                              40
  T  F  M  T  G  V  R  N  A  M  S  D  A  A  N  G  V  A  K  L  D  I  V  D  S  Q  N  A  Q  P  T  Q  N
ATACCTTCATGACAGGCGTTCGAAACGCGATGAGCGATGCAGCGAACGGTGTAGCGAAACTGGACATCGTGGATTCGCAAAACGCCCAACCGACCCAGAA
TATGGAAGTACTGTCCGCAAGCTTTGCGCTACTCGCTACGTCGCTTGCCACATCGCTTTGACCTGTAGCACCTAAGCGTTTTGCGGGTTGGCTGGGTCTT
       210       220       230       240       250       260       270       280       290       300

            50                              60                              70
 E  K  I  D  L  F  I  S  K  K  Y  S  S  M  I  I  N  P  V  D  R  T  A  A  G  V  I  I  D  K  A  K  T
CGAGAAAATCGACCTGTTCATCAGCAAAAAGTACAGCAGCATGATCATCAACCCCGTTGATCGTACCGCAGCTGGCGTCATCATCGACAAAGCCAAAACC
GCTCTTTTAGCTGGACAAGTAGTCGTTTTTCATGTCGTCGTACTAGTAGTTGGGGCAACTAGCATGGCGTCGACCGCAGTAGTAGCTGTTTCGGTTTTGG
       310       320       330       340       350       360       370       380       390       400

   80                             90                             100                             110
A  N  T  P  V  V  F  L  N  R  E  P  I  A  E  D  M  N  K  W  D  K  V  Y  Y  V  G  A  K  A  E  E  S  G
GCCAATACCCCGGTGGTTTTCCTGAATCGCGAACCGATTGCGGAAGACATGAACAAATGGGACAAGGTGTACTATGTCGGTGCCAAAGCGGAGGAAAGCG
CGGTTATGGGGCCACCAAAAGGACTTAGCGCTTGGCTAACGCCTTCTGTACTTGTTTACCCTGTTCCACATGATACAGCCACGGTTTCGCCTCCTTTCGC
       410       420       430       440       450       460       470       480       490       500

                      120                             130                             140
  T  I  S  G  Q  L  I  V  D  Y  W  K  A  N  P  K  A  D  K  N  G  D  G  K  L  Q  Y  V  L  L  Q  G  E
GTACCATCAGCGGTCAGCTGATCGTGGACTACTGGAAAGCGAACCCGAAAGCCGACAAGAACGGAGATGGCAAACTGCAGTACGTGCTGTTGCAGGGTGA
CATGGTAGTCGCCAGTCGACTAGCACCTGATGACCTTTCGCTTGGGCTTTCGGCTGTTCTTGCCTCTACCGTTTGACGTCATGCACGACAACGTCCCACT
       510       520       530       540       550       560       570       580       590       600

            150                             160                             170
 P  G  H  Q  D  A  E  L  R  T  K  F  S  V  Q  A  I  Q  D  A  G  I  E  V  E  A  L  A  V  D  T  A  M
ACCGGGTCATCAGGATGCCGAACTGCGTACCAAGTTCAGCGTTCAGGCTATCCAGGATGCAGGCATCGAGGTGGAAGCGTTAGCGGTGGATACCGCTATG
TGGCCCAGTAGTCCTACGGCTTGACGCATGGTTCAAGTCGCAAGTCCGATAGGTCCTACGTCCGTAGCTCCACCTTCGCAATCGCCACCTATGGCGATAC
       610       620       630       640       650       660       670       680       690       700
```

FIG. 32 (cont.)

```
    180                                     190                                     200                                     210
W  D  R  V  K  G  Q  E  K  M  Q  T  F  L  A  S  H  G  D  K  I  E  A  V  L  A  N  N  D  D  M  A  L  G
TGGGATCGTGTGAAAGGGCAGGAAAAGATGCAGACCTTCCTTGCGTCTCATGGCGACAAAATCGAAGCGGTTCTGGCGAACAACGACGATATGGCGTTAG
ACCCTAGCACACTTTCCCGTCCTTTTCTACGTCTGGAAGGAACGCAGAGTACCGCTGTTTTAGCTTCGCCAAGACCGCTTGTTGCTGCTATACCGCAATC
         710       720       730       740       750       760       770       780       790       800

                                   220                                     230                                     240
  A  I  E  A  L  K  A  A  G  Y  F  S  G  D  K  Y  M  P  V  V  G  V  D  A  T  A  P  A  V  Q  A  L  E
GAGCGATTGAGGCCTTGAAAGCTGCAGGCTACTTCAGTGGCGATAAGTACATGCCGGTGGTTGGTGTGGATGCAACCGCTCCAGCCGTTCAGGCGCTGGA
CTCGCTAACTCCGGAACTTTCGACGTCCGATGAAGTCACCGCTATTCATGTACGGCCACCAACCACACCTACGTTGGCGAGGTCGGCAAGTCCGCGACCT
         810       820       830       840       850       860       870       880       890       900

                      250                                     260                                     270
 D  G  T  L  L  G  T  V  L  N  D  A  K  S  Q  G  K  A  S  V  A  I  A  A  A  L  S  K  G  E  A  P  N
AGATGGCACATTGCTCGGAACCGTGCTCAACGACGCGAAAAGCCAGGGCAAAGCGAGTGTTGCGATAGCAGCGGCGCTTTCGAAGGGTGAAGCGCCGAAC
TCTACCGTGTAACGAGCCTTGGCACGAGTTGCTGCGCTTTTCGGTCCCGTTTCGCTCACAACGCTATCGTCGCCGCGAAAGCTTCCCACTTCGCGGCTTG
         910       920       930       940       950       960       970       980       990      1000

    280                                     290                                     300                                     310
K  E  N  T  G  F  D  I  T  D  G  K  Y  V  W  I  A  Y  K  K  I  T  K  D  N  I  A  D  A  K  G  G  S  H
AAAGAGAACACCGGTTTCGACATCACCGATGGGAAGTACGTGTGGATTGCGTACAAGAAGATCACCAAAGATAATATTGCAGATGCTAAAGGCGGCAGCC
TTTCTCTTGTGGCCAAAGCTGTAGTGGCTACCCTTCATGCACACCTAACGCATGTTCTTCTAGTGGTTTCTATTATAACGTCTACGATTTCCGCCGTCGG
        1010      1020      1030      1040      1050      1060      1070      1080      1090      1100

  H  H  H  H  H  *  *  *
ATCATCATCATCATCATTAATGATAAAAGGGCGATATCCAGCACACTGGCGGCCGTTACTAGTGGATCCGGCTGCTAACAAAGCCCGAAAGGAAGCTGAG
TAGTAGTAGTAGTAGTAATTACTATTTTCCCGCTATAGGTCGTGTGACCGCCGGCAATGATCACCTAGGCCGACGATTGTTTCGGGCTTTCCTTCGACTC
        1110      1120      1130      1140      1150      1160      1170      1180      1190      1200

TTGGCTGCTGCCACCGCTGAGCAATAACTAGCATAACCCCTTGGGGCCTCTAAACGGGTCTTGAGGGGTTTTTTGCTGAAAGGAGGAACTATATCCGGAG
AACCGACGACGGTGGCGACTCGTTATTGATCGTATTGGGGAACCCCGGAGATTTGCCCAGAACTCCCCAAAAAACGACTTTCCTCCTTGATATAGGCCTC
        1210      1220      1230      1240      1250      1260      1270      1280      1290      1300

CGACTCCCACGGCACGTTGGCAAGCTCG
GCTGAGGGTGCCGTGCAACCGTTCGAGC
        1310      1320
```

FIG. 33

```
>Exemplary ttGGBP11C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                         10                            20
                                                     M  K  Q  L  N  I  G  V  A  I  C  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTGCAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAACGTTTAAGCTGCTGTGTAAGTACTGACCCCAGGCCTTACG
       130       140       150       160       170       180       190       200       210       220       230       240

                   30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

                   70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

                  110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

                  150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 33 (cont.)

```
          190                 200                 210                 220
 V T A H D K M A A W L S S F G D K I E A V F A N N D D M A L G A I E A L K S A G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730        740        750        760        770        780        790        800        810        820        830        840

          230                 240                 250                 260
 Y F T G N K Y I P V V G V D A T A P G I Q A I K D G T L L G T V L N D A K N Q A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850        860        870        880        890        900        910        920        930        940        950        960

          270                 280                 290                 300
 K A T F N I A Y E L A Q G I T P T K D N I G Y D I T D G K Y V W I P Y K K I T K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970        980        990       1000       1010       1020       1030       1040       1050       1060       1070       1080

          310                 320
 D N I S D A E Q G G S H H H H H H * *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090       1100       1110       1120       1130       1140       1150       1160       1170       1180       1190       1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210       1220       1230       1240       1250       1260       1270       1280       1290       1300       1310       1320

ACGGCACGTTGGCAAGCTCG
TGCCGTGCAACCGTTCGAGC
      1330       1340
```

FIG. 34

```
>Exemplary ttGGBP16C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                            20
                                                        M  K  Q  L  N  I  G  V  A  I  Y  K  F  D  D  C  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACTGCTTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGACGAAGTACTGACCCCAGGCCTTACG
       130       140       150       160       170       180       190       200       210       220       230       240

        30                            40                            50                            60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

        70                            80                            90                           100
N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

       110                           120                           130                           140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

       150                           160                           170                           180
L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 34 (cont.)

```
         190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

         230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

         270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

         310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320


ACGGCACGTTGGCAAGCTCG
TGCCGTGCAACCGTTCGAGC
      1330      1340
```

FIG. 35

```
>Exemplary ttGGBP17C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                                    10                            20
                                                          M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
        130       140       150       160       170       180       190       200       210       220       230       240

              30                            40                            50                            60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
        250       260       270       280       290       300       310       320       330       340       350       360

              70                            80                            90                            100
N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
        370       380       390       400       410       420       430       440       450       460       470       480

             110                           120                           130                           140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
        490       500       510       520       530       540       550       560       570       580       590       600

             150                           160                           170                           180
L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
        610       620       630       640       650       660       670       680       690       700       710       720
```

FIG. 35 (cont.)

```
        190                                     200                                     210                                     220
V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

        230                                     240                                     250                                     260
Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

        270                                     280                                     290                                     300
K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

        310                                     320
D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 36

```
>Exemplary ttGGBP42C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                            20
                                                    M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

                    30                            40                            50                            60
 M  T  A  E  A  Q  G  K  A  K  L  N  M  V  D  S  Q  C  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGTGCTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCACGAGTGTTGGATGTGTTTTACTAGTCCAGCTGGAGAAGTAGTGCTTTTTTTACTTACGCAACCGTTA
       250       260       270       280       290       300       310       320       330       340       350       360

                    70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

                   110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

                   150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 36 (cont.)

```
            190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
          730       740       750       760       770       780       790       800       810       820       830       840

            230                                     240                                     250                                     260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
          850       860       870       880       890       900       910       920       930       940       950       960

            270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
          970       980       990      1000      1010      1020      1030      1040      1050      1060      1070      1080

            310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
         1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
         1210      1220      1230      1240      1250      1260      1270      1280      1290      1300      1310      1320

ACGGCACGTTGGCAAGCTCG
TGCCGTGCAACCGTTCGAGC
         1330      1340
```

FIG. 37

>Exemplary ttGGBP67C Cysteine Scan Mutant (Table 3) Expression Construct

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                    10                            20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

                       30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

                       70                            80                            90                           100
 N  P  C  D  R  T  A  A  G  T  I  I  D  K  A  K  Q  A  N  I  P  V  V  F  F  N  R  E  P  L  P  E  D  M  K  K  W  D  K  V
CAACCCTTGCGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGAACGCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

                      110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

                      150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 37 (cont.)

```
         190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

         230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

         270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

         310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 38

```
>Exemplary ttGGBP91C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                     10                            20
                                                          M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

       30                            40                            50                            60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

       70                            80                            90                           100
N  P  V  D  R  T  A  A  G  T  I  I  D  K  A  K  Q  A  N  I  P  V  V  F  F  N  C  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACTGCGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGACGCTTGGAAATGGTCTTCTGTACTTTTTTACCCTATTCCA
       370       380       390       400       410       420       430       440       450       460       470       480

      110                           120                           130                           140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

      150                           160                           170                           180
L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 38 (cont.)

```
            190                             200                             210                             220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

            230                             240                             250                             260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

            270                             280                             290                             300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

            310                             320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320


ACGGCACGTTGGCAAGCTCG
TGCCGTGCAACCGTTCGAGC
      1330      1340
```

FIG. 39

```
>Exemplary ttGGBP92C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                10                            20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

              30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                            80                            90                            100
 N  P  V  D  R  T  A  A  G  T  I  I  D  K  A  K  Q  A  N  I  P  V  V  F  F  N  R  C  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGTGCCCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCACGGGAAATGGTCTTCTGTACTTTTTTACCCTATTCCA
       370       380       390       400       410       420       430       440       450       460       470       480

             110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 39 (cont.)

```
          190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
         730        740        750        760        770        780        790        800        810        820        830        840

          230                                     240                                     250                                     260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
         850        860        870        880        890        900        910        920        930        940        950        960

          270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
         970        980        990       1000       1010       1020       1030       1040       1050       1060       1070       1080

          310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
        1090       1100       1110       1120       1130       1140       1150       1160       1170       1180       1190       1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
        1210       1220       1230       1240       1250       1260       1270       1280       1290       1300       1310       1320


ACGGCACGTTGGCAAGCTCG
TGCCGTGCAACCGTTCGAGC
        1330       1340
```

FIG. 40

```
>Exemplary ttGGBP111C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                          10                            20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

              30                            40                            50                            60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                            80                            90                           100
N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       430       450       460       470       480

             110                           120                           130                           140
Y  Y  V  G  A  K  C  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGTGCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCACGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                           160                           170                           180
L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 40 (cont.)

```
          190                             200                             210                             220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

          230                             240                             250                             260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

          270                             280                             290                             300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

          310                             320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 41

```
>Exemplary ttGGBP148C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

                30                            40                            50                            60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

                70                            80                            90                           100
N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

               110                           120                           130                           140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

               150                           160                           170                           180
L  M  G  C  P  G  H  Q  D  A  I  L  R  T  Q  Y  S  I  Q  T  V  K  D  A  G  I  K  V  Q  E  L  A  K  D  Y  A  N  W  D  R
GTTAATGGGCTGCCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGACGGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 41 (cont.)

```
             190                                     200                                     210                                     220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

             230                                     240                                     250                                     260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850       860       870       880       890       900       910       920       930       940       950       960

             270                                     280                                     290                                     300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

             310                                     320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320


ACGGCACGTTGGCAAGCTCG
TGCCGTGCAACCGTTCGAGC
       1330      1340
```

FIG. 42

>Exemplary ttGGBP151C Cysteine Scan Mutant (Table 3) Expression Construct

CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
10 20 30 40 50 60 70 80 90 100 110 120

10 20
M K Q L N I G V A I Y K F D D T F M T G V R N A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
130 140 150 160 170 180 190 200 210 220 230 240

30 40 50 60
M T A E A Q G K A K L N M V D S Q N S Q P T Q N D Q V D L F I T K K M N A L A I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
250 260 270 280 290 300 310 320 330 340 350 360

70 80 90 100
N P V D R T A A G T I I D K A K Q A N I P V V F F N R E P L P E D M K K W D K V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
370 380 390 400 410 420 430 440 450 460 470 480

110 120 130 140
Y Y V G A K A E Q S G I L Q G Q I M A D Y W K A H P E A D K N H D G V M Q Y V M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
490 500 510 520 530 540 550 560 570 580 590 600

150 160 170 180
L M G Q P G C Q D A I L R T Q Y S I Q T V K D A G I K V Q E L A K D Y A N W D R
GTTAATGGGCCAGCCGGGGTGCCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCACGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
610 620 630 640 650 660 670 680 690 700 710 720

FIG. 42 (cont.)

```
                   190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

                   230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

                   270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

                   310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320


ACGGCACGTTGGCAAGCTCG
TGCCGTGCAACCGTTCGAGC
      1330      1340
```

FIG. 43

```
>Exemplary ttGGBP152C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                            10                            20
                                                       M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

              30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

             110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                           160                           170                           180
 L  M  G  Q  P  G  H  C  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACTGCGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGACGCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 43 (cont.)

```
         190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

         230                                     240                                     250                                     260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

         270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

         310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 44

```
>Exemplary ttGGBP181C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                              20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

              30                             40                             50                             60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                             80                             90                            100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

             110                            120                            130                            140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                            160                            170                            180
 L  M  G  Q  P  G  H  Q  D  A  I  L  R  T  Q  Y  S  I  Q  T  V  K  D  A  G  I  K  V  Q  E  L  A  K  D  Y  A  C  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCTGCTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGACGACCCTAGC
       610       620       630       640       650       660       670       680       690       700       710       720
```

FIG. 44 (cont.)

```
         190                       200                       210                       220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

         230                       240                       250                       260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850       860       870       880       890       900       910       920       930       940       950       960

         270                       280                       290                       300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

         310                       320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320


ACGGCACGTTGGCAAGCTCG
TGCCGTGCAACCGTTCGAGC
       1330      1340
```

FIG. 45

```
>Exemplary ttGGBP182C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                          M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

                 30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

                 70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

                110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

                150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  C  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 45 (cont.)

```
          190                                     200                                     210                                     220
V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730         740         750         760         770         780         790         800         810         820         830         840

          230                                     240                                     250                                     260
Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850         860         870         880         890         900         910         920         930         940         950         960

          270                                     280                                     290                                     300
K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970         980         990        1000        1010        1020        1030        1040        1050        1060        1070        1080

          310                                     320
D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090        1100        1110        1120        1130        1140        1150        1160        1170        1180        1190        1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210        1220        1230        1240        1250        1260        1270        1280        1290        1300        1310        1320


ACGGCACGTTGGCAAGCTCG
TGCCGTGCAACCGTTCGAGC
       1330        1340
```

FIG. 46

```
>Exemplary ttGGBP183C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                               10                            20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

                 30                            40                            50                            60
  M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

                 70                            80                            90                           100
  N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

                110                           120                           130                           140
  Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

                150                           160                           170                           180
  L  M  G  Q  P  G  H  Q  D  A  I  L  R  T  Q  Y  S  I  Q  T  V  K  D  A  G  I  K  V  Q  E  L  A  K  D  Y  A  N  W  C  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGTGCCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCACGGC
       610       620       630       640       650       660       670       680       690       700       710       720
```

FIG. 46 (cont.)

```
          190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

          230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

          270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

          310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 47

>Exemplary ttGGBP257C Cysteine Scan Mutant (Table 3) Expression Construct

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                  20
                                                       M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

            30                            40                            50                            60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTTACTTACGCAACCGTTA
       250       260       270       280       290       300       310       320       330       340       350       360

            70                            80                            90                           100
N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

           110                           120                           130                           140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

           150                           160                           170                           180
L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 47 (cont.)

```
                 190                                                     200                                                     210                                                     220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

                 230                                                     240                                                     250                                                     260
 Y  F  T  G  N  K  Y  I  P  V  V  G  V  D  A  T  A  P  G  I  Q  A  I  K  D  G  T  L  L  G  T  V  C  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCTGCAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGACGTTGCTGCGGTTTTTGGTCCG
       850       860       870       880       890       900       910       920       930       940       950       960

                 270                                                     280                                                     290                                                     300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

                 310                                                     320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 48

```
>Exemplary ttGGBP259C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                 10                            20
                                                         M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

               30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

               70                            80                            90                            100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

              110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

              150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 48 (cont.)

```
         190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

         230                           240                           250                           260
 Y  F  T  G  N  K  Y  I  P  V  V  G  V  D  A  T  A  P  G  I  Q  A  I  K  D  G  T  L  L  G  T  V  L  N  C  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACTGCGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGACGCGGTTTTTGGTCCG
        850       860       870       880       890       900       910       920       930       940       950       960

         270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

         310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320


ACGGCACGTTGGCAAGCTCG
TGCCGTGCAACCGTTCGAGC
       1330      1340
```

FIG. 49

```
>Exemplary ttGGBP300C Cysteine Scan Mutant (Table 3) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                                 10                            20
                                                         M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
        130       140       150       160       170       180       190       200       210       220       230       240

                 30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
        250       260       270       280       290       300       310       320       330       340       350       360

                 70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
        370       380       390       400       410       420       430       440       450       460       470       480

                110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
        490       500       510       520       530       540       550       560       570       580       590       600

                150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
        610       620       630       640       650       660       670       680       690       700       710       720
```

FIG. 49 (cont.)

```
                190                                    200                                    210                                    220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730         740         750         760         770         780         790         800         810         820         830         840

                230                                    240                                    250                                    260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850         860         870         880         890         900         910         920         930         940         950         960

                270                                    280                                    290                                    300
 K   A   T   F   N   I   A   Y   E   L   A   Q   G   I   T   P   T   K   D   N   I   G   Y   D   I   T   D   G   K   Y   V   W   I   P   Y   C   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATTGCAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATAACGTTTTAATGTTT
        970         980         990        1000        1010        1020        1030        1040        1050        1060        1070        1080

                310                                    320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090        1100        1110        1120        1130        1140        1150        1160        1170        1180        1190        1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210        1220        1230        1240        1250        1260        1270        1280        1290        1300        1310        1320

ACGGCACGTTGGCAAGCTCG
TGCCGTGCAACCGTTCGAGC
       1330        1340
```

FIG. 50

```
>Exemplary ttGGBP17C.1 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                         10                            20
                                                     M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

       30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

       70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

      110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

      150                           160                           170                           180
 L  M  G  E  P  G  H  Q  D  A  I  L  R  T  Q  Y  S  I  Q  T  V  K  D  A  G  I  K  V  Q  E  L  A  K  D  Y  A  N  W  D  R
GTTAATGGGCGAACCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGCTTGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 50 (cont.)

```
         190                                200                                210                                220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

         230                                240                                250                                260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

         270                                280                                290                                300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

         310                                320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320


ACGGCACGTTGGCAAGCTCG
TGCCGTGCAACCGTTCGAGC
      1330      1340
```

FIG. 51

```
>Exemplary ttGGBP17C.2 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                            20
                                                         M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

                30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

                70                            80                            90                           100
 N  P  V  D  P  T  A  A  G  T  I  I  D  K  A  K  Q  A  N  I  P  V  V  F  F  N  R  E  P  L  P  E  D  M  K  K  W  D  K  V
CAACCCTGTAGATCCGACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGGCTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

               110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

               150                           160                           170                           180
 L  M  G  Q  P  G  H  P  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCCGGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGGCCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 51 (cont.)

```
        190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

        230                                     240                                     250                                     260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

        270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

        310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320


ACGGCACGTTGGCAAGCTCG
TGCCGTGCAACCGTTCGAGC
      1330      1340
```

FIG. 52

```
>Exemplary ttGGBP17C.3 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                                    10                            20
                                                         M  K  Q  L  N  I  G  V  A  I  Y  K  F  D  D  N  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACAACTGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTTGACGTACTGACCCCAGGCCTTACG
        130       140       150       160       170       180       190       200       210       220       230       240

                        30                            40                            50                            60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
        250       260       270       280       290       300       310       320       330       340       350       360

                        70                            80                            90                            100
N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
        370       380       390       400       410       420       430       440       450       460       470       480

                       110                           120                           130                           140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
        490       500       510       520       530       540       550       560       570       580       590       600

                       150                           160                           170                           180
L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
        610       620       630       640       650       660       670       680       690       700       710       720
```

FIG. 52 (cont.)

```
          190                           200                           210                           220
 V  T  A  H  D  K  M  A  A  W  L  S  S  F  G  D  K  I  E  A  V  F  A  N  N  D  A  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGCGATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCGCTACCGGGACCCACGGTAACTTCGGGAGTTCAGACGACC
        730       740       750       760       770       780       790       800       810       820       830       840

          230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850       860       870       880       890       900       910       920       930       940       950       960

          270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

          310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320

ACGGCACGTTGGCAAGCTCG
TGCCGTGCAACCGTTCGAGC
       1330      1340
```

FIG. 53

```
>Exemplary ttGGBP17C.4 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                                      10                            20
                                                         M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
        130       140       150       160       170       180       190       200       210       220       230       240

               30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
        250       260       270       280       290       300       310       320       330       340       350       360

               70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
        370       380       390       400       410       420       430       440       450       460       470       480

              110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
        490       500       510       520       530       540       550       560       570       580       590       600

              150                           160                           170                           180
 L  M  G  Q  P  G  Q  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCAGCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTCGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
        610       620       630       640       650       660       670       680       690       700       710       720
```

FIG. 53 (cont.)

```
              190                             200                             210                             220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

              230                             240                             250                             260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

              270                             280                             290                             300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

              310                             320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 54

```
>Exemplary ttGGBP17C.5 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                        M  K  Q  L  N  I  G  V  A  I  Y  K  F  D  A  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGCGACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCGCTGTACGTACTGACCCCAGGCCTTACG
       130       140       150       160       170       180       190       200       210       220       230       240

              30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                            80                            90                            100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

              110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

              150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 54 (cont.)

```
         190                                200                                210                                220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

         230                                240                                250                                260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

         270                                280                                290                                300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

         310                                320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 55

```
>Exemplary ttGGBP17C.6 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                            20
                                                        M  K  Q  L  N  I  G  V  A  I  Y  K  F  D  E  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGAAACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTTTGTACGTACTGACCCCAGGCCTTACG
       130       140       150       160       170       180       190       200       210       220       230       240

            30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

            70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

           110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

           150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 55 (cont.)

```
         190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

         230                                     240                                     250                                     260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

         270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

         310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 56

```
>Exemplary ttGGBP17C.7 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                               10                            20
                                                         M  K  Q  L  N  I  G  V  A  I  Y  K  F  D  N  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACAACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGTTGTGTACGTACTGACCCCAGGCCTTACG
        130       140       150       160       170       180       190       200       210       220       230       240

                 30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
        250       260       270       280       290       300       310       320       330       340       350       360

                 70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
        370       380       390       400       410       420       430       440       450       460       470       480

                110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
        490       500       510       520       530       540       550       560       570       580       590       600

                150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
        610       620       630       640       650       660       670       680       690       700       710       720
```

FIG. 56 (cont.)

```
             190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

             230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

             270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

             310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320


ACGGCACGTTGGCAAGCTCG
TGCCGTGCAACCGTTCGAGC
      1330      1340
```

FIG. 57

```
>Exemplary ttGGBP17C.8 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                       M  K  Q  L  N  I  G  V  A  I  Y  K  F  D  D  N  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACAACTGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTTGACGTACTGACCCCAGGCCTTACG
       130       140       150       160       170       180       190       200       210       220       230       240

                      30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

                      70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

                     110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

                     150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 57 (cont.)

```
            190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

            230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

            270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

            310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320


ACGGCACGTTGGCAAGCTCG
TGCCGTGCAACCGTTCGAGC
      1330      1340
```

FIG. 58

```
>Exemplary ttGGBP17C.9 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                10                            20
                                                         M  K  Q  L  N  I  G  V  A  I  Y  K  F  D  D  S  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACAGCTGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTCGACGTACTGACCCCAGGCCTTACG
       130       140       150       160       170       180       190       200       210       220       230       240

             30                            40                            50                            60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

            110                           120                           130                           140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 58 (cont.)

```
             190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

             230                                     240                                     250                                     260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850       860       870       880       890       900       910       920       930       940       950       960

             270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

             310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320


ACGGCACGTTGGCAAGCTCG
TGCCGTGCAACCGTTCGAGC
       1330      1340
```

FIG. 59

>Exemplary ttGGBP17C.10 Affinity-Tuning Mutant (17C background) (Table 6) Expression Construct

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                             10                            20
                                                          M  K  Q  L  N  I  G  V  A  I  Y  K  F  D  D  T  C  M  T  A  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGCGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACGCCAGGCCTTACG
        130       140       150       160       170       180       190       200       210       220       230       240

                30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
        250       260       270       280       290       300       310       320       330       340       350       360

                70                            80                            90                            100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
        370       380       390       400       410       420       430       440       450       460       470       480

               110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
        490       500       510       520       530       540       550       560       570       580       590       600

               150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
        610       620       630       640       650       660       670       680       690       700       710       720
```

FIG. 59 (cont.)

```
           190                           200                           210                           220
V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

           230                           240                           250                           260
Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

           270                           280                           290                           300
K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

           310                           320
D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 60

```
>Exemplary ttGGBP17C.11 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
10 20 30 40 50 60 70 80 90 100 110 120

10 20
M K Q L N I G V A I Y K F D D T C M T G V R N A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
130 140 150 160 170 180 190 200 210 220 230 240

30 40 50 60
M T A E A Q G K A K L N M V D S Q N S Q P T Q N D Q V D L F I T K K M N A L A I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
250 260 270 280 290 300 310 320 330 340 350 360

70 80 90 100
N P V D R T A A G T I I D K A K Q A N I P V V F F N R E P L P E D M K K W D K V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
370 380 390 400 410 420 430 440 450 460 470 480

110 120 130 140
Y Y V G A K A E Q S G I L Q G Q I M A D Y W K A H P E A D K N H D G V M Q Y V M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
490 500 510 520 530 540 550 560 570 580 590 600

150 160 170 180
L M G Q P G H Q D A I L R T Q Y S I Q T V K D A G I K V Q E L A K D Y A N W D R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
610 620 630 640 650 660 670 680 690 700 710 720
```

FIG. 60 (cont.)

```
         190                                200                                210                                220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

         230                                240                                250                                260
 Y  F  T  G  N  K  Y  I  P  V  V  G  V  D  A  A  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCGCGGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGCGCCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

         270                                280                                290                                300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

         310                                320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 61

```
>Exemplary ttGGBP17C.19 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                               10                            20
                                                          M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

                 30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

                 70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

                110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

                150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 61 (cont.)

```
          190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

          230                           240                           250                           260
 Y  F  T  G  N  K  Y  I  P  V  V  G  V  D  A  T  A  P  G  I  Q  A  I  K  D  G  T  L  L  G  T  V  L  D  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGGATGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACCTACTGCGGTTTTTGGTCCG
        850       860       870       880       890       900       910       920       930       940       950       960

          270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

          310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320


ACGGCACGTTGGCAAGCTCG
TGCCGTGCAACCGTTCGAGC
       1330      1340
```

FIG. 62

```
>Exemplary ttGGBP17C.20 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                            20
                                                        M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

              30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

             110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 62 (cont.)

```
          190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

          230                           240                           250                           260
 Y  F  T  G  N  K  Y  I  P  V  V  G  V  D  A  T  A  P  G  I  Q  A  I  K  D  G  T  L  L  G  T  V  L  S  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAGCGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTCGCTGCGGTTTTTGGTCCG
       850       860       870       880       890       900       910       920       930       940       950       960

          270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

          310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 63

```
>Exemplary ttGGBP17C.21 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                        M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 63 (cont.)

```
              190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
      730       740       750       760       770       780       790       800       810       820       830       840

              230                           240                           250                           260
 Y  F  T  G  N  K  Y  I  P  V  V  G  V  D  A  T  A  P  G  I  Q  A  I  K  D  G  T  L  L  G  T  V  L  A  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGGCGGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACCGCCTGCGGTTTTTGGTCCG
      850       860       870       880       890       900       910       920       930       940       950       960

              270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
      970       980       990      1000      1010      1020      1030      1040      1050      1060      1070      1080

              310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
     1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
     1210      1220      1230      1240      1250      1260      1270      1280      1290      1300      1310      1320


ACGGCACGTTGGCAAGCTCG
TGCCGTGCAACCGTTCGAGC
     1330      1340
```

FIG. 64

```
>Exemplary ttGGBP17C.22 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                         M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

              30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

             110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 64 (cont.)

```
            190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

            230                                     240                                     250                                     260
 Y   F   T   G   N   K   Y   I   P   V   V   G   V   D   A   T   A   P   G   I   Q   A   I   K   D   G   T   L   L   G   T   V   L   N   D   N   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACAACAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGTTGTTTTTGGTCCG
        850       860       870       880       890       900       910       920       930       940       950       960

            270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

            310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320

ACGGCACGTTGGCAAGCTCG
TGCCGTGCAACCGTTCGAGC
       1330      1340
```

FIG. 65

```
>Exemplary ttGGBP17C.23 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                            20
                                                        M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

           30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

           70                            80                            90                            100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

          110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

          150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 65 (cont.)

```
                190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

                230                                     240                                     250                                     260
 Y   F   T   G   N   K   Y   I   P   V   V   G   V   D   A   T   A   P   G   I   Q   A   I   K   D   G   T   L   L   G   T   V   L   N   D   Q   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACCAGAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGGTCTTTTTGGTCCG
        850       860       870       880       890       900       910       920       930       940       950       960

                270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

                310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320

ACGGCACGTTGGCAAGCTCG
TGCCGTGCAACCGTTCGAGC
       1330      1340
```

FIG. 66

```
>Exemplary ttGGBP17C.24 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                            20
                                                        M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 66 (cont.)

190 200 210 220
V T A H D K M A A W L S S F G D K I E A V F A N N D D M A L G A I E A L K S A G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
730 740 750 760 770 780 790 800 810 820 830 840

230 240 250 260
Y F T G N K Y I P V V G V D A T A P G I Q A I K D G T L L G T V L N D R K N Q A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACCGCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGGCGTTTTTGGTCCG
850 860 870 880 890 900 910 920 930 940 950 960

270 280 290 300
K A T F N I A Y E L A Q G I T P T K D N I G Y D I T D G K Y V W I P Y K K I T K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
970 980 990 1000 1010 1020 1030 1040 1050 1060 1070 1080

310 320
D N I S D A E Q G G S H H H H H H * *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
1090 1100 1110 1120 1130 1140 1150 1160 1170 1180 1190 1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
1210 1220 1230 1240 1250 1260 1270 1280 1290 1300 1310 1320

ACGGCACGTTGGCAAGCTCG
TGCCGTGCAACCGTTCGAGC
1330 1340

FIG. 67

```
>Exemplary ttGGBP17C.25 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                                10                                      20
                                                         M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
        130       140       150       160       170       180       190       200       210       220       230       240

                    30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
        250       260       270       280       290       300       310       320       330       340       350       360

                    70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
        370       380       390       400       410       420       430       440       450       460       470       480

                   110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
        490       500       510       520       530       540       550       560       570       580       590       600

                   150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
        610       620       630       640       650       660       670       680       690       700       710       720
```

FIG. 67 (cont.)

```
               190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

               230                           240                           250                           260
 Y  F  T  G  N  K  Y  I  P  V  V  G  V  D  A  T  A  P  G  I  Q  A  I  K  D  G  T  L  L  G  T  V  L  N  D  K  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACAAAAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGTTTTTTTTGGTCCG
       850       860       870       880       890       900       910       920       930       940       950       960

               270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

               310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 68

```
>Exemplary ttGGBP17C.26 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                                 10                            20
                                                         M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
        130       140       150       160       170       180       190       200       210       220       230       240

                      30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
        250       260       270       280       290       300       310       320       330       340       350       360

                      70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
        370       380       390       400       410       420       430       440       450       460       470       480

                     110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
        490       500       510       520       530       540       550       560       570       580       590       600

                     150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
        610       620       630       640       650       660       670       680       690       700       710       720
```

FIG. 68 (cont.)

```
             190                                     200                                     210                                     220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

             230                                     240                                     250                                     260
 Y  F  T  G  N  K  Y  I  P  V  V  G  V  D  A  T  A  P  G  I  Q  A  I  K  D  G  T  L  L  G  T  V  L  N  D  W  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACTGGAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGACCTTTTTGGTCCG
       850       860       870       880       890       900       910       920       930       940       950       960

             270                                     280                                     290                                     300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

             310                                     320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 69

```
>Exemplary ttGGBP17C.27 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                       10                            20
                                                        M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 69 (cont.)

```
              190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
      730       740       750       760       770       780       790       800       810       820       830       840

              230                           240                           250                           260
 Y  F  T  G  N  K  Y  I  P  V  V  G  V  D  A  T  A  P  G  I  Q  A  I  K  D  G  T  L  L  G  T  V  L  N  D  F  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACTTTAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGAAATTTTTGGTCCG
      850       860       870       880       890       900       910       920       930       940       950       960

              270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
      970       980       990      1000      1010      1020      1030      1040      1050      1060      1070      1080

              310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
     1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
     1210      1220      1230      1240      1250      1260      1270      1280      1290      1300      1310      1320


ACGGCACGTTGGCAAGCTCG
TGCCGTGCAACCGTTCGAGC
     1330      1340
```

FIG. 70

```
>Exemplary ttGGBP17C.28 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                        M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

              30                             40                             50                             60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                             80                             90                            100
N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

             110                            120                            130                            140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                            160                            170                            180
L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 70 (cont.)

```
          190                                     200                                     210                                     220
V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

          230                                     240                                     250                                     260
Y  F  T  G  N  K  Y  I  P  V  V  G  V  D  A  T  A  P  G  I  Q  A  I  K  D  G  T  L  L  G  T  V  L  N  D  Y  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACTATAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGATATTTTTGGTCCG
        850       860       870       880       890       900       910       920       930       940       950       960

          270                                     280                                     290                                     300
K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

          310                                     320
D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320


ACGGCACGTTGGCAAGCTCG
TGCCGTGCAACCGTTCGAGC
       1330      1340
```

FIG. 71

```
>Exemplary ttGGBP17C.29 Affinity-Tuning Mutant (17C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                  10                            20
                                                          M  K  Q  L  N  I  G  V  A  I  Y  K  F  D  D  T  C  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATGCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTACGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  W  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGGGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACCCTAGC
       610       620       630       640       650       660       670       680       690       700       710       720
```

FIG. 71 (cont.)

```
              190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730         740         750         760         770         780         790         800         810         820         830         840

              230                                     240                                     250                                     260
 Y   F   T   G   N   K   Y   I   P   V   V   G   V   D   A   T   A   P   G   I   Q   A   I   K   D   G   T   L   L   G   T   V   L   N   D   S   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACAGCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGTCGTTTTTGGTCCG
        850         860         870         880         890         900         910         920         930         940         950         960

              270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970         980         990        1000        1010        1020        1030        1040        1050        1060        1070        1080

              310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090        1100        1110        1120        1130        1140        1150        1160        1170        1180        1190        1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210        1220        1230        1240        1250        1260        1270        1280        1290        1300        1310        1320

ACGGCACGTTGGCAAGCTCG
TGCCGTGCAACCGTTCGAGC
       1330        1340
```

FIG. 72

```
>Exemplary ttGGBP182C.2.0 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                 M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  E  P  G  H  Q  D  A  I  L  R  T  Q  Y  S  I  Q  T  V  K  D  A  G  I  K  V  Q  E  L  A  K  D  Y  A  N  C  D  R
GTTAATGGGCGAACCGGGGCACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 72 (cont.)

```
                190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

                230                                     240                                     250                                     260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

                270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

                310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 73

```
>Exemplary ttGGBP182C.2.1 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

            30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

            70                            80                            90                         100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

           110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

           150                           160                           170                           180
 L  M  G  E  P  G  H  Q  D  S  I  L  R  T  Q  Y  S  I  Q  T  V  K  D  A  G  I  K  V  Q  E  L  A  K  D  Y  A  N  C  D  R
GTTAATGGGCGAACCGGGGCACCAAGACAGCATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCGTGGTTCTGTCGTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 73 (cont.)

```
                190                                                   200                                                   210                                                   220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
         730       740       750       760       770       780       790       800       810       820       830       840

                230                                                   240                                                   250                                                   260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
         850       860       870       880       890       900       910       920       930       940       950       960

                270                                                   280                                                   290                                                   300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
         970       980       990      1000      1010      1020      1030      1040      1050      1060      1070      1080

                310                                                   320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
        1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
        1210      1220      1230      1240      1250      1260      1270      1280      1290      1300      1310      1320

ACGGCACGTTGGCAAGCTCG
TGCCGTGCAACCGTTCGAGC
        1330      1340
```

FIG. 74

```
>Exemplary ttGGBP182C.2.3 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                         M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

              30                             40                             50                             60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                             80                             90                            100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

             110                            120                            130                            140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                            160                            170                            180
 L  M  G  E  P  G  H  Q  D  N  I  L  R  T  Q  Y  S  I  Q  T  V  K  D  A  G  I  K  V  Q  E  L  A  K  D  Y  A  N  C  D  R
GTTAATGGGCGAACCGGGGCACCAAGACAACATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCGTGGTTCTGTTGTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 74 (cont.)

```
          190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

          230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850       860       870       880       890       900       910       920       930       940       950       960

          270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

          310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320

ACGGCACGTTGGCAAGCTCG
TGCCGTGCAACCGTTCGAGC
       1330      1340
```

FIG. 75

```
>Exemplary ttGGBP182C.2.4 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                 10                            20
                                                         M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

              30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

             110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                           160                           170                           180
 L  M  G  E  P  G  H  Q  D  M  I  L  R  T  Q  Y  S  I  Q  T  V  K  D  A  G  I  K  V  Q  E  L  A  K  D  Y  A  N  C  D  R
GTTAATGGGCGAACCGGGGCACCAAGACATGATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCGTGGTTCTGTACTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 75 (cont.)

```
                  190                                200                                210                                220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

                  230                                240                                250                                260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850       860       870       880       890       900       910       920       930       940       950       960

                  270                                280                                290                                300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

                  310                                320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320

ACGGCACGTTGGCAAGCTCG
TGCCGTGCAACCGTTCGAGC
       1330      1340
```

FIG. 76

```
>Exemplary ttGGBP182C.2.5 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                  10                            20
                                                         M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

               30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

               70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

              110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

              150                           160                           170                           180
 L  M  G  E  P  G  Q  Q  D  A  I  L  R  T  Q  Y  S  I  Q  T  V  K  D  A  G  I  K  V  Q  E  L  A  K  D  Y  A  N  C  D  R
GTTAATGGGCGAACCGGGGCAGCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCGTCGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 76 (cont.)

```
          190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

          230                                     240                                     250                                     260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850       860       870       880       890       900       910       920       930       940       950       960

          270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

          310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320

ACGGCACGTTGGCAAGCTCG
TGCCGTGCAACCGTTCGAGC
       1330      1340
```

FIG. 77

```
>Exemplary ttGGBP182C.2.6 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  E  P  G  N  Q  D  A  I  L  R  T  Q  Y  S  I  Q  T  V  K  D  A  G  I  K  V  Q  E  L  A  K  D  Y  A  N  C  D  R
GTTAATGGGCGAACCGGGGAACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCTTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 77 (cont.)

```
            190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

            230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

            270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

            310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 78

```
>Exemplary ttGGBP182C.2.7 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                            10                            20
                                                         M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  E  P  G  F  Q  D  A  I  L  R  T  Q  Y  S  I  Q  T  V  K  D  A  G  I  K  V  Q  E  L  A  K  D  Y  A  N  C  D  R
GTTAATGGGCGAACCGGGGTTTCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCAAAGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 78 (cont.)

```
          190                                200                                210                                220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730         740         750         760         770         780         790         800         810         820         830         840

          230                                240                                250                                260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850         860         870         880         890         900         910         920         930         940         950         960

          270                                280                                290                                300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970         980         990        1000        1010        1020        1030        1040        1050        1060        1070        1080

          310                                320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090        1100        1110        1120        1130        1140        1150        1160        1170        1180        1190        1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210        1220        1230        1240        1250        1260        1270        1280        1290        1300        1310        1320

ACGGCACGTTGGCAAGCTCG
TGCCGTGCAACCGTTCGAGC
       1330        1340
```

FIG. 79

```
>Exemplary ttGGBP182C.2.8 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                 10                            20
                                                         M  K  Q  L  N  I  G  V  A  I  Y  K  F  D  N  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACAACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGTTGTGTAAGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  E  P  G  H  Q  D  A  I  L  R  T  Q  Y  S  I  Q  T  V  K  D  A  G  I  K  V  Q  E  L  A  K  D  Y  A  N  C  D  R
GTTAATGGGCGAACCGGGGCACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 79 (cont.)

```
           190                           200                           210                           220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

           230                           240                           250                           260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

           270                           280                           290                           300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

           310                           320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 80

```
>Exemplary ttGGBP182C.2.9 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                  20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  E  P  G  H  Q  D  F  I  L  R  T  Q  Y  S  I  Q  T  V  K  D  A  G  I  K  V  Q  E  L  A  K  D  Y  A  N  C  D  R
GTTAATGGGCGAACCGGGGCACCAAGACTTTATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCGTGGTTCTGAAATAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 80 (cont.)

```
          190                            200                            210                            220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

          230                            240                            250                            260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

          270                            280                            290                            300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

          310                            320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 81

```
>Exemplary ttGGBP182C.3 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
         10        20        30        40        50        60        70        80        90       100       110       120

                                                                                   10                            20
                                                           M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
        130       140       150       160       170       180       190       200       210       220       230       240

            30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
        250       260       270       280       290       300       310       320       330       340       350       360

            70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
        370       380       390       400       410       420       430       440       450       460       470       480

           110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
        490       500       510       520       530       540       550       560       570       580       590       600

           150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  C  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
        610       620       630       640       650       660       670       680       690       700       710       720
```

FIG. 81 (cont.)

```
          190                                 200                                 210                                 220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

          230                                 240                                 250                                 260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

          270                                 280                                 290                                 300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

          310                                 320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320


ACGGCACGTTGGCAAGCTCG
TGCCGTGCAACCGTTCGAGC
      1330      1340
```

FIG. 82

```
>Exemplary ttGGBP182C.4 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                  20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

       30                            40                            50                            60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

       70                            80                            90                           100
N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

      110                           120                           130                           140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

      150                           160                           170                           180
L  M  G  E  P  G  H  Q  D  A  I  L  R  T  Q  Y  S  I  Q  T  V  K  D  A  G  I  K  V  Q  E  L  A  K  D  Y  A  N  C  D  R
GTTAATGGGCGAACCGGGGCACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGCTTGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 82 (cont.)

190 200 210 220
V T A H D K M A A W L S S F G D K I E A V F A N N D D M A L G A I E A L K S A G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
730 740 750 760 770 780 790 800 810 820 830 840

230 240 250 260
Y F T G N K Y I P V V G V D A T A P G I Q A I K D G T L L G T V L N D A K N Q A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
850 860 870 880 890 900 910 920 930 940 950 960

270 280 290 300
K A T F N I A Y E L A Q G I T P T K D N I G Y D I T D G K Y V W I P Y K K I T K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
970 980 990 1000 1010 1020 1030 1040 1050 1060 1070 1080

310 320
D N I S D A E Q G G S H H H H H H * *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
1090 1100 1110 1120 1130 1140 1150 1160 1170 1180 1190 1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
1210 1220 1230 1240 1250 1260 1270 1280 1290 1300 1310 1320

ACGGCACGTTGGCAAGCTCG
TGCCGTGCAACCGTTCGAGC
1330 1340

FIG. 83

```
>Exemplary ttGGBP182C.5 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                              20
                                                         M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

                      30                             40                             50                             60
M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

                      70                             80                             90                            100
N  P  V  D  P  T  A  A  G  T  I  I  D  K  A  K  Q  A  N  I  P  V  V  F  F  N  R  E  P  L  P  E  D  M  K  K  W  D  K  V
CAACCCTGTAGATCCGACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGGCTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

                     110                            120                            130                            140
Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

                     150                            160                            170                            180
L  M  G  Q  P  G  H  P  D  A  I  L  R  T  Q  Y  S  I  Q  T  V  K  D  A  G  I  K  V  Q  E  L  A  K  D  Y  A  N  C  D  R
GTTAATGGGCCAGCCGGGGCACCCGGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGGTCGGCCCCGTGGGCCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 83 (cont.)

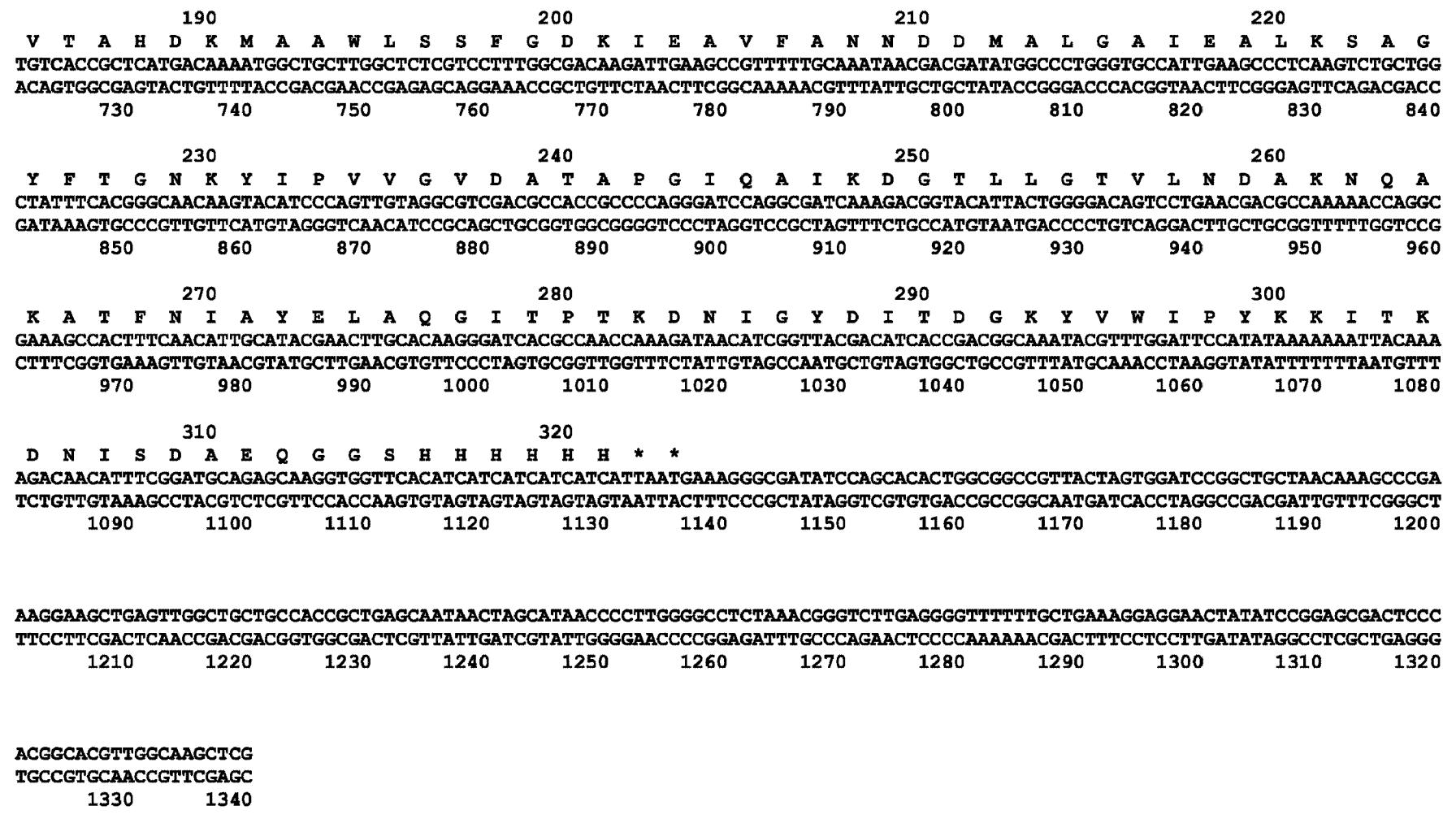

```
         190                                200                                210                                220
 V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

         230                                240                                250                                260
 Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

         270                                280                                290                                300
 K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

         310                                320
 D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 84

```
>Exemplary ttGGBP182C.6 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                            20
                                                         M  K  Q  L  N  I  G  V  A  I  Y  K  F  D  D  N  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACAACTTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTTGAAGTACTGACCCCAGGCCTTACG
       130       140       150       160       170       180       190       200       210       220       230       240

              30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

              70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

             110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

             150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  C  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 84 (cont.)

```
          190                 200                 210                 220
V  T  A  H  D  K  M  A  A  W  L  S  S  F  G  D  K  I  E  A  V  F  A  N  N  D  A  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGCGATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCGCTACCGGGACCCACGGTAACTTCGGGAGTTCAGACGACC
       730       740       750       760       770       780       790       800       810       820       830       840

          230                 240                 250                 260
Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

          270                 280                 290                 300
K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

          310                 320
D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

FIG. 85

```
>Exemplary ttGGBP182C.7 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                           10                            20
                                                         M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  S  P  G  H  Q  D  A  I  L  R  T  Q  Y  S  I  Q  T  V  K  D  A  G  I  K  V  Q  E  L  A  K  D  Y  A  N  C  D  R
GTTAATGGGCAGCCCGGGGCACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGTCGGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 85 (cont.)

```
                190                                     200                                     210                                     220
V  T  A  H  D  K  M  A  A  W  L  S  S  F  G  D  K  I  E  A  V  F  A  N  N  D  D  M  A  L  G  A  I  E  A  L  K  S  A  G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

                230                                     240                                     250                                     260
Y  F  T  G  N  K  Y  I  P  V  V  G  V  D  A  T  A  P  G  I  Q  A  I  K  D  G  T  L  L  G  T  V  L  N  D  A  K  N  Q  A
CTATTTCACGGGCAACAAGTACATCCCAGTTGTAGGCGTCGACGCCACCGCCCCAGGGATCCAGGCGATCAAAGACGGTACATTACTGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850       860       870       880       890       900       910       920       930       940       950       960

                270                                     280                                     290                                     300
K  A  T  F  N  I  A  Y  E  L  A  Q  G  I  T  P  T  K  D  N  I  G  Y  D  I  T  D  G  K  Y  V  W  I  P  Y  K  K  I  T  K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

                310                                     320
D  N  I  S  D  A  E  Q  G  G  S  H  H  H  H  H  H  *  *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320


ACGGCACGTTGGCAAGCTCG
TGCCGTGCAACCGTTCGAGC
       1330      1340
```

FIG. 86

```
>Exemplary ttGGBP182C.8 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                               10                            20
                                                        M  K  Q  L  N  I  G  V  A  I  Y  K  F  D  D  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACGACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGCTGTGTAAGTACTGACCCCAGGCCTTACG
       130       140       150       160       170       180       190       200       210       220       230       240

             30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

             70                            80                            90                           100
 N  P  V  D  R  T  A  A  G  T  I  I  D  K  A  K  Q  A  N  I  P  V  V  F  F  N  K  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACAAAGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGTTTCTTGGAAATGGTCTTCTGTACTTTTTTACCCTATTCCA
       370       380       390       400       410       420       430       440       450       460       470       480

            110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

            150                           160                           170                           180
 L  M  G  K  P  G  H  Q  D  A  I  L  R  T  Q  Y  S  I  Q  T  V  K  D  A  G  I  K  V  Q  E  L  A  K  D  Y  A  N  C  D  R
GTTAATGGGCAAACCGGGGCACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGTTTGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 86 (cont.)

```
          190                                     200                                     210                                     220
 V   T   A   H   D   K   M   A   A   W   L   S   S   F   G   D   K   I   E   A   V   F   A   N   N   D   D   M   A   L   G   A   I   E   A   L   K   S   A   G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
        730       740       750       760       770       780       790       800       810       820       830       840

          230                                     240                                     250                                     260
 Y   F   T   G   N   K   Y   I   P   V   V   G   V   D   A   T   A   P   G   I   Q   A   I   K   D   G   T   L   L   G   T   V   L   N   D   A   K   N   Q   A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
        850       860       870       880       890       900       910       920       930       940       950       960

          270                                     280                                     290                                     300
 K   A   T   F   N   I   A   Y   E   L   A   Q   G   I   T   P   T   K   D   N   I   G   Y   D   I   T   D   G   K   Y   V   W   I   P   Y   K   K   I   T   K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
        970       980       990      1000      1010      1020      1030      1040      1050      1060      1070      1080

          310                                     320
 D   N   I   S   D   A   E   Q   G   G   S   H   H   H   H   H   H   *   *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
       1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210      1220      1230      1240      1250      1260      1270      1280      1290      1300      1310      1320

ACGGCACGTTGGCAAGCTCG
TGCCGTGCAACCGTTCGAGC
       1330      1340
```

FIG. 87

```
>Exemplary ttGGBP182C.9 Affinity-Tuning Mutant (182C background) (Table 6) Expression Construct
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                             10                            20
                                                        M  K  Q  L  N  I  G  V  A  I  Y  K  F  D  N  T  F  M  T  G  V  R  N  A
GGTTTCCCTCTAGAAATAATTTTGTTTAACTTTAAGAAGGAGATATACCATGAAACAACTCAATATCGGTGTAGCTATTTATAAATTCGACAACACATTCATGACTGGGGTCCGGAATGC
CCAAAGGGAGATCTTTATTAAAACAAATTGAAATTCTTCCTCTATATGGTACTTTGTTGAGTTATAGCCACATCGATAAATATTTAAGCTGTTGTGTAAGTACTGACCCCAGGCCTTACG
       130       140       150       160       170       180       190       200       210       220       230       240

           30                            40                            50                            60
 M  T  A  E  A  Q  G  K  A  K  L  N  M  V  D  S  Q  N  S  Q  P  T  Q  N  D  Q  V  D  L  F  I  T  K  K  M  N  A  L  A  I
TATGACCGCAGAAGCCCAAGGCAAGGCCAAGTTAAACATGGTAGACAGTCAGAACTCACAACCTACACAAAATGATCAGGTCGACCTCTTCATCACGAAAAAAATGAATGCGTTGGCAAT
ATACTGGCGTCTTCGGGTTCCGTTCCGGTTCAATTTGTACCATCTGTCAGTCTTGAGTGTTGGATGTGTTTTACTAGTCCAGCTGGAGAAGTAGTGCTTTTTTTACTTACGCAACCGTTA
       250       260       270       280       290       300       310       320       330       340       350       360

           70                            80                            90                           100
 N  P  V  D  R  T  A  A  G  T  I  I  D  K  A  K  Q  A  N  I  P  V  V  F  F  N  R  E  P  L  P  E  D  M  K  K  W  D  K  V
CAACCCTGTAGATCGCACCGCAGCTGGGACTATCATCGACAAGGCAAAGCAAGCAAATATCCCTGTAGTGTTCTTCAACCGGGAACCTTTACCAGAAGACATGAAAAAATGGGATAAGGT
GTTGGGACATCTAGCGTGGCGTCGACCCTGATAGTAGCTGTTCCGTTTCGTTCGTTTATAGGGACATCACAAGAAGTTGGCCCTTGGAAATGGTCTTCTGTACTTTTTTACCCTATTCCA
       370       380       390       400       410       420       430       440       450       460       470       480

          110                           120                           130                           140
 Y  Y  V  G  A  K  A  E  Q  S  G  I  L  Q  G  Q  I  M  A  D  Y  W  K  A  H  P  E  A  D  K  N  H  D  G  V  M  Q  Y  V  M
ATATTACGTAGGCGCAAAGGCCGAACAGAGTGGCATTCTCCAAGGTCAAATCATGGCTGATTATTGGAAAGCTCATCCGGAAGCGGACAAGAACCACGACGGGGTTATGCAATATGTCAT
TATAATGCATCCGCGTTTCCGGCTTGTCTCACCGTAAGAGGTTCCAGTTTAGTACCGACTAATAACCTTTCGAGTAGGCCTTCGCCTGTTCTTGGTGCTGCCCCAATACGTTATACAGTA
       490       500       510       520       530       540       550       560       570       580       590       600

          150                           160                           170                           180
 L  M  G  Q  P  G  H  Q  D  A  I  L  R  T  Q  Y  S  I  Q  T  V  K  D  A  G  I  K  V  Q  E  L  A  K  D  Y  A  N  C  D  R
GTTAATGGGCCAGCCGGGGCACCAAGACGCAATCTTACGTACGCAATACTCGATCCAAACCGTGAAAGATGCAGGCATCAAGGTCCAGGAGCTGGCTAAAGACTACGCCAATTGCGATCG
CAATTACCCGGTCGGCCCCGTGGTTCTGCGTTAGAATGCATGCGTTATGAGCTAGGTTTGGCACTTTCTACGTCCGTAGTTCCAGGTCCTCGACCGATTTCTGATGCGGTTAACGCTAGC
       610       620       630       640       650       660       670       680       690       700       710       720
```

FIG. 87 (cont.)

```
           190                                                     200                                                     210                                                     220
V T A H D K M A A W L S S F G D K I E A V F A N N D D M A L G A I E A L K S A G
TGTCACCGCTCATGACAAAATGGCTGCTTGGCTCTCGTCCTTTGGCGACAAGATTGAAGCCGTTTTTGCAAATAACGACGATATGGCCCTGGGTGCCATTGAAGCCCTCAAGTCTGCTGG
ACAGTGGCGAGTACTGTTTTACCGACGAACCGAGAGCAGGAAACCGCTGTTCTAACTTCGGCAAAAACGTTTATTGCTGCTATACCGGGACCCACGGTAACTTCGGGAGTTCAGACGACC
       730       740       750       760       770       780       790       800       810       820       830       840

           230                                                     240                                                     250                                                     260
Y F T G N K Y I P V V G V D A T A P G I Q A I K D G T L L G T V L N D A K N Q A
CTATTTCACGGGCAACAAGTACATCCCAGTTGTAGGCGTCGACGCCACCGCCCCAGGGATCCAGGCGATCAAAGACGGTACATTACTGGGGACAGTCCTGAACGACGCCAAAAACCAGGC
GATAAAGTGCCCGTTGTTCATGTAGGGTCAACATCCGCAGCTGCGGTGGCGGGGTCCCTAGGTCCGCTAGTTTCTGCCATGTAATGACCCCTGTCAGGACTTGCTGCGGTTTTTGGTCCG
       850       860       870       880       890       900       910       920       930       940       950       960

           270                                                     280                                                     290                                                     300
K A T F N I A Y E L A Q G I T P T K D N I G Y D I T D G K Y V W I P Y K K I T K
GAAAGCCACTTTCAACATTGCATACGAACTTGCACAAGGGATCACGCCAACCAAAGATAACATCGGTTACGACATCACCGACGGCAAATACGTTTGGATTCCATATAAAAAAATTACAAA
CTTTCGGTGAAAGTTGTAACGTATGCTTGAACGTGTTCCCTAGTGCGGTTGGTTTCTATTGTAGCCAATGCTGTAGTGGCTGCCGTTTATGCAAACCTAAGGTATATTTTTTTAATGTTT
       970       980       990      1000      1010      1020      1030      1040      1050      1060      1070      1080

           310                                                     320
D N I S D A E Q G G S H H H H H H * *
AGACAACATTTCGGATGCAGAGCAAGGTGGTTCACATCATCATCATCATCATTAATGAAAGGGCGATATCCAGCACACTGGCGGCCGTTACTAGTGGATCCGGCTGCTAACAAAGCCCGA
TCTGTTGTAAAGCCTACGTCTCGTTCCACCAAGTGTAGTAGTAGTAGTAGTAATTACTTTCCCGCTATAGGTCGTGTGACCGCCGGCAATGATCACCTAGGCCGACGATTGTTTCGGGCT
      1090      1100      1110      1120      1130      1140      1150      1160      1170      1180      1190      1200

AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
      1210      1220      1230      1240      1250      1260      1270      1280      1290      1300      1310      1320

ACGGCACGTTGGCAAGCTCG
TGCCGTGCAACCGTTCGAGC
      1330      1340
```

GLUCOSE BIOSENSORS AND USES THEREOF

RELATED APPLICATIONS

This application is a national stage application, filed under 35 U.S.C. § 371, of International Application No. PCT/US2016/050297 filed Sep. 2, 2016, which claims benefit of priority to U.S. Provisional Application No. 62/257,796, filed Nov. 20, 2015, and U.S. Provisional Application No. 62/257,784, filed Nov. 20, 2015, the entire contents of each of which are incorporated herein by reference.

INCORPORATION-BY-REFERENCE OF SEQUENCE LISTING

The contents of the text file named "35327-516001WO_Sequence_Listing.txt", which was created on Sep. 2, 2016 and is 587 KB in size, is hereby incorporated by reference in its entirety.

FIELD OF THE INVENTION

The present invention relates to compositions and methods for detecting and determining the concentration of glucose and/or galactose.

BACKGROUND

Biosensors are analytical tools that can be used to measure the presence of a single molecular species in a complex mixture by combining the exquisite molecular recognition properties of biological macromolecules with signal transduction mechanisms that couple ligand binding to readily detectable physical changes (Hall, Biosensors, Prentice-Hall, Englewood Cliffs, N.J.; Scheller et al., Curr. Op. Biotech. 12:35-40, 2001). Ideally, a biosensor is reagentless and, in contrast to enzyme-based assays or competitive immunoassays, does not change composition as a consequence of making the measurement (Hellinga & Marvin, Trends Biotech. 16:183-189, 1998). Most biosensors combine a naturally occurring macromolecule such as an enzyme or an antibody, with the identification of a suitable physical signal particular to the molecule in question, and the construction of a detector specific to that system (Meadows, Adv. Drug Deliv. Rev. 21:177-189, 1996). Recently, molecular engineering techniques have been explored to develop macromolecules that combine a wide range of binding specificities and affinities with a common signal transduction mechanism, to construct a generic detection system for many different analytes (Hellinga & Marvin, Trends Biotech. 16:183-189, 1998).

*Escherichia coli* periplasmic binding proteins are members of a protein superfamily (bacterial periplasmic binding proteins, bPBPs) (Tam & Saier, Microbiol. Rev. 57:320-346, 1993). These proteins comprise two domains linked by a hinge region (Quiocho & Ledvina, Molec. Microbiol. 20:17-25, 1996). The ligand-binding site is located at the interface between the two domains. The proteins typically adopt two conformations: a ligand-free open form, and a ligand-bound closed form, which interconvert via a hinge-bending mechanism upon ligand binding. This global, ligand-mediated conformational change has been exploited to couple ligand binding to changes in fluorescence intensity by positioning single, environmentally sensitive fluorophores in locations that undergo local conformational changes in concert with the global change (Brune et al., Biochemistry 33:8262-8271, 1994; Gilardi et al., Prot. Eng. 10:479-486, 1997; Gilardi et al., Anal. Chem. 66:3840-3847, 1994; Marvin et al., Proc. Natl. Acad. Sci. USA 94:4366-4371, 1997, Marvin and Hellinga, J. Am. Chem. Soc. 120:7-11, 1998; Tolosa et al., Anal. Biochem. 267:114-120, 1999; Dattelbaum & Lakowicz, Anal. Biochem. 291:89-95, 2001; Marvin & Hellinga, Proc. Natl. Acad. Sci. USA 98:4955-4960, 2001; Salins et al., Anal. Biochem. 294:19-26, 2001).

SUMMARY OF THE INVENTION

The invention provides improved biosensors that rapidly, reliably, and accurately detect and quantify glucose and/or galactose with significant advantages over previous systems. The present disclosure provides a biosensor for ligand, comprising a ligand-binding protein that is attached to a reporter group. The ligand may be glucose and/or galactose, and the ligand-binding protein includes a domain that binds the glucose and/or the galactose. The binding of a ligand to the ligand-binding domain of the ligand-binding protein causes a change in signaling by the reporter group. In various implementations, the biosensor may produce a signal when a ligand is bound to the ligand binding domain that is not produced (and/or that is different from a signal that is produced) when the ligand is absent from the ligand binding domain. These biosensors have widespread utility including in clinical, industrial, and environmental settings.

The glucose-binding proteins (biosensors) described herein are characterized by one conformational shape when bound to glucose and a different conformational shape when unbound to glucose, this change in shape affects the signal of a detectable label such as a fluorophore. The proteins are engineered to include a single cysteine to which the detectable label, e.g., a fluorophore is covalently attached. The biosensors are reagentless in that their monitoring mechanism requires neither additional substrates for a signal to develop, nor measurement of substrate consumption or product generation rates to determine glucose concentrations.

Among the advantages of these fluorophone-containing protein constructs is their high durability. The constructs retain their ability to bind glucose, change shape and thus detect the analyte, glucose, (a) even when immobilized (directly or indirectly) onto a solid surface such as a bead, plate, or sheet; (b) even after dessication (and subsequent reconstitution in a physiological buffer solution); (c) even when subjected to ambient conditions, e.g., conditions that can be encountered in storage and/or transportation; and (d) even when aged/stored for extended periods of time, e.g., weeks, months, or even years. Thus, the biosensors do not require refrigeration or a cold chain for distribution, permitting a wider range of applicability such as in-the-field use and reducing the cost of the sensor product.

For clinical applications, microliter volumes, e.g., 10 μl or less of a bodily fluid such as blood may be used. Moreover compared to conventional enzyme-based or antibody based assay systems, the results are achieved virtually instantaneously, e.g., within 30-60 seconds. A further advantage is that the sensors consistently and reliably bind to and detect the analyte (glucose) in complex fluids such as whole blood. Thus in a clinical setting, whole blood need not be processed, thereby reducing time and cost of the diagnostic procedure.

In non-clinical situations, e.g., industrial of commercial settings such as analysis of waste water, food or beverage production, or bioreactor/fermentation monitoring, the samples to be analyzed can be used directly upon sampling without further purification or processing, similarly reducing time and expense of the test. Moreover, the immobilized sensors need not be washed to remove unbound material following contacting the test sample with the sensors, because the unbound material ("contaminants") do not materially affect the production of a precise, reliable detectable assay signal.

The glucose biosensors produce a dichromatic, ratiometric signal, i.e., the signal is defined as the quotient of the intensities at two independent wavelengths. The advantage of such a signal is that it provides an internally consistent reference. The self-calibrating nature of a ratiometric measurement removes the necessity for carrying out on-board calibration tests prior to each measurement.

Thus, reagentless, fluorescently responsive glucose sensors present a number of advantages over enzyme-based biosensors, including elimination of chemical transformations, elimination of substrate requirements, and self-calibration, which together lead to rapid response times, continuous monitoring capabilities, simple sample-handling, and lower cost due to simplified manufacturing and distribution processes.

Ligand-Binding Proteins

Aspects of the present subject matter provide biosensors comprising a ligand-binding protein that binds glucose and/or galactose. Ligand binding proteins that bind both glucose and galactose may be referred to herein as "glucose-galactose binding proteins" (GGBPs). Typically, a natural GGBP has a glucose dissociation constant (KD) of about 10 μM or less at room temperature. However, GGBPs may be selected, designed, or engineered to detect different (e.g., higher or lower) levels of glucose and/or galactose. The ligand-binding protein may comprise a naturally occurring protein or a protein that is modified compared to a naturally occurring protein. For example, the ligand-binding protein may comprise one or more mutations compared to a naturally occurring protein. In some embodiments, the naturally occurring protein is a naturally occurring counterpart of the ligand-binding protein (e.g., the ligand-binding protein is a mutant of the naturally occurring counterpart).

A "naturally occurring counterpart" of a mutant polypeptide is a polypeptide produced in nature from which the mutant polypeptide has been or may be derived (e.g., by one or more mutations). For example, the naturally occurring counterpart is an endogenous polypeptide produced by an organism in nature, wherein the endogenous polypeptide typically does not have one or more of the mutations present in the mutant polypeptide. For convenience and depending on context, a naturally occurring counterpart may be referred to herein for the purpose of comparison and to illustrate the location and/or presence of one or more mutations, binding activities, and/or structural features.

As used herein, a "mutation" is a difference between the amino acid sequence of a modified polypeptide/protein and a naturally occurring counterpart. A polypeptide having a mutation may be referred to as a "mutant." Non-limiting examples of mutations include insertions, deletions, and substitutions. However, the term "mutation" excludes (i) the addition of amino acids to the N-terminus or C-terminus of a polypeptide, and (ii) the omission/deletion/replacement of a polypeptide's signal peptide (e.g., replacement with another signal peptide or with a methionine).

The addition of amino acids to the N-terminus or C-terminus of a protein via a peptide bond may be referred to herein as a "fusion" of the amino acids to the protein. Similarly, an exogenous protein fused to amino acids (e.g., another protein, a fragment, a tag, or a polypeptide moiety) at its N-terminus or C-terminus may be referred to as a "fusion protein." The added amino acids may comprise a heterologous polypeptide, e.g., a polypeptide reporter group such as a fluorescent protein, a moiety that facilitates the isolation or modification of a polypeptide, or a moiety that facilitates the attachment of a polypeptide to a substrate or surface. As used herein, "heterologous" when referring to the added amino acids (e.g., a "polypeptide") of a fusion protein indicates that the polypeptide is not naturally part of the protein to which it is fused in the fusion protein. For example, the sequence of a heterologous polypeptide ("added amino acids") that is fused to a protein is encoded by an organism other than the organism from which the protein is derived, is not known to be naturally encoded by any organism, or is encoded by a gene other than the wild-type gene that encodes an endogenous version of the protein.

As used herein the term "signal peptide" refers to a short (e.g., 5-30 or 10-60 amino acids long) stretch of amino acids at the N-terminus of a protein that directs the transport of the protein. In various embodiments, the signal peptide is cleaved off during the post-translational modification of a protein by a cell. Signal peptides may also be referred to as "targeting signals," "leader sequences," "signal sequences," "transit peptides," or "localization signals." In instances where a signal peptide is not defined for a GGBP discussed herein, the signal peptide may optionally be considered to be, e.g., the first 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus of the translated protein (compared to a protein that has not had the signal peptide removed, e.g., compared to a naturally occurring protein).

In some embodiments, the ligand-binding protein comprises 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100 or more mutations compared to a naturally occurring protein while retaining at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity of the naturally occurring protein. Mutations include but are not limited to substitutions, insertions, and deletions. Non-limiting examples of ligand-binding proteins may have 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100, or more substitution mutations compared to a naturally occurring protein while retaining at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity of the naturally occurring protein. In embodiments, at least one amino acid of the ligand-binding protein has been substituted with a cysteine. Alternatively or in addition, a ligand-binding protein may include one or more mutations that remove a cysteine, e.g., 1, 2, 3, 4, 5, 6, 7, 8, 9, 10 or more substitutions or deletions of a cysteine compared to a naturally occurring protein.

Alternatively, the ligand-binding protein is not a mutant. For example, a reporter group is fused to the N-terminus or the C-terminus of the ligand-binding protein.

In various embodiments, a ligand-binding protein may comprise a stretch of amino acids (e.g., the entire length of the ligand-binding protein or a portion comprising at least about 50, 100, 200, 250, 300, or 350 amino acids) in a sequence that is at least about 90%, 91%, 92%, 93%, 94%, 95%, 96%, 97%, 98%, 99%, 99.1%, 99.2%, 99.3%, 99.4%, or 99.5% identical to an amino acid sequence of a naturally occurring protein.

In some embodiments, the mutations are conservative, and the present subject matter includes many ligand-binding proteins in which the only mutations are substitution mutations. In non-limiting examples, a ligand-binding protein has no deletions or insertions compared to a naturally occurring protein (e.g., a naturally occurring counterpart). Alternatively, a ligand-binding protein may have (i) less than about 5, 4, 3, 2, or 1 inserted amino acids, and/or (ii) less than about 5, 4, 3, 2, or 1 deleted amino acids compared to a naturally occurring protein.

In various embodiments, a naturally occurring protein to which a ligand-binding protein is compared or has been derived (e.g., by mutation, fusion, or other modification) from a prokaryotic ligand-binding protein such as a bacterial ligand-binding protein. For example, the prokaryotic ligand-binding protein is a mutant, fragment, or variant of a natural (i.e., wild-type) bacterial protein. In various embodiments, the bacterial ligand-binding protein is from a thermophilic, mesophilic, or cryophilic prokaryotic microorganism (e.g., a thermophilic, mesophilic, or cryophilic bacterium).

A microorganism is "thermophilic" if it is capable of surviving, growing, and reproducing at temperatures between 41 and 140° C. (106 and 284° F.), inclusive. In various embodiments, a thermophilic organism has an optimal growth temperature between 41 and 140° C., or that is at least about 45, 50, 55, 60, 65, 70, 75, 80, 85, 90, 95, 100, 105, 110, 115, 120, 125, 130, 135, or 140° C. Many thermophiles are archaea. Thermophilic eubacteria are suggested to have been among the earliest bacteria. Thermophiles are found in various geothermally heated regions of the Earth, such as hot springs and deep sea hydrothermal vents, as well as decaying plant matter, such as peat bogs and compost. Unlike other types of microorganisms, thermophiles can survive at much hotter temperatures, whereas other bacteria would be damaged and sometimes killed if exposed to the same temperatures. Thermophiles may be classified into three groups: (1) obligate thermophiles; (2) facultative thermophiles; and (3) hyperthermophiles. Obligate thermophiles (also called extreme thermophiles) require such high temperatures for growth, whereas facultative thermophiles (also called moderate thermophiles) can thrive at high temperatures, but also at lower temperatures (e.g. below 50° C.). Hyperthermophiles are particularly extreme thermophiles for which the optimal temperatures are above 80° C. Some microorganisms can live at temperatures higher than 100° C. at large depths in the ocean where water does not boil because of high pressure. Many hyperthermophiles are also able to withstand other environmental extremes such as high acidity or radiation levels. A compound (e.g., a protein or biosensor) is "thermotolerant" if it is capable of surviving exposure to temperatures above 41° C. For example, in some embodiments a thermotolerant biosensor retains its function and does not become denatured when exposed to a temperature of about 45, 50, 55, 60, 65, 70, 75, 80, 85, 90, 95, 100, 105, 110, 115, 120, 125, 130, 135, or 140° C. for at least about 1, 2, 3, 4, 5, 6, 7, 8, 9, 10, 15, 20, 25, 30 or more minutes. In some embodiments, the thermotolerant compound survives exposure to 45, 50, 55, 60, 65, 70, 75, 80, 85, 90, 95, 100, 105, 110, 115, 120, 125, 130, 135, or 140° C. under pressure.

A microorganism is "mesophilic" if it is capable of surviving, growing, and reproducing at temperatures between 20 and 40° C. (68 and 104° F.), inclusive. "Psychrophiles" or "cryophiles" are microorganisms that are capable of growth and reproduction in cold temperatures. In various embodiments, a psychrophile is capable of growth and reproduction at a temperature of 10° C. or less, e.g., between −20° C. and +10° C.

In some embodiments, the microbial protein is produced by a bacterial microorganism, an archaean microorganism, an algal microorganism, a protozoan microorganism, or a fungal microorganism. In non-limiting examples, the microbial protein is produced by a Gram-positive bacterium or a Gram-negative bacterium. In various embodiments, a biosensor comprises a modified (e.g., mutated, fused, and/or conjugated) periplasmic binding protein or a cytoplasmic binding protein.

In non-limiting examples in which the ligand-binding protein is (1) an *Escherichia coli* (*E. coli*) glucose-galactose binding protein (GGBP) (e.g., has been derived from an *E. coli* GGBP via mutation) or (2) has an amino acid sequence that is at least 95%, 96, 97%, 98%, or 99% identical to the amino acid sequence of *E. coli* GGBP, the ligand-binding protein comprises a mutation other than a mutation of amino acid Y10, D14, N15, F16, N91, K92, E93, S112, S115, E149, H152, D154, A155, R158, M182, W183, N211, D236, L255, N256, D257, P294, or V296, wherein each amino acid position is numbered as in (SEQ ID NO: 17).

In certain embodiments, the ligand-binding protein is not derived from (e.g., by mutation, fusion, or other modification) an *E. coli* protein (such as ecGGBP) and does not comprise an amino acid sequence that is identical to the amino acid sequence of ecGGBP. For example, the naturally occurring counterpart of the ligand-binding protein is not an *E. coli* GGBP (e.g., the ligand-binding protein is not a mutant of, fusion protein comprising, or other variant of an *E. coli* GGBP). In some embodiments, the amino acid sequence of the ligand-binding protein is less than about 100%, 99%, 98%, 97%, 96%, 95%, 90%, 85%, 80%, 75%, 70%, 65%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, or 15% identical to an *E. coli* GGBP protein having amino acids in the sequence set forth as SEQ ID NO: 1, 16, or 17.

Aspects of the present subject matter provide a ligand-binding protein with a mutation that alters the interaction of the ligand-binding protein with a ligand (e.g., glucose and/or galactose). For example, the ligand-binding protein comprises a mutation that alters the interaction of the ligand-binding protein with the ligand compared to a naturally occurring counterpart. In some embodiments, the ligand-binding protein comprises a mutation that alters the interaction of an amino acid of the ligand-binding protein with a water molecule compared to a naturally occurring counterpart.

In some embodiments, the ligand-binding protein does not comprise a signal peptide. For example, the signal peptide (e.g., that is present in a naturally occurring counterpart) may be replaced with a methionine.

Exemplary implementations relate to a ligand such as glucose or galactose, wherein the ligand-binding protein comprises a GGBP. For example, the GGBP may comprise a mutant of, a fragment of, or a fusion protein comprising a microbial GGBP. In embodiments, the GGBP is not a mutant or fragment to which a heterologous polypeptide has been attached or added. In some embodiments, the ligand-binding protein has an affinity (KD) for glucose and/or galactose within the concentration range of glucose and/or galactose in a subject. In certain embodiments, the ligand-binding protein has an affinity (KD) for glucose in the range of about 0.2 mM to about 100 mM, about 0.1 mmol/L to about 120 mmol/L, or about 4 mmol/L to about 33 mmol/L. In various embodiments, the ligand-binding protein has an affinity (KD) for galactose in the range of about 0.8 mM to about 100 mM or about 0.2 mM to about 400 mM. The biosensor is capable of detecting glucose in, e.g. the hypoglycemic, euglycemic, hyperglycemic, or hyperglycemic-hyperosmotic range. Thus, unlike previous glucose sensors, the ratiometric reagentless glucose biosensors produce precise measurements over an extended glucose concentration range from hypoglycemic, euglycemic, hyperglycemic, as well as the hyperglycemic-hyperosmotic range in sample volumes of less than 10 In some embodiments, the ligand-binding protein comprises a mutation that alters (e.g., increases or decreases) the interaction of the mutant with bound glucose compared to a naturally occurring protein (e.g., a microbial GGBP), wherein the interaction is with a portion of the glucose selected from the group consisting of 1-hydroxyl, 2-hydroxyl, 3-hydroxyl, 4-hydoxyl, 6-hydroxyl, pyranose ring, or any combination thereof. In non-limiting examples, the ligand-binding protein comprises a mutation that alters (e.g., increases or decreases) the mutant's affinity and/or specificity for glucose and/or galactose compared to a the unmutated ligand-binding protein (e.g., a microbial GGBP). In certain embodiments, the ligand-binding protein comprises a mutation that alters the interaction between the protein and bound glucose and/or galactose, a mutation that alters the equilibrium between the open and closed states of the ligand-binding protein, a mutation that alters the interaction between the ligand-binding protein and a reporter group (such as a fluorescent conjugate, e.g., the interaction with a carbonyl group or a naphthalene ring of a prodan-derived fluorophore such as Acrylodan or Badan), and/or a mutation that impacts indirect interactions that alter the geometry of the ligand binding site. In various embodiments, the mutation does not reduce, or negligibly impacts, the thermostability of the ligand-binding protein. In some embodiments, the mutation alters the thermostability of the ligand-binding protein by less than about 1, 2, 3, 4, 5, or 10° C.

The present subject matter provides a GGBP that is or is a mutant of: an *Escherichia* sp. (e.g., *E. albertii, E. coli, E. fergusonii, E. hermannii*, or *E. vulneris*) GGBP; a *Thermoanaerobacter* sp. (e.g., *T. acetoethylicus, T. brockii, T. ethanolicus, T. italicus, T. kivui, T. mathranii, T. pseudethanolicus, T. siderophilus, T. sulfurigignens, T. sulfurophilus, T. thermocopriae, T. thermohydrosulfuricus, T. thermosaccharolyticum, T. uzonensis*, or *T. wiegelii*) GGBP; a *Clostridium* sp. (e.g., *C. absonum, C. aceticum, C. acetireducens, C. acetobutylicum, C. acidisoli, C. aciditolerans, C. acidurici, C. aerotolerans, C. aestuarii, C. akagii, C. aldenense, C. aldrichii, C. algidicarni, C. algidixylanolyticum, C. algifaecis, C. algoriphilum, C. alkalicellulosi, C. aminophilum, C. aminovalericum, C. amygdalinum, C. amylolyticum, C. arbusti, C. arcticum, C. argentinense, C. asparagiforme, C. aurantibutyricum, C. autoethanogenum, C. baratii, C. barkeri, C. bartlettii, C. beijerinckii, C. bifermentans, C. bolteae, C. bornimense, C. botulinum, C. bowmanii, C. bryantii, C. butyricum, C. cadaveris, C. caenicola, C. caminithermale, C. carboxidivorans, C. carnis, C. cavendishii, C. celatum, C. celerecrescens, C. cellobioparum, C. cellulofermentans, C. cellulolyticum, C. cellulosi, C. cellulovorans, C. chartatabidum, C. chauvoei, C. chromiireducens, C. citroniae, C. clariflavum, C. clostridioforme, C. coccoides, C. cochlearium, C. colletant, C. colicanis, C. colinum, C. collagenovorans, C. cylindrosporum, C. difficile, C. diolis, C. disporicum, C. drakei, C. durum, C. estertheticum, C. estertheticum estertheticum, C. estertheticum laramiense, C. fallax, C. felsineum, C. fervidum, C. fimetarium, C. formicaceticum, C. frigidicarnis, C. frigoris, C. ganghwense, C. gasigenes, C. ghonii, C. glycolicum, C. glycyrrhizinilyticum, C. grantii, C. haemolyticum, C. halophilum, C. hastiforme, C. hathewayi, C. herbivorans, C. hiranonis, C. histolyticum, C. homopropionicum, C. huakuii, C. hungatei, C. hydrogeniformans, C. hydroxybenzoicum, C. hylemonae, C. jejuense, C. indolis, C. innocuum, C. intestinale, C. irregulare, C. isatidis, C. josui, C. kluyveri, C. lactatifermentans, C. lacusfryxellense, C. laramiense, C. lavalense, C. lentocellum, C. lentoputrescens, C. leptum, C. limosum, C. litorale, C. lituseburense, C. ljungdahlii, C. lortetii, C. lundense, C. magnum, C. malenominatum, C. mangenotii, C. mayombei, C. methoxybenzovorans, C. methylpentosum, C. neopropionicum, C. nexile, C. nitrophenolicum, C. novyi, C. oceanicum, C. orbiscindens, C. oroticum, C. oxalicum, C. papyrosolvens, C. paradoxum, C. paraperfringens, C. paraputrificum, C. pascui, C. pasteurianum, C. peptidivorans, C. perenne, C. perfringens, C. pfennigii, C. phytofermentans, C. piliforme, C. polysaccharolyticum, C. populeti, C. propionicum, C. proteoclasticum, C. proteolyticum, C. psychrophilum, C. puniceum, C. purinilyticum, C. putrefaciens, C. putrificum, C. quercicolum, C. quinii, C. ramosum, C. rectum, C. roseum, C. saccharobutylicum, C. saccharogumia, C. saccharolyticum, C. saccharoperbutylacetonicum, C. sardiniense, C. sartagoforme, C. scatologenes, C. schirmacherense, C. scindens, C. septicum, C. sordellii, C. sphenoides, C. spiroforme, C. sporogenes, C. sporosphaeroides, C. stercorarium, C. stercorarium leptospartum, C. stercorarium stercorarium, C. stercorarium thermolacticum, C. sticklandii, C. straminisolvens, C. subterminale, C. sufflavum, C. sulfidigenes, C. symbiosum, C. tagluense, C. tepidiprofundi, C. termitidis, C. tertium, C. tetani, Clostridium tetanomorphum, C. thermaceticum, C. thermautotrophicum, C. thermoalcaliphilum, C. thermobutyricum, C. thermocellum, C. thermocopriae, C. thermohydrosulfuricum, C. thermolacticum, C. thermopalmarium, C. thermopapyrolyticum, C. thermosaccharolyticum, C. thermosuccinogenes, C. thermosulfurigenes, C. thiosulfatireducens, C. tyrobutyricum, C. uliginosum, C. ultunense, C. villosum, C. vincentii, C. viride, C. xylanolyticum*, or *C. xylanovorans*) GGBP; a *Salmonella* sp. [e.g., *S. bongori, S. enterica, S. enterica* subspecies *enterica, S. enterica* subspecies *salamae, S. enterica* subspecies *arizonae, S. enterica* subspecies *diarizonae, S. enterica* subspecies *houtenae, S. enterica* subspecies *indica*, or *S. enterica* subspecies *enterica* serovar *Typhimurium* (*S. typhimurium*)] GGBP; a *Caldicellulosiruptor* sp. (e.g., *C. saccharolyticus, C. acetigenus, C. bescii, C. changbaiensis, C. hydrothermalis, Caldicellulosiruptor hydrother, C. kristjanssonii, C. kronotskyensis, C. lactoaceticus, C. owensensis*, or *C. obsidiansis*) GGBP; a *Paenibacillus* sp. (e.g., *P. agarexedens, P. agaridevorans, P. alginolyticus, P. alkaliterrae, P. alvei, P. amylolyticus, P. anaericanus, P. antarcticus, P. assamensis, P. azoreducens, P. azotofixans, P. barcinonensis, P. borealis, P. brasilensis, P. brassicae, P. campinasensis, P. chinjuensis, P. chitinolyticus, P. chondroitinus, P. cineris, P. cookii, P. curdlanolyticus, P. daejeonensis, P. dendritiformis, P. durum, P. ehimensis, P. elgii, P. favisporus, P. glucanolyticus, P. glycanilyticus, P. gordonae, P. graminis, P. granivorans, P. hodogayensis, P. illinoisensis, P. jamilae, P. kobensis, P. koleovorans, P. koreensis, P. kribbensis, P. lactis, P. larvae, P. lautus, P. lentimorbus, P. macerans, P. macquariensis, P. massiliensis, P. mendelii, P. motobuensis, P. naphthalenovorans, P. nematophilus, P. odorifer, P. pabuli, P.*

*peoriae, P. phoenicis, P. phyllosphaerae, P. polymyxa, P. popilliae, P. pulvifaciens, P. rhizosphaerae, P. sanguinis, P. stellifer, P. terrae, P. thiaminolyticus, P. timonensis, P. tylopili, P. turicensis, P. validus, P. vortex, P. vulneris, P. wynnii, P. xylanilyticus*) GGBP; a *Butyrivibrio* sp. (e.g., *B. proteoclasticus, B. crossotus, B. fibrisolvens*, or *B. hungatei*) GGBP; a *Roseburia* sp. (e.g., *R. intestinalis, R. faecis, R. hominis*, or *R. inulinivorans*) GGBP; a *Faecalibacterium* sp. (e.g., *F. prausnitzii*) GGBP; an *Erysipelothrix* sp. (e.g., *E. rhusiopathiae, E. inopinata*, or *E. tonsillarum*) GGBP; or an *Eubacterium* sp. (e.g., *E. rectale, E. acidaminophilum, E. nodatum, E. oxidoreducens*, or *E. foedans*) GGBP.

In various embodiments, a biosensor comprises a GGBP that is or is a mutant of: an *Escherichia coli* GGBP (ecGGBP; SEQ ID NO: 1), a *Thermoanaerobacter thermosaccharolyticum* GGBP (ttGGBP; SEQ ID NO: 2), a *Salmonella typhimurium* GGBP (stGGBP; SEQ ID NO: 3), a *Caldicellulosiruptor hydrothermalis* GGBP (chyGGBP; SEQ ID NO: 4), a *Caldicellulosiruptor obsidiansis* GGBP (cobGGBP; SEQ ID NO: 5), a *Paenibacillus* sp. GGBP (pspGGBP; SEQ ID NO: 6); a *Clostridium saccharolyticum* GGBP (csaGGBP; SEQ ID NO: 7); a *Clostridium autoethanogenum* GGBP (cauGGBP; SEQ ID NO: 12); a *Clostridium ljungdahlii* GGBP (cljGGBP; SEQ ID NO: 11); a *Butyrivibrio proteoclasticus* GGBP (bprGGBP; SEQ ID NO: 8); a *Roseburia intestinalis* GGBP (rinGGBP_A; SEQ ID NO: 9 or rinGGBP_B; SEQ ID NO: 13); a *Faecalibacterium prausnitzii* GGBP (fprGGBP; SEQ ID NO: 10); a *Erysipelothrix rhusiopathiae* GGBP (erhGGBP; SEQ ID NO: 14); or a *Eubacterium rectale* GGBP (ereGGBP; SEQ ID NO: 15). In some embodiments, the GGBP comprises an amino acid sequence that is between 75% and 10% identical (e.g., between 25% and 50% identical) to the amino acid sequence of ecGGBP (SEQ ID NO: 1 or 17), ttGGBP (SEQ ID NO: 2 or 18), stGGBP (SEQ ID NO: 3 or 19), chyGGBP (SEQ ID NO: 4 or 20), pspGGBP (SEQ ID NO: 6 or 22); csaGGBP (SEQ ID NO: 7 or 23); bprGGBP (SEQ ID NO: 8 or 24); rinGGBP_A (SEQ ID NO: 9 or 25); rinGGBP_B (SEQ ID NO: 13 or 29); fprGGBP (SEQ ID NO: 10 or 26); cljGGBP (SEQ ID NO: 11 or 27); cauGGBP (SEQ ID NO: 12 or 28); erhGGBP (SEQ ID NO: 14 or 30); and/or ereGGBP (SEQ ID NO: 15 or 31).

Aspects of the present subject matter include a GGBP that is or is a mutant of a protein listed in Table 1, e.g., the protein numbered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138 in Table 1.

With regard to a defined polypeptide, % identity figures higher or lower than those provided herein will encompass various embodiments. Thus, where applicable, in light of a minimum % identity figure, a polypeptide may comprises an amino acid sequence which is at least 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the reference SEQ ID NO or to each of the reference SEQ ID NOs. Where applicable, in light of a maximum % identity to a reference sequence, a polypeptide may comprise an amino acid sequence which is less than 75%, 70%, 65%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, or 15% identical to the reference SEQ ID NO or to each of the reference SEQ ID NOs. In certain embodiments, a polypeptide comprises amino acids in a sequence that is preferably at least about 10%, 11%, 12%, 13%, 14%, 15%, 16%, 17%, 18%, 19%, 20%, 21%, 22%, 23%, 24%, 25%, 26%, 27%, 28%, 29%, or 30% and less than about 75%, 70%, 65%, 60%, 55%, 50%, 45%, 44%, 43%, 42%, 41%, 40%, 39%, 38%, 37%, 36%, 35%, 34%, 33%, 32%, 31%, or 30% identical to the reference SEQ ID NO or to each of the reference SEQ ID NOs. Non-limiting examples of reference proteins and amino acid sequences disclosed herein include:

(i) a glucose-galactose binding protein from *Escherichia coli* (ecGGBP; genome, NC_002695; protein, WP_032329053, SEQ ID NO: 1);

(ii) a glucose-galactose binding protein from *Thermoanaerobacterium thermosaccharolyticum* (ttGGBP; genome, NC_014410; protein, YP_003852930.1, SEQ ID NO: 2);

(iii) a glucose-galactose binding protein from *Salmonella typhimurium* (stGGBP; genome, NC_003197; protein, WP_001036943, SEQ ID NO: 3);

(iv) a glucose-galactose binding protein from *Caldicellulosiruptor hydrothermalis* (chyGGBP; genome, NC_014652; protein identifier, YP_003991244.1, SEQ ID NO: 4);

(v) a glucose-galactose binding protein from *Caldicellulosiruptor* obsidiansis (cobGGBP; genome, NC_014392; protein, YP_003839461.1, SEQ ID NO: 5);

(vi) a glucose-galactose binding protein from *Paenibacillus* sp. (pspGGBP; genome, NC_013406; protein, YP_003243743.1, SEQ ID NO: 6);

(vii) a glucose-galactose binding protein from *Clostridium saccharolyticum* (csaGGBP; genome, NC_014376; protein, YP_003822565.1, SEQ ID NO: 7);

(viii) a glucose-galactose binding protein from *Butyrivibrio proteoclasticus* (bprGGBP; genome, NC_014387; protein, YP_003830205.1, SEQ ID NO: 8);

(ix) a glucose-galactose binding protein from *Roseburia intestinalis* (rinGGBP_A; genome, NC_021012; protein, YP_007778116.1, SEQ ID NO: 9);

(x) a glucose-galactose binding protein from *Faecalibacterium prausnitzii* (fprGGBP; genome, NC_021020; protein, YP_007799070.1, SEQ ID NO: 10);

(xi) a glucose-galactose binding protein from *Clostridium ljungdahlii* (cljGGBP; genome, NC_014328; protein, CLJU_c08950, SEQ ID NO: 11);

(xii) a glucose-galactose binding protein from *Clostridium autoethanogenum* (cauGGBP; genome, NC_022592; protein, CAETHG_2989, SEQ ID NO: 12);

(xiii) a glucose-galactose binding protein from *Roseburia intestinalis* (rinGGBP_B; genome, NC_021012; protein, YP_007778124.1, SEQ ID NO: 13);

(xiv) a glucose-galactose binding protein from *Erysipelothrix rhusiopathiae* (erhGGBP; genome, NC_015601; protein, YP_004561181.1, SEQ ID NO: 14); and (xv) a glucose-galactose binding protein from *Eubacterium rectale* (ereGGBP; genome, NC_012781; protein, YP_002936409.1, SEQ ID NO: 15).

The GGBPs disclosed herein may optionally be fused (e.g., at their N-terminal and/or C-terminal ends) to a motif comprising a stretch of amino acids that facilitates the isolation or other manipulation such as conjugation to a moiety or immobilization on a substrate such as a plastic, a cellulose product such as paper, polymer, metal, noble metal, semi-conductor, or quantum dot (e.g., a fluorescent quantum dot). A non-limiting example of such a stretch of amino acids has the sequence: GGSHHHHHH (SEQ ID NO: 104). This motif is not required for and is not believed to influence or affect ligand-binding activity or signal transduction. For example, each of SEQ ID NOs: 32-103 (and the non-limiting examples of other proteins used in the experiments disclosed herein) comprises this motif (SEQ ID NO: 104). Alternatively or in addition, a ligand-binding protein may be fused to a heterologous polypeptide or “added amino acids” that facilitates the attachment thereof to a surface, such as the surface of a device.

In some embodiments, a polypeptide comprises 1, 2, 3, 4, 5, or more substitutions or deletions of a cysteine compared to the naturally occurring counterpart of the polypeptide (i.e., 1, 2, 3, 4, 5, or more native cysteines have been removed), e.g., 1, 2, 3, 4, 5, or more cysteine to alanine substitutions compared to the naturally occurring counterpart of the polypeptide. In some embodiments, all of cysteines of a polypeptide have been deleted and/or substituted compared to its natural counterpart.

In embodiments, the amino acid sequence of a protein comprises no more than 1, 2, 3, 4, 5, 6, 7, 8, 9, 10, 15, 20, or 25 mutations compared to its naturally occurring counterpart. In some embodiments, less than 25, 20, 15, 10, 9, 8, 7, 6, 5, 4, 3, or 2 of the mutations is a deletion or insertion of 1, 2, 3, 4, or 5 or no more than 1, 2, 3, 4, or 5 amino acids. In some embodiments, 1, 2, 3, 4, 5, 6, 7, 8, 9, 10, 15, 20, 25, or more of the mutations is a substitution mutation. In certain embodiments, every mutation to a protein compared to its naturally occurring counterpart is a substitution mutation. In various embodiments, 1, 2, 3, 4, 5, 6, 7, 8, 9, 10, 15, 20, 25 or more or all of the mutations to a protein compared to its naturally occurring counterpart is a conservative substitution mutation.

In various embodiments, a polypeptide does not have any insertion or deletion compared to its natural counterpart, other than (optionally) the removal of the signal peptide and/or the fusion of compounds such as another polypeptide at the N-terminus or C-terminus thereof.

Ligand-Binding Proteins Comprising a Primary Complementary Surface (PCS)

The following BLAST parameters are used to identify sequence homologues of GGBP: (1) Expect threshold is 10.0; (2) Gap cost is Existence: 11 and Extension: 1; (3) The Matrix employed is BLOSUM62; (4) The filter for low complexity regions is “on.” Such an alignment may be generated using the ProteinHunter program. The ProteinHunter package always executes BLAST searches, with the following command “blastall-p blastp-m 8-b 50000-d % s-i<INPUT FILE>-o<OUTPUT FILE>”

where <INPUT FILE> and <OUTPUT FILE> specify the input and output files, respectively for a given calculation. This command executes the BLAST alignment program for protein sequences with default parameters, intrinsically set by the program. The BLAST program version is 2.2.24.

Sequence homologues of GGBP identified using BLAST may be aligned with ecGGBP using ClustalW to identify homologues that share a PCS with ecGGBP as discussed below.

Aspects of the present subject matter provide ligand-binding proteins that share a PCS with a GGBP disclosed herein. In embodiments, the PCS comprises at least about 5, 6, 7, 8, 9, or 10 amino acid positions used to identify a glucose-galactose binding protein. For example, the PCS of ecGGBP may comprise positions 14, 16, 91, 152, 154, 158, 183, 211, 236, and 256, wherein each position is counted as in SEQ ID NO: 17. In various embodiments, a protein shares a PCS with ecGGBP if the amino acid sequence of the protein has (i) D or N at the position that aligns with position 14 of ecGGBP;

(ii) F, Y, or W at the position that aligns with position 16 of ecGGBP;

(iii) N or D at the position that aligns with position 91 of ecGGBP;

(iv) H, N, or Q at the position that aligns with position 152 of ecGGBP;

(v) D or N at the position that aligns with position 154 of ecGGBP;

(vi) R at the position that aligns with position 158 of ecGGBP;

(vii) W, F, or Y at the position that aligns with position 183 of ecGGBP;

(viii) N or D at the position that aligns with position 211 of ecGGBP;

(ix) D or N at the position that aligns with position 236 of ecGGBP; and (x) N or D at the position that aligns with position 256 of ecGGBP, wherein the alignment between ecGGBP (SEQ ID NO: 17) and the protein is constructed using the ClustalW alignment program.

The ProteinHunter package always executes multiple sequence alignments with the following command “clustalw-infile=<INPUT FILE>-outfile=<OUTPUTFILE>-align-quiet”

This command executes the CLUSTALW multi-sequence alignment program for protein sequences. There are no user-specified parameter settings that alter the alignment behavior of the program. The CLUSTALW program version is 2.1.

For convenience and depending on context, a position that aligns with a stated position of ecGGBP may be referred to herein as “equivalent” to the stated position.

Exemplary Ligand-Binding Proteins

Various biosensors provided herein comprise glucose-galactose binding proteins, such as glucose-galactose binding proteins that have altered amino acid sequences compared to their naturally occurring counterparts. In embodiments, such proteins are conjugated to reporter groups. ecGGBP is a non-limiting reference protein respect to glucose-galactose binding proteins. An alignment of ecGGBP with other polypeptides is provided in FIG. 3.

In various embodiments, a polypeptide of the present disclosure comprises (a) an amino acid that is preferably (i) at least about 10%, 11%, 12%, 13%, 14%, 15%, 16%, 17%, 18%, 19%, 20%, 21%, 22%, 23%, 24%, 25%, 26%, 27%, 28%, 29%, or 30%, and (ii) less than about 75%, 70%, 65%, 60%, 55%, 50%, 45%, 44%, 43%, 42%, 41%, 40%, 39%, 38%, 37%, 36%, or 35% identical to ecGGBP;

(b) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 183 of ecGGBP (e.g., a tryptophan to cysteine substitution);

(c) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 14 of ecGGBP;

(d) a stretch of amino acids in the sequence a. IYK$X_1$DD$X_2$FM (where $X_1$ is any amino acid, or where $X_1$ is Y, F, Q, or K; and where $X_2$ is any amino acid, or where $X_2$ is N or T) (SEQ ID NO: 182), b. YK$X_1$DD$X_2$FM (where $X_1$ is any amino acid, or where $X_1$ is Y, F, Q, or K; and where $X_2$ is any amino acid, or where $X_2$ is N or T) (SEQ ID NO: 183), c. YK$X_1$DD$X_2$F (where $X_1$ is any amino acid, or where $X_1$ is Y, F, Q, or K; and where $X_2$ is any amino acid, or where $X_2$ is N or T) (SEQ ID NO: 184), d. K$X_1$DD$X_2$F (where $X_1$ is any amino acid, or where $X_1$ is Y, F, Q, or K; and where $X_2$ is any amino acid, or where $X_2$ is N or T) (SEQ ID NO: 185), e. YKXDD (where X is any amino acid, or where X is Y, F, Q, or K) (SEQ ID NO: 186), f. KXDD (where X is any amino acid, or where X is Y, F, Q, or K) (SEQ ID NO: 187), g. DDXF (where X is any amino acid, or where X is N or T) (SEQ ID NO: 188), h. D$X_1$FM$X_2X_3$VR (where $X_1$ is any amino acid, or where $X_1$ is N or T; where $X_2$ is any amino acid, or where $X_2$ is S, T, G; and where $X_3$ is any amino acid, or where $X_3$ is V, G, E, or L) (SEQ ID NO: 189), i. D$X_1$FM$X_2X_3$V (where $X_1$ is any amino acid, or where $X_1$ is N or T; where $X_2$ is any amino acid, or where $X_2$ is S, T, G; and where $X_3$ is any amino acid, or where $X_3$ is V, G, E, or L) (SEQ ID NO: 190), j. DXFM (where X is any amino acid, or where X is N or T) (SEQ ID NO: 191), k. IYK$X_1$DN$X_2$FM (where $X_1$ is any amino acid, or where $X_1$ is Y, F, Q, or K; and where $X_2$ is any amino acid, or where $X_2$ is N or T) (SEQ ID NO: 192), l. YK$X_1$DN$X_2$FM (where $X_1$ is any amino acid, or where $X_1$ is Y, F, Q, or K; and where $X_2$ is any amino acid, or where $X_2$ is N or T) (SEQ ID NO: 193), m. YK$X_1$DN$X_2$F (where $X_1$ is any amino acid, or where $X_1$ is Y, F, Q, or K; and where $X_2$ is any amino acid, or where $X_2$ is N or T) (SEQ ID NO: 194), n. K$X_1$DN$X_2$F (where $X_1$ is any amino acid, or where $X_1$ is Y, F, Q, or K; and where $X_2$ is any amino acid, or where $X_2$ is N or T) (SEQ ID NO: 195), o. YKXDN (where X is any amino acid, or where X is Y, F, Q, or K) (SEQ ID NO: 196), p. KXDN (where X is any amino acid, or where X is Y, F, Q, or K) (SEQ ID NO: 197), q. DNXF (where X is any amino acid, or where X is N or T) (SEQ ID NO: 198), r. N$X_1$FM$X_2X_3$VR (where $X_1$ is any amino acid, or where $X_1$ is N or T; where $X_2$ is any amino acid, or where $X_2$ is S, T, G; and where $X_3$ is any amino acid, or where $X_3$ is V, G, E, or L) (SEQ ID NO: 199), s. N$X_1$FM$X_2X_3$V (where $X_1$ is any amino acid, or where $X_1$ is N or T; where $X_2$ is any amino acid, or where $X_2$ is S, T, G; and where $X_3$ is any amino acid, or where $X_3$ is V, G, E, or L) (SEQ ID NO: 200), t. NXFM (where X is any amino acid, or where X is N or T) (SEQ ID NO: 201);

(e) a stretch of amino acids in the sequence a. IYK$X_1$DD$X_2$FM (where $X_1$ is any amino acid, or where $X_1$ is Y, F, Q, or K; and where $X_2$ is any amino acid, or where $X_2$ is N or T) (SEQ ID NO: 182), b. YK$X_1$DD$X_2$FM (where $X_1$ is any amino acid, or where $X_1$ is Y, F, Q, or K; and where $X_2$ is any amino acid, or where $X_2$ is N or T) (SEQ ID NO: 183), c. YK$X_1$DD$X_2$F (where $X_1$ is any amino acid, or where $X_1$ is Y, F, Q, or K; and where $X_2$ is any amino acid, or where $X_2$ is N or T) (SEQ ID NO: 184), d. K$X_1$DD$X_2$F (where $X_1$ is any amino acid, or where $X_1$ is Y, F, Q, or K; and where $X_2$ is any amino acid, or where $X_2$ is N or T) (SEQ ID NO: 185), e. YKXDD (where X is any amino acid, or where X is Y, F, Q, or K) (SEQ ID NO: 186), f. KXDD (where X is any amino acid, or where X is Y, F, Q, or K) (SEQ ID NO: 187), g. DDXF (where X is any amino acid, or where X is N or T) (SEQ ID NO: 188), h. D$X_1$FM$X_2X_3$VR (where $X_1$ is any amino acid, or where $X_1$ is N or T; where $X_2$ is any amino acid, or where $X_2$ is S, T, G; and where $X_3$ is any amino acid, or where $X_3$ is V, G, E, or L) (SEQ ID NO: 189), i. D$X_1$FM$X_2X_3$V (where $X_1$ is any amino acid, or where $X_1$ is N or T; where $X_2$ is any amino acid, or where $X_2$ is S, T, G; and where $X_3$ is any amino acid, or where $X_3$ is V, G, E, or L) (SEQ ID NO: 190), j. DXFM (where X is any amino acid, or where X is N or T) (SEQ ID NO: 191), k. IYK$X_1$DN$X_2$FM (where $X_1$ is any amino acid, or where $X_1$ is Y, F, Q, or K; and where $X_2$ is any amino acid, or where $X_2$ is N or T) (SEQ ID NO: 192), l. YK$X_1$DN$X_2$FM (where $X_1$ is any amino acid, or where $X_1$ is Y, F, Q, or K; and where $X_2$ is any amino acid, or where $X_2$ is N or T) (SEQ ID NO: 193), m. YK$X_1$DN$X_2$F (where $X_1$ is any amino acid, or where $X_1$ is Y, F, Q, or K; and where $X_2$ is any amino acid, or where $X_2$ is N or T) (SEQ ID NO: 194), n. K$X_1$DN$X_2$F (where $X_1$ is any amino acid, or where $X_1$ is Y, F, Q, or K; and where $X_2$ is any amino acid, or where $X_2$ is N or T) (SEQ ID NO: 195), o. YKXDN (where X is any amino acid, or where X is Y, F, Q, or K) (SEQ ID NO: 196), p. KXDN (where X is any amino acid, or where X is Y, F, Q, or K) (SEQ ID NO: 197), q. DNXF (where X is any amino acid, or where X is N or T) (SEQ ID NO: 198), r. N$X_1$FM$X_2X_3$VR (where $X_1$ is any amino acid, or where $X_1$ is N or T; where $X_2$ is any amino acid, or where $X_2$ is S, T, G; and where $X_3$ is any amino acid, or where $X_3$ is V, G, E, or L) (SEQ ID NO: 199), s. N$X_1$FM$X_2X_3$V (where $X_1$ is any amino acid, or where $X_1$ is N or T; where $X_2$ is any amino acid, or where $X_2$ is S, T, G; and where $X_3$ is any amino acid, or where $X_3$ is V, G, E, or L) (SEQ ID NO: 200), or t. NXFM (where X is any amino acid, or where X is N or T) (SEQ ID NO: 201), within about 50, 45, 40, 35, 20, or 15 amino acids of the N-terminus of the polypeptide, including or not including the amino acids of the signal peptide (also referred to herein as the leader peptide) of its natural counterpart;

(f) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 91 of ecGGBP (g) a stretch of amino acids having the sequence a. PVVFFNKEP (SEQ ID NO: 202), b. PVVFXNKEP (where X is any amino acid, or where X is F, L, V, or I) (SEQ ID NO: 203), c. PVVFFNXEP (where X is any amino acid, or where X is K, R, E, or G) (SEQ ID NO: 204),
d. PVVF$X_1$N$X_2$EP (where $X_1$ is any amino acid, or where $X_1$ is F, L, V, or I; and where $X_2$ is any amino acid, or where $X_2$ is K, R, E, or G) (SEQ ID NO: 205),
e. VVF$X_1$N$X_2$EP (where $X_1$ is any amino acid, or where $X_1$ is F, L, V, or I; and where $X_2$ is any amino acid, or where $X_2$ is K, R, E, or G) (SEQ ID NO: 206),
f. VF$X_1$N$X_2$EP (where $X_1$ is any amino acid, or where $X_1$ is F, L, V, or I; and where $X_2$ is any amino acid, or where $X_2$ is K, R, E, or G) (SEQ ID NO: 207),
g. PVVF$X_1$N$X_2$E (where $X_1$ is any amino acid, or where $X_1$ is F, L, V, or I; and where $X_2$ is any amino acid, or where $X_2$ is K, R, E, or G) (SEQ ID NO: 208),
h. PVVFXN (where X is any amino acid, or where X is F, L, V, or I) (SEQ ID NO: 209),
i. P$X_1$VF$X_2$N (where $X_1$ is any amino acid, or where $X_1$ is V, I, L, or T; and where $X_2$ is any amino acid, or where $X_2$ is F, L, V, or I) (SEQ ID NO: 210),
j. PV$X_1$F$X_2$N (where $X_1$ is any amino acid, or where $X_1$ is V, I, L, or T; and where $X_2$ is any amino acid, or where $X_2$ is F, L, V, or I) (SEQ ID NO: 211),
k. F$X_1$N$X_2$EP (where $X_1$ is any amino acid, or where $X_1$ is F, L, V, or I; and where $X_2$ is any amino acid, or where $X_2$ is K, R, E, or G) (SEQ ID NO: 212), or
l. F$X_1$N$X_2$E (where $X_1$ is any amino acid, or where $X_1$ is F, L, V, or I; and where $X_2$ is any amino acid, or where $X_2$ is K, R, E, or G) (SEQ ID NO: 213);

(h) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 150, 155, or 160 of ecGGBP;

(i) a stretch of amino acids having the sequence
a. PGHPDAEART (SEQ ID NO: 214),
b. PGH$X_1$DA$X_2$$X_3$RT (where $X_1$ is any amino acid, or where $X_1$ is P, Q, V, I, or E; where $X_2$ is any amino acid, or where $X_2$ is E, I, K, or Q; and where $X_3$ is any amino acid, or where $X_3$ is A, L, V, K, Q, or Y) (SEQ ID NO: 215),
c. GH$X_1$DA$X_2$$X_3$RT (where $X_1$ is any amino acid, or where $X_1$ is P, Q, V, I, or E; where $X_2$ is any amino acid, or where $X_2$ is E, I, K, or Q; and where $X_3$ is any amino acid, or where $X_3$ is A, L, V, K, Q, or Y) (SEQ ID NO: 216),
d. H$X_1$DA$X_2$$X_3$RT (where $X_1$ is any amino acid, or where $X_1$ is P, Q, V, I, or E; where $X_2$ is any amino acid, or where $X_2$ is E, I, K, or Q; and where $X_3$ is any amino acid, or where $X_3$ is A, L, V, K, Q, or Y) (SEQ ID NO: 217),
e. DA$X_1$$X_2$RT (where $X_1$ is any amino acid, or where $X_1$ is E, I, K, or Q; and where $X_2$ is any amino acid, or where $X_2$ is A, L, V, K, Q, or Y) (SEQ ID NO: 218),
f. PGH$X_1$DA$X_2$$X_3$R (where $X_1$ is any amino acid, or where $X_1$ is P, Q, V, I, or E; where $X_2$ is any amino acid, or where $X_2$ is E, I, K, or Q; and where $X_3$ is any amino acid, or where $X_3$ is A, L, V, K, Q, or Y) (SEQ ID NO: 219),
g. PGHXDA (where X is any amino acid, or where X is P, Q, V, I, or E) (SEQ ID NO: 220),
h. PGHXD (where X is any amino acid, or where X is P, Q, V, I, or E) (SEQ ID NO: 221),
i. PGNPDAEART (SEQ ID NO: 222),
j. PGN$X_1$DA$X_2$$X_3$RT (where $X_1$ is any amino acid, or where $X_1$ is P, Q, V, I, or E; where $X_2$ is any amino acid, or where $X_2$ is E, I, K, or Q; and where $X_3$ is any amino acid, or where $X_3$ is A, L, V, K, Q, or Y) (SEQ ID NO: 223),
k. GN$X_1$DA$X_2$$X_3$RT (where $X_1$ is any amino acid, or where $X_1$ is P, Q, V, I, or E; where $X_2$ is any amino acid, or where $X_2$ is E, I, K, or Q; and where $X_3$ is any amino acid, or where $X_3$ is A, L, V, K, Q, or Y) (SEQ ID NO: 224),
l. N$X_1$DA$X_2$$X_3$RT (where $X_1$ is any amino acid, or where $X_1$ is P, Q, V, I, or E; where $X_2$ is any amino acid, or where $X_2$ is E, I, K, or Q; and where $X_3$ is any amino acid, or where $X_3$ is A, L, V, K, Q, or Y) (SEQ ID NO: 225),
m. PGN$X_1$DA$X_2$$X_3$R (where $X_1$ is any amino acid, or where $X_1$ is P, Q, V, I, or E; where $X_2$ is any amino acid, or where $X_2$ is E, I, K, or Q; and where $X_3$ is any amino acid, or where $X_3$ is A, L, V, K, Q, or Y) (SEQ ID NO: 226),
n. PGNXDA (where X is any amino acid, or where X is P, Q, V, I, or E) (SEQ ID NO: 227), or
o. PGNXD (where X is any amino acid, or where X is P, Q, V, I, or E) (SEQ ID NO: 228);

(j) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 183 of ecGGBP;

(k) a stretch of amino acids having the sequence
a. DTAMWD (SEQ ID NO: 229),
b. DTAMCD (SEQ ID NO: 230),
c. DTAMW (SEQ ID NO: 231),
d. DTAMC (SEQ ID NO: 232),
e. TAMWD (SEQ ID NO: 233),
f. TAMCD (SEQ ID NO: 234),
g. A$X_1$W$X_2$$X_3$ (where $X_1$ is any amino acid, or where $X_1$ is M or N; where $X_2$ is any amino acid, or where $X_2$ is D or N; and where $X_3$ is any amino acid, or where $X_3$ is T or R) (SEQ ID NO: 235), or
h. A$X_1$C$X_2$$X_3$ (where $X_1$ is any amino acid, or where $X_1$ is M or N; where $X_2$ is any amino acid, or where $X_2$ is D or N; and where $X_3$ is any amino acid, or where $X_3$ is T or R) (SEQ ID NO: 236);

(l) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 210 of ecGGBP;

(m) a stretch of amino acids having the sequence
a. IEVVIANND (SEQ ID NO: 237),
b. EVVIANND (SEQ ID NO: 238),
c. IEVVIANN (SEQ ID NO: 239),
d. EVVIANN (SEQ ID NO: 240),
e. IE$X_1$V$X_2$$X_3$NND (where $X_1$ is any amino acid, or where $X_1$ is V, A, L, or C; where $X_2$ is any amino acid, or where $X_2$ is I, F, or L; and where $X_3$ is any amino acid, or where $X_3$ is A or C) (SEQ ID NO: 241),
f. IE$X_1$V$X_2$$X_3$NN (where $X_1$ is any amino acid, or where $X_1$ is V, A, L, or C; where $X_2$ is any amino acid, or where $X_2$ is I, F, or L; and where $X_3$ is any amino acid, or where $X_3$ is A or C) (SEQ ID NO: 242),
g. E$X_1$V$X_2$$X_3$NND (where $X_1$ is any amino acid, or where $X_1$ is V, A, L, or C; where $X_2$ is any amino acid, or where $X_2$ is I, F, or L; and where $X_3$ is any amino acid, or where $X_3$ is A or C) (SEQ ID NO: 243), or h. $EX_1VX_2X_3NN$ (where $X_1$ is any amino acid, or where $X_1$ is V, A, L, or C; where $X_2$ is any amino acid, or where $X_2$ is I, F, or L; and where $X_3$ is any amino acid, or where $X_3$ is A or C) (SEQ ID NO: 244);

(n) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 235 or 240 of ecGGBP;

(o) a stretch of amino acids having the sequence
   a. PVFGVDA (SEQ ID NO: 245),
   b. VFGVDA (SEQ ID NO: 246),
   c. PVFGVD (SEQ ID NO: 247),
   d. FGVDA (SEQ ID NO: 248),
   e. PVXGVDA (where X is any amino acid or where X is F, V, or I) (SEQ ID NO: 249),
   f. VXGVDA (where X is any amino acid or where X is F, V, or I) (SEQ ID NO: 250),
   g. PVXGVD (where X is any amino acid or where X is F, V, or I) (SEQ ID NO: 251), or
   h. VXGVD (where X is any amino acid or where X is F, V, or I) (SEQ ID NO: 252);

(p) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 255 or 260 of ecGGBP (q) a stretch of amino acids having the sequence GTVLNDA (SEQ ID NO: 253), GTVLND (SEQ ID NO: 254), GTVLN (SEQ ID NO: 255), or TVLND (SEQ ID NO: 256);

(r) no more than 1, 2, 3, 4, 5, 6, 7, 8, 9, 10, or 15 deleted or inserted amino acids compared to ecGGBP, not including added amino acids added to the N-terminus or C-terminus of the polypeptide compared to its natural counterpart, and including or not including the signal peptide of the natural counterpart of the polypeptide;

(s) at least 8, 9, 10, or 11, or exactly 8, 9, 10, or 11 α-helices; and/or (t) at least 9, 10, 11, or 12 β-sheets or exactly 9, 10, 11, or 12 β-sheets.

In embodiments, two or more or each of features (c)-(q) above occurs in the polypeptide in the order listed above as the amino acid sequence of the polypeptide is viewed or read from the N-terminus to the C-terminus (with additional features and/or amino acid sequences therebetween). For example, the polypeptide may have an N-terminus, followed by feature (c), (d), or (e), followed by feature (f) or (g), followed by feature (h) or (i), followed by feature (j) or (k), followed by feature (l) or (m), followed by feature (n) or (o), followed by feature (p) or (q), followed by the C-terminus.

As used herein when referring to the order of features in an amino acid read from the N terminus to the C-terminus, a first feature is "followed by" a second feature when the second feature occurs after the first feature in the amino acid sequence. The words "followed by" do not require that the second feature immediately follow or be close to the first feature. For example, the N-terminus is followed by the C-terminus.

The features listed above are not limiting and may be combined with any other relevant features disclosed herein, including those listed below.

In some embodiments the polypeptide has the following sequence:

```
ZZZZ!GVXIY K%DDXFMXXV RXAXXXXXXX XXXX#XXZZD
XQNXQXXQN# X!DXXXXKXX XX$XINXVDX XAAGXXI#KA
XXXNXPVVFX NXEPXXXX$X XXDKXYYVGX XXX#SGXXXG
#XXXXXWXXX XXXDXNX#GX x#%V$xxG#P GHXDAxxRTX
%X!XXXXXXG IXXXXLXXDX AXWDXXXXXX KMXXXLXXZX
X#XIEXVXXN NDXMA$GA!E ALKXZZZZXX XXXXPVXGVD
AXXXXXXXXX XGX$XGTVLN DAXXQXKAXX XXAXXLXXGZ
XXXX#XXXXX IZ#XKX!X!X YXX!XKDNXX #ZZZZZZZZ
```

wherein each
Z is, individually, any amino acid or is absent,
X is, individually, any amino acid,
! is, individually, I or V,
$ is, individually, L or M,
% is, individually, F or Y, and
# is, individually, N, D, Q, or E.

In a non-limiting example, the glucose-galactose binding polypeptide comprises an N-terminal domain and a C-terminal domain connected by a flexible hinge, with the ligand-binding site (the ligand binding domain) located in the cleft between the N-terminal and the C-terminal domain.

In some embodiments, the glucose-galactose binding polypeptide comprises, from the N-terminus to the C-terminus, a first β-sheet (β1), followed by a first α-helix (α1), followed by a second β-sheet (β2), followed by a second α-helix (α2), followed by a third β-sheet (β3), followed by a third α-helix (α3), followed by a fourth β-sheet (β4), followed by a fourth α-helix (α4), followed by a fifth β-sheet (β5), followed by a first inter-domain hinge segment (h1), followed by a fifth α-helix (α5), followed by a sixth β-sheet (β6), followed by a sixth α-helix (α6), followed by a seventh β-sheet (β7), followed by a seventh α-helix (α7), followed by an eighth β-sheet (β8), followed by an eighth α-helix (α8), followed by a ninth β-sheet (β9), followed by a ninth α-helix (α9), followed by a tenth β-sheet (β10), followed by a second inter-domain hinge segment (h2), followed by a tenth α-helix (α10), followed by a third inter-domain hinge segment (h3), followed by an eleventh β-sheet (β11). In some embodiments, the polypeptide comprises (i) 1, 2, or 3 amino acid substitutions between β1 and α1; (ii) 1, 2, or 3 amino acid substitutions between β2 and α2; (iii) 1, 2, or 3 amino acid substitutions between the β3 and α3; (iv) 1, 2, or 3 amino acid substitutions between the β4 and α4; (v) 1, 2, or 3 amino acid substitutions in β6; (vi) 1, 2, or 3 amino acid substitutions in α6; (vii) 1, 2, or 3 amino acid substitutions between the β7 and α7; (viii) 1, 2, or 3, amino acid substitutions in α8; and/or (ix) 1, 2, or 3 amino acid substitutions between the β9 and α9. In some embodiments, the substitutions are conservative substitutions. In various embodiments, the polypeptide comprises a cysteine substitution at β7, α7, or between β7 and α7.

The glucose-galactose binding polypeptide may further comprise 1, 2, or more $Ca^{2+}$ binding sites.

In various embodiments, the $C_\alpha$ root-mean-square deviation (RMSD) between the backbone of the glucose-galactose binding polypeptide and ecGGBP, ttGGBP, stGGBP, chyGGBP, cobGGBP, pspGGBP, csaGGBP, bprGGBP, rinGGBP_A, rinGGBP_B, fprGGBP, cljGGBP, cauGGBP, erhGGBP, ereGGBP, and/or chyGGBP is, e.g., between about 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. In some embodiments, the $C_\alpha$ RMSD between the N-terminal domain (i.e., the portion of the protein at the N-terminal side of the binding domain hinge) backbone of the glucose-galactose binding polypeptide and the corresponding domain of ecGGBP, ttGGBP, stGGBP, chyGGBP, cobGGBP, and/or pspGGBP is, e.g., between about 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. In certain embodiments, the $C_\alpha$ RMSD between the C-terminal domain (i.e., the portion of the protein at the C-terminal side of the binding domain hinge) backbone of the glucose-galactose binding polypeptide and the corresponding domain of ecGGBP, ttGGBP, stGGBP, chyGGBP, cobGGBP, pspGGBP, csaGGBP, bprGGBP, rinGGBP_A, rinGGBP_B, fprGGBP, cljGGBP, cauGGBP, erhGGBP, ereGGBP, and/or chyGGBP is, e.g., between about 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. Non-limiting considerations relating to the sequence and structural differences between homologous proteins are discussed in Chothia and Lesk (1986) *The EMBO Journal,* 5(4):823-826, the entire content of which is incorporated herein by reference.

Non-limiting examples of glucose-galactose binding polypeptides that are useful in biosensors provided herein include ecGGBP, ttGGBP, stGGBP, chyGGBP, cobGGBP, pspGGBP, csaGGBP, bprGGBP, rinGGBP_A, rinGGBP_B, fprGGBP, cljGGBP, cauGGBP, erhGGBP, ereGGBP, and chyGGBP. In embodiments, a biosensor comprises a modified ecGGBP, ttGGBP, stGGBP, chyGGBP, cobGGBP, pspGGBP, csaGGBP, bprGGBP, rinGGBP_A, rinGGBP_B, fprGGBP, cljGGBP, cauGGBP, erhGGBP, ereGGBP, or chyGGBP polypeptide having an amino acid substitution compared to its naturally occurring counterpart, such that the polypeptide has a cysteine at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 270, 271, 272, 273, 274, 275, 276, 277, 278, 279, 280, 281, 282, 283, 284, 285, 286, 287, 288, 289, 290, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, or 383 or any combination of 1, 2, 3, 4, or 5 thereof, wherein the position corresponds a SEQ ID NO disclosed herein for ecGGBP, ttGGBP, stGGBP, chyGGBP, cobGGBP, pspGGBP, csaGGBP, bprGGBP, rinGGBP_A, rinGGBP_B, fprGGBP, cljGGBP, cauGGBP, erhGGBP, ereGGBP, or chyGGBP. In embodiments, the cysteine is conjugated to a reporter group.

In embodiments, a biosensor comprises a modified ecGGBP. In non-limiting examples, the modified ecGGBP may comprise one or more, or any combination of the following substitutions compared to its naturally occurring counterpart: Y10X, D14X, N15X, F16X, P70X, N91X, K92X, S112X, S115X, E149X, H152X, P153X, D154X, A155X, R158X, M182X, W183X, N211X, D212X, D236X, L238X, D257X, P294X, and V296X, where X is any amino acid, an amino acid that results in a conservative substitution, or a cysteine, and where each position is counted in ecGGBP without including the signal peptide (SEQ ID NO: 17). In some embodiments, the modified ecGGBP comprises 1, 2, 3, 4, 5, 6, 7, 8, 9, 10, or 11 of the following substitutions: Y10A, Y10C, D14C, D14A, D14Q, D14N, D145, D14T, D14E, D14H, D14L, D14Y, D14F, F16L, F16A, F16C, N91C, N91A, K92A, K92C, E149C, E149K, E149Q, E149S, H152C, H152A, H152F, H152Q, H152N, D154C, D154A, D154N, A155C, A155S, A155H, A155L, A155F, A155Y, A155N, A155K, A155M, A155W, A155Q, R158C, R158A, R158K, M182C, M182W, W183C, N211C, N211F, N211W, N211K, N211Q, N211S, N211H, N211M, N211C, D212C, L238C, D236C, D236A, D236N, N256A, N256D, D257C, P294C, and V293C.

In various embodiments, a biosensor comprises a modified ttGGBP. In non-limiting examples, the modified ttGGBP may comprise one or more, or any combination of the following substitutions compared to its naturally occurring counterpart: Y11X, D15X, T16X, F17X, G20X, N42X, V67X, R69X, R91X, E92X, A111X, Q148X, H151X, Q152X, A154X, N181X, W182X, D183X, D211X, T237X, T240X, L257X, N258X, D259X, A260X, and K300X where X is any amino acid, an amino acid that results in a conservative substitution, or a cysteine, and where each position is counted in ttGGBP with the signal peptide replaced with a methionine (SEQ ID NO: 18). In some embodiments, the modified ttGGBP comprises 1, 2, 3, 4, 5, 6, 7, 8, 9, 10, or 11 of the following substitutions: Y11C, D15A, D15E, D15N, DISC, T165, T16N, T16C, F17C, G20A, G20C, N42C, V67C, R69P, R69C, R91K, E92C, A111C, Q148S, Q148K, Q148E, Q148C, H151Q, H151N, H151F, H151C, Q152P, Q152C, A154S, A154N, A154M, A154F, A154C, N181C, W182C, D183C, D211A, D211C, T237C, T240A, L257C, N258D, N258S, N258A, N258C, D259C, A260N, A260Q, A260R, A260K, A260W, A260F, A260Y, A260S, A260C, and K300C.

In embodiments, a biosensor comprises a modified stGGBP. In non-limiting examples, the modified stGGBP may comprise one or more, or any combination of the following substitutions compared to its naturally occurring counterpart: Y11X, Y13X, D15X, N16X, F17X, P71X, N92X, K93X, P113X, S116X, E150X, H153X, P154X, D155X, A156X, R159X, M183X, W184X, N211X, N212X, D213X, A214X, D237X, L239X, D258X, P295X, and V297X where X is any amino acid, an amino acid that results in a conservative substitution, or a cysteine, and where each position is counted in stGGBP with the signal peptide replaced with a methionine (SEQ ID NO: 19). In some embodiments, the modified stGGBP comprises 1, 2 or 3 of the following mutations: Y13C, F17C, and W184C.

In embodiments, a biosensor comprises a modified chyGGBP. In non-limiting examples, the modified chyGGBP may comprise one or more, or any combination of the following substitutions compared to its naturally occurring counterpart: F12X, D14X, T15X, F16X, R68X, N89X, R90X, A110X, S113X, E147X, H150X, Q151X, D152X, A153X, R156X, M180X, W181X, N207X, N208X, D209X, D210X, D237X, T239X, D258X, V296X, and Y298X where X is any amino acid, an amino acid that results in a conservative substitution, or a cysteine, and where each position is counted in chyGGBP with the signal peptide replaced with a methionine (SEQ ID NO: 20). In some embodiments, the modified chyGGBP comprises 1, 2, or 3 of the following mutations: F12C, F16C, C39A, W181C, and C206A.

In embodiments, a biosensor comprises a modified cobGGBP. In non-limiting examples, the modified cobGGBP may comprise one or more, or any combination of the following substitutions compared to its naturally occurring counterpart: F12X, D14X, T15X, F16X, C39X, R68X, N89X, R90X, A110X, S113X, E147X, H150X, Q151X, D152X, A153X, R156X, C173X, M180X, W181X, C206X, N207X, N208X, D209X, D210X, D237X, T239X, D258X, P297X, and Q299X where X is any amino acid, an amino acid that results in a conservative substitution, or a cysteine, and where each position is counted in cobGGBP with the signal peptide replaced with a methionine (SEQ ID NO: 21). In some embodiments, the modified cobGGBP comprises 1, 2, or 3 of the following mutations: F12C, F16C, C39A, C173A, W181C, and C206A.

In embodiments, a biosensor comprises a modified pspGGBP. In non-limiting examples, the modified pspGGBP may comprise one or more, or any combination of the following substitutions compared to its naturally occurring counterpart: F9X, D11X, T12X, F13X, R65X, N86X, R87X, A107X, S110X, E144X, H147X, Q148X, D149X, A150X, R153X, M177X, W178X, N204X, N205X, D206X, D207X, D234X, T236X, 255X, A294X, and K296X where X is any amino acid, an amino acid that results in a conservative substitution, or a cysteine, and where each position is counted in pspGGBP with the signal peptide replaced with a methionine (SEQ ID NO: 22). In some embodiments, the modified pspGGBP comprises 1, 2, or 3 of the following mutations: F9C, F13C, and W178C.

In embodiments, a biosensor comprises a modified csaGGBP. In non-limiting examples, the modified csaGGBP may comprise one or more, or any combination of the following substitutions compared to its naturally occurring counterpart: Y14X, D16X, F18X, C62X, I72X, C82X, N93X, R94X, C113A, S118X, A121X, E152X, N155X, E156X, D157X, S158X, R161X, N185X, W186X, C211X, D241X, L243X, D262X, D290X, I292X, I297X, F299X, Q301X, and T302X where X is any amino acid, an amino acid that results in a conservative substitution, or a cysteine, and where each position is counted in csaGGBP with the signal peptide replaced with a methionine (SEQ ID NO: 23). In some embodiments, the modified csaGGBP comprises 1, 2, 3, 4, 5, 6, 7, or 8 of the following mutations: Y14C, F18C, C62A, C82A, C113A, W186C, and C211A.

In embodiments, a biosensor comprises a modified bprGGBP. In non-limiting examples, the modified bprGGBP may comprise one or more, or any combination of the following substitutions compared to its naturally occurring counterpart: C8X, K12X, D14X, N15X, F16X, S72X, N93X, R94X, C112X, C116X, A118X, 5121X, A153X, N156X, I157X, D158X, A159X, C179X, N186X, W187X, C211X, N212X, N213X, D214X, A215X, D241X, D243X, K251X, C289X, D290X, and V292X where X is any amino acid, an amino acid that results in a conservative substitution, or a cysteine, and where each position is counted in bprGGBP with the signal peptide replaced with a methionine (SEQ ID NO: 24). In some embodiments, the modified bprGGBP comprises 1, 2, 3, 4, 5, 6, 7, 8, or 9 of the following mutations: C8A, K12C, F16C, C112A, C116A, C179A, W187C, C211A, and C289A.

In embodiments, a biosensor comprises a modified rinGGBP_A. In non-limiting examples, the modified rinGGBP_A may comprise one or more, or any combination of the following substitutions compared to its naturally occurring counterpart: C6X, F10X, D12X, N13X, F14X, 570X, N91X, R92X, C114X, A116X, Q118X, D151X, N154X, V155X, D156X, A157X, R160X, C177X, N184X, W185X, C210X, N211X, N212X, D213X, A214X, D240X, L242X, L250X, C288X, D289X, and V291X where X is any amino acid, an amino acid that results in a conservative substitution, or a cysteine, and where each position is counted in rinGGBP_A with the signal peptide replaced with a methionine (SEQ ID NO: 25). In some embodiments, the modified rinGGBP_A comprises 1, 2, 3, 4, 5, 6, 7, or 8 of the following mutations: C6A, F10C, F14C, C114A, C177A, W185C, C210A, and C288A.

In embodiments, a biosensor comprises a modified rinGGBP_B. In non-limiting examples, the modified rinGGBP_B may comprise one or more, or any combination of the following substitutions compared to its naturally occurring counterpart: Q13X, D15X, T16X, F17X, C66X, C70A, R76X, N97X, R98X, A118X, 5121X, E155X, H158X, Q159X, D160X, A161X, R164X, N188X, W189X, N215X, N216X, D217X, D218X, D244X, T246X, D265X, P301X, A303X, and C306X where X is any amino acid, an amino acid that results in a conservative substitution, or a cysteine, and where each position is counted in rinGGBP_B with the signal peptide replaced with a methionine (SEQ ID NO: 29). In some embodiments, the modified rinGGBP_B comprises 1, 2, 3, 4, 5, or 6 of the following mutations: Q13C, F17C, C66A, C70A, W189C, and C306A.

In embodiments, a biosensor comprises a modified fprGGBP. In non-limiting examples, the modified fprGGBP may comprise one or more, or any combination of the following substitutions compared to its naturally occurring counterpart: C8A, F12X, D14X, N15X, F16X, T69X, N90X, R91X, C105X, C106X, A113X, S116X, C143X, D146X, N149X, I150X, D151X, A152X, R155X, N179X, W180X, C205A, N206X, N207X, D208X, A209X, D235X, L237X, N243X, D284X, and V286X where X is any amino acid, an amino acid that results in a conservative substitution, or a cysteine, and where each position is counted in fprGGBP with the signal peptide replaced with a methionine (SEQ ID NO: 26). In some embodiments, the modified fprGGBP comprises 1, 2, 3, 4, 5, 6, or 7 of the following mutations: C8A, F12C, F16C, C105A, C106A, C143A, W180C, and C205A.

In embodiments, a biosensor comprises a modified cljGGBP. In non-limiting examples, the modified cljGGBP may comprise one or more, or any combination of the following substitutions compared to its naturally occurring counterpart: F11x, N13X, T14X, W15X, V67X, C77X, N88X, R89X, A109X, S112X, E142X, N145X, Q146X, D147X, A148X, R151X, M175X, W176X, C198X, N201X, N202X, D203X, D204X, D231X, T233X, D252X, D291X, and K294X where X is any amino acid, an amino acid that results in a conservative substitution, or a cysteine, and where each position is counted in cljGGBP with the signal peptide replaced with a methionine (SEQ ID NO: 27). In some embodiments, the modified cljGGBP comprises 1, 2, 3, 4, or 5 of the following mutations: F11C, W15C, C77A, W176C, and C198A.

In embodiments, a biosensor comprises a modified cauGGBP. In non-limiting examples, the modified cauGGBP may comprise one or more, or any combination of the following substitutions compared to its naturally occurring counterpart: F12X, N14X, T15X, W16X, V68X, C78X, N89X, R90X, A110X, S113X, E143X, N146X, Q147X, D148X, A149X, R152X, M176X, W177X, C199X, N203X, N204X, D205X, D206X, D233X, T235X, D254X, D293X, and K295X where X is any amino acid, an amino acid that results in a conservative substitution, or a cysteine, and where each position is counted in cauGGBP with the signal peptide replaced with a methionine (SEQ ID NO: 28). In some embodiments, the modified cauGGBP comprises 1, 2, 3, 4, or 5 of the following mutations: F12C, W16C, C78A, W177C, and C199A.

In embodiments, a biosensor comprises a modified erhGGBP. In non-limiting examples, the modified erhGGBP may comprise one or more, or any combination of the following substitutions compared to its naturally occurring counterpart: F13X, D15X, N16X, F17X, P76X, N97X, R98X, A119X, S122X, D153X, N156X, V157X, D158X, A159X, R162X, M187X, W188X, N214X, N215X, D216X, G217X, D243X, I245X, D264X, E312X, and V314X where X is any amino acid, an amino acid that results in a conservative substitution, or a cysteine, and where each position is counted in erhGGBP with the signal peptide replaced with a methionine (SEQ ID NO: 30). In some embodiments, the modified erhGGBP comprises 1, 2, or 3 of the following mutations: F13C, F17C, and W188C.

In embodiments, a biosensor comprises a modified ereGGBP. In non-limiting examples, the modified ereGGBP may comprise one or more, or any combination of the following substitutions compared to its naturally occurring counterpart: Q13X, D15X, T16X, F17X, C29X, C65X, C69X, R75X, N96X, R97, A117X, 5120X, E154X, H157X, Q158X, D159X, A160X, R163X, C183X, N187X, W188X, N214X, N215X, D216X, A217X, D243X, T245X, D264X, P301X, and E303X where X is any amino acid, an amino acid that results in a conservative substitution, or a cysteine, and where each position is counted in ereGGBP with the signal peptide replaced with a methionine (SEQ ID NO: 31). In some embodiments, the modified ereGGBP comprises 1, 2, 3, 4, 5, 6, 7, or 8 of the following mutations: C10A, Q13C, F17C, C29A, C65A, C69A, C183A, and W188C.

In various embodiments, the mutant glucose-galactose binding polypeptide's glucose and/or galactose disassociation constant differs by at least about 1 μM, 5 μM, 10 μM, 20 μM, 25 μM, 30 μM, 35 μM, 40 μM, 45 μM, 50 μM, 75 μM, 100 μM, 200 μM, 300 μM, 400 μM, 500 μM, 600 μM, 700 μM, 800 μM, 900 μM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, or 100 mM (increase or decrease) compared to its naturally occurring counterpart.

The biosensors and ligand-binding proteins provided herein are robust and useful at a wide range of physical conditions, e.g., pressure, temperature, salinity, osmolality, and pH conditions. For example, biosensors and ligand-binding proteins provided herein may survive substantial periods of time after being dried or exposed to high temperatures. In some embodiments, the biosensor maintains at least about 75%, 80%, 85%, 90%, 95%, 96%, 97%, 98%, 99%, 99.5%, 99.9%, or more of its signal transduction activity after exposure to a temperature of about 40, 45, 50, 55, 60, 65, 70, 75, 80, 85, 90, 95, 100, 105, 110, 115, 120, or 125, or 40-125° C. for about 1, 2, 3, 4, 5, 6, 15, 30, 60, 120, 180, 240, or 360 minutes. In certain embodiments, the biosensor maintains at least about 75%, 80%, 85%, 90%, 95%, 96%, 97%, 98%, 99%, 99.5%, 99.9%, or more of its signal transduction activity after 1, 2, 3, 4, or 5 freeze-thaw cycles in an aqueous solution. In various embodiments, the biosensor maintains at least about 75%, 80%, 85%, 90%, 95%, 96%, 97%, 98%, 99%, 99.5%, 99.9%, or more of its signal transduction activity after storage at a temperature of between 20-37° C. for about 1, 2, 3, 4, 5, 6, 7, 8, 9, 10, 11, 12, 18, 24, or 1-24 months in dry form. In some embodiments, the optimal functional temperature of the biosensor is between 41 and 122° C., between 20 and 40° C., or less than about 10° C. (e.g., between −20 and +10° C.). Devices, compositions, and biosensors provided herein may be stored, e.g., with or without protection from exposure to light. In some embodiments, the devices, compositions, and biosensors are stored in the dark, e.g., with protection from light.

Reporter Group Attachment

Aspects of the present subject matter provide a biosensor that comprises a one or more reporter groups attached to a ligand-binding protein, wherein binding of a ligand to a ligand-binding domain of the ligand-binding protein causes a change in signaling by the reporter group. In various embodiments, the reporter group is attached to an endosteric site, an allosteric site, or a peristeric site of the ligand-binding protein. In embodiments, the reporter group is covalently or noncovalently attached to the ligand-binding protein.

For convenience and depending on context, a reporter group may be referred to by a name of an unattached form of the reporter group regardless of whether the reporter group is attached to a ligand-binding protein. For example, a compound known as "Compound A" when in an unconjugated form may be referred to herein as "Compound A" when in a form that is attached to a ligand-binding protein. In a specific example, the term "Acrylodan" is used to refer to unreacted/unconjugated Acrylodan, as well as Acrylodan that is conjugated to a ligand-binding protein.

In certain embodiments, a biosensor comprises a reporter group that is conjugated to a ligand-binding protein, and the reporter group is conjugated to an amino acid of the protein that is at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 4, 6, 8, 10, 11, 12, 13, 14, 15, 16, 17, 18, 19, 20, 25, 30, 35, 40, 45, 50, 55, 60, 65, 70, 75, 80, 85, 90, 95, or 100 angstroms (Å) from the ligand when the ligand is bound to the protein. In some embodiments, the reporter group is conjugated to an amino acid of the protein that is within an α-helix or a β-sheet. In some embodiments, the reporter group is conjugated to an amino acid that (i) is not within an α-helix or a β-sheet, but is within about 10, 9, 8, 7, 6, 5, 4, 3, 2, or 1 amino acids of an amino acid of the protein's amino acid sequence that is within α-helix or β-sheet. In some embodiments, the reporter group is conjugated to an amino acid that is in an inter-domain hinge amino acid region between two domains of a protein. In some embodiments, the reporter group is conjugated to an amino acid that is in an inter-domain hinge amino acid region between (i) α-helix and a β-sheet; (ii) two α-helixes; or (iii) two β-sheets of a protein. In some embodiments, the reporter group is conjugated to an amino acid (e.g., a cysteine such as a cysteine added by substitution compared to a naturally corresponding polypeptide) between positions 1-25, 25-50, 50-75, 75-100, 100-125, 125-150, 150-175, 175-200, 200-225, 225-250, 250-275, 275-350, 275-300, 275-325, 300-325, 300-350, 300-383, or 350-383 (inclusive) of a polypeptide (e.g., not including N-terminal fusion proteins compared to the polypeptide's naturally occurring counterpart).

Direct signaling relationships between proteins and reporter groups are readily designed by replacing a residue known to form a ligand contact with a cysteine to which the fluorophore is attached ("endosteric" attachment site). Other, indirect signaling relationships can be established in two ways. The first relies on visual inspection of the ligand complex structure, and identifying residues that are located in the vicinity of the binding site, but do not interact directly with the ligand, and that are likely to be involved in conformational changes. Typically, such "peristeric" sites are located adjacent to the residues that form direct contacts with the bound ligand. In the case of the bPBPs, such residues are located at the perimeter of the inter-domain cleft that forms the ligand binding site. The environment of these peristeric sites changes significantly upon formation of the closed state. These are examples of positions which are proximal to the ligand-binding pocket/domain. The second, most general, approach identifies sites in the protein structure that are located anywhere in the protein, including locations at some distance away from the ligand-binding site (i.e., distal to the ligand-binding pocket/domain), and undergo a local conformational change in concert with ligand binding. If the structures of both the open and closed states are known, then such "allosteric" sites can be identified using a computational method that analyzes the conformational changes that accompany ligand binding (Marvin et al., Proc. Natl. Acad. Sci. USA 94:4366-4371, 1997). Alternatively, once allosteric sites have been identified in one bPBP, modeling and structural homology arguments can be invoked to identify such sites in other bPBPs in which only one state has been characterized (Marvin & Hellinga, J. Am. Chem. Soc. 120:7-11, 1998). This generalized conformational analysis also may identify peristeric and endosteric sites, which were identified and classified by visual inspection.

In non-limiting implementations, the reporter group is attached to said ligand-binding protein via a biotin-avidin interaction. The reporter group may be, e.g., conjugated to biotin and the ligand-binding protein is conjugated to avidin. In an example, the avidin is bound to four biotin molecules wherein each biotin molecule is individually conjugated to a reporter group. Alternatively, the reporter group is conjugated to avidin and the ligand-binding protein is conjugated to biotin. For example, the avidin is bound to four biotin molecules, wherein each biotin molecule is individually conjugated to a ligand-binding protein.

As used herein, "conjugated" means covalently attached. One compound may be directly conjugated to another compound, or indirectly conjugated, e.g., via a linker.

In some embodiments, the reporter group is directly attached to said ligand-binding protein. In various embodiments, the reporter group is attached to an amino acid of the ligand-binding protein that is at least about 2, 4, 6, 8, 10, 11, 12, 13, 14, 15, 16, 17, 18, 19, 20, 25, 30, 35, 40, 45, 50, 55, 60, 65, 70, 75, 80, 85, 90, 95, or 100 angstroms (Å) from the ligand when the ligand is bound to the ligand-binding protein. In certain embodiments, the reporter group is conjugated to an amino acid having a position within positions 1-25, 25-50, 50-75, 75-100, 100-125, 125-150, 150-175, 175-200, 200-225, 225-250, 250-275, or 275-300 of the ligand-binding protein, wherein position 1 is the N-terminal amino acid of the ligand-binding protein. In non-limiting examples, the reporter group is conjugated to an amino acid of the ligand-binding protein that is (a) within an α-helix or a β-sheet of the ligand-binding protein; (b) not within an α-helix; (c) not within a β-sheet; (d) within about 5 or 10 amino acids of an amino acid that is within an α-helix or β-sheet; (e) within a stretch of consecutive amino acids that links two domains of the ligand-binding protein; (f) within a stretch of consecutive amino acids that links an α-helix and a β-sheet; (g) within a stretch of consecutive amino acids that links two α-helices; or (h) within a stretch of consecutive amino acids that links two β-sheets. In some embodiments, the reporter group is directly attached to the N-terminus or the C-terminus of the ligand-binding protein.

The reporter group may be conjugated to the ligand-binding protein a variety of linkers or bonds, including (but not limited to) a disulfide bond, an ester bond, a thioester bond, an amide bond, or a bond that has been formed by a click reaction. In some embodiments, the click reaction is a reaction between (a) an azide and an alkyne; (b) an azide and an alkyne in the presence of Cu(I); (c) an azide and a strained cyclooctyne; (d) an azide and a dibenzylcyclooctyne, a difluorooctyne, or a biarylazacyclooctynone; (e) a diaryl-strained-cyclooctyne and a 1,3-nitrone; (f) an azide, a tetrazine, or a tetrazole and a strained alkene; (g) an azide, a tetrazine, or a tretrazole and a oxanorbornadiene, a cyclooctene, or a trans-cycloalkene; (h) a tetrazole and an alkene; or (i) a tetrazole with an amino or styryl group that is activated by ultraviolet light and an alkene. These exemplary click chemistry reactions have high specificity, efficient kinetics, and occur in vivo under physiological conditions. See, e.g., Baskin et al. Proc. Natl. Acad. Sci. USA 104(2007):16793; Oneto et al. Acta biomaterilia (2014); Neves et al. Bioconjugate chemistry 24(2013):934; Koo et al. Angewandte Chemie 51(2012):11836; Rossin et al. Angewandte Chemie 49(2010):3375, and U.S. Patent Application Publication No. 20160220686, published Aug. 4, 2016, the entire content of each of which is incorporated herein by reference. For a review of a wide variety of click chemistry reactions and their methodologies, see e.g., Nwe K and Brechbiel M W, 2009 Cancer Biotherapy and Radiopharmaceuticals, 24(3): 289-302; Kolb H C et al., 2001 Angew. Chem. Int. Ed. 40: 2004-2021. The entire contents of each of the foregoing references are incorporated herein by reference.

As used herein, the term "linker" refers to a molecule or sequence (such as an amino acid sequence), that attaches, as in a bridge, one molecule or sequence to another molecule or sequence. "Linked" means attached or bound by covalent bonds, or non-covalent bonds, or other bonds, such as van der Waals forces. In some embodiments, a linker comprises a chemical structure that has resulted from a reaction used to attach one molecule to another.

In various implementations of the present subject matter, the reporter group is conjugated to a cysteine of the ligand-binding protein. The cysteine may be present on a natural counterpart or version of the ligand-binding protein or added to the ligand-binding protein by a substitution mutation. In some embodiments, the cysteine is at the N-terminus or the C-terminus of said ligand-binding protein.

Non-limiting examples relate to the conjugation of a reporter group to a primary amine of the ligand-binding protein. In certain embodiments, the primary amine is present in a lysine of said ligand-binding protein. The lysine may be present on a natural counterpart or version of the ligand-binding protein or added to the ligand-binding protein by a substitution mutation. In various embodiments, the lysine is at the N-terminus or the C-terminus of the ligand-binding protein.

Aspects of the present subject matter provide a biosensor in which the reporter group is attached to the ligand-binding protein via a linker. In some embodiments, the linker comprises an organic compound that is less than about 30, 20, 15, or 10 Å long. Non-limiting examples of spacers include O, S, NH, PH, and alkyl spacers.

"Alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value. The term "alkyl" includes both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety. Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

In some embodiments, the linker comprises a bond formed by a chemical reaction involving a reactive group such as a maleimide group. Alternatively or in addition, the linker comprises a stretch of amino acids. In a non-limiting example, the linker comprises a polyglycine linker. In embodiments, the polyglycine linker comprises 2, 3, 4, 5, or more glycines. Optionally, the polyglycine linker further comprises a serine.

In various implementations, the reporter group is attached to a linker via a covalent bond and the linker is attached to a ligand-binding protein via a covalent bond. In embodiments, the covalent bond between the linker and the reporter group and/or the covalent bond between the linker and the ligand-binding protein is a disulfide bond, an ester bond, a thioester bond, an amide bond, a carbamate bond, or a bond that has been formed by a click reaction. Non-limiting examples of click reactions include reactions between an azide and an alkyne; an azide and an alkyne in the presence of Cu(I); an azide and a strained cyclooctyne; an azide and a dibenzylcyclooctyne, a difluorooctyne, or a biarylazacyclooctynone; a diaryl-strained-cyclooctyne and a 1,3-nitrone; an azide, a tetrazine, or a tetrazole and a strained alkene; an azide, a tetrazine, or a tretrazole and a oxanorbornadiene, a cyclooctene, or a trans-cycloalkene; a tetrazole and an alkene; or a tetrazole with an amino or styryl group that is activated by ultraviolet light and an alkene.

Reporter Groups

Various types of reporter groups may be used in embodiments of the present subject matter. For example, the reporter group may comprise a fluorophore that produces a fluorescent signal. Biosensors comprising a fluorophore may be referred to herein as fluorescently responsive sensors (FRSs).

Preferably, the binding of ligand to an FRS results in a change in ratiometric ΔR in the signal from a reporter group. A ratiometric signal ($R_{1,2}$) is defined as the quotient of two intensities, $I_{\lambda 1}$ and $I_{\lambda 2}$, measured at two independent wavelengths, $\lambda_1$ and $\lambda_2$ and may be calculated according to the following equation:

$$R_{1,2}=I_{\lambda 1}/I_{\lambda 2}$$

In some embodiments, intensities are integrated over a range of wavelengths in a recorded emission spectrum. In some embodiments, intensities are integrated over 10-nm, 15-nm, 20-nm, 25-nm, 30-nm, 35-nm, 40-nm, 45-nm, 50-nm, 75-nm, 100-nm, 10-40-nm, 10-50-nm, 20-50-nm, or 10-100-nm regions, centered between 400-800 nm, e.g. between 420 nm and 520 nm for $\lambda_1$, and 400-800 nm, e.g. between 500 nm to 600 nm for $\lambda_2$. In some embodiments, intensities are recorded through a bandpass filter. A non-limiting example of a bandpass filter is a 10-nm, 15-nm, 20-nm, 25-nm, 30-nm, 35-nm, 40-nm, 45-nm, 50-nm, 75-nm, 100-nm, 10-40-nm, 10-50-nm, 20-50-nm, or 10-100-nm bandpass filter, centered between 400-800 nm, e.g. at 452 nm for $\lambda_1$ and at 400-800 nm, e.g. at 528 nm ($\lambda_2$).

Aspects of the present subject matter provide FRSs whose emission spectra change (e.g., the shape of the emission spectra change) in response to ligand binding. In various embodiments, the ratio of intensities at two chosen wavelengths of an FRS's emission spectrum changes upon ligand binding. In some embodiments, the emission wavelength and/or intensity of the fluorophore changes when the position of atoms within the fluorophore changes with respect to each other (e.g., due to the rotation of bound atoms with respect to each other or a change in the angle of a bond). In non-limiting examples, the emission wavelength and/or intensity of the fluorophore changes when (i) one portion of the fluorophore rotates around a bond axis compared to another portion of the fluorophore and/or (ii) when the angle of a bond between two atoms of said fluorophore changes. In a non-limiting example, the fluorophore is a prodan-derived fluorophore (e.g., Acrylodan or Badan) and binding of ligand alters the orientation of a dimethylamino group, a naphthalene ring, and/or a carbonyl with respect to the ligand-binding protein and/or each other. In a non-limiting example, the degree of polarization of a dipole on the fluorophore changes in response to ligand binding. In various embodiments, the emission wavelength and/or intensity of the fluorophore changes when an atom electrostatically interacts with said fluorophore. For example, the emission wavelength and/or intensity of the fluorophore changes when the source of a positive or negative charge changes its distance with respect to the fluorophore within about 1, 2, 3, 4, 5, or 10 Å of the fluorophore. In some embodiments, the fluorophore exhibits hypsochromicity or bathochromicity upon ligand binding to the ligand-binding domain of the ligand-binding protein. In certain embodiments, the fluorophore has an emission wavelength comprising a wavelength of about 550 nanometers (nm), 575 nm, 600 nm, 625 nm, 650 nm, or 550-650 nm.

In some embodiments, the signal comprises the emission intensity of the fluorophore recorded at a single wavelength or range of wavelengths. The change in signal may be a shift in the single wavelength or range of wavelengths. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 105 nm, at least about 110 nm, at least about 115 nm, at least about 120 nm, at least about 125 nm, or at least about 130 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 130 nm.

In certain embodiments, the signal comprises the ratio or quotient of the emission intensities recorded at two distinct wavelengths or ranges of wavelengths, i.e., a ratiometric signal. For example, as shown in FIGS. 1A-C, ligand binding may be determined by measuring the ratio of blue to green emission intensities. The change in signal may be decreased emission intensity at one wavelength, and no change in emission intensity at the other wavelength. The change in signal may be increased emission intensity at one wavelength, and no change in emission intensity at the other wavelength. The change in signal may be increased emission intensity at one wavelength, and increased emission intensity at the other wavelength. The change in signal may be decreased emission intensity at one wavelength, and decreased emission intensity at the other wavelength. The change in signal may be increased emission intensity at one wavelength, and decreased emission intensity at the other wavelength. In some embodiments, the change in ratio of the emission intensities recorded at two distinct wavelengths or ranges of wavelengths may be at least about 1.1-fold, at least about 1.2-fold, at least about 1.4-fold, at least about 1.6-fold, at least about 1.8-fold, at least about 2.0-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 12-fold, at least about 14-fold, at least about 16-fold, at least about 18-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold. In some embodiments, the change in ratio of the emission intensities recorded at two distinct wavelengths or ranges of wavelengths may be a decrease of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, or of 5-25%, 25-50%, 25-75%, 50-75%, 50-90%, or 75-99% or the reciprocal thereof.

The change in signal may be a change in the ratio of the two distinct wavelengths or ranges of wavelengths. The change in signal may be a shift in the two distinct wavelengths or ranges of wavelengths. In some embodiments, one wavelength shifts. In some embodiments, both wavelengths shift. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 105 nm, at least about 110 nm, at least about 115 nm, at least about 120 nm, at least about 125 nm, or at least about 130 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 130 nm.

A fluorophore may comprise, e.g., a fluorescent protein or an organic compound having a molecular weight less than about 2000 Daltons (Da). Non-limiting examples of commercially available fluorophores include such as 5-iodoacetamidofluorescein (5IAF) or 6-iodoacetamidofluorescein (6IAF), rhodamine, Oregon Green, eosin, Texas Red, indocarbocyanine, oxacarbocyanine, thiacarbocyanine, merocyanine, Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD), N-((2-(iodoacetoxy)ethyl)-N-methy-1)amino-7-nitrobenz-2-oxa-1,3-diazole (NBDE), Acrylodan, JPW4039, JPW4042, JPW4045, Oregon Green, Pacific Blue, CPM, N,N'-Dimethyl-N-(Iodoacetyl)-N-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545, BODIPY 499/508, Alexa 432, Alexa488, Alexa532, Alexa546, Cy5, or 1-(2-maleimidylethyl)-4-(5-(4-methoxyphenyl)oxazol-2-yl)pyridinium methanesulfonate (PyMPO maleimide) (PyMPO). In various embodiments, the reporter group was thiol-reactive prior to being conjugated to a polypeptide disclosed herein. In embodiments, the reporter group is linked to a polypeptide disclosed herein via a disulfide bond. Additional non-limiting examples of commercially available fluorophores include fluorescent proteins such as Blue Fluorescent Protein (BFP), TagBFP, mTagBFP2, Azurite, Enhanced Blue Florescent Protein 2 (EBFP2), mKalama1, Sirius, Sapphire, T-Sapphire, Cyan Fluorescent Protein (CFP); Enhanced Cyan Fluorescent Protein (ECFP), Cerulean, SCFP3A, mTurquoise, mTurquoise2, monomeric Midoriishi-Cyan, TagCFP, mTFP1, AmCyan1, Green Fluorescent Protein (GFP), Enhanced Green Fluorescent Protein (EGFP), Emerald, Superfolder GFP, AcGFP1, ZsGreen1, Monomeric Azami Green, TagGFP2, mUKG, mWasabi, Clover, mNeonGreen, Yellow Fluorescent Protein (YFP), Enhanced Yellow Fluorescent Protein (EYFP), Citrine, Venus, Super Yellow Fluorescent Protein 2 (SYFP2), TagYFP, ZsYellow1, mBanana, Orange Fluorescetn Protein (OFP), Monomeric Kusabira-Orange (mKO), mKOK, mKO2, mOrange, mOrange2, Red Fluorescent Protein (RFP), DsRed-Express, DsRed-Express2, DsRed2, AsRed2, mRaspberry, mCherry, mStrawberry, mTangerine, tdTomato, TagRFP, TagRFP-T, mApple, mRuby, mRuby2, mPlum, HcRed-Tandem, mKate2, mNeptune, HcRed1, E2-Crimson, NirFP, TagRFP657, IFP1.4, or iRFP.

In some embodiments, the fluorophore comprises xanthene, a xanthene derivative, cyanine, a cyanine derivative, squaraine, a squaraine derivative, naphthalene, a naphthalene derivative, coumarin, a coumarin derivative, oxadiazole, an oxadiazole derivative, anthracene, an anthracene derivative, a boradiazaindacine (BODIPY) family fluorophore, pyrene, a pyrene derivative, acridine, an acridine derivative, arylmethine, an arylmethine derivative, tetrapyrrole, or a tetrapyrrole derivative. For example, the fluorophore may comprise a xanthene derivative comprising fluorescein or a fluorescein derivative, rhodamine, Oregon Green, eosin, or Texas Red. Non-limiting examples of fluorescein derivatives include 5-fluorescein, 6-carboxyfluorescein, 3'6-carboxyfluorescein, 5(6)-carboxyfluorescein, 6-hexachlorofluorescein, 6-tetrachlorofluorescein, or isothiocyanate. In some embodiments, the fluorophore comprises a cyanine derivative comprising indocarbocyanine, oxacarbocyanine, thiacarbocyanine, or merocyanine. In certain embodiments, the fluorophore comprises a squaraine derivative comprising a ring-substituted squaraine. In various embodiments, the fluorophore comprises a naphthalene derivative comprising a dansyl or prodan naphthalene derivative. In a non-limiting example, the fluorophore comprises prodan or a derivative thereof. In certain embodiments, the fluorophore comprises Badan, Acrylodan, or N-(Iodoacetaminoethyl)-1-naphthylamine-5-sulfonic acid (IAEDANS). In some embodiments, the fluorophore comprises a coumarin derivative such as 3-cyano-7-hydroxycoumarin, 7-hydroxycoumarin-3-carboxylic acid, 6,8-difluoro-7-hydroxy-4-methylcoumarin (DiFMU), or 7-amino-4-methylcoumarin. In various embodiments, the fluorophore comprises an oxadiazole derivative such as pyridyloxazole, nitrobenzoxadiazole, or benzoxadiazole. In certain embodiments, the fluorophore comprises an anthracene derivative comprising an anthraquinone such as DRAQ5, DRAQ7, or CyTRAK Orange. In various embodiments, the fluorophore comprises a pyrene derivative comprising cascade blue. In non-limiting examples the fluorophore comprises an oxazine derivative such as Nile red, Nile blue, cresyl violet, or oxazine 170. In some embodiments, the fluorophore comprises an acridine derivative such as proflavin, acridine orange, or acridine yellow. In certain embodiments, the fluorophore comprises an arylmethine derivative such as auramine, crystal violet, or malachite green. In various embodiments, the fluorophore comprises a tetrapyrrole derivative comprising porphin, phthalocyanine, or bilirubin.

Aspects of the present subject matter relate to the use of fluorophores that may readily be attached to a ligand-binding protein disclosed herein, e.g., at a cysteine residue. For example, a fluorophore may comprise a sulfhydryl group prior to attachment to a ligand-binding protein that is reacted with a moiety of the ligand-binding protein to attach the fluorophore to the ligand-binding protein. In some embodiments, the fluorophore comprised a thiol group prior to attachment to the ligand-binding protein. For example, the fluorophore was thiol reactive prior to attachment to said ligand-binding protein. Non-limiting examples of fluorophores that may readily be attached to ligand-binding proteins using thiol reactions include fluorescein, pyrene, NBD, NBDE, Acrylodan (6-acryloyl-2-dimethylaminonaphthalene), Badan (6-bromo-acetyl-2-dimethylamino-naphthalene), JPW4039, JPW4042, or JPW4045.

In certain embodiments, the fluorophore comprises a derivative of a Prodan-based fluorophore such as Acrylodan or Badan. The excitation and emission properties of the Prodan-based fluorophores Acrylodan and Badan can be altered by manipulating the fluorescent ring system, while preserving the dimethylamino donor group, and the twistable carbonyl acceptor (Klymchenko 2013 *Progress in Molecular Biology and Translational Science,* 35-58). Replacement of the two-ring naphthalene with a three-ring anthracene (Lu 2006 *J. Org. Chem.,* 71, 9651-9657), fluorene (Kucherak 2010 *J. Phys. Chem. Lett.,* 1, 616-620), pyrene (Niko 2013 *Chem. Eur. J.,* 19, 9760-9765), or styrene (Benedetti 2012 *J. Am. Chem. Soc.,* 134, 12418-12421) cores significantly red-shift the excitation and emission properties, and in the case of the latter two, improve brightness through improvements in their excitation peak extinction coefficients. The entire content of each of the references cited above (as well as all other references referred to herein including the contents of nucleic acid and amino acid sequence accession number references) are incorporated herein by reference. Non-limiting examples of prodan analogues include 2-cyano-6-dihexylaminoanthracene and 2-propionyl-6-dihexylaminoanthracene, as well as fluorophores comprising the following structures:

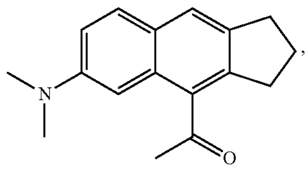
,

-continued

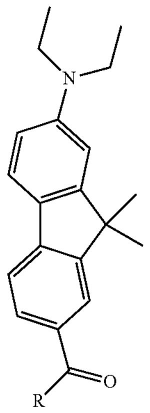

or

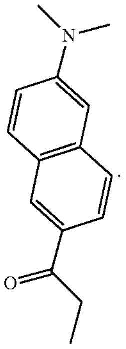

In some embodiments, the fluorophore comprises a fluorescent protein. Fluorescent proteins that emit blue, cyan, green, yellow, orange, red, far-red, or near infrared radiation when contacted with excitation radiation are known in the art and commercially available as proteins and via the expression of vectors that encode the fluorescent protein. Non-limiting examples of fluorescent proteins include Blue Fluorescent Protein (BFP), TagBFP, mTagBFP2, Azurite, Enhanced Blue Florescent Protein 2 (EBFP2), mKalama1, Sirius, Sapphire, T-Sapphire, Cyan Fluorescent Protein (CFP); Enhanced Cyan Fluorescent Protein (ECFP), Cerulean, SCFP3A, mTurquoise, mTurquoise2, monomeric Midoriishi-Cyan, TagCFP, mTFP1, AmCyan1, Green Fluorescent Protein (GFP), Enhanced Green Fluorescent Protein (EGFP), Emerald, Superfolder GFP, AcGFP1, ZsGreen1, Monomeric Azami Green, TagGFP2, mUKG, mWasabi, Clover, mNeonGreen, Yellow Fluorescent Protein (YFP), Enhanced Yellow Fluorescent Protein (EYFP), Citrin, Venus, Super Yellow Fluorescent Protein 2 (SYFP2), TagYFP, ZsYellow1, mBanana, Orange Fluorescetn Protein (OFP), Monomeric Kusabira-Orange (mKO), mKOK, mKO2, mOrange, mOrange2, Red Fluorescent Protein (RFP), DsRed-Express, DsRed-Express2, DsRed2, AsRed2, mRaspberry, mCherry, mStrawberry, mTangerine, tdTomato, TagRFP, TagRFP-T, mApple, mRuby, mRuby2, mPlum, HcRed-Tandem, mKate2, mNeptune, HcRed1, E2-Crimson, NirFP, TagRFP657, IFP1.4, or iRFP.

In some embodiments, the fluorophore comprises a quantum dot (Medintz et al. 2005) (Sapsford, Berti and Medintz 2006 Angew Chem Int Ed Engl, 45, 4562-89; Resch-Genger et al. 2008 Nat Methods, 5, 763-75). In some embodiments the emission properties of the conjugated protein are enhanced by immobilization on or near metallic nanoparticles (Zeng et al. 2014 *Chem Soc Rev,* 43, 3426-52; Shen et al. 2015 *Nanoscale,* 7, 20132-41).

In various embodiments, the peak emission wavelength and/or the emission intensity of the biosensor change when the ligand binds to the ligand-binding protein. In some embodiments, the biosensor exhibits a dichromatic signaling change when the ligand binds to the ligand-binding protein. In various embodiments, the peak emission wavelength of the biosensor shifts by at least about 5, 10, 15, 20, 30, 40, 50, or by about 5-50 nm when the biosensor binds to ligand. In certain embodiments, the emission intensity of the biosensor increases by at least about 5%, 10%, 20%, 30%, 40%, 50%, 60%, 70%, 80%, 90%, 100%, 150%, 200%, or 300% when the biosensor binds to ligand. In various embodiments, the signal produced by said reporter group persists for at least 1 nanoseconds (ns), 5 ns, 10 ns, 25 ns, 50 ns, 75 ns, 100 ns, 200 ns, 300 ns, 400 ns, 500 ns, 600 ns, 700 ns, 800 ns, 900 ns, 0.001 milliseconds (ms), 0.01 ms, 0.1 ms, 1 ms, 5 ms, 10 ms, 20 ms, 25 ms, 50 ms, 100 ms, or 500 ms when the ligand binds to the ligand-binding protein.

Exemplary Methods of Using Biosensors Provided Herein

Aspects of the present subject matter provide a method of assaying for a ligand in a sample. The method may include contacting the sample with a biosensor disclosed herein under conditions such that the ligand-binding protein of the biosensor binds to the ligand if ligand is present in said sample. The method also comprises detecting (i) whether a signal is produced by a reporter group of the biosensor; and/or (ii) the a signal produced by a reporter group of the biosensor. In a non-limiting example, a reporter group of the biosensor is fluorescent, and the method further comprises contacting the reporter group with electromagnetic radiation having a wavelength that comprises a wavelength within the band of excitation wavelengths of the reporter group.

In various embodiments, the method further comprises (i) comparing a signal produced by a reporter group of the biosensor when the biosensor is contacted with the sample with a signal produced by a control sample containing a known quantity of ligand; and (ii) detecting the presence or absence of ligand in said sample based on this comparison. Alternatively or in addition, the method further comprises (i) comparing a signal produced by a reporter group of the biosensor when the biosensor is contacted with the sample with signals produced by a series of control samples containing known quantities of ligand; and (ii) determining the quantity of ligand in the sample based on this comparison. In some embodiments, the series of control samples comprises at least 2, 3, 4, 5, 6, 7, 8, 9, or 10 control samples, and wherein each control sample comprises a different quantity of ligand. Alternatively or in addition, the method further comprises determining the concentration of a ligand in a sample, wherein determining the concentration of the ligand in the sample comprises comparing the signal to a standard hyperbolic ligand binding curve to determine the concentration of the ligand in the test sample, wherein the standard hyperbolic ligand binding curve is prepared by measuring the signal produced by the reporter group of the biosensor when the biosensor is contacted with control samples containing known concentrations of ligand. In various embodiments, the method comprises (i) measuring a ratiometric change ($\Delta R$) and/or an intensity change ($\Delta I$) of a signal produced by the reporter group. In some embodiments, the method includes quantitating the level of ligand present in said sample.

In various embodiments, the ligand comprises glucose and/or galactose and said ligand-binding protein comprises a glucose-galactose binding protein.

Aspects of the present subject matter also provide a method of assaying for multiple ligands in a sample, wherein the multiple ligands comprise a first ligand and a second ligand. Such a method may include contacting the sample with (i) a first biosensor a first ligand provided herein and (ii) a second biosensor for said second ligand, under conditions such that the ligand-binding protein of said first biosensor binds to said first ligand, if said first ligand is present in said sample, and detecting (i) a signal produced by a reporter group of said first biosensor, or (ii) whether a signal is produced by a reporter group of said first biosensor. In some embodiments, the second biosensor is also a biosensor provided herein, and the second biosensor is contacted with the second ligand under conditions such that the ligand-binding protein of the second biosensor binds to the second ligand it is present in the sample. The method may further comprise detecting (i) a signal produced by a reporter group of the second biosensor, or (ii) whether a signal is produced by a reporter group of the second biosensor.

In some embodiments, the signal produced by the reporter group of said first biosensor is different than the signal produced by the reporter group of said second biosensor. In a non-limiting example, the reporter group of said first biosensor and the reporter group of said second biosensor are each fluorescent, and the peak emission wavelength of the reporter group of the first biosensor is at least about 10, 25, 50, 75, or 100 nm greater or lower than the peak emission wavelength of the reporter group of the second biosensor.

Non-limiting examples of biosensors that may be used as the second biosensor include biosensors with ligand-binding proteins comprising a GGBP (e.g., an *E. coli* GGBP) or a derivative or mutant thereof; (ii) an *E. coli* arabinose binding protein (e.g., an *E. coli* arabinose binding protein) or a derivative or mutant thereof; (iii) a dipeptide binding protein (e.g., an *E. coli* dipeptide binding protein) or a derivative or mutant thereof; (iv) a histidine binding protein (e.g., an *E. coli*, histidine binding protein) or a derivative or mutant thereof; (v) a ribose binding protein (e.g., an *E. coli* ribose binding protein) or a derivative or mutant thereof; (vi) a sulfate binding protein (e.g., an *E. coli* sulfate binding protein) or a derivative or mutant thereof; (vii) a maltose binding protein (e.g., an *E. coli* maltose binding protein) or a derivative or mutant thereof; (viii) a glutamine binding protein (e.g., an *E. coli* glutamine binding protein) or a derivative or mutant thereof; (ix) a glutamate/aspartate binding protein (e.g., an *E. coli* glutamate/aspartate binding protein) or a derivative or mutant thereof; (x) a phosphate binding protein (e.g., an *E. coli* phosphate binding protein) or a derivative or mutant thereof; or (xi) an iron binding protein [e.g., a *Haemophilus* influenza (*H. influenzae*) iron binding protein] or a derivative or mutant thereof. For example, the second biosensor comprises an *E. coli* GGBP having a Y10C, Y10A, D14A, D14Q, D14N, D14S, D14T, D14E, D14H, D14L, D14Y, D14F, N15C, F16L, F16A, F16Y, K92A, N91A, E93C, S112A, S115A, E149C, E149K, E149Q, E149S, H152A, H152F, H152Q, H152N, H152C, D154A, D154N, A155S, A155H, A155L, A155F, A155Y, A155N, A155K, A155M, A155W, A155Q, R158A, R158K, M182W, W183C, W183A, N211F, N211W, N211K, N211Q, N211S, N211H, N211M, D236A, D236N, L255C, N256A, N256D, D257C, P294C, or V296C mutation (e.g., comprising 1, 2, 3, 4, 5 or more of these mutations), wherein each amino acid position is numbered as in (SEQ ID NO: 17); (ii) an *E. coli* arabinose binding protein having a D257C, F23C, K301C, L253C, or L298C mutation (e.g., comprising 1, 2, 3, 4, or 5 of these mutations) (see, e.g., U.S. Patent Application Publication No. 2004/0118681, the entire contents of which are incorporated herein by reference) (see, e.g., U.S. Patent Application Publication No. 2004/0118681, the entire contents of which are incorporated herein by reference); (iii) an *E. coli* dipeptide binding protein having a D450C, K394C, R141C, S111C, T44C, or W315C mutation (e.g., comprising 1, 2, 3, 4, 5 or 6 of these mutations) (see, e.g., U.S. Patent Application Publication No. 2004/0118681, the entire contents of which are incorporated herein by reference); (iv) an *E. coli*, histidine binding protein having a E167C, K229C, V163C, Y230C, F231C, Y88C mutation (e.g., comprising 1, 2, 3, 4, 5 or 6 of these mutations) (see, e.g., U.S. Patent Application Publication No. 2004/0118681, the entire contents of which are incorporated herein by reference); (v) an *E. coli* ribose binding protein having a T135C, D165C, E192C, A234C, L236C, or L265C mutation (e.g., comprising 1, 2, 3, 4, 5 or 6 of these mutations) (see, e.g., U.S. Patent Application Publication No. 2004/0118681, the entire contents of which are incorporated herein by reference); (vi) an *E. coli* sulfate binding protein having a L65C, N70C, Q294C, R134C, W290C, or Y67C mutation (e.g., comprising 1, 2, 3, 4, 5 or 6 of these mutations) (see, e.g., U.S. Patent Application Publication No. 2004/0118681 the entire content of which is incorporated herein by reference); (vii) an *E. coli* maltose binding protein having a D95C, F92C, E163C, G174C, I329C, or S233C mutation (e.g., comprising 1, 2, 3, 4, 5 or 6 of these mutations) (see, e.g., U.S. Patent Application Publication No. 2004/0118681 the entire content of which is incorporated herein by reference); (viii) an *E. coli* glutamine binding protein having a N160C, F221C, K219C, L162C, W220C, Y163C, or Y86C mutation (e.g., comprising 1, 2, 3, 4, 5 or more of these mutations) (see, e.g., U.S. Patent Application Publication No. 2004/0118681 the entire content of which is incorporated herein by reference); (ix) an *E. coli* glutamate/aspartate binding protein having a A207C, A210C, E119C, F126C, F131C, F270C, G211C, K268C, Q123C, or T129C mutation (e.g., comprising 1, 2, 3, 4, 5 or more of these mutations) (see, e.g., U.S. Patent Application Publication No. 2004/0118681 the entire content of which is incorporated herein by reference); (x) an *E. coli* phosphate binding protein having a A225C, N223C, N226C, S164C, or S39C mutation (e.g., comprising 1, 2, 3, 4, or 5 of these mutations) (see, e.g., U.S. Patent Application Publication No. 2004/0118681 the entire content of which is incorporated herein by reference); or (xi) a *Haemophilus influenza* (*H. influenzae*) iron binding protein having a E203C, K202C, K85C, or V287C mutation (e.g., comprising 1, 2, 3, or 4 of these mutations) (see, e.g., U.S. Patent Application Publication No. 2004/0118681 the entire content of which is incorporated herein by reference). In various embodiments, the sample is suspected of comprising glucose or galactose.

References and PDB[a] files for bPBP structures, genes, and ligand binding

| bPBP | crystal structure: open form | crystal structure: closed form | DNA sequence | ligand affinity |
|---|---|---|---|---|
| arabinose BP | | Quiocho and Vyas, 1984 1ABE | Scripture et al., 1987 | Clark et al., 1982; Miller et al., 1983 |
| dipeptide BP | Nickitenko et al., 1995 1DPE | Dunten & Mowbray, 1995 1DPP | Abouhamad et al., 1991 | Guyer et al., 1986; Smith et al., 1999 |
| Glu/Asp BP | | | | Barash Halpern, 1975; Willis Furlong, 1975 |

-continued

References and PDB[a] files for bPBP structures, genes, and ligand binding

| bPBP | crystal structure open form | crystal structure closed form | DNA sequence | ligand affinity |
|---|---|---|---|---|
| Fe(III) BP | Bruns et al., 2001 1D9V | Bruns et al., 1997 1MRP | Sanders et al., 1994 | Adhikari et al., 1995 |
| glucose BP | | Vyas et al., 1988; Vyas et al., 1994 1GLG | Scholle et al., 1987 | Anraku, 1968 |
| histidine BP | | Yao et al., 1994 1HSL | Joshi & Ames 1996 | Miller et al., 1983 |
| maltose BP | Sharff et al., 1992 1OMP | Spurlino et al., 1991; Quiocho et al., 1997 1ANF | Duplay et al., 1984 | Schwartz et al., 1976 |
| phosphate BP | Ledvina et al., 1996 1OIB | Luecke & Quiocho, 1990 1IXH | Magota et al., 1984 | Medveczky & Rosenberg, 1969 |
| glutamine BP | Hsiao et al., 1996 1GGG | Sun et al., 1998 1WDN | Nohno et al., 1986 | Weiner et al., 1971 |
| ribose BP | Bjorkman & Mowbray, 1998 1URP | Mowbray & Cole, 1992 2DRI | Groarke et al., 1983 | Willis & Furlong, 1974 |
| sulfate BP | | Pflugrath & Quiocho, 1985; He & Quiocho, 1993 1SBP | Hellinga & Evans, 1985 | Jacobson & Quiocho, 1988 |

[a]Protein Data Bank (Berman et al., 2000)

Abouhamad et al., Molec. Microbial. 5: 1035-1047 (1991)
Adhikari et al., J. Biol. Chem. 270: 25142-25149 (1995)
Anraku, J. Biol. Chem. 243: 3116-3122 (1968)
Barash & Halpern, Biochim. Biophys. Acta 386: 168-180 (1975)
Bjorkman & Mowbray, J. Mol. Biol. 279: 651-664 (1998)
Bruns et al., Biochemistry 40: 15631-15637 (2001)
Bruns et al., Nat. Struct. Biol. 4: 919-924 (1997)
Clark et al., Biochemistry 21: 2227-2233 (1982)
Dunten & Mowbray, Protein Sci. 4: 2327-2334 (1995)
Duplay et al., J. Biol. Chem. 259: 10606-10613 (1984)
Groarke et al., J. Biol. Chem. 258: 12952-12956 (1983)
Guyer et al., J. Bacteriol. 168: 775-779 (1986)
He & Quiocho, Protein Sci. 2: 1643-1647 (1993)
Hellinga & Evans, Eur. J. Biochem. 149: 363-373 (1985)
Hsiao et al., J. Mol. Biol. 262: 225-242 (1996)
Jacobson & Quiocho, J. Mol. Biol. 204: 783-787 (1988)
Joshi & Ames, GenBank Accession Number U47027 (1996)
Ledvina et al., Proc. Natl. Acad. Sci. USA 93: 6786-6791 (1996)
Luecke & Quiocho, Nature 347: 402-406 (1990)
Magota et al., J. Bacteriol. 157: 909-917 (1984)
Medveczky & Rosenberg, Biochim. Biophys. Acta 192: 369-371 (1969)
Miller et al., J. Biol. Chem. 258: 13665-13672 (1983)
Mowbray & Cole, J. Mol. Biol. 225: 155-175 (1992)
Nickitenko et al., Biochemistry 34: 16585-16595 (1995)
Nohno et al., Molec. Gen. Genet. 205: 260-269 (1986)
Pflugrath & Quiocho, Nature 314: 257-260 (1985)
Quiocho et al., Structure 5: 997-1015 (1997)
Quiocho & Vyas, Nature 310: 381-386 (1984)
Sanders et al., Infect. Immun. 62: 4515-4525 (1994)
Scholle et al., Molec. Gen. Genet. 208: 247-253 (1987)
Scripture et al., J. Mol. Biol. 197: 37-46 (1987)
Schwartz et al., Eur. J. Biochem. 71: 167-170 (1976)
Sharff et al., Biochemistry 31: 10657-10663 (1992)
Smith et al., Microbiology 145: 2891-2901 (1999)
Spurlino et al., J. Biol. Chem. 266: 5202-5219 (1991)
Sun et al., J. Mol. Biol. 278: 219-229 (1998)
Vyas et al., Biochemistry 33: 4762-4768 (1994)
Vyas et al., Science 242: 1290-1295 (1988)
Weiner et al., Arch. Biochem. Biophys. 142: 715-717 (1971)
Willis & Furlong, J. Biol. Chem. 249: 6926-6929 (1974)
Willis & Furlong, J. Biol. Chem. 250: 2574-2580 (1975)
Yao et al., Biochemistry 33: 4769-4779 (1994)

Various types of samples may be used in methods provided herein. In non-limiting examples, a sample may comprise a reaction product, a buffer, and/or a solvent. In some embodiments, the solvent is an aqueous solvent. In some embodiments, the solvent comprises a non-polar solvent, a polar aprotic solvent, and/or a polar protic solvent. For example, a sample may comprise water, liquid ammonia, liquid sulfur dioxide, sulfuryl chloride, sulfuryl chloride fluoride, phosphoryl chloride, dinitrogen tetroxide, antimony trichloride, bromine pentafluoride, hydrogen fluoride, dimethyl sulfoxide, hexane, benzene, toluene, 1,4-dioxane, chlorogorm, diethyl ether, dichloromethane, N-methylpyrrolidone, tetrahydrofuran, ethyl acetate, acetone, dimethylformamide, acetonitrile, tormic acid, n-butanol, isopropanol, nitromethane, ethanol, methanol, and/or acetic acid.

In embodiments, a sample comprises a Newtonian liquid, a shear thickening liquid, a shear thinning liquid, a thixotropic liquid, a rheopectic liquid, or a Bingham plastic. In some implementations, a sample has a dynamic viscosity of at least about 0.5, 0.6, 0.7, 0.8, 0.9, 1, 1.1, 1.2, 1.3, 1.4, 1.5, or 2 pascal-seconds (Pa·s) or less than about 2, 1.5, 1.4, 1.3, 1.2, 1.1, 1, 0.9, 0.8, 0.7, 0.6, 0.5 Pa·s; and/or a kinematic viscosity of at least about 0.5, 0.6, 0.7, 0.8, 0.9, 1, 1.1, 1.2, 1.3, 1.4, 1.5, or 2 centistokes (cSt) or less than about 2, 1.5, 1.4, 1.3, 1.2, 1.1, 1, 0.9, 0.8, 0.7, 0.6, 0.5 cSt.

In various embodiments, the sample comprises a biological sample. The sample may comprise, e.g., a clinical sample (i.e., a sample collected in a clinical or veterinary setting, e.g., by or at the request or supervision or direction of a doctor, nurse, aid worker, or medic) and/or a physiological sample (a sample collected from an organism, e.g., a mammal such as a human) In certain embodiments, the biological sample comprises or has been provided or obtained from a skin surface or a mucosal surface. In some embodiments, the biological sample comprises a biological fluid. Non-limiting examples of biological fluids include sweat, tear fluid, blood, serum, plasma, interstitial fluid, amniotic fluid, sputum, gastric lavage, skin oil, milk, fecal matter, emesis, bile, saliva, urine, mucous, semen, lymph, spinal fluid, synovial fluid, a cell lysate, venom, hemolymph, and fluid obtained from plants such as the fluid transported in xylem cells or phloem sieve tube elements of a plant (e.g. sap).

The present subject matter also provides biosensors, methods, compositions, and devices useful for measuring the level of a ligand within a liquid solution or suspension or composition comprising cultured cells or tissue or a supernatant of such a solution or suspension, e.g., a sample of conditioned media or a sample of growth media in which a population of cells was cultured. In some embodiments, the sample is within a culture (e.g., inserted into a bioreactor) or provided from a media, culture, or reaction, e.g., in a bioreactor. For example, the sample may be within or provided from a fermenter such as a culture or culture supernatant from a fermentation reaction (e.g., an ongoing fermentation). Thus, the level of a ligand can be assayed at a timepoint of interest or at a series of timepoints over the duration of cell culture, e.g. continuously, in or from a reaction or culture. Bioreactors include devices or systems that support a biologically active environment. For example, a bioreactor may comprise a vessel in which a chemical process is carried out which involves organisms or biochemically active substances derived from such organisms. Such a process can either be aerobic or anaerobic. Organisms growing in bioreactors may be, e.g., submerged or suspended in liquid medium or may be attached to the surface of a solid medium. Submerged cultures may be suspended or immobilized. Suspension bioreactors can use a wider variety of organisms, since special attachment surfaces are not needed, and can operate at much larger scale than immobilized cultures. However, in a continuously operated process the organisms will be removed from the reactor with the effluent Immobilization is a general term describing a wide variety of cell or particle attachment or entrapment. It can be applied to basically all types of biocatalysis including enzymes, cellular organelles, and cells (e.g., animal cells, plant cells, fungal cells, and bacterial cells) Immobilization is useful for continuously operated processes, since the organisms will not be removed with the reactor effluent, but is limited in scale because the cells are only present on the surfaces of the vessel. A bioreactor may also refer to a device or system meant to grow cells or tissues in the context of cell culture. The interogation and/or monitoring of glucose levels in such samples permits the evaluation of the status of growth of the cells or production of secreted products by the cells to inform harvest or feeding or other modification of the culture.

Aspects of the present subject matter relate to the use of methods and biosensors provided herein to detect contamination.

In some embodiments, the sample comprises an environmental sample. Depending on context, there are instances in which a biological sample may also be, or may be within, an environmental sample. In certain embodiments, an environmental sample comprises a solute obtained from a biological composition, such as bone, nail, hair, shell, or cartilage. In various embodiments, an environmental sample comprises a solute obtained from an environmental substance and/or an environmental surface. For example, the solute may be dissolved/obtained from the environmental substance and/or an environmental surface using an aqueous or nonaqueous solution. In some embodiments, an aqueous may optionally comprise a nonaqueous solvent (e.g., mixed with an aqueous solvent). Non-limiting examples of environmental substances include rock, soil, clay, sand, meteorites, asteroids, dust, plastic, metal, mineral, fossils, sediment, and wood. Non-limiting examples of environmental surfaces include the surface of a vehicle such as a civilian vehicle (e.g., a satellite, a bike, a rocket, an automobile, a truck, a motorcycle, a yacht, a bus, or a plane) or a military vehicle (e.g., a tank, an armored personell carrier, a transport truck, a jeep, a mobile artillery unit, a mobile antiaircraft unit, a minesweeper, a Mine-Resistant Ambush Protected (MRAP) vehicle, a lightweight tactical all-terrain vehicle, a high mobility multipurpose wheeled vehicle, a mobile multiple rocket launch system, an amphibious landing vehicle, a ship, a hovercraft, a submarine, a transport plane, a fighterjet, a helicopter, a rocket, or an Unmanned Arial Vehicle), a drone, a robot, a building, furniture, or an organism other than a human. In some embodiments, the sample comprises an environmental fluid. Non-limiting examples of environmental fluids include marine water, well water, drinking well water, water at the bottom of well dug for petroleum extraction or exploration, melted ice water, pond water, aquarium water, pool water, lake water, mud, stream water, river water, brook water, waste water, treated waste water, reservoir water, rain water, and ground water. In some embodiments, waste water comprises sewage water, septic tank water, agricultural runoff, water from an area in which chemical or oil spill has or is suspected of having occurred (e.g., an oil spill into a marine environment), water from an area where a radiation leak has or is suspected of having occurred (e.g., coolant from a nuclear reactor), water within the plumbing of a building, water within or exiting a research facility, and/or water within or exiting a manufacturing facility such as a factory.

In certain embodiments, the sample comprises a food or beverage additive and/or a food or beverage composition. In some embodiments, the food or beverage composition comprises a fermented composition. In various embodiments, the sample comprises a fluid obtained from a food composition. Alternatively or in addition, the sample may comprise a solute dissolved from a food composition. In some examples, a solute is or has been dissolved from a food composition with an aqueous or nonaqueous solution. In various implementations, an aqueous solution may optionally comprise a nonaqueous solvent. In certain embodiments, a sample comprises a food composition in semisolid or liquid form. Non-limiting examples of such compositions include yogurt, soup, ice cream, a broth, a puree, a shake, a smoothie, a batter, a condiment, a sauce, and any combination thereof. In some implementations, a sample is a food engineering process (e.g., obtained from a food design, storage, transport, or production process or from equipment intended to process, transport, or store food). A food composition may comprise, e.g., a plant or a composition isolated from a plant, and/or an animal or a composition isolated from an animal. In various embodiments, a sample comprises a beverage composition. Non-limiting examples of beverage compositions include soft drinks, fountain beverages, water, coffee, tea, milk, dairy-based beverages, soy-based beverages (e.g., soy milk), almond-based beverages (e.g., almond milk), vegetable juice, fruit juice, fruit juice-flavored drinks, energy drinks, sports and fitness drinks, alcoholic products, and beverages comprising any combination thereof. Non-limiting examples of beverage compositions comprising water include purified water (e.g., filtered water, distilled water, or water purified by reverse osmosis), flavored water, mineral water, spring water, sparkling water, tonic water, and any combination thereof. In various embodiments, the sample comprises alcohol. Non-limiting examples of such samples include samples comprising or obtained/provided from beer, malt beverages, liqueur, wine, spirits, and any combination thereof.

In some embodiments, a sample comprises a nutritional or supplement composition. In certain implementations, the nutritional or supplement composition comprises an omega-3 fatty acid, a vitamin, a mineral, a protein powder, or a meal supplement.

In certain embodiments, a biosensor is implanted in a subject's body. For example, a biosensor may be implanted in a subject's blood vessel, vein, eye, natural or artificial pancreas, alimentary canal, stomach, intestine, esophagus, or skin (e.g., within the skin or under the skin). In various embodiments, the biosensor is configured within or on the surface of a contact lens. In some embodiments, the biosensor is configured to be implanted in or under the skin. In non-limiting examples, the biosensor is implanted in a subject with an optode and/or a microbead. In certain embodiments, the biosensor generates a signal transdermally.

Aspects of the present subject matter provide a method for assaying the level of glucose in a subject. The method may comprise contacting a biological sample from the subject with a biosensor for glucose under conditions such that the biosensor binds to glucose present in the biological sample. The biosensor comprises a glucose-galactose binding protein attached to a reporter group, and binding of glucose to a glucose-binding domain of the glucose-galactose binding protein causes a change in signaling by the reporter group. In various embodiments, the subject has or is suspected of having diabetes, such as Type I diabetes or Type II diabetes. In some embodiments, the biological sample comprises blood, plasma, serum, sweat, tear fluid, or urine. In certain embodiments, the biological sample is present in or on the surface of said subject. In various implementations, the biosensor is applied onto or inserted into the subject. For example, the biosensor may be tattooed into the subject or is in or on a device that is implanted into said subject. In some embodiments, the biosensor may be present in or on a contact lens that is worn by the subject. Methods for determining the level of glucose, e.g. in a subject who has or is suspected of having diabetes, may be performed without other testing related to diabetes performed as part of a battery of clinical testing.

The present subject matter includes a method for monitoring the level of a ligand, comprising periodically or continuously detecting the level of the ligand, wherein detecting the level of the ligand comprises (a) providing or obtaining a sample; (b) contacting said sample with a biosensor for said ligand according to claim 1 under conditions such that the ligand-binding protein of said biosensor binds to said ligand, and (c) detecting a signal produced by said biosensor.

Aspects of the present subject matter also provide a method for monitoring the level of a ligand (e.g., glucose and/or galactose) in a subject, comprising periodically detecting the level of the ligand in the subject. Detecting the level of the ligand in the subject may comprise (a) providing or obtaining a biological sample from said subject; (b) contacting the biological sample with a biosensor for the ligand provided herein under conditions such that the ligand-binding protein of the biosensor binds to the ligand, if the ligand is present in said biological sample, and (c) detecting (i) a signal produced by a reporter group of said biosensor, or (ii) whether a signal is produced by a reporter group of said biosensor. The level of said ligand may be detected, e.g., at least once every 1, 2, 3, 6, or 12 hours, at least once every 1, 2, 3, or 4 days, at least once every 1, 2, or three weeks, or at least once every 1, 2, 3, 4, 6, or 12 months.

The present subject matter also provides a method for monitoring the level of a ligand in a subject. The method comprises (a) administering a biosensor provided herein or a device comprising a biosensor provided herein to said subject, wherein after administration the biosensor is in contact with a bodily fluid or surface that typically comprises said ligand, and (b) detecting (i) a signal produced by a reporter group of the biosensor continuously or repeatedly at intervals less than about 30 minutes (m), 15 m, 10 m, 5 m, 1 m, 30 seconds (s), 15 s, 10 s, 5 s, 1 s, 0.1 s, 0.001 s, 0.0001 s, or 0.00001 apart, and/or (ii) whether a signal is produced by a reporter group of the biosensor continuously or repeatedly at intervals less than about 30 m, 15 m, 10 m, 5 m, 1 m, 30 s, 15 s, 10 s, 5 s, 1 s, 0.1 s, 0.001 s, 0.0001 s, or 0.00001 apart.

Non-limiting aspects of continuously monitoring glucose levels are described in Weidemaier et al. (2011) Biosensors and Bioelectronics 26, 4117-4123 and Judge et al. (2011) Diabetes Technology & Therapeutics, 13(3):309-317, the entire contents of each of which are hereby incorporated herein by reference.

Also within the invention is a composition comprising a purified thermostable, glucose-binding fluorescently-responsive sensor protein and a solid substrate, e.g., a particle, a bead such as a magnetic bead, or a planar surface such as a chip or slide, wherein the sensor protein is immobilized onto the solid substrate. An exemplary solid substrate solid substrate comprises a cyclic olefin copolymer.

The sensor protein contains a single cysteine residue, with the single cysteine residue being located in a glucose-contacting site of protein. A thermostable glucose sensor protein is one in which the activity (glucose binding) is unaffected by relatively high temperatures. For example, the glucose sensor protein comprises a mid-point thermal melt transition greater than 50° C., greater than 60° C., greater than 70° C., greater than 80° C., greater than 90° C., or greater than 100° C. In some examples, the protein comprises the amino acid sequence of SEQ ID NO: 298, and in some examples, the single cysteine is conjugated to Badan, Acrylodan, or a derivative thereof. For example, the derivative comprises a replacement of the two-ring naphthalene of Acrylodan or Badan with a three-ring anthracene, a fluorene, or a styrene. A reporter group is covalently bound to the single cysteine. In some situations, the solid substrate comprises a plurality of sensor proteins, each of which comprises a different dissociation constant ($K_D$) for glucose, e.g., for detecting and quantifying glucose levels across many ranges of concentrations.

The invention also includes a composition comprising purified glucose sensor protein with less than 65% identity and greater than 27% identity (e.g., 44-48% sequence identity) to SEQ ID NO: 1, 16, or 17, wherein the sensor protein comprises a single cysteine residue, said residue being located in a glucose-contacting site of the protein, and a solid substrate, such that the sensor protein is immobilized onto said solid substrate. As described above, a reporter group is covalently bound to the single cysteine. In some example, the solid substrate comprises a plurality of sensor proteins, each of which comprises a different dissociation constant ($K_D$) for glucose for sensing over a wide range or ranges of glucose concentrations.

A method of detecting the presence of or the quantity of glucose in a test sample is carried out using the following steps: contacting the testsample with the biosensor or sensor protein/solid support construct to yield a complex of glucose and the ligand-binding protein or biosensor protein; contacting the complex with an excitation light; measuring an emission intensity of the reporter group from at least two wavelengths; computing a ratiometric signal from the two (or more) wavelengths; and comparing the signal to a known glucose binding curve of signals to identify the presence of or calculate the quantity of glucose in the test sample. The test sample may be obtained from a variety of sources. For example, the test sample is selected from a bodily fluid, a food, a beverage, or a bioreactor culture broth. The testing method may be carried out in vivo, e.g., using an implantable device or dermal patch, or ex vivo.

In various embodiments, the subject to be tested is a mammal, e.g., a primate (such as a human, a monkey, a chimpanzee, or a gorilla), a fish, a bird, a reptile, an amphibian, or an arthropod. In some embodiments, the subject is a fish, a cow, a pig, a camel, a llama, a horse, a race horse, a work horse, a goat, a rabbit, a sheep, a hamster, a guinea pig, a cat, a wolf, a dog (e.g., a pet dog, a work dog, a police dog, or a military dog), a rat, a mouse, a seal, a whale, a manatee, a lizard, a snake, a chicken, a goose, a swan, a duck, or a penguin.

Exemplary Devices and Compositions Comprising Biosensors

Aspects of the present subject matter provide a device comprising one or more biosensors provided herein. Such devices may be, e.g., wearable, implantable, portable, or fixed.

In some embodiments, the device is a nanoparticle or a microparticle comprising said biosensor. Non-limiting examples of devices include devices comprising a test strip, patch, plate, bead, or chip comprising a biosensor provided herein. In certain embodiments, a device may comprise a desiccated biosensor.

The present subject matter also provides a contact lens or a skin patch comprising a biosensor provided herein. In some embodiments, the biosensor is throughout the contact lens or skin patch or within a particular region or zone of a contact lens or skin patch (e.g., in one or more shapes (e.g., a square, circle, or star), dots, lines, or zones, located at the periphery or a portion of the periphery of a contact lens or patch). In some embodiments, the skin patch comprises an adhesive that facilitates attachment of the patch to the surface of skin.

Devices provided herein may include a variety of structural compositions. For example, many polymers (including copolymers), and plastics may be used. Non-limiting examples of compositions useful in certain devices include glass, polystyrene, polypropylene, cyclic olefin copolymers, ethylene-norbornene copolymers, polyethylene, dextran, nylon, amylase, paper, a natural cellulose, a modified cellulose, a polyacrylamide, gabbros, gold, and magnetite (as well as combinations thereof). In some embodiments, the device comprises a hydrogel, a cryogel, or a soluble gel. For example, the biosensor may be incorporated into or onto the hydrogel, cryogel, or soluble gel. In various embodiments, the device comprises a matrix comprising nanopores, micropores, and/or macropores. In certain embodiments, the surface of a device comprises a polymer. In an embodiment, the surface comprises the surface of a particle or a bead having a diameter of about 0.001-1, 0.001-0.1, 0.01-0.1, 0.001-0.01, 0.1-1, 0.1-0.5, or 0.01-0.5 centimeters (cm). For example, the particle comprises a nanoparticle or a microparticle.

Non-limiting examples of polymers include cyclic olefin copolymers, ethylene-norbornene copolymers, polylactic acid, polyglycolic acid, agarose, alginate, poly(lactide-co-glycolide), gelatin, collagen, agarose, natural and synthetic polysaccharides, polyamino acids, poly(lysine), polyesters, polyhydroxybutyrates, polyanhydrides, polyphosphazines, polyvinyl alcohol, polyalkylene oxide, polyethylene oxide, polyallylamines, polyacrylates, modified styrene polymers, poly(4-aminomethylstyrene), pluronic polyols, polyoxamers, polyuronic acid, and polyvinylpyrrolidone.

In some embodiments, the device comprises a plastic polymer comprising cyclic olefin copolymer (COC), such as e.g. TOPAS® COC. Several types of cyclic olefin copolymers are available based on different types of cyclic monomers and polymerization methods. Cyclic olefin copolymers are produced by chain copolymerization of cyclic monomers such as 8,9,10-trinorborn-2-ene (norbornene) or 1,2,3,4,4a,5,8,8a-octahydro-1,4:5,8-dimethanonaphthalene (tetracyclododecene) with ethene (such as TOPAS Advanced Polymer's TOPAS, Mitsui Chemical's APEL), or by ring-opening metathesis polymerization of various cyclic monomers followed by hydrogenation (Japan Synthetic Rubber's ARTON, Zeon Chemical's Zeonex and Zeonor). See, e.g., International Union of Pure and Applied Chemistry (2005) *Purr. Appl. Chem.* 77(5):801-814. These later materials using a single type of monomer may be referred to as cyclic olefin polymers (COPs). A CAS Registry number for COC is 26007-43-2.

In certain embodiments, the device is attached to a surface of a device or is not attached to a surface of said device (e.g., the biosensor is present loosely within the device as a component of a solution or powder).

A biosensor may be attached to a device via a variety or means, e.g., via attachment motif. In some embodiments, the attachment motif is attached to the N-terminus or the C-terminus of the biosensor. In certain embodiments, the biosensor is linked to an attachment motif via a covalent bond. In various embodiments, the biosensor is linked to said attachment motif via a linker. A non-limiting example of a linker is a polyglycine comprising 2, 3, 4, 5, or more glycines and optionally further comprising a serine. In some embodiments, the attachment motif comprises a polypeptide. Non-limiting examples of polypeptides useful in attachment moieties include hexahistidine peptides, hexalysine peptides, zinc-finger domains (ZF-QNKs), and disulfide-containing truncated zinc fingers (βZifs). An example of a hexalysine peptide comprises amino acids in the sequence of SEQ ID NO: 296, an example of a ZF-QNK comprises amino acids in the sequence of SEQ ID NO: 294, and an example of a βZif comprises amino acids in the sequence of SEQ ID NO: 293. In some embodiments, the attachment motif comprises a polypeptide that binds to plastic or cellulose.

The hexahistidine, hexalysine, βZif and QNK-ZF fusions (SEQ ID NOS: 173 and 175-181) enable FRSs to be immobilized onto chemically functionalized surfaces. Non-limiting aspects of chemically functionalized surfaces are discussed in Biju, V. (2014) *Chem Soc Rev,* 43, 744-64 and McDonagh (2008) *Chem Rev,* 108, 400-422, the entire contents of which are incorporated herein by reference. Directed evolution methods have been used to develop peptides that bind directly to non-functionalized surfaces (Care, Bergquist and Sunna 2015 *Trends Biotechnol,* 33, 259-68; Baneyx 2007 *Curr. Opin. Biotechnol.,* 18, 312-317;

Gunay and Klok 2015 *Bioconjug Chem,* 26, 2002-15), including various plastics (Adey et al. 1995 *Gene,* 156, 27-31; Serizawa et al. 2005 J Am Chem Soc, 127, 13780-1; Serizawa, Sawada and Kitayama 2007a *Angew Chem Int Ed Engl,* 46, 723-6; Serizawa, Sawada and Matsuno 2007b *Langmuir,* 23, 11127-33; Serizawa, Techawanitchai and Matsuno 2007c *Chembiochem,* 8, 989-93; Matsuno et al. 2008 *Langmuir,* 24, 6399-403; Chen, Serizawa and Komiyama 2011 *J Pept Sci,* 17, 163-8; Kumada 2010 *J. Biosci. and BioEng.,* 109, 583-587; Date et al. 2011 *ACS Appl Mater Interfaces,* 3, 351-9; Kumada 2012, Vodnik, Strukelj and Lunder 2012 *J. Biotech.,* 160, 222-228; Kumada 2014 *Biochem. et Biophys. Acta,* 1844, 1960-1969; Ejima, Matsuno and Serizawa 2010 *Langmuir,* 26, 17278-85), inorganic materials (Hnilova 2012 *Soft Matter,* 8, 4327-4334; Care et al. 2015 *Trends Biotechnol,* 33, 259-68), nanoparticles (Avvakumova et al. 2014 *Trends Biotechnol,* 32, 11-20), and cellulosic paper (Guo et al. 2013 *Biomacromolecules,* 14, 1795-805). Such peptides, or natural material-binding domains (Oliveira et al. 2015 *Biotechnol Adv,* 33, 358-69), also can be fused to FRSs to direct site-specific, oriented immobilization on their target materials while preserving FRS function. For instance, plastic-binding peptides have been developed that direct immobilization on polystyrene (Adey et al. 1995 *Gene,* 156, 27-31; Serizawa et al. 2007c *Chembiochem,* 8, 989-93; Kumada 2010 *Biochem. et Biophys. Acta,* 1844, 1960-1969; Vodnik et al. 2012 *Anal Biochem,* 424, 83-6), polymethyl acrylate (Serizawa et al. 2005 *J Am Chem Soc,* 127, 13780-1; Serizawa et al. 2007a *Angew Chem Int Ed Engl,* 46, 723-6; Serizawa et al. 2007b *Langmuir,* 23, 11127-33; Kumada 2014 *Biochem. et Biophys. Acta,* 1844, 1960-1969), polycarbonate (Kumada 2012 *J. Biotech.,* 160, 222-228), polylactide (Matsuno et al. 2008 *Langmuir,* 24, 6399-403), and polyphenylene vinylene (Ejima et al. 2010 *Langmuir,* 26, 17278-85). Cellulose-binding peptides (Guo et al. 2013 *Biomacromolecules,* 14, 1795-805) and natural domains (Oliveira et al. 2015 *Biotechnol Adv,* 33, 358-69; Shoseyov, Shani and Levy 2006 *Microbiol Mol Biol Rev,* 70, 283-95) can be used to immobilize fusion proteins on paper. Inorganic material include noble metals (Hnilova 2012 *Soft Matter,* 8, 4327-4334), semi-conductors (Care et al. 2015 *Trends Biotechnol,* 33, 259-68), and fluorescent quantum dots (Medintz et al. 2005 *Nat Mater,* 4, 435-46; Lee et al. 2002 *Science,* 296, 892-5). The entire contents of each of the references above (and all other references herein) is incorporated herein by reference.

In some embodiments, the attachment motif is attached to a device surface and/or within a matrix of the device. In some embodiments, a biosensor is attached to an attachment motif via a covalent bond and the attachment motif is attached to a device via a covalent bond. Non-limiting examples of covalent bonds include disulfide bonds, ester bonds, thioester bonds, amide bonds, and bonds that have been formed by click reactions. Non-limiting examples of a click reaction include a reaction between an azide and an alkyne; an azide and an alkyne in the presence of Cu(I); an azide and a strained cyclooctyne; an azide and a dibenzylcyclooctyne, a difluorooctyne, or a biarylazacyclooctynone; a diaryl-strained-cyclooctyne and a 1,3-nitrone; an azide, a tetrazine, or a tetrazole and a strained alkene; an azide, a tetrazine, or a tretrazole and a oxanorbornadiene, a cyclooctene, or a trans-cycloalkene; a tetrazole and an alkene; or a tetrazole with an amino or styryl group that is activated by ultraviolet light and an alkene.

Alternatively or in addition, a surface of a device may be modified to contain a moiety (e.g. a reactive group) what facilitates the attachment of a biosensor and/or binds to the biosensor. In some embodiments, the biosensor is attached to a surface via a biotin-avidin interaction.

In various implementations, the device comprises a first region for receiving a sample and second a region that comprises the biosensor, wherein said first region is separated from said second region by a filter. In some examples, the filter is impermeable to compounds greater than about 1, 2, 3, 4, 5, 10, 50, 200, or 250 kiloDalton (kDa) in size. The sample may comprise, e.g., a tube, such as a tube that is configured for centrifugation. When sample is placed into the first region and the device is centrifuged, then a portion of the sample comprising a ligand flows through the filter into the second region where the biosensor is contacted.

Non-limiting examples of devices provided herein include endoscopy probes and colonoscopy probes.

In some embodiments, the device comprises an optode. In non-limiting examples, the optode comprises an optical fiber and a single biosensor or composite biosensor. In certain embodiments, the single biosensor or composite biosensor is immobilized on the surface or at an end of the optical fiber. In some embodiments, the optode is configured for implantation into a subject. Alternatively or in addition, the optode is configured for insertion into a sample.

The devices provided herein may optionally comprise a biosensor panel, a composite sensor, a sensor array, and/or a composition comprising a plurality of biosensors. In various embodiments, a device comprises multiple glucose and/or galactose biosensors that detect a range of different glucose and/or galactose concentrations in a single sample and/or assay run (i.e., each biosensor has a different affinity for glucose and/or galactose). Devices may provide spatial localization of multiple biosensors to provide the necessary addressability of different elements in a multi-sensor array comprising sensors that differ in their engineered affinities for coverage of a wide range of glucose concentrations, or sensors that each detects distinct analytes.

Aspects of the present subject matter provide a biosensor panel comprising a plurality of biosensors, wherein said plurality of biosensors comprises at least one biosensor disclosed herein. In some embodiments, the plurality comprises at least about 2, 3, 4, 5, 10, 20, 30, 40, 50, 60, 70, 80, 90, or 100 biosensors.

The present subject matter also provides a composite sensor. The composite sensor may comprise a sensor element, wherein the sensor element comprises 2 or more biosensors, wherein at least 1 of said 2 or more biosensors is a biosensor disclosed herein. In some embodiments, the biosensors are not spatially separated in the sensor element, e.g., the biosensors are mixed within a solution or on a surface of the sensor element. In various embodiments, the composite sensor comprises a plurality of sensor elements, wherein each sensor element of the plurality of sensor elements comprises 2 or more biosensors, wherein at least 1 of the 2 or more biosensors is a biosensor provided herein. In some embodiments, the plurality of sensor elements comprises at least about 2, 3, 4, 5, 10, 20, 30, 40, 50, 60, 70, 80, 90, or 100 sensor elements.

Also included herein is a sensor array comprising a plurality of biosensors of the present subject matter. The sensor array may include, e.g., multichannel array or a multiplexed array. In some embodiments, the biosensors of the plurality of biosensors are spatially separated from each other. In certain embodiments, the biosensors are arranged linearly or in a grid on a surface of said array.

The present subject matter provides a composition comprising a plurality of biosensors including at least one biosensor disclosed herein. Also provided is a non-human mammal comprising a biosensor or device disclosed herein.

Exemplary Polypeptides and Polynucleotides

The present subject matter provides polynucleotides encoding any one of the polypeptides disclosed herein. The polypeptides are also provided. In various embodiments, the polynucleotides are codon-optimized for expression in a desired host cell, such as bacterial cells (e.g., *E. coli*), yeast, insect cells, plant cells, algal cells, or mammalian cells. The polypeptides provided herein include polypeptides comprising the amino acid sequence of any one of SEQ ID NOS: 1-103, 157-292, 197, or 198. The polynucleotides provided herein include polynucleotides encoding a polypeptide comprising the amino acid sequence of any one of SEQ ID NOS: 1-103, 157-292, 197, or 198.

The polypeptides and biosensors provided herein may be in a variety of forms, e.g., purified in solution, dried (e.g. lyophilized) such as in the form of a powder, and in the form of a crystal (e.g., a crystal suitable for x-ray crystallography). Thus, aspects of the present subject matter provide crystal structures and crystalized forms of the ligand-binding proteins and biosensors disclosed herein. Such crystal structures and crystalized proteins are useful for designing and optimizing biosensors using principles and methods discussed herein.

Also provided are expression vectors comprising a polynucleotide of the present subject matter and/or encoding a polypeptide disclosed herein. Non-limiting examples of expression vectors include viral vectors and plasmid vectors. In some embodiments, an expression vector comprises nucleotides in the sequence set forth as SEQ ID NO: 105-156. In various embodiments, a polynucleotide encoding a ligand-binding protein and/or biosensor is operably linked to a promoter. The promoter may be expressed, e.g., in a prokaryotic and/or a eukaryotic cell.

The subject matter further includes an isolated cell comprising an expression vector provided herein. The isolated cell may be, e.g., a bacterial cell, a yeast cell, an algal cell, a plant cell, an insect cell, or a mammalian cell. Also included is a non-human multicellular organism such as a plant or an animal (e.g., an insect, a mammal, a worm, a fish, a bird, or a reptile) comprising an expression vector disclosed herein.

Exemplary Methods for Designing Biosensors

Aspects of the present subject matter provide method of identifying a candidate ligand-binding protein for use in a biosensor, comprising: (a) selecting a first protein having a known amino acid sequence (seed sequence), wherein the first protein is a glucose-galactose binding protein; (b) identifying a second protein having an amino acid sequence (hit sequence) with at least 15% sequence identity to the seed sequence; (c) aligning the seed amino acid sequence and the hit sequence, and comparing the hit sequence with the seed sequence at positions of the seed sequence that correspond to at least 5 primary complementary surface (PCS) amino acids, wherein each of the at least 5 PCS amino acids has a hydrogen bond interaction or a van der Waals interaction with glucose when glucose is bound to the first protein; and (d) identifying the second protein to be a candidate ligand-binding protein if the hit sequence comprises at least 5 amino acids that are consistent with the PCS.

The present subject matter also includes a method for constructing a candidate biosensor, comprising: (a) providing a candidate ligand-binding protein; (b) generating a structure of the second protein; (c) identifying at least one putative allosteric, endosteric, or peristeric site of the second protein based on the structure; (d) mutating the second protein to substitute an amino acid at said at least one putative allosteric, endosteric, or peristeric site of the second protein with a cysteine; and (e) conjugating a fluorescent compound to the cysteine. In some embodiments, the structure comprises a homology model of the second protein generated using a structure of the first protein. In some embodiments, the structure comprises a structure experimentally determined by nuclear magnetic resonance spectroscopy or X-ray crystallography.

Aspects of the present subject matter further provide a method for constructing a biosensor comprising a desired dissociation constant (KD) for glucose, comprising: (a) providing an initial biosensor that does not comprise the desired KD for glucose, wherein said initial biosensor is a biosensor provided herein; (b) mutating the initial biosensor to (i) alter a direct interaction in the PCS between the initial biosensor and bound glucose; (ii) manipulate the equilibrium between open and closed states of the initial biosensor; (iii) alter an interaction between the ligand-binding protein and the reporter group of the initial biosensor; or (iv) alter an indirect interaction that alters the geometry of the binding site of the biosensor, to produce a modified biosensor; and (c) selecting the modified biosensor if the modified biosensor comprises the desired KD for glucose. In some embodiments, the reporter comprises Acrylodan, Badan, or a derivative thereof, and mutating the initial biosensor in (b) comprises altering an interaction between the ligand-binding protein and a carbonyl group of the Acrylodan, Badan, or derivative thereof. In some embodiments, the reporter group comprises Acrylodan, Badan, or a derivative thereof, and mutating the initial biosensor in (b) comprises altering an interaction between the ligand-binding protein and a naphthalene ring of the Acrylodan, Badan, or derivative thereof. In some embodiments, mutating the initial biosensor comprises introducing a substitution mutation into said initial biosensor. In some embodiments, the method further comprises immobilizing said affinity-tuned biosensor on a substrate.

In some embodiments, the second protein comprises (i) amino acids in the sequence of SEQ ID NO: 1-15 or 17-31; (ii) a stretch of amino acids in a sequence that is least about 95, 96, 97, 98, or 99% identical to the sequence of SEQ ID NO: 1-31; (iii) a stretch of at least about 50, 100, 150, 200, 250, 300, or 350 amino acids in a sequence that is at least about 95, 96, 97, 98, or 99% identical to a sequence within SEQ ID NO: 1-31; or (iv) a stretch of at least about 50, 100, 150, 200, 250, 300, or 350 amino acids in a sequence that is identical to a sequence within SEQ ID NO: 1-31. In various embodiments, attaching the reporter group to the putative allosteric, endosteric, or peristeric site of the first protein comprises substituting a cysteine at the site with a cysteine. For example, the reporter group is conjugated to the cysteine. Preferably, attaching a reporter group to the corresponding amino acid of the second protein produces a functional biosensor.

The selected first protein (e.g., the amino acid sequence thereof) may be novel or known. However, in many instances, the function of the first protein will not be known. In a non-limiting example, identifying a protein not previously known to have glucose binding activity may comprise a structurally assisted functional evaluation (SAFE) homolog search method comprising the following steps:

(1) Collecting a sequence homology set using a BLAST sequence alignment tool starting with glucose-galactose binding protein (GGBP) sequence disclosed herein as a seed. Permissive settings are used, such that pairwise hits are required to have a minimum of only, e.g., 20%, 25%, 30%, 35% or 40% sequence identity with the seed sequence. The lengths of the hit and seed are mutually constrained such that the alignment covers at least, e.g., 60%, 65%, 70%, 85%, or 90% within each partner.

(2) Structure-based encoding of biological function: A primary complementary surface (PCS) comprising the protein residues that form hydrogen bonds and van der Waals contacts with a bound glucose is defined using computer-assisted, visual inspection of the three-dimensional structure of the GGBP-glucose complex. This definition specifies residue positions and their permitted amino acid identity. Multiple amino acid identities are permitted at each position to encode functionally equivalent residues. This definition establishes a search filter for the accurate prediction of glucose-binding proteins within the universe of sequence homologs collected in (1). For example, a candidate's residue corresponding to position 14 of ecGGBP may be D or N, a candidate's residue corresponding to position 16 of ecGGBP may be F, Y, or W, a candidate's residue corresponding to position 91 of ecGGBP may be N or D, a candidate's residue corresponding to position 152 of ecGGBP may be H, N, or Q, a candidate's residue corresponding to position 154 of ecGGBP may be D or N, a candidate's residue corresponding to position 158 of ecGGBP may be R, a candidate's residue corresponding to position 183 of ecGGBP may be W, F, or Y, a candidate's residue corresponding to position 211 of ecGGBP may be N or D, a candidate's residue corresponding to position 236 of ecGGBP may be D or N, and a candidate's residue corresponding to position 256 of ecGGBP may be N or D.

(3) Accurate sequence alignment: Tools such as ClustalW are used to construct an accurate alignment of all the sequence homologs. The GGBP seed sequence is included in the alignment. This multiple sequence alignment establishes the equivalent positions of the seed GGBP (primary complementary surface) PCS in each sequence homolog.

(4) Function evaluation: The glucose-binding properties of each of the aligned sequence homologs is determined by measuring their compliance with the PCS sequence filter. A "Hamming distance", H, is assigned for each homolog, which specifies the degree of sequence identity of all the residues at the aligned PCS positions. A value of H=0 indicates that the identities of all the residues at the aligned PCS positions match the amino acid(s) allowed in the PCS search filter; H>0, indicates that one or more aligned positions have disallowed residues. Sequences for which H=0 are predicted to encode glucose-binding proteins.

(5) Selection of representative SAFE homologs: The sequence homologs are ordered by (a) identity with the seed PCS, as measured by the Hamming distance, (b) fractional overall sequence identity with the seed sequence. A subset for sequences with H=0, sampling the fractional overall sequence identity is selected for experimental verification.

In a non-limiting example, identifying a protein not previously known to have glucose binding activity may comprises the following steps:

(1) performing a computational search of sequence databases to define a broad group of simple sequence or structural homologs of any known, glucose-galactose binding protein;

(2) using the list from step (1), deriving a search profile containing common sequence and/or structural motifs shared by the members of the list [e.g. by using computer programs such as MEME (Multiple Em for Motif Elicitation available at meme.sdsc.edu/meme/cgi-bin/meme.cgi) or BLAST];

(3) searching sequence/structural databases, using a derived search profile based on the common sequence or structural motif from step (2) as query (e.g., using computer programs such as BLAST, or MAST (Motif Alignment Search Tool available at meme.sdsc.edu/meme/cgi-bin/mast.cgi), and identifying a candidate sequence, wherein a sequence homology and/or structural similarity to a reference glucose-galactose binding protein is a predetermined percentage threshold;

(4) compiling a list of candidate sequences to generate a list of candidate glucose-galactose binding proteins;

(5) expressing the candidate glucose-binding proteins in a host organism; and (6) testing for glucose and/or galactose binding activity, wherein detection of glucose and/or galactose binding in said organism (or the media thereof) indicates that the candidate sequence comprises a novel glucose and/or galactose binding protein.

In non-limiting examples, the MEME suite of sequence analysis tools (meme.sdsc.edu/meme/cgi-bin/meme.cgi) can also be used as an alternative to BLAST. Sequence motifs are discovered using the program "MEME". These motifs can then be used to search sequence databases using the program "MAST." The BLAST search algorithm is well-known.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

ecGGBP, 2, NC_013654|YP_003350022.1, *Escherichia coli,* 100%;

ttGGBP, 96, NC_014410|YP_003852930.1, *Thermoanearobacterium thermosaccharolyticum,* 48%;

cobGGBP, 94, NC_014392|YP_003839461.1, *Caldicellosiruptor obsidiansis,* 48%;

chyGGBP, 101, NC_014652|YP_003991244.1, *Caldicellulosiruptor hydrothermalis,* 47%;

pspGGBP, 112, NC_013406|YP_003243743.1, *Paenibacillus* sp., 44%;

ereGGBP, 123, NC_012781|YP_002936409.1, *Eubacterium rectale,* 37%;

cauGGBP, 127, NC_022592|CAETHG_2982, *Clostridium autoethanogenum,* 36%;

erhGGBP, 124, N_015601|YP_004561181.1, *Erysipelthrix rhusiopathiae,* 36%;

rinGGBP_B, 126, NC_021012|YP_00777811241, *Roseburia intestinalis,* 36%;

cljGGBP, 128, NC_014328|CLJU_c08950, *Clostridium ljunghaldii,* 35%;

fprGGBP, 129, NC_021020|YP_007799070.1, *Faecalibacterium prausnitzii,* 34%;

rinGGBP_A, 132, NC_021012|YP_007778116.1, *Roseburia intestinalis,* 33%;

bprGGBP, 137, NC_014387|YP_003830205.1, *Butyvibrio proteoclasticus,* 30%;

csaGGBP, 138, NC_014376|YP_003822565.1, *Clostridium saccharolyticum,* 29%.

Numbering according to ecGGBP. Light grey: leader peptides; dark grey, primary complementary surface (PCS) residues; -, position of insertions. Positions of the α helices ($\alpha_x$), β sheets ($\beta_x$) inter-domain hinge segments ($h_x$), and calcium binding site EF hand (EF) observed in the ecGGBP structure are indicated.

Figure 4A:
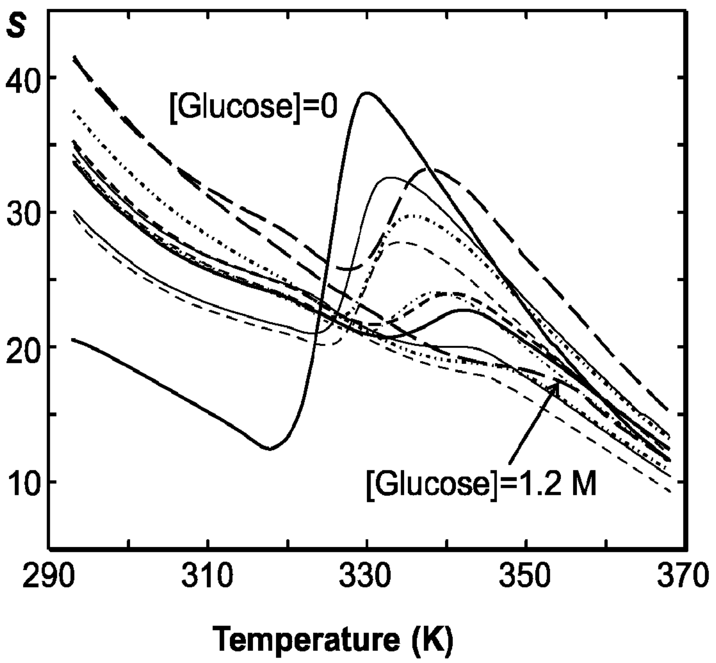
Figure 4B:
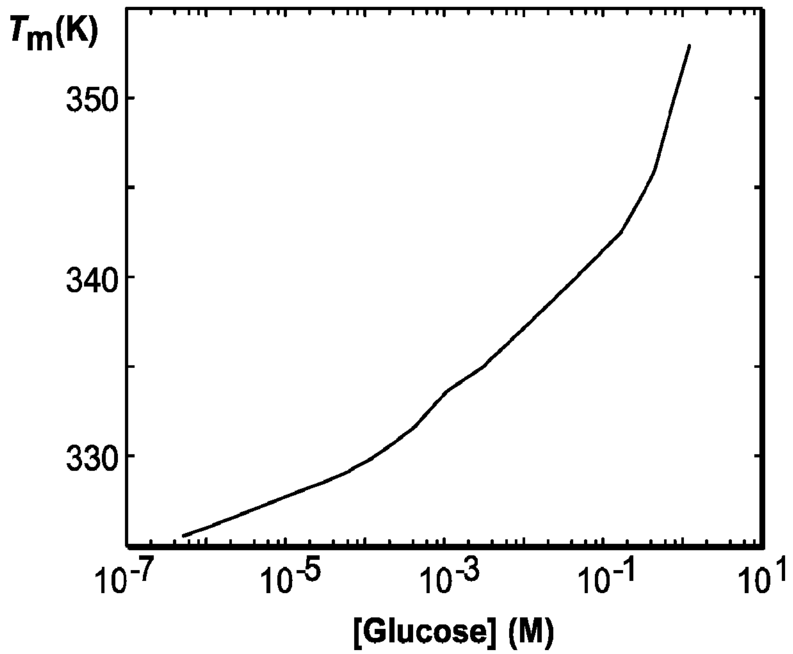
Figure 5:
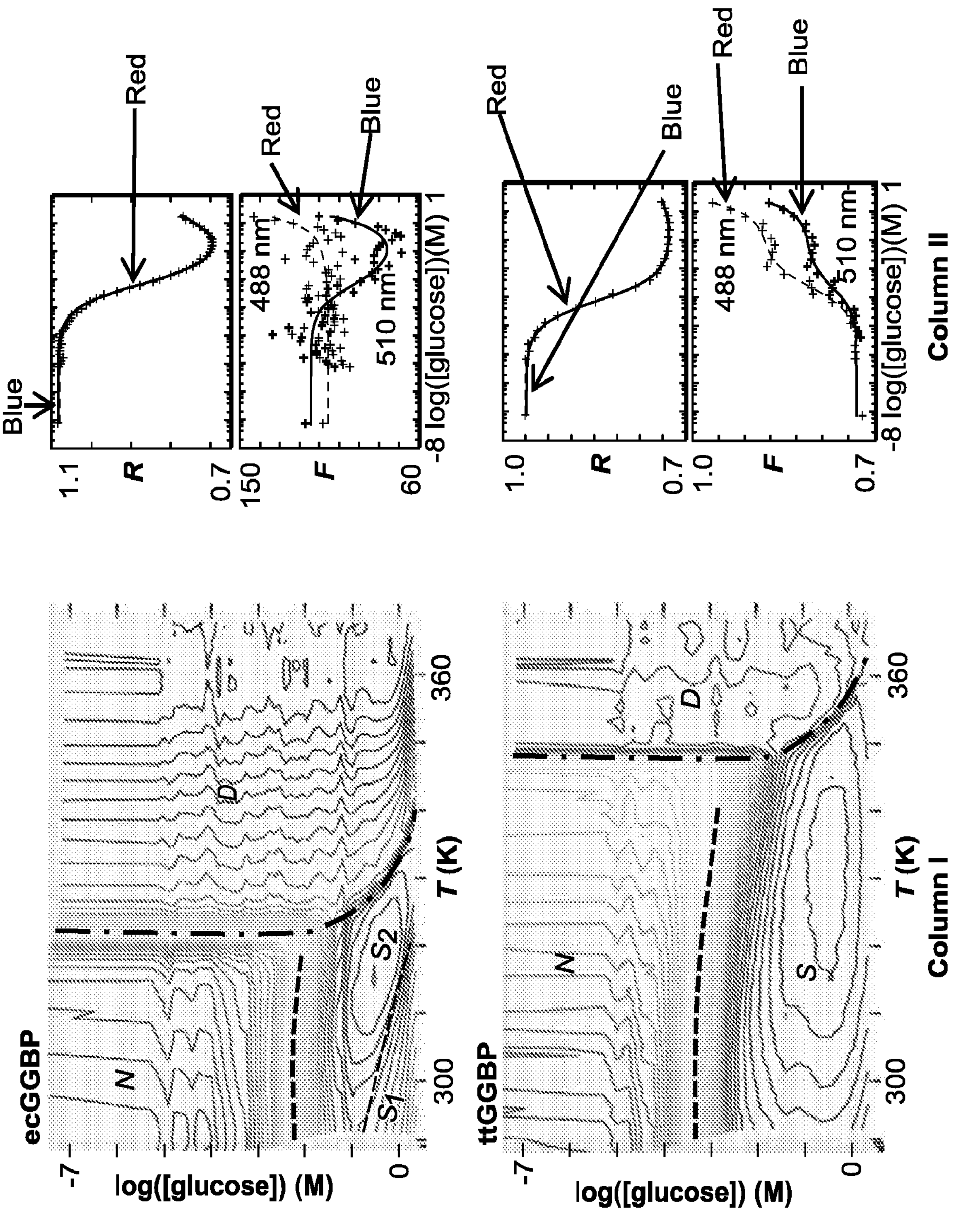
Figure 5:
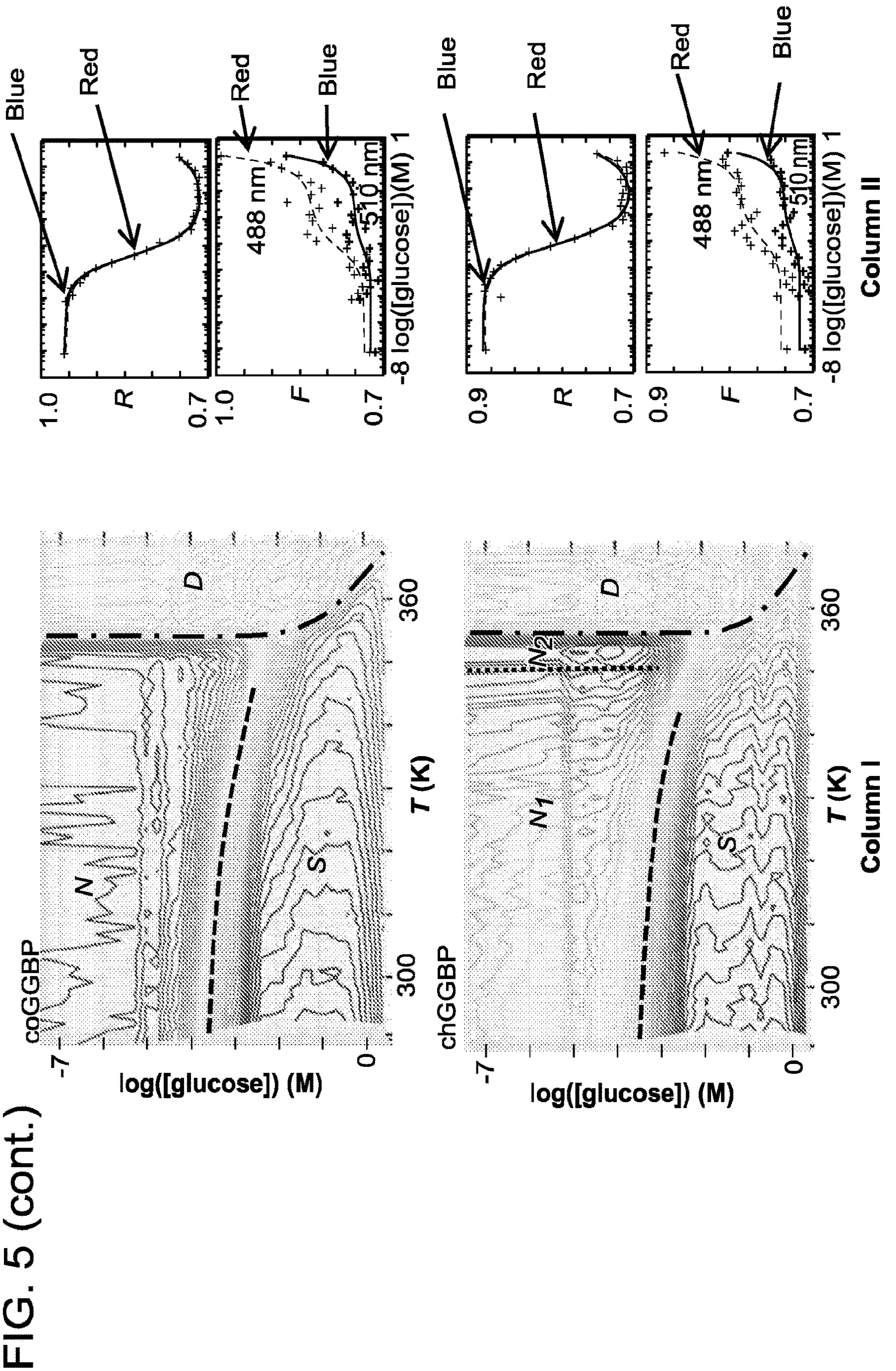

FIGS. 4A and 4B are graphs relating to the analysis of glucose binding by ligand-mediated increases in protein thermostability. Protein (un)folding is monitored by binding of SYPRO to the unfolded state as a function of temperature. Fluorescence intensity increases upon binding of SYPRO by the unfolded state. (A) Temperature dependence of fluorescence emission intensity of csaGGBP (see Tables 1 and 2) in the presence of varying amounts of glucose. (B) The midpoint denaturation temperature, $T_m$, increases upon addition of glucose, indicative of glucose binding to the folded state of csaGGBP, as predicted FIG. 5 is a series of graphs showing temperature- and glucose-dependent ratiometric fluorescent landscapes of the Acrylodan conjugates of GGBP homologs. Rows correspond to the *E. coli* (ecGGBP), *T. thermosaccharolyticum* (ttGGBP), *C. obsidiansis* (cobGGBP), and *C. hydrothermalis* (chyGGBP) glucose-galactose binding proteins site-specifically labeled with Acrylodan at the endosteric cysteine mutation replacing the tryptophan that contacts the glucose pyranose ring (W183 in ecGGPB). Column I: Three-dimensional landscapes representing the ratio of fluorescence emission intensities (Z axis) at 488 nm and 510 nm as a function of temperature and glucose concentration. Indicated are the main equilibrium states: N, native apo-protein; D, denatured protein; S, saturated glucose complex. Subscripts indicate temperature-dependent conformational substates (see main text). Dotted lines indicate approximate mid-points (i.e. ΔG=0) for the equilibria of the underlying reactions: black lines (----), binding; red (-•-•-), thermal denaturation; purple (••••), thermal conformational changes. Column II: Examples of isothermal glucose-binding curves, determined at 310 K (37° C.). For each protein, two panels are shown: top, fit to the ratiometric signal (red line, fit to the ratiometric data only; blue line, joint fit to ratiometric and monochromatic emission intensities); bottom, fit to monochromatic emission intensities (red, 488 nm; blue, 510 nm).

Figure 6A:
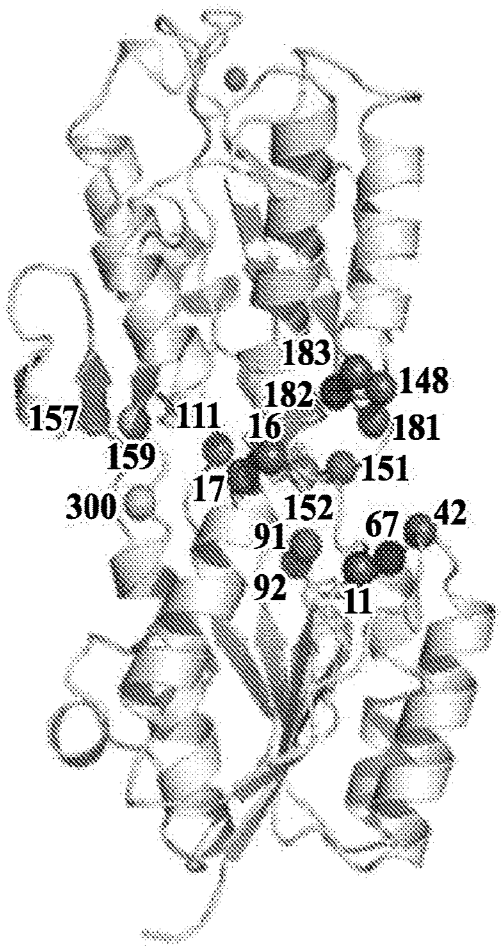
Figure 6B:
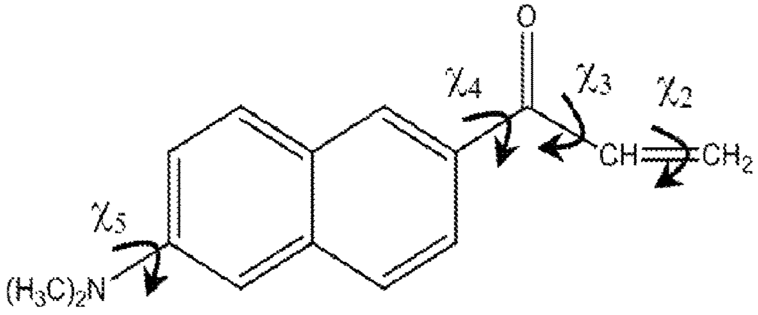
Figure 6C:
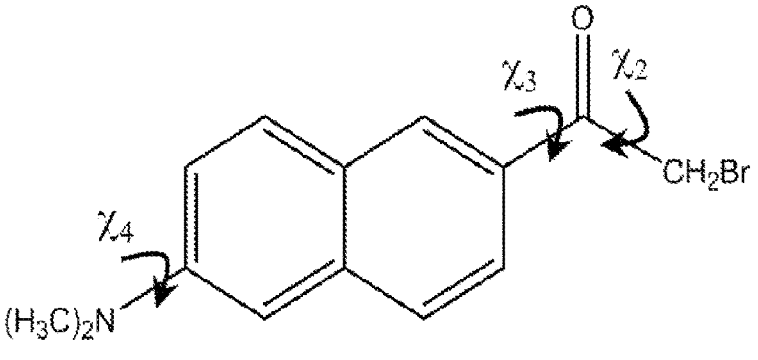

FIG. 6A is a structure showing exemplary positions for introducing cysteine mutations to which fluorophores can be covalently coupled for reagentless biosensor construction are indicated: positions 157, 159, and 300, endosteric; positions 11, 16, 42, 67, 92, 111, 148, 181, and 183, peristeric; positions 17, 91, 151, and 182, allosteric. FIG. 6B shows a structure of Acrylodan. FIG. 6C shows a structure of Badan.

FIG. 7A-F is a series of graphs for glucose-dependent emission spectra of Acrylodan and Badan conjugates of Y11C, F17C and W182C mutants of ttGGBP. Corrected spectra (apo-protein, red; saturated glucose, purple; intermediate glucose concentrations, black): left column, Acrylodan; right column, Badan. Insets, fit of the ratiometric signal (equation 1 and 2; 20 nm integration bandwidth): blue circles, experimentally observed ratios; black line, calculated fit (baselines; apo-protein, constant; saturated glucose complex, linear). (A) Y11C•Acrylodan (isochromic; $\lambda_1$, 458 nm; $\lambda_2$, 511 nm; ${}^{app}K_d$, 0.14 mM); (B) Y11C•Badan (hypsochromic; $\lambda_1$, 492 nm; $\lambda_2$, 528 nm; ${}^{app}K_d$, 0.28 mM); (C) F17C•Acrylodan (hypsochromic; $\lambda_1$, 482 nm; $\lambda_2$, 545 nm; ${}^{app}K_d$, 0.08 mM); (D) F17C•Badan (hypsochromic; $\lambda_1$, 470 nm; $\lambda_2$, 542 nm; ${}^{app}K_d$, 0.18 mM); (E) F182C•Acrylodan (bathochromic; $\lambda_1$, 475 nm; $\lambda_2$, 545 nm; ${}^{app}K_d$, 2.2 mM); (F) F182C•Badan (isochromic; $\lambda_1$, 474 nm; $\lambda_2$, 518 nm; ${}^{app}K_d$, 26 mM).

Figure 8A:
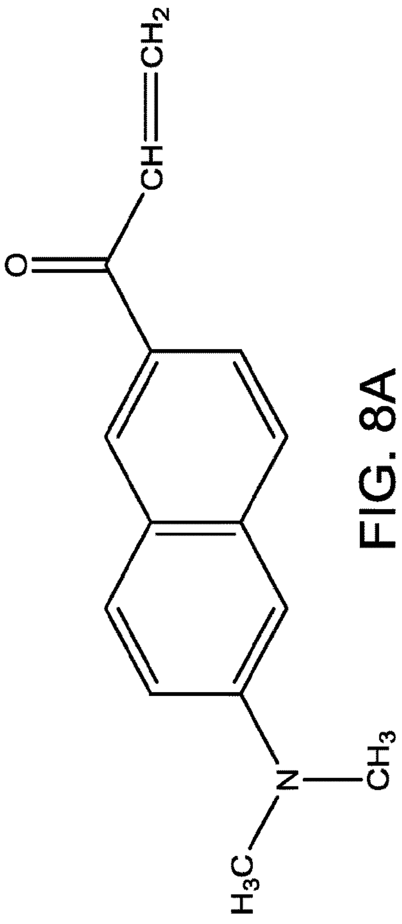
Figure 8B:
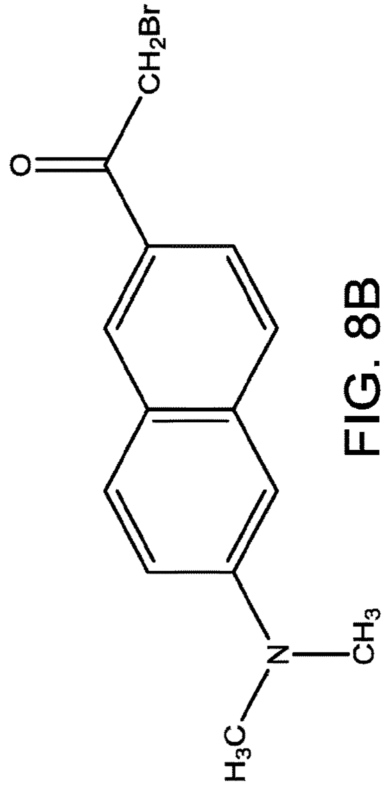
Figure 8C:
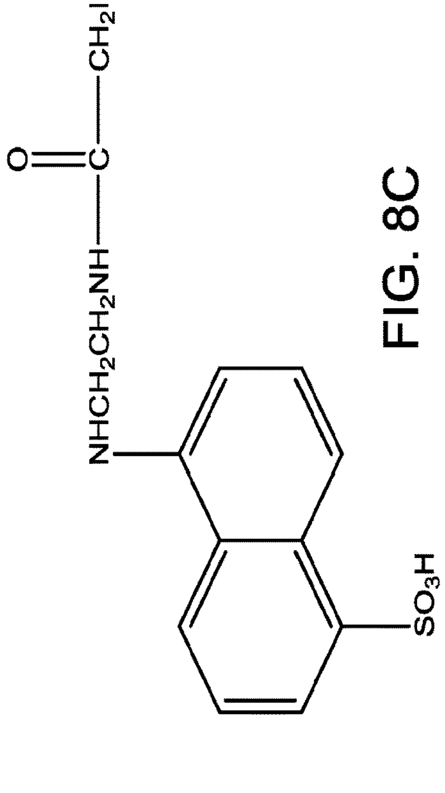
Figure 8D:
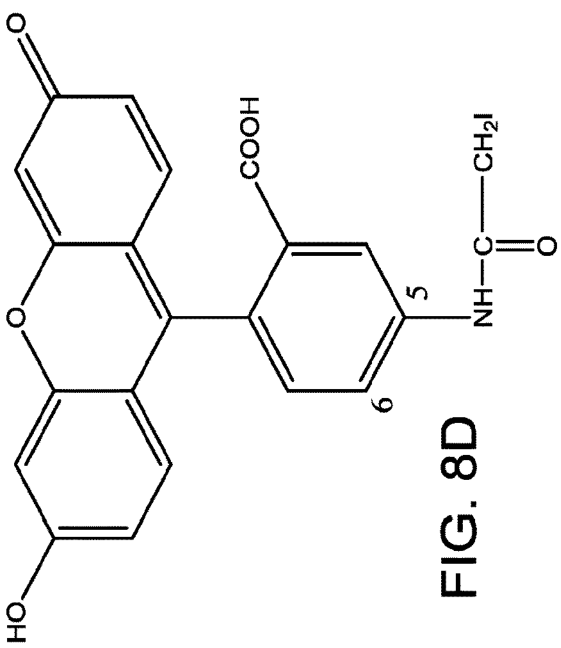
Figure 8E:
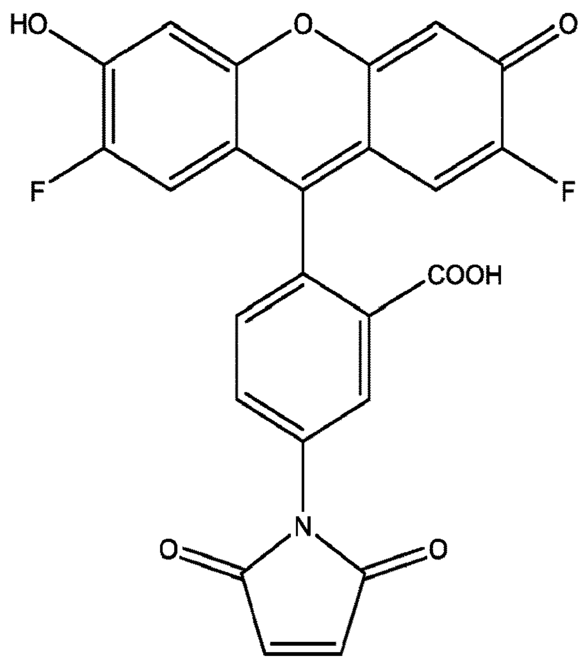
Figure 8F:
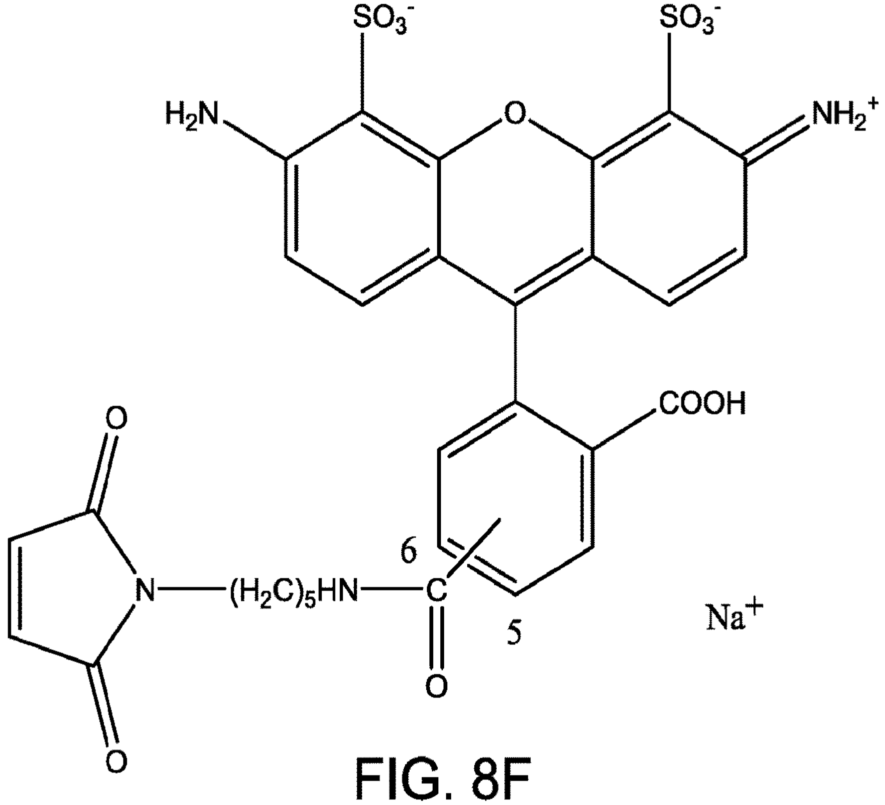
Figure 8G:
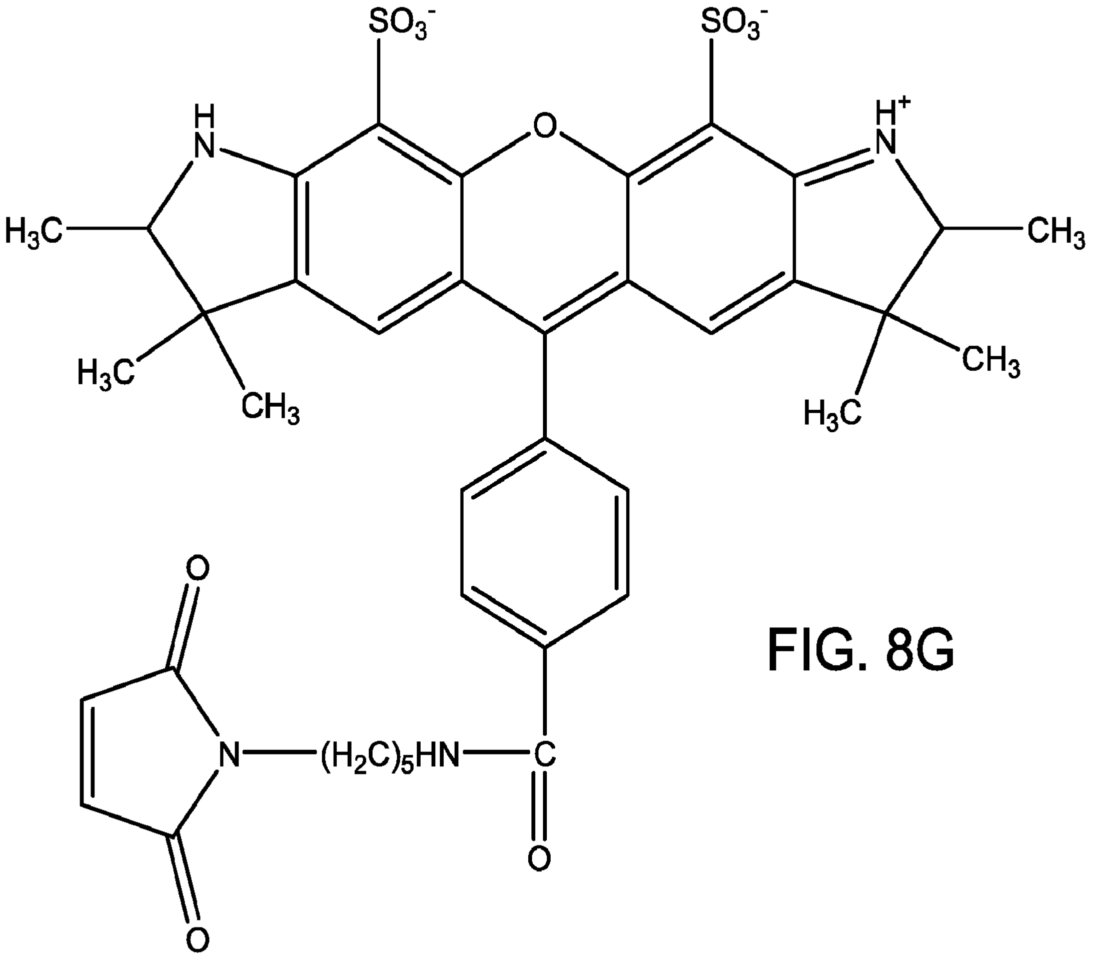
Figure 8H:
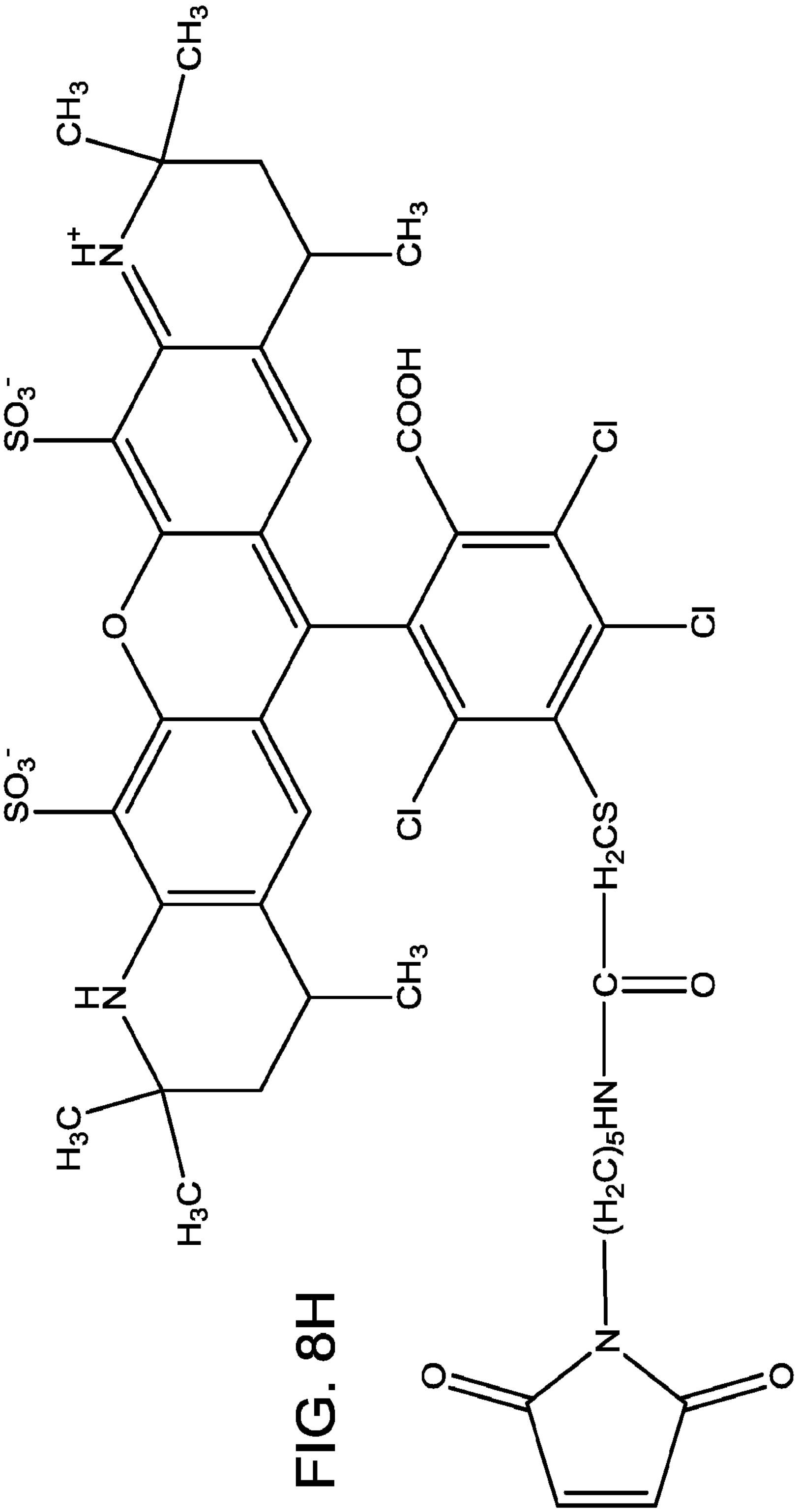
Figure 8I:
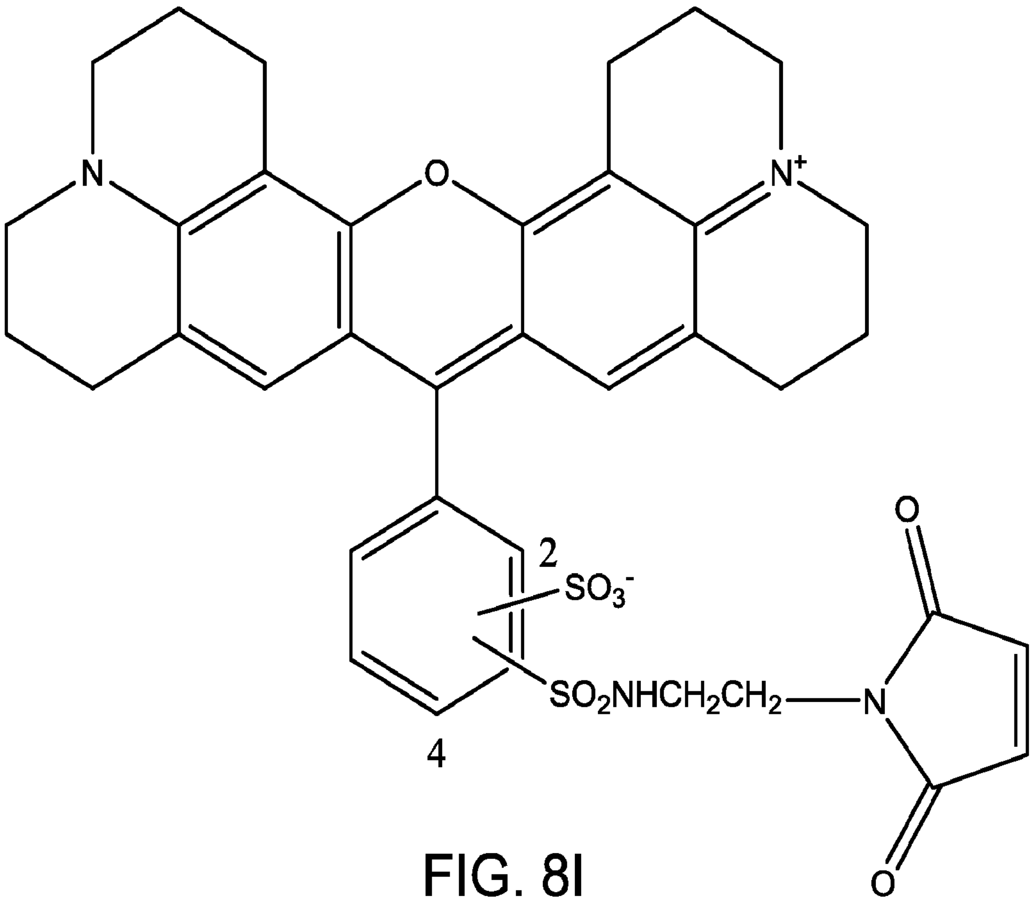
Figure 8J:
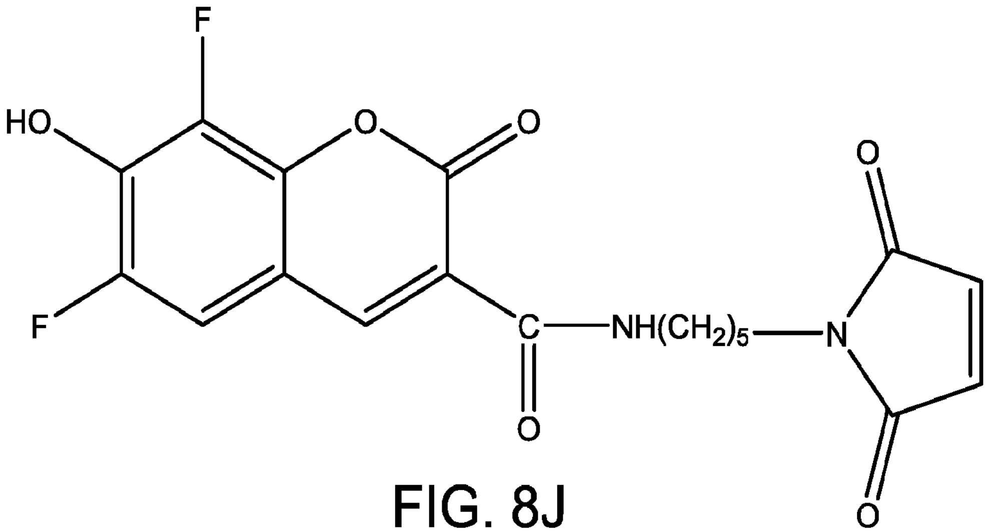
Figure 8K:
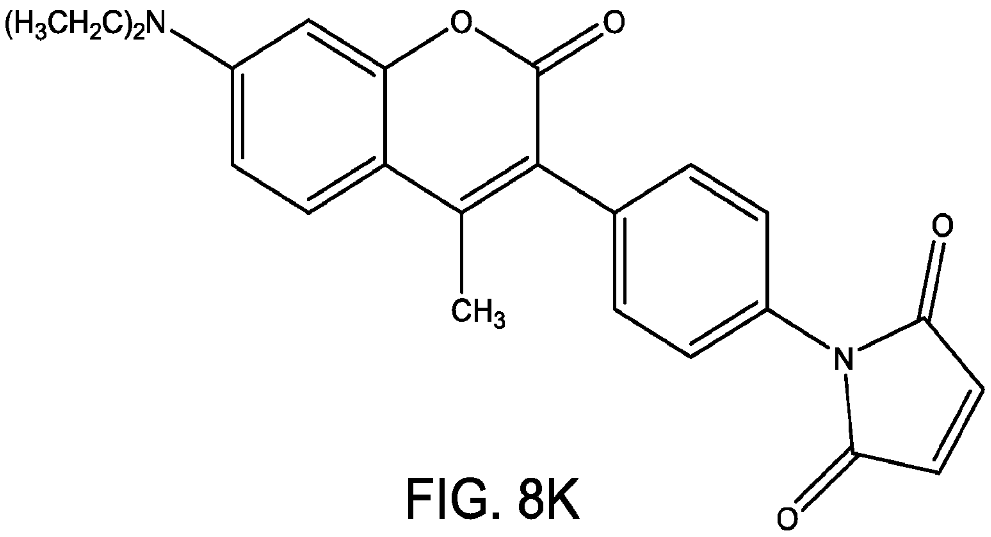
Figure 8L:
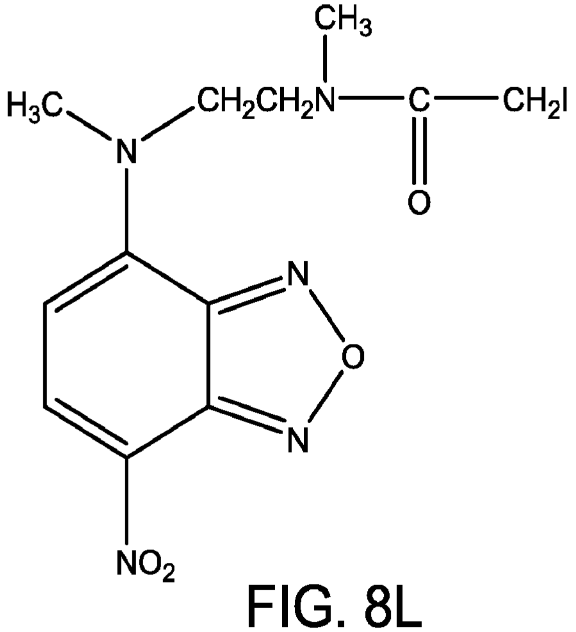
Figure 8M:
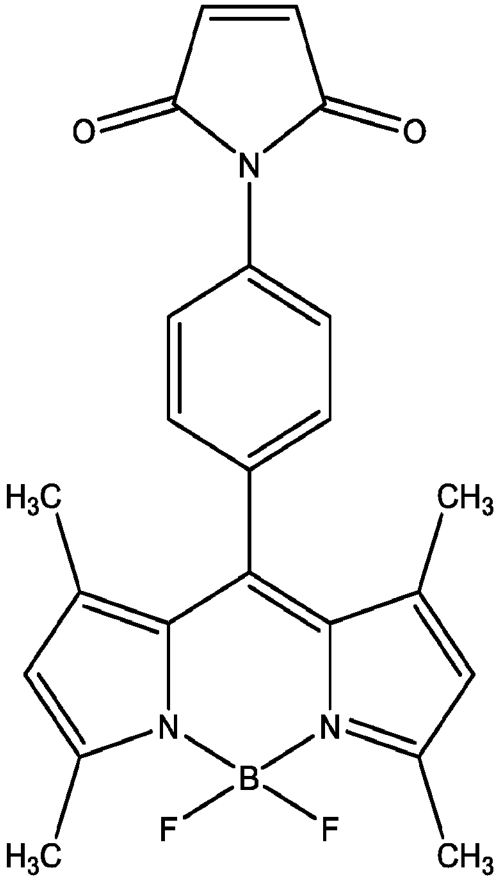
Figure 8N:
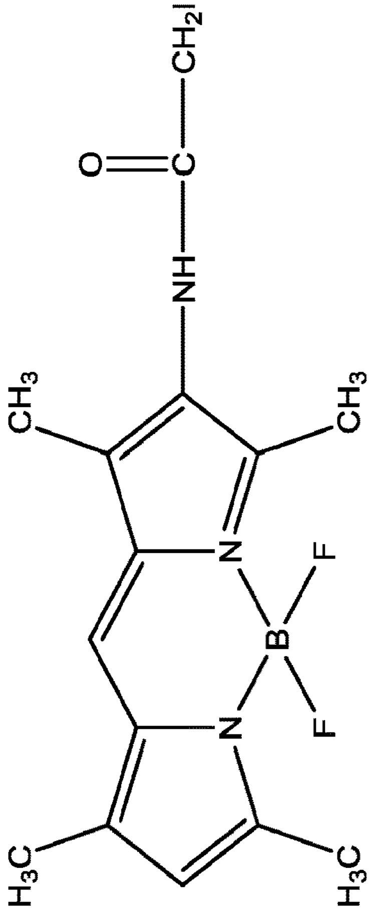
Figure 8O:
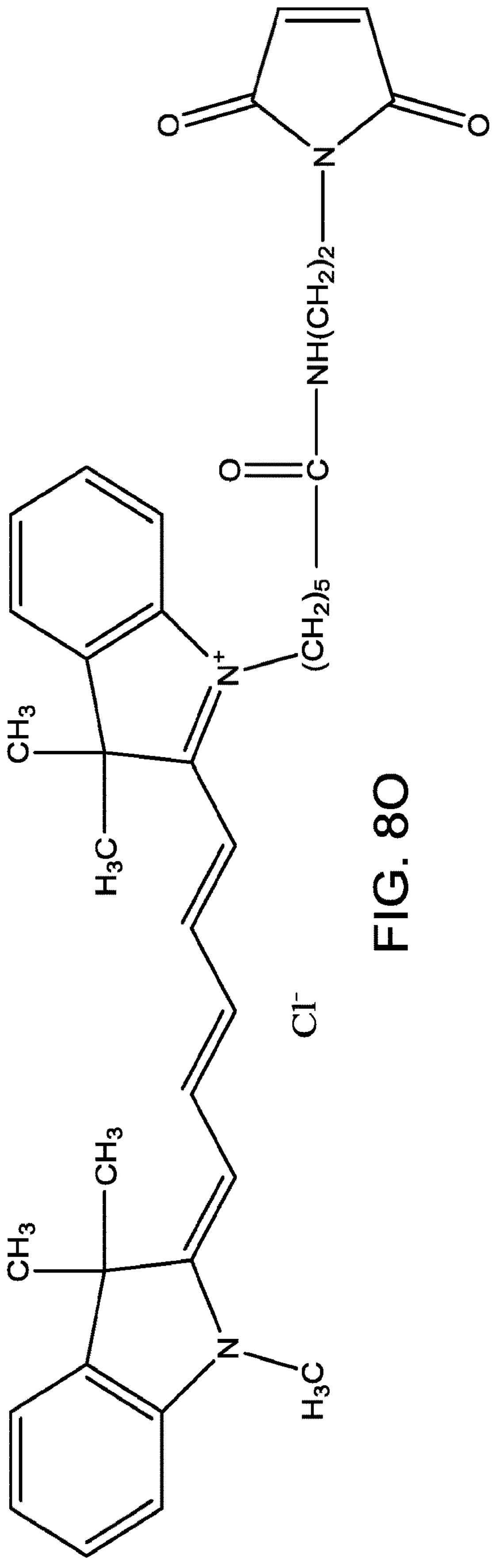
Figure 8P:
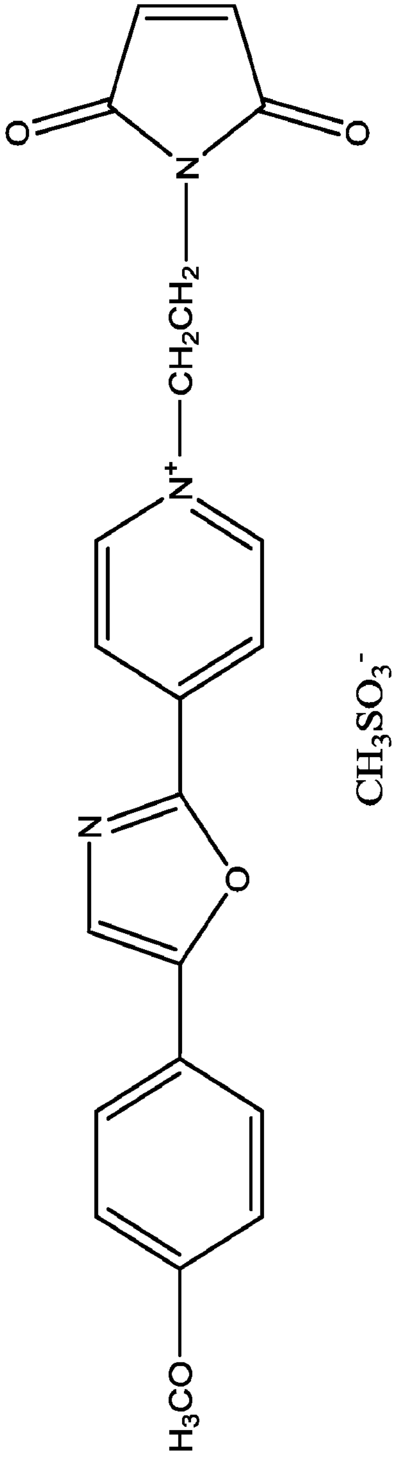

FIGS. 8A-P are illustrations of fluorophore structures. Naphthalene family: (A) Acrylodan; (B) Badan; (C) IAEDANS. Xanthene family: (D) Fluorescein (5-IAF and 6-IAF); (E) Oregon Green; (F) Alexa 432; (G) Alexa 532; (H) Alexa 546; (I) Texas Red. Coumarin family: (J) Pacific Blue; (K) CPM. Benzoxadiazole family: (L) IANBD. Boradiazaindacine (BODIPY) family: (M) BODIPY 499/508; (N) BODIPY 507/545. Cyanine family: (O) Cy5. Miscellaneous: (P) PyMPO.

FIGS. 9A-H are illustrations of structures of ttGGBP conjugates determined by X-ray crystallography. (A) Overview of the ttGGBP F17C•Badan conjugate, viewed from the back of the protein looking through the three hinge strands ($h_1$-$h_3$). W182 (magenta) forms extensive van der Waals contacts (translucent surface) with the bound glucose (cyan). The F17C mutation removes the wild-type contacts (translucent surface) between the benzene ring and glucose. The Badan conjugate (blue) points out of the glucose-binding site into the solvent. (B) Overview of the ttGGBP182C2.0•Acrylodan conjugate (note that the view point is different from (A). The conjugated Acrylodan also points out into solution. (C) Cutaway illustrating the channels surrounding the bound glucose within which Badan, Acrylodan, and the galactoside R-group (Sooriyaarachchi et al. 2009) (dark gray) are placed. The view is down the long axis of ttGGBP, looking at the glucose-binding surface of the N-terminal domain. The C-terminal domain (with $Ca^{2+}$ site) has been cut away (bisecting the hinge). (D) The electronic densities of the Badan fluorophore and bound sugar are well defined (gray lines, $2F_o$-$F_c$ electron density at 1σ contour levels). (E) Close-up side-view of Badan illustrates that the fluorophore carbonyl is twisted out the of the naphthalene ring plane. (F) End view, looking down the linker towards the exterior of the binding site shows that the carbonyl torsion is ~28° (gray lines, $2F_o$-$F_c$ electron density at 1σ contour levels; arrow, cysteine thiol). (G) The same view of the ecGGBP W183C•Acrylodan shows that in this fluorophore the carbonyl is co-planar with the naphthalene ring (blue lines, $2F_o$-$F_c$ electron density at 1σ contour levels; arrow, cysteine thiol). (H) Close-up view of the fit between the fluorophore carbonyl knob into the hole (translucent surface) formed by van der Waals contacts with D238 and N258.

Figure 10A:
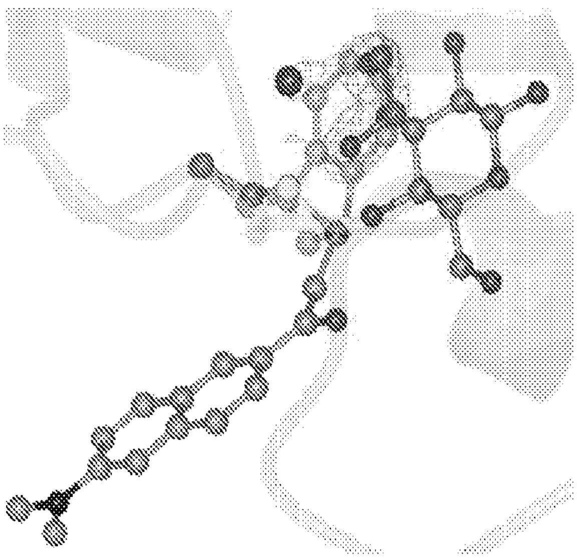

FIGS. 10A and B are structures relating to structure-guided design of affinity mutants. (A) The ttGGBP182C2.0 Acrylodan conjugate structure reveals the presence of a cavity filled with water and the cryoprotectant ethylene glycol, replacing the indole ring of the mutated tryptophan. (B) Inter-domain hydrogen bonds that have been mutated.

FIGS. 11A-C are graphs relating to the determination of ${}^{true}K_d$ and ${}^{app}K_d$ values for glucose in ttGGBP182C.2.0 (see Table 5). (A) Glucose dependence of the fluorescence emission intensities for the ttGGBP182C.2.0•Acrylodan mutant conjugate (see Table 4). Arrows indicate direction of change with increased glucose concentrations. (B) Determination of ${}^{app}K_d$ using ratiometry the emission intensities (R) at 475 nm and 545 nm (20 nm bandwidth). (C) Determination of ${}^{true}K_d$ by monochromatic fits the two ratiometric intensities (I(λ): green, 475 nm; red, 545 nm). Values for ${}^{app}K_d$ (4.5 mM) and ${}^{true}K_d$ (6.0 mM) were simultaneously fit to the three experimental binding isotherms using equations 1 and 5 using constant baselines for both the apo- and saturated protein, with the two monochromatic isotherms sharing the same ${}^{true}K_d$ value.

Figure 12A:
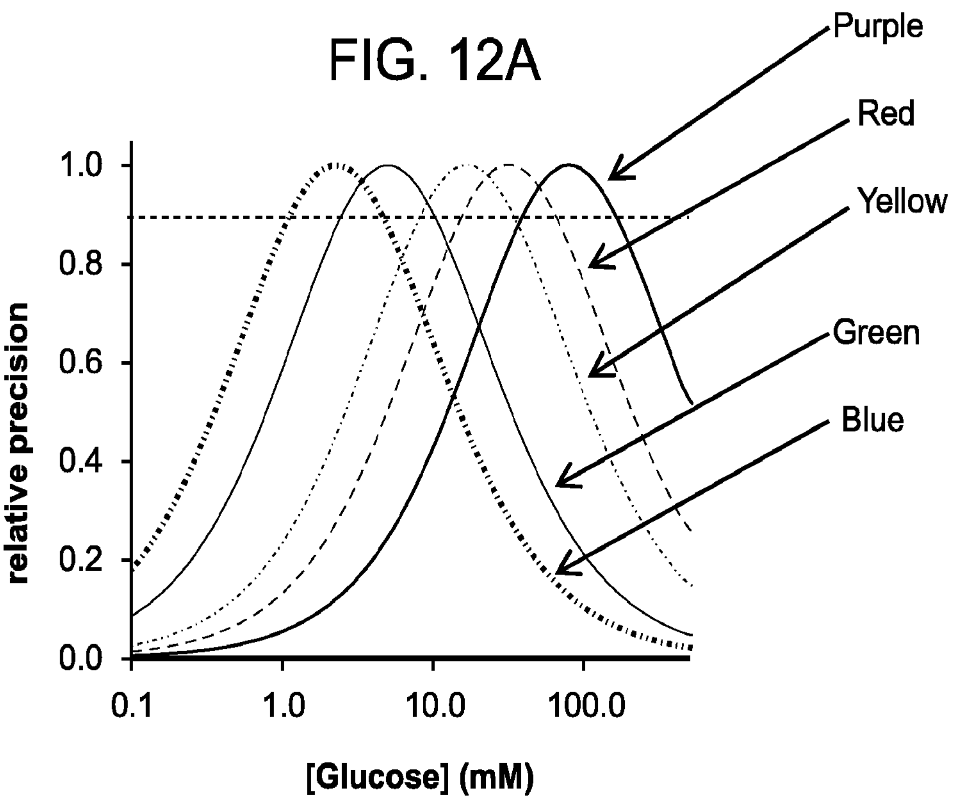
Figure 13:
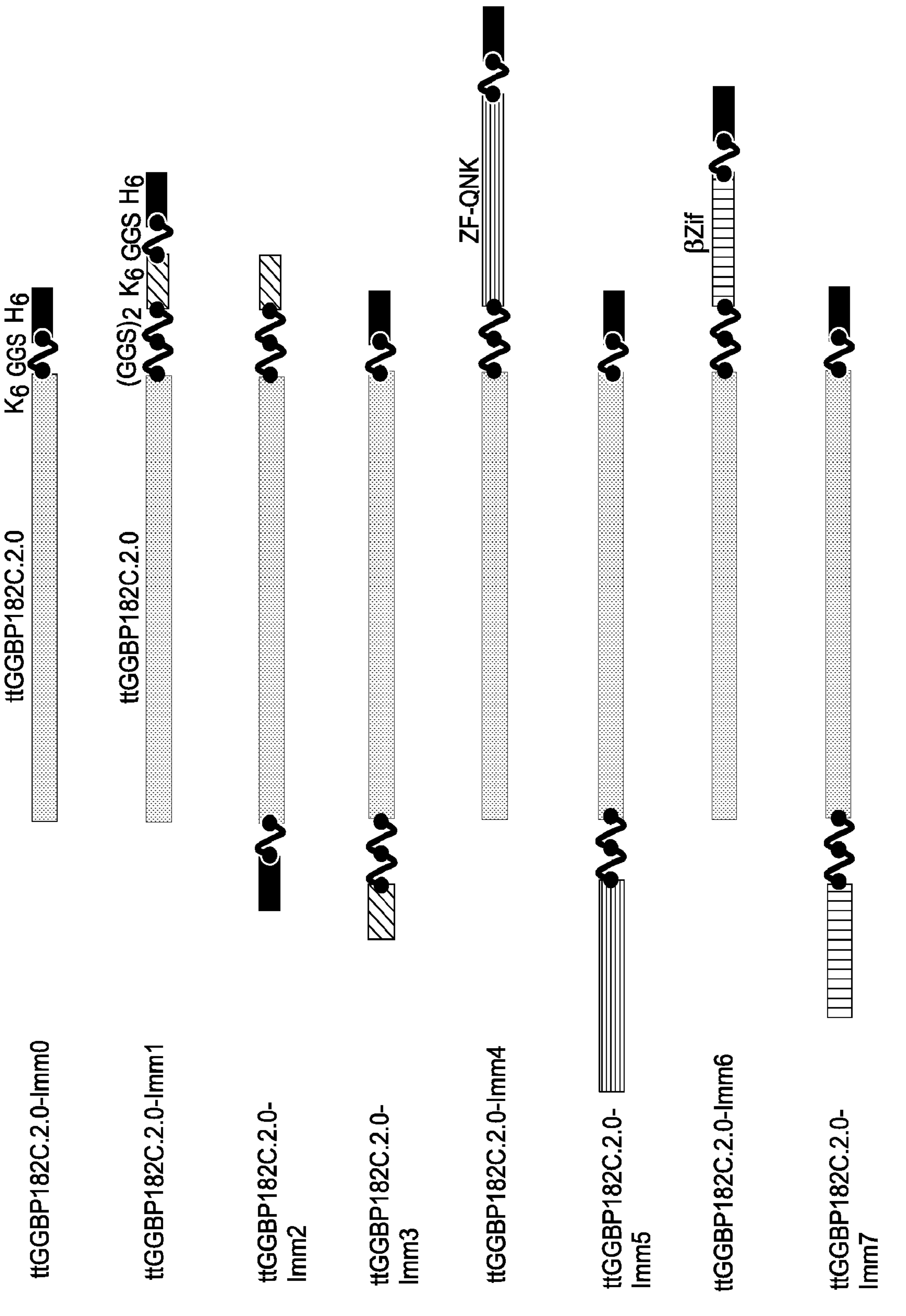

FIGS. 12A and B are graphs showing that a sensor arrays that combine several ttGGBP mutants (Table 6) could span the full pathophysiological range at better than 90% of maximal possible precision. (A) Mutants in the ttGGBP182C Acrylodan background. The responses are shown as relative precision, calculated from the fits to the experimental data according to equation 8, from left to right: ttGBP182C, hypoglycemia; ttGGBP182C.2.0, euglycemia; ttGGBP182C.2.3, mild hyperglycemia; ttGGBP182C.8, severe hyperglycemia; ttGGBP182C.9, hyperosmolar hyperglycemic state. (B) Mutants in the ttGGBP17C Badan background. Ratiometric signals are shown from left to right: ttGGBP 17C•Acrylodan (${}^{app}K_d$=0.06 mM), ttGGBP 17C.1•Badan (${}^{app}K_d$=1.2 mM), ttGGBP 17C.3•Badan (${}^{app}K_d$=3.9 mM), ttGGBP 17C.5•Badan (${}^{app}K_d$=19.3 mM). Black circles: experimental data points FIG. 13 is a set of cartoons showing fusion constructs for sensor immobilization. Light gray, ttGGBP182C.2.0; diagonal striped, hexa-lysine immobilization tag; dark gray, hexa-histidine affinity purification tag; horizontal striped, ZF-QNK zinc finger domain; vertical striped, truncated zinc finger βZif domain; wavy line, Gly-Gly-Ser linker (two segments, indicate Gly-Gly-Ser-Gly-Gly-Ser). Left column, names of constructs.

FIGS. 14A-F are graphs showing that the immobilization of ttGGBP182C2.0•Acrylodan does not affect its thermostability. Thermostabilities were determined by measuring the ratio fluorescence emission intensities through 488 nm and 510 nm filters as a function of temperature in a Roche LightCycler. Panels A-C: ttGBP182C.2.0-Imm0; Panels D-F: ttGBP182C.2.0-Imm1 (see FIG. 13). (A) Solution ($T_m$=347.6K). (B) Immobilized on Nickel-nitriloacetic acid (Ni-NTA) beads ($T_m$=346.7K). (C) Reconstituted, desiccated Ni-NTA beads ($T_m$=347.6K). (D) Fluorescence response of ttGGBP5.2 Imm1 immobilized on NHS-functionalized agarose beads. Data was collected on a Roche LightCycler real-time PCS instrument, recording emission intensities at 488 nm and 510 nm as a function of temperature in a 384-well microtiter plate. Wells contain beads with labelled, immobilized protein in hydrogel at different glucose concentrations. Temperature melts of twelve different wells. Apo protein thermostability as reported by the denaturation mid-point temperature is 349 K, similar to the protein free in solution. (E) The three-dimensional landscape showing ratiometric signal as a function of glucose concentration and temperature is essentially indistinguishable from the protein free in solution. (F) Representative Langmuir ligand-binding curve extracted from the three-dimensional data. The $K_d$ (glucose) value at 25° C. is 4.8 mM, which is similar to the protein free in solution.

Figure 15:
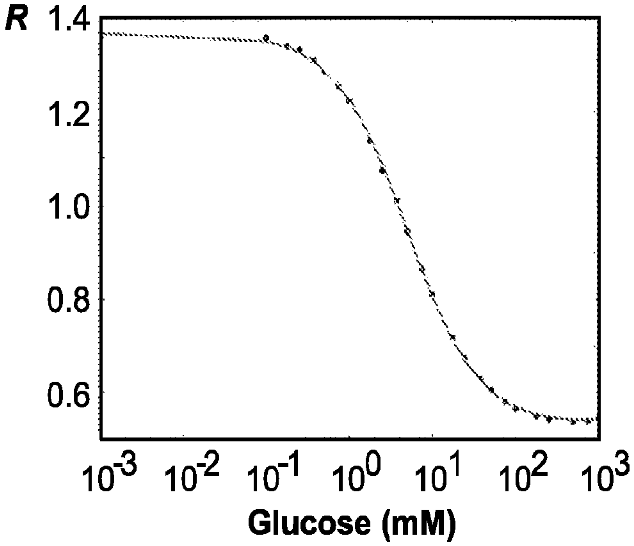

FIG. 15 is a graph of a glucose titration curve determined for magnetic Ni-NTA beads coated with immobilized ttGGBP182C2.0•Acrylodan. Data were highly precise, being reproducible <0.2% coefficient of variance.

FIGS. 16A-F are graphs showing the singular value decomposition of the glucose-dependent corrected spectra of Acrylodan and Badan conjugates of Y11C, F17C and W182C mutants of ttGGBP. (A) Y11C•Acrylodan; (B) Y11C•Badan; (C) F17C•Acrylodan; (D) F17C•Badan; (E) F182C•Acrylodan; (F) F182C•Badan. Frequency transformations of the spectra (equation 11) were decomposed into principal components (equation 12). The contribution of the first component, $C_1$ (black), is largely invariant with glucose concentration, whereas the second component, $C_2$ (gray), encode accounts for the glucose-dependent changes in the spectra (component contributions are given in Table 1). Inserts, glucose dependence of the fractional contribution of each component (equation 13).

Figure 16A:
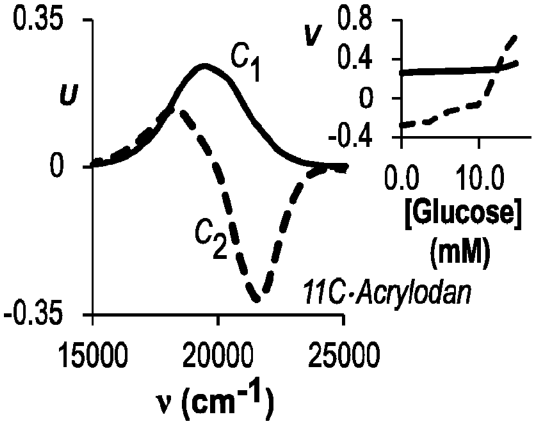
Figure 16B:
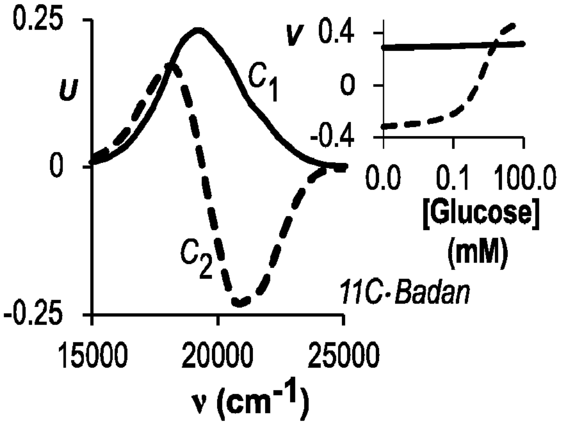
Figure 16C:
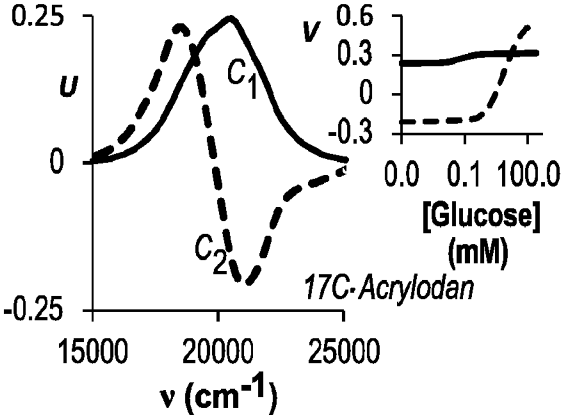
Figure 16D:
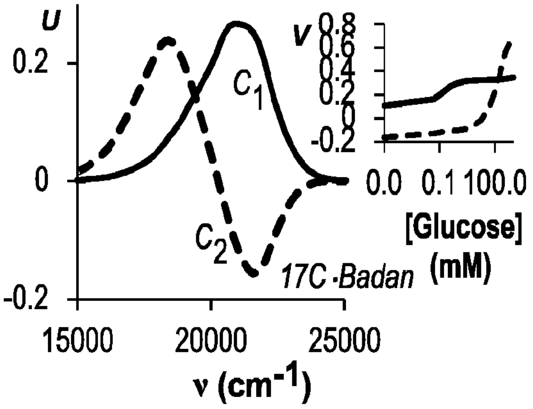
Figure 16E:
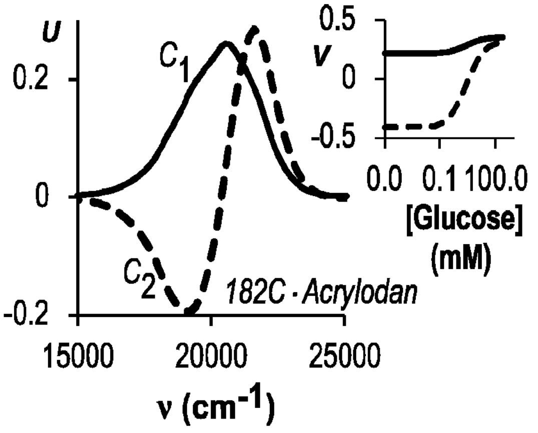
Figure 16F:
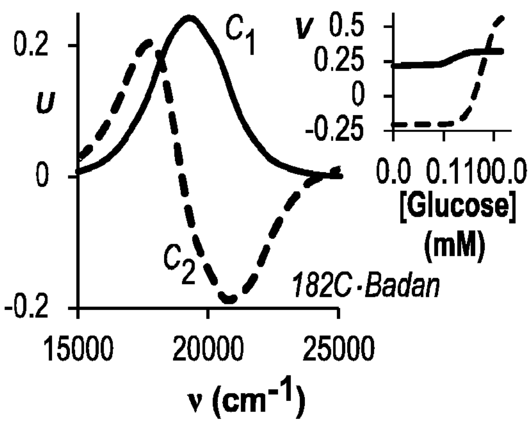
Figures 17A, 17B, 17C, 17D:
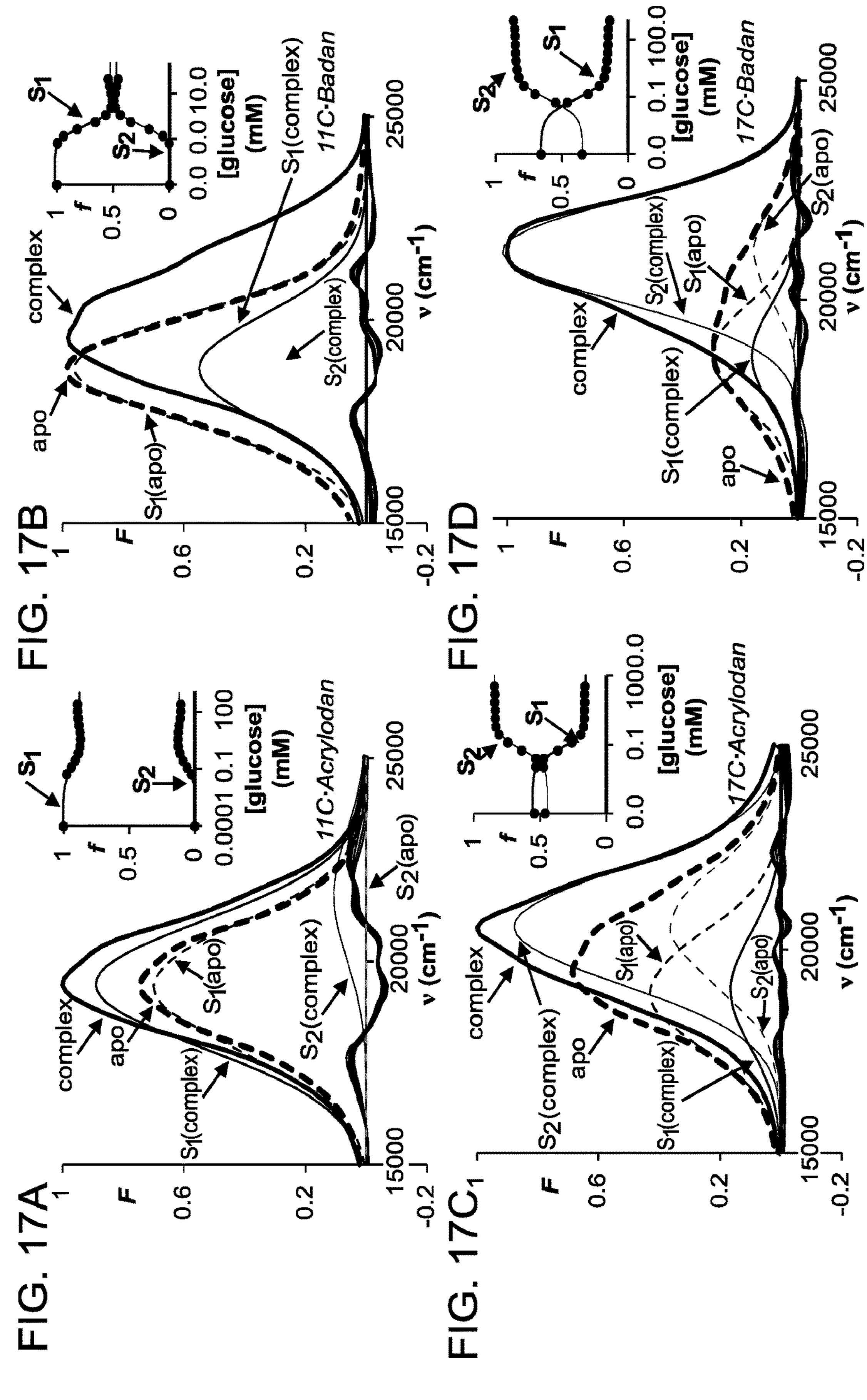
Figure 17F:
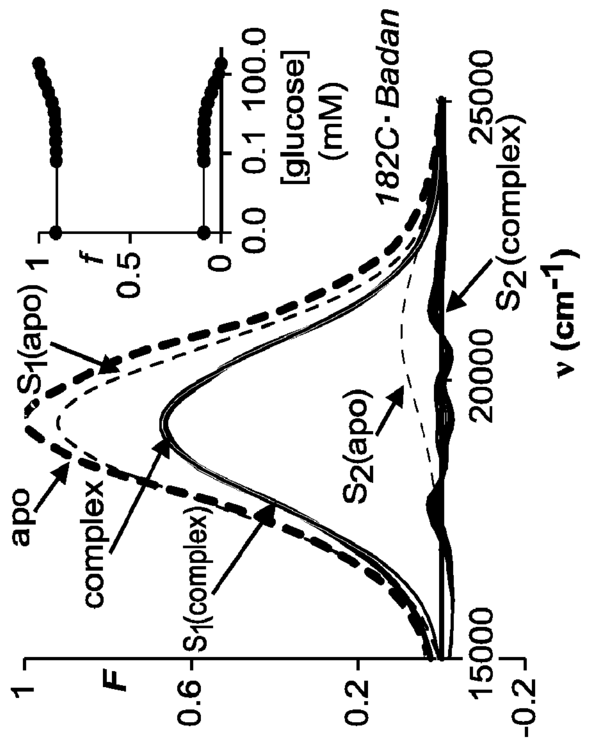
Figure 17E:
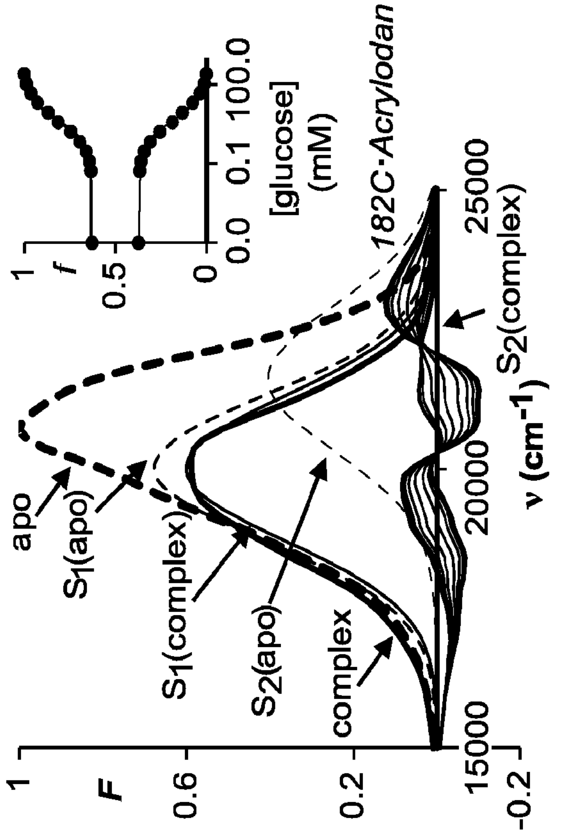
Figure 18A:
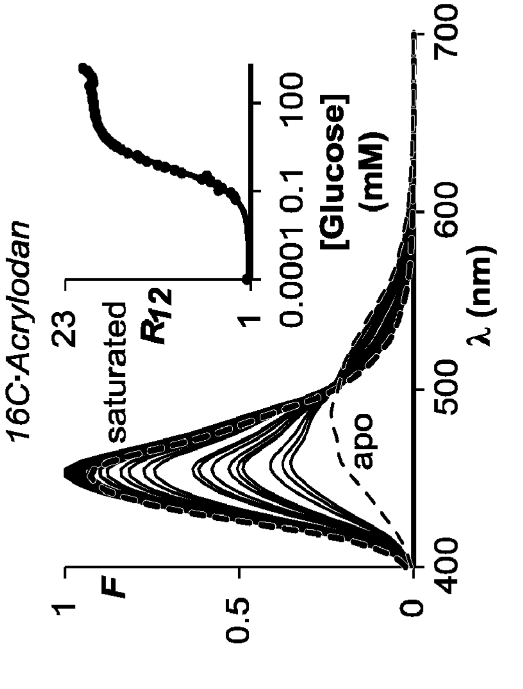
Figure 18B:
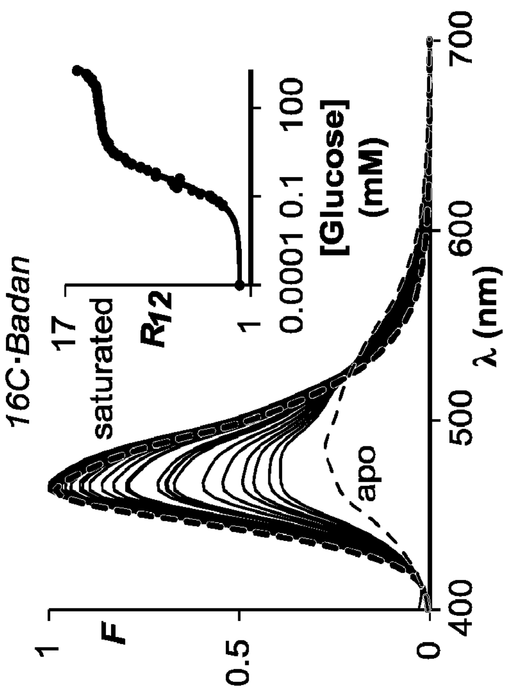
Figure 18C:
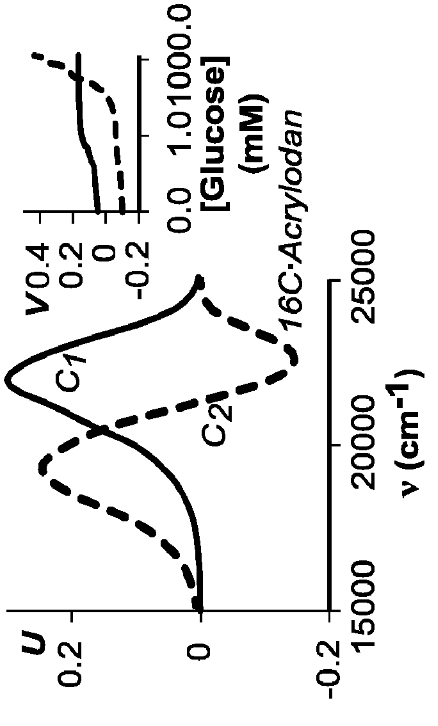
Figure 18D:
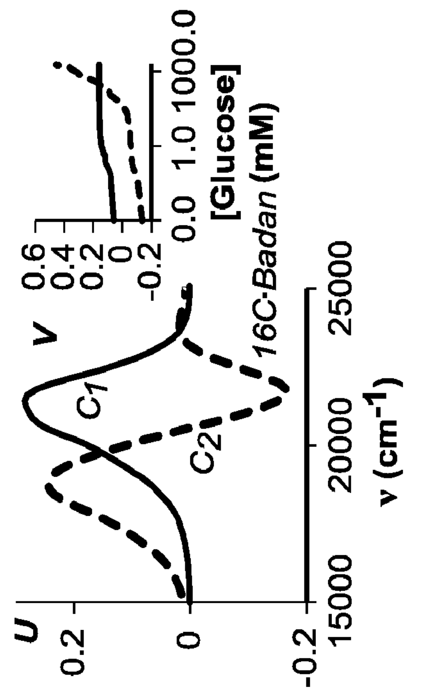
Figure 18E:
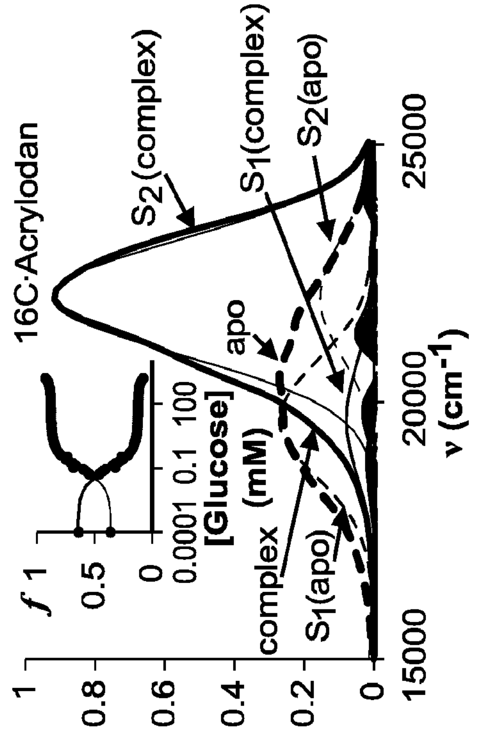
Figure 18F:
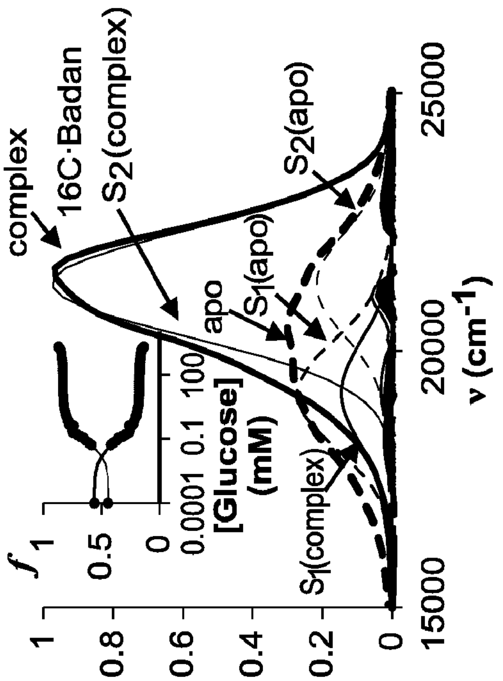
Figure 18G:
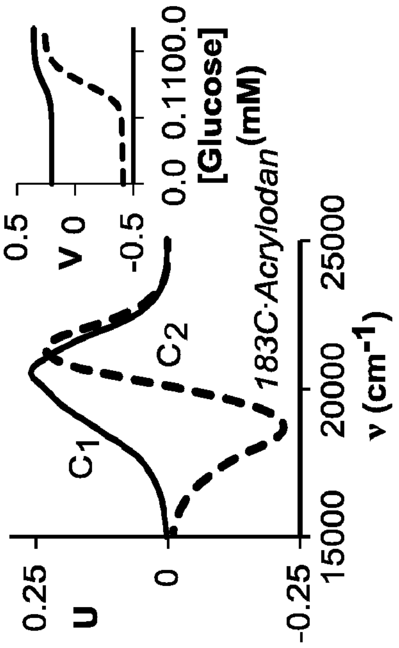
Figure 18H:
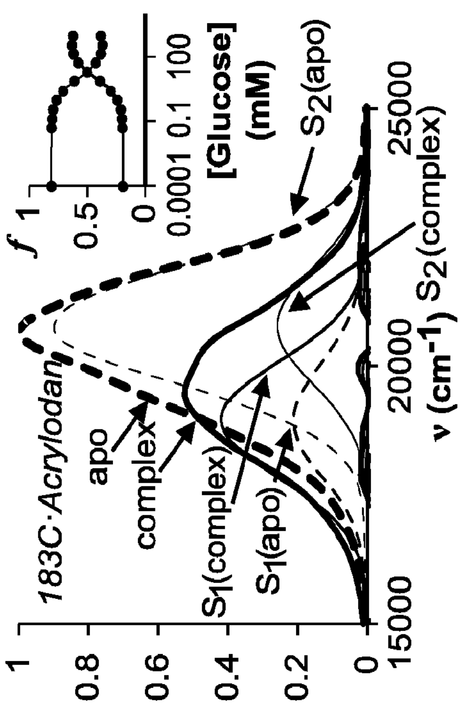
Figure 19A:
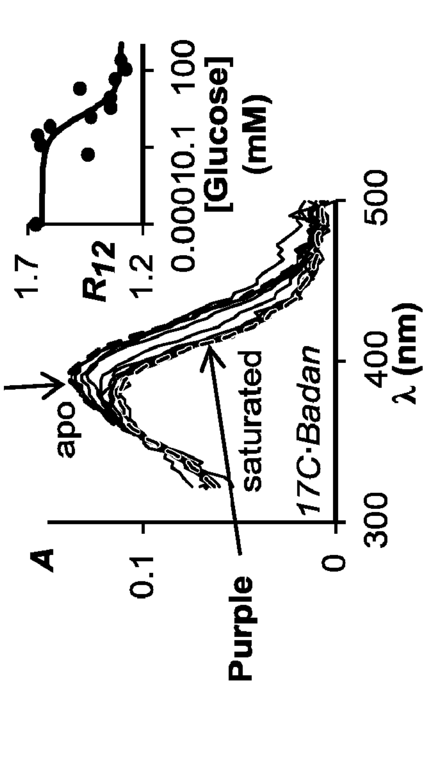
Figure 19B:
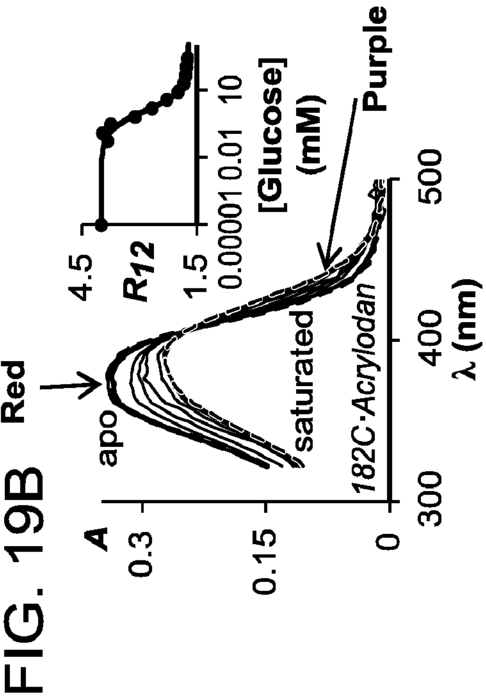
Figure 19C:
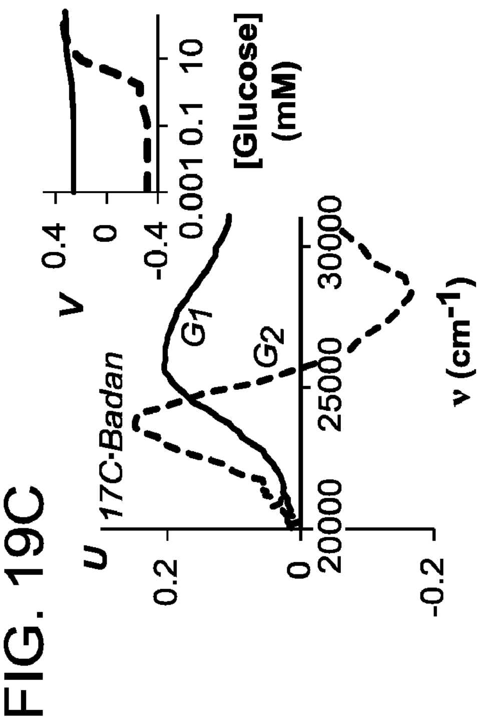
Figure 19D:
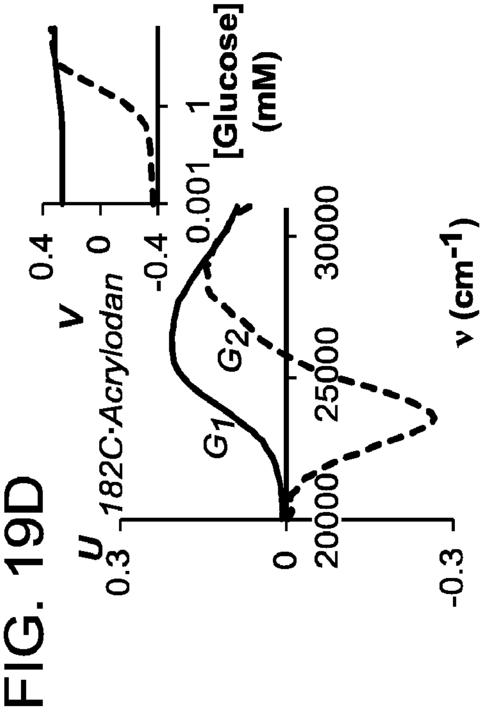
Figure 19E:
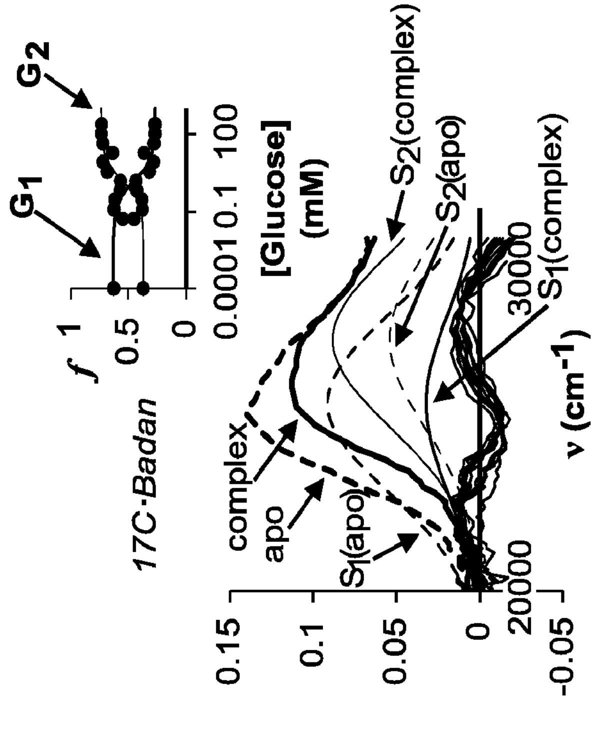
Figure 19F:
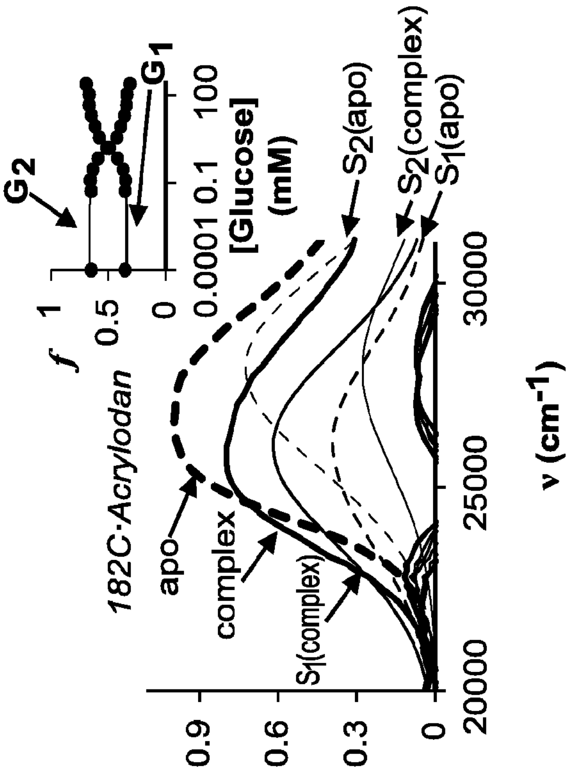

FIGS. 17A-F are graphs showing glucose dependence of electronic transitions in the fluorescence emission intensity spectra of Acrylodan and Badan conjugates of Y11C, F17C and W182C mutants of ttGGBP. (A) Y11C•Acrylodan; (B) Y11C•Badan; (C) F17C•Acrylodan; (D) F17C•Badan; (E) F182C•Acrylodan; (F) F182C•Badan. The emission intensities can be accounted for to a first approximation by two excited state electronic transitions (FIG. 16): a low-energy, green, $S_1$ (Acrylodan: 521±9 nm; Badan: 530±14 nm) and a high-energy, blue, $S_2$ (Acrylodan: 477±14 nm; Badan: 477±16 nm) transition. The $S_1$ transition is present in all spectra; $S_2$ is present in all the glucose-responsive and 36% of the non-responsive conjugates (Table 7 and 8). In conjugates that exhibit glucose-responsive changes in fluorescence emission intensities, glucose binding shifts the population of these excited states. At each titration point, the experimentally observed emission intensities were modeled with Gaussians fits (equation 14) for $S_1$ and $S_2$ electronic transition (model parameter values in Table 3). Experimental emission spectra and Gaussian fits are shown only for the apo-protein, and saturated glucose complex. Emission spectra: dashed black line, apo-protein; solid black line, glucose complex. Gaussians ($S_1$, green lines; $S_2$, blue lines): dashed lines, apo-protein; solid lines, glucose complex. Thin black lines: residuals (equation 16) at each titration point. Inserts show the population fractions (equation 15) of the $S_1$ and $S_2$ transitions extracted from the spectra at each titration point (black circles) fit to Langmuir binding isotherms (solid lines) with ${}^{aPP}K_d$ values constrained to be the same for both populations. As a first approximation, the wavelengths of $S_1$ or $S_2$ transitions are the same in apo-protein and the saturated glucose complex. The residuals indicate that this approximation does not hold for all conjugates, and a more extensive treatment is required in which the $S_1$ and $S_2$ are split into multiple transitions (see discussion below). Wavelength shifts occur if there is a significant redistribution of the two excited state populations in the apo-protein and the saturated ligand complexes. In the bathochromic ratiometric 182C•Acrylodan conjugate, the $S_1$ state dominates in the glucose complex (panel E); in the hypsochromic conjugates 17C•Badan (panel D) and 17C•Acrylodan (panel C), apo-proteins comprise a mixture of the two states, whereas their glucose complexes contain almost exclusively the $S_2$ state. In the hypsochromic 11C•Badan sensor (panel B), the system shifts from a predominantly $S_1$ in the absence of glucose to almost equally populated $S_1$ and $S_2$ states in the glucose complex. Shifts in the fraction of $S_1$ and $S_2$ populations also occur in conjugates that did not exhibit overt shifts in the wavelengths of their emission intensity maxima. For instance, neither 11C•Acrylodan nor 182C•Badan exhibited significant shifts in emission maxima upon binding glucose. Nevertheless, SVD analysis revealed similar changes in the variable $C_2$ component as observed for the overtly ratiometric sensors, but with a smaller contribution (FIGS. 16A and F). Gaussian analysis revealed small shifts in the $S_1$ and $S_2$ populations in response to glucose (panel A and F). This pattern also was observed in other non-ratiometrically responsive conjugates (Table 7 and 8). Wavelength shifts were observed if the $C_2$ component constitutes >5% of the total contribution.

FIGS. 18A-H is a series of graphs showing Glucose dependence of the $S_1$ and $S_2$ electronic transition contributions to the fluorescence emission intensity spectra of *E. coli* GGBP Acrylodan and Badan conjugates. Color schemes, symbols and line representation as in FIGS. 2-4. 16C•Acrylodan: (A) emission spectra (hypsochromic) and ratiometric glucose-binding curve (inset: $\lambda_1$, 454 nm; $\lambda_2$, 540 nm; ${}^{app}K_d$, 1.0 mM); (C) singular value decomposition; (E) Gausssian fits and glucose dependence of the $S_1$ and $S_2$ populations (inset). 16C•Badan: (B) emission spectra (hypsochromic) and ratiometric glucose-binding curve (inset: $\lambda_1$, 465 nm; $\lambda_2$, 555 nm; ${}^{app}K_d$, 0.4 mM); (D) singular value decomposition; (F) Gausssian fits and glucose dependence of the $S_1$ and $S_2$ populations (inset). 182C•Acrylodan: (G) singular value decomposition; (H) Gausssian fits and glucose dependence of the $S_1$ and $S_2$ populations (inset).

FIGS. 19A-F are graphs showing glucose dependence of the absorption spectra of ttGGBP Acrylodan and Badan conjugates that undergo wavelength shifts in their fluorescence emission intensities in response to ligand binding. ttGGBP F17C•Badan: (A) Absorption spectra (red, no glucose; purple, saturating glucose; black, intermediate glucose concentrations). Hypsochromic response was modeled by fit of a Langmuir ligand-binding isotherm (equation 1) to ratiometric analysis of the absorption intensities (inset: $\lambda_1$, 390 nm; $\lambda_2$, 340 nm; ${}^{app}K_d$, 1.7 mM); (C) singular value decomposition (components: black, $C_1$; gray, $C_2$); (E) Fit of Gaussian representations of electronic transitions to absorption spectra (dashed black line, apo-protein; solid black line, glucose complex) of $G_1$ (386 nm green; apo-protein, dashed; glucose complex, solid) and $G_2$ (359 nm, blue; apo-protein, dashed; glucose complex, solid) ground state electronic transitions. Inset, glucose dependence of population fractions at each glucose titration (black circles) of the $G_1$ and $G_2$ transitions fit to Langmuir binding isotherms (solid lines) with ${}^{app}K_d$ values constrained to be the same for both populations (residuals, thin lines). ttGGBP F182C•Acrylodan (color scheme, line representations, symbols, as above): (B) Absorption spectra (bathochromic response) and glucose binding (inset: $\lambda_1$, 375 nm; $\lambda_2$, 430 nm; ${}^{app}K_d$, 1.1 mM; ${}^{true}K_d$, 1.9 mM); (D) singular value decomposition; (F) $G_1$ and $G_2$ electronic transitions and populations. The residuals indicate that the maximal wavelength of the $G_1$ and $G_2$ transitions is different in the apo-protein and glucose (also see legend to FIG. 17).

FIG. 20 shows the sequence of an exemplary csaGGBP (Table 2) expression construct (SEQ ID NO: 105).

FIG. 21 shows the sequence of an exemplary bprGGBP (Table 2) expression construct (SEQ ID NO: 106).

FIG. 22 shows the sequence of an exemplary rinGGBP_A (Table 2) expression construct (SEQ ID NO: 107).

FIG. 23 shows the sequence of an exemplary fprGGBP (Table 2) expression construct (SEQ ID NO: 108).

FIG. 24 shows the sequence of an exemplary cljGGBP (Table 2) expression construct (SEQ ID NO: 109).

FIG. 25 shows the sequence of an exemplary cauGGBP (Table 2) expression construct (SEQ ID NO: 110).

FIG. 26 shows the sequence of an exemplary rinGGBP_B (Table 2) expression construct (SEQ ID NO: 111).

FIG. 27 shows the sequence of an exemplary erhGGBP (Table 2) expression construct (SEQ ID NO: 112).

FIG. 28 shows the sequence of an exemplary ereGGBP (Table 2) expression construct (SEQ ID NO: 113).

FIG. 29 shows the sequence of an exemplary ttGGBP (Table 2) expression construct (SEQ ID NO: 114).

FIG. 30 shows the sequence of an exemplary cobGGBP (Table 2) expression construct (SEQ ID NO: 115).

FIG. 31 shows the sequence of an exemplary chyGGBP (Table 2) expression construct (SEQ ID NO: 116).

FIG. 32 shows the sequence of an exemplary pspGGBP (Table 2) expression construct (SEQ ID NO: 117).

FIG. 33 shows the sequence of an exemplary ttGGBP11C Cysteine Scan Mutant (Table 3) expression construct (SEQ ID NO: 118).

FIG. 34 shows the sequence of an exemplary ttGGBP16C Cysteine Scan Mutant (Table 3) expression construct (SEQ ID NO: 119).

FIG. 35 shows the sequence of an exemplary ttGGBP17C Cysteine Scan Mutant (Table 3) expression construct (SEQ ID NO: 120).

FIG. 36 shows the sequence of an exemplary ttGGBP42C Cysteine Scan Mutant (Table 3) expression construct (SEQ ID NO: 121).

FIG. 37 shows the sequence of an exemplary ttGGBP67C Cysteine Scan Mutant (Table 3) expression construct (SEQ ID NO: 122).

FIG. 38 shows the sequence of an exemplary ttGGBP91C Cysteine Scan Mutant (Table 3) expression construct (SEQ ID NO: 123).

FIG. 39 shows the sequence of an exemplary ttGGBP92C Cysteine Scan Mutant (Table 3) expression construct (SEQ ID NO: 124).

FIG. 40 shows the sequence of an exemplary ttGGBP111C Cysteine Scan Mutant (Table 3) expression construct (SEQ ID NO: 125).

FIG. 41 shows the sequence of an exemplary ttGGBP148C Cysteine Scan Mutant (Table 3) expression construct (SEQ ID NO: 126).

FIG. 42 shows the sequence of an exemplary ttGGBP151C Cysteine Scan Mutant (Table 3) expression construct (SEQ ID NO: 127).

FIG. 43 shows the sequence of an exemplary ttGGBP152C Cysteine Scan Mutant (Table 3) expression construct (SEQ ID NO: 128).

FIG. 44 shows the sequence of an exemplary ttGGBP181C Cysteine Scan Mutant (Table 3) expression construct (SEQ ID NO: 129).

FIG. 45 shows the sequence of an exemplary ttGGBP182C Cysteine Scan Mutant (Table 3) expression construct (SEQ ID NO: 130).

FIG. 46 shows the sequence of an exemplary ttGGBP183C Cysteine Scan Mutant (Table 3) expression construct (SEQ ID NO: 131).

FIG. 47 shows the sequence of an exemplary ttGGBP257C Cysteine Scan Mutant (Table 3) expression construct (SEQ ID NO: 132).

FIG. 48 shows the sequence of an exemplary ttGGBP259C Cysteine Scan Mutant (Table 3) expression construct (SEQ ID NO: 133).

FIG. 49 shows the sequence of an exemplary ttGGBP300C Cysteine Scan Mutant (Table 3) expression construct (SEQ ID NO: 134).

FIG. 50 shows the sequence of an exemplary ttGGBP17C.1 Affinity-Tuning Mutant (17C background) (Table 6) expression construct (SEQ ID NO: 135).

FIG. 51 shows the sequence of an exemplary ttGGBP17C.2 Affinity-Tuning Mutant (17C background) (Table 6) expression construct (SEQ ID NO: 136).

FIG. 52 shows the sequence of an exemplary ttGGBP17C.3 Affinity-Tuning Mutant (17C background) (Table 6) expression construct (SEQ ID NO: 137).

FIG. 53 shows the sequence of an exemplary ttGGBP17C.4 Affinity-Tuning Mutant (17C background) (Table 6) expression construct (SEQ ID NO: 138).

FIG. 54 shows the sequence of an exemplary ttGGBP17C.5 Affinity-Tuning Mutant (17C background) (Table 6) expression construct (SEQ ID NO: 139).

FIG. 55 shows the sequence of an exemplary ttGGBP17C.6 Affinity-Tuning Mutant (17C background) (Table 6) expression construct (SEQ ID NO: 140).

FIG. 56 shows the sequence of an exemplary ttGGBP17C.7 Affinity-Tuning Mutant (17C background) (Table 6) expression construct (SEQ ID NO: 141).

FIG. 57 shows the sequence of an exemplary ttGGBP17C.8 Affinity-Tuning Mutant (17C background) (Table 6) expression construct (SEQ ID NO: 142).

FIG. 58 shows the sequence of an exemplary ttGGBP17C.9 Affinity-Tuning Mutant (17C background) (Table 6) expression construct (SEQ ID NO: 143).

FIG. 59 shows the sequence of an exemplary ttGGBP17C.10 Affinity-Tuning Mutant (17C background) (Table 6) expression construct (SEQ ID NO: 144).

FIG. 60 shows the sequence of an exemplary ttGGBP17C.11 Affinity-Tuning Mutant (17C background) (Table 6) expression construct (SEQ ID NO: 145).

FIG. 61 shows the sequence of an exemplary ttGGBP17C.19 Affinity-Tuning Mutant (17C background) (Table 6) expression construct (SEQ ID NO: 146).

FIG. 62 shows the sequence of an exemplary ttGGBP17C.20 Affinity-Tuning Mutant (17C background) (Table 6) expression construct (SEQ ID NO: 147).

FIG. 63 shows the sequence of an exemplary ttGGBP17C.21 Affinity-Tuning Mutant (17C background) (Table 6) expression construct (SEQ ID NO: 148).

FIG. 64 shows the sequence of an exemplary ttGGBP17C.22 Affinity-Tuning Mutant (17C background) (Table 6) expression construct (SEQ ID NO: 149).

FIG. 65 shows the sequence of an exemplary ttGGBP17C.23 Affinity-Tuning Mutant (17C background) (Table 6) expression construct (SEQ ID NO: 150).

FIG. 66 shows the sequence of an exemplary ttGGBP17C.24 Affinity-Tuning Mutant (17C background) (Table 6) expression construct (SEQ ID NO: 151).

FIG. 67 shows the sequence of an exemplary ttGGBP17C.25 Affinity-Tuning Mutant (17C background) (Table 6) expression construct (SEQ ID NO: 152).

FIG. 68 shows the sequence of an exemplary ttGGBP17C.26 Affinity-Tuning Mutant (17C background) (Table 6) expression construct (SEQ ID NO: 153).

FIG. 69 shows the sequence of an exemplary ttGGBP17C.27 Affinity-Tuning Mutant (17C background) (Table 6) expression construct (SEQ ID NO: 154).

FIG. 70 shows the sequence of an exemplary ttGGBP17C.28 Affinity-Tuning Mutant (17C background) (Table 6) expression construct (SEQ ID NO: 155).

FIG. 71 shows the sequence of an exemplary ttGGBP17C.29 Affinity-Tuning Mutant (17C background) (Table 6) expression construct (SEQ ID NO: 156).

FIG. 72 shows the sequence of an exemplary ttGGBP182C.2.0 Affinity-Tuning Mutant (182C background) (Table 6) expression construct (SEQ ID NO: 157).

FIG. 73 shows the sequence of an exemplary ttGGBP182C.2.1 Affinity-Tuning Mutant (182C background) (Table 6) expression construct (SEQ ID NO: 158).

FIG. 74 shows the sequence of an exemplary ttGGBP182C.2.3 Affinity-Tuning Mutant (182C background) (Table 6) expression construct (SEQ ID NO: 159).

FIG. 75 shows the sequence of an exemplary ttGGBP182C.2.4 Affinity-Tuning Mutant (182C background) (Table 6) expression construct (SEQ ID NO: 160).

FIG. 76 shows the sequence of an exemplary ttGGBP182C.2.5 Affinity-Tuning Mutant (182C background) (Table 6) expression construct (SEQ ID NO: 161).

FIG. 77 shows the sequence of an exemplary ttGGBP182C.2.6 Affinity-Tuning Mutant (182C background) (Table 6) expression construct (SEQ ID NO: 162).

FIG. 78 shows the sequence of an exemplary ttGGBP182C.2.7 Affinity-Tuning Mutant (182C background) (Table 6) expression construct (SEQ ID NO: 163).

FIG. 79 shows the sequence of an exemplary ttGGBP182C.2.8 Affinity-Tuning Mutant (182C background) (Table 6) expression construct (SEQ ID NO: 164).

FIG. 80 shows the sequence of an exemplary ttGGBP182C.2.9 Affinity-Tuning Mutant (182C background) (Table 6) expression construct (SEQ ID NO: 165).

FIG. 81 shows the sequence of an exemplary ttGGBP182C.3 Affinity-Tuning Mutant (182C background) (Table 6) expression construct (SEQ ID NO: 166).

FIG. 82 shows the sequence of an exemplary ttGGBP182C.4 Affinity-Tuning Mutant (182C background) (Table 6) expression construct (SEQ ID NO: 167).

FIG. 83 shows the sequence of an exemplary ttGGBP182C.5 Affinity-Tuning Mutant (182C background) (Table 6) expression construct (SEQ ID NO: 168).

FIG. 84 shows the sequence of an exemplary ttGGBP182C.6 Affinity-Tuning Mutant (182C background) (Table 6) expression construct (SEQ ID NO: 169).

FIG. 85 shows the sequence of an exemplary ttGGBP182C.7 Affinity-Tuning Mutant (182C background) (Table 6) expression construct (SEQ ID NO: 170).

FIG. 86 shows the sequence of an exemplary ttGGBP182C.8 Affinity-Tuning Mutant (182C background) (Table 6) expression construct (SEQ ID NO: 171).

FIG. 87 shows the sequence of an exemplary ttGGBP182C.9 Affinity-Tuning Mutant (182C background) (Table 6) expression construct (SEQ ID NO: 172).

Figure 88:
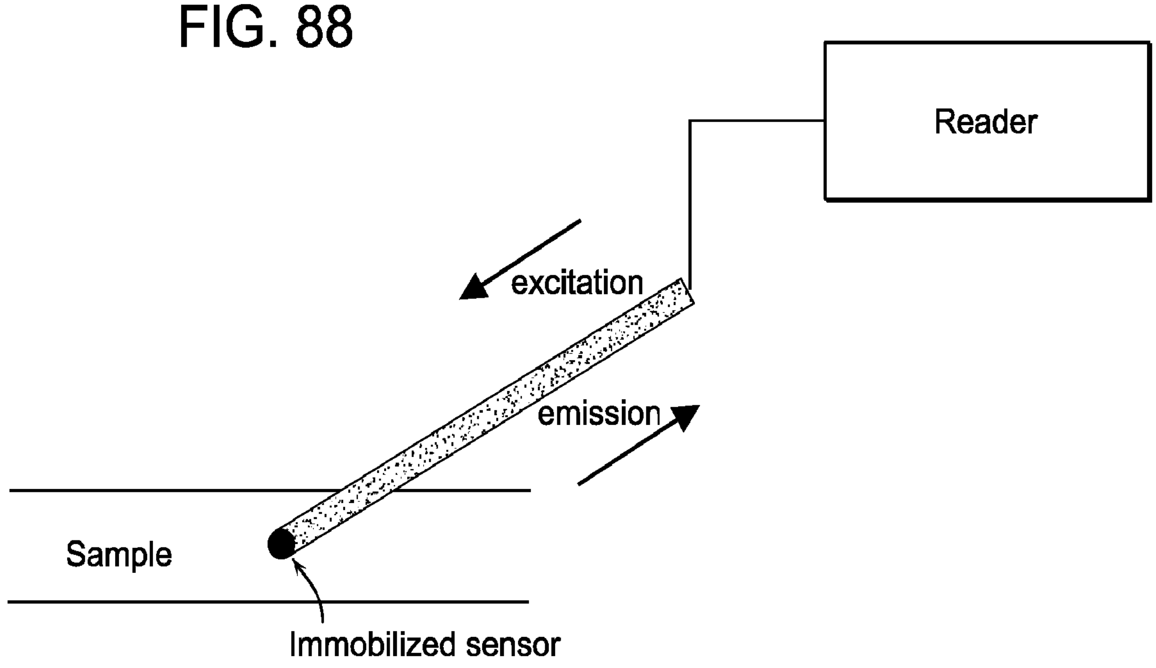

FIG. 88 is a cartoon illustrating non-limiting aspects of continuous glucose monitoring.

Figure 89:
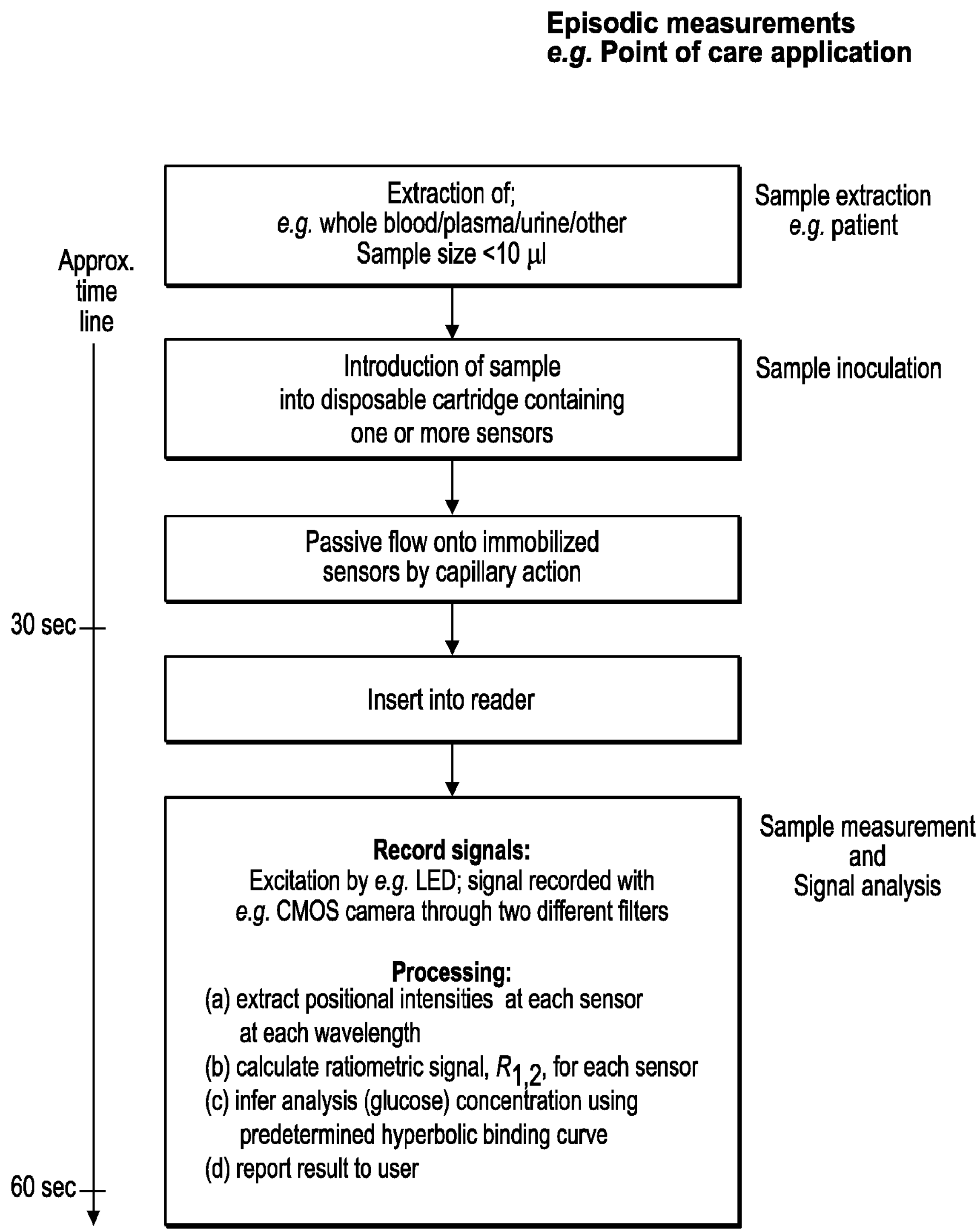

FIG. 89 is a cartoon illustrating a non-limiting example of sample analysis with a biosensor.

DETAILED DESCRIPTION

Fluorescently responsive sensors (FRSs) based on engineered proteins that couple ligand-binding events to changes in the emission properties of intrinsic or semi-synthetically incorporated chromophores have wide-ranging applications in cell biology and analytical chemistry. If the fluorescence emission spectrum of an engineered FRS changes shape in response to ligand binding such that the ratio of intensities at two appropriately chosen wavelengths reports on ligand concentration (dichromatic response), then ratiometric measurements can be used to monitor analyte concentrations. Ratiometry Advantage is essential for devices that rely on changes in fluorescence emission intensities, because it provides an internally consistent reference. The self-calibrating nature of a ratiometric measurement removes the necessity for carrying out on-board calibration tests prior to each measurement, obviating the need for multiple components and fluidic circuitry. Accordingly, reagentless, ratiometric fluorescent sensors have many uses in process engineering, environmental or clinical chemistry, including single-use point-of-care applications, wearable devices, or implanted "tattoos" that are interrogated transdermally.

Figure 1A:
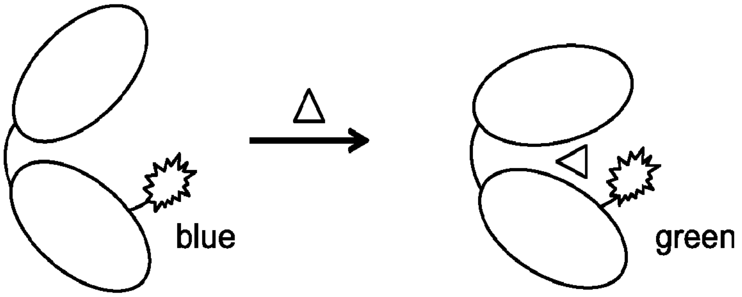
FIGS. 1A-C are a cartoon and graphs illustrating emission spectra changes upon ligand binding to FRSs. (A) FRSs can be constructed by site-specifically attaching a fluorophore to a protein that undergoes a conformational change upon binding ligand (triangle), such that the shape and intensities of the fluorescent conjugate emission spectra changes. (B) In the absence of ligand, the emitted fluorescence color is predominantly blue, whereas the ligand complex fluoresces green. Arrows indicate the direction of change upon ligand addition. (C) Ligand binding is determined by measuring the ratio of blue to green emission intensities.
Figure 1B:
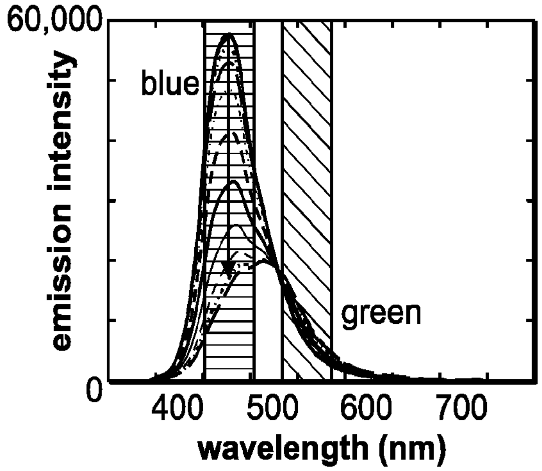
Figure 1C:
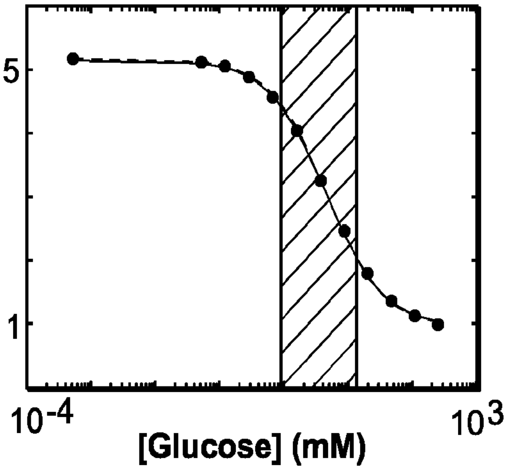

The periplasmic binding protein (PBP) superfamily provide a rich source of FRSs, because PBPs combine a large diversity of ligand specificities with a common structural mechanism that is well suited to the construction of fluorescence signal transduction schemes. The three-dimensional PBP monomer structure comprises two α/β domains linked by a β-strand hinge FIG. 1A. Binding of ligand is accompanied by a large hinge-bending motion that transitions the protein from an open to a closed state in which the ligand is enveloped within a cleft between the two domains. Semi-synthetic FRSs can be engineered with PBPs by site-specifically attaching single, thiol-reactive, environmentally sensitive fluorophores that respond to the ligand-mediated conformational change (FIGS. 1A-C). Here we describe the construction of robust, ratiometric, fluorescently responsive glucose sensors derived from thermostable members of a family of glucose-binding PBPs.

Glucose monitoring is essential for the management of diabetes mellitus, a disease that affects at least 366 million people world-wide, increasing every year. The majority of current glucose-monitoring technologies rely on enzymes for which glucose is one of the substrates. Glucose concentration measurements are therefore subject to variations in second substrate concentrations consumed in the enzyme reaction, such as oxygen in the case of glucose oxidase. Additional complications arise in systems where reaction rates are measured for enzymes immobilized on electrodes. In such arrangements, accuracy is compromised by factors that alter the rate at which glucose arrives at the electrode surface interfere with accuracy, such as hematocrit levels, or surface "fouling" by deposition of proteins and cells in the foreign body response. Ratiometric fluorescent glucose sensors obviate these problems, and accordingly have been incorporated successfully in optodes for continuous glucose monitoring in animals and humans.

In FRS-based sensors, signals arise from reversible binding equilibria of the analyte (ligand) to a receptor. These signals are most precise at ligand concentrations that match the receptor ligand-disassociation constant. Precision is maintained to within ~80% of this maximal level over a concentration range approximately 3-fold above or below this point. Construction of effective FRS therefore requires matching of ligand-binding affinities to the relevant analyte concentrations. Arrays of multiple sensors may have to be used in concert to cover wide concentration ranges. Clinically relevant glucose levels vary approximately 100-fold (from ~1 mM in extreme hypoglycemia, to ~100 mM for the hyperosmolar, hyperglycemic condition, with healthy, euglycemic levels at ~6 mM (Association 2000 *Clinical Diabetes,* 18; Pasquel 2014 *Diabetes Care,* 37, 3124-3131), requiring an array of multiple FRS sensors with distinct glucose affinities to report directly on the full range of clinically relevant glucose concentrations with high precision. Here we report a set of appropriately tuned thermostable, glucose-responsive FRSs, constructed by mutating their glucose-binding site.

Immobilization of FRSs on solid surfaces with minimal perturbation of the molecular sensing mechanism is an important step for incorporating biosensors into devices. Immobilization enables retention of the sensor within the sampling element (e.g. optode surface or implanted bead for in vivo sensing applications; or in a sample-handling cartridge for ex vivo sensing) Immobilization also may provide spatial localization to provide the necessary addressability of different elements in a multi-sensor array comprising sensors that differ in their engineered affinities for coverage of a wide range of glucose concentrations, or sensors that each detect distinct analytes.

Ex vivo clinical chemistries such as point-of-care applications require that the FRS is incorporated into a cartridge into which a sample is introduced at the time of measurement. Such "disposables" need to have a long shelf life that preferably does not require temperature control (e.g. refrigeration) for storage or distribution. It is preferable to incorporate immobilized protein in a stable, dried form in such disposables. The inherent resistance to denaturation of thermostable proteins minimizes the need for temperature control during manufacturing and storage, and may extend to the long-term stability of a desiccated state. The protein sensors described herein meet these requirements.

The spectral response, binding affinity, and thermostability of the robust thermostable glucose FRSs reported here are maintained following site-specific immobilization on a substrate such as beads. Furthermore, these properties are recovered rapidly upon reconstitution following drying and prolonged storage under accelerated aging conditions. These engineered proteins therefore are useful for high-precision, wide-dynamic range glucose sensing applications, including continuous monitoring, point-of-care, wearable sensor systems.

Biosensors

Biosensors are molecular recognition elements that transduce ligand-binding events into physical signals. Biosensors as detailed herein bind at least one ligand and emit a signal. A ligand-bound biosensor results in a signal that is different from the unbound biosensor. This difference facilitates detection of the at least one ligand and/or determination of ligand concentration. The biosensors may be used without the assistance of other reagents.

Described herein are novel engineered biosensors. These biosensors may have altered ligand-binding affinities, tailored ligand-binding specificities, and/or temperature dependencies of ligand binding or stability. For example, the herein described engineered glucose and galactose biosensors provide high-accuracy information related to extended glucose concentration ranges.

Binding of ligand mediates conformational changes in the biosensor, such as hinge-bending motions of the polypeptide. The conformational changes affect the environment of the reporter such that a change in the reporter-generated signal occurs. That is, without ligand bound, the biosensor results in signal generated from the reporter, and when ligand is bound, the signal generated from the reporter changes. The ligand-bound biosensor results in a reporter-generated signal that is different from the unbound biosensor.

In some embodiments, the methods and compositions include a plurality of a single type of biosensor. The biosensors may be identical in structure and function. For example, the biosensors of a single type may have the same polypeptide, the same reporter, and the same ligand affinity.

In other embodiments, the methods and compositions include a plurality of different types of biosensors. A plurality of these different types of biosensors may be arranged or incorporated in a panel. As used herein, a "panel" refers to two or more biosensors. The two or more biosensors may be different from each other. The biosensors may differ in structure and/or function. Biosensors may differ in polypeptide sequence, reporter, ligand affinities, or a combination thereof. Accordingly, there may be different types of biosensors. In some embodiments, each biosensor in the panel comprises the same reporter group. In some embodiments, each biosensor in the panel comprises a different reporter group. The panel may include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, or at least 100 biosensors.

The panel of biosensors includes at least one sensor element. "Sensor element" refers to a single spot, site, location, or well for the at least one biosensor, to which a sample or aliquot thereof may be applied. The panel may be a composite sensor or an array.

In some embodiments, the panel is a composite sensor. In a composite sensor, each sensor element includes a mixture of two or more different biosensors. In some embodiments, the composite sensor includes one sensor element. In some embodiments, the composite sensor includes two or more sensor elements. In some embodiments, signals are measured from a composite sensor in which the signals arise from one or more biosensors in the sensor element. For example, signals may be measured from a composite sensor in which the signals arise from a subset of the total number of biosensors in the sensor element. For example, signals may be measured from a composite sensor in which the signals arise from two of five biosensors in the sensor element.

In some embodiments, the panel is an array. In an array, each sensor element includes a single type of biosensor. An array comprises a plurality of individually and spatially localized sensor elements. Each sensor element includes a biosensor that is different than or the same as the biosensor of a different sensor element. In some embodiments, signals are measured from an array in which the signals arise separately from two or more selected biosensors in separate sensor elements. An array may comprise a plurality of sensor elements of a variety of sizes and configurations. An array may comprise a plurality of sensor elements arranged linearly. For example, an array may comprise a plurality of micrometer-sized sensor elements arranged in a single row. An array may comprise a plurality of sensor elements arranged in a grid. The grid may be two- or three-dimensional. In some embodiments, the grid is a spatially addressable grid. In some embodiments, the biosensors are incorporated into an array, such as a multichannel or multiplexed array.

The biosensors of the present disclosure can be used in any setting where glucose detection is required or desired, such a medical setting (e.g., determining the level of blood glucose in a subject), environmental setting (e.g., determining the level of glucose in an environmental sample), biological setting (e.g., determining the presence or amount of glucose in a reaction), or in process engineering, such as monitoring the amount of glucose in a fermentation reaction (e.g., beer/wine production, etc.). Other examples include, but are not limited to, uses in the food industry (Suleiman et al, In: Biosensor Design and Application: Mathewson and Finley Eds; American Chemical Society, Washington, D.C. 1992, vol. 511); in clinical chemistry (Wilkins et al., Med. Eng. Phys. 1996, 18, 273-288; Pickup, Tr. Biotech. 1993, 11, 285-291; Meyerhoff et al., Endricon 1966, 6, 51-58; Riklin et al., Nature 1995, 376, 672-675); Willner et al., J. Am. Chem. Soc. 1996, 118, 10321-10322); as the basis for the construction of a fluorescent flow cell containing immobilized GGBP-FAST conjugates (see, e.g., Wilkins et al., Med. Eng. Phys. 1966, 18, 273-288; Pickup, Tr. Biotech. 1993, 11, 285-291; Meyerhoff et al., Endricon. 1966, 6, 51; Group, New Engl. J. Med. 1993, 329, 977-986; Gough et al., Diabetes 1995, 44, 1005-1009); and in an implantable devices, such as those suitable for use as an artificial pancreas.

The biosensors as detailed herein may be administered in a variety of ways known by those of skill in the art, as appropriate for each application. Biosensors may be provided in a solution. The solution may be buffered. Biosensors may be provided in a solution and mixed directly with a sample. In some embodiments, a biosensor is immobilized onto a surface. Biosensors may be immobilized within a disposable cartridge into which a sample may be introduced or applied. Biosensors may be implanted or incorporated in a wearable device. The biosensor may be provided as an optode.

The biosensor may be attached to or incorporated in a wearable device. Wearable devices may include, for example, adhesive strips, patches, and contact lenses. The biosensor may be configured for placement in contact with a subject's skin or mucosal surface. In some embodiments, the biosensor is configured as an adhesive strip. In some embodiments, the biosensor is configured within or on the surface of a contact lens. In some embodiments, the contact lens is formed from a transparent substrate shaped to be worn directly over a subject's eye, as described in, for example, U.S. Pat. No. 8,608,310.

The biosensor may be implanted. The biosensor may be implanted in a subject's body. The biosensor may be implanted in a subject's blood vessel, vein, eye, natural or artificial pancreas, skin, or anywhere in the alimentary canal including the stomach, intestine and esophagus. The biosensor may be implanted in a subject with a microbead. In some embodiments, the biosensor is configured to be implanted in the skin. The biosensor may be implanted in a subject sub-dermally. The biosensor may generate the signal transdermally. In some embodiments, the biosensor may be implanted in a subject with transdermal microbeads, wherein the optical signals can be transmitted remotely between the biosensor and detecting device.

In some embodiments, the biosensor is administered as an optode. As used herein, "optode" refers to an optical fiber with a single biosensor, or a composite biosensor, immobilized at the surface or at the end. An "optode" may also be referred to as an "optrode." In some embodiments, the biosensor is implanted in a subject as an optode. The optode may be incorporated with or into a needle. The optode may be incorporated with a probe such as endoscopy or colonoscopy probes. The optode may be used in a tumor, near a tumor, or at the periphery of a tumor. In some embodiments, the biosensor may be implanted in a subject as an optode, wherein the optical signals can be transmitted between the biosensor and detecting device using physical links. In some embodiments, the biosensor is administered as an optode to a sample or reaction. The optode may be contacted with a sample or reaction. In some embodiments, an optode is used to continuously or episodically monitor a ligand in a sample or reaction.

Methods of Detecting the Presence of a Ligand

Provided herein is a method of detecting the presence of a ligand in a sample. The method may include contacting the biosensor with the sample; measuring a signal from the biosensor; and comparing the signal to a ligand-free control. A difference in signal indicates the presence of ligand in the sample.

Also provided herein is a method of detecting the presence of glucose in a sample. The method may include (a) providing a glucose biosensor disclosed herein in which the reporter group is attached the GGBP so that a signal transduced by the reporter group when the GGBP is bound to glucose differs from a signal transduced by the reporter group when the GGBP is not bound to glucose; (b) contacting the biosensor with the test sample under conditions such that the biosensor can bind to glucose present in the test sample; and (c) comparing the signal transduced by the reporter group when the biosensor is contacted with the test sample with the signal transduced by the reporter group when the biosensor is contacted with a glucose-free control sample, wherein a difference in the signal transduced by the reporter group when the biosensor is contacted with the test sample, as compared to when the biosensor is contacted with the control sample, indicates that the test sample contains glucose.

Methods of Determining the Concentration of a Ligand

Provided herein is a method of determining the concentration of a ligand in a sample. The method may include contacting the biosensor with the sample; measuring a signal from the biosensor; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of determining the concentration of glucose in a test sample comprising, consisting of, or consisting essentially of: (a) providing a glucose biosensor comprising a glucose biosensor as described herein in which the reporter group is attached the GGBP so that a signal transduced by the reporter group when the GGBP is bound to glucose differs from a signal transduced by the reporter group when the GGBP is not bound to glucose; (b) contacting the biosensor with the test sample under conditions such that the biosensor can bind to glucose present in the test sample; and (c) comparing the signal transduced by the reporter group when the biosensor is contacted with the test sample with a standard hyperbolic glucose binding curve prepared by measuring the signal transduced by the reporter group when the biosensor is contacted with control samples containing known quantities of glucose to determine the concentration of glucose in the test sample.

Methods of Monitoring the Presence of a Ligand

The present invention is directed to a method of episodically or continuously monitoring the presence of a ligand in a reaction. In certain embodiments, the biosensors may be used in the continuous monitoring of glucose in a reaction. In certain embodiments, the glucose sensors may be used in episodic monitoring of sample aliquots.

The method of episodically or continuously monitoring the presence of a ligand in a reaction may include contacting the biosensor with the reaction; maintaining the reaction under conditions such that the polypeptide is capable of binding ligand present in the reaction; and episodically or continuously monitoring the signal from the biosensor in the reaction.

The method of episodically or continuously monitoring the presence of a ligand in a reaction may include contacting the biosensor with the reaction; maintaining the reaction under conditions such that the polypeptide is capable of binding ligand present in the reaction; episodically or continuously monitoring the signal from the biosensor in the reaction; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

In some embodiments, the method further includes comparing the signal to a ligand-free control, wherein a difference in signal indicates the presence of ligand in the reaction.

In some embodiments, the method further includes comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of continuously monitoring the presence of glucose in a reaction comprising, consisting of, or consisting essentially of: (a) providing a glucose biosensor as described herein in which the reporter group is attached the GGBP so that a signal transduced by the reporter group when the GGBP is bound to glucose differs from a signal transduced by the reporter group when the GGBP is not bound to glucose; (b) maintaining the biosensor within the reaction and under conditions such that the biosensor can bind to glucose present in the reaction; (c) continuously monitoring the signal transduced by the reporter group when the biosensor is contacted with the glucose present in the reaction; and optionally (d) comparing the signal transduced by the reporter group when the biosensor is contacted with the glucose present in the reaction with the signal transduced by the reporter group when the biosensor is contacted with a glucose-free control sample, wherein a difference in the signal transduced by the reporter group when the biosensor is contacted with the glucose present in the reaction, as compared to when the biosensor is contacted with the control sample, indicates glucose is present in the reaction.

Yet another aspect of the present disclosure provides a method of continuously monitoring the concentration of glucose in a reaction comprising, consisting of, or consisting essentially of: (a) providing a glucose biosensor comprising a glucose biosensor as described herein in which the reporter group is attached the GGBP so that a signal transduced by the reporter group when the GGBP is bound to glucose differs from a signal transduced by the reporter group when the GGBP is not bound to glucose; (b) maintaining the biosensor within the reaction under conditions such that the biosensor can bind to glucose present in the reaction; and (c) continuously monitoring the signal transduced by the reporter group when the biosensor is contacted with the glucose present in the reaction; and (d) comparing the signal transduced by the reporter group when the biosensor is contacted with the glucose present in the reaction with a standard hyperbolic glucose binding curve prepared by measuring the signal transduced by the reporter group when the biosensor is contacted with control samples containing known quantities of glucose to determine the concentration of glucose in the reaction.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes/nucleic acids or sequences/amino acids that flank it in its naturally-occurring state. Purified also defines a degree of sterility that is safe for administration to a human subject, e.g., lacking infectious or toxic agents. In the case of tumor antigens, the antigen may be purified or a processed preparation such as a tumor cell lysate.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

"Subject" as used herein refers to any organism from which a biological sample is obtained. For example, the sample is a biological fluid or tissue. For example, a subject is one who wants or is in need of detecting ligand or determining the concentration of ligand with the herein described biosensors. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

As used herein, an "expression vector" is a DNA or RNA vector that is capable of effecting expression of one or more polynucleotides. Preferably, the expression vector is also capable of replicating within the host cell. Expression vectors can be either prokaryotic or eukaryotic, and are typically include plasmids. Expression vectors of the present invention include any vectors that function (i.e., direct gene expression) in host cells of the present invention, including in one of the prokaryotic or eukaryotic cells described herein, e.g., gram-positive, gram-negative, pathogenic, non-pathogenic, commensal, cocci, *bacillus*, or spiral-shaped bacterial cells; archaeal cells; or protozoan, algal, fungi, yeast, plant, animal, vertebrate, invertebrate, arthropod, mammalian, rodent, primate, or human cells. Expression vectors of the present invention contain regulatory sequences such as transcription control sequences, translation control sequences, origins of replication, and other regulatory sequences that are compatible with the host cell and that control the expression of a polynucleotide. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the cells of the present invention. A variety of such transcription control sequences are known to those skilled in the art.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

The term "diagnosis" refers to a determination that a disease is present in the subject. Similarly, the term "prognosis" refers to a relative probability that a certain future outcome may occur in the subject. For example, in the context of the present disclosure, prognosis can refer to the likelihood that an individual will develop a disease, or the likely severity of the disease (e.g., severity of symptoms, rate of functional decline, survival, etc.).

Depending on context, the terms "polypeptide" and "protein" may be used interchangeably.

A polypeptide or class of polypeptides may be defined by the extent of identity (% identity) of its amino acid sequence to a reference amino acid sequence, or by having a greater % identity to one reference amino acid sequence than to another. A variant of any of genes or gene products disclosed herein may have, e.g., 50%, 55%, 60%, 65%, 70%, 75%, 80%, 85%, 90%, 95%, 96%, 97%, 98%, or 99% sequence identity to the nucleic acid or amino acid sequences described herein. The term "% identity," in the context of two or more nucleic acid or polypeptide sequences, refers to two or more sequences or subsequences that are the same or have a specified percentage of amino acid residues or nucleotides that are the same, when compared and aligned for maximum correspondence, as measured using a sequence comparison algorithm or by visual inspection. For example, % identity is relative to the entire length of the coding regions of the sequences being compared, or the length of a particular fragment or functional domain thereof. Variants as disclosed herein also include homologs, orthologs, or paralogs of the genes or gene products described herein. In some embodiments, variants may demonstrate a percentage of homology or identity, for example, at least about 50%, 55%, 60%, 65%, 70%, 75%, 80%, 85%, 90%, 95%, 96%, 97%, 98%, or 99% identity conserved domains important for biological function, e.g., in a functional domain, e.g. a ligand-binding or catalytic domain.

For sequence comparison, one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity is determined using BLAST. For the BLAST searches, the following parameters were employed: (1) Expect threshold is 10; (2) Gap cost is Existence: 11 and Extension: 1; (3) The Matrix employed is BLOSUM62; (4) The filter for low complexity regions is "on."

The present invention also provides for functional fragments of the genes or gene products described herein. A fragment of a protein is characterized by a length (number of amino acids) that is less than the length of the full length mature form of the protein. A fragment, in the case of these sequences and all others provided herein, may be a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

For example, fragments of any of the proteins or enzymes disclosed herein or encoded by any of the genes disclosed herein can be 10 to 20 amino acids, 10 to 30 amino acids, 10 to 40 amino acids, 10 to 50 amino acids, 10 to 60 amino acids, 10 to 70 amino acids, 10 to 80 amino acids, 10 to 90 amino acids, 10 to 100 amino acids, 50 to 100 amino acids, 75 to 125 amino acids, 100 to 150 amino acids, 150 to 200 amino acids, 200 to 250 amino acids, 250 to 300 amino acids, or 300 to 350 amino acids. The fragments encompassed in the present subject matter comprise fragments that retain functional fragments. As such, the fragments preferably retain the binding domains that are required or are important for functional activity. Fragments can be determined or generated by using the sequence information herein, and the fragments can be tested for functional activity using standard methods known in the art. For example, the encoded protein can be expressed by any recombinant technology known in the art and the binding activity of the protein can be determined.

As used herein a "biologically active" fragment is a portion of a polypeptide which maintains an activity of a full-length reference polypeptide. Biologically active fragments as used herein exclude the full-length polypeptide. Biologically active fragments can be any size as long as they maintain the defined activity. Preferably, the biologically active fragment maintains at least 10%, at least 50%, at least 75% or at least 90%, of the activity of the full length protein.

Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired activity and/or specificity.

Mutant (altered) peptides can be prepared using any technique known in the art. For example, a polynucleotide defined herein can be subjected to in vitro mutagenesis or DNA shuffling techniques as broadly described by Harayama (1998). Products derived from mutated/altered DNA can readily be screened using techniques described herein to determine if they possess, for example, glucose and/or galactose binding activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues. In some embodiments, a mutated or modified protein does not comprise any deletions or insertions. In various embodiments, a mutated or modified protein has less than about 10, 9, 8, 7, 6, 5, 4, 3, or 2 deleted or inserted amino acids.

Substitution mutants have at least one amino acid residue in the polypeptide molecule removed and a different residue inserted in its place. Sites may be substituted in a relatively conservative manner in order to maintain activity and/or specificity. Such conservative substitutions are shown in the table below under the heading of "exemplary substitutions."

In certain embodiments, a mutant/variant polypeptide has only, or not more than, one or two or three or four conservative amino acid changes when compared to a naturally occurring polypeptide. Details of conservative amino acid changes are provided in the table below. As the skilled person would be aware, such minor changes can reasonably be predicted not to alter the activity of the polypeptide when expressed in a recombinant cell.

Exemplary Substitutions

| Original Residue | Exemplary Substitutions |
|---|---|
| Alanine (Ala) | Val; Leu; Ile; Gly |
| Arginine (Arg) | Lys |
| Asparagine (Asn) | Gln; His |
| Cysteine (Cys) | Ser |
| Glutamine (Gln) | Asn; His |
| Glutamic Acid (Glu) | Asp |
| Glycine (Gly) | Pro; Ala |
| Histidine (His) | Asn; Gln |
| Isoleucine (Ile) | Leu; Val; Ala |
| Leucine (Leu) | Ile; Val; Met; Ala; Phe |
| Lysine (Lys) | Arg |
| Methionine (Met) | Leu; Phe |
| Phenylalanine (Phe) | Leu; Val; Ala |
| Proline (Pro) | Gly |
| Serine (Ser) | Thr |
| Threonine (Thr) | Ser |
| Tryptophan (Trp) | Tyr |
| Tyrosine (Tyr) | Trp; Phe |
| Valine (Val) | Ile; Leu; Met; Phe; Ala |

Mutations can be introduced into a nucleic acid sequence such that the encoded amino acid sequence is altered by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g., alanine, valine, leucine, isoleucine, proline, phenylalanine, methionine, tyrosine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a given polypeptide is replaced with another amino acid residue from the same side chain family. Alternatively, in another embodiment, mutations can be introduced randomly along all or part of a given coding sequence, such as by saturation mutagenesis, and the resultant mutants can be screened for given polypeptide biological activity to identify mutants that retain activity. Conversely, the invention also provides for variants with mutations that enhance or increase the endogenous biological activity. Following mutagenesis of the nucleic acid sequence, the encoded protein can be expressed by any recombinant technology known in the art and the activity/specificity of the protein can be determined. An increase, decrease, or elimination of a given biological activity of the variants disclosed herein can be readily measured by the ordinary person skilled in the art, i.e., by measuring the capability for binding a ligand and/or signal transduction.

In various embodiments, a polypeptide comprises mutations such that 1, 2, 3, 4, 5, 6, 7, 8, 9, or 10, or less than about 10, 9, 8, 7, 6, 5, 4, 3, or 2 amino acids is substituted with a cysteine and/or a lysine.

Polypeptides can be produced in a variety of ways, including production and recovery of natural polypeptides or recombinant polypeptides according to methods known in the art. In one embodiment, a recombinant polypeptide is produced by culturing a cell capable of expressing the polypeptide under conditions effective to produce the polypeptide, such as a host cell defined herein.

Key to the Sequence Listing

| SEQ ID NO | Sequence Name |
|---|---|
| 1 | ecGGBP [U.S. National Center for Biotechnology Information (NCBI) Accession No. WP_032329053] |
| 2 | ttGGBP (NCBI Accession Nos. YP_003852930.1 and WP_013298803.1) |
| 3 | stGGBP (NCBI Accession No. WP_001036943) |
| 4 | chyGGBP (NCBI Accession Nos. WP_013402088.1 and YP_003991244.1) |
| 5 | cobGGBP (NCBI Accession Nos. WP_013289482.1 and YP_003839461.1) |
| 6 | pspGGBP (NCBI Accession Nos. WP_015735911.1 and YP_003243743.1) |
| 7 | csaGGBP (NCBI Accession Nos. WP_013273028.1 and YP_003822565.1) |
| 8 | bprGGBP (NCBI Accession Nos. WP_013280279.1 and YP_003830205.1) |
| 9 | rinGGBP_A (NCBI Accession Nos. WP_006855636.1 and YP_007778116.1) |

-continued

| SEQ ID NO | Sequence Name |
|---|---|
| 10 | fprGGBP (NCBI Accession Nos. WP_015536639.1 and YP_007799070.1) |
| 11 | cljGGBP (NCBI Accession No. CLJU_c08950) |
| 12 | cauGGBP (NCBI Accession No. CAETHG_2989) |
| 13 | rinGGBP_B (NCBI Accession Nos. WP_006855628.1 and YP_007778124.1) |
| 14 | erhGGBP (NCBI Accession Nos. WP_003775352.1 and YP_004561181.1) |
| 15 | ereGGBP (NCBI Accession Nos. WP_012741392.1 and YP_002936409.1) |
| 16 | ecGGBP (with signal peptide replaced with M) |
| 17 | ecGGBP (with signal sequence removed) |
| 18 | ttGGBP (with signal peptide replaced with M) |
| 19 | stGGBP (with signal peptide replaced with M) |
| 20 | chyGGBP (with signal peptide replaced with M) |
| 21 | cobGGBP (with signal peptide replaced with M) |
| 22 | pspGGBP (with signal peptide replaced with M) |
| 23 | csaGGBP (with signal peptide replaced with M) |
| 24 | bprGGBP (with signal peptide replaced with M) |
| 25 | rinGGBP_A (with signal peptide replaced with M) |
| 26 | fprGGBP (with signal peptide replaced with M) |
| 27 | cljGGBP (with signal peptide replaced with M) |
| 28 | cauGGBP (with signal peptide replaced with M) |
| 29 | rinGGBP_b (with signal peptide replaced with M) |
| 30 | erhGGBP (with signal peptide replaced with M) |
| 31 | ereGGBP (with signal peptide replaced with M) |
| 32 | ecGGBPW183C (with signal peptide replaced with M; a W183C mutation; and a GGSHHHHHH at C-terminus) |
| 33 | ecGGBP (with signal peptide replaced with M and a GGSHHHHHH at C-terminus) |
| 34 | csaGGBP (with signal peptide replaced with M and a GGSHHHHHH at C-terminus) |
| 35 | bprGGBP (with signal peptide replaced with M and a GGSHHHHHH at C-terminus) |
| 36 | rinGGBP_A (with signal peptide replaced with M and a GGSHHHHHH at C-terminus) |
| 37 | fprGGBP (with signal peptide replaced with M and a GGSHHHHHH at C-terminus) |
| 38 | cljGGBP (with signal peptide replaced with M and a GGSHHHHHH at C-terminus) |
| 39 | cauGGBP (with signal peptide replaced with M and a GGSHHHHHH at C-terminus) |
| 40 | rinGGBP_B (with signal peptide replaced with M and a GGSHHHHHH at C-terminus) |
| 41 | erhGGBP (with signal peptide replaced with M and a GGSHHHHHH at C-terminus) |
| 42 | ereGGBP (with signal peptide replaced with M and a GGSHHHHHH at C-terminus) |
| 43 | ttGGBP (with signal peptide replaced with M and a GGSHHHHHH at C-terminus) |
| 44 | cobGGBP (with signal peptide replaced with M and a GGSHHHHHH at C-terminus) |
| 45 | chyGGBP (with signal peptide replaced with M and a GGSHHHHHH at C-terminus) |
| 46 | pspGGBP (with signal peptide replaced with M and a GGSHHHHHH at C-terminus) |
| 47 | cobGGBP.W181C (Signaling cys mutant of cobGGBP with signal peptide replaced with M and GGSHHHHHH at C-terminus) |
| 48 | chyGGBP.W181C (Signaling cys mutants of chyGGBP with signal peptide replaced with M and GGSHHHHHH at C-terminus) |
| 49 | ttGGBP11C (ttGGBP cys mutant with signal peptide replaced with M and GGSHHHHHH at C-terminus) |
| 50 | ttGGBP16C (ttGGBP cys mutant with signal peptide replaced with M and GGSHHHHHH at C-terminus) |
| 51 | ttGGBP17C (ttGGBP cys mutant with signal peptide replaced with M and GGSHHHHHH at C-terminus) |
| 52 | ttGGBP42C (ttGGBP cys mutant with signal peptide replaced with M and GGSHHHHHH at C-terminus) |
| 53 | ttGGBP67C (ttGGBP cys mutant with signal peptide replaced with M and GGSHHHHHH at C-terminus) |
| 54 | ttGGBP91C (ttGGBP cys mutant with signal peptide replaced with M and GGSHHHHHH at C-terminus) |
| 55 | ttGGBP92C (ttGGBP cys mutant with signal peptide replaced with M and GGSHHHHHH at C-terminus) |
| 56 | ttGGBP111C (ttGGBP cys mutant with signal peptide replaced with M and GGSHHHHHH at C-terminus) |

-continued

| SEQ ID NO | Sequence Name |
|---|---|
| 57 | ttGGBP148C (ttGGBP cys mutant with signal peptide replaced with M and GGSHHHHHH at C-terminus) |
| 58 | ttGGBP151C (ttGGBP cys mutant with signal peptide replaced with M and GGSHHHHHH at C-terminus) |
| 59 | ttGGBP152C (ttGGBP cys mutant with signal peptide replaced with M and GGSHHHHHH at C-terminus) |
| 60 | ttGGBP181C (ttGGBP cys mutant with signal peptide replaced with M and GGSHHHHHH at C-terminus) |
| 61 | ttGGBP182C (ttGGBP cys mutant with signal peptide replaced with M and GGSHHHHHH at C-terminus) |
| 62 | ttGGBP183C (ttGGBP cys mutant with signal peptide replaced with M and GGSHHHHHH at C-terminus) |
| 63 | ttGGBP257C (ttGGBP cys mutant with signal peptide replaced with M and GGSHHHHHH at C-terminus) |
| 64 | ttGGBP259C (ttGGBP cys mutant with signal peptide replaced with M and GGSHHHHHH at C-terminus) |
| 65 | ttGGBP300C (ttGGBP cys mutant with signal peptide replaced with M and GGSHHHHHH at C-terminus) |
| 66 | ttGGBP17C.1 (affinity-tuning mutant, 17C background (Table 6) with signal peptide replaced with M and GGSHHHHHH at C-terminus) |
| 67 | ttGGBP17C.2 (affinity-tuning mutant, 17C background (Table 6) with signal peptide replaced with M and GGSHHHHHH at C-terminus) |
| 68 | ttGGBP17C.3 (affinity-tuning mutant, 17C background (Table 6) with signal peptide replaced with M and GGSHHHHHH at C-terminus) |
| 69 | ttGGBP17C.4 (affinity-tuning mutant, 17C background (Table 6) with signal peptide replaced with M and GGSHHHHHH at C-terminus) |
| 70 | ttGGBP17C.5 (affinity-tuning mutant, 17C background (Table 6) with signal peptide replaced with M and GGSHHHHHH at C-terminus) |
| 71 | ttGGBP17C.6 (affinity-tuning mutant, 17C background (Table 6) with signal peptide replaced with M and GGSHHHHHH at C-terminus) |
| 72 | ttGGBP17C.7 (affinity-tuning mutant, 17C background (Table 6) with signal peptide replaced with M and GGSHHHHHH at C-terminus) |
| 73 | ttGGBP17C.8 (affinity-tuning mutant, 17C background (Table 6) with signal peptide replaced with M and GGSHHHHHH at C-terminus) |
| 74 | ttGGBP17C.9 (affinity-tuning mutant, 17C background (Table 6) with signal peptide replaced with M and GGSHHHHHH at C-terminus) |
| 75 | ttGGBP17C.10 (affinity-tuning mutant, 17C background (Table 6) with signal peptide replaced with M and GGSHHHHHH at C-terminus) |
| 76 | ttGGBP17C.11 (affinity-tuning mutant, 17C background (Table 6) with signal peptide replaced with M and GGSHHHHHH at C-terminus) |
| 77 | ttGGBP17C.19 (affinity-tuning mutant, 17C background (Table 6) with signal peptide replaced with M and GGSHHHHHH at C-terminus) |
| 78 | ttGGBP17C.20 (affinity-tuning mutant, 17C background (Table 6) with signal peptide replaced with M and GGSHHHHHH at C-terminus) |
| 79 | ttGGBP17C.21 (affinity-tuning mutant, 17C background (Table 6) with signal peptide replaced with M and GGSHHHHHH at C-terminus) |
| 80 | ttGGBP17C.22 (affinity-tuning mutant, 17C background (Table 6) with signal peptide replaced with M and GGSHHHHHH at C-terminus) |
| 81 | ttGGBP17C.23 (affinity-tuning mutant, 17C background (Table 6) with signal peptide replaced with M and GGSHHHHHH at C-terminus) |
| 82 | ttGGBP17C.24 (affinity-tuning mutant, 17C background (Table 6) with signal peptide replaced with M and GGSHHHHHH at C-terminus) |
| 83 | ttGGBP17C.25 (affinity-tuning mutant, 17C background (Table 6) with signal peptide replaced with M and GGSHHHHHH at C-terminus) |
| 84 | ttGGBP17C.26 (affinity-tuning mutant, 17C background (Table 6) with signal peptide replaced with M and GGSHHHHHH at C-terminus) |
| 85 | ttGGBP17C.27 (affinity-tuning mutant, 17C background (Table 6) with signal peptide replaced with M and GGSHHHHHH at C-terminus) |
| 86 | ttGGBP17C.28 (affinity-tuning mutant, 17C background (Table 6) with signal peptide replaced with M and GGSHHHHHH at C-terminus) |
| 87 | ttGGBP17C.29 (affinity-tuning mutant, 17C background (Table 6) with signal peptide replaced with M and GGSHHHHHH at C-terminus) |
| 88 | ttGGBP182C.2.0 (affinity-tuning mutant, 182C background (Table 6) with signal peptide replaced with M and GGSHHHHHH at C-terminus) |
| 89 | ttGGBP182C.2.1 (affinity-tuning mutant, 182C background (Table 6) with signal peptide replaced with M and GGSHHHHHH at C-terminus) |
| 90 | ttGGBP182C.2.3 (affinity-tuning mutant, 182C background (Table 6) with signal peptide replaced with M and GGSHHHHHH at C-terminus) |
| 91 | ttGGBP182C.2.4 (affinity-tuning mutant, 182C background (Table 6) with signal peptide replaced with M and GGSHHHHHH at C-terminus) |
| 92 | ttGGBP182C.2.5 (affinity-tuning mutant, 182C background (Table 6) with signal peptide replaced with M and GGSHHHHHH at C-terminus) |
| 93 | ttGGBP182C.2.6 (affinity-tuning mutant, 182C background (Table 6) with signal peptide replaced with M and GGSHHHHHH at C-terminus) |
| 94 | ttGGBP182C.2.7 (affinity-tuning mutant, 182C background (Table 6) with signal peptide replaced with M and GGSHHHHHH at C-terminus) |

-continued

| SEQ ID NO | Sequence Name |
|---|---|
| 95 | ttGGBP182C.2.8 (affinity-tuning mutant, 182C background (Table 6) with signal peptide replaced with M and GGSHHHHHH at C-terminus) |
| 96 | ttGGBP182C.2.9 (affinity-tuning mutant, 182C background (Table 6) with signal peptide replaced with M and GGSHHHHHH at C-terminus) |
| 97 | ttGGBP182C.3 (affinity-tuning mutant, 182C background (Table 6) with signal peptide replaced with M and GGSHHHHHH at C-terminus) |
| 98 | ttGGBP182C.4 (affinity-tuning mutant, 182C background (Table 6) with signal peptide replaced with M and GGSHHHHHH at C-terminus) |
| 99 | ttGGBP182C.5 (affinity-tuning mutant, 182C background (Table 6) with signal peptide replaced with M and GGSHHHHHH at C-terminus) |
| 100 | ttGGBP182C.6 (affinity-tuning mutant, 182C background (Table 6) with signal peptide replaced with M and GGSHHHHHH at C-terminus) |
| 101 | ttGGBP182C.7 (affinity-tuning mutant, 182C background (Table 6) with signal peptide replaced with M and GGSHHHHHH at C-terminus) |
| 102 | ttGGBP182C.8 (affinity-tuning mutant, 182C background (Table 6) with signal peptide replaced with M and GGSHHHHHH at C-terminus) |
| 103 | ttGGBP182C.9 (affinity-tuning mutant, 182C background (Table 6) with signal peptide replaced with M and GGSHHHHHH at C-terminus) |
| 104 | GGSHHHHHH |
| 105 | csaGGBP Exemplary Expression Construct (Table 2) |
| 106 | bprGGBP Exemplary Expression Construct (Table 2) |
| 107 | rinGGBP__A Exemplary Expression Construct (Table 2) |
| 108 | fprGGBP Exemplary Expression Construct (Table 2) |
| 109 | cljGGBP Exemplary Expression Construct (Table 2) |
| 110 | cauGGBP Exemplary Expression Construct (Table 2) |
| 111 | rinGGBP__B Exemplary Expression Construct (Table 2) |
| 112 | erhGGBP Exemplary Expression Construct (Table 2) |
| 113 | ereGGBP Exemplary Expression Construct (Table 2) |
| 114 | ttGGBP Exemplary Expression Construct (Table 2) |
| 115 | cobGGBP Exemplary Expression Construct (Table 2) |
| 116 | chyGGBP Exemplary Expression Construct (Table 2) |
| 117 | pspGGBP23 Exemplary Expression Construct (Table 2) |
| 118 | ttGGBP11C Exemplary Cysteine Scan Mutant Expression Construct (Table 3) |
| 119 | ttGGBP16C Exemplary Cysteine Scan Mutant Expression Construct (Table 3) |
| 120 | ttGGBP17C Exemplary Cysteine Scan Mutant Expression Construct (Table 3) |
| 121 | ttGGBP42C Exemplary Cysteine Scan Mutant Expression Construct (Table 3) |
| 122 | ttGGBP67C Exemplary Cysteine Scan Mutant Expression Construct (Table 3) |
| 123 | ttGGBP91C Exemplary Cysteine Scan Mutant Expression Construct (Table 3) |
| 124 | ttGGBP92C Exemplary Cysteine Scan Mutant Expression Construct (Table 3) |
| 125 | ttGGBP111C Exemplary Cysteine Scan Mutant Expression Construct (Table 3) |
| 126 | ttGGBP148C Exemplary Cysteine Scan Mutant Expression Construct (Table 3) |
| 127 | ttGGBP151C Exemplary Cysteine Scan Mutant Expression Construct (Table 3) |
| 128 | ttGGBP152C Exemplary Cysteine Scan Mutant Expression Construct (Table 3) |
| 129 | ttGGBP181C Exemplary Cysteine Scan Mutant Expression Construct (Table 3) |
| 130 | ttGGBP182C Exemplary Cysteine Scan Mutant Expression Construct (Table 3) |
| 131 | ttGGBP183C Exemplary Cysteine Scan Mutant Expression Construct (Table 3) |
| 132 | ttGGBP257C Exemplary Cysteine Scan Mutant Expression Construct (Table 3) |
| 133 | ttGGBP259C Exemplary Cysteine Scan Mutant Expression Construct (Table 3) |
| 134 | ttGGBP300C Exemplary Cysteine Scan Mutant Expression Construct (Table 3) |
| 135 | ttGGBP17C.1 Exemplary Affinity-Tuning mutant (17C Background) Expression Construct (Table 6) |
| 136 | ttGGBP17C.2 Exemplary Affinity-Tuning mutant (17C Background) Expression Construct (Table 6) |
| 137 | ttGGBP17C.3 Exemplary Affinity-Tuning mutant (17C Background) Expression Construct (Table 6) |
| 138 | ttGGBP17C.4 Exemplary Affinity-Tuning mutant (17C Background) Expression Construct (Table 6) |
| 139 | ttGGBP17C.5 Exemplary Affinity-Tuning mutant (17C Background) Expression Construct (Table 6) |

-continued

| SEQ ID NO | Sequence Name |
|---|---|
| 140 | ttGGBP17C.6 Exemplary Affinity-Tuning mutant (17C Background) Expression Construct (Table 6) |
| 141 | ttGGBP17C.7 Exemplary Affinity-Tuning mutant (17C Background) Expression Construct (Table 6) |
| 142 | ttGGBP17C.8 Exemplary Affinity-Tuning mutant (17C Background) Expression Construct (Table 6) |
| 143 | ttGGBP17C.9 Exemplary Affinity-Tuning mutant (17C Background) Expression Construct (Table 6) |
| 144 | ttGGBP17C.10 Exemplary Affinity-Tuning mutant (17C Background) Expression Construct (Table 6) |
| 145 | ttGGBP17C.11 Exemplary Affinity-Tuning mutant (17C Background) Expression Construct (Table 6) |
| 146 | ttGGBP17C.19 Exemplary Affinity-Tuning mutant (17C Background) Expression Construct (Table 6) |
| 147 | ttGGBP17C.20 Exemplary Affinity-Tuning mutant (17C Background) Expression Construct (Table 6) |
| 148 | ttGGBP17C.21 Exemplary Affinity-Tuning mutant (17C Background) Expression Construct (Table 6) |
| 149 | ttGGBP17C.22 Exemplary Affinity-Tuning mutant (17C Background) Expression Construct (Table 6) |
| 150 | ttGGBP17C.23 Exemplary Affinity-Tuning mutant (17C Background) Expression Construct (Table 6) |
| 151 | ttGGBP17C.24 Exemplary Affinity-Tuning mutant (17C Background) Expression Construct (Table 6) |
| 152 | ttGGBP17C.25 Exemplary Affinity-Tuning mutant (17C Background) Expression Construct (Table 6) |
| 153 | ttGGBP17C.26 Exemplary Affinity-Tuning mutant (17C Background) Expression Construct (Table 6) |
| 154 | ttGGBP17C.27 Exemplary Affinity-Tuning mutant (17C Background) Expression Construct (Table 6) |
| 155 | ttGGBP17C.28 Exemplary Affinity-Tuning mutant (17C Background) Expression Construct (Table 6) |
| 156 | ttGGBP17C.29 Exemplary Affinity-Tuning mutant (17C Background) Expression Construct (Table 6) |
| 157 | ttGGBP182C.2.0 Exemplary Affinity-Tuning mutant (182C Background) Expression Construct (Table 6) |
| 158 | ttGGBP182C.2.1 Exemplary Affinity-Tuning mutant (182C Background) Expression Construct (Table 6) |
| 159 | ttGGBP182C.2.3 Exemplary Affinity-Tuning mutant (182C Background) Expression Construct (Table 6) |
| 160 | ttGGBP182C.2.4 Exemplary Affinity-Tuning mutant (182C Background) Expression Construct (Table 6) |
| 161 | ttGGBP182C.2.5 Exemplary Affinity-Tuning mutant (182C Background) Expression Construct (Table 6) |
| 162 | ttGGBP182C.2.6 Exemplary Affinity-Tuning mutant (182C Background) Expression Construct (Table 6) |
| 163 | ttGGBP182C.2.7 Exemplary Affinity-Tuning mutant (182C Background) Expression Construct (Table 6) |
| 164 | ttGGBP182C.2.8 Exemplary Affinity-Tuning mutant (182C Background) Expression Construct (Table 6) |
| 165 | ttGGBP182C.2.9 Exemplary Affinity-Tuning mutant (182C Background) Expression Construct (Table 6) |
| 166 | ttGGBP182C.3 Exemplary Affinity-Tuning mutant (182C Background) Expression Construct (Table 6) |
| 167 | ttGGBP182C.4 Exemplary Affinity-Tuning mutant (182C Background) Expression Construct (Table 6) |
| 168 | ttGGBP182C.5 Exemplary Affinity-Tuning mutant (182C Background) Expression Construct (Table 6) |
| 169 | ttGGBP182C.6 Exemplary Affinity-Tuning mutant (182C Background) Expression Construct (Table 6) |
| 170 | ttGGBP182C.7 Exemplary Affinity-Tuning mutant (182C Background) Expression Construct (Table 6) |
| 171 | ttGGBP182C.8 Exemplary Affinity-Tuning mutant (182C Background) Expression Construct (Table 6) |
| 172 | ttGGBP182C.9 Exemplary Affinity-Tuning mutant (182C Background) Expression Construct (Table 6) |
| 173 | ttGGBP182C.2.0_Imm0 |
| 174 | ttGGBP, R91K, Q148E |
| 175 | ttGGBP182C.2.0_Imm1 |
| 176 | ttGGBP182C.2.0_Imm2 |
| 177 | ttGGBP182C.2.0_Imm3 |
| 178 | ttGGBP182C.2.0_Imm4 |
| 179 | ttGGBP182C.2.0_Imm5 |
| 180 | ttGGBP182C.2.0_Imm6 |
| 181 | ttGGBP182C.2.0_Imm7 |
| 182 | IYKXDDXFM (Conserved Sequence) |
| 183 | YKXDDXFM (Conserved Sequence) |

-continued

| SEQ ID NO | Sequence Name |
|---|---|
| 184 | YKXDDXF (Conserved Sequence) |
| 185 | KXDDXF (Conserved Sequence) |
| 186 | YKXDD (Conserved Sequence) |
| 187 | KXDD (Conserved Sequence) |
| 188 | DDXF (Conserved Sequence) |
| 189 | DXFMXXVR (Conserved Sequence) |
| 190 | DXFMXXV (Conserved Sequence) |
| 191 | DXFM (Conserved Sequence) |
| 192 | IYKXDNXFM (Conserved Sequence) |
| 193 | YKXDNXFM (Conserved Sequence) |
| 194 | YKXDNXF (Conserved Sequence) |
| 195 | KXDNXF (Conserved Sequence) |
| 196 | YKXDN (Conserved Sequence) |
| 197 | KXDN (Conserved Sequence) |
| 198 | DNXF (Conserved Sequence) |
| 199 | NXFMXXVR (Conserved Sequence) |
| 200 | NXFMXXV (Conserved Sequence) |
| 201 | NXFM (Conserved Sequence) |
| 202 | PVVFFNKEP (Conserved Sequence) |
| 203 | PVVFXNKEP (Conserved Sequence) |
| 204 | PVVFFNXEP (Conserved Sequence) |
| 205 | PVVFXNXEP (Conserved Sequence) |
| 206 | VVFXNXEP (Conserved Sequence) |
| 207 | VFXNXEP (Conserved Sequence) |
| 208 | PVVFXNXE (Conserved Sequence) |
| 209 | PVVFXN (Conserved Sequence) |
| 210 | PXVFXN (Conserved Sequence) |
| 211 | PVXFXN (Conserved Sequence) |
| 212 | FXNXEP (Conserved Sequence) |
| 213 | FXNXE (Conserved Sequence) |
| 214 | PGHPDAEART (Conserved Sequence) |
| 215 | PGHXDAXXRT (Conserved Sequence) |
| 216 | GHXDAXXRT (Conserved Sequence) |
| 217 | HXDAXXRT (Conserved Sequence) |
| 218 | DAXXRT (Conserved Sequence) |
| 219 | PGHXDAXXR (Conserved Sequence) |
| 220 | PGHXDA (Conserved Sequence) |
| 221 | PGHXD (Conserved Sequence) |
| 222 | PGNPDAEART (Conserved Sequence) |
| 223 | PGNXDAXXRT (Conserved Sequence) |
| 224 | GNXDAXXRT (Conserved Sequence) |
| 225 | NXDAXXRT (Conserved Sequence) |
| 226 | PGNXDAXXR (Conserved Sequence) |
| 227 | PGNXDA (Conserved Sequence) |
| 228 | PGNXD (Conserved Sequence) |
| 229 | DTAMWD (Conserved Sequence) |
| 230 | DTAMCD (Conserved Sequence) |
| 231 | DTAMW (Conserved Sequence) |
| 232 | DTAMC (Conserved Sequence) |
| 233 | TAMWD (Conserved Sequence) |
| 234 | TAMCD (Conserved Sequence) |
| 235 | AXWXX (Conserved Sequence) |
| 236 | AXCXX (Conserved Sequence) |
| 237 | IEVVIANND (Conserved Sequence) |
| 238 | EVVIANND (Conserved Sequence) |
| 239 | IEVVIANN (Conserved Sequence) |
| 240 | EVVIANN (Conserved Sequence) |
| 241 | IEXVXXNND (Conserved Sequence) |
| 242 | IEXVXXNN (Conserved Sequence) |
| 243 | EXVXXNND (Conserved Sequence) |
| 244 | EXVXXNN (Conserved Sequence) |
| 245 | PVFGVDA (Conserved Sequence) |
| 246 | VFGVDA (Conserved Sequence) |
| 247 | PVFGVD (Conserved Sequence) |
| 248 | FGVDA (Conserved Sequence) |
| 249 | PVXGVDA (Conserved Sequence) |
| 250 | VXGVDA (Conserved Sequence) |
| 251 | PVXGVD (Conserved Sequence) |
| 252 | VXGVD (Conserved Sequence) |
| 253 | GTVLNDA (Conserved Sequence) |
| 254 | GTVLND (Conserved Sequence) |
| 255 | GTVLN (Conserved Sequence) |
| 256 | TVLND (Conserved Sequence) |
| 257 | chyGGBP_F12C (chGGBP with signal sequence replaced with M; F12C, C39A, and C206A mutations; and GGSHHHHHH at C-terminus) |
| 258 | chyGGBP_F16C (chGGBP with signal sequence replaced with M; F16C, C39A, and C206A mutations; and GGSHHHHHH at C-terminus) |

-continued

| SEQ ID NO | Sequence Name |
|---|---|
| 259 | chyGGBP_W181C (chGGBP with signal sequence replaced with M; W181C, C39A, and C206A mutations; and GGSHHHHHH at C-terminus) |
| 260 | cobGGBP_F12C (cobGGBP with signal sequence replaced with M; F12C, C39A, C173A, and C206A mutations; and GGSHHHHHH at C-terminus) |
| 261 | cobGGBP_F16C (cobGGBP with signal sequence replaced with M; F16C, C39A, C173A, and C206A mutations; and GGSHHHHHH at C-terminus) |
| 262 | cobGGBP_W181C (cobGGBP with signal sequence replaced with M, W181C, C39A, C173A, and C206A mutations; and GGSHHHHHH at C-terminus) |
| 263 | pspGGPB_F13C (pspGGBP with signal sequence replaced with M; F13C mutation; and GGSHHHHHH at C-terminus) |
| 264 | pspGGPB_F9C (pspGGBP with signal sequence replaced with M; F9C mutation; and GGSHHHHHH at C-terminus) |
| 265 | pspGGPB_W178C (pspGGBP with signal sequence replaced with M; W178C mutation; and GGSHHHHHH at C-terminus) |
| 266 | csaGGBP_F18C (csaGGBP with signal sequence replaced with M; F18C, C62A, C82A, C113A, and C211A mutations; and GGSHHHHHH at C-terminus) |
| 267 | csaGGBP_W186C (csaGGBP with signal sequence replaced with M; W186C, C62A, C82A, C113A, and C211A mutations; and GGSHHHHHH at C-terminus) |
| 268 | csaGGBP_Y14C (csaGGBP with signal sequence replaced with M; Y14C, C62A, C82A, C113A, and C211A mutations; and GGSHHHHHH at C-terminus) |
| 269 | bprGGBP_F16C (bprGGBP with signal sequence replaced with M; F16C, C8A, C112A, C116A, C179A, C211A, and C289A mutations; and GGSHHHHHH at C-terminus) |
| 270 | bprGGBP_K12C (bprGGBP with signal sequence replaced with M; K12C, C8A, C112A, C116A, C179A, C211A, and C289A mutations; and GGSHHHHHH at C-terminus) |
| 271 | bprGGBP_W187C (bprGGBP with signal sequence replaced with M; W187C, C8A, C112A, C116A, C179A, C211A, and C289A mutations; and GGSHHHHHH at C-terminus) |
| 272 | rinGGBP_A_F10C (rinGGBP_A with signal sequence replaced with M; F10C, C6A, C114A, C177A, C210A, and C288A mutations; and GGSHHHHHH at C-terminus) |
| 273 | rinGGBP_A_F14C (rinGGBP_A with signal sequence replaced with M; F14C, C6A, C114A, C177A, C210A, and C288A mutations; and GGSHHHHHH at C-terminus) |
| 274 | rinGGBP_A_W185C (rinGGBP_A with signal sequence replaced with M; W185C, C6A, C114A, C177A, C210A, and C288A mutations; and GGSHHHHHH at C-terminus) |
| 275 | rinGGBP_B_F17C (rinGGBP_B with signal sequence replaced with M; F17C, C66A, C70A, and C306A; and GGSHHHHHH at C-terminus) |
| 276 | rinGGBP_B_Q13C (rinGGBP_B with signal sequence replaced with M; Q13C, C66A, C70A, and C306A mutations; and GGSHHHHHH at C-terminus) |
| 277 | rinGGBP_B_W189C (rinGGBP_B with signal sequence replaced with M; W189C, C66A, C70A, and C306A mutations; and GGSHHHHHH at C-terminus) |
| 278 | fprGGBP_F12C (fprGGBP with signal sequence replaced with M; F12C, C8A, C105A, C106A, C143A, and C205A mutations; and GGSHHHHHH at C-terminus) |
| 279 | fprGGBP_F16C (fprGGBP with signal sequence replaced with M; F16C, C8A, C105A, C106A, C143A, and C205A mutations; and GGSHHHHHH at C-terminus) |
| 280 | fprGGBP_W180C (fprGGBP with signal sequence replaced with M; W180C, C8A, C105A, C106A, C143A, and C205A mutations; and GGSHHHHHH at C-terminus) |
| 281 | cljGGBP_F11C (cljGGBP with signal sequence replaced with M; F11C, C77A, and C198A mutations; and GGSHHHHHH at C-terminus) |
| 282 | cljGGBP_W15C (cljGGBP with signal sequence replaced with M; W15C, C77A, and C198A mutations; and GGSHHHHHH at C-terminus) |
| 283 | cljGGBP_W176C (cljGGBP with signal sequence replaced with M; W176C, C77A, and C198A mutations; and GGSHHHHHH at C-terminus) |
| 284 | cauGGBP_F12C (cauGGBP with signal sequence replaced with M; F12C, C78A, and C199A mutations; and GGSHHHHHH at C-terminus) |
| 285 | cauGGBP_W16C (cauGGBP with signal sequence replaced with M; W16C, C78A, and C199A mutations; and GGSHHHHHH at C-terminus) |
| 286 | cauGGBP_W177C (cauGGBP with signal sequence replaced with M; W177C, C78A, and C199A mutations; and GGSHHHHHH at C-terminus) |
| 287 | erhGGBP_F13C (erhGGBP with signal sequence replaced with M; F13C mutation; and GGSHHHHHH at C-terminus) |
| 288 | erhGGBP_F17C (erhGGBP with signal sequence replaced with M; F17C mutation; and GGSHHHHHH at C-terminus) |

-continued

| SEQ ID NO | Sequence Name |
|---|---|
| 289 | erhGGBP_W188C (erhGGBP with signal sequence replaced with M; W188C mutation; and GGSHHHHHH at C-terminus) |
| 290 | ereGGBP_F17C (ereGGBP with signal sequence replaced with M; F17C, C10A, C29A, C65A, C69A, and C183A mutations; and GGSHHHHHH at C-terminus) |
| 291 | ereGGBP_Q13C (ereGGBP with signal sequence replaced with M; Q13C, C10A, C29A, C65A, C69A, and C183A mutations; and GGSHHHHHH at C-terminus) |
| 292 | ereGGBP_W188C (ereGGBP with signal sequence replaced with M; W188C, C10A, C29A, C65A, C69A, and C183A mutations; and GGSHHHHHH at C-terminus) |
| 293 | βZif |
| 294 | ZF-QNK |
| 295 | Hexahistidine Tag |
| 296 | Hexalysine Tag |
| 297 | ecGGBP.F16C (with signal peptide replaced with M; a F16C mutation; and a GGSHHHHHH at C-terminus) |
| 298 | ttGGBP182C.2.0 (affinity-tuning mutant, 182C background (Table 6) with signal peptide replaced with M) |

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1. Fluorescently Responsive Sensor Engineering Phases

The engineering of FRSs can be divided into five phases:

1. Binding protein discovery. A set of glucose-binding protein sequence homologs is identified. Accurate assignment of their ligand-binding function utilizes application of a prediction method that incorporates information encoded in the experimentally determined three-dimensional structure of periplasmic glucose-binding proteins.
2. Experimental lead validation. Synthetic genes are constructed, which are optimized for heterologous expression in *Escherichia coli* of one or more predicted glucose-binding protein sequences. The glucose-binding properties and thermostabilities of the corresponding expressed, purified proteins are evaluated.
3. Engineering of fluorescent responses. Semisynthetic fluorescent conjugates of the experimentally validated leads are constructed by attaching fluorophores to single cysteine mutants. The effect of glucose binding on the fluorescence emission properties of those conjugates is evaluated. Those conjugates that evince strong, ratiometric responses are selected as FRSs.
4. Affinity tuning. Single or multiple mutations are introduced by site-directed mutagenesis to alter the glucose-binding affinities of glucose-responsive FRSs. A set of FRS variants is selected that together cover the clinical glucose concentration range with high accuracy.
5. Device integration. FRSs are immobilized in the sampling component of the analytical device in a manner that preserves their fluorescent response and glucose affinity. Long-term storage conditions are established.

Example 2. Identification of a Family of Periplasmic Glucose-Binding Proteins Homologs Using Structurally Assisted Function Evaluation (Phase Step 1)

As a first step in constructing robust glucose sensor candidates, we examined bacterial genomic sequences to identify periplasmic glucose-binding protein sequences in known thermophiles. Homologs from such organisms are likely to encode thermostable proteins. Analysis of enzyme families has shown that overall sequence identity below ~60% is a weak predictor of function conservation (Todd 2001 *J. Mol. Biol.*, 307, 1113-1143; Tian 2003 *J. Mol. Biol.*, 333, 863-882). Furthermore, functional assignments based on sequence homology alone are known to be particularly problematic in the PBP superfamily. For instance, PBPs that by overall sequence identity are predicted to bind oligopeptides were found to bind oligosaccharides. Enzyme functional assignments are improved greatly if a sequence selection filter based on conservation of catalytic residues identified from protein structures is included. Such catalytic residues comprise a subset of all the residues that contact an enzyme substrate or inhibitor. In the case of the PBPs, functional selection filters need to take into account all the protein-ligand contacts that encode the ligand-binding function. Accordingly, we have developed a structurally assisted functional evaluation (SAFE) method to identify PBP sequence homologs with accurately predicted function. The SAFE homolog search method consists of five steps encoded in the ProteinHunter software package:

1. Sequence homolog set is collected using the BLAST sequence alignment tool (Altschul et al. 1990) with standard settings (expect threshold: 10.0; gap cost existence: 11; gap extension: 1; substitution matrix: Blosum62; filter for low complexity regions on), starting with *Escherichia coli* periplasmic glucose-galactose binding protein (ecGGBP) sequence (SEQ ID NO: 17) as a seed (Vyas, Vyas and Quiocho 1988 *Science,* 242, 1290-5). The ProteinHunter program selects only those pairwise BLAST alignments that (a) share a minimum of 20% sequence identity, and (b) have 70% coverage of their entire sequence length by the aligned region. This set of sequences defines a universe of possible glucose-binding proteins without assigning function.
2. Structure-based encoding of biological function. A PCS comprising the protein residues that form hydrogen bonds and van der Waals contacts with the bound glucose is defined using computer-assisted, visual inspection of the three-dimensional structure of the ecGGBP-glucose complex. ProteinHunter identifies if the calculated distance between any of their atoms and any glucose atom is less than 5 Å, and the distances between their backbone $C_\alpha$ and any atom in glucose is greater than that of their $C_\beta$ atom and any atom in glucose. Secondary shell residues that do not form hydrogen bonds or van der Waals contacts are removed by inspection from the resulting set. The choice of allowed residues is guided by the identity of the residue in the structure, and mutants that are likely to maintain that interaction. The resulting definition specifies residue positions and their permitted amino acid identity. Multiple amino acid identities are permitted at each position to encode functionally equivalent residues. This definition establishes a search filter for the accurate prediction of glucose-binding proteins within the universe of sequence homologs collected in (1).

3. Accurate sequence alignment. Tools such as ClustalW (Chenna et al. 2003 Nucleic Acids Res, 31, 3497-500) are used to construct an accurate alignment of all the sequence homologs. The ecGGBP seed sequence is included in this alignment. This multiple sequence alignment establishes the equivalent positions of the ecGGBP PCS in each sequence homolog.
4. Function evaluation. The glucose-binding properties of each of the aligned sequence homologs is determined by measuring their compliance with the PCS sequence filter. A "Hamming distance", H, is assigned for each homolog by the ProteinHunter program, which specifies the degree of sequence identity of all the residues at the aligned PCS positions. A value of H=0 indicates that the identities of all the residues at the aligned PCS positions match the amino acid(s) allowed in the PCS search filter; H>0, indicates that one or more aligned positions have disallowed residues. Sequences for which H=0 are predicted to encode glucose-binding proteins.
5. Selection of representative SAFE homologs. The sequence homologs are ordered by (a) identity with the seed PCS, as measured by the Hamming distance, (b) fractional overall sequence identity with the seed sequence. A subset for sequences with H=0, sampling the fractional overall sequence identity is selected for experimental verification.

The ProteinHunter software tool encodes the flow of execution, applies the PCS search filter, and visualizes the results that include organism annotations such as thermophilicity, and Gram stain status.

These steps are encoded in the ProteinHunter software tool, which encodes the flow of execution, applies the PCS search filter, and visualizes the results, and handles organism annotations such as thermophilicity, and Gram stain status.

Annotated genomic and plasmid sequences of 5062 prokaryotes were downloaded from the National Center of Biotechnology Information (download date: May 17, 2015; ftp://ftp.ncbi.nih.gov/genomes/Bacteria/all.gbk.tar.gz). The protein sequence for the *E. coli* glucose-galactose binding protein (ecGGBP) was extracted from the protein structure file 2gbp (Vyas et al. 1988 *Science,* 242, 1290-5), and used as the seed sequence for the BLAST search described above. A total of 1822 sequence homologs were identified.

Figure 2A:
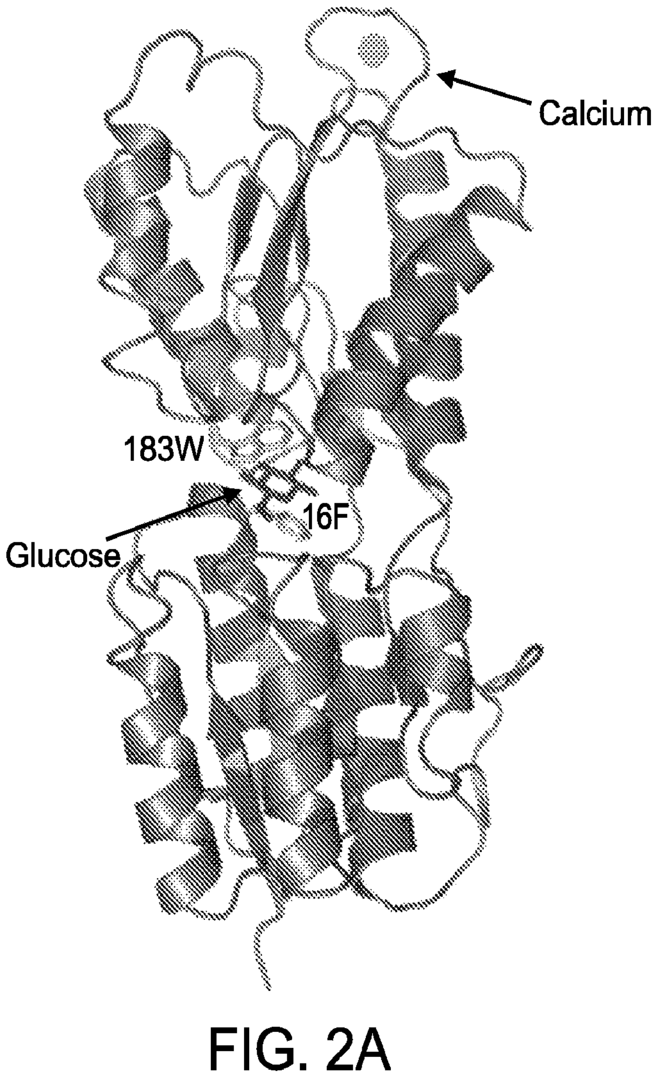
FIGS. 2A-C are structural illustrations and a table showing exemplary features of the *E. coli* glucose-galactose binding protein (ecGGBP). (A) The glucose and calcium complex [PDB identifier 2gbp (Vyas et al. 1988)], glucose is sandwiched by van der Waals contacts with the rings of Phe16 and Trp183. (B) Residues that form hydrogen bonds with the bound glucose. The primary complementary surface (PCS) comprises the aromatic sandwich and the hydrogen-bonding residues. (C) The PCS sequence filter used to identify the subset of glucose-binding proteins within a family of sequence ecGGBP homologs. Note redundancies in the allowed residues at each position (the first amino acid listed corresponds to the wild-type ecGGBP sequence).
Figures 2B, 2C:
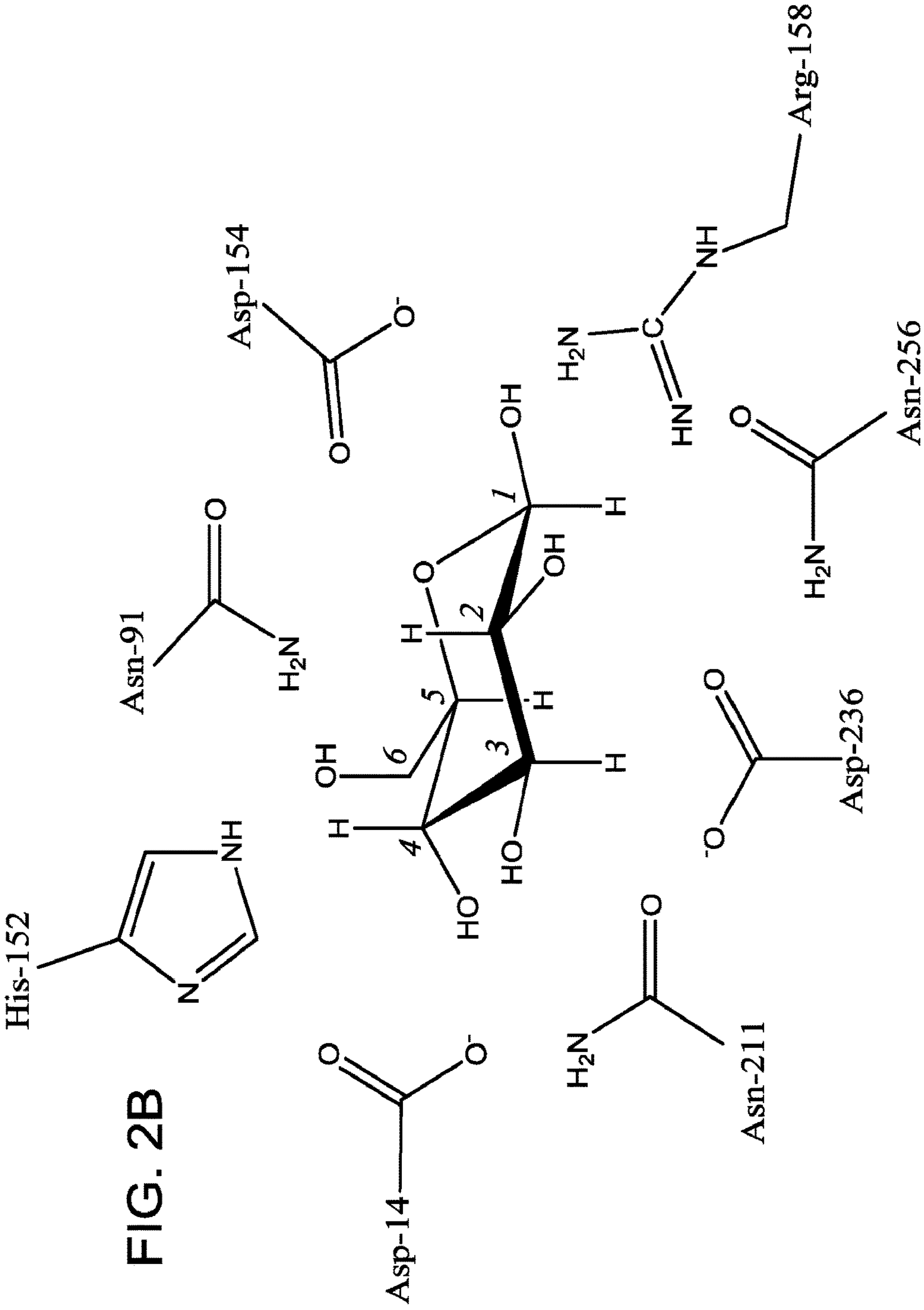
Figure 3:
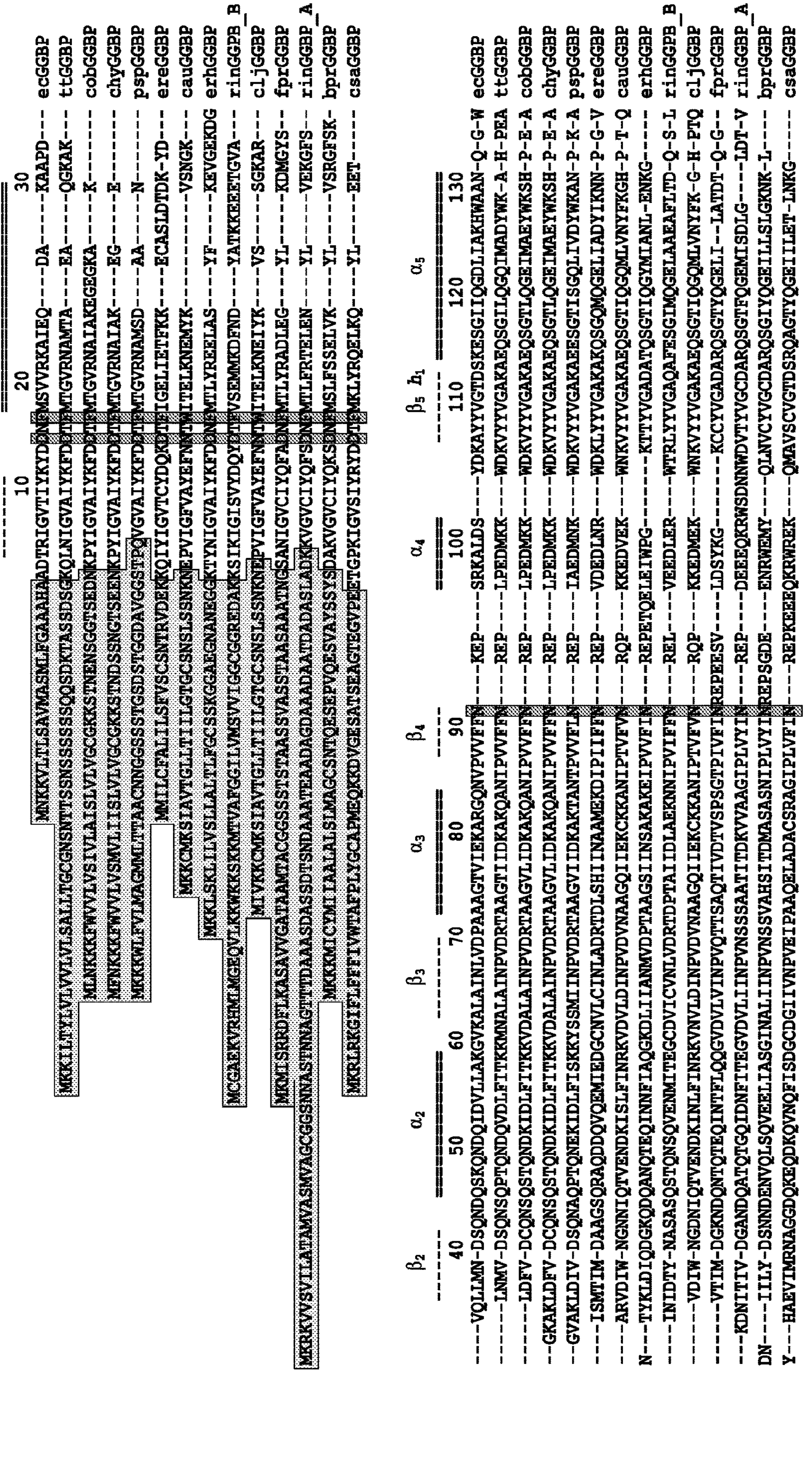
FIG. 3 is an alignment of the homologs predicted to be glucose-binding proteins (alignment generated by ClustalW; ordered by fractional sequence identity to the ecGGBP seed sequence). Sequences taken from Table 1 (name, line number in Table 1, accession code, species, fractional identity to ecGGBP)

In ecGGBP, glucose binding is encoded by a PCS comprising ten residues. Two aromatic residues (F16, W182) sandwich the bound glucose through extensive van der Waals interactions with either surface of the pyranose ring. The other eight residues form hydrogen bonds with all the glucose hydroxyls. A PCS filter specifying multiple amino acids at these 10 positions was used to predict glucose-binding proteins (FIGS. 2A-C). A total of 139 homologs were predicted to encode glucose-binding proteins, on the basis of their Hamming distance scores (H=0). The overall sequence identities of these homologs relative to the ecGGBP seed varied from 100% to 29% (Table 1).

Example 3. Lead Protein Validation Using Ligand-Mediated Thermostability Shifts (Phase Step 2)

Thirteen homologs that were predicted to be glucose-binding proteins (FIG. 3) were selected to probe different degrees of sequence identity to the ecGGBP seed, and their glucose-binding properties were determined experimentally (Table 2). These experiments comprise four successive steps:

1. Synthetic gene construction. The amino acid sequence of the homology leads are backtranslated into DNA sequences. These are optimized for directing heterologous cytoplasmic expression of the protein homologues in *E. coli*, using either the OrfOpt, (U.S. Patent Publication No. 2011/0171737), hereby incorporated by reference or OrfMorph (described herein) programs. These programs predict mRNA sequences that direct high-level protein expression in *E. coli*. The predicted gene sequences are assembled de novo from synthetic oligonucleotides.
2. Heterologous protein expression of the homologues in *E. coli*. Plasmids carrying the synthetic expression constructs (see above) were transformed into KRX (*E-Coli* K12 Derivative Strain) competent cells (Promega, Technical Bulletin TB352). Protein production was induced in bacterial cultures of these cultures, as described in the Materials and Methods.
3. Purification of successfully expressed protein using immobilized metal affinity chromatography, as described in Materials and Methods.
4. Verification of glucose binding. Determination of the glucose-binding properties of the purified proteins using a thermal stability shift assay, as described in Materials and Methods.

Seven of the thirteen synthetic expression constructs successfully directed heterologous cytoplasmic expression of a GGBP homolog in *E. coli*. The glucose-binding properties of five of these were confirmed directly using the thermal shift assay (FIGS. 4A-B). The thermostability of two homologs was too high ($^{app}T_m$>90° C.) for this assay to be applicable. Their glucose-binding properties were confirmed by measuring the temperature-dependent fluorescence responses of Acrylodan-labeled single cysteine mutants (see section 5) to glucose (FIGS. 5A-B).

Surprisingly, the sequence identity of all these experimentally verified glucose-binding homologs relative the ecGGBP seed are considerably below the 60% threshold, ranging from 29% to 48%. Several use alternate amino acids in the PCS at position 152, demonstrating the predictive power of allowing functionally equivalent residues. These results therefore demonstrate that biological function can be predicted accurately with the SAFE technique, even in sequence homologs with low fractional identities to the original seed.

Three of the experimentally verified GGBP homologs exhibit mid-point thermal denaturation temperatures ($T_m$ values) in the 347-350 K range, which is at least 25 K more stable than the ecGGBP seed ($T_m$=322 K). Of these, the homolog from *Thermoanaerobacter thermosaccharolyticum* (ttGGBP) was produced at the highest level by heterologous expression in *E. coli*. This protein was selected as the candidate for constructing robust glucose sensors.

Example 4. Cysteine Mutant Scans and Fluorophore Screening to Identify Fluorescently Responsive Glucose Sensors (Phase Step 3)

Semi-synthetic FRSs were engineered by site-specifically attaching thiol-reactive, environmentally sensitive fluorophores that respond to ligand-mediated conformational changes. Identification of FRS candidates that are useful for sensing applications comprises three steps:

1. Cysteine scan. Mutant glucose-binding proteins containing single cysteines are constructed for site-specific attachment of thiol-reactive fluorophores. Positions in PBPs where attached single fluorophores are likely to exhibit ligand-dependent responses were determined (de Lorimier et al. 2002 *Protein Sci,* 11, 2655-75). Candidate positions fall into three classes: endosteric, replacing a residue that contacts the ligand directly; peristeric, located at the rim of the binding site; allosteric (Marvin et al. 1997 *Proc Natl Acad Sci USA,* 94, 4366-71; Marvin 1998 *J Am Chem Soc,* 120, 7-11), located outside the binding site at sites that undergo local structural changes in concert with the hinge-bending motion.
2. Fluorophore screening. Thiol-reactive, environmentally sensitive fluorophores are attached to each cysteine mutant prepared in step 1.
3. Evaluation of the glucose-mediated change of all the fluorescent conjugates prepared in step 2. Responses to ligand binding in which there is both a change in fluorescence emission intensity and spectral shape was essential for chemometric applications, because such changes enable ratiometric measurements. Changes in spectral shape typically are accompanied by a shift in the wavelength of the emission intensity maxima. Three classes of fluorescent responses are possible:
   - i. No response.
   - ii. Monochromatic response (emission intensity increases or decreases without a change in spectral shape)
   - iii. Dichromatic response (both intensity and spectral shape changes) which can be classified into two sub-classes:
     - i. Hypsochromatic: emission intensity shifts to shorter wavelengths upon binding glucose ("blue shift").
     - ii. Bathochromatic: emission intensity shifts to longer wavelengths upon binding glucose ("red shift").

We constructed seventeen single cysteine mutants in ttGGBP, exploring four endosteric, ten peristeric, and three allosteric positions (FIGS. 6A-B). At each position, we attached the Prodan-derived fluorophores such as Acrylodan and Badan, which differ by one methylene group in their thiol-reactive linking moiety. The fluorescence emission intensities of seven Acrylodan and five Badan conjugates responded to glucose at seven attachment positions (Table 3). At only four attachment positions were the responses of both fluorophores qualitatively similar, and never quantitatively. We also tested for glucose binding by measuring ligand-mediated shifts in protein thermal stability (Table 3). By this criterion, the majority of the non-responsive conjugates bound glucose. The two conjugates that did not bind glucose (N42C•Badan, V67C•Badan) also exhibited large losses in overall thermostability (28-30 K decrease in apo $T_m$ values), indicating that the attached fluorophore adversely affected their structural integrity. By contrast, all other conjugates exhibited only small variations in apo-protein thermostability (1-4 K), indicating that the fluorophore causes minimal perturbations instability.

Endosteric attachment positions exhibited the most pronounced changes in fluorescence emissions in response to ligand binding. Conjugates at three of the ten peristeric positions were responsive to glucose. No allosteric conjugates exhibited fluorescence responses to glucose.

Figure 7A:
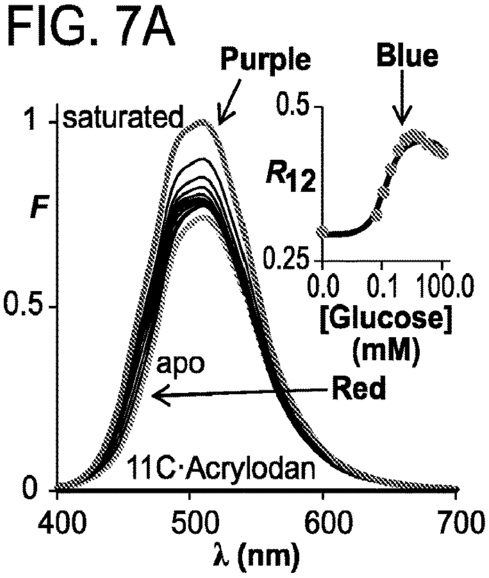
Figure 7B:
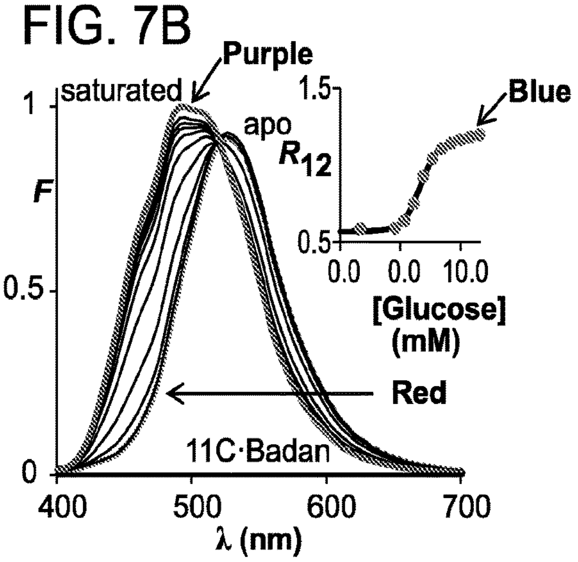
Figure 7C:
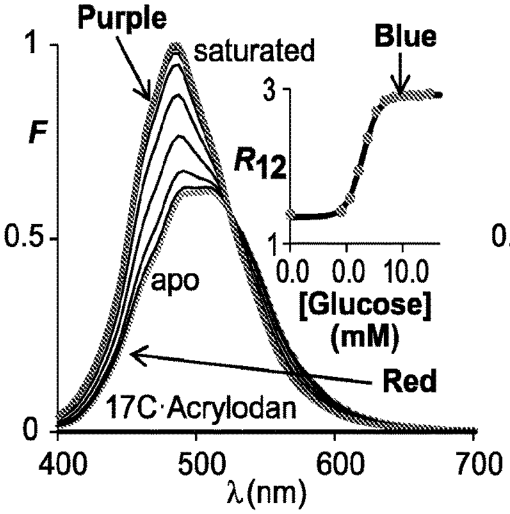
Figure 7D:
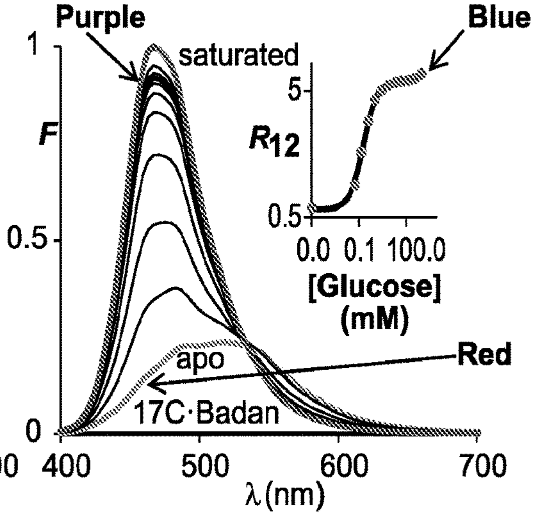
Figure 7E:
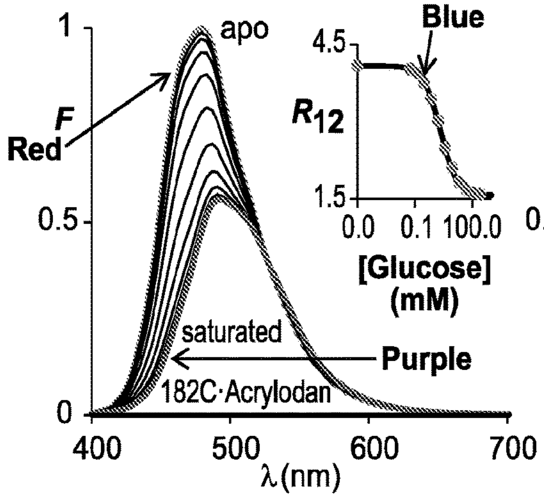
Figure 7F:
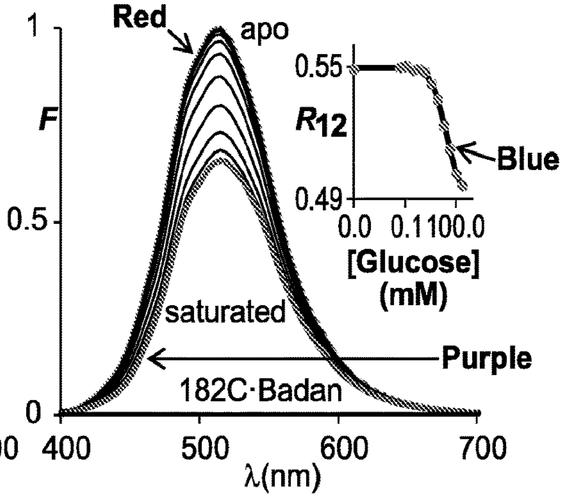

We observed ligand-dependent shifts in the wavelengths of emission intensity maxima at one peristeric (Y11C) and two endosteric (F17C, W182C) sites (FIGS. 7A-F), enabling dichromatic ratiometric measurements; the maximum intensity of other glucose-responsive conjugates remained the same (monochromatic responses). Wavelengths shifts occurred in both directions: in the ttGGBP W182C•Acrylodan conjugate the apo-protein spectrum converted from a short- to a long-wavelength emission state upon binding glucose (bathochromic shift), whereas the emissions in F17C•Acrylodan, F17C•Badan and Y11C•Badan conjugates shifted to shorter wavelengths (hypsochromic shift). The Badan and Acrylodan conjugates attached to F17C and W182C, respectively, exhibited the largest, wavelength-dependent changes in fluorescence emission intensities, (FIGS. 7A-C).

The responses to glucose of a number of other fluorophores (FIGS. 8A-P) were also tested at positions 182C and 17C (Table 4). Several conjugates exhibited significant changes in emission intensity upon glucose addition, but none of these were accompanied by large wavelengths shifts of their maxima. Both increases and decreases in fluorescence were observed.

The most effective sensors that were discovered are the Badan and Acrylodan conjugates attached to the endosteric cysteine mutations F17C and W182C, respectively. For example, peptides with SEQ ID No:61 (ttGGBP182C), SEQ ID NO:88 (ttGGBP182C.2.0), SEQ ID NO:90 (ttGGBP182C.2.3), and SEQ ID NO:102 (ttGGBP182C.8) are particularly useful for clinical diagnostics, because they span hypoglycemia, euglycemia, mild hyperglycemia, severe hyperglycemia, and hyperosmolar hyperglycemic glucose concentrations respectively. These two fluorophores differ only in their linker geometry, but this small difference determines whether dichromatic or monochromatic responses are observed for a particular conjugate. At position 17C, only the Badan and not the Acrylodan conjugate evinces a dichromatic response; at 182C; surprisingly, the reverse case is observed. Within a given bacterial periplasmic binding protein, some attachment sites are more effective than others, and within a given attachment site, some fluorophores are more effective than others (DeLorimier et al., 2002, Protein Science 11:2655-2675). Thus, the nature of the responses therefore is idiosyncratic, and therefore the choice of which site to mutate (e.g., substitute with a single cysteine) and which fluorophore to use at a particular site is nonobvious. Changes in linker geometry and chromophore modifications give rise to significant differences in the detailed interactions of particular fluorophores with the protein, even within families of closely related molecules, thereby significantly impacting sensor characteristics, consistent with previous observations.

Example 5: Determination of Exemplary Fluorescent Conjugate Structures

The structures of the fluorescent conjugates with pronounced dichromatic responses, ttGGBP17C•Badan and ttGGBP182C.2.0•Acrylodan (SEQ ID NO: 88) (this is a variant in which the glucose-binding affinity has been manipulated), were determined by X-ray crystallography (Table 5; FIG. 9). The structure of the *E. coli* GGBP homolog conjugate, ecGGBP W183C•Acrylodan (ecGGBP W183C, SEQ ID NO: 32), was determined also.

Like all members of the periplasmic-binding protein (PBP) superfamily, GGBPs comprise two domains connected by a flexible hinge, with the ligand-binding site located in a cleft between the two domains. In the absence of ligand, PBPs adopt an open conformation, in which the two domains move apart and the cleft is wide. In ligand complexes, hinge-bending motions move the two domains closer together, forming a binding site that completely envelops the ligand, reminiscent of a protein interior. The overall structures of the ecGGBP and ttGGBP conjugates are similar with a backbone $C_\alpha$ RMSD of 0.6 Å and 0.9 Å for the N- and C-terminal domains respectively (C-terminal domain contains the $Ca^{2+}$-binding site) as expected for proteins that are 48% identical (Chothia 1986 EMBO J., 5, 823-826). Small variations in the degree of closure can affect critical inter-domain hydrogen-bonding interactions. With the exception of mutated aromatic groups, the interactions between the protein and bound glucose are conserved. The structures of these conjugates enabled us to determine the interactions between the protein and the fluorophore and the internal conformation of the fluorophore. These sets of observations guided the choice of mutations for manipulating glucose affinities.

Figure 9A:
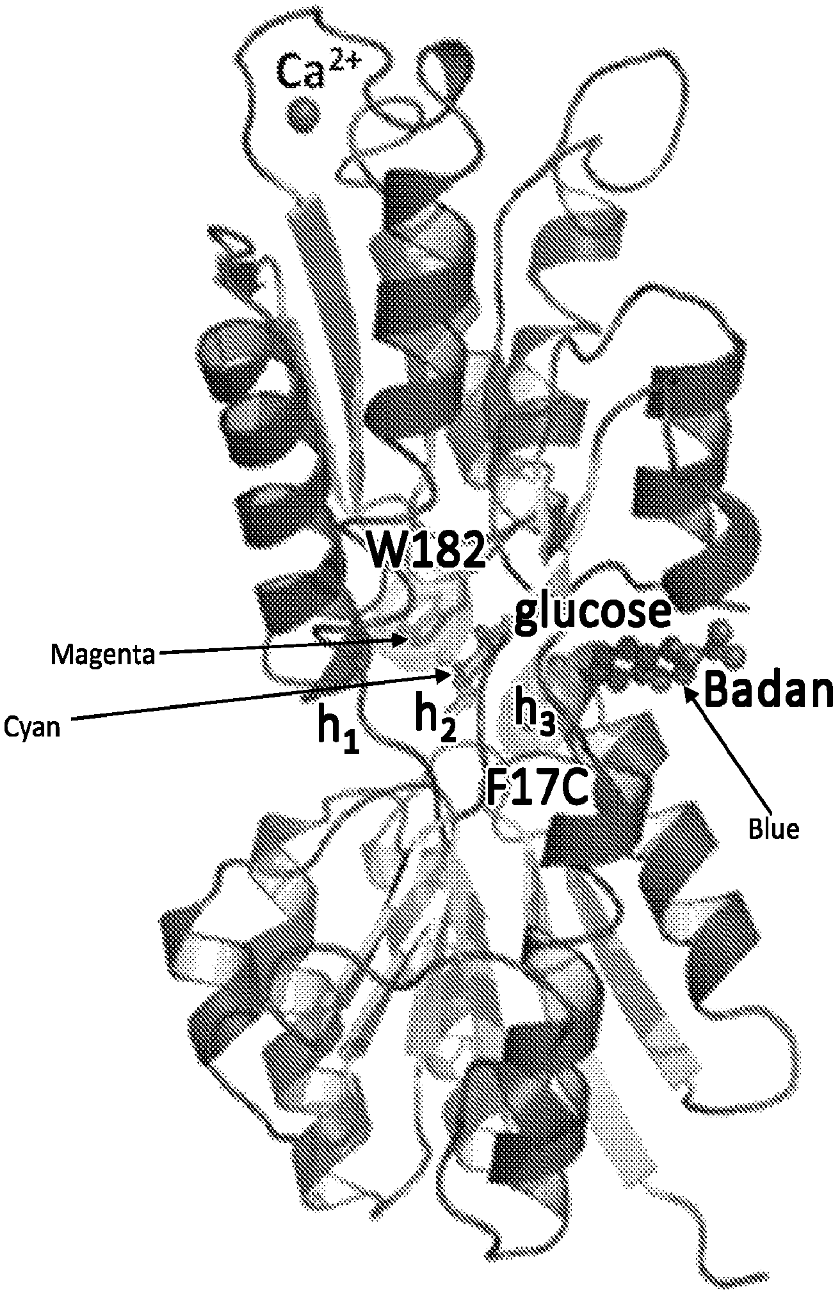
Figure 9B:
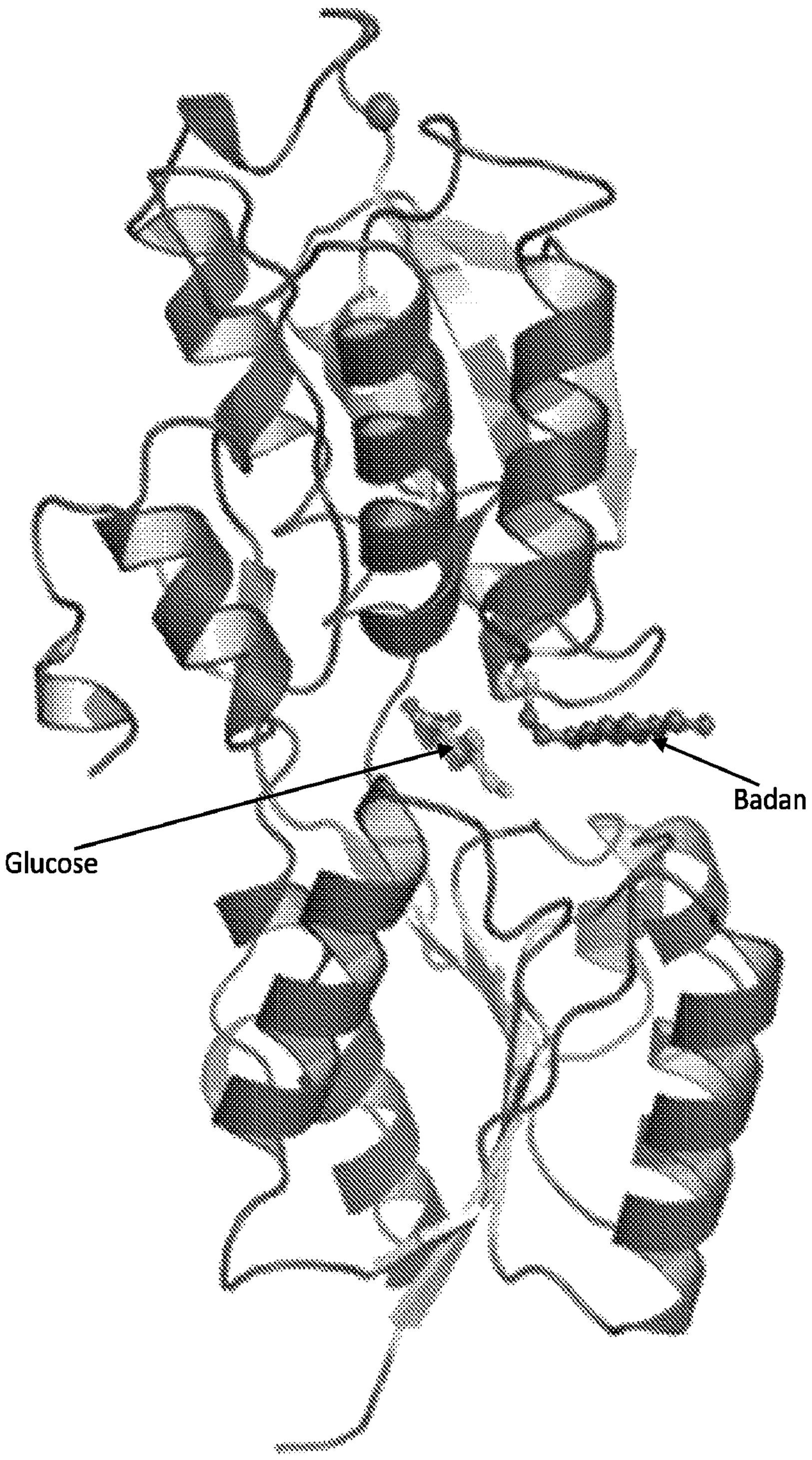
Figure 9C:
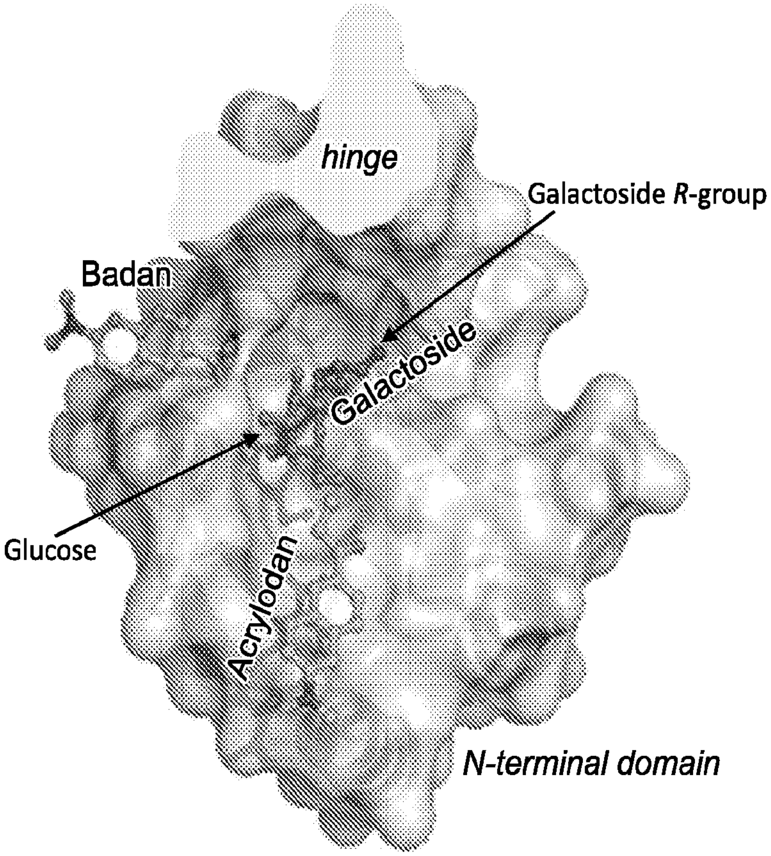

In both F17C•Badan and W182C•Acrylodan, the conjugated fluorophores point out into solution. A view down the long axis of ttGGBP from the C-terminal towards the N-terminal domain into the ligand-binding site reveals that three channels, each approximately 120° apart, connect the centrally located bound monosaccharide to the protein surface (FIG. 9*c*). One channel is occupied by the R-group of the natural galactoside ligand (this position is occupied by water in the glucose and galactose complexes), the other two are filled by Badan and Acrylodan in their respective conjugates.

In the wild-type protein, the rings of F17 and W182 form extensive van der Waals contact with the bound glucose. The outward orientation of the fluorophore in the W182C•Acrylodan conjugate leaves a cavity vacated by the indole ring, which is filled with water and cryoprotectant. The cavity created by the loss of the smaller benzyl ring in F17C•Badan is largely filled with the linker; no water or cryoprotectant was observed.

Figure 9D:
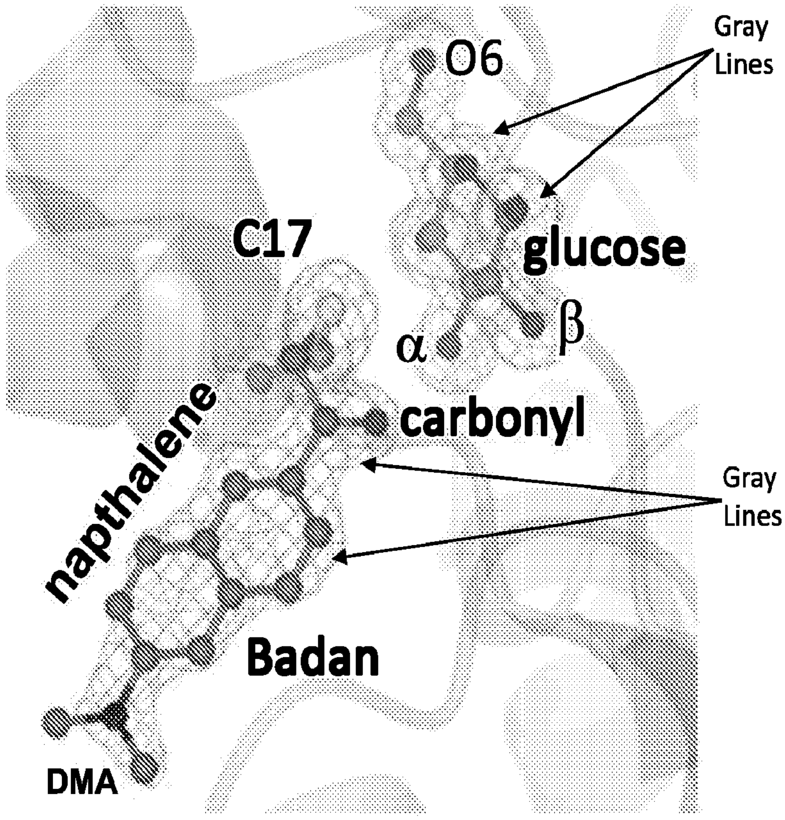
Figure 9F:
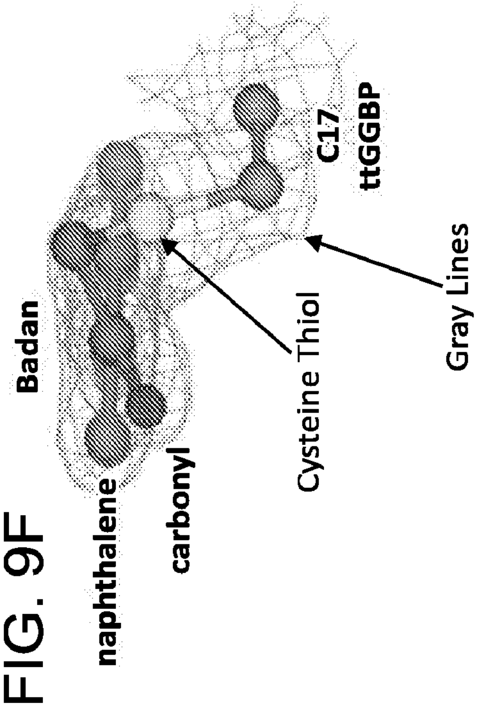
Figure 9H:
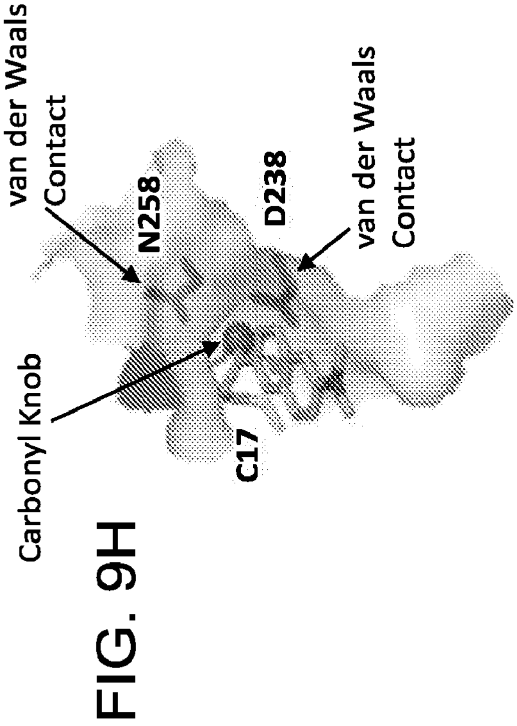
Figure 9E:
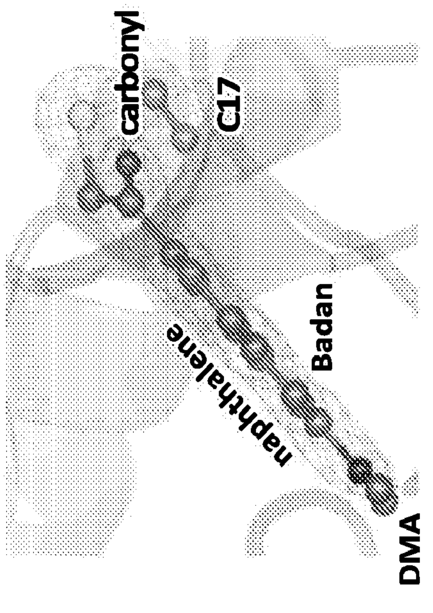
Figure 9G:
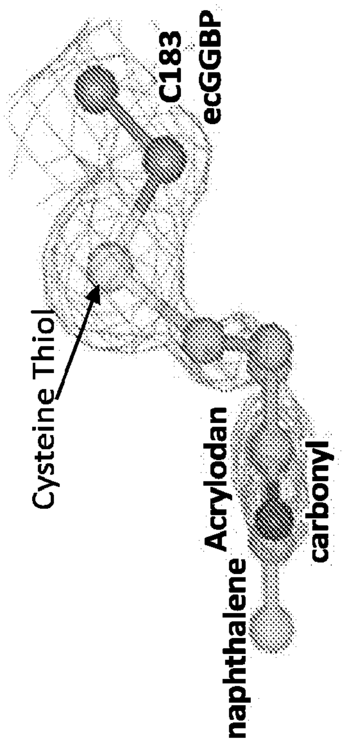

The Acrylodan and Badan fluorophores contain two important internal degrees of freedom (FIGS. 6*a-c*): the twist of the dimethylamino group, and the carbonyl. The state of these two angles influences the fluorescence properties of the fluorophore, by altering the extent of electronic conjugation within the system, and the degree of polarization of the excited dipole. The electron density of Badan in the ttGGBP F17C conjugate was well defined, enabling us to determine the internal fluorophore conformation with high confidence (FIG. 9*d-f*). The dimethyl amino group is co-planar with the naphthalene ring. The carbonyl group is twisted out of plane by approximately 30°. By contrast, in ecGGBP.183C•Acrylodan the carbonyl is co-planar (FIG. 9*g*). This group is probably also co-planar in the ttGGBP.182C•Acrylodan structure, but the partial occupancy of the conjugate in this structure precluded a definitive conclusion. Nevertheless, the high degree of similarity in structure and spectral properties of the ecGGBP 183C and ttGGBP 182C Acrylodan conjugates suggests that the Acrylodan carbonyl is co-planar in both homolog conjugates.

In both ttGGBP 17C•Badan and 182C•Acrylodan (and ecGGBP 183C•Acrylodan) conjugates, the pocket in which the fluorophore carbonyl is located comprises residues contributed by each domain, and is fully formed only in the closed, glucose-bound protein conformation. No hydrogen bonds are observed between the fluorophore carbonyl and the protein at either attachment position. In ttGGBP 17C•Badan the "knob" of the twisted carbonyl conformation is bound in a small "hole" formed by residues also contributed by both domains (FIG. 9*h*). The carbonyl is held in place by van der Waals interactions proximal to the attachment site with residues located in the domain opposite to the F17C site: the $C_\beta$ carbon of N258 touches the carbonyl; the backbone atoms of residues 239-241 interact with one of the two naphthalene rings faces. The twisted ttGGBP F17C•Badan conformation therefore is stabilized by interactions of the protein with both the naphthalene ring and the carbonyl. These interactions are fully formed in the closed state only. By contrast, in ecGGBP 183C•Acrylodan the carbonyl hole is not well defined. The carbonyl is flanked by E149 (same domain as attachment site), and K92 (opposite domain), but these residues form no direct contacts in the structure. Neither the carbonyl nor the naphthalene rings of this planar conjugate are constrained by clear interactions in the protein closed conformation.

Example 6. Affinity Tuning (Phase Step 4)

Blood glucose concentrations range from ~3 mM (hypoglycemia) to ~30 mM (hyperglycemia) and up to ~100 mM for the hyperosmolar hyperglycemic state (HHS), with healthy levels at around 6 mM (euglycemia). Measurements using reagentless sensors are most sensitive at analyte concentrations that match the dissociation constant. The glucose affinity of ttGGBP182C•Acrylodan is too high and must therefore be "tuned" by raising the $K_d$ value.

The mutations that alter glucose affinities fall into four classes:

1. Alteration of direct interactions in the PCS between the protein and the bound glucose.
2. Manipulation of the equilibrium between the open and closed states.
3. Alteration of interactions between the protein and the fluorescent conjugate. Two sub-classes can be distinguished:
   a. Interactions with the carbonyl group
   b. Interactions with the naphthalene ring
4. Indirect interactions that alter the geometry of the binding site.

Representatives of mutant classes 1-3 were constructed in the ttGGBP182C and ttGGBP17C backgrounds, using Acrylodan and Badan conjugates to evaluate their effects on glucose binding (Table 6).

Mutations in the PCS residues (Class 1) do not afford many opportunities for manipulating affinity subtly. Mutagenesis of ecGGBP has demonstrated that most PCS positions are intolerant of mutations, with the exception of histidine that interacts with the 6-hydroxyl, and the aspartate that binds the epimeric 4-hydroxyl. In ttGGBP182C•Acrylodan, the H151Q mutations subtly lower the affinity into the middle of the pathophysiological concentration range, whereas in ttGGBP17C•Badan H151Q lowers affinity, but nearly abolishes ratiometry. In ttGGBP182C•Acrylodan, D15N weakens glucose binding into the HHS range and increases discrimination between glucose and galactose. In ttGGBP17C•Badan, D15A weakens ligand binding and enhances the dichromatic response.

Uniquely in ttGGBP182C•Acrylodan, the PCS also can be manipulated by mutating position 154 adjacent to the cavity vacated by the missing indole ring of W182 (FIG. 10*a*). Three mutations in Ala154 alter the affinity 50-fold, spanning the entire pathophysiological glucose concentration range. The A154M mutation increases the affinity ~10-fold, presumably by (partially) restoring direct van der Waals interactions between the protein and bound glucose, which were lost upon removal of the tryptophan. The 154S mutation causes a 19 K decrease in thermostability; the other mutations exhibit negligible effects on thermostability.

Figure 10B:
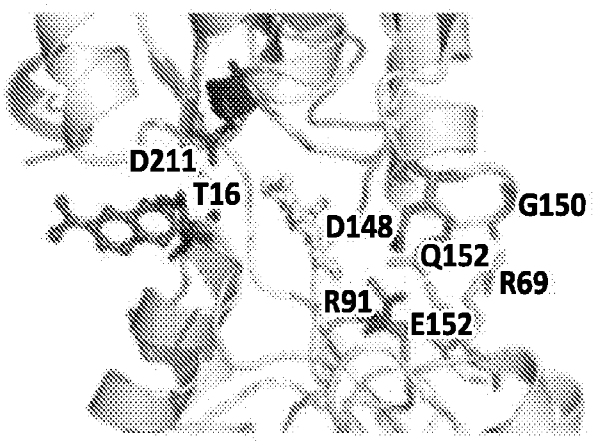

The conformational equilibrium can be altered by manipulating those hydrogen bonds between the N- and C-terminal domains that are predicted to form in the closed, but not the open state (Class 2 mutations). Four locations form inter-domain hydrogen bonds in the protein closed conformation (FIG. 10*b*) of ttGGBP: T16-D211, R69-G150 (main-chain), R91-Q148, and E92 (main-chain)-Q152. The first of these interactions is located between the Badan and Acrylodan channels, whereas the other three are positioned between the Acrylodan and galactoside R-group channels (FIG. 9*c*). Disruption of inter-domain interactions alters the intrinsic equilibrium between the open and closed conformations, thereby decreasing ligand affinity. Accordingly, in the ttGGBP W182C•Acrylodan conjugate mutants, glucose affinities are lowered ($K_d$ values raised) in the class 2 mutations. These mutations also alter the fluorescence emission spectra. In all the class 2 mutants of both ttGGBPF17C Acrylodan and Badan conjugates the spectral responses are altered, either enhancing or abolish wavelength shifts. These observations indicate that mutations of the inter-domain hydrogen bonds cause (small) changes in the structure of the closed state, which affect the fluorophore environment.

Mutations in the interactions between the protein and the conjugated fluorophore (Class 3 mutants), changing either the carbonyl hole (Class 3a) or the fluorophore channel walls (Class 3b), have large effects on glucose binding and fluorescence spectra. In ttGGBP17C•Badan, most of the N258 mutants in the carbonyl hole do not respond to glucose. The absence of shifts in thermal stability in the presence of glucose indicates that these mutants no longer bind ligand. The 17C•Acrylodan N258S mutant conjugate is the exception: it binds and responds to glucose, but binding does not evoke a fluorescent response. Mutations in residues located on either side of the channel wall strongly influence spectral properties of the fluorescent conjugates. In ttGGBP17C•Badan, with the exception of A260W, mutations in A260 convert dichromatic to monochromatic responses. In ttGGBP182C•Acrylodan, the behavior of mutations in the R91 and Q148 interaction is complex, because these potentially affect both inter-domain hydrogen bonding and interactions between the protein and the conjugated fluorophore. The fluorophore blocks the formation of R91K-Q148E in the ttGGBP182C.2.0•Acrylodan double mutant structure, but in ecGGBP183C•Acrylodan E149-K92 is present, reflecting subtle differences in fluorophore conformation and inter-domain closure angles. The two single Q148E and R91K mutants both exhibit a modest increase of glucose affinities in ttGGBP182C•Acrylodan, suggesting that this inter-domain is maintained, and slightly improved. By contrast, the Q148E+R91K double mutant exhibits a 2.6-fold decrease in affinity, consistent with the observed loss of interaction in the ttGGBP182C2.0•Acrylodan double mutant structure (SEQ ID NO: 88). The glucose affinity of the ttGGBP182C.2.0•Acrylodan double mutant (SEQ ID NO: 88) falls within the euglycemic concentration range (FIG. 13), which is why this variant was selected for structural analysis (FIG. 11).

Affinity-tuning mutations introduced in both the ttGGBP17C•Badan or ttGGBP182C•Acrylodan backgrounds yield a collection of dichromatic sensors that cover the wide range of glucose concentrations encountered in clinical chemistry.

Example 7. Sensor Arrays for Detecting a Wide Range of Glucose Concentrations

Figure 12B:
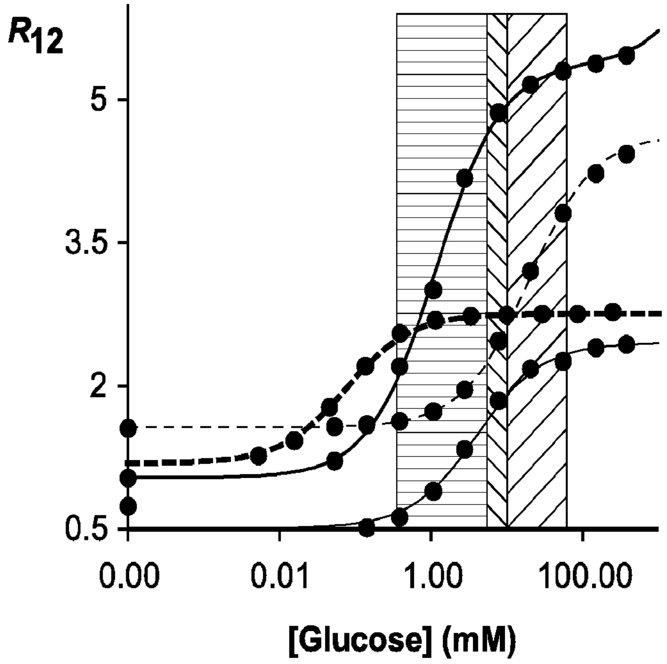

The precision (reciprocal of the error) of individual sensor precision is maximal at the $K_d$ value, and decreases at lower or higher glucose concentrations (Marvin et al. 1997 *Proc Natl Acad Sci USA,* 94, 4366-71). Construction of a high-precision sensor capable of spanning the entire 100-fold clinical concentration range from extreme hypoglycemia to the HHS therefore requires combining several sensors together to maintain a high precision level. In the ttGGBP182C•Acrylodan background, a suite of five affinity mutants can be combined that together provide high-precision coverage from 1-100 mM (FIG. 12). A suite of four mutants in the ttGGBP17C•Badan background provides similar coverage. It should be noted that the ttGGBP17C•Badan variants switch from dim green to bright blue upon binding glucose, whereas the ttGGBP182C•Acrylodan variants switch from bright blue to dim green. These opposing changes in color and brightness in response to glucose binding provide additional internal checks on the integrity of the observations in an array that combines sensors derived from both backgrounds.

Example 8. Device Integration (Phase Step 5)

Protein immobilization on solid surfaces, e.g. a polymeric planar structure or bead structure, paper, glass, silica or metal, is an important step for incorporating biosensors into devices. Immobilization enables (i) spatial localization, (ii) control over the presentation of the sensors to the reader (e.g. by encoding geometries for optical readouts), (iii) selective retention in sample separation procedures. It is advantageous to control the geometry of the protein attachment to the solid surface, in order to minimize perturbation of the fluorescence sensing mechanism. Such constructs fuse an N- or C-terminal protein domain that can mediate site-specific attachment to an appropriately chemically activated surface. For instance, hexa-histidine peptide for metal-mediated immobilization, a hexa-lysine peptide for attachment to amine-reactive groups, or a zinc-finger domain (ZF-QNK) (Smith et al. 2005 *Protein Sci,* 14, 64-73), or a disulfide-containing truncated zinc finger (βZif) (Smith et al. 2005 *Protein Sci,* 14, 64-73) at N- or C-termini of the FRS to thiol-reactive groups (FIG. 13). Here we show that site-specific attachment of a robust glucose sensor to suitably derivatized agarose beads conserves its emission fluorescence spectral response, binding affinity, and thermostability.

Figure 14A:
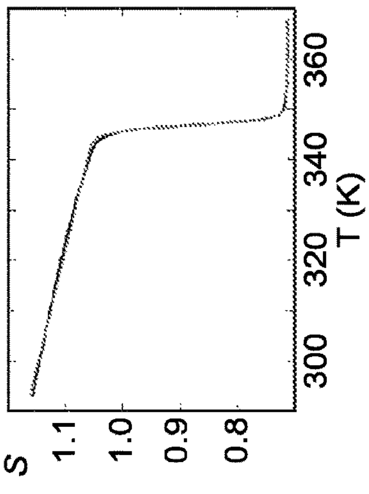
Figure 14B:
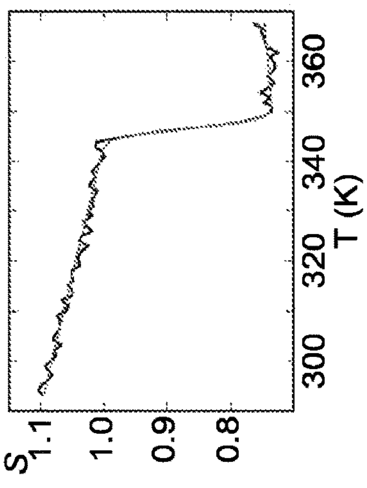
Figure 14C:
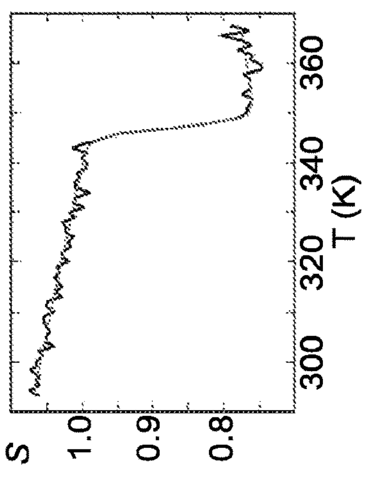
Figure 14D:
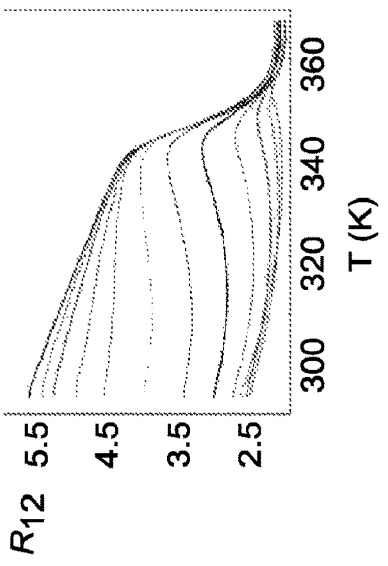
Figure 14E:
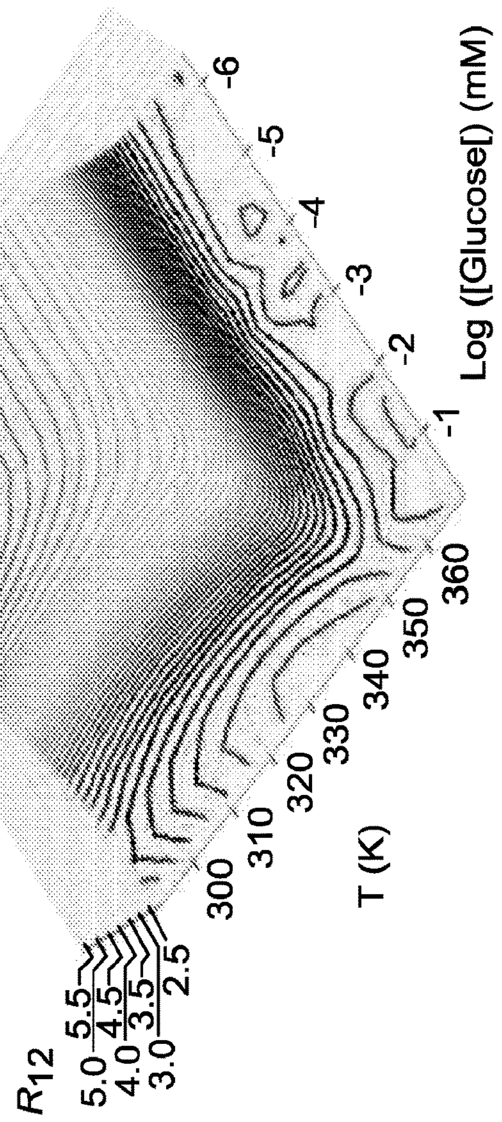
Figure 14F:
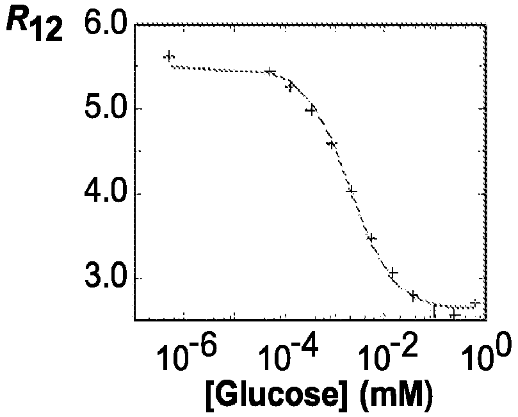

The ttGGBP182C.2.0•Acrylodan protein was site-specifically immobilized through its C-terminal hexa-histidine tag on commercially available magnetic beads coated with Ni-NTA. The use of magnetic beads affords a straightforward means for holding the beads in place within their respective sensor patches in the sampling cartridge with a magnetic field. Site-specific immobilization minimizes perturbation of the sensing mechanism. Comparison of protein thermostabilities determined in solution and on beads shows that protein is stability is not perturbed by immobilization (FIG. 14A-F) These glucose-responsive magnetic beads also useful to measure highly precise glucose titration curves (FIG. 15). Similarly, hexa-lysine fusion domains were immobilized on agarose beads derivatized with N-hydroxysuccinimide, and the QNK- or βZif-fusion on iodacetyl-derivatized beads. These fusion proteins also maintained their spectral, glucose affinities, and thermostabilities (FIG. 14D-F).

The glucose-responsive magnetic beads were dried by incubation at 50° C. for 20 minutes, using an aqueous ammonium bicarbonate buffer. The stability properties of the sensor were recovered completely upon rehydration (FIG. 14*c*). The dried beads were aged in situ inside fully assembled sample-handling cartridges by incubation for up to 7 days at 25° C., 37° C., and 50° C. in the dark. Fluorescence and glucose-responsive properties were tested in cartridges stored for 1, 2 and 7 days. At all temperatures, the fluorescence ratio in the absence of glucose, and the glucose affinities remained unchanged within the error of the observation. Therefore, a significant advantage of ttGGBP-based FRSs is that they are sufficiently robust to be handled at ambient temperatures in a desiccated state, greatly simplifying manufacturing, distribution, and long-term storage conditions.

Example 9. Fluorescence Mechanism

The most effective glucose-sensing FRSs identified are based on singly labeled Acrylodan and Badan conjugates. These two dyes, and their parent, Prodan (Weber 1979 *Biochemistry,* 18, 3075-3078), belong to a class of fluorophores that can undergo internal rotations which change the electronic structures of excited state dipoles (Rettig 1986 *Angew. Chem. Int. Ed. Engl.,* 25, 971-988; Grabowski et al. 2003 *Chem Rev,* 103, 3899-4032). The X-ray structure of Prodan shows that in the absence of external factors, the dimethyl amino (DMA) and carbonyl groups are coplanar with the naphthalene core, and the system is maximally conjugated. However, the DMA or carbonyl groups can twist out of plane, diminishing the extent of conjugation within the system, and increasing the degree of polarization of these groups. This enhanced polarization increases the magnitude of the excited state dipole, and correspondingly its sensitivity to the polarity of its surroundings, which manifests itself as general solvatochromic effects and responses to specific hydrogen-bonding interactions. There has been considerable debate regarding the magnitude of the dipole in the polarized state in Prodan (Weber 1979 *Biochemistry,* 18, 3075-3078; Baiter 1988 *Chem. Phys. Lett.,* 143, 565-570; Catalan 1991 *Journal of Fluorescence,* 1, 215-223; Nemkovich 2007 *Journal of Photochemistry and Photobiology A: Chemistry,* 185, 26-31; Samanta 2000 *Journal of Physical Chemistry,* 104, 8972-8975; Kawski 2001 *Zeitschrift fur Naturforschung,* 56a, 407-411; Kawski 2002 *Zeitschrift fur Naturforschung,* 57a, 716-722), whether the molecule undergoes twisting in the excited state, and if so, whether the carbonyl or the DMA groups twist (Nowak 1986 *Journal of Molecular Structure,* 139, 13-23; Heisel 1987 *Chemical Physics Letters,* 138, 321-326; Parusel 1997 *J. Molec. Struct.,* 398, 341-346; Parusel 1998b *Journal of Physical Chemistry,* 102, 7149-7156; Parusel 1998a *J. Chem. Soc., Faraday Trans.,* 94, 2923-2927; Mennucci 2008 *Journal of Physical Chemistry,* 112, 414-423; Adhikary 2009 *Journal of Physical Chemistry,* 113, 11999-12004; Marini 2010 *Journal of Physical Chemistry,* 114, 17128-17135; Pederzoli 2014 *Chemical Physics Letters,* 597, 57-62; Cwiklik 2011 *J. Phys. Chem.,* 115, 11428-11437; Fukuda 2012 *Chem. Phys. Lett.,* 552, 53-57; Barucha-Kraszewska 2010 *Biochim Biophys Acta,* 1798, 1724-1734; Nitschke 2012 *J. Phys. Chem.,* 116, 2713-2721). A series of derivatives in which the DMA (Lobo 2003 *Journal of Physical Chemistry,* 107, 10938-10943; Davis 2005 *J. Phys. Chem.,* 109, 1295-1298) or carbonyl (Everett 2010 *Journal of Physical Chemistry,* 114, 4946-4950) groups are held in planar or out-of-plane conformations have shown that it is twisting of the carbonyl and not the DMA group that alters Prodan polarization.

The collection of Acrylodan and Badan conjugates of mutant ecGGBP and ttGGBPs constructed and described herein contains several semi-synthetic glucose sensors that exhibit wavelength-dependent changes in fluorescence emission intensity in response to glucose binding. The best responses were observed for conjugates attached to ttGGBP F17C (SEQ ID NO: 51) and ttGGBP W182C (SEQ ID NO: 61) cysteines endosteric mutants that replace residues which form van der Waals contacts with the pyranose glucose ring. Remarkably, the emission intensity maxima shift in opposite directions at these two positions: glucose binding evinces a bathochromic shift for ttGGBP W182C and ecGGBP W183C Acrylodan conjugates, whereas at ttGGBP F17C and ecGGBP F16C both Acrylodan and Badan exhibit hypsochromic responses. Analysis of their ligand-mediated changes in the populations of excited state and ground state electronic transitions in combination with the X-ray structures of three different conjugates has enabled us to describe a mechanism for the fluorescence response to glucose binding.

Analysis of the emission intensity (FIGS. 16-18, Tables 7 and 8) and absorption spectra (FIG. 19) indicated that glucose binding alters the populations of two dominant electronic transitions in both the excited ($S_1$ and $S_2$) and ground ($G_1$ and $G_2$) states. In hypsochromic responses, the dominant excited state electronic transition shifts from $S_1$ (green) in the apo-protein, to $S_2$ (blue) in the glucose complex; in bathochromic responses, the opposite redistribution is observed, and the glucose complex is dominated by the $S_1$ (green) excited state. Similarly, in the ground state, hypsochromic responses shift the electronic transitions in the absorbance spectra from a low- ($G_1$) to a high-energy state ($G_2$); for bathochromic responses, the shift is $G_2 \rightarrow G_1$. Comparison of high-resolution X-ray structures of the ttGGBP F17C•Badan (hypsochromic response) and ttGGBP W182C•Acrylodan or ecGGBP W183C•Acrylodan (bathochromic responses) revealed that the fluorophore structures of the glucose complexes differ in these conjugates (FIGS. 9 and 10). From these observations we deduced that the $G_1$ ground state in ecGGBP W183C•Acrylodan corresponds to a planar fluorophore, whereas the $G_2$ state of F17C•Badan corresponds to twisted fluorophore carbonyl in which the carbonyl has repositioned out of the plane of the naphthalene ring.

These observations indicate that the changes in fluorescence intensities of glucose-responsive Acrylodan and Badan conjugates arise as a consequence of conformational coupling between ligand-mediated shifts in the population of protein conformations and internal twisting of the fluorophore carbonyl relative to its naphthalene ring. Like all periplasmic binding proteins, GGBP undergoes a large, ligand-mediated conformational change from an open to a closed state in which the ligand is enveloped between two domains that are linked by a flexible hinge. The protein conformations of the glucose complexes of the ttGGBP F17C•Badan, ttGGBP W182C•Acrylodan and ecGGBP W183C•Acrylodan conjugates are as closed as the unmodified, wild-type proteins. The fluorophores do not occupy the positions of the wild-type aromatic rings that they replace, but instead point outwards into the solvent such that their dimethylamino groups make no contacts with the protein and is coplanar with naphthalene ring (e.g., in the case of ttGGBP17C•Badan, where the structure of this group is unambiguous). By contrast, the carbonyl is located at the end of the linker through which the fluorophore is coupled to the protein cysteine. The torsion between it and the naphthalene ring therefore is affected by a combination of interactions with residues proximal to the attachment site and distal interactions with the ring. Ligand-mediated signaling occurs if two conditions are satisfied: (i) the protein interacts with both the naphthalene and the carbonyl, stabilizing their relative twist, and (ii) these interactions differ in the open and closed states.

Analysis of the spectra of all conjugates (Tables 7 and 8) showed that these signaling conditions are satisfied most commonly if the fluorophore is planar in the open, ligand-free protein conformation and twists in the closed conformation of the glucose complex. In the case of F17C•Badan structure, the closed protein conformation stabilizes the twisted form by interactions with both the carbonyl and the naphthalene ring. These interactions are contributed by distal residues in the domain located opposite the fluorophore attachment point, and therefore are likely to be present in the closed but not open protein conformation. Less commonly, the fluorophore twists in the open protein conformation through proximal interactions, and becomes untwisted in the closed conformation. The ttGGBP W182C•Acrylodan and ecGGBP W183C•Acrylodan conjugates represent this case. The interactions that stabilize the twisted state in the open protein conformation have not been identified, but the structure of the closed conformation reveals an absence of interactions that twist the naphthalene ring and carbonyl relative to each other and the fluorophore adopts a low-energy planar state.

Mutations that affect ligand binding (Table 6) also can influence spectroscopic properties (Table 8). In the Class 1 PCS mutant H151Q ratiometry is abolished, by diminishing the fraction of $S_2$ that forms in the glucose complex. In D15A the redistribution of the two excited populations enhances ratiometric responses in both conjugates. In Class 2 mutants, the intrinsic equilibrium between the open and closed conformations is manipulated. In all the Class 2 mutants of both F17C Acrylodan and Badan conjugates, the fraction of the $S_1$ state in the apo-protein $^{apo}f(S_1)$) is altered. These effects can both enhance or abolish wavelength shifts (Table 7 and 8). For instance, shifts are strengthened in the mutant Badan conjugates, but abolished in the Acrylodan conjugates as evidenced by the magnitude of the $C_2$ component. Mutations in the carbonyl hole (Class 3a) and the fluorophore channel walls (Class 3b) have large effects on glucose binding and fluorescence spectra. Many of the N258 mutants in the carbonyl hole do not respond to glucose. The absence of shifts in thermal stability in the presence of glucose indicates that these mutants no longer bind ligand. The 17C•Acrylodan N258S mutant conjugate is the exception: it binds and responds to glucose, but binding does not alter the distribution of excited state populations. Mutations in residues located on either side of the channel wall strongly influence both the distributions of the excited states in the ligand-free protein, and their ligand-mediated redistribution. Mutations in A260 all switch the 17C•Badan conjugate from a mixture of $S_1$ and $S_2$ states in the apo-protein to a predominantly $S_1$ state that exhibit small redistributions in response to glucose. Accordingly, most mutant conjugates exhibit isochromic instead of hypsochromic responses to glucose, with exception of 17C•Badan A260W which retains (diminished) hypsochromicity. By contrast, the 17C•Acrylodan A260 mutants retain the mixed $S_1$ and $S_2$ population in the apo-protein, but all response to glucose binding.

Although conformational coupling between the open and closed forms of the protein and the fluorophore internal torsional equilibrium is a major factor in determining the ligand-responsive changes in fluorescence of the Acrylodan and Badan conjugates, environmental effects on excited state dipole strengths also contribute, as evidenced by the presence of fine structure in the residuals between the models and observations (FIGS. 17 and 18). The conjugates or their mutants differ in the degree to which fine structure is present in the emission spectra and responsive to glucose. This fine structure is due to changes in the energies of the $S_1$ and $S_2$ excited states associated with differences of their local environment in the open and closed conformations. The analysis presented here treats these differences as an ensemble average approximation.

The mechanism described is consistent with observations of the experimental properties of Prodan derivatives in which the twisted state of either the DMA or the carbonyl groups were controlled by synthesis of conformationally constrained groups (Lobo 2003 *Journal of Physical Chemistry,* 107, 10938-10943; Davis 2005 *J. Phys. Chem.,* 109, 1295-1298; Green 2012 *J. Org. Chem.,* 78, 1784-1789; Everett 2010 *Journal of Physical Chemistry,* 114, 4946-4950; Naughton 2013 *J. Phys. Chem.,* 117, 3323-3327; Nikitina 2013 *J. Phys. Chem.,* 117, 9189-9195; Daneri 2015 *Journal of Photochemistry and Photobiology A: Chemistry,* 310, 106-112).

Semisynthetic, fluorescently responsive proteins are useful in the development of reagentless biosensors with a wide variety of applications. However, in the absence of design principles that guide choice and placement of fluorophores, systematic identification of suitable fluorescent conjugates remains a significant challenge in their construction. The mechanistic insights described herein have revealed three key aspects of the fluorescence signal transduction mechanism that enable, inform, and direct rational engineering of fluorescent responses:

1. Signaling is controlled by the twisting of the carbonyl group, and changes in the specific interactions between it and the protein matrix via ligand-mediated protein conformational changes.
2. The linker length and concomitant degrees of torsional freedom determine the effectiveness of the ligand-mediated conformational coupling between the protein and the carbonyl at a given attachment position.
3. The planar ring system which determines the wavelength absorption and emission characteristics is not constrained by the protein matrix, but points outwards into the solvent.

The first two observations enable and direct structure-based approaches for identifying attachment positions and optimizing the functionalized linker for covalent modification. In such approaches, the internal flexibility of the linker is modeled, and the resulting library of fluorophore conformations are placed in a three-dimensional model of a protein host, checked for steric compatibility with their environment, and attachment sites and possible additional mutations identified that (de)stabilize a particular conformation or hydrogen bond with the protein exclusively in the apo-protein or ligand complex. The third observation indicates that the feasibility of introducing alternative chromophore structures that alter the fluorescence characteristics of the basic Prodan framework, while maintaining ligand-responsive signaling, provided the structural characteristics of the carbonyl and linker are maintained. Of particular interest are the design and construction of chromophore variants with wavelengths in the transparent window of blood (>600 nm). These principles are applied not only to periplasmic binding proteins and Prodan derivatives, but also to establish conformational coupling of any suitably placed, internally twisting fluorophore in proteins that undergo ligand-mediated changes in protein conformations.

TABLE 1

| | | | PCS position and sequence | | | |
|---|---|---|---|---|---|---|
| # | Accession code | Species | 14 | 16 | 91 | 152 |
| 1 | 2GBP (seed structure) | *Escherichia coli* | D | F | N | H |
| 2 | NC_013654\|YP_003350022.1 | *Escherichia coli* | D | F | N | H |
| 3 | NC_016822\|YP_005457115.1 | *Shigella sonnei* | D | F | N | H |
| 4 | NC_017328\|YP_005727882.1 | *Shigella flexneri* | D | F | N | H |
| 5 | NC_011740\|YP_002383354.1 | *Escherichia fergusonii* | D | F | N | H |
| 6 | NC_010658\|YP_001879517.1 | *Shigella boydii* | D | F | N | H |
| 7 | NC_022912\|Asd1617_02874 | *Shigella dysenteriae* | D | F | N | H |
| 8 | NC_013716\|YP_003365823.1 | *Citrobacter rodentium* | D | F | N | H |
| 9 | NC_009792\|YP_001452231.1 | *Citrobacter koseri* | D | F | N | H |
| 10 | NC_021500\|H650_06520 | *Enterobacter* sp. | D | F | N | H |
| 11 | NC_014121\|ECL_03459 | *Enterobacter cloacae* | D | F | N | H |
| 12 | NC_015968\|YP_004829427.1 | *Enterobacter asburiae* | D | F | N | H |
| 13 | NC_009778\|YP_001437192.1 | *Cronobacter sakazakii* | D | F | N | H |
| 14 | NC_016514\|YP_004952913.1 | *Enterobacter cloacae* | D | F | N | H |
| 15 | NC_011283\|YP_002237430.1 | *Klebsiella pneumoniae* | D | F | N | H |
| 16 | NC_020063\|YP_007339667.1 | *Enterobacteriaceae bacterium* | D | F | N | H |
| 17 | NC_016810\|YP_005182060.1 | *Salmonella enterica* | D | F | N | H |
| 18 | NC_013850\|YP_003438413.1 | *Klebsiella variicola* | D | F | N | H |
| 19 | NC_013282\|YP_003211183.1 | *Cronobacter turicensis* | D | F | N | H |
| 20 | NC_021232\|YP_007990486.1 | *Klebsiella pneumoniae* | D | F | N | H |
| 21 | NC_015761\|YP_004730836.1 | *Salmonella bongori* | D | F | N | H |
| 22 | NC_016612\|YP_005021097.1 | *Klebsiella oxytoca* | D | F | N | H |
| 23 | NC_009436\|YP_001177466.1 | *Enterobacter* sp. | D | F | N | H |
| 24 | NC_011147\|YP_002141464.1 | *Salmonella enterica* | D | F | N | H |
| 25 | NC_021066\|YP_007872566.1 | *Raoultella ornithinolytica* | D | F | N | H |
| 26 | NC_015663\|YP_004594960.1 | *Enterobacter aerogenes* | D | F | N | H |
| 27 | NC_014618\|YP_003941097.1 | *Enterobacter lignolyticus* | D | F | N | H |
| 28 | NC_015224\|YP_004297664.1 | *Yersinia enterocolitica* | D | F | N | H |
| 29 | NC_020211\|YP_007405370.1 | *Serratia marcescens* | D | F | N | H |
| 30 | NC_021741\|M495_07335 | *Serratia liguefaciens* | D | F | N | H |
| 31 | NC_014029\|YP_003567546.1 | *Yersinia pestis* | D | F | N | H |
| 32 | NC_010634\|YP_001872058.1 | *Yersinia pseudotuberculosis* | D | F | N | H |
| 33 | NC_009832\|YP_001477795.1 | *Serratia proteamaculans* | D | F | N | H |
| 34 | NC_015567\|YP_004504928.1 | *Serratia plymuthica* | D | F | N | H |
| 35 | NC_015566\|YP_004499976.1 | *Serratia* sp. | D | F | N | H |
| 36 | NC_015061\|YP_004212168.1 | *Rahnella* sp. | D | F | N | H |
| 37 | NC_016818\|YP_005199494.1 | *Rahnella aquatilis* | D | F | N | H |
| 38 | NC_007712\|YP_454643.1 | *Sodalis glossinidius* | D | F | N | H |
| 39 | NC_020418\|YP_007506508.1 | *Morganella morganii* | D | F | N | H |
| 40 | NC_021290\|YP_008045423.1 | *Aeromonas hydrophila* | D | F | N | H |
| 41 | NC_012912\|YP_003005296.1 | *Dickeya zeae* | D | F | N | H |
| 42 | NC_014562\|YP_003931657.1 | *Pantoea vagans* | D | F | N | H |
| 43 | NC_014837\|YP_004116494.1 | *Pantoea* sp. | D | F | N | H |
| 44 | NC_014500\|YP_003882024.1 | *Dickeya dadantii* | D | F | N | H |
| 45 | NC_014306\|YP_003742362.1 | *Erwinia billingiae* | D | F | N | H |
| 46 | NC_015424\|YP_004390764.1 | *Aeromonas veronii* | D | F | N | H |
| 47 | NC_013956\|YP_003520836.1 | *Pantoea ananatis* | D | F | N | H |
| 48 | NC_022546\|YP_008651638.1 | *Plautia stali* | D | F | N | H |
| 49 | NC_009348\|YP_001140155.1 | *Aeromonas salmonicida* | D | F | N | H |
| 50 | NC_010694\|YP_001907230.1 | *Erwinia tasmaniensis* | D | F | N | H |
| 51 | NC_013961\|YP_003531646.1 | *Erwinia amylovora* | D | F | N | H |
| 52 | NC_022268\|YP_008522161.1 | *Serratia* sp. | D | F | N | H |
| 53 | NC_012691\|YP_002893819.1 | *Tolumonas auensis* | D | F | N | H |
| 54 | NC_006371\|YP_133522.1 | *Photobacterium profundum* | D | F | N | H |
| 55 | NC_020802\|YP_007640992.1 | *Psychromonas* sp. | D | F | N | H |
| 56 | NC_022223\|N175_08855 | *Listonella anguillarum* | D | F | N | H |
| 57 | NC_015633\|YP_004566361.1 | *Vibrio anguillarum* | D | F | N | H |
| 58 | NC_016445\|YP_004936985.1 | *Vibrio cholerae* | D | F | N | H |
| 59 | NC_016602\|YP_004992976.1 | *Vibrio furnissii* | D | F | N | H |
| 60 | NC_015460\|YP_004420811.1 | *Gallibacterium anatis* | D | F | N | H |
| 61 | NC_014966\|YP_004190360.1 | *Vibrio vulnificus* | D | F | N | H |
| 62 | NC_006300\|YP_087835.1 | *Mannheimia succiniciproducens* | D | F | N | H |
| 63 | NC_015964\|YP_004822812.1 | *Haemophilus parainfluenzae* | D | F | N | H |
| 64 | NC_012913\|YP_003007706.1 | *Aggregatibacter aphrophilus* | D | F | N | H |
| 65 | NC_000907\|NP_438982.2 | *Haemophilus influenzae* | D | F | N | H |
| 66 | NC_009655\|YP_001345182.1 | *Actinobacillus succinogenes* | D | F | N | H |
| 67 | NC_014920\|YP_004135881.1 | *Haemophilus influenza* | D | F | N | H |
| 68 | NC_016513\|YP_004948894.1 | *Aggregatibacter actinomycetemc* | D | F | N | H |

TABLE 1-continued

| | | | | | | |
|---|---|---|---|---|---|---|
| 69 | NC_010939\|YP_001969307.1 | *Actinobacillus pleuropneumonia* | D | F | N | H |
| 70 | NC_016808\|YP_005176051.1 | *Pasteurella multocida* | D | F | N | H |
| 71 | NC_010519\|YP_001783460.1 | *Haemophilus somnus* | D | F | N | H |
| 72 | NC_021082\|YP_007882660.1 | *Mannheimia haemolytica* | D | F | N | H |
| 73 | NC_017846\|YP_006287121.1 | *Aggregatibacter actinomycetemc* | D | F | N | H |
| 74 | NC_018690\|YP_006818133.1 | *Actinobacillus suis* | D | F | N | H |
| 75 | NC_011852\|YP_002475059.1 | *Haemophilus parasuis* | D | F | N | H |
| 76 | NC_008312\|YP_720691.1 | *Trichodesmium erythraeum* | D | F | N | H |
| 77 | NC_020515\|YP_007548075.1 | *Bibersteinia trehalosi* | D | F | N | H |
| 78 | NC_022524\|N288_24375 | *Bacillus infantis* | D | F | N | H |
| 79 | NC_021281\|YP_008019649.1 | *Fusobacterium nucleatum* | D | F | N | H |
| 80 | NC_003454\|NP_604062.1 | *Fusobacterium nucleatum* | D | F | N | H |
| 81 | NC_003366\|NP_562257.1 | *Clostridium perfringens* | D | F | N | H |
| 82 | NC_018607\|YP_006708369.1 | *Brachyspira pilosicoli* | D | F | N | H |
| 83 | NC_019908\|YP_007234804.1 | *Brachyspira pilosicoli* | D | F | N | H |
| 84 | NC_012225\|YP_002722709.1 | *Brachyspira hyodysenteriae* | D | F | N | H |
| 85 | NC_017243\|YP_005593986.1 | *Brachyspira intermedia* | D | F | N | H |
| 86 | NC_014150\|YP_003634598.1 | *Brachyspira murdochii* | D | F | N | H |
| 87 | NC_014330\|YP_003786208.1 | *Brachyspira pilosicoli* | D | F | N | H |
| 88 | NC_012491\|YP_002770161.1 | *Brevibacillus brevis* | D | F | N | H |
| 89 | NC_015732\|YP_004698509.1 | *Treponema caldaria* | D | F | N | H |
| 90 | NC_020291\|Cspa_c46680 | *Clostridium saccharoperbutylac* | D | F | N | H |
| 91 | NC_009617\|YP_001311499.1 | *Clostridium beijerinckii* | D | F | N | H |
| 92 | NC_014364\|YP_003802961.1 | *Spirochaeta smaragdinae* | D | Y | N | H |
| 93 | NC_015152\|YP_004246106.1 | *Sphaerochaeta globosa* | D | F | N | H |
| 94 | NC_014392\|YP_003839461.1 | *Caldicellulosiruptor obsidians* | D | F | N | H |
| 95 | NC_015578\|YP_004532181.1 | *Treponema primitia* | D | F | N | H |
| 96 | NC_014410\|YP_003852930.1 | *Thermoanaerobacterium thermosa* | D | F | N | H |
| 97 | NC_012914\|YP_003010600.1 | *Paenibacillus* sp. | D | F | N | H |
| 98 | NC_010278\|YP_001651502.1 | *Actinobacillus pleuropneumonia* | D | F | N | H |
| 99 | NC_016633\|YP_005062659.1 | *Sphaerochaeta pleomorpha* | D | F | N | H |
| 100 | NC_014393\|YP_003845273.1 | *Clostridium cellulovorans* | D | F | N | H |
| 101 | NC_014652\|YP_003991244.1 | *Caldicellulosiruptor hydrother* | D | F | N | H |
| 102 | NC_022777\|YP_008772951.1 | *Clostridium tetani* | D | F | N | H |
| 103 | NC_018690\|YP_006817320.1 | *Actinobacillus suis* | D | F | N | H |
| 104 | NC_009053\|YP_001053159.1 | *Actinobacillus pleuropneumonia* | D | F | N | H |
| 105 | NC_014393\|YP_003845272.1 | *Clostridium cellulovorans* | D | F | N | N |
| 106 | NC_010939\|YP_001968321.1 | *Actinobacillus pleuropneumonia* | D | F | N | H |
| 107 | NC_021658\|SCE1572_01005 | *Sorangium cellulosum* | N | F | N | H |
| 108 | NC_015690\|YP_004645360.1 | *Paenibacillus mucilaginosus* | D | F | N | H |
| 109 | NC_016935\|YP_005316341.1 | *Paenibacillus mucilaginosus* | D | F | N | H |
| 110 | NC_012914\|YP_003013039.1 | *Paenibacillus* sp. | D | F | N | H |
| 111 | NC_015519\|YP_004460241.1 | *Tepidanaerobacter acetatoxydan* | D | F | N | H |
| 112 | NC_013406\|YP_003243743.1 | *Paenibacillus* sp. | D | F | N | H |
| 113 | NC_015519\|YP_004461277.1 | *Tepidanaerobacter acetatoxydan* | D | F | N | H |
| 114 | NC_013517\|YP_003308491.1 | *Sebaldella termitidis* | D | F | N | H |
| 115 | NC_014150\|YP_003634599.1 | *Brachyspira murdochii* | D | F | N | H |
| 116 | NC_015436\|YP_004411990.1 | *Sphaerochaeta coccoides* | D | F | N | H |
| 117 | NC_021038\|YP_007827124.1 | *Fretibacterium fastidiosum* | D | F | N | H |
| 118 | NC_020291\|Cspa_c46620 | *Clostridium saccharoperbutylac* | D | F | N | H |
| 119 | NC_009617\|YP_001311493.1 | *Clostridium beijerinckii* | D | F | N | H |
| 120 | NC_015977\|YP_004837837.1 | *Roseburia hominis* | D | F | N | H |
| 121 | NC_021018\|YP_007796707.1 | *Coprococcus* sp. | D | F | N | H |
| 122 | NC_021042\|YP_007838599.1 | *Faecalibacterium prausnitzii* | D | F | N | N |
| 123 | NC_012781\|YP_002936409.1 | *Eubacterium rectale* | D | F | N | H |
| 124 | NC_015601\|YP_004561181.1 | *Erysipelothrix rhusiopathiae* | D | F | N | N |
| 125 | NC_021354\|YP_008073256.1 | *Erysipelothrix rhusiopathiae* | D | F | N | N |
| 126 | NC_021012\|YP_007778124.1 | *Roseburia intestinalis* | D | F | N | H |
| 127 | NC_022592\|CAETHG_2989 | *Clostridium autoethanogenum* | N | W | N | N |
| 128 | NC_014328\|CLJU_c08950 | *Clostridium ljungdahlii* | N | W | N | N |
| 129 | NC_021020\|YP_007799070.1 | *Faecalibacterium prausnitzii* | D | F | N | N |
| 130 | NC_021040\|YP_007833443.1 | *Roseburia intestinalis* | D | F | N | H |
| 131 | NC_021035\|YP_007824422.1 | butyrate-producing bacterium | D | F | N | N |
| 132 | NC_021012\|YP_007778116.1 | *Roseburia intestinalis* | D | F | N | N |
| 133 | NC_015977\|YP_004837830.1 | *Roseburia hominis* | D | F | N | N |
| 134 | NC_021040\|YP_007833436.1 | *Roseburia intestinalis* | D | F | N | N |
| 135 | NC_014376\|YP_003822569.1 | *Clostridium saccharolyticum* | D | F | N | N |
| 136 | NC_022549\|YP_008656214.1 | *Acholeplasma brassicae* | D | F | N | H |
| 137 | NC_014387\|YP_003830205.1 | *Butyrivibrio proteoclasticus* | D | F | N | N |
| 138 | NC_014376\|YP_003822565.1 | *Clostridium saccharolyticum* | D | F | N | N |

| | PCS position and sequence | | | | | | | | |
|---|---|---|---|---|---|---|---|---|---|
| # | 154 | 158 | 183 | 211 | 236 | 256 | Identity | Thermophilicity | Gram |
| 1 | D | R | W | N | D | N | | | |
| 2 | D | R | W | N | D | N | 1.00 | Mesophilic | – |
| 3 | D | R | W | N | D | N | 1.00 | Mesophilic | – |
| 4 | D | R | W | N | D | N | 1.00 | Mesophilic | – |
| 5 | D | R | W | N | D | N | 1.00 | Mesophilic | – |

TABLE 1-continued

| | | | | | | | | | |
|---|---|---|---|---|---|---|---|---|---|
| 6 | D | R | W | N | D | N | 1.00 | Mesophilic | − |
| 7 | D | R | W | N | D | N | 1.00 | Mesophilic | − |
| 8 | D | R | W | N | D | N | 0.97 | Mesophilic | − |
| 9 | D | R | W | N | D | N | 0.96 | Mesophilic | − |
| 10 | D | R | W | N | D | N | 0.95 | Mesophilic | − |
| 11 | D | R | W | N | D | N | 0.95 | Mesophilic | − |
| 12 | D | R | W | N | D | N | 0.95 | Mesophilic | − |
| 13 | D | R | W | N | D | N | 0.94 | Mesophilic | − |
| 14 | D | R | W | N | D | N | 0.94 | Mesophilic | − |
| 15 | D | R | W | N | D | N | 0.94 | Mesophilic | − |
| 16 | D | R | W | N | D | N | 0.94 | Mesophilic | + |
| 17 | D | R | W | N | D | N | 0.94 | Mesophilic | − |
| 18 | D | R | W | N | D | N | 0.94 | Mesophilic | − |
| 19 | D | R | W | N | D | N | 0.94 | Mesophilic | − |
| 20 | D | R | W | N | D | N | 0.94 | Mesophilic | − |
| 21 | D | R | W | N | D | N | 0.94 | Mesophilic | − |
| 22 | D | R | W | N | D | N | 0.94 | Mesophilic | − |
| 23 | D | R | W | N | D | N | 0.94 | Mesophilic | − |
| 24 | D | R | W | N | D | N | 0.94 | Mesophilic | − |
| 25 | D | R | W | N | D | N | 0.93 | Mesophilic | + |
| 26 | D | R | W | N | D | N | 0.93 | Mesophilic | − |
| 27 | D | R | W | N | D | N | 0.93 | Mesophilic | − |
| 28 | D | R | W | N | D | N | 0.90 | Mesophilic | − |
| 29 | D | R | W | N | D | N | 0.88 | Mesophilic | + |
| 30 | D | R | W | N | D | N | 0.88 | Mesophilic | + |
| 31 | D | R | W | N | D | N | 0.87 | Mesophilic | − |
| 32 | D | R | W | N | D | N | 0.87 | Mesophilic | − |
| 33 | D | R | W | N | D | N | 0.87 | Mesophilic | + |
| 34 | D | R | W | N | D | N | 0.86 | Mesophilic | + |
| 35 | D | R | W | N | D | N | 0.86 | ? | + |
| 36 | D | R | W | N | D | N | 0.86 | Mesophilic | + |
| 37 | D | R | W | N | D | N | 0.85 | Mesophilic | + |
| 38 | D | R | W | N | D | N | 0.84 | Mesophilic | − |
| 39 | D | R | W | N | D | N | 0.82 | Mesophilic | + |
| 40 | D | R | W | N | D | N | 0.82 | Mesophilic | − |
| 41 | D | R | W | N | D | N | 0.82 | Mesophilic | − |
| 42 | D | R | W | N | D | N | 0.81 | Mesophilic | − |
| 43 | D | R | W | N | D | N | 0.81 | Mesophilic | − |
| 44 | D | R | W | N | D | N | 0.81 | Mesophilic | − |
| 45 | D | R | W | N | D | N | 0.81 | Mesophilic | − |
| 46 | D | R | W | N | D | N | 0.81 | Mesophilic | − |
| 47 | D | R | W | N | D | N | 0.81 | Mesophilic | − |
| 48 | D | R | W | N | D | N | 0.80 | Mesophilic | + |
| 49 | D | R | W | N | D | N | 0.80 | Mesophilic | − |
| 50 | D | R | W | N | D | N | 0.80 | Mesophilic | − |
| 51 | D | R | W | N | D | N | 0.79 | Mesophilic | − |
| 52 | D | R | W | N | D | N | 0.78 | ? | + |
| 53 | D | R | W | N | D | N | 0.76 | Mesophilic | − |
| 54 | D | R | W | N | D | N | 0.74 | Psychrophilic | − |
| 55 | D | R | W | N | D | N | 0.72 | Mesophilic | + |
| 56 | D | R | W | N | D | N | 0.72 | Mesophilic | + |
| 57 | D | R | W | N | D | N | 0.72 | Mesophilic | − |
| 58 | D | R | W | N | D | N | 0.72 | Mesophilic | − |
| 59 | D | R | W | N | D | N | 0.71 | Mesophilic | − |
| 60 | D | R | W | N | D | N | 0.71 | Mesophilic | − |
| 61 | D | R | W | N | D | N | 0.71 | Mesophilic | − |
| 62 | D | R | W | N | D | N | 0.70 | Mesophilic | + |
| 63 | D | R | W | N | D | N | 0.70 | Mesophilic | − |
| 64 | D | R | W | N | D | N | 0.69 | Mesophilic | − |
| 65 | D | R | W | N | D | N | 0.69 | Mesophilic | − |
| 66 | D | R | W | N | D | N | 0.69 | Mesophilic | − |
| 67 | D | R | W | N | D | N | 0.69 | Mesophilic | − |
| 68 | D | R | W | N | D | N | 0.68 | Mesophilic | − |
| 69 | D | R | W | N | D | N | 0.68 | Mesophilic | − |
| 70 | D | R | W | N | D | N | 0.68 | Mesophilic | − |
| 71 | D | R | W | N | D | N | 0.68 | Mesophilic | − |
| 72 | D | R | W | N | D | N | 0.68 | Mesophilic | + |
| 73 | D | R | W | N | D | N | 0.68 | Mesophilic | − |
| 74 | D | R | W | N | D | N | 0.67 | Mesophilic | − |
| 75 | D | R | W | N | D | N | 0.66 | Mesophilic | − |
| 76 | D | R | W | N | D | N | 0.59 | Mesophilic | − |
| 77 | D | R | W | N | D | N | 0.58 | Mesophilic | + |
| 78 | D | R | W | N | D | N | 0.58 | Mesophilic | + |
| 79 | D | R | W | N | D | N | 0.58 | Mesophilic | − |
| 80 | D | R | W | N | D | N | 0.57 | Mesophilic | − |
| 81 | D | R | W | N | D | N | 0.56 | Mesophilic | + |
| 82 | D | R | W | N | D | N | 0.53 | Mesophilic | − |
| 83 | D | R | W | N | D | N | 0.52 | Mesophilic | − |
| 84 | D | R | W | N | D | N | 0.52 | Mesophilic | − |
| 85 | D | R | W | N | D | N | 0.52 | ? | − |

TABLE 1-continued

| | | | | | | | | | |
|---|---|---|---|---|---|---|---|---|---|
| 86 | D | R | W | N | D | N | 0.52 | Mesophilic | – |
| 87 | D | R | W | N | D | N | 0.51 | Mesophilic | – |
| 88 | D | R | W | N | D | N | 0.50 | Mesophilic | + |
| 89 | D | R | W | N | D | N | 0.50 | Mesophilic | – |
| 90 | D | R | W | N | D | N | 0.49 | Mesophilic | + |
| 91 | D | R | W | N | D | N | 0.49 | Mesophilic | + |
| 92 | D | R | W | N | D | N | 0.49 | Mesophilic | – |
| 93 | D | R | W | N | D | N | 0.48 | Mesophilic | + |
| 94 | D | R | W | N | D | N | 0.48 | Hyperthermophilic | + |
| 95 | D | R | W | N | D | N | 0.48 | Mesophilic | – |
| 96 | D | R | W | N | D | N | 0.48 | Thermophilic | + |
| 97 | D | R | W | N | D | N | 0.48 | Mesophilic | + |
| 98 | D | R | W | N | D | N | 0.48 | Mesophilic | – |
| 99 | D | R | W | N | D | N | 0.48 | Mesophilic | + |
| 100 | D | R | W | N | D | N | 0.47 | Mesophilic | + |
| 101 | D | R | W | N | D | N | 0.47 | Hyperthermophilic | + |
| 102 | D | R | W | N | D | N | 0.47 | Mesophilic | + |
| 103 | D | R | W | N | D | N | 0.47 | Mesophilic | – |
| 104 | D | R | W | N | D | N | 0.47 | Mesophilic | – |
| 105 | D | R | W | N | D | N | 0.47 | Mesophilic | + |
| 106 | D | R | W | N | D | N | 0.46 | Mesophilic | – |
| 107 | D | R | W | N | D | N | 0.46 | Mesophilic | – |
| 108 | D | R | W | N | D | N | 0.46 | Mesophilic | + |
| 109 | D | R | W | N | D | N | 0.45 | Mesophilic | + |
| 110 | D | R | W | N | D | N | 0.44 | Mesophilic | + |
| 111 | D | R | W | N | D | N | 0.44 | Mesophilic | + |
| 112 | D | R | W | N | D | N | 0.44 | Mesophilic | + |
| 113 | D | R | W | N | D | N | 0.43 | Mesophilic | + |
| 114 | D | R | W | N | D | N | 0.43 | Mesophilic | – |
| 115 | D | R | W | N | D | N | 0.43 | Mesophilic | – |
| 116 | D | R | W | N | D | N | 0.41 | Mesophilic | + |
| 117 | D | R | W | N | D | N | 0.41 | Mesophilic | + |
| 118 | D | R | W | N | D | N | 0.40 | Mesophilic | + |
| 119 | D | R | W | N | D | N | 0.39 | Mesophilic | + |
| 120 | D | R | W | N | D | N | 0.38 | Mesophilic | + |
| 121 | D | R | W | N | D | N | 0.38 | Mesophilic | + |
| 122 | D | R | W | N | D | N | 0.37 | Mesophilic | – |
| 123 | D | R | W | N | D | N | 0.37 | Mesophilic | + |
| 124 | D | R | W | N | D | N | 0.36 | Mesophilic | + |
| 125 | D | R | W | N | D | N | 0.36 | Mesophilic | + |
| 126 | D | R | W | N | D | N | 0.36 | Mesophilic | + |
| 127 | D | R | W | N | D | N | 0.36 | Mesophilic | + |
| 128 | D | R | W | N | D | N | 0.35 | Mesophilic | + |
| 129 | D | R | W | N | D | N | 0.34 | Mesophilic | – |
| 130 | D | R | W | N | D | N | 0.34 | Mesophilic | + |
| 131 | D | R | W | N | D | N | 0.33 | Mesophilic | ? |
| 132 | D | R | W | N | D | N | 0.33 | Mesophilic | + |
| 133 | D | R | W | N | D | N | 0.33 | Mesophilic | + |
| 134 | D | R | W | N | D | N | 0.32 | Mesophilic | + |
| 135 | D | R | W | N | D | N | 0.31 | Mesophilic | + |
| 136 | D | R | W | N | D | N | 0.31 | Mesophilic | + |
| 137 | D | R | W | N | D | N | 0.30 | Mesophilic | + |
| 138 | D | R | W | N | D | N | 0.29 | Mesophilic | + |

Each nucleotide and amino acid sequence associated with the accession numbers listed in Table 1 is hereby incorporated by reference in its entirety.

TABLE 2

Glucose-binding properties of *E. coli* GGBP SAFE sequence homologs.

| Accession number | Protein name | Expression[a] | $T_m$ shift with Glucose[a] | Percent Identity |
|---|---|---|---|---|
| NC_013654\|YP_003350022.1 | ecGGBP | Y | Y | 100 |
| NC_014376\|YP_003822565.1 | csaGGBP | Y | Y | 29 |
| NC_014387\|YP_003830205.1 | bprGGBP | N | | 30 |
| NC_021012\|YP_007778116.1 | rinGGBP_A | N | | 33 |
| NC_021020\|YP_007799070.1 | fprGGBP | Y | Y | 34 |
| NC_014328\|CLJU_c08950 | cljGGBP | N | | 35 |
| NC_022592\|CAETHG_2989 | cauGGBP | N | | 36 |
| NC_021012\|YP_007778124.1 | rinGGBP_B | Y | Y | 36 |
| NC_015601\|YP_004561181.1 | erhGGBP | Y | Y | 36 |
| NC_012781\|YP_002936409.1 | ereGGBP | N | | 37 |

TABLE 2-continued

| Glucose-binding properties of *E. coli* GGBP SAFE sequence homologs. | | | | |
|---|---|---|---|---|
| Accession number | Protein name | Expression[a] | $T_m$ shift with Glucose[a] | Percent Identity |
| NC_014410\|YP_003852930.1 | ttGGBP | Y | Y | 48 |
| NC_014392\|YP_003839461.1 | cobGGBP | Y | Too thermostable[b] | 48 |
| NC_014652\|YP_003991244.1 | chyGGBP | Y | Too thermostable[b] | 47 |
| NC_013406\|YP_003243743.1 | pspGGBP | N | | 44 |

[a]Y, Yes; N, No.
[b]Determined using fluorescent Acrylodan conjugates (see text).

TABLE 3

Glucose response of Acrylodan and Badan conjugates in a cysteine scan of the ttGGBP scaffold.

| Mutation | Class[a] | Shape[b] | Conjugate[c] | $^{apo}T_m$ (K) | Emission Wavelength (nm) λ1 | Emission Wavelength (nm) λ2 | $K_d^{d,e}$ (mM) $^{app}K_d$ | $K_d^{d,e}$ (mM) $^{true}K_d$ |
|---|---|---|---|---|---|---|---|---|
| Y11C | p | m | A | 351 | 511 | 470 | 0.12 | 0.16 |
| | | d | B | 349 | 492 | 528 | 0.28 | 0.24 |
| T16C | p | m | A | 351 | 519 | 460 | 8.8 | 12 |
| | | m | B | 349 | — | — | nb | nb |
| F17C | e | d | A | 349 | 482 | 542 | 0.08 | 0.06 |
| | | d | B | 346 | 467 | 491 | 0.087 | 0.26 |
| N42C | p | | A | 350 | — | — | nb | nb |
| | | | B | 324 | — | — | nb | nb |
| V67C | p | | A | 350 | — | — | nb | nb |
| | | | B | 322 | — | — | nb | nb |
| R91C | e | m | A | 349 | 491 | 540 | 0.18 | 0.17 |
| | | | B | 348 | — | — | nb[d] | nb[d] |
| E92C | p | | A | 350 | — | — | nb | nb |
| | | | B | 346 | — | — | nb | nb |
| A111C | p | m | A | 350 | 515 | 550 | 0.19[d] | 0.11[d] |
| | | m/d | B | 348 | 523 | 550 | 0.64 | 0.55 |
| Q148C | p | | A | 351 | — | — | nb | nb |
| | | | B | 349 | — | — | nb | nb |
| H151C | e | m | A | 351 | 511 | 489 | 0.012 | 0.025 |
| | | m | B | 348 | 523 | 550 | 0.018[d] | 0.027[d] |
| Q152C | p | | A | 351 | — | — | nb[d] | nb[d] |
| | | | B | 349 | — | — | nb | nb |
| N181C | p | | A | 350 | — | — | nb | nb |
| | | | B | 349 | — | — | nb | nb |
| W182C | e | d | A | 347 | 479 | 526 | 2.3 | 2.3 |
| | | m | B | 347 | 515 | 550 | 27 | 19 |
| D183C | p | | A | 348 | — | — | nb[d] | nb[d] |
| | | | B | 348 | — | — | nb | nb |
| L257C | a | | A | 352 | — | — | nb | nb |
| | | | B | 348 | — | — | nb | nb |
| D259C | a | | A | 349 | — | — | nb | nb |
| | | | B | 347 | — | — | nb | nb |
| K300C | a | | A | 349 | — | — | nb | nb |
| | | | B | 348 | — | — | nb | nb |

[a]a, allosteric; e, endosteric; p, peristeric.
[b]m, monochromatic; d, dichromatic (i.e. spectral shape change).
[c]A, Acrylodan; B, Badan.
[d]noisy data and or bad fit.
[e]nb; no binding, nd; not determined.

TABLE 4

Responses of fluorophores conjugated to F17C and W182C mutants of ttGGBP[a].

| Position | Fluorophore[b] | $\lambda_{ex}$ (nm)[c] | $^{apo}\lambda_{max}$ (nm) | $^{apo}I_{max}$ (AU ×1000) | $^{sat}\lambda_{max}$ (nm) | $^{sat}I_{max}$ (AU ×1000) | $^{true}K_d$ (mM) |
|---|---|---|---|---|---|---|---|
| 17C | Acrylodan | 391 | 487 | 15.9 | 487 | 20.0 | 0.2 |
| | Badan | 391 | 519 | 12.8 | 467 | 52.6 | 0.1 |
| | 5-IAF | 491 | 523 | 64.3 | 523 | 70.6 | 61.3 |
| | Oregon green | 496 | 523 | 101.9 | 523 | 91.7 | — |
| | CPM | 384 | 471 | 78.5 | 467 | 90.9 | 17.0 |
| | IANBD | 478 | 531 | 15.3 | 535 | 19.8 | 11.8 |
| | IAEDANS | 336 | 467 | 12.5 | 467 | 14.4 | — |
| | Pacific Blue | 410 | 451 | 28.6 | 455 | 108.6 | 60.7 |
| 182C | Acrylodan | 391 | 479 | 55.0 | 515 | 17.2 | 6.0 |
| | Badan | 391 | 515 | 16.8 | 515 | 11.9 | 64.9 |
| | 5-IAF | 491 | 519 | 255.0 | 519 | 453.2 | 5.0 |
| | 6-IAF | 491 | 513 | 50.4 | 513 | 63.1 | 750 |
| | Oregon green | 496 | 519 | 78.2 | 519 | 186.2 | 20.0 |
| | CPM | 384 | 479 | 49.5 | 483 | 40.3 | 6.8 |
| | IANBD | 478 | 543 | 29.1 | 547 | 12.5 | 210 |
| | IAEDANS | 336 | 487 | 3.7 | 483 | 7.9 | 0.2 |
| | Pacific Blue | 410 | 455 | 115.0 | 455 | 119.4 | — |
| | BODIPY 499 | 499 | 519 | 40.1 | 515 | 80.2 | 30.7 |
| | BODIPY 507 | 507 | 531 | 32.9 | 535 | 31.4 | 11.0 |
| | Alexa 488 | 495 | 519 | 211.6 | 519 | 182.2 | — |
| | Alexa 532 | 532 | 551 | 63.0 | 551 | 61.0 | — |
| | Alexa 546 | 546 | 571 | 152.1 | 571 | 150.2 | — |
| | Texas Red | 595 | 611 | 23.3 | 611 | 23.5 | — |
| | Cy 5 | 646 | 663 | 19.2 | 663 | 23.3 | 210 |
| | PyPMPO | 415 | 555 | 3.7 | 559 | 4.2 | 20.6 |

[a]$\lambda_{ex}$, preferred excitation wavelength (from supplier); $^{apo}\lambda_{max}$, observed maximum emission wavelength of the apo-protein; $^{apo}I_{max}$, observed intensity at $^{apo}\lambda_{max}$; $^{apo}\lambda_{max}$, observed maximum emission wavelength of the glucose complex; $^{sat}I_{max}$, observed intensity at $^{sat}\lambda_{max}$; $^{true}K_d$, affinity determined from fit of equation 1 to the monochromatic emission intensities. Emission spectra were measured on the Nanodrop3300, using ~10 μM protein. The observed absolute emission intensities are a rough guide to the brightness of the conjugate, because the protein concentration was approximately the same for each experiment.
[b]Abbreviations, chemical names and supplier catalogue numbers as follows: Acrylodan (A433); Badan (B6057); 5-IAF (I30451); Oregon Green 488 (O6034); CPM (D346); IANBD (D2004); IAEDANS (I14); Pacific Blue (P30506); BODIPY 499 (D20350); BODIPY 507 (D6004); BODIPY 577 (D20351); Alexa 532 (A10255); Alexa 555 (A20346); Texas Red (T6008); PyMPO (M6026) from Life Technologies and Cy5 (13080) from Lumiprobe.
[c]The Nanodrop3300 fixed wavelength LED that most closely matched $\lambda_{ex}$ was used (see Materials and Methods).

TABLE 5

Crystallographic data collection and refinement statistics.[a]

| | ttGGBP17C-Badan | ttGGBP182C.2.0-Acrylodan | ecGGBP183C-Acrylodan |
|---|---|---|---|
| X-ray source | 22-ID, SER-CAT, APS | 22-ID, SER-CAT, APS | 22-BM, SER-CAT, APS |
| Wavelength (Å) | 1.0 | 1.0 | 1.0 |
| Space Group | $P2_12_12_1$ | $P2_12_12_1$ | C121 |
| Unit Cell parameters (Å) | | | |
| a, b, c | 45.49, 53.06, 134.32 | 45.67, 53.17, 133.57 | 119.58, 36.53, 79.90 |
| | | | 90.00 (α), 124.13 (β), 90.00 (γ) |
| Resolution range (Å) | 41.63-1.59 (1.62-1.59) | 33.70-1.39 | 50.00-1.53 (1.56-1.53) |
| Completeness (%) | 99.8 (99.3) | 98.9 (94.9) | 98.8 (94.6) |
| No. of unique reflections | 44590 | 65108 (9969) | 43030 |
| Wilson B-factor (Å$^2$) | 15.50 | 11.50 | 12.60 |
| Multiplicity | 7.21 (7.22) | 5.29 (5.17) | 6.5 (5.1) |
| R-sym (%) | 0.08 (0.69) | 0.08 (0.76) | 0.06 (0.29) |
| R-pim (%) | 0.03 (0.25) | 0.04 (0.34) | 0.025 (0.131) |
| Mean I/σ (I) | 16.40 (3.58) | 13.71 (2.87) | 25.54 (3.99) |
| Refinement statistics | | | |
| R factor (%) | 15.11 | 15.88 | 15.04 |
| Free_R_factor (%) | 17.07 | 17.74 | 16.75 |
| Average B-factor (Å$^2$) | 20.10 | 17.90 | 18.60 |
| Macromolecules | 17.70 | 15.30 | 15.90 |
| Water | 34.30 | 34.10 | 34.60 |
| Glucose/Fluorophore | 9.50/39.90 | 8.60/39.10 | 22.70/64.50 |

TABLE 5-continued

| Crystallographic data collection and refinement statistics.[a] | ttGGBP17C-Badan | ttGGBP182C.2.0-Acrylodan | ecGGBP183C-Acrylodan |
|---|---|---|---|
| Number of non-hydrogen atoms | | | |
| Macromolecule | 2471 | 2493 | 2358 |
| Glucose | 24[b] | 24[b] | 72[c] |
| Calcium | 1 | 1 | 1 |
| Fluorophore | 16 | 17 | 17 |
| Water | 407 | 391 | 325 |
| RMS deviations | | | |
| RMS (bonds) | 0.007 | 0.005 | 0.006 |
| RMS (angles) | 1.112 | 0.822 | 1.060 |
| Ramachandran favoured (%) | 97.81 | 98.44 | 98.71 |
| Ramachandran allowed (%) | 1.88 | 1.25 | 0.97 |
| Ramachandran outliers (%) | 0.31 | 0.31 | 0.32 |
| Rotamer outliers (%) | 0.00 | 0.00 | 0.00 |
| Clashscore | 1.60 | 0.79 | 1.03 |

[a]Values for highest resolution shell are given in parentheses.
[b]Two conformations.
[c]Five molecules.

TABLE 6

Responses of mutant HGGBP17C and ttGGBP182C conjugates[a].

| Protein | Mutation | Class[b] | Conjugate[c] | $^{apo}T_m$ (K) | Emission wavelength (nm) λ1 | Emission wavelength (nm) λ2 | Glucose[d] $^{app}K_d$ (mM) | Glucose[d] $^{true}K_d$ (mM) | Galactose[d] $^{true}K_d$ (mM) | S |
|---|---|---|---|---|---|---|---|---|---|---|
| ttGBP17C | | | B | 346 | 467 | 519 | 0.10 | 0.15 | 0.19 | 1.3 |
| " | | | A | 349 | 487 | 515 | 0.08 | 0.09 | 3.8 | 43 |
| ttGGBP17C.1 | R91K, Q148E | 2 | B | | 463 | 515 | 0.6 | 0.8 | 0.4 | 0.46 |
| ttGGBP17C.2 | R69P, Q152P | 2 | B | 350 | 479 | 523 | 8.6 | 10.8 | 5.2 | 0.48 |
| " | " | 2 | A | | 492 | 515 | 15 | 18 | 5.0 | 0.28 |
| ttGGBP17C.3 | T16N, D211A | 2 | B | 346 | 471 | 531 | 3.4 | 4.1 | 2.5 | 0.61 |
| " | " | 2 | A | | 495 | 529 | 1.4 | 1.5 | 0.53 | 0.35 |
| ttGGBP17C.4 | H151Q | 1 | B | 347 | 511 | 457 | 16 | 6.4 | 14 | 2.2 |
| " | " | 1 | A | | 488 | 550 | 50 | 48 | 14 | 0.29 |
| ttGGBP17C.5 | D15A | 1 | B | 345 | 487 | 530 | 16 | 16 | 4.2 | 0.26 |
| " | " | 1 | A | 348 | 483 | 498 | 6 | 6 | 2.4 | 0.41 |
| ttGGBP17C.6 | D15E | 1 | B | 346 | 467 | 525 | 3.3 | 3.6 | 3.6[e] | 1 |
| ttGGBP17C.7 | D15N | 1 | B | 347 | 483 | 515 | 0.75 | 1.0 | 0.64 | 0.64 |
| " | " | 1 | A | 348 | 483 | 515 | 0.3 | 0.3 | 0.3 | 0.91 |
| ttGGBP17C.8 | T16N | 2 | A | 348 | 487 | 529 | 0.61 | 0.60 | 0.26 | 0.43 |
| ttGGBP17C.9 | T16S | 2 | A | | 487 | 520 | 0.2 | 0.20 | nd | |
| ttGGBP17C.10 | G20A | 3 | A | 351 | 487 | 520 | 0.4 | 0.4 | nd | |
| ttGGBP17C.11 | T240A | 3 | A | 348 | 487 | 500 | 0.04 | 0.04 | nd | |
| ttGGBP17C.19 | N258D | 3 | B | 344 | | | nb[e] | nb[e] | nb[e] | |
| ttGGBP17C.20 | N258S | 3 | B | 344 | | | nb[e] | nb[e] | nb[e] | |
| ttGGBP17C.21 | N258A | 3 | B | 345 | 532 | 494 | 61 | 69 | nb | |
| ttGGBP17C.22 | A260N | 3 | B | 343 | 523 | 492 | 12 | 15 | 530[e] | |
| ttGGBP17C.23 | A260Q | 3 | B | 344 | 527 | 490 | 15 | 18 | nb[c] | |
| ttGGBP17C.24 | A260R | 3 | B | 344 | 490 | 515 | 1.8 | 1.7 | 29 | 17 |
| ttGGBP17C.25 | A260K | 3 | B | | 515 | 493 | 3.2 | 3.7 | nb[e] | |
| ttGGBP17C.26 | A260W | 3 | B | 346 | 523 | 509 | 0.9 | 0.9 | 14 | 16 |
| ttGGBP17C.27 | A260F | 3 | B | 346 | 523 | 490 | 0.2 | 0.3 | 8.8 | 33 |
| ttGGBP17C.28 | A260Y | 3 | B | 346 | 523 | 494 | 0.06 | 0.07 | 2.6 | 37 |
| ttGGBP17C.29 | A260S | 3 | B | 343 | 527 | 496 | 2.1 | 2.2 | 250 | 114 |
| ttGGBP182C | | | A | 347 | 472 | 535 | 2.2 | 2.3 | 3.3 | 1.4 |
| ttGGBP182C.2.0[f] | R91K Q148E | 2, 3 | A | 346 | 475 | 545 | 4.5 | 6.0 | 18.5 | 3.1 |
| ttGGBP182C.2.1[g] | A154S | 1 | A | 328 | 480 | 552 | 3.0 | 4.1 | 13.1 | 3.2 |
| ttGGBP182C.2.3[g] | A154N | 1 | A | 346 | 470 | 537 | 16.3 | 19.0 | 207 | 10.9 |
| ttGGBP182C.2.4[g] | A154M | 1 | A | 346 | 472 | 540 | 0.4 | 0.4 | 4.5 | 11.2 |
| ttGGBP182C.2.5[g] | H151Q | 1 | A | 346 | 477 | 542 | 10.8 | 13.0 | 20.3 | 1.6 |
| ttGGBP182C.2.6[g] | H151N | 1 | A | 347 | 475 | 537 | 19.2 | 17.9 | 52.6 | 2.9 |
| ttGGBP182C.2.7[g] | H151F | 1 | A | 346 | 475 | 545 | 121 | 124 | | |
| ttGGBP182C.2.8[g] | D15N | 1 | A | 343 | 474 | 542 | 179 | 209 | 372 | 1.8 |
| ttGGBP182C.2.9[g] | A154F | 1 | A | 345 | 512 | 477 | 0.4 | 0.3 | 1.6 | 4.0 |
| ttGGBP182C.3[f] | R91K | 2 | A | 346 | 494 | 459 | 1.8 | 0.9 | 3.1 | 3.4 |

TABLE 6-continued

| Responses of mutant HGGBP17C and ttGGBP182C conjugates[a]. | | | | | | | | | | |
|---|---|---|---|---|---|---|---|---|---|---|
| | | | | | Emission | | Glucose[d] | | Galactose[d] | |
| | | | | $^{apo}T_m$ | wavelength (nm) | | $^{app}K_d$ | $^{true}K_d$ | $^{true}K_d$ | |
| Protein | Mutation | Class[b] | Conjugate[c] | (K) | λ1 | λ2 | (mM) | (mM) | (mM) | S |
| ttGGBP182C.4[f] | Q148E | 2 | A | 347 | 475 | 542 | 0.6 | 0.8 | 6.5 | 8.1 |
| ttGGBP182C.5[f] | R69P Q152P | 2 | A | 349 | 477 | 535 | 7.5 | 8.8 | 7.4 | 0.8 |
| ttGGBP182C.6[f] | T16N D211A | 2 | A | 345 | 472 | 530 | 21.6 | 27.6 | 81 | 2.9 |
| ttGGBP182C.7[f] | R91K Q148S | 2, 3 | A | 346 | 478 | 550 | 0.3 | 0.4 | 1.1 | 3.7 |
| ttGGBP182C.8[f] | R91K Q148K | 2, 3 | A | 346 | 475 | 545 | 28.7 | 44.2 | 256 | 5.8 |
| ttGGBP182C.9[f] | D15N | 1 | A | 343 | 475 | 540 | 75.1 | 76.4 | 282 | 3.7 |

[a]Measured on the Nanodrop at room temperature. $\lambda_{max}$ is the wavelength corresponding to the maximum emission intensity. Optimal ratiometry wavelengths are determined according to the analysis described in Materials and Methods (equation 7). The $^{true}K_d$ is determined from monochromatic titration curves; $^{app}K_d$ from dichromatic ratiometry (equations 5 and 6). Average relative error in the $^{true}K_d$ values is 5%, in the $^{app}K_d$ values, 1%. S is the selectivity between glucose and galactose, S = $^{true}K_d$(galactose)/$^{true}K_d$(glucose); S > 1, selective for glucose.
[b]1, PCS; 2, inter-domain interaction; 3, contact between protein and fluorophore
[c]A, Acrylodan; B, Badan.
[d]nb, no bonding; nd, not determined.
[e]Noisy data or bad fit.
[f]Additional mutation constructed in ttGGBP182C.
[g]Additional mutation constructed in ttGGBP182C.2.0.

TABLE 7

| Spectral analysis of ttGGBP and ecGGBP Acrylodan and Badan conjugates[a]. | | | | | | | | |
|---|---|---|---|---|---|---|---|---|
| | | | SVD component | | Gaussians | | | |
| Muta- | | | fractions | | Peaks (nm) | | Fraction f(S$_1$) | |
| tion | Conjugate[b] | | C$_1$ | C$_2$ | S$_1$ | S$_2$ | Apo | Sat |
| Y11C | A | r (h) | 0.97 | 0.03 | 515 | 463 | 1.00 | 0.88 |
| | B | r (h) | 0.84 | 0.16 | 532 | 484 | 1.00 | 0.47 |
| T16C | A | n | — | — | 518 | — | 1.00 | — |
| | B | n | — | — | 539 | 446 | 0.96 | — |
| F17C | A | r (h) | 0.90 | 0.09 | 527 | 486 | 0.56 | 0.16 |
| | B | r (h) | 0.89 | 0.10 | 535 | 474 | 0.66 | 0.15 |
| F16C (Ec) | A | r (h) | 0.91 | 0.08 | 509 | 454 | 0.63 | 0.10 |
| | B | r (h) | 0.92 | 0.06 | 522 | 469 | 0.56 | 0.14 |
| N42C | A | n | — | — | 518 | — | 1.00 | — |
| | B | n | — | — | 516 | — | 1.00 | — |
| V67C | A | n | — | — | 522 | 464 | 0.59 | — |
| | B | n | — | — | 523 | 480 | 0.38 | — |
| R91C | A | i | 0.97 | 0.02 | 533 | 488 | 0.43 | 0.92 |
| | B | n | — | — | 522 | 476 | 0.51 | — |
| E92C | A | n | — | — | 520 | — | 1.00 | — |
| | B | n | — | — | 522 | — | 1.00 | — |
| A111C | A | d | 0.98 | 0.01 | 520 | 474 | 0.98 | 0.95 |
| | B | d | 0.98 | 0.02 | 529 | 467 | 0.91 | 0.84 |
| Q148C | A | n | — | — | 537 | 491 | 0.26 | — |
| | B | n | — | — | 576 | 519 | 0.15 | — |

TABLE 7-continued

| Spectral analysis of ttGGBP and ecGGBP Acrylodan and Badan conjugates[a]. | | | | | | | | |
|---|---|---|---|---|---|---|---|---|
| | | | SVD component | | Gaussians | | | |
| Muta- | | | fractions | | Peaks (nm) | | Fraction f(S$_1$) | |
| tion | Conjugate[b] | | C$_1$ | C$_2$ | S$_1$ | S$_2$ | Apo | Sat |
| H151C | A | i | 0.97 | 0.02 | 520 | 490 | 1.00 | 0.86 |
| | B | i | 0.98 | 0.01 | 533 | 477 | 0.98 | 1.00 |
| Q152C | A | n | — | — | 520 | — | 1.00 | — |
| | B | n | — | — | 524 | 472 | 0.74 | — |
| N181C | A | n | — | — | 527 | — | 1.00 | — |
| | B | n | — | — | 545 | — | 1.00 | — |
| W182C | A | r (b) | 0.87 | 0.13 | 500 | 463 | 0.63 | 0.99 |
| | B | d | 0.98 | 0.02 | 521 | 479 | 0.91 | 1.00 |
| W183C (Ec) | A | r (b) | 0.84 | 0.15 | 527 | 481 | 0.37 | 0.81 |
| D183C | A | d | | | 523 | — | 1.00 | — |
| | B | n | — | — | 530 | 477 | 0.61 | — |
| L257C | A | n | — | — | 533 | 496 | 0.29 | — |
| | B | n | — | — | 516 | — | 1.00 | — |
| D259C | A | n | — | — | 516 | — | 1.00 | — |
| | B | n | — | — | 521 | — | 1.00 | — |
| K300C | A | n | — | — | 520 | — | 1.00 | — |
| | B | n | — | — | 528 | — | 1.00 | — |

[a]Emission spectra determined on Nanodrop3300. SVD analysis according to equations 11-13. Gaussian fits according to equations 14-15.
[b]A, Acrylodan; B, Badan; n, no observed response to glucose; r (h), ratiometric (hypsochromic shift); r (b), ratiometric (bathochromic shift); i, intensity increase only; d, intensity decrease only.

TABLE 8

| Spectral analysis of ttGGBP.17C Acrylodan and Badan conjugates[a]. | | | | | | | | | |
|---|---|---|---|---|---|---|---|---|---|
| | | | | SVD component | | Gaussians | | | |
| | | | | fractions | | Peaks (nm) | | Fraction f(S$_1$) | |
| Protein | Mutation | Conjugate[b] | | C$_1$ | C$_2$ | S$_1$ | S$_2$ | Apo | Sat |
| ttGGBP17C.1 | R91K, Q148E | A | d | 0.95 | 0.04 | 518 | 490 | 0.71 | 0.60 |
| " | " | B | r(h) | 0.85 | 0.14 | 532 | 472 | 0.64 | 0.15 |
| ttGGBP17C.2 | R69P, Q152P | A | d | 0.92 | 0.06 | 528 | 462 | 0.88 | 0.73 |
| " | " | B | r(h) | 0.86 | 0.13 | 542 | 476 | 0.64 | 0.36 |
| ttGGBP17C.3 | T16N, D211A | A | d | 0.94 | 0.05 | 519 | 458 | 0.83 | 0.70 |
| " | " | B | r(h) | 0.81 | 0.18 | 540 | 474 | 0.70 | 0.30 |

TABLE 8-continued

Spectral analysis of ttGGBP.17C Acrylodan and Badan conjugates[a].

| Protein | Mutation | Conjugate[b] | | SVD component fractions $C_1$ | $C_2$ | Gaussians Peaks (nm) $S_1$ | $S_2$ | Fraction $f(S_1)$ Apo | Sat |
|---|---|---|---|---|---|---|---|---|---|
| ttGGBP17C.8 | T16N | A | r(h) | 0.93 | 0.07 | 533 | 496 | 0.30 | 0.00 |
| ttGGBP17C.9 | T16S | A | r(h) | 0.94 | 0.06 | 510 | 488 | 1.00 | 0.43 |
| ttGGBP17C.4 | H151Q | A | r(h) | 0.95 | 0.04 | 526 | 485 | 0.65 | 0.52 |
| " | " | B | r(h) | 0.95 | 0.04 | 540 | 486 | 0.50 | 0.39 |
| ttGGBP17C.5 | D15A | A | r(h) | 0.87 | 0.13 | 491 | 465 | 0.98 | 0.22 |
| " | " | B | r(h) | 0.84 | 0.15 | 525 | 470 | 0.58 | 0.16 |
| ttGGBP17C.6 | D15E | A | n | — | — | 511 | 448 | 0.72 | — |
| " | " | B | r(h) | 0.90 | 0.09 | 525 | 473 | 0.39 | 0.15 |
| ttGGBP17C.7 | D15N | A | d | 0.97 | 0.02 | 492 | 464 | 0.86 | 1.00 |
| " | " | B | d | 0.92 | 0.05 | 533 | 480 | 0.22 | 0.16 |
| ttGGBP17C.19 | N258D | A | n | — | — | 525 | 475 | 0.30 | — |
| " | " | B | n | — | — | 523 | — | 1.00 | — |
| ttGGBP17C.20 | N258S | A | d | 0.99 | 0.00 | 530 | 479 | 0.37 | 0.36 |
| " | " | B | n | — | — | 524 | — | 1.00 | — |
| ttGGBP17C.21 | N258A | A | n | — | — | 526 | 475 | 0.33 | — |
| " | " | B | n | — | — | 523 | — | 1.00 | — |
| ttGGBP17C.10 | G20A | A | d | 0.95 | 0.04 | 534 | 487 | 0.28 | 0.21 |
| ttGGBP17C.11 | T240A | A | d | 0.95 | 0.03 | 541 | 487 | 0.35 | 0.25 |
| ttGGBP17C.22 | A260N | A | n | — | — | 528 | 475 | 0.33 | — |
| " | " | B | i | 0.97 | 0.03 | 531 | 480 | 0.96 | 0.85 |
| ttGGBP17C.23 | A260Q | A | i | — | — | 526 | 474 | 0.31 | — |
| " | " | B | i | 0.97 | 0.03 | 532 | 475 | 0.95 | 0.85 |
| ttGGBP17C.24 | A260R | A | n | — | — | 525 | 474 | 0.26 | — |
| " | " | B | i | 0.96 | 0.03 | 523 | 483 | 0.90 | 0.75 |
| ttGGBP17C.25 | A260K | A | n | — | — | 526 | 473 | 0.24 | — |
| " | " | B | i | 0.96 | 0.03 | 519 | 482 | 0.90 | 0.76 |
| ttGGBP17C.26 | A260W | A | i | 0.99 | 0.01 | 530 | 479 | 0.42 | 0.41 |
| " | " | B | r(h) | 0.96 | 0.04 | 529 | 478 | 1.00 | 0.87 |
| ttGGBP17C.27 | A260F | A | n | — | — | 523 | 477 | 0.38 | — |
| " | " | B | i | 0.96 | 0.04 | 529 | 487 | 1.00 | 0.82 |
| ttGGBP17C.28 | A260Y | A | n | — | — | 523 | 477 | 0.38 | — |
| " | " | B | i | 0.97 | 0.03 | 530 | 480 | 1.00 | 0.87 |
| ttGGBP17C.29 | A260S | A | n | — | — | 526 | 474 | 0.32 | — |
| " | " | B | i | 0.96 | 0.03 | 533 | 478 | 0.95 | 0.83 |

[a]Emission spectra determined on Nanodrop3300. SVD analysis according to equations 11-13. Gaussian fits according to equations 14-15.
[b]A, Acrylodan; B, Badan; n, no observed response to glucose; r(h), ratiometric (hypsochromic shift); r(b), ratiometric (bathochromic shift); i, intensity increase only; d, intensity decrease only.

Example 10. Crystal Structure Coordinates for an *E. coli* Glucose-Galactose Binding Protein: ecGGBP183C (Acrylodan Attached to W183C Mutant)

Naming is standard three-letter amino acid code.

Atom positions are provided as Cartesian coordinates, using standard Protein Databank (PDB) format. ATOM records refer to amino acid atoms; HETATM records refer to non-amino acid atoms.

Column 1: record type (ATOM or HETATM); column 2: atom number; column 3 atom name (standard naming scheme for amino acids); column 4: residue name (ATOM records), or component name (HETATM records); column 5: chain identifier (A, B, C, . . . ); column 6: amino acid residue sequence number (ATOM records), or component number (HETATM records); columns 7-9: x,y,z atomic Cartesian positional coordinates; column 10: fractional occupancy (set to 1.0 in this listing); column 11: B-factor (ignored in this listing); column 12: file identifier (ignored in this listing); column 13: line number (same as atom number in this listing).

For heteroatom (HETATM) records, the component name (column 4) is as follows:

| |
|---|
| CA, calcium |
| HOH, Water |
| ACR, Acrylodan |
| K, potassium |
| EDO, ethylene glycol |

| | | | | | | | | | | | | |
|---|---|---|---|---|---|---|---|---|---|---|---|---|
| ATOM | 1 | O | ALA | A | 2 | 106.533 | −15.459 | 75.201 | 1.00 | 0.00 | xxxx | 1 |
| ATOM | 2 | N | ALA | A | 2 | 107.059 | −18.172 | 74.462 | 1.00 | 0.00 | xxxx | 2 |
| ATOM | 3 | CA | ALA | A | 2 | 105.803 | −17.753 | 75.070 | 1.00 | 0.00 | xxxx | 3 |
| ATOM | 4 | C | ALA | A | 2 | 105.616 | −16.243 | 74.951 | 1.00 | 0.00 | xxxx | 4 |
| ATOM | 5 | CB | ALA | A | 2 | 105.744 | −18.181 | 76.527 | 1.00 | 0.00 | xxxx | 5 |
| ATOM | 6 | N | THR | A | 3 | 104.414 | −15.847 | 74.566 | 1.00 | 0.00 | xxxx | 6 |
| ATOM | 7 | CA | THR | A | 3 | 104.079 | −14.441 | 74.397 | 1.00 | 0.00 | xxxx | 7 |
| ATOM | 8 | C | THR | A | 3 | 103.547 | −13.847 | 75.689 | 1.00 | 0.00 | xxxx | 8 |
| ATOM | 9 | O | THR | A | 3 | 102.489 | −14.249 | 76.156 | 1.00 | 0.00 | xxxx | 9 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 10 | CB | THR | A | 3 | 103.023 | −14.268 | 73.301 | 1.00 | 0.00 | xxxx | 10 |
| ATOM | 11 | OG1 | THR | A | 3 | 103.556 | −14.752 | 72.060 | 1.00 | 0.00 | xxxx | 11 |
| ATOM | 12 | CG2 | THR | A | 3 | 102.616 | −12.817 | 73.168 | 1.00 | 0.00 | xxxx | 12 |
| ATOM | 13 | N | ARG | A | 4 | 104.268 | −12.892 | 76.272 | 1.00 | 0.00 | xxxx | 13 |
| ATOM | 14 | CA | ARG | A | 4 | 103.781 | −12.274 | 77.501 | 1.00 | 0.00 | xxxx | 14 |
| ATOM | 15 | C | ARG | A | 4 | 102.892 | −11.082 | 77.169 | 1.00 | 0.00 | xxxx | 15 |
| ATOM | 16 | O | ARG | A | 4 | 103.286 | −10.224 | 76.378 | 1.00 | 0.00 | xxxx | 16 |
| ATOM | 17 | CB | ARG | A | 4 | 104.947 | −11.827 | 78.392 | 1.00 | 0.00 | xxxx | 17 |
| ATOM | 18 | CG | ARG | A | 4 | 105.839 | −12.971 | 78.910 | 1.00 | 0.00 | xxxx | 18 |
| ATOM | 19 | CD | ARG | A | 4 | 106.999 | −12.408 | 79.742 | 1.00 | 0.00 | xxxx | 19 |
| ATOM | 20 | NE | ARG | A | 4 | 107.840 | −13.464 | 80.300 | 1.00 | 0.00 | xxxx | 20 |
| ATOM | 21 | CZ | ARG | A | 4 | 108.891 | −13.259 | 81.091 | 1.00 | 0.00 | xxxx | 21 |
| ATOM | 22 | NH1 | ARG | A | 4 | 109.247 | −12.027 | 81.435 | 1.00 | 0.00 | xxxx | 22 |
| ATOM | 23 | NH2 | ARG | A | 4 | 109.589 | −14.293 | 81.541 | 1.00 | 0.00 | xxxx | 23 |
| ATOM | 24 | N | ILE | A | 5 | 101.699 | −11.040 | 77.760 | 1.00 | 0.00 | xxxx | 24 |
| ATOM | 25 | CA | ILE | A | 5 | 100.798 | −9.892 | 77.638 | 1.00 | 0.00 | xxxx | 25 |
| ATOM | 26 | C | ILE | A | 5 | 100.536 | −9.303 | 79.016 | 1.00 | 0.00 | xxxx | 26 |
| ATOM | 27 | O | ILE | A | 5 | 100.148 | −10.025 | 79.938 | 1.00 | 0.00 | xxxx | 27 |
| ATOM | 28 | CB | ILE | A | 5 | 99.484 | −10.290 | 76.931 | 1.00 | 0.00 | xxxx | 28 |
| ATOM | 29 | CG2 | ILE | A | 5 | 98.491 | −9.115 | 76.932 | 1.00 | 0.00 | xxxx | 29 |
| ATOM | 30 | CG1 | ILE | A | 5 | 99.787 | −10.790 | 75.514 | 1.00 | 0.00 | xxxx | 30 |
| ATOM | 31 | CD1 | ILE | A | 5 | 98.552 | −11.286 | 74.772 | 1.00 | 0.00 | xxxx | 31 |
| ATOM | 32 | N | GLY | A | 6 | 100.775 | −8.001 | 79.158 | 1.00 | 0.00 | xxxx | 32 |
| ATOM | 33 | CA | GLY | A | 6 | 100.613 | −7.324 | 80.436 | 1.00 | 0.00 | xxxx | 33 |
| ATOM | 34 | C | GLY | A | 6 | 99.242 | −6.689 | 80.534 | 1.00 | 0.00 | xxxx | 34 |
| ATOM | 35 | O | GLY | A | 6 | 98.785 | −6.074 | 79.579 | 1.00 | 0.00 | xxxx | 35 |
| ATOM | 36 | N | VAL | A | 7 | 98.583 | −6.847 | 81.678 | 1.00 | 0.00 | xxxx | 36 |
| ATOM | 37 | CA | VAL | A | 7 | 97.232 | −6.313 | 81.871 | 1.00 | 0.00 | xxxx | 37 |
| ATOM | 38 | C | VAL | A | 7 | 97.186 | −5.551 | 83.186 | 1.00 | 0.00 | xxxx | 38 |
| ATOM | 39 | O | VAL | A | 7 | 97.627 | −6.074 | 84.212 | 1.00 | 0.00 | xxxx | 39 |
| ATOM | 40 | CB | VAL | A | 7 | 96.160 | −7.449 | 81.885 | 1.00 | 0.00 | xxxx | 40 |
| ATOM | 41 | CG1 | VAL | A | 7 | 94.781 | −6.891 | 82.114 | 1.00 | 0.00 | xxxx | 41 |
| ATOM | 42 | CG2 | VAL | A | 7 | 96.199 | −8.257 | 80.605 | 1.00 | 0.00 | xxxx | 42 |
| ATOM | 43 | N | THR | A | 8 | 96.645 | −4.333 | 83.183 | 1.00 | 0.00 | xxxx | 43 |
| ATOM | 44 | CA | THR | A | 8 | 96.381 | −3.648 | 84.448 | 1.00 | 0.00 | xxxx | 44 |
| ATOM | 45 | C | THR | A | 8 | 94.872 | −3.426 | 84.569 | 1.00 | 0.00 | xxxx | 45 |
| ATOM | 46 | O | THR | A | 8 | 94.217 | −2.977 | 83.620 | 1.00 | 0.00 | xxxx | 46 |
| ATOM | 47 | CB | THR | A | 8 | 97.147 | −2.294 | 84.570 | 1.00 | 0.00 | xxxx | 47 |
| ATOM | 48 | OG1 | THR | A | 8 | 96.693 | −1.384 | 83.556 | 1.00 | 0.00 | xxxx | 48 |
| ATOM | 49 | CG2 | THR | A | 8 | 98.676 | −2.510 | 84.446 | 1.00 | 0.00 | xxxx | 49 |
| ATOM | 50 | N | ILE | A | 9 | 94.335 | −3.761 | 85.739 | 1.00 | 0.00 | xxxx | 50 |
| ATOM | 51 | CA | ILE | A | 9 | 92.933 | −3.546 | 86.095 | 1.00 | 0.00 | xxxx | 51 |
| ATOM | 52 | C | ILE | A | 9 | 92.893 | −2.377 | 87.059 | 1.00 | 0.00 | xxxx | 52 |
| ATOM | 53 | O | ILE | A | 9 | 93.694 | −2.340 | 87.986 | 1.00 | 0.00 | xxxx | 53 |
| ATOM | 54 | CB | ILE | A | 9 | 92.334 | −4.809 | 86.743 | 1.00 | 0.00 | xxxx | 54 |
| ATOM | 55 | CG1 | ILE | A | 9 | 92.474 | −6.004 | 85.801 | 1.00 | 0.00 | xxxx | 55 |
| ATOM | 56 | CG2 | ILE | A | 9 | 90.886 | −4.563 | 87.149 | 1.00 | 0.00 | xxxx | 56 |
| ATOM | 57 | CD1 | ILE | A | 9 | 91.634 | −5.899 | 84.523 | 1.00 | 0.00 | xxxx | 57 |
| ATOM | 58 | N | TYR | A | 10 | 91.994 | −1.411 | 86.871 | 1.00 | 0.00 | xxxx | 58 |
| ATOM | 59 | CA | TYR | A | 10 | 92.119 | −0.166 | 87.630 | 1.00 | 0.00 | xxxx | 59 |
| ATOM | 60 | C | TYR | A | 10 | 91.894 | −0.426 | 89.119 | 1.00 | 0.00 | xxxx | 60 |
| ATOM | 61 | O | TYR | A | 10 | 92.540 | 0.190 | 89.952 | 1.00 | 0.00 | xxxx | 61 |
| ATOM | 62 | CB | TYR | A | 10 | 91.159 | 0.920 | 87.078 | 1.00 | 0.00 | xxxx | 62 |
| ATOM | 63 | CG | TYR | A | 10 | 89.811 | 1.015 | 87.771 | 1.00 | 0.00 | xxxx | 63 |
| ATOM | 64 | CD1 | TYR | A | 10 | 89.599 | 1.932 | 88.799 | 1.00 | 0.00 | xxxx | 64 |
| ATOM | 65 | CD2 | TYR | A | 10 | 88.745 | 0.201 | 87.388 | 1.00 | 0.00 | xxxx | 65 |
| ATOM | 66 | CE1 | TYR | A | 10 | 88.382 | 2.034 | 89.441 | 1.00 | 0.00 | xxxx | 66 |
| ATOM | 67 | CE2 | TYR | A | 10 | 87.514 | 0.286 | 88.034 | 1.00 | 0.00 | xxxx | 67 |
| ATOM | 68 | CZ | TYR | A | 10 | 87.340 | 1.210 | 89.055 | 1.00 | 0.00 | xxxx | 68 |
| ATOM | 69 | OH | TYR | A | 10 | 86.139 | 1.297 | 89.724 | 1.00 | 0.00 | xxxx | 69 |
| ATOM | 70 | N | LYS | A | 11 | 91.014 | −1.375 | 89.430 | 1.00 | 0.00 | xxxx | 70 |
| ATOM | 71 | CA | LYS | A | 11 | 90.672 | −1.735 | 90.799 | 1.00 | 0.00 | xxxx | 71 |
| ATOM | 72 | C | LYS | A | 11 | 90.059 | −3.128 | 90.779 | 1.00 | 0.00 | xxxx | 72 |
| ATOM | 73 | O | LYS | A | 11 | 88.993 | −3.327 | 90.195 | 1.00 | 0.00 | xxxx | 73 |
| ATOM | 74 | CB | LYS | A | 11 | 89.705 | −0.687 | 91.376 | 1.00 | 0.00 | xxxx | 74 |
| ATOM | 75 | CG | LYS | A | 11 | 88.958 | −1.080 | 92.621 | 1.00 | 0.00 | xxxx | 75 |
| ATOM | 76 | CD | LYS | A | 11 | 88.090 | 0.094 | 93.073 | 1.00 | 0.00 | xxxx | 76 |
| ATOM | 77 | CE | LYS | A | 11 | 87.341 | −0.224 | 94.359 | 1.00 | 0.00 | xxxx | 77 |
| ATOM | 78 | NZ | LYS | A | 11 | 88.210 | −0.910 | 95.353 | 1.00 | 0.00 | xxxx | 78 |
| ATOM | 79 | N | TYR | A | 12 | 90.728 | −4.107 | 91.389 | 1.00 | 0.00 | xxxx | 79 |
| ATOM | 80 | CA | TYR | A | 12 | 90.288 | −5.500 | 91.239 | 1.00 | 0.00 | xxxx | 80 |
| ATOM | 81 | C | TYR | A | 12 | 88.895 | −5.769 | 91.789 | 1.00 | 0.00 | xxxx | 81 |
| ATOM | 82 | O | TYR | A | 12 | 88.194 | −6.643 | 91.273 | 1.00 | 0.00 | xxxx | 82 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 83 | CB | TYR | A | 12 | 91.252 | −6.472 | 91.934 | 1.00 | 0.00 | xxxx | 83 |
| ATOM | 84 | CG | TYR | A | 12 | 92.199 | −7.239 | 91.032 | 1.00 | 0.00 | xxxx | 84 |
| ATOM | 85 | CD1 | TYR | A | 12 | 92.817 | −6.627 | 89.945 | 1.00 | 0.00 | xxxx | 85 |
| ATOM | 86 | CD2 | TYR | A | 12 | 92.527 | −8.558 | 91.317 | 1.00 | 0.00 | xxxx | 86 |
| ATOM | 87 | CE1 | TYR | A | 12 | 93.724 | −7.315 | 89.146 | 1.00 | 0.00 | xxxx | 87 |
| ATOM | 88 | CE2 | TYR | A | 12 | 93.421 | −9.258 | 90.532 | 1.00 | 0.00 | xxxx | 88 |
| ATOM | 89 | CZ | TYR | A | 12 | 94.012 | −8.626 | 89.443 | 1.00 | 0.00 | xxxx | 89 |
| ATOM | 90 | OH | TYR | A | 12 | 94.917 | −9.315 | 88.675 | 1.00 | 0.00 | xxxx | 90 |
| ATOM | 91 | N | ASP | A | 13 | 88.491 | −5.051 | 92.831 | 1.00 | 0.00 | xxxx | 91 |
| ATOM | 92 | CA | ASP | A | 13 | 87.206 | −5.393 | 93.433 | 1.00 | 0.00 | xxxx | 92 |
| ATOM | 93 | C | ASP | A | 13 | 86.059 | −4.494 | 92.973 | 1.00 | 0.00 | xxxx | 93 |
| ATOM | 94 | O | ASP | A | 13 | 84.973 | −4.560 | 93.535 | 1.00 | 0.00 | xxxx | 94 |
| ATOM | 95 | CB | ASP | A | 13 | 87.311 | −5.409 | 94.960 | 1.00 | 0.00 | xxxx | 95 |
| ATOM | 96 | CG | ASP | A | 13 | 87.822 | −4.115 | 95.535 | 1.00 | 0.00 | xxxx | 96 |
| ATOM | 97 | OD1 | ASP | A | 13 | 88.328 | −3.272 | 94.778 | 1.00 | 0.00 | xxxx | 97 |
| ATOM | 98 | OD2 | ASP | A | 13 | 87.738 | −3.962 | 96.775 | 1.00 | 0.00 | xxxx | 98 |
| ATOM | 99 | N | ASP | A | 14 | 86.279 | −3.693 | 91.933 | 1.00 | 0.00 | xxxx | 99 |
| ATOM | 100 | CA | ASP | A | 14 | 85.161 | −3.118 | 91.169 | 1.00 | 0.00 | xxxx | 100 |
| ATOM | 101 | C | ASP | A | 14 | 84.313 | −4.302 | 90.691 | 1.00 | 0.00 | xxxx | 101 |
| ATOM | 102 | O | ASP | A | 14 | 84.858 | −5.221 | 90.091 | 1.00 | 0.00 | xxxx | 102 |
| ATOM | 103 | CB | ASP | A | 14 | 85.698 | −2.279 | 90.001 | 1.00 | 0.00 | xxxx | 103 |
| ATOM | 104 | CG | ASP | A | 14 | 84.601 | −1.711 | 89.124 | 1.00 | 0.00 | xxxx | 104 |
| ATOM | 105 | OD1 | ASP | A | 14 | 84.259 | −0.523 | 89.295 | 1.00 | 0.00 | xxxx | 105 |
| ATOM | 106 | OD2 | ASP | A | 14 | 84.090 | −2.449 | 88.260 | 1.00 | 0.00 | xxxx | 106 |
| ATOM | 107 | N | ASN | A | 15 | 83.007 | −4.316 | 90.980 | 1.00 | 0.00 | xxxx | 107 |
| ATOM | 108 | CA | ASN | A | 15 | 82.192 | −5.510 | 90.688 | 1.00 | 0.00 | xxxx | 108 |
| ATOM | 109 | C | ASN | A | 15 | 82.248 | −5.882 | 89.215 | 1.00 | 0.00 | xxxx | 109 |
| ATOM | 110 | O | ASN | A | 15 | 82.458 | −7.045 | 88.857 | 1.00 | 0.00 | xxxx | 110 |
| ATOM | 111 | CB | ASN | A | 15 | 80.724 | −5.312 | 91.091 | 1.00 | 0.00 | xxxx | 111 |
| ATOM | 112 | CG | ASN | A | 15 | 80.549 | −5.010 | 92.562 | 1.00 | 0.00 | xxxx | 112 |
| ATOM | 113 | OD1 | ASN | A | 15 | 81.029 | −3.996 | 93.054 | 1.00 | 0.00 | xxxx | 113 |
| ATOM | 114 | ND2 | ASN | A | 15 | 79.794 | −5.859 | 93.257 | 1.00 | 0.00 | xxxx | 114 |
| ATOM | 115 | N | PHE | A | 16 | 82.069 | −4.897 | 88.348 | 1.00 | 0.00 | xxxx | 115 |
| ATOM | 116 | CA | PHE | A | 16 | 82.097 | −5.199 | 86.927 | 1.00 | 0.00 | xxxx | 116 |
| ATOM | 117 | C | PHE | A | 16 | 83.483 | −5.634 | 86.450 | 1.00 | 0.00 | xxxx | 117 |
| ATOM | 118 | O | PHE | A | 16 | 83.621 | −6.611 | 85.693 | 1.00 | 0.00 | xxxx | 118 |
| ATOM | 119 | CB | PHE | A | 16 | 81.629 | −3.995 | 86.120 | 1.00 | 0.00 | xxxx | 119 |
| ATOM | 120 | CG | PHE | A | 16 | 81.657 | −4.235 | 84.646 | 1.00 | 0.00 | xxxx | 120 |
| ATOM | 121 | CD1 | PHE | A | 16 | 80.744 | −5.096 | 84.058 | 1.00 | 0.00 | xxxx | 121 |
| ATOM | 122 | CD2 | PHE | A | 16 | 82.608 | −3.621 | 83.856 | 1.00 | 0.00 | xxxx | 122 |
| ATOM | 123 | CE1 | PHE | A | 16 | 80.778 | −5.335 | 82.689 | 1.00 | 0.00 | xxxx | 123 |
| ATOM | 124 | CE2 | PHE | A | 16 | 82.649 | −3.859 | 82.482 | 1.00 | 0.00 | xxxx | 124 |
| ATOM | 125 | CZ | PHE | A | 16 | 81.731 | −4.720 | 81.909 | 1.00 | 0.00 | xxxx | 125 |
| ATOM | 126 | N | MET | A | 17 | 84.521 | −4.922 | 86.876 | 1.00 | 0.00 | xxxx | 126 |
| ATOM | 127 | CA | MET | A | 17 | 85.854 | −5.278 | 86.404 | 1.00 | 0.00 | xxxx | 127 |
| ATOM | 128 | C | MET | A | 17 | 86.328 | −6.622 | 86.968 | 1.00 | 0.00 | xxxx | 128 |
| ATOM | 129 | O | MET | A | 17 | 87.231 | −7.255 | 86.403 | 1.00 | 0.00 | xxxx | 129 |
| ATOM | 130 | CB | MET | A | 17 | 86.862 | −4.169 | 86.715 | 1.00 | 0.00 | xxxx | 130 |
| ATOM | 131 | CG | MET | A | 17 | 86.681 | −2.912 | 85.854 | 1.00 | 0.00 | xxxx | 131 |
| ATOM | 132 | SD | MET | A | 17 | 86.502 | −3.231 | 84.091 | 1.00 | 0.00 | xxxx | 132 |
| ATOM | 133 | CE | MET | A | 17 | 88.089 | −3.976 | 83.741 | 1.00 | 0.00 | xxxx | 133 |
| ATOM | 134 | N | SER | A | 18 | 85.738 | −7.047 | 88.082 | 1.00 | 0.00 | xxxx | 134 |
| ATOM | 135 | CA | SER | A | 18 | 85.999 | −8.383 | 88.605 | 1.00 | 0.00 | xxxx | 135 |
| ATOM | 136 | C | SER | A | 18 | 85.524 | −9.424 | 87.590 | 1.00 | 0.00 | xxxx | 136 |
| ATOM | 137 | O | SER | A | 18 | 86.219 | −10.411 | 87.320 | 1.00 | 0.00 | xxxx | 137 |
| ATOM | 138 | CB | SER | A | 18 | 85.309 | −8.577 | 89.957 | 1.00 | 0.00 | xxxx | 138 |
| ATOM | 139 | OG | SER | A | 18 | 85.592 | −9.854 | 90.498 | 1.00 | 0.00 | xxxx | 139 |
| ATOM | 140 | N | VAL | A | 19 | 84.352 | −9.186 | 87.004 | 1.00 | 0.00 | xxxx | 140 |
| ATOM | 141 | CA | VAL | A | 19 | 83.817 | −10.081 | 85.982 | 1.00 | 0.00 | xxxx | 141 |
| ATOM | 142 | C | VAL | A | 19 | 84.735 | −10.048 | 84.754 | 1.00 | 0.00 | xxxx | 142 |
| ATOM | 143 | O | VAL | A | 19 | 85.083 | −11.091 | 84.201 | 1.00 | 0.00 | xxxx | 143 |
| ATOM | 144 | CB | VAL | A | 19 | 82.362 | −9.716 | 85.597 | 1.00 | 0.00 | xxxx | 144 |
| ATOM | 145 | CG1 | VAL | A | 19 | 81.813 | −10.737 | 84.609 | 1.00 | 0.00 | xxxx | 145 |
| ATOM | 146 | CG2 | VAL | A | 19 | 81.465 | −9.656 | 86.832 | 1.00 | 0.00 | xxxx | 146 |
| ATOM | 147 | N | VAL | A | 20 | 85.130 | −8.851 | 84.331 | 1.00 | 0.00 | xxxx | 147 |
| ATOM | 148 | CA | VAL | A | 20 | 85.985 | −8.708 | 83.147 | 1.00 | 0.00 | xxxx | 148 |
| ATOM | 149 | C | VAL | A | 20 | 87.335 | −9.385 | 83.329 | 1.00 | 0.00 | xxxx | 149 |
| ATOM | 150 | O | VAL | A | 20 | 87.796 | −10.106 | 82.434 | 1.00 | 0.00 | xxxx | 150 |
| ATOM | 151 | CB | VAL | A | 20 | 86.174 | −7.219 | 82.781 | 1.00 | 0.00 | xxxx | 151 |
| ATOM | 152 | CG1 | VAL | A | 20 | 87.190 | −7.051 | 81.650 | 1.00 | 0.00 | xxxx | 152 |
| ATOM | 153 | CG2 | VAL | A | 20 | 84.842 | −6.607 | 82.385 | 1.00 | 0.00 | xxxx | 153 |
| ATOM | 154 | N | ARG | A | 21 | 87.983 | −9.163 | 84.468 | 1.00 | 0.00 | xxxx | 154 |
| ATOM | 155 | CA | ARG | A | 21 | 89.339 | −9.679 | 84.636 | 1.00 | 0.00 | xxxx | 155 |

-continued

| | | | | | | | | | | | |
|---|---|---|---|---|---|---|---|---|---|---|---|
| CA, calcium<br>HOH, Water<br>ACR, Acrylodan<br>K, potassium<br>EDO, ethylene glycol | | | | | | | | | | | |
| ATOM | 156 | C | ARG | A | 21 | 89.329 | −11.196 | 84.697 | 1.00 | 0.00 xxxx | 156 |
| ATOM | 157 | O | ARG | A | 21 | 90.244 | −11.850 | 84.184 | 1.00 | 0.00 xxxx | 157 |
| ATOM | 158 | CB | ARG | A | 21 | 90.007 | −9.074 | 85.875 | 1.00 | 0.00 xxxx | 158 |
| ATOM | 159 | CG | ARG | A | 21 | 89.441 | −9.508 | 87.206 | 1.00 | 0.00 xxxx | 159 |
| ATOM | 160 | CD | ARG | A | 21 | 90.137 | −8.696 | 88.303 | 1.00 | 0.00 xxxx | 160 |
| ATOM | 161 | NE | ARG | A | 21 | 89.427 | −8.720 | 89.582 | 1.00 | 0.00 xxxx | 161 |
| ATOM | 162 | CZ | ARG | A | 21 | 89.481 | −9.725 | 90.450 | 1.00 | 0.00 xxxx | 162 |
| ATOM | 163 | NH1 | ARG | A | 21 | 90.195 | −10.809 | 90.165 | 1.00 | 0.00 xxxx | 163 |
| ATOM | 164 | NH2 | ARG | A | 21 | 88.817 | −9.652 | 91.599 | 1.00 | 0.00 xxxx | 164 |
| ATOM | 165 | N | LYS | A | 22 | 88.279 | −11.766 | 85.280 | 1.00 | 0.00 xxxx | 165 |
| ATOM | 166 | CA | LYS | A | 22 | 88.183 | −13.214 | 85.344 | 1.00 | 0.00 xxxx | 166 |
| ATOM | 167 | C | LYS | A | 22 | 87.954 | −13.790 | 83.955 | 1.00 | 0.00 xxxx | 167 |
| ATOM | 168 | O | LYS | A | 22 | 88.479 | −14.857 | 83.616 | 1.00 | 0.00 xxxx | 168 |
| ATOM | 169 | CB | LYS | A | 22 | 87.079 | −13.628 | 86.315 | 1.00 | 0.00 xxxx | 169 |
| ATOM | 170 | CG | LYS | A | 22 | 87.475 | −13.286 | 87.751 | 1.00 | 0.00 xxxx | 170 |
| ATOM | 171 | CD | LYS | A | 22 | 86.396 | −13.653 | 88.756 | 1.00 | 0.00 xxxx | 171 |
| ATOM | 172 | CE | LYS | A | 22 | 86.756 | −13.110 | 90.132 | 1.00 | 0.00 xxxx | 172 |
| ATOM | 173 | NZ | LYS | A | 22 | 85.780 | −13.518 | 91.180 | 1.00 | 0.00 xxxx | 173 |
| ATOM | 174 | N | ALA | A | 23 | 87.209 | −13.060 | 83.132 | 1.00 | 0.00 xxxx | 174 |
| ATOM | 175 | CA | ALA | A | 23 | 86.967 | −13.508 | 81.769 | 1.00 | 0.00 xxxx | 175 |
| ATOM | 176 | C | ALA | A | 23 | 88.242 | −13.417 | 80.920 | 1.00 | 0.00 xxxx | 176 |
| ATOM | 177 | O | ALA | A | 23 | 88.526 | −14.326 | 80.142 | 1.00 | 0.00 xxxx | 177 |
| ATOM | 178 | CB | ALA | A | 23 | 85.836 | −12.705 | 81.144 | 1.00 | 0.00 xxxx | 178 |
| ATOM | 179 | N | ILE | A | 24 | 89.023 | −12.349 | 81.084 | 1.00 | 0.00 xxxx | 179 |
| ATOM | 180 | CA | ILE | A | 24 | 90.285 | −12.217 | 80.348 | 1.00 | 0.00 xxxx | 180 |
| ATOM | 181 | C | ILE | A | 24 | 91.210 | −13.367 | 80.728 | 1.00 | 0.00 xxxx | 181 |
| ATOM | 182 | O | ILE | A | 24 | 91.874 | −13.963 | 79.873 | 1.00 | 0.00 xxxx | 182 |
| ATOM | 183 | CB | ILE | A | 24 | 90.973 | −10.856 | 80.630 | 1.00 | 0.00 xxxx | 183 |
| ATOM | 184 | CG1 | ILE | A | 24 | 90.144 | −9.700 | 80.088 | 1.00 | 0.00 xxxx | 184 |
| ATOM | 185 | CD1 | ILE | A | 24 | 90.752 | −8.339 | 80.389 | 1.00 | 0.00 xxxx | 185 |
| ATOM | 186 | CG2 | ILE | A | 24 | 92.403 | −10.829 | 80.060 | 1.00 | 0.00 xxxx | 186 |
| ATOM | 187 | N | GLU | A | 25 | 91.258 | −13.684 | 82.019 | 1.00 | 0.00 xxxx | 187 |
| ATOM | 188 | CA | GLU | A | 25 | 92.092 | −14.790 | 82.474 | 1.00 | 0.00 xxxx | 188 |
| ATOM | 189 | C | GLU | A | 25 | 91.698 | −16.104 | 81.797 | 1.00 | 0.00 xxxx | 189 |
| ATOM | 190 | O | GLU | A | 25 | 92.564 | −16.883 | 81.400 | 1.00 | 0.00 xxxx | 190 |
| ATOM | 191 | CB | GLU | A | 25 | 92.012 | −14.942 | 83.990 | 1.00 | 0.00 xxxx | 191 |
| ATOM | 192 | CG | GLU | A | 25 | 93.068 | −15.883 | 84.537 | 1.00 | 0.00 xxxx | 192 |
| ATOM | 193 | CD | GLU | A | 25 | 92.979 | −16.034 | 86.033 | 1.00 | 0.00 xxxx | 193 |
| ATOM | 194 | OE1 | GLU | A | 25 | 92.080 | −16.763 | 86.503 | 1.00 | 0.00 xxxx | 194 |
| ATOM | 195 | OE2 | GLU | A | 25 | 93.794 | −15.401 | 86.738 | 1.00 | 0.00 xxxx | 195 |
| ATOM | 196 | N | GLN | A | 26 | 90.399 | −16.344 | 81.657 | 1.00 | 0.00 xxxx | 196 |
| ATOM | 197 | CA | GLN | A | 26 | 89.935 | −17.567 | 81.007 | 1.00 | 0.00 xxxx | 197 |
| ATOM | 198 | C | GLN | A | 26 | 90.310 | −17.606 | 79.525 | 1.00 | 0.00 xxxx | 198 |
| ATOM | 199 | O | GLN | A | 26 | 90.686 | −18.654 | 79.004 | 1.00 | 0.00 xxxx | 199 |
| ATOM | 200 | CB | GLN | A | 26 | 88.425 | −17.719 | 81.176 | 1.00 | 0.00 xxxx | 200 |
| ATOM | 201 | CG | GLN | A | 26 | 88.009 | −17.965 | 82.613 | 1.00 | 0.00 xxxx | 201 |
| ATOM | 202 | CD | GLN | A | 26 | 88.675 | −19.193 | 83.206 | 1.00 | 0.00 xxxx | 202 |
| ATOM | 203 | OE1 | GLN | A | 26 | 89.258 | −19.136 | 84.288 | 1.00 | 0.00 xxxx | 203 |
| ATOM | 204 | NE2 | GLN | A | 26 | 88.589 | −20.314 | 82.497 | 1.00 | 0.00 xxxx | 204 |
| ATOM | 205 | N | ASP | A | 27 | 90.225 | −16.464 | 78.850 | 1.00 | 0.00 xxxx | 205 |
| ATOM | 206 | CA | ASP | A | 27 | 90.642 | −16.386 | 77.454 | 1.00 | 0.00 xxxx | 206 |
| ATOM | 207 | C | ASP | A | 27 | 92.129 | −16.674 | 77.293 | 1.00 | 0.00 xxxx | 207 |
| ATOM | 208 | O | ASP | A | 27 | 92.544 | −17.394 | 76.367 | 1.00 | 0.00 xxxx | 208 |
| ATOM | 209 | CB | ASP | A | 27 | 90.318 | −15.009 | 76.874 | 1.00 | 0.00 xxxx | 209 |
| ATOM | 210 | CG | ASP | A | 27 | 88.819 | −14.753 | 76.777 | 1.00 | 0.00 xxxx | 210 |
| ATOM | 211 | OD1 | ASP | A | 27 | 88.073 | −15.718 | 76.515 | 1.00 | 0.00 xxxx | 211 |
| ATOM | 212 | OD2 | ASP | A | 27 | 88.386 | −13.591 | 76.968 | 1.00 | 0.00 xxxx | 212 |
| ATOM | 213 | N | ALA | A | 28 | 92.941 | −16.146 | 78.202 | 1.00 | 0.00 xxxx | 213 |
| ATOM | 214 | CA | ALA | A | 28 | 94.386 | −16.360 | 78.126 | 1.00 | 0.00 xxxx | 214 |
| ATOM | 215 | C | ALA | A | 28 | 94.736 | −17.813 | 78.417 | 1.00 | 0.00 xxxx | 215 |
| ATOM | 216 | O | ALA | A | 28 | 95.608 | −18.381 | 77.762 | 1.00 | 0.00 xxxx | 216 |
| ATOM | 217 | CB | ALA | A | 28 | 95.123 | −15.427 | 79.088 | 1.00 | 0.00 xxxx | 217 |
| ATOM | 218 | N | LYS | A | 29 | 94.047 | −18.412 | 79.388 | 1.00 | 0.00 xxxx | 218 |
| ATOM | 219 | CA | LYS | A | 29 | 94.249 | −19.820 | 79.742 | 1.00 | 0.00 xxxx | 219 |
| ATOM | 220 | C | LYS | A | 29 | 94.004 | −20.738 | 78.556 | 1.00 | 0.00 xxxx | 220 |
| ATOM | 221 | O | LYS | A | 29 | 94.648 | −21.784 | 78.416 | 1.00 | 0.00 xxxx | 221 |
| ATOM | 222 | CB | LYS | A | 29 | 93.326 | −20.223 | 80.895 | 1.00 | 0.00 xxxx | 222 |
| ATOM | 223 | CG | LYS | A | 29 | 93.781 | −19.726 | 82.256 | 1.00 | 0.00 xxxx | 223 |
| ATOM | 224 | CD | LYS | A | 29 | 92.810 | −20.153 | 83.347 | 1.00 | 0.00 xxxx | 224 |
| ATOM | 225 | CE | LYS | A | 29 | 93.250 | −19.641 | 84.712 | 1.00 | 0.00 xxxx | 225 |
| ATOM | 226 | NZ | LYS | A | 29 | 94.578 | −20.190 | 85.114 | 1.00 | 0.00 xxxx | 226 |
| ATOM | 227 | N | ALA | A | 30 | 93.067 | −20.343 | 77.703 | 1.00 | 0.00 xxxx | 227 |
| ATOM | 228 | CA | ALA | A | 30 | 92.696 | −21.144 | 76.544 | 1.00 | 0.00 xxxx | 228 |

-continued

| CA, calcium<br>HOH, Water<br>ACR, Acrylodan<br>K, potassium<br>EDO, ethylene glycol | | | | | | | | | | | |
|---|---|---|---|---|---|---|---|---|---|---|---|
| ATOM | 229 | C | ALA | A | 30 | 93.770 | −21.106 | 75.461 | 1.00 | 0.00 xxxx | 229 |
| ATOM | 230 | O | ALA | A | 30 | 93.772 | −21.936 | 74.549 | 1.00 | 0.00 xxxx | 230 |
| ATOM | 231 | CB | ALA | A | 30 | 91.364 | −20.665 | 75.982 | 1.00 | 0.00 xxxx | 231 |
| ATOM | 232 | N | ALA | A | 31 | 94.675 | −20.137 | 75.562 | 1.00 | 0.00 xxxx | 232 |
| ATOM | 233 | CA | ALA | A | 31 | 95.722 | −19.923 | 74.566 | 1.00 | 0.00 xxxx | 233 |
| ATOM | 234 | C | ALA | A | 31 | 97.061 | −20.427 | 75.093 | 1.00 | 0.00 xxxx | 234 |
| ATOM | 235 | O | ALA | A | 31 | 97.695 | −19.760 | 75.905 | 1.00 | 0.00 xxxx | 235 |
| ATOM | 236 | CB | ALA | A | 31 | 95.813 | −18.437 | 74.210 | 1.00 | 0.00 xxxx | 236 |
| ATOM | 237 | N | PRO | A | 32 | 97.511 | −21.593 | 74.622 | 1.00 | 0.00 xxxx | 237 |
| ATOM | 238 | CA | PRO | A | 32 | 98.679 | −22.204 | 75.270 | 1.00 | 0.00 xxxx | 238 |
| ATOM | 239 | C | PRO | A | 32 | 99.986 | −21.419 | 75.097 | 1.00 | 0.00 xxxx | 239 |
| ATOM | 240 | O | PRO | A | 32 | 100.924 | −21.659 | 75.859 | 1.00 | 0.00 xxxx | 240 |
| ATOM | 241 | CB | PRO | A | 32 | 98.775 | −23.576 | 74.592 | 1.00 | 0.00 xxxx | 241 |
| ATOM | 242 | CG | PRO | A | 32 | 98.064 | −23.417 | 73.288 | 1.00 | 0.00 xxxx | 242 |
| ATOM | 243 | CD | PRO | A | 32 | 96.963 | −22.433 | 73.545 | 1.00 | 0.00 xxxx | 243 |
| ATOM | 244 | N | ASP | A | 33 | 100.043 | −20.498 | 74.139 | 1.00 | 0.00 xxxx | 244 |
| ATOM | 245 | CA | ASP | A | 33 | 101.282 | −19.774 | 73.856 | 1.00 | 0.00 xxxx | 245 |
| ATOM | 246 | C | ASP | A | 33 | 101.348 | −18.412 | 74.543 | 1.00 | 0.00 xxxx | 246 |
| ATOM | 247 | O | ASP | A | 33 | 102.256 | −17.629 | 74.271 | 1.00 | 0.00 xxxx | 247 |
| ATOM | 248 | CB | ASP | A | 33 | 101.469 | −19.593 | 72.345 | 1.00 | 0.00 xxxx | 248 |
| ATOM | 249 | CG | ASP | A | 33 | 100.328 | −18.833 | 71.692 | 1.00 | 0.00 xxxx | 249 |
| ATOM | 250 | OD1 | ASP | A | 33 | 99.197 | −18.858 | 72.222 | 1.00 | 0.00 xxxx | 250 |
| ATOM | 251 | OD2 | ASP | A | 33 | 100.564 | −18.214 | 70.629 | 1.00 | 0.00 xxxx | 251 |
| ATOM | 252 | N | VAL | A | 34 | 100.404 | −18.145 | 75.442 | 1.00 | 0.00 xxxx | 252 |
| ATOM | 253 | CA | VAL | A | 34 | 100.292 | −16.842 | 76.101 | 1.00 | 0.00 xxxx | 253 |
| ATOM | 254 | C | VAL | A | 34 | 100.593 | −16.957 | 77.589 | 1.00 | 0.00 xxxx | 254 |
| ATOM | 255 | O | VAL | A | 34 | 100.154 | −17.901 | 78.247 | 1.00 | 0.00 xxxx | 255 |
| ATOM | 256 | CB | VAL | A | 34 | 98.890 | −16.238 | 75.893 | 1.00 | 0.00 xxxx | 256 |
| ATOM | 257 | CG1 | VAL | A | 34 | 98.702 | −14.981 | 76.733 | 1.00 | 0.00 xxxx | 257 |
| ATOM | 258 | CG2 | VAL | A | 34 | 98.670 | −15.936 | 74.435 | 1.00 | 0.00 xxxx | 258 |
| ATOM | 259 | N | GLN | A | 35 | 101.361 | −16.004 | 78.108 | 1.00 | 0.00 xxxx | 259 |
| ATOM | 260 | CA | GLN | A | 35 | 101.497 | −15.833 | 79.544 | 1.00 | 0.00 xxxx | 260 |
| ATOM | 261 | C | GLN | A | 35 | 100.909 | −14.485 | 79.915 | 1.00 | 0.00 xxxx | 261 |
| ATOM | 262 | O | GLN | A | 35 | 101.363 | −13.445 | 79.433 | 1.00 | 0.00 xxxx | 262 |
| ATOM | 263 | CB | GLN | A | 35 | 102.946 | −15.910 | 79.997 | 1.00 | 0.00 xxxx | 263 |
| ATOM | 264 | CG | GLN | A | 35 | 103.098 | −15.718 | 81.497 | 1.00 | 0.00 xxxx | 264 |
| ATOM | 265 | CD | GLN | A | 35 | 104.544 | −15.694 | 81.942 | 1.00 | 0.00 xxxx | 265 |
| ATOM | 266 | OE1 | GLN | A | 35 | 105.461 | −15.777 | 81.125 | 1.00 | 0.00 xxxx | 266 |
| ATOM | 267 | NE2 | GLN | A | 35 | 104.757 | −15.577 | 83.249 | 1.00 | 0.00 xxxx | 267 |
| ATOM | 268 | N | LEU | A | 36 | 99.886 | −14.513 | 80.755 | 1.00 | 0.00 xxxx | 268 |
| ATOM | 269 | CA | LEU | A | 36 | 99.221 | −13.304 | 81.202 | 1.00 | 0.00 xxxx | 269 |
| ATOM | 270 | C | LEU | A | 36 | 99.905 | −12.748 | 82.449 | 1.00 | 0.00 xxxx | 270 |
| ATOM | 271 | O | LEU | A | 36 | 100.128 | −13.494 | 83.396 | 1.00 | 0.00 xxxx | 271 |
| ATOM | 272 | CB | LEU | A | 36 | 97.760 | −13.610 | 81.499 | 1.00 | 0.00 xxxx | 272 |
| ATOM | 273 | CG | LEU | A | 36 | 96.815 | −12.427 | 81.600 | 1.00 | 0.00 xxxx | 273 |
| ATOM | 274 | CD1 | LEU | A | 36 | 96.635 | −11.829 | 80.218 | 1.00 | 0.00 xxxx | 274 |
| ATOM | 275 | CD2 | LEU | A | 36 | 95.484 | −12.898 | 82.173 | 1.00 | 0.00 xxxx | 275 |
| ATOM | 276 | N | LEU | A | 37 | 100.264 | −11.462 | 82.445 | 1.00 | 0.00 xxxx | 276 |
| ATOM | 277 | CA | LEU | A | 37 | 100.825 | −10.832 | 83.641 | 1.00 | 0.00 xxxx | 277 |
| ATOM | 278 | C | LEU | A | 37 | 99.845 | −9.749 | 84.060 | 1.00 | 0.00 xxxx | 278 |
| ATOM | 279 | O | LEU | A | 37 | 99.835 | −8.664 | 83.473 | 1.00 | 0.00 xxxx | 279 |
| ATOM | 280 | CB | LEU | A | 37 | 102.215 | −10.236 | 83.379 | 1.00 | 0.00 xxxx | 280 |
| ATOM | 281 | CG | LEU | A | 37 | 103.399 | −11.161 | 83.055 | 1.00 | 0.00 xxxx | 281 |
| ATOM | 282 | CD1 | LEU | A | 37 | 103.232 | −11.921 | 81.751 | 1.00 | 0.00 xxxx | 282 |
| ATOM | 283 | CD2 | LEU | A | 37 | 104.663 | −10.338 | 82.976 | 1.00 | 0.00 xxxx | 283 |
| ATOM | 284 | N | MET | A | 38 | 99.015 | −10.023 | 85.063 | 1.00 | 0.00 xxxx | 284 |
| ATOM | 285 | CA | MET | A | 38 | 97.926 | −9.095 | 85.382 | 1.00 | 0.00 xxxx | 285 |
| ATOM | 286 | C | MET | A | 38 | 98.051 | −8.491 | 86.779 | 1.00 | 0.00 xxxx | 286 |
| ATOM | 287 | O | MET | A | 38 | 98.323 | −9.194 | 87.751 | 1.00 | 0.00 xxxx | 287 |
| ATOM | 288 | CB | MET | A | 38 | 96.567 | −9.791 | 85.224 | 1.00 | 0.00 xxxx | 288 |
| ATOM | 289 | CG | MET | A | 38 | 95.373 | −8.825 | 85.176 | 1.00 | 0.00 xxxx | 289 |
| ATOM | 290 | SD | MET | A | 38 | 93.881 | −9.536 | 84.433 | 1.00 | 0.00 xxxx | 290 |
| ATOM | 291 | CE | MET | A | 38 | 93.470 | −10.772 | 85.662 | 1.00 | 0.00 xxxx | 291 |
| ATOM | 292 | N | ASN | A | 39 | 97.827 | −7.180 | 86.849 | 1.00 | 0.00 xxxx | 292 |
| ATOM | 293 | CA | ASN | A | 39 | 98.037 | −6.372 | 88.051 | 1.00 | 0.00 xxxx | 293 |
| ATOM | 294 | C | ASN | A | 39 | 96.781 | −5.654 | 88.498 | 1.00 | 0.00 xxxx | 294 |
| ATOM | 295 | O | ASN | A | 39 | 95.965 | −5.230 | 87.672 | 1.00 | 0.00 xxxx | 295 |
| ATOM | 296 | CB | ASN | A | 39 | 99.110 | −5.310 | 87.811 | 1.00 | 0.00 xxxx | 296 |
| ATOM | 297 | CG | ASN | A | 39 | 100.506 | −5.893 | 87.698 | 1.00 | 0.00 xxxx | 297 |
| ATOM | 298 | OD1 | ASN | A | 39 | 101.171 | −5.706 | 86.692 | 1.00 | 0.00 xxxx | 298 |
| ATOM | 299 | ND2 | ASN | A | 39 | 100.961 | −6.585 | 88.746 | 1.00 | 0.00 xxxx | 299 |
| ATOM | 300 | N | ASP | A | 40 | 96.664 | −5.511 | 89.812 | 1.00 | 0.00 xxxx | 300 |
| ATOM | 301 | CA | ASP | A | 40 | 95.672 | −4.650 | 90.460 | 1.00 | 0.00 xxxx | 301 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 302 | C | ASP | A | 40 | 96.287 | −3.286 | 90.729 | 1.00 | 0.00 | xxxx | 302 |
| ATOM | 303 | O | ASP | A | 40 | 97.214 | −3.168 | 91.537 | 1.00 | 0.00 | xxxx | 303 |
| ATOM | 304 | CB | ASP | A | 40 | 95.198 | −5.300 | 91.771 | 1.00 | 0.00 | xxxx | 304 |
| ATOM | 305 | CG | ASP | A | 40 | 94.113 | −4.502 | 92.473 | 1.00 | 0.00 | xxxx | 305 |
| ATOM | 306 | OD1 | ASP | A | 40 | 93.553 | −3.564 | 91.862 | 1.00 | 0.00 | xxxx | 306 |
| ATOM | 307 | OD2 | ASP | A | 40 | 93.809 | −4.848 | 93.635 | 1.00 | 0.00 | xxxx | 307 |
| ATOM | 308 | N | SER | A | 41 | 95.772 | −2.247 | 90.076 | 1.00 | 0.00 | xxxx | 308 |
| ATOM | 309 | CA | SER | A | 41 | 96.320 | −0.910 | 90.271 | 1.00 | 0.00 | xxxx | 309 |
| ATOM | 310 | C | SER | A | 41 | 95.785 | −0.231 | 91.531 | 1.00 | 0.00 | xxxx | 310 |
| ATOM | 311 | O | SER | A | 41 | 96.189 | 0.875 | 91.841 | 1.00 | 0.00 | xxxx | 311 |
| ATOM | 312 | CB | SER | A | 41 | 96.033 | −0.043 | 89.042 | 1.00 | 0.00 | xxxx | 312 |
| ATOM | 313 | OG | SER | A | 41 | 96.652 | −0.624 | 87.893 | 1.00 | 0.00 | xxxx | 313 |
| ATOM | 314 | N | GLN | A | 42 | 94.886 | −0.899 | 92.258 | 1.00 | 0.00 | xxxx | 314 |
| ATOM | 315 | CA | GLN | A | 42 | 94.410 | −0.381 | 93.547 | 1.00 | 0.00 | xxxx | 315 |
| ATOM | 316 | C | GLN | A | 42 | 93.869 | 1.053 | 93.455 | 1.00 | 0.00 | xxxx | 316 |
| ATOM | 317 | O | GLN | A | 42 | 94.044 | 1.857 | 94.371 | 1.00 | 0.00 | xxxx | 317 |
| ATOM | 318 | CB | GLN | A | 42 | 95.537 | −0.455 | 94.588 | 1.00 | 0.00 | xxxx | 318 |
| ATOM | 319 | CG | GLN | A | 42 | 96.023 | −1.898 | 94.793 | 1.00 | 0.00 | xxxx | 319 |
| ATOM | 320 | CD | GLN | A | 42 | 96.973 | −2.066 | 95.967 | 1.00 | 0.00 | xxxx | 320 |
| ATOM | 321 | OE1 | GLN | A | 42 | 97.611 | −1.116 | 96.411 | 1.00 | 0.00 | xxxx | 321 |
| ATOM | 322 | NE2 | GLN | A | 42 | 97.071 | −3.296 | 96.474 | 1.00 | 0.00 | xxxx | 322 |
| ATOM | 323 | N | ASN | A | 43 | 93.207 | 1.350 | 92.336 | 1.00 | 0.00 | xxxx | 323 |
| ATOM | 324 | CA | ASN | A | 43 | 92.564 | 2.646 | 92.099 | 1.00 | 0.00 | xxxx | 324 |
| ATOM | 325 | C | ASN | A | 43 | 93.531 | 3.835 | 92.253 | 1.00 | 0.00 | xxxx | 325 |
| ATOM | 326 | O | ASN | A | 43 | 93.151 | 4.906 | 92.726 | 1.00 | 0.00 | xxxx | 326 |
| ATOM | 327 | CB | ASN | A | 43 | 91.361 | 2.817 | 93.037 | 1.00 | 0.00 | xxxx | 327 |
| ATOM | 328 | CG | ASN | A | 43 | 90.360 | 3.824 | 92.517 | 1.00 | 0.00 | xxxx | 328 |
| ATOM | 329 | OD1 | ASN | A | 43 | 90.301 | 4.088 | 91.319 | 1.00 | 0.00 | xxxx | 329 |
| ATOM | 330 | ND2 | ASN | A | 43 | 89.572 | 4.405 | 93.423 | 1.00 | 0.00 | xxxx | 330 |
| ATOM | 331 | N | ASP | A | 44 | 94.777 | 3.646 | 91.829 | 1.00 | 0.00 | xxxx | 331 |
| ATOM | 332 | CA | ASP | A | 44 | 95.807 | 4.677 | 91.943 | 1.00 | 0.00 | xxxx | 332 |
| ATOM | 333 | C | ASP | A | 44 | 96.592 | 4.708 | 90.630 | 1.00 | 0.00 | xxxx | 333 |
| ATOM | 334 | O | ASP | A | 44 | 97.292 | 3.749 | 90.300 | 1.00 | 0.00 | xxxx | 334 |
| ATOM | 335 | CB | ASP | A | 44 | 96.709 | 4.362 | 93.149 | 1.00 | 0.00 | xxxx | 335 |
| ATOM | 336 | CG | ASP | A | 44 | 97.743 | 5.434 | 93.437 | 1.00 | 0.00 | xxxx | 336 |
| ATOM | 337 | OD1 | ASP | A | 44 | 98.249 | 6.082 | 92.510 | 1.00 | 0.00 | xxxx | 337 |
| ATOM | 338 | OD2 | ASP | A | 44 | 98.075 | 5.609 | 94.631 | 1.00 | 0.00 | xxxx | 338 |
| ATOM | 339 | N | GLN | A | 45 | 96.493 | 5.798 | 89.872 | 1.00 | 0.00 | xxxx | 339 |
| ATOM | 340 | CA | GLN | A | 45 | 97.187 | 5.839 | 88.587 | 1.00 | 0.00 | xxxx | 340 |
| ATOM | 341 | C | GLN | A | 45 | 98.708 | 5.795 | 88.731 | 1.00 | 0.00 | xxxx | 341 |
| ATOM | 342 | O | GLN | A | 45 | 99.393 | 5.237 | 87.860 | 1.00 | 0.00 | xxxx | 342 |
| ATOM | 343 | CB | GLN | A | 45 | 96.780 | 7.085 | 87.788 | 1.00 | 0.00 | xxxx | 343 |
| ATOM | 344 | CG | GLN | A | 45 | 97.318 | 7.082 | 86.362 | 1.00 | 0.00 | xxxx | 344 |
| ATOM | 345 | CD | GLN | A | 45 | 96.752 | 5.928 | 85.546 | 1.00 | 0.00 | xxxx | 345 |
| ATOM | 346 | OE1 | GLN | A | 45 | 95.544 | 5.714 | 85.521 | 1.00 | 0.00 | xxxx | 346 |
| ATOM | 347 | NE2 | GLN | A | 45 | 97.630 | 5.174 | 84.884 | 1.00 | 0.00 | xxxx | 347 |
| ATOM | 348 | N | SER | A | 46 | 99.237 | 6.372 | 89.811 | 1.00 | 0.00 | xxxx | 348 |
| ATOM | 349 | CA | SER | A | 46 | 100.680 | 6.340 | 90.048 | 1.00 | 0.00 | xxxx | 349 |
| ATOM | 350 | C | SER | A | 46 | 101.150 | 4.901 | 90.204 | 1.00 | 0.00 | xxxx | 350 |
| ATOM | 351 | O | SER | A | 46 | 102.185 | 4.522 | 89.662 | 1.00 | 0.00 | xxxx | 351 |
| ATOM | 352 | CB | SER | A | 46 | 101.059 | 7.151 | 91.287 | 1.00 | 0.00 | xxxx | 352 |
| ATOM | 353 | OG | SER | A | 46 | 100.720 | 8.514 | 91.110 | 1.00 | 0.00 | xxxx | 353 |
| ATOM | 354 | N | LYS | A | 47 | 100.378 | 4.093 | 90.931 | 1.00 | 0.00 | xxxx | 354 |
| ATOM | 355 | CA | LYS | A | 47 | 100.684 | 2.667 | 91.039 | 1.00 | 0.00 | xxxx | 355 |
| ATOM | 356 | C | LYS | A | 47 | 100.614 | 1.975 | 89.685 | 1.00 | 0.00 | xxxx | 356 |
| ATOM | 357 | O | LYS | A | 47 | 101.463 | 1.146 | 89.362 | 1.00 | 0.00 | xxxx | 357 |
| ATOM | 358 | CB | LYS | A | 47 | 99.735 | 1.977 | 92.029 | 1.00 | 0.00 | xxxx | 358 |
| ATOM | 359 | CG | LYS | A | 47 | 99.961 | 2.404 | 93.475 | 1.00 | 0.00 | xxxx | 359 |
| ATOM | 360 | CD | LYS | A | 47 | 98.985 | 1.704 | 94.410 | 1.00 | 0.00 | xxxx | 360 |
| ATOM | 361 | CE | LYS | A | 47 | 99.264 | 2.081 | 95.854 | 1.00 | 0.00 | xxxx | 361 |
| ATOM | 362 | NZ | LYS | A | 47 | 98.268 | 1.501 | 96.800 | 1.00 | 0.00 | xxxx | 362 |
| ATOM | 363 | N | GLN | A | 48 | 99.592 | 2.305 | 88.898 | 1.00 | 0.00 | xxxx | 363 |
| ATOM | 364 | CA | GLN | A | 48 | 99.460 | 1.726 | 87.578 | 1.00 | 0.00 | xxxx | 364 |
| ATOM | 365 | C | GLN | A | 48 | 100.663 | 2.079 | 86.686 | 1.00 | 0.00 | xxxx | 365 |
| ATOM | 366 | O | GLN | A | 48 | 101.166 | 1.233 | 85.952 | 1.00 | 0.00 | xxxx | 366 |
| ATOM | 367 | CB | GLN | A | 48 | 98.160 | 2.189 | 86.915 | 1.00 | 0.00 | xxxx | 367 |
| ATOM | 368 | CG | GLN | A | 48 | 97.943 | 1.513 | 85.563 | 1.00 | 0.00 | xxxx | 368 |
| ATOM | 369 | CD | GLN | A | 48 | 96.543 | 1.713 | 85.022 | 1.00 | 0.00 | xxxx | 369 |
| ATOM | 370 | OE1 | GLN | A | 48 | 96.302 | 2.594 | 84.194 | 1.00 | 0.00 | xxxx | 370 |
| ATOM | 371 | NE2 | GLN | A | 48 | 95.611 | 0.888 | 85.477 | 1.00 | 0.00 | xxxx | 371 |
| ATOM | 372 | N | ASN | A | 49 | 101.128 | 3.320 | 86.760 | 1.00 | 0.00 | xxxx | 372 |
| ATOM | 373 | CA | ASN | A | 49 | 102.247 | 3.745 | 85.917 | 1.00 | 0.00 | xxxx | 373 |
| ATOM | 374 | C | ASN | A | 49 | 103.500 | 2.936 | 86.271 | 1.00 | 0.00 | xxxx | 374 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 375 | O | ASN | A | 49 | 104.240 | 2.525 | 85.382 | 1.00 | 0.00 | xxxx | 375 |
| ATOM | 376 | CB | ASN | A | 49 | 102.506 | 5.251 | 86.061 | 1.00 | 0.00 | xxxx | 376 |
| ATOM | 377 | CG | ASN | A | 49 | 101.367 | 6.102 | 85.492 | 1.00 | 0.00 | xxxx | 377 |
| ATOM | 378 | OD1 | ASN | A | 49 | 100.536 | 5.616 | 84.729 | 1.00 | 0.00 | xxxx | 378 |
| ATOM | 379 | ND2 | ASN | A | 49 | 101.333 | 7.379 | 85.870 | 1.00 | 0.00 | xxxx | 379 |
| ATOM | 380 | N | ASP | A | 50 | 103.725 | 2.698 | 87.562 | 1.00 | 0.00 | xxxx | 380 |
| ATOM | 381 | CA | ASP | A | 50 | 104.856 | 1.874 | 87.982 | 1.00 | 0.00 | xxxx | 381 |
| ATOM | 382 | C | ASP | A | 50 | 104.697 | 0.440 | 87.487 | 1.00 | 0.00 | xxxx | 382 |
| ATOM | 383 | O | ASP | A | 50 | 105.672 | −0.216 | 87.089 | 1.00 | 0.00 | xxxx | 383 |
| ATOM | 384 | CB | ASP | A | 50 | 104.998 | 1.875 | 89.502 | 1.00 | 0.00 | xxxx | 384 |
| ATOM | 385 | CG | ASP | A | 50 | 105.413 | 3.222 | 90.053 | 1.00 | 0.00 | xxxx | 385 |
| ATOM | 386 | OD1 | ASP | A | 50 | 105.848 | 4.091 | 89.267 | 1.00 | 0.00 | xxxx | 386 |
| ATOM | 387 | OD2 | ASP | A | 50 | 105.311 | 3.403 | 91.286 | 1.00 | 0.00 | xxxx | 387 |
| ATOM | 388 | N | GLN | A | 51 | 103.464 | −0.055 | 87.526 | 1.00 | 0.00 | xxxx | 388 |
| ATOM | 389 | CA | GLN | A | 51 | 103.189 | −1.410 | 87.060 | 1.00 | 0.00 | xxxx | 389 |
| ATOM | 390 | C | GLN | A | 51 | 103.516 | −1.541 | 85.581 | 1.00 | 0.00 | xxxx | 390 |
| ATOM | 391 | O | GLN | A | 51 | 104.057 | −2.559 | 85.142 | 1.00 | 0.00 | xxxx | 391 |
| ATOM | 392 | CB | GLN | A | 51 | 101.725 | −1.778 | 87.334 | 1.00 | 0.00 | xxxx | 392 |
| ATOM | 393 | CG | GLN | A | 51 | 101.498 | −2.034 | 88.824 | 1.00 | 0.00 | xxxx | 393 |
| ATOM | 394 | CD | GLN | A | 51 | 100.046 | −2.147 | 89.231 | 1.00 | 0.00 | xxxx | 394 |
| ATOM | 395 | OE1 | GLN | A | 51 | 99.148 | −1.628 | 88.557 | 1.00 | 0.00 | xxxx | 395 |
| ATOM | 396 | NE2 | GLN | A | 51 | 99.806 | −2.809 | 90.361 | 1.00 | 0.00 | xxxx | 396 |
| ATOM | 397 | N | ILE | A | 52 | 103.182 | −0.515 | 84.811 | 1.00 | 0.00 | xxxx | 397 |
| ATOM | 398 | CA | ILE | A | 52 | 103.475 | −0.559 | 83.388 | 1.00 | 0.00 | xxxx | 398 |
| ATOM | 399 | C | ILE | A | 52 | 104.991 | −0.557 | 83.135 | 1.00 | 0.00 | xxxx | 399 |
| ATOM | 400 | O | ILE | A | 52 | 105.474 | −1.287 | 82.267 | 1.00 | 0.00 | xxxx | 400 |
| ATOM | 401 | CB | ILE | A | 52 | 102.741 | 0.587 | 82.668 | 1.00 | 0.00 | xxxx | 401 |
| ATOM | 402 | CG1 | ILE | A | 52 | 101.226 | 0.330 | 82.728 | 1.00 | 0.00 | xxxx | 402 |
| ATOM | 403 | CG2 | ILE | A | 52 | 103.220 | 0.723 | 81.220 | 1.00 | 0.00 | xxxx | 403 |
| ATOM | 404 | CD1 | ILE | A | 52 | 100.376 | 1.551 | 82.399 | 1.00 | 0.00 | xxxx | 404 |
| ATOM | 405 | N | ASP | A | 53 | 105.747 | 0.215 | 83.917 | 1.00 | 0.00 | xxxx | 405 |
| ATOM | 406 | CA | ASP | A | 53 | 107.214 | 0.162 | 83.824 | 1.00 | 0.00 | xxxx | 406 |
| ATOM | 407 | C | ASP | A | 53 | 107.728 | −1.266 | 84.031 | 1.00 | 0.00 | xxxx | 407 |
| ATOM | 408 | O | ASP | A | 53 | 108.629 | −1.727 | 83.310 | 1.00 | 0.00 | xxxx | 408 |
| ATOM | 409 | CB | ASP | A | 53 | 107.869 | 1.079 | 84.857 | 1.00 | 0.00 | xxxx | 409 |
| ATOM | 410 | CG | ASP | A | 53 | 107.717 | 2.547 | 84.531 | 1.00 | 0.00 | xxxx | 410 |
| ATOM | 411 | OD1 | ASP | A | 53 | 107.558 | 2.886 | 83.345 | 1.00 | 0.00 | xxxx | 411 |
| ATOM | 412 | OD2 | ASP | A | 53 | 107.786 | 3.365 | 85.474 | 1.00 | 0.00 | xxxx | 412 |
| ATOM | 413 | N | VAL | A | 54 | 107.188 | −1.952 | 85.036 | 1.00 | 0.00 | xxxx | 413 |
| ATOM | 414 | CA | VAL | A | 54 | 107.601 | −3.323 | 85.328 | 1.00 | 0.00 | xxxx | 414 |
| ATOM | 415 | C | VAL | A | 54 | 107.221 | −4.290 | 84.200 | 1.00 | 0.00 | xxxx | 415 |
| ATOM | 416 | O | VAL | A | 54 | 108.024 | −5.137 | 83.808 | 1.00 | 0.00 | xxxx | 416 |
| ATOM | 417 | CB | VAL | A | 54 | 107.011 | −3.791 | 86.677 | 1.00 | 0.00 | xxxx | 417 |
| ATOM | 418 | CG1 | VAL | A | 54 | 107.249 | −5.283 | 86.887 | 1.00 | 0.00 | xxxx | 418 |
| ATOM | 419 | CG2 | VAL | A | 54 | 107.617 | −2.982 | 87.823 | 1.00 | 0.00 | xxxx | 419 |
| ATOM | 420 | N | LEU | A | 55 | 106.011 | −4.156 | 83.664 | 1.00 | 0.00 | xxxx | 420 |
| ATOM | 421 | CA | LEU | A | 55 | 105.582 | −5.031 | 82.577 | 1.00 | 0.00 | xxxx | 421 |
| ATOM | 422 | C | LEU | A | 55 | 106.493 | −4.847 | 81.362 | 1.00 | 0.00 | xxxx | 422 |
| ATOM | 423 | O | LEU | A | 55 | 106.877 | −5.820 | 80.704 | 1.00 | 0.00 | xxxx | 423 |
| ATOM | 424 | CB | LEU | A | 55 | 104.120 | −4.747 | 82.216 | 1.00 | 0.00 | xxxx | 424 |
| ATOM | 425 | CG | LEU | A | 55 | 103.107 | −5.160 | 83.289 | 1.00 | 0.00 | xxxx | 425 |
| ATOM | 426 | CD1 | LEU | A | 55 | 101.717 | −4.586 | 83.008 | 1.00 | 0.00 | xxxx | 426 |
| ATOM | 427 | CD2 | LEU | A | 55 | 103.031 | −6.669 | 83.414 | 1.00 | 0.00 | xxxx | 427 |
| ATOM | 428 | N | LEU | A | 56 | 106.841 | −3.599 | 81.059 | 1.00 | 0.00 | xxxx | 428 |
| ATOM | 429 | CA | LEU | A | 56 | 107.753 | −3.336 | 79.949 | 1.00 | 0.00 | xxxx | 429 |
| ATOM | 430 | C | LEU | A | 56 | 109.150 | −3.903 | 80.226 | 1.00 | 0.00 | xxxx | 430 |
| ATOM | 431 | O | LEU | A | 56 | 109.793 | −4.445 | 79.325 | 1.00 | 0.00 | xxxx | 431 |
| ATOM | 432 | CB | LEU | A | 56 | 107.814 | −1.839 | 79.657 | 1.00 | 0.00 | xxxx | 432 |
| ATOM | 433 | CG | LEU | A | 56 | 106.512 | −1.310 | 79.039 | 1.00 | 0.00 | xxxx | 433 |
| ATOM | 434 | CD1 | LEU | A | 56 | 106.505 | 0.221 | 78.986 | 1.00 | 0.00 | xxxx | 434 |
| ATOM | 435 | CD2 | LEU | A | 56 | 106.269 | −1.906 | 77.650 | 1.00 | 0.00 | xxxx | 435 |
| ATOM | 436 | N | ALA | A | 57 | 109.615 | −3.812 | 81.472 | 1.00 | 0.00 | xxxx | 436 |
| ATOM | 437 | CA | ALA | A | 57 | 110.899 | −4.396 | 81.829 | 1.00 | 0.00 | xxxx | 437 |
| ATOM | 438 | C | ALA | A | 57 | 110.876 | −5.912 | 81.636 | 1.00 | 0.00 | xxxx | 438 |
| ATOM | 439 | O | ALA | A | 57 | 111.914 | −6.521 | 81.319 | 1.00 | 0.00 | xxxx | 439 |
| ATOM | 440 | CB | ALA | A | 57 | 111.272 | −4.039 | 83.279 | 1.00 | 0.00 | xxxx | 440 |
| ATOM | 441 | N | LYS | A | 58 | 109.699 | −6.511 | 81.821 | 1.00 | 0.00 | xxxx | 441 |
| ATOM | 442 | CA | LYS | A | 58 | 109.515 | −7.953 | 81.661 | 1.00 | 0.00 | xxxx | 442 |
| ATOM | 443 | C | LYS | A | 58 | 109.301 | −8.363 | 80.208 | 1.00 | 0.00 | xxxx | 443 |
| ATOM | 444 | O | LYS | A | 58 | 109.065 | −9.536 | 79.919 | 1.00 | 0.00 | xxxx | 444 |
| ATOM | 445 | CB | LYS | A | 58 | 108.349 | −8.439 | 82.523 | 1.00 | 0.00 | xxxx | 445 |
| ATOM | 446 | CG | LYS | A | 58 | 108.644 | −8.364 | 84.017 | 1.00 | 0.00 | xxxx | 446 |
| ATOM | 447 | CD | LYS | A | 58 | 107.485 | −8.852 | 84.854 | 1.00 | 0.00 | xxxx | 447 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 448 | CE | LYS | A | 58 | 107.877 | −8.918 | 86.324 | 1.00 | 0.00 | xxxx | 448 |
| ATOM | 449 | NZ | LYS | A | 58 | 106.777 | −9.443 | 87.171 | 1.00 | 0.00 | xxxx | 449 |
| ATOM | 450 | N | GLY | A | 59 | 109.405 | −7.399 | 79.300 | 1.00 | 0.00 | xxxx | 450 |
| ATOM | 451 | CA | GLY | A | 59 | 109.364 | −7.687 | 77.882 | 1.00 | 0.00 | xxxx | 451 |
| ATOM | 452 | C | GLY | A | 59 | 108.011 | −8.128 | 77.353 | 1.00 | 0.00 | xxxx | 452 |
| ATOM | 453 | O | GLY | A | 59 | 107.951 | −8.956 | 76.442 | 1.00 | 0.00 | xxxx | 453 |
| ATOM | 454 | N | VAL | A | 60 | 106.925 | −7.596 | 77.908 | 1.00 | 0.00 | xxxx | 454 |
| ATOM | 455 | CA | VAL | A | 60 | 105.607 | −7.915 | 77.365 | 1.00 | 0.00 | xxxx | 455 |
| ATOM | 456 | C | VAL | A | 60 | 105.555 | −7.444 | 75.916 | 1.00 | 0.00 | xxxx | 456 |
| ATOM | 457 | O | VAL | A | 60 | 106.153 | −6.430 | 75.552 | 1.00 | 0.00 | xxxx | 457 |
| ATOM | 458 | CB | VAL | A | 60 | 104.460 | −7.298 | 78.184 | 1.00 | 0.00 | xxxx | 458 |
| ATOM | 459 | CG1 | VAL | A | 60 | 104.425 | −7.880 | 79.587 | 1.00 | 0.00 | xxxx | 459 |
| ATOM | 460 | CG2 | VAL | A | 60 | 104.512 | −5.757 | 78.190 | 1.00 | 0.00 | xxxx | 460 |
| ATOM | 461 | N | LYS | A | 61 | 104.831 | −8.195 | 75.093 | 1.00 | 0.00 | xxxx | 461 |
| ATOM | 462 | CA | LYS | A | 61 | 104.708 | −7.860 | 73.679 | 1.00 | 0.00 | xxxx | 462 |
| ATOM | 463 | C | LYS | A | 61 | 103.444 | −7.049 | 73.388 | 1.00 | 0.00 | xxxx | 463 |
| ATOM | 464 | O | LYS | A | 61 | 103.270 | −6.551 | 72.280 | 1.00 | 0.00 | xxxx | 464 |
| ATOM | 465 | CB | LYS | A | 61 | 104.736 | −9.135 | 72.830 | 1.00 | 0.00 | xxxx | 465 |
| ATOM | 466 | CG | LYS | A | 61 | 106.049 | −9.896 | 72.930 | 1.00 | 0.00 | xxxx | 466 |
| ATOM | 467 | CD | LYS | A | 61 | 106.112 | −11.014 | 71.902 | 1.00 | 0.00 | xxxx | 467 |
| ATOM | 468 | CE | LYS | A | 61 | 106.273 | −10.456 | 70.491 | 1.00 | 0.00 | xxxx | 468 |
| ATOM | 469 | NZ | LYS | A | 61 | 106.157 | −11.505 | 69.426 | 1.00 | 0.00 | xxxx | 469 |
| ATOM | 470 | N | ALA | A | 62 | 102.561 | −6.938 | 74.374 | 1.00 | 0.00 | xxxx | 470 |
| ATOM | 471 | CA | ALA | A | 62 | 101.392 | −6.064 | 74.278 | 1.00 | 0.00 | xxxx | 471 |
| ATOM | 472 | C | ALA | A | 62 | 100.930 | −5.706 | 75.670 | 1.00 | 0.00 | xxxx | 472 |
| ATOM | 473 | O | ALA | A | 62 | 101.185 | −6.447 | 76.623 | 1.00 | 0.00 | xxxx | 473 |
| ATOM | 474 | CB | ALA | A | 62 | 100.254 | −6.732 | 73.503 | 1.00 | 0.00 | xxxx | 474 |
| ATOM | 475 | N | LEU | A | 63 | 100.280 | −4.553 | 75.787 | 1.00 | 0.00 | xxxx | 475 |
| ATOM | 476 | CA | LEU | A | 63 | 99.649 | −4.122 | 77.034 | 1.00 | 0.00 | xxxx | 476 |
| ATOM | 477 | C | LEU | A | 63 | 98.146 | −3.994 | 76.833 | 1.00 | 0.00 | xxxx | 477 |
| ATOM | 478 | O | LEU | A | 63 | 97.712 | −3.472 | 75.820 | 1.00 | 0.00 | xxxx | 478 |
| ATOM | 479 | CB | LEU | A | 63 | 100.211 | −2.774 | 77.479 | 1.00 | 0.00 | xxxx | 479 |
| ATOM | 480 | CG | LEU | A | 63 | 101.669 | −2.776 | 77.919 | 1.00 | 0.00 | xxxx | 480 |
| ATOM | 481 | CD1 | LEU | A | 63 | 102.226 | −1.365 | 77.884 | 1.00 | 0.00 | xxxx | 481 |
| ATOM | 482 | CD2 | LEU | A | 63 | 101.797 | −3.368 | 79.321 | 1.00 | 0.00 | xxxx | 482 |
| ATOM | 483 | N | ALA | A | 64 | 97.360 | −4.466 | 77.798 | 1.00 | 0.00 | xxxx | 483 |
| ATOM | 484 | CA | ALA | A | 64 | 95.934 | −4.163 | 77.857 | 1.00 | 0.00 | xxxx | 484 |
| ATOM | 485 | C | ALA | A | 64 | 95.720 | −3.374 | 79.139 | 1.00 | 0.00 | xxxx | 485 |
| ATOM | 486 | O | ALA | A | 64 | 95.967 | −3.887 | 80.233 | 1.00 | 0.00 | xxxx | 486 |
| ATOM | 487 | CB | ALA | A | 64 | 95.091 | −5.442 | 77.841 | 1.00 | 0.00 | xxxx | 487 |
| ATOM | 488 | N | ILE | A | 65 | 95.281 | −2.125 | 79.008 | 1.00 | 0.00 | xxxx | 488 |
| ATOM | 489 | CA | ILE | A | 65 | 95.305 | −1.184 | 80.125 | 1.00 | 0.00 | xxxx | 489 |
| ATOM | 490 | C | ILE | A | 65 | 93.900 | −0.669 | 80.430 | 1.00 | 0.00 | xxxx | 490 |
| ATOM | 491 | O | ILE | A | 65 | 93.240 | −0.078 | 79.579 | 1.00 | 0.00 | xxxx | 491 |
| ATOM | 492 | CB | ILE | A | 65 | 96.250 | 0.003 | 79.819 | 1.00 | 0.00 | xxxx | 492 |
| ATOM | 493 | CG1 | ILE | A | 65 | 97.671 | −0.497 | 79.500 | 1.00 | 0.00 | xxxx | 493 |
| ATOM | 494 | CG2 | ILE | A | 65 | 96.178 | 1.044 | 80.964 | 1.00 | 0.00 | xxxx | 494 |
| ATOM | 495 | CD1 | ILE | A | 65 | 98.341 | −1.250 | 80.648 | 1.00 | 0.00 | xxxx | 495 |
| ATOM | 496 | N | ASN | A | 66 | 93.433 | −0.941 | 81.640 | 1.00 | 0.00 | xxxx | 496 |
| ATOM | 497 | CA | ASN | A | 66 | 92.196 | −0.377 | 82.162 | 1.00 | 0.00 | xxxx | 497 |
| ATOM | 498 | C | ASN | A | 66 | 92.595 | 0.789 | 83.070 | 1.00 | 0.00 | xxxx | 498 |
| ATOM | 499 | O | ASN | A | 66 | 92.954 | 0.574 | 84.227 | 1.00 | 0.00 | xxxx | 499 |
| ATOM | 500 | CB | ASN | A | 66 | 91.427 | −1.500 | 82.892 | 1.00 | 0.00 | xxxx | 500 |
| ATOM | 501 | CG | ASN | A | 66 | 90.188 | −1.022 | 83.635 | 1.00 | 0.00 | xxxx | 501 |
| ATOM | 502 | OD1 | ASN | A | 66 | 89.988 | −1.389 | 84.797 | 1.00 | 0.00 | xxxx | 502 |
| ATOM | 503 | ND2 | ASN | A | 66 | 89.317 | −0.271 | 82.953 | 1.00 | 0.00 | xxxx | 503 |
| ATOM | 504 | N | LEU | A | 67 | 92.595 | 2.007 | 82.519 | 1.00 | 0.00 | xxxx | 504 |
| ATOM | 505 | CA | LEU | A | 67 | 93.111 | 3.187 | 83.213 | 1.00 | 0.00 | xxxx | 505 |
| ATOM | 506 | C | LEU | A | 67 | 92.402 | 3.474 | 84.526 | 1.00 | 0.00 | xxxx | 506 |
| ATOM | 507 | O | LEU | A | 67 | 91.196 | 3.295 | 84.638 | 1.00 | 0.00 | xxxx | 507 |
| ATOM | 508 | CB | LEU | A | 67 | 92.999 | 4.416 | 82.306 | 1.00 | 0.00 | xxxx | 508 |
| ATOM | 509 | CG | LEU | A | 67 | 93.959 | 4.418 | 81.114 | 1.00 | 0.00 | xxxx | 509 |
| ATOM | 510 | CD1 | LEU | A | 67 | 93.473 | 5.426 | 80.071 | 1.00 | 0.00 | xxxx | 510 |
| ATOM | 511 | CD2 | LEU | A | 67 | 95.356 | 4.773 | 81.575 | 1.00 | 0.00 | xxxx | 511 |
| ATOM | 512 | N | VAL | A | 68 | 93.164 | 3.908 | 85.529 | 1.00 | 0.00 | xxxx | 512 |
| ATOM | 513 | CA | VAL | A | 68 | 92.548 | 4.499 | 86.712 | 1.00 | 0.00 | xxxx | 513 |
| ATOM | 514 | C | VAL | A | 68 | 92.007 | 5.883 | 86.328 | 1.00 | 0.00 | xxxx | 514 |
| ATOM | 515 | O | VAL | A | 68 | 90.839 | 6.205 | 86.572 | 1.00 | 0.00 | xxxx | 515 |
| ATOM | 516 | CB | VAL | A | 68 | 93.543 | 4.601 | 87.879 | 1.00 | 0.00 | xxxx | 516 |
| ATOM | 517 | CG1 | VAL | A | 68 | 92.888 | 5.299 | 89.074 | 1.00 | 0.00 | xxxx | 517 |
| ATOM | 518 | CG2 | VAL | A | 68 | 94.045 | 3.214 | 88.276 | 1.00 | 0.00 | xxxx | 518 |
| ATOM | 519 | N | ASP | A | 69 | 92.881 | 6.688 | 85.728 | 1.00 | 0.00 | xxxx | 519 |
| ATOM | 520 | CA | ASP | A | 69 | 92.566 | 8.048 | 85.273 | 1.00 | 0.00 | xxxx | 520 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 521 | C | ASP | A | 69 | 92.653 | 8.091 | 83.749 | 1.00 | 0.00 | xxxx | 521 |
| ATOM | 522 | O | ASP | A | 69 | 93.722 | 7.908 | 83.182 | 1.00 | 0.00 | xxxx | 522 |
| ATOM | 523 | CB | ASP | A | 69 | 93.534 | 9.049 | 85.904 | 1.00 | 0.00 | xxxx | 523 |
| ATOM | 524 | CG | ASP | A | 69 | 93.300 | 10.481 | 85.454 | 1.00 | 0.00 | xxxx | 524 |
| ATOM | 525 | OD1 | ASP | A | 69 | 92.338 | 10.757 | 84.700 | 1.00 | 0.00 | xxxx | 525 |
| ATOM | 526 | OD2 | ASP | A | 69 | 94.096 | 11.344 | 85.886 | 1.00 | 0.00 | xxxx | 526 |
| ATOM | 527 | N | PRO | A | 70 | 91.519 | 8.324 | 83.081 | 1.00 | 0.00 | xxxx | 527 |
| ATOM | 528 | CA | PRO | A | 70 | 91.546 | 8.357 | 81.613 | 1.00 | 0.00 | xxxx | 528 |
| ATOM | 529 | C | PRO | A | 70 | 92.534 | 9.376 | 81.041 | 1.00 | 0.00 | xxxx | 529 |
| ATOM | 530 | O | PRO | A | 70 | 93.051 | 9.184 | 79.938 | 1.00 | 0.00 | xxxx | 530 |
| ATOM | 531 | CB | PRO | A | 70 | 90.108 | 8.731 | 81.247 | 1.00 | 0.00 | xxxx | 531 |
| ATOM | 532 | CG | PRO | A | 70 | 89.289 | 8.251 | 82.394 | 1.00 | 0.00 | xxxx | 532 |
| ATOM | 533 | CD | PRO | A | 70 | 90.154 | 8.424 | 83.624 | 1.00 | 0.00 | xxxx | 533 |
| ATOM | 534 | N | ALA | A | 71 | 92.813 | 10.440 | 81.784 | 1.00 | 0.00 | xxxx | 534 |
| ATOM | 535 | CA | ALA | A | 71 | 93.717 | 11.475 | 81.292 | 1.00 | 0.00 | xxxx | 535 |
| ATOM | 536 | C | ALA | A | 71 | 95.163 | 10.987 | 81.229 | 1.00 | 0.00 | xxxx | 536 |
| ATOM | 537 | O | ALA | A | 71 | 96.015 | 11.647 | 80.638 | 1.00 | 0.00 | xxxx | 537 |
| ATOM | 538 | CB | ALA | A | 71 | 93.618 | 12.724 | 82.166 | 1.00 | 0.00 | xxxx | 538 |
| ATOM | 539 | N | ALA | A | 72 | 95.439 | 9.831 | 81.834 | 1.00 | 0.00 | xxxx | 539 |
| ATOM | 540 | CA | ALA | A | 72 | 96.795 | 9.299 | 81.874 | 1.00 | 0.00 | xxxx | 540 |
| ATOM | 541 | C | ALA | A | 72 | 97.136 | 8.467 | 80.655 | 1.00 | 0.00 | xxxx | 541 |
| ATOM | 542 | O | ALA | A | 72 | 98.216 | 7.874 | 80.598 | 1.00 | 0.00 | xxxx | 542 |
| ATOM | 543 | CB | ALA | A | 72 | 96.998 | 8.462 | 83.127 | 1.00 | 0.00 | xxxx | 543 |
| ATOM | 544 | N | ALA | A | 73 | 96.221 | 8.396 | 79.693 | 1.00 | 0.00 | xxxx | 544 |
| ATOM | 545 | CA | ALA | A | 73 | 96.492 | 7.631 | 78.472 | 1.00 | 0.00 | xxxx | 545 |
| ATOM | 546 | C | ALA | A | 73 | 97.802 | 8.065 | 77.811 | 1.00 | 0.00 | xxxx | 546 |
| ATOM | 547 | O | ALA | A | 73 | 98.565 | 7.229 | 77.328 | 1.00 | 0.00 | xxxx | 547 |
| ATOM | 548 | CB | ALA | A | 73 | 95.333 | 7.765 | 77.492 | 1.00 | 0.00 | xxxx | 548 |
| ATOM | 549 | N | GLY | A | 74 | 98.058 | 9.373 | 77.788 | 1.00 | 0.00 | xxxx | 549 |
| ATOM | 550 | CA | GLY | A | 74 | 99.286 | 9.886 | 77.203 | 1.00 | 0.00 | xxxx | 550 |
| ATOM | 551 | C | GLY | A | 74 | 100.541 | 9.357 | 77.875 | 1.00 | 0.00 | xxxx | 551 |
| ATOM | 552 | O | GLY | A | 74 | 101.514 | 8.988 | 77.214 | 1.00 | 0.00 | xxxx | 552 |
| ATOM | 553 | N | THR | A | 75 | 100.518 | 9.335 | 79.204 | 1.00 | 0.00 | xxxx | 553 |
| ATOM | 554 | CA | THR | A | 75 | 101.631 | 8.825 | 79.990 | 1.00 | 0.00 | xxxx | 554 |
| ATOM | 555 | C | THR | A | 75 | 101.904 | 7.368 | 79.631 | 1.00 | 0.00 | xxxx | 555 |
| ATOM | 556 | O | THR | A | 75 | 103.051 | 6.971 | 79.433 | 1.00 | 0.00 | xxxx | 556 |
| ATOM | 557 | CB | THR | A | 75 | 101.340 | 8.945 | 81.489 | 1.00 | 0.00 | xxxx | 557 |
| ATOM | 558 | OG1 | THR | A | 75 | 101.223 | 10.330 | 81.831 | 1.00 | 0.00 | xxxx | 558 |
| ATOM | 559 | CG2 | THR | A | 75 | 102.458 | 8.299 | 82.317 | 1.00 | 0.00 | xxxx | 559 |
| ATOM | 560 | N | VAL | A | 76 | 100.838 | 6.576 | 79.550 | 1.00 | 0.00 | xxxx | 560 |
| ATOM | 561 | CA | VAL | A | 76 | 100.961 | 5.165 | 79.228 | 1.00 | 0.00 | xxxx | 561 |
| ATOM | 562 | C | VAL | A | 76 | 101.516 | 4.973 | 77.818 | 1.00 | 0.00 | xxxx | 562 |
| ATOM | 563 | O | VAL | A | 76 | 102.418 | 4.160 | 77.598 | 1.00 | 0.00 | xxxx | 563 |
| ATOM | 564 | CB | VAL | A | 76 | 99.600 | 4.457 | 79.384 | 1.00 | 0.00 | xxxx | 564 |
| ATOM | 565 | CG1 | VAL | A | 76 | 99.679 | 3.013 | 78.879 | 1.00 | 0.00 | xxxx | 565 |
| ATOM | 566 | CG2 | VAL | A | 76 | 99.164 | 4.498 | 80.850 | 1.00 | 0.00 | xxxx | 566 |
| ATOM | 567 | N | ILE | A | 77 | 100.990 | 5.747 | 76.874 | 1.00 | 0.00 | xxxx | 567 |
| ATOM | 568 | CA | ILE | A | 77 | 101.426 | 5.663 | 75.477 | 1.00 | 0.00 | xxxx | 568 |
| ATOM | 569 | C | ILE | A | 77 | 102.916 | 5.991 | 75.341 | 1.00 | 0.00 | xxxx | 569 |
| ATOM | 570 | O | ILE | A | 77 | 103.650 | 5.327 | 74.601 | 1.00 | 0.00 | xxxx | 570 |
| ATOM | 571 | CB | ILE | A | 77 | 100.580 | 6.595 | 74.594 | 1.00 | 0.00 | xxxx | 571 |
| ATOM | 572 | CG1 | ILE | A | 77 | 99.207 | 5.972 | 74.345 | 1.00 | 0.00 | xxxx | 572 |
| ATOM | 573 | CG2 | ILE | A | 77 | 101.303 | 6.905 | 73.287 | 1.00 | 0.00 | xxxx | 573 |
| ATOM | 574 | CD1 | ILE | A | 77 | 98.218 | 6.927 | 73.704 | 1.00 | 0.00 | xxxx | 574 |
| ATOM | 575 | N | GLU | A | 78 | 103.371 | 7.007 | 76.065 | 1.00 | 0.00 | xxxx | 575 |
| ATOM | 576 | C | GLU | A | 78 | 105.680 | 6.225 | 76.455 | 1.00 | 0.00 | xxxx | 576 |
| ATOM | 577 | 0 | GLU | A | 78 | 106.718 | 5.967 | 75.839 | 1.00 | 0.00 | xxxx | 577 |
| ATOM | 578 | CA | GLU | A | 78 | 104.781 | 7.389 | 76.018 | 1.00 | 0.00 | xxxx | 578 |
| ATOM | 579 | CB | GLU | A | 78 | 105.029 | 8.620 | 76.899 | 1.00 | 0.00 | xxxx | 579 |
| ATOM | 580 | CG | GLU | A | 78 | 106.383 | 9.281 | 76.690 | 1.00 | 0.00 | xxxx | 580 |
| ATOM | 581 | CD | GLU | A | 78 | 107.463 | 8.732 | 77.605 | 1.00 | 0.00 | xxxx | 581 |
| ATOM | 582 | OE1 | GLU | A | 78 | 107.122 | 8.181 | 78.674 | 1.00 | 0.00 | xxxx | 582 |
| ATOM | 583 | OE2 | GLU | A | 78 | 108.658 | 8.853 | 77.255 | 1.00 | 0.00 | xxxx | 583 |
| ATOM | 584 | N | LYS | A | 79 | 105.275 | 5.512 | 77.504 | 1.00 | 0.00 | xxxx | 584 |
| ATOM | 585 | CA | LYS | A | 79 | 106.071 | 4.387 | 77.979 | 1.00 | 0.00 | xxxx | 585 |
| ATOM | 586 | C | LYS | A | 79 | 106.086 | 3.283 | 76.931 | 1.00 | 0.00 | xxxx | 586 |
| ATOM | 587 | O | LYS | A | 79 | 107.145 | 2.742 | 76.596 | 1.00 | 0.00 | xxxx | 587 |
| ATOM | 588 | CB | LYS | A | 79 | 105.533 | 3.860 | 79.310 | 1.00 | 0.00 | xxxx | 588 |
| ATOM | 589 | CG | LYS | A | 79 | 105.667 | 4.829 | 80.472 | 1.00 | 0.00 | xxxx | 589 |
| ATOM | 590 | CD | LYS | A | 79 | 104.967 | 4.284 | 81.707 | 1.00 | 0.00 | xxxx | 590 |
| ATOM | 591 | CE | LYS | A | 79 | 105.041 | 5.261 | 82.886 | 1.00 | 0.00 | xxxx | 591 |
| ATOM | 592 | NZ | LYS | A | 79 | 106.441 | 5.513 | 83.323 | 1.00 | 0.00 | xxxx | 592 |
| ATOM | 593 | N | ALA | A | 80 | 104.912 | 2.963 | 76.396 | 1.00 | 0.00 | xxxx | 593 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 594 | CA | ALA | A | 80 | 104.798 | 1.881 | 75.427 | 1.00 | 0.00 | xxxx | 594 |
| ATOM | 595 | C | ALA | A | 80 | 105.539 | 2.204 | 74.126 | 1.00 | 0.00 | xxxx | 595 |
| ATOM | 596 | O | ALA | A | 80 | 106.202 | 1.333 | 73.546 | 1.00 | 0.00 | xxxx | 596 |
| ATOM | 597 | CB | ALA | A | 80 | 103.346 | 1.591 | 75.143 | 1.00 | 0.00 | xxxx | 597 |
| ATOM | 598 | O | ARG | A | 81 | 108.081 | 3.246 | 71.373 | 1.00 | 0.00 | xxxx | 598 |
| ATOM | 599 | N | ARG | A | 81 | 105.423 | 3.453 | 73.679 | 1.00 | 0.00 | xxxx | 599 |
| ATOM | 600 | CA | ARG | A | 81 | 106.016 | 3.886 | 72.408 | 1.00 | 0.00 | xxxx | 600 |
| ATOM | 601 | C | ARG | A | 81 | 107.524 | 3.653 | 72.391 | 1.00 | 0.00 | xxxx | 601 |
| ATOM | 602 | CB | ARG | A | 81 | 105.708 | 5.365 | 72.151 | 1.00 | 0.00 | xxxx | 602 |
| ATOM | 603 | CG | ARG | A | 81 | 106.197 | 5.872 | 70.789 | 1.00 | 0.00 | xxxx | 603 |
| ATOM | 604 | CD | ARG | A | 81 | 106.272 | 7.394 | 70.728 | 1.00 | 0.00 | xxxx | 604 |
| ATOM | 605 | NE | ARG | A | 81 | 105.027 | 8.050 | 71.122 | 1.00 | 0.00 | xxxx | 605 |
| ATOM | 606 | CZ | ARG | A | 81 | 104.003 | 8.258 | 70.302 | 1.00 | 0.00 | xxxx | 606 |
| ATOM | 607 | NH1 | ARG | A | 81 | 102.913 | 8.870 | 70.752 | 1.00 | 0.00 | xxxx | 607 |
| ATOM | 608 | NH2 | ARG | A | 81 | 104.058 | 7.843 | 69.041 | 1.00 | 0.00 | xxxx | 608 |
| ATOM | 609 | N | GLY | A | 82 | 108.172 | 3.884 | 73.530 | 1.00 | 0.00 | xxxx | 609 |
| ATOM | 610 | CA | GLY | A | 82 | 109.614 | 3.736 | 73.627 | 1.00 | 0.00 | xxxx | 610 |
| ATOM | 611 | C | GLY | A | 82 | 110.090 | 2.319 | 73.370 | 1.00 | 0.00 | xxxx | 611 |
| ATOM | 612 | O | GLY | A | 82 | 111.231 | 2.085 | 72.969 | 1.00 | 0.00 | xxxx | 612 |
| ATOM | 613 | N | GLN | A | 83 | 109.204 | 1.360 | 73.605 | 1.00 | 0.00 | xxxx | 613 |
| ATOM | 614 | CA | GLN | A | 83 | 109.538 | −0.043 | 73.423 | 1.00 | 0.00 | xxxx | 614 |
| ATOM | 615 | C | GLN | A | 83 | 108.786 | −0.651 | 72.231 | 1.00 | 0.00 | xxxx | 615 |
| ATOM | 616 | O | GLN | A | 83 | 108.819 | −1.862 | 72.010 | 1.00 | 0.00 | xxxx | 616 |
| ATOM | 617 | CB | GLN | A | 83 | 109.222 | −0.811 | 74.710 | 1.00 | 0.00 | xxxx | 617 |
| ATOM | 618 | CG | GLN | A | 83 | 110.081 | −2.042 | 74.937 | 1.00 | 0.00 | xxxx | 618 |
| ATOM | 619 | CD | GLN | A | 83 | 110.165 | −2.422 | 76.404 | 1.00 | 0.00 | xxxx | 619 |
| ATOM | 620 | OE1 | GLN | A | 83 | 110.622 | −1.635 | 77.235 | 1.00 | 0.00 | xxxx | 620 |
| ATOM | 621 | NE2 | GLN | A | 83 | 109.712 | −3.626 | 76.730 | 1.00 | 0.00 | xxxx | 621 |
| ATOM | 622 | N | ASN | A | 84 | 108.101 | 0.202 | 71.474 | 1.00 | 0.00 | xxxx | 622 |
| ATOM | 623 | CA | ASN | A | 84 | 107.310 | −0.224 | 70.321 | 1.00 | 0.00 | xxxx | 623 |
| ATOM | 624 | C | ASN | A | 84 | 106.233 | −1.246 | 70.709 | 1.00 | 0.00 | xxxx | 624 |
| ATOM | 625 | O | ASN | A | 84 | 105.928 | −2.157 | 69.939 | 1.00 | 0.00 | xxxx | 625 |
| ATOM | 626 | CB | ASN | A | 84 | 108.221 | −0.799 | 69.228 | 1.00 | 0.00 | xxxx | 626 |
| ATOM | 627 | CG | ASN | A | 84 | 109.380 | 0.118 | 68.896 | 1.00 | 0.00 | xxxx | 627 |
| ATOM | 628 | OD1 | ASN | A | 84 | 109.186 | 1.296 | 68.588 | 1.00 | 0.00 | xxxx | 628 |
| ATOM | 629 | ND2 | ASN | A | 84 | 110.600 | −0.413 | 68.978 | 1.00 | 0.00 | xxxx | 629 |
| ATOM | 630 | N | VAL | A | 85 | 105.647 | −1.074 | 71.891 | 1.00 | 0.00 | xxxx | 630 |
| ATOM | 631 | CA | VAL | A | 85 | 104.676 | −2.033 | 72.419 | 1.00 | 0.00 | xxxx | 631 |
| ATOM | 632 | C | VAL | A | 85 | 103.254 | −1.525 | 72.172 | 1.00 | 0.00 | xxxx | 632 |
| ATOM | 633 | O | VAL | A | 85 | 102.932 | −0.393 | 72.508 | 1.00 | 0.00 | xxxx | 633 |
| ATOM | 634 | CB | VAL | A | 85 | 104.952 | −2.294 | 73.920 | 1.00 | 0.00 | xxxx | 634 |
| ATOM | 635 | CG1 | VAL | A | 85 | 103.787 | −3.044 | 74.592 | 1.00 | 0.00 | xxxx | 635 |
| ATOM | 636 | CG2 | VAL | A | 85 | 106.258 | −3.072 | 74.068 | 1.00 | 0.00 | xxxx | 636 |
| ATOM | 637 | N | PRO | A | 86 | 102.388 | −2.363 | 71.577 | 1.00 | 0.00 | xxxx | 637 |
| ATOM | 638 | CA | PRO | A | 86 | 101.004 | −1.920 | 71.366 | 1.00 | 0.00 | xxxx | 638 |
| ATOM | 639 | C | PRO | A | 86 | 100.209 | −1.854 | 72.666 | 1.00 | 0.00 | xxxx | 639 |
| ATOM | 640 | O | PRO | A | 86 | 100.501 | −2.592 | 73.621 | 1.00 | 0.00 | xxxx | 640 |
| ATOM | 641 | CB | PRO | A | 86 | 100.421 | −2.989 | 70.437 | 1.00 | 0.00 | xxxx | 641 |
| ATOM | 642 | CG | PRO | A | 86 | 101.291 | −4.205 | 70.660 | 1.00 | 0.00 | xxxx | 642 |
| ATOM | 643 | CD | PRO | A | 86 | 102.672 | −3.668 | 70.951 | 1.00 | 0.00 | xxxx | 643 |
| ATOM | 644 | N | VAL | A | 87 | 99.215 | −0.973 | 72.707 | 1.00 | 0.00 | xxxx | 644 |
| ATOM | 645 | CA | VAL | A | 87 | 98.377 | −0.792 | 73.891 | 1.00 | 0.00 | xxxx | 645 |
| ATOM | 646 | C | VAL | A | 87 | 96.907 | −0.896 | 73.513 | 1.00 | 0.00 | xxxx | 646 |
| ATOM | 647 | O | VAL | A | 87 | 96.432 | −0.123 | 72.687 | 1.00 | 0.00 | xxxx | 647 |
| ATOM | 648 | CB | VAL | A | 87 | 98.626 | 0.567 | 74.572 | 1.00 | 0.00 | xxxx | 648 |
| ATOM | 649 | CG1 | VAL | A | 87 | 97.751 | 0.707 | 75.828 | 1.00 | 0.00 | xxxx | 649 |
| ATOM | 650 | CG2 | VAL | A | 87 | 100.070 | 0.724 | 74.941 | 1.00 | 0.00 | xxxx | 650 |
| ATOM | 651 | N | VAL | A | 88 | 96.192 | −1.820 | 74.149 | 1.00 | 0.00 | xxxx | 651 |
| ATOM | 652 | CA | VAL | A | 88 | 94.740 | −1.888 | 74.015 | 1.00 | 0.00 | xxxx | 652 |
| ATOM | 653 | C | VAL | A | 88 | 94.141 | −1.351 | 75.308 | 1.00 | 0.00 | xxxx | 653 |
| ATOM | 654 | O | VAL | A | 88 | 94.129 | −2.049 | 76.335 | 1.00 | 0.00 | xxxx | 654 |
| ATOM | 655 | CB | VAL | A | 88 | 94.255 | −3.317 | 73.725 | 1.00 | 0.00 | xxxx | 655 |
| ATOM | 656 | CG1 | VAL | A | 88 | 92.734 | −3.331 | 73.544 | 1.00 | 0.00 | xxxx | 656 |
| ATOM | 657 | CG2 | VAL | A | 88 | 94.938 | −3.884 | 72.472 | 1.00 | 0.00 | xxxx | 657 |
| ATOM | 658 | N | PHE | A | 89 | 93.667 | −0.108 | 75.279 | 1.00 | 0.00 | xxxx | 658 |
| ATOM | 659 | CA | PHE | A | 89 | 92.946 | 0.445 | 76.426 | 1.00 | 0.00 | xxxx | 659 |
| ATOM | 660 | C | PHE | A | 89 | 91.574 | −0.204 | 76.508 | 1.00 | 0.00 | xxxx | 660 |
| ATOM | 661 | O | PHE | A | 89 | 90.982 | −0.520 | 75.470 | 1.00 | 0.00 | xxxx | 661 |
| ATOM | 662 | CB | PHE | A | 89 | 92.804 | 1.958 | 76.293 | 1.00 | 0.00 | xxxx | 662 |
| ATOM | 663 | CG | PHE | A | 89 | 94.107 | 2.702 | 76.394 | 1.00 | 0.00 | xxxx | 663 |
| ATOM | 664 | CD1 | PHE | A | 89 | 94.708 | 2.899 | 77.625 | 1.00 | 0.00 | xxxx | 664 |
| ATOM | 665 | CD2 | PHE | A | 89 | 94.734 | 3.190 | 75.259 | 1.00 | 0.00 | xxxx | 665 |
| ATOM | 666 | CE1 | PHE | A | 89 | 95.910 | 3.578 | 77.726 | 1.00 | 0.00 | xxxx | 666 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 667 | CE2 | PHE | A | 89 | 95.936 | 3.879 | 75.355 | 1.00 | 0.00 | xxxx | 667 |
| ATOM | 668 | CZ | PHE | A | 89 | 96.523 | 4.077 | 76.594 | 1.00 | 0.00 | xxxx | 668 |
| ATOM | 669 | N | PHE | A | 90 | 91.048 | −0.413 | 77.712 | 1.00 | 0.00 | xxxx | 669 |
| ATOM | 670 | CA | PHE | A | 90 | 89.680 | −0.944 | 77.785 | 1.00 | 0.00 | xxxx | 670 |
| ATOM | 671 | C | PHE | A | 90 | 88.926 | −0.412 | 78.992 | 1.00 | 0.00 | xxxx | 671 |
| ATOM | 672 | O | PHE | A | 90 | 89.525 | −0.062 | 80.010 | 1.00 | 0.00 | xxxx | 672 |
| ATOM | 673 | CB | PHE | A | 90 | 89.660 | −2.510 | 77.730 | 1.00 | 0.00 | xxxx | 673 |
| ATOM | 674 | CG | PHE | A | 90 | 90.339 | −3.225 | 78.894 | 1.00 | 0.00 | xxxx | 674 |
| ATOM | 675 | CD1 | PHE | A | 90 | 89.573 | −3.927 | 79.824 | 1.00 | 0.00 | xxxx | 675 |
| ATOM | 676 | CD2 | PHE | A | 90 | 91.729 | −3.261 | 79.015 | 1.00 | 0.00 | xxxx | 676 |
| ATOM | 677 | CE1 | PHE | A | 90 | 90.184 | −4.611 | 80.886 | 1.00 | 0.00 | xxxx | 677 |
| ATOM | 678 | CE2 | PHE | A | 90 | 92.349 | −3.934 | 80.071 | 1.00 | 0.00 | xxxx | 678 |
| ATOM | 679 | CZ | PHE | A | 90 | 91.574 | −4.614 | 81.001 | 1.00 | 0.00 | xxxx | 679 |
| ATOM | 680 | N | ASN | A | 91 | 87.616 | −0.279 | 78.791 | 1.00 | 0.00 | xxxx | 680 |
| ATOM | 681 | CA | ASN | A | 91 | 86.590 | 0.085 | 79.786 | 1.00 | 0.00 | xxxx | 681 |
| ATOM | 682 | C | ASN | A | 91 | 86.587 | 1.542 | 80.258 | 1.00 | 0.00 | xxxx | 682 |
| ATOM | 683 | O | ASN | A | 91 | 85.510 | 2.087 | 80.492 | 1.00 | 0.00 | xxxx | 683 |
| ATOM | 684 | CB | ASN | A | 91 | 86.660 | −0.854 | 80.998 | 1.00 | 0.00 | xxxx | 684 |
| ATOM | 685 | CG | ASN | A | 91 | 85.830 | −0.351 | 82.182 | 1.00 | 0.00 | xxxx | 685 |
| ATOM | 686 | OD1 | ASN | A | 91 | 86.370 | 0.228 | 83.120 | 1.00 | 0.00 | xxxx | 686 |
| ATOM | 687 | ND2 | ASN | A | 91 | 84.522 | −0.592 | 82.147 | 1.00 | 0.00 | xxxx | 687 |
| ATOM | 688 | N | LYS | A | 92 | 87.752 | 2.160 | 80.423 | 1.00 | 0.00 | xxxx | 688 |
| ATOM | 689 | CA | LYS | A | 92 | 87.828 | 3.594 | 80.690 | 1.00 | 0.00 | xxxx | 689 |
| ATOM | 690 | C | LYS | A | 92 | 88.391 | 4.250 | 79.446 | 1.00 | 0.00 | xxxx | 690 |
| ATOM | 691 | O | LYS | A | 92 | 89.554 | 4.061 | 79.097 | 1.00 | 0.00 | xxxx | 691 |
| ATOM | 692 | CB | LYS | A | 92 | 88.682 | 3.903 | 81.918 | 1.00 | 0.00 | xxxx | 692 |
| ATOM | 693 | CG | LYS | A | 92 | 88.035 | 3.444 | 83.217 | 1.00 | 0.00 | xxxx | 693 |
| ATOM | 694 | CD | LYS | A | 92 | 88.252 | 4.447 | 84.327 | 1.00 | 0.00 | xxxx | 694 |
| ATOM | 695 | CE | LYS | A | 92 | 88.017 | 3.795 | 85.679 | 1.00 | 0.00 | xxxx | 695 |
| ATOM | 696 | NZ | LYS | A | 92 | 88.338 | 4.731 | 86.803 | 1.00 | 0.00 | xxxx | 696 |
| ATOM | 697 | N | GLU | A | 93 | 87.546 | 5.014 | 78.770 | 1.00 | 0.00 | xxxx | 697 |
| ATOM | 698 | CA | GLU | A | 93 | 87.872 | 5.464 | 77.422 | 1.00 | 0.00 | xxxx | 698 |
| ATOM | 699 | C | GLU | A | 93 | 88.806 | 6.685 | 77.393 | 1.00 | 0.00 | xxxx | 699 |
| ATOM | 700 | O | GLU | A | 93 | 88.495 | 7.729 | 77.986 | 1.00 | 0.00 | xxxx | 700 |
| ATOM | 701 | CB | GLU | A | 93 | 86.585 | 5.765 | 76.656 | 1.00 | 0.00 | xxxx | 701 |
| ATOM | 702 | CG | GLU | A | 93 | 86.840 | 6.151 | 75.212 | 1.00 | 0.00 | xxxx | 702 |
| ATOM | 703 | CD | GLU | A | 93 | 85.572 | 6.254 | 74.396 | 1.00 | 0.00 | xxxx | 703 |
| ATOM | 704 | OE1 | GLU | A | 93 | 84.503 | 5.840 | 74.887 | 1.00 | 0.00 | xxxx | 704 |
| ATOM | 705 | OE2 | GLU | A | 93 | 85.652 | 6.749 | 73.252 | 1.00 | 0.00 | xxxx | 705 |
| ATOM | 706 | N | PRO | A | 94 | 89.950 | 6.563 | 76.701 | 1.00 | 0.00 | xxxx | 706 |
| ATOM | 707 | CA | PRO | A | 94 | 90.860 | 7.705 | 76.521 | 1.00 | 0.00 | xxxx | 707 |
| ATOM | 708 | C | PRO | A | 94 | 90.311 | 8.706 | 75.520 | 1.00 | 0.00 | xxxx | 708 |
| ATOM | 709 | O | PRO | A | 94 | 89.374 | 8.385 | 74.787 | 1.00 | 0.00 | xxxx | 709 |
| ATOM | 710 | CB | PRO | A | 94 | 92.143 | 7.073 | 75.966 | 1.00 | 0.00 | xxxx | 710 |
| ATOM | 711 | CG | PRO | A | 94 | 91.946 | 5.593 | 76.036 | 1.00 | 0.00 | xxxx | 711 |
| ATOM | 712 | CD | PRO | A | 94 | 90.473 | 5.342 | 76.071 | 1.00 | 0.00 | xxxx | 712 |
| ATOM | 713 | N | SER | A | 95 | 90.901 | 9.897 | 75.465 | 1.00 | 0.00 | xxxx | 713 |
| ATOM | 714 | CA | SER | A | 95 | 90.489 | 10.879 | 74.474 | 1.00 | 0.00 | xxxx | 714 |
| ATOM | 715 | C | SER | A | 95 | 90.814 | 10.412 | 73.058 | 1.00 | 0.00 | xxxx | 715 |
| ATOM | 716 | O | SER | A | 95 | 91.716 | 9.616 | 72.837 | 1.00 | 0.00 | xxxx | 716 |
| ATOM | 717 | CB | SER | A | 95 | 91.157 | 12.234 | 74.741 | 1.00 | 0.00 | xxxx | 717 |
| ATOM | 718 | OG | SER | A | 95 | 92.546 | 12.172 | 74.450 | 1.00 | 0.00 | xxxx | 718 |
| ATOM | 719 | N | ARG | A | 96 | 90.052 | 10.923 | 72.100 | 1.00 | 0.00 | xxxx | 719 |
| ATOM | 720 | CA | ARG | A | 96 | 90.334 | 10.701 | 70.685 | 1.00 | 0.00 | xxxx | 720 |
| ATOM | 721 | C | ARG | A | 96 | 91.758 | 11.141 | 70.337 | 1.00 | 0.00 | xxxx | 721 |
| ATOM | 722 | O | ARG | A | 96 | 92.484 | 10.443 | 69.625 | 1.00 | 0.00 | xxxx | 722 |
| ATOM | 723 | CB | ARG | A | 96 | 89.310 | 11.451 | 69.839 | 1.00 | 0.00 | xxxx | 723 |
| ATOM | 724 | CG | ARG | A | 96 | 89.369 | 11.185 | 68.347 | 1.00 | 0.00 | xxxx | 724 |
| ATOM | 725 | CD | ARG | A | 96 | 88.887 | 9.781 | 68.062 | 1.00 | 0.00 | xxxx | 725 |
| ATOM | 726 | NE | ARG | A | 96 | 89.980 | 8.914 | 67.664 | 1.00 | 0.00 | xxxx | 726 |
| ATOM | 727 | CZ | ARG | A | 96 | 89.860 | 7.604 | 67.479 | 1.00 | 0.00 | xxxx | 727 |
| ATOM | 728 | NH1 | ARG | A | 96 | 88.689 | 7.005 | 67.678 | 1.00 | 0.00 | xxxx | 728 |
| ATOM | 729 | NH2 | ARG | A | 96 | 90.914 | 6.900 | 67.099 | 1.00 | 0.00 | xxxx | 729 |
| ATOM | 730 | N | LYS | A | 97 | 92.165 | 12.301 | 70.845 | 1.00 | 0.00 | xxxx | 730 |
| ATOM | 731 | CA | LYS | A | 97 | 93.506 | 12.809 | 70.578 | 1.00 | 0.00 | xxxx | 731 |
| ATOM | 732 | C | LYS | A | 97 | 94.572 | 11.850 | 71.084 | 1.00 | 0.00 | xxxx | 732 |
| ATOM | 733 | O | LYS | A | 97 | 95.597 | 11.648 | 70.428 | 1.00 | 0.00 | xxxx | 733 |
| ATOM | 734 | CB | LYS | A | 97 | 93.707 | 14.180 | 71.227 | 1.00 | 0.00 | xxxx | 734 |
| ATOM | 735 | CG | LYS | A | 97 | 92.951 | 15.304 | 70.545 | 1.00 | 0.00 | xxxx | 735 |
| ATOM | 736 | CD | LYS | A | 97 | 93.178 | 16.635 | 71.271 | 1.00 | 0.00 | xxxx | 736 |
| ATOM | 737 | CE | LYS | A | 97 | 92.407 | 17.759 | 70.595 | 1.00 | 0.00 | xxxx | 737 |
| ATOM | 738 | NZ | LYS | A | 97 | 92.712 | 19.098 | 71.206 | 1.00 | 0.00 | xxxx | 738 |
| ATOM | 739 | N | ALA | A | 98 | 94.344 | 11.277 | 72.264 | 1.00 | 0.00 | xxxx | 739 |

-continued

| | | | | | | | | | | | |
|---|---|---|---|---|---|---|---|---|---|---|---|
| CA, calcium<br>HOH, Water<br>ACR, Acrylodan<br>K, potassium<br>EDO, ethylene glycol | | | | | | | | | | | |
| ATOM | 740 | CA | ALA | A | 98 | 95.304 | 10.315 | 72.803 | 1.00 | 0.00 xxxx | 740 |
| ATOM | 741 | C | ALA | A | 98 | 95.394 | 9.077 | 71.917 | 1.00 | 0.00 xxxx | 741 |
| ATOM | 742 | O | ALA | A | 98 | 96.488 | 8.650 | 71.553 | 1.00 | 0.00 xxxx | 742 |
| ATOM | 743 | CB | ALA | A | 98 | 94.942 | 9.925 | 74.237 | 1.00 | 0.00 xxxx | 743 |
| ATOM | 744 | N | LEU | A | 99 | 94.246 | 8.518 | 71.551 | 1.00 | 0.00 xxxx | 744 |
| ATOM | 745 | CA | LEU | A | 99 | 94.233 | 7.346 | 70.673 | 1.00 | 0.00 xxxx | 745 |
| ATOM | 746 | C | LEU | A | 99 | 94.941 | 7.608 | 69.346 | 1.00 | 0.00 xxxx | 746 |
| ATOM | 747 | O | LEU | A | 99 | 95.665 | 6.754 | 68.837 | 1.00 | 0.00 xxxx | 747 |
| ATOM | 748 | CB | LEU | A | 99 | 92.801 | 6.895 | 70.397 | 1.00 | 0.00 xxxx | 748 |
| ATOM | 749 | CG | LEU | A | 99 | 92.063 | 6.297 | 71.584 | 1.00 | 0.00 xxxx | 749 |
| ATOM | 750 | CD1 | LEU | A | 99 | 90.656 | 5.872 | 71.158 | 1.00 | 0.00 xxxx | 750 |
| ATOM | 751 | CD2 | LEU | A | 99 | 92.829 | 5.105 | 72.167 | 1.00 | 0.00 xxxx | 751 |
| ATOM | 752 | N | ASP | A | 100 | 94.725 | 8.790 | 68.779 | 1.00 | 0.00 xxxx | 752 |
| ATOM | 753 | CA | ASP | A | 100 | 95.310 | 9.129 | 67.489 | 1.00 | 0.00 xxxx | 753 |
| ATOM | 754 | C | ASP | A | 100 | 96.808 | 9.421 | 67.547 | 1.00 | 0.00 xxxx | 754 |
| ATOM | 755 | O | ASP | A | 100 | 97.473 | 9.473 | 66.508 | 1.00 | 0.00 xxxx | 755 |
| ATOM | 756 | CB | ASP | A | 100 | 94.579 | 10.332 | 66.887 | 1.00 | 0.00 xxxx | 756 |
| ATOM | 757 | CG | ASP | A | 100 | 93.189 | 9.971 | 66.389 | 1.00 | 0.00 xxxx | 757 |
| ATOM | 758 | OD1 | ASP | A | 100 | 92.927 | 8.762 | 66.198 | 1.00 | 0.00 xxxx | 758 |
| ATOM | 759 | OD2 | ASP | A | 100 | 92.362 | 10.887 | 66.199 | 1.00 | 0.00 xxxx | 759 |
| ATOM | 760 | N | SER | A | 101 | 97.343 | 9.599 | 68.750 | 1.00 | 0.00 xxxx | 760 |
| ATOM | 761 | CA | SER | A | 101 | 98.739 | 9.990 | 68.902 | 1.00 | 0.00 xxxx | 761 |
| ATOM | 762 | C | SER | A | 101 | 99.714 | 8.818 | 68.752 | 1.00 | 0.00 xxxx | 762 |
| ATOM | 763 | O | SER | A | 101 | 100.925 | 9.023 | 68.654 | 1.00 | 0.00 xxxx | 763 |
| ATOM | 764 | CB | SER | A | 101 | 98.958 | 10.666 | 70.263 | 1.00 | 0.00 xxxx | 764 |
| ATOM | 765 | OG | SER | A | 101 | 98.904 | 9.725 | 71.329 | 1.00 | 0.00 xxxx | 765 |
| ATOM | 766 | N | TYR | A | 102 | 99.187 | 7.595 | 68.740 | 1.00 | 0.00 xxxx | 766 |
| ATOM | 767 | CA | TYR | A | 102 | 100.022 | 6.395 | 68.694 | 1.00 | 0.00 xxxx | 767 |
| ATOM | 768 | C | TYR | A | 102 | 99.397 | 5.398 | 67.737 | 1.00 | 0.00 xxxx | 768 |
| ATOM | 769 | O | TYR | A | 102 | 98.228 | 5.037 | 67.906 | 1.00 | 0.00 xxxx | 769 |
| ATOM | 770 | CB | TYR | A | 102 | 100.154 | 5.792 | 70.096 | 1.00 | 0.00 xxxx | 770 |
| ATOM | 771 | CG | TYR | A | 102 | 101.138 | 4.640 | 70.265 | 1.00 | 0.00 xxxx | 771 |
| ATOM | 772 | CD1 | TYR | A | 102 | 100.853 | 3.593 | 71.138 | 1.00 | 0.00 xxxx | 772 |
| ATOM | 773 | CD2 | TYR | A | 102 | 102.352 | 4.614 | 69.596 | 1.00 | 0.00 xxxx | 773 |
| ATOM | 774 | CE1 | TYR | A | 102 | 101.740 | 2.541 | 71.330 | 1.00 | 0.00 xxxx | 774 |
| ATOM | 775 | CE2 | TYR | A | 102 | 103.260 | 3.563 | 69.780 | 1.00 | 0.00 xxxx | 775 |
| ATOM | 776 | CZ | TYR | A | 102 | 102.941 | 2.531 | 70.660 | 1.00 | 0.00 xxxx | 776 |
| ATOM | 777 | OH | TYR | A | 102 | 103.832 | 1.493 | 70.862 | 1.00 | 0.00 xxxx | 777 |
| ATOM | 778 | N | ASP | A | 103 | 100.165 | 4.951 | 66.739 | 1.00 | 0.00 xxxx | 778 |
| ATOM | 779 | CA | ASP | A | 103 | 99.602 | 4.085 | 65.707 | 1.00 | 0.00 xxxx | 779 |
| ATOM | 780 | C | ASP | A | 103 | 99.207 | 2.719 | 66.273 | 1.00 | 0.00 xxxx | 780 |
| ATOM | 781 | O | ASP | A | 103 | 98.417 | 2.008 | 65.670 | 1.00 | 0.00 xxxx | 781 |
| ATOM | 782 | CB | ASP | A | 103 | 100.573 | 3.912 | 64.519 | 1.00 | 0.00 xxxx | 782 |
| ATOM | 783 | CG | ASP | A | 103 | 101.943 | 3.400 | 64.934 | 1.00 | 0.00 xxxx | 783 |
| ATOM | 784 | OD1 | ASP | A | 103 | 102.138 | 3.062 | 66.120 | 1.00 | 0.00 xxxx | 784 |
| ATOM | 785 | OD2 | ASP | A | 103 | 102.834 | 3.328 | 64.057 | 1.00 | 0.00 xxxx | 785 |
| ATOM | 786 | N | LYS | A | 104 | 99.732 | 2.361 | 67.440 | 1.00 | 0.00 xxxx | 786 |
| ATOM | 787 | CA | LYS | A | 104 | 99.415 | 1.066 | 68.020 | 1.00 | 0.00 xxxx | 787 |
| ATOM | 788 | C | LYS | A | 104 | 98.553 | 1.168 | 69.286 | 1.00 | 0.00 xxxx | 788 |
| ATOM | 789 | O | LYS | A | 104 | 98.544 | 0.235 | 70.094 | 1.00 | 0.00 xxxx | 789 |
| ATOM | 790 | CB | LYS | A | 104 | 100.710 | 0.295 | 68.321 | 1.00 | 0.00 xxxx | 790 |
| ATOM | 791 | CG | LYS | A | 104 | 101.487 | −0.125 | 67.063 | 1.00 | 0.00 xxxx | 791 |
| ATOM | 792 | CD | LYS | A | 104 | 102.803 | −0.812 | 67.409 | 1.00 | 0.00 xxxx | 792 |
| ATOM | 793 | CE | LYS | A | 104 | 103.833 | 0.175 | 67.931 | 1.00 | 0.00 xxxx | 793 |
| ATOM | 794 | NZ | LYS | A | 104 | 104.492 | 0.950 | 66.837 | 1.00 | 0.00 xxxx | 794 |
| ATOM | 795 | N | ALA | A | 105 | 97.822 | 2.277 | 69.446 | 1.00 | 0.00 xxxx | 795 |
| ATOM | 796 | CA | ALA | A | 105 | 96.825 | 2.410 | 70.515 | 1.00 | 0.00 xxxx | 796 |
| ATOM | 797 | C | ALA | A | 105 | 95.419 | 2.078 | 70.019 | 1.00 | 0.00 xxxx | 797 |
| ATOM | 798 | O | ALA | A | 105 | 95.012 | 2.542 | 68.957 | 1.00 | 0.00 xxxx | 798 |
| ATOM | 799 | CB | ALA | A | 105 | 96.852 | 3.822 | 71.107 | 1.00 | 0.00 xxxx | 799 |
| ATOM | 800 | N | TYR | A | 106 | 94.685 | 1.279 | 70.797 | 1.00 | 0.00 xxxx | 800 |
| ATOM | 801 | CA | TYR | A | 106 | 93.312 | 0.880 | 70.483 | 1.00 | 0.00 xxxx | 801 |
| ATOM | 802 | C | TYR | A | 106 | 92.440 | 1.016 | 71.729 | 1.00 | 0.00 xxxx | 802 |
| ATOM | 803 | O | TYR | A | 106 | 92.966 | 1.198 | 72.826 | 1.00 | 0.00 xxxx | 803 |
| ATOM | 804 | CB | TYR | A | 106 | 93.268 | −0.567 | 69.975 | 1.00 | 0.00 xxxx | 804 |
| ATOM | 805 | CG | TYR | A | 106 | 93.943 | −0.752 | 68.640 | 1.00 | 0.00 xxxx | 805 |
| ATOM | 806 | CD1 | TYR | A | 106 | 93.197 | −0.796 | 67.479 | 1.00 | 0.00 xxxx | 806 |
| ATOM | 807 | CD2 | TYR | A | 106 | 95.323 | −0.852 | 68.546 | 1.00 | 0.00 xxxx | 807 |
| ATOM | 808 | CE1 | TYR | A | 106 | 93.807 | −0.942 | 66.245 | 1.00 | 0.00 xxxx | 808 |
| ATOM | 809 | CE2 | TYR | A | 106 | 95.945 | −1.003 | 67.320 | 1.00 | 0.00 xxxx | 809 |
| ATOM | 810 | CZ | TYR | A | 106 | 95.180 | −1.045 | 66.181 | 1.00 | 0.00 xxxx | 810 |
| ATOM | 811 | OH | TYR | A | 106 | 95.776 | −1.190 | 64.941 | 1.00 | 0.00 xxxx | 811 |
| ATOM | 812 | N | TYR | A | 107 | 91.120 | 0.911 | 71.562 | 1.00 | 0.00 xxxx | 812 |

-continued

| | | | | | | | | | | | |
|---|---|---|---|---|---|---|---|---|---|---|---|
| CA, calcium<br>HOH, Water<br>ACR, Acrylodan<br>K, potassium<br>EDO, ethylene glycol | | | | | | | | | | | |
| ATOM | 813 | CA | TYR | A | 107 | 90.212 | 0.931 | 72.709 | 1.00 | 0.00 xxxx | 813 |
| ATOM | 814 | C | TYR | A | 107 | 89.090 | −0.082 | 72.540 | 1.00 | 0.00 xxxx | 814 |
| ATOM | 815 | O | TYR | A | 107 | 88.493 | −0.173 | 71.477 | 1.00 | 0.00 xxxx | 815 |
| ATOM | 816 | CB | TYR | A | 107 | 89.587 | 2.325 | 72.927 | 1.00 | 0.00 xxxx | 816 |
| ATOM | 817 | CG | TYR | A | 107 | 88.629 | 2.324 | 74.109 | 1.00 | 0.00 xxxx | 817 |
| ATOM | 818 | CD1 | TYR | A | 107 | 89.110 | 2.165 | 75.405 | 1.00 | 0.00 xxxx | 818 |
| ATOM | 819 | CD2 | TYR | A | 107 | 87.255 | 2.445 | 73.935 | 1.00 | 0.00 xxxx | 819 |
| ATOM | 820 | CE1 | TYR | A | 107 | 88.257 | 2.135 | 76.488 | 1.00 | 0.00 xxxx | 820 |
| ATOM | 821 | CE2 | TYR | A | 107 | 86.387 | 2.414 | 75.024 | 1.00 | 0.00 xxxx | 821 |
| ATOM | 822 | CZ | TYR | A | 107 | 86.906 | 2.261 | 76.297 | 1.00 | 0.00 xxxx | 822 |
| ATOM | 823 | OH | TYR | A | 107 | 86.058 | 2.217 | 77.383 | 1.00 | 0.00 xxxx | 823 |
| ATOM | 824 | N | VAL | A | 108 | 88.797 | −0.817 | 73.612 | 1.00 | 0.00 xxxx | 824 |
| ATOM | 825 | CA | VAL | A | 108 | 87.650 | −1.721 | 73.661 | 1.00 | 0.00 xxxx | 825 |
| ATOM | 826 | C | VAL | A | 108 | 86.720 | −1.294 | 74.784 | 1.00 | 0.00 xxxx | 826 |
| ATOM | 827 | O | VAL | A | 108 | 87.141 | −1.184 | 75.934 | 1.00 | 0.00 xxxx | 827 |
| ATOM | 828 | CB | VAL | A | 108 | 88.087 | −3.174 | 73.877 | 1.00 | 0.00 xxxx | 828 |
| ATOM | 829 | CG1 | VAL | A | 108 | 86.848 | −4.086 | 74.051 | 1.00 | 0.00 xxxx | 829 |
| ATOM | 830 | CG2 | VAL | A | 108 | 88.972 | −3.674 | 72.718 | 1.00 | 0.00 xxxx | 830 |
| ATOM | 831 | N | GLY | A | 109 | 85.460 | −1.060 | 74.457 | 1.00 | 0.00 xxxx | 831 |
| ATOM | 832 | CA | GLY | A | 109 | 84.492 | −0.672 | 75.470 | 1.00 | 0.00 xxxx | 832 |
| ATOM | 833 | C | GLY | A | 109 | 83.079 | −0.729 | 74.934 | 1.00 | 0.00 xxxx | 833 |
| ATOM | 834 | O | GLY | A | 109 | 82.682 | −1.717 | 74.321 | 1.00 | 0.00 xxxx | 834 |
| ATOM | 835 | N | THR | A | 110 | 82.328 | 0.335 | 75.196 | 1.00 | 0.00 xxxx | 835 |
| ATOM | 836 | CA | THR | A | 110 | 80.915 | 0.410 | 74.843 | 1.00 | 0.00 xxxx | 836 |
| ATOM | 837 | C | THR | A | 110 | 80.556 | 1.792 | 74.323 | 1.00 | 0.00 xxxx | 837 |
| ATOM | 838 | O | THR | A | 110 | 81.343 | 2.734 | 74.442 | 1.00 | 0.00 xxxx | 838 |
| ATOM | 839 | CB | THR | A | 110 | 80.007 | 0.132 | 76.056 | 1.00 | 0.00 xxxx | 839 |
| ATOM | 840 | OG1 | THR | A | 110 | 80.096 | 1.231 | 76.975 | 1.00 | 0.00 xxxx | 840 |
| ATOM | 841 | CG2 | THR | A | 110 | 80.418 | −1.153 | 76.784 | 1.00 | 0.00 xxxx | 841 |
| ATOM | 842 | N | ASP | A | 111 | 79.354 | 1.912 | 73.755 | 1.00 | 0.00 xxxx | 842 |
| ATOM | 843 | CA | ASP | A | 111 | 78.733 | 3.209 | 73.500 | 1.00 | 0.00 xxxx | 843 |
| ATOM | 844 | C | ASP | A | 111 | 77.968 | 3.609 | 74.757 | 1.00 | 0.00 xxxx | 844 |
| ATOM | 845 | O | ASP | A | 111 | 76.852 | 3.152 | 74.977 | 1.00 | 0.00 xxxx | 845 |
| ATOM | 846 | CB | ASP | A | 111 | 77.803 | 3.122 | 72.295 | 1.00 | 0.00 xxxx | 846 |
| ATOM | 847 | CG | ASP | A | 111 | 77.151 | 4.443 | 71.945 | 1.00 | 0.00 xxxx | 847 |
| ATOM | 848 | OD1 | ASP | A | 111 | 77.546 | 5.492 | 72.494 | 1.00 | 0.00 xxxx | 848 |
| ATOM | 849 | OD2 | ASP | A | 111 | 76.245 | 4.423 | 71.089 | 1.00 | 0.00 xxxx | 849 |
| ATOM | 850 | N | SER | A | 112 | 78.584 | 4.441 | 75.593 | 1.00 | 0.00 xxxx | 850 |
| ATOM | 851 | CA | SER | A | 112 | 78.050 | 4.710 | 76.928 | 1.00 | 0.00 xxxx | 851 |
| ATOM | 852 | C | SER | A | 112 | 76.588 | 5.181 | 76.924 | 1.00 | 0.00 xxxx | 852 |
| ATOM | 853 | O | SER | A | 112 | 75.783 | 4.735 | 77.743 | 1.00 | 0.00 xxxx | 853 |
| ATOM | 854 | CB | SER | A | 112 | 78.938 | 5.743 | 77.632 | 1.00 | 0.00 xxxx | 854 |
| ATOM | 855 | OG | SER | A | 112 | 80.282 | 5.273 | 77.722 | 1.00 | 0.00 xxxx | 855 |
| ATOM | 856 | N | LYS | A | 113 | 76.241 | 6.053 | 75.980 | 1.00 | 0.00 xxxx | 856 |
| ATOM | 857 | CA | LYS | A | 113 | 74.895 | 6.620 | 75.943 | 1.00 | 0.00 xxxx | 857 |
| ATOM | 858 | C | LYS | A | 113 | 73.836 | 5.534 | 75.701 | 1.00 | 0.00 xxxx | 858 |
| ATOM | 859 | O | LYS | A | 113 | 72.714 | 5.640 | 76.197 | 1.00 | 0.00 xxxx | 859 |
| ATOM | 860 | CB | LYS | A | 113 | 74.799 | 7.711 | 74.877 | 1.00 | 0.00 xxxx | 860 |
| ATOM | 861 | CG | LYS | A | 113 | 74.780 | 7.203 | 73.457 | 1.00 | 0.00 xxxx | 861 |
| ATOM | 862 | CD | LYS | A | 113 | 74.286 | 8.278 | 72.499 | 1.00 | 0.00 xxxx | 862 |
| ATOM | 863 | CE | LYS | A | 113 | 74.040 | 7.701 | 71.113 | 1.00 | 0.00 xxxx | 863 |
| ATOM | 864 | NZ | LYS | A | 113 | 75.238 | 6.994 | 70.575 | 1.00 | 0.00 xxxx | 864 |
| ATOM | 865 | N | GLU | A | 114 | 74.207 | 4.479 | 74.975 | 1.00 | 0.00 xxxx | 865 |
| ATOM | 866 | CA | GLU | A | 114 | 73.270 | 3.394 | 74.699 | 1.00 | 0.00 xxxx | 866 |
| ATOM | 867 | C | GLU | A | 114 | 72.725 | 2.781 | 75.978 | 1.00 | 0.00 xxxx | 867 |
| ATOM | 868 | O | GLU | A | 114 | 71.543 | 2.448 | 76.065 | 1.00 | 0.00 xxxx | 868 |
| ATOM | 869 | CB | GLU | A | 114 | 73.926 | 2.311 | 73.843 | 1.00 | 0.00 xxxx | 869 |
| ATOM | 870 | CG | GLU | A | 114 | 72.990 | 1.167 | 73.486 | 1.00 | 0.00 xxxx | 870 |
| ATOM | 871 | CD | GLU | A | 114 | 73.671 | 0.061 | 72.706 | 1.00 | 0.00 xxxx | 871 |
| ATOM | 872 | OE1 | GLU | A | 114 | 74.705 | −0.457 | 73.172 | 1.00 | 0.00 xxxx | 872 |
| ATOM | 873 | OE2 | GLU | A | 114 | 73.176 | −0.290 | 71.615 | 1.00 | 0.00 xxxx | 873 |
| ATOM | 874 | N | SER | A | 115 | 73.574 | 2.631 | 76.987 | 1.00 | 0.00 xxxx | 874 |
| ATOM | 875 | CA | SER | A | 115 | 73.103 | 2.025 | 78.228 | 1.00 | 0.00 xxxx | 875 |
| ATOM | 876 | C | SER | A | 115 | 72.096 | 2.924 | 78.953 | 1.00 | 0.00 xxxx | 876 |
| ATOM | 877 | O | SER | A | 115 | 71.162 | 2.423 | 79.559 | 1.00 | 0.00 xxxx | 877 |
| ATOM | 878 | CB | SER | A | 115 | 74.274 | 1.673 | 79.162 | 1.00 | 0.00 xxxx | 878 |
| ATOM | 879 | OG | SER | A | 115 | 75.073 | 2.791 | 79.501 | 1.00 | 0.00 xxxx | 879 |
| ATOM | 880 | N | GLY | A | 116 | 72.282 | 4.240 | 78.880 | 1.00 | 0.00 xxxx | 880 |
| ATOM | 881 | CA | GLY | A | 116 | 71.305 | 5.160 | 79.446 | 1.00 | 0.00 xxxx | 881 |
| ATOM | 882 | C | GLY | A | 116 | 69.965 | 5.122 | 78.724 | 1.00 | 0.00 xxxx | 882 |
| ATOM | 883 | O | GLY | A | 116 | 68.903 | 5.120 | 79.354 | 1.00 | 0.00 xxxx | 883 |
| ATOM | 884 | N | ILE | A | 117 | 70.015 | 5.109 | 77.396 | 1.00 | 0.00 xxxx | 884 |
| ATOM | 885 | CA | ILE | A | 117 | 68.807 | 5.008 | 76.584 | 1.00 | 0.00 xxxx | 885 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 886 | C | ILE | A | 117 | 68.071 | 3.700 | 76.894 | 1.00 | 0.00 | xxxx | 886 |
| ATOM | 887 | O | ILE | A | 117 | 66.856 | 3.699 | 77.111 | 1.00 | 0.00 | xxxx | 887 |
| ATOM | 888 | CB | ILE | A | 117 | 69.147 | 5.119 | 75.093 | 1.00 | 0.00 | xxxx | 888 |
| ATOM | 889 | CG2 | ILE | A | 117 | 67.908 | 4.856 | 74.240 | 1.00 | 0.00 | xxxx | 889 |
| ATOM | 890 | CG1 | ILE | A | 117 | 69.742 | 6.498 | 74.792 | 1.00 | 0.00 | xxxx | 890 |
| ATOM | 891 | CD1 | ILE | A | 117 | 70.257 | 6.656 | 73.391 | 1.00 | 0.00 | xxxx | 891 |
| ATOM | 892 | N | ILE | A | 118 | 68.800 | 2.586 | 76.914 | 1.00 | 0.00 | xxxx | 892 |
| ATOM | 893 | CA | ILE | A | 118 | 68.164 | 1.304 | 77.208 | 1.00 | 0.00 | xxxx | 893 |
| ATOM | 894 | C | ILE | A | 118 | 67.565 | 1.302 | 78.609 | 1.00 | 0.00 | xxxx | 894 |
| ATOM | 895 | O | ILE | A | 118 | 66.458 | 0.799 | 78.810 | 1.00 | 0.00 | xxxx | 895 |
| ATOM | 896 | CB | ILE | A | 118 | 69.142 | 0.147 | 77.015 | 1.00 | 0.00 | xxxx | 896 |
| ATOM | 897 | CG1 | ILE | A | 118 | 69.483 | 0.027 | 75.528 | 1.00 | 0.00 | xxxx | 897 |
| ATOM | 898 | CG2 | ILE | A | 118 | 68.535 | −1.155 | 77.531 | 1.00 | 0.00 | xxxx | 898 |
| ATOM | 899 | CD1 | ILE | A | 118 | 70.562 | −1.000 | 75.227 | 1.00 | 0.00 | xxxx | 899 |
| ATOM | 900 | N | GLN | A | 119 | 68.272 | 1.879 | 79.579 | 1.00 | 0.00 | xxxx | 900 |
| ATOM | 901 | CA | GLN | A | 119 | 67.736 | 1.916 | 80.932 | 1.00 | 0.00 | xxxx | 901 |
| ATOM | 902 | C | GLN | A | 119 | 66.448 | 2.738 | 80.996 | 1.00 | 0.00 | xxxx | 902 |
| ATOM | 903 | O | GLN | A | 119 | 65.490 | 2.339 | 81.649 | 1.00 | 0.00 | xxxx | 903 |
| ATOM | 904 | CB | GLN | A | 119 | 68.773 | 2.472 | 81.915 | 1.00 | 0.00 | xxxx | 904 |
| ATOM | 905 | CG | GLN | A | 119 | 68.356 | 2.257 | 83.375 | 1.00 | 0.00 | xxxx | 905 |
| ATOM | 906 | CD | GLN | A | 119 | 69.334 | 2.890 | 84.345 | 1.00 | 0.00 | xxxx | 906 |
| ATOM | 907 | OE1 | GLN | A | 119 | 69.729 | 4.042 | 84.172 | 1.00 | 0.00 | xxxx | 907 |
| ATOM | 908 | NE2 | GLN | A | 119 | 69.722 | 2.145 | 85.371 | 1.00 | 0.00 | xxxx | 908 |
| ATOM | 909 | N | GLY | A | 120 | 66.422 | 3.866 | 80.296 | 1.00 | 0.00 | xxxx | 909 |
| ATOM | 910 | CA | GLY | A | 120 | 65.229 | 4.697 | 80.240 | 1.00 | 0.00 | xxxx | 910 |
| ATOM | 911 | C | GLY | A | 120 | 64.057 | 3.986 | 79.584 | 1.00 | 0.00 | xxxx | 911 |
| ATOM | 912 | O | GLY | A | 120 | 62.917 | 4.111 | 80.032 | 1.00 | 0.00 | xxxx | 912 |
| ATOM | 913 | N | ASP | A | 121 | 64.323 | 3.268 | 78.502 | 1.00 | 0.00 | xxxx | 913 |
| ATOM | 914 | CA | ASP | A | 121 | 63.258 | 2.583 | 77.780 | 1.00 | 0.00 | xxxx | 914 |
| ATOM | 915 | C | ASP | A | 121 | 62.695 | 1.453 | 78.634 | 1.00 | 0.00 | xxxx | 915 |
| ATOM | 916 | O | ASP | A | 121 | 61.505 | 1.142 | 78.573 | 1.00 | 0.00 | xxxx | 916 |
| ATOM | 917 | CB | ASP | A | 121 | 63.779 | 2.051 | 76.446 | 1.00 | 0.00 | xxxx | 917 |
| ATOM | 918 | CG | ASP | A | 121 | 62.776 | 1.169 | 75.740 | 1.00 | 0.00 | xxxx | 918 |
| ATOM | 919 | OD1 | ASP | A | 121 | 61.896 | 1.712 | 75.040 | 1.00 | 0.00 | xxxx | 919 |
| ATOM | 920 | OD2 | ASP | A | 121 | 62.875 | −0.068 | 75.881 | 1.00 | 0.00 | xxxx | 920 |
| ATOM | 921 | N | LEU | A | 122 | 63.564 | 0.857 | 79.444 | 1.00 | 0.00 | xxxx | 921 |
| ATOM | 922 | CA | LEU | A | 122 | 63.166 | −0.201 | 80.362 | 1.00 | 0.00 | xxxx | 922 |
| ATOM | 923 | C | LEU | A | 122 | 62.257 | 0.340 | 81.468 | 1.00 | 0.00 | xxxx | 923 |
| ATOM | 924 | O | LEU | A | 122 | 61.190 | −0.218 | 81.734 | 1.00 | 0.00 | xxxx | 924 |
| ATOM | 925 | CB | LEU | A | 122 | 64.407 | −0.866 | 80.964 | 1.00 | 0.00 | xxxx | 925 |
| ATOM | 926 | CG | LEU | A | 122 | 64.182 | −2.202 | 81.667 | 1.00 | 0.00 | xxxx | 926 |
| ATOM | 927 | CD1 | LEU | A | 122 | 63.510 | −3.183 | 80.713 | 1.00 | 0.00 | xxxx | 927 |
| ATOM | 928 | CD2 | LEU | A | 122 | 65.509 | −2.750 | 82.177 | 1.00 | 0.00 | xxxx | 928 |
| ATOM | 929 | N | ILE | A | 123 | 62.684 | 1.429 | 82.108 | 1.00 | 0.00 | xxxx | 929 |
| ATOM | 930 | CA | ILE | A | 123 | 61.890 | 2.097 | 83.132 | 1.00 | 0.00 | xxxx | 930 |
| ATOM | 931 | C | ILE | A | 123 | 60.524 | 2.474 | 82.561 | 1.00 | 0.00 | xxxx | 931 |
| ATOM | 932 | O | ILE | A | 123 | 59.499 | 2.260 | 83.206 | 1.00 | 0.00 | xxxx | 932 |
| ATOM | 933 | CB | ILE | A | 123 | 62.622 | 3.325 | 83.692 | 1.00 | 0.00 | xxxx | 933 |
| ATOM | 934 | CG1 | ILE | A | 123 | 63.881 | 2.881 | 84.437 | 1.00 | 0.00 | xxxx | 934 |
| ATOM | 935 | CG2 | ILE | A | 123 | 61.692 | 4.122 | 84.624 | 1.00 | 0.00 | xxxx | 935 |
| ATOM | 936 | CD1 | ILE | A | 123 | 64.782 | 4.037 | 84.868 | 1.00 | 0.00 | xxxx | 936 |
| ATOM | 937 | N | ALA | A | 124 | 60.501 | 3.010 | 81.346 | 1.00 | 0.00 | xxxx | 937 |
| ATOM | 938 | CA | ALA | A | 124 | 59.229 | 3.381 | 80.715 | 1.00 | 0.00 | xxxx | 938 |
| ATOM | 939 | C | ALA | A | 124 | 58.288 | 2.187 | 80.553 | 1.00 | 0.00 | xxxx | 939 |
| ATOM | 940 | O | ALA | A | 124 | 57.078 | 2.294 | 80.797 | 1.00 | 0.00 | xxxx | 940 |
| ATOM | 941 | CB | ALA | A | 124 | 59.483 | 4.037 | 79.367 | 1.00 | 0.00 | xxxx | 941 |
| ATOM | 942 | N | LYS | A | 125 | 58.845 | 1.052 | 80.141 | 1.00 | 0.00 | xxxx | 942 |
| ATOM | 943 | CA | LYS | A | 125 | 58.071 | −0.168 | 79.945 | 1.00 | 0.00 | xxxx | 943 |
| ATOM | 944 | C | LYS | A | 125 | 57.428 | −0.619 | 81.251 | 1.00 | 0.00 | xxxx | 944 |
| ATOM | 945 | O | LYS | A | 125 | 56.235 | −0.954 | 81.296 | 1.00 | 0.00 | xxxx | 945 |
| ATOM | 946 | CB | LYS | A | 125 | 58.978 | −1.267 | 79.381 | 1.00 | 0.00 | xxxx | 946 |
| ATOM | 947 | CG | LYS | A | 125 | 58.334 | −2.651 | 79.292 | 1.00 | 0.00 | xxxx | 947 |
| ATOM | 948 | CD | LYS | A | 125 | 59.409 | −3.705 | 79.021 | 1.00 | 0.00 | xxxx | 948 |
| ATOM | 949 | CE | LYS | A | 125 | 58.828 | −5.103 | 79.036 | 1.00 | 0.00 | xxxx | 949 |
| ATOM | 950 | NZ | LYS | A | 125 | 59.892 | −6.128 | 78.877 | 1.00 | 0.00 | xxxx | 950 |
| ATOM | 951 | N | HIS | A | 126 | 58.221 | −0.622 | 82.320 | 1.00 | 0.00 | xxxx | 951 |
| ATOM | 952 | CA | HIS | A | 126 | 57.741 | −1.131 | 83.596 | 1.00 | 0.00 | xxxx | 952 |
| ATOM | 953 | C | HIS | A | 126 | 56.831 | −0.138 | 84.296 | 1.00 | 0.00 | xxxx | 953 |
| ATOM | 954 | O | HIS | A | 126 | 55.894 | −0.543 | 84.980 | 1.00 | 0.00 | xxxx | 954 |
| ATOM | 955 | CB | HIS | A | 126 | 58.922 | −1.523 | 84.478 | 1.00 | 0.00 | xxxx | 955 |
| ATOM | 956 | CG | HIS | A | 126 | 59.593 | −2.778 | 84.016 | 1.00 | 0.00 | xxxx | 956 |
| ATOM | 957 | ND1 | HIS | A | 126 | 59.266 | −4.020 | 84.514 | 1.00 | 0.00 | xxxx | 957 |
| ATOM | 958 | CD2 | HIS | A | 126 | 60.510 | −2.990 | 83.041 | 1.00 | 0.00 | xxxx | 958 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 959 | CE1 | HIS | A | 126 | 59.983 | −4.943 | 83.893 | 1.00 | 0.00 | xxxx | 959 |
| ATOM | 960 | NE2 | HIS | A | 126 | 60.744 | −4.343 | 82.995 | 1.00 | 0.00 | xxxx | 960 |
| ATOM | 961 | N | TRP | A | 127 | 57.089 | 1.154 | 84.103 | 1.00 | 0.00 | xxxx | 961 |
| ATOM | 962 | CA | TRP | A | 127 | 56.206 | 2.213 | 84.605 | 1.00 | 0.00 | xxxx | 962 |
| ATOM | 963 | C | TRP | A | 127 | 54.805 | 2.083 | 84.022 | 1.00 | 0.00 | xxxx | 963 |
| ATOM | 964 | O | TRP | A | 127 | 53.803 | 2.171 | 84.746 | 1.00 | 0.00 | xxxx | 964 |
| ATOM | 965 | CB | TRP | A | 127 | 56.807 | 3.583 | 84.262 | 1.00 | 0.00 | xxxx | 965 |
| ATOM | 966 | CG | TRP | A | 127 | 56.008 | 4.805 | 84.674 | 1.00 | 0.00 | xxxx | 966 |
| ATOM | 967 | CD1 | TRP | A | 127 | 55.272 | 5.607 | 83.854 | 1.00 | 0.00 | xxxx | 967 |
| ATOM | 968 | CD2 | TRP | A | 127 | 55.927 | 5.383 | 85.982 | 1.00 | 0.00 | xxxx | 968 |
| ATOM | 969 | NE1 | TRP | A | 127 | 54.716 | 6.642 | 84.574 | 1.00 | 0.00 | xxxx | 969 |
| ATOM | 970 | CE2 | TRP | A | 127 | 55.110 | 6.527 | 85.882 | 1.00 | 0.00 | xxxx | 970 |
| ATOM | 971 | CE3 | TRP | A | 127 | 56.469 | 5.045 | 87.229 | 1.00 | 0.00 | xxxx | 971 |
| ATOM | 972 | CZ2 | TRP | A | 127 | 54.818 | 7.335 | 86.982 | 1.00 | 0.00 | xxxx | 972 |
| ATOM | 973 | CZ3 | TRP | A | 127 | 56.183 | 5.849 | 88.320 | 1.00 | 0.00 | xxxx | 973 |
| ATOM | 974 | CH2 | TRP | A | 127 | 55.360 | 6.980 | 88.191 | 1.00 | 0.00 | xxxx | 974 |
| ATOM | 975 | N | ALA | A | 128 | 54.730 | 1.869 | 82.713 | 1.00 | 0.00 | xxxx | 975 |
| ATOM | 976 | CA | ALA | A | 128 | 53.439 | 1.684 | 82.051 | 1.00 | 0.00 | xxxx | 976 |
| ATOM | 977 | C | ALA | A | 128 | 52.691 | 0.465 | 82.606 | 1.00 | 0.00 | xxxx | 977 |
| ATOM | 978 | O | ALA | A | 128 | 51.459 | 0.480 | 82.734 | 1.00 | 0.00 | xxxx | 978 |
| ATOM | 979 | CB | ALA | A | 128 | 53.635 | 1.546 | 80.545 | 1.00 | 0.00 | xxxx | 979 |
| ATOM | 980 | N | ALA | A | 129 | 53.438 | −0.580 | 82.946 | 1.00 | 0.00 | xxxx | 980 |
| ATOM | 981 | CA | ALA | A | 129 | 52.859 | −1.837 | 83.413 | 1.00 | 0.00 | xxxx | 981 |
| ATOM | 982 | C | ALA | A | 129 | 52.549 | −1.841 | 84.911 | 1.00 | 0.00 | xxxx | 982 |
| ATOM | 983 | O | ALA | A | 129 | 51.876 | −2.744 | 85.401 | 1.00 | 0.00 | xxxx | 983 |
| ATOM | 984 | CB | ALA | A | 129 | 53.793 | −2.995 | 83.084 | 1.00 | 0.00 | xxxx | 984 |
| ATOM | 985 | N | ASN | A | 130 | 53.053 | −0.847 | 85.636 | 1.00 | 0.00 | xxxx | 985 |
| ATOM | 986 | CA | ASN | A | 130 | 52.878 | −0.801 | 87.086 | 1.00 | 0.00 | xxxx | 986 |
| ATOM | 987 | C | ASN | A | 130 | 52.454 | 0.593 | 87.527 | 1.00 | 0.00 | xxxx | 987 |
| ATOM | 988 | O | ASN | A | 130 | 53.226 | 1.290 | 88.173 | 1.00 | 0.00 | xxxx | 988 |
| ATOM | 989 | CB | ASN | A | 130 | 54.179 | −1.189 | 87.808 | 1.00 | 0.00 | xxxx | 989 |
| ATOM | 990 | CG | ASN | A | 130 | 54.592 | −2.629 | 87.551 | 1.00 | 0.00 | xxxx | 990 |
| ATOM | 991 | OD1 | ASN | A | 130 | 54.189 | −3.538 | 88.283 | 1.00 | 0.00 | xxxx | 991 |
| ATOM | 992 | ND2 | ASN | A | 130 | 55.397 | −2.847 | 86.509 | 1.00 | 0.00 | xxxx | 992 |
| ATOM | 993 | N | GLN | A | 131 | 51.236 | 1.005 | 87.192 | 1.00 | 0.00 | xxxx | 993 |
| ATOM | 994 | CA | GLN | A | 131 | 50.836 | 2.377 | 87.493 | 1.00 | 0.00 | xxxx | 994 |
| ATOM | 995 | C | GLN | A | 131 | 50.664 | 2.616 | 88.994 | 1.00 | 0.00 | xxxx | 995 |
| ATOM | 996 | O | GLN | A | 131 | 50.591 | 3.756 | 89.434 | 1.00 | 0.00 | xxxx | 996 |
| ATOM | 997 | CB | GLN | A | 131 | 49.558 | 2.737 | 86.743 | 1.00 | 0.00 | xxxx | 997 |
| ATOM | 998 | CG | GLN | A | 131 | 49.811 | 3.113 | 85.287 | 1.00 | 0.00 | xxxx | 998 |
| ATOM | 999 | CD | GLN | A | 131 | 50.666 | 4.365 | 85.145 | 1.00 | 0.00 | xxxx | 999 |
| ATOM | 1000 | OE1 | GLN | A | 131 | 50.176 | 5.486 | 85.303 | 1.00 | 0.00 | xxxx | 1000 |
| ATOM | 1001 | NE2 | GLN | A | 131 | 51.949 | 4.180 | 84.848 | 1.00 | 0.00 | xxxx | 1001 |
| ATOM | 1002 | N | GLY | A | 132 | 50.627 | 1.541 | 89.773 | 1.00 | 0.00 | xxxx | 1002 |
| ATOM | 1003 | CA | GLY | A | 132 | 50.664 | 1.661 | 91.218 | 1.00 | 0.00 | xxxx | 1003 |
| ATOM | 1004 | C | GLY | A | 132 | 51.957 | 2.255 | 91.741 | 1.00 | 0.00 | xxxx | 1004 |
| ATOM | 1005 | O | GLY | A | 132 | 52.014 | 2.708 | 92.886 | 1.00 | 0.00 | xxxx | 1005 |
| ATOM | 1006 | N | TRP | A | 133 | 52.999 | 2.266 | 90.906 | 1.00 | 0.00 | xxxx | 1006 |
| ATOM | 1007 | CA | TRP | A | 133 | 54.265 | 2.885 | 91.281 | 1.00 | 0.00 | xxxx | 1007 |
| ATOM | 1008 | C | TRP | A | 133 | 54.179 | 4.410 | 91.375 | 1.00 | 0.00 | xxxx | 1008 |
| ATOM | 1009 | O | TRP | A | 133 | 55.021 | 5.042 | 92.004 | 1.00 | 0.00 | xxxx | 1009 |
| ATOM | 1010 | CB | TRP | A | 133 | 55.369 | 2.526 | 90.279 | 1.00 | 0.00 | xxxx | 1010 |
| ATOM | 1011 | CG | TRP | A | 133 | 55.859 | 1.107 | 90.312 | 1.00 | 0.00 | xxxx | 1011 |
| ATOM | 1012 | CD1 | TRP | A | 133 | 55.501 | 0.119 | 91.186 | 1.00 | 0.00 | xxxx | 1012 |
| ATOM | 1013 | CD2 | TRP | A | 133 | 56.818 | 0.531 | 89.423 | 1.00 | 0.00 | xxxx | 1013 |
| ATOM | 1014 | NE1 | TRP | A | 133 | 56.190 | −1.045 | 90.890 | 1.00 | 0.00 | xxxx | 1014 |
| ATOM | 1015 | CE2 | TRP | A | 133 | 56.997 | −0.816 | 89.806 | 1.00 | 0.00 | xxxx | 1015 |
| ATOM | 1016 | CE3 | TRP | A | 133 | 57.544 | 1.025 | 88.334 | 1.00 | 0.00 | xxxx | 1016 |
| ATOM | 1017 | CZ2 | TRP | A | 133 | 57.877 | −1.674 | 89.140 | 1.00 | 0.00 | xxxx | 1017 |
| ATOM | 1018 | CZ3 | TRP | A | 133 | 58.422 | 0.170 | 87.671 | 1.00 | 0.00 | xxxx | 1018 |
| ATOM | 1019 | CH2 | TRP | A | 133 | 58.574 | −1.165 | 88.079 | 1.00 | 0.00 | xxxx | 1019 |
| ATOM | 1020 | N | ASP | A | 134 | 53.175 | 4.985 | 90.714 | 1.00 | 0.00 | xxxx | 1020 |
| ATOM | 1021 | CA | ASP | A | 134 | 52.940 | 6.423 | 90.756 | 1.00 | 0.00 | xxxx | 1021 |
| ATOM | 1022 | C | ASP | A | 134 | 52.241 | 6.760 | 92.070 | 1.00 | 0.00 | xxxx | 1022 |
| ATOM | 1023 | O | ASP | A | 134 | 51.022 | 6.966 | 92.112 | 1.00 | 0.00 | xxxx | 1023 |
| ATOM | 1024 | CB | ASP | A | 134 | 52.105 | 6.842 | 89.543 | 1.00 | 0.00 | xxxx | 1024 |
| ATOM | 1025 | CG | ASP | A | 134 | 51.978 | 8.350 | 89.382 | 1.00 | 0.00 | xxxx | 1025 |
| ATOM | 1026 | OD1 | ASP | A | 134 | 52.701 | 9.111 | 90.044 | 1.00 | 0.00 | xxxx | 1026 |
| ATOM | 1027 | OD2 | ASP | A | 134 | 51.151 | 8.771 | 88.554 | 1.00 | 0.00 | xxxx | 1027 |
| ATOM | 1028 | N | LEU | A | 135 | 53.031 | 6.800 | 93.141 | 1.00 | 0.00 | xxxx | 1028 |
| ATOM | 1029 | CA | LEU | A | 135 | 52.494 | 6.901 | 94.496 | 1.00 | 0.00 | xxxx | 1029 |
| ATOM | 1030 | C | LEU | A | 135 | 51.661 | 8.154 | 94.723 | 1.00 | 0.00 | xxxx | 1030 |
| ATOM | 1031 | O | LEU | A | 135 | 50.639 | 8.093 | 95.418 | 1.00 | 0.00 | xxxx | 1031 |

-continued

| CA, calcium<br>HOH, Water<br>ACR, Acrylodan<br>K, potassium<br>EDO, ethylene glycol | | | | | | | | | | | |
|---|---|---|---|---|---|---|---|---|---|---|---|
| ATOM | 1032 | CB | LEU | A | 135 | 53.636 | 6.852 | 95.513 | 1.00 | 0.00 xxxx | 1032 |
| ATOM | 1033 | CG | LEU | A | 135 | 54.522 | 5.609 | 95.486 | 1.00 | 0.00 xxxx | 1033 |
| ATOM | 1034 | CD1 | LEU | A | 135 | 55.586 | 5.739 | 96.573 | 1.00 | 0.00 xxxx | 1034 |
| ATOM | 1035 | CD2 | LEU | A | 135 | 53.695 | 4.365 | 95.696 | 1.00 | 0.00 xxxx | 1035 |
| ATOM | 1036 | N | ASN | A | 136 | 52.068 | 9.286 | 94.148 | 1.00 | 0.00 xxxx | 1036 |
| ATOM | 1037 | CA | ASN | A | 136 | 51.282 | 10.512 | 94.345 | 1.00 | 0.00 xxxx | 1037 |
| ATOM | 1038 | C | ASN | A | 136 | 50.294 | 10.778 | 93.208 | 1.00 | 0.00 xxxx | 1038 |
| ATOM | 1039 | O | ASN | A | 136 | 49.642 | 11.827 | 93.183 | 1.00 | 0.00 xxxx | 1039 |
| ATOM | 1040 | CB | ASN | A | 136 | 52.193 | 11.729 | 94.543 | 1.00 | 0.00 xxxx | 1040 |
| ATOM | 1041 | CG | ASN | A | 136 | 52.931 | 12.144 | 93.274 | 1.00 | 0.00 xxxx | 1041 |
| ATOM | 1042 | OD1 | ASN | A | 136 | 53.028 | 11.386 | 92.307 | 1.00 | 0.00 xxxx | 1042 |
| ATOM | 1043 | ND2 | ASN | A | 136 | 53.477 | 13.362 | 93.289 | 1.00 | 0.00 xxxx | 1043 |
| ATOM | 1044 | N | LYS | A | 137 | 50.197 | 9.830 | 92.280 | 1.00 | 0.00 xxxx | 1044 |
| ATOM | 1045 | CA | LYS | A | 137 | 49.160 | 9.856 | 91.239 | 1.00 | 0.00 xxxx | 1045 |
| ATOM | 1046 | C | LYS | A | 137 | 49.225 | 11.109 | 90.363 | 1.00 | 0.00 xxxx | 1046 |
| ATOM | 1047 | O | LYS | A | 137 | 48.189 | 11.578 | 89.883 | 1.00 | 0.00 xxxx | 1047 |
| ATOM | 1048 | CB | LYS | A | 137 | 47.770 | 9.736 | 91.883 | 1.00 | 0.00 xxxx | 1048 |
| ATOM | 1049 | CG | LYS | A | 137 | 47.571 | 8.425 | 92.630 | 1.00 | 0.00 xxxx | 1049 |
| ATOM | 1050 | CD | LYS | A | 137 | 46.208 | 8.359 | 93.303 | 1.00 | 0.00 xxxx | 1050 |
| ATOM | 1051 | CE | LYS | A | 137 | 45.091 | 8.308 | 92.284 | 1.00 | 0.00 xxxx | 1051 |
| ATOM | 1052 | NZ | LYS | A | 137 | 45.115 | 7.052 | 91.487 | 1.00 | 0.00 xxxx | 1052 |
| ATOM | 1053 | N | ASP | A | 138 | 50.428 | 11.638 | 90.135 | 1.00 | 0.00 xxxx | 1053 |
| ATOM | 1054 | CA | ASP | A | 138 | 50.554 | 12.869 | 89.344 | 1.00 | 0.00 xxxx | 1054 |
| ATOM | 1055 | C | ASP | A | 138 | 51.009 | 12.636 | 87.901 | 1.00 | 0.00 xxxx | 1055 |
| ATOM | 1056 | O | ASP | A | 138 | 51.184 | 13.594 | 87.148 | 1.00 | 0.00 xxxx | 1056 |
| ATOM | 1057 | CB | ASP | A | 138 | 51.499 | 13.865 | 90.041 | 1.00 | 0.00 xxxx | 1057 |
| ATOM | 1058 | CG | ASP | A | 138 | 52.965 | 13.447 | 90.011 | 1.00 | 0.00 xxxx | 1058 |
| ATOM | 1059 | OD1 | ASP | A | 138 | 53.285 | 12.308 | 89.603 | 1.00 | 0.00 xxxx | 1059 |
| ATOM | 1060 | OD2 | ASP | A | 138 | 53.812 | 14.281 | 90.431 | 1.00 | 0.00 xxxx | 1060 |
| ATOM | 1061 | N | GLY | A | 139 | 51.196 | 11.374 | 87.519 | 1.00 | 0.00 xxxx | 1061 |
| ATOM | 1062 | CA | GLY | A | 139 | 51.634 | 11.030 | 86.174 | 1.00 | 0.00 xxxx | 1062 |
| ATOM | 1063 | C | GLY | A | 139 | 53.104 | 11.282 | 85.887 | 1.00 | 0.00 xxxx | 1063 |
| ATOM | 1064 | O | GLY | A | 139 | 53.555 | 11.086 | 84.757 | 1.00 | 0.00 xxxx | 1064 |
| ATOM | 1065 | N | GLN | A | 140 | 53.859 | 11.686 | 86.910 | 1.00 | 0.00 xxxx | 1065 |
| ATOM | 1066 | CA | GLN | A | 140 | 55.299 | 11.929 | 86.779 | 1.00 | 0.00 xxxx | 1066 |
| ATOM | 1067 | C | GLN | A | 140 | 56.057 | 10.927 | 87.603 | 1.00 | 0.00 xxxx | 1067 |
| ATOM | 1068 | O | GLN | A | 140 | 55.531 | 10.447 | 88.612 | 1.00 | 0.00 xxxx | 1068 |
| ATOM | 1069 | CB | GLN | A | 140 | 55.682 | 13.327 | 87.258 | 1.00 | 0.00 xxxx | 1069 |
| ATOM | 1070 | CG | GLN | A | 140 | 54.808 | 14.436 | 86.722 | 1.00 | 0.00 xxxx | 1070 |
| ATOM | 1071 | CD | GLN | A | 140 | 55.319 | 15.804 | 87.115 | 1.00 | 0.00 xxxx | 1071 |
| ATOM | 1072 | OE1 | GLN | A | 140 | 56.517 | 15.992 | 87.328 | 1.00 | 0.00 xxxx | 1072 |
| ATOM | 1073 | NE2 | GLN | A | 140 | 54.412 | 16.769 | 87.222 | 1.00 | 0.00 xxxx | 1073 |
| ATOM | 1074 | N | ILE | A | 141 | 57.275 | 10.594 | 87.178 | 1.00 | 0.00 xxxx | 1074 |
| ATOM | 1075 | CA | ILE | A | 141 | 58.146 | 9.760 | 88.003 | 1.00 | 0.00 xxxx | 1075 |
| ATOM | 1076 | C | ILE | A | 141 | 58.978 | 10.606 | 88.964 | 1.00 | 0.00 xxxx | 1076 |
| ATOM | 1077 | O | ILE | A | 141 | 59.856 | 11.347 | 88.538 | 1.00 | 0.00 xxxx | 1077 |
| ATOM | 1078 | CB | ILE | A | 141 | 59.090 | 8.899 | 87.162 | 1.00 | 0.00 xxxx | 1078 |
| ATOM | 1079 | CG1 | ILE | A | 141 | 58.300 | 7.990 | 86.223 | 1.00 | 0.00 xxxx | 1079 |
| ATOM | 1080 | CD1 | ILE | A | 141 | 59.209 | 7.121 | 85.330 | 1.00 | 0.00 xxxx | 1080 |
| ATOM | 1081 | CG2 | ILE | A | 141 | 60.002 | 8.087 | 88.090 | 1.00 | 0.00 xxxx | 1081 |
| ATOM | 1082 | N | GLN | A | 142 | 58.695 | 10.497 | 90.256 | 1.00 | 0.00 xxxx | 1082 |
| ATOM | 1083 | CA | GLN | A | 142 | 59.568 | 11.073 | 91.274 | 1.00 | 0.00 xxxx | 1083 |
| ATOM | 1084 | C | GLN | A | 142 | 60.693 | 10.084 | 91.528 | 1.00 | 0.00 xxxx | 1084 |
| ATOM | 1085 | O | GLN | A | 142 | 60.453 | 8.970 | 92.000 | 1.00 | 0.00 xxxx | 1085 |
| ATOM | 1086 | CB | GLN | A | 142 | 58.795 | 11.361 | 92.562 | 1.00 | 0.00 xxxx | 1086 |
| ATOM | 1087 | CG | GLN | A | 142 | 58.111 | 12.718 | 92.607 | 1.00 | 0.00 xxxx | 1087 |
| ATOM | 1088 | CD | GLN | A | 142 | 56.877 | 12.796 | 91.716 | 1.00 | 0.00 xxxx | 1088 |
| ATOM | 1089 | OE1 | GLN | A | 142 | 56.161 | 11.805 | 91.524 | 1.00 | 0.00 xxxx | 1089 |
| ATOM | 1090 | NE2 | GLN | A | 142 | 56.611 | 13.987 | 91.190 | 1.00 | 0.00 xxxx | 1090 |
| ATOM | 1091 | N | PHE | A | 143 | 61.916 | 10.468 | 91.183 | 1.00 | 0.00 xxxx | 1091 |
| ATOM | 1092 | CA | PHE | A | 143 | 63.031 | 9.530 | 91.267 | 1.00 | 0.00 xxxx | 1092 |
| ATOM | 1093 | C | PHE | A | 143 | 64.180 | 10.041 | 92.119 | 1.00 | 0.00 xxxx | 1093 |
| ATOM | 1094 | O | PHE | A | 143 | 64.290 | 11.237 | 92.391 | 1.00 | 0.00 xxxx | 1094 |
| ATOM | 1095 | CB | PHE | A | 143 | 63.561 | 9.192 | 89.856 | 1.00 | 0.00 xxxx | 1095 |
| ATOM | 1096 | CG | PHE | A | 143 | 64.318 | 10.321 | 89.187 | 1.00 | 0.00 xxxx | 1096 |
| ATOM | 1097 | CD1 | PHE | A | 143 | 65.710 | 10.383 | 89.259 | 1.00 | 0.00 xxxx | 1097 |
| ATOM | 1098 | CD2 | PHE | A | 143 | 63.647 | 11.301 | 88.475 | 1.00 | 0.00 xxxx | 1098 |
| ATOM | 1099 | CE1 | PHE | A | 143 | 66.415 | 11.409 | 88.638 | 1.00 | 0.00 xxxx | 1099 |
| ATOM | 1100 | CE2 | PHE | A | 143 | 64.342 | 12.332 | 87.852 | 1.00 | 0.00 xxxx | 1100 |
| ATOM | 1101 | CZ | PHE | A | 143 | 65.730 | 12.386 | 87.936 | 1.00 | 0.00 xxxx | 1101 |
| ATOM | 1102 | N | VAL | A | 144 | 65.038 | 9.116 | 92.534 | 1.00 | 0.00 xxxx | 1102 |
| ATOM | 1103 | CA | VAL | A | 144 | 66.359 | 9.480 | 93.032 | 1.00 | 0.00 xxxx | 1103 |
| ATOM | 1104 | C | VAL | A | 144 | 67.364 | 8.774 | 92.143 | 1.00 | 0.00 xxxx | 1104 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1105 | O | VAL | A | 144 | 67.052 | 7.737 | 91.557 | 1.00 | 0.00 | xxxx | 1105 |
| ATOM | 1106 | CB | VAL | A | 144 | 66.579 | 9.111 | 94.511 | 1.00 | 0.00 | xxxx | 1106 |
| ATOM | 1107 | CG1 | VAL | A | 144 | 65.579 | 9.852 | 95.400 | 1.00 | 0.00 | xxxx | 1107 |
| ATOM | 1108 | CG2 | VAL | A | 144 | 66.496 | 7.598 | 94.726 | 1.00 | 0.00 | xxxx | 1108 |
| ATOM | 1109 | N | LEU | A | 145 | 68.556 | 9.348 | 92.009 | 1.00 | 0.00 | xxxx | 1109 |
| ATOM | 1110 | CA | LEU | A | 145 | 69.551 | 8.754 | 91.118 | 1.00 | 0.00 | xxxx | 1110 |
| ATOM | 1111 | C | LEU | A | 145 | 70.913 | 8.649 | 91.792 | 1.00 | 0.00 | xxxx | 1111 |
| ATOM | 1112 | O | LEU | A | 145 | 71.429 | 9.620 | 92.348 | 1.00 | 0.00 | xxxx | 1112 |
| ATOM | 1113 | CB | LEU | A | 145 | 69.651 | 9.557 | 89.808 | 1.00 | 0.00 | xxxx | 1113 |
| ATOM | 1114 | CG | LEU | A | 145 | 70.503 | 8.946 | 88.676 | 1.00 | 0.00 | xxxx | 1114 |
| ATOM | 1115 | CD1 | LEU | A | 145 | 69.943 | 9.329 | 87.311 | 1.00 | 0.00 | xxxx | 1115 |
| ATOM | 1116 | CD2 | LEU | A | 145 | 71.965 | 9.353 | 88.771 | 1.00 | 0.00 | xxxx | 1116 |
| ATOM | 1117 | N | LEU | A | 146 | 71.462 | 7.438 | 91.735 | 1.00 | 0.00 | xxxx | 1117 |
| ATOM | 1118 | CA | LEU | A | 146 | 72.791 | 7.139 | 92.259 | 1.00 | 0.00 | xxxx | 1118 |
| ATOM | 1119 | C | LEU | A | 146 | 73.792 | 7.143 | 91.107 | 1.00 | 0.00 | xxxx | 1119 |
| ATOM | 1120 | O | LEU | A | 146 | 73.759 | 6.267 | 90.238 | 1.00 | 0.00 | xxxx | 1120 |
| ATOM | 1121 | CB | LEU | A | 146 | 72.770 | 5.788 | 92.984 | 1.00 | 0.00 | xxxx | 1121 |
| ATOM | 1122 | CG | LEU | A | 146 | 71.969 | 5.854 | 94.285 | 1.00 | 0.00 | xxxx | 1122 |
| ATOM | 1123 | CD1 | LEU | A | 146 | 71.464 | 4.479 | 94.688 | 1.00 | 0.00 | xxxx | 1123 |
| ATOM | 1124 | CD2 | LEU | A | 146 | 72.845 | 6.450 | 95.380 | 1.00 | 0.00 | xxxx | 1124 |
| ATOM | 1125 | N | LYS | A | 147 | 74.662 | 8.147 | 91.095 | 1.00 | 0.00 | xxxx | 1125 |
| ATOM | 1126 | CA | LYS | A | 147 | 75.583 | 8.361 | 89.986 | 1.00 | 0.00 | xxxx | 1126 |
| ATOM | 1127 | C | LYS | A | 147 | 76.939 | 7.700 | 90.244 | 1.00 | 0.00 | xxxx | 1127 |
| ATOM | 1128 | O | LYS | A | 147 | 77.365 | 7.565 | 91.391 | 1.00 | 0.00 | xxxx | 1128 |
| ATOM | 1129 | CB | LYS | A | 147 | 75.739 | 9.871 | 89.754 | 1.00 | 0.00 | xxxx | 1129 |
| ATOM | 1130 | CG | LYS | A | 147 | 76.634 | 10.249 | 88.595 | 1.00 | 0.00 | xxxx | 1130 |
| ATOM | 1131 | CD | LYS | A | 147 | 76.509 | 11.741 | 88.309 | 1.00 | 0.00 | xxxx | 1131 |
| ATOM | 1132 | CE | LYS | A | 147 | 77.457 | 12.148 | 87.189 | 1.00 | 0.00 | xxxx | 1132 |
| ATOM | 1133 | NZ | LYS | A | 147 | 77.409 | 13.623 | 86.951 | 1.00 | 0.00 | xxxx | 1133 |
| ATOM | 1134 | N | GLY | A | 148 | 77.607 | 7.268 | 89.174 | 1.00 | 0.00 | xxxx | 1134 |
| ATOM | 1135 | CA | GLY | A | 148 | 78.973 | 6.778 | 89.262 | 1.00 | 0.00 | xxxx | 1135 |
| ATOM | 1136 | C | GLY | A | 148 | 80.004 | 7.876 | 89.465 | 1.00 | 0.00 | xxxx | 1136 |
| ATOM | 1137 | O | GLY | A | 148 | 79.660 | 8.999 | 89.844 | 1.00 | 0.00 | xxxx | 1137 |
| ATOM | 1138 | N | GLU | A | 149 | 81.269 | 7.544 | 89.201 | 1.00 | 0.00 | xxxx | 1138 |
| ATOM | 1139 | CA | GLU | A | 149 | 82.387 | 8.479 | 89.315 | 1.00 | 0.00 | xxxx | 1139 |
| ATOM | 1140 | C | GLU | A | 149 | 82.189 | 9.673 | 88.390 | 1.00 | 0.00 | xxxx | 1140 |
| ATOM | 1141 | O | GLU | A | 149 | 82.058 | 9.502 | 87.185 | 1.00 | 0.00 | xxxx | 1141 |
| ATOM | 1142 | CB | GLU | A | 149 | 83.705 | 7.763 | 88.982 | 1.00 | 0.00 | xxxx | 1142 |
| ATOM | 1143 | CG | GLU | A | 149 | 84.892 | 8.693 | 88.733 | 1.00 | 0.00 | xxxx | 1143 |
| ATOM | 1144 | CD | GLU | A | 149 | 86.163 | 7.955 | 88.312 | 1.00 | 0.00 | xxxx | 1144 |
| ATOM | 1145 | OE1 | GLU | A | 149 | 86.160 | 7.257 | 87.269 | 1.00 | 0.00 | xxxx | 1145 |
| ATOM | 1146 | OE2 | GLU | A | 149 | 87.176 | 8.078 | 89.032 | 1.00 | 0.00 | xxxx | 1146 |
| ATOM | 1147 | N | PRO | A | 150 | 82.139 | 10.889 | 88.954 | 1.00 | 0.00 | xxxx | 1147 |
| ATOM | 1148 | CA | PRO | A | 150 | 81.976 | 12.064 | 88.090 | 1.00 | 0.00 | xxxx | 1148 |
| ATOM | 1149 | C | PRO | A | 150 | 83.076 | 12.150 | 87.034 | 1.00 | 0.00 | xxxx | 1149 |
| ATOM | 1150 | O | PRO | A | 150 | 84.254 | 11.966 | 87.346 | 1.00 | 0.00 | xxxx | 1150 |
| ATOM | 1151 | CB | PRO | A | 150 | 82.054 | 13.233 | 89.076 | 1.00 | 0.00 | xxxx | 1151 |
| ATOM | 1152 | CG | PRO | A | 150 | 81.585 | 12.636 | 90.382 | 1.00 | 0.00 | xxxx | 1152 |
| ATOM | 1153 | CD | PRO | A | 150 | 82.150 | 11.246 | 90.383 | 1.00 | 0.00 | xxxx | 1153 |
| ATOM | 1154 | N | GLY | A | 151 | 82.686 | 12.388 | 85.786 | 1.00 | 0.00 | xxxx | 1154 |
| ATOM | 1155 | CA | GLY | A | 151 | 83.636 | 12.431 | 84.690 | 1.00 | 0.00 | xxxx | 1155 |
| ATOM | 1156 | C | GLY | A | 151 | 83.867 | 11.116 | 83.969 | 1.00 | 0.00 | xxxx | 1156 |
| ATOM | 1157 | O | GLY | A | 151 | 84.386 | 11.100 | 82.852 | 1.00 | 0.00 | xxxx | 1157 |
| ATOM | 1158 | N | HIS | A | 152 | 83.505 | 10.008 | 84.610 | 1.00 | 0.00 | xxxx | 1158 |
| ATOM | 1159 | CA | HIS | A | 152 | 83.556 | 8.702 | 83.962 | 1.00 | 0.00 | xxxx | 1159 |
| ATOM | 1160 | C | HIS | A | 152 | 82.542 | 8.753 | 82.832 | 1.00 | 0.00 | xxxx | 1160 |
| ATOM | 1161 | O | HIS | A | 152 | 81.397 | 9.117 | 83.066 | 1.00 | 0.00 | xxxx | 1161 |
| ATOM | 1162 | CB | HIS | A | 152 | 83.232 | 7.586 | 84.968 | 1.00 | 0.00 | xxxx | 1162 |
| ATOM | 1163 | CG | HIS | A | 152 | 83.493 | 6.196 | 84.467 | 1.00 | 0.00 | xxxx | 1163 |
| ATOM | 1164 | ND1 | HIS | A | 152 | 82.885 | 5.674 | 83.345 | 1.00 | 0.00 | xxxx | 1164 |
| ATOM | 1165 | CD2 | HIS | A | 152 | 84.270 | 5.205 | 84.966 | 1.00 | 0.00 | xxxx | 1165 |
| ATOM | 1166 | CE1 | HIS | A | 152 | 83.290 | 4.429 | 83.162 | 1.00 | 0.00 | xxxx | 1166 |
| ATOM | 1167 | NE2 | HIS | A | 152 | 84.131 | 4.120 | 84.134 | 1.00 | 0.00 | xxxx | 1167 |
| ATOM | 1168 | N | PRO | A | 153 | 82.963 | 8.418 | 81.602 | 1.00 | 0.00 | xxxx | 1168 |
| ATOM | 1169 | CA | PRO | A | 153 | 82.057 | 8.494 | 80.450 | 1.00 | 0.00 | xxxx | 1169 |
| ATOM | 1170 | C | PRO | A | 153 | 80.746 | 7.753 | 80.671 | 1.00 | 0.00 | xxxx | 1170 |
| ATOM | 1171 | O | PRO | A | 153 | 79.684 | 8.243 | 80.282 | 1.00 | 0.00 | xxxx | 1171 |
| ATOM | 1172 | CB | PRO | A | 153 | 82.867 | 7.831 | 79.330 | 1.00 | 0.00 | xxxx | 1172 |
| ATOM | 1173 | CG | PRO | A | 153 | 84.262 | 8.052 | 79.713 | 1.00 | 0.00 | xxxx | 1173 |
| ATOM | 1174 | CD | PRO | A | 153 | 84.313 | 7.980 | 81.209 | 1.00 | 0.00 | xxxx | 1174 |
| ATOM | 1175 | N | ASP | A | 154 | 80.818 | 6.585 | 81.300 | 1.00 | 0.00 | xxxx | 1175 |
| ATOM | 1176 | CA | ASP | A | 154 | 79.619 | 5.782 | 81.532 | 1.00 | 0.00 | xxxx | 1176 |
| ATOM | 1177 | C | ASP | A | 154 | 78.681 | 6.459 | 82.518 | 1.00 | 0.00 | xxxx | 1177 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1178 | O | ASP | A | 154 | 77.477 | 6.478 | 82.308 | 1.00 | 0.00 | xxxx | 1178 |
| ATOM | 1179 | CB | ASP | A | 154 | 79.969 | 4.382 | 82.041 | 1.00 | 0.00 | xxxx | 1179 |
| ATOM | 1180 | CG | ASP | A | 154 | 80.549 | 3.488 | 80.956 | 1.00 | 0.00 | xxxx | 1180 |
| ATOM | 1181 | OD1 | ASP | A | 154 | 80.282 | 3.727 | 79.756 | 1.00 | 0.00 | xxxx | 1181 |
| ATOM | 1182 | OD2 | ASP | A | 154 | 81.262 | 2.524 | 81.298 | 1.00 | 0.00 | xxxx | 1182 |
| ATOM | 1183 | N | ALA | A | 155 | 79.225 | 6.992 | 83.609 | 1.00 | 0.00 | xxxx | 1183 |
| ATOM | 1184 | CA | ALA | A | 155 | 78.391 | 7.677 | 84.597 | 1.00 | 0.00 | xxxx | 1184 |
| ATOM | 1185 | C | ALA | A | 155 | 77.702 | 8.915 | 84.010 | 1.00 | 0.00 | xxxx | 1185 |
| ATOM | 1186 | O | ALA | A | 155 | 76.509 | 9.131 | 84.215 | 1.00 | 0.00 | xxxx | 1186 |
| ATOM | 1187 | CB | ALA | A | 155 | 79.220 | 8.067 | 85.819 | 1.00 | 0.00 | xxxx | 1187 |
| ATOM | 1188 | N | GLU | A | 156 | 78.455 | 9.731 | 83.276 | 1.00 | 0.00 | xxxx | 1188 |
| ATOM | 1189 | CA | GLU | A | 156 | 77.885 | 10.946 | 82.720 | 1.00 | 0.00 | xxxx | 1189 |
| ATOM | 1190 | C | GLU | A | 156 | 76.799 | 10.637 | 81.693 | 1.00 | 0.00 | xxxx | 1190 |
| ATOM | 1191 | O | GLU | A | 156 | 75.725 | 11.221 | 81.738 | 1.00 | 0.00 | xxxx | 1191 |
| ATOM | 1192 | CB | GLU | A | 156 | 78.973 | 11.814 | 82.091 | 1.00 | 0.00 | xxxx | 1192 |
| ATOM | 1193 | CG | GLU | A | 156 | 80.011 | 12.322 | 83.083 | 1.00 | 0.00 | xxxx | 1193 |
| ATOM | 1194 | CD | GLU | A | 156 | 79.422 | 13.168 | 84.199 | 1.00 | 0.00 | xxxx | 1194 |
| ATOM | 1195 | OE1 | GLU | A | 156 | 78.347 | 13.780 | 84.009 | 1.00 | 0.00 | xxxx | 1195 |
| ATOM | 1196 | OE2 | GLU | A | 156 | 80.049 | 13.224 | 85.276 | 1.00 | 0.00 | xxxx | 1196 |
| ATOM | 1197 | N | ALA | A | 157 | 77.090 | 9.729 | 80.765 | 1.00 | 0.00 | xxxx | 1197 |
| ATOM | 1198 | CA | ALA | A | 157 | 76.121 | 9.347 | 79.745 | 1.00 | 0.00 | xxxx | 1198 |
| ATOM | 1199 | C | ALA | A | 157 | 74.890 | 8.658 | 80.332 | 1.00 | 0.00 | xxxx | 1199 |
| ATOM | 1200 | O | ALA | A | 157 | 73.761 | 8.943 | 79.922 | 1.00 | 0.00 | xxxx | 1200 |
| ATOM | 1201 | CB | ALA | A | 157 | 76.775 | 8.439 | 78.713 | 1.00 | 0.00 | xxxx | 1201 |
| ATOM | 1202 | N | ARG | A | 158 | 75.085 | 7.754 | 81.286 | 1.00 | 0.00 | xxxx | 1202 |
| ATOM | 1203 | CA | ARG | A | 158 | 73.946 | 7.028 | 81.836 | 1.00 | 0.00 | xxxx | 1203 |
| ATOM | 1204 | C | ARG | A | 158 | 73.015 | 7.947 | 82.600 | 1.00 | 0.00 | xxxx | 1204 |
| ATOM | 1205 | O | ARG | A | 158 | 71.795 | 7.761 | 82.596 | 1.00 | 0.00 | xxxx | 1205 |
| ATOM | 1206 | CB | ARG | A | 158 | 74.413 | 5.885 | 82.742 | 1.00 | 0.00 | xxxx | 1206 |
| ATOM | 1207 | CG | ARG | A | 158 | 74.963 | 4.718 | 81.960 | 1.00 | 0.00 | xxxx | 1207 |
| ATOM | 1208 | CD | ARG | A | 158 | 75.686 | 3.742 | 82.866 | 1.00 | 0.00 | xxxx | 1208 |
| ATOM | 1209 | NE | ARG | A | 158 | 76.454 | 2.793 | 82.073 | 1.00 | 0.00 | xxxx | 1209 |
| ATOM | 1210 | CZ | ARG | A | 158 | 77.307 | 1.917 | 82.597 | 1.00 | 0.00 | xxxx | 1210 |
| ATOM | 1211 | NH1 | ARG | A | 158 | 77.475 | 1.869 | 83.918 | 1.00 | 0.00 | xxxx | 1211 |
| ATOM | 1212 | NH2 | ARG | A | 158 | 78.000 | 1.104 | 81.808 | 1.00 | 0.00 | xxxx | 1212 |
| ATOM | 1213 | N | THR | A | 159 | 73.595 | 8.932 | 83.272 | 1.00 | 0.00 | xxxx | 1213 |
| ATOM | 1214 | CA | THR | A | 159 | 72.812 | 9.858 | 84.072 | 1.00 | 0.00 | xxxx | 1214 |
| ATOM | 1215 | C | THR | A | 159 | 72.016 | 10.787 | 83.165 | 1.00 | 0.00 | xxxx | 1215 |
| ATOM | 1216 | O | THR | A | 159 | 70.829 | 11.022 | 83.385 | 1.00 | 0.00 | xxxx | 1216 |
| ATOM | 1217 | CB | THR | A | 159 | 73.723 | 10.662 | 85.000 | 1.00 | 0.00 | xxxx | 1217 |
| ATOM | 1218 | OG1 | THR | A | 159 | 74.339 | 9.767 | 85.931 | 1.00 | 0.00 | xxxx | 1218 |
| ATOM | 1219 | CG2 | THR | A | 159 | 72.930 | 11.692 | 85.772 | 1.00 | 0.00 | xxxx | 1219 |
| ATOM | 1220 | N | THR | A | 160 | 72.673 | 11.288 | 82.128 | 1.00 | 0.00 | xxxx | 1220 |
| ATOM | 1221 | CA | THR | A | 160 | 72.007 | 12.189 | 81.196 | 1.00 | 0.00 | xxxx | 1221 |
| ATOM | 1222 | C | THR | A | 160 | 70.915 | 11.488 | 80.402 | 1.00 | 0.00 | xxxx | 1222 |
| ATOM | 1223 | O | THR | A | 160 | 69.805 | 12.009 | 80.263 | 1.00 | 0.00 | xxxx | 1223 |
| ATOM | 1224 | CB | THR | A | 160 | 73.011 | 12.800 | 80.207 | 1.00 | 0.00 | xxxx | 1224 |
| ATOM | 1225 | OG1 | THR | A | 160 | 73.939 | 13.636 | 80.914 | 1.00 | 0.00 | xxxx | 1225 |
| ATOM | 1226 | CG2 | THR | A | 160 | 72.289 | 13.625 | 79.137 | 1.00 | 0.00 | xxxx | 1226 |
| ATOM | 1227 | N | TYR | A | 161 | 71.237 | 10.319 | 79.853 | 1.00 | 0.00 | xxxx | 1227 |
| ATOM | 1228 | CA | TYR | A | 161 | 70.351 | 9.740 | 78.847 | 1.00 | 0.00 | xxxx | 1228 |
| ATOM | 1229 | C | TYR | A | 161 | 69.210 | 8.901 | 79.417 | 1.00 | 0.00 | xxxx | 1229 |
| ATOM | 1230 | O | TYR | A | 161 | 68.202 | 8.711 | 78.729 | 1.00 | 0.00 | xxxx | 1230 |
| ATOM | 1231 | CB | TYR | A | 161 | 71.169 | 8.925 | 77.829 | 1.00 | 0.00 | xxxx | 1231 |
| ATOM | 1232 | CG | TYR | A | 161 | 71.871 | 9.815 | 76.830 | 1.00 | 0.00 | xxxx | 1232 |
| ATOM | 1233 | CD1 | TYR | A | 161 | 71.230 | 10.222 | 75.669 | 1.00 | 0.00 | xxxx | 1233 |
| ATOM | 1234 | CD2 | TYR | A | 161 | 73.154 | 10.285 | 77.067 | 1.00 | 0.00 | xxxx | 1234 |
| ATOM | 1235 | CE1 | TYR | A | 161 | 71.864 | 11.051 | 74.756 | 1.00 | 0.00 | xxxx | 1235 |
| ATOM | 1236 | CE2 | TYR | A | 161 | 73.792 | 11.120 | 76.162 | 1.00 | 0.00 | xxxx | 1236 |
| ATOM | 1237 | CZ | TYR | A | 161 | 73.142 | 11.496 | 75.012 | 1.00 | 0.00 | xxxx | 1237 |
| ATOM | 1238 | OH | TYR | A | 161 | 73.775 | 12.323 | 74.112 | 1.00 | 0.00 | xxxx | 1238 |
| ATOM | 1239 | N | VAL | A | 162 | 69.310 | 8.434 | 80.659 | 1.00 | 0.00 | xxxx | 1239 |
| ATOM | 1240 | CA | VAL | A | 162 | 68.155 | 7.734 | 81.220 | 1.00 | 0.00 | xxxx | 1240 |
| ATOM | 1241 | C | VAL | A | 162 | 66.970 | 8.708 | 81.360 | 1.00 | 0.00 | xxxx | 1241 |
| ATOM | 1242 | O | VAL | A | 162 | 65.832 | 8.370 | 81.008 | 1.00 | 0.00 | xxxx | 1242 |
| ATOM | 1243 | CB | VAL | A | 162 | 68.495 | 7.027 | 82.564 | 1.00 | 0.00 | xxxx | 1243 |
| ATOM | 1244 | CG1 | VAL | A | 162 | 68.829 | 8.019 | 83.681 | 1.00 | 0.00 | xxxx | 1244 |
| ATOM | 1245 | CG2 | VAL | A | 162 | 67.339 | 6.120 | 82.992 | 1.00 | 0.00 | xxxx | 1245 |
| ATOM | 1246 | N | ILE | A | 163 | 67.249 | 9.926 | 81.817 | 1.00 | 0.00 | xxxx | 1246 |
| ATOM | 1247 | CA | ILE | A | 163 | 66.213 | 10.941 | 81.981 | 1.00 | 0.00 | xxxx | 1247 |
| ATOM | 1248 | C | ILE | A | 163 | 65.767 | 11.478 | 80.631 | 1.00 | 0.00 | xxxx | 1248 |
| ATOM | 1249 | O | ILE | A | 163 | 64.561 | 11.682 | 80.412 | 1.00 | 0.00 | xxxx | 1249 |
| ATOM | 1250 | CB | ILE | A | 163 | 66.702 | 12.073 | 82.917 | 1.00 | 0.00 | xxxx | 1250 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1251 | CG1 | ILE | A | 163 | 67.019 | 11.507 | 84.306 | 1.00 | 0.00 | xxxx | 1251 |
| ATOM | 1252 | CG2 | ILE | A | 163 | 65.663 | 13.205 | 83.013 | 1.00 | 0.00 | xxxx | 1252 |
| ATOM | 1253 | CD1 | ILE | A | 163 | 65.913 | 10.626 | 84.897 | 1.00 | 0.00 | xxxx | 1253 |
| ATOM | 1254 | N | LYS | A | 164 | 66.717 | 11.716 | 79.730 | 1.00 | 0.00 | xxxx | 1254 |
| ATOM | 1255 | CA | LYS | A | 164 | 66.365 | 12.228 | 78.410 | 1.00 | 0.00 | xxxx | 1255 |
| ATOM | 1256 | C | LYS | A | 164 | 65.417 | 11.261 | 77.700 | 1.00 | 0.00 | xxxx | 1256 |
| ATOM | 1257 | O | LYS | A | 164 | 64.434 | 11.676 | 77.079 | 1.00 | 0.00 | xxxx | 1257 |
| ATOM | 1258 | CB | LYS | A | 164 | 67.619 | 12.461 | 77.565 | 1.00 | 0.00 | xxxx | 1258 |
| ATOM | 1259 | CG | LYS | A | 164 | 67.313 | 13.048 | 76.199 | 1.00 | 0.00 | xxxx | 1259 |
| ATOM | 1260 | CD | LYS | A | 164 | 68.579 | 13.299 | 75.394 | 1.00 | 0.00 | xxxx | 1260 |
| ATOM | 1261 | CE | LYS | A | 164 | 68.249 | 13.646 | 73.948 | 1.00 | 0.00 | xxxx | 1261 |
| ATOM | 1262 | NZ | LYS | A | 164 | 67.187 | 14.687 | 73.850 | 1.00 | 0.00 | xxxx | 1262 |
| ATOM | 1263 | N | GLU | A | 165 | 65.703 | 9.969 | 77.807 | 1.00 | 0.00 | xxxx | 1263 |
| ATOM | 1264 | CA | GLU | A | 165 | 64.888 | 8.978 | 77.119 | 1.00 | 0.00 | xxxx | 1264 |
| ATOM | 1265 | C | GLU | A | 165 | 63.478 | 8.925 | 77.699 | 1.00 | 0.00 | xxxx | 1265 |
| ATOM | 1266 | O | GLU | A | 165 | 62.496 | 8.895 | 76.948 | 1.00 | 0.00 | xxxx | 1266 |
| ATOM | 1267 | CB | GLU | A | 165 | 65.548 | 7.595 | 77.174 | 1.00 | 0.00 | xxxx | 1267 |
| ATOM | 1268 | CG | GLU | A | 165 | 64.772 | 6.517 | 76.425 | 1.00 | 0.00 | xxxx | 1268 |
| ATOM | 1269 | CD | GLU | A | 165 | 64.739 | 6.725 | 74.909 | 1.00 | 0.00 | xxxx | 1269 |
| ATOM | 1270 | OE1 | GLU | A | 165 | 65.462 | 7.595 | 74.383 | 1.00 | 0.00 | xxxx | 1270 |
| ATOM | 1271 | OE2 | GLU | A | 165 | 63.978 | 6.001 | 74.234 | 1.00 | 0.00 | xxxx | 1271 |
| ATOM | 1272 | N | LEU | A | 166 | 63.367 | 8.943 | 79.024 | 1.00 | 0.00 | xxxx | 1272 |
| ATOM | 1273 | CA | LEU | A | 166 | 62.055 | 8.996 | 79.661 | 1.00 | 0.00 | xxxx | 1273 |
| ATOM | 1274 | C | LEU | A | 166 | 61.286 | 10.233 | 79.214 | 1.00 | 0.00 | xxxx | 1274 |
| ATOM | 1275 | O | LEU | A | 166 | 60.137 | 10.134 | 78.784 | 1.00 | 0.00 | xxxx | 1275 |
| ATOM | 1276 | CB | LEU | A | 166 | 62.196 | 8.980 | 81.185 | 1.00 | 0.00 | xxxx | 1276 |
| ATOM | 1277 | CG | LEU | A | 166 | 62.545 | 7.614 | 81.779 | 1.00 | 0.00 | xxxx | 1277 |
| ATOM | 1278 | CD1 | LEU | A | 166 | 63.027 | 7.747 | 83.220 | 1.00 | 0.00 | xxxx | 1278 |
| ATOM | 1279 | CD2 | LEU | A | 166 | 61.331 | 6.689 | 81.686 | 1.00 | 0.00 | xxxx | 1279 |
| ATOM | 1280 | N | ASN | A | 167 | 61.932 | 11.393 | 79.281 | 1.00 | 0.00 | xxxx | 1280 |
| ATOM | 1281 | CA | ASN | A | 167 | 61.263 | 12.636 | 78.902 | 1.00 | 0.00 | xxxx | 1281 |
| ATOM | 1282 | C | ASN | A | 167 | 60.872 | 12.639 | 77.421 | 1.00 | 0.00 | xxxx | 1282 |
| ATOM | 1283 | O | ASN | A | 167 | 59.788 | 13.121 | 77.071 | 1.00 | 0.00 | xxxx | 1283 |
| ATOM | 1284 | CB | ASN | A | 167 | 62.147 | 13.848 | 79.210 | 1.00 | 0.00 | xxxx | 1284 |
| ATOM | 1285 | CG | ASN | A | 167 | 62.376 | 14.059 | 80.705 | 1.00 | 0.00 | xxxx | 1285 |
| ATOM | 1286 | OD1 | ASN | A | 167 | 61.698 | 13.473 | 81.558 | 1.00 | 0.00 | xxxx | 1286 |
| ATOM | 1287 | ND2 | ASN | A | 167 | 63.329 | 14.915 | 81.024 | 1.00 | 0.00 | xxxx | 1287 |
| ATOM | 1288 | N | ASP | A | 168 | 61.730 | 12.088 | 76.558 | 1.00 | 0.00 | xxxx | 1288 |
| ATOM | 1289 | CA | ASP | A | 168 | 61.453 | 12.062 | 75.119 | 1.00 | 0.00 | xxxx | 1289 |
| ATOM | 1290 | C | ASP | A | 168 | 60.230 | 11.206 | 74.833 | 1.00 | 0.00 | xxxx | 1290 |
| ATOM | 1291 | O | ASP | A | 168 | 59.505 | 11.452 | 73.863 | 1.00 | 0.00 | xxxx | 1291 |
| ATOM | 1292 | CB | ASP | A | 168 | 62.658 | 11.534 | 74.332 | 1.00 | 0.00 | xxxx | 1292 |
| ATOM | 1293 | CG | ASP | A | 168 | 63.759 | 12.576 | 74.153 | 1.00 | 0.00 | xxxx | 1293 |
| ATOM | 1294 | OD1 | ASP | A | 168 | 63.522 | 13.772 | 74.436 | 1.00 | 0.00 | xxxx | 1294 |
| ATOM | 1295 | OD2 | ASP | A | 168 | 64.861 | 12.194 | 73.707 | 1.00 | 0.00 | xxxx | 1295 |
| ATOM | 1296 | N | LYS | A | 169 | 60.003 | 10.207 | 75.685 | 1.00 | 0.00 | xxxx | 1296 |
| ATOM | 1297 | CA | LYS | A | 169 | 58.855 | 9.311 | 75.552 | 1.00 | 0.00 | xxxx | 1297 |
| ATOM | 1298 | C | LYS | A | 169 | 57.585 | 9.897 | 76.161 | 1.00 | 0.00 | xxxx | 1298 |
| ATOM | 1299 | O | LYS | A | 169 | 56.543 | 9.243 | 76.175 | 1.00 | 0.00 | xxxx | 1299 |
| ATOM | 1300 | CB | LYS | A | 169 | 59.153 | 7.958 | 76.203 | 1.00 | 0.00 | xxxx | 1300 |
| ATOM | 1301 | CG | LYS | A | 169 | 60.182 | 7.127 | 75.469 | 1.00 | 0.00 | xxxx | 1301 |
| ATOM | 1302 | CD | LYS | A | 169 | 60.315 | 5.756 | 76.107 | 1.00 | 0.00 | xxxx | 1302 |
| ATOM | 1303 | CE | LYS | A | 169 | 60.991 | 4.783 | 75.159 | 1.00 | 0.00 | xxxx | 1303 |
| ATOM | 1304 | NZ | LYS | A | 169 | 60.305 | 4.701 | 73.837 | 1.00 | 0.00 | xxxx | 1304 |
| ATOM | 1305 | N | GLY | A | 170 | 57.667 | 11.127 | 76.657 | 1.00 | 0.00 | xxxx | 1305 |
| ATOM | 1306 | CA | GLY | A | 170 | 56.509 | 11.790 | 77.233 | 1.00 | 0.00 | xxxx | 1306 |
| ATOM | 1307 | C | GLY | A | 170 | 56.263 | 11.489 | 78.698 | 1.00 | 0.00 | xxxx | 1307 |
| ATOM | 1308 | O | GLY | A | 170 | 55.179 | 11.753 | 79.220 | 1.00 | 0.00 | xxxx | 1308 |
| ATOM | 1309 | N | ILE | A | 171 | 57.272 | 10.945 | 79.370 | 1.00 | 0.00 | xxxx | 1309 |
| ATOM | 1310 | CA | ILE | A | 171 | 57.172 | 10.698 | 80.804 | 1.00 | 0.00 | xxxx | 1310 |
| ATOM | 1311 | C | ILE | A | 171 | 57.941 | 11.780 | 81.540 | 1.00 | 0.00 | xxxx | 1311 |
| ATOM | 1312 | O | ILE | A | 171 | 59.177 | 11.813 | 81.507 | 1.00 | 0.00 | xxxx | 1312 |
| ATOM | 1313 | CB | ILE | A | 171 | 57.683 | 9.305 | 81.178 | 1.00 | 0.00 | xxxx | 1313 |
| ATOM | 1314 | CG1 | ILE | A | 171 | 56.891 | 8.229 | 80.423 | 1.00 | 0.00 | xxxx | 1314 |
| ATOM | 1315 | CD1 | ILE | A | 171 | 57.515 | 6.856 | 80.496 | 1.00 | 0.00 | xxxx | 1315 |
| ATOM | 1316 | CG2 | ILE | A | 171 | 57.608 | 9.094 | 82.690 | 1.00 | 0.00 | xxxx | 1316 |
| ATOM | 1317 | N | LYS | A | 172 | 57.208 | 12.683 | 82.187 | 1.00 | 0.00 | xxxx | 1317 |
| ATOM | 1318 | CA | LYS | A | 172 | 57.825 | 13.718 | 83.004 | 1.00 | 0.00 | xxxx | 1318 |
| ATOM | 1319 | C | LYS | A | 172 | 58.452 | 13.117 | 84.241 | 1.00 | 0.00 | xxxx | 1319 |
| ATOM | 1320 | O | LYS | A | 172 | 57.946 | 12.143 | 84.804 | 1.00 | 0.00 | xxxx | 1320 |
| ATOM | 1321 | CB | LYS | A | 172 | 56.805 | 14.770 | 83.417 | 1.00 | 0.00 | xxxx | 1321 |
| ATOM | 1322 | CG | LYS | A | 172 | 56.199 | 15.537 | 82.261 | 1.00 | 0.00 | xxxx | 1322 |
| ATOM | 1323 | CD | LYS | A | 172 | 55.181 | 16.549 | 82.783 | 1.00 | 0.00 | xxxx | 1323 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1324 | CE | LYS | A | 172 | 54.534 | 17.326 | 81.650 | 1.00 | 0.00 | xxxx | 1324 |
| ATOM | 1325 | NZ | LYS | A | 172 | 55.536 | 18.060 | 80.827 | 1.00 | 0.00 | xxxx | 1325 |
| ATOM | 1326 | N | THR | A | 173 | 59.548 | 13.723 | 84.672 | 1.00 | 0.00 | xxxx | 1326 |
| ATOM | 1327 | CA | THR | A | 173 | 60.320 | 13.197 | 85.792 | 1.00 | 0.00 | xxxx | 1327 |
| ATOM | 1328 | C | THR | A | 173 | 60.618 | 14.325 | 86.761 | 1.00 | 0.00 | xxxx | 1328 |
| ATOM | 1329 | O | THR | A | 173 | 60.759 | 15.480 | 86.353 | 1.00 | 0.00 | xxxx | 1329 |
| ATOM | 1330 | CB | THR | A | 173 | 61.635 | 12.548 | 85.320 | 1.00 | 0.00 | xxxx | 1330 |
| ATOM | 1331 | OG1 | THR | A | 173 | 62.379 | 13.472 | 84.508 | 1.00 | 0.00 | xxxx | 1331 |
| ATOM | 1332 | CG2 | THR | A | 173 | 61.352 | 11.291 | 84.503 | 1.00 | 0.00 | xxxx | 1332 |
| ATOM | 1333 | N | GLU | A | 174 | 60.673 | 13.995 | 88.047 | 1.00 | 0.00 | xxxx | 1333 |
| ATOM | 1334 | CA | GLU | A | 174 | 61.057 | 14.966 | 89.058 | 1.00 | 0.00 | xxxx | 1334 |
| ATOM | 1335 | C | GLU | A | 174 | 62.205 | 14.408 | 89.878 | 1.00 | 0.00 | xxxx | 1335 |
| ATOM | 1336 | O | GLU | A | 174 | 62.055 | 13.407 | 90.580 | 1.00 | 0.00 | xxxx | 1336 |
| ATOM | 1337 | CB | GLU | A | 174 | 59.894 | 15.330 | 89.985 | 1.00 | 0.00 | xxxx | 1337 |
| ATOM | 1338 | CG | GLU | A | 174 | 60.320 | 16.389 | 91.020 | 1.00 | 0.00 | xxxx | 1338 |
| ATOM | 1339 | CD | GLU | A | 174 | 59.264 | 16.733 | 92.064 | 1.00 | 0.00 | xxxx | 1339 |
| ATOM | 1340 | OE1 | GLU | A | 174 | 58.196 | 16.086 | 92.123 | 1.00 | 0.00 | xxxx | 1340 |
| ATOM | 1341 | OE2 | GLU | A | 174 | 59.516 | 17.671 | 92.848 | 1.00 | 0.00 | xxxx | 1341 |
| ATOM | 1342 | N | GLN | A | 175 | 63.350 | 15.074 | 89.787 | 1.00 | 0.00 | xxxx | 1342 |
| ATOM | 1343 | CA | GLN | A | 175 | 64.556 | 14.661 | 90.510 | 1.00 | 0.00 | xxxx | 1343 |
| ATOM | 1344 | C | GLN | A | 175 | 64.469 | 15.050 | 91.980 | 1.00 | 0.00 | xxxx | 1344 |
| ATOM | 1345 | O | GLN | A | 175 | 64.574 | 16.234 | 92.315 | 1.00 | 0.00 | xxxx | 1345 |
| ATOM | 1346 | CB | GLN | A | 175 | 65.783 | 15.304 | 89.874 | 1.00 | 0.00 | xxxx | 1346 |
| ATOM | 1347 | CG | GLN | A | 175 | 67.103 | 14.879 | 90.484 | 1.00 | 0.00 | xxxx | 1347 |
| ATOM | 1348 | CD | GLN | A | 175 | 68.250 | 15.684 | 89.923 | 1.00 | 0.00 | xxxx | 1348 |
| ATOM | 1349 | OE1 | GLN | A | 175 | 68.903 | 16.442 | 90.641 | 1.00 | 0.00 | xxxx | 1349 |
| ATOM | 1350 | NE2 | GLN | A | 175 | 68.483 | 15.545 | 88.629 | 1.00 | 0.00 | xxxx | 1350 |
| ATOM | 1351 | N | LEU | A | 176 | 64.262 | 14.067 | 92.850 | 1.00 | 0.00 | xxxx | 1351 |
| ATOM | 1352 | CA | LEU | A | 176 | 64.183 | 14.350 | 94.293 | 1.00 | 0.00 | xxxx | 1352 |
| ATOM | 1353 | C | LEU | A | 176 | 65.546 | 14.387 | 94.955 | 1.00 | 0.00 | xxxx | 1353 |
| ATOM | 1354 | O | LEU | A | 176 | 65.767 | 15.180 | 95.866 | 1.00 | 0.00 | xxxx | 1354 |
| ATOM | 1355 | CB | LEU | A | 176 | 63.312 | 13.305 | 94.999 | 1.00 | 0.00 | xxxx | 1355 |
| ATOM | 1356 | CG | LEU | A | 176 | 61.856 | 13.217 | 94.549 | 1.00 | 0.00 | xxxx | 1356 |
| ATOM | 1357 | CD1 | LEU | A | 176 | 61.175 | 12.071 | 95.308 | 1.00 | 0.00 | xxxx | 1357 |
| ATOM | 1358 | CD2 | LEU | A | 176 | 61.139 | 14.546 | 94.788 | 1.00 | 0.00 | xxxx | 1358 |
| ATOM | 1359 | N | GLN | A | 177 | 66.435 | 13.483 | 94.545 | 1.00 | 0.00 | xxxx | 1359 |
| ATOM | 1360 | CA | GLN | A | 177 | 67.817 | 13.462 | 95.029 | 1.00 | 0.00 | xxxx | 1360 |
| ATOM | 1361 | C | GLN | A | 177 | 68.693 | 12.943 | 93.896 | 1.00 | 0.00 | xxxx | 1361 |
| ATOM | 1362 | O | GLN | A | 177 | 68.228 | 12.150 | 93.071 | 1.00 | 0.00 | xxxx | 1362 |
| ATOM | 1363 | CB | GLN | A | 177 | 68.011 | 12.551 | 96.262 | 1.00 | 0.00 | xxxx | 1363 |
| ATOM | 1364 | CG | GLN | A | 177 | 66.981 | 12.631 | 97.393 | 1.00 | 0.00 | xxxx | 1364 |
| ATOM | 1365 | CD | GLN | A | 177 | 67.126 | 13.831 | 98.332 | 1.00 | 0.00 | xxxx | 1365 |
| ATOM | 1366 | OE1 | GLN | A | 177 | 66.270 | 14.034 | 99.194 | 1.00 | 0.00 | xxxx | 1366 |
| ATOM | 1367 | NE2 | GLN | A | 177 | 68.204 | 14.605 | 98.189 | 1.00 | 0.00 | xxxx | 1367 |
| ATOM | 1368 | N | LEU | A | 178 | 69.944 | 13.386 | 93.865 | 1.00 | 0.00 | xxxx | 1368 |
| ATOM | 1369 | CA | LEU | A | 178 | 70.942 | 12.869 | 92.930 | 1.00 | 0.00 | xxxx | 1369 |
| ATOM | 1370 | C | LEU | A | 178 | 72.319 | 13.073 | 93.530 | 1.00 | 0.00 | xxxx | 1370 |
| ATOM | 1371 | O | LEU | A | 178 | 72.658 | 14.177 | 93.954 | 1.00 | 0.00 | xxxx | 1371 |
| ATOM | 1372 | CB | LEU | A | 178 | 70.848 | 13.555 | 91.561 | 1.00 | 0.00 | xxxx | 1372 |
| ATOM | 1373 | CG | LEU | A | 178 | 71.737 | 12.993 | 90.440 | 1.00 | 0.00 | xxxx | 1373 |
| ATOM | 1374 | CD1 | LEU | A | 178 | 71.094 | 13.273 | 89.093 | 1.00 | 0.00 | xxxx | 1374 |
| ATOM | 1375 | CD2 | LEU | A | 178 | 73.146 | 13.573 | 90.458 | 1.00 | 0.00 | xxxx | 1375 |
| ATOM | 1376 | N | ASP | A | 179 | 73.110 | 12.011 | 93.565 | 1.00 | 0.00 | xxxx | 1376 |
| ATOM | 1377 | CA | ASP | A | 179 | 74.449 | 12.118 | 94.146 | 1.00 | 0.00 | xxxx | 1377 |
| ATOM | 1378 | C | ASP | A | 179 | 75.281 | 10.939 | 93.713 | 1.00 | 0.00 | xxxx | 1378 |
| ATOM | 1379 | O | ASP | A | 179 | 74.745 | 9.903 | 93.320 | 1.00 | 0.00 | xxxx | 1379 |
| ATOM | 1380 | CB | ASP | A | 179 | 74.373 | 12.174 | 95.674 | 1.00 | 0.00 | xxxx | 1380 |
| ATOM | 1381 | CG | ASP | A | 179 | 75.519 | 12.961 | 96.307 | 1.00 | 0.00 | xxxx | 1381 |
| ATOM | 1382 | OD1 | ASP | A | 179 | 76.586 | 13.168 | 95.674 | 1.00 | 0.00 | xxxx | 1382 |
| ATOM | 1383 | OD2 | ASP | A | 179 | 75.343 | 13.385 | 97.470 | 1.00 | 0.00 | xxxx | 1383 |
| ATOM | 1384 | N | THR | A | 180 | 76.599 | 11.086 | 93.801 | 1.00 | 0.00 | xxxx | 1384 |
| ATOM | 1385 | CA | THR | A | 180 | 77.473 | 9.975 | 93.475 | 1.00 | 0.00 | xxxx | 1385 |
| ATOM | 1386 | C | THR | A | 180 | 77.575 | 9.026 | 94.662 | 1.00 | 0.00 | xxxx | 1386 |
| ATOM | 1387 | O | THR | A | 180 | 77.531 | 9.442 | 95.826 | 1.00 | 0.00 | xxxx | 1387 |
| ATOM | 1388 | CB | THR | A | 180 | 78.880 | 10.457 | 93.069 | 1.00 | 0.00 | xxxx | 1388 |
| ATOM | 1389 | OG1 | THR | A | 180 | 79.674 | 9.327 | 92.674 | 1.00 | 0.00 | xxxx | 1389 |
| ATOM | 1390 | CG2 | THR | A | 180 | 79.568 | 11.183 | 94.230 | 1.00 | 0.00 | xxxx | 1390 |
| ATOM | 1391 | N | ALA | A | 181 | 77.682 | 7.739 | 94.364 | 1.00 | 0.00 | xxxx | 1391 |
| ATOM | 1392 | CA | ALA | A | 181 | 78.063 | 6.770 | 95.369 | 1.00 | 0.00 | xxxx | 1392 |
| ATOM | 1393 | C | ALA | A | 181 | 79.237 | 5.967 | 94.826 | 1.00 | 0.00 | xxxx | 1393 |
| ATOM | 1394 | O | ALA | A | 181 | 79.492 | 4.850 | 95.269 | 1.00 | 0.00 | xxxx | 1394 |
| ATOM | 1395 | CB | ALA | A | 181 | 76.890 | 5.868 | 95.738 | 1.00 | 0.00 | xxxx | 1395 |
| ATOM | 1396 | N | MET | A | 182 | 79.941 | 6.564 | 93.859 | 1.00 | 0.00 | xxxx | 1396 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1397 | CA | MET | A | 182 | 81.259 | 6.101 | 93.418 | 1.00 | 0.00 | xxxx | 1397 |
| ATOM | 1398 | C | MET | A | 182 | 81.306 | 4.625 | 93.052 | 1.00 | 0.00 | xxxx | 1398 |
| ATOM | 1399 | O | MET | A | 182 | 82.284 | 3.931 | 93.358 | 1.00 | 0.00 | xxxx | 1399 |
| ATOM | 1400 | CB | MET | A | 182 | 82.300 | 6.394 | 94.501 | 1.00 | 0.00 | xxxx | 1400 |
| ATOM | 1401 | CG | MET | A | 182 | 82.438 | 7.896 | 94.802 | 1.00 | 0.00 | xxxx | 1401 |
| ATOM | 1402 | SD | MET | A | 182 | 83.054 | 8.899 | 93.419 | 1.00 | 0.00 | xxxx | 1402 |
| ATOM | 1403 | CE | MET | A | 182 | 84.811 | 8.596 | 93.549 | 1.00 | 0.00 | xxxx | 1403 |
| ATOM | 1404 | N | CYS | A | 183 | 80.232 | 4.159 | 92.419 | 1.00 | 0.00 | xxxx | 1404 |
| ATOM | 1405 | CA | CYS | A | 183 | 80.152 | 2.815 | 91.855 | 1.00 | 0.00 | xxxx | 1405 |
| ATOM | 1406 | C | CYS | A | 183 | 80.215 | 1.715 | 92.915 | 1.00 | 0.00 | xxxx | 1406 |
| ATOM | 1407 | O | CYS | A | 183 | 80.418 | 0.555 | 92.578 | 1.00 | 0.00 | xxxx | 1407 |
| ATOM | 1408 | CB | CYS | A | 183 | 81.268 | 2.616 | 90.816 | 1.00 | 0.00 | xxxx | 1408 |
| ATOM | 1409 | SG | CYS | A | 183 | 81.332 | 4.000 | 89.637 | 1.00 | 0.00 | xxxx | 1409 |
| ATOM | 1410 | N | ASP | A | 184 | 79.976 | 2.079 | 94.179 | 1.00 | 0.00 | xxxx | 1410 |
| ATOM | 1411 | CA | ASP | A | 184 | 80.214 | 1.203 | 95.330 | 1.00 | 0.00 | xxxx | 1411 |
| ATOM | 1412 | C | ASP | A | 184 | 78.923 | 0.838 | 96.079 | 1.00 | 0.00 | xxxx | 1412 |
| ATOM | 1413 | O | ASP | A | 184 | 78.117 | 1.714 | 96.375 | 1.00 | 0.00 | xxxx | 1413 |
| ATOM | 1414 | CB | ASP | A | 184 | 81.210 | 1.895 | 96.281 | 1.00 | 0.00 | xxxx | 1414 |
| ATOM | 1415 | CG | ASP | A | 184 | 81.539 | 1.069 | 97.504 | 1.00 | 0.00 | xxxx | 1415 |
| ATOM | 1416 | OD1 | ASP | A | 184 | 82.395 | 0.168 | 97.414 | 1.00 | 0.00 | xxxx | 1416 |
| ATOM | 1417 | OD2 | ASP | A | 184 | 80.969 | 1.338 | 98.574 | 1.00 | 0.00 | xxxx | 1417 |
| ATOM | 1418 | N | THR | A | 185 | 78.740 | −0.444 | 96.401 | 1.00 | 0.00 | xxxx | 1418 |
| ATOM | 1419 | CA | THR | A | 185 | 77.520 | −0.913 | 97.077 | 1.00 | 0.00 | xxxx | 1419 |
| ATOM | 1420 | C | THR | A | 185 | 77.309 | −0.291 | 98.464 | 1.00 | 0.00 | xxxx | 1420 |
| ATOM | 1421 | O | THR | A | 185 | 76.217 | 0.206 | 98.768 | 1.00 | 0.00 | xxxx | 1421 |
| ATOM | 1422 | CB | THR | A | 185 | 77.519 | −2.460 | 97.230 | 1.00 | 0.00 | xxxx | 1422 |
| ATOM | 1423 | OG1 | THR | A | 185 | 77.522 | −3.072 | 95.931 | 1.00 | 0.00 | xxxx | 1423 |
| ATOM | 1424 | CG2 | THR | A | 185 | 76.289 | −2.934 | 97.982 | 1.00 | 0.00 | xxxx | 1424 |
| ATOM | 1425 | N | ALA | A | 186 | 78.331 | −0.330 | 99.312 | 1.00 | 0.00 | xxxx | 1425 |
| ATOM | 1426 | CA | ALA | A | 186 | 78.187 | 0.212 | 100.664 | 1.00 | 0.00 | xxxx | 1426 |
| ATOM | 1427 | C | ALA | A | 186 | 77.948 | 1.725 | 100.657 | 1.00 | 0.00 | xxxx | 1427 |
| ATOM | 1428 | O | ALA | A | 186 | 77.117 | 2.229 | 101.429 | 1.00 | 0.00 | xxxx | 1428 |
| ATOM | 1429 | CB | ALA | A | 186 | 79.412 | −0.129 | 101.507 | 1.00 | 0.00 | xxxx | 1429 |
| ATOM | 1430 | N | GLN | A | 187 | 78.647 | 2.454 | 99.792 | 1.00 | 0.00 | xxxx | 1430 |
| ATOM | 1431 | CA | GLN | A | 187 | 78.406 | 3.895 | 99.687 | 1.00 | 0.00 | xxxx | 1431 |
| ATOM | 1432 | C | GLN | A | 187 | 76.977 | 4.178 | 99.226 | 1.00 | 0.00 | xxxx | 1432 |
| ATOM | 1433 | O | GLN | A | 187 | 76.335 | 5.126 | 99.694 | 1.00 | 0.00 | xxxx | 1433 |
| ATOM | 1434 | CB | GLN | A | 187 | 79.390 | 4.562 | 98.725 | 1.00 | 0.00 | xxxx | 1434 |
| ATOM | 1435 | CG | GLN | A | 187 | 80.818 | 4.676 | 99.221 | 1.00 | 0.00 | xxxx | 1435 |
| ATOM | 1436 | CD | GLN | A | 187 | 81.613 | 5.683 | 98.408 | 1.00 | 0.00 | xxxx | 1436 |
| ATOM | 1437 | OE1 | GLN | A | 187 | 81.082 | 6.715 | 97.987 | 1.00 | 0.00 | xxxx | 1437 |
| ATOM | 1438 | NE2 | GLN | A | 187 | 82.885 | 5.385 | 98.173 | 1.00 | 0.00 | xxxx | 1438 |
| ATOM | 1439 | N | ALA | A | 188 | 76.470 | 3.356 | 98.313 | 1.00 | 0.00 | xxxx | 1439 |
| ATOM | 1440 | CA | ALA | A | 188 | 75.100 | 3.522 | 97.820 | 1.00 | 0.00 | xxxx | 1440 |
| ATOM | 1441 | C | ALA | A | 188 | 74.053 | 3.210 | 98.891 | 1.00 | 0.00 | xxxx | 1441 |
| ATOM | 1442 | O | ALA | A | 188 | 73.034 | 3.888 | 98.979 | 1.00 | 0.00 | xxxx | 1442 |
| ATOM | 1443 | CB | ALA | A | 188 | 74.877 | 2.642 | 96.604 | 1.00 | 0.00 | xxxx | 1443 |
| ATOM | 1444 | N | LYS | A | 189 | 74.302 | 2.173 | 99.690 | 1.00 | 0.00 | xxxx | 1444 |
| ATOM | 1445 | CA | LYS | A | 189 | 73.401 | 1.832 | 100.789 | 1.00 | 0.00 | xxxx | 1445 |
| ATOM | 1446 | C | LYS | A | 189 | 73.337 | 3.005 | 101.764 | 1.00 | 0.00 | xxxx | 1446 |
| ATOM | 1447 | O | LYS | A | 189 | 72.250 | 3.385 | 102.219 | 1.00 | 0.00 | xxxx | 1447 |
| ATOM | 1448 | CB | LYS | A | 189 | 73.860 | 0.551 | 101.506 | 1.00 | 0.00 | xxxx | 1448 |
| ATOM | 1449 | CG | LYS | A | 189 | 72.930 | 0.137 | 102.642 | 1.00 | 0.00 | xxxx | 1449 |
| ATOM | 1450 | CD | LYS | A | 189 | 73.420 | −1.084 | 103.397 | 1.00 | 0.00 | xxxx | 1450 |
| ATOM | 1451 | CE | LYS | A | 189 | 72.458 | −1.431 | 104.524 | 1.00 | 0.00 | xxxx | 1451 |
| ATOM | 1452 | NZ | LYS | A | 189 | 72.884 | −2.636 | 105.292 | 1.00 | 0.00 | xxxx | 1452 |
| ATOM | 1453 | N | ASP | A | 190 | 74.502 | 3.586 | 102.066 | 1.00 | 0.00 | xxxx | 1453 |
| ATOM | 1454 | CA | ASP | A | 190 | 74.553 | 4.737 | 102.971 | 1.00 | 0.00 | xxxx | 1454 |
| ATOM | 1455 | C | ASP | A | 190 | 73.784 | 5.927 | 102.397 | 1.00 | 0.00 | xxxx | 1455 |
| ATOM | 1456 | O | ASP | A | 190 | 73.018 | 6.591 | 103.106 | 1.00 | 0.00 | xxxx | 1456 |
| ATOM | 1457 | CB | ASP | A | 190 | 75.996 | 5.149 | 103.260 | 1.00 | 0.00 | xxxx | 1457 |
| ATOM | 1458 | CG | ASP | A | 190 | 76.070 | 6.413 | 104.082 | 1.00 | 0.00 | xxxx | 1458 |
| ATOM | 1459 | OD1 | ASP | A | 190 | 75.855 | 6.332 | 105.307 | 1.00 | 0.00 | xxxx | 1459 |
| ATOM | 1460 | OD2 | ASP | A | 190 | 76.329 | 7.489 | 103.500 | 1.00 | 0.00 | xxxx | 1460 |
| ATOM | 1461 | N | LYS | A | 191 | 73.983 | 6.197 | 101.113 | 1.00 | 0.00 | xxxx | 1461 |
| ATOM | 1462 | CA | LYS | A | 191 | 73.330 | 7.344 | 100.479 | 1.00 | 0.00 | xxxx | 1462 |
| ATOM | 1463 | C | LYS | A | 191 | 71.811 | 7.147 | 100.415 | 1.00 | 0.00 | xxxx | 1463 |
| ATOM | 1464 | O | LYS | A | 191 | 71.035 | 8.050 | 100.762 | 1.00 | 0.00 | xxxx | 1464 |
| ATOM | 1465 | CB | LYS | A | 191 | 73.908 | 7.553 | 99.072 | 1.00 | 0.00 | xxxx | 1465 |
| ATOM | 1466 | CG | LYS | A | 191 | 73.374 | 8.747 | 98.322 | 1.00 | 0.00 | xxxx | 1466 |
| ATOM | 1467 | CD | LYS | A | 191 | 73.720 | 10.087 | 98.980 | 1.00 | 0.00 | xxxx | 1467 |
| ATOM | 1468 | CE | LYS | A | 191 | 75.228 | 10.258 | 99.200 | 1.00 | 0.00 | xxxx | 1468 |
| ATOM | 1469 | NZ | LYS | A | 191 | 75.550 | 11.651 | 99.690 | 1.00 | 0.00 | xxxx | 1469 |

-continued

| | | | | | | | | | | | | |
|---|---|---|---|---|---|---|---|---|---|---|---|---|
| CA, calcium<br>HOH, Water<br>ACR, Acrylodan<br>K, potassium<br>EDO, ethylene glycol | | | | | | | | | | | | |
| ATOM | 1470 | N | MET | A | 192 | 71.391 | 5.958 | 99.994 | 1.00 | 0.00 | xxxx | 1470 |
| ATOM | 1471 | CA | MET | A | 192 | 69.970 | 5.658 | 99.924 | 1.00 | 0.00 | xxxx | 1471 |
| ATOM | 1472 | C | MET | A | 192 | 69.313 | 5.698 | 101.304 | 1.00 | 0.00 | xxxx | 1472 |
| ATOM | 1473 | O | MET | A | 192 | 68.208 | 6.231 | 101.459 | 1.00 | 0.00 | xxxx | 1473 |
| ATOM | 1474 | CB | MET | A | 192 | 69.752 | 4.289 | 99.270 | 1.00 | 0.00 | xxxx | 1474 |
| ATOM | 1475 | CG | MET | A | 192 | 68.289 | 3.992 | 98.975 | 1.00 | 0.00 | xxxx | 1475 |
| ATOM | 1476 | SD | MET | A | 192 | 67.643 | 5.014 | 97.628 | 1.00 | 0.00 | xxxx | 1476 |
| ATOM | 1477 | CE | MET | A | 192 | 65.900 | 4.966 | 98.028 | 1.00 | 0.00 | xxxx | 1477 |
| ATOM | 1478 | N | ASP | A | 193 | 69.997 | 5.149 | 102.305 | 1.00 | 0.00 | xxxx | 1478 |
| ATOM | 1479 | CA | ASP | A | 193 | 69.495 | 5.202 | 103.671 | 1.00 | 0.00 | xxxx | 1479 |
| ATOM | 1480 | C | ASP | A | 193 | 69.318 | 6.653 | 104.133 | 1.00 | 0.00 | xxxx | 1480 |
| ATOM | 1481 | O | ASP | A | 193 | 68.323 | 6.989 | 104.793 | 1.00 | 0.00 | xxxx | 1481 |
| ATOM | 1482 | CB | ASP | A | 193 | 70.432 | 4.460 | 104.621 | 1.00 | 0.00 | xxxx | 1482 |
| ATOM | 1483 | CG | ASP | A | 193 | 69.987 | 4.572 | 106.057 | 1.00 | 0.00 | xxxx | 1483 |
| ATOM | 1484 | OD1 | ASP | A | 193 | 70.516 | 5.447 | 106.762 | 1.00 | 0.00 | xxxx | 1484 |
| ATOM | 1485 | OD2 | ASP | A | 193 | 69.077 | 3.814 | 106.469 | 1.00 | 0.00 | xxxx | 1485 |
| ATOM | 1486 | N | ALA | A | 194 | 70.274 | 7.516 | 103.797 | 1.00 | 0.00 | xxxx | 1486 |
| ATOM | 1487 | CA | ALA | A | 194 | 70.134 | 8.929 | 104.139 | 1.00 | 0.00 | xxxx | 1487 |
| ATOM | 1488 | C | ALA | A | 194 | 68.870 | 9.526 | 103.503 | 1.00 | 0.00 | xxxx | 1488 |
| ATOM | 1489 | O | ALA | A | 194 | 68.095 | 10.221 | 104.167 | 1.00 | 0.00 | xxxx | 1489 |
| ATOM | 1490 | CB | ALA | A | 194 | 71.377 | 9.712 | 103.703 | 1.00 | 0.00 | xxxx | 1490 |
| ATOM | 1491 | N | TRP | A | 195 | 68.656 | 9.239 | 102.224 | 1.00 | 0.00 | xxxx | 1491 |
| ATOM | 1492 | CA | TRP | A | 195 | 67.502 | 9.766 | 101.511 | 1.00 | 0.00 | xxxx | 1492 |
| ATOM | 1493 | C | TRP | A | 195 | 66.187 | 9.244 | 102.097 | 1.00 | 0.00 | xxxx | 1493 |
| ATOM | 1494 | O | TRP | A | 195 | 65.198 | 9.973 | 102.188 | 1.00 | 0.00 | xxxx | 1494 |
| ATOM | 1495 | CB | TRP | A | 195 | 67.624 | 9.412 | 100.034 | 1.00 | 0.00 | xxxx | 1495 |
| ATOM | 1496 | CG | TRP | A | 195 | 68.764 | 10.131 | 99.346 | 1.00 | 0.00 | xxxx | 1496 |
| ATOM | 1497 | CD1 | TRP | A | 195 | 69.427 | 11.225 | 99.801 | 1.00 | 0.00 | xxxx | 1497 |
| ATOM | 1498 | CD2 | TRP | A | 195 | 69.350 | 9.802 | 98.079 | 1.00 | 0.00 | xxxx | 1498 |
| ATOM | 1499 | NE1 | TRP | A | 195 | 70.403 | 11.602 | 98.894 | 1.00 | 0.00 | xxxx | 1499 |
| ATOM | 1500 | CE2 | TRP | A | 195 | 70.374 | 10.742 | 97.833 | 1.00 | 0.00 | xxxx | 1500 |
| ATOM | 1501 | CE3 | TRP | A | 195 | 69.116 | 8.799 | 97.135 | 1.00 | 0.00 | xxxx | 1501 |
| ATOM | 1502 | CZ2 | TRP | A | 195 | 71.149 | 10.719 | 96.668 | 1.00 | 0.00 | xxxx | 1502 |
| ATOM | 1503 | CZ3 | TRP | A | 195 | 69.898 | 8.779 | 95.971 | 1.00 | 0.00 | xxxx | 1503 |
| ATOM | 1504 | CH2 | TRP | A | 195 | 70.892 | 9.733 | 95.755 | 1.00 | 0.00 | xxxx | 1504 |
| ATOM | 1505 | N | LEU | A | 196 | 66.189 | 7.980 | 102.514 | 1.00 | 0.00 | xxxx | 1505 |
| ATOM | 1506 | CA | LEU | A | 196 | 65.022 | 7.406 | 103.164 | 1.00 | 0.00 | xxxx | 1506 |
| ATOM | 1507 | C | LEU | A | 196 | 64.808 | 7.957 | 104.566 | 1.00 | 0.00 | xxxx | 1507 |
| ATOM | 1508 | O | LEU | A | 196 | 63.775 | 7.692 | 105.177 | 1.00 | 0.00 | xxxx | 1508 |
| ATOM | 1509 | CB | LEU | A | 196 | 65.141 | 5.879 | 103.217 | 1.00 | 0.00 | xxxx | 1509 |
| ATOM | 1510 | CG | LEU | A | 196 | 65.043 | 5.236 | 101.832 | 1.00 | 0.00 | xxxx | 1510 |
| ATOM | 1511 | CD1 | LEU | A | 196 | 65.477 | 3.771 | 101.881 | 1.00 | 0.00 | xxxx | 1511 |
| ATOM | 1512 | CD2 | LEU | A | 196 | 63.614 | 5.360 | 101.304 | 1.00 | 0.00 | xxxx | 1512 |
| ATOM | 1513 | N | SER | A | 197 | 65.792 | 8.703 | 105.073 | 1.00 | 0.00 | xxxx | 1513 |
| ATOM | 1514 | CA | SER | A | 197 | 65.721 | 9.321 | 106.390 | 1.00 | 0.00 | xxxx | 1514 |
| ATOM | 1515 | C | SER | A | 197 | 65.516 | 10.830 | 106.277 | 1.00 | 0.00 | xxxx | 1515 |
| ATOM | 1516 | O | SER | A | 197 | 65.524 | 11.527 | 107.294 | 1.00 | 0.00 | xxxx | 1516 |
| ATOM | 1517 | CB | SER | A | 197 | 66.992 | 9.043 | 107.198 | 1.00 | 0.00 | xxxx | 1517 |
| ATOM | 1518 | OG | SER | A | 197 | 67.260 | 7.649 | 107.316 | 1.00 | 0.00 | xxxx | 1518 |
| ATOM | 1519 | N | GLY | A | 198 | 65.321 | 11.322 | 105.050 | 1.00 | 0.00 | xxxx | 1519 |
| ATOM | 1520 | CA | GLY | A | 198 | 65.148 | 12.751 | 104.807 | 1.00 | 0.00 | xxxx | 1520 |
| ATOM | 1521 | C | GLY | A | 198 | 63.742 | 13.078 | 104.341 | 1.00 | 0.00 | xxxx | 1521 |
| ATOM | 1522 | O | GLY | A | 198 | 62.900 | 12.186 | 104.216 | 1.00 | 0.00 | xxxx | 1522 |
| ATOM | 1523 | N | PRO | A | 199 | 63.478 | 14.363 | 104.074 | 1.00 | 0.00 | xxxx | 1523 |
| ATOM | 1524 | CA | PRO | A | 199 | 62.106 | 14.833 | 103.839 | 1.00 | 0.00 | xxxx | 1524 |
| ATOM | 1525 | C | PRO | A | 199 | 61.464 | 14.338 | 102.545 | 1.00 | 0.00 | xxxx | 1525 |
| ATOM | 1526 | O | PRO | A | 199 | 60.239 | 14.456 | 102.417 | 1.00 | 0.00 | xxxx | 1526 |
| ATOM | 1527 | CB | PRO | A | 199 | 62.254 | 16.364 | 103.800 | 1.00 | 0.00 | xxxx | 1527 |
| ATOM | 1528 | CG | PRO | A | 199 | 63.581 | 16.657 | 104.428 | 1.00 | 0.00 | xxxx | 1528 |
| ATOM | 1529 | CD | PRO | A | 199 | 64.450 | 15.464 | 104.162 | 1.00 | 0.00 | xxxx | 1529 |
| ATOM | 1530 | N | ASN | A | 200 | 62.245 | 13.815 | 101.604 | 1.00 | 0.00 | xxxx | 1530 |
| ATOM | 1531 | CA | ASN | A | 200 | 61.655 | 13.290 | 100.370 | 1.00 | 0.00 | xxxx | 1531 |
| ATOM | 1532 | C | ASN | A | 200 | 61.381 | 11.791 | 100.423 | 1.00 | 0.00 | xxxx | 1532 |
| ATOM | 1533 | O | ASN | A | 200 | 60.945 | 11.220 | 99.420 | 1.00 | 0.00 | xxxx | 1533 |
| ATOM | 1534 | CB | ASN | A | 200 | 62.557 | 13.582 | 99.166 | 1.00 | 0.00 | xxxx | 1534 |
| ATOM | 1535 | CG | ASN | A | 200 | 62.652 | 15.068 | 98.858 | 1.00 | 0.00 | xxxx | 1535 |
| ATOM | 1536 | OD1 | ASN | A | 200 | 61.657 | 15.795 | 98.911 | 1.00 | 0.00 | xxxx | 1536 |
| ATOM | 1537 | ND2 | ASN | A | 200 | 63.854 | 15.527 | 98.550 | 1.00 | 0.00 | xxxx | 1537 |
| ATOM | 1538 | N | ALA | A | 201 | 61.644 | 11.147 | 101.563 | 1.00 | 0.00 | xxxx | 1538 |
| ATOM | 1539 | CA | ALA | A | 201 | 61.533 | 9.689 | 101.645 | 1.00 | 0.00 | xxxx | 1539 |
| ATOM | 1540 | C | ALA | A | 201 | 60.185 | 9.168 | 101.122 | 1.00 | 0.00 | xxxx | 1540 |
| ATOM | 1541 | O | ALA | A | 201 | 60.157 | 8.216 | 100.329 | 1.00 | 0.00 | xxxx | 1541 |
| ATOM | 1542 | CB | ALA | A | 201 | 61.745 | 9.228 | 103.059 | 1.00 | 0.00 | xxxx | 1542 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1543 | N | ASN | A | 202 | 59.097 | 9.813 | 101.547 | 1.00 | 0.00 | xxxx | 1543 |
| ATOM | 1544 | CA | ASN | A | 202 | 57.746 | 9.334 | 101.237 | 1.00 | 0.00 | xxxx | 1544 |
| ATOM | 1545 | C | ASN | A | 202 | 57.364 | 9.580 | 99.785 | 1.00 | 0.00 | xxxx | 1545 |
| ATOM | 1546 | O | ASN | A | 202 | 56.394 | 8.997 | 99.291 | 1.00 | 0.00 | xxxx | 1546 |
| ATOM | 1547 | CB | ASN | A | 202 | 56.705 | 9.988 | 102.165 | 1.00 | 0.00 | xxxx | 1547 |
| ATOM | 1548 | CG | ASN | A | 202 | 56.603 | 11.501 | 101.979 | 1.00 | 0.00 | xxxx | 1548 |
| ATOM | 1549 | OD1 | ASN | A | 202 | 57.530 | 12.243 | 102.302 | 1.00 | 0.00 | xxxx | 1549 |
| ATOM | 1550 | ND2 | ASN | A | 202 | 55.465 | 11.961 | 101.474 | 1.00 | 0.00 | xxxx | 1550 |
| ATOM | 1551 | N | LYS | A | 203 | 58.134 | 10.428 | 99.110 | 1.00 | 0.00 | xxxx | 1551 |
| ATOM | 1552 | CA | LYS | A | 203 | 57.851 | 10.816 | 97.730 | 1.00 | 0.00 | xxxx | 1552 |
| ATOM | 1553 | C | LYS | A | 203 | 58.576 | 9.978 | 96.686 | 1.00 | 0.00 | xxxx | 1553 |
| ATOM | 1554 | O | LYS | A | 203 | 58.195 | 10.012 | 95.514 | 1.00 | 0.00 | xxxx | 1554 |
| ATOM | 1555 | CB | LYS | A | 203 | 58.218 | 12.287 | 97.509 | 1.00 | 0.00 | xxxx | 1555 |
| ATOM | 1556 | CG | LYS | A | 203 | 57.499 | 13.250 | 98.431 | 1.00 | 0.00 | xxxx | 1556 |
| ATOM | 1557 | CD | LYS | A | 203 | 57.973 | 14.674 | 98.189 | 1.00 | 0.00 | xxxx | 1557 |
| ATOM | 1558 | CE | LYS | A | 203 | 58.639 | 15.242 | 99.431 | 1.00 | 0.00 | xxxx | 1558 |
| ATOM | 1559 | NZ | LYS | A | 203 | 57.791 | 15.088 | 100.650 | 1.00 | 0.00 | xxxx | 1559 |
| ATOM | 1560 | N | ILE | A | 204 | 59.623 | 9.250 | 97.090 | 1.00 | 0.00 | xxxx | 1560 |
| ATOM | 1561 | CA | ILE | A | 204 | 60.423 | 8.457 | 96.146 | 1.00 | 0.00 | xxxx | 1561 |
| ATOM | 1562 | C | ILE | A | 204 | 59.602 | 7.349 | 95.500 | 1.00 | 0.00 | xxxx | 1562 |
| ATOM | 1563 | O | ILE | A | 204 | 59.039 | 6.510 | 96.207 | 1.00 | 0.00 | xxxx | 1563 |
| ATOM | 1564 | CB | ILE | A | 204 | 61.645 | 7.841 | 96.839 | 1.00 | 0.00 | xxxx | 1564 |
| ATOM | 1565 | CG1 | ILE | A | 204 | 62.522 | 8.943 | 97.425 | 1.00 | 0.00 | xxxx | 1565 |
| ATOM | 1566 | CD1 | ILE | A | 204 | 63.655 | 8.425 | 98.336 | 1.00 | 0.00 | xxxx | 1566 |
| ATOM | 1567 | CG2 | ILE | A | 204 | 62.435 | 6.991 | 95.839 | 1.00 | 0.00 | xxxx | 1567 |
| ATOM | 1568 | N | GLU | A | 205 | 59.555 | 7.333 | 94.165 | 1.00 | 0.00 | xxxx | 1568 |
| ATOM | 1569 | CA | GLU | A | 205 | 58.783 | 6.322 | 93.451 | 1.00 | 0.00 | xxxx | 1569 |
| ATOM | 1570 | C | GLU | A | 205 | 59.667 | 5.317 | 92.719 | 1.00 | 0.00 | xxxx | 1570 |
| ATOM | 1571 | O | GLU | A | 205 | 59.304 | 4.147 | 92.612 | 1.00 | 0.00 | xxxx | 1571 |
| ATOM | 1572 | CB | GLU | A | 205 | 57.816 | 6.995 | 92.459 | 1.00 | 0.00 | xxxx | 1572 |
| ATOM | 1573 | CG | GLU | A | 205 | 56.791 | 7.866 | 93.156 | 1.00 | 0.00 | xxxx | 1573 |
| ATOM | 1574 | CD | GLU | A | 205 | 55.895 | 8.673 | 92.223 | 1.00 | 0.00 | xxxx | 1574 |
| ATOM | 1575 | OE1 | GLU | A | 205 | 56.191 | 8.828 | 91.021 | 1.00 | 0.00 | xxxx | 1575 |
| ATOM | 1576 | OE2 | GLU | A | 205 | 54.874 | 9.172 | 92.719 | 1.00 | 0.00 | xxxx | 1576 |
| ATOM | 1577 | N | VAL | A | 206 | 60.811 | 5.774 | 92.213 | 1.00 | 0.00 | xxxx | 1577 |
| ATOM | 1578 | CA | VAL | A | 206 | 61.734 | 4.913 | 91.459 | 1.00 | 0.00 | xxxx | 1578 |
| ATOM | 1579 | C | VAL | A | 206 | 63.168 | 5.264 | 91.838 | 1.00 | 0.00 | xxxx | 1579 |
| ATOM | 1580 | O | VAL | A | 206 | 63.503 | 6.441 | 91.935 | 1.00 | 0.00 | xxxx | 1580 |
| ATOM | 1581 | CB | VAL | A | 206 | 61.525 | 5.069 | 89.927 | 1.00 | 0.00 | xxxx | 1581 |
| ATOM | 1582 | CG1 | VAL | A | 206 | 62.548 | 4.245 | 89.139 | 1.00 | 0.00 | xxxx | 1582 |
| ATOM | 1583 | CG2 | VAL | A | 206 | 60.096 | 4.661 | 89.499 | 1.00 | 0.00 | xxxx | 1583 |
| ATOM | 1584 | N | VAL | A | 207 | 64.011 | 4.250 | 92.037 | 1.00 | 0.00 | xxxx | 1584 |
| ATOM | 1585 | CA | VAL | A | 207 | 65.445 | 4.454 | 92.239 | 1.00 | 0.00 | xxxx | 1585 |
| ATOM | 1586 | C | VAL | A | 207 | 66.179 | 4.084 | 90.958 | 1.00 | 0.00 | xxxx | 1586 |
| ATOM | 1587 | O | VAL | A | 207 | 66.022 | 2.963 | 90.447 | 1.00 | 0.00 | xxxx | 1587 |
| ATOM | 1588 | CB | VAL | A | 207 | 65.991 | 3.618 | 93.404 | 1.00 | 0.00 | xxxx | 1588 |
| ATOM | 1589 | CG1 | VAL | A | 207 | 67.508 | 3.828 | 93.547 | 1.00 | 0.00 | xxxx | 1589 |
| ATOM | 1590 | CG2 | VAL | A | 207 | 65.272 | 3.946 | 94.703 | 1.00 | 0.00 | xxxx | 1590 |
| ATOM | 1591 | N | ILE | A | 208 | 66.982 | 5.022 | 90.448 | 1.00 | 0.00 | xxxx | 1591 |
| ATOM | 1592 | CA | ILE | A | 208 | 67.799 | 4.793 | 89.254 | 1.00 | 0.00 | xxxx | 1592 |
| ATOM | 1593 | C | ILE | A | 208 | 69.268 | 4.780 | 89.640 | 1.00 | 0.00 | xxxx | 1593 |
| ATOM | 1594 | O | ILE | A | 208 | 69.739 | 5.726 | 90.263 | 1.00 | 0.00 | xxxx | 1594 |
| ATOM | 1595 | CB | ILE | A | 208 | 67.549 | 5.872 | 88.194 | 1.00 | 0.00 | xxxx | 1595 |
| ATOM | 1596 | CG1 | ILE | A | 208 | 66.056 | 5.937 | 87.844 | 1.00 | 0.00 | xxxx | 1596 |
| ATOM | 1597 | CD1 | ILE | A | 208 | 65.698 | 7.103 | 86.935 | 1.00 | 0.00 | xxxx | 1597 |
| ATOM | 1598 | CG2 | ILE | A | 208 | 68.438 | 5.621 | 86.957 | 1.00 | 0.00 | xxxx | 1598 |
| ATOM | 1599 | N | ALA | A | 209 | 69.999 | 3.721 | 89.294 | 1.00 | 0.00 | xxxx | 1599 |
| ATOM | 1600 | CA | ALA | A | 209 | 71.437 | 3.691 | 89.582 | 1.00 | 0.00 | xxxx | 1600 |
| ATOM | 1601 | C | ALA | A | 209 | 72.264 | 3.519 | 88.307 | 1.00 | 0.00 | xxxx | 1601 |
| ATOM | 1602 | O | ALA | A | 209 | 71.869 | 2.778 | 87.405 | 1.00 | 0.00 | xxxx | 1602 |
| ATOM | 1603 | CB | ALA | A | 209 | 71.766 | 2.567 | 90.573 | 1.00 | 0.00 | xxxx | 1603 |
| ATOM | 1604 | N | ASN | A | 210 | 73.415 | 4.187 | 88.240 | 1.00 | 0.00 | xxxx | 1604 |
| ATOM | 1605 | CA | ASN | A | 210 | 74.296 | 4.064 | 87.076 | 1.00 | 0.00 | xxxx | 1605 |
| ATOM | 1606 | C | ASN | A | 210 | 74.921 | 2.682 | 86.965 | 1.00 | 0.00 | xxxx | 1606 |
| ATOM | 1607 | O | ASN | A | 210 | 75.438 | 2.334 | 85.907 | 1.00 | 0.00 | xxxx | 1607 |
| ATOM | 1608 | CB | ASN | A | 210 | 75.461 | 5.062 | 87.115 | 1.00 | 0.00 | xxxx | 1608 |
| ATOM | 1609 | CG | ASN | A | 210 | 75.095 | 6.511 | 86.761 | 1.00 | 0.00 | xxxx | 1609 |
| ATOM | 1610 | OD1 | ASN | A | 210 | 75.978 | 7.361 | 86.862 | 1.00 | 0.00 | xxxx | 1610 |
| ATOM | 1611 | ND2 | ASN | A | 210 | 73.853 | 6.799 | 86.348 | 1.00 | 0.00 | xxxx | 1611 |
| ATOM | 1612 | N | ASN | A | 211 | 74.967 | 1.918 | 88.058 | 1.00 | 0.00 | xxxx | 1612 |
| ATOM | 1613 | CA | ASN | A | 211 | 75.459 | 0.541 | 87.934 | 1.00 | 0.00 | xxxx | 1613 |
| ATOM | 1614 | C | ASN | A | 211 | 74.811 | −0.377 | 88.967 | 1.00 | 0.00 | xxxx | 1614 |
| ATOM | 1615 | O | ASN | A | 211 | 74.096 | 0.077 | 89.878 | 1.00 | 0.00 | xxxx | 1615 |

-continued

| | | | | | | | | | | | |
|---|---|---|---|---|---|---|---|---|---|---|---|
| CA, calcium<br>HOH, Water<br>ACR, Acrylodan<br>K, potassium<br>EDO, ethylene glycol | | | | | | | | | | | |
| ATOM | 1616 | CB | ASN | A | 211 | 77.011 | 0.482 | 87.984 | 1.00 | 0.00 xxxx | 1616 |
| ATOM | 1617 | CG | ASN | A | 211 | 77.609 | 0.592 | 89.395 | 1.00 | 0.00 xxxx | 1617 |
| ATOM | 1618 | OD1 | ASN | A | 211 | 76.925 | 0.869 | 90.383 | 1.00 | 0.00 xxxx | 1618 |
| ATOM | 1619 | ND2 | ASN | A | 211 | 78.929 | 0.407 | 89.473 | 1.00 | 0.00 xxxx | 1619 |
| ATOM | 1620 | N | ASP | A | 212 | 75.007 | −1.674 | 88.780 | 1.00 | 0.00 xxxx | 1620 |
| ATOM | 1621 | CA | ASP | A | 212 | 74.353 | −2.659 | 89.644 | 1.00 | 0.00 xxxx | 1621 |
| ATOM | 1622 | C | ASP | A | 212 | 74.900 | −2.644 | 91.056 | 1.00 | 0.00 xxxx | 1622 |
| ATOM | 1623 | O | ASP | A | 212 | 74.155 | −2.907 | 91.989 | 1.00 | 0.00 xxxx | 1623 |
| ATOM | 1624 | CB | ASP | A | 212 | 74.504 | −4.073 | 89.085 | 1.00 | 0.00 xxxx | 1624 |
| ATOM | 1625 | CG | ASP | A | 212 | 73.580 | −4.354 | 87.923 | 1.00 | 0.00 xxxx | 1625 |
| ATOM | 1626 | OD1 | ASP | A | 212 | 72.644 | −3.571 | 87.653 | 1.00 | 0.00 xxxx | 1626 |
| ATOM | 1627 | OD2 | ASP | A | 212 | 73.801 | −5.394 | 87.285 | 1.00 | 0.00 xxxx | 1627 |
| ATOM | 1628 | N | ALA | A | 213 | 76.201 | −2.392 | 91.216 | 1.00 | 0.00 xxxx | 1628 |
| ATOM | 1629 | CA | ALA | A | 213 | 76.769 | −2.347 | 92.563 | 1.00 | 0.00 xxxx | 1629 |
| ATOM | 1630 | C | ALA | A | 213 | 75.986 | −1.340 | 93.403 | 1.00 | 0.00 xxxx | 1630 |
| ATOM | 1631 | O | ALA | A | 213 | 75.579 | −1.630 | 94.539 | 1.00 | 0.00 xxxx | 1631 |
| ATOM | 1632 | CB | ALA | A | 213 | 78.250 | −1.988 | 92.519 | 1.00 | 0.00 xxxx | 1632 |
| ATOM | 1633 | N | MET | A | 214 | 75.725 | −0.174 | 92.827 | 1.00 | 0.00 xxxx | 1633 |
| ATOM | 1634 | CA | MET | A | 214 | 74.991 | 0.841 | 93.567 | 1.00 | 0.00 xxxx | 1634 |
| ATOM | 1635 | C | MET | A | 214 | 73.513 | 0.481 | 93.707 | 1.00 | 0.00 xxxx | 1635 |
| ATOM | 1636 | O | MET | A | 214 | 72.916 | 0.724 | 94.758 | 1.00 | 0.00 xxxx | 1636 |
| ATOM | 1637 | CB | MET | A | 214 | 75.173 | 2.215 | 92.911 | 1.00 | 0.00 xxxx | 1637 |
| ATOM | 1638 | CG | MET | A | 214 | 76.604 | 2.734 | 93.068 | 1.00 | 0.00 xxxx | 1638 |
| ATOM | 1639 | SD | MET | A | 214 | 76.846 | 4.394 | 92.423 | 1.00 | 0.00 xxxx | 1639 |
| ATOM | 1640 | CE | MET | A | 214 | 76.387 | 4.154 | 90.695 | 1.00 | 0.00 xxxx | 1640 |
| ATOM | 1641 | N | ALA | A | 215 | 72.917 | −0.091 | 92.665 | 1.00 | 0.00 xxxx | 1641 |
| ATOM | 1642 | CA | ALA | A | 215 | 71.533 | −0.549 | 92.767 | 1.00 | 0.00 xxxx | 1642 |
| ATOM | 1643 | C | ALA | A | 215 | 71.363 | −1.525 | 93.930 | 1.00 | 0.00 xxxx | 1643 |
| ATOM | 1644 | O | ALA | A | 215 | 70.377 | −1.458 | 94.675 | 1.00 | 0.00 xxxx | 1644 |
| ATOM | 1645 | CB | ALA | A | 215 | 71.087 | −1.196 | 91.455 | 1.00 | 0.00 xxxx | 1645 |
| ATOM | 1646 | N | MET | A | 216 | 72.321 | −2.433 | 94.098 | 1.00 | 0.00 xxxx | 1646 |
| ATOM | 1647 | CA | MET | A | 216 | 72.202 | −3.437 | 95.149 | 1.00 | 0.00 xxxx | 1647 |
| ATOM | 1648 | C | MET | A | 216 | 72.310 | −2.813 | 96.539 | 1.00 | 0.00 xxxx | 1648 |
| ATOM | 1649 | O | MET | A | 216 | 71.693 | −3.301 | 97.484 | 1.00 | 0.00 xxxx | 1649 |
| ATOM | 1650 | CB | MET | A | 216 | 73.251 | −4.534 | 94.967 | 1.00 | 0.00 xxxx | 1650 |
| ATOM | 1651 | CG | MET | A | 216 | 72.994 | −5.385 | 93.737 | 1.00 | 0.00 xxxx | 1651 |
| ATOM | 1652 | SD | MET | A | 216 | 74.066 | −6.832 | 93.600 | 1.00 | 0.00 xxxx | 1652 |
| ATOM | 1653 | CE | MET | A | 216 | 75.688 | −6.071 | 93.652 | 1.00 | 0.00 xxxx | 1653 |
| ATOM | 1654 | N | GLY | A | 217 | 73.077 | −1.733 | 96.661 | 1.00 | 0.00 xxxx | 1654 |
| ATOM | 1655 | CA | GLY | A | 217 | 73.106 | −0.975 | 97.904 | 1.00 | 0.00 xxxx | 1655 |
| ATOM | 1656 | C | GLY | A | 217 | 71.764 | −0.328 | 98.196 | 1.00 | 0.00 xxxx | 1656 |
| ATOM | 1657 | O | GLY | A | 217 | 71.289 | −0.344 | 99.337 | 1.00 | 0.00 xxxx | 1657 |
| ATOM | 1658 | N | ALA | A | 218 | 71.139 | 0.244 | 97.170 | 1.00 | 0.00 xxxx | 1658 |
| ATOM | 1659 | CA | ALA | A | 218 | 69.812 | 0.848 | 97.344 | 1.00 | 0.00 xxxx | 1659 |
| ATOM | 1660 | C | ALA | A | 218 | 68.782 | −0.201 | 97.750 | 1.00 | 0.00 xxxx | 1660 |
| ATOM | 1661 | O | ALA | A | 218 | 67.937 | 0.070 | 98.601 | 1.00 | 0.00 xxxx | 1661 |
| ATOM | 1662 | CB | ALA | A | 218 | 69.368 | 1.554 | 96.064 | 1.00 | 0.00 xxxx | 1662 |
| ATOM | 1663 | N | VAL | A | 219 | 68.859 | −1.393 | 97.149 | 1.00 | 0.00 xxxx | 1663 |
| ATOM | 1664 | CA | VAL | A | 219 | 67.943 | −2.494 | 97.483 | 1.00 | 0.00 xxxx | 1664 |
| ATOM | 1665 | C | VAL | A | 219 | 68.054 | −2.817 | 98.970 | 1.00 | 0.00 xxxx | 1665 |
| ATOM | 1666 | O | VAL | A | 219 | 67.038 | −3.007 | 99.651 | 1.00 | 0.00 xxxx | 1666 |
| ATOM | 1667 | CB | VAL | A | 219 | 68.231 | −3.743 | 96.618 | 1.00 | 0.00 xxxx | 1667 |
| ATOM | 1668 | CG1 | VAL | A | 219 | 67.526 | −4.976 | 97.198 | 1.00 | 0.00 xxxx | 1668 |
| ATOM | 1669 | CG2 | VAL | A | 219 | 67.771 | −3.509 | 95.187 | 1.00 | 0.00 xxxx | 1669 |
| ATOM | 1670 | N | GLU | A | 220 | 69.283 | −2.856 | 99.481 | 1.00 | 0.00 xxxx | 1670 |
| ATOM | 1671 | CA | GLU | A | 220 | 69.508 | −3.155 | 100.894 | 1.00 | 0.00 xxxx | 1671 |
| ATOM | 1672 | C | GLU | A | 220 | 68.901 | −2.089 | 101.804 | 1.00 | 0.00 xxxx | 1672 |
| ATOM | 1673 | O | GLU | A | 220 | 68.284 | −2.411 | 102.827 | 1.00 | 0.00 xxxx | 1673 |
| ATOM | 1674 | CB | GLU | A | 220 | 70.998 | −3.275 | 101.196 | 1.00 | 0.00 xxxx | 1674 |
| ATOM | 1675 | CG | GLU | A | 220 | 71.680 | −4.536 | 100.690 | 1.00 | 0.00 xxxx | 1675 |
| ATOM | 1676 | CD | GLU | A | 220 | 73.107 | −4.637 | 101.220 | 1.00 | 0.00 xxxx | 1676 |
| ATOM | 1677 | OE1 | GLU | A | 220 | 73.282 | −4.770 | 102.453 | 1.00 | 0.00 xxxx | 1677 |
| ATOM | 1678 | OE2 | GLU | A | 220 | 74.055 | −4.552 | 100.413 | 1.00 | 0.00 xxxx | 1678 |
| ATOM | 1679 | N | ALA | A | 221 | 69.094 | −0.825 | 101.450 | 1.00 | 0.00 xxxx | 1679 |
| ATOM | 1680 | CA | ALA | A | 221 | 68.532 | 0.265 | 102.247 | 1.00 | 0.00 xxxx | 1680 |
| ATOM | 1681 | C | ALA | A | 221 | 67.006 | 0.221 | 102.244 | 1.00 | 0.00 xxxx | 1681 |
| ATOM | 1682 | O | ALA | A | 221 | 66.362 | 0.410 | 103.284 | 1.00 | 0.00 xxxx | 1682 |
| ATOM | 1683 | CB | ALA | A | 221 | 69.035 | 1.623 | 101.735 | 1.00 | 0.00 xxxx | 1683 |
| ATOM | 1684 | N | LEU | A | 222 | 66.419 | −0.050 | 101.085 | 1.00 | 0.00 xxxx | 1684 |
| ATOM | 1685 | CA | LEU | A | 222 | 64.967 | −0.103 | 100.981 | 1.00 | 0.00 xxxx | 1685 |
| ATOM | 1686 | C | LEU | A | 222 | 64.414 | −1.218 | 101.847 | 1.00 | 0.00 xxxx | 1686 |
| ATOM | 1687 | O | LEU | A | 222 | 63.394 | −1.040 | 102.523 | 1.00 | 0.00 xxxx | 1687 |
| ATOM | 1688 | CB | LEU | A | 222 | 64.534 | −0.285 | 99.521 | 1.00 | 0.00 xxxx | 1688 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1689 | CG | LEU | A | 222 | 64.657 | 0.972 | 98.647 | 1.00 | 0.00 | xxxx | 1689 |
| ATOM | 1690 | CD1 | LEU | A | 222 | 64.575 | 0.602 | 97.175 | 1.00 | 0.00 | xxxx | 1690 |
| ATOM | 1691 | CD2 | LEU | A | 222 | 63.573 | 1.992 | 98.994 | 1.00 | 0.00 | xxxx | 1691 |
| ATOM | 1692 | N | LYS | A | 223 | 65.098 | −2.360 | 101.853 | 1.00 | 0.00 | xxxx | 1692 |
| ATOM | 1693 | CA | LYS | A | 223 | 64.672 | −3.492 | 102.687 | 1.00 | 0.00 | xxxx | 1693 |
| ATOM | 1694 | C | LYS | A | 223 | 64.691 | −3.123 | 104.174 | 1.00 | 0.00 | xxxx | 1694 |
| ATOM | 1695 | O | LYS | A | 223 | 63.776 | −3.473 | 104.932 | 1.00 | 0.00 | xxxx | 1695 |
| ATOM | 1696 | CB | LYS | A | 223 | 65.558 | −4.718 | 102.435 | 1.00 | 0.00 | xxxx | 1696 |
| ATOM | 1697 | CG | LYS | A | 223 | 65.379 | −5.837 | 103.462 | 1.00 | 0.00 | xxxx | 1697 |
| ATOM | 1698 | CD | LYS | A | 223 | 66.047 | −7.129 | 103.009 | 1.00 | 0.00 | xxxx | 1698 |
| ATOM | 1699 | CE | LYS | A | 223 | 67.535 | −6.935 | 102.773 | 1.00 | 0.00 | xxxx | 1699 |
| ATOM | 1700 | NZ | LYS | A | 223 | 68.181 | −8.167 | 102.241 | 1.00 | 0.00 | xxxx | 1700 |
| ATOM | 1701 | N | ALA | A | 224 | 65.724 | −2.401 | 104.585 | 1.00 | 0.00 | xxxx | 1701 |
| ATOM | 1702 | CA | ALA | A | 224 | 65.845 | −1.978 | 105.975 | 1.00 | 0.00 | xxxx | 1702 |
| ATOM | 1703 | C | ALA | A | 224 | 64.728 | −1.013 | 106.394 | 1.00 | 0.00 | xxxx | 1703 |
| ATOM | 1704 | O | ALA | A | 224 | 64.380 | −0.950 | 107.574 | 1.00 | 0.00 | xxxx | 1704 |
| ATOM | 1705 | CB | ALA | A | 224 | 67.209 | −1.344 | 106.206 | 1.00 | 0.00 | xxxx | 1705 |
| ATOM | 1706 | N | HIS | A | 225 | 64.162 | −0.281 | 105.437 | 1.00 | 0.00 | xxxx | 1706 |
| ATOM | 1707 | CA | HIS | A | 225 | 63.105 | 0.692 | 105.703 | 1.00 | 0.00 | xxxx | 1707 |
| ATOM | 1708 | C | HIS | A | 225 | 61.712 | 0.158 | 105.372 | 1.00 | 0.00 | xxxx | 1708 |
| ATOM | 1709 | O | HIS | A | 225 | 60.742 | 0.921 | 105.364 | 1.00 | 0.00 | xxxx | 1709 |
| ATOM | 1710 | CB | HIS | A | 225 | 63.340 | 1.974 | 104.904 | 1.00 | 0.00 | xxxx | 1710 |
| ATOM | 1711 | CG | HIS | A | 225 | 64.419 | 2.844 | 105.462 | 1.00 | 0.00 | xxxx | 1711 |
| ATOM | 1712 | ND1 | HIS | A | 225 | 64.152 | 3.941 | 106.253 | 1.00 | 0.00 | xxxx | 1712 |
| ATOM | 1713 | CD2 | HIS | A | 225 | 65.767 | 2.774 | 105.352 | 1.00 | 0.00 | xxxx | 1713 |
| ATOM | 1714 | CE1 | HIS | A | 225 | 65.292 | 4.512 | 106.605 | 1.00 | 0.00 | xxxx | 1714 |
| ATOM | 1715 | NE2 | HIS | A | 225 | 66.287 | 3.823 | 106.074 | 1.00 | 0.00 | xxxx | 1715 |
| ATOM | 1716 | N | ASN | A | 226 | 61.631 | −1.139 | 105.081 | 1.00 | 0.00 | xxxx | 1716 |
| ATOM | 1717 | CA | ASN | A | 226 | 60.369 | −1.793 | 104.741 | 1.00 | 0.00 | xxxx | 1717 |
| ATOM | 1718 | C | ASN | A | 226 | 59.709 | −1.111 | 103.554 | 1.00 | 0.00 | xxxx | 1718 |
| ATOM | 1719 | O | ASN | A | 226 | 58.492 | −0.887 | 103.539 | 1.00 | 0.00 | xxxx | 1719 |
| ATOM | 1720 | CB | ASN | A | 226 | 59.430 | −1.807 | 105.947 | 1.00 | 0.00 | xxxx | 1720 |
| ATOM | 1721 | CG | ASN | A | 226 | 60.045 | −2.499 | 107.142 | 1.00 | 0.00 | xxxx | 1721 |
| ATOM | 1722 | OD1 | ASN | A | 226 | 60.652 | −3.561 | 107.007 | 1.00 | 0.00 | xxxx | 1722 |
| ATOM | 1723 | ND2 | ASN | A | 226 | 59.909 | −1.893 | 108.317 | 1.00 | 0.00 | xxxx | 1723 |
| ATOM | 1724 | N | LYS | A | 227 | 60.537 | −0.777 | 102.565 | 1.00 | 0.00 | xxxx | 1724 |
| ATOM | 1725 | CA | LYS | A | 227 | 60.095 | −0.116 | 101.349 | 1.00 | 0.00 | xxxx | 1725 |
| ATOM | 1726 | C | LYS | A | 227 | 60.554 | −0.907 | 100.120 | 1.00 | 0.00 | xxxx | 1726 |
| ATOM | 1727 | O | LYS | A | 227 | 60.903 | −0.320 | 99.095 | 1.00 | 0.00 | xxxx | 1727 |
| ATOM | 1728 | CB | LYS | A | 227 | 60.642 | 1.319 | 101.285 | 1.00 | 0.00 | xxxx | 1728 |
| ATOM | 1729 | CG | LYS | A | 227 | 60.066 | 2.283 | 102.323 | 1.00 | 0.00 | xxxx | 1729 |
| ATOM | 1730 | CD | LYS | A | 227 | 58.656 | 2.733 | 101.966 | 1.00 | 0.00 | xxxx | 1730 |
| ATOM | 1731 | CE | LYS | A | 227 | 58.656 | 3.636 | 100.738 | 1.00 | 0.00 | xxxx | 1731 |
| ATOM | 1732 | NZ | LYS | A | 227 | 57.319 | 4.258 | 100.483 | 1.00 | 0.00 | xxxx | 1732 |
| ATOM | 1733 | N | SER | A | 228 | 60.548 | −2.232 | 100.216 | 1.00 | 0.00 | xxxx | 1733 |
| ATOM | 1734 | CA | SER | A | 228 | 61.005 | −3.057 | 99.100 | 1.00 | 0.00 | xxxx | 1734 |
| ATOM | 1735 | C | SER | A | 228 | 60.051 | −3.004 | 97.906 | 1.00 | 0.00 | xxxx | 1735 |
| ATOM | 1736 | O | SER | A | 228 | 60.369 | −3.529 | 96.837 | 1.00 | 0.00 | xxxx | 1736 |
| ATOM | 1737 | CB | SER | A | 228 | 61.196 | −4.502 | 99.550 | 1.00 | 0.00 | xxxx | 1737 |
| ATOM | 1738 | OG | SER | A | 228 | 62.308 | −4.609 | 100.420 | 1.00 | 0.00 | xxxx | 1738 |
| ATOM | 1739 | N | SER | A | 229 | 58.902 | −2.360 | 98.089 | 1.00 | 0.00 | xxxx | 1739 |
| ATOM | 1740 | CA | SER | A | 229 | 57.932 | −2.158 | 97.014 | 1.00 | 0.00 | xxxx | 1740 |
| ATOM | 1741 | C | SER | A | 229 | 58.391 | −1.094 | 96.013 | 1.00 | 0.00 | xxxx | 1741 |
| ATOM | 1742 | O | SER | A | 229 | 57.823 | −0.972 | 94.930 | 1.00 | 0.00 | xxxx | 1742 |
| ATOM | 1743 | CB | SER | A | 229 | 56.570 | −1.768 | 97.604 | 1.00 | 0.00 | xxxx | 1743 |
| ATOM | 1744 | OG | SER | A | 229 | 56.710 | −0.696 | 98.528 | 1.00 | 0.00 | xxxx | 1744 |
| ATOM | 1745 | N | ILE | A | 230 | 59.404 | −0.317 | 96.393 | 1.00 | 0.00 | xxxx | 1745 |
| ATOM | 1746 | CA | ILE | A | 230 | 59.980 | 0.706 | 95.516 | 1.00 | 0.00 | xxxx | 1746 |
| ATOM | 1747 | C | ILE | A | 230 | 60.940 | 0.056 | 94.525 | 1.00 | 0.00 | xxxx | 1747 |
| ATOM | 1748 | O | ILE | A | 230 | 61.918 | −0.553 | 94.936 | 1.00 | 0.00 | xxxx | 1748 |
| ATOM | 1749 | CB | ILE | A | 230 | 60.719 | 1.781 | 96.334 | 1.00 | 0.00 | xxxx | 1749 |
| ATOM | 1750 | CG2 | ILE | A | 230 | 61.325 | 2.840 | 95.416 | 1.00 | 0.00 | xxxx | 1750 |
| ATOM | 1751 | CG1 | ILE | A | 230 | 59.795 | 2.397 | 97.395 | 1.00 | 0.00 | xxxx | 1751 |
| ATOM | 1752 | CD1 | ILE | A | 230 | 58.589 | 3.105 | 96.823 | 1.00 | 0.00 | xxxx | 1752 |
| ATOM | 1753 | N | PRO | A | 231 | 60.674 | 0.191 | 93.219 | 1.00 | 0.00 | xxxx | 1753 |
| ATOM | 1754 | CA | PRO | A | 231 | 61.546 | −0.457 | 92.223 | 1.00 | 0.00 | xxxx | 1754 |
| ATOM | 1755 | C | PRO | A | 231 | 62.907 | 0.219 | 92.060 | 1.00 | 0.00 | xxxx | 1755 |
| ATOM | 1756 | O | PRO | A | 231 | 63.019 | 1.446 | 92.161 | 1.00 | 0.00 | xxxx | 1756 |
| ATOM | 1757 | CB | PRO | A | 231 | 60.746 | −0.329 | 90.932 | 1.00 | 0.00 | xxxx | 1757 |
| ATOM | 1758 | CG | PRO | A | 231 | 59.952 | 0.924 | 91.123 | 1.00 | 0.00 | xxxx | 1758 |
| ATOM | 1759 | CD | PRO | A | 231 | 59.570 | 0.934 | 92.587 | 1.00 | 0.00 | xxxx | 1759 |
| ATOM | 1760 | N | VAL | A | 232 | 63.918 | −0.603 | 91.789 | 1.00 | 0.00 | xxxx | 1760 |
| ATOM | 1761 | CA | VAL | A | 232 | 65.289 | −0.161 | 91.571 | 1.00 | 0.00 | xxxx | 1761 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1762 | C | VAL | A | 232 | 65.746 | −0.630 | 90.193 | 1.00 | 0.00 | xxxx | 1762 |
| ATOM | 1763 | O | VAL | A | 232 | 65.467 | −1.756 | 89.787 | 1.00 | 0.00 | xxxx | 1763 |
| ATOM | 1764 | CB | VAL | A | 232 | 66.224 | −0.701 | 92.662 | 1.00 | 0.00 | xxxx | 1764 |
| ATOM | 1765 | CG1 | VAL | A | 232 | 67.645 | −0.189 | 92.454 | 1.00 | 0.00 | xxxx | 1765 |
| ATOM | 1766 | CG2 | VAL | A | 232 | 65.710 | −0.305 | 94.046 | 1.00 | 0.00 | xxxx | 1766 |
| ATOM | 1767 | N | PHE | A | 233 | 66.444 | 0.246 | 89.479 | 1.00 | 0.00 | xxxx | 1767 |
| ATOM | 1768 | CA | PHE | A | 233 | 67.018 | −0.105 | 88.177 | 1.00 | 0.00 | xxxx | 1768 |
| ATOM | 1769 | C | PHE | A | 233 | 68.529 | 0.093 | 88.187 | 1.00 | 0.00 | xxxx | 1769 |
| ATOM | 1770 | O | PHE | A | 233 | 69.029 | 1.058 | 88.763 | 1.00 | 0.00 | xxxx | 1770 |
| ATOM | 1771 | CB | PHE | A | 233 | 66.384 | 0.735 | 87.069 | 1.00 | 0.00 | xxxx | 1771 |
| ATOM | 1772 | CG | PHE | A | 233 | 64.923 | 0.445 | 86.854 | 1.00 | 0.00 | xxxx | 1772 |
| ATOM | 1773 | CD1 | PHE | A | 233 | 64.525 | −0.446 | 85.872 | 1.00 | 0.00 | xxxx | 1773 |
| ATOM | 1774 | CD2 | PHE | A | 233 | 63.955 | 1.050 | 87.647 | 1.00 | 0.00 | xxxx | 1774 |
| ATOM | 1775 | CE1 | PHE | A | 233 | 63.175 | −0.719 | 85.664 | 1.00 | 0.00 | xxxx | 1775 |
| ATOM | 1776 | CE2 | PHE | A | 233 | 62.612 | 0.777 | 87.459 | 1.00 | 0.00 | xxxx | 1776 |
| ATOM | 1777 | CZ | PHE | A | 233 | 62.217 | −0.110 | 86.470 | 1.00 | 0.00 | xxxx | 1777 |
| ATOM | 1778 | N | GLY | A | 234 | 69.252 | −0.834 | 87.556 | 1.00 | 0.00 | xxxx | 1778 |
| ATOM | 1779 | CA | GLY | A | 234 | 70.704 | −0.748 | 87.481 | 1.00 | 0.00 | xxxx | 1779 |
| ATOM | 1780 | C | GLY | A | 234 | 71.251 | −0.871 | 86.071 | 1.00 | 0.00 | xxxx | 1780 |
| ATOM | 1781 | O | GLY | A | 234 | 70.506 | −0.818 | 85.087 | 1.00 | 0.00 | xxxx | 1781 |
| ATOM | 1782 | N | VAL | A | 235 | 72.572 | −1.000 | 85.997 | 1.00 | 0.00 | xxxx | 1782 |
| ATOM | 1783 | CA | VAL | A | 235 | 73.304 | −1.326 | 84.767 | 1.00 | 0.00 | xxxx | 1783 |
| ATOM | 1784 | C | VAL | A | 235 | 74.447 | −2.269 | 85.103 | 1.00 | 0.00 | xxxx | 1784 |
| ATOM | 1785 | O | VAL | A | 235 | 75.187 | −2.003 | 86.057 | 1.00 | 0.00 | xxxx | 1785 |
| ATOM | 1786 | CB | VAL | A | 235 | 73.881 | −0.073 | 84.066 | 1.00 | 0.00 | xxxx | 1786 |
| ATOM | 1787 | CG1 | VAL | A | 235 | 74.730 | −0.490 | 82.870 | 1.00 | 0.00 | xxxx | 1787 |
| ATOM | 1788 | CG2 | VAL | A | 235 | 72.785 | 0.883 | 83.642 | 1.00 | 0.00 | xxxx | 1788 |
| ATOM | 1789 | N | ASP | A | 236 | 74.550 | −3.356 | 84.329 | 1.00 | 0.00 | xxxx | 1789 |
| ATOM | 1790 | CA | ASP | A | 236 | 75.711 | −4.274 | 84.192 | 1.00 | 0.00 | xxxx | 1790 |
| ATOM | 1791 | C | ASP | A | 236 | 75.229 | −5.706 | 83.994 | 1.00 | 0.00 | xxxx | 1791 |
| ATOM | 1792 | O | ASP | A | 236 | 75.867 | −6.481 | 83.286 | 1.00 | 0.00 | xxxx | 1792 |
| ATOM | 1793 | CB | ASP | A | 236 | 76.688 | −4.255 | 85.385 | 1.00 | 0.00 | xxxx | 1793 |
| ATOM | 1794 | CG | ASP | A | 236 | 77.665 | −3.089 | 85.333 | 1.00 | 0.00 | xxxx | 1794 |
| ATOM | 1795 | OD1 | ASP | A | 236 | 77.845 | −2.486 | 84.251 | 1.00 | 0.00 | xxxx | 1795 |
| ATOM | 1796 | OD2 | ASP | A | 236 | 78.254 | −2.760 | 86.388 | 1.00 | 0.00 | xxxx | 1796 |
| ATOM | 1797 | N | ALA | A | 237 | 74.107 | −6.042 | 84.628 | 1.00 | 0.00 | xxxx | 1797 |
| ATOM | 1798 | CA | ALA | A | 237 | 73.631 | −7.418 | 84.752 | 1.00 | 0.00 | xxxx | 1798 |
| ATOM | 1799 | C | ALA | A | 237 | 74.721 | −8.308 | 85.339 | 1.00 | 0.00 | xxxx | 1799 |
| ATOM | 1800 | O | ALA | A | 237 | 75.071 | −9.350 | 84.775 | 1.00 | 0.00 | xxxx | 1800 |
| ATOM | 1801 | CB | ALA | A | 237 | 73.144 | −7.963 | 83.398 | 1.00 | 0.00 | xxxx | 1801 |
| ATOM | 1802 | N | LEU | A | 238 | 75.253 | −7.893 | 86.487 | 1.00 | 0.00 | xxxx | 1802 |
| ATOM | 1803 | CA | LEU | A | 238 | 76.190 | −8.722 | 87.231 | 1.00 | 0.00 | xxxx | 1803 |
| ATOM | 1804 | C | LEU | A | 238 | 75.508 | −10.035 | 87.568 | 1.00 | 0.00 | xxxx | 1804 |
| ATOM | 1805 | O | LEU | A | 238 | 74.304 | −10.059 | 87.782 | 1.00 | 0.00 | xxxx | 1805 |
| ATOM | 1806 | CB | LEU | A | 238 | 76.642 | −8.041 | 88.525 | 1.00 | 0.00 | xxxx | 1806 |
| ATOM | 1807 | CG | LEU | A | 238 | 77.270 | −6.648 | 88.486 | 1.00 | 0.00 | xxxx | 1807 |
| ATOM | 1808 | CD1 | LEU | A | 238 | 77.388 | −6.142 | 89.909 | 1.00 | 0.00 | xxxx | 1808 |
| ATOM | 1809 | CD2 | LEU | A | 238 | 78.643 | −6.698 | 87.820 | 1.00 | 0.00 | xxxx | 1809 |
| ATOM | 1810 | N | PRO | A | 239 | 76.280 | −11.130 | 87.626 | 1.00 | 0.00 | xxxx | 1810 |
| ATOM | 1811 | CA | PRO | A | 239 | 75.700 | −12.410 | 88.037 | 1.00 | 0.00 | xxxx | 1811 |
| ATOM | 1812 | C | PRO | A | 239 | 74.853 | −12.285 | 89.303 | 1.00 | 0.00 | xxxx | 1812 |
| ATOM | 1813 | O | PRO | A | 239 | 73.767 | −12.852 | 89.361 | 1.00 | 0.00 | xxxx | 1813 |
| ATOM | 1814 | CB | PRO | A | 239 | 76.932 | −13.286 | 88.276 | 1.00 | 0.00 | xxxx | 1814 |
| ATOM | 1815 | CG | PRO | A | 239 | 77.965 | −12.728 | 87.363 | 1.00 | 0.00 | xxxx | 1815 |
| ATOM | 1816 | CD | PRO | A | 239 | 77.718 | −11.238 | 87.325 | 1.00 | 0.00 | xxxx | 1816 |
| ATOM | 1817 | N | GLU | A | 240 | 75.322 | −11.516 | 90.284 | 1.00 | 0.00 | xxxx | 1817 |
| ATOM | 1818 | CA | GLU | A | 240 | 74.596 | −11.373 | 91.544 | 1.00 | 0.00 | xxxx | 1818 |
| ATOM | 1819 | C | GLU | A | 240 | 73.346 | −10.497 | 91.399 | 1.00 | 0.00 | xxxx | 1819 |
| ATOM | 1820 | O | GLU | A | 240 | 72.385 | −10.645 | 92.152 | 1.00 | 0.00 | xxxx | 1820 |
| ATOM | 1821 | CB | GLU | A | 240 | 75.518 | −10.812 | 92.638 | 1.00 | 0.00 | xxxx | 1821 |
| ATOM | 1822 | CG | GLU | A | 240 | 76.280 | −9.539 | 92.268 | 1.00 | 0.00 | xxxx | 1822 |
| ATOM | 1823 | CD | GLU | A | 240 | 77.688 | −9.807 | 91.744 | 1.00 | 0.00 | xxxx | 1823 |
| ATOM | 1824 | OE1 | GLU | A | 240 | 77.872 | −10.780 | 90.977 | 1.00 | 0.00 | xxxx | 1824 |
| ATOM | 1825 | OE2 | GLU | A | 240 | 78.614 | −9.041 | 92.101 | 1.00 | 0.00 | xxxx | 1825 |
| ATOM | 1826 | N | ALA | A | 241 | 73.349 | −9.599 | 90.421 | 1.00 | 0.00 | xxxx | 1826 |
| ATOM | 1827 | CA | ALA | A | 241 | 72.181 | −8.751 | 90.182 | 1.00 | 0.00 | xxxx | 1827 |
| ATOM | 1828 | C | ALA | A | 241 | 71.053 | −9.528 | 89.496 | 1.00 | 0.00 | xxxx | 1828 |
| ATOM | 1829 | O | ALA | A | 241 | 69.870 | −9.257 | 89.712 | 1.00 | 0.00 | xxxx | 1829 |
| ATOM | 1830 | CB | ALA | A | 241 | 72.572 | −7.540 | 89.350 | 1.00 | 0.00 | xxxx | 1830 |
| ATOM | 1831 | N | LEU | A | 242 | 71.423 | −10.495 | 88.663 | 1.00 | 0.00 | xxxx | 1831 |
| ATOM | 1832 | CA | LEU | A | 242 | 70.431 | −11.298 | 87.963 | 1.00 | 0.00 | xxxx | 1832 |
| ATOM | 1833 | C | LEU | A | 242 | 69.530 | −12.038 | 88.950 | 1.00 | 0.00 | xxxx | 1833 |
| ATOM | 1834 | O | LEU | A | 242 | 68.339 | −12.213 | 88.703 | 1.00 | 0.00 | xxxx | 1834 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1835 | CB | LEU | A | 242 | 71.118 | −12.279 | 87.010 | 1.00 | 0.00 | xxxx | 1835 |
| ATOM | 1836 | CG | LEU | A | 242 | 71.898 | −11.594 | 85.884 | 1.00 | 0.00 | xxxx | 1836 |
| ATOM | 1837 | CD1 | LEU | A | 242 | 72.501 | −12.613 | 84.916 | 1.00 | 0.00 | xxxx | 1837 |
| ATOM | 1838 | CD2 | LEU | A | 242 | 71.012 | −10.605 | 85.142 | 1.00 | 0.00 | xxxx | 1838 |
| ATOM | 1839 | N | ALA | A | 243 | 70.095 | −12.448 | 90.081 | 1.00 | 0.00 | xxxx | 1839 |
| ATOM | 1840 | CA | ALA | A | 243 | 69.326 | −13.136 | 91.107 | 1.00 | 0.00 | xxxx | 1840 |
| ATOM | 1841 | C | ALA | A | 243 | 68.253 | −12.225 | 91.705 | 1.00 | 0.00 | xxxx | 1841 |
| ATOM | 1842 | O | ALA | A | 243 | 67.158 | −12.675 | 92.032 | 1.00 | 0.00 | xxxx | 1842 |
| ATOM | 1843 | CB | ALA | A | 243 | 70.249 | −13.654 | 92.196 | 1.00 | 0.00 | xxxx | 1843 |
| ATOM | 1844 | N | LEU | A | 244 | 68.574 | −10.940 | 91.839 | 1.00 | 0.00 | xxxx | 1844 |
| ATOM | 1845 | CA | LEU | A | 244 | 67.627 | −9.962 | 92.351 | 1.00 | 0.00 | xxxx | 1845 |
| ATOM | 1846 | C | LEU | A | 244 | 66.537 | −9.636 | 91.338 | 1.00 | 0.00 | xxxx | 1846 |
| ATOM | 1847 | O | LEU | A | 244 | 65.422 | −9.284 | 91.715 | 1.00 | 0.00 | xxxx | 1847 |
| ATOM | 1848 | CB | LEU | A | 244 | 68.346 | −8.675 | 92.751 | 1.00 | 0.00 | xxxx | 1848 |
| ATOM | 1849 | CG | LEU | A | 244 | 69.396 | −8.786 | 93.856 | 1.00 | 0.00 | xxxx | 1849 |
| ATOM | 1850 | CD1 | LEU | A | 244 | 70.017 | −7.425 | 94.111 | 1.00 | 0.00 | xxxx | 1850 |
| ATOM | 1851 | CD2 | LEU | A | 244 | 68.793 | −9.348 | 95.137 | 1.00 | 0.00 | xxxx | 1851 |
| ATOM | 1852 | N | VAL | A | 245 | 66.867 | −9.713 | 90.050 | 1.00 | 0.00 | xxxx | 1852 |
| ATOM | 1853 | CA | VAL | A | 245 | 65.847 | −9.540 | 89.027 | 1.00 | 0.00 | xxxx | 1853 |
| ATOM | 1854 | C | VAL | A | 245 | 64.835 | −10.677 | 89.141 | 1.00 | 0.00 | xxxx | 1854 |
| ATOM | 1855 | O | VAL | A | 245 | 63.629 | −10.467 | 89.025 | 1.00 | 0.00 | xxxx | 1855 |
| ATOM | 1856 | CB | VAL | A | 245 | 66.460 | −9.483 | 87.612 | 1.00 | 0.00 | xxxx | 1856 |
| ATOM | 1857 | CG1 | VAL | A | 245 | 65.348 | −9.436 | 86.568 | 1.00 | 0.00 | xxxx | 1857 |
| ATOM | 1858 | CG2 | VAL | A | 245 | 67.385 | −8.263 | 87.487 | 1.00 | 0.00 | xxxx | 1858 |
| ATOM | 1859 | N | LYS | A | 246 | 65.342 | −11.882 | 89.377 | 1.00 | 0.00 | xxxx | 1859 |
| ATOM | 1860 | CA | LYS | A | 246 | 64.486 | −13.053 | 89.565 | 1.00 | 0.00 | xxxx | 1860 |
| ATOM | 1861 | C | LYS | A | 246 | 63.547 | −12.843 | 90.752 | 1.00 | 0.00 | xxxx | 1861 |
| ATOM | 1862 | O | LYS | A | 246 | 62.342 | −13.073 | 90.651 | 1.00 | 0.00 | xxxx | 1862 |
| ATOM | 1863 | CB | LYS | A | 246 | 65.339 | −14.313 | 89.764 | 1.00 | 0.00 | xxxx | 1863 |
| ATOM | 1864 | CG | LYS | A | 246 | 64.560 | −15.639 | 89.744 | 1.00 | 0.00 | xxxx | 1864 |
| ATOM | 1865 | CD | LYS | A | 246 | 64.000 | −16.017 | 91.119 | 1.00 | 0.00 | xxxx | 1865 |
| ATOM | 1866 | CE | LYS | A | 246 | 62.993 | −17.166 | 91.028 | 1.00 | 0.00 | xxxx | 1866 |
| ATOM | 1867 | NZ | LYS | A | 246 | 62.123 | −17.249 | 92.240 | 1.00 | 0.00 | xxxx | 1867 |
| ATOM | 1868 | N | SER | A | 247 | 64.105 | −12.396 | 91.874 | 1.00 | 0.00 | xxxx | 1868 |
| ATOM | 1869 | CA | SER | A | 247 | 63.342 | −12.267 | 93.110 | 1.00 | 0.00 | xxxx | 1869 |
| ATOM | 1870 | C | SER | A | 247 | 62.398 | −11.073 | 93.075 | 1.00 | 0.00 | xxxx | 1870 |
| ATOM | 1871 | O | SER | A | 247 | 61.460 | −10.990 | 93.870 | 1.00 | 0.00 | xxxx | 1871 |
| ATOM | 1872 | CB | SER | A | 247 | 64.286 | −12.144 | 94.308 | 1.00 | 0.00 | xxxx | 1872 |
| ATOM | 1873 | OG | SER | A | 247 | 64.953 | −10.894 | 94.307 | 1.00 | 0.00 | xxxx | 1873 |
| ATOM | 1874 | N | GLY | A | 248 | 62.647 | −10.151 | 92.152 | 1.00 | 0.00 | xxxx | 1874 |
| ATOM | 1875 | CA | GLY | A | 248 | 61.848 | −8.948 | 92.052 | 1.00 | 0.00 | xxxx | 1875 |
| ATOM | 1876 | C | GLY | A | 248 | 62.402 | −7.796 | 92.873 | 1.00 | 0.00 | xxxx | 1876 |
| ATOM | 1877 | O | GLY | A | 248 | 61.832 | −6.709 | 92.881 | 1.00 | 0.00 | xxxx | 1877 |
| ATOM | 1878 | N | ALA | A | 249 | 63.517 | −8.035 | 93.561 | 1.00 | 0.00 | xxxx | 1878 |
| ATOM | 1879 | CA | ALA | A | 249 | 64.176 | −6.992 | 94.350 | 1.00 | 0.00 | xxxx | 1879 |
| ATOM | 1880 | C | ALA | A | 249 | 64.775 | −5.920 | 93.447 | 1.00 | 0.00 | xxxx | 1880 |
| ATOM | 1881 | O | ALA | A | 249 | 64.873 | −4.756 | 93.827 | 1.00 | 0.00 | xxxx | 1881 |
| ATOM | 1882 | CB | ALA | A | 249 | 65.253 | −7.598 | 95.238 | 1.00 | 0.00 | xxxx | 1882 |
| ATOM | 1883 | N | LEU | A | 250 | 65.185 | −6.328 | 92.249 | 1.00 | 0.00 | xxxx | 1883 |
| ATOM | 1884 | CA | LEU | A | 250 | 65.663 | −5.410 | 91.230 | 1.00 | 0.00 | xxxx | 1884 |
| ATOM | 1885 | C | LEU | A | 250 | 64.692 | −5.468 | 90.058 | 1.00 | 0.00 | xxxx | 1885 |
| ATOM | 1886 | O | LEU | A | 250 | 64.411 | −6.547 | 89.548 | 1.00 | 0.00 | xxxx | 1886 |
| ATOM | 1887 | CB | LEU | A | 250 | 67.085 | −5.785 | 90.790 | 1.00 | 0.00 | xxxx | 1887 |
| ATOM | 1888 | CG | LEU | A | 250 | 67.898 | −4.821 | 89.938 | 1.00 | 0.00 | xxxx | 1888 |
| ATOM | 1889 | CD1 | LEU | A | 250 | 68.214 | −3.556 | 90.736 | 1.00 | 0.00 | xxxx | 1889 |
| ATOM | 1890 | CD2 | LEU | A | 250 | 69.171 | −5.513 | 89.483 | 1.00 | 0.00 | xxxx | 1890 |
| ATOM | 1891 | N | ALA | A | 251 | 64.174 | −4.319 | 89.633 | 1.00 | 0.00 | xxxx | 1891 |
| ATOM | 1892 | CA | ALA | A | 251 | 63.132 | −4.291 | 88.613 | 1.00 | 0.00 | xxxx | 1892 |
| ATOM | 1893 | C | ALA | A | 251 | 63.704 | −4.469 | 87.215 | 1.00 | 0.00 | xxxx | 1893 |
| ATOM | 1894 | O | ALA | A | 251 | 63.030 | −4.971 | 86.310 | 1.00 | 0.00 | xxxx | 1894 |
| ATOM | 1895 | CB | ALA | A | 251 | 62.332 | −2.985 | 88.696 | 1.00 | 0.00 | xxxx | 1895 |
| ATOM | 1896 | N | GLY | A | 252 | 64.944 | −4.045 | 87.024 | 1.00 | 0.00 | xxxx | 1896 |
| ATOM | 1897 | CA | GLY | A | 252 | 65.556 | −4.215 | 85.724 | 1.00 | 0.00 | xxxx | 1897 |
| ATOM | 1898 | C | GLY | A | 252 | 66.982 | −3.738 | 85.694 | 1.00 | 0.00 | xxxx | 1898 |
| ATOM | 1899 | O | GLY | A | 252 | 67.396 | −2.934 | 86.528 | 1.00 | 0.00 | xxxx | 1899 |
| ATOM | 1900 | N | THR | A | 253 | 67.743 | −4.243 | 84.733 | 1.00 | 0.00 | xxxx | 1900 |
| ATOM | 1901 | CA | THR | A | 253 | 69.114 | −3.796 | 84.577 | 1.00 | 0.00 | xxxx | 1901 |
| ATOM | 1902 | C | THR | A | 253 | 69.496 | −3.891 | 83.101 | 1.00 | 0.00 | xxxx | 1902 |
| ATOM | 1903 | O | THR | A | 253 | 68.648 | −4.124 | 82.251 | 1.00 | 0.00 | xxxx | 1903 |
| ATOM | 1904 | CB | THR | A | 253 | 70.078 | −4.617 | 85.488 | 1.00 | 0.00 | xxxx | 1904 |
| ATOM | 1905 | OG1 | THR | A | 253 | 71.414 | −4.114 | 85.371 | 1.00 | 0.00 | xxxx | 1905 |
| ATOM | 1906 | CG2 | THR | A | 253 | 70.046 | −6.088 | 85.134 | 1.00 | 0.00 | xxxx | 1906 |
| ATOM | 1907 | N | VAL | A | 254 | 70.761 | −3.655 | 82.788 | 1.00 | 0.00 | xxxx | 1907 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1908 | CA | VAL | A | 254 | 71.210 | −3.611 | 81.398 | 1.00 | 0.00 | xxxx | 1908 |
| ATOM | 1909 | C | VAL | A | 254 | 72.503 | −4.399 | 81.301 | 1.00 | 0.00 | xxxx | 1909 |
| ATOM | 1910 | O | VAL | A | 254 | 73.468 | −4.053 | 81.986 | 1.00 | 0.00 | xxxx | 1910 |
| ATOM | 1911 | CB | VAL | A | 254 | 71.438 | −2.156 | 80.931 | 1.00 | 0.00 | xxxx | 1911 |
| ATOM | 1912 | CG1 | VAL | A | 254 | 71.966 | −2.120 | 79.492 | 1.00 | 0.00 | xxxx | 1912 |
| ATOM | 1913 | CG2 | VAL | A | 254 | 70.181 | −1.298 | 81.103 | 1.00 | 0.00 | xxxx | 1913 |
| ATOM | 1914 | N | LEU | A | 255 | 72.552 | −5.426 | 80.454 | 1.00 | 0.00 | xxxx | 1914 |
| ATOM | 1915 | CA | LEU | A | 255 | 73.785 | −6.208 | 80.315 | 1.00 | 0.00 | xxxx | 1915 |
| ATOM | 1916 | C | LEU | A | 255 | 74.913 | −5.348 | 79.768 | 1.00 | 0.00 | xxxx | 1916 |
| ATOM | 1917 | O | LEU | A | 255 | 74.817 | −4.771 | 78.689 | 1.00 | 0.00 | xxxx | 1917 |
| ATOM | 1918 | CB | LEU | A | 255 | 73.580 | −7.439 | 79.413 | 1.00 | 0.00 | xxxx | 1918 |
| ATOM | 1919 | CG | LEU | A | 255 | 74.896 | −8.169 | 79.088 | 1.00 | 0.00 | xxxx | 1919 |
| ATOM | 1920 | CD1 | LEU | A | 255 | 75.517 | −8.756 | 80.351 | 1.00 | 0.00 | xxxx | 1920 |
| ATOM | 1921 | CD2 | LEU | A | 255 | 74.714 | −9.252 | 78.028 | 1.00 | 0.00 | xxxx | 1921 |
| ATOM | 1922 | N | ASN | A | 256 | 75.962 | −5.224 | 80.567 | 1.00 | 0.00 | xxxx | 1922 |
| ATOM | 1923 | CA | ASN | A | 256 | 77.230 | −4.676 | 80.127 | 1.00 | 0.00 | xxxx | 1923 |
| ATOM | 1924 | C | ASN | A | 256 | 78.070 | −5.920 | 79.866 | 1.00 | 0.00 | xxxx | 1924 |
| ATOM | 1925 | O | ASN | A | 256 | 78.364 | −6.686 | 80.785 | 1.00 | 0.00 | xxxx | 1925 |
| ATOM | 1926 | CB | ASN | A | 256 | 77.809 | −3.752 | 81.206 | 1.00 | 0.00 | xxxx | 1926 |
| ATOM | 1927 | CG | ASN | A | 256 | 79.029 | −2.990 | 80.750 | 1.00 | 0.00 | xxxx | 1927 |
| ATOM | 1928 | OD1 | ASN | A | 256 | 79.481 | −3.121 | 79.606 | 1.00 | 0.00 | xxxx | 1928 |
| ATOM | 1929 | ND2 | ASN | A | 256 | 79.565 | −2.163 | 81.641 | 1.00 | 0.00 | xxxx | 1929 |
| ATOM | 1930 | N | ASP | A | 257 | 78.380 | −6.168 | 78.598 | 1.00 | 0.00 | xxxx | 1930 |
| ATOM | 1931 | CA | ASP | A | 257 | 78.822 | −7.494 | 78.170 | 1.00 | 0.00 | xxxx | 1931 |
| ATOM | 1932 | C | ASP | A | 257 | 80.300 | −7.722 | 78.470 | 1.00 | 0.00 | xxxx | 1932 |
| ATOM | 1933 | O | ASP | A | 257 | 81.161 | −7.511 | 77.613 | 1.00 | 0.00 | xxxx | 1933 |
| ATOM | 1934 | CB | ASP | A | 257 | 78.534 | −7.665 | 76.672 | 1.00 | 0.00 | xxxx | 1934 |
| ATOM | 1935 | CG | ASP | A | 257 | 78.715 | −9.097 | 76.179 | 1.00 | 0.00 | xxxx | 1935 |
| ATOM | 1936 | OD1 | ASP | A | 257 | 79.319 | −9.930 | 76.887 | 1.00 | 0.00 | xxxx | 1936 |
| ATOM | 1937 | OD2 | ASP | A | 257 | 78.240 | −9.391 | 75.055 | 1.00 | 0.00 | xxxx | 1937 |
| ATOM | 1938 | N | ALA | A | 258 | 80.572 | −8.161 | 79.697 | 1.00 | 0.00 | xxxx | 1938 |
| ATOM | 1939 | CA | ALA | A | 258 | 81.936 | −8.390 | 80.176 | 1.00 | 0.00 | xxxx | 1939 |
| ATOM | 1940 | C | ALA | A | 258 | 82.663 | −9.456 | 79.370 | 1.00 | 0.00 | xxxx | 1940 |
| ATOM | 1941 | O | ALA | A | 258 | 83.844 | −9.286 | 79.049 | 1.00 | 0.00 | xxxx | 1941 |
| ATOM | 1942 | CB | ALA | A | 258 | 81.915 | −8.787 | 81.645 | 1.00 | 0.00 | xxxx | 1942 |
| ATOM | 1943 | N | ASN | A | 259 | 81.969 | −10.547 | 79.044 | 1.00 | 0.00 | xxxx | 1943 |
| ATOM | 1944 | CA | ASN | A | 259 | 82.608 | −11.662 | 78.360 | 1.00 | 0.00 | xxxx | 1944 |
| ATOM | 1945 | C | ASN | A | 259 | 83.116 | −11.236 | 76.988 | 1.00 | 0.00 | xxxx | 1945 |
| ATOM | 1946 | O | ASN | A | 259 | 84.233 | −11.586 | 76.606 | 1.00 | 0.00 | xxxx | 1946 |
| ATOM | 1947 | CB | ASN | A | 259 | 81.649 | −12.850 | 78.230 | 1.00 | 0.00 | xxxx | 1947 |
| ATOM | 1948 | CG | ASN | A | 259 | 81.281 | −13.441 | 79.572 | 1.00 | 0.00 | xxxx | 1948 |
| ATOM | 1949 | OD1 | ASN | A | 259 | 82.086 | −13.437 | 80.505 | 1.00 | 0.00 | xxxx | 1949 |
| ATOM | 1950 | ND2 | ASN | A | 259 | 80.055 | −13.946 | 79.683 | 1.00 | 0.00 | xxxx | 1950 |
| ATOM | 1951 | N | ASN | A | 260 | 82.323 | −10.460 | 76.251 | 1.00 | 0.00 | xxxx | 1951 |
| ATOM | 1952 | CA | ASN | A | 260 | 82.768 | −10.060 | 74.925 | 1.00 | 0.00 | xxxx | 1952 |
| ATOM | 1953 | C | ASN | A | 260 | 83.762 | −8.902 | 74.974 | 1.00 | 0.00 | xxxx | 1953 |
| ATOM | 1954 | O | ASN | A | 260 | 84.652 | −8.842 | 74.128 | 1.00 | 0.00 | xxxx | 1954 |
| ATOM | 1955 | CB | ASN | A | 260 | 81.570 | −9.722 | 74.037 | 1.00 | 0.00 | xxxx | 1955 |
| ATOM | 1956 | CG | ASN | A | 260 | 80.950 | −10.969 | 73.440 | 1.00 | 0.00 | xxxx | 1956 |
| ATOM | 1957 | OD1 | ASN | A | 260 | 81.669 | −11.860 | 72.978 | 1.00 | 0.00 | xxxx | 1957 |
| ATOM | 1958 | ND2 | ASN | A | 260 | 79.627 | −11.059 | 73.469 | 1.00 | 0.00 | xxxx | 1958 |
| ATOM | 1959 | N | GLN | A | 261 | 83.665 | −8.012 | 75.961 | 1.00 | 0.00 | xxxx | 1959 |
| ATOM | 1960 | CA | GLN | A | 261 | 84.693 | −6.975 | 76.100 | 1.00 | 0.00 | xxxx | 1960 |
| ATOM | 1961 | C | GLN | A | 261 | 86.041 | −7.609 | 76.481 | 1.00 | 0.00 | xxxx | 1961 |
| ATOM | 1962 | O | GLN | A | 261 | 87.080 | −7.215 | 75.948 | 1.00 | 0.00 | xxxx | 1962 |
| ATOM | 1963 | CB | GLN | A | 261 | 84.267 | −5.916 | 77.107 | 1.00 | 0.00 | xxxx | 1963 |
| ATOM | 1964 | CG | GLN | A | 261 | 83.183 | −5.025 | 76.535 | 1.00 | 0.00 | xxxx | 1964 |
| ATOM | 1965 | CD | GLN | A | 261 | 82.627 | −4.079 | 77.569 | 1.00 | 0.00 | xxxx | 1965 |
| ATOM | 1966 | OE1 | GLN | A | 261 | 83.322 | −3.172 | 78.048 | 1.00 | 0.00 | xxxx | 1966 |
| ATOM | 1967 | NE2 | GLN | A | 261 | 81.361 | −4.287 | 77.928 | 1.00 | 0.00 | xxxx | 1967 |
| ATOM | 1968 | N | ALA | A | 262 | 86.022 | −8.615 | 77.350 | 1.00 | 0.00 | xxxx | 1968 |
| ATOM | 1969 | CA | ALA | A | 262 | 87.239 | −9.362 | 77.682 | 1.00 | 0.00 | xxxx | 1969 |
| ATOM | 1970 | C | ALA | A | 262 | 87.835 | −10.048 | 76.459 | 1.00 | 0.00 | xxxx | 1970 |
| ATOM | 1971 | O | ALA | A | 262 | 89.052 | −10.010 | 76.237 | 1.00 | 0.00 | xxxx | 1971 |
| ATOM | 1972 | CB | ALA | A | 262 | 86.955 | −10.397 | 78.744 | 1.00 | 0.00 | xxxx | 1972 |
| ATOM | 1973 | N | LYS | A | 263 | 86.970 | −10.684 | 75.672 | 1.00 | 0.00 | xxxx | 1973 |
| ATOM | 1974 | CA | LYS | A | 263 | 87.416 | −11.447 | 74.515 | 1.00 | 0.00 | xxxx | 1974 |
| ATOM | 1975 | C | LYS | A | 263 | 88.009 | −10.539 | 73.440 | 1.00 | 0.00 | xxxx | 1975 |
| ATOM | 1976 | O | LYS | A | 263 | 89.046 | −10.860 | 72.858 | 1.00 | 0.00 | xxxx | 1976 |
| ATOM | 1977 | CB | LYS | A | 263 | 86.259 | −12.264 | 73.932 | 1.00 | 0.00 | xxxx | 1977 |
| ATOM | 1978 | CG | LYS | A | 263 | 86.690 | −13.251 | 72.851 | 1.00 | 0.00 | xxxx | 1978 |
| ATOM | 1979 | CD | LYS | A | 263 | 87.848 | −14.112 | 73.339 | 1.00 | 0.00 | xxxx | 1979 |
| ATOM | 1980 | CE | LYS | A | 263 | 88.295 | −15.120 | 72.290 | 1.00 | 0.00 | xxxx | 1980 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 1981 | NZ | LYS | A | 263 | 89.591 | −15.754 | 72.673 | 1.00 | 0.00 | xxxx | 1981 |
| ATOM | 1982 | N | ALA | A | 264 | 87.346 | −9.415 | 73.170 | 1.00 | 0.00 | xxxx | 1982 |
| ATOM | 1983 | CA | ALA | A | 264 | 87.865 | −8.451 | 72.197 | 1.00 | 0.00 | xxxx | 1983 |
| ATOM | 1984 | C | ALA | A | 264 | 89.197 | −7.862 | 72.657 | 1.00 | 0.00 | xxxx | 1984 |
| ATOM | 1985 | O | ALA | A | 264 | 90.134 | −7.739 | 71.857 | 1.00 | 0.00 | xxxx | 1985 |
| ATOM | 1986 | CB | ALA | A | 264 | 86.854 | −7.334 | 71.958 | 1.00 | 0.00 | xxxx | 1986 |
| ATOM | 1987 | N | THR | A | 265 | 89.288 | −7.509 | 73.937 | 1.00 | 0.00 | xxxx | 1987 |
| ATOM | 1988 | CA | THR | A | 265 | 90.530 | −6.975 | 74.485 | 1.00 | 0.00 | xxxx | 1988 |
| ATOM | 1989 | C | THR | A | 265 | 91.656 | −7.994 | 74.318 | 1.00 | 0.00 | xxxx | 1989 |
| ATOM | 1990 | O | THR | A | 265 | 92.733 | −7.662 | 73.813 | 1.00 | 0.00 | xxxx | 1990 |
| ATOM | 1991 | CB | THR | A | 265 | 90.350 | −6.589 | 75.958 | 1.00 | 0.00 | xxxx | 1991 |
| ATOM | 1992 | OG1 | THR | A | 265 | 89.369 | −5.554 | 76.042 | 1.00 | 0.00 | xxxx | 1992 |
| ATOM | 1993 | CG2 | THR | A | 265 | 91.662 | −6.075 | 76.577 | 1.00 | 0.00 | xxxx | 1993 |
| ATOM | 1994 | N | PHE | A | 266 | 91.393 | −9.243 | 74.688 | 1.00 | 0.00 | xxxx | 1994 |
| ATOM | 1995 | CA | PHE | A | 266 | 92.401 | −10.285 | 74.533 | 1.00 | 0.00 | xxxx | 1995 |
| ATOM | 1996 | C | PHE | A | 266 | 92.778 | −10.530 | 73.063 | 1.00 | 0.00 | xxxx | 1996 |
| ATOM | 1997 | O | PHE | A | 266 | 93.968 | −10.657 | 72.742 | 1.00 | 0.00 | xxxx | 1997 |
| ATOM | 1998 | CB | PHE | A | 266 | 91.942 | −11.607 | 75.163 | 1.00 | 0.00 | xxxx | 1998 |
| ATOM | 1999 | CG | PHE | A | 266 | 92.949 | −12.702 | 75.008 | 1.00 | 0.00 | xxxx | 1999 |
| ATOM | 2000 | CD1 | PHE | A | 266 | 94.016 | −12.804 | 75.883 | 1.00 | 0.00 | xxxx | 2000 |
| ATOM | 2001 | CD2 | PHE | A | 266 | 92.858 | −13.593 | 73.959 | 1.00 | 0.00 | xxxx | 2001 |
| ATOM | 2002 | CE1 | PHE | A | 266 | 94.970 | −13.800 | 75.724 | 1.00 | 0.00 | xxxx | 2002 |
| ATOM | 2003 | CE2 | PHE | A | 266 | 93.813 | −14.595 | 73.789 | 1.00 | 0.00 | xxxx | 2003 |
| ATOM | 2004 | CZ | PHE | A | 266 | 94.864 | −14.688 | 74.679 | 1.00 | 0.00 | xxxx | 2004 |
| ATOM | 2005 | N | ASP | A | 267 | 91.780 | −10.616 | 72.181 | 1.00 | 0.00 | xxxx | 2005 |
| ATOM | 2006 | CA | ASP | A | 267 | 92.046 | −10.959 | 70.785 | 1.00 | 0.00 | xxxx | 2006 |
| ATOM | 2007 | C | ASP | A | 267 | 92.907 | −9.884 | 70.132 | 1.00 | 0.00 | xxxx | 2007 |
| ATOM | 2008 | O | ASP | A | 267 | 93.848 | −10.181 | 69.389 | 1.00 | 0.00 | xxxx | 2008 |
| ATOM | 2009 | CB | ASP | A | 267 | 90.743 | −11.105 | 69.995 | 1.00 | 0.00 | xxxx | 2009 |
| ATOM | 2010 | CG | ASP | A | 267 | 89.994 | −12.396 | 70.299 | 1.00 | 0.00 | xxxx | 2010 |
| ATOM | 2011 | OD1 | ASP | A | 267 | 90.559 | −13.321 | 70.923 | 1.00 | 0.00 | xxxx | 2011 |
| ATOM | 2012 | OD2 | ASP | A | 267 | 88.826 | −12.487 | 69.876 | 1.00 | 0.00 | xxxx | 2012 |
| ATOM | 2013 | N | LEU | A | 268 | 92.549 | −8.632 | 70.388 | 1.00 | 0.00 | xxxx | 2013 |
| ATOM | 2014 | CA | LEU | A | 268 | 93.291 | −7.518 | 69.797 | 1.00 | 0.00 | xxxx | 2014 |
| ATOM | 2015 | C | LEU | A | 268 | 94.706 | −7.476 | 70.360 | 1.00 | 0.00 | xxxx | 2015 |
| ATOM | 2016 | O | LEU | A | 268 | 95.670 | −7.316 | 69.614 | 1.00 | 0.00 | xxxx | 2016 |
| ATOM | 2017 | CB | LEU | A | 268 | 92.593 | −6.175 | 70.054 | 1.00 | 0.00 | xxxx | 2017 |
| ATOM | 2018 | CG | LEU | A | 268 | 91.587 | −5.752 | 68.976 | 1.00 | 0.00 | xxxx | 2018 |
| ATOM | 2019 | CD1 | LEU | A | 268 | 90.516 | −6.801 | 68.720 | 1.00 | 0.00 | xxxx | 2019 |
| ATOM | 2020 | CD2 | LEU | A | 268 | 90.943 | −4.413 | 69.351 | 1.00 | 0.00 | xxxx | 2020 |
| ATOM | 2021 | N | ALA | A | 269 | 94.841 | −7.635 | 71.673 | 1.00 | 0.00 | xxxx | 2021 |
| ATOM | 2022 | CA | ALA | A | 269 | 96.166 | −7.604 | 72.289 | 1.00 | 0.00 | xxxx | 2022 |
| ATOM | 2023 | C | ALA | A | 269 | 97.052 | −8.722 | 71.752 | 1.00 | 0.00 | xxxx | 2023 |
| ATOM | 2024 | O | ALA | A | 269 | 98.217 | −8.486 | 71.430 | 1.00 | 0.00 | xxxx | 2024 |
| ATOM | 2025 | CB | ALA | A | 269 | 96.046 | −7.696 | 73.795 | 1.00 | 0.00 | xxxx | 2025 |
| ATOM | 2026 | N | LYS | A | 270 | 96.498 | −9.927 | 71.627 | 1.00 | 0.00 | xxxx | 2026 |
| ATOM | 2027 | CA | LYS | A | 270 | 97.277 | −11.069 | 71.131 | 1.00 | 0.00 | xxxx | 2027 |
| ATOM | 2028 | C | LYS | A | 270 | 97.678 | −10.875 | 69.665 | 1.00 | 0.00 | xxxx | 2028 |
| ATOM | 2029 | O | LYS | A | 270 | 98.828 | −11.149 | 69.297 | 1.00 | 0.00 | xxxx | 2029 |
| ATOM | 2030 | CB | LYS | A | 270 | 96.484 | −12.377 | 71.325 | 1.00 | 0.00 | xxxx | 2030 |
| ATOM | 2031 | CG | LYS | A | 270 | 97.152 | −13.678 | 70.800 | 1.00 | 0.00 | xxxx | 2031 |
| ATOM | 2032 | CD | LYS | A | 270 | 98.569 | −13.884 | 71.306 | 1.00 | 0.00 | xxxx | 2032 |
| ATOM | 2033 | CE | LYS | A | 270 | 99.013 | −15.346 | 71.115 | 1.00 | 0.00 | xxxx | 2033 |
| ATOM | 2034 | NZ | LYS | A | 270 | 98.873 | −15.867 | 69.718 | 1.00 | 0.00 | xxxx | 2034 |
| ATOM | 2035 | N | ASN | A | 271 | 96.752 | −10.396 | 68.830 | 1.00 | 0.00 | xxxx | 2035 |
| ATOM | 2036 | CA | ASN | A | 271 | 97.104 | −10.119 | 67.433 | 1.00 | 0.00 | xxxx | 2036 |
| ATOM | 2037 | C | ASN | A | 271 | 98.197 | −9.061 | 67.332 | 1.00 | 0.00 | xxxx | 2037 |
| ATOM | 2038 | O | ASN | A | 271 | 99.155 | −9.216 | 66.560 | 1.00 | 0.00 | xxxx | 2038 |
| ATOM | 2039 | CB | ASN | A | 271 | 95.880 | −9.661 | 66.643 | 1.00 | 0.00 | xxxx | 2039 |
| ATOM | 2040 | CG | ASN | A | 271 | 95.079 | −10.814 | 66.078 | 1.00 | 0.00 | xxxx | 2040 |
| ATOM | 2041 | OD1 | ASN | A | 271 | 95.622 | −11.879 | 65.774 | 1.00 | 0.00 | xxxx | 2041 |
| ATOM | 2042 | ND2 | ASN | A | 271 | 93.778 | −10.592 | 65.903 | 1.00 | 0.00 | xxxx | 2042 |
| ATOM | 2043 | N | LEU | A | 272 | 98.069 | −8.000 | 68.120 | 1.00 | 0.00 | xxxx | 2043 |
| ATOM | 2044 | CA | LEU | A | 272 | 99.074 | −6.935 | 68.080 | 1.00 | 0.00 | xxxx | 2044 |
| ATOM | 2045 | C | LEU | A | 272 | 100.412 | −7.448 | 68.626 | 1.00 | 0.00 | xxxx | 2045 |
| ATOM | 2046 | O | LEU | A | 272 | 101.483 | −7.126 | 68.080 | 1.00 | 0.00 | xxxx | 2046 |
| ATOM | 2047 | CB | LEU | A | 272 | 98.574 | −5.719 | 68.853 | 1.00 | 0.00 | xxxx | 2047 |
| ATOM | 2048 | CG | LEU | A | 272 | 97.416 | −5.022 | 68.138 | 1.00 | 0.00 | xxxx | 2048 |
| ATOM | 2049 | CD1 | LEU | A | 272 | 96.725 | −4.072 | 69.117 | 1.00 | 0.00 | xxxx | 2049 |
| ATOM | 2050 | CD2 | LEU | A | 272 | 97.875 | −4.262 | 66.893 | 1.00 | 0.00 | xxxx | 2050 |
| ATOM | 2051 | N | ALA | A | 273 | 100.373 | −8.263 | 69.681 | 1.00 | 0.00 | xxxx | 2051 |
| ATOM | 2052 | CA | ALA | A | 273 | 101.606 | −8.878 | 70.188 | 1.00 | 0.00 | xxxx | 2052 |
| ATOM | 2053 | C | ALA | A | 273 | 102.310 | −9.679 | 69.093 | 1.00 | 0.00 | xxxx | 2053 |

-continued

CA, calcium
HOH, Water
ACR, Acrylodan
K, potassium
EDO, ethylene glycol

| | | | | | | | | | | | |
|---|---|---|---|---|---|---|---|---|---|---|---|
| ATOM | 2054 | O | ALA | A | 273 | 103.544 | −9.724 | 69.024 | 1.00 | 0.00 | xxxx | 2054 |
| ATOM | 2055 | CB | ALA | A | 273 | 101.302 | −9.785 | 71.385 | 1.00 | 0.00 | xxxx | 2055 |
| ATOM | 2056 | N | ASP | A | 274 | 101.506 | −10.311 | 68.240 | 1.00 | 0.00 | xxxx | 2056 |
| ATOM | 2057 | CA | ASP | A | 274 | 102.014 | −11.193 | 67.195 | 1.00 | 0.00 | xxxx | 2057 |
| ATOM | 2058 | C | ASP | A | 274 | 102.445 | −10.407 | 65.958 | 1.00 | 0.00 | xxxx | 2058 |
| ATOM | 2059 | O | ASP | A | 274 | 102.948 | −10.989 | 64.988 | 1.00 | 0.00 | xxxx | 2059 |
| ATOM | 2060 | CB | ASP | A | 274 | 100.951 | −12.229 | 66.796 | 1.00 | 0.00 | xxxx | 2060 |
| ATOM | 2061 | CG | ASP | A | 274 | 100.725 | −13.303 | 67.854 | 1.00 | 0.00 | xxxx | 2061 |
| ATOM | 2062 | OD1 | ASP | A | 274 | 101.565 | −13.470 | 68.771 | 1.00 | 0.00 | xxxx | 2062 |
| ATOM | 2063 | OD2 | ASP | A | 274 | 99.701 | −14.013 | 67.747 | 1.00 | 0.00 | xxxx | 2063 |
| ATOM | 2064 | N | GLY | A | 275 | 102.244 | −9.094 | 65.978 | 1.00 | 0.00 | xxxx | 2064 |
| ATOM | 2065 | CA | GLY | A | 275 | 102.602 | −8.263 | 64.843 | 1.00 | 0.00 | xxxx | 2065 |
| ATOM | 2066 | C | GLY | A | 275 | 101.597 | −8.298 | 63.706 | 1.00 | 0.00 | xxxx | 2066 |
| ATOM | 2067 | O | GLY | A | 275 | 101.895 | −7.887 | 62.570 | 1.00 | 0.00 | xxxx | 2067 |
| ATOM | 2068 | N | LYS | A | 276 | 100.398 | −8.797 | 64.002 | 1.00 | 0.00 | xxxx | 2068 |
| ATOM | 2069 | CA | LYS | A | 276 | 99.324 | −8.872 | 63.018 | 1.00 | 0.00 | xxxx | 2069 |
| ATOM | 2070 | C | LYS | A | 276 | 98.397 | −7.670 | 63.100 | 1.00 | 0.00 | xxxx | 2070 |
| ATOM | 2071 | O | LYS | A | 276 | 98.509 | −6.852 | 64.015 | 1.00 | 0.00 | xxxx | 2071 |
| ATOM | 2072 | CB | LYS | A | 276 | 98.504 | −10.146 | 63.207 | 1.00 | 0.00 | xxxx | 2072 |
| ATOM | 2073 | CG | LYS | A | 276 | 99.297 | −11.425 | 63.092 | 1.00 | 0.00 | xxxx | 2073 |
| ATOM | 2074 | CD | LYS | A | 276 | 98.417 | −12.580 | 63.509 | 1.00 | 0.00 | xxxx | 2074 |
| ATOM | 2075 | CE | LYS | A | 276 | 99.157 | −13.890 | 63.440 | 1.00 | 0.00 | xxxx | 2075 |
| ATOM | 2076 | NZ | LYS | A | 276 | 98.229 | −15.011 | 63.774 | 1.00 | 0.00 | xxxx | 2076 |
| ATOM | 2077 | N | GLY | A | 277 | 97.474 | −7.581 | 62.143 | 1.00 | 0.00 | xxxx | 2077 |
| ATOM | 2078 | CA | GLY | A | 277 | 96.403 | −6.605 | 62.226 | 1.00 | 0.00 | xxxx | 2078 |
| ATOM | 2079 | C | GLY | A | 277 | 95.544 | −6.908 | 63.435 | 1.00 | 0.00 | xxxx | 2079 |
| ATOM | 2080 | O | GLY | A | 277 | 95.335 | −8.070 | 63.769 | 1.00 | 0.00 | xxxx | 2080 |
| ATOM | 2081 | N | ALA | A | 278 | 95.058 | −5.866 | 64.095 | 1.00 | 0.00 | xxxx | 2081 |
| ATOM | 2082 | CA | ALA | A | 278 | 94.383 | −6.019 | 65.376 | 1.00 | 0.00 | xxxx | 2082 |
| ATOM | 2083 | C | ALA | A | 278 | 93.204 | −6.995 | 65.344 | 1.00 | 0.00 | xxxx | 2083 |
| ATOM | 2084 | O | ALA | A | 278 | 93.006 | −7.747 | 66.303 | 1.00 | 0.00 | xxxx | 2084 |
| ATOM | 2085 | CB | ALA | A | 278 | 93.915 | −4.652 | 65.881 | 1.00 | 0.00 | xxxx | 2085 |
| ATOM | 2086 | N | ALA | A | 279 | 92.432 | −6.986 | 64.256 | 1.00 | 0.00 | xxxx | 2086 |
| ATOM | 2087 | CA | ALA | A | 279 | 91.224 | −7.808 | 64.177 | 1.00 | 0.00 | xxxx | 2087 |
| ATOM | 2088 | C | ALA | A | 279 | 91.413 | −9.072 | 63.342 | 1.00 | 0.00 | xxxx | 2088 |
| ATOM | 2089 | O | ALA | A | 279 | 90.444 | −9.783 | 63.071 | 1.00 | 0.00 | xxxx | 2089 |
| ATOM | 2090 | CB | ALA | A | 279 | 90.071 | −6.989 | 63.612 | 1.00 | 0.00 | xxxx | 2090 |
| ATOM | 2091 | N | ASP | A | 280 | 92.650 | −9.355 | 62.949 | 1.00 | 0.00 | xxxx | 2091 |
| ATOM | 2092 | CA | ASP | A | 280 | 92.942 | −10.490 | 62.077 | 1.00 | 0.00 | xxxx | 2092 |
| ATOM | 2093 | C | ASP | A | 280 | 92.365 | −11.800 | 62.633 | 1.00 | 0.00 | xxxx | 2093 |
| ATOM | 2094 | O | ASP | A | 280 | 92.561 | −12.136 | 63.802 | 1.00 | 0.00 | xxxx | 2094 |
| ATOM | 2095 | CB | ASP | A | 280 | 94.454 | −10.610 | 61.864 | 1.00 | 0.00 | xxxx | 2095 |
| ATOM | 2096 | CG | ASP | A | 280 | 95.004 | −9.556 | 60.903 | 1.00 | 0.00 | xxxx | 2096 |
| ATOM | 2097 | OD1 | ASP | A | 280 | 94.263 | −8.604 | 60.560 | 1.00 | 0.00 | xxxx | 2097 |
| ATOM | 2098 | OD2 | ASP | A | 280 | 96.184 | −9.677 | 60.491 | 1.00 | 0.00 | xxxx | 2098 |
| ATOM | 2099 | N | GLY | A | 281 | 91.611 | −12.511 | 61.802 | 1.00 | 0.00 | xxxx | 2099 |
| ATOM | 2100 | CA | GLY | A | 281 | 91.057 | −13.796 | 62.188 | 1.00 | 0.00 | xxxx | 2100 |
| ATOM | 2101 | C | GLY | A | 281 | 89.859 | −13.718 | 63.117 | 1.00 | 0.00 | xxxx | 2101 |
| ATOM | 2102 | O | GLY | A | 281 | 89.405 | −14.734 | 63.649 | 1.00 | 0.00 | xxxx | 2102 |
| ATOM | 2103 | N | THR | A | 282 | 89.338 | −12.511 | 63.313 | 1.00 | 0.00 | xxxx | 2103 |
| ATOM | 2104 | CA | THR | A | 282 | 88.194 | −12.309 | 64.193 | 1.00 | 0.00 | xxxx | 2104 |
| ATOM | 2105 | C | THR | A | 282 | 87.072 | −11.603 | 63.460 | 1.00 | 0.00 | xxxx | 2105 |
| ATOM | 2106 | O | THR | A | 282 | 87.253 | −11.154 | 62.333 | 1.00 | 0.00 | xxxx | 2106 |
| ATOM | 2107 | CB | THR | A | 282 | 88.542 | −11.459 | 65.418 | 1.00 | 0.00 | xxxx | 2107 |
| ATOM | 2108 | OG1 | THR | A | 282 | 88.572 | −10.079 | 65.029 | 1.00 | 0.00 | xxxx | 2108 |
| ATOM | 2109 | CG2 | THR | A | 282 | 89.899 | −11.850 | 65.993 | 1.00 | 0.00 | xxxx | 2109 |
| ATOM | 2110 | N | ASN | A | 283 | 85.923 | −11.488 | 64.117 | 1.00 | 0.00 | xxxx | 2110 |
| ATOM | 2111 | CA | ASN | A | 283 | 84.809 | −10.731 | 63.558 | 1.00 | 0.00 | xxxx | 2111 |
| ATOM | 2112 | C | ASN | A | 283 | 84.590 | −9.426 | 64.305 | 1.00 | 0.00 | xxxx | 2112 |
| ATOM | 2113 | O | ASN | A | 283 | 83.523 | −8.824 | 64.199 | 1.00 | 0.00 | xxxx | 2113 |
| ATOM | 2114 | CB | ASN | A | 283 | 83.525 | −11.561 | 63.574 | 1.00 | 0.00 | xxxx | 2114 |
| ATOM | 2115 | CG | ASN | A | 283 | 83.481 | −12.583 | 62.453 | 1.00 | 0.00 | xxxx | 2115 |
| ATOM | 2116 | OD1 | ASN | A | 283 | 83.915 | −12.311 | 61.331 | 1.00 | 0.00 | xxxx | 2116 |
| ATOM | 2117 | ND2 | ASN | A | 283 | 82.959 | −13.768 | 62.751 | 1.00 | 0.00 | xxxx | 2117 |
| ATOM | 2118 | N | TRP | A | 284 | 85.595 | −8.977 | 65.059 | 1.00 | 0.00 | xxxx | 2118 |
| ATOM | 2119 | CA | TRP | A | 284 | 85.470 | −7.704 | 65.755 | 1.00 | 0.00 | xxxx | 2119 |
| ATOM | 2120 | C | TRP | A | 284 | 85.444 | −6.558 | 64.757 | 1.00 | 0.00 | xxxx | 2120 |
| ATOM | 2121 | O | TRP | A | 284 | 86.250 | −6.505 | 63.823 | 1.00 | 0.00 | xxxx | 2121 |
| ATOM | 2122 | CB | TRP | A | 284 | 86.608 | −7.493 | 66.762 | 1.00 | 0.00 | xxxx | 2122 |
| ATOM | 2123 | CG | TRP | A | 284 | 86.637 | −8.542 | 67.829 | 1.00 | 0.00 | xxxx | 2123 |
| ATOM | 2124 | CD1 | TRP | A | 284 | 87.626 | −9.461 | 68.055 | 1.00 | 0.00 | xxxx | 2124 |
| ATOM | 2125 | CD2 | TRP | A | 284 | 85.610 | −8.815 | 68.793 | 1.00 | 0.00 | xxxx | 2125 |
| ATOM | 2126 | NE1 | TRP | A | 284 | 87.278 | −10.280 | 69.101 | 1.00 | 0.00 | xxxx | 2126 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 2127 | CE2 | TRP | A | 284 | 86.047 | −9.900 | 69.574 | 1.00 | 0.00 | xxxx | 2127 |
| ATOM | 2128 | CE3 | TRP | A | 284 | 84.360 | −8.242 | 69.069 | 1.00 | 0.00 | xxxx | 2128 |
| ATOM | 2129 | CZ2 | TRP | A | 284 | 85.283 | −10.432 | 70.607 | 1.00 | 0.00 | xxxx | 2129 |
| ATOM | 2130 | CZ3 | TRP | A | 284 | 83.605 | −8.766 | 70.106 | 1.00 | 0.00 | xxxx | 2130 |
| ATOM | 2131 | CH2 | TRP | A | 284 | 84.069 | −9.846 | 70.861 | 1.00 | 0.00 | xxxx | 2131 |
| ATOM | 2132 | N | LYS | A | 285 | 84.499 | −5.649 | 64.971 | 1.00 | 0.00 | xxxx | 2132 |
| ATOM | 2133 | CA | LYS | A | 285 | 84.365 | −4.451 | 64.160 | 1.00 | 0.00 | xxxx | 2133 |
| ATOM | 2134 | C | LYS | A | 285 | 85.161 | −3.326 | 64.800 | 1.00 | 0.00 | xxxx | 2134 |
| ATOM | 2135 | O | LYS | A | 285 | 84.763 | −2.787 | 65.829 | 1.00 | 0.00 | xxxx | 2135 |
| ATOM | 2136 | CB | LYS | A | 285 | 82.895 | −4.057 | 64.030 | 1.00 | 0.00 | xxxx | 2136 |
| ATOM | 2137 | CG | LYS | A | 285 | 82.649 | −2.809 | 63.208 | 1.00 | 0.00 | xxxx | 2137 |
| ATOM | 2138 | CD | LYS | A | 285 | 81.294 | −2.189 | 63.538 | 1.00 | 0.00 | xxxx | 2138 |
| ATOM | 2139 | CE | LYS | A | 285 | 80.195 | −3.244 | 63.631 | 1.00 | 0.00 | xxxx | 2139 |
| ATOM | 2140 | NZ | LYS | A | 285 | 80.057 | −4.036 | 62.376 | 1.00 | 0.00 | xxxx | 2140 |
| ATOM | 2141 | N | ILE | A | 286 | 86.301 | −2.995 | 64.206 | 1.00 | 0.00 | xxxx | 2141 |
| ATOM | 2142 | CA | ILE | A | 286 | 87.124 | −1.913 | 64.718 | 1.00 | 0.00 | xxxx | 2142 |
| ATOM | 2143 | C | ILE | A | 286 | 86.816 | −0.677 | 63.901 | 1.00 | 0.00 | xxxx | 2143 |
| ATOM | 2144 | O | ILE | A | 286 | 86.990 | −0.675 | 62.677 | 1.00 | 0.00 | xxxx | 2144 |
| ATOM | 2145 | CB | ILE | A | 286 | 88.618 | −2.254 | 64.662 | 1.00 | 0.00 | xxxx | 2145 |
| ATOM | 2146 | CGI | ILE | A | 286 | 88.915 | −3.557 | 65.408 | 1.00 | 0.00 | xxxx | 2146 |
| ATOM | 2147 | CG2 | ILE | A | 286 | 89.437 | −1.152 | 65.286 | 1.00 | 0.00 | xxxx | 2147 |
| ATOM | 2148 | CD1 | ILE | A | 286 | 90.402 | −3.902 | 65.442 | 1.00 | 0.00 | xxxx | 2148 |
| ATOM | 2149 | N | ASP | A | 287 | 86.329 | 0.363 | 64.570 | 1.00 | 0.00 | xxxx | 2149 |
| ATOM | 2150 | CA | ASP | A | 287 | 86.022 | 1.631 | 63.916 | 1.00 | 0.00 | xxxx | 2150 |
| ATOM | 2151 | C | ASP | A | 287 | 86.955 | 2.709 | 64.451 | 1.00 | 0.00 | xxxx | 2151 |
| ATOM | 2152 | O | ASP | A | 287 | 86.837 | 3.105 | 65.616 | 1.00 | 0.00 | xxxx | 2152 |
| ATOM | 2153 | CB | ASP | A | 287 | 84.563 | 2.017 | 64.150 | 1.00 | 0.00 | xxxx | 2153 |
| ATOM | 2154 | CG | ASP | A | 287 | 84.222 | 3.391 | 63.604 | 1.00 | 0.00 | xxxx | 2154 |
| ATOM | 2155 | OD1 | ASP | A | 287 | 83.193 | 3.952 | 64.034 | 1.00 | 0.00 | xxxx | 2155 |
| ATOM | 2156 | OD2 | ASP | A | 287 | 84.976 | 3.911 | 62.754 | 1.00 | 0.00 | xxxx | 2156 |
| ATOM | 2157 | N | ASN | A | 288 | 87.874 | 3.167 | 63.603 | 1.00 | 0.00 | xxxx | 2157 |
| ATOM | 2158 | CA | ASN | A | 288 | 88.884 | 4.149 | 63.997 | 1.00 | 0.00 | xxxx | 2158 |
| ATOM | 2159 | C | ASN | A | 288 | 89.522 | 3.727 | 65.319 | 1.00 | 0.00 | xxxx | 2159 |
| ATOM | 2160 | O | ASN | A | 288 | 89.561 | 4.490 | 66.282 | 1.00 | 0.00 | xxxx | 2160 |
| ATOM | 2161 | CB | ASN | A | 288 | 88.279 | 5.547 | 64.118 | 1.00 | 0.00 | xxxx | 2161 |
| ATOM | 2162 | CG | ASN | A | 288 | 89.326 | 6.645 | 64.007 | 1.00 | 0.00 | xxxx | 2162 |
| ATOM | 2163 | OD1 | ASN | A | 288 | 90.478 | 6.391 | 63.649 | 1.00 | 0.00 | xxxx | 2163 |
| ATOM | 2164 | ND2 | ASN | A | 288 | 88.926 | 7.874 | 64.312 | 1.00 | 0.00 | xxxx | 2164 |
| ATOM | 2165 | N | LYS | A | 289 | 89.969 | 2.475 | 65.337 | 1.00 | 0.00 | xxxx | 2165 |
| ATOM | 2166 | CA | LYS | A | 289 | 90.722 | 1.852 | 66.426 | 1.00 | 0.00 | xxxx | 2166 |
| ATOM | 2167 | C | LYS | A | 289 | 89.913 | 1.565 | 67.685 | 1.00 | 0.00 | xxxx | 2167 |
| ATOM | 2168 | O | LYS | A | 289 | 90.494 | 1.252 | 68.706 | 1.00 | 0.00 | xxxx | 2168 |
| ATOM | 2169 | CB | LYS | A | 289 | 91.943 | 2.703 | 66.761 | 1.00 | 0.00 | xxxx | 2169 |
| ATOM | 2170 | CG | LYS | A | 289 | 92.803 | 2.945 | 65.519 | 1.00 | 0.00 | xxxx | 2170 |
| ATOM | 2171 | CD | LYS | A | 289 | 94.224 | 3.241 | 65.877 | 1.00 | 0.00 | xxxx | 2171 |
| ATOM | 2172 | CE | LYS | A | 289 | 94.317 | 4.511 | 66.697 | 1.00 | 0.00 | xxxx | 2172 |
| ATOM | 2173 | NZ | LYS | A | 289 | 95.738 | 4.684 | 67.101 | 1.00 | 0.00 | xxxx | 2173 |
| ATOM | 2174 | N | VAL | A | 290 | 88.585 | 1.619 | 67.581 | 1.00 | 0.00 | xxxx | 2174 |
| ATOM | 2175 | CA | VAL | A | 290 | 87.691 | 1.387 | 68.712 | 1.00 | 0.00 | xxxx | 2175 |
| ATOM | 2176 | C | VAL | A | 290 | 86.720 | 0.237 | 68.435 | 1.00 | 0.00 | xxxx | 2176 |
| ATOM | 2177 | O | VAL | A | 290 | 86.116 | 0.171 | 67.356 | 1.00 | 0.00 | xxxx | 2177 |
| ATOM | 2178 | CB | VAL | A | 290 | 86.903 | 2.664 | 69.053 | 1.00 | 0.00 | xxxx | 2178 |
| ATOM | 2179 | CG1 | VAL | A | 290 | 85.925 | 2.394 | 70.204 | 1.00 | 0.00 | xxxx | 2179 |
| ATOM | 2180 | CG2 | VAL | A | 290 | 87.847 | 3.824 | 69.381 | 1.00 | 0.00 | xxxx | 2180 |
| ATOM | 2181 | N | VAL | A | 291 | 86.578 | −0.658 | 69.414 | 1.00 | 0.00 | xxxx | 2181 |
| ATOM | 2182 | CA | VAL | A | 291 | 85.515 | −1.666 | 69.437 | 1.00 | 0.00 | xxxx | 2182 |
| ATOM | 2183 | C | VAL | A | 291 | 84.489 | −1.292 | 70.498 | 1.00 | 0.00 | xxxx | 2183 |
| ATOM | 2184 | O | VAL | A | 291 | 84.852 | −1.110 | 71.657 | 1.00 | 0.00 | xxxx | 2184 |
| ATOM | 2185 | CB | VAL | A | 291 | 86.066 | −3.066 | 69.726 | 1.00 | 0.00 | xxxx | 2185 |
| ATOM | 2186 | CG1 | VAL | A | 291 | 84.922 | −4.078 | 69.847 | 1.00 | 0.00 | xxxx | 2186 |
| ATOM | 2187 | CG2 | VAL | A | 291 | 87.077 | −3.484 | 68.661 | 1.00 | 0.00 | xxxx | 2187 |
| ATOM | 2188 | N | ARG | A | 292 | 83.218 | −1.198 | 70.124 | 1.00 | 0.00 | xxxx | 2188 |
| ATOM | 2189 | CA | ARG | A | 292 | 82.153 | −0.990 | 71.106 | 1.00 | 0.00 | xxxx | 2189 |
| ATOM | 2190 | C | ARG | A | 292 | 81.193 | −2.177 | 71.103 | 1.00 | 0.00 | xxxx | 2190 |
| ATOM | 2191 | O | ARG | A | 292 | 80.611 | −2.524 | 70.072 | 1.00 | 0.00 | xxxx | 2191 |
| ATOM | 2192 | CB | ARG | A | 292 | 81.410 | 0.318 | 70.830 | 1.00 | 0.00 | xxxx | 2192 |
| ATOM | 2193 | CG | ARG | A | 292 | 82.339 | 1.527 | 70.900 | 1.00 | 0.00 | xxxx | 2193 |
| ATOM | 2194 | CD | ARG | A | 292 | 81.619 | 2.864 | 70.873 | 1.00 | 0.00 | xxxx | 2194 |
| ATOM | 2195 | NE | ARG | A | 292 | 82.583 | 3.942 | 70.642 | 1.00 | 0.00 | xxxx | 2195 |
| ATOM | 2196 | CZ | ARG | A | 292 | 83.265 | 4.572 | 71.597 | 1.00 | 0.00 | xxxx | 2196 |
| ATOM | 2197 | NH1 | ARG | A | 292 | 83.082 | 4.260 | 72.880 | 1.00 | 0.00 | xxxx | 2197 |
| ATOM | 2198 | NH2 | ARG | A | 292 | 84.133 | 5.524 | 71.270 | 1.00 | 0.00 | xxxx | 2198 |
| ATOM | 2199 | N | VAL | A | 293 | 81.035 | −2.795 | 72.270 | 1.00 | 0.00 | xxxx | 2199 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 2200 | CA | VAL | A | 293 | 80.206 | −3.979 | 72.446 | 1.00 | 0.00 | xxxx | 2200 |
| ATOM | 2201 | C | VAL | A | 293 | 78.823 | −3.541 | 72.921 | 1.00 | 0.00 | xxxx | 2201 |
| ATOM | 2202 | O | VAL | A | 293 | 78.716 | −2.749 | 73.854 | 1.00 | 0.00 | xxxx | 2202 |
| ATOM | 2203 | CB | VAL | A | 293 | 80.868 | −4.953 | 73.451 | 1.00 | 0.00 | xxxx | 2203 |
| ATOM | 2204 | CG1 | VAL | A | 293 | 80.007 | −6.186 | 73.661 | 1.00 | 0.00 | xxxx | 2204 |
| ATOM | 2205 | CG2 | VAL | A | 293 | 82.286 | −5.342 | 72.966 | 1.00 | 0.00 | xxxx | 2205 |
| ATOM | 2206 | N | PRO | A | 294 | 77.763 | −4.028 | 72.264 | 1.00 | 0.00 | xxxx | 2206 |
| ATOM | 2207 | CA | PRO | A | 294 | 76.400 | −3.585 | 72.591 | 1.00 | 0.00 | xxxx | 2207 |
| ATOM | 2208 | C | PRO | A | 294 | 75.942 | −3.913 | 74.009 | 1.00 | 0.00 | xxxx | 2208 |
| ATOM | 2209 | O | PRO | A | 294 | 76.295 | −4.954 | 74.569 | 1.00 | 0.00 | xxxx | 2209 |
| ATOM | 2210 | CB | PRO | A | 294 | 75.530 | −4.347 | 71.592 | 1.00 | 0.00 | xxxx | 2210 |
| ATOM | 2211 | CG | PRO | A | 294 | 76.441 | −4.689 | 70.475 | 1.00 | 0.00 | xxxx | 2211 |
| ATOM | 2212 | CD | PRO | A | 294 | 77.791 | −4.917 | 71.094 | 1.00 | 0.00 | xxxx | 2212 |
| ATOM | 2213 | N | TYR | A | 295 | 75.146 | −3.004 | 74.563 | 1.00 | 0.00 | xxxx | 2213 |
| ATOM | 2214 | CA | TYR | A | 295 | 74.359 | −3.271 | 75.761 | 1.00 | 0.00 | xxxx | 2214 |
| ATOM | 2215 | C | TYR | A | 295 | 73.038 | −3.956 | 75.407 | 1.00 | 0.00 | xxxx | 2215 |
| ATOM | 2216 | O | TYR | A | 295 | 72.542 | −3.815 | 74.291 | 1.00 | 0.00 | xxxx | 2216 |
| ATOM | 2217 | CB | TYR | A | 295 | 74.047 | −1.974 | 76.497 | 1.00 | 0.00 | xxxx | 2217 |
| ATOM | 2218 | CG | TYR | A | 295 | 75.211 | −1.244 | 77.128 | 1.00 | 0.00 | xxxx | 2218 |
| ATOM | 2219 | CD1 | TYR | A | 295 | 75.657 | −1.576 | 78.401 | 1.00 | 0.00 | xxxx | 2219 |
| ATOM | 2220 | CD2 | TYR | A | 295 | 75.805 | −0.160 | 76.490 | 1.00 | 0.00 | xxxx | 2220 |
| ATOM | 2221 | CE1 | TYR | A | 295 | 76.699 | −0.880 | 79.010 | 1.00 | 0.00 | xxxx | 2221 |
| ATOM | 2222 | CE2 | TYR | A | 295 | 76.839 | 0.540 | 77.088 | 1.00 | 0.00 | xxxx | 2222 |
| ATOM | 2223 | CZ | TYR | A | 295 | 77.287 | 0.179 | 78.349 | 1.00 | 0.00 | xxxx | 2223 |
| ATOM | 2224 | OH | TYR | A | 295 | 78.304 | 0.888 | 78.944 | 1.00 | 0.00 | xxxx | 2224 |
| ATOM | 2225 | N | VAL | A | 296 | 72.448 | −4.668 | 76.368 | 1.00 | 0.00 | xxxx | 2225 |
| ATOM | 2226 | CA | VAL | A | 296 | 71.141 | −5.312 | 76.180 | 1.00 | 0.00 | xxxx | 2226 |
| ATOM | 2227 | C | VAL | A | 296 | 70.270 | −5.142 | 77.430 | 1.00 | 0.00 | xxxx | 2227 |
| ATOM | 2228 | O | VAL | A | 296 | 70.722 | −5.438 | 78.526 | 1.00 | 0.00 | xxxx | 2228 |
| ATOM | 2229 | CB | VAL | A | 296 | 71.290 | −6.820 | 75.854 | 1.00 | 0.00 | xxxx | 2229 |
| ATOM | 2230 | CG1 | VAL | A | 296 | 69.929 | −7.427 | 75.553 | 1.00 | 0.00 | xxxx | 2230 |
| ATOM | 2231 | CG2 | VAL | A | 296 | 72.262 | −7.048 | 74.700 | 1.00 | 0.00 | xxxx | 2231 |
| ATOM | 2232 | N | GLY | A | 297 | 69.024 | −4.691 | 77.273 | 1.00 | 0.00 | xxxx | 2232 |
| ATOM | 2233 | CA | GLY | A | 297 | 68.127 | −4.557 | 78.417 | 1.00 | 0.00 | xxxx | 2233 |
| ATOM | 2234 | C | GLY | A | 297 | 67.730 | −5.896 | 79.010 | 1.00 | 0.00 | xxxx | 2234 |
| ATOM | 2235 | O | GLY | A | 297 | 67.462 | −6.840 | 78.271 | 1.00 | 0.00 | xxxx | 2235 |
| ATOM | 2236 | N | VAL | A | 298 | 67.682 | −5.980 | 80.341 | 1.00 | 0.00 | xxxx | 2236 |
| ATOM | 2237 | CA | VAL | A | 298 | 67.368 | −7.232 | 81.032 | 1.00 | 0.00 | xxxx | 2237 |
| ATOM | 2238 | C | VAL | A | 298 | 66.268 | −7.038 | 82.073 | 1.00 | 0.00 | xxxx | 2238 |
| ATOM | 2239 | O | VAL | A | 298 | 66.392 | −6.199 | 82.965 | 1.00 | 0.00 | xxxx | 2239 |
| ATOM | 2240 | CB | VAL | A | 298 | 68.630 | −7.827 | 81.717 | 1.00 | 0.00 | xxxx | 2240 |
| ATOM | 2241 | CG1 | VAL | A | 298 | 68.279 | −9.124 | 82.444 | 1.00 | 0.00 | xxxx | 2241 |
| ATOM | 2242 | CG2 | VAL | A | 298 | 69.751 | −8.070 | 80.706 | 1.00 | 0.00 | xxxx | 2242 |
| ATOM | 2243 | N | ASP | A | 299 | 65.203 | −7.826 | 81.982 | 1.00 | 0.00 | xxxx | 2243 |
| ATOM | 2244 | CA | ASP | A | 299 | 64.227 | −7.885 | 83.067 | 1.00 | 0.00 | xxxx | 2244 |
| ATOM | 2245 | C | ASP | A | 299 | 63.676 | −9.302 | 83.204 | 1.00 | 0.00 | xxxx | 2245 |
| ATOM | 2246 | O | ASP | A | 299 | 64.224 | −10.238 | 82.626 | 1.00 | 0.00 | xxxx | 2246 |
| ATOM | 2247 | CB | ASP | A | 299 | 63.100 | −6.871 | 82.852 | 1.00 | 0.00 | xxxx | 2247 |
| ATOM | 2248 | CG | ASP | A | 299 | 62.370 | −7.052 | 81.526 | 1.00 | 0.00 | xxxx | 2248 |
| ATOM | 2249 | OD1 | ASP | A | 299 | 62.441 | −8.141 | 80.921 | 1.00 | 0.00 | xxxx | 2249 |
| ATOM | 2250 | OD2 | ASP | A | 299 | 61.711 | −6.090 | 81.088 | 1.00 | 0.00 | xxxx | 2250 |
| ATOM | 2251 | N | LYS | A | 300 | 62.601 | −9.459 | 83.969 | 1.00 | 0.00 | xxxx | 2251 |
| ATOM | 2252 | CA | LYS | A | 300 | 62.028 | −10.784 | 84.188 | 1.00 | 0.00 | xxxx | 2252 |
| ATOM | 2253 | C | LYS | A | 300 | 61.629 | −11.480 | 82.887 | 1.00 | 0.00 | xxxx | 2253 |
| ATOM | 2254 | O | LYS | A | 300 | 61.693 | −12.708 | 82.795 | 1.00 | 0.00 | xxxx | 2254 |
| ATOM | 2255 | CB | LYS | A | 300 | 60.817 | −10.692 | 85.117 | 1.00 | 0.00 | xxxx | 2255 |
| ATOM | 2256 | CG | LYS | A | 300 | 61.178 | −10.695 | 86.589 | 1.00 | 0.00 | xxxx | 2256 |
| ATOM | 2257 | CD | LYS | A | 300 | 59.943 | −10.846 | 87.458 | 1.00 | 0.00 | xxxx | 2257 |
| ATOM | 2258 | CE | LYS | A | 300 | 60.317 | −11.060 | 88.913 | 1.00 | 0.00 | xxxx | 2258 |
| ATOM | 2259 | NZ | LYS | A | 300 | 59.113 | −11.141 | 89.790 | 1.00 | 0.00 | xxxx | 2259 |
| ATOM | 2260 | N | ASP | A | 301 | 61.237 | −10.703 | 81.881 | 1.00 | 0.00 | xxxx | 2260 |
| ATOM | 2261 | CA | ASP | A | 301 | 60.716 | −11.282 | 80.637 | 1.00 | 0.00 | xxxx | 2261 |
| ATOM | 2262 | C | ASP | A | 301 | 61.778 | −12.014 | 79.811 | 1.00 | 0.00 | xxxx | 2262 |
| ATOM | 2263 | O | ASP | A | 301 | 61.472 | −13.011 | 79.157 | 1.00 | 0.00 | xxxx | 2263 |
| ATOM | 2264 | CB | ASP | A | 301 | 60.063 | −10.203 | 79.770 | 1.00 | 0.00 | xxxx | 2264 |
| ATOM | 2265 | CG | ASP | A | 301 | 58.783 | −9.660 | 80.375 | 1.00 | 0.00 | xxxx | 2265 |
| ATOM | 2266 | OD1 | ASP | A | 301 | 58.198 | −10.330 | 81.253 | 1.00 | 0.00 | xxxx | 2266 |
| ATOM | 2267 | OD2 | ASP | A | 301 | 58.354 | −8.562 | 79.961 | 1.00 | 0.00 | xxxx | 2267 |
| ATOM | 2268 | N | ASN | A | 302 | 63.016 | −11.527 | 79.825 | 1.00 | 0.00 | xxxx | 2268 |
| ATOM | 2269 | CA | ASN | A | 302 | 64.069 | −12.161 | 79.033 | 1.00 | 0.00 | xxxx | 2269 |
| ATOM | 2270 | C | ASN | A | 302 | 65.214 | −12.678 | 79.899 | 1.00 | 0.00 | xxxx | 2270 |
| ATOM | 2271 | O | ASN | A | 302 | 66.301 | −12.953 | 79.397 | 1.00 | 0.00 | xxxx | 2271 |
| ATOM | 2272 | CB | ASN | A | 302 | 64.607 | −11.195 | 77.961 | 1.00 | 0.00 | xxxx | 2272 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| ATOM | 2273 | CG | ASN | A | 302 | 65.396 | −10.021 | 78.546 | 1.00 | 0.00 | xxxx | 2273 |
| ATOM | 2274 | OD1 | ASN | A | 302 | 65.258 | −9.690 | 79.720 | 1.00 | 0.00 | xxxx | 2274 |
| ATOM | 2275 | ND2 | ASN | A | 302 | 66.218 | −9.383 | 77.714 | 1.00 | 0.00 | xxxx | 2275 |
| ATOM | 2276 | N | LEU | A | 303 | 64.950 | −12.842 | 81.192 | 1.00 | 0.00 | xxxx | 2276 |
| ATOM | 2277 | CA | LEU | A | 303 | 65.989 | −13.194 | 82.159 | 1.00 | 0.00 | xxxx | 2277 |
| ATOM | 2278 | C | LEU | A | 303 | 66.640 | −14.545 | 81.863 | 1.00 | 0.00 | xxxx | 2278 |
| ATOM | 2279 | O | LEU | A | 303 | 67.844 | −14.722 | 82.055 | 1.00 | 0.00 | xxxx | 2279 |
| ATOM | 2280 | CB | LEU | A | 303 | 65.406 | −13.204 | 83.575 | 1.00 | 0.00 | xxxx | 2280 |
| ATOM | 2281 | CG | LEU | A | 303 | 66.412 | −13.453 | 84.698 | 1.00 | 0.00 | xxxx | 2281 |
| ATOM | 2282 | CD1 | LEU | A | 303 | 67.491 | −12.378 | 84.690 | 1.00 | 0.00 | xxxx | 2282 |
| ATOM | 2283 | CD2 | LEU | A | 303 | 65.705 | −13.529 | 86.046 | 1.00 | 0.00 | xxxx | 2283 |
| ATOM | 2284 | N | ALA | A | 304 | 65.835 | −15.486 | 81.382 | 1.00 | 0.00 | xxxx | 2284 |
| ATOM | 2285 | CA | ALA | A | 304 | 66.295 | −16.847 | 81.119 | 1.00 | 0.00 | xxxx | 2285 |
| ATOM | 2286 | C | ALA | A | 304 | 67.334 | −16.907 | 79.999 | 1.00 | 0.00 | xxxx | 2286 |
| ATOM | 2287 | O | ALA | A | 304 | 68.003 | −17.926 | 79.822 | 1.00 | 0.00 | xxxx | 2287 |
| ATOM | 2288 | CB | ALA | A | 304 | 65.110 | −17.741 | 80.783 | 1.00 | 0.00 | xxxx | 2288 |
| ATOM | 2289 | O | GLU | A | 305 | 70.668 | −15.086 | 77.723 | 1.00 | 0.00 | xxxx | 2289 |
| ATOM | 2290 | N | GLU | A | 305 | 67.465 | −15.817 | 79.248 | 1.00 | 0.00 | xxxx | 2290 |
| ATOM | 2291 | CA | GLU | A | 305 | 68.405 | −15.758 | 78.133 | 1.00 | 0.00 | xxxx | 2291 |
| ATOM | 2292 | C | GLU | A | 305 | 69.808 | −15.338 | 78.567 | 1.00 | 0.00 | xxxx | 2292 |
| ATOM | 2293 | CB | GLU | A | 305 | 67.897 | −14.793 | 77.060 | 1.00 | 0.00 | xxxx | 2293 |
| ATOM | 2294 | CG | GLU | A | 305 | 66.535 | −15.149 | 76.491 | 1.00 | 0.00 | xxxx | 2294 |
| ATOM | 2295 | CD | GLU | A | 305 | 65.997 | −14.081 | 75.556 | 1.00 | 0.00 | xxxx | 2295 |
| ATOM | 2296 | OE1 | GLU | A | 305 | 66.778 | −13.194 | 75.150 | 1.00 | 0.00 | xxxx | 2296 |
| ATOM | 2297 | OE2 | GLU | A | 305 | 64.790 | −14.124 | 75.230 | 1.00 | 0.00 | xxxx | 2297 |
| ATOM | 2298 | N | PHE | A | 306 | 70.042 | −15.263 | 79.874 | 1.00 | 0.00 | xxxx | 2298 |
| ATOM | 2299 | CA | PHE | A | 306 | 71.332 | −14.800 | 80.384 | 1.00 | 0.00 | xxxx | 2299 |
| ATOM | 2300 | C | PHE | A | 306 | 71.923 | −15.759 | 81.414 | 1.00 | 0.00 | xxxx | 2300 |
| ATOM | 2301 | O | PHE | A | 306 | 71.297 | −16.063 | 82.430 | 1.00 | 0.00 | xxxx | 2301 |
| ATOM | 2302 | CB | PHE | A | 306 | 71.190 | −13.397 | 80.983 | 1.00 | 0.00 | xxxx | 2302 |
| ATOM | 2303 | CG | PHE | A | 306 | 70.743 | −12.366 | 79.989 | 1.00 | 0.00 | xxxx | 2303 |
| ATOM | 2304 | CD1 | PHE | A | 306 | 71.669 | −11.643 | 79.258 | 1.00 | 0.00 | xxxx | 2304 |
| ATOM | 2305 | CD2 | PHE | A | 306 | 69.394 | −12.139 | 79.766 | 1.00 | 0.00 | xxxx | 2305 |
| ATOM | 2306 | CE1 | PHE | A | 306 | 71.259 | −10.703 | 78.330 | 1.00 | 0.00 | xxxx | 2306 |
| ATOM | 2307 | CE2 | PHE | A | 306 | 68.979 | −11.206 | 78.839 | 1.00 | 0.00 | xxxx | 2307 |
| ATOM | 2308 | CZ | PHE | A | 306 | 69.912 | −10.488 | 78.118 | 1.00 | 0.00 | xxxx | 2308 |
| ATOM | 2309 | N | SER | A | 307 | 73.135 | −16.234 | 81.137 | 1.00 | 0.00 | xxxx | 2309 |
| ATOM | 2310 | CA | SER | A | 307 | 73.836 | −17.143 | 82.037 | 1.00 | 0.00 | xxxx | 2310 |
| ATOM | 2311 | C | SER | A | 307 | 74.912 | −16.399 | 82.823 | 1.00 | 0.00 | xxxx | 2311 |
| ATOM | 2312 | O | SER | A | 307 | 74.852 | −15.178 | 82.974 | 1.00 | 0.00 | xxxx | 2312 |
| ATOM | 2313 | CB | SER | A | 307 | 74.460 | −18.305 | 81.257 | 1.00 | 0.00 | xxxx | 2313 |
| ATOM | 2314 | OG | SER | A | 307 | 73.468 | −19.075 | 80.596 | 1.00 | 0.00 | xxxx | 2314 |
| HETATM | 2315 | C2 | GLC | B | 1 | 92.690 | −2.746 | 98.842 | 1.00 | 0.00 | xxxx | 2315 |
| HETATM | 2316 | C3 | GLC | B | 1 | 92.583 | −2.324 | 97.414 | 1.00 | 0.00 | xxxx | 2316 |
| HETATM | 2317 | C4 | GLC | B | 1 | 92.596 | −3.496 | 96.471 | 1.00 | 0.00 | xxxx | 2317 |
| HETATM | 2318 | C5 | GLC | B | 1 | 91.481 | −4.463 | 96.869 | 1.00 | 0.00 | xxxx | 2318 |
| HETATM | 2319 | C6 | GLC | B | 1 | 91.486 | −5.686 | 96.009 | 1.00 | 0.00 | xxxx | 2319 |
| HETATM | 2320 | C1 | GLC | B | 1 | 91.608 | −3.754 | 99.186 | 1.00 | 0.00 | xxxx | 2320 |
| HETATM | 2321 | O1 | GLC | B | 1 | 91.764 | −4.278 | 100.438 | 1.00 | 0.00 | xxxx | 2321 |
| HETATM | 2322 | O2 | GLC | B | 1 | 92.488 | −1.602 | 99.689 | 1.00 | 0.00 | xxxx | 2322 |
| HETATM | 2323 | O3 | GLC | B | 1 | 93.663 | −1.404 | 97.079 | 1.00 | 0.00 | xxxx | 2323 |
| HETATM | 2324 | O4 | GLC | B | 1 | 92.389 | −3.037 | 95.130 | 1.00 | 0.00 | xxxx | 2324 |
| HETATM | 2325 | O5 | GLC | B | 1 | 91.680 | −4.901 | 98.250 | 1.00 | 0.00 | xxxx | 2325 |
| HETATM | 2326 | O6 | GLC | B | 1 | 90.408 | −6.542 | 96.329 | 1.00 | 0.00 | xxxx | 2326 |
| HETATM | 2327 | C2 | GLC | B | 1 | 83.021 | −4.575 | 97.570 | 1.00 | 0.00 | xxxx | 2327 |
| HETATM | 2328 | C3 | GLC | B | 1 | 81.832 | −4.206 | 96.753 | 1.00 | 0.00 | xxxx | 2328 |
| HETATM | 2329 | C4 | GLC | B | 1 | 81.920 | −2.801 | 96.215 | 1.00 | 0.00 | xxxx | 2329 |
| HETATM | 2330 | C5 | GLC | B | 1 | 83.229 | −2.630 | 95.437 | 1.00 | 0.00 | xxxx | 2330 |
| HETATM | 2331 | C6 | GLC | B | 1 | 83.321 | −1.238 | 94.879 | 1.00 | 0.00 | xxxx | 2331 |
| HETATM | 2332 | C1 | GLC | B | 1 | 84.339 | −4.267 | 96.878 | 1.00 | 0.00 | xxxx | 2332 |
| HETATM | 2333 | O1 | GLC | B | 1 | 85.348 | −4.414 | 97.783 | 1.00 | 0.00 | xxxx | 2333 |
| HETATM | 2334 | O2 | GLC | B | 1 | 82.974 | −5.984 | 97.880 | 1.00 | 0.00 | xxxx | 2334 |
| HETATM | 2335 | O3 | GLC | B | 1 | 80.691 | −4.345 | 97.633 | 1.00 | 0.00 | xxxx | 2335 |
| HETATM | 2336 | O4 | GLC | B | 1 | 80.814 | −2.458 | 95.361 | 1.00 | 0.00 | xxxx | 2336 |
| HETATM | 2337 | O5 | GLC | B | 1 | 84.362 | −2.867 | 96.341 | 1.00 | 0.00 | xxxx | 2337 |
| HETATM | 2338 | O6 | GLC | B | 1 | 84.340 | −1.167 | 93.916 | 1.00 | 0.00 | xxxx | 2338 |
| HETATM | 2339 | C2 | GLC | B | 1 | 80.567 | −0.156 | 84.804 | 1.00 | 0.00 | xxxx | 2339 |
| HETATM | 2340 | C3 | GLC | B | 1 | 80.797 | 0.238 | 86.214 | 1.00 | 0.00 | xxxx | 2340 |
| HETATM | 2341 | C4 | GLC | B | 1 | 82.268 | 0.274 | 86.520 | 1.00 | 0.00 | xxxx | 2341 |
| HETATM | 2342 | C5 | GLC | B | 1 | 83.019 | 1.200 | 85.560 | 1.00 | 0.00 | xxxx | 2342 |
| HETATM | 2343 | C6 | GLC | B | 1 | 84.494 | 1.071 | 85.797 | 1.00 | 0.00 | xxxx | 2343 |
| HETATM | 2344 | C1 | GLC | B | 1 | 81.296 | 0.784 | 83.863 | 1.00 | 0.00 | xxxx | 2344 |
| HETATM | 2345 | O1 | GLC | B | 1 | 81.119 | 0.356 | 82.586 | 1.00 | 0.00 | xxxx | 2345 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| HETATM | 2346 | O2 | GLC | B | 1 | 79.162 | −0.097 | 84.487 | 1.00 | 0.00 | xxxx | 2346 |
| HETATM | 2347 | O3 | GLC | B | 1 | 80.162 | −0.738 | 87.080 | 1.00 | 0.00 | xxxx | 2347 |
| HETATM | 2348 | O4 | GLC | B | 1 | 82.448 | 0.724 | 87.865 | 1.00 | 0.00 | xxxx | 2348 |
| HETATM | 2349 | O5 | GLC | B | 1 | 82.760 | 0.835 | 84.165 | 1.00 | 0.00 | xxxx | 2349 |
| HETATM | 2350 | O6 | GLC | B | 1 | 85.215 | 1.890 | 84.906 | 1.00 | 0.00 | xxxx | 2350 |
| HETATM | 2351 | C01 | ACR | H | 1 | 89.320 | 8.265 | 96.523 | 1.00 | 0.00 | xxxx | 2351 |
| HETATM | 2352 | N02 | ACR | H | 1 | 88.307 | 7.240 | 96.350 | 1.00 | 0.00 | xxxx | 2352 |
| HETATM | 2353 | C03 | ACR | H | 1 | 87.743 | 6.573 | 97.511 | 1.00 | 0.00 | xxxx | 2353 |
| HETATM | 2354 | C04 | ACR | H | 1 | 87.854 | 6.877 | 95.019 | 1.00 | 0.00 | xxxx | 2354 |
| HETATM | 2355 | C05 | ACR | H | 1 | 86.887 | 5.890 | 94.867 | 1.00 | 0.00 | xxxx | 2355 |
| HETATM | 2356 | C06 | ACR | H | 1 | 86.444 | 5.530 | 93.561 | 1.00 | 0.00 | xxxx | 2356 |
| HETATM | 2357 | C07 | ACR | H | 1 | 86.959 | 6.149 | 92.460 | 1.00 | 0.00 | xxxx | 2357 |
| HETATM | 2358 | C08 | ACR | H | 1 | 87.951 | 7.162 | 92.617 | 1.00 | 0.00 | xxxx | 2358 |
| HETATM | 2359 | C09 | ACR | H | 1 | 88.389 | 7.511 | 93.893 | 1.00 | 0.00 | xxxx | 2359 |
| HETATM | 2360 | C10 | ACR | H | 1 | 86.503 | 5.785 | 91.156 | 1.00 | 0.00 | xxxx | 2360 |
| HETATM | 2361 | C11 | ACR | H | 1 | 85.537 | 4.795 | 91.016 | 1.00 | 0.00 | xxxx | 2361 |
| HETATM | 2362 | C12 | ACR | H | 1 | 85.018 | 4.165 | 92.145 | 1.00 | 0.00 | xxxx | 2362 |
| HETATM | 2363 | C13 | ACR | H | 1 | 85.455 | 4.521 | 93.413 | 1.00 | 0.00 | xxxx | 2363 |
| HETATM | 2364 | C14 | ACR | H | 1 | 85.016 | 4.366 | 89.647 | 1.00 | 0.00 | xxxx | 2364 |
| HETATM | 2365 | O15 | ACR | H | 1 | 85.422 | 4.856 | 88.645 | 1.00 | 0.00 | xxxx | 2365 |
| HETATM | 2366 | C16 | ACR | H | 1 | 83.949 | 3.277 | 89.605 | 1.00 | 0.00 | xxxx | 2366 |
| HETATM | 2367 | C17 | ACR | H | 1 | 82.796 | 3.601 | 88.672 | 1.00 | 0.00 | xxxx | 2367 |
| HETATM | 2368 | C2 | GLC | E | 1 | 74.043 | 3.534 | 106.784 | 1.00 | 0.00 | xxxx | 2368 |
| HETATM | 2369 | C3 | GLC | E | 1 | 73.870 | 4.007 | 108.173 | 1.00 | 0.00 | xxxx | 2369 |
| HETATM | 2370 | C4 | GLC | E | 1 | 72.769 | 3.314 | 108.911 | 1.00 | 0.00 | xxxx | 2370 |
| HETATM | 2371 | C5 | GLC | E | 1 | 72.652 | 1.800 | 108.679 | 1.00 | 0.00 | xxxx | 2371 |
| HETATM | 2372 | C6 | GLC | E | 1 | 71.229 | 1.409 | 108.957 | 1.00 | 0.00 | xxxx | 2372 |
| HETATM | 2373 | C1 | GLC | E | 1 | 74.196 | 2.025 | 106.743 | 1.00 | 0.00 | xxxx | 2373 |
| HETATM | 2374 | O1 | GLC | E | 1 | 74.348 | 1.636 | 105.448 | 1.00 | 0.00 | xxxx | 2374 |
| HETATM | 2375 | O2 | GLC | E | 1 | 75.235 | 4.143 | 106.253 | 1.00 | 0.00 | xxxx | 2375 |
| HETATM | 2376 | O3 | GLC | E | 1 | 73.539 | 5.421 | 108.139 | 1.00 | 0.00 | xxxx | 2376 |
| HETATM | 2377 | O4 | GLC | E | 1 | 73.014 | 3.548 | 110.299 | 1.00 | 0.00 | xxxx | 2377 |
| HETATM | 2378 | O5 | GLC | E | 1 | 72.987 | 1.347 | 107.318 | 1.00 | 0.00 | xxxx | 2378 |
| HETATM | 2379 | O6 | GLC | E | 1 | 70.837 | 0.351 | 108.121 | 1.00 | 0.00 | xxxx | 2379 |
| HETATM | 2380 | C2 | GLC | E | 1 | 63.097 | −3.500 | 75.382 | 1.00 | 0.00 | xxxx | 2380 |
| HETATM | 2381 | C3 | GLC | E | 1 | 64.434 | −4.145 | 75.413 | 1.00 | 0.00 | xxxx | 2381 |
| HETATM | 2382 | C4 | GLC | E | 1 | 64.610 | −5.099 | 76.560 | 1.00 | 0.00 | xxxx | 2382 |
| HETATM | 2383 | C5 | GLC | E | 1 | 63.418 | −6.043 | 76.763 | 1.00 | 0.00 | xxxx | 2383 |
| HETATM | 2384 | C6 | GLC | E | 1 | 63.551 | −6.742 | 78.085 | 1.00 | 0.00 | xxxx | 2384 |
| HETATM | 2385 | C1 | GLC | E | 1 | 61.987 | −4.531 | 75.469 | 1.00 | 0.00 | xxxx | 2385 |
| HETATM | 2386 | O1 | GLC | E | 1 | 60.787 | −3.891 | 75.460 | 1.00 | 0.00 | xxxx | 2386 |
| HETATM | 2387 | O2 | GLC | E | 1 | 62.942 | −2.769 | 74.151 | 1.00 | 0.00 | xxxx | 2387 |
| HETATM | 2388 | O3 | GLC | E | 1 | 65.458 | −3.110 | 75.509 | 1.00 | 0.00 | xxxx | 2388 |
| HETATM | 2389 | O4 | GLC | E | 1 | 65.777 | −5.887 | 76.302 | 1.00 | 0.00 | xxxx | 2389 |
| HETATM | 2390 | O5 | GLC | E | 1 | 62.124 | −5.342 | 76.723 | 1.00 | 0.00 | xxxx | 2390 |
| HETATM | 2391 | O6 | GLC | E | 1 | 62.509 | −7.677 | 78.244 | 1.00 | 0.00 | xxxx | 2391 |
| HETATM | 2392 | CA | CA | M | 1 | 54.443 | 10.528 | 90.671 | 1.00 | 0.00 | xxxx | 2392 |
| HETATM | 2393 | O | HOH | S | 1 | 64.967 | 12.689 | 101.419 | 1.00 | 0.00 | xxxx | 2393 |
| HETATM | 2394 | O | HOH | S | 2 | 71.563 | 5.785 | 84.976 | 1.00 | 0.00 | xxxx | 2394 |
| HETATM | 2395 | O | HOH | S | 3 | 80.923 | −2.340 | 89.295 | 1.00 | 0.00 | xxxx | 2395 |
| HETATM | 2396 | O | HOH | S | 4 | 56.757 | 3.515 | 93.548 | 1.00 | 0.00 | xxxx | 2396 |
| HETATM | 2397 | O | HOH | S | 5 | 95.702 | −5.521 | 95.382 | 1.00 | 0.00 | xxxx | 2397 |
| HETATM | 2398 | O | HOH | S | 6 | 78.131 | −2.907 | 89.098 | 1.00 | 0.00 | xxxx | 2398 |
| HETATM | 2399 | O | HOH | S | 7 | 78.263 | −4.245 | 76.555 | 1.00 | 0.00 | xxxx | 2399 |
| HETATM | 2400 | O | HOH | S | 8 | 93.988 | −3.398 | 102.054 | 1.00 | 0.00 | xxxx | 2400 |
| HETATM | 2401 | O | HOH | S | 9 | 83.364 | 2.281 | 77.076 | 1.00 | 0.00 | xxxx | 2401 |
| HETATM | 2402 | O | HOH | S | 10 | 55.561 | 10.622 | 95.053 | 1.00 | 0.00 | xxxx | 2402 |
| HETATM | 2403 | O | HOH | S | 11 | 56.036 | 1.251 | 94.793 | 1.00 | 0.00 | xxxx | 2403 |
| HETATM | 2404 | O | HOH | S | 12 | 92.822 | 10.636 | 77.633 | 1.00 | 0.00 | xxxx | 2404 |
| HETATM | 2405 | O | HOH | S | 13 | 103.721 | −4.910 | 86.930 | 1.00 | 0.00 | xxxx | 2405 |
| HETATM | 2406 | O | HOH | S | 14 | 84.655 | 4.673 | 79.569 | 1.00 | 0.00 | xxxx | 2406 |
| HETATM | 2407 | O | HOH | S | 15 | 86.063 | −2.878 | 78.146 | 1.00 | 0.00 | xxxx | 2407 |
| HETATM | 2408 | O | HOH | S | 16 | 63.999 | 15.452 | 85.780 | 1.00 | 0.00 | xxxx | 2408 |
| HETATM | 2409 | O | HOH | S | 17 | 97.891 | −19.300 | 78.614 | 1.00 | 0.00 | xxxx | 2409 |
| HETATM | 2410 | O | HOH | S | 18 | 60.292 | 16.203 | 83.158 | 1.00 | 0.00 | xxxx | 2410 |
| HETATM | 2411 | O | HOH | S | 19 | 83.019 | 4.976 | 77.084 | 1.00 | 0.00 | xxxx | 2411 |
| HETATM | 2412 | O | HOH | S | 20 | 78.782 | −5.387 | 95.995 | 1.00 | 0.00 | xxxx | 2412 |
| HETATM | 2413 | O | HOH | S | 21 | 82.607 | −1.435 | 80.011 | 1.00 | 0.00 | xxxx | 2413 |
| HETATM | 2414 | O | HOH | S | 22 | 63.199 | 16.555 | 83.175 | 1.00 | 0.00 | xxxx | 2414 |
| HETATM | 2415 | O | HOH | S | 23 | 97.299 | −13.937 | 66.671 | 1.00 | 0.00 | xxxx | 2415 |
| HETATM | 2416 | O | HOH | S | 24 | 77.647 | −0.308 | 73.329 | 1.00 | 0.00 | xxxx | 2416 |
| HETATM | 2417 | O | HOH | S | 25 | 72.956 | 6.465 | 105.943 | 1.00 | 0.00 | xxxx | 2417 |
| HETATM | 2418 | O | HOH | S | 26 | 54.476 | 12.405 | 82.647 | 1.00 | 0.00 | xxxx | 2418 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| HETATM | 2419 | O | HOH | S | 27 | 103.889 | −13.594 | 65.061 | 1.00 | 0.00 | xxxx | 2419 |
| HETATM | 2420 | O | HOH | S | 28 | 69.798 | 6.225 | 109.324 | 1.00 | 0.00 | xxxx | 2420 |
| HETATM | 2421 | O | HOH | S | 29 | 82.160 | −1.182 | 91.535 | 1.00 | 0.00 | xxxx | 2421 |
| HETATM | 2422 | O | HOH | S | 30 | 95.116 | −13.976 | 64.095 | 1.00 | 0.00 | xxxx | 2422 |
| HETATM | 2423 | O | HOH | S | 31 | 63.291 | −3.325 | 92.624 | 1.00 | 0.00 | xxxx | 2423 |
| HETATM | 2424 | O | HOH | S | 32 | 51.558 | 16.241 | 86.760 | 1.00 | 0.00 | xxxx | 2424 |
| HETATM | 2425 | O | HOH | S | 33 | 82.692 | 1.250 | 79.488 | 1.00 | 0.00 | xxxx | 2425 |
| HETATM | 2426 | O | HOH | S | 34 | 58.233 | 14.653 | 79.027 | 1.00 | 0.00 | xxxx | 2426 |
| HETATM | 2427 | O | HOH | S | 35 | 76.576 | −7.589 | 73.550 | 1.00 | 0.00 | xxxx | 2427 |
| HETATM | 2428 | O | HOH | S | 36 | 101.994 | −4.603 | 91.215 | 1.00 | 0.00 | xxxx | 2428 |
| HETATM | 2429 | O | HOH | S | 37 | 52.930 | 8.706 | 83.603 | 1.00 | 0.00 | xxxx | 2429 |
| HETATM | 2430 | O | HOH | S | 38 | 104.304 | −4.180 | 89.612 | 1.00 | 0.00 | xxxx | 2430 |
| HETATM | 2431 | O | HOH | S | 39 | 87.731 | 8.186 | 72.461 | 1.00 | 0.00 | xxxx | 2431 |
| HETATM | 2432 | O | HOH | S | 40 | 63.628 | 17.345 | 87.950 | 1.00 | 0.00 | xxxx | 2432 |
| HETATM | 2433 | O | HOH | S | 41 | 79.089 | −10.881 | 79.735 | 1.00 | 0.00 | xxxx | 2433 |
| HETATM | 2434 | O | HOH | S | 42 | 85.636 | −13.717 | 77.361 | 1.00 | 0.00 | xxxx | 2434 |
| HETATM | 2435 | O | HOH | S | 43 | 82.637 | −1.836 | 67.270 | 1.00 | 0.00 | xxxx | 2435 |
| HETATM | 2436 | O | HOH | S | 44 | 83.873 | −13.593 | 84.483 | 1.00 | 0.00 | xxxx | 2436 |
| HETATM | 2437 | O | HOH | S | 45 | 58.492 | 6.346 | 98.905 | 1.00 | 0.00 | xxxx | 2437 |
| HETATM | 2438 | O | HOH | S | 46 | 102.773 | −0.145 | 91.513 | 1.00 | 0.00 | xxxx | 2438 |
| HETATM | 2439 | O | HOH | S | 47 | 95.927 | −3.173 | 63.290 | 1.00 | 0.00 | xxxx | 2439 |
| HETATM | 2440 | O | HOH | S | 48 | 95.651 | 2.686 | 96.406 | 1.00 | 0.00 | xxxx | 2440 |
| HETATM | 2441 | O | HOH | S | 49 | 94.768 | 8.045 | 90.644 | 1.00 | 0.00 | xxxx | 2441 |
| HETATM | 2442 | O | HOH | S | 50 | 110.557 | −0.277 | 81.899 | 1.00 | 0.00 | xxxx | 2442 |
| HETATM | 2443 | O | HOH | S | 51 | 89.666 | −8.773 | 94.962 | 1.00 | 0.00 | xxxx | 2443 |
| HETATM | 2444 | O | HOH | S | 52 | 78.271 | 11.349 | 100.263 | 1.00 | 0.00 | xxxx | 2444 |
| HETATM | 2445 | O | HOH | S | 53 | 90.013 | 14.373 | 72.022 | 1.00 | 0.00 | xxxx | 2445 |
| HETATM | 2446 | O | HOH | S | 54 | 54.686 | −1.991 | 79.584 | 1.00 | 0.00 | xxxx | 2446 |
| HETATM | 2447 | O | HOH | S | 55 | 54.060 | 10.208 | 97.384 | 1.00 | 0.00 | xxxx | 2447 |
| HETATM | 2448 | O | HOH | S | 56 | 59.790 | 16.417 | 80.364 | 1.00 | 0.00 | xxxx | 2448 |
| HETATM | 2449 | O | HOH | S | 57 | 77.401 | 7.520 | 100.770 | 1.00 | 0.00 | xxxx | 2449 |
| HETATM | 2450 | O | HOH | S | 58 | 51.231 | 7.595 | 85.998 | 1.00 | 0.00 | xxxx | 2450 |
| HETATM | 2451 | O | HOH | S | 59 | 82.426 | −6.107 | 67.060 | 1.00 | 0.00 | xxxx | 2451 |
| HETATM | 2452 | O | HOH | S | 60 | 68.071 | −3.957 | 74.775 | 1.00 | 0.00 | xxxx | 2452 |
| HETATM | 2453 | O | HOH | S | 61 | 61.816 | −7.423 | 86.024 | 1.00 | 0.00 | xxxx | 2453 |
| HETATM | 2454 | O | HOH | S | 62 | 62.403 | −8.118 | 88.651 | 1.00 | 0.00 | xxxx | 2454 |
| HETATM | 2455 | O | HOH | S | 63 | 91.608 | −17.642 | 73.896 | 1.00 | 0.00 | xxxx | 2455 |
| HETATM | 2456 | O | HOH | S | 64 | 78.078 | −8.136 | 83.415 | 1.00 | 0.00 | xxxx | 2456 |
| HETATM | 2457 | O | HOH | S | 65 | 64.474 | −4.069 | 98.736 | 1.00 | 0.00 | xxxx | 2457 |
| HETATM | 2458 | O | HOH | S | 66 | 102.228 | 10.529 | 75.052 | 1.00 | 0.00 | xxxx | 2458 |
| HETATM | 2459 | O | HOH | S | 67 | 78.259 | 7.764 | 74.423 | 1.00 | 0.00 | xxxx | 2459 |
| HETATM | 2460 | O | HOH | S | 68 | 50.503 | −1.277 | 89.513 | 1.00 | 0.00 | xxxx | 2460 |
| HETATM | 2461 | O | HOH | S | 69 | 104.992 | −1.785 | 90.522 | 1.00 | 0.00 | xxxx | 2461 |
| HETATM | 2462 | O | HOH | S | 70 | 91.823 | −11.886 | 88.298 | 1.00 | 0.00 | xxxx | 2462 |
| HETATM | 2463 | O | HOH | S | 71 | 99.237 | −12.571 | 86.653 | 1.00 | 0.00 | xxxx | 2463 |
| HETATM | 2464 | O | HOH | S | 72 | 55.772 | 13.625 | 95.460 | 1.00 | 0.00 | xxxx | 2464 |
| HETATM | 2465 | O | HOH | S | 73 | 102.895 | 6.060 | 66.290 | 1.00 | 0.00 | xxxx | 2465 |
| HETATM | 2466 | O | HOH | S | 74 | 101.101 | 10.601 | 72.687 | 1.00 | 0.00 | xxxx | 2466 |
| HETATM | 2467 | O | HOH | S | 75 | 90.600 | 1.190 | 62.778 | 1.00 | 0.00 | xxxx | 2467 |
| HETATM | 2468 | O | HOH | S | 76 | 46.025 | 12.655 | 90.998 | 1.00 | 0.00 | xxxx | 2468 |
| HETATM | 2469 | O | HOH | S | 77 | 89.016 | 5.541 | 89.546 | 1.00 | 0.00 | xxxx | 2469 |
| HETATM | 2470 | O | HOH | S | 78 | 55.575 | 1.314 | 97.525 | 1.00 | 0.00 | xxxx | 2470 |
| HETATM | 2471 | O | HOH | S | 79 | 106.870 | −11.908 | 75.592 | 1.00 | 0.00 | xxxx | 2471 |
| HETATM | 2472 | O | HOH | S | 80 | 106.021 | 5.208 | 86.640 | 1.00 | 0.00 | xxxx | 2472 |
| HETATM | 2473 | O | HOH | S | 81 | 85.474 | 5.243 | 66.632 | 1.00 | 0.00 | xxxx | 2473 |
| HETATM | 2474 | O | HOH | S | 82 | 108.949 | 2.324 | 81.288 | 1.00 | 0.00 | xxxx | 2474 |
| HETATM | 2475 | O | HOH | S | 83 | 93.941 | −13.080 | 68.593 | 1.00 | 0.00 | xxxx | 2475 |
| HETATM | 2476 | O | HOH | S | 84 | 98.669 | 11.594 | 80.048 | 1.00 | 0.00 | xxxx | 2476 |
| HETATM | 2477 | O | HOH | S | 85 | 105.364 | 8.545 | 80.194 | 1.00 | 0.00 | xxxx | 2477 |
| HETATM | 2478 | O | HOH | S | 86 | 76.737 | 1.253 | 103.989 | 1.00 | 0.00 | xxxx | 2478 |
| HETATM | 2479 | O | HOH | S | 87 | 53.290 | 10.371 | 100.636 | 1.00 | 0.00 | xxxx | 2479 |
| HETATM | 2480 | O | HOH | S | 88 | 102.105 | −8.780 | 86.538 | 1.00 | 0.00 | xxxx | 2480 |
| HETATM | 2481 | O | HOH | S | 89 | 108.979 | 2.590 | 87.807 | 1.00 | 0.00 | xxxx | 2481 |
| HETATM | 2482 | O | HOH | S | 90 | 101.811 | −4.625 | 66.928 | 1.00 | 0.00 | xxxx | 2482 |
| HETATM | 2483 | O | HOH | S | 91 | 86.952 | −8.105 | 61.791 | 1.00 | 0.00 | xxxx | 2483 |
| HETATM | 2484 | O | HOH | S | 92 | 75.709 | −11.553 | 83.231 | 1.00 | 0.00 | xxxx | 2484 |
| HETATM | 2485 | O | HOH | S | 93 | 69.623 | 1.107 | 105.573 | 1.00 | 0.00 | xxxx | 2485 |
| HETATM | 2486 | O | HOH | S | 94 | 56.876 | 15.613 | 94.651 | 1.00 | 0.00 | xxxx | 2486 |
| HETATM | 2487 | O | HOH | S | 95 | 77.223 | −1.392 | 104.142 | 1.00 | 0.00 | xxxx | 2487 |
| HETATM | 2488 | O | HOH | S | 96 | 68.977 | 14.567 | 81.003 | 1.00 | 0.00 | xxxx | 2488 |
| HETATM | 2489 | O | HOH | S | 97 | 103.530 | 8.231 | 87.832 | 1.00 | 0.00 | xxxx | 2489 |
| HETATM | 2490 | O | HOH | S | 98 | 53.398 | 16.767 | 91.322 | 1.00 | 0.00 | xxxx | 2490 |
| HETATM | 2491 | O | HOH | S | 99 | 66.904 | 10.170 | 74.460 | 1.00 | 0.00 | xxxx | 2491 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| HETATM | 2492 | O | HOH | S | 100 | 66.427 | 6.432 | 109.335 | 1.00 | 0.00 | xxxx | 2492 |
| HETATM | 2493 | O | HOH | S | 101 | 51.878 | 17.923 | 84.653 | 1.00 | 0.00 | xxxx | 2493 |
| HETATM | 2494 | O | HOH | S | 102 | 69.516 | −7.765 | 98.830 | 1.00 | 0.00 | xxxx | 2494 |
| HETATM | 2495 | O | HOH | S | 103 | 71.156 | −6.045 | 97.297 | 1.00 | 0.00 | xxxx | 2495 |
| HETATM | 2496 | O | HOH | S | 104 | 92.484 | 1.110 | 96.863 | 1.00 | 0.00 | xxxx | 2496 |
| HETATM | 2497 | O | HOH | S | 105 | 104.523 | −7.523 | 86.656 | 1.00 | 0.00 | xxxx | 2497 |
| HETATM | 2498 | O | HOH | S | 106 | 53.427 | 0.356 | 94.420 | 1.00 | 0.00 | xxxx | 2498 |
| HETATM | 2499 | O | HOH | S | 107 | 92.617 | −5.406 | 61.831 | 1.00 | 0.00 | xxxx | 2499 |
| HETATM | 2500 | O | HOH | S | 108 | 54.889 | −4.851 | 79.692 | 1.00 | 0.00 | xxxx | 2500 |
| HETATM | 2501 | O | HOH | S | 109 | 100.399 | −5.002 | 64.314 | 1.00 | 0.00 | xxxx | 2501 |
| HETATM | 2502 | O | HOH | S | 110 | 66.574 | 15.836 | 85.863 | 1.00 | 0.00 | xxxx | 2502 |
| HETATM | 2503 | O | HOH | S | 111 | 89.301 | −16.735 | 85.704 | 1.00 | 0.00 | xxxx | 2503 |
| HETATM | 2504 | O | HOH | S | 112 | 76.257 | −2.694 | 101.852 | 1.00 | 0.00 | xxxx | 2504 |
| HETATM | 2505 | O | HOH | S | 113 | 76.407 | 13.842 | 79.480 | 1.00 | 0.00 | xxxx | 2505 |
| HETATM | 2506 | O | HOH | S | 114 | 77.812 | −8.591 | 71.367 | 1.00 | 0.00 | xxxx | 2506 |
| HETATM | 2507 | O | HOH | S | 115 | 62.041 | 10.695 | 106.347 | 1.00 | 0.00 | xxxx | 2507 |
| HETATM | 2508 | O | HOH | S | 116 | 87.607 | 2.895 | 60.722 | 1.00 | 0.00 | xxxx | 2508 |
| HETATM | 2509 | O | HOH | S | 117 | 51.846 | −1.707 | 79.894 | 1.00 | 0.00 | xxxx | 2509 |
| HETATM | 2510 | O | HOH | S | 118 | 96.615 | 13.271 | 68.468 | 1.00 | 0.00 | xxxx | 2510 |
| HETATM | 2511 | O | HOH | S | 119 | 68.883 | −4.447 | 104.456 | 1.00 | 0.00 | xxxx | 2511 |
| HETATM | 2512 | O | HOH | S | 120 | 78.507 | 14.813 | 89.197 | 1.00 | 0.00 | xxxx | 2512 |
| HETATM | 2513 | O | HOH | S | 121 | 53.335 | 12.886 | 98.107 | 1.00 | 0.00 | xxxx | 2513 |
| HETATM | 2514 | O | HOH | S | 122 | 56.296 | −5.318 | 85.105 | 1.00 | 0.00 | xxxx | 2514 |
| HETATM | 2515 | O | HOH | S | 123 | 88.573 | −1.610 | 98.089 | 1.00 | 0.00 | xxxx | 2515 |
| HETATM | 2516 | O | HOH | S | 124 | 106.958 | 2.835 | 68.585 | 1.00 | 0.00 | xxxx | 2516 |
| HETATM | 2517 | O | HOH | S | 125 | 91.128 | −0.551 | 95.036 | 1.00 | 0.00 | xxxx | 2517 |
| HETATM | 2518 | O | HOH | S | 126 | 87.174 | 11.082 | 80.269 | 1.00 | 0.00 | xxxx | 2518 |
| HETATM | 2519 | O | HOH | S | 127 | 68.707 | 10.512 | 72.620 | 1.00 | 0.00 | xxxx | 2519 |
| HETATM | 2520 | O | HOH | S | 128 | 98.671 | −0.829 | 64.980 | 1.00 | 0.00 | xxxx | 2520 |
| HETATM | 2521 | O | HOH | S | 129 | 65.315 | 15.486 | 79.330 | 1.00 | 0.00 | xxxx | 2521 |
| HETATM | 2522 | O | HOH | S | 130 | 80.811 | −3.719 | 67.559 | 1.00 | 0.00 | xxxx | 2522 |
| HETATM | 2523 | O | HOH | S | 131 | 90.555 | 10.401 | 64.329 | 1.00 | 0.00 | xxxx | 2523 |
| HETATM | 2524 | O | HOH | S | 132 | 103.855 | 1.624 | 92.996 | 1.00 | 0.00 | xxxx | 2524 |
| HETATM | 2525 | O | HOH | S | 133 | 83.476 | −11.583 | 89.782 | 1.00 | 0.00 | xxxx | 2525 |
| HETATM | 2526 | O | HOH | S | 134 | 64.555 | −6.773 | 98.920 | 1.00 | 0.00 | xxxx | 2526 |
| HETATM | 2527 | O | HOH | S | 135 | 92.827 | 13.344 | 66.990 | 1.00 | 0.00 | xxxx | 2527 |
| HETATM | 2528 | O | HOH | S | 136 | 79.777 | 10.104 | 78.338 | 1.00 | 0.00 | xxxx | 2528 |
| HETATM | 2529 | O | HOH | S | 137 | 111.897 | −1.398 | 79.647 | 1.00 | 0.00 | xxxx | 2529 |
| HETATM | 2530 | O | HOH | S | 138 | 71.797 | 16.681 | 93.656 | 1.00 | 0.00 | xxxx | 2530 |
| HETATM | 2531 | O | HOH | S | 139 | 85.233 | −15.957 | 83.898 | 1.00 | 0.00 | xxxx | 2531 |
| HETATM | 2532 | O | HOH | S | 140 | 65.068 | −1.301 | 77.154 | 1.00 | 0.00 | xxxx | 2532 |
| HETATM | 2533 | O | HOH | S | 141 | 97.222 | −19.132 | 71.009 | 1.00 | 0.00 | xxxx | 2533 |
| HETATM | 2534 | O | HOH | S | 142 | 78.384 | −12.495 | 76.563 | 1.00 | 0.00 | xxxx | 2534 |
| HETATM | 2535 | O | HOH | S | 143 | 86.982 | 8.225 | 70.003 | 1.00 | 0.00 | xxxx | 2535 |
| HETATM | 2536 | O | HOH | S | 144 | 95.144 | 19.750 | 70.827 | 1.00 | 0.00 | xxxx | 2536 |
| HETATM | 2537 | O | HOH | S | 145 | 53.003 | 4.985 | 80.845 | 1.00 | 0.00 | xxxx | 2537 |
| HETATM | 2538 | O | HOH | S | 146 | 59.733 | 3.617 | 106.080 | 1.00 | 0.00 | xxxx | 2538 |
| HETATM | 2539 | O | HOH | S | 147 | 55.600 | 4.084 | 79.973 | 1.00 | 0.00 | xxxx | 2539 |
| HETATM | 2540 | O | HOH | S | 148 | 70.047 | 13.700 | 84.283 | 1.00 | 0.00 | xxxx | 2540 |
| HETATM | 2541 | O | HOH | S | 149 | 64.010 | −3.472 | 96.174 | 1.00 | 0.00 | xxxx | 2541 |
| HETATM | 2542 | O | HOH | S | 150 | 76.709 | 15.830 | 97.974 | 1.00 | 0.00 | xxxx | 2542 |
| HETATM | 2543 | O | HOH | S | 151 | 87.946 | 12.867 | 72.908 | 1.00 | 0.00 | xxxx | 2543 |
| HETATM | 2544 | O | HOH | S | 152 | 77.629 | 11.855 | 77.995 | 1.00 | 0.00 | xxxx | 2544 |
| HETATM | 2545 | O | HOH | S | 153 | 81.571 | −9.261 | 90.403 | 1.00 | 0.00 | xxxx | 2545 |
| HETATM | 2546 | O | HOH | S | 154 | 86.206 | −15.823 | 79.020 | 1.00 | 0.00 | xxxx | 2546 |
| HETATM | 2547 | O | HOH | S | 155 | 59.732 | 1.153 | 76.797 | 1.00 | 0.00 | xxxx | 2547 |
| HETATM | 2548 | O | HOH | S | 156 | 62.121 | −2.955 | 94.978 | 1.00 | 0.00 | xxxx | 2548 |
| HETATM | 2549 | O | HOH | S | 157 | 89.746 | −21.133 | 79.527 | 1.00 | 0.00 | xxxx | 2549 |
| HETATM | 2550 | O | HOH | S | 158 | 50.330 | 17.743 | 88.856 | 1.00 | 0.00 | xxxx | 2550 |
| HETATM | 2551 | O | HOH | S | 159 | 112.731 | −8.840 | 80.143 | 1.00 | 0.00 | xxxx | 2551 |
| HETATM | 2552 | O | HOH | S | 160 | 77.512 | −0.547 | 70.389 | 1.00 | 0.00 | xxxx | 2552 |
| HETATM | 2553 | O | HOH | S | 161 | 107.467 | −0.669 | 90.868 | 1.00 | 0.00 | xxxx | 2553 |
| HETATM | 2554 | O | HOH | S | 162 | 80.928 | 6.192 | 74.700 | 1.00 | 0.00 | xxxx | 2554 |
| HETATM | 2555 | O | HOH | S | 163 | 101.626 | 13.065 | 71.737 | 1.00 | 0.00 | xxxx | 2555 |
| HETATM | 2556 | O | HOH | S | 164 | 66.816 | −8.640 | 98.431 | 1.00 | 0.00 | xxxx | 2556 |
| HETATM | 2557 | O | HOH | S | 165 | 52.660 | 7.548 | 81.180 | 1.00 | 0.00 | xxxx | 2557 |
| HETATM | 2558 | O | HOH | S | 166 | 97.162 | 12.117 | 78.436 | 1.00 | 0.00 | xxxx | 2558 |
| HETATM | 2559 | O | HOH | S | 167 | 100.084 | 13.362 | 78.661 | 1.00 | 0.00 | xxxx | 2559 |
| HETATM | 2560 | O | HOH | S | 168 | 112.469 | 3.315 | 71.207 | 1.00 | 0.00 | xxxx | 2560 |
| HETATM | 2561 | O | HOH | S | 169 | 108.102 | 0.594 | 88.724 | 1.00 | 0.00 | xxxx | 2561 |
| HETATM | 2562 | O | HOH | S | 170 | 83.349 | 1.004 | 67.252 | 1.00 | 0.00 | xxxx | 2562 |
| HETATM | 2563 | O | HOH | S | 171 | 82.593 | 1.925 | 100.618 | 1.00 | 0.00 | xxxx | 2563 |
| HETATM | 2564 | O | HOH | S | 172 | 48.628 | 5.314 | 90.692 | 1.00 | 0.00 | xxxx | 2564 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| HETATM | 2565 | O | HOH | S | 173 | 61.875 | −5.472 | 104.466 | 1.00 | 0.00 | xxxx | 2565 |
| HETATM | 2566 | O | HOH | S | 174 | 100.676 | −10.021 | 88.842 | 1.00 | 0.00 | xxxx | 2566 |
| HETATM | 2567 | O | HOH | S | 175 | 55.519 | 15.322 | 78.594 | 1.00 | 0.00 | xxxx | 2567 |
| HETATM | 2568 | O | HOH | S | 176 | 86.065 | −0.576 | 97.523 | 1.00 | 0.00 | xxxx | 2568 |
| HETATM | 2569 | O | HOH | S | 177 | 97.201 | −12.062 | 59.918 | 1.00 | 0.00 | xxxx | 2569 |
| HETATM | 2570 | O | HOH | S | 178 | 47.342 | 5.542 | 85.607 | 1.00 | 0.00 | xxxx | 2570 |
| HETATM | 2571 | O | HOH | S | 179 | 76.468 | −12.251 | 74.660 | 1.00 | 0.00 | xxxx | 2571 |
| HETATM | 2572 | O | HOH | S | 180 | 57.423 | 18.345 | 88.406 | 1.00 | 0.00 | xxxx | 2572 |
| HETATM | 2573 | O | HOH | S | 181 | 80.597 | −2.205 | 99.237 | 1.00 | 0.00 | xxxx | 2573 |
| HETATM | 2574 | O | HOH | S | 182 | 103.774 | −12.854 | 69.894 | 1.00 | 0.00 | xxxx | 2574 |
| HETATM | 2575 | O | HOH | S | 183 | 72.156 | −11.814 | 94.679 | 1.00 | 0.00 | xxxx | 2575 |
| HETATM | 2576 | O | HOH | S | 184 | 81.554 | −13.910 | 83.030 | 1.00 | 0.00 | xxxx | 2576 |
| HETATM | 2577 | O | HOH | S | 185 | 95.027 | 12.134 | 77.203 | 1.00 | 0.00 | xxxx | 2577 |
| HETATM | 2578 | O | HOH | S | 186 | 68.570 | 3.287 | 109.073 | 1.00 | 0.00 | xxxx | 2578 |
| HETATM | 2579 | O | HOH | S | 187 | 51.200 | 7.008 | 83.661 | 1.00 | 0.00 | xxxx | 2579 |
| HETATM | 2580 | O | HOH | S | 188 | 61.837 | −9.774 | 76.675 | 1.00 | 0.00 | xxxx | 2580 |
| HETATM | 2581 | O | HOH | S | 189 | 86.757 | 8.270 | 84.402 | 1.00 | 0.00 | xxxx | 2581 |
| HETATM | 2582 | O | HOH | S | 190 | 49.987 | 3.480 | 94.412 | 1.00 | 0.00 | xxxx | 2582 |
| HETATM | 2583 | O | HOH | S | 191 | 91.500 | 2.394 | 79.859 | 1.00 | 0.00 | xxxx | 2583 |
| HETATM | 2584 | O | HOH | S | 192 | 97.145 | −21.675 | 79.236 | 1.00 | 0.00 | xxxx | 2584 |
| HETATM | 2585 | O | HOH | S | 193 | 87.618 | −4.559 | 62.051 | 1.00 | 0.00 | xxxx | 2585 |
| HETATM | 2586 | O | HOH | S | 194 | 68.160 | 14.469 | 86.588 | 1.00 | 0.00 | xxxx | 2586 |
| HETATM | 2587 | O | HOH | S | 195 | 66.364 | −10.527 | 74.836 | 1.00 | 0.00 | xxxx | 2587 |
| HETATM | 2588 | O | HOH | S | 196 | 74.004 | −10.006 | 96.016 | 1.00 | 0.00 | xxxx | 2588 |
| HETATM | 2589 | O | HOH | S | 197 | 82.968 | −13.859 | 87.332 | 1.00 | 0.00 | xxxx | 2589 |
| HETATM | 2590 | O | HOH | S | 198 | 108.974 | 5.718 | 85.007 | 1.00 | 0.00 | xxxx | 2590 |
| HETATM | 2591 | O | HOH | S | 199 | 92.041 | 7.360 | 91.914 | 1.00 | 0.00 | xxxx | 2591 |
| HETATM | 2592 | O | HOH | S | 200 | 82.751 | −1.455 | 100.240 | 1.00 | 0.00 | xxxx | 2592 |
| HETATM | 2593 | O | HOH | S | 201 | 99.141 | 11.984 | 83.418 | 1.00 | 0.00 | xxxx | 2593 |
| HETATM | 2594 | O | HOH | S | 202 | 49.427 | 14.666 | 93.898 | 1.00 | 0.00 | xxxx | 2594 |
| HETATM | 2595 | O | HOH | S | 203 | 83.900 | −7.265 | 93.778 | 1.00 | 0.00 | xxxx | 2595 |
| HETATM | 2596 | O | HOH | S | 204 | 61.447 | 5.704 | 104.520 | 1.00 | 0.00 | xxxx | 2596 |
| HETATM | 2597 | O | HOH | S | 205 | 97.789 | 8.951 | 91.262 | 1.00 | 0.00 | xxxx | 2597 |
| HETATM | 2598 | O | HOH | S | 206 | 87.751 | 14.201 | 75.052 | 1.00 | 0.00 | xxxx | 2598 |
| HETATM | 2599 | O | HOH | S | 207 | 106.770 | 8.139 | 82.289 | 1.00 | 0.00 | xxxx | 2599 |
| HETATM | 2600 | O | HOH | S | 208 | 65.822 | −10.575 | 96.934 | 1.00 | 0.00 | xxxx | 2600 |
| HETATM | 2601 | O | HOH | S | 209 | 81.050 | −5.890 | 69.224 | 1.00 | 0.00 | xxxx | 2601 |
| HETATM | 2602 | O | HOH | S | 210 | 74.647 | 14.640 | 86.026 | 1.00 | 0.00 | xxxx | 2602 |
| HETATM | 2603 | O | HOH | S | 211 | 108.674 | −5.814 | 74.673 | 1.00 | 0.00 | xxxx | 2603 |
| HETATM | 2604 | O | HOH | S | 212 | 77.264 | 7.891 | 71.418 | 1.00 | 0.00 | xxxx | 2604 |
| HETATM | 2605 | O | HOH | S | 213 | 60.198 | −3.619 | 94.101 | 1.00 | 0.00 | xxxx | 2605 |
| HETATM | 2606 | O | HOH | S | 214 | 89.676 | −4.554 | 61.123 | 1.00 | 0.00 | xxxx | 2606 |
| HETATM | 2607 | O | HOH | S | 215 | 92.651 | −14.696 | 70.145 | 1.00 | 0.00 | xxxx | 2607 |
| HETATM | 2608 | O | HOH | S | 216 | 99.635 | 9.883 | 85.489 | 1.00 | 0.00 | xxxx | 2608 |
| HETATM | 2609 | O | HOH | S | 217 | 59.538 | −4.151 | 102.501 | 1.00 | 0.00 | xxxx | 2609 |
| HETATM | 2610 | O | HOH | S | 218 | 72.310 | −20.773 | 82.100 | 1.00 | 0.00 | xxxx | 2610 |
| HETATM | 2611 | O | HOH | S | 219 | 84.674 | 0.825 | 92.224 | 1.00 | 0.00 | xxxx | 2611 |
| HETATM | 2612 | O | HOH | S | 220 | 104.507 | 9.632 | 73.559 | 1.00 | 0.00 | xxxx | 2612 |
| HETATM | 2613 | O | HOH | S | 221 | 84.194 | 1.903 | 94.312 | 1.00 | 0.00 | xxxx | 2613 |
| HETATM | 2614 | O | HOH | S | 222 | 108.610 | 6.829 | 81.349 | 1.00 | 0.00 | xxxx | 2614 |
| HETATM | 2615 | O | HOH | S | 223 | 98.648 | 14.172 | 82.300 | 1.00 | 0.00 | xxxx | 2615 |
| HETATM | 2616 | O | HOH | S | 224 | 90.832 | 12.419 | 78.701 | 1.00 | 0.00 | xxxx | 2616 |
| HETATM | 2617 | O | HOH | S | 225 | 52.540 | 11.909 | 76.002 | 1.00 | 0.00 | xxxx | 2617 |
| HETATM | 2618 | O | HOH | S | 226 | 105.324 | −4.324 | 67.888 | 1.00 | 0.00 | xxxx | 2618 |
| HETATM | 2619 | O | HOH | S | 227 | 79.297 | 16.150 | 98.557 | 1.00 | 0.00 | xxxx | 2619 |
| HETATM | 2620 | O | HOH | S | 228 | 85.157 | −12.672 | 66.545 | 1.00 | 0.00 | xxxx | 2620 |
| HETATM | 2621 | O | HOH | S | 229 | 105.404 | −6.081 | 70.536 | 1.00 | 0.00 | xxxx | 2621 |
| HETATM | 2622 | O | HOH | S | 230 | 107.613 | −4.792 | 71.045 | 1.00 | 0.00 | xxxx | 2622 |
| HETATM | 2623 | O | HOH | S | 231 | 109.758 | 3.007 | 77.248 | 1.00 | 0.00 | xxxx | 2623 |
| HETATM | 2624 | O | HOH | S | 232 | 78.855 | 9.433 | 98.137 | 1.00 | 0.00 | xxxx | 2624 |
| HETATM | 2625 | O | HOH | S | 233 | 77.983 | 14.271 | 92.424 | 1.00 | 0.00 | xxxx | 2625 |
| HETATM | 2626 | O | HOH | S | 234 | 59.982 | −1.213 | 75.290 | 1.00 | 0.00 | xxxx | 2626 |
| HETATM | 2627 | O | HOH | S | 235 | 78.032 | −13.631 | 72.697 | 1.00 | 0.00 | xxxx | 2627 |
| HETATM | 2628 | O | HOH | S | 236 | 104.192 | −6.382 | 61.840 | 1.00 | 0.00 | xxxx | 2628 |
| HETATM | 2629 | O | HOH | S | 237 | 60.735 | 10.512 | 108.811 | 1.00 | 0.00 | xxxx | 2629 |
| HETATM | 2630 | O | HOH | S | 238 | 74.989 | −1.300 | 69.668 | 1.00 | 0.00 | xxxx | 2630 |
| HETATM | 2631 | O | HOH | S | 239 | 86.035 | −17.451 | 85.940 | 1.00 | 0.00 | xxxx | 2631 |
| HETATM | 2632 | O | HOH | S | 240 | 99.535 | −10.757 | 59.554 | 1.00 | 0.00 | xxxx | 2632 |
| HETATM | 2633 | O | HOH | S | 241 | 75.396 | 13.835 | 83.611 | 1.00 | 0.00 | xxxx | 2633 |
| HETATM | 2634 | O | HOH | S | 242 | 90.731 | 12.998 | 84.625 | 1.00 | 0.00 | xxxx | 2634 |
| HETATM | 2635 | O | HOH | S | 243 | 52.818 | 14.956 | 95.847 | 1.00 | 0.00 | xxxx | 2635 |
| HETATM | 2636 | O | HOH | S | 244 | 80.322 | 3.758 | 85.850 | 1.00 | 0.00 | xxxx | 2636 |
| HETATM | 2637 | O | HOH | S | 245 | 55.785 | 17.408 | 92.655 | 1.00 | 0.00 | xxxx | 2637 |

-continued

CA, calcium
HOH, Water
ACR, Acrylodan
K, potassium
EDO, ethylene glycol

| | | | | | | | | | | | | |
|---|---|---|---|---|---|---|---|---|---|---|---|---|
| HETATM | 2638 | O | HOH | S | 246 | 115.056 | 3.055 | 70.761 | 1.00 | 0.00 | xxxx | 2638 |
| HETATM | 2639 | O | HOH | S | 247 | 87.204 | 8.691 | 79.775 | 1.00 | 0.00 | xxxx | 2639 |
| HETATM | 2640 | O | HOH | S | 248 | 67.929 | 19.944 | 86.779 | 1.00 | 0.00 | xxxx | 2640 |
| HETATM | 2641 | O | HOH | S | 249 | 77.278 | −12.670 | 79.318 | 1.00 | 0.00 | xxxx | 2641 |
| HETATM | 2642 | O | HOH | S | 250 | 89.042 | −7.911 | 60.104 | 1.00 | 0.00 | xxxx | 2642 |
| HETATM | 2643 | O | HOH | S | 251 | 66.522 | 19.073 | 85.218 | 1.00 | 0.00 | xxxx | 2643 |
| HETATM | 2644 | O | HOH | S | 252 | 61.727 | 4.783 | 107.347 | 1.00 | 0.00 | xxxx | 2644 |
| HETATM | 2645 | O | HOH | S | 253 | 106.736 | −16.531 | 79.420 | 1.00 | 0.00 | xxxx | 2645 |
| HETATM | 2646 | O | HOH | S | 254 | 73.924 | 0.038 | 67.798 | 1.00 | 0.00 | xxxx | 2646 |
| HETATM | 2647 | O | HOH | S | 255 | 69.573 | 20.378 | 85.052 | 1.00 | 0.00 | xxxx | 2647 |
| HETATM | 2648 | O | HOH | S | 256 | 60.911 | 17.953 | 97.183 | 1.00 | 0.00 | xxxx | 2648 |
| HETATM | 2649 | O | HOH | S | 257 | 64.462 | 17.633 | 96.231 | 1.00 | 0.00 | xxxx | 2649 |
| HETATM | 2650 | O | HOH | S | 258 | 62.233 | 18.287 | 95.393 | 1.00 | 0.00 | xxxx | 2650 |
| HETATM | 2651 | O | HOH | S | 259 | 56.704 | 6.246 | 102.901 | 1.00 | 0.00 | xxxx | 2651 |
| HETATM | 2652 | O | HOH | S | 260 | 100.155 | 8.120 | 65.189 | 1.00 | 0.00 | xxxx | 2652 |
| HETATM | 2653 | O | HOH | S | 261 | 68.662 | 4.614 | 111.034 | 1.00 | 0.00 | xxxx | 2653 |
| HETATM | 2654 | O | HOH | S | 262 | 85.282 | 6.689 | 68.710 | 1.00 | 0.00 | xxxx | 2654 |
| HETATM | 2655 | O | HOH | S | 263 | 53.059 | 13.136 | 78.511 | 1.00 | 0.00 | xxxx | 2655 |
| HETATM | 2656 | O | HOH | S | 264 | 57.271 | −2.144 | 100.780 | 1.00 | 0.00 | xxxx | 2656 |
| HETATM | 2657 | O | HOH | S | 265 | 52.474 | −2.587 | 90.434 | 1.00 | 0.00 | xxxx | 2657 |
| HETATM | 2658 | O | HOH | S | 266 | 80.171 | 6.190 | 71.814 | 1.00 | 0.00 | xxxx | 2658 |
| HETATM | 2659 | O | HOH | S | 267 | 99.575 | −11.497 | 56.975 | 1.00 | 0.00 | xxxx | 2659 |
| HETATM | 2660 | O | HOH | S | 268 | 99.589 | 0.394 | 99.299 | 1.00 | 0.00 | xxxx | 2660 |
| HETATM | 2661 | O | HOH | S | 269 | 69.687 | 19.479 | 91.009 | 1.00 | 0.00 | xxxx | 2661 |
| HETATM | 2662 | O | HOH | S | 270 | 57.793 | 0.261 | 108.756 | 1.00 | 0.00 | xxxx | 2662 |
| HETATM | 2663 | O | HOH | S | 271 | 81.987 | −13.534 | 70.405 | 1.00 | 0.00 | xxxx | 2663 |
| HETATM | 2664 | O | HOH | S | 272 | 68.352 | 16.666 | 93.708 | 1.00 | 0.00 | xxxx | 2664 |
| HETATM | 2665 | O | HOH | S | 273 | 52.337 | −1.842 | 99.213 | 1.00 | 0.00 | xxxx | 2665 |
| HETATM | 2666 | O | HOH | S | 274 | 113.989 | 4.886 | 71.455 | 1.00 | 0.00 | xxxx | 2666 |
| HETATM | 2667 | O | HOH | S | 275 | 78.548 | −9.578 | 81.802 | 1.00 | 0.00 | xxxx | 2667 |
| HETATM | 2668 | O | HOH | S | 276 | 71.504 | −3.457 | 71.931 | 1.00 | 0.00 | xxxx | 2668 |
| HETATM | 2669 | O | HOH | S | 277 | 81.373 | −7.989 | 65.925 | 1.00 | 0.00 | xxxx | 2669 |
| HETATM | 2670 | O | HOH | S | 278 | 75.743 | 2.240 | 69.380 | 1.00 | 0.00 | xxxx | 2670 |
| HETATM | 2671 | O | HOH | S | 279 | 106.824 | −16.531 | 84.712 | 1.00 | 0.00 | xxxx | 2671 |
| HETATM | 2672 | O | HOH | S | 280 | 85.750 | 6.704 | 62.252 | 1.00 | 0.00 | xxxx | 2672 |
| HETATM | 2673 | O | HOH | S | 281 | 85.615 | −16.056 | 74.909 | 1.00 | 0.00 | xxxx | 2673 |
| HETATM | 2674 | O | HOH | S | 282 | 54.694 | 7.097 | 100.323 | 1.00 | 0.00 | xxxx | 2674 |
| HETATM | 2675 | O | HOH | S | 283 | 82.416 | −9.126 | 92.690 | 1.00 | 0.00 | xxxx | 2675 |
| HETATM | 2676 | O | HOH | S | 284 | 104.688 | −6.624 | 68.238 | 1.00 | 0.00 | xxxx | 2676 |
| HETATM | 2677 | O | HOH | S | 285 | 104.352 | 6.757 | 89.424 | 1.00 | 0.00 | xxxx | 2677 |
| HETATM | 2678 | O | HOH | S | 286 | 69.910 | 20.393 | 88.915 | 1.00 | 0.00 | xxxx | 2678 |
| HETATM | 2679 | O | HOH | S | 287 | 61.958 | −7.213 | 97.165 | 1.00 | 0.00 | xxxx | 2679 |
| HETATM | 2680 | O | HOH | S | 288 | 94.529 | −0.882 | 102.773 | 1.00 | 0.00 | xxxx | 2680 |
| HETATM | 2681 | O | HOH | S | 289 | 77.902 | −11.183 | 83.158 | 1.00 | 0.00 | xxxx | 2681 |
| HETATM | 2682 | O | HOH | S | 290 | 107.822 | −15.668 | 77.566 | 1.00 | 0.00 | xxxx | 2682 |
| HETATM | 2683 | O | HOH | S | 291 | 95.725 | 5.302 | 96.902 | 1.00 | 0.00 | xxxx | 2683 |
| HETATM | 2684 | O | HOH | S | 292 | 64.133 | 3.617 | 72.467 | 1.00 | 0.00 | xxxx | 2684 |
| HETATM | 2685 | O | HOH | S | 293 | 108.451 | −6.376 | 72.578 | 1.00 | 0.00 | xxxx | 2685 |
| HETATM | 2686 | O | HOH | S | 294 | 46.400 | 14.955 | 93.071 | 1.00 | 0.00 | xxxx | 2686 |
| HETATM | 2687 | O | HOH | S | 295 | 58.303 | 17.796 | 86.218 | 1.00 | 0.00 | xxxx | 2687 |
| HETATM | 2688 | O | HOH | S | 296 | 59.171 | 18.585 | 83.785 | 1.00 | 0.00 | xxxx | 2688 |
| HETATM | 2689 | O | HOH | S | 297 | 97.679 | −18.685 | 80.897 | 1.00 | 0.00 | xxxx | 2689 |
| HETATM | 2690 | O | HOH | S | 298 | 77.741 | −14.710 | 81.359 | 1.00 | 0.00 | xxxx | 2690 |
| HETATM | 2691 | O | HOH | S | 299 | 92.006 | 10.014 | 61.925 | 1.00 | 0.00 | xxxx | 2691 |
| HETATM | 2692 | O | HOH | S | 300 | 61.301 | 17.558 | 78.643 | 1.00 | 0.00 | xxxx | 2692 |
| HETATM | 2693 | O | HOH | S | 301 | 52.821 | 0.688 | 97.645 | 1.00 | 0.00 | xxxx | 2693 |
| HETATM | 2694 | O | HOH | S | 302 | 84.779 | −15.819 | 76.983 | 1.00 | 0.00 | xxxx | 2694 |
| HETATM | 2695 | O | HOH | S | 303 | 101.048 | −19.438 | 80.682 | 1.00 | 0.00 | xxxx | 2695 |
| HETATM | 2696 | O | HOH | S | 304 | 96.756 | 10.671 | 86.678 | 1.00 | 0.00 | xxxx | 2696 |
| HETATM | 2697 | O | HOH | S | 305 | 52.337 | 7.315 | 99.213 | 1.00 | 0.00 | xxxx | 2697 |
| HETATM | 2698 | O | HOH | S | 306 | 66.714 | −10.256 | 100.388 | 1.00 | 0.00 | xxxx | 2698 |
| HETATM | 2699 | O | HOH | S | 307 | 68.541 | 17.330 | 99.380 | 1.00 | 0.00 | xxxx | 2699 |
| HETATM | 2700 | O | HOH | S | 308 | 73.679 | −7.075 | 68.628 | 1.00 | 0.00 | xxxx | 2700 |
| HETATM | 2701 | O | HOH | S | 309 | 82.946 | 3.923 | 67.908 | 1.00 | 0.00 | xxxx | 2701 |
| HETATM | 2702 | O | HOH | S | 310 | 87.530 | −16.979 | 69.522 | 1.00 | 0.00 | xxxx | 2702 |
| HETATM | 2703 | O | HOH | S | 311 | 90.650 | −11.119 | 59.389 | 1.00 | 0.00 | xxxx | 2703 |
| HETATM | 2704 | O | HOH | S | 312 | 102.333 | −10.420 | 90.408 | 1.00 | 0.00 | xxxx | 2704 |
| HETATM | 2705 | O | HOH | S | 313 | 76.300 | 15.569 | 93.317 | 1.00 | 0.00 | xxxx | 2705 |
| HETATM | 2706 | O | HOH | S | 314 | 49.384 | −0.292 | 85.440 | 1.00 | 0.00 | xxxx | 2706 |
| HETATM | 2707 | O | HOH | S | 315 | 94.144 | −22.571 | 85.773 | 1.00 | 0.00 | xxxx | 2707 |
| HETATM | 2708 | O | HOH | S | 316 | 86.915 | −14.572 | 69.472 | 1.00 | 0.00 | xxxx | 2708 |
| HETATM | 2709 | O | HOH | S | 317 | 95.100 | 0.697 | 100.381 | 1.00 | 0.00 | xxxx | 2709 |
| HETATM | 2710 | O | HOH | S | 318 | 69.328 | −3.518 | 72.553 | 1.00 | 0.00 | xxxx | 2710 |

-continued

| | | | | | | | | | | | | |
|---|---|---|---|---|---|---|---|---|---|---|---|---|
| CA, calcium<br>HOH, Water<br>ACR, Acrylodan<br>K, potassium<br>EDO, ethylene glycol | | | | | | | | | | | | |
| HETATM | 2711 | O | HOH | S | 319 | 80.753 | 6.983 | 69.069 | 1.00 | 0.00 | xxxx | 2711 |
| HETATM | 2712 | O | HOH | S | 320 | 46.258 | 17.814 | 93.974 | 1.00 | 0.00 | xxxx | 2712 |
| HETATM | 2713 | O | HOH | S | 321 | 81.726 | −12.988 | 89.021 | 1.00 | 0.00 | xxxx | 2713 |
| HETATM | 2714 | O | HOH | S | 322 | 57.011 | −2.865 | 93.361 | 1.00 | 0.00 | xxxx | 2714 |
| HETATM | 2715 | O | HOH | S | 323 | 87.257 | 7.473 | 60.108 | 1.00 | 0.00 | xxxx | 2715 |
| HETATM | 2716 | O | HOH | S | 324 | 51.673 | 3.931 | 78.235 | 1.00 | 0.00 | xxxx | 2716 |
| HETATM | 2717 | O | HOH | S | 325 | 100.177 | 9.710 | 88.414 | 1.00 | 0.00 | xxxx | 2717 |

Example 11. Crystal Structure Coordinates for a *T. thermosaccharolyticum* Glucose-Galactose Binding Protein: ttGGBP.17C.Badan (Badan Attached to F17C Mutant)

Naming is standard three-letter amino acid code.

Atom positions are provided as Cartesian coordinates, using standard Protein Databank (PDB) format. ATOM records refer to amino acid atoms; HETATM records refer to non-amino acid atoms.

Column 1: record type (ATOM or HETATM); column 2: atom number; column 3 atom name (standard naming scheme for amino acids); column 4: residue name (ATOM records), or component name (HETATM records); column 5: chain identifier (A, B, C, . . . ); column 6: amino acid residue sequence number (ATOM records), or component number (HETATM records); columns 7-9: x,y,z atomic Cartesian positional coordinates; column 10: fractional occupancy (set to 1.0 in this listing); column 11: B-factor (ignored in this listing); column 12: file identifier (ignored in this listing); column 13: line number (same as atom number in this listing).

For heteroatom (HETATM) records, the component name (column 4) is as follows:

| | | | | | | | | | | | | |
|---|---|---|---|---|---|---|---|---|---|---|---|---|
| CA, calcium<br>HOH, water<br>BAD, Badan<br>K, potassium<br>EDO, ethylene glycol | | | | | | | | | | | | |
| ATOM | 1 | N | MET | A | 1 | 68.218 | 89.131 | 176.853 | 1.00 | 0.00 | xxxx | 1 |
| ATOM | 2 | CA | MET | A | 1 | 68.822 | 88.646 | 175.620 | 1.00 | 0.00 | xxxx | 2 |
| ATOM | 3 | CB | MET | A | 1 | 68.234 | 87.289 | 175.227 | 1.00 | 0.00 | xxxx | 3 |
| ATOM | 4 | CG | MET | A | 1 | 68.484 | 86.177 | 176.231 | 1.00 | 0.00 | xxxx | 4 |
| ATOM | 5 | SD | MET | A | 1 | 70.237 | 85.791 | 176.409 | 1.00 | 0.00 | xxxx | 5 |
| ATOM | 6 | CE | MET | A | 1 | 70.690 | 85.435 | 174.710 | 1.00 | 0.00 | xxxx | 6 |
| ATOM | 7 | C | MET | A | 1 | 68.615 | 89.642 | 174.487 | 1.00 | 0.00 | xxxx | 7 |
| ATOM | 8 | O | MET | A | 1 | 67.712 | 90.472 | 174.536 | 1.00 | 0.00 | xxxx | 8 |
| ATOM | 9 | N | LYS | A | 2 | 69.465 | 89.548 | 173.473 | 1.00 | 0.00 | xxxx | 9 |
| ATOM | 10 | CA | LYS | A | 2 | 69.300 | 90.303 | 172.238 | 1.00 | 0.00 | xxxx | 10 |
| ATOM | 11 | CB | LYS | A | 2 | 70.554 | 90.146 | 171.376 | 1.00 | 0.00 | xxxx | 11 |
| ATOM | 12 | CG | LYS | A | 2 | 70.717 | 91.140 | 170.251 | 1.00 | 0.00 | xxxx | 12 |
| ATOM | 13 | CD | LYS | A | 2 | 72.082 | 90.940 | 169.607 | 1.00 | 0.00 | xxxx | 13 |
| ATOM | 14 | CE | LYS | A | 2 | 72.374 | 91.980 | 168.546 | 1.00 | 0.00 | xxxx | 14 |
| ATOM | 15 | NZ | LYS | A | 2 | 73.735 | 91.788 | 167.968 | 1.00 | 0.00 | xxxx | 15 |
| ATOM | 16 | C | LYS | A | 2 | 68.064 | 89.811 | 171.487 | 1.00 | 0.00 | xxxx | 16 |
| ATOM | 17 | O | LYS | A | 2 | 67.828 | 88.604 | 171.408 | 1.00 | 0.00 | xxxx | 17 |
| ATOM | 18 | N | GLN | A | 3 | 67.265 | 90.725 | 170.943 | 1.00 | 0.00 | xxxx | 18 |
| ATOM | 19 | CA | GLN | A | 3 | 66.123 | 90.302 | 170.146 | 1.00 | 0.00 | xxxx | 19 |
| ATOM | 20 | CB | GLN | A | 3 | 65.033 | 91.374 | 170.089 | 1.00 | 0.00 | xxxx | 20 |
| ATOM | 21 | CG | GLN | A | 3 | 63.827 | 90.924 | 169.251 | 1.00 | 0.00 | xxxx | 21 |
| ATOM | 22 | CD | GLN | A | 3 | 62.685 | 91.932 | 169.246 | 1.00 | 0.00 | xxxx | 22 |
| ATOM | 23 | OE1 | GLN | A | 3 | 62.731 | 92.936 | 168.535 | 1.00 | 0.00 | xxxx | 23 |
| ATOM | 24 | NE2 | GLN | A | 3 | 61.652 | 91.663 | 170.041 | 1.00 | 0.00 | xxxx | 24 |
| ATOM | 25 | C | GLN | A | 3 | 66.591 | 89.955 | 168.744 | 1.00 | 0.00 | xxxx | 25 |
| ATOM | 26 | O | GLN | A | 3 | 67.319 | 90.713 | 168.106 | 1.00 | 0.00 | xxxx | 26 |
| ATOM | 27 | N | LEU | A | 4 | 66.192 | 88.779 | 168.289 | 1.00 | 0.00 | xxxx | 27 |
| ATOM | 28 | CA | LEU | A | 4 | 66.449 | 88.350 | 166.930 | 1.00 | 0.00 | xxxx | 28 |
| ATOM | 29 | CB | LEU | A | 4 | 67.079 | 86.957 | 166.908 | 1.00 | 0.00 | xxxx | 29 |
| ATOM | 30 | CG | LEU | A | 4 | 68.443 | 86.858 | 167.587 | 1.00 | 0.00 | xxxx | 30 |
| ATOM | 31 | CD1 | LEU | A | 4 | 68.891 | 85.408 | 167.634 | 1.00 | 0.00 | xxxx | 31 |
| ATOM | 32 | CD2 | LEU | A | 4 | 69.469 | 87.729 | 166.877 | 1.00 | 0.00 | xxxx | 32 |
| ATOM | 33 | C | LEU | A | 4 | 65.126 | 88.356 | 166.199 | 1.00 | 0.00 | xxxx | 33 |
| ATOM | 34 | O | LEU | A | 4 | 64.123 | 87.874 | 166.725 | 1.00 | 0.00 | xxxx | 34 |
| ATOM | 35 | N | ASN | A | 5 | 65.123 | 88.914 | 164.994 | 1.00 | 0.00 | xxxx | 35 |
| ATOM | 36 | CA | ASN | A | 5 | 63.908 | 89.001 | 164.199 | 1.00 | 0.00 | xxxx | 36 |
| ATOM | 37 | CB | ASN | A | 5 | 63.626 | 90.440 | 163.778 | 1.00 | 0.00 | xxxx | 37 |
| ATOM | 38 | CG | ASN | A | 5 | 62.959 | 91.237 | 164.865 | 1.00 | 0.00 | xxxx | 38 |
| ATOM | 39 | OD1 | ASN | A | 5 | 61.748 | 91.138 | 165.064 | 1.00 | 0.00 | xxxx | 39 |
| ATOM | 40 | ND2 | ASN | A | 5 | 63.739 | 92.035 | 165.577 | 1.00 | 0.00 | xxxx | 40 |
| ATOM | 41 | C | ASN | A | 5 | 64.027 | 88.139 | 162.970 | 1.00 | 0.00 | xxxx | 41 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 42 | O | ASN | A | 5 | 64.981 | 88.276 | 162.206 | 1.00 | 0.00 | xxxx | 42 |
| ATOM | 43 | N | ILE | A | 6 | 63.056 | 87.256 | 162.775 | 1.00 | 0.00 | xxxx | 43 |
| ATOM | 44 | CA | ILE | A | 6 | 63.039 | 86.413 | 161.588 | 1.00 | 0.00 | xxxx | 44 |
| ATOM | 45 | CB | ILE | A | 6 | 63.099 | 84.931 | 161.964 | 1.00 | 0.00 | xxxx | 45 |
| ATOM | 46 | CG1 | ILE | A | 6 | 64.396 | 84.647 | 162.738 | 1.00 | 0.00 | xxxx | 46 |
| ATOM | 47 | CD1 | ILE | A | 6 | 64.417 | 83.296 | 163.418 | 1.00 | 0.00 | xxxx | 47 |
| ATOM | 48 | CG2 | ILE | A | 6 | 62.994 | 84.065 | 160.713 | 1.00 | 0.00 | xxxx | 48 |
| ATOM | 49 | C | ILE | A | 6 | 61.792 | 86.731 | 160.780 | 1.00 | 0.00 | xxxx | 49 |
| ATOM | 50 | O | ILE | A | 6 | 60.685 | 86.727 | 161.315 | 1.00 | 0.00 | xxxx | 50 |
| ATOM | 51 | N | GLY | A | 7 | 61.977 | 87.040 | 159.498 | 1.00 | 0.00 | xxxx | 51 |
| ATOM | 52 | CA | GLY | A | 7 | 60.844 | 87.251 | 158.614 | 1.00 | 0.00 | xxxx | 52 |
| ATOM | 53 | C | GLY | A | 7 | 60.351 | 85.930 | 158.044 | 1.00 | 0.00 | xxxx | 53 |
| ATOM | 54 | O | GLY | A | 7 | 61.110 | 85.211 | 157.403 | 1.00 | 0.00 | xxxx | 54 |
| ATOM | 55 | N | VAL | A | 8 | 59.086 | 85.596 | 158.285 | 1.00 | 0.00 | xxxx | 55 |
| ATOM | 56 | CA | VAL | A | 8 | 58.543 | 84.323 | 157.803 | 1.00 | 0.00 | xxxx | 56 |
| ATOM | 57 | CB | VAL | A | 8 | 58.067 | 83.416 | 158.961 | 1.00 | 0.00 | xxxx | 57 |
| ATOM | 58 | CG1 | VAL | A | 8 | 57.613 | 82.063 | 158.425 | 1.00 | 0.00 | xxxx | 58 |
| ATOM | 59 | CG2 | VAL | A | 8 | 59.164 | 83.248 | 160.003 | 1.00 | 0.00 | xxxx | 59 |
| ATOM | 60 | C | VAL | A | 8 | 57.389 | 84.593 | 156.862 | 1.00 | 0.00 | xxxx | 60 |
| ATOM | 61 | O | VAL | A | 8 | 56.422 | 85.258 | 157.249 | 1.00 | 0.00 | xxxx | 61 |
| ATOM | 62 | N | ALA | A | 9 | 57.485 | 84.095 | 155.633 | 1.00 | 0.00 | xxxx | 62 |
| ATOM | 63 | CA | ALA | A | 9 | 56.372 | 84.227 | 154.688 | 1.00 | 0.00 | xxxx | 63 |
| ATOM | 64 | CB | ALA | A | 9 | 56.826 | 84.935 | 153.410 | 1.00 | 0.00 | xxxx | 64 |
| ATOM | 65 | C | ALA | A | 9 | 55.789 | 82.854 | 154.364 | 1.00 | 0.00 | xxxx | 65 |
| ATOM | 66 | O | ALA | A | 9 | 56.511 | 81.948 | 153.948 | 1.00 | 0.00 | xxxx | 66 |
| ATOM | 67 | N | ILE | A | 10 | 54.479 | 82.709 | 154.583 | 1.00 | 0.00 | xxxx | 67 |
| ATOM | 68 | CA | ILE | A | 10 | 53.745 | 81.456 | 154.338 | 1.00 | 0.00 | xxxx | 68 |
| ATOM | 69 | CB | ILE | A | 10 | 52.776 | 81.151 | 155.498 | 1.00 | 0.00 | xxxx | 69 |
| ATOM | 70 | CG1 | ILE | A | 10 | 53.533 | 81.091 | 156.827 | 1.00 | 0.00 | xxxx | 70 |
| ATOM | 71 | CD1 | ILE | A | 10 | 54.530 | 79.969 | 156.898 | 1.00 | 0.00 | xxxx | 71 |
| ATOM | 72 | CG2 | ILE | A | 10 | 52.018 | 79.850 | 155.243 | 1.00 | 0.00 | xxxx | 72 |
| ATOM | 73 | C | ILE | A | 10 | 52.993 | 81.609 | 153.025 | 1.00 | 0.00 | xxxx | 73 |
| ATOM | 74 | O | ILE | A | 10 | 52.393 | 82.657 | 152.808 | 1.00 | 0.00 | xxxx | 74 |
| ATOM | 75 | N | TYR | A | 11 | 53.007 | 80.606 | 152.144 | 1.00 | 0.00 | xxxx | 75 |
| ATOM | 76 | CA | TYR | A | 11 | 52.490 | 80.856 | 150.790 | 1.00 | 0.00 | xxxx | 76 |
| ATOM | 77 | CB | TYR | A | 11 | 52.778 | 79.669 | 149.840 | 1.00 | 0.00 | xxxx | 77 |
| ATOM | 78 | CG | TYR | A | 11 | 51.675 | 78.630 | 149.715 | 1.00 | 0.00 | xxxx | 78 |
| ATOM | 79 | CD1 | TYR | A | 11 | 50.763 | 78.682 | 148.666 | 1.00 | 0.00 | xxxx | 79 |
| ATOM | 80 | CE1 | TYR | A | 11 | 49.747 | 77.740 | 148.540 | 1.00 | 0.00 | xxxx | 80 |
| ATOM | 81 | CZ | TYR | A | 11 | 49.635 | 76.725 | 149.476 | 1.00 | 0.00 | xxxx | 81 |
| ATOM | 82 | OH | TYR | A | 11 | 48.625 | 75.805 | 149.339 | 1.00 | 0.00 | xxxx | 82 |
| ATOM | 83 | CE2 | TYR | A | 11 | 50.532 | 76.638 | 150.529 | 1.00 | 0.00 | xxxx | 83 |
| ATOM | 84 | CD2 | TYR | A | 11 | 51.556 | 77.595 | 150.639 | 1.00 | 0.00 | xxxx | 84 |
| ATOM | 85 | C | TYR | A | 11 | 50.993 | 81.211 | 150.837 | 1.00 | 0.00 | xxxx | 85 |
| ATOM | 86 | O | TYR | A | 11 | 50.560 | 82.095 | 150.112 | 1.00 | 0.00 | xxxx | 86 |
| ATOM | 87 | N | LYS | A | 12 | 50.229 | 80.560 | 151.712 | 1.00 | 0.00 | xxxx | 87 |
| ATOM | 88 | CA | LYS | A | 12 | 48.875 | 81.018 | 152.025 | 1.00 | 0.00 | xxxx | 88 |
| ATOM | 89 | CB | LYS | A | 12 | 47.879 | 80.636 | 150.911 | 1.00 | 0.00 | xxxx | 89 |
| ATOM | 90 | CG | LYS | A | 12 | 47.377 | 79.208 | 150.906 | 1.00 | 0.00 | xxxx | 90 |
| ATOM | 91 | CD | LYS | A | 12 | 46.460 | 78.984 | 149.692 | 1.00 | 0.00 | xxxx | 91 |
| ATOM | 92 | CE | LYS | A | 12 | 45.753 | 77.645 | 149.771 | 1.00 | 0.00 | xxxx | 92 |
| ATOM | 93 | NZ | LYS | A | 12 | 44.896 | 77.401 | 148.570 | 1.00 | 0.00 | xxxx | 93 |
| ATOM | 94 | C | LYS | A | 12 | 48.454 | 80.462 | 153.383 | 1.00 | 0.00 | xxxx | 94 |
| ATOM | 95 | O | LYS | A | 12 | 48.834 | 79.349 | 153.753 | 1.00 | 0.00 | xxxx | 95 |
| ATOM | 96 | N | PHE | A | 13 | 47.707 | 81.256 | 154.148 | 1.00 | 0.00 | xxxx | 96 |
| ATOM | 97 | CA | PHE | A | 13 | 47.311 | 80.834 | 155.494 | 1.00 | 0.00 | xxxx | 97 |
| ATOM | 98 | CB | PHE | A | 13 | 46.861 | 82.032 | 156.338 | 1.00 | 0.00 | xxxx | 98 |
| ATOM | 99 | CG | PHE | A | 13 | 47.980 | 82.737 | 157.069 | 1.00 | 0.00 | xxxx | 99 |
| ATOM | 100 | CD1 | PHE | A | 13 | 49.311 | 82.494 | 156.765 | 1.00 | 0.00 | xxxx | 100 |
| ATOM | 101 | CE1 | PHE | A | 13 | 50.332 | 83.161 | 157.445 | 1.00 | 0.00 | xxxx | 101 |
| ATOM | 102 | CZ | PHE | A | 13 | 50.021 | 84.077 | 158.439 | 1.00 | 0.00 | xxxx | 102 |
| ATOM | 103 | CE2 | PHE | A | 13 | 48.697 | 84.321 | 158.754 | 1.00 | 0.00 | xxxx | 103 |
| ATOM | 104 | CD2 | PHE | A | 13 | 47.687 | 83.654 | 158.075 | 1.00 | 0.00 | xxxx | 104 |
| ATOM | 105 | C | PHE | A | 13 | 46.197 | 79.784 | 155.469 | 1.00 | 0.00 | xxxx | 105 |
| ATOM | 106 | O | PHE | A | 13 | 46.102 | 78.969 | 156.384 | 1.00 | 0.00 | xxxx | 106 |
| ATOM | 107 | N | ASP | A | 14 | 45.364 | 79.795 | 154.433 | 1.00 | 0.00 | xxxx | 107 |
| ATOM | 108 | CA | ASP | A | 14 | 44.280 | 78.822 | 154.342 | 1.00 | 0.00 | xxxx | 108 |
| ATOM | 109 | CB | ASP | A | 14 | 43.065 | 79.419 | 153.613 | 1.00 | 0.00 | xxxx | 109 |
| ATOM | 110 | CG | ASP | A | 14 | 43.364 | 79.839 | 152.179 | 1.00 | 0.00 | xxxx | 110 |
| ATOM | 111 | OD1 | ASP | A | 14 | 44.501 | 80.270 | 151.888 | 1.00 | 0.00 | xxxx | 111 |
| ATOM | 112 | OD2 | ASP | A | 14 | 42.439 | 79.751 | 151.338 | 1.00 | 0.00 | xxxx | 112 |
| ATOM | 113 | C | ASP | A | 14 | 44.742 | 77.532 | 153.659 | 1.00 | 0.00 | xxxx | 113 |
| ATOM | 114 | O | ASP | A | 14 | 44.102 | 77.032 | 152.731 | 1.00 | 0.00 | xxxx | 114 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 115 | N | ASP | A | 15 | 45.873 | 77.016 | 154.128 | 1.00 | 0.00 | xxxx | 115 |
| ATOM | 116 | CA | ASP | A | 15 | 46.391 | 75.711 | 153.722 | 1.00 | 0.00 | xxxx | 116 |
| ATOM | 117 | CB | ASP | A | 15 | 47.749 | 75.858 | 153.018 | 1.00 | 0.00 | xxxx | 117 |
| ATOM | 118 | CG | ASP | A | 15 | 48.339 | 74.519 | 152.567 | 1.00 | 0.00 | xxxx | 118 |
| ATOM | 119 | OD1 | ASP | A | 15 | 48.195 | 74.183 | 151.376 | 1.00 | 0.00 | xxxx | 119 |
| ATOM | 120 | OD2 | ASP | A | 15 | 48.969 | 73.816 | 153.391 | 1.00 | 0.00 | xxxx | 120 |
| ATOM | 121 | C | ASP | A | 15 | 46.506 | 74.883 | 154.999 | 1.00 | 0.00 | xxxx | 121 |
| ATOM | 122 | O | ASP | A | 15 | 47.150 | 75.308 | 155.957 | 1.00 | 0.00 | xxxx | 122 |
| ATOM | 123 | N | THR | A | 16 | 45.874 | 73.715 | 155.023 | 1.00 | 0.00 | xxxx | 123 |
| ATOM | 124 | CA | THR | A | 16 | 45.811 | 72.911 | 156.243 | 1.00 | 0.00 | xxxx | 124 |
| ATOM | 125 | CB | THR | A | 16 | 44.916 | 71.675 | 156.040 | 1.00 | 0.00 | xxxx | 125 |
| ATOM | 126 | OG1 | THR | A | 16 | 43.607 | 72.109 | 155.636 | 1.00 | 0.00 | xxxx | 126 |
| ATOM | 127 | CG2 | THR | A | 16 | 44.800 | 70.863 | 157.334 | 1.00 | 0.00 | xxxx | 127 |
| ATOM | 128 | C | THR | A | 16 | 47.191 | 72.473 | 156.724 | 1.00 | 0.00 | xxxx | 128 |
| ATOM | 129 | O | THR | A | 16 | 47.536 | 72.673 | 157.887 | 1.00 | 0.00 | xxxx | 129 |
| ATOM | 130 | N | CYS | A | 17 | 47.992 | 71.894 | 155.838 | 1.00 | 0.00 | xxxx | 130 |
| ATOM | 131 | CA | CYS | A | 17 | 49.347 | 71.505 | 156.221 | 1.00 | 0.00 | xxxx | 131 |
| ATOM | 132 | CB | CYS | A | 17 | 50.024 | 70.780 | 155.054 | 1.00 | 0.00 | xxxx | 132 |
| ATOM | 133 | SG | CYS | A | 17 | 51.834 | 70.624 | 155.124 | 1.00 | 0.00 | xxxx | 133 |
| ATOM | 134 | C | CYS | A | 17 | 50.200 | 72.693 | 156.684 | 1.00 | 0.00 | xxxx | 134 |
| ATOM | 135 | O | CYS | A | 17 | 50.850 | 72.624 | 157.731 | 1.00 | 0.00 | xxxx | 135 |
| ATOM | 136 | N | MET | A | 18 | 50.199 | 73.789 | 155.933 | 1.00 | 0.00 | xxxx | 136 |
| ATOM | 137 | CA | MET | A | 18 | 51.103 | 74.876 | 156.280 | 1.00 | 0.00 | xxxx | 137 |
| ATOM | 138 | CB | MET | A | 18 | 51.261 | 75.855 | 155.112 | 1.00 | 0.00 | xxxx | 138 |
| ATOM | 139 | CG | MET | A | 18 | 52.133 | 75.302 | 153.980 | 1.00 | 0.00 | xxxx | 139 |
| ATOM | 140 | SD | MET | A | 18 | 53.707 | 74.616 | 154.560 | 1.00 | 0.00 | xxxx | 140 |
| ATOM | 141 | CE | MET | A | 18 | 54.419 | 76.060 | 155.321 | 1.00 | 0.00 | xxxx | 141 |
| ATOM | 142 | C | MET | A | 18 | 50.645 | 75.594 | 157.549 | 1.00 | 0.00 | xxxx | 142 |
| ATOM | 143 | O | MET | A | 18 | 51.443 | 76.258 | 158.200 | 1.00 | 0.00 | xxxx | 143 |
| ATOM | 144 | N | THR | A | 19 | 49.368 | 75.455 | 157.906 | 1.00 | 0.00 | xxxx | 144 |
| ATOM | 145 | CA | THR | A | 19 | 48.891 | 75.959 | 159.200 | 1.00 | 0.00 | xxxx | 145 |
| ATOM | 146 | CB | THR | A | 19 | 47.364 | 75.855 | 159.317 | 1.00 | 0.00 | xxxx | 146 |
| ATOM | 147 | OG1 | THR | A | 19 | 46.762 | 76.756 | 158.377 | 1.00 | 0.00 | xxxx | 147 |
| ATOM | 148 | CG2 | THR | A | 19 | 46.895 | 76.207 | 160.727 | 1.00 | 0.00 | xxxx | 148 |
| ATOM | 149 | C | THR | A | 19 | 49.567 | 75.194 | 160.331 | 1.00 | 0.00 | xxxx | 149 |
| ATOM | 150 | O | THR | A | 19 | 49.973 | 75.778 | 161.337 | 1.00 | 0.00 | xxxx | 150 |
| ATOM | 151 | N | GLY | A | 20 | 49.704 | 73.885 | 160.157 | 1.00 | 0.00 | xxxx | 151 |
| ATOM | 152 | CA | GLY | A | 20 | 50.429 | 73.080 | 161.118 | 1.00 | 0.00 | xxxx | 152 |
| ATOM | 153 | C | GLY | A | 20 | 51.880 | 73.503 | 161.211 | 1.00 | 0.00 | xxxx | 153 |
| ATOM | 154 | O | GLY | A | 20 | 52.445 | 73.588 | 162.298 | 1.00 | 0.00 | xxxx | 154 |
| ATOM | 155 | N | VAL | A | 21 | 52.492 | 73.769 | 160.062 | 1.00 | 0.00 | xxxx | 155 |
| ATOM | 156 | CA | VAL | A | 21 | 53.899 | 74.148 | 160.051 | 1.00 | 0.00 | xxxx | 156 |
| ATOM | 157 | CB | VAL | A | 21 | 54.473 | 74.174 | 158.622 | 1.00 | 0.00 | xxxx | 157 |
| ATOM | 158 | CG1 | VAL | A | 21 | 55.881 | 74.758 | 158.637 | 1.00 | 0.00 | xxxx | 158 |
| ATOM | 159 | CG2 | VAL | A | 21 | 54.492 | 72.778 | 158.037 | 1.00 | 0.00 | xxxx | 159 |
| ATOM | 160 | C | VAL | A | 21 | 54.084 | 75.495 | 160.742 | 1.00 | 0.00 | xxxx | 160 |
| ATOM | 161 | O | VAL | A | 21 | 54.950 | 75.639 | 161.606 | 1.00 | 0.00 | xxxx | 161 |
| ATOM | 162 | N | ARG | A | 22 | 53.277 | 76.492 | 160.401 | 1.00 | 0.00 | xxxx | 162 |
| ATOM | 163 | CA | ARG | A | 22 | 53.521 | 77.790 | 161.025 | 1.00 | 0.00 | xxxx | 163 |
| ATOM | 164 | CB | ARG | A | 22 | 52.779 | 78.906 | 160.292 | 1.00 | 0.00 | xxxx | 164 |
| ATOM | 165 | CG | ARG | A | 22 | 51.295 | 78.771 | 160.203 | 1.00 | 0.00 | xxxx | 165 |
| ATOM | 166 | CD | ARG | A | 22 | 50.786 | 79.812 | 159.223 | 1.00 | 0.00 | xxxx | 166 |
| ATOM | 167 | NE | ARG | A | 22 | 49.387 | 79.609 | 158.882 | 1.00 | 0.00 | xxxx | 167 |
| ATOM | 168 | CZ | ARG | A | 22 | 48.385 | 80.204 | 159.512 | 1.00 | 0.00 | xxxx | 168 |
| ATOM | 169 | NH1 | ARG | A | 22 | 48.638 | 81.038 | 160.511 | 1.00 | 0.00 | xxxx | 169 |
| ATOM | 170 | NH2 | ARG | A | 22 | 47.135 | 79.968 | 159.144 | 1.00 | 0.00 | xxxx | 170 |
| ATOM | 171 | C | ARG | A | 22 | 53.182 | 77.798 | 162.525 | 1.00 | 0.00 | xxxx | 171 |
| ATOM | 172 | O | ARG | A | 22 | 53.855 | 78.479 | 163.294 | 1.00 | 0.00 | xxxx | 172 |
| ATOM | 173 | N | ASN | A | 23 | 52.185 | 77.027 | 162.960 | 1.00 | 0.00 | xxxx | 173 |
| ATOM | 174 | CA | ASN | A | 23 | 51.922 | 76.894 | 164.395 | 1.00 | 0.00 | xxxx | 174 |
| ATOM | 175 | CB | ASN | A | 23 | 50.650 | 76.086 | 164.644 | 1.00 | 0.00 | xxxx | 175 |
| ATOM | 176 | CG | ASN | A | 23 | 49.403 | 76.841 | 164.242 | 1.00 | 0.00 | xxxx | 176 |
| ATOM | 177 | OD1 | ASN | A | 23 | 49.447 | 78.053 | 164.024 | 1.00 | 0.00 | xxxx | 177 |
| ATOM | 178 | ND2 | ASN | A | 23 | 48.283 | 76.132 | 164.141 | 1.00 | 0.00 | xxxx | 178 |
| ATOM | 179 | C | ASN | A | 23 | 53.096 | 76.244 | 165.119 | 1.00 | 0.00 | xxxx | 179 |
| ATOM | 180 | O | ASN | A | 23 | 53.463 | 76.656 | 166.221 | 1.00 | 0.00 | xxxx | 180 |
| ATOM | 181 | N | ALA | A | 24 | 53.693 | 75.234 | 164.496 | 1.00 | 0.00 | xxxx | 181 |
| ATOM | 182 | CA | ALA | A | 24 | 54.832 | 74.554 | 165.107 | 1.00 | 0.00 | xxxx | 182 |
| ATOM | 183 | CB | ALA | A | 24 | 55.132 | 73.256 | 164.378 | 1.00 | 0.00 | xxxx | 183 |
| ATOM | 184 | C | ALA | A | 24 | 56.060 | 75.467 | 165.123 | 1.00 | 0.00 | xxxx | 184 |
| ATOM | 185 | O | ALA | A | 24 | 56.841 | 75.441 | 166.077 | 1.00 | 0.00 | xxxx | 185 |
| ATOM | 186 | N | MET | A | 25 | 56.231 | 76.266 | 164.073 | 1.00 | 0.00 | xxxx | 186 |
| ATOM | 187 | CA | MET | A | 25 | 57.317 | 77.247 | 164.038 | 1.00 | 0.00 | xxxx | 187 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 188 | CB | MET | A | 25 | 57.376 | 77.945 | 162.680 | 1.00 | 0.00 | xxxx | 188 |
| ATOM | 189 | CG | MET | A | 25 | 57.910 | 77.046 | 161.580 | 1.00 | 0.00 | xxxx | 189 |
| ATOM | 190 | SD | MET | A | 25 | 58.065 | 77.901 | 160.004 | 1.00 | 0.00 | xxxx | 190 |
| ATOM | 191 | CE | MET | A | 25 | 59.335 | 79.085 | 160.417 | 1.00 | 0.00 | xxxx | 191 |
| ATOM | 192 | C | MET | A | 25 | 57.157 | 78.270 | 165.152 | 1.00 | 0.00 | xxxx | 192 |
| ATOM | 193 | O | MET | A | 25 | 58.121 | 78.614 | 165.837 | 1.00 | 0.00 | xxxx | 193 |
| ATOM | 194 | N | THR | A | 26 | 55.933 | 78.746 | 165.333 | 1.00 | 0.00 | xxxx | 194 |
| ATOM | 195 | CA | THR | A | 26 | 55.656 | 79.711 | 166.388 | 1.00 | 0.00 | xxxx | 195 |
| ATOM | 196 | CB | THR | A | 26 | 54.196 | 80.194 | 166.321 | 1.00 | 0.00 | xxxx | 196 |
| ATOM | 197 | OG1 | THR | A | 26 | 53.990 | 80.881 | 165.080 | 1.00 | 0.00 | xxxx | 197 |
| ATOM | 198 | CG2 | THR | A | 26 | 53.895 | 81.138 | 167.480 | 1.00 | 0.00 | xxxx | 198 |
| ATOM | 199 | C | THR | A | 26 | 55.966 | 79.100 | 167.758 | 1.00 | 0.00 | xxxx | 199 |
| ATOM | 200 | O | THR | A | 26 | 56.518 | 79.775 | 168.636 | 1.00 | 0.00 | xxxx | 200 |
| ATOM | 201 | N | ALA | A | 27 | 55.660 | 77.814 | 167.930 | 1.00 | 0.00 | xxxx | 201 |
| ATOM | 202 | CA | ALA | A | 27 | 55.944 | 77.135 | 169.194 | 1.00 | 0.00 | xxxx | 202 |
| ATOM | 203 | CB | ALA | A | 27 | 55.284 | 75.757 | 169.219 | 1.00 | 0.00 | xxxx | 203 |
| ATOM | 204 | C | ALA | A | 27 | 57.451 | 77.008 | 169.440 | 1.00 | 0.00 | xxxx | 204 |
| ATOM | 205 | O | ALA | A | 27 | 57.929 | 77.222 | 170.555 | 1.00 | 0.00 | xxxx | 205 |
| ATOM | 206 | N | GLU | A | 28 | 58.198 | 76.661 | 168.396 | 1.00 | 0.00 | xxxx | 206 |
| ATOM | 207 | CA | GLU | A | 28 | 59.646 | 76.522 | 168.525 | 1.00 | 0.00 | xxxx | 207 |
| ATOM | 208 | CB | GLU | A | 28 | 60.236 | 75.939 | 167.244 | 1.00 | 0.00 | xxxx | 208 |
| ATOM | 209 | CG | GLU | A | 28 | 59.853 | 74.496 | 166.998 | 1.00 | 0.00 | xxxx | 209 |
| ATOM | 210 | CD | GLU | A | 28 | 60.289 | 73.586 | 168.133 | 1.00 | 0.00 | xxxx | 210 |
| ATOM | 211 | OE1 | GLU | A | 28 | 61.391 | 73.800 | 168.691 | 1.00 | 0.00 | xxxx | 211 |
| ATOM | 212 | OE2 | GLU | A | 28 | 59.520 | 72.662 | 168.472 | 1.00 | 0.00 | xxxx | 212 |
| ATOM | 213 | C | GLU | A | 28 | 60.334 | 77.847 | 168.846 | 1.00 | 0.00 | xxxx | 213 |
| ATOM | 214 | O | GLU | A | 28 | 61.358 | 77.871 | 169.533 | 1.00 | 0.00 | xxxx | 214 |
| ATOM | 215 | N | ALA | A | 29 | 59.765 | 78.941 | 168.347 | 1.00 | 0.00 | xxxx | 215 |
| ATOM | 216 | CA | ALA | A | 29 | 60.377 | 80.260 | 168.470 | 1.00 | 0.00 | xxxx | 216 |
| ATOM | 217 | CB | ALA | A | 29 | 59.882 | 81.168 | 167.363 | 1.00 | 0.00 | xxxx | 217 |
| ATOM | 218 | C | ALA | A | 29 | 60.122 | 80.920 | 169.818 | 1.00 | 0.00 | xxxx | 218 |
| ATOM | 219 | O | ALA | A | 29 | 60.847 | 81.841 | 170.197 | 1.00 | 0.00 | xxxx | 219 |
| ATOM | 220 | N | GLN | A | 30 | 59.088 | 80.469 | 170.527 | 1.00 | 0.00 | xxxx | 220 |
| ATOM | 221 | C | GLN | A | 30 | 59.944 | 81.122 | 172.747 | 1.00 | 0.00 | xxxx | 221 |
| ATOM | 222 | O | GLN | A | 30 | 60.601 | 80.114 | 173.019 | 1.00 | 0.00 | xxxx | 222 |
| ATOM | 223 | CA | GLN | A | 30 | 58.724 | 80.991 | 171.843 | 1.00 | 0.00 | xxxx | 223 |
| ATOM | 224 | CB | GLN | A | 30 | 57.685 | 80.064 | 172.494 | 1.00 | 0.00 | xxxx | 224 |
| ATOM | 225 | CG | GLN | A | 30 | 57.220 | 80.480 | 173.885 | 1.00 | 0.00 | xxxx | 225 |
| ATOM | 226 | CD | GLN | A | 30 | 56.502 | 79.356 | 174.622 | 1.00 | 0.00 | xxxx | 226 |
| ATOM | 227 | OE1 | GLN | A | 30 | 57.126 | 78.385 | 175.055 | 1.00 | 0.00 | xxxx | 227 |
| ATOM | 228 | NE2 | GLN | A | 30 | 55.186 | 79.483 | 174.768 | 1.00 | 0.00 | xxxx | 228 |
| ATOM | 229 | N | GLY | A | 31 | 60.247 | 82.330 | 173.213 | 1.00 | 0.00 | xxxx | 229 |
| ATOM | 230 | CA | GLY | A | 31 | 61.366 | 82.552 | 174.111 | 1.00 | 0.00 | xxxx | 230 |
| ATOM | 231 | C | GLY | A | 31 | 62.735 | 82.629 | 173.456 | 1.00 | 0.00 | xxxx | 231 |
| ATOM | 232 | O | GLY | A | 31 | 63.740 | 82.816 | 174.142 | 1.00 | 0.00 | xxxx | 232 |
| ATOM | 233 | N | LYS | A | 32 | 62.784 | 82.500 | 172.134 | 1.00 | 0.00 | xxxx | 233 |
| ATOM | 234 | CA | LYS | A | 32 | 64.065 | 82.426 | 171.430 | 1.00 | 0.00 | xxxx | 234 |
| ATOM | 235 | CB | LYS | A | 32 | 64.214 | 81.071 | 170.728 | 1.00 | 0.00 | xxxx | 235 |
| ATOM | 236 | CG | LYS | A | 32 | 64.340 | 79.880 | 171.664 | 1.00 | 0.00 | xxxx | 236 |
| ATOM | 237 | CD | LYS | A | 32 | 64.685 | 78.617 | 170.878 | 1.00 | 0.00 | xxxx | 237 |
| ATOM | 238 | CE | LYS | A | 32 | 64.614 | 77.382 | 171.758 | 1.00 | 0.00 | xxxx | 238 |
| ATOM | 239 | NZ | LYS | A | 32 | 63.207 | 77.104 | 172.173 | 1.00 | 0.00 | xxxx | 239 |
| ATOM | 240 | C | LYS | A | 32 | 64.248 | 83.539 | 170.403 | 1.00 | 0.00 | xxxx | 240 |
| ATOM | 241 | O | LYS | A | 32 | 65.297 | 84.184 | 170.351 | 1.00 | 0.00 | xxxx | 241 |
| ATOM | 242 | N | ALA | A | 33 | 63.233 | 83.742 | 169.573 | 1.00 | 0.00 | xxxx | 242 |
| ATOM | 243 | CA | ALA | A | 33 | 63.301 | 84.738 | 168.511 | 1.00 | 0.00 | xxxx | 243 |
| ATOM | 244 | CB | ALA | A | 33 | 63.997 | 84.168 | 167.288 | 1.00 | 0.00 | xxxx | 244 |
| ATOM | 245 | C | ALA | A | 33 | 61.908 | 85.222 | 168.148 | 1.00 | 0.00 | xxxx | 245 |
| ATOM | 246 | O | ALA | A | 33 | 60.927 | 84.505 | 168.321 | 1.00 | 0.00 | xxxx | 246 |
| ATOM | 247 | N | LYS | A | 34 | 61.829 | 86.448 | 167.648 | 1.00 | 0.00 | xxxx | 247 |
| ATOM | 248 | CA | LYS | A | 34 | 60.563 | 87.009 | 167.217 | 1.00 | 0.00 | xxxx | 248 |
| ATOM | 249 | CB | LYS | A | 34 | 60.564 | 88.530 | 167.390 | 1.00 | 0.00 | xxxx | 249 |
| ATOM | 250 | CG | LYS | A | 34 | 59.308 | 89.220 | 166.878 | 1.00 | 0.00 | xxxx | 250 |
| ATOM | 251 | CD | LYS | A | 34 | 59.300 | 90.688 | 167.274 | 1.00 | 0.00 | xxxx | 251 |
| ATOM | 252 | CE | LYS | A | 34 | 58.087 | 91.411 | 166.704 | 1.00 | 0.00 | xxxx | 252 |
| ATOM | 253 | NZ | LYS | A | 34 | 58.078 | 92.851 | 167.064 | 1.00 | 0.00 | xxxx | 253 |
| ATOM | 254 | C | LYS | A | 34 | 60.309 | 86.641 | 165.765 | 1.00 | 0.00 | xxxx | 254 |
| ATOM | 255 | O | LYS | A | 34 | 61.115 | 86.966 | 164.889 | 1.00 | 0.00 | xxxx | 255 |
| ATOM | 256 | N | LEU | A | 35 | 59.210 | 85.933 | 165.513 | 1.00 | 0.00 | xxxx | 256 |
| ATOM | 257 | CA | LEU | A | 35 | 58.799 | 85.667 | 164.139 | 1.00 | 0.00 | xxxx | 257 |
| ATOM | 258 | CB | LEU | A | 35 | 58.088 | 84.320 | 164.016 | 1.00 | 0.00 | xxxx | 258 |
| ATOM | 259 | CG | LEU | A | 35 | 58.834 | 83.075 | 164.493 | 1.00 | 0.00 | xxxx | 259 |
| ATOM | 260 | CD1 | LEU | A | 35 | 58.058 | 81.826 | 164.102 | 1.00 | 0.00 | xxxx | 260 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 261 | CD2 | LEU | A | 35 | 60.256 | 83.025 | 163.946 | 1.00 | 0.00 | xxxx | 261 |
| ATOM | 262 | C | LEU | A | 35 | 57.883 | 86.779 | 163.660 | 1.00 | 0.00 | xxxx | 262 |
| ATOM | 263 | O | LEU | A | 35 | 56.903 | 87.131 | 164.328 | 1.00 | 0.00 | xxxx | 263 |
| ATOM | 264 | N | ASN | A | 36 | 58.214 | 87.342 | 162.508 | 1.00 | 0.00 | xxxx | 264 |
| ATOM | 265 | CA | ASN | A | 36 | 57.350 | 88.298 | 161.851 | 1.00 | 0.00 | xxxx | 265 |
| ATOM | 266 | CB | ASN | A | 36 | 58.146 | 89.516 | 161.395 | 1.00 | 0.00 | xxxx | 266 |
| ATOM | 267 | CG | ASN | A | 36 | 58.825 | 90.224 | 162.557 | 1.00 | 0.00 | xxxx | 267 |
| ATOM | 268 | OD1 | ASN | A | 36 | 58.214 | 91.050 | 163.229 | 1.00 | 0.00 | xxxx | 268 |
| ATOM | 269 | ND2 | ASN | A | 36 | 60.083 | 89.879 | 162.812 | 1.00 | 0.00 | xxxx | 269 |
| ATOM | 270 | C | ASN | A | 36 | 56.696 | 87.561 | 160.692 | 1.00 | 0.00 | xxxx | 270 |
| ATOM | 271 | O | ASN | A | 36 | 57.265 | 87.452 | 159.612 | 1.00 | 0.00 | xxxx | 271 |
| ATOM | 272 | N | MET | A | 37 | 55.507 | 87.023 | 160.943 | 1.00 | 0.00 | xxxx | 272 |
| ATOM | 273 | CA | MET | A | 37 | 54.933 | 86.040 | 160.028 | 1.00 | 0.00 | xxxx | 273 |
| ATOM | 274 | CB | MET | A | 37 | 54.441 | 84.820 | 160.796 | 1.00 | 0.00 | xxxx | 274 |
| ATOM | 275 | CG | MET | A | 37 | 54.241 | 83.606 | 159.905 | 1.00 | 0.00 | xxxx | 275 |
| ATOM | 276 | SD | MET | A | 37 | 53.741 | 82.201 | 160.891 | 1.00 | 0.00 | xxxx | 276 |
| ATOM | 277 | CE | MET | A | 37 | 55.317 | 81.666 | 161.542 | 1.00 | 0.00 | xxxx | 277 |
| ATOM | 278 | C | MET | A | 37 | 53.804 | 86.631 | 159.210 | 1.00 | 0.00 | xxxx | 278 |
| ATOM | 279 | O | MET | A | 37 | 52.875 | 87.236 | 159.754 | 1.00 | 0.00 | xxxx | 279 |
| ATOM | 280 | N | VAL | A | 38 | 53.891 | 86.443 | 157.900 | 1.00 | 0.00 | xxxx | 280 |
| ATOM | 281 | CA | VAL | A | 38 | 52.949 | 87.050 | 156.969 | 1.00 | 0.00 | xxxx | 281 |
| ATOM | 282 | CB | VAL | A | 38 | 53.619 | 88.173 | 156.151 | 1.00 | 0.00 | xxxx | 282 |
| ATOM | 283 | CG1 | VAL | A | 38 | 54.158 | 89.253 | 157.081 | 1.00 | 0.00 | xxxx | 283 |
| ATOM | 284 | CG2 | VAL | A | 38 | 54.728 | 87.611 | 155.267 | 1.00 | 0.00 | xxxx | 284 |
| ATOM | 285 | C | VAL | A | 38 | 52.346 | 86.011 | 156.038 | 1.00 | 0.00 | xxxx | 285 |
| ATOM | 286 | O | VAL | A | 38 | 52.937 | 84.963 | 155.770 | 1.00 | 0.00 | xxxx | 286 |
| ATOM | 287 | N | ASP | A | 39 | 51.157 | 86.340 | 155.550 | 1.00 | 0.00 | xxxx | 287 |
| ATOM | 288 | CA | ASP | A | 39 | 50.355 | 85.500 | 154.667 | 1.00 | 0.00 | xxxx | 288 |
| ATOM | 289 | CB | ASP | A | 39 | 48.890 | 85.561 | 155.133 | 1.00 | 0.00 | xxxx | 289 |
| ATOM | 290 | CG | ASP | A | 39 | 47.925 | 84.752 | 154.270 | 1.00 | 0.00 | xxxx | 290 |
| ATOM | 291 | OD1 | ASP | A | 39 | 48.357 | 84.004 | 153.366 | 1.00 | 0.00 | xxxx | 291 |
| ATOM | 292 | OD2 | ASP | A | 39 | 46.700 | 84.868 | 154.522 | 1.00 | 0.00 | xxxx | 292 |
| ATOM | 293 | C | ASP | A | 39 | 50.516 | 86.011 | 153.238 | 1.00 | 0.00 | xxxx | 293 |
| ATOM | 294 | O | ASP | A | 39 | 50.115 | 87.138 | 152.935 | 1.00 | 0.00 | xxxx | 294 |
| ATOM | 295 | N | SER | A | 40 | 51.092 | 85.197 | 152.362 | 1.00 | 0.00 | xxxx | 295 |
| ATOM | 296 | CA | SER | A | 40 | 51.324 | 85.649 | 150.988 | 1.00 | 0.00 | xxxx | 296 |
| ATOM | 297 | CB | SER | A | 40 | 52.541 | 84.930 | 150.390 | 1.00 | 0.00 | xxxx | 297 |
| ATOM | 298 | OG | SER | A | 40 | 53.719 | 85.267 | 151.122 | 1.00 | 0.00 | xxxx | 298 |
| ATOM | 299 | C | SER | A | 40 | 50.087 | 85.467 | 150.102 | 1.00 | 0.00 | xxxx | 299 |
| ATOM | 300 | O | SER | A | 40 | 50.092 | 85.867 | 148.938 | 1.00 | 0.00 | xxxx | 300 |
| ATOM | 301 | N | GLN | A | 41 | 49.018 | 84.901 | 150.661 | 1.00 | 0.00 | xxxx | 301 |
| ATOM | 302 | CA | GLN | A | 41 | 47.725 | 84.784 | 149.963 | 1.00 | 0.00 | xxxx | 302 |
| ATOM | 303 | CB | GLN | A | 41 | 47.038 | 86.155 | 149.887 | 1.00 | 0.00 | xxxx | 303 |
| ATOM | 304 | CG | GLN | A | 41 | 46.765 | 86.792 | 151.256 | 1.00 | 0.00 | xxxx | 304 |
| ATOM | 305 | CD | GLN | A | 41 | 45.986 | 88.102 | 151.146 | 1.00 | 0.00 | xxxx | 305 |
| ATOM | 306 | OE1 | GLN | A | 41 | 46.553 | 89.182 | 151.285 | 1.00 | 0.00 | xxxx | 306 |
| ATOM | 307 | NE2 | GLN | A | 41 | 44.684 | 88.004 | 150.891 | 1.00 | 0.00 | xxxx | 307 |
| ATOM | 308 | C | GLN | A | 41 | 47.842 | 84.186 | 148.553 | 1.00 | 0.00 | xxxx | 308 |
| ATOM | 309 | O | GLN | A | 41 | 47.128 | 84.599 | 147.624 | 1.00 | 0.00 | xxxx | 309 |
| ATOM | 310 | N | ASN | A | 42 | 48.747 | 83.218 | 148.412 | 1.00 | 0.00 | xxxx | 310 |
| ATOM | 311 | CA | ASN | A | 42 | 48.961 | 82.480 | 147.165 | 1.00 | 0.00 | xxxx | 311 |
| ATOM | 312 | CB | ASN | A | 42 | 47.737 | 81.614 | 146.848 | 1.00 | 0.00 | xxxx | 312 |
| ATOM | 313 | CG | ASN | A | 42 | 48.036 | 80.518 | 145.852 | 1.00 | 0.00 | xxxx | 313 |
| ATOM | 314 | OD1 | ASN | A | 42 | 49.133 | 79.957 | 145.819 | 1.00 | 0.00 | xxxx | 314 |
| ATOM | 315 | ND2 | ASN | A | 42 | 47.053 | 80.213 | 145.015 | 1.00 | 0.00 | xxxx | 315 |
| ATOM | 316 | C | ASN | A | 42 | 49.282 | 83.417 | 146.002 | 1.00 | 0.00 | xxxx | 316 |
| ATOM | 317 | O | ASN | A | 42 | 48.898 | 83.167 | 144.855 | 1.00 | 0.00 | xxxx | 317 |
| ATOM | 318 | N | SER | A | 43 | 49.993 | 84.498 | 146.311 | 1.00 | 0.00 | xxxx | 318 |
| ATOM | 319 | CA | SER | A | 43 | 50.388 | 85.490 | 145.320 | 1.00 | 0.00 | xxxx | 319 |
| ATOM | 320 | CB | SER | A | 43 | 49.588 | 86.785 | 145.512 | 1.00 | 0.00 | xxxx | 320 |
| ATOM | 321 | OG | SER | A | 43 | 50.124 | 87.836 | 144.719 | 1.00 | 0.00 | xxxx | 321 |
| ATOM | 322 | C | SER | A | 43 | 51.878 | 85.789 | 145.427 | 1.00 | 0.00 | xxxx | 322 |
| ATOM | 323 | O | SER | A | 43 | 52.328 | 86.321 | 146.445 | 1.00 | 0.00 | xxxx | 323 |
| ATOM | 324 | N | GLN | A | 44 | 52.653 | 85.458 | 144.399 | 1.00 | 0.00 | xxxx | 324 |
| ATOM | 325 | CA | GLN | A | 44 | 54.073 | 85.793 | 144.453 | 1.00 | 0.00 | xxxx | 325 |
| ATOM | 326 | CB | GLN | A | 44 | 54.850 | 85.140 | 143.310 | 1.00 | 0.00 | xxxx | 326 |
| ATOM | 327 | CG | GLN | A | 44 | 56.368 | 85.194 | 143.524 | 1.00 | 0.00 | xxxx | 327 |
| ATOM | 328 | CD | GLN | A | 44 | 56.808 | 84.502 | 144.807 | 1.00 | 0.00 | xxxx | 328 |
| ATOM | 329 | OE1 | GLN | A | 44 | 56.407 | 83.371 | 145.086 | 1.00 | 0.00 | xxxx | 329 |
| ATOM | 330 | NE2 | GLN | A | 44 | 57.639 | 85.182 | 145.599 | 1.00 | 0.00 | xxxx | 330 |
| ATOM | 331 | C | GLN | A | 44 | 54.314 | 87.315 | 144.446 | 1.00 | 0.00 | xxxx | 331 |
| ATOM | 332 | O | GLN | A | 44 | 55.211 | 87.782 | 145.147 | 1.00 | 0.00 | xxxx | 332 |
| ATOM | 333 | N | PRO | A | 45 | 53.541 | 88.087 | 143.657 | 1.00 | 0.00 | xxxx | 333 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 334 | CA | PRO | A | 45 | 53.746 | 89.539 | 143.776 | 1.00 | 0.00 | xxxx | 334 |
| ATOM | 335 | CB | PRO | A | 45 | 52.693 | 90.113 | 142.824 | 1.00 | 0.00 | xxxx | 335 |
| ATOM | 336 | CG | PRO | A | 45 | 52.587 | 89.055 | 141.760 | 1.00 | 0.00 | xxxx | 336 |
| ATOM | 337 | CD | PRO | A | 45 | 52.642 | 87.762 | 142.526 | 1.00 | 0.00 | xxxx | 337 |
| ATOM | 338 | C | PRO | A | 45 | 53.549 | 90.045 | 145.204 | 1.00 | 0.00 | xxxx | 338 |
| ATOM | 339 | O | PRO | A | 45 | 54.320 | 90.882 | 145.667 | 1.00 | 0.00 | xxxx | 339 |
| ATOM | 340 | N | THR | A | 46 | 52.555 | 89.511 | 145.903 | 1.00 | 0.00 | xxxx | 340 |
| ATOM | 341 | CA | THR | A | 46 | 52.363 | 89.856 | 147.308 | 1.00 | 0.00 | xxxx | 341 |
| ATOM | 342 | CB | THR | A | 46 | 51.108 | 89.171 | 147.863 | 1.00 | 0.00 | xxxx | 342 |
| ATOM | 343 | OG1 | THR | A | 46 | 49.954 | 89.728 | 147.216 | 1.00 | 0.00 | xxxx | 343 |
| ATOM | 344 | CG2 | THR | A | 46 | 51.004 | 89.373 | 149.368 | 1.00 | 0.00 | xxxx | 344 |
| ATOM | 345 | C | THR | A | 46 | 53.581 | 89.474 | 148.151 | 1.00 | 0.00 | xxxx | 345 |
| ATOM | 346 | O | THR | A | 46 | 54.094 | 90.284 | 148.941 | 1.00 | 0.00 | xxxx | 346 |
| ATOM | 347 | N | GLN | A | 47 | 54.057 | 88.247 | 147.966 | 1.00 | 0.00 | xxxx | 347 |
| ATOM | 348 | CA | GLN | A | 47 | 55.214 | 87.777 | 148.706 | 1.00 | 0.00 | xxxx | 348 |
| ATOM | 349 | CB | GLN | A | 47 | 55.459 | 86.299 | 148.425 | 1.00 | 0.00 | xxxx | 349 |
| ATOM | 350 | CG | GLN | A | 47 | 56.539 | 85.727 | 149.310 | 1.00 | 0.00 | xxxx | 350 |
| ATOM | 351 | CD | GLN | A | 47 | 56.655 | 84.234 | 149.145 | 1.00 | 0.00 | xxxx | 351 |
| ATOM | 352 | OE1 | GLN | A | 47 | 57.354 | 83.750 | 148.255 | 1.00 | 0.00 | xxxx | 352 |
| ATOM | 353 | NE2 | GLN | A | 47 | 55.963 | 83.490 | 149.997 | 1.00 | 0.00 | xxxx | 353 |
| ATOM | 354 | C | GLN | A | 47 | 56.472 | 88.582 | 148.381 | 1.00 | 0.00 | xxxx | 354 |
| ATOM | 355 | O | GLN | A | 47 | 57.287 | 88.818 | 149.255 | 1.00 | 0.00 | xxxx | 355 |
| ATOM | 356 | N | ASN | A | 48 | 56.625 | 88.998 | 147.127 | 1.00 | 0.00 | xxxx | 356 |
| ATOM | 357 | CA | ASN | A | 48 | 57.794 | 89.793 | 146.754 | 1.00 | 0.00 | xxxx | 357 |
| ATOM | 358 | CB | ASN | A | 48 | 57.820 | 90.061 | 145.251 | 1.00 | 0.00 | xxxx | 358 |
| ATOM | 359 | CG | ASN | A | 48 | 58.164 | 88.820 | 144.434 | 1.00 | 0.00 | xxxx | 359 |
| ATOM | 360 | OD1 | ASN | A | 48 | 58.698 | 87.839 | 144.954 | 1.00 | 0.00 | xxxx | 360 |
| ATOM | 361 | ND2 | ASN | A | 48 | 57.881 | 88.879 | 143.135 | 1.00 | 0.00 | xxxx | 361 |
| ATOM | 362 | C | ASN | A | 48 | 57.802 | 91.113 | 147.527 | 1.00 | 0.00 | xxxx | 362 |
| ATOM | 363 | O | ASN | A | 48 | 58.854 | 91.563 | 147.987 | 1.00 | 0.00 | xxxx | 363 |
| ATOM | 364 | N | ASP | A | 49 | 56.626 | 91.724 | 147.670 | 1.00 | 0.00 | xxxx | 364 |
| ATOM | 365 | CA | ASP | A | 49 | 56.486 | 92.945 | 148.462 | 1.00 | 0.00 | xxxx | 365 |
| ATOM | 366 | CB | ASP | A | 49 | 55.059 | 93.504 | 148.364 | 1.00 | 0.00 | xxxx | 366 |
| ATOM | 367 | CG | ASP | A | 49 | 54.752 | 94.096 | 147.000 | 1.00 | 0.00 | xxxx | 367 |
| ATOM | 368 | OD1 | ASP | A | 49 | 55.700 | 94.468 | 146.275 | 1.00 | 0.00 | xxxx | 368 |
| ATOM | 369 | OD2 | ASP | A | 49 | 53.555 | 94.210 | 146.653 | 1.00 | 0.00 | xxxx | 369 |
| ATOM | 370 | C | ASP | A | 49 | 56.833 | 92.672 | 149.922 | 1.00 | 0.00 | xxxx | 370 |
| ATOM | 371 | O | ASP | A | 49 | 57.471 | 93.483 | 150.580 | 1.00 | 0.00 | xxxx | 371 |
| ATOM | 372 | N | GLN | A | 50 | 56.416 | 91.513 | 150.421 | 1.00 | 0.00 | xxxx | 372 |
| ATOM | 373 | CA | GLN | A | 50 | 56.674 | 91.169 | 151.817 | 1.00 | 0.00 | xxxx | 373 |
| ATOM | 374 | CB | GLN | A | 50 | 55.875 | 89.922 | 152.210 | 1.00 | 0.00 | xxxx | 374 |
| ATOM | 375 | CG | GLN | A | 50 | 54.378 | 90.222 | 152.317 | 1.00 | 0.00 | xxxx | 375 |
| ATOM | 376 | CD | GLN | A | 50 | 53.499 | 88.981 | 152.264 | 1.00 | 0.00 | xxxx | 376 |
| ATOM | 377 | OE1 | GLN | A | 50 | 53.886 | 87.941 | 151.732 | 1.00 | 0.00 | xxxx | 377 |
| ATOM | 378 | NE2 | GLN | A | 50 | 52.298 | 89.098 | 152.816 | 1.00 | 0.00 | xxxx | 378 |
| ATOM | 379 | C | GLN | A | 50 | 58.164 | 90.962 | 152.055 | 1.00 | 0.00 | xxxx | 379 |
| ATOM | 380 | O | GLN | A | 50 | 58.705 | 91.402 | 153.067 | 1.00 | 0.00 | xxxx | 380 |
| ATOM | 381 | N | VAL | A | 51 | 58.823 | 90.294 | 151.112 | 1.00 | 0.00 | xxxx | 381 |
| ATOM | 382 | CA | VAL | A | 51 | 60.260 | 90.081 | 151.211 | 1.00 | 0.00 | xxxx | 382 |
| ATOM | 383 | CB | VAL | A | 51 | 60.764 | 89.156 | 150.098 | 1.00 | 0.00 | xxxx | 383 |
| ATOM | 384 | CG1 | VAL | A | 51 | 62.308 | 89.153 | 150.045 | 1.00 | 0.00 | xxxx | 384 |
| ATOM | 385 | CG2 | VAL | A | 51 | 60.231 | 87.736 | 150.309 | 1.00 | 0.00 | xxxx | 385 |
| ATOM | 386 | C | VAL | A | 51 | 60.984 | 91.419 | 151.177 | 1.00 | 0.00 | xxxx | 386 |
| ATOM | 387 | O | VAL | A | 51 | 61.912 | 91.644 | 151.963 | 1.00 | 0.00 | xxxx | 387 |
| ATOM | 388 | N | ASP | A | 52 | 60.562 | 92.310 | 150.280 | 1.00 | 0.00 | xxxx | 388 |
| ATOM | 389 | CA | ASP | A | 52 | 61.167 | 93.640 | 150.219 | 1.00 | 0.00 | xxxx | 389 |
| ATOM | 390 | CB | ASP | A | 52 | 60.525 | 94.504 | 149.132 | 1.00 | 0.00 | xxxx | 390 |
| ATOM | 391 | CG | ASP | A | 52 | 60.923 | 94.080 | 147.729 | 1.00 | 0.00 | xxxx | 391 |
| ATOM | 392 | OD1 | ASP | A | 52 | 61.889 | 93.306 | 147.580 | 1.00 | 0.00 | xxxx | 392 |
| ATOM | 393 | OD2 | ASP | A | 52 | 60.268 | 94.536 | 146.767 | 1.00 | 0.00 | xxxx | 393 |
| ATOM | 394 | C | ASP | A | 52 | 61.056 | 94.347 | 151.563 | 1.00 | 0.00 | xxxx | 394 |
| ATOM | 395 | O | ASP | A | 52 | 62.012 | 94.987 | 152.006 | 1.00 | 0.00 | xxxx | 395 |
| ATOM | 396 | N | LEU | A | 53 | 59.905 | 94.221 | 152.222 | 1.00 | 0.00 | xxxx | 396 |
| ATOM | 397 | CA | LEU | A | 53 | 59.703 | 94.897 | 153.504 | 1.00 | 0.00 | xxxx | 397 |
| ATOM | 398 | CB | LEU | A | 53 | 58.222 | 94.893 | 153.895 | 1.00 | 0.00 | xxxx | 398 |
| ATOM | 399 | CG | LEU | A | 53 | 57.869 | 95.753 | 155.115 | 1.00 | 0.00 | xxxx | 399 |
| ATOM | 400 | CD1 | LEU | A | 53 | 58.301 | 97.208 | 154.909 | 1.00 | 0.00 | xxxx | 400 |
| ATOM | 401 | CD2 | LEU | A | 53 | 56.381 | 95.663 | 155.432 | 1.00 | 0.00 | xxxx | 401 |
| ATOM | 402 | C | LEU | A | 53 | 60.547 | 94.264 | 154.619 | 1.00 | 0.00 | xxxx | 402 |
| ATOM | 403 | O | LEU | A | 53 | 61.093 | 94.987 | 155.466 | 1.00 | 0.00 | xxxx | 403 |
| ATOM | 404 | N | PHE | A | 54 | 60.636 | 92.933 | 154.629 | 1.00 | 0.00 | xxxx | 404 |
| ATOM | 405 | CA | PHE | A | 54 | 61.515 | 92.214 | 155.560 | 1.00 | 0.00 | xxxx | 405 |
| ATOM | 406 | CB | PHE | A | 54 | 61.561 | 90.708 | 155.254 | 1.00 | 0.00 | xxxx | 406 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 407 | CG | PHE | A | 54 | 60.346 | 89.933 | 155.713 | 1.00 | 0.00 | xxxx | 407 |
| ATOM | 408 | CD1 | PHE | A | 54 | 59.575 | 90.367 | 156.776 | 1.00 | 0.00 | xxxx | 408 |
| ATOM | 409 | CE1 | PHE | A | 54 | 58.461 | 89.633 | 157.192 | 1.00 | 0.00 | xxxx | 409 |
| ATOM | 410 | CZ | PHE | A | 54 | 58.131 | 88.452 | 156.551 | 1.00 | 0.00 | xxxx | 410 |
| ATOM | 411 | CE2 | PHE | A | 54 | 58.905 | 87.998 | 155.491 | 1.00 | 0.00 | xxxx | 411 |
| ATOM | 412 | CD2 | PHE | A | 54 | 60.010 | 88.737 | 155.089 | 1.00 | 0.00 | xxxx | 412 |
| ATOM | 413 | C | PHE | A | 54 | 62.929 | 92.783 | 155.465 | 1.00 | 0.00 | xxxx | 413 |
| ATOM | 414 | O | PHE | A | 54 | 63.604 | 93.023 | 156.477 | 1.00 | 0.00 | xxxx | 414 |
| ATOM | 415 | N | ILE | A | 55 | 63.373 | 93.007 | 154.233 | 1.00 | 0.00 | xxxx | 415 |
| ATOM | 416 | CA | ILE | A | 55 | 64.732 | 93.479 | 153.993 | 1.00 | 0.00 | xxxx | 416 |
| ATOM | 417 | CB | ILE | A | 55 | 65.098 | 93.302 | 152.511 | 1.00 | 0.00 | xxxx | 417 |
| ATOM | 418 | CG1 | ILE | A | 55 | 65.222 | 91.807 | 152.197 | 1.00 | 0.00 | xxxx | 418 |
| ATOM | 419 | CD1 | ILE | A | 55 | 65.409 | 91.487 | 150.726 | 1.00 | 0.00 | xxxx | 419 |
| ATOM | 420 | CG2 | ILE | A | 55 | 66.377 | 94.055 | 152.177 | 1.00 | 0.00 | xxxx | 420 |
| ATOM | 421 | C | ILE | A | 55 | 64.902 | 94.924 | 154.457 | 1.00 | 0.00 | xxxx | 421 |
| ATOM | 422 | O | ILE | A | 55 | 65.902 | 95.266 | 155.093 | 1.00 | 0.00 | xxxx | 422 |
| ATOM | 423 | N | THR | A | 56 | 63.916 | 95.763 | 154.159 | 1.00 | 0.00 | xxxx | 423 |
| ATOM | 424 | CA | THR | A | 56 | 63.933 | 97.154 | 154.592 | 1.00 | 0.00 | xxxx | 424 |
| ATOM | 425 | CB | THR | A | 56 | 62.713 | 97.923 | 154.040 | 1.00 | 0.00 | xxxx | 425 |
| ATOM | 426 | OG1 | THR | A | 56 | 62.796 | 97.967 | 152.611 | 1.00 | 0.00 | xxxx | 426 |
| ATOM | 427 | CG2 | THR | A | 56 | 62.676 | 99.344 | 154.581 | 1.00 | 0.00 | xxxx | 427 |
| ATOM | 428 | C | THR | A | 56 | 63.951 | 97.232 | 156.116 | 1.00 | 0.00 | xxxx | 428 |
| ATOM | 429 | O | THR | A | 56 | 64.620 | 98.091 | 156.700 | 1.00 | 0.00 | xxxx | 429 |
| ATOM | 430 | N | LYS | A | 57 | 63.230 | 96.315 | 156.755 | 1.00 | 0.00 | xxxx | 430 |
| ATOM | 431 | CA | LYS | A | 57 | 63.159 | 96.274 | 158.214 | 1.00 | 0.00 | xxxx | 431 |
| ATOM | 432 | CB | LYS | A | 57 | 61.850 | 95.617 | 158.655 | 1.00 | 0.00 | xxxx | 432 |
| ATOM | 433 | CG | LYS | A | 57 | 60.626 | 96.490 | 158.452 | 1.00 | 0.00 | xxxx | 433 |
| ATOM | 434 | CD | LYS | A | 57 | 59.376 | 95.824 | 159.010 | 1.00 | 0.00 | xxxx | 434 |
| ATOM | 435 | CE | LYS | A | 57 | 58.180 | 96.769 | 158.976 | 1.00 | 0.00 | xxxx | 435 |
| ATOM | 436 | NZ | LYS | A | 57 | 56.935 | 96.105 | 159.456 | 1.00 | 0.00 | xxxx | 436 |
| ATOM | 437 | C | LYS | A | 57 | 64.344 | 95.549 | 158.864 | 1.00 | 0.00 | xxxx | 437 |
| ATOM | 438 | O | LYS | A | 57 | 64.375 | 95.392 | 160.084 | 1.00 | 0.00 | xxxx | 438 |
| ATOM | 439 | N | LYS | A | 58 | 65.309 | 95.129 | 158.048 | 1.00 | 0.00 | xxxx | 439 |
| ATOM | 440 | CA | LYS | A | 58 | 66.553 | 94.503 | 158.516 | 1.00 | 0.00 | xxxx | 440 |
| ATOM | 441 | CB | LYS | A | 58 | 67.433 | 95.534 | 159.234 | 1.00 | 0.00 | xxxx | 441 |
| ATOM | 442 | CG | LYS | A | 58 | 67.875 | 96.673 | 158.318 | 1.00 | 0.00 | xxxx | 442 |
| ATOM | 443 | CD | LYS | A | 58 | 68.881 | 97.591 | 158.989 | 1.00 | 0.00 | xxxx | 443 |
| ATOM | 444 | CE | LYS | A | 58 | 69.136 | 98.827 | 158.137 | 1.00 | 0.00 | xxxx | 444 |
| ATOM | 445 | NZ | LYS | A | 58 | 69.258 | 98.481 | 156.688 | 1.00 | 0.00 | xxxx | 445 |
| ATOM | 446 | C | LYS | A | 58 | 66.313 | 93.289 | 159.416 | 1.00 | 0.00 | xxxx | 446 |
| ATOM | 447 | O | LYS | A | 58 | 66.865 | 93.191 | 160.516 | 1.00 | 0.00 | xxxx | 447 |
| ATOM | 448 | N | MET | A | 59 | 65.483 | 92.368 | 158.939 | 1.00 | 0.00 | xxxx | 448 |
| ATOM | 449 | CA | MET | A | 59 | 65.349 | 91.068 | 159.584 | 1.00 | 0.00 | xxxx | 449 |
| ATOM | 450 | CB | MET | A | 59 | 64.430 | 90.136 | 158.784 | 1.00 | 0.00 | xxxx | 450 |
| ATOM | 451 | CG | MET | A | 59 | 62.963 | 90.542 | 158.691 | 1.00 | 0.00 | xxxx | 451 |
| ATOM | 452 | SD | MET | A | 59 | 62.059 | 90.456 | 160.248 | 1.00 | 0.00 | xxxx | 452 |
| ATOM | 453 | CE | MET | A | 59 | 62.015 | 92.191 | 160.689 | 1.00 | 0.00 | xxxx | 453 |
| ATOM | 454 | C | MET | A | 59 | 66.728 | 90.444 | 159.704 | 1.00 | 0.00 | xxxx | 454 |
| ATOM | 455 | O | MET | A | 59 | 67.582 | 90.663 | 158.846 | 1.00 | 0.00 | xxxx | 455 |
| ATOM | 456 | N | ASN | A | 60 | 66.951 | 89.661 | 160.756 | 1.00 | 0.00 | xxxx | 456 |
| ATOM | 457 | CA | ASN | A | 60 | 68.228 | 88.965 | 160.908 | 1.00 | 0.00 | xxxx | 457 |
| ATOM | 458 | CB | ASN | A | 60 | 68.446 | 88.589 | 162.372 | 1.00 | 0.00 | xxxx | 458 |
| ATOM | 459 | CG | ASN | A | 60 | 68.464 | 89.801 | 163.279 | 1.00 | 0.00 | xxxx | 459 |
| ATOM | 460 | OD1 | ASN | A | 60 | 67.465 | 90.128 | 163.918 | 1.00 | 0.00 | xxxx | 460 |
| ATOM | 461 | ND2 | ASN | A | 60 | 69.599 | 90.491 | 163.318 | 1.00 | 0.00 | xxxx | 461 |
| ATOM | 462 | C | ASN | A | 60 | 68.341 | 87.719 | 160.026 | 1.00 | 0.00 | xxxx | 462 |
| ATOM | 463 | O | ASN | A | 60 | 69.445 | 87.289 | 159.692 | 1.00 | 0.00 | xxxx | 463 |
| ATOM | 464 | N | ALA | A | 61 | 67.193 | 87.142 | 159.669 | 1.00 | 0.00 | xxxx | 464 |
| ATOM | 465 | CA | ALA | A | 61 | 67.123 | 86.004 | 158.756 | 1.00 | 0.00 | xxxx | 465 |
| ATOM | 466 | CB | ALA | A | 61 | 67.477 | 84.693 | 159.470 | 1.00 | 0.00 | xxxx | 466 |
| ATOM | 467 | C | ALA | A | 61 | 65.727 | 85.920 | 158.155 | 1.00 | 0.00 | xxxx | 467 |
| ATOM | 468 | O | ALA | A | 61 | 64.780 | 86.490 | 158.689 | 1.00 | 0.00 | xxxx | 468 |
| ATOM | 469 | N | LEU | A | 62 | 65.616 | 85.209 | 157.036 | 1.00 | 0.00 | xxxx | 469 |
| ATOM | 470 | CA | LEU | A | 62 | 64.332 | 84.994 | 156.379 | 1.00 | 0.00 | xxxx | 470 |
| ATOM | 471 | CB | LEU | A | 62 | 64.337 | 85.542 | 154.955 | 1.00 | 0.00 | xxxx | 471 |
| ATOM | 472 | CG | LEU | A | 62 | 64.779 | 86.990 | 154.745 | 1.00 | 0.00 | xxxx | 472 |
| ATOM | 473 | CD1 | LEU | A | 62 | 64.760 | 87.308 | 153.264 | 1.00 | 0.00 | xxxx | 473 |
| ATOM | 474 | CD2 | LEU | A | 62 | 63.876 | 87.937 | 155.498 | 1.00 | 0.00 | xxxx | 474 |
| ATOM | 475 | C | LEU | A | 62 | 64.027 | 83.511 | 156.334 | 1.00 | 0.00 | xxxx | 475 |
| ATOM | 476 | O | LEU | A | 62 | 64.923 | 82.701 | 156.109 | 1.00 | 0.00 | xxxx | 476 |
| ATOM | 477 | N | ALA | A | 63 | 62.762 | 83.165 | 156.553 | 1.00 | 0.00 | xxxx | 477 |
| ATOM | 478 | CA | ALA | A | 63 | 62.273 | 81.813 | 156.314 | 1.00 | 0.00 | xxxx | 478 |
| ATOM | 479 | CB | ALA | A | 63 | 61.842 | 81.136 | 157.624 | 1.00 | 0.00 | xxxx | 479 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 480 | C | ALA | A | 63 | 61.105 | 81.935 | 155.348 | 1.00 | 0.00 | xxxx | 480 |
| ATOM | 481 | O | ALA | A | 63 | 60.050 | 82.455 | 155.711 | 1.00 | 0.00 | xxxx | 481 |
| ATOM | 482 | N | ILE | A | 64 | 61.300 | 81.468 | 154.120 | 1.00 | 0.00 | xxxx | 482 |
| ATOM | 483 | CA | ILE | A | 64 | 60.337 | 81.715 | 153.050 | 1.00 | 0.00 | xxxx | 483 |
| ATOM | 484 | CB | ILE | A | 64 | 60.994 | 82.522 | 151.905 | 1.00 | 0.00 | xxxx | 484 |
| ATOM | 485 | CG1 | ILE | A | 64 | 61.607 | 83.830 | 152.432 | 1.00 | 0.00 | xxxx | 485 |
| ATOM | 486 | CD1 | ILE | A | 64 | 60.611 | 84.779 | 153.082 | 1.00 | 0.00 | xxxx | 486 |
| ATOM | 487 | CG2 | ILE | A | 64 | 59.989 | 82.759 | 150.772 | 1.00 | 0.00 | xxxx | 487 |
| ATOM | 488 | C | ILE | A | 64 | 59.743 | 80.418 | 152.501 | 1.00 | 0.00 | xxxx | 488 |
| ATOM | 489 | O | ILE | A | 64 | 60.463 | 79.495 | 152.140 | 1.00 | 0.00 | xxxx | 489 |
| ATOM | 490 | N | ASN | A | 65 | 58.414 | 80.373 | 152.463 | 1.00 | 0.00 | xxxx | 490 |
| ATOM | 491 | CA | ASN | A | 65 | 57.649 | 79.299 | 151.833 | 1.00 | 0.00 | xxxx | 491 |
| ATOM | 492 | CB | ASN | A | 65 | 56.519 | 78.881 | 152.806 | 1.00 | 0.00 | xxxx | 492 |
| ATOM | 493 | CG | ASN | A | 65 | 55.548 | 77.840 | 152.252 | 1.00 | 0.00 | xxxx | 493 |
| ATOM | 494 | OD1 | ASN | A | 65 | 54.331 | 78.040 | 152.335 | 1.00 | 0.00 | xxxx | 494 |
| ATOM | 495 | ND2 | ASN | A | 65 | 56.055 | 76.722 | 151.762 | 1.00 | 0.00 | xxxx | 495 |
| ATOM | 496 | C | ASN | A | 65 | 57.157 | 79.892 | 150.497 | 1.00 | 0.00 | xxxx | 496 |
| ATOM | 497 | O | ASN | A | 65 | 56.116 | 80.535 | 150.451 | 1.00 | 0.00 | xxxx | 497 |
| ATOM | 498 | N | PRO | A | 66 | 57.946 | 79.739 | 149.413 | 1.00 | 0.00 | xxxx | 498 |
| ATOM | 499 | CA | PRO | A | 66 | 57.699 | 80.580 | 148.231 | 1.00 | 0.00 | xxxx | 499 |
| ATOM | 500 | CB | PRO | A | 66 | 58.934 | 80.329 | 147.357 | 1.00 | 0.00 | xxxx | 500 |
| ATOM | 501 | CG | PRO | A | 66 | 59.372 | 78.935 | 147.731 | 1.00 | 0.00 | xxxx | 501 |
| ATOM | 502 | CD | PRO | A | 66 | 59.106 | 78.847 | 149.232 | 1.00 | 0.00 | xxxx | 502 |
| ATOM | 503 | C | PRO | A | 66 | 56.425 | 80.206 | 147.478 | 1.00 | 0.00 | xxxx | 503 |
| ATOM | 504 | O | PRO | A | 66 | 56.155 | 79.020 | 147.299 | 1.00 | 0.00 | xxxx | 504 |
| ATOM | 505 | N | VAL | A | 67 | 55.650 | 81.199 | 147.049 | 1.00 | 0.00 | xxxx | 505 |
| ATOM | 506 | CA | VAL | A | 67 | 54.412 | 80.915 | 146.326 | 1.00 | 0.00 | xxxx | 506 |
| ATOM | 507 | CB | VAL | A | 67 | 53.585 | 82.188 | 146.099 | 1.00 | 0.00 | xxxx | 507 |
| ATOM | 508 | CG1 | VAL | A | 67 | 52.372 | 81.865 | 145.252 | 1.00 | 0.00 | xxxx | 508 |
| ATOM | 509 | CG2 | VAL | A | 67 | 53.154 | 82.764 | 147.427 | 1.00 | 0.00 | xxxx | 509 |
| ATOM | 510 | C | VAL | A | 67 | 54.743 | 80.241 | 145.004 | 1.00 | 0.00 | xxxx | 510 |
| ATOM | 511 | O | VAL | A | 67 | 54.246 | 79.156 | 144.698 | 1.00 | 0.00 | xxxx | 511 |
| ATOM | 512 | N | ASP | A | 68 | 55.592 | 80.903 | 144.226 | 1.00 | 0.00 | xxxx | 512 |
| ATOM | 513 | CA | ASP | A | 68 | 56.154 | 80.356 | 143.001 | 1.00 | 0.00 | xxxx | 513 |
| ATOM | 514 | CB | ASP | A | 68 | 56.103 | 81.413 | 141.895 | 1.00 | 0.00 | xxxx | 514 |
| ATOM | 515 | CG | ASP | A | 68 | 56.745 | 80.970 | 140.598 | 1.00 | 0.00 | xxxx | 515 |
| ATOM | 516 | OD1 | ASP | A | 68 | 57.339 | 79.872 | 140.524 | 1.00 | 0.00 | xxxx | 516 |
| ATOM | 517 | OD2 | ASP | A | 68 | 56.652 | 81.758 | 139.624 | 1.00 | 0.00 | xxxx | 517 |
| ATOM | 518 | C | ASP | A | 68 | 57.580 | 79.951 | 143.345 | 1.00 | 0.00 | xxxx | 518 |
| ATOM | 519 | O | ASP | A | 68 | 58.439 | 80.805 | 143.546 | 1.00 | 0.00 | xxxx | 519 |
| ATOM | 520 | N | ARG | A | 69 | 57.842 | 78.656 | 143.450 | 1.00 | 0.00 | xxxx | 520 |
| ATOM | 521 | CA | ARG | A | 69 | 59.166 | 78.263 | 143.896 | 1.00 | 0.00 | xxxx | 521 |
| ATOM | 522 | CB | ARG | A | 69 | 59.214 | 76.759 | 144.204 | 1.00 | 0.00 | xxxx | 522 |
| ATOM | 523 | CG | ARG | A | 69 | 59.157 | 75.863 | 142.992 | 1.00 | 0.00 | xxxx | 523 |
| ATOM | 524 | CD | ARG | A | 69 | 58.691 | 74.465 | 143.413 | 1.00 | 0.00 | xxxx | 524 |
| ATOM | 525 | NE | ARG | A | 69 | 58.616 | 73.547 | 142.288 | 1.00 | 0.00 | xxxx | 525 |
| ATOM | 526 | CZ | ARG | A | 69 | 59.624 | 72.786 | 141.865 | 1.00 | 0.00 | xxxx | 526 |
| ATOM | 527 | NH1 | ARG | A | 69 | 60.814 | 72.830 | 142.465 | 1.00 | 0.00 | xxxx | 527 |
| ATOM | 528 | NH2 | ARG | A | 69 | 59.440 | 71.977 | 140.833 | 1.00 | 0.00 | xxxx | 528 |
| ATOM | 529 | C | ARG | A | 69 | 60.249 | 78.666 | 142.881 | 1.00 | 0.00 | xxxx | 529 |
| ATOM | 530 | O | ARG | A | 69 | 61.413 | 78.803 | 143.263 | 1.00 | 0.00 | xxxx | 530 |
| ATOM | 531 | N | THR | A | 70 | 59.879 | 78.923 | 141.625 | 1.00 | 0.00 | xxxx | 531 |
| ATOM | 532 | CA | THR | A | 70 | 60.878 | 79.411 | 140.661 | 1.00 | 0.00 | xxxx | 532 |
| ATOM | 533 | CB | THR | A | 70 | 60.392 | 79.267 | 139.184 | 1.00 | 0.00 | xxxx | 533 |
| ATOM | 534 | OG1 | THR | A | 70 | 59.329 | 80.188 | 138.896 | 1.00 | 0.00 | xxxx | 534 |
| ATOM | 535 | CG2 | THR | A | 70 | 59.919 | 77.842 | 138.933 | 1.00 | 0.00 | xxxx | 535 |
| ATOM | 536 | C | THR | A | 70 | 61.284 | 80.865 | 140.955 | 1.00 | 0.00 | xxxx | 536 |
| ATOM | 537 | O | THR | A | 70 | 62.320 | 81.333 | 140.480 | 1.00 | 0.00 | xxxx | 537 |
| ATOM | 538 | N | ALA | A | 71 | 60.510 | 81.559 | 141.788 | 1.00 | 0.00 | xxxx | 538 |
| ATOM | 539 | CA | ALA | A | 71 | 60.861 | 82.923 | 142.190 | 1.00 | 0.00 | xxxx | 539 |
| ATOM | 540 | CB | ALA | A | 71 | 59.612 | 83.672 | 142.667 | 1.00 | 0.00 | xxxx | 540 |
| ATOM | 541 | C | ALA | A | 71 | 61.937 | 82.971 | 143.274 | 1.00 | 0.00 | xxxx | 541 |
| ATOM | 542 | O | ALA | A | 71 | 62.404 | 84.052 | 143.644 | 1.00 | 0.00 | xxxx | 542 |
| ATOM | 543 | N | ALA | A | 72 | 62.341 | 81.808 | 143.779 | 1.00 | 0.00 | xxxx | 543 |
| ATOM | 544 | CA | ALA | A | 72 | 63.334 | 81.764 | 144.846 | 1.00 | 0.00 | xxxx | 544 |
| ATOM | 545 | CB | ALA | A | 72 | 63.557 | 80.321 | 145.328 | 1.00 | 0.00 | xxxx | 545 |
| ATOM | 546 | C | ALA | A | 72 | 64.654 | 82.393 | 144.397 | 1.00 | 0.00 | xxxx | 546 |
| ATOM | 547 | O | ALA | A | 72 | 65.361 | 82.986 | 145.207 | 1.00 | 0.00 | xxxx | 547 |
| ATOM | 548 | N | GLY | A | 73 | 64.973 | 82.284 | 143.106 | 1.00 | 0.00 | xxxx | 548 |
| ATOM | 549 | CA | GLY | A | 73 | 66.187 | 82.877 | 142.574 | 1.00 | 0.00 | xxxx | 549 |
| ATOM | 550 | C | GLY | A | 73 | 66.250 | 84.379 | 142.794 | 1.00 | 0.00 | xxxx | 550 |
| ATOM | 551 | O | GLY | A | 73 | 67.258 | 84.908 | 143.264 | 1.00 | 0.00 | xxxx | 551 |
| ATOM | 552 | N | THR | A | 74 | 65.167 | 85.071 | 142.457 | 1.00 | 0.00 | xxxx | 552 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 553 | CA | THR | A | 74 | 65.101 | 86.515 | 142.667 | 1.00 | 0.00 | xxxx | 553 |
| ATOM | 554 | CB | THR | A | 74 | 63.836 | 87.112 | 142.007 | 1.00 | 0.00 | xxxx | 554 |
| ATOM | 555 | OG1 | THR | A | 74 | 63.900 | 86.893 | 140.591 | 1.00 | 0.00 | xxxx | 555 |
| ATOM | 556 | CG2 | THR | A | 74 | 63.743 | 88.608 | 142.273 | 1.00 | 0.00 | xxxx | 556 |
| ATOM | 557 | C | THR | A | 74 | 65.130 | 86.863 | 144.158 | 1.00 | 0.00 | xxxx | 557 |
| ATOM | 558 | O | THR | A | 74 | 65.742 | 87.855 | 144.560 | 1.00 | 0.00 | xxxx | 558 |
| ATOM | 559 | N | ILE | A | 75 | 64.492 | 86.035 | 144.980 | 1.00 | 0.00 | xxxx | 559 |
| ATOM | 560 | CA | ILE | A | 75 | 64.502 | 86.251 | 146.423 | 1.00 | 0.00 | xxxx | 560 |
| ATOM | 561 | CB | ILE | A | 75 | 63.521 | 85.295 | 147.133 | 1.00 | 0.00 | xxxx | 561 |
| ATOM | 562 | CG1 | ILE | A | 75 | 62.077 | 85.609 | 146.730 | 1.00 | 0.00 | xxxx | 562 |
| ATOM | 563 | CD1 | ILE | A | 75 | 61.072 | 84.586 | 147.234 | 1.00 | 0.00 | xxxx | 563 |
| ATOM | 564 | CG2 | ILE | A | 75 | 63.693 | 85.377 | 148.649 | 1.00 | 0.00 | xxxx | 564 |
| ATOM | 565 | C | ILE | A | 75 | 65.924 | 86.099 | 146.973 | 1.00 | 0.00 | xxxx | 565 |
| ATOM | 566 | O | ILE | A | 75 | 66.351 | 86.874 | 147.829 | 1.00 | 0.00 | xxxx | 566 |
| ATOM | 567 | N | ILE | A | 76 | 66.654 | 85.101 | 146.479 | 1.00 | 0.00 | xxxx | 567 |
| ATOM | 568 | CA | ILE | A | 76 | 68.037 | 84.902 | 146.899 | 1.00 | 0.00 | xxxx | 568 |
| ATOM | 569 | CB | ILE | A | 76 | 68.615 | 83.585 | 146.343 | 1.00 | 0.00 | xxxx | 569 |
| ATOM | 570 | CG1 | ILE | A | 76 | 67.917 | 82.387 | 146.999 | 1.00 | 0.00 | xxxx | 570 |
| ATOM | 571 | CD1 | ILE | A | 76 | 68.122 | 81.063 | 146.273 | 1.00 | 0.00 | xxxx | 571 |
| ATOM | 572 | CG2 | ILE | A | 76 | 70.123 | 83.526 | 146.570 | 1.00 | 0.00 | xxxx | 572 |
| ATOM | 573 | C | ILE | A | 76 | 68.884 | 86.109 | 146.491 | 1.00 | 0.00 | xxxx | 573 |
| ATOM | 574 | O | ILE | A | 76 | 69.702 | 86.583 | 147.280 | 1.00 | 0.00 | xxxx | 574 |
| ATOM | 575 | N | ASP | A | 77 | 68.675 | 86.622 | 145.276 | 1.00 | 0.00 | xxxx | 575 |
| ATOM | 576 | CA | ASP | A | 77 | 69.396 | 87.818 | 144.827 | 1.00 | 0.00 | xxxx | 576 |
| ATOM | 577 | CB | ASP | A | 77 | 68.917 | 88.274 | 143.447 | 1.00 | 0.00 | xxxx | 577 |
| ATOM | 578 | CG | ASP | A | 77 | 69.400 | 87.373 | 142.329 | 1.00 | 0.00 | xxxx | 578 |
| ATOM | 579 | OD1 | ASP | A | 77 | 70.394 | 86.651 | 142.530 | 1.00 | 0.00 | xxxx | 579 |
| ATOM | 580 | OD2 | ASP | A | 77 | 68.786 | 87.399 | 141.241 | 1.00 | 0.00 | xxxx | 580 |
| ATOM | 581 | C | ASP | A | 77 | 69.236 | 88.971 | 145.812 | 1.00 | 0.00 | xxxx | 581 |
| ATOM | 582 | O | ASP | A | 77 | 70.217 | 89.600 | 146.202 | 1.00 | 0.00 | xxxx | 582 |
| ATOM | 583 | N | LYS | A | 78 | 67.993 | 89.238 | 146.206 | 1.00 | 0.00 | xxxx | 583 |
| ATOM | 584 | CA | LYS | A | 78 | 67.697 | 90.340 | 147.114 | 1.00 | 0.00 | xxxx | 584 |
| ATOM | 585 | CB | LYS | A | 78 | 66.187 | 90.539 | 147.253 | 1.00 | 0.00 | xxxx | 585 |
| ATOM | 586 | CG | LYS | A | 78 | 65.482 | 91.006 | 145.993 | 1.00 | 0.00 | xxxx | 586 |
| ATOM | 587 | CD | LYS | A | 78 | 63.968 | 90.934 | 146.185 | 1.00 | 0.00 | xxxx | 587 |
| ATOM | 588 | CE | LYS | A | 78 | 63.205 | 91.440 | 144.968 | 1.00 | 0.00 | xxxx | 588 |
| ATOM | 589 | NZ | LYS | A | 78 | 63.228 | 92.922 | 144.844 | 1.00 | 0.00 | xxxx | 589 |
| ATOM | 590 | C | LYS | A | 78 | 68.309 | 90.094 | 148.485 | 1.00 | 0.00 | xxxx | 590 |
| ATOM | 591 | O | LYS | A | 78 | 68.882 | 91.000 | 149.095 | 1.00 | 0.00 | xxxx | 591 |
| ATOM | 592 | N | ALA | A | 79 | 68.177 | 88.864 | 148.962 | 1.00 | 0.00 | xxxx | 592 |
| ATOM | 593 | CA | ALA | A | 79 | 68.713 | 88.492 | 150.266 | 1.00 | 0.00 | xxxx | 593 |
| ATOM | 594 | CB | ALA | A | 79 | 68.272 | 87.087 | 150.631 | 1.00 | 0.00 | xxxx | 594 |
| ATOM | 595 | C | ALA | A | 79 | 70.237 | 88.597 | 150.290 | 1.00 | 0.00 | xxxx | 595 |
| ATOM | 596 | O | ALA | A | 79 | 70.813 | 89.107 | 151.251 | 1.00 | 0.00 | xxxx | 596 |
| ATOM | 597 | N | LYS | A | 80 | 70.885 | 88.117 | 149.231 | 1.00 | 0.00 | xxxx | 597 |
| ATOM | 598 | CA | LYS | A | 80 | 72.346 | 88.192 | 149.124 | 1.00 | 0.00 | xxxx | 598 |
| ATOM | 599 | CB | LYS | A | 80 | 72.829 | 87.505 | 147.843 | 1.00 | 0.00 | xxxx | 599 |
| ATOM | 600 | CG | LYS | A | 80 | 74.345 | 87.412 | 147.695 | 1.00 | 0.00 | xxxx | 600 |
| ATOM | 601 | CD | LYS | A | 80 | 74.716 | 86.576 | 146.474 | 1.00 | 0.00 | xxxx | 601 |
| ATOM | 602 | CE | LYS | A | 80 | 76.222 | 86.416 | 146.331 | 1.00 | 0.00 | xxxx | 602 |
| ATOM | 603 | NZ | LYS | A | 80 | 76.901 | 87.724 | 146.158 | 1.00 | 0.00 | xxxx | 603 |
| ATOM | 604 | C | LYS | A | 80 | 72.823 | 89.638 | 149.149 | 1.00 | 0.00 | xxxx | 604 |
| ATOM | 605 | O | LYS | A | 80 | 73.796 | 89.968 | 149.826 | 1.00 | 0.00 | xxxx | 605 |
| ATOM | 606 | N | GLN | A | 81 | 72.127 | 90.497 | 148.410 | 1.00 | 0.00 | xxxx | 606 |
| ATOM | 607 | CA | GLN | A | 81 | 72.466 | 91.910 | 148.354 | 1.00 | 0.00 | xxxx | 607 |
| ATOM | 608 | CB | GLN | A | 81 | 71.571 | 92.629 | 147.344 | 1.00 | 0.00 | xxxx | 608 |
| ATOM | 609 | CG | GLN | A | 81 | 71.899 | 94.102 | 147.167 | 1.00 | 0.00 | xxxx | 609 |
| ATOM | 610 | CD | GLN | A | 81 | 73.342 | 94.340 | 146.750 | 1.00 | 0.00 | xxxx | 610 |
| ATOM | 611 | OE1 | GLN | A | 81 | 73.913 | 93.578 | 145.966 | 1.00 | 0.00 | xxxx | 611 |
| ATOM | 612 | NE2 | GLN | A | 81 | 73.940 | 95.403 | 147.279 | 1.00 | 0.00 | xxxx | 612 |
| ATOM | 613 | C | GLN | A | 81 | 72.344 | 92.550 | 149.735 | 1.00 | 0.00 | xxxx | 613 |
| ATOM | 614 | O | GLN | A | 81 | 73.172 | 93.369 | 150.123 | 1.00 | 0.00 | xxxx | 614 |
| ATOM | 615 | N | ALA | A | 82 | 71.326 | 92.145 | 150.487 | 1.00 | 0.00 | xxxx | 615 |
| ATOM | 616 | CA | ALA | A | 82 | 71.095 | 92.689 | 151.823 | 1.00 | 0.00 | xxxx | 616 |
| ATOM | 617 | CB | ALA | A | 82 | 69.618 | 92.589 | 152.166 | 1.00 | 0.00 | xxxx | 617 |
| ATOM | 618 | C | ALA | A | 82 | 71.928 | 91.984 | 152.900 | 1.00 | 0.00 | xxxx | 618 |
| ATOM | 619 | O | ALA | A | 82 | 71.942 | 92.409 | 154.058 | 1.00 | 0.00 | xxxx | 619 |
| ATOM | 620 | N | ASN | A | 83 | 72.609 | 90.911 | 152.506 | 1.00 | 0.00 | xxxx | 620 |
| ATOM | 621 | CA | ASN | A | 83 | 73.337 | 90.025 | 153.419 | 1.00 | 0.00 | xxxx | 621 |
| ATOM | 622 | CB | ASN | A | 83 | 74.565 | 90.740 | 154.004 | 1.00 | 0.00 | xxxx | 622 |
| ATOM | 623 | CG | ASN | A | 83 | 75.580 | 89.772 | 154.579 | 1.00 | 0.00 | xxxx | 623 |
| ATOM | 624 | OD1 | ASN | A | 83 | 75.617 | 88.597 | 154.209 | 1.00 | 0.00 | xxxx | 624 |
| ATOM | 625 | ND2 | ASN | A | 83 | 76.400 | 90.256 | 155.498 | 1.00 | 0.00 | xxxx | 625 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 626 | C | ASN | A | 83 | 72.436 | 89.487 | 154.540 | 1.00 | 0.00 | xxxx | 626 |
| ATOM | 627 | O | ASN | A | 83 | 72.835 | 89.408 | 155.699 | 1.00 | 0.00 | xxxx | 627 |
| ATOM | 628 | N | ILE | A | 84 | 71.215 | 89.108 | 154.173 | 1.00 | 0.00 | xxxx | 628 |
| ATOM | 629 | CA | ILE | A | 84 | 70.283 | 88.471 | 155.098 | 1.00 | 0.00 | xxxx | 629 |
| ATOM | 630 | CB | ILE | A | 84 | 68.926 | 89.201 | 155.137 | 1.00 | 0.00 | xxxx | 630 |
| ATOM | 631 | CG1 | ILE | A | 84 | 69.110 | 90.662 | 155.557 | 1.00 | 0.00 | xxxx | 631 |
| ATOM | 632 | CD1 | ILE | A | 84 | 67.799 | 91.458 | 155.568 | 1.00 | 0.00 | xxxx | 632 |
| ATOM | 633 | CG2 | ILE | A | 84 | 67.970 | 88.472 | 156.085 | 1.00 | 0.00 | xxxx | 633 |
| ATOM | 634 | C | ILE | A | 84 | 70.096 | 87.022 | 154.673 | 1.00 | 0.00 | xxxx | 634 |
| ATOM | 635 | O | ILE | A | 84 | 69.549 | 86.760 | 153.605 | 1.00 | 0.00 | xxxx | 635 |
| ATOM | 636 | N | PRO | A | 85 | 70.566 | 86.072 | 155.494 | 1.00 | 0.00 | xxxx | 636 |
| ATOM | 637 | CA | PRO | A | 85 | 70.477 | 84.653 | 155.134 | 1.00 | 0.00 | xxxx | 637 |
| ATOM | 638 | CB | PRO | A | 85 | 71.146 | 83.939 | 156.313 | 1.00 | 0.00 | xxxx | 638 |
| ATOM | 639 | CG | PRO | A | 85 | 71.926 | 84.981 | 157.018 | 1.00 | 0.00 | xxxx | 639 |
| ATOM | 640 | CD | PRO | A | 85 | 71.196 | 86.272 | 156.807 | 1.00 | 0.00 | xxxx | 640 |
| ATOM | 641 | C | PRO | A | 85 | 69.036 | 84.200 | 154.989 | 1.00 | 0.00 | xxxx | 641 |
| ATOM | 642 | O | PRO | A | 85 | 68.147 | 84.804 | 155.588 | 1.00 | 0.00 | xxxx | 642 |
| ATOM | 643 | N | VAL | A | 86 | 68.805 | 83.152 | 154.208 | 1.00 | 0.00 | xxxx | 643 |
| ATOM | 644 | CA | VAL | A | 86 | 67.445 | 82.710 | 153.973 | 1.00 | 0.00 | xxxx | 644 |
| ATOM | 645 | CB | VAL | A | 86 | 66.891 | 83.341 | 152.664 | 1.00 | 0.00 | xxxx | 645 |
| ATOM | 646 | CG1 | VAL | A | 86 | 67.839 | 83.113 | 151.486 | 1.00 | 0.00 | xxxx | 646 |
| ATOM | 647 | CG2 | VAL | A | 86 | 65.501 | 82.813 | 152.349 | 1.00 | 0.00 | xxxx | 647 |
| ATOM | 648 | C | VAL | A | 86 | 67.355 | 81.197 | 153.939 | 1.00 | 0.00 | xxxx | 648 |
| ATOM | 649 | O | VAL | A | 86 | 68.173 | 80.523 | 153.316 | 1.00 | 0.00 | xxxx | 649 |
| ATOM | 650 | N | VAL | A | 87 | 66.358 | 80.670 | 154.637 | 1.00 | 0.00 | xxxx | 650 |
| ATOM | 651 | CA | VAL | A | 87 | 66.011 | 79.268 | 154.517 | 1.00 | 0.00 | xxxx | 651 |
| ATOM | 652 | CB | VAL | A | 87 | 66.050 | 78.545 | 155.891 | 1.00 | 0.00 | xxxx | 652 |
| ATOM | 653 | CG1 | VAL | A | 87 | 65.197 | 79.281 | 156.950 | 1.00 | 0.00 | xxxx | 653 |
| ATOM | 654 | CG2 | VAL | A | 87 | 65.647 | 77.059 | 155.757 | 1.00 | 0.00 | xxxx | 654 |
| ATOM | 655 | C | VAL | A | 87 | 64.642 | 79.193 | 153.854 | 1.00 | 0.00 | xxxx | 655 |
| ATOM | 656 | O | VAL | A | 87 | 63.702 | 79.888 | 154.250 | 1.00 | 0.00 | xxxx | 656 |
| ATOM | 657 | N | PHE | A | 88 | 64.545 | 78.376 | 152.815 | 1.00 | 0.00 | xxxx | 657 |
| ATOM | 658 | CA | PHE | A | 88 | 63.271 | 78.124 | 152.168 | 1.00 | 0.00 | xxxx | 658 |
| ATOM | 659 | CB | PHE | A | 88 | 63.426 | 78.003 | 150.652 | 1.00 | 0.00 | xxxx | 659 |
| ATOM | 660 | CG | PHE | A | 88 | 63.847 | 79.285 | 149.980 | 1.00 | 0.00 | xxxx | 660 |
| ATOM | 661 | CD1 | PHE | A | 88 | 65.194 | 79.564 | 149.773 | 1.00 | 0.00 | xxxx | 661 |
| ATOM | 662 | CE1 | PHE | A | 88 | 65.594 | 80.743 | 149.161 | 1.00 | 0.00 | xxxx | 662 |
| ATOM | 663 | CZ | PHE | A | 88 | 64.633 | 81.661 | 148.744 | 1.00 | 0.00 | xxxx | 663 |
| ATOM | 664 | CE2 | PHE | A | 88 | 63.286 | 81.391 | 148.944 | 1.00 | 0.00 | xxxx | 664 |
| ATOM | 665 | CD2 | PHE | A | 88 | 62.900 | 80.209 | 149.564 | 1.00 | 0.00 | xxxx | 665 |
| ATOM | 666 | C | PHE | A | 88 | 62.705 | 76.841 | 152.739 | 1.00 | 0.00 | xxxx | 666 |
| ATOM | 667 | O | PHE | A | 88 | 63.451 | 76.004 | 153.249 | 1.00 | 0.00 | xxxx | 667 |
| ATOM | 668 | N | PHE | A | 89 | 61.393 | 76.672 | 152.658 | 1.00 | 0.00 | xxxx | 668 |
| ATOM | 669 | CA | PHE | A | 89 | 60.818 | 75.423 | 153.159 | 1.00 | 0.00 | xxxx | 669 |
| ATOM | 670 | CB | PHE | A | 89 | 60.593 | 75.478 | 154.697 | 1.00 | 0.00 | xxxx | 670 |
| ATOM | 671 | CG | PHE | A | 89 | 59.650 | 76.566 | 155.184 | 1.00 | 0.00 | xxxx | 671 |
| ATOM | 672 | CD1 | PHE | A | 89 | 60.063 | 77.896 | 155.266 | 1.00 | 0.00 | xxxx | 672 |
| ATOM | 673 | CE1 | PHE | A | 89 | 59.200 | 78.894 | 155.744 | 1.00 | 0.00 | xxxx | 673 |
| ATOM | 674 | CZ | PHE | A | 89 | 57.931 | 78.557 | 156.176 | 1.00 | 0.00 | xxxx | 674 |
| ATOM | 675 | CE2 | PHE | A | 89 | 57.517 | 77.232 | 156.118 | 1.00 | 0.00 | xxxx | 675 |
| ATOM | 676 | CD2 | PHE | A | 89 | 58.373 | 76.246 | 155.627 | 1.00 | 0.00 | xxxx | 676 |
| ATOM | 677 | C | PHE | A | 89 | 59.535 | 75.069 | 152.426 | 1.00 | 0.00 | xxxx | 677 |
| ATOM | 678 | O | PHE | A | 89 | 58.814 | 75.946 | 151.946 | 1.00 | 0.00 | xxxx | 678 |
| ATOM | 679 | N | ASN | A | 90 | 59.332 | 73.754 | 152.289 | 1.00 | 0.00 | xxxx | 679 |
| ATOM | 680 | CA | ASN | A | 90 | 58.098 | 73.099 | 151.807 | 1.00 | 0.00 | xxxx | 680 |
| ATOM | 681 | CB | ASN | A | 90 | 56.883 | 73.575 | 152.622 | 1.00 | 0.00 | xxxx | 681 |
| ATOM | 682 | CG | ASN | A | 90 | 55.556 | 73.178 | 151.972 | 1.00 | 0.00 | xxxx | 682 |
| ATOM | 683 | OD1 | ASN | A | 90 | 54.938 | 73.975 | 151.266 | 1.00 | 0.00 | xxxx | 683 |
| ATOM | 684 | ND2 | ASN | A | 90 | 55.117 | 71.939 | 152.207 | 1.00 | 0.00 | xxxx | 684 |
| ATOM | 685 | C | ASN | A | 90 | 57.807 | 73.246 | 150.302 | 1.00 | 0.00 | xxxx | 685 |
| ATOM | 686 | O | ASN | A | 90 | 57.298 | 72.315 | 149.681 | 1.00 | 0.00 | xxxx | 686 |
| ATOM | 687 | N | ARG | A | 91 | 58.125 | 74.403 | 149.724 | 1.00 | 0.00 | xxxx | 687 |
| ATOM | 688 | CA | ARG | A | 91 | 58.036 | 74.592 | 148.280 | 1.00 | 0.00 | xxxx | 688 |
| ATOM | 689 | C | ARG | A | 91 | 59.468 | 74.816 | 147.794 | 1.00 | 0.00 | xxxx | 689 |
| ATOM | 690 | O | ARG | A | 91 | 60.124 | 75.773 | 148.202 | 1.00 | 0.00 | xxxx | 690 |
| ATOM | 691 | CB | ARG | A | 91 | 57.087 | 75.751 | 147.949 | 1.00 | 0.00 | xxxx | 691 |
| ATOM | 692 | CG | ARG | A | 91 | 55.655 | 75.433 | 148.407 | 1.00 | 0.00 | xxxx | 692 |
| ATOM | 693 | CD | ARG | A | 91 | 54.789 | 76.659 | 148.670 | 1.00 | 0.00 | xxxx | 693 |
| ATOM | 694 | NE | ARG | A | 91 | 54.151 | 77.190 | 147.458 | 1.00 | 0.00 | xxxx | 694 |
| ATOM | 695 | CZ | ARG | A | 91 | 53.015 | 76.739 | 146.941 | 1.00 | 0.00 | xxxx | 695 |
| ATOM | 696 | NH1 | ARG | A | 91 | 52.362 | 75.719 | 147.501 | 1.00 | 0.00 | xxxx | 696 |
| ATOM | 697 | NH2 | ARG | A | 91 | 52.519 | 77.309 | 145.846 | 1.00 | 0.00 | xxxx | 697 |
| ATOM | 698 | N | GLU | A | 92 | 59.968 | 73.890 | 146.977 | 1.00 | 0.00 | xxxx | 698 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 699 | CA | GLU | A | 92 | 61.422 | 73.749 | 146.804 | 1.00 | 0.00 | xxxx | 699 |
| ATOM | 700 | CB | GLU | A | 92 | 61.763 | 72.272 | 146.560 | 1.00 | 0.00 | xxxx | 700 |
| ATOM | 701 | CG | GLU | A | 92 | 63.259 | 71.978 | 146.579 | 1.00 | 0.00 | xxxx | 701 |
| ATOM | 702 | CD | GLU | A | 92 | 63.581 | 70.526 | 146.255 | 1.00 | 0.00 | xxxx | 702 |
| ATOM | 703 | OE1 | GLU | A | 92 | 62.669 | 69.664 | 146.317 | 1.00 | 0.00 | xxxx | 703 |
| ATOM | 704 | OE2 | GLU | A | 92 | 64.758 | 70.244 | 145.929 | 1.00 | 0.00 | xxxx | 704 |
| ATOM | 705 | C | GLU | A | 92 | 62.045 | 74.601 | 145.689 | 1.00 | 0.00 | xxxx | 705 |
| ATOM | 706 | O | GLU | A | 92 | 61.686 | 74.480 | 144.528 | 1.00 | 0.00 | xxxx | 706 |
| ATOM | 707 | N | PRO | A | 93 | 63.012 | 75.455 | 146.038 | 1.00 | 0.00 | xxxx | 707 |
| ATOM | 708 | CA | PRO | A | 93 | 63.750 | 76.176 | 144.988 | 1.00 | 0.00 | xxxx | 708 |
| ATOM | 709 | CB | PRO | A | 93 | 64.800 | 76.963 | 145.766 | 1.00 | 0.00 | xxxx | 709 |
| ATOM | 710 | CG | PRO | A | 93 | 64.178 | 77.136 | 147.143 | 1.00 | 0.00 | xxxx | 710 |
| ATOM | 711 | CD | PRO | A | 93 | 63.424 | 75.864 | 147.392 | 1.00 | 0.00 | xxxx | 711 |
| ATOM | 712 | C | PRO | A | 93 | 64.435 | 75.237 | 144.017 | 1.00 | 0.00 | xxxx | 712 |
| ATOM | 713 | O | PRO | A | 93 | 64.810 | 74.123 | 144.393 | 1.00 | 0.00 | xxxx | 713 |
| ATOM | 714 | N | LEU | A | 94 | 64.606 | 75.690 | 142.781 | 1.00 | 0.00 | xxxx | 714 |
| ATOM | 715 | CA | LEU | A | 94 | 65.328 | 74.912 | 141.787 | 1.00 | 0.00 | xxxx | 715 |
| ATOM | 716 | CB | LEU | A | 94 | 65.233 | 75.591 | 140.425 | 1.00 | 0.00 | xxxx | 716 |
| ATOM | 717 | CG | LEU | A | 94 | 63.785 | 75.791 | 139.968 | 1.00 | 0.00 | xxxx | 717 |
| ATOM | 718 | CD1 | LEU | A | 94 | 63.734 | 76.670 | 138.728 | 1.00 | 0.00 | xxxx | 718 |
| ATOM | 719 | CD2 | LEU | A | 94 | 63.095 | 74.455 | 139.709 | 1.00 | 0.00 | xxxx | 719 |
| ATOM | 720 | C | LEU | A | 94 | 66.781 | 74.727 | 142.223 | 1.00 | 0.00 | xxxx | 720 |
| ATOM | 721 | O | LEU | A | 94 | 67.381 | 75.624 | 142.813 | 1.00 | 0.00 | xxxx | 721 |
| ATOM | 722 | N | PRO | A | 95 | 67.340 | 73.542 | 141.956 | 1.00 | 0.00 | xxxx | 722 |
| ATOM | 723 | CA | PRO | A | 95 | 68.666 | 73.193 | 142.475 | 1.00 | 0.00 | xxxx | 723 |
| ATOM | 724 | CB | PRO | A | 95 | 68.930 | 71.809 | 141.863 | 1.00 | 0.00 | xxxx | 724 |
| ATOM | 725 | CG | PRO | A | 95 | 67.860 | 71.592 | 140.834 | 1.00 | 0.00 | xxxx | 725 |
| ATOM | 726 | CD | PRO | A | 95 | 66.697 | 72.411 | 141.269 | 1.00 | 0.00 | xxxx | 726 |
| ATOM | 727 | C | PRO | A | 95 | 69.755 | 74.205 | 142.096 | 1.00 | 0.00 | xxxx | 727 |
| ATOM | 728 | O | PRO | A | 95 | 70.580 | 74.519 | 142.943 | 1.00 | 0.00 | xxxx | 728 |
| ATOM | 729 | N | GLU | A | 96 | 69.737 | 74.741 | 140.877 | 1.00 | 0.00 | xxxx | 729 |
| ATOM | 730 | CA | GLU | A | 96 | 70.756 | 75.714 | 140.488 | 1.00 | 0.00 | xxxx | 730 |
| ATOM | 731 | CB | GLU | A | 96 | 70.749 | 75.933 | 138.974 | 1.00 | 0.00 | xxxx | 731 |
| ATOM | 732 | CG | GLU | A | 96 | 71.164 | 74.707 | 138.180 | 1.00 | 0.00 | xxxx | 732 |
| ATOM | 733 | CD | GLU | A | 96 | 72.488 | 74.139 | 138.652 | 1.00 | 0.00 | xxxx | 733 |
| ATOM | 734 | OE1 | GLU | A | 96 | 73.461 | 74.918 | 138.775 | 1.00 | 0.00 | xxxx | 734 |
| ATOM | 735 | OE2 | GLU | A | 96 | 72.550 | 72.919 | 138.920 | 1.00 | 0.00 | xxxx | 735 |
| ATOM | 736 | C | GLU | A | 96 | 70.574 | 77.050 | 141.213 | 1.00 | 0.00 | xxxx | 736 |
| ATOM | 737 | O | GLU | A | 96 | 71.546 | 77.766 | 141.459 | 1.00 | 0.00 | xxxx | 737 |
| ATOM | 738 | N | ASP | A | 97 | 69.336 | 77.386 | 141.566 | 1.00 | 0.00 | xxxx | 738 |
| ATOM | 739 | CA | ASP | A | 97 | 69.094 | 78.607 | 142.328 | 1.00 | 0.00 | xxxx | 739 |
| ATOM | 740 | CB | ASP | A | 97 | 67.596 | 78.919 | 142.410 | 1.00 | 0.00 | xxxx | 740 |
| ATOM | 741 | CG | ASP | A | 97 | 67.067 | 79.559 | 141.140 | 1.00 | 0.00 | xxxx | 741 |
| ATOM | 742 | OD1 | ASP | A | 97 | 67.891 | 79.972 | 140.292 | 1.00 | 0.00 | xxxx | 742 |
| ATOM | 743 | OD2 | ASP | A | 97 | 65.832 | 79.670 | 141.000 | 1.00 | 0.00 | xxxx | 743 |
| ATOM | 744 | C | ASP | A | 97 | 69.694 | 78.493 | 143.725 | 1.00 | 0.00 | xxxx | 744 |
| ATOM | 745 | O | ASP | A | 97 | 70.181 | 79.480 | 144.271 | 1.00 | 0.00 | xxxx | 745 |
| ATOM | 746 | N | MET | A | 98 | 69.684 | 77.279 | 144.278 | 1.00 | 0.00 | xxxx | 746 |
| ATOM | 747 | CA | MET | A | 98 | 70.254 | 77.018 | 145.599 | 1.00 | 0.00 | xxxx | 747 |
| ATOM | 748 | CB | MET | A | 98 | 69.955 | 75.577 | 146.039 | 1.00 | 0.00 | xxxx | 748 |
| ATOM | 749 | CG | MET | A | 98 | 68.467 | 75.284 | 146.309 | 1.00 | 0.00 | xxxx | 749 |
| ATOM | 750 | SD | MET | A | 98 | 67.801 | 76.201 | 147.721 | 1.00 | 0.00 | xxxx | 750 |
| ATOM | 751 | CE | MET | A | 98 | 68.810 | 75.553 | 149.068 | 1.00 | 0.00 | xxxx | 751 |
| ATOM | 752 | C | MET | A | 98 | 71.768 | 77.275 | 145.614 | 1.00 | 0.00 | xxxx | 752 |
| ATOM | 753 | O | MET | A | 98 | 72.340 | 77.557 | 146.664 | 1.00 | 0.00 | xxxx | 753 |
| ATOM | 754 | N | LYS | A | 99 | 72.410 | 77.193 | 144.452 | 1.00 | 0.00 | xxxx | 754 |
| ATOM | 755 | CA | LYS | A | 99 | 73.858 | 77.393 | 144.374 | 1.00 | 0.00 | xxxx | 755 |
| ATOM | 756 | CB | LYS | A | 99 | 74.431 | 76.572 | 143.221 | 1.00 | 0.00 | xxxx | 756 |
| ATOM | 757 | CG | LYS | A | 99 | 74.265 | 75.078 | 143.389 | 1.00 | 0.00 | xxxx | 757 |
| ATOM | 758 | CD | LYS | A | 99 | 74.964 | 74.331 | 142.266 | 1.00 | 0.00 | xxxx | 758 |
| ATOM | 759 | CE | LYS | A | 99 | 74.695 | 72.840 | 142.343 | 1.00 | 0.00 | xxxx | 759 |
| ATOM | 760 | NZ | LYS | A | 99 | 75.280 | 72.127 | 141.177 | 1.00 | 0.00 | xxxx | 760 |
| ATOM | 761 | C | LYS | A | 99 | 74.280 | 78.858 | 144.211 | 1.00 | 0.00 | xxxx | 761 |
| ATOM | 762 | O | LYS | A | 99 | 75.475 | 79.153 | 144.093 | 1.00 | 0.00 | xxxx | 762 |
| ATOM | 763 | N | LYS | A | 100 | 73.312 | 79.774 | 144.212 | 1.00 | 0.00 | xxxx | 763 |
| ATOM | 764 | CA | LYS | A | 100 | 73.601 | 81.195 | 144.001 | 1.00 | 0.00 | xxxx | 764 |
| ATOM | 765 | CB | LYS | A | 100 | 72.302 | 81.956 | 143.700 | 1.00 | 0.00 | xxxx | 765 |
| ATOM | 766 | CG | LYS | A | 100 | 71.752 | 81.702 | 142.304 | 1.00 | 0.00 | xxxx | 766 |
| ATOM | 767 | CD | LYS | A | 100 | 70.279 | 82.067 | 142.192 | 1.00 | 0.00 | xxxx | 767 |
| ATOM | 768 | CE | LYS | A | 100 | 70.069 | 83.561 | 142.148 | 1.00 | 0.00 | xxxx | 768 |
| ATOM | 769 | NZ | LYS | A | 100 | 70.519 | 84.144 | 140.855 | 1.00 | 0.00 | xxxx | 769 |
| ATOM | 770 | C | LYS | A | 100 | 74.313 | 81.856 | 145.186 | 1.00 | 0.00 | xxxx | 770 |
| ATOM | 771 | O | LYS | A | 100 | 74.978 | 82.878 | 145.026 | 1.00 | 0.00 | xxxx | 771 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 772 | N | TRP | A | 101 | 74.173 | 81.273 | 146.372 | 1.00 | 0.00 | xxxx | 772 |
| ATOM | 773 | CA | TRP | A | 101 | 74.705 | 81.880 | 147.591 | 1.00 | 0.00 | xxxx | 773 |
| ATOM | 774 | CB | TRP | A | 101 | 73.730 | 82.932 | 148.125 | 1.00 | 0.00 | xxxx | 774 |
| ATOM | 775 | CG | TRP | A | 101 | 74.285 | 83.873 | 149.158 | 1.00 | 0.00 | xxxx | 775 |
| ATOM | 776 | CD1 | TRP | A | 101 | 75.590 | 84.247 | 149.326 | 1.00 | 0.00 | xxxx | 776 |
| ATOM | 777 | NE1 | TRP | A | 101 | 75.697 | 85.135 | 150.378 | 1.00 | 0.00 | xxxx | 777 |
| ATOM | 778 | CE2 | TRP | A | 101 | 74.451 | 85.343 | 150.909 | 1.00 | 0.00 | xxxx | 778 |
| ATOM | 779 | CD2 | TRP | A | 101 | 73.536 | 84.567 | 150.165 | 1.00 | 0.00 | xxxx | 779 |
| ATOM | 780 | CE3 | TRP | A | 101 | 72.181 | 84.603 | 150.512 | 1.00 | 0.00 | xxxx | 780 |
| ATOM | 781 | CZ3 | TRP | A | 101 | 71.785 | 85.406 | 151.573 | 1.00 | 0.00 | xxxx | 781 |
| ATOM | 782 | CH2 | TRP | A | 101 | 72.716 | 86.169 | 152.289 | 1.00 | 0.00 | xxxx | 782 |
| ATOM | 783 | CZ2 | TRP | A | 101 | 74.051 | 86.153 | 151.975 | 1.00 | 0.00 | xxxx | 783 |
| ATOM | 784 | C | TRP | A | 101 | 74.948 | 80.804 | 148.638 | 1.00 | 0.00 | xxxx | 784 |
| ATOM | 785 | O | TRP | A | 101 | 74.258 | 79.784 | 148.642 | 1.00 | 0.00 | xxxx | 785 |
| ATOM | 786 | N | ASP | A | 102 | 75.911 | 81.031 | 149.529 | 1.00 | 0.00 | xxxx | 786 |
| ATOM | 787 | CA | ASP | A | 102 | 76.271 | 80.015 | 150.516 | 1.00 | 0.00 | xxxx | 787 |
| ATOM | 788 | CB | ASP | A | 102 | 77.797 | 79.937 | 150.667 | 1.00 | 0.00 | xxxx | 788 |
| ATOM | 789 | CG | ASP | A | 102 | 78.411 | 81.214 | 151.221 | 1.00 | 0.00 | xxxx | 789 |
| ATOM | 790 | OD1 | ASP | A | 102 | 77.731 | 82.261 | 151.270 | 1.00 | 0.00 | xxxx | 790 |
| ATOM | 791 | OD2 | ASP | A | 102 | 79.603 | 81.170 | 151.607 | 1.00 | 0.00 | xxxx | 791 |
| ATOM | 792 | C | ASP | A | 102 | 75.612 | 80.254 | 151.872 | 1.00 | 0.00 | xxxx | 792 |
| ATOM | 793 | O | ASP | A | 102 | 76.036 | 79.692 | 152.882 | 1.00 | 0.00 | xxxx | 793 |
| ATOM | 794 | N | LYS | A | 103 | 74.569 | 81.079 | 151.888 | 1.00 | 0.00 | xxxx | 794 |
| ATOM | 795 | CA | LYS | A | 103 | 73.775 | 81.274 | 153.099 | 1.00 | 0.00 | xxxx | 795 |
| ATOM | 796 | CB | LYS | A | 103 | 73.948 | 82.698 | 153.648 | 1.00 | 0.00 | xxxx | 796 |
| ATOM | 797 | CG | LYS | A | 103 | 75.400 | 83.028 | 154.036 | 1.00 | 0.00 | xxxx | 797 |
| ATOM | 798 | CD | LYS | A | 103 | 75.491 | 84.301 | 154.862 | 1.00 | 0.00 | xxxx | 798 |
| ATOM | 799 | CE | LYS | A | 103 | 76.930 | 84.638 | 155.211 | 1.00 | 0.00 | xxxx | 799 |
| ATOM | 800 | NZ | LYS | A | 103 | 77.020 | 85.940 | 155.922 | 1.00 | 0.00 | xxxx | 800 |
| ATOM | 801 | C | LYS | A | 103 | 72.314 | 80.970 | 152.799 | 1.00 | 0.00 | xxxx | 801 |
| ATOM | 802 | O | LYS | A | 103 | 71.412 | 81.586 | 153.365 | 1.00 | 0.00 | xxxx | 802 |
| ATOM | 803 | N | VAL | A | 104 | 72.094 | 80.004 | 151.909 | 1.00 | 0.00 | xxxx | 803 |
| ATOM | 804 | CA | VAL | A | 104 | 70.753 | 79.586 | 151.511 | 1.00 | 0.00 | xxxx | 804 |
| ATOM | 805 | CB | VAL | A | 104 | 70.521 | 79.835 | 150.010 | 1.00 | 0.00 | xxxx | 805 |
| ATOM | 806 | CG1 | VAL | A | 104 | 69.112 | 79.405 | 149.604 | 1.00 | 0.00 | xxxx | 806 |
| ATOM | 807 | CG2 | VAL | A | 104 | 70.758 | 81.302 | 149.682 | 1.00 | 0.00 | xxxx | 807 |
| ATOM | 808 | C | VAL | A | 104 | 70.528 | 78.111 | 151.844 | 1.00 | 0.00 | xxxx | 808 |
| ATOM | 809 | O | VAL | A | 104 | 71.358 | 77.265 | 151.521 | 1.00 | 0.00 | xxxx | 809 |
| ATOM | 810 | N | TYR | A | 105 | 69.388 | 77.809 | 152.466 | 1.00 | 0.00 | xxxx | 810 |
| ATOM | 811 | CA | TYR | A | 105 | 69.059 | 76.444 | 152.853 | 1.00 | 0.00 | xxxx | 811 |
| ATOM | 812 | CB | TYR | A | 105 | 69.228 | 76.265 | 154.376 | 1.00 | 0.00 | xxxx | 812 |
| ATOM | 813 | CG | TYR | A | 105 | 70.671 | 76.389 | 154.807 | 1.00 | 0.00 | xxxx | 813 |
| ATOM | 814 | CD1 | TYR | A | 105 | 71.253 | 77.636 | 154.992 | 1.00 | 0.00 | xxxx | 814 |
| ATOM | 815 | CE1 | TYR | A | 105 | 72.581 | 77.756 | 155.351 | 1.00 | 0.00 | xxxx | 815 |
| ATOM | 816 | CZ | TYR | A | 105 | 73.346 | 76.619 | 155.527 | 1.00 | 0.00 | xxxx | 816 |
| ATOM | 817 | OH | TYR | A | 105 | 74.672 | 76.740 | 155.883 | 1.00 | 0.00 | xxxx | 817 |
| ATOM | 818 | CE2 | TYR | A | 105 | 72.793 | 75.365 | 155.342 | 1.00 | 0.00 | xxxx | 818 |
| ATOM | 819 | CD2 | TYR | A | 105 | 71.467 | 75.257 | 154.980 | 1.00 | 0.00 | xxxx | 819 |
| ATOM | 820 | C | TYR | A | 105 | 67.638 | 76.081 | 152.436 | 1.00 | 0.00 | xxxx | 820 |
| ATOM | 821 | O | TYR | A | 105 | 66.846 | 76.955 | 152.088 | 1.00 | 0.00 | xxxx | 821 |
| ATOM | 822 | N | TYR | A | 106 | 67.328 | 74.787 | 152.466 | 1.00 | 0.00 | xxxx | 822 |
| ATOM | 823 | CA | TYR | A | 106 | 65.968 | 74.320 | 152.202 | 1.00 | 0.00 | xxxx | 823 |
| ATOM | 824 | CB | TYR | A | 106 | 65.805 | 73.799 | 150.766 | 1.00 | 0.00 | xxxx | 824 |
| ATOM | 825 | CG | TYR | A | 106 | 64.400 | 73.263 | 150.542 | 1.00 | 0.00 | xxxx | 825 |
| ATOM | 826 | CD1 | TYR | A | 106 | 63.320 | 74.136 | 150.424 | 1.00 | 0.00 | xxxx | 826 |
| ATOM | 827 | CE1 | TYR | A | 106 | 62.021 | 73.665 | 150.254 | 1.00 | 0.00 | xxxx | 827 |
| ATOM | 828 | CZ | TYR | A | 106 | 61.779 | 72.307 | 150.206 | 1.00 | 0.00 | xxxx | 828 |
| ATOM | 829 | OH | TYR | A | 106 | 60.486 | 71.885 | 150.034 | 1.00 | 0.00 | xxxx | 829 |
| ATOM | 830 | CE2 | TYR | A | 106 | 62.821 | 71.409 | 150.321 | 1.00 | 0.00 | xxxx | 830 |
| ATOM | 831 | CD2 | TYR | A | 106 | 64.140 | 71.890 | 150.506 | 1.00 | 0.00 | xxxx | 831 |
| ATOM | 832 | C | TYR | A | 106 | 65.611 | 73.206 | 153.170 | 1.00 | 0.00 | xxxx | 832 |
| ATOM | 833 | O | TYR | A | 106 | 66.406 | 72.284 | 153.372 | 1.00 | 0.00 | xxxx | 833 |
| ATOM | 834 | N | VAL | A | 107 | 64.421 | 73.298 | 153.763 | 1.00 | 0.00 | xxxx | 834 |
| ATOM | 835 | CA | VAL | A | 107 | 63.878 | 72.225 | 154.590 | 1.00 | 0.00 | xxxx | 835 |
| ATOM | 836 | CB | VAL | A | 107 | 63.576 | 72.705 | 156.023 | 1.00 | 0.00 | xxxx | 836 |
| ATOM | 837 | CG1 | VAL | A | 107 | 62.977 | 71.559 | 156.841 | 1.00 | 0.00 | xxxx | 837 |
| ATOM | 838 | CG2 | VAL | A | 107 | 64.837 | 73.246 | 156.691 | 1.00 | 0.00 | xxxx | 838 |
| ATOM | 839 | C | VAL | A | 107 | 62.621 | 71.650 | 153.968 | 1.00 | 0.00 | xxxx | 839 |
| ATOM | 840 | O | VAL | A | 107 | 61.683 | 72.388 | 153.638 | 1.00 | 0.00 | xxxx | 840 |
| ATOM | 841 | N | GLY | A | 108 | 62.582 | 70.329 | 153.842 | 1.00 | 0.00 | xxxx | 841 |
| ATOM | 842 | CA | GLY | A | 108 | 61.396 | 69.675 | 153.322 | 1.00 | 0.00 | xxxx | 842 |
| ATOM | 843 | C | GLY | A | 108 | 61.471 | 68.179 | 153.492 | 1.00 | 0.00 | xxxx | 843 |
| ATOM | 844 | O | GLY | A | 108 | 61.937 | 67.673 | 154.513 | 1.00 | 0.00 | xxxx | 844 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 845 | N | ALA | A | 109 | 61.009 | 67.467 | 152.473 | 1.00 | 0.00 | xxxx | 845 |
| ATOM | 846 | CA | ALA | A | 109 | 60.962 | 66.021 | 152.524 | 1.00 | 0.00 | xxxx | 846 |
| ATOM | 847 | CB | ALA | A | 109 | 59.693 | 65.555 | 153.212 | 1.00 | 0.00 | xxxx | 847 |
| ATOM | 848 | C | ALA | A | 109 | 61.050 | 65.499 | 151.101 | 1.00 | 0.00 | xxxx | 848 |
| ATOM | 849 | O | ALA | A | 109 | 60.772 | 66.233 | 150.154 | 1.00 | 0.00 | xxxx | 849 |
| ATOM | 850 | N | LYS | A | 110 | 61.447 | 64.244 | 150.951 | 1.00 | 0.00 | xxxx | 850 |
| ATOM | 851 | CA | LYS | A | 110 | 61.636 | 63.675 | 149.621 | 1.00 | 0.00 | xxxx | 851 |
| ATOM | 852 | CB | LYS | A | 110 | 62.642 | 62.528 | 149.664 | 1.00 | 0.00 | xxxx | 852 |
| ATOM | 853 | CG | LYS | A | 110 | 64.070 | 62.996 | 149.934 | 1.00 | 0.00 | xxxx | 853 |
| ATOM | 854 | CD | LYS | A | 110 | 64.508 | 63.980 | 148.850 | 1.00 | 0.00 | xxxx | 854 |
| ATOM | 855 | CE | LYS | A | 110 | 66.018 | 64.004 | 148.679 | 1.00 | 0.00 | xxxx | 855 |
| ATOM | 856 | NZ | LYS | A | 110 | 66.526 | 62.763 | 148.039 | 1.00 | 0.00 | xxxx | 856 |
| ATOM | 857 | C | LYS | A | 110 | 60.300 | 63.210 | 149.074 | 1.00 | 0.00 | xxxx | 857 |
| ATOM | 858 | O | LYS | A | 110 | 59.803 | 62.153 | 149.444 | 1.00 | 0.00 | xxxx | 858 |
| ATOM | 859 | N | ALA | A | 111 | 59.726 | 64.006 | 148.173 | 1.00 | 0.00 | xxxx | 859 |
| ATOM | 860 | CA | ALA | A | 111 | 58.378 | 63.731 | 147.687 | 1.00 | 0.00 | xxxx | 860 |
| ATOM | 861 | CB | ALA | A | 111 | 57.933 | 64.817 | 146.714 | 1.00 | 0.00 | xxxx | 861 |
| ATOM | 862 | C | ALA | A | 111 | 58.276 | 62.352 | 147.025 | 1.00 | 0.00 | xxxx | 862 |
| ATOM | 863 | O | ALA | A | 111 | 57.214 | 61.731 | 147.064 | 1.00 | 0.00 | xxxx | 863 |
| ATOM | 864 | N | GLU | A | 112 | 59.371 | 61.894 | 146.409 | 1.00 | 0.00 | xxxx | 864 |
| ATOM | 865 | CA | GLU | A | 112 | 59.416 | 60.558 | 145.815 | 1.00 | 0.00 | xxxx | 865 |
| ATOM | 866 | C | GLU | A | 112 | 59.013 | 59.494 | 146.832 | 1.00 | 0.00 | xxxx | 866 |
| ATOM | 867 | O | GLU | A | 112 | 58.281 | 58.552 | 146.520 | 1.00 | 0.00 | xxxx | 867 |
| ATOM | 868 | CB | GLU | A | 112 | 60.820 | 60.239 | 145.276 | 1.00 | 0.00 | xxxx | 868 |
| ATOM | 869 | CG | GLU | A | 112 | 61.342 | 61.190 | 144.209 | 1.00 | 0.00 | xxxx | 869 |
| ATOM | 870 | CD | GLU | A | 112 | 62.128 | 62.364 | 144.774 | 1.00 | 0.00 | xxxx | 870 |
| ATOM | 871 | OE1 | GLU | A | 112 | 61.879 | 62.772 | 145.933 | 1.00 | 0.00 | xxxx | 871 |
| ATOM | 872 | OE2 | GLU | A | 112 | 63.009 | 62.882 | 144.047 | 1.00 | 0.00 | xxxx | 872 |
| ATOM | 873 | N | GLN | A | 113 | 59.510 | 59.649 | 148.054 | 1.00 | 0.00 | xxxx | 873 |
| ATOM | 874 | C | GLN | A | 113 | 57.749 | 58.688 | 149.484 | 1.00 | 0.00 | xxxx | 874 |
| ATOM | 875 | O | GLN | A | 113 | 57.153 | 57.624 | 149.697 | 1.00 | 0.00 | xxxx | 875 |
| ATOM | 876 | CA | GLN | A | 113 | 59.241 | 58.715 | 149.144 | 1.00 | 0.00 | xxxx | 876 |
| ATOM | 877 | CB | GLN | A | 113 | 60.077 | 59.090 | 150.385 | 1.00 | 0.00 | xxxx | 877 |
| ATOM | 878 | CG | GLN | A | 113 | 59.812 | 58.227 | 151.626 | 1.00 | 0.00 | xxxx | 878 |
| ATOM | 879 | CD | GLN | A | 113 | 60.629 | 58.637 | 152.864 | 1.00 | 0.00 | xxxx | 879 |
| ATOM | 880 | OE1 | GLN | A | 113 | 60.781 | 59.826 | 153.183 | 1.00 | 0.00 | xxxx | 880 |
| ATOM | 881 | NE2 | GLN | A | 113 | 61.153 | 57.640 | 153.567 | 1.00 | 0.00 | xxxx | 881 |
| ATOM | 882 | N | SER | A | 114 | 57.135 | 59.870 | 149.559 | 1.00 | 0.00 | xxxx | 882 |
| ATOM | 883 | CA | SER | A | 114 | 55.708 | 59.885 | 149.877 | 1.00 | 0.00 | xxxx | 883 |
| ATOM | 884 | CB | SER | A | 114 | 55.192 | 61.303 | 150.175 | 1.00 | 0.00 | xxxx | 884 |
| ATOM | 885 | OG | SER | A | 114 | 55.337 | 62.195 | 149.078 | 1.00 | 0.00 | xxxx | 885 |
| ATOM | 886 | C | SER | A | 114 | 54.891 | 59.240 | 148.752 | 1.00 | 0.00 | xxxx | 886 |
| ATOM | 887 | O | SER | A | 114 | 53.912 | 58.554 | 149.022 | 1.00 | 0.00 | xxxx | 887 |
| ATOM | 888 | N | GLY | A | 115 | 55.302 | 59.440 | 147.504 | 1.00 | 0.00 | xxxx | 888 |
| ATOM | 889 | CA | GLY | A | 115 | 54.639 | 58.793 | 146.382 | 1.00 | 0.00 | xxxx | 889 |
| ATOM | 890 | C | GLY | A | 115 | 54.745 | 57.275 | 146.440 | 1.00 | 0.00 | xxxx | 890 |
| ATOM | 891 | O | GLY | A | 115 | 53.756 | 56.555 | 146.241 | 1.00 | 0.00 | xxxx | 891 |
| ATOM | 892 | N | ILE | A | 116 | 55.950 | 56.787 | 146.718 | 1.00 | 0.00 | xxxx | 892 |
| ATOM | 893 | CA | ILE | A | 116 | 56.167 | 55.351 | 146.855 | 1.00 | 0.00 | xxxx | 893 |
| ATOM | 894 | CB | ILE | A | 116 | 57.644 | 55.034 | 147.118 | 1.00 | 0.00 | xxxx | 894 |
| ATOM | 895 | CG1 | ILE | A | 116 | 58.482 | 55.388 | 145.876 | 1.00 | 0.00 | xxxx | 895 |
| ATOM | 896 | CD1 | ILE | A | 116 | 59.970 | 55.429 | 146.116 | 1.00 | 0.00 | xxxx | 896 |
| ATOM | 897 | CG2 | ILE | A | 116 | 57.816 | 53.563 | 147.498 | 1.00 | 0.00 | xxxx | 897 |
| ATOM | 898 | C | ILE | A | 116 | 55.285 | 54.778 | 147.960 | 1.00 | 0.00 | xxxx | 898 |
| ATOM | 899 | O | ILE | A | 116 | 54.631 | 53.756 | 147.766 | 1.00 | 0.00 | xxxx | 899 |
| ATOM | 900 | N | LEU | A | 117 | 55.258 | 55.431 | 149.120 | 1.00 | 0.00 | xxxx | 900 |
| ATOM | 901 | CA | LEU | A | 117 | 54.491 | 54.889 | 150.236 | 1.00 | 0.00 | xxxx | 901 |
| ATOM | 902 | CB | LEU | A | 117 | 54.789 | 55.673 | 151.520 | 1.00 | 0.00 | xxxx | 902 |
| ATOM | 903 | CG | LEU | A | 117 | 56.224 | 55.505 | 152.034 | 1.00 | 0.00 | xxxx | 903 |
| ATOM | 904 | CD1 | LEU | A | 117 | 56.507 | 56.501 | 153.152 | 1.00 | 0.00 | xxxx | 904 |
| ATOM | 905 | CD2 | LEU | A | 117 | 56.470 | 54.082 | 152.518 | 1.00 | 0.00 | xxxx | 905 |
| ATOM | 906 | C | LEU | A | 117 | 52.991 | 54.878 | 149.916 | 1.00 | 0.00 | xxxx | 906 |
| ATOM | 907 | O | LEU | A | 117 | 52.282 | 53.928 | 150.270 | 1.00 | 0.00 | xxxx | 907 |
| ATOM | 908 | N | GLN | A | 118 | 52.514 | 55.931 | 149.255 | 1.00 | 0.00 | xxxx | 908 |
| ATOM | 909 | CA | GLN | A | 118 | 51.141 | 55.976 | 148.746 | 1.00 | 0.00 | xxxx | 909 |
| ATOM | 910 | CB | GLN | A | 118 | 50.901 | 57.223 | 147.902 | 1.00 | 0.00 | xxxx | 910 |
| ATOM | 911 | CG | GLN | A | 118 | 50.449 | 58.426 | 148.646 | 1.00 | 0.00 | xxxx | 911 |
| ATOM | 912 | CD | GLN | A | 118 | 49.879 | 59.451 | 147.701 | 1.00 | 0.00 | xxxx | 912 |
| ATOM | 913 | OE1 | GLN | A | 118 | 50.580 | 59.948 | 146.809 | 1.00 | 0.00 | xxxx | 913 |
| ATOM | 914 | NE2 | GLN | A | 118 | 48.596 | 59.751 | 147.861 | 1.00 | 0.00 | xxxx | 914 |
| ATOM | 915 | C | GLN | A | 118 | 50.837 | 54.774 | 147.884 | 1.00 | 0.00 | xxxx | 915 |
| ATOM | 916 | O | GLN | A | 118 | 49.828 | 54.083 | 148.072 | 1.00 | 0.00 | xxxx | 916 |
| ATOM | 917 | N | GLY | A | 119 | 51.710 | 54.554 | 146.908 | 1.00 | 0.00 | xxxx | 917 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 918 | CA | GLY | A | 119 | 51.531 | 53.469 | 145.958 | 1.00 | 0.00 | xxxx | 918 |
| ATOM | 919 | C | GLY | A | 119 | 51.496 | 52.113 | 146.637 | 1.00 | 0.00 | xxxx | 919 |
| ATOM | 920 | O | GLY | A | 119 | 50.727 | 51.240 | 146.249 | 1.00 | 0.00 | xxxx | 920 |
| ATOM | 921 | N | GLN | A | 120 | 52.328 | 51.939 | 147.659 | 1.00 | 0.00 | xxxx | 921 |
| ATOM | 922 | CA | GLN | A | 120 | 52.344 | 50.681 | 148.396 | 1.00 | 0.00 | xxxx | 922 |
| ATOM | 923 | CB | GLN | A | 120 | 53.474 | 50.671 | 149.420 | 1.00 | 0.00 | xxxx | 923 |
| ATOM | 924 | CG | GLN | A | 120 | 54.836 | 50.619 | 148.765 | 1.00 | 0.00 | xxxx | 924 |
| ATOM | 925 | CD | GLN | A | 120 | 55.953 | 50.609 | 149.768 | 1.00 | 0.00 | xxxx | 925 |
| ATOM | 926 | OE1 | GLN | A | 120 | 55.725 | 50.749 | 150.967 | 1.00 | 0.00 | xxxx | 926 |
| ATOM | 927 | NE2 | GLN | A | 120 | 57.179 | 50.439 | 149.284 | 1.00 | 0.00 | xxxx | 927 |
| ATOM | 928 | C | GLN | A | 120 | 51.007 | 50.421 | 149.087 | 1.00 | 0.00 | xxxx | 928 |
| ATOM | 929 | O | GLN | A | 120 | 50.520 | 49.297 | 149.080 | 1.00 | 0.00 | xxxx | 929 |
| ATOM | 930 | N | ILE | A | 121 | 50.424 | 51.463 | 149.674 | 1.00 | 0.00 | xxxx | 930 |
| ATOM | 931 | CA | ILE | A | 121 | 49.140 | 51.321 | 150.354 | 1.00 | 0.00 | xxxx | 931 |
| ATOM | 932 | CB | ILE | A | 121 | 48.686 | 52.659 | 150.977 | 1.00 | 0.00 | xxxx | 932 |
| ATOM | 933 | CG1 | ILE | A | 121 | 49.633 | 53.085 | 152.095 | 1.00 | 0.00 | xxxx | 933 |
| ATOM | 934 | CD1 | ILE | A | 121 | 49.463 | 54.550 | 152.512 | 1.00 | 0.00 | xxxx | 934 |
| ATOM | 935 | CG2 | ILE | A | 121 | 47.244 | 52.556 | 151.489 | 1.00 | 0.00 | xxxx | 935 |
| ATOM | 936 | C | ILE | A | 121 | 48.095 | 50.799 | 149.377 | 1.00 | 0.00 | xxxx | 936 |
| ATOM | 937 | O | ILE | A | 121 | 47.365 | 49.831 | 149.663 | 1.00 | 0.00 | xxxx | 937 |
| ATOM | 938 | N | MET | A | 122 | 48.027 | 51.433 | 148.213 | 1.00 | 0.00 | xxxx | 938 |
| ATOM | 939 | CA | MET | A | 122 | 47.014 | 51.056 | 147.233 | 1.00 | 0.00 | xxxx | 939 |
| ATOM | 940 | CB | MET | A | 122 | 46.928 | 52.108 | 146.118 | 1.00 | 0.00 | xxxx | 940 |
| ATOM | 941 | CG | MET | A | 122 | 45.735 | 51.898 | 145.188 | 1.00 | 0.00 | xxxx | 941 |
| ATOM | 942 | SD | MET | A | 122 | 44.169 | 52.297 | 146.002 | 1.00 | 0.00 | xxxx | 942 |
| ATOM | 943 | CE | MET | A | 122 | 44.193 | 54.082 | 145.894 | 1.00 | 0.00 | xxxx | 943 |
| ATOM | 944 | C | MET | A | 122 | 47.289 | 49.677 | 146.640 | 1.00 | 0.00 | xxxx | 944 |
| ATOM | 945 | O | MET | A | 122 | 46.362 | 48.898 | 146.428 | 1.00 | 0.00 | xxxx | 945 |
| ATOM | 946 | N | ALA | A | 123 | 48.557 | 49.374 | 146.366 | 1.00 | 0.00 | xxxx | 946 |
| ATOM | 947 | CA | ALA | A | 123 | 48.899 | 48.085 | 145.771 | 1.00 | 0.00 | xxxx | 947 |
| ATOM | 948 | CB | ALA | A | 123 | 50.363 | 48.040 | 145.366 | 1.00 | 0.00 | xxxx | 948 |
| ATOM | 949 | C | ALA | A | 123 | 48.590 | 46.950 | 146.730 | 1.00 | 0.00 | xxxx | 949 |
| ATOM | 950 | O | ALA | A | 123 | 48.059 | 45.914 | 146.332 | 1.00 | 0.00 | xxxx | 950 |
| ATOM | 951 | N | ASP | A | 124 | 48.920 | 47.150 | 148.000 | 1.00 | 0.00 | xxxx | 951 |
| ATOM | 952 | CA | ASP | A | 124 | 48.670 | 46.114 | 148.993 | 1.00 | 0.00 | xxxx | 952 |
| ATOM | 953 | CB | ASP | A | 124 | 49.330 | 46.479 | 150.319 | 1.00 | 0.00 | xxxx | 953 |
| ATOM | 954 | CG | ASP | A | 124 | 50.841 | 46.290 | 150.288 | 1.00 | 0.00 | xxxx | 954 |
| ATOM | 955 | OD1 | ASP | A | 124 | 51.333 | 45.512 | 149.430 | 1.00 | 0.00 | xxxx | 955 |
| ATOM | 956 | OD2 | ASP | A | 124 | 51.528 | 46.902 | 151.132 | 1.00 | 0.00 | xxxx | 956 |
| ATOM | 957 | C | ASP | A | 124 | 47.170 | 45.881 | 149.179 | 1.00 | 0.00 | xxxx | 957 |
| ATOM | 958 | O | ASP | A | 124 | 46.724 | 44.736 | 149.314 | 1.00 | 0.00 | xxxx | 958 |
| ATOM | 959 | N | TYR | A | 125 | 46.388 | 46.960 | 149.168 | 1.00 | 0.00 | xxxx | 959 |
| ATOM | 960 | CA | TYR | A | 125 | 44.936 | 46.818 | 149.209 | 1.00 | 0.00 | xxxx | 960 |
| ATOM | 961 | CB | TYR | A | 125 | 44.248 | 48.197 | 149.260 | 1.00 | 0.00 | xxxx | 961 |
| ATOM | 962 | CG | TYR | A | 125 | 42.757 | 48.059 | 149.036 | 1.00 | 0.00 | xxxx | 962 |
| ATOM | 963 | CD1 | TYR | A | 125 | 41.909 | 47.716 | 150.080 | 1.00 | 0.00 | xxxx | 963 |
| ATOM | 964 | CE1 | TYR | A | 125 | 40.544 | 47.555 | 149.867 | 1.00 | 0.00 | xxxx | 964 |
| ATOM | 965 | CZ | TYR | A | 125 | 40.038 | 47.721 | 148.584 | 1.00 | 0.00 | xxxx | 965 |
| ATOM | 966 | OH | TYR | A | 125 | 38.691 | 47.570 | 148.331 | 1.00 | 0.00 | xxxx | 966 |
| ATOM | 967 | CE2 | TYR | A | 125 | 40.867 | 48.050 | 147.541 | 1.00 | 0.00 | xxxx | 967 |
| ATOM | 968 | CD2 | TYR | A | 125 | 42.214 | 48.216 | 147.768 | 1.00 | 0.00 | xxxx | 968 |
| ATOM | 969 | C | TYR | A | 125 | 44.427 | 46.015 | 147.999 | 1.00 | 0.00 | xxxx | 969 |
| ATOM | 970 | O | TYR | A | 125 | 43.628 | 45.081 | 148.146 | 1.00 | 0.00 | xxxx | 970 |
| ATOM | 971 | N | TRP | A | 126 | 44.895 | 46.387 | 146.810 | 1.00 | 0.00 | xxxx | 971 |
| ATOM | 972 | CA | TRP | A | 126 | 44.453 | 45.762 | 145.565 | 1.00 | 0.00 | xxxx | 972 |
| ATOM | 973 | CB | TRP | A | 126 | 45.160 | 46.427 | 144.377 | 1.00 | 0.00 | xxxx | 973 |
| ATOM | 974 | CG | TRP | A | 126 | 44.797 | 45.873 | 143.033 | 1.00 | 0.00 | xxxx | 974 |
| ATOM | 975 | CD1 | TRP | A | 126 | 45.447 | 44.883 | 142.351 | 1.00 | 0.00 | xxxx | 975 |
| ATOM | 976 | NE1 | TRP | A | 126 | 44.821 | 44.649 | 141.150 | 1.00 | 0.00 | xxxx | 976 |
| ATOM | 977 | CE2 | TRP | A | 126 | 43.755 | 45.503 | 141.032 | 1.00 | 0.00 | xxxx | 977 |
| ATOM | 978 | CD2 | TRP | A | 126 | 43.709 | 46.289 | 142.199 | 1.00 | 0.00 | xxxx | 978 |
| ATOM | 979 | CE3 | TRP | A | 126 | 42.695 | 47.242 | 142.333 | 1.00 | 0.00 | xxxx | 979 |
| ATOM | 980 | CZ3 | TRP | A | 126 | 41.773 | 47.380 | 141.304 | 1.00 | 0.00 | xxxx | 980 |
| ATOM | 981 | CH2 | TRP | A | 126 | 41.849 | 46.584 | 140.159 | 1.00 | 0.00 | xxxx | 981 |
| ATOM | 982 | CZ2 | TRP | A | 126 | 42.829 | 45.642 | 140.001 | 1.00 | 0.00 | xxxx | 982 |
| ATOM | 983 | C | TRP | A | 126 | 44.722 | 44.254 | 145.590 | 1.00 | 0.00 | xxxx | 983 |
| ATOM | 984 | O | TRP | A | 126 | 43.852 | 43.445 | 145.266 | 1.00 | 0.00 | xxxx | 984 |
| ATOM | 985 | N | LYS | A | 127 | 45.926 | 43.882 | 146.013 | 1.00 | 0.00 | xxxx | 985 |
| ATOM | 986 | CA | LYS | A | 127 | 46.315 | 42.481 | 146.073 | 1.00 | 0.00 | xxxx | 986 |
| ATOM | 987 | CB | LYS | A | 127 | 47.795 | 42.368 | 146.436 | 1.00 | 0.00 | xxxx | 987 |
| ATOM | 988 | CG | LYS | A | 127 | 48.710 | 42.840 | 145.322 | 1.00 | 0.00 | xxxx | 988 |
| ATOM | 989 | CD | LYS | A | 127 | 50.162 | 42.861 | 145.766 | 1.00 | 0.00 | xxxx | 989 |
| ATOM | 990 | CE | LYS | A | 127 | 51.067 | 43.232 | 144.613 | 1.00 | 0.00 | xxxx | 990 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 991 | NZ | LYS | A | 127 | 52.478 | 43.303 | 145.057 | 1.00 | 0.00 | xxxx | 991 |
| ATOM | 992 | C | LYS | A | 127 | 45.460 | 41.674 | 147.058 | 1.00 | 0.00 | xxxx | 992 |
| ATOM | 993 | O | LYS | A | 127 | 45.192 | 40.492 | 146.829 | 1.00 | 0.00 | xxxx | 993 |
| ATOM | 994 | N | ALA | A | 128 | 45.005 | 42.316 | 148.132 | 1.00 | 0.00 | xxxx | 994 |
| ATOM | 995 | CA | ALA | A | 128 | 44.264 | 41.614 | 149.176 | 1.00 | 0.00 | xxxx | 995 |
| ATOM | 996 | CB | ALA | A | 128 | 44.547 | 42.243 | 150.529 | 1.00 | 0.00 | xxxx | 996 |
| ATOM | 997 | C | ALA | A | 128 | 42.759 | 41.588 | 148.924 | 1.00 | 0.00 | xxxx | 997 |
| ATOM | 998 | O | ALA | A | 128 | 42.032 | 40.867 | 149.606 | 1.00 | 0.00 | xxxx | 998 |
| ATOM | 999 | N | HIS | A | 129 | 42.298 | 42.367 | 147.951 | 1.00 | 0.00 | xxxx | 999 |
| ATOM | 1000 | CA | HIS | A | 129 | 40.862 | 42.522 | 147.715 | 1.00 | 0.00 | xxxx | 1000 |
| ATOM | 1001 | CB | HIS | A | 129 | 40.403 | 43.904 | 148.198 | 1.00 | 0.00 | xxxx | 1001 |
| ATOM | 1002 | CG | HIS | A | 129 | 40.528 | 44.091 | 149.674 | 1.00 | 0.00 | xxxx | 1002 |
| ATOM | 1003 | ND1 | HIS | A | 129 | 41.703 | 44.486 | 150.278 | 1.00 | 0.00 | xxxx | 1003 |
| ATOM | 1004 | CE1 | HIS | A | 129 | 41.524 | 44.548 | 151.586 | 1.00 | 0.00 | xxxx | 1004 |
| ATOM | 1005 | NE2 | HIS | A | 129 | 40.280 | 44.196 | 151.854 | 1.00 | 0.00 | xxxx | 1005 |
| ATOM | 1006 | CD2 | HIS | A | 129 | 39.635 | 43.900 | 150.677 | 1.00 | 0.00 | xxxx | 1006 |
| ATOM | 1007 | C | HIS | A | 129 | 40.481 | 42.338 | 146.249 | 1.00 | 0.00 | xxxx | 1007 |
| ATOM | 1008 | O | HIS | A | 129 | 40.392 | 43.311 | 145.504 | 1.00 | 0.00 | xxxx | 1008 |
| ATOM | 1009 | N | PRO | A | 130 | 40.237 | 41.086 | 145.838 | 1.00 | 0.00 | xxxx | 1009 |
| ATOM | 1010 | CA | PRO | A | 130 | 39.859 | 40.757 | 144.457 | 1.00 | 0.00 | xxxx | 1010 |
| ATOM | 1011 | CB | PRO | A | 130 | 39.548 | 39.259 | 144.526 | 1.00 | 0.00 | xxxx | 1011 |
| ATOM | 1012 | CG | PRO | A | 130 | 40.266 | 38.768 | 145.740 | 1.00 | 0.00 | xxxx | 1012 |
| ATOM | 1013 | CD | PRO | A | 130 | 40.234 | 39.900 | 146.712 | 1.00 | 0.00 | xxxx | 1013 |
| ATOM | 1014 | C | PRO | A | 130 | 38.634 | 41.537 | 143.984 | 1.00 | 0.00 | xxxx | 1014 |
| ATOM | 1015 | O | PRO | A | 130 | 38.508 | 41.859 | 142.797 | 1.00 | 0.00 | xxxx | 1015 |
| ATOM | 1016 | N | GLU | A | 131 | 37.744 | 41.846 | 144.920 | 1.00 | 0.00 | xxxx | 1016 |
| ATOM | 1017 | CA | GLU | A | 131 | 36.507 | 42.546 | 144.601 | 1.00 | 0.00 | xxxx | 1017 |
| ATOM | 1018 | CB | GLU | A | 131 | 35.560 | 42.526 | 145.810 | 1.00 | 0.00 | xxxx | 1018 |
| ATOM | 1019 | CG | GLU | A | 131 | 35.970 | 43.431 | 146.972 | 1.00 | 0.00 | xxxx | 1019 |
| ATOM | 1020 | CD | GLU | A | 131 | 36.909 | 42.764 | 147.977 | 1.00 | 0.00 | xxxx | 1020 |
| ATOM | 1021 | OE1 | GLU | A | 131 | 37.546 | 41.737 | 147.647 | 1.00 | 0.00 | xxxx | 1021 |
| ATOM | 1022 | OE2 | GLU | A | 131 | 37.011 | 43.280 | 149.111 | 1.00 | 0.00 | xxxx | 1022 |
| ATOM | 1023 | C | GLU | A | 131 | 36.759 | 43.993 | 144.149 | 1.00 | 0.00 | xxxx | 1023 |
| ATOM | 1024 | O | GLU | A | 131 | 35.864 | 44.653 | 143.613 | 1.00 | 0.00 | xxxx | 1024 |
| ATOM | 1025 | N | ALA | A | 132 | 37.978 | 44.487 | 144.354 | 1.00 | 0.00 | xxxx | 1025 |
| ATOM | 1026 | CA | ALA | A | 132 | 38.301 | 45.870 | 143.999 | 1.00 | 0.00 | xxxx | 1026 |
| ATOM | 1027 | CB | ALA | A | 132 | 39.637 | 46.271 | 144.588 | 1.00 | 0.00 | xxxx | 1027 |
| ATOM | 1028 | C | ALA | A | 132 | 38.312 | 46.075 | 142.483 | 1.00 | 0.00 | xxxx | 1028 |
| ATOM | 1029 | O | ALA | A | 132 | 38.063 | 47.180 | 141.992 | 1.00 | 0.00 | xxxx | 1029 |
| ATOM | 1030 | N | ASP | A | 133 | 38.606 | 45.008 | 141.751 | 1.00 | 0.00 | xxxx | 1030 |
| ATOM | 1031 | CA | ASP | A | 133 | 38.589 | 45.039 | 140.296 | 1.00 | 0.00 | xxxx | 1031 |
| ATOM | 1032 | CB | ASP | A | 133 | 39.523 | 43.960 | 139.753 | 1.00 | 0.00 | xxxx | 1032 |
| ATOM | 1033 | CG | ASP | A | 133 | 39.634 | 43.977 | 138.253 | 1.00 | 0.00 | xxxx | 1033 |
| ATOM | 1034 | OD1 | ASP | A | 133 | 39.298 | 45.010 | 137.645 | 1.00 | 0.00 | xxxx | 1034 |
| ATOM | 1035 | OD2 | ASP | A | 133 | 40.082 | 42.949 | 137.695 | 1.00 | 0.00 | xxxx | 1035 |
| ATOM | 1036 | C | ASP | A | 133 | 37.141 | 44.847 | 139.833 | 1.00 | 0.00 | xxxx | 1036 |
| ATOM | 1037 | O | ASP | A | 133 | 36.727 | 43.749 | 139.436 | 1.00 | 0.00 | xxxx | 1037 |
| ATOM | 1038 | N | LYS | A | 134 | 36.381 | 45.936 | 139.891 | 1.00 | 0.00 | xxxx | 1038 |
| ATOM | 1039 | C | LYS | A | 134 | 34.486 | 45.450 | 138.329 | 1.00 | 0.00 | xxxx | 1039 |
| ATOM | 1040 | O | LYS | A | 134 | 33.414 | 44.858 | 138.173 | 1.00 | 0.00 | xxxx | 1040 |
| ATOM | 1041 | CA | LYS | A | 134 | 34.932 | 45.889 | 139.723 | 1.00 | 0.00 | xxxx | 1041 |
| ATOM | 1042 | CB | LYS | A | 134 | 34.341 | 47.257 | 140.067 | 1.00 | 0.00 | xxxx | 1042 |
| ATOM | 1043 | CG | LYS | A | 134 | 34.547 | 47.627 | 141.529 | 1.00 | 0.00 | xxxx | 1043 |
| ATOM | 1044 | CD | LYS | A | 134 | 34.923 | 49.089 | 141.712 | 1.00 | 0.00 | xxxx | 1044 |
| ATOM | 1045 | CE | LYS | A | 134 | 33.833 | 50.003 | 141.212 | 1.00 | 0.00 | xxxx | 1045 |
| ATOM | 1046 | NZ | LYS | A | 134 | 33.897 | 51.369 | 141.799 | 1.00 | 0.00 | xxxx | 1046 |
| ATOM | 1047 | N | ASN | A | 135 | 35.297 | 45.724 | 137.310 | 1.00 | 0.00 | xxxx | 1047 |
| ATOM | 1048 | CA | ASN | A | 135 | 34.922 | 45.292 | 135.961 | 1.00 | 0.00 | xxxx | 1048 |
| ATOM | 1049 | CB | ASN | A | 135 | 35.113 | 46.438 | 134.955 | 1.00 | 0.00 | xxxx | 1049 |
| ATOM | 1050 | CG | ASN | A | 135 | 36.566 | 46.696 | 134.618 | 1.00 | 0.00 | xxxx | 1050 |
| ATOM | 1051 | OD1 | ASN | A | 135 | 37.458 | 46.418 | 135.414 | 1.00 | 0.00 | xxxx | 1051 |
| ATOM | 1052 | ND2 | ASN | A | 135 | 36.813 | 47.232 | 133.425 | 1.00 | 0.00 | xxxx | 1052 |
| ATOM | 1053 | C | ASN | A | 135 | 35.693 | 44.043 | 135.519 | 1.00 | 0.00 | xxxx | 1053 |
| ATOM | 1054 | O | ASN | A | 135 | 35.605 | 43.631 | 134.364 | 1.00 | 0.00 | xxxx | 1054 |
| ATOM | 1055 | N | HIS | A | 136 | 36.439 | 43.448 | 136.450 | 1.00 | 0.00 | xxxx | 1055 |
| ATOM | 1056 | CA | HIS | A | 136 | 37.083 | 42.144 | 136.243 | 1.00 | 0.00 | xxxx | 1056 |
| ATOM | 1057 | CB | HIS | A | 136 | 36.021 | 41.045 | 136.121 | 1.00 | 0.00 | xxxx | 1057 |
| ATOM | 1058 | CG | HIS | A | 136 | 34.940 | 41.132 | 137.151 | 1.00 | 0.00 | xxxx | 1058 |
| ATOM | 1059 | ND1 | HIS | A | 136 | 35.154 | 40.840 | 138.482 | 1.00 | 0.00 | xxxx | 1059 |
| ATOM | 1060 | CE1 | HIS | A | 136 | 34.029 | 41.006 | 139.153 | 1.00 | 0.00 | xxxx | 1060 |
| ATOM | 1061 | NE2 | HIS | A | 136 | 33.090 | 41.389 | 138.305 | 1.00 | 0.00 | xxxx | 1061 |
| ATOM | 1062 | CD2 | HIS | A | 136 | 33.635 | 41.476 | 137.047 | 1.00 | 0.00 | xxxx | 1062 |
| ATOM | 1063 | C | HIS | A | 136 | 37.993 | 42.069 | 135.021 | 1.00 | 0.00 | xxxx | 1063 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1064 | O | HIS | A | 136 | 38.072 | 41.013 | 134.378 | 1.00 | 0.00 | xxxx | 1064 |
| ATOM | 1065 | N | ASP | A | 137 | 38.672 | 43.166 | 134.695 | 1.00 | 0.00 | xxxx | 1065 |
| ATOM | 1066 | CA | ASP | A | 137 | 39.557 | 43.181 | 133.529 | 1.00 | 0.00 | xxxx | 1066 |
| ATOM | 1067 | CB | ASP | A | 137 | 39.354 | 44.472 | 132.712 | 1.00 | 0.00 | xxxx | 1067 |
| ATOM | 1068 | CG | ASP | A | 137 | 39.756 | 45.740 | 133.464 | 1.00 | 0.00 | xxxx | 1068 |
| ATOM | 1069 | OD1 | ASP | A | 137 | 40.114 | 45.670 | 134.658 | 1.00 | 0.00 | xxxx | 1069 |
| ATOM | 1070 | OD2 | ASP | A | 137 | 39.711 | 46.818 | 132.834 | 1.00 | 0.00 | xxxx | 1070 |
| ATOM | 1071 | C | ASP | A | 137 | 41.033 | 43.012 | 133.892 | 1.00 | 0.00 | xxxx | 1071 |
| ATOM | 1072 | O | ASP | A | 137 | 41.893 | 43.016 | 133.011 | 1.00 | 0.00 | xxxx | 1072 |
| ATOM | 1073 | N | GLY | A | 138 | 41.320 | 42.860 | 135.183 | 1.00 | 0.00 | xxxx | 1073 |
| ATOM | 1074 | CA | GLY | A | 138 | 42.687 | 42.694 | 135.654 | 1.00 | 0.00 | xxxx | 1074 |
| ATOM | 1075 | C | GLY | A | 138 | 43.523 | 43.962 | 135.602 | 1.00 | 0.00 | xxxx | 1075 |
| ATOM | 1076 | O | GLY | A | 138 | 44.754 | 43.909 | 135.600 | 1.00 | 0.00 | xxxx | 1076 |
| ATOM | 1077 | N | VAL | A | 139 | 42.844 | 45.104 | 135.556 | 1.00 | 0.00 | xxxx | 1077 |
| ATOM | 1078 | CA | VAL | A | 139 | 43.486 | 46.412 | 135.479 | 1.00 | 0.00 | xxxx | 1078 |
| ATOM | 1079 | CB | VAL | A | 139 | 43.348 | 47.030 | 134.067 | 1.00 | 0.00 | xxxx | 1079 |
| ATOM | 1080 | CG1 | VAL | A | 139 | 44.016 | 48.399 | 134.003 | 1.00 | 0.00 | xxxx | 1080 |
| ATOM | 1081 | CG2 | VAL | A | 139 | 43.922 | 46.100 | 133.009 | 1.00 | 0.00 | xxxx | 1081 |
| ATOM | 1082 | C | VAL | A | 139 | 42.863 | 47.329 | 136.526 | 1.00 | 0.00 | xxxx | 1082 |
| ATOM | 1083 | O | VAL | A | 139 | 41.644 | 47.336 | 136.699 | 1.00 | 0.00 | xxxx | 1083 |
| ATOM | 1084 | N | MET | A | 140 | 43.691 | 48.096 | 137.228 | 1.00 | 0.00 | xxxx | 1084 |
| ATOM | 1085 | CA | MET | A | 140 | 43.187 | 49.070 | 138.191 | 1.00 | 0.00 | xxxx | 1085 |
| ATOM | 1086 | CB | MET | A | 140 | 44.219 | 49.322 | 139.293 | 1.00 | 0.00 | xxxx | 1086 |
| ATOM | 1087 | CG | MET | A | 140 | 43.815 | 50.406 | 140.290 | 1.00 | 0.00 | xxxx | 1087 |
| ATOM | 1088 | SD | MET | A | 140 | 45.208 | 50.999 | 141.305 | 1.00 | 0.00 | xxxx | 1088 |
| ATOM | 1089 | CE | MET | A | 140 | 45.540 | 49.546 | 142.295 | 1.00 | 0.00 | xxxx | 1089 |
| ATOM | 1090 | C | MET | A | 140 | 42.822 | 50.389 | 137.511 | 1.00 | 0.00 | xxxx | 1090 |
| ATOM | 1091 | O | MET | A | 140 | 43.702 | 51.147 | 137.098 | 1.00 | 0.00 | xxxx | 1091 |
| ATOM | 1092 | N | GLN | A | 141 | 41.525 | 50.655 | 137.382 | 1.00 | 0.00 | xxxx | 1092 |
| ATOM | 1093 | CA | GLN | A | 141 | 41.067 | 51.947 | 136.863 | 1.00 | 0.00 | xxxx | 1093 |
| ATOM | 1094 | CB | GLN | A | 141 | 39.638 | 51.857 | 136.329 | 1.00 | 0.00 | xxxx | 1094 |
| ATOM | 1095 | CG | GLN | A | 141 | 39.516 | 51.404 | 134.879 | 1.00 | 0.00 | xxxx | 1095 |
| ATOM | 1096 | CD | GLN | A | 141 | 39.714 | 49.912 | 134.703 | 1.00 | 0.00 | xxxx | 1096 |
| ATOM | 1097 | OE1 | GLN | A | 141 | 39.282 | 49.108 | 135.530 | 1.00 | 0.00 | xxxx | 1097 |
| ATOM | 1098 | NE2 | GLN | A | 141 | 40.352 | 49.531 | 133.602 | 1.00 | 0.00 | xxxx | 1098 |
| ATOM | 1099 | C | GLN | A | 141 | 41.121 | 52.998 | 137.958 | 1.00 | 0.00 | xxxx | 1099 |
| ATOM | 1100 | O | GLN | A | 141 | 40.443 | 52.855 | 138.974 | 1.00 | 0.00 | xxxx | 1100 |
| ATOM | 1101 | N | TYR | A | 142 | 41.888 | 54.065 | 137.752 | 1.00 | 0.00 | xxxx | 1101 |
| ATOM | 1102 | CA | TYR | A | 142 | 42.048 | 55.073 | 138.803 | 1.00 | 0.00 | xxxx | 1102 |
| ATOM | 1103 | CB | TYR | A | 142 | 43.434 | 54.948 | 139.458 | 1.00 | 0.00 | xxxx | 1103 |
| ATOM | 1104 | CG | TYR | A | 142 | 44.589 | 55.439 | 138.600 | 1.00 | 0.00 | xxxx | 1104 |
| ATOM | 1105 | CD1 | TYR | A | 142 | 45.024 | 56.767 | 138.666 | 1.00 | 0.00 | xxxx | 1105 |
| ATOM | 1106 | CE1 | TYR | A | 142 | 46.083 | 57.218 | 137.867 | 1.00 | 0.00 | xxxx | 1106 |
| ATOM | 1107 | CZ | TYR | A | 142 | 46.718 | 56.325 | 137.013 | 1.00 | 0.00 | xxxx | 1107 |
| ATOM | 1108 | OH | TYR | A | 142 | 47.762 | 56.736 | 136.211 | 1.00 | 0.00 | xxxx | 1108 |
| ATOM | 1109 | CE2 | TYR | A | 142 | 46.299 | 55.011 | 136.936 | 1.00 | 0.00 | xxxx | 1109 |
| ATOM | 1110 | CD2 | TYR | A | 142 | 45.249 | 54.574 | 137.728 | 1.00 | 0.00 | xxxx | 1110 |
| ATOM | 1111 | C | TYR | A | 142 | 41.857 | 56.500 | 138.303 | 1.00 | 0.00 | xxxx | 1111 |
| ATOM | 1112 | O | TYR | A | 142 | 41.923 | 56.769 | 137.102 | 1.00 | 0.00 | xxxx | 1112 |
| ATOM | 1113 | N | VAL | A | 143 | 41.623 | 57.415 | 139.242 | 1.00 | 0.00 | xxxx | 1113 |
| ATOM | 1114 | CA | VAL | A | 143 | 41.694 | 58.845 | 138.964 | 1.00 | 0.00 | xxxx | 1114 |
| ATOM | 1115 | CB | VAL | A | 143 | 40.337 | 59.563 | 139.132 | 1.00 | 0.00 | xxxx | 1115 |
| ATOM | 1116 | CG1 | VAL | A | 143 | 39.321 | 59.038 | 138.114 | 1.00 | 0.00 | xxxx | 1116 |
| ATOM | 1117 | CG2 | VAL | A | 143 | 39.815 | 59.418 | 140.565 | 1.00 | 0.00 | xxxx | 1117 |
| ATOM | 1118 | C | VAL | A | 143 | 42.743 | 59.449 | 139.882 | 1.00 | 0.00 | xxxx | 1118 |
| ATOM | 1119 | O | VAL | A | 143 | 43.052 | 58.898 | 140.939 | 1.00 | 0.00 | xxxx | 1119 |
| ATOM | 1120 | N | MET | A | 144 | 43.264 | 60.599 | 139.471 | 1.00 | 0.00 | xxxx | 1120 |
| ATOM | 1121 | CA | MET | A | 144 | 44.388 | 61.232 | 140.145 | 1.00 | 0.00 | xxxx | 1121 |
| ATOM | 1122 | CB | MET | A | 144 | 45.668 | 61.030 | 139.321 | 1.00 | 0.00 | xxxx | 1122 |
| ATOM | 1123 | CG | MET | A | 144 | 46.876 | 61.829 | 139.818 | 1.00 | 0.00 | xxxx | 1123 |
| ATOM | 1124 | SD | MET | A | 144 | 47.606 | 61.247 | 141.367 | 1.00 | 0.00 | xxxx | 1124 |
| ATOM | 1125 | CE | MET | A | 144 | 48.305 | 59.674 | 140.848 | 1.00 | 0.00 | xxxx | 1125 |
| ATOM | 1126 | C | MET | A | 144 | 44.118 | 62.717 | 140.359 | 1.00 | 0.00 | xxxx | 1126 |
| ATOM | 1127 | O | MET | A | 144 | 43.926 | 63.463 | 139.390 | 1.00 | 0.00 | xxxx | 1127 |
| ATOM | 1128 | N | LEU | A | 145 | 44.094 | 63.130 | 141.623 | 1.00 | 0.00 | xxxx | 1128 |
| ATOM | 1129 | CA | LEU | A | 145 | 43.927 | 64.537 | 141.981 | 1.00 | 0.00 | xxxx | 1129 |
| ATOM | 1130 | CB | LEU | A | 145 | 42.971 | 64.684 | 143.162 | 1.00 | 0.00 | xxxx | 1130 |
| ATOM | 1131 | CG | LEU | A | 145 | 41.522 | 64.394 | 142.788 | 1.00 | 0.00 | xxxx | 1131 |
| ATOM | 1132 | CD1 | LEU | A | 145 | 40.733 | 63.931 | 144.017 | 1.00 | 0.00 | xxxx | 1132 |
| ATOM | 1133 | CD2 | LEU | A | 145 | 40.908 | 65.648 | 142.174 | 1.00 | 0.00 | xxxx | 1133 |
| ATOM | 1134 | C | LEU | A | 145 | 45.291 | 65.124 | 142.311 | 1.00 | 0.00 | xxxx | 1134 |
| ATOM | 1135 | O | LEU | A | 145 | 45.892 | 64.771 | 143.333 | 1.00 | 0.00 | xxxx | 1135 |
| ATOM | 1136 | N | MET | A | 146 | 45.789 | 65.995 | 141.435 | 1.00 | 0.00 | xxxx | 1136 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1137 | CA | MET | A | 146 | 47.123 | 66.570 | 141.610 | 1.00 | 0.00 | xxxx | 1137 |
| ATOM | 1138 | CB | MET | A | 146 | 47.793 | 66.784 | 140.258 | 1.00 | 0.00 | xxxx | 1138 |
| ATOM | 1139 | CG | MET | A | 146 | 47.928 | 65.499 | 139.472 | 1.00 | 0.00 | xxxx | 1139 |
| ATOM | 1140 | SD | MET | A | 146 | 48.716 | 65.741 | 137.878 | 1.00 | 0.00 | xxxx | 1140 |
| ATOM | 1141 | CE | MET | A | 146 | 47.451 | 66.667 | 136.991 | 1.00 | 0.00 | xxxx | 1141 |
| ATOM | 1142 | C | MET | A | 146 | 47.070 | 67.882 | 142.377 | 1.00 | 0.00 | xxxx | 1142 |
| ATOM | 1143 | O | MET | A | 146 | 46.039 | 68.531 | 142.425 | 1.00 | 0.00 | xxxx | 1143 |
| ATOM | 1144 | N | GLY | A | 147 | 48.197 | 68.261 | 142.974 | 1.00 | 0.00 | xxxx | 1144 |
| ATOM | 1145 | CA | GLY | A | 147 | 48.327 | 69.550 | 143.634 | 1.00 | 0.00 | xxxx | 1145 |
| ATOM | 1146 | C | GLY | A | 147 | 48.417 | 70.715 | 142.657 | 1.00 | 0.00 | xxxx | 1146 |
| ATOM | 1147 | O | GLY | A | 147 | 47.771 | 70.705 | 141.619 | 1.00 | 0.00 | xxxx | 1147 |
| ATOM | 1148 | N | GLN | A | 148 | 49.205 | 71.732 | 142.986 | 1.00 | 0.00 | xxxx | 1148 |
| ATOM | 1149 | CA | GLN | A | 148 | 49.395 | 72.843 | 142.055 | 1.00 | 0.00 | xxxx | 1149 |
| ATOM | 1150 | CB | GLN | A | 148 | 49.902 | 74.083 | 142.796 | 1.00 | 0.00 | xxxx | 1150 |
| ATOM | 1151 | CG | GLN | A | 148 | 48.868 | 74.706 | 143.724 | 1.00 | 0.00 | xxxx | 1151 |
| ATOM | 1152 | CD | GLN | A | 148 | 49.487 | 75.729 | 144.659 | 1.00 | 0.00 | xxxx | 1152 |
| ATOM | 1153 | OE1 | GLN | A | 148 | 50.471 | 75.444 | 145.347 | 1.00 | 0.00 | xxxx | 1153 |
| ATOM | 1154 | NE2 | GLN | A | 148 | 48.921 | 76.939 | 144.678 | 1.00 | 0.00 | xxxx | 1154 |
| ATOM | 1155 | C | GLN | A | 148 | 50.374 | 72.477 | 140.953 | 1.00 | 0.00 | xxxx | 1155 |
| ATOM | 1156 | O | GLN | A | 148 | 51.385 | 71.828 | 141.210 | 1.00 | 0.00 | xxxx | 1156 |
| ATOM | 1157 | N | PRO | A | 149 | 50.104 | 72.936 | 139.721 | 1.00 | 0.00 | xxxx | 1157 |
| ATOM | 1158 | CA | PRO | A | 149 | 51.021 | 72.653 | 138.610 | 1.00 | 0.00 | xxxx | 1158 |
| ATOM | 1159 | CB | PRO | A | 149 | 50.440 | 73.464 | 137.451 | 1.00 | 0.00 | xxxx | 1159 |
| ATOM | 1160 | CG | PRO | A | 149 | 49.015 | 73.676 | 137.798 | 1.00 | 0.00 | xxxx | 1160 |
| ATOM | 1161 | CD | PRO | A | 149 | 48.921 | 73.696 | 139.294 | 1.00 | 0.00 | xxxx | 1161 |
| ATOM | 1162 | C | PRO | A | 149 | 52.447 | 73.111 | 138.915 | 1.00 | 0.00 | xxxx | 1162 |
| ATOM | 1163 | O | PRO | A | 149 | 52.656 | 74.234 | 139.367 | 1.00 | 0.00 | xxxx | 1163 |
| ATOM | 1164 | N | GLY | A | 150 | 53.414 | 72.235 | 138.687 | 1.00 | 0.00 | xxxx | 1164 |
| ATOM | 1165 | CA | GLY | A | 150 | 54.802 | 72.622 | 138.876 | 1.00 | 0.00 | xxxx | 1165 |
| ATOM | 1166 | C | GLY | A | 150 | 55.350 | 72.563 | 140.290 | 1.00 | 0.00 | xxxx | 1166 |
| ATOM | 1167 | O | GLY | A | 150 | 56.548 | 72.731 | 140.491 | 1.00 | 0.00 | xxxx | 1167 |
| ATOM | 1168 | N | HIS | A | 151 | 54.485 | 72.346 | 141.271 | 1.00 | 0.00 | xxxx | 1168 |
| ATOM | 1169 | CA | HIS | A | 151 | 54.938 | 72.119 | 142.640 | 1.00 | 0.00 | xxxx | 1169 |
| ATOM | 1170 | CB | HIS | A | 151 | 53.705 | 72.145 | 143.550 | 1.00 | 0.00 | xxxx | 1170 |
| ATOM | 1171 | CG | HIS | A | 151 | 53.984 | 72.117 | 145.018 | 1.00 | 0.00 | xxxx | 1171 |
| ATOM | 1172 | ND1 | HIS | A | 151 | 54.669 | 71.099 | 145.648 | 1.00 | 0.00 | xxxx | 1172 |
| ATOM | 1173 | CE1 | HIS | A | 151 | 54.689 | 71.325 | 146.947 | 1.00 | 0.00 | xxxx | 1173 |
| ATOM | 1174 | NE2 | HIS | A | 151 | 54.032 | 72.449 | 147.188 | 1.00 | 0.00 | xxxx | 1174 |
| ATOM | 1175 | CD2 | HIS | A | 151 | 53.580 | 72.963 | 146.001 | 1.00 | 0.00 | xxxx | 1175 |
| ATOM | 1176 | C | HIS | A | 151 | 55.671 | 70.774 | 142.681 | 1.00 | 0.00 | xxxx | 1176 |
| ATOM | 1177 | O | HIS | A | 151 | 55.152 | 69.796 | 142.145 | 1.00 | 0.00 | xxxx | 1177 |
| ATOM | 1178 | N | GLN | A | 152 | 56.857 | 70.706 | 143.293 | 1.00 | 0.00 | xxxx | 1178 |
| ATOM | 1179 | CA | GLN | A | 152 | 57.634 | 69.455 | 143.237 | 1.00 | 0.00 | xxxx | 1179 |
| ATOM | 1180 | CB | GLN | A | 152 | 59.023 | 69.636 | 143.877 | 1.00 | 0.00 | xxxx | 1180 |
| ATOM | 1181 | CG | GLN | A | 152 | 59.071 | 69.521 | 145.405 | 1.00 | 0.00 | xxxx | 1181 |
| ATOM | 1182 | CD | GLN | A | 152 | 58.525 | 70.739 | 146.127 | 1.00 | 0.00 | xxxx | 1182 |
| ATOM | 1183 | OE1 | GLN | A | 152 | 58.442 | 71.832 | 145.566 | 1.00 | 0.00 | xxxx | 1183 |
| ATOM | 1184 | NE2 | GLN | A | 152 | 58.159 | 70.552 | 147.391 | 1.00 | 0.00 | xxxx | 1184 |
| ATOM | 1185 | C | GLN | A | 152 | 56.899 | 68.263 | 143.880 | 1.00 | 0.00 | xxxx | 1185 |
| ATOM | 1186 | O | GLN | A | 152 | 57.065 | 67.118 | 143.452 | 1.00 | 0.00 | xxxx | 1186 |
| ATOM | 1187 | N | ASP | A | 153 | 56.078 | 68.516 | 144.891 | 1.00 | 0.00 | xxxx | 1187 |
| ATOM | 1188 | CA | ASP | A | 153 | 55.357 | 67.426 | 145.527 | 1.00 | 0.00 | xxxx | 1188 |
| ATOM | 1189 | CB | ASP | A | 153 | 54.754 | 67.867 | 146.859 | 1.00 | 0.00 | xxxx | 1189 |
| ATOM | 1190 | CG | ASP | A | 153 | 55.813 | 68.166 | 147.909 | 1.00 | 0.00 | xxxx | 1190 |
| ATOM | 1191 | OD1 | ASP | A | 153 | 56.988 | 67.774 | 147.732 | 1.00 | 0.00 | xxxx | 1191 |
| ATOM | 1192 | OD2 | ASP | A | 153 | 55.472 | 68.791 | 148.934 | 1.00 | 0.00 | xxxx | 1192 |
| ATOM | 1193 | C | ASP | A | 153 | 54.257 | 66.902 | 144.617 | 1.00 | 0.00 | xxxx | 1193 |
| ATOM | 1194 | O | ASP | A | 153 | 53.980 | 65.708 | 144.612 | 1.00 | 0.00 | xxxx | 1194 |
| ATOM | 1195 | N | ALA | A | 154 | 53.627 | 67.791 | 143.852 | 1.00 | 0.00 | xxxx | 1195 |
| ATOM | 1196 | CA | ALA | A | 154 | 52.591 | 67.356 | 142.925 | 1.00 | 0.00 | xxxx | 1196 |
| ATOM | 1197 | CB | ALA | A | 154 | 51.830 | 68.554 | 142.337 | 1.00 | 0.00 | xxxx | 1197 |
| ATOM | 1198 | C | ALA | A | 154 | 53.233 | 66.521 | 141.820 | 1.00 | 0.00 | xxxx | 1198 |
| ATOM | 1199 | O | ALA | A | 154 | 52.750 | 65.438 | 141.503 | 1.00 | 0.00 | xxxx | 1199 |
| ATOM | 1200 | N | ILE | A | 155 | 54.338 | 67.008 | 141.258 | 1.00 | 0.00 | xxxx | 1200 |
| ATOM | 1201 | CA | ILE | A | 155 | 55.012 | 66.292 | 140.177 | 1.00 | 0.00 | xxxx | 1201 |
| ATOM | 1202 | CB | ILE | A | 155 | 56.235 | 67.079 | 139.660 | 1.00 | 0.00 | xxxx | 1202 |
| ATOM | 1203 | CG1 | ILE | A | 155 | 55.791 | 68.403 | 139.039 | 1.00 | 0.00 | xxxx | 1203 |
| ATOM | 1204 | CD1 | ILE | A | 155 | 56.916 | 69.404 | 138.848 | 1.00 | 0.00 | xxxx | 1204 |
| ATOM | 1205 | CG2 | ILE | A | 155 | 57.012 | 66.273 | 138.618 | 1.00 | 0.00 | xxxx | 1205 |
| ATOM | 1206 | C | ILE | A | 155 | 55.431 | 64.905 | 140.652 | 1.00 | 0.00 | xxxx | 1206 |
| ATOM | 1207 | O | ILE | A | 155 | 55.131 | 63.892 | 140.014 | 1.00 | 0.00 | xxxx | 1207 |
| ATOM | 1208 | N | LEU | A | 156 | 56.125 | 64.864 | 141.785 | 1.00 | 0.00 | xxxx | 1208 |
| ATOM | 1209 | CA | LEU | A | 156 | 56.755 | 63.617 | 142.208 | 1.00 | 0.00 | xxxx | 1209 |

-continued

| CA, calcium<br>HOH, water<br>BAD, Badan<br>K, potassium<br>EDO, ethylene glycol | | | | | | | | | | | |
|---|---|---|---|---|---|---|---|---|---|---|---|
| ATOM | 1210 | CB | LEU | A | 156 | 57.933 | 63.924 | 143.141 | 1.00 | 0.00 xxxx | 1210 |
| ATOM | 1211 | CG | LEU | A | 156 | 59.079 | 64.620 | 142.408 | 1.00 | 0.00 xxxx | 1211 |
| ATOM | 1212 | CD1 | LEU | A | 156 | 60.088 | 65.153 | 143.415 | 1.00 | 0.00 xxxx | 1212 |
| ATOM | 1213 | CD2 | LEU | A | 156 | 59.740 | 63.664 | 141.396 | 1.00 | 0.00 xxxx | 1213 |
| ATOM | 1214 | C | LEU | A | 156 | 55.776 | 62.638 | 142.868 | 1.00 | 0.00 xxxx | 1214 |
| ATOM | 1215 | O | LEU | A | 156 | 55.900 | 61.428 | 142.671 | 1.00 | 0.00 xxxx | 1215 |
| ATOM | 1216 | N | ARG | A | 157 | 54.800 | 63.124 | 143.631 | 1.00 | 0.00 xxxx | 1216 |
| ATOM | 1217 | CA | ARG | A | 157 | 53.834 | 62.195 | 144.216 | 1.00 | 0.00 xxxx | 1217 |
| ATOM | 1218 | CB | ARG | A | 157 | 52.940 | 62.892 | 145.235 | 1.00 | 0.00 xxxx | 1218 |
| ATOM | 1219 | CG | ARG | A | 157 | 53.664 | 63.219 | 146.531 | 1.00 | 0.00 xxxx | 1219 |
| ATOM | 1220 | CD | ARG | A | 157 | 52.800 | 64.102 | 147.399 | 1.00 | 0.00 xxxx | 1220 |
| ATOM | 1221 | NE | ARG | A | 157 | 53.528 | 64.587 | 148.570 | 1.00 | 0.00 xxxx | 1221 |
| ATOM | 1222 | CZ | ARG | A | 157 | 53.102 | 65.579 | 149.343 | 1.00 | 0.00 xxxx | 1222 |
| ATOM | 1223 | NH1 | ARG | A | 157 | 51.958 | 66.183 | 149.071 | 1.00 | 0.00 xxxx | 1223 |
| ATOM | 1224 | NH2 | ARG | A | 157 | 53.823 | 65.977 | 150.380 | 1.00 | 0.00 xxxx | 1224 |
| ATOM | 1225 | C | ARG | A | 157 | 52.995 | 61.548 | 143.128 | 1.00 | 0.00 xxxx | 1225 |
| ATOM | 1226 | O | ARG | A | 157 | 52.681 | 60.361 | 143.205 | 1.00 | 0.00 xxxx | 1226 |
| ATOM | 1227 | N | THR | A | 158 | 52.654 | 62.321 | 142.104 | 1.00 | 0.00 xxxx | 1227 |
| ATOM | 1228 | CA | THR | A | 158 | 51.861 | 61.804 | 140.992 | 1.00 | 0.00 xxxx | 1228 |
| ATOM | 1229 | CB | THR | A | 158 | 51.466 | 62.932 | 140.027 | 1.00 | 0.00 xxxx | 1229 |
| ATOM | 1230 | OG1 | THR | A | 158 | 50.646 | 63.877 | 140.737 | 1.00 | 0.00 xxxx | 1230 |
| ATOM | 1231 | CG2 | THR | A | 158 | 50.680 | 62.386 | 138.858 | 1.00 | 0.00 xxxx | 1231 |
| ATOM | 1232 | C | THR | A | 158 | 52.626 | 60.721 | 140.239 | 1.00 | 0.00 xxxx | 1232 |
| ATOM | 1233 | O | THR | A | 158 | 52.078 | 59.654 | 139.931 | 1.00 | 0.00 xxxx | 1233 |
| ATOM | 1234 | N | GLN | A | 159 | 53.896 | 60.997 | 139.954 | 1.00 | 0.00 xxxx | 1234 |
| ATOM | 1235 | CA | GLN | A | 159 | 54.742 | 60.073 | 139.220 | 1.00 | 0.00 xxxx | 1235 |
| ATOM | 1236 | CB | GLN | A | 159 | 56.065 | 60.756 | 138.868 | 1.00 | 0.00 xxxx | 1236 |
| ATOM | 1237 | CG | GLN | A | 159 | 57.079 | 59.851 | 138.200 | 1.00 | 0.00 xxxx | 1237 |
| ATOM | 1238 | CD | GLN | A | 159 | 58.397 | 60.554 | 137.958 | 1.00 | 0.00 xxxx | 1238 |
| ATOM | 1239 | OE1 | GLN | A | 159 | 58.507 | 61.772 | 138.132 | 1.00 | 0.00 xxxx | 1239 |
| ATOM | 1240 | NE2 | GLN | A | 159 | 59.411 | 59.789 | 137.566 | 1.00 | 0.00 xxxx | 1240 |
| ATOM | 1241 | C | GLN | A | 159 | 55.002 | 58.794 | 140.016 | 1.00 | 0.00 xxxx | 1241 |
| ATOM | 1242 | O | GLN | A | 159 | 54.830 | 57.686 | 139.506 | 1.00 | 0.00 xxxx | 1242 |
| ATOM | 1243 | N | TYR | A | 160 | 55.436 | 58.943 | 141.261 | 1.00 | 0.00 xxxx | 1243 |
| ATOM | 1244 | CA | TYR | A | 160 | 55.930 | 57.774 | 141.985 | 1.00 | 0.00 xxxx | 1244 |
| ATOM | 1245 | CB | TYR | A | 160 | 56.932 | 58.207 | 143.074 | 1.00 | 0.00 xxxx | 1245 |
| ATOM | 1246 | CG | TYR | A | 160 | 58.324 | 58.434 | 142.513 | 1.00 | 0.00 xxxx | 1246 |
| ATOM | 1247 | CD1 | TYR | A | 160 | 58.656 | 59.629 | 141.880 | 1.00 | 0.00 xxxx | 1247 |
| ATOM | 1248 | CE1 | TYR | A | 160 | 59.922 | 59.829 | 141.345 | 1.00 | 0.00 xxxx | 1248 |
| ATOM | 1249 | CZ | TYR | A | 160 | 60.872 | 58.831 | 141.445 | 1.00 | 0.00 xxxx | 1249 |
| ATOM | 1250 | OH | TYR | A | 160 | 62.141 | 59.022 | 140.925 | 1.00 | 0.00 xxxx | 1250 |
| ATOM | 1251 | CE2 | TYR | A | 160 | 60.565 | 57.634 | 142.059 | 1.00 | 0.00 xxxx | 1251 |
| ATOM | 1252 | CD2 | TYR | A | 160 | 59.292 | 57.440 | 142.587 | 1.00 | 0.00 xxxx | 1252 |
| ATOM | 1253 | C | TYR | A | 160 | 54.823 | 56.906 | 142.578 | 1.00 | 0.00 xxxx | 1253 |
| ATOM | 1254 | O | TYR | A | 160 | 55.029 | 55.709 | 142.755 | 1.00 | 0.00 xxxx | 1254 |
| ATOM | 1255 | N | SER | A | 161 | 53.653 | 57.473 | 142.867 | 1.00 | 0.00 xxxx | 1255 |
| ATOM | 1256 | CA | SER | A | 161 | 52.555 | 56.642 | 143.365 | 1.00 | 0.00 xxxx | 1256 |
| ATOM | 1257 | CB | SER | A | 161 | 51.334 | 57.481 | 143.755 | 1.00 | 0.00 xxxx | 1257 |
| ATOM | 1258 | OG | SER | A | 161 | 50.896 | 58.302 | 142.672 | 1.00 | 0.00 xxxx | 1258 |
| ATOM | 1259 | C | SER | A | 161 | 52.170 | 55.606 | 142.317 | 1.00 | 0.00 xxxx | 1259 |
| ATOM | 1260 | O | SER | A | 161 | 52.085 | 54.412 | 142.615 | 1.00 | 0.00 xxxx | 1260 |
| ATOM | 1261 | N | ILE | A | 162 | 51.975 | 56.056 | 141.081 | 1.00 | 0.00 xxxx | 1261 |
| ATOM | 1262 | CA | ILE | A | 162 | 51.519 | 55.152 | 140.043 | 1.00 | 0.00 xxxx | 1262 |
| ATOM | 1263 | CB | ILE | A | 162 | 50.948 | 55.919 | 138.835 | 1.00 | 0.00 xxxx | 1263 |
| ATOM | 1264 | CG1 | ILE | A | 162 | 49.767 | 56.797 | 139.266 | 1.00 | 0.00 xxxx | 1264 |
| ATOM | 1265 | CD1 | ILE | A | 162 | 48.691 | 56.079 | 140.082 | 1.00 | 0.00 xxxx | 1265 |
| ATOM | 1266 | CG2 | ILE | A | 162 | 50.522 | 54.942 | 137.737 | 1.00 | 0.00 xxxx | 1266 |
| ATOM | 1267 | C | ILE | A | 162 | 52.650 | 54.215 | 139.615 | 1.00 | 0.00 xxxx | 1267 |
| ATOM | 1268 | O | ILE | A | 162 | 52.418 | 53.028 | 139.407 | 1.00 | 0.00 xxxx | 1268 |
| ATOM | 1269 | N | GLN | A | 163 | 53.876 | 54.725 | 139.497 | 1.00 | 0.00 xxxx | 1269 |
| ATOM | 1270 | CA | GLN | A | 163 | 54.979 | 53.845 | 139.124 | 1.00 | 0.00 xxxx | 1270 |
| ATOM | 1271 | CB | GLN | A | 163 | 56.292 | 54.614 | 138.981 | 1.00 | 0.00 xxxx | 1271 |
| ATOM | 1272 | CG | GLN | A | 163 | 57.425 | 53.743 | 138.413 | 1.00 | 0.00 xxxx | 1272 |
| ATOM | 1273 | CD | GLN | A | 163 | 57.069 | 53.143 | 137.053 | 1.00 | 0.00 xxxx | 1273 |
| ATOM | 1274 | OE1 | GLN | A | 163 | 56.595 | 53.845 | 136.160 | 1.00 | 0.00 xxxx | 1274 |
| ATOM | 1275 | NE2 | GLN | A | 163 | 57.275 | 51.836 | 136.903 | 1.00 | 0.00 xxxx | 1275 |
| ATOM | 1276 | C | GLN | A | 163 | 55.141 | 52.726 | 140.150 | 1.00 | 0.00 xxxx | 1276 |
| ATOM | 1277 | O | GLN | A | 163 | 55.471 | 51.597 | 139.790 | 1.00 | 0.00 xxxx | 1277 |
| ATOM | 1278 | N | THR | A | 164 | 54.865 | 53.035 | 141.418 | 1.00 | 0.00 xxxx | 1278 |
| ATOM | 1279 | CA | THR | A | 164 | 55.003 | 52.045 | 142.476 | 1.00 | 0.00 xxxx | 1279 |
| ATOM | 1280 | CB | THR | A | 164 | 54.952 | 52.716 | 143.864 | 1.00 | 0.00 xxxx | 1280 |
| ATOM | 1281 | OG1 | THR | A | 164 | 56.123 | 53.530 | 144.020 | 1.00 | 0.00 xxxx | 1281 |
| ATOM | 1282 | CG2 | THR | A | 164 | 54.924 | 51.673 | 144.980 | 1.00 | 0.00 xxxx | 1282 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1283 | C | THR | A | 164 | 53.940 | 50.949 | 142.361 | 1.00 | 0.00 | xxxx | 1283 |
| ATOM | 1284 | O | THR | A | 164 | 54.239 | 49.769 | 142.563 | 1.00 | 0.00 | xxxx | 1284 |
| ATOM | 1285 | N | VAL | A | 165 | 52.712 | 51.338 | 142.017 | 1.00 | 0.00 | xxxx | 1285 |
| ATOM | 1286 | CA | VAL | A | 165 | 51.667 | 50.354 | 141.732 | 1.00 | 0.00 | xxxx | 1286 |
| ATOM | 1287 | CB | VAL | A | 165 | 50.323 | 51.038 | 141.438 | 1.00 | 0.00 | xxxx | 1287 |
| ATOM | 1288 | CG1 | VAL | A | 165 | 49.261 | 49.993 | 141.094 | 1.00 | 0.00 | xxxx | 1288 |
| ATOM | 1289 | CG2 | VAL | A | 165 | 49.889 | 51.838 | 142.653 | 1.00 | 0.00 | xxxx | 1289 |
| ATOM | 1290 | C | VAL | A | 165 | 52.081 | 49.447 | 140.565 | 1.00 | 0.00 | xxxx | 1290 |
| ATOM | 1291 | O | VAL | A | 165 | 51.934 | 48.224 | 140.647 | 1.00 | 0.00 | xxxx | 1291 |
| ATOM | 1292 | N | LYS | A | 166 | 52.596 | 50.028 | 139.482 | 1.00 | 0.00 | xxxx | 1292 |
| ATOM | 1293 | CA | LYS | A | 166 | 53.042 | 49.206 | 138.357 | 1.00 | 0.00 | xxxx | 1293 |
| ATOM | 1294 | CB | LYS | A | 166 | 53.510 | 50.065 | 137.180 | 1.00 | 0.00 | xxxx | 1294 |
| ATOM | 1295 | CG | LYS | A | 166 | 52.445 | 50.933 | 136.540 | 1.00 | 0.00 | xxxx | 1295 |
| ATOM | 1296 | CD | LYS | A | 166 | 53.072 | 51.745 | 135.414 | 1.00 | 0.00 | xxxx | 1296 |
| ATOM | 1297 | CE | LYS | A | 166 | 52.078 | 52.671 | 134.758 | 1.00 | 0.00 | xxxx | 1297 |
| ATOM | 1298 | NZ | LYS | A | 166 | 52.729 | 53.514 | 133.706 | 1.00 | 0.00 | xxxx | 1298 |
| ATOM | 1299 | C | LYS | A | 166 | 54.179 | 48.276 | 138.777 | 1.00 | 0.00 | xxxx | 1299 |
| ATOM | 1300 | O | LYS | A | 166 | 54.214 | 47.105 | 138.386 | 1.00 | 0.00 | xxxx | 1300 |
| ATOM | 1301 | N | ASP | A | 167 | 55.107 | 48.802 | 139.571 | 1.00 | 0.00 | xxxx | 1301 |
| ATOM | 1302 | CA | ASP | A | 167 | 56.255 | 48.020 | 140.029 | 1.00 | 0.00 | xxxx | 1302 |
| ATOM | 1303 | CB | ASP | A | 167 | 57.224 | 48.907 | 140.805 | 1.00 | 0.00 | xxxx | 1303 |
| ATOM | 1304 | CG | ASP | A | 167 | 57.973 | 49.879 | 139.907 | 1.00 | 0.00 | xxxx | 1304 |
| ATOM | 1305 | OD1 | ASP | A | 167 | 57.921 | 49.715 | 138.667 | 1.00 | 0.00 | xxxx | 1305 |
| ATOM | 1306 | OD2 | ASP | A | 167 | 58.618 | 50.801 | 140.447 | 1.00 | 0.00 | xxxx | 1306 |
| ATOM | 1307 | C | ASP | A | 167 | 55.820 | 46.832 | 140.892 | 1.00 | 0.00 | xxxx | 1307 |
| ATOM | 1308 | O | ASP | A | 167 | 56.531 | 45.832 | 140.998 | 1.00 | 0.00 | xxxx | 1308 |
| ATOM | 1309 | N | ALA | A | 168 | 54.642 | 46.951 | 141.502 | 1.00 | 0.00 | xxxx | 1309 |
| ATOM | 1310 | CA | ALA | A | 168 | 54.075 | 45.895 | 142.326 | 1.00 | 0.00 | xxxx | 1310 |
| ATOM | 1311 | CB | ALA | A | 168 | 53.060 | 46.481 | 143.302 | 1.00 | 0.00 | xxxx | 1311 |
| ATOM | 1312 | C | ALA | A | 168 | 53.428 | 44.798 | 141.477 | 1.00 | 0.00 | xxxx | 1312 |
| ATOM | 1313 | O | ALA | A | 168 | 52.883 | 43.830 | 142.008 | 1.00 | 0.00 | xxxx | 1313 |
| ATOM | 1314 | N | GLY | A | 169 | 53.476 | 44.965 | 140.157 | 1.00 | 0.00 | xxxx | 1314 |
| ATOM | 1315 | CA | GLY | A | 169 | 52.955 | 43.965 | 139.241 | 1.00 | 0.00 | xxxx | 1315 |
| ATOM | 1316 | C | GLY | A | 169 | 51.511 | 44.173 | 138.819 | 1.00 | 0.00 | xxxx | 1316 |
| ATOM | 1317 | O | GLY | A | 169 | 50.890 | 43.274 | 138.249 | 1.00 | 0.00 | xxxx | 1317 |
| ATOM | 1318 | N | ILE | A | 170 | 50.979 | 45.360 | 139.091 | 1.00 | 0.00 | xxxx | 1318 |
| ATOM | 1319 | CA | ILE | A | 170 | 49.571 | 45.657 | 138.823 | 1.00 | 0.00 | xxxx | 1319 |
| ATOM | 1320 | CB | ILE | A | 170 | 48.918 | 46.348 | 140.042 | 1.00 | 0.00 | xxxx | 1320 |
| ATOM | 1321 | CG1 | ILE | A | 170 | 48.984 | 45.434 | 141.273 | 1.00 | 0.00 | xxxx | 1321 |
| ATOM | 1322 | CD1 | ILE | A | 170 | 48.785 | 46.204 | 142.574 | 1.00 | 0.00 | xxxx | 1322 |
| ATOM | 1323 | CG2 | ILE | A | 170 | 47.468 | 46.788 | 139.749 | 1.00 | 0.00 | xxxx | 1323 |
| ATOM | 1324 | C | ILE | A | 170 | 49.440 | 46.523 | 137.575 | 1.00 | 0.00 | xxxx | 1324 |
| ATOM | 1325 | O | ILE | A | 170 | 50.110 | 47.543 | 137.457 | 1.00 | 0.00 | xxxx | 1325 |
| ATOM | 1326 | N | LYS | A | 171 | 48.578 | 46.111 | 136.647 | 1.00 | 0.00 | xxxx | 1326 |
| ATOM | 1327 | CA | LYS | A | 171 | 48.273 | 46.927 | 135.474 | 1.00 | 0.00 | xxxx | 1327 |
| ATOM | 1328 | CB | LYS | A | 171 | 47.663 | 46.079 | 134.357 | 1.00 | 0.00 | xxxx | 1328 |
| ATOM | 1329 | CG | LYS | A | 171 | 48.611 | 45.042 | 133.779 | 1.00 | 0.00 | xxxx | 1329 |
| ATOM | 1330 | CD | LYS | A | 171 | 47.900 | 44.207 | 132.722 | 1.00 | 0.00 | xxxx | 1330 |
| ATOM | 1331 | CE | LYS | A | 171 | 48.757 | 43.051 | 132.242 | 1.00 | 0.00 | xxxx | 1331 |
| ATOM | 1332 | NZ | LYS | A | 171 | 47.987 | 42.147 | 131.340 | 1.00 | 0.00 | xxxx | 1332 |
| ATOM | 1333 | C | LYS | A | 171 | 47.314 | 48.042 | 135.859 | 1.00 | 0.00 | xxxx | 1333 |
| ATOM | 1334 | O | LYS | A | 171 | 46.385 | 47.832 | 136.642 | 1.00 | 0.00 | xxxx | 1334 |
| ATOM | 1335 | N | VAL | A | 172 | 47.536 | 49.231 | 135.310 | 1.00 | 0.00 | xxxx | 1335 |
| ATOM | 1336 | CA | VAL | A | 172 | 46.716 | 50.378 | 135.681 | 1.00 | 0.00 | xxxx | 1336 |
| ATOM | 1337 | CB | VAL | A | 172 | 47.507 | 51.384 | 136.554 | 1.00 | 0.00 | xxxx | 1337 |
| ATOM | 1338 | CG1 | VAL | A | 172 | 48.094 | 50.686 | 137.780 | 1.00 | 0.00 | xxxx | 1338 |
| ATOM | 1339 | CG2 | VAL | A | 172 | 48.598 | 52.069 | 135.743 | 1.00 | 0.00 | xxxx | 1339 |
| ATOM | 1340 | C | VAL | A | 172 | 46.164 | 51.080 | 134.451 | 1.00 | 0.00 | xxxx | 1340 |
| ATOM | 1341 | O | VAL | A | 172 | 46.700 | 50.963 | 133.346 | 1.00 | 0.00 | xxxx | 1341 |
| ATOM | 1342 | N | GLN | A | 173 | 45.080 | 51.818 | 134.661 | 1.00 | 0.00 | xxxx | 1342 |
| ATOM | 1343 | CA | GLN | A | 173 | 44.502 | 52.657 | 133.631 | 1.00 | 0.00 | xxxx | 1343 |
| ATOM | 1344 | CB | GLN | A | 173 | 43.334 | 51.963 | 132.930 | 1.00 | 0.00 | xxxx | 1344 |
| ATOM | 1345 | CG | GLN | A | 173 | 42.782 | 52.813 | 131.799 | 1.00 | 0.00 | xxxx | 1345 |
| ATOM | 1346 | CD | GLN | A | 173 | 41.612 | 52.175 | 131.091 | 1.00 | 0.00 | xxxx | 1346 |
| ATOM | 1347 | OE1 | GLN | A | 173 | 40.758 | 51.538 | 131.713 | 1.00 | 0.00 | xxxx | 1347 |
| ATOM | 1348 | NE2 | GLN | A | 173 | 41.567 | 52.334 | 129.773 | 1.00 | 0.00 | xxxx | 1348 |
| ATOM | 1349 | C | GLN | A | 173 | 44.033 | 53.957 | 134.253 | 1.00 | 0.00 | xxxx | 1349 |
| ATOM | 1350 | O | GLN | A | 173 | 43.168 | 53.956 | 135.129 | 1.00 | 0.00 | xxxx | 1350 |
| ATOM | 1351 | N | GLU | A | 174 | 44.604 | 55.060 | 133.783 | 1.00 | 0.00 | xxxx | 1351 |
| ATOM | 1352 | CA | GLU | A | 174 | 44.240 | 56.389 | 134.240 | 1.00 | 0.00 | xxxx | 1352 |
| ATOM | 1353 | CB | GLU | A | 174 | 45.385 | 57.356 | 133.963 | 1.00 | 0.00 | xxxx | 1353 |
| ATOM | 1354 | CG | GLU | A | 174 | 45.220 | 58.707 | 134.592 | 1.00 | 0.00 | xxxx | 1354 |
| ATOM | 1355 | CD | GLU | A | 174 | 46.487 | 59.534 | 134.440 | 1.00 | 0.00 | xxxx | 1355 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1356 | OE1 | GLU | A | 174 | 46.579 | 60.296 | 133.463 | 1.00 | 0.00 | xxxx | 1356 |
| ATOM | 1357 | OE2 | GLU | A | 174 | 47.400 | 59.384 | 135.278 | 1.00 | 0.00 | xxxx | 1357 |
| ATOM | 1358 | C | GLU | A | 174 | 42.967 | 56.881 | 133.552 | 1.00 | 0.00 | xxxx | 1358 |
| ATOM | 1359 | O | GLU | A | 174 | 42.996 | 57.233 | 132.374 | 1.00 | 0.00 | xxxx | 1359 |
| ATOM | 1360 | N | LEU | A | 175 | 41.852 | 56.899 | 134.274 | 1.00 | 0.00 | xxxx | 1360 |
| ATOM | 1361 | CA | LEU | A | 175 | 40.604 | 57.387 | 133.681 | 1.00 | 0.00 | xxxx | 1361 |
| ATOM | 1362 | CB | LEU | A | 175 | 39.398 | 56.922 | 134.498 | 1.00 | 0.00 | xxxx | 1362 |
| ATOM | 1363 | CG | LEU | A | 175 | 39.121 | 55.423 | 134.515 | 1.00 | 0.00 | xxxx | 1363 |
| ATOM | 1364 | CD1 | LEU | A | 175 | 37.913 | 55.154 | 135.402 | 1.00 | 0.00 | xxxx | 1364 |
| ATOM | 1365 | CD2 | LEU | A | 175 | 38.873 | 54.925 | 133.104 | 1.00 | 0.00 | xxxx | 1365 |
| ATOM | 1366 | C | LEU | A | 175 | 40.586 | 58.906 | 133.569 | 1.00 | 0.00 | xxxx | 1366 |
| ATOM | 1367 | O | LEU | A | 175 | 40.021 | 59.462 | 132.624 | 1.00 | 0.00 | xxxx | 1367 |
| ATOM | 1368 | N | ALA | A | 176 | 41.186 | 59.574 | 134.550 | 1.00 | 0.00 | xxxx | 1368 |
| ATOM | 1369 | CA | ALA | A | 176 | 41.232 | 61.036 | 134.576 | 1.00 | 0.00 | xxxx | 1369 |
| ATOM | 1370 | CB | ALA | A | 176 | 39.880 | 61.605 | 134.965 | 1.00 | 0.00 | xxxx | 1370 |
| ATOM | 1371 | C | ALA | A | 176 | 42.285 | 61.520 | 135.544 | 1.00 | 0.00 | xxxx | 1371 |
| ATOM | 1372 | O | ALA | A | 176 | 42.571 | 60.864 | 136.535 | 1.00 | 0.00 | xxxx | 1372 |
| ATOM | 1373 | N | LYS | A | 177 | 42.860 | 62.676 | 135.254 | 1.00 | 0.00 | xxxx | 1373 |
| ATOM | 1374 | CA | LYS | A | 177 | 43.719 | 63.346 | 136.213 | 1.00 | 0.00 | xxxx | 1374 |
| ATOM | 1375 | CB | LYS | A | 177 | 45.181 | 62.923 | 136.061 | 1.00 | 0.00 | xxxx | 1375 |
| ATOM | 1376 | CG | LYS | A | 177 | 45.871 | 63.428 | 134.814 | 1.00 | 0.00 | xxxx | 1376 |
| ATOM | 1377 | CD | LYS | A | 177 | 47.373 | 63.195 | 134.903 | 1.00 | 0.00 | xxxx | 1377 |
| ATOM | 1378 | CE | LYS | A | 177 | 48.041 | 63.494 | 133.577 | 1.00 | 0.00 | xxxx | 1378 |
| ATOM | 1379 | NZ | LYS | A | 177 | 49.468 | 63.096 | 133.605 | 1.00 | 0.00 | xxxx | 1379 |
| ATOM | 1380 | C | LYS | A | 177 | 43.561 | 64.833 | 136.011 | 1.00 | 0.00 | xxxx | 1380 |
| ATOM | 1381 | O | LYS | A | 177 | 43.310 | 65.291 | 134.901 | 1.00 | 0.00 | xxxx | 1381 |
| ATOM | 1382 | N | ASP | A | 178 | 43.663 | 65.595 | 137.089 | 1.00 | 0.00 | xxxx | 1382 |
| ATOM | 1383 | CA | ASP | A | 178 | 43.572 | 67.044 | 136.961 | 1.00 | 0.00 | xxxx | 1383 |
| ATOM | 1384 | CB | ASP | A | 178 | 42.114 | 67.492 | 136.772 | 1.00 | 0.00 | xxxx | 1384 |
| ATOM | 1385 | CG | ASP | A | 178 | 41.987 | 68.845 | 136.073 | 1.00 | 0.00 | xxxx | 1385 |
| ATOM | 1386 | OD1 | ASP | A | 178 | 43.015 | 69.536 | 135.869 | 1.00 | 0.00 | xxxx | 1386 |
| ATOM | 1387 | OD2 | ASP | A | 178 | 40.839 | 69.229 | 135.735 | 1.00 | 0.00 | xxxx | 1387 |
| ATOM | 1388 | C | ASP | A | 178 | 44.166 | 67.669 | 138.200 | 1.00 | 0.00 | xxxx | 1388 |
| ATOM | 1389 | O | ASP | A | 178 | 44.343 | 67.010 | 139.226 | 1.00 | 0.00 | xxxx | 1389 |
| ATOM | 1390 | N | TYR | A | 179 | 44.462 | 68.956 | 138.084 | 1.00 | 0.00 | xxxx | 1390 |
| ATOM | 1391 | CA | TYR | A | 179 | 44.969 | 69.751 | 139.184 | 1.00 | 0.00 | xxxx | 1391 |
| ATOM | 1392 | CB | TYR | A | 179 | 45.795 | 70.923 | 138.647 | 1.00 | 0.00 | xxxx | 1392 |
| ATOM | 1393 | CG | TYR | A | 179 | 47.028 | 70.506 | 137.884 | 1.00 | 0.00 | xxxx | 1393 |
| ATOM | 1394 | CD1 | TYR | A | 179 | 48.176 | 70.081 | 138.553 | 1.00 | 0.00 | xxxx | 1394 |
| ATOM | 1395 | CE1 | TYR | A | 179 | 49.308 | 69.699 | 137.851 | 1.00 | 0.00 | xxxx | 1395 |
| ATOM | 1396 | CZ | TYR | A | 179 | 49.294 | 69.751 | 136.473 | 1.00 | 0.00 | xxxx | 1396 |
| ATOM | 1397 | OH | TYR | A | 179 | 50.413 | 69.378 | 135.756 | 1.00 | 0.00 | xxxx | 1397 |
| ATOM | 1398 | CE2 | TYR | A | 179 | 48.175 | 70.174 | 135.792 | 1.00 | 0.00 | xxxx | 1398 |
| ATOM | 1399 | CD2 | TYR | A | 179 | 47.049 | 70.545 | 136.495 | 1.00 | 0.00 | xxxx | 1399 |
| ATOM | 1400 | C | TYR | A | 179 | 43.834 | 70.278 | 140.038 | 1.00 | 0.00 | xxxx | 1400 |
| ATOM | 1401 | O | TYR | A | 179 | 42.921 | 70.928 | 139.524 | 1.00 | 0.00 | xxxx | 1401 |
| ATOM | 1402 | N | ALA | A | 180 | 43.899 | 70.014 | 141.344 | 1.00 | 0.00 | xxxx | 1402 |
| ATOM | 1403 | CA | ALA | A | 180 | 42.958 | 70.631 | 142.268 | 1.00 | 0.00 | xxxx | 1403 |
| ATOM | 1404 | CB | ALA | A | 180 | 42.086 | 69.574 | 142.946 | 1.00 | 0.00 | xxxx | 1404 |
| ATOM | 1405 | C | ALA | A | 180 | 43.674 | 71.497 | 143.305 | 1.00 | 0.00 | xxxx | 1405 |
| ATOM | 1406 | O | ALA | A | 180 | 43.052 | 71.949 | 144.258 | 1.00 | 0.00 | xxxx | 1406 |
| ATOM | 1407 | N | ASN | A | 181 | 44.977 | 71.723 | 143.111 | 1.00 | 0.00 | xxxx | 1407 |
| ATOM | 1408 | CA | ASN | A | 181 | 45.678 | 72.840 | 143.766 | 1.00 | 0.00 | xxxx | 1408 |
| ATOM | 1409 | CB | ASN | A | 181 | 45.029 | 74.165 | 143.361 | 1.00 | 0.00 | xxxx | 1409 |
| ATOM | 1410 | CG | ASN | A | 181 | 44.936 | 74.317 | 141.862 | 1.00 | 0.00 | xxxx | 1410 |
| ATOM | 1411 | OD1 | ASN | A | 181 | 45.904 | 74.057 | 141.140 | 1.00 | 0.00 | xxxx | 1411 |
| ATOM | 1412 | ND2 | ASN | A | 181 | 43.759 | 74.698 | 141.378 | 1.00 | 0.00 | xxxx | 1412 |
| ATOM | 1413 | C | ASN | A | 181 | 45.728 | 72.755 | 145.284 | 1.00 | 0.00 | xxxx | 1413 |
| ATOM | 1414 | O | ASN | A | 181 | 45.785 | 73.792 | 145.959 | 1.00 | 0.00 | xxxx | 1414 |
| ATOM | 1415 | N | TRP | A | 182 | 45.695 | 71.520 | 145.796 | 1.00 | 0.00 | xxxx | 1415 |
| ATOM | 1416 | CA | TRP | A | 182 | 45.769 | 71.207 | 147.235 | 1.00 | 0.00 | xxxx | 1416 |
| ATOM | 1417 | CB | TRP | A | 182 | 46.918 | 71.965 | 147.932 | 1.00 | 0.00 | xxxx | 1417 |
| ATOM | 1418 | CG | TRP | A | 182 | 48.266 | 71.865 | 147.262 | 1.00 | 0.00 | xxxx | 1418 |
| ATOM | 1419 | CD1 | TRP | A | 182 | 49.010 | 72.896 | 146.766 | 1.00 | 0.00 | xxxx | 1419 |
| ATOM | 1420 | NE1 | TRP | A | 182 | 50.186 | 72.424 | 146.240 | 1.00 | 0.00 | xxxx | 1420 |
| ATOM | 1421 | CE2 | TRP | A | 182 | 50.237 | 71.065 | 146.408 | 1.00 | 0.00 | xxxx | 1421 |
| ATOM | 1422 | CD2 | TRP | A | 182 | 49.041 | 70.676 | 147.049 | 1.00 | 0.00 | xxxx | 1422 |
| ATOM | 1423 | CE3 | TRP | A | 182 | 48.840 | 69.321 | 147.344 | 1.00 | 0.00 | xxxx | 1423 |
| ATOM | 1424 | CZ3 | TRP | A | 182 | 49.825 | 68.411 | 146.987 | 1.00 | 0.00 | xxxx | 1424 |
| ATOM | 1425 | CH2 | TRP | A | 182 | 51.010 | 68.831 | 146.342 | 1.00 | 0.00 | xxxx | 1425 |
| ATOM | 1426 | CZ2 | TRP | A | 182 | 51.234 | 70.149 | 146.052 | 1.00 | 0.00 | xxxx | 1426 |
| ATOM | 1427 | C | TRP | A | 182 | 44.475 | 71.519 | 147.973 | 1.00 | 0.00 | xxxx | 1427 |
| ATOM | 1428 | O | TRP | A | 182 | 44.418 | 71.383 | 149.201 | 1.00 | 0.00 | xxxx | 1428 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1429 | N | ASP | A | 183 | 43.448 | 71.898 | 147.218 | 1.00 | 0.00 | xxxx | 1429 |
| ATOM | 1430 | CA | ASP | A | 183 | 42.214 | 72.426 | 147.783 | 1.00 | 0.00 | xxxx | 1430 |
| ATOM | 1431 | CB | ASP | A | 183 | 41.686 | 73.566 | 146.907 | 1.00 | 0.00 | xxxx | 1431 |
| ATOM | 1432 | CG | ASP | A | 183 | 40.491 | 74.259 | 147.514 | 1.00 | 0.00 | xxxx | 1432 |
| ATOM | 1433 | OD1 | ASP | A | 183 | 40.565 | 74.648 | 148.697 | 1.00 | 0.00 | xxxx | 1433 |
| ATOM | 1434 | OD2 | ASP | A | 183 | 39.463 | 74.411 | 146.815 | 1.00 | 0.00 | xxxx | 1434 |
| ATOM | 1435 | C | ASP | A | 183 | 41.146 | 71.348 | 147.935 | 1.00 | 0.00 | xxxx | 1435 |
| ATOM | 1436 | O | ASP | A | 183 | 40.932 | 70.529 | 147.039 | 1.00 | 0.00 | xxxx | 1436 |
| ATOM | 1437 | N | ARG | A | 184 | 40.477 | 71.355 | 149.081 | 1.00 | 0.00 | xxxx | 1437 |
| ATOM | 1438 | C | ARG | A | 184 | 38.200 | 70.639 | 148.421 | 1.00 | 0.00 | xxxx | 1438 |
| ATOM | 1439 | O | ARG | A | 184 | 37.716 | 69.714 | 147.782 | 1.00 | 0.00 | xxxx | 1439 |
| ATOM | 1440 | CA | ARG | A | 184 | 39.402 | 70.411 | 149.347 | 1.00 | 0.00 | xxxx | 1440 |
| ATOM | 1441 | CB | ARG | A | 184 | 38.978 | 70.522 | 150.818 | 1.00 | 0.00 | xxxx | 1441 |
| ATOM | 1442 | CG | ARG | A | 184 | 37.971 | 69.475 | 151.277 | 1.00 | 0.00 | xxxx | 1442 |
| ATOM | 1443 | CD | ARG | A | 184 | 37.897 | 69.420 | 152.808 | 1.00 | 0.00 | xxxx | 1443 |
| ATOM | 1444 | NE | ARG | A | 184 | 36.959 | 68.400 | 153.274 | 1.00 | 0.00 | xxxx | 1444 |
| ATOM | 1445 | CZ | ARG | A | 184 | 36.970 | 67.868 | 154.492 | 1.00 | 0.00 | xxxx | 1445 |
| ATOM | 1446 | NH1 | ARG | A | 184 | 37.877 | 68.251 | 155.382 | 1.00 | 0.00 | xxxx | 1446 |
| ATOM | 1447 | NH2 | ARG | A | 184 | 36.070 | 66.948 | 154.820 | 1.00 | 0.00 | xxxx | 1447 |
| ATOM | 1448 | N | VAL | A | 185 | 37.723 | 71.878 | 148.352 | 1.00 | 0.00 | xxxx | 1448 |
| ATOM | 1449 | CA | VAL | A | 185 | 36.511 | 72.147 | 147.575 | 1.00 | 0.00 | xxxx | 1449 |
| ATOM | 1450 | CB | VAL | A | 185 | 35.988 | 73.561 | 147.828 | 1.00 | 0.00 | xxxx | 1450 |
| ATOM | 1451 | CG1 | VAL | A | 185 | 34.800 | 73.869 | 146.907 | 1.00 | 0.00 | xxxx | 1451 |
| ATOM | 1452 | CG2 | VAL | A | 185 | 35.568 | 73.687 | 149.283 | 1.00 | 0.00 | xxxx | 1452 |
| ATOM | 1453 | C | VAL | A | 185 | 36.750 | 71.902 | 146.088 | 1.00 | 0.00 | xxxx | 1453 |
| ATOM | 1454 | O | VAL | A | 185 | 35.893 | 71.334 | 145.400 | 1.00 | 0.00 | xxxx | 1454 |
| ATOM | 1455 | N | THR | A | 186 | 37.914 | 72.300 | 145.591 | 1.00 | 0.00 | xxxx | 1455 |
| ATOM | 1456 | CA | THR | A | 186 | 38.221 | 72.061 | 144.181 | 1.00 | 0.00 | xxxx | 1456 |
| ATOM | 1457 | CB | THR | A | 186 | 39.561 | 72.715 | 143.790 | 1.00 | 0.00 | xxxx | 1457 |
| ATOM | 1458 | OG1 | THR | A | 186 | 39.532 | 74.100 | 144.155 | 1.00 | 0.00 | xxxx | 1458 |
| ATOM | 1459 | CG2 | THR | A | 186 | 39.794 | 72.603 | 142.287 | 1.00 | 0.00 | xxxx | 1459 |
| ATOM | 1460 | C | THR | A | 186 | 38.258 | 70.567 | 143.864 | 1.00 | 0.00 | xxxx | 1460 |
| ATOM | 1461 | O | THR | A | 186 | 37.718 | 70.117 | 142.852 | 1.00 | 0.00 | xxxx | 1461 |
| ATOM | 1462 | N | ALA | A | 187 | 38.887 | 69.790 | 144.739 | 1.00 | 0.00 | xxxx | 1462 |
| ATOM | 1463 | CA | ALA | A | 187 | 38.937 | 68.349 | 144.555 | 1.00 | 0.00 | xxxx | 1463 |
| ATOM | 1464 | CB | ALA | A | 187 | 39.807 | 67.725 | 145.626 | 1.00 | 0.00 | xxxx | 1464 |
| ATOM | 1465 | C | ALA | A | 187 | 37.535 | 67.743 | 144.583 | 1.00 | 0.00 | xxxx | 1465 |
| ATOM | 1466 | O | ALA | A | 187 | 37.211 | 66.866 | 143.789 | 1.00 | 0.00 | xxxx | 1466 |
| ATOM | 1467 | N | HIS | A | 188 | 36.712 | 68.216 | 145.511 | 1.00 | 0.00 | xxxx | 1467 |
| ATOM | 1468 | CA | HIS | A | 188 | 35.322 | 67.782 | 145.572 | 1.00 | 0.00 | xxxx | 1468 |
| ATOM | 1469 | CB | HIS | A | 188 | 34.566 | 68.533 | 146.659 | 1.00 | 0.00 | xxxx | 1469 |
| ATOM | 1470 | CG | HIS | A | 188 | 33.084 | 68.377 | 146.558 | 1.00 | 0.00 | xxxx | 1470 |
| ATOM | 1471 | ND1 | HIS | A | 188 | 32.305 | 69.204 | 145.780 | 1.00 | 0.00 | xxxx | 1471 |
| ATOM | 1472 | CE1 | HIS | A | 188 | 31.041 | 68.820 | 145.871 | 1.00 | 0.00 | xxxx | 1472 |
| ATOM | 1473 | NE2 | HIS | A | 188 | 30.981 | 67.775 | 146.677 | 1.00 | 0.00 | xxxx | 1473 |
| ATOM | 1474 | CD2 | HIS | A | 188 | 32.247 | 67.473 | 147.117 | 1.00 | 0.00 | xxxx | 1474 |
| ATOM | 1475 | C | HIS | A | 188 | 34.633 | 67.985 | 144.232 | 1.00 | 0.00 | xxxx | 1475 |
| ATOM | 1476 | O | HIS | A | 188 | 33.967 | 67.082 | 143.731 | 1.00 | 0.00 | xxxx | 1476 |
| ATOM | 1477 | N | ASP | A | 189 | 34.806 | 69.170 | 143.657 | 1.00 | 0.00 | xxxx | 1477 |
| ATOM | 1478 | CA | ASP | A | 189 | 34.119 | 69.515 | 142.419 | 1.00 | 0.00 | xxxx | 1478 |
| ATOM | 1479 | CB | ASP | A | 189 | 34.260 | 71.012 | 142.121 | 1.00 | 0.00 | xxxx | 1479 |
| ATOM | 1480 | CG | ASP | A | 189 | 33.530 | 71.898 | 143.134 | 1.00 | 0.00 | xxxx | 1480 |
| ATOM | 1481 | OD1 | ASP | A | 189 | 32.775 | 71.381 | 143.997 | 1.00 | 0.00 | xxxx | 1481 |
| ATOM | 1482 | OD2 | ASP | A | 189 | 33.715 | 73.134 | 143.065 | 1.00 | 0.00 | xxxx | 1482 |
| ATOM | 1483 | C | ASP | A | 189 | 34.648 | 68.674 | 141.252 | 1.00 | 0.00 | xxxx | 1483 |
| ATOM | 1484 | O | ASP | A | 189 | 33.864 | 68.214 | 140.414 | 1.00 | 0.00 | xxxx | 1484 |
| ATOM | 1485 | N | LYS | A | 190 | 35.966 | 68.462 | 141.195 | 1.00 | 0.00 | xxxx | 1485 |
| ATOM | 1486 | CA | LYS | A | 190 | 36.543 | 67.604 | 140.153 | 1.00 | 0.00 | xxxx | 1486 |
| ATOM | 1487 | CB | LYS | A | 190 | 38.076 | 67.575 | 140.244 | 1.00 | 0.00 | xxxx | 1487 |
| ATOM | 1488 | CG | LYS | A | 190 | 38.773 | 68.916 | 140.085 | 1.00 | 0.00 | xxxx | 1488 |
| ATOM | 1489 | CD | LYS | A | 190 | 38.692 | 69.446 | 138.665 | 1.00 | 0.00 | xxxx | 1489 |
| ATOM | 1490 | CE | LYS | A | 190 | 39.552 | 70.698 | 138.487 | 1.00 | 0.00 | xxxx | 1490 |
| ATOM | 1491 | NZ | LYS | A | 190 | 39.457 | 71.199 | 137.081 | 1.00 | 0.00 | xxxx | 1491 |
| ATOM | 1492 | C | LYS | A | 190 | 36.000 | 66.178 | 140.260 | 1.00 | 0.00 | xxxx | 1492 |
| ATOM | 1493 | O | LYS | A | 190 | 35.587 | 65.570 | 139.263 | 1.00 | 0.00 | xxxx | 1493 |
| ATOM | 1494 | N | MET | A | 191 | 35.997 | 65.645 | 141.475 | 1.00 | 0.00 | xxxx | 1494 |
| ATOM | 1495 | CA | MET | A | 191 | 35.572 | 64.268 | 141.705 | 1.00 | 0.00 | xxxx | 1495 |
| ATOM | 1496 | CB | MET | A | 191 | 35.859 | 63.859 | 143.152 | 1.00 | 0.00 | xxxx | 1496 |
| ATOM | 1497 | CG | MET | A | 191 | 35.582 | 62.396 | 143.438 | 1.00 | 0.00 | xxxx | 1497 |
| ATOM | 1498 | SD | MET | A | 191 | 36.879 | 61.354 | 142.734 | 1.00 | 0.00 | xxxx | 1498 |
| ATOM | 1499 | CE | MET | A | 191 | 36.062 | 59.764 | 142.708 | 1.00 | 0.00 | xxxx | 1499 |
| ATOM | 1500 | C | MET | A | 191 | 34.089 | 64.078 | 141.388 | 1.00 | 0.00 | xxxx | 1500 |
| ATOM | 1501 | O | MET | A | 191 | 33.701 | 63.057 | 140.822 | 1.00 | 0.00 | xxxx | 1501 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1502 | N | ALA | A | 192 | 33.261 | 65.061 | 141.743 | 1.00 | 0.00 | xxxx | 1502 |
| ATOM | 1503 | CA | ALA | A | 192 | 31.831 | 64.962 | 141.469 | 1.00 | 0.00 | xxxx | 1503 |
| ATOM | 1504 | CB | ALA | A | 192 | 31.089 | 66.163 | 142.050 | 1.00 | 0.00 | xxxx | 1504 |
| ATOM | 1505 | C | ALA | A | 192 | 31.577 | 64.848 | 139.966 | 1.00 | 0.00 | xxxx | 1505 |
| ATOM | 1506 | O | ALA | A | 192 | 30.724 | 64.067 | 139.528 | 1.00 | 0.00 | xxxx | 1506 |
| ATOM | 1507 | N | ALA | A | 193 | 32.317 | 65.628 | 139.182 | 1.00 | 0.00 | xxxx | 1507 |
| ATOM | 1508 | CA | ALA | A | 193 | 32.166 | 65.611 | 137.730 | 1.00 | 0.00 | xxxx | 1508 |
| ATOM | 1509 | CB | ALA | A | 193 | 32.935 | 66.779 | 137.089 | 1.00 | 0.00 | xxxx | 1509 |
| ATOM | 1510 | C | ALA | A | 193 | 32.636 | 64.273 | 137.159 | 1.00 | 0.00 | xxxx | 1510 |
| ATOM | 1511 | O | ALA | A | 193 | 31.990 | 63.693 | 136.281 | 1.00 | 0.00 | xxxx | 1511 |
| ATOM | 1512 | N | TRP | A | 194 | 33.769 | 63.781 | 137.647 | 1.00 | 0.00 | xxxx | 1512 |
| ATOM | 1513 | CA | TRP | A | 194 | 34.223 | 62.454 | 137.258 | 1.00 | 0.00 | xxxx | 1513 |
| ATOM | 1514 | CB | TRP | A | 194 | 35.542 | 62.121 | 137.944 | 1.00 | 0.00 | xxxx | 1514 |
| ATOM | 1515 | CG | TRP | A | 194 | 36.704 | 62.930 | 137.447 | 1.00 | 0.00 | xxxx | 1515 |
| ATOM | 1516 | CD1 | TRP | A | 194 | 36.801 | 63.607 | 136.258 | 1.00 | 0.00 | xxxx | 1516 |
| ATOM | 1517 | NE1 | TRP | A | 194 | 38.028 | 64.222 | 136.163 | 1.00 | 0.00 | xxxx | 1517 |
| ATOM | 1518 | CE2 | TRP | A | 194 | 38.742 | 63.957 | 137.306 | 1.00 | 0.00 | xxxx | 1518 |
| ATOM | 1519 | CD2 | TRP | A | 194 | 37.945 | 63.143 | 138.128 | 1.00 | 0.00 | xxxx | 1519 |
| ATOM | 1520 | CE3 | TRP | A | 194 | 38.448 | 62.727 | 139.368 | 1.00 | 0.00 | xxxx | 1520 |
| ATOM | 1521 | CZ3 | TRP | A | 194 | 39.729 | 63.114 | 139.724 | 1.00 | 0.00 | xxxx | 1521 |
| ATOM | 1522 | CH2 | TRP | A | 194 | 40.505 | 63.930 | 138.887 | 1.00 | 0.00 | xxxx | 1522 |
| ATOM | 1523 | CZ2 | TRP | A | 194 | 40.037 | 64.356 | 137.671 | 1.00 | 0.00 | xxxx | 1523 |
| ATOM | 1524 | C | TRP | A | 194 | 33.194 | 61.363 | 137.577 | 1.00 | 0.00 | xxxx | 1524 |
| ATOM | 1525 | O | TRP | A | 194 | 33.000 | 60.453 | 136.773 | 1.00 | 0.00 | xxxx | 1525 |
| ATOM | 1526 | N | LEU | A | 195 | 32.539 | 61.445 | 138.734 | 1.00 | 0.00 | xxxx | 1526 |
| ATOM | 1527 | CA | LEU | A | 195 | 31.555 | 60.419 | 139.101 | 1.00 | 0.00 | xxxx | 1527 |
| ATOM | 1528 | CB | LEU | A | 195 | 31.105 | 60.591 | 140.555 | 1.00 | 0.00 | xxxx | 1528 |
| ATOM | 1529 | CG | LEU | A | 195 | 32.194 | 60.179 | 141.550 | 1.00 | 0.00 | xxxx | 1529 |
| ATOM | 1530 | CD1 | LEU | A | 195 | 31.930 | 60.776 | 142.929 | 1.00 | 0.00 | xxxx | 1530 |
| ATOM | 1531 | CD2 | LEU | A | 195 | 32.294 | 58.658 | 141.647 | 1.00 | 0.00 | xxxx | 1531 |
| ATOM | 1532 | C | LEU | A | 195 | 30.351 | 60.446 | 138.156 | 1.00 | 0.00 | xxxx | 1532 |
| ATOM | 1533 | O | LEU | A | 195 | 29.782 | 59.403 | 137.827 | 1.00 | 0.00 | xxxx | 1533 |
| ATOM | 1534 | N | SER | A | 196 | 29.971 | 61.638 | 137.717 | 1.00 | 0.00 | xxxx | 1534 |
| ATOM | 1535 | CA | SER | A | 196 | 28.892 | 61.757 | 136.749 | 1.00 | 0.00 | xxxx | 1535 |
| ATOM | 1536 | CB | SER | A | 196 | 28.511 | 63.223 | 136.553 | 1.00 | 0.00 | xxxx | 1536 |
| ATOM | 1537 | OG | SER | A | 196 | 27.466 | 63.342 | 135.607 | 1.00 | 0.00 | xxxx | 1537 |
| ATOM | 1538 | C | SER | A | 196 | 29.292 | 61.137 | 135.412 | 1.00 | 0.00 | xxxx | 1538 |
| ATOM | 1539 | O | SER | A | 196 | 28.492 | 60.464 | 134.759 | 1.00 | 0.00 | xxxx | 1539 |
| ATOM | 1540 | N | SER | A | 197 | 30.534 | 61.370 | 135.006 | 1.00 | 0.00 | xxxx | 1540 |
| ATOM | 1541 | CA | SER | A | 197 | 31.015 | 60.884 | 133.710 | 1.00 | 0.00 | xxxx | 1541 |
| ATOM | 1542 | CB | SER | A | 197 | 32.301 | 61.614 | 133.315 | 1.00 | 0.00 | xxxx | 1542 |
| ATOM | 1543 | OG | SER | A | 197 | 32.056 | 62.978 | 133.022 | 1.00 | 0.00 | xxxx | 1543 |
| ATOM | 1544 | C | SER | A | 197 | 31.278 | 59.380 | 133.665 | 1.00 | 0.00 | xxxx | 1544 |
| ATOM | 1545 | O | SER | A | 197 | 30.903 | 58.712 | 132.700 | 1.00 | 0.00 | xxxx | 1545 |
| ATOM | 1546 | N | PHE | A | 198 | 31.933 | 58.857 | 134.706 | 1.00 | 0.00 | xxxx | 1546 |
| ATOM | 1547 | CA | PHE | A | 198 | 32.506 | 57.513 | 134.659 | 1.00 | 0.00 | xxxx | 1547 |
| ATOM | 1548 | CB | PHE | A | 198 | 34.024 | 57.551 | 134.909 | 1.00 | 0.00 | xxxx | 1548 |
| ATOM | 1549 | CG | PHE | A | 198 | 34.792 | 58.382 | 133.926 | 1.00 | 0.00 | xxxx | 1549 |
| ATOM | 1550 | CD1 | PHE | A | 198 | 34.956 | 57.953 | 132.613 | 1.00 | 0.00 | xxxx | 1550 |
| ATOM | 1551 | CE1 | PHE | A | 198 | 35.672 | 58.712 | 131.702 | 1.00 | 0.00 | xxxx | 1551 |
| ATOM | 1552 | CZ | PHE | A | 198 | 36.244 | 59.908 | 132.104 | 1.00 | 0.00 | xxxx | 1552 |
| ATOM | 1553 | CE2 | PHE | A | 198 | 36.093 | 60.340 | 133.413 | 1.00 | 0.00 | xxxx | 1553 |
| ATOM | 1554 | CD2 | PHE | A | 198 | 35.374 | 59.576 | 134.314 | 1.00 | 0.00 | xxxx | 1554 |
| ATOM | 1555 | C | PHE | A | 198 | 31.877 | 56.591 | 135.681 | 1.00 | 0.00 | xxxx | 1555 |
| ATOM | 1556 | O | PHE | A | 198 | 31.911 | 55.370 | 135.529 | 1.00 | 0.00 | xxxx | 1556 |
| ATOM | 1557 | N | GLY | A | 199 | 31.334 | 57.179 | 136.741 | 1.00 | 0.00 | xxxx | 1557 |
| ATOM | 1558 | CA | GLY | A | 199 | 30.585 | 56.415 | 137.720 | 1.00 | 0.00 | xxxx | 1558 |
| ATOM | 1559 | C | GLY | A | 199 | 31.304 | 55.216 | 138.300 | 1.00 | 0.00 | xxxx | 1559 |
| ATOM | 1560 | O | GLY | A | 199 | 32.402 | 55.331 | 138.867 | 1.00 | 0.00 | xxxx | 1560 |
| ATOM | 1561 | N | ASP | A | 200 | 30.704 | 54.043 | 138.136 | 1.00 | 0.00 | xxxx | 1561 |
| ATOM | 1562 | C | ASP | A | 200 | 32.465 | 52.304 | 138.046 | 1.00 | 0.00 | xxxx | 1562 |
| ATOM | 1563 | O | ASP | A | 200 | 32.968 | 51.244 | 138.394 | 1.00 | 0.00 | xxxx | 1563 |
| ATOM | 1564 | CA | ASP | A | 200 | 31.249 | 52.859 | 138.788 | 1.00 | 0.00 | xxxx | 1564 |
| ATOM | 1565 | CB | ASP | A | 200 | 30.181 | 51.771 | 138.933 | 1.00 | 0.00 | xxxx | 1565 |
| ATOM | 1566 | CG | ASP | A | 200 | 30.510 | 50.778 | 140.040 | 1.00 | 0.00 | xxxx | 1566 |
| ATOM | 1567 | OD1 | ASP | A | 200 | 30.918 | 51.218 | 141.140 | 1.00 | 0.00 | xxxx | 1567 |
| ATOM | 1568 | OD2 | ASP | A | 200 | 30.372 | 49.560 | 139.805 | 1.00 | 0.00 | xxxx | 1568 |
| ATOM | 1569 | N | LYS | A | 201 | 32.957 | 53.030 | 137.045 | 1.00 | 0.00 | xxxx | 1569 |
| ATOM | 1570 | CA | LYS | A | 201 | 34.201 | 52.610 | 136.394 | 1.00 | 0.00 | xxxx | 1570 |
| ATOM | 1571 | CB | LYS | A | 201 | 34.411 | 53.325 | 135.062 | 1.00 | 0.00 | xxxx | 1571 |
| ATOM | 1572 | CG | LYS | A | 201 | 33.528 | 52.841 | 133.934 | 1.00 | 0.00 | xxxx | 1572 |
| ATOM | 1573 | CD | LYS | A | 201 | 33.955 | 53.489 | 132.626 | 1.00 | 0.00 | xxxx | 1573 |
| ATOM | 1574 | CE | LYS | A | 201 | 33.291 | 52.805 | 131.449 | 1.00 | 0.00 | xxxx | 1574 |

-continued

| | | | | | | | | | | | | |
|---|---|---|---|---|---|---|---|---|---|---|---|---|
| CA, calcium<br>HOH, water<br>BAD, Badan<br>K, potassium<br>EDO, ethylene glycol | | | | | | | | | | | | |
| ATOM | 1575 | NZ | LYS | A | 201 | 33.633 | 51.346 | 131.404 | 1.00 | 0.00 | xxxx | 1575 |
| ATOM | 1576 | C | LYS | A | 201 | 35.416 | 52.875 | 137.282 | 1.00 | 0.00 | xxxx | 1576 |
| ATOM | 1577 | O | LYS | A | 201 | 36.447 | 52.213 | 137.141 | 1.00 | 0.00 | xxxx | 1577 |
| ATOM | 1578 | N | ILE | A | 202 | 35.299 | 53.852 | 138.180 | 1.00 | 0.00 | xxxx | 1578 |
| ATOM | 1579 | CA | ILE | A | 202 | 36.416 | 54.249 | 139.025 | 1.00 | 0.00 | xxxx | 1579 |
| ATOM | 1580 | CB | ILE | A | 202 | 36.185 | 55.625 | 139.660 | 1.00 | 0.00 | xxxx | 1580 |
| ATOM | 1581 | CG1 | ILE | A | 202 | 35.829 | 56.664 | 138.591 | 1.00 | 0.00 | xxxx | 1581 |
| ATOM | 1582 | CD1 | ILE | A | 202 | 35.524 | 58.048 | 139.164 | 1.00 | 0.00 | xxxx | 1582 |
| ATOM | 1583 | CG2 | ILE | A | 202 | 37.425 | 56.056 | 140.438 | 1.00 | 0.00 | xxxx | 1583 |
| ATOM | 1584 | C | ILE | A | 202 | 36.651 | 53.204 | 140.107 | 1.00 | 0.00 | xxxx | 1584 |
| ATOM | 1585 | O | ILE | A | 202 | 35.737 | 52.884 | 140.865 | 1.00 | 0.00 | xxxx | 1585 |
| ATOM | 1586 | N | GLU | A | 203 | 37.878 | 52.694 | 140.188 | 1.00 | 0.00 | xxxx | 1586 |
| ATOM | 1587 | CA | GLU | A | 203 | 38.199 | 51.627 | 141.135 | 1.00 | 0.00 | xxxx | 1587 |
| ATOM | 1588 | CB | GLU | A | 203 | 38.778 | 50.417 | 140.384 | 1.00 | 0.00 | xxxx | 1588 |
| ATOM | 1589 | CG | GLU | A | 203 | 37.772 | 49.792 | 139.416 | 1.00 | 0.00 | xxxx | 1589 |
| ATOM | 1590 | CD | GLU | A | 203 | 38.353 | 48.684 | 138.547 | 1.00 | 0.00 | xxxx | 1590 |
| ATOM | 1591 | OE1 | GLU | A | 203 | 39.595 | 48.539 | 138.479 | 1.00 | 0.00 | xxxx | 1591 |
| ATOM | 1592 | OE2 | GLU | A | 203 | 37.561 | 47.942 | 137.920 | 1.00 | 0.00 | xxxx | 1592 |
| ATOM | 1593 | C | GLU | A | 203 | 39.158 | 52.075 | 142.233 | 1.00 | 0.00 | xxxx | 1593 |
| ATOM | 1594 | O | GLU | A | 203 | 39.313 | 51.390 | 143.245 | 1.00 | 0.00 | xxxx | 1594 |
| ATOM | 1595 | N | ALA | A | 204 | 39.778 | 53.235 | 142.051 | 1.00 | 0.00 | xxxx | 1595 |
| ATOM | 1596 | CA | ALA | A | 204 | 40.764 | 53.731 | 143.000 | 1.00 | 0.00 | xxxx | 1596 |
| ATOM | 1597 | CB | ALA | A | 204 | 42.099 | 53.007 | 142.809 | 1.00 | 0.00 | xxxx | 1597 |
| ATOM | 1598 | C | ALA | A | 204 | 40.944 | 55.236 | 142.834 | 1.00 | 0.00 | xxxx | 1598 |
| ATOM | 1599 | O | ALA | A | 204 | 40.877 | 55.761 | 141.720 | 1.00 | 0.00 | xxxx | 1599 |
| ATOM | 1600 | N | VAL | A | 205 | 41.167 | 55.934 | 143.945 | 1.00 | 0.00 | xxxx | 1600 |
| ATOM | 1601 | CA | VAL | A | 205 | 41.404 | 57.370 | 143.911 | 1.00 | 0.00 | xxxx | 1601 |
| ATOM | 1602 | CB | VAL | A | 205 | 40.278 | 58.154 | 144.615 | 1.00 | 0.00 | xxxx | 1602 |
| ATOM | 1603 | CG1 | VAL | A | 205 | 40.605 | 59.641 | 144.631 | 1.00 | 0.00 | xxxx | 1603 |
| ATOM | 1604 | CG2 | VAL | A | 205 | 38.935 | 57.899 | 143.941 | 1.00 | 0.00 | xxxx | 1604 |
| ATOM | 1605 | C | VAL | A | 205 | 42.724 | 57.692 | 144.578 | 1.00 | 0.00 | xxxx | 1605 |
| ATOM | 1606 | O | VAL | A | 205 | 42.915 | 57.366 | 145.749 | 1.00 | 0.00 | xxxx | 1606 |
| ATOM | 1607 | N | PHE | A | 206 | 43.621 | 58.331 | 143.835 | 1.00 | 0.00 | xxxx | 1607 |
| ATOM | 1608 | CA | PHE | A | 206 | 44.862 | 58.884 | 144.392 | 1.00 | 0.00 | xxxx | 1608 |
| ATOM | 1609 | CB | PHE | A | 206 | 46.082 | 58.571 | 143.509 | 1.00 | 0.00 | xxxx | 1609 |
| ATOM | 1610 | CG | PHE | A | 206 | 46.410 | 57.109 | 143.392 | 1.00 | 0.00 | xxxx | 1610 |
| ATOM | 1611 | CD1 | PHE | A | 206 | 47.402 | 56.542 | 144.172 | 1.00 | 0.00 | xxxx | 1611 |
| ATOM | 1612 | CE1 | PHE | A | 206 | 47.714 | 55.194 | 144.046 | 1.00 | 0.00 | xxxx | 1612 |
| ATOM | 1613 | CZ | PHE | A | 206 | 47.034 | 54.416 | 143.126 | 1.00 | 0.00 | xxxx | 1613 |
| ATOM | 1614 | CE2 | PHE | A | 206 | 46.037 | 54.971 | 142.339 | 1.00 | 0.00 | xxxx | 1614 |
| ATOM | 1615 | CD2 | PHE | A | 206 | 45.738 | 56.312 | 142.466 | 1.00 | 0.00 | xxxx | 1615 |
| ATOM | 1616 | C | PHE | A | 206 | 44.733 | 60.397 | 144.508 | 1.00 | 0.00 | xxxx | 1616 |
| ATOM | 1617 | O | PHE | A | 206 | 44.292 | 61.053 | 143.565 | 1.00 | 0.00 | xxxx | 1617 |
| ATOM | 1618 | N | ALA | A | 207 | 45.142 | 60.957 | 145.645 | 1.00 | 0.00 | xxxx | 1618 |
| ATOM | 1619 | CA | ALA | A | 207 | 45.225 | 62.416 | 145.769 | 1.00 | 0.00 | xxxx | 1619 |
| ATOM | 1620 | CB | ALA | A | 207 | 44.123 | 62.950 | 146.678 | 1.00 | 0.00 | xxxx | 1620 |
| ATOM | 1621 | C | ALA | A | 207 | 46.594 | 62.810 | 146.306 | 1.00 | 0.00 | xxxx | 1621 |
| ATOM | 1622 | O | ALA | A | 207 | 47.122 | 62.146 | 147.201 | 1.00 | 0.00 | xxxx | 1622 |
| ATOM | 1623 | N | ASN | A | 208 | 47.162 | 63.896 | 145.787 | 1.00 | 0.00 | xxxx | 1623 |
| ATOM | 1624 | CA | ASN | A | 208 | 48.502 | 64.291 | 146.219 | 1.00 | 0.00 | xxxx | 1624 |
| ATOM | 1625 | CB | ASN | A | 208 | 49.103 | 65.400 | 145.344 | 1.00 | 0.00 | xxxx | 1625 |
| ATOM | 1626 | CG | ASN | A | 208 | 49.459 | 64.984 | 143.909 | 1.00 | 0.00 | xxxx | 1626 |
| ATOM | 1627 | OD1 | ASN | A | 208 | 49.763 | 65.868 | 143.121 | 1.00 | 0.00 | xxxx | 1627 |
| ATOM | 1628 | ND2 | ASN | A | 208 | 49.449 | 63.689 | 143.571 | 1.00 | 0.00 | xxxx | 1628 |
| ATOM | 1629 | C | ASN | A | 208 | 48.517 | 64.796 | 147.679 | 1.00 | 0.00 | xxxx | 1629 |
| ATOM | 1630 | O | ASN | A | 208 | 49.590 | 64.903 | 148.269 | 1.00 | 0.00 | xxxx | 1630 |
| ATOM | 1631 | N | ASN | A | 209 | 47.365 | 65.153 | 148.253 | 1.00 | 0.00 | xxxx | 1631 |
| ATOM | 1632 | CA | ASN | A | 209 | 47.342 | 65.466 | 149.688 | 1.00 | 0.00 | xxxx | 1632 |
| ATOM | 1633 | CB | ASN | A | 209 | 47.691 | 66.955 | 149.969 | 1.00 | 0.00 | xxxx | 1633 |
| ATOM | 1634 | CG | ASN | A | 209 | 46.526 | 67.920 | 149.719 | 1.00 | 0.00 | xxxx | 1634 |
| ATOM | 1635 | OD1 | ASN | A | 209 | 45.537 | 67.573 | 149.075 | 1.00 | 0.00 | xxxx | 1635 |
| ATOM | 1636 | ND2 | ASN | A | 209 | 46.667 | 69.158 | 150.209 | 1.00 | 0.00 | xxxx | 1636 |
| ATOM | 1637 | C | ASN | A | 209 | 46.007 | 65.097 | 150.320 | 1.00 | 0.00 | xxxx | 1637 |
| ATOM | 1638 | O | ASN | A | 209 | 45.059 | 64.713 | 149.633 | 1.00 | 0.00 | xxxx | 1638 |
| ATOM | 1639 | N | ASP | A | 210 | 45.958 | 65.204 | 151.644 | 1.00 | 0.00 | xxxx | 1639 |
| ATOM | 1640 | CA | ASP | A | 210 | 44.773 | 64.808 | 152.391 | 1.00 | 0.00 | xxxx | 1640 |
| ATOM | 1641 | CB | ASP | A | 210 | 45.055 | 64.800 | 153.892 | 1.00 | 0.00 | xxxx | 1641 |
| ATOM | 1642 | CG | ASP | A | 210 | 45.798 | 63.549 | 154.341 | 1.00 | 0.00 | xxxx | 1642 |
| ATOM | 1643 | OD1 | ASP | A | 210 | 46.085 | 62.662 | 153.499 | 1.00 | 0.00 | xxxx | 1643 |
| ATOM | 1644 | OD2 | ASP | A | 210 | 46.092 | 63.456 | 155.547 | 1.00 | 0.00 | xxxx | 1644 |
| ATOM | 1645 | C | ASP | A | 210 | 43.581 | 65.701 | 152.100 | 1.00 | 0.00 | xxxx | 1645 |
| ATOM | 1646 | O | ASP | A | 210 | 42.472 | 65.208 | 151.978 | 1.00 | 0.00 | xxxx | 1646 |
| ATOM | 1647 | N | ASP | A | 211 | 43.791 | 67.008 | 151.985 | 1.00 | 0.00 | xxxx | 1647 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1648 | CA | ASP | A | 211 | 42.638 | 67.877 | 151.766 | 1.00 | 0.00 | xxxx | 1648 |
| ATOM | 1649 | CB | ASP | A | 211 | 43.052 | 69.350 | 151.760 | 1.00 | 0.00 | xxxx | 1649 |
| ATOM | 1650 | CG | ASP | A | 211 | 42.782 | 70.029 | 153.091 | 1.00 | 0.00 | xxxx | 1650 |
| ATOM | 1651 | OD1 | ASP | A | 211 | 42.301 | 69.349 | 154.028 | 1.00 | 0.00 | xxxx | 1651 |
| ATOM | 1652 | OD2 | ASP | A | 211 | 43.055 | 71.240 | 153.210 | 1.00 | 0.00 | xxxx | 1652 |
| ATOM | 1653 | C | ASP | A | 211 | 41.921 | 67.506 | 150.469 | 1.00 | 0.00 | xxxx | 1653 |
| ATOM | 1654 | O | ASP | A | 211 | 40.698 | 67.469 | 150.421 | 1.00 | 0.00 | xxxx | 1654 |
| ATOM | 1655 | N | MET | A | 212 | 42.680 | 67.193 | 149.427 | 1.00 | 0.00 | xxxx | 1655 |
| ATOM | 1656 | CA | MET | A | 212 | 42.048 | 66.791 | 148.177 | 1.00 | 0.00 | xxxx | 1656 |
| ATOM | 1657 | CB | MET | A | 212 | 43.069 | 66.817 | 147.034 | 1.00 | 0.00 | xxxx | 1657 |
| ATOM | 1658 | CG | MET | A | 212 | 43.477 | 68.258 | 146.686 | 1.00 | 0.00 | xxxx | 1658 |
| ATOM | 1659 | SD | MET | A | 212 | 44.495 | 68.384 | 145.210 | 1.00 | 0.00 | xxxx | 1659 |
| ATOM | 1660 | CE | MET | A | 212 | 45.912 | 67.363 | 145.682 | 1.00 | 0.00 | xxxx | 1660 |
| ATOM | 1661 | C | MET | A | 212 | 41.397 | 65.419 | 148.310 | 1.00 | 0.00 | xxxx | 1661 |
| ATOM | 1662 | O | MET | A | 212 | 40.318 | 65.194 | 147.763 | 1.00 | 0.00 | xxxx | 1662 |
| ATOM | 1663 | N | ALA | A | 213 | 42.031 | 64.506 | 149.047 | 1.00 | 0.00 | xxxx | 1663 |
| ATOM | 1664 | CA | ALA | A | 213 | 41.423 | 63.195 | 149.279 | 1.00 | 0.00 | xxxx | 1664 |
| ATOM | 1665 | CB | ALA | A | 213 | 42.346 | 62.289 | 150.078 | 1.00 | 0.00 | xxxx | 1665 |
| ATOM | 1666 | C | ALA | A | 213 | 40.094 | 63.354 | 150.002 | 1.00 | 0.00 | xxxx | 1666 |
| ATOM | 1667 | O | ALA | A | 213 | 39.126 | 62.658 | 149.683 | 1.00 | 0.00 | xxxx | 1667 |
| ATOM | 1668 | N | LEU | A | 214 | 40.048 | 64.282 | 150.964 | 1.00 | 0.00 | xxxx | 1668 |
| ATOM | 1669 | CA | LEU | A | 214 | 38.842 | 64.516 | 151.759 | 1.00 | 0.00 | xxxx | 1669 |
| ATOM | 1670 | CB | LEU | A | 214 | 39.158 | 65.434 | 152.947 | 1.00 | 0.00 | xxxx | 1670 |
| ATOM | 1671 | CG | LEU | A | 214 | 40.111 | 64.799 | 153.966 | 1.00 | 0.00 | xxxx | 1671 |
| ATOM | 1672 | CD1 | LEU | A | 214 | 40.612 | 65.821 | 154.986 | 1.00 | 0.00 | xxxx | 1672 |
| ATOM | 1673 | CD2 | LEU | A | 214 | 39.464 | 63.609 | 154.670 | 1.00 | 0.00 | xxxx | 1673 |
| ATOM | 1674 | C | LEU | A | 214 | 37.717 | 65.104 | 150.922 | 1.00 | 0.00 | xxxx | 1674 |
| ATOM | 1675 | O | LEU | A | 214 | 36.555 | 64.746 | 151.102 | 1.00 | 0.00 | xxxx | 1675 |
| ATOM | 1676 | N | GLY | A | 215 | 38.066 | 66.001 | 150.004 | 1.00 | 0.00 | xxxx | 1676 |
| ATOM | 1677 | CA | GLY | A | 215 | 37.088 | 66.537 | 149.067 | 1.00 | 0.00 | xxxx | 1677 |
| ATOM | 1678 | C | GLY | A | 215 | 36.551 | 65.438 | 148.168 | 1.00 | 0.00 | xxxx | 1678 |
| ATOM | 1679 | O | GLY | A | 215 | 35.345 | 65.377 | 147.911 | 1.00 | 0.00 | xxxx | 1679 |
| ATOM | 1680 | N | ALA | A | 216 | 37.442 | 64.573 | 147.688 | 1.00 | 0.00 | xxxx | 1680 |
| ATOM | 1681 | CA | ALA | A | 216 | 37.020 | 63.429 | 146.885 | 1.00 | 0.00 | xxxx | 1681 |
| ATOM | 1682 | CB | ALA | A | 216 | 38.230 | 62.655 | 146.374 | 1.00 | 0.00 | xxxx | 1682 |
| ATOM | 1683 | C | ALA | A | 216 | 36.090 | 62.516 | 147.688 | 1.00 | 0.00 | xxxx | 1683 |
| ATOM | 1684 | O | ALA | A | 216 | 35.066 | 62.062 | 147.170 | 1.00 | 0.00 | xxxx | 1684 |
| ATOM | 1685 | N | ILE | A | 217 | 36.424 | 62.270 | 148.952 | 1.00 | 0.00 | xxxx | 1685 |
| ATOM | 1686 | CA | ILE | A | 217 | 35.583 | 61.438 | 149.805 | 1.00 | 0.00 | xxxx | 1686 |
| ATOM | 1687 | CB | ILE | A | 217 | 36.275 | 61.186 | 151.167 | 1.00 | 0.00 | xxxx | 1687 |
| ATOM | 1688 | CG1 | ILE | A | 217 | 37.406 | 60.171 | 150.988 | 1.00 | 0.00 | xxxx | 1688 |
| ATOM | 1689 | CD1 | ILE | A | 217 | 38.425 | 60.184 | 152.118 | 1.00 | 0.00 | xxxx | 1689 |
| ATOM | 1690 | CG2 | ILE | A | 217 | 35.265 | 60.695 | 152.221 | 1.00 | 0.00 | xxxx | 1690 |
| ATOM | 1691 | C | ILE | A | 217 | 34.187 | 62.049 | 149.971 | 1.00 | 0.00 | xxxx | 1691 |
| ATOM | 1692 | O | ILE | A | 217 | 33.188 | 61.327 | 149.967 | 1.00 | 0.00 | xxxx | 1692 |
| ATOM | 1693 | N | GLU | A | 218 | 34.089 | 63.371 | 150.075 | 1.00 | 0.00 | xxxx | 1693 |
| ATOM | 1694 | C | GLU | A | 218 | 31.948 | 63.832 | 148.945 | 1.00 | 0.00 | xxxx | 1694 |
| ATOM | 1695 | O | GLU | A | 218 | 30.736 | 63.621 | 149.019 | 1.00 | 0.00 | xxxx | 1695 |
| ATOM | 1696 | CA | GLU | A | 218 | 32.781 | 64.001 | 150.218 | 1.00 | 0.00 | xxxx | 1696 |
| ATOM | 1697 | CB | GLU | A | 218 | 32.925 | 65.482 | 150.574 | 1.00 | 0.00 | xxxx | 1697 |
| ATOM | 1698 | CG | GLU | A | 218 | 33.457 | 65.727 | 151.983 | 1.00 | 0.00 | xxxx | 1698 |
| ATOM | 1699 | CD | GLU | A | 218 | 32.729 | 64.911 | 153.046 | 1.00 | 0.00 | xxxx | 1699 |
| ATOM | 1700 | OE1 | GLU | A | 218 | 31.482 | 64.948 | 153.089 | 1.00 | 0.00 | xxxx | 1700 |
| ATOM | 1701 | OE2 | GLU | A | 218 | 33.401 | 64.221 | 153.840 | 1.00 | 0.00 | xxxx | 1701 |
| ATOM | 1702 | N | ALA | A | 219 | 32.593 | 63.921 | 147.783 | 1.00 | 0.00 | xxxx | 1702 |
| ATOM | 1703 | CA | ALA | A | 219 | 31.881 | 63.696 | 146.531 | 1.00 | 0.00 | xxxx | 1703 |
| ATOM | 1704 | CB | ALA | A | 219 | 32.763 | 64.063 | 145.327 | 1.00 | 0.00 | xxxx | 1704 |
| ATOM | 1705 | C | ALA | A | 219 | 31.431 | 62.237 | 146.444 | 1.00 | 0.00 | xxxx | 1705 |
| ATOM | 1706 | O | ALA | A | 219 | 30.321 | 61.945 | 145.997 | 1.00 | 0.00 | xxxx | 1706 |
| ATOM | 1707 | N | LEU | A | 220 | 32.294 | 61.329 | 146.890 | 1.00 | 0.00 | xxxx | 1707 |
| ATOM | 1708 | CA | LEU | A | 220 | 31.957 | 59.907 | 146.898 | 1.00 | 0.00 | xxxx | 1708 |
| ATOM | 1709 | CB | LEU | A | 220 | 33.175 | 59.083 | 147.291 | 1.00 | 0.00 | xxxx | 1709 |
| ATOM | 1710 | CG | LEU | A | 220 | 34.251 | 59.007 | 146.209 | 1.00 | 0.00 | xxxx | 1710 |
| ATOM | 1711 | CD1 | LEU | A | 220 | 35.601 | 58.672 | 146.812 | 1.00 | 0.00 | xxxx | 1711 |
| ATOM | 1712 | CD2 | LEU | A | 220 | 33.837 | 57.986 | 145.144 | 1.00 | 0.00 | xxxx | 1712 |
| ATOM | 1713 | C | LEU | A | 220 | 30.793 | 59.605 | 147.836 | 1.00 | 0.00 | xxxx | 1713 |
| ATOM | 1714 | O | LEU | A | 220 | 29.876 | 58.868 | 147.475 | 1.00 | 0.00 | xxxx | 1714 |
| ATOM | 1715 | N | LYS | A | 221 | 30.824 | 60.164 | 149.045 | 1.00 | 0.00 | xxxx | 1715 |
| ATOM | 1716 | CA | LYS | A | 221 | 29.687 | 60.015 | 149.962 | 1.00 | 0.00 | xxxx | 1716 |
| ATOM | 1717 | CB | LYS | A | 221 | 29.930 | 60.789 | 151.258 | 1.00 | 0.00 | xxxx | 1717 |
| ATOM | 1718 | CG | LYS | A | 221 | 30.943 | 60.170 | 152.186 | 1.00 | 0.00 | xxxx | 1718 |
| ATOM | 1719 | CD | LYS | A | 221 | 31.170 | 61.087 | 153.369 | 1.00 | 0.00 | xxxx | 1719 |
| ATOM | 1720 | CE | LYS | A | 221 | 32.082 | 60.452 | 154.396 | 1.00 | 0.00 | xxxx | 1720 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1721 | NZ | LYS | A | 221 | 32.368 | 61.404 | 155.504 | 1.00 | 0.00 | xxxx | 1721 |
| ATOM | 1722 | C | LYS | A | 221 | 28.379 | 60.492 | 149.320 | 1.00 | 0.00 | xxxx | 1722 |
| ATOM | 1723 | O | LYS | A | 221 | 27.353 | 59.801 | 149.365 | 1.00 | 0.00 | xxxx | 1723 |
| ATOM | 1724 | N | SER | A | 222 | 28.431 | 61.671 | 148.709 | 1.00 | 0.00 | xxxx | 1724 |
| ATOM | 1725 | CA | SER | A | 222 | 27.258 | 62.263 | 148.063 | 1.00 | 0.00 | xxxx | 1725 |
| ATOM | 1726 | CB | SER | A | 222 | 27.626 | 63.620 | 147.450 | 1.00 | 0.00 | xxxx | 1726 |
| ATOM | 1727 | OG | SER | A | 222 | 26.484 | 64.308 | 146.967 | 1.00 | 0.00 | xxxx | 1727 |
| ATOM | 1728 | C | SER | A | 222 | 26.670 | 61.340 | 146.992 | 1.00 | 0.00 | xxxx | 1728 |
| ATOM | 1729 | O | SER | A | 222 | 25.451 | 61.321 | 146.773 | 1.00 | 0.00 | xxxx | 1729 |
| ATOM | 1730 | N | ALA | A | 223 | 27.539 | 60.569 | 146.346 | 1.00 | 0.00 | xxxx | 1730 |
| ATOM | 1731 | CA | ALA | A | 223 | 27.144 | 59.633 | 145.295 | 1.00 | 0.00 | xxxx | 1731 |
| ATOM | 1732 | CB | ALA | A | 223 | 28.227 | 59.565 | 144.226 | 1.00 | 0.00 | xxxx | 1732 |
| ATOM | 1733 | C | ALA | A | 223 | 26.844 | 58.224 | 145.823 | 1.00 | 0.00 | xxxx | 1733 |
| ATOM | 1734 | O | ALA | A | 223 | 26.640 | 57.299 | 145.039 | 1.00 | 0.00 | xxxx | 1734 |
| ATOM | 1735 | N | GLY | A | 224 | 26.837 | 58.055 | 147.143 | 1.00 | 0.00 | xxxx | 1735 |
| ATOM | 1736 | CA | GLY | A | 224 | 26.391 | 56.803 | 147.737 | 1.00 | 0.00 | xxxx | 1736 |
| ATOM | 1737 | C | GLY | A | 224 | 27.439 | 55.849 | 148.286 | 1.00 | 0.00 | xxxx | 1737 |
| ATOM | 1738 | O | GLY | A | 224 | 27.099 | 54.754 | 148.749 | 1.00 | 0.00 | xxxx | 1738 |
| ATOM | 1739 | N | TYR | A | 225 | 28.705 | 56.254 | 148.247 | 1.00 | 0.00 | xxxx | 1739 |
| ATOM | 1740 | CA | TYR | A | 225 | 29.790 | 55.423 | 148.772 | 1.00 | 0.00 | xxxx | 1740 |
| ATOM | 1741 | CB | TYR | A | 225 | 31.126 | 55.823 | 148.132 | 1.00 | 0.00 | xxxx | 1741 |
| ATOM | 1742 | CG | TYR | A | 225 | 31.231 | 55.438 | 146.673 | 1.00 | 0.00 | xxxx | 1742 |
| ATOM | 1743 | CD1 | TYR | A | 225 | 30.582 | 56.178 | 145.691 | 1.00 | 0.00 | xxxx | 1743 |
| ATOM | 1744 | CE1 | TYR | A | 225 | 30.666 | 55.826 | 144.354 | 1.00 | 0.00 | xxxx | 1744 |
| ATOM | 1745 | CZ | TYR | A | 225 | 31.403 | 54.721 | 143.983 | 1.00 | 0.00 | xxxx | 1745 |
| ATOM | 1746 | OH | TYR | A | 225 | 31.483 | 54.376 | 142.652 | 1.00 | 0.00 | xxxx | 1746 |
| ATOM | 1747 | CE2 | TYR | A | 225 | 32.056 | 53.963 | 144.937 | 1.00 | 0.00 | xxxx | 1747 |
| ATOM | 1748 | CD2 | TYR | A | 225 | 31.963 | 54.321 | 146.276 | 1.00 | 0.00 | xxxx | 1748 |
| ATOM | 1749 | C | TYR | A | 225 | 29.901 | 55.507 | 150.290 | 1.00 | 0.00 | xxxx | 1749 |
| ATOM | 1750 | O | TYR | A | 225 | 29.427 | 56.464 | 150.907 | 1.00 | 0.00 | xxxx | 1750 |
| ATOM | 1751 | N | PHE | A | 226 | 30.514 | 54.479 | 150.874 | 1.00 | 0.00 | xxxx | 1751 |
| ATOM | 1752 | CA | PHE | A | 226 | 30.855 | 54.433 | 152.295 | 1.00 | 0.00 | xxxx | 1752 |
| ATOM | 1753 | CB | PHE | A | 226 | 31.676 | 55.662 | 152.679 | 1.00 | 0.00 | xxxx | 1753 |
| ATOM | 1754 | CG | PHE | A | 226 | 32.925 | 55.809 | 151.866 | 1.00 | 0.00 | xxxx | 1754 |
| ATOM | 1755 | CD1 | PHE | A | 226 | 33.835 | 54.764 | 151.787 | 1.00 | 0.00 | xxxx | 1755 |
| ATOM | 1756 | CE1 | PHE | A | 226 | 34.990 | 54.881 | 151.019 | 1.00 | 0.00 | xxxx | 1756 |
| ATOM | 1757 | CZ | PHE | A | 226 | 35.233 | 56.055 | 150.313 | 1.00 | 0.00 | xxxx | 1757 |
| ATOM | 1758 | CE2 | PHE | A | 226 | 34.318 | 57.101 | 150.383 | 1.00 | 0.00 | xxxx | 1758 |
| ATOM | 1759 | CD2 | PHE | A | 226 | 33.174 | 56.972 | 151.150 | 1.00 | 0.00 | xxxx | 1759 |
| ATOM | 1760 | C | PHE | A | 226 | 29.627 | 54.297 | 153.184 | 1.00 | 0.00 | xxxx | 1760 |
| ATOM | 1761 | O | PHE | A | 226 | 29.662 | 54.619 | 154.369 | 1.00 | 0.00 | xxxx | 1761 |
| ATOM | 1762 | N | THR | A | 227 | 28.547 | 53.815 | 152.583 | 1.00 | 0.00 | xxxx | 1762 |
| ATOM | 1763 | CA | THR | A | 227 | 27.374 | 53.347 | 153.311 | 1.00 | 0.00 | xxxx | 1763 |
| ATOM | 1764 | CB | THR | A | 227 | 26.239 | 54.382 | 153.335 | 1.00 | 0.00 | xxxx | 1764 |
| ATOM | 1765 | OG1 | THR | A | 227 | 25.133 | 53.854 | 154.076 | 1.00 | 0.00 | xxxx | 1765 |
| ATOM | 1766 | CG2 | THR | A | 227 | 25.785 | 54.714 | 151.924 | 1.00 | 0.00 | xxxx | 1766 |
| ATOM | 1767 | C | THR | A | 227 | 26.930 | 52.070 | 152.610 | 1.00 | 0.00 | xxxx | 1767 |
| ATOM | 1768 | O | THR | A | 227 | 27.137 | 51.920 | 151.405 | 1.00 | 0.00 | xxxx | 1768 |
| ATOM | 1769 | N | GLY | A | 228 | 26.331 | 51.145 | 153.349 | 1.00 | 0.00 | xxxx | 1769 |
| ATOM | 1770 | CA | GLY | A | 228 | 26.122 | 49.818 | 152.804 | 1.00 | 0.00 | xxxx | 1770 |
| ATOM | 1771 | C | GLY | A | 228 | 27.484 | 49.199 | 152.547 | 1.00 | 0.00 | xxxx | 1771 |
| ATOM | 1772 | O | GLY | A | 228 | 28.433 | 49.473 | 153.281 | 1.00 | 0.00 | xxxx | 1772 |
| ATOM | 1773 | N | ASN | A | 229 | 27.601 | 48.384 | 151.505 | 1.00 | 0.00 | xxxx | 1773 |
| ATOM | 1774 | CA | ASN | A | 229 | 28.884 | 47.756 | 151.200 | 1.00 | 0.00 | xxxx | 1774 |
| ATOM | 1775 | CB | ASN | A | 229 | 28.697 | 46.259 | 150.932 | 1.00 | 0.00 | xxxx | 1775 |
| ATOM | 1776 | CG | ASN | A | 229 | 27.629 | 45.977 | 149.888 | 1.00 | 0.00 | xxxx | 1776 |
| ATOM | 1777 | OD1 | ASN | A | 229 | 27.160 | 46.885 | 149.199 | 1.00 | 0.00 | xxxx | 1777 |
| ATOM | 1778 | ND2 | ASN | A | 229 | 27.241 | 44.711 | 149.766 | 1.00 | 0.00 | xxxx | 1778 |
| ATOM | 1779 | C | ASN | A | 229 | 29.591 | 48.414 | 150.013 | 1.00 | 0.00 | xxxx | 1779 |
| ATOM | 1780 | O | ASN | A | 229 | 30.509 | 47.831 | 149.435 | 1.00 | 0.00 | xxxx | 1780 |
| ATOM | 1781 | N | LYS | A | 230 | 29.165 | 49.627 | 149.661 | 1.00 | 0.00 | xxxx | 1781 |
| ATOM | 1782 | CA | LYS | A | 230 | 29.696 | 50.331 | 148.491 | 1.00 | 0.00 | xxxx | 1782 |
| ATOM | 1783 | CB | LYS | A | 230 | 28.645 | 51.284 | 147.926 | 1.00 | 0.00 | xxxx | 1783 |
| ATOM | 1784 | CG | LYS | A | 230 | 29.049 | 51.957 | 146.625 | 1.00 | 0.00 | xxxx | 1784 |
| ATOM | 1785 | CD | LYS | A | 230 | 27.920 | 52.840 | 146.108 | 1.00 | 0.00 | xxxx | 1785 |
| ATOM | 1786 | CE | LYS | A | 230 | 28.136 | 53.249 | 144.662 | 1.00 | 0.00 | xxxx | 1786 |
| ATOM | 1787 | NZ | LYS | A | 230 | 27.043 | 54.140 | 144.184 | 1.00 | 0.00 | xxxx | 1787 |
| ATOM | 1788 | C | LYS | A | 230 | 30.975 | 51.104 | 148.820 | 1.00 | 0.00 | xxxx | 1788 |
| ATOM | 1789 | O | LYS | A | 230 | 30.931 | 52.156 | 149.455 | 1.00 | 0.00 | xxxx | 1789 |
| ATOM | 1790 | N | TYR | A | 231 | 32.107 | 50.592 | 148.352 | 1.00 | 0.00 | xxxx | 1790 |
| ATOM | 1791 | CA | TYR | A | 231 | 33.403 | 51.068 | 148.820 | 1.00 | 0.00 | xxxx | 1791 |
| ATOM | 1792 | CB | TYR | A | 231 | 34.020 | 50.021 | 149.742 | 1.00 | 0.00 | xxxx | 1792 |
| ATOM | 1793 | CG | TYR | A | 231 | 35.396 | 50.366 | 150.248 | 1.00 | 0.00 | xxxx | 1793 |

-continued

| CA, calcium<br>HOH, water<br>BAD, Badan<br>K, potassium<br>EDO, ethylene glycol | | | | | | | | | | | |
|---|---|---|---|---|---|---|---|---|---|---|---|
| ATOM | 1794 | CD1 | TYR | A | 231 | 35.558 | 51.179 | 151.358 | 1.00 | 0.00 | xxxx | 1794 |
| ATOM | 1795 | CE1 | TYR | A | 231 | 36.809 | 51.500 | 151.828 | 1.00 | 0.00 | xxxx | 1795 |
| ATOM | 1796 | CZ | TYR | A | 231 | 37.927 | 50.995 | 151.187 | 1.00 | 0.00 | xxxx | 1796 |
| ATOM | 1797 | OH | TYR | A | 231 | 39.183 | 51.307 | 151.656 | 1.00 | 0.00 | xxxx | 1797 |
| ATOM | 1798 | CE2 | TYR | A | 231 | 37.790 | 50.178 | 150.084 | 1.00 | 0.00 | xxxx | 1798 |
| ATOM | 1799 | CD2 | TYR | A | 231 | 36.533 | 49.867 | 149.624 | 1.00 | 0.00 | xxxx | 1799 |
| ATOM | 1800 | C | TYR | A | 231 | 34.359 | 51.383 | 147.680 | 1.00 | 0.00 | xxxx | 1800 |
| ATOM | 1801 | O | TYR | A | 231 | 34.282 | 50.778 | 146.616 | 1.00 | 0.00 | xxxx | 1801 |
| ATOM | 1802 | N | ILE | A | 232 | 35.259 | 52.334 | 147.914 | 1.00 | 0.00 | xxxx | 1802 |
| ATOM | 1803 | CA | ILE | A | 232 | 36.330 | 52.633 | 146.976 | 1.00 | 0.00 | xxxx | 1803 |
| ATOM | 1804 | CB | ILE | A | 232 | 35.913 | 53.708 | 145.951 | 1.00 | 0.00 | xxxx | 1804 |
| ATOM | 1805 | CG1 | ILE | A | 232 | 37.027 | 53.945 | 144.941 | 1.00 | 0.00 | xxxx | 1805 |
| ATOM | 1806 | CD1 | ILE | A | 232 | 36.591 | 54.744 | 143.743 | 1.00 | 0.00 | xxxx | 1806 |
| ATOM | 1807 | CG2 | ILE | A | 232 | 35.555 | 55.020 | 146.649 | 1.00 | 0.00 | xxxx | 1807 |
| ATOM | 1808 | C | ILE | A | 232 | 37.548 | 53.063 | 147.793 | 1.00 | 0.00 | xxxx | 1808 |
| ATOM | 1809 | O | ILE | A | 232 | 37.413 | 53.817 | 148.754 | 1.00 | 0.00 | xxxx | 1809 |
| ATOM | 1810 | N | PRO | A | 233 | 38.739 | 52.558 | 147.441 | 1.00 | 0.00 | xxxx | 1810 |
| ATOM | 1811 | CA | PRO | A | 233 | 39.939 | 52.965 | 148.184 | 1.00 | 0.00 | xxxx | 1811 |
| ATOM | 1812 | CB | PRO | A | 233 | 40.955 | 51.880 | 147.820 | 1.00 | 0.00 | xxxx | 1812 |
| ATOM | 1813 | CG | PRO | A | 233 | 40.537 | 51.453 | 146.432 | 1.00 | 0.00 | xxxx | 1813 |
| ATOM | 1814 | CD | PRO | A | 233 | 39.026 | 51.487 | 146.470 | 1.00 | 0.00 | xxxx | 1814 |
| ATOM | 1815 | C | PRO | A | 233 | 40.438 | 54.344 | 147.769 | 1.00 | 0.00 | xxxx | 1815 |
| ATOM | 1816 | O | PRO | A | 233 | 40.593 | 54.627 | 146.578 | 1.00 | 0.00 | xxxx | 1816 |
| ATOM | 1817 | N | VAL | A | 234 | 40.678 | 55.196 | 148.762 | 1.00 | 0.00 | xxxx | 1817 |
| ATOM | 1818 | CA | VAL | A | 234 | 41.174 | 56.546 | 148.544 | 1.00 | 0.00 | xxxx | 1818 |
| ATOM | 1819 | CB | VAL | A | 234 | 40.142 | 57.602 | 148.976 | 1.00 | 0.00 | xxxx | 1819 |
| ATOM | 1820 | CG1 | VAL | A | 234 | 40.678 | 58.996 | 148.715 | 1.00 | 0.00 | xxxx | 1820 |
| ATOM | 1821 | CG2 | VAL | A | 234 | 38.804 | 57.384 | 148.267 | 1.00 | 0.00 | xxxx | 1821 |
| ATOM | 1822 | C | VAL | A | 234 | 42.452 | 56.709 | 149.345 | 1.00 | 0.00 | xxxx | 1822 |
| ATOM | 1823 | O | VAL | A | 234 | 42.484 | 56.346 | 150.522 | 1.00 | 0.00 | xxxx | 1823 |
| ATOM | 1824 | N | VAL | A | 235 | 43.501 | 57.258 | 148.732 | 1.00 | 0.00 | xxxx | 1824 |
| ATOM | 1825 | CA | VAL | A | 235 | 44.757 | 57.491 | 149.447 | 1.00 | 0.00 | xxxx | 1825 |
| ATOM | 1826 | CB | VAL | A | 235 | 45.869 | 56.539 | 148.964 | 1.00 | 0.00 | xxxx | 1826 |
| ATOM | 1827 | CG1 | VAL | A | 235 | 45.519 | 55.097 | 149.324 | 1.00 | 0.00 | xxxx | 1827 |
| ATOM | 1828 | CG2 | VAL | A | 235 | 46.099 | 56.699 | 147.468 | 1.00 | 0.00 | xxxx | 1828 |
| ATOM | 1829 | C | VAL | A | 235 | 45.189 | 58.952 | 149.316 | 1.00 | 0.00 | xxxx | 1829 |
| ATOM | 1830 | O | VAL | A | 235 | 44.972 | 59.583 | 148.280 | 1.00 | 0.00 | xxxx | 1830 |
| ATOM | 1831 | N | GLY | A | 236 | 45.764 | 59.496 | 150.387 | 1.00 | 0.00 | xxxx | 1831 |
| ATOM | 1832 | CA | GLY | A | 236 | 46.282 | 60.856 | 150.371 | 1.00 | 0.00 | xxxx | 1832 |
| ATOM | 1833 | C | GLY | A | 236 | 47.705 | 60.961 | 150.892 | 1.00 | 0.00 | xxxx | 1833 |
| ATOM | 1834 | O | GLY | A | 236 | 48.418 | 59.958 | 150.963 | 1.00 | 0.00 | xxxx | 1834 |
| ATOM | 1835 | N | VAL | A | 237 | 48.119 | 62.185 | 151.231 | 1.00 | 0.00 | xxxx | 1835 |
| ATOM | 1836 | CA | VAL | A | 237 | 49.399 | 62.461 | 151.893 | 1.00 | 0.00 | xxxx | 1836 |
| ATOM | 1837 | CB | VAL | A | 237 | 50.527 | 62.876 | 150.914 | 1.00 | 0.00 | xxxx | 1837 |
| ATOM | 1838 | CG1 | VAL | A | 237 | 51.746 | 63.309 | 151.700 | 1.00 | 0.00 | xxxx | 1838 |
| ATOM | 1839 | CG2 | VAL | A | 237 | 50.896 | 61.745 | 149.967 | 1.00 | 0.00 | xxxx | 1839 |
| ATOM | 1840 | C | VAL | A | 237 | 49.189 | 63.600 | 152.885 | 1.00 | 0.00 | xxxx | 1840 |
| ATOM | 1841 | O | VAL | A | 237 | 48.552 | 64.589 | 152.520 | 1.00 | 0.00 | xxxx | 1841 |
| ATOM | 1842 | N | ASP | A | 238 | 49.692 | 63.425 | 154.113 | 1.00 | 0.00 | xxxx | 1842 |
| ATOM | 1843 | CA | ASP | A | 238 | 49.966 | 64.468 | 155.127 | 1.00 | 0.00 | xxxx | 1843 |
| ATOM | 1844 | CB | ASP | A | 238 | 49.128 | 65.746 | 154.971 | 1.00 | 0.00 | xxxx | 1844 |
| ATOM | 1845 | CG | ASP | A | 238 | 49.636 | 66.668 | 153.871 | 1.00 | 0.00 | xxxx | 1845 |
| ATOM | 1846 | OD1 | ASP | A | 238 | 50.792 | 66.524 | 153.414 | 1.00 | 0.00 | xxxx | 1846 |
| ATOM | 1847 | OD2 | ASP | A | 238 | 48.841 | 67.527 | 153.432 | 1.00 | 0.00 | xxxx | 1847 |
| ATOM | 1848 | C | ASP | A | 238 | 49.713 | 63.921 | 156.526 | 1.00 | 0.00 | xxxx | 1848 |
| ATOM | 1849 | O | ASP | A | 238 | 50.480 | 64.184 | 157.447 | 1.00 | 0.00 | xxxx | 1849 |
| ATOM | 1850 | N | ALA | A | 239 | 48.611 | 63.191 | 156.679 | 1.00 | 0.00 | xxxx | 1850 |
| ATOM | 1851 | CA | ALA | A | 239 | 48.125 | 62.740 | 157.989 | 1.00 | 0.00 | xxxx | 1851 |
| ATOM | 1852 | CB | ALA | A | 239 | 49.145 | 61.812 | 158.674 | 1.00 | 0.00 | xxxx | 1852 |
| ATOM | 1853 | C | ALA | A | 239 | 47.783 | 63.936 | 158.881 | 1.00 | 0.00 | xxxx | 1853 |
| ATOM | 1854 | O | ALA | A | 239 | 48.171 | 64.008 | 160.055 | 1.00 | 0.00 | xxxx | 1854 |
| ATOM | 1855 | N | THR | A | 240 | 47.049 | 64.883 | 158.301 | 1.00 | 0.00 | xxxx | 1855 |
| ATOM | 1856 | CA | THR | A | 240 | 46.483 | 65.989 | 159.060 | 1.00 | 0.00 | xxxx | 1856 |
| ATOM | 1857 | CB | THR | A | 240 | 45.850 | 67.040 | 158.148 | 1.00 | 0.00 | xxxx | 1857 |
| ATOM | 1858 | OG1 | THR | A | 240 | 44.789 | 66.424 | 157.409 | 1.00 | 0.00 | xxxx | 1858 |
| ATOM | 1859 | CG2 | THR | A | 240 | 46.883 | 67.627 | 157.184 | 1.00 | 0.00 | xxxx | 1859 |
| ATOM | 1860 | C | THR | A | 240 | 45.408 | 65.453 | 159.994 | 1.00 | 0.00 | xxxx | 1860 |
| ATOM | 1861 | O | THR | A | 240 | 45.001 | 64.297 | 159.883 | 1.00 | 0.00 | xxxx | 1861 |
| ATOM | 1862 | N | ALA | A | 241 | 44.948 | 66.295 | 160.914 | 1.00 | 0.00 | xxxx | 1862 |
| ATOM | 1863 | CA | ALA | A | 241 | 43.896 | 65.887 | 161.837 | 1.00 | 0.00 | xxxx | 1863 |
| ATOM | 1864 | CB | ALA | A | 241 | 43.531 | 67.044 | 162.781 | 1.00 | 0.00 | xxxx | 1864 |
| ATOM | 1865 | C | ALA | A | 241 | 42.648 | 65.357 | 161.094 | 1.00 | 0.00 | xxxx | 1865 |
| ATOM | 1866 | O | ALA | A | 241 | 42.175 | 64.264 | 161.408 | 1.00 | 0.00 | xxxx | 1866 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1867 | N | PRO | A | 242 | 42.131 | 66.098 | 160.089 | 1.00 | 0.00 | xxxx | 1867 |
| ATOM | 1868 | CA | PRO | A | 242 | 40.978 | 65.500 | 159.401 | 1.00 | 0.00 | xxxx | 1868 |
| ATOM | 1869 | CB | PRO | A | 242 | 40.446 | 66.648 | 158.532 | 1.00 | 0.00 | xxxx | 1869 |
| ATOM | 1870 | CG | PRO | A | 242 | 41.594 | 67.555 | 158.345 | 1.00 | 0.00 | xxxx | 1870 |
| ATOM | 1871 | CD | PRO | A | 242 | 42.406 | 67.464 | 159.607 | 1.00 | 0.00 | xxxx | 1871 |
| ATOM | 1872 | C | PRO | A | 242 | 41.340 | 64.283 | 158.544 | 1.00 | 0.00 | xxxx | 1872 |
| ATOM | 1873 | O | PRO | A | 242 | 40.493 | 63.415 | 158.346 | 1.00 | 0.00 | xxxx | 1873 |
| ATOM | 1874 | N | GLY | A | 243 | 42.577 | 64.202 | 158.063 | 1.00 | 0.00 | xxxx | 1874 |
| ATOM | 1875 | CA | GLY | A | 243 | 43.011 | 62.995 | 157.379 | 1.00 | 0.00 | xxxx | 1875 |
| ATOM | 1876 | C | GLY | A | 243 | 42.969 | 61.786 | 158.305 | 1.00 | 0.00 | xxxx | 1876 |
| ATOM | 1877 | O | GLY | A | 243 | 42.437 | 60.724 | 157.961 | 1.00 | 0.00 | xxxx | 1877 |
| ATOM | 1878 | N | ILE | A | 244 | 43.533 | 61.955 | 159.499 | 1.00 | 0.00 | xxxx | 1878 |
| ATOM | 1879 | CA | ILE | A | 244 | 43.549 | 60.895 | 160.500 | 1.00 | 0.00 | xxxx | 1879 |
| ATOM | 1880 | CB | ILE | A | 244 | 44.333 | 61.342 | 161.748 | 1.00 | 0.00 | xxxx | 1880 |
| ATOM | 1881 | CG1 | ILE | A | 244 | 45.826 | 61.443 | 161.425 | 1.00 | 0.00 | xxxx | 1881 |
| ATOM | 1882 | CD1 | ILE | A | 244 | 46.597 | 62.226 | 162.456 | 1.00 | 0.00 | xxxx | 1882 |
| ATOM | 1883 | CG2 | ILE | A | 244 | 44.076 | 60.408 | 162.929 | 1.00 | 0.00 | xxxx | 1883 |
| ATOM | 1884 | C | ILE | A | 244 | 42.120 | 60.491 | 160.841 | 1.00 | 0.00 | xxxx | 1884 |
| ATOM | 1885 | O | ILE | A | 244 | 41.808 | 59.306 | 160.941 | 1.00 | 0.00 | xxxx | 1885 |
| ATOM | 1886 | N | GLN | A | 245 | 41.241 | 61.475 | 160.982 | 1.00 | 0.00 | xxxx | 1886 |
| ATOM | 1887 | CA | GLN | A | 245 | 39.851 | 61.177 | 161.287 | 1.00 | 0.00 | xxxx | 1887 |
| ATOM | 1888 | CB | GLN | A | 245 | 39.063 | 62.469 | 161.501 | 1.00 | 0.00 | xxxx | 1888 |
| ATOM | 1889 | CG | GLN | A | 245 | 37.649 | 62.224 | 161.982 | 1.00 | 0.00 | xxxx | 1889 |
| ATOM | 1890 | CD | GLN | A | 245 | 37.621 | 61.498 | 163.314 | 1.00 | 0.00 | xxxx | 1890 |
| ATOM | 1891 | OE1 | GLN | A | 245 | 38.162 | 61.987 | 164.309 | 1.00 | 0.00 | xxxx | 1891 |
| ATOM | 1892 | NE2 | GLN | A | 245 | 37.011 | 60.315 | 163.335 | 1.00 | 0.00 | xxxx | 1892 |
| ATOM | 1893 | C | GLN | A | 245 | 39.192 | 60.328 | 160.189 | 1.00 | 0.00 | xxxx | 1893 |
| ATOM | 1894 | O | GLN | A | 245 | 38.414 | 59.418 | 160.494 | 1.00 | 0.00 | xxxx | 1894 |
| ATOM | 1895 | N | ALA | A | 246 | 39.521 | 60.598 | 158.924 | 1.00 | 0.00 | xxxx | 1895 |
| ATOM | 1896 | CA | ALA | A | 246 | 38.941 | 59.829 | 157.819 | 1.00 | 0.00 | xxxx | 1896 |
| ATOM | 1897 | CB | ALA | A | 246 | 39.202 | 60.523 | 156.490 | 1.00 | 0.00 | xxxx | 1897 |
| ATOM | 1898 | C | ALA | A | 246 | 39.478 | 58.396 | 157.783 | 1.00 | 0.00 | xxxx | 1898 |
| ATOM | 1899 | O | ALA | A | 246 | 38.764 | 57.472 | 157.390 | 1.00 | 0.00 | xxxx | 1899 |
| ATOM | 1900 | N | ILE | A | 247 | 40.734 | 58.206 | 158.193 | 1.00 | 0.00 | xxxx | 1900 |
| ATOM | 1901 | CA | ILE | A | 247 | 41.272 | 56.854 | 158.343 | 1.00 | 0.00 | xxxx | 1901 |
| ATOM | 1902 | CB | ILE | A | 247 | 42.765 | 56.866 | 158.712 | 1.00 | 0.00 | xxxx | 1902 |
| ATOM | 1903 | CG1 | ILE | A | 247 | 43.583 | 57.467 | 157.566 | 1.00 | 0.00 | xxxx | 1903 |
| ATOM | 1904 | CD1 | ILE | A | 247 | 45.054 | 57.286 | 157.705 | 1.00 | 0.00 | xxxx | 1904 |
| ATOM | 1905 | CG2 | ILE | A | 247 | 43.249 | 55.456 | 159.063 | 1.00 | 0.00 | xxxx | 1905 |
| ATOM | 1906 | C | ILE | A | 247 | 40.469 | 56.101 | 159.392 | 1.00 | 0.00 | xxxx | 1906 |
| ATOM | 1907 | O | ILE | A | 247 | 40.092 | 54.951 | 159.199 | 1.00 | 0.00 | xxxx | 1907 |
| ATOM | 1908 | N | LYS | A | 248 | 40.209 | 56.767 | 160.509 | 1.00 | 0.00 | xxxx | 1908 |
| ATOM | 1909 | CA | LYS | A | 248 | 39.428 | 56.166 | 161.578 | 1.00 | 0.00 | xxxx | 1909 |
| ATOM | 1910 | CB | LYS | A | 248 | 39.441 | 57.071 | 162.803 | 1.00 | 0.00 | xxxx | 1910 |
| ATOM | 1911 | CG | LYS | A | 248 | 40.813 | 57.187 | 163.463 | 1.00 | 0.00 | xxxx | 1911 |
| ATOM | 1912 | CD | LYS | A | 248 | 40.756 | 58.156 | 164.623 | 1.00 | 0.00 | xxxx | 1912 |
| ATOM | 1913 | CE | LYS | A | 248 | 42.102 | 58.310 | 165.291 | 1.00 | 0.00 | xxxx | 1913 |
| ATOM | 1914 | NZ | LYS | A | 248 | 42.032 | 59.317 | 166.388 | 1.00 | 0.00 | xxxx | 1914 |
| ATOM | 1915 | C | LYS | A | 248 | 37.988 | 55.882 | 161.142 | 1.00 | 0.00 | xxxx | 1915 |
| ATOM | 1916 | O | LYS | A | 248 | 37.416 | 54.866 | 161.539 | 1.00 | 0.00 | xxxx | 1916 |
| ATOM | 1917 | N | ASP | A | 249 | 37.424 | 56.776 | 160.329 | 1.00 | 0.00 | xxxx | 1917 |
| ATOM | 1918 | CA | ASP | A | 249 | 36.057 | 56.640 | 159.803 | 1.00 | 0.00 | xxxx | 1918 |
| ATOM | 1919 | CB | ASP | A | 249 | 35.598 | 57.937 | 159.114 | 1.00 | 0.00 | xxxx | 1919 |
| ATOM | 1920 | CG | ASP | A | 249 | 35.429 | 59.101 | 160.078 | 1.00 | 0.00 | xxxx | 1920 |
| ATOM | 1921 | OD1 | ASP | A | 249 | 35.413 | 60.260 | 159.603 | 1.00 | 0.00 | xxxx | 1921 |
| ATOM | 1922 | OD2 | ASP | A | 249 | 35.308 | 58.871 | 161.301 | 1.00 | 0.00 | xxxx | 1922 |
| ATOM | 1923 | C | ASP | A | 249 | 35.949 | 55.489 | 158.798 | 1.00 | 0.00 | xxxx | 1923 |
| ATOM | 1924 | O | ASP | A | 249 | 34.853 | 55.002 | 158.507 | 1.00 | 0.00 | xxxx | 1924 |
| ATOM | 1925 | N | GLY | A | 250 | 37.091 | 55.085 | 158.251 | 1.00 | 0.00 | xxxx | 1925 |
| ATOM | 1926 | CA | GLY | A | 250 | 37.138 | 54.047 | 157.237 | 1.00 | 0.00 | xxxx | 1926 |
| ATOM | 1927 | C | GLY | A | 250 | 36.984 | 54.551 | 155.809 | 1.00 | 0.00 | xxxx | 1927 |
| ATOM | 1928 | O | GLY | A | 250 | 36.947 | 53.755 | 154.876 | 1.00 | 0.00 | xxxx | 1928 |
| ATOM | 1929 | N | THR | A | 251 | 36.900 | 55.868 | 155.636 | 1.00 | 0.00 | xxxx | 1929 |
| ATOM | 1930 | CA | THR | A | 251 | 36.671 | 56.458 | 154.313 | 1.00 | 0.00 | xxxx | 1930 |
| ATOM | 1931 | CB | THR | A | 251 | 35.837 | 57.756 | 154.403 | 1.00 | 0.00 | xxxx | 1931 |
| ATOM | 1932 | OG1 | THR | A | 251 | 36.531 | 58.731 | 155.198 | 1.00 | 0.00 | xxxx | 1932 |
| ATOM | 1933 | CG2 | THR | A | 251 | 34.449 | 57.472 | 154.995 | 1.00 | 0.00 | xxxx | 1933 |
| ATOM | 1934 | C | THR | A | 251 | 37.972 | 56.777 | 153.566 | 1.00 | 0.00 | xxxx | 1934 |
| ATOM | 1935 | O | THR | A | 251 | 37.973 | 56.923 | 152.346 | 1.00 | 0.00 | xxxx | 1935 |
| ATOM | 1936 | N | LEU | A | 252 | 39.070 | 56.900 | 154.306 | 1.00 | 0.00 | xxxx | 1936 |
| ATOM | 1937 | CA | LEU | A | 252 | 40.393 | 57.080 | 153.715 | 1.00 | 0.00 | xxxx | 1937 |
| ATOM | 1938 | CB | LEU | A | 252 | 41.089 | 58.317 | 154.297 | 1.00 | 0.00 | xxxx | 1938 |
| ATOM | 1939 | CG | LEU | A | 252 | 42.427 | 58.752 | 153.692 | 1.00 | 0.00 | xxxx | 1939 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 1940 | CD1 | LEU | A | 252 | 42.273 | 59.128 | 152.211 | 1.00 | 0.00 | xxxx | 1940 |
| ATOM | 1941 | CD2 | LEU | A | 252 | 43.008 | 59.929 | 154.472 | 1.00 | 0.00 | xxxx | 1941 |
| ATOM | 1942 | C | LEU | A | 252 | 41.195 | 55.812 | 153.989 | 1.00 | 0.00 | xxxx | 1942 |
| ATOM | 1943 | O | LEU | A | 252 | 41.347 | 55.412 | 155.139 | 1.00 | 0.00 | xxxx | 1943 |
| ATOM | 1944 | N | LEU | A | 253 | 41.685 | 55.169 | 152.934 | 1.00 | 0.00 | xxxx | 1944 |
| ATOM | 1945 | CA | LEU | A | 253 | 42.397 | 53.903 | 153.086 | 1.00 | 0.00 | xxxx | 1945 |
| ATOM | 1946 | CB | LEU | A | 253 | 42.601 | 53.240 | 151.717 | 1.00 | 0.00 | xxxx | 1946 |
| ATOM | 1947 | CG | LEU | A | 253 | 43.518 | 52.011 | 151.707 | 1.00 | 0.00 | xxxx | 1947 |
| ATOM | 1948 | CD1 | LEU | A | 253 | 42.917 | 50.848 | 152.514 | 1.00 | 0.00 | xxxx | 1948 |
| ATOM | 1949 | CD2 | LEU | A | 253 | 43.811 | 51.593 | 150.278 | 1.00 | 0.00 | xxxx | 1949 |
| ATOM | 1950 | C | LEU | A | 253 | 43.742 | 54.105 | 153.776 | 1.00 | 0.00 | xxxx | 1950 |
| ATOM | 1951 | O | LEU | A | 253 | 44.149 | 53.333 | 154.648 | 1.00 | 0.00 | xxxx | 1951 |
| ATOM | 1952 | N | GLY | A | 254 | 44.441 | 55.157 | 153.389 | 1.00 | 0.00 | xxxx | 1952 |
| ATOM | 1953 | CA | GLY | A | 254 | 45.749 | 55.381 | 153.958 | 1.00 | 0.00 | xxxx | 1953 |
| ATOM | 1954 | C | GLY | A | 254 | 46.259 | 56.739 | 153.579 | 1.00 | 0.00 | xxxx | 1954 |
| ATOM | 1955 | O | GLY | A | 254 | 45.695 | 57.409 | 152.710 | 1.00 | 0.00 | xxxx | 1955 |
| ATOM | 1956 | N | THR | A | 255 | 47.328 | 57.144 | 154.249 | 1.00 | 0.00 | xxxx | 1956 |
| ATOM | 1957 | CA | THR | A | 255 | 47.980 | 58.395 | 153.941 | 1.00 | 0.00 | xxxx | 1957 |
| ATOM | 1958 | CB | THR | A | 255 | 47.293 | 59.602 | 154.650 | 1.00 | 0.00 | xxxx | 1958 |
| ATOM | 1959 | OG1 | THR | A | 255 | 47.875 | 60.829 | 154.206 | 1.00 | 0.00 | xxxx | 1959 |
| ATOM | 1960 | CG2 | THR | A | 255 | 47.392 | 59.517 | 156.170 | 1.00 | 0.00 | xxxx | 1960 |
| ATOM | 1961 | C | THR | A | 255 | 49.445 | 58.255 | 154.340 | 1.00 | 0.00 | xxxx | 1961 |
| ATOM | 1962 | O | THR | A | 255 | 49.913 | 57.156 | 154.636 | 1.00 | 0.00 | xxxx | 1962 |
| ATOM | 1963 | N | VAL | A | 256 | 50.169 | 59.363 | 154.283 | 1.00 | 0.00 | xxxx | 1963 |
| ATOM | 1964 | CA | VAL | A | 256 | 51.593 | 59.376 | 154.584 | 1.00 | 0.00 | xxxx | 1964 |
| ATOM | 1965 | CB | VAL | A | 256 | 52.434 | 59.484 | 153.297 | 1.00 | 0.00 | xxxx | 1965 |
| ATOM | 1966 | CG1 | VAL | A | 256 | 53.924 | 59.449 | 153.622 | 1.00 | 0.00 | xxxx | 1966 |
| ATOM | 1967 | CG2 | VAL | A | 256 | 52.054 | 58.386 | 152.302 | 1.00 | 0.00 | xxxx | 1967 |
| ATOM | 1968 | C | VAL | A | 256 | 51.827 | 60.559 | 155.495 | 1.00 | 0.00 | xxxx | 1968 |
| ATOM | 1969 | O | VAL | A | 256 | 51.471 | 61.677 | 155.149 | 1.00 | 0.00 | xxxx | 1969 |
| ATOM | 1970 | N | LEU | A | 257 | 52.399 | 60.316 | 156.668 | 1.00 | 0.00 | xxxx | 1970 |
| ATOM | 1971 | CA | LEU | A | 257 | 52.679 | 61.405 | 157.585 | 1.00 | 0.00 | xxxx | 1971 |
| ATOM | 1972 | CB | LEU | A | 257 | 53.143 | 60.875 | 158.938 | 1.00 | 0.00 | xxxx | 1972 |
| ATOM | 1973 | CG | LEU | A | 257 | 53.668 | 61.969 | 159.872 | 1.00 | 0.00 | xxxx | 1973 |
| ATOM | 1974 | CD1 | LEU | A | 257 | 52.555 | 62.938 | 160.270 | 1.00 | 0.00 | xxxx | 1974 |
| ATOM | 1975 | CD2 | LEU | A | 257 | 54.331 | 61.346 | 161.102 | 1.00 | 0.00 | xxxx | 1975 |
| ATOM | 1976 | C | LEU | A | 257 | 53.734 | 62.335 | 157.011 | 1.00 | 0.00 | xxxx | 1976 |
| ATOM | 1977 | O | LEU | A | 257 | 54.852 | 61.915 | 156.704 | 1.00 | 0.00 | xxxx | 1977 |
| ATOM | 1978 | N | ASN | A | 258 | 53.348 | 63.593 | 156.841 | 1.00 | 0.00 | xxxx | 1978 |
| ATOM | 1979 | CA | ASN | A | 258 | 54.252 | 64.663 | 156.459 | 1.00 | 0.00 | xxxx | 1979 |
| ATOM | 1980 | CB | ASN | A | 258 | 53.592 | 65.620 | 155.458 | 1.00 | 0.00 | xxxx | 1980 |
| ATOM | 1981 | CG | ASN | A | 258 | 54.584 | 66.574 | 154.797 | 1.00 | 0.00 | xxxx | 1981 |
| ATOM | 1982 | OD1 | ASN | A | 258 | 55.805 | 66.410 | 154.900 | 1.00 | 0.00 | xxxx | 1982 |
| ATOM | 1983 | ND2 | ASN | A | 258 | 54.054 | 67.560 | 154.084 | 1.00 | 0.00 | xxxx | 1983 |
| ATOM | 1984 | C | ASN | A | 258 | 54.577 | 65.344 | 157.771 | 1.00 | 0.00 | xxxx | 1984 |
| ATOM | 1985 | O | ASN | A | 258 | 53.705 | 65.942 | 158.400 | 1.00 | 0.00 | xxxx | 1985 |
| ATOM | 1986 | N | ASP | A | 259 | 55.822 | 65.207 | 158.207 | 1.00 | 0.00 | xxxx | 1986 |
| ATOM | 1987 | CA | ASP | A | 259 | 56.197 | 65.545 | 159.576 | 1.00 | 0.00 | xxxx | 1987 |
| ATOM | 1988 | CB | ASP | A | 259 | 57.455 | 64.762 | 159.955 | 1.00 | 0.00 | xxxx | 1988 |
| ATOM | 1989 | CG | ASP | A | 259 | 57.789 | 64.844 | 161.431 | 1.00 | 0.00 | xxxx | 1989 |
| ATOM | 1990 | OD1 | ASP | A | 259 | 57.216 | 65.690 | 162.151 | 1.00 | 0.00 | xxxx | 1990 |
| ATOM | 1991 | OD2 | ASP | A | 259 | 58.660 | 64.056 | 161.860 | 1.00 | 0.00 | xxxx | 1991 |
| ATOM | 1992 | C | ASP | A | 259 | 56.415 | 67.048 | 159.739 | 1.00 | 0.00 | xxxx | 1992 |
| ATOM | 1993 | O | ASP | A | 259 | 57.549 | 67.531 | 159.710 | 1.00 | 0.00 | xxxx | 1993 |
| ATOM | 1994 | N | ALA | A | 260 | 55.314 | 67.772 | 159.923 | 1.00 | 0.00 | xxxx | 1994 |
| ATOM | 1995 | CA | ALA | A | 260 | 55.334 | 69.218 | 160.026 | 1.00 | 0.00 | xxxx | 1995 |
| ATOM | 1996 | CB | ALA | A | 260 | 53.903 | 69.762 | 160.105 | 1.00 | 0.00 | xxxx | 1996 |
| ATOM | 1997 | C | ALA | A | 260 | 56.135 | 69.680 | 161.231 | 1.00 | 0.00 | xxxx | 1997 |
| ATOM | 1998 | O | ALA | A | 260 | 56.814 | 70.704 | 161.175 | 1.00 | 0.00 | xxxx | 1998 |
| ATOM | 1999 | N | LYS | A | 261 | 56.045 | 68.940 | 162.330 | 1.00 | 0.00 | xxxx | 1999 |
| ATOM | 2000 | CA | LYS | A | 261 | 56.710 | 69.369 | 163.549 | 1.00 | 0.00 | xxxx | 2000 |
| ATOM | 2001 | CB | LYS | A | 261 | 56.311 | 68.484 | 164.731 | 1.00 | 0.00 | xxxx | 2001 |
| ATOM | 2002 | CG | LYS | A | 261 | 54.865 | 68.702 | 165.160 | 1.00 | 0.00 | xxxx | 2002 |
| ATOM | 2003 | CD | LYS | A | 261 | 54.537 | 68.016 | 166.478 | 1.00 | 0.00 | xxxx | 2003 |
| ATOM | 2004 | CE | LYS | A | 261 | 53.071 | 68.221 | 166.846 | 1.00 | 0.00 | xxxx | 2004 |
| ATOM | 2005 | NZ | LYS | A | 261 | 52.725 | 67.634 | 168.170 | 1.00 | 0.00 | xxxx | 2005 |
| ATOM | 2006 | C | LYS | A | 261 | 58.224 | 69.387 | 163.372 | 1.00 | 0.00 | xxxx | 2006 |
| ATOM | 2007 | O | LYS | A | 261 | 58.870 | 70.364 | 163.743 | 1.00 | 0.00 | xxxx | 2007 |
| ATOM | 2008 | N | ASN | A | 262 | 58.800 | 68.333 | 162.797 | 1.00 | 0.00 | xxxx | 2008 |
| ATOM | 2009 | CA | ASN | A | 262 | 60.248 | 68.328 | 162.610 | 1.00 | 0.00 | xxxx | 2009 |
| ATOM | 2010 | CB | ASN | A | 262 | 60.767 | 66.905 | 162.398 | 1.00 | 0.00 | xxxx | 2010 |
| ATOM | 2011 | CG | ASN | A | 262 | 60.950 | 66.161 | 163.715 | 1.00 | 0.00 | xxxx | 2011 |
| ATOM | 2012 | OD1 | ASN | A | 262 | 61.734 | 66.572 | 164.571 | 1.00 | 0.00 | xxxx | 2012 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 2013 | ND2 | ASN | A | 262 | 60.231 | 65.060 | 163.878 | 1.00 | 0.00 | xxxx | 2013 |
| ATOM | 2014 | C | ASN | A | 262 | 60.688 | 69.230 | 161.460 | 1.00 | 0.00 | xxxx | 2014 |
| ATOM | 2015 | O | ASN | A | 262 | 61.773 | 69.810 | 161.513 | 1.00 | 0.00 | xxxx | 2015 |
| ATOM | 2016 | N | GLN | A | 263 | 59.846 | 69.388 | 160.444 | 1.00 | 0.00 | xxxx | 2016 |
| ATOM | 2017 | CA | GLN | A | 263 | 60.182 | 70.338 | 159.392 | 1.00 | 0.00 | xxxx | 2017 |
| ATOM | 2018 | CB | GLN | A | 263 | 59.218 | 70.222 | 158.212 | 1.00 | 0.00 | xxxx | 2018 |
| ATOM | 2019 | CG | GLN | A | 263 | 59.489 | 68.968 | 157.391 | 1.00 | 0.00 | xxxx | 2019 |
| ATOM | 2020 | CD | GLN | A | 263 | 58.548 | 68.809 | 156.221 | 1.00 | 0.00 | xxxx | 2020 |
| ATOM | 2021 | OE1 | GLN | A | 263 | 58.355 | 69.734 | 155.431 | 1.00 | 0.00 | xxxx | 2021 |
| ATOM | 2022 | NE2 | GLN | A | 263 | 57.948 | 67.632 | 156.107 | 1.00 | 0.00 | xxxx | 2022 |
| ATOM | 2023 | C | GLN | A | 263 | 60.197 | 71.754 | 159.974 | 1.00 | 0.00 | xxxx | 2023 |
| ATOM | 2024 | O | GLN | A | 263 | 61.091 | 72.548 | 159.664 | 1.00 | 0.00 | xxxx | 2024 |
| ATOM | 2025 | N | ALA | A | 264 | 59.242 | 72.058 | 160.852 | 1.00 | 0.00 | xxxx | 2025 |
| ATOM | 2026 | CA | ALA | A | 264 | 59.205 | 73.371 | 161.488 | 1.00 | 0.00 | xxxx | 2026 |
| ATOM | 2027 | CB | ALA | A | 264 | 57.929 | 73.540 | 162.298 | 1.00 | 0.00 | xxxx | 2027 |
| ATOM | 2028 | C | ALA | A | 264 | 60.423 | 73.593 | 162.385 | 1.00 | 0.00 | xxxx | 2028 |
| ATOM | 2029 | O | ALA | A | 264 | 61.001 | 74.682 | 162.396 | 1.00 | 0.00 | xxxx | 2029 |
| ATOM | 2030 | N | LYS | A | 265 | 60.797 | 72.576 | 163.158 | 1.00 | 0.00 | xxxx | 2030 |
| ATOM | 2031 | C | LYS | A | 265 | 63.235 | 72.909 | 163.247 | 1.00 | 0.00 | xxxx | 2031 |
| ATOM | 2032 | O | LYS | A | 265 | 64.056 | 73.762 | 163.597 | 1.00 | 0.00 | xxxx | 2032 |
| ATOM | 2033 | CA | LYS | A | 265 | 61.955 | 72.688 | 164.042 | 1.00 | 0.00 | xxxx | 2033 |
| ATOM | 2034 | CB | LYS | A | 265 | 62.109 | 71.443 | 164.921 | 1.00 | 0.00 | xxxx | 2034 |
| ATOM | 2035 | CG | LYS | A | 265 | 60.962 | 71.194 | 165.866 | 1.00 | 0.00 | xxxx | 2035 |
| ATOM | 2036 | CD | LYS | A | 265 | 61.328 | 70.146 | 166.902 | 1.00 | 0.00 | xxxx | 2036 |
| ATOM | 2037 | CE | LYS | A | 265 | 60.117 | 69.716 | 167.711 | 1.00 | 0.00 | xxxx | 2037 |
| ATOM | 2038 | NZ | LYS | A | 265 | 60.514 | 68.939 | 168.913 | 1.00 | 0.00 | xxxx | 2038 |
| ATOM | 2039 | N | ALA | A | 266 | 63.409 | 72.146 | 162.171 | 1.00 | 0.00 | xxxx | 2039 |
| ATOM | 2040 | CA | ALA | A | 266 | 64.607 | 72.292 | 161.350 | 1.00 | 0.00 | xxxx | 2040 |
| ATOM | 2041 | CB | ALA | A | 266 | 64.661 | 71.209 | 160.261 | 1.00 | 0.00 | xxxx | 2041 |
| ATOM | 2042 | C | ALA | A | 266 | 64.656 | 73.682 | 160.727 | 1.00 | 0.00 | xxxx | 2042 |
| ATOM | 2043 | O | ALA | A | 266 | 65.702 | 74.325 | 160.708 | 1.00 | 0.00 | xxxx | 2043 |
| ATOM | 2044 | N | THR | A | 267 | 63.519 | 74.139 | 160.214 | 1.00 | 0.00 | xxxx | 2044 |
| ATOM | 2045 | CA | THR | A | 267 | 63.451 | 75.457 | 159.590 | 1.00 | 0.00 | xxxx | 2045 |
| ATOM | 2046 | CB | THR | A | 267 | 62.071 | 75.717 | 158.972 | 1.00 | 0.00 | xxxx | 2046 |
| ATOM | 2047 | OG1 | THR | A | 267 | 61.793 | 74.702 | 158.001 | 1.00 | 0.00 | xxxx | 2047 |
| ATOM | 2048 | CG2 | THR | A | 267 | 62.050 | 77.087 | 158.298 | 1.00 | 0.00 | xxxx | 2048 |
| ATOM | 2049 | C | THR | A | 267 | 63.769 | 76.550 | 160.594 | 1.00 | 0.00 | xxxx | 2049 |
| ATOM | 2050 | O | THR | A | 267 | 64.613 | 77.413 | 160.341 | 1.00 | 0.00 | xxxx | 2050 |
| ATOM | 2051 | N | PHE | A | 268 | 63.097 | 76.514 | 161.739 | 1.00 | 0.00 | xxxx | 2051 |
| ATOM | 2052 | CA | PHE | A | 268 | 63.396 | 77.493 | 162.764 | 1.00 | 0.00 | xxxx | 2052 |
| ATOM | 2053 | CB | PHE | A | 268 | 62.517 | 77.332 | 164.001 | 1.00 | 0.00 | xxxx | 2053 |
| ATOM | 2054 | CG | PHE | A | 268 | 62.907 | 78.279 | 165.090 | 1.00 | 0.00 | xxxx | 2054 |
| ATOM | 2055 | CD1 | PHE | A | 268 | 62.579 | 79.619 | 164.989 | 1.00 | 0.00 | xxxx | 2055 |
| ATOM | 2056 | CE1 | PHE | A | 268 | 62.971 | 80.513 | 165.958 | 1.00 | 0.00 | xxxx | 2056 |
| ATOM | 2057 | CZ | PHE | A | 268 | 63.722 | 80.073 | 167.033 | 1.00 | 0.00 | xxxx | 2057 |
| ATOM | 2058 | CE2 | PHE | A | 268 | 64.076 | 78.746 | 167.131 | 1.00 | 0.00 | xxxx | 2058 |
| ATOM | 2059 | CD2 | PHE | A | 268 | 63.679 | 77.855 | 166.161 | 1.00 | 0.00 | xxxx | 2059 |
| ATOM | 2060 | C | PHE | A | 268 | 64.858 | 77.423 | 163.204 | 1.00 | 0.00 | xxxx | 2060 |
| ATOM | 2061 | O | PHE | A | 268 | 65.507 | 78.456 | 163.318 | 1.00 | 0.00 | xxxx | 2061 |
| ATOM | 2062 | N | ASN | A | 269 | 65.367 | 76.219 | 163.467 | 1.00 | 0.00 | xxxx | 2062 |
| ATOM | 2063 | CA | ASN | A | 269 | 66.732 | 76.097 | 163.977 | 1.00 | 0.00 | xxxx | 2063 |
| ATOM | 2064 | CB | ASN | A | 269 | 67.074 | 74.636 | 164.290 | 1.00 | 0.00 | xxxx | 2064 |
| ATOM | 2065 | CG | ASN | A | 269 | 66.398 | 74.148 | 165.556 | 1.00 | 0.00 | xxxx | 2065 |
| ATOM | 2066 | OD1 | ASN | A | 269 | 65.773 | 74.931 | 166.270 | 1.00 | 0.00 | xxxx | 2066 |
| ATOM | 2067 | ND2 | ASN | A | 269 | 66.531 | 72.858 | 165.852 | 1.00 | 0.00 | xxxx | 2067 |
| ATOM | 2068 | C | ASN | A | 269 | 67.744 | 76.682 | 162.996 | 1.00 | 0.00 | xxxx | 2068 |
| ATOM | 2069 | O | ASN | A | 269 | 68.693 | 77.350 | 163.408 | 1.00 | 0.00 | xxxx | 2069 |
| ATOM | 2070 | N | ILE | A | 270 | 67.527 | 76.457 | 161.705 | 1.00 | 0.00 | xxxx | 2070 |
| ATOM | 2071 | CA | ILE | A | 270 | 68.428 | 77.004 | 160.704 | 1.00 | 0.00 | xxxx | 2071 |
| ATOM | 2072 | CB | ILE | A | 270 | 68.120 | 76.434 | 159.308 | 1.00 | 0.00 | xxxx | 2072 |
| ATOM | 2073 | CG1 | ILE | A | 270 | 68.529 | 74.959 | 159.220 | 1.00 | 0.00 | xxxx | 2073 |
| ATOM | 2074 | CD1 | ILE | A | 270 | 68.081 | 74.296 | 157.903 | 1.00 | 0.00 | xxxx | 2074 |
| ATOM | 2075 | CG2 | ILE | A | 270 | 68.811 | 77.279 | 158.217 | 1.00 | 0.00 | xxxx | 2075 |
| ATOM | 2076 | C | ILE | A | 270 | 68.360 | 78.532 | 160.701 | 1.00 | 0.00 | xxxx | 2076 |
| ATOM | 2077 | O | ILE | A | 270 | 69.394 | 79.200 | 160.723 | 1.00 | 0.00 | xxxx | 2077 |
| ATOM | 2078 | N | ALA | A | 271 | 67.148 | 79.083 | 160.699 | 1.00 | 0.00 | xxxx | 2078 |
| ATOM | 2079 | CA | ALA | A | 271 | 66.969 | 80.538 | 160.675 | 1.00 | 0.00 | xxxx | 2079 |
| ATOM | 2080 | CB | ALA | A | 271 | 65.482 | 80.900 | 160.547 | 1.00 | 0.00 | xxxx | 2080 |
| ATOM | 2081 | C | ALA | A | 271 | 67.569 | 81.163 | 161.928 | 1.00 | 0.00 | xxxx | 2081 |
| ATOM | 2082 | O | ALA | A | 271 | 68.144 | 82.248 | 161.877 | 1.00 | 0.00 | xxxx | 2082 |
| ATOM | 2083 | N | TYR | A | 272 | 67.439 | 80.457 | 163.047 | 1.00 | 0.00 | xxxx | 2083 |
| ATOM | 2084 | CA | TYR | A | 272 | 67.902 | 80.941 | 164.340 | 1.00 | 0.00 | xxxx | 2084 |
| ATOM | 2085 | CB | TYR | A | 272 | 67.345 | 80.034 | 165.445 | 1.00 | 0.00 | xxxx | 2085 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 2086 | CG | TYR | A | 272 | 67.624 | 80.441 | 166.876 | 1.00 | 0.00 | xxxx | 2086 |
| ATOM | 2087 | CD1 | TYR | A | 272 | 67.292 | 81.704 | 167.345 | 1.00 | 0.00 | xxxx | 2087 |
| ATOM | 2088 | CE1 | TYR | A | 272 | 67.527 | 82.060 | 168.663 | 1.00 | 0.00 | xxxx | 2088 |
| ATOM | 2089 | CZ | TYR | A | 272 | 68.082 | 81.142 | 169.528 | 1.00 | 0.00 | xxxx | 2089 |
| ATOM | 2090 | OH | TYR | A | 272 | 68.318 | 81.500 | 170.838 | 1.00 | 0.00 | xxxx | 2090 |
| ATOM | 2091 | CE2 | TYR | A | 272 | 68.407 | 79.877 | 169.092 | 1.00 | 0.00 | xxxx | 2091 |
| ATOM | 2092 | CD2 | TYR | A | 272 | 68.165 | 79.529 | 167.773 | 1.00 | 0.00 | xxxx | 2092 |
| ATOM | 2093 | C | TYR | A | 272 | 69.426 | 80.990 | 164.382 | 1.00 | 0.00 | xxxx | 2093 |
| ATOM | 2094 | O | TYR | A | 272 | 70.008 | 81.970 | 164.852 | 1.00 | 0.00 | xxxx | 2094 |
| ATOM | 2095 | N | GLU | A | 273 | 70.076 | 79.939 | 163.879 | 1.00 | 0.00 | xxxx | 2095 |
| ATOM | 2096 | CA | GLU | A | 273 | 71.533 | 79.939 | 163.820 | 1.00 | 0.00 | xxxx | 2096 |
| ATOM | 2097 | CB | GLU | A | 273 | 72.076 | 78.576 | 163.385 | 1.00 | 0.00 | xxxx | 2097 |
| ATOM | 2098 | CG | GLU | A | 273 | 71.808 | 77.455 | 164.387 | 1.00 | 0.00 | xxxx | 2098 |
| ATOM | 2099 | CD | GLU | A | 273 | 72.396 | 77.727 | 165.771 | 1.00 | 0.00 | xxxx | 2099 |
| ATOM | 2100 | OE1 | GLU | A | 273 | 73.574 | 78.132 | 165.864 | 1.00 | 0.00 | xxxx | 2100 |
| ATOM | 2101 | OE2 | GLU | A | 273 | 71.674 | 77.533 | 166.771 | 1.00 | 0.00 | xxxx | 2101 |
| ATOM | 2102 | C | GLU | A | 273 | 72.017 | 81.037 | 162.873 | 1.00 | 0.00 | xxxx | 2102 |
| ATOM | 2103 | O | GLU | A | 273 | 72.927 | 81.795 | 163.210 | 1.00 | 0.00 | xxxx | 2103 |
| ATOM | 2104 | N | LEU | A | 274 | 71.394 | 81.136 | 161.701 | 1.00 | 0.00 | xxxx | 2104 |
| ATOM | 2105 | CA | LEU | A | 274 | 71.817 | 82.128 | 160.715 | 1.00 | 0.00 | xxxx | 2105 |
| ATOM | 2106 | CB | LEU | A | 274 | 71.085 | 81.928 | 159.385 | 1.00 | 0.00 | xxxx | 2106 |
| ATOM | 2107 | CG | LEU | A | 274 | 71.476 | 80.692 | 158.562 | 1.00 | 0.00 | xxxx | 2107 |
| ATOM | 2108 | CD1 | LEU | A | 274 | 70.465 | 80.446 | 157.451 | 1.00 | 0.00 | xxxx | 2108 |
| ATOM | 2109 | CD2 | LEU | A | 274 | 72.894 | 80.826 | 158.000 | 1.00 | 0.00 | xxxx | 2109 |
| ATOM | 2110 | C | LEU | A | 274 | 71.592 | 83.545 | 161.240 | 1.00 | 0.00 | xxxx | 2110 |
| ATOM | 2111 | O | LEU | A | 274 | 72.384 | 84.450 | 160.968 | 1.00 | 0.00 | xxxx | 2111 |
| ATOM | 2112 | N | ALA | A | 275 | 70.533 | 83.727 | 162.023 | 1.00 | 0.00 | xxxx | 2112 |
| ATOM | 2113 | CA | ALA | A | 275 | 70.234 | 85.034 | 162.599 | 1.00 | 0.00 | xxxx | 2113 |
| ATOM | 2114 | CB | ALA | A | 275 | 68.877 | 85.021 | 163.283 | 1.00 | 0.00 | xxxx | 2114 |
| ATOM | 2115 | C | ALA | A | 275 | 71.323 | 85.449 | 163.585 | 1.00 | 0.00 | xxxx | 2115 |
| ATOM | 2116 | O | ALA | A | 275 | 71.541 | 86.641 | 163.813 | 1.00 | 0.00 | xxxx | 2116 |
| ATOM | 2117 | N | GLN | A | 276 | 71.997 | 84.458 | 164.165 | 1.00 | 0.00 | xxxx | 2117 |
| ATOM | 2118 | CA | GLN | A | 276 | 73.079 | 84.706 | 165.120 | 1.00 | 0.00 | xxxx | 2118 |
| ATOM | 2119 | CB | GLN | A | 276 | 73.124 | 83.613 | 166.189 | 1.00 | 0.00 | xxxx | 2119 |
| ATOM | 2120 | CG | GLN | A | 276 | 71.901 | 83.542 | 167.092 | 1.00 | 0.00 | xxxx | 2120 |
| ATOM | 2121 | CD | GLN | A | 276 | 71.914 | 82.318 | 167.986 | 1.00 | 0.00 | xxxx | 2121 |
| ATOM | 2122 | OE1 | GLN | A | 276 | 71.240 | 81.323 | 167.708 | 1.00 | 0.00 | xxxx | 2122 |
| ATOM | 2123 | NE2 | GLN | A | 276 | 72.690 | 82.381 | 169.066 | 1.00 | 0.00 | xxxx | 2123 |
| ATOM | 2124 | C | GLN | A | 276 | 74.442 | 84.790 | 164.440 | 1.00 | 0.00 | xxxx | 2124 |
| ATOM | 2125 | O | GLN | A | 276 | 75.461 | 84.971 | 165.110 | 1.00 | 0.00 | xxxx | 2125 |
| ATOM | 2126 | N | GLY | A | 277 | 74.461 | 84.662 | 163.119 | 1.00 | 0.00 | xxxx | 2126 |
| ATOM | 2127 | CA | GLY | A | 277 | 75.708 | 84.670 | 162.372 | 1.00 | 0.00 | xxxx | 2127 |
| ATOM | 2128 | C | GLY | A | 277 | 76.469 | 83.358 | 162.461 | 1.00 | 0.00 | xxxx | 2128 |
| ATOM | 2129 | O | GLY | A | 277 | 77.673 | 83.303 | 162.200 | 1.00 | 0.00 | xxxx | 2129 |
| ATOM | 2130 | N | ILE | A | 278 | 75.762 | 82.293 | 162.823 | 1.00 | 0.00 | xxxx | 2130 |
| ATOM | 2131 | CA | ILE | A | 278 | 76.368 | 80.971 | 162.968 | 1.00 | 0.00 | xxxx | 2131 |
| ATOM | 2132 | CB | ILE | A | 278 | 75.943 | 80.326 | 164.299 | 1.00 | 0.00 | xxxx | 2132 |
| ATOM | 2133 | CG1 | ILE | A | 278 | 76.389 | 81.209 | 165.470 | 1.00 | 0.00 | xxxx | 2133 |
| ATOM | 2134 | CD1 | ILE | A | 278 | 75.767 | 80.832 | 166.795 | 1.00 | 0.00 | xxxx | 2134 |
| ATOM | 2135 | CG2 | ILE | A | 278 | 76.495 | 78.904 | 164.424 | 1.00 | 0.00 | xxxx | 2135 |
| ATOM | 2136 | C | ILE | A | 278 | 75.998 | 80.078 | 161.782 | 1.00 | 0.00 | xxxx | 2136 |
| ATOM | 2137 | O | ILE | A | 278 | 74.836 | 80.015 | 161.380 | 1.00 | 0.00 | xxxx | 2137 |
| ATOM | 2138 | N | THR | A | 279 | 76.988 | 79.390 | 161.221 | 1.00 | 0.00 | xxxx | 2138 |
| ATOM | 2139 | CA | THR | A | 279 | 76.737 | 78.469 | 160.112 | 1.00 | 0.00 | xxxx | 2139 |
| ATOM | 2140 | CB | THR | A | 279 | 78.040 | 78.105 | 159.374 | 1.00 | 0.00 | xxxx | 2140 |
| ATOM | 2141 | OG1 | THR | A | 279 | 78.635 | 79.296 | 158.841 | 1.00 | 0.00 | xxxx | 2141 |
| ATOM | 2142 | CG2 | THR | A | 279 | 77.760 | 77.132 | 158.245 | 1.00 | 0.00 | xxxx | 2142 |
| ATOM | 2143 | C | THR | A | 279 | 76.078 | 77.186 | 160.609 | 1.00 | 0.00 | xxxx | 2143 |
| ATOM | 2144 | O | THR | A | 279 | 76.610 | 76.533 | 161.506 | 1.00 | 0.00 | xxxx | 2144 |
| ATOM | 2145 | N | PRO | A | 280 | 74.920 | 76.819 | 160.027 | 1.00 | 0.00 | xxxx | 2145 |
| ATOM | 2146 | CA | PRO | A | 280 | 74.256 | 75.568 | 160.417 | 1.00 | 0.00 | xxxx | 2146 |
| ATOM | 2147 | CB | PRO | A | 280 | 73.070 | 75.489 | 159.450 | 1.00 | 0.00 | xxxx | 2147 |
| ATOM | 2148 | CG | PRO | A | 280 | 72.751 | 76.924 | 159.144 | 1.00 | 0.00 | xxxx | 2148 |
| ATOM | 2149 | CD | PRO | A | 280 | 74.092 | 77.612 | 159.097 | 1.00 | 0.00 | xxxx | 2149 |
| ATOM | 2150 | C | PRO | A | 280 | 75.140 | 74.329 | 160.279 | 1.00 | 0.00 | xxxx | 2150 |
| ATOM | 2151 | O | PRO | A | 280 | 75.859 | 74.177 | 159.290 | 1.00 | 0.00 | xxxx | 2151 |
| ATOM | 2152 | N | THR | A | 281 | 75.102 | 73.472 | 161.295 | 1.00 | 0.00 | xxxx | 2152 |
| ATOM | 2153 | CA | THR | A | 281 | 75.739 | 72.155 | 161.265 | 1.00 | 0.00 | xxxx | 2153 |
| ATOM | 2154 | CB | THR | A | 281 | 77.009 | 72.086 | 162.122 | 1.00 | 0.00 | xxxx | 2154 |
| ATOM | 2155 | OG1 | THR | A | 281 | 76.650 | 72.211 | 163.503 | 1.00 | 0.00 | xxxx | 2155 |
| ATOM | 2156 | CG2 | THR | A | 281 | 77.978 | 73.199 | 161.759 | 1.00 | 0.00 | xxxx | 2156 |
| ATOM | 2157 | C | THR | A | 281 | 74.728 | 71.158 | 161.808 | 1.00 | 0.00 | xxxx | 2157 |
| ATOM | 2158 | O | THR | A | 281 | 73.770 | 71.560 | 162.466 | 1.00 | 0.00 | xxxx | 2158 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 2159 | N | LYS | A | 282 | 74.939 | 69.868 | 161.558 | 1.00 | 0.00 | xxxx | 2159 |
| ATOM | 2160 | CA | LYS | A | 282 | 74.074 | 68.851 | 162.146 | 1.00 | 0.00 | xxxx | 2160 |
| ATOM | 2161 | CB | LYS | A | 282 | 74.540 | 67.441 | 161.777 | 1.00 | 0.00 | xxxx | 2161 |
| ATOM | 2162 | CG | LYS | A | 282 | 73.709 | 66.356 | 162.445 | 1.00 | 0.00 | xxxx | 2162 |
| ATOM | 2163 | CD | LYS | A | 282 | 74.069 | 64.971 | 161.951 | 1.00 | 0.00 | xxxx | 2163 |
| ATOM | 2164 | CE | LYS | A | 282 | 73.131 | 63.935 | 162.548 | 1.00 | 0.00 | xxxx | 2164 |
| ATOM | 2165 | NZ | LYS | A | 282 | 73.423 | 62.568 | 162.033 | 1.00 | 0.00 | xxxx | 2165 |
| ATOM | 2166 | C | LYS | A | 282 | 74.026 | 68.995 | 163.667 | 1.00 | 0.00 | xxxx | 2166 |
| ATOM | 2167 | O | LYS | A | 282 | 72.974 | 68.811 | 164.278 | 1.00 | 0.00 | xxxx | 2167 |
| ATOM | 2168 | N | ASP | A | 283 | 75.156 | 69.342 | 164.274 | 1.00 | 0.00 | xxxx | 2168 |
| ATOM | 2169 | CA | ASP | A | 283 | 75.208 | 69.504 | 165.719 | 1.00 | 0.00 | xxxx | 2169 |
| ATOM | 2170 | CB | ASP | A | 283 | 76.646 | 69.739 | 166.193 | 1.00 | 0.00 | xxxx | 2170 |
| ATOM | 2171 | CG | ASP | A | 283 | 77.478 | 68.474 | 166.201 | 1.00 | 0.00 | xxxx | 2171 |
| ATOM | 2172 | OD1 | ASP | A | 283 | 76.920 | 67.381 | 165.965 | 1.00 | 0.00 | xxxx | 2172 |
| ATOM | 2173 | OD2 | ASP | A | 283 | 78.698 | 68.576 | 166.461 | 1.00 | 0.00 | xxxx | 2173 |
| ATOM | 2174 | C | ASP | A | 283 | 74.329 | 70.651 | 166.217 | 1.00 | 0.00 | xxxx | 2174 |
| ATOM | 2175 | O | ASP | A | 283 | 73.639 | 70.501 | 167.228 | 1.00 | 0.00 | xxxx | 2175 |
| ATOM | 2176 | N | ASN | A | 284 | 74.353 | 71.799 | 165.539 | 1.00 | 0.00 | xxxx | 2176 |
| ATOM | 2177 | CA | ASN | A | 284 | 73.670 | 72.962 | 166.110 | 1.00 | 0.00 | xxxx | 2177 |
| ATOM | 2178 | CB | ASN | A | 284 | 74.506 | 74.254 | 165.920 | 1.00 | 0.00 | xxxx | 2178 |
| ATOM | 2179 | CG | ASN | A | 284 | 74.696 | 74.658 | 164.461 | 1.00 | 0.00 | xxxx | 2179 |
| ATOM | 2180 | OD1 | ASN | A | 284 | 73.869 | 74.373 | 163.603 | 1.00 | 0.00 | xxxx | 2180 |
| ATOM | 2181 | ND2 | ASN | A | 284 | 75.793 | 75.361 | 164.188 | 1.00 | 0.00 | xxxx | 2181 |
| ATOM | 2182 | C | ASN | A | 284 | 72.237 | 73.163 | 165.593 | 1.00 | 0.00 | xxxx | 2182 |
| ATOM | 2183 | O | ASN | A | 284 | 71.515 | 73.997 | 166.135 | 1.00 | 0.00 | xxxx | 2183 |
| ATOM | 2184 | N | ILE | A | 285 | 71.805 | 72.403 | 164.581 | 1.00 | 0.00 | xxxx | 2184 |
| ATOM | 2185 | CA | ILE | A | 285 | 70.383 | 72.428 | 164.228 | 1.00 | 0.00 | xxxx | 2185 |
| ATOM | 2186 | CB | ILE | A | 285 | 70.154 | 72.786 | 162.739 | 1.00 | 0.00 | xxxx | 2186 |
| ATOM | 2187 | CG1 | ILE | A | 285 | 70.630 | 71.667 | 161.808 | 1.00 | 0.00 | xxxx | 2187 |
| ATOM | 2188 | CD1 | ILE | A | 285 | 70.062 | 71.779 | 160.390 | 1.00 | 0.00 | xxxx | 2188 |
| ATOM | 2189 | CG2 | ILE | A | 285 | 70.809 | 74.122 | 162.399 | 1.00 | 0.00 | xxxx | 2189 |
| ATOM | 2190 | C | ILE | A | 285 | 69.662 | 71.116 | 164.557 | 1.00 | 0.00 | xxxx | 2190 |
| ATOM | 2191 | O | ILE | A | 285 | 68.431 | 71.087 | 164.592 | 1.00 | 0.00 | xxxx | 2191 |
| ATOM | 2192 | N | GLY | A | 286 | 70.414 | 70.040 | 164.782 | 1.00 | 0.00 | xxxx | 2192 |
| ATOM | 2193 | CA | GLY | A | 286 | 69.830 | 68.779 | 165.210 | 1.00 | 0.00 | xxxx | 2193 |
| ATOM | 2194 | C | GLY | A | 286 | 69.321 | 67.841 | 164.134 | 1.00 | 0.00 | xxxx | 2194 |
| ATOM | 2195 | O | GLY | A | 286 | 68.576 | 66.908 | 164.437 | 1.00 | 0.00 | xxxx | 2195 |
| ATOM | 2196 | N | TYR | A | 287 | 69.718 | 68.088 | 162.883 | 1.00 | 0.00 | xxxx | 2196 |
| ATOM | 2197 | CA | TYR | A | 287 | 69.293 | 67.281 | 161.736 | 1.00 | 0.00 | xxxx | 2197 |
| ATOM | 2198 | CB | TYR | A | 287 | 68.093 | 67.922 | 161.026 | 1.00 | 0.00 | xxxx | 2198 |
| ATOM | 2199 | CG | TYR | A | 287 | 66.884 | 68.058 | 161.911 | 1.00 | 0.00 | xxxx | 2199 |
| ATOM | 2200 | CD1 | TYR | A | 287 | 66.708 | 69.188 | 162.701 | 1.00 | 0.00 | xxxx | 2200 |
| ATOM | 2201 | CE1 | TYR | A | 287 | 65.613 | 69.318 | 163.527 | 1.00 | 0.00 | xxxx | 2201 |
| ATOM | 2202 | CZ | TYR | A | 287 | 64.674 | 68.312 | 163.570 | 1.00 | 0.00 | xxxx | 2202 |
| ATOM | 2203 | OH | TYR | A | 287 | 63.586 | 68.449 | 164.405 | 1.00 | 0.00 | xxxx | 2203 |
| ATOM | 2204 | CE2 | TYR | A | 287 | 64.823 | 67.171 | 162.795 | 1.00 | 0.00 | xxxx | 2204 |
| ATOM | 2205 | CD2 | TYR | A | 287 | 65.923 | 67.052 | 161.965 | 1.00 | 0.00 | xxxx | 2205 |
| ATOM | 2206 | C | TYR | A | 287 | 70.428 | 67.138 | 160.738 | 1.00 | 0.00 | xxxx | 2206 |
| ATOM | 2207 | O | TYR | A | 287 | 71.245 | 68.048 | 160.609 | 1.00 | 0.00 | xxxx | 2207 |
| ATOM | 2208 | N | ASP | A | 288 | 70.469 | 66.004 | 160.034 | 1.00 | 0.00 | xxxx | 2208 |
| ATOM | 2209 | CA | ASP | A | 288 | 71.399 | 65.819 | 158.918 | 1.00 | 0.00 | xxxx | 2209 |
| ATOM | 2210 | CB | ASP | A | 288 | 71.210 | 64.445 | 158.269 | 1.00 | 0.00 | xxxx | 2210 |
| ATOM | 2211 | CG | ASP | A | 288 | 71.732 | 63.318 | 159.118 | 1.00 | 0.00 | xxxx | 2211 |
| ATOM | 2212 | OD1 | ASP | A | 288 | 72.927 | 63.343 | 159.473 | 1.00 | 0.00 | xxxx | 2212 |
| ATOM | 2213 | OD2 | ASP | A | 288 | 70.942 | 62.397 | 159.416 | 1.00 | 0.00 | xxxx | 2213 |
| ATOM | 2214 | C | ASP | A | 288 | 71.203 | 66.877 | 157.843 | 1.00 | 0.00 | xxxx | 2214 |
| ATOM | 2215 | O | ASP | A | 288 | 70.071 | 67.186 | 157.466 | 1.00 | 0.00 | xxxx | 2215 |
| ATOM | 2216 | N | ILE | A | 289 | 72.311 | 67.412 | 157.340 | 1.00 | 0.00 | xxxx | 2216 |
| ATOM | 2217 | CA | ILE | A | 289 | 72.280 | 68.351 | 156.219 | 1.00 | 0.00 | xxxx | 2217 |
| ATOM | 2218 | CB | ILE | A | 289 | 73.095 | 69.615 | 156.517 | 1.00 | 0.00 | xxxx | 2218 |
| ATOM | 2219 | CG1 | ILE | A | 289 | 72.558 | 70.310 | 157.769 | 1.00 | 0.00 | xxxx | 2219 |
| ATOM | 2220 | CD1 | ILE | A | 289 | 73.458 | 71.434 | 158.271 | 1.00 | 0.00 | xxxx | 2220 |
| ATOM | 2221 | CG2 | ILE | A | 289 | 73.059 | 70.575 | 155.321 | 1.00 | 0.00 | xxxx | 2221 |
| ATOM | 2222 | C | ILE | A | 289 | 72.810 | 67.618 | 154.995 | 1.00 | 0.00 | xxxx | 2222 |
| ATOM | 2223 | O | ILE | A | 289 | 73.862 | 66.978 | 155.052 | 1.00 | 0.00 | xxxx | 2223 |
| ATOM | 2224 | N | THR | A | 290 | 72.066 | 67.701 | 153.898 | 1.00 | 0.00 | xxxx | 2224 |
| ATOM | 2225 | CA | THR | A | 290 | 72.393 | 66.983 | 152.668 | 1.00 | 0.00 | xxxx | 2225 |
| ATOM | 2226 | CB | THR | A | 290 | 71.173 | 66.165 | 152.178 | 1.00 | 0.00 | xxxx | 2226 |
| ATOM | 2227 | OG1 | THR | A | 290 | 70.769 | 65.253 | 153.204 | 1.00 | 0.00 | xxxx | 2227 |
| ATOM | 2228 | CG2 | THR | A | 290 | 71.496 | 65.377 | 150.909 | 1.00 | 0.00 | xxxx | 2228 |
| ATOM | 2229 | C | THR | A | 290 | 72.829 | 67.970 | 151.588 | 1.00 | 0.00 | xxxx | 2229 |
| ATOM | 2230 | O | THR | A | 290 | 72.252 | 69.046 | 151.462 | 1.00 | 0.00 | xxxx | 2230 |
| ATOM | 2231 | N | ASP | A | 291 | 73.872 | 67.620 | 150.841 | 1.00 | 0.00 | xxxx | 2231 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 2232 | CA | ASP | A | 291 | 74.367 | 68.479 | 149.764 | 1.00 | 0.00 | xxxx | 2232 |
| ATOM | 2233 | CB | ASP | A | 291 | 73.338 | 68.541 | 148.614 | 1.00 | 0.00 | xxxx | 2233 |
| ATOM | 2234 | CG | ASP | A | 291 | 73.206 | 67.219 | 147.865 | 1.00 | 0.00 | xxxx | 2234 |
| ATOM | 2235 | OD1 | ASP | A | 291 | 74.245 | 66.647 | 147.474 | 1.00 | 0.00 | xxxx | 2235 |
| ATOM | 2236 | OD2 | ASP | A | 291 | 72.065 | 66.754 | 147.659 | 1.00 | 0.00 | xxxx | 2236 |
| ATOM | 2237 | C | ASP | A | 291 | 74.696 | 69.891 | 150.274 | 1.00 | 0.00 | xxxx | 2237 |
| ATOM | 2238 | O | ASP | A | 291 | 74.624 | 70.873 | 149.532 | 1.00 | 0.00 | xxxx | 2238 |
| ATOM | 2239 | N | GLY | A | 292 | 75.068 | 69.984 | 151.546 | 1.00 | 0.00 | xxxx | 2239 |
| ATOM | 2240 | CA | GLY | A | 292 | 75.441 | 71.251 | 152.152 | 1.00 | 0.00 | xxxx | 2240 |
| ATOM | 2241 | C | GLY | A | 292 | 74.328 | 72.257 | 152.390 | 1.00 | 0.00 | xxxx | 2241 |
| ATOM | 2242 | O | GLY | A | 292 | 74.558 | 73.299 | 153.006 | 1.00 | 0.00 | xxxx | 2242 |
| ATOM | 2243 | N | LYS | A | 293 | 73.118 | 71.958 | 151.920 | 1.00 | 0.00 | xxxx | 2243 |
| ATOM | 2244 | CA | LYS | A | 293 | 72.054 | 72.963 | 151.908 | 1.00 | 0.00 | xxxx | 2244 |
| ATOM | 2245 | CB | LYS | A | 293 | 71.920 | 73.565 | 150.505 | 1.00 | 0.00 | xxxx | 2245 |
| ATOM | 2246 | CG | LYS | A | 293 | 73.118 | 74.371 | 150.044 | 1.00 | 0.00 | xxxx | 2246 |
| ATOM | 2247 | CD | LYS | A | 293 | 72.954 | 74.836 | 148.612 | 1.00 | 0.00 | xxxx | 2247 |
| ATOM | 2248 | CE | LYS | A | 293 | 74.246 | 75.471 | 148.090 | 1.00 | 0.00 | xxxx | 2248 |
| ATOM | 2249 | NZ | LYS | A | 293 | 74.399 | 76.899 | 148.510 | 1.00 | 0.00 | xxxx | 2249 |
| ATOM | 2250 | C | LYS | A | 293 | 70.676 | 72.474 | 152.330 | 1.00 | 0.00 | xxxx | 2250 |
| ATOM | 2251 | O | LYS | A | 293 | 69.810 | 73.296 | 152.635 | 1.00 | 0.00 | xxxx | 2251 |
| ATOM | 2252 | N | TYR | A | 294 | 70.456 | 71.161 | 152.316 | 1.00 | 0.00 | xxxx | 2252 |
| ATOM | 2253 | CA | TYR | A | 294 | 69.104 | 70.620 | 152.456 | 1.00 | 0.00 | xxxx | 2253 |
| ATOM | 2254 | CB | TYR | A | 294 | 68.762 | 69.680 | 151.294 | 1.00 | 0.00 | xxxx | 2254 |
| ATOM | 2255 | CG | TYR | A | 294 | 68.805 | 70.293 | 149.917 | 1.00 | 0.00 | xxxx | 2255 |
| ATOM | 2256 | CD1 | TYR | A | 294 | 69.996 | 70.361 | 149.205 | 1.00 | 0.00 | xxxx | 2256 |
| ATOM | 2257 | CE1 | TYR | A | 294 | 70.032 | 70.915 | 147.941 | 1.00 | 0.00 | xxxx | 2257 |
| ATOM | 2258 | CZ | TYR | A | 294 | 68.863 | 71.389 | 147.366 | 1.00 | 0.00 | xxxx | 2258 |
| ATOM | 2259 | OH | TYR | A | 294 | 68.908 | 71.929 | 146.098 | 1.00 | 0.00 | xxxx | 2259 |
| ATOM | 2260 | CE2 | TYR | A | 294 | 67.672 | 71.319 | 148.046 | 1.00 | 0.00 | xxxx | 2260 |
| ATOM | 2261 | CD2 | TYR | A | 294 | 67.651 | 70.777 | 149.318 | 1.00 | 0.00 | xxxx | 2261 |
| ATOM | 2262 | C | TYR | A | 294 | 68.910 | 69.839 | 153.739 | 1.00 | 0.00 | xxxx | 2262 |
| ATOM | 2263 | O | TYR | A | 294 | 69.782 | 69.065 | 154.135 | 1.00 | 0.00 | xxxx | 2263 |
| ATOM | 2264 | N | VAL | A | 295 | 67.751 | 70.013 | 154.365 | 1.00 | 0.00 | xxxx | 2264 |
| ATOM | 2265 | CA | VAL | A | 295 | 67.357 | 69.122 | 155.445 | 1.00 | 0.00 | xxxx | 2265 |
| ATOM | 2266 | CB | VAL | A | 295 | 67.101 | 69.874 | 156.749 | 1.00 | 0.00 | xxxx | 2266 |
| ATOM | 2267 | CG1 | VAL | A | 295 | 66.510 | 68.914 | 157.789 | 1.00 | 0.00 | xxxx | 2267 |
| ATOM | 2268 | CG2 | VAL | A | 295 | 68.402 | 70.504 | 157.263 | 1.00 | 0.00 | xxxx | 2268 |
| ATOM | 2269 | C | VAL | A | 295 | 66.116 | 68.350 | 155.008 | 1.00 | 0.00 | xxxx | 2269 |
| ATOM | 2270 | O | VAL | A | 295 | 65.059 | 68.939 | 154.769 | 1.00 | 0.00 | xxxx | 2270 |
| ATOM | 2271 | N | TRP | A | 296 | 66.274 | 67.037 | 154.876 | 1.00 | 0.00 | xxxx | 2271 |
| ATOM | 2272 | CA | TRP | A | 296 | 65.187 | 66.147 | 154.483 | 1.00 | 0.00 | xxxx | 2272 |
| ATOM | 2273 | CB | TRP | A | 296 | 65.668 | 65.135 | 153.441 | 1.00 | 0.00 | xxxx | 2273 |
| ATOM | 2274 | CG | TRP | A | 296 | 66.233 | 65.760 | 152.203 | 1.00 | 0.00 | xxxx | 2274 |
| ATOM | 2275 | CD1 | TRP | A | 296 | 67.529 | 65.712 | 151.778 | 1.00 | 0.00 | xxxx | 2275 |
| ATOM | 2276 | NE1 | TRP | A | 296 | 67.665 | 66.395 | 150.595 | 1.00 | 0.00 | xxxx | 2276 |
| ATOM | 2277 | CE2 | TRP | A | 296 | 66.449 | 66.922 | 150.244 | 1.00 | 0.00 | xxxx | 2277 |
| ATOM | 2278 | CD2 | TRP | A | 296 | 65.522 | 66.542 | 151.235 | 1.00 | 0.00 | xxxx | 2278 |
| ATOM | 2279 | CE3 | TRP | A | 296 | 64.192 | 66.955 | 151.110 | 1.00 | 0.00 | xxxx | 2279 |
| ATOM | 2280 | CZ3 | TRP | A | 296 | 63.831 | 67.718 | 150.011 | 1.00 | 0.00 | xxxx | 2280 |
| ATOM | 2281 | CH2 | TRP | A | 296 | 64.776 | 68.082 | 149.041 | 1.00 | 0.00 | xxxx | 2281 |
| ATOM | 2282 | CZ2 | TRP | A | 296 | 66.091 | 67.694 | 149.141 | 1.00 | 0.00 | xxxx | 2282 |
| ATOM | 2283 | C | TRP | A | 296 | 64.626 | 65.422 | 155.691 | 1.00 | 0.00 | xxxx | 2283 |
| ATOM | 2284 | O | TRP | A | 296 | 65.356 | 64.767 | 156.437 | 1.00 | 0.00 | xxxx | 2284 |
| ATOM | 2285 | N | ILE | A | 297 | 63.319 | 65.556 | 155.886 | 1.00 | 0.00 | xxxx | 2285 |
| ATOM | 2286 | CA | ILE | A | 297 | 62.625 | 64.918 | 156.991 | 1.00 | 0.00 | xxxx | 2286 |
| ATOM | 2287 | CB | ILE | A | 297 | 61.670 | 65.912 | 157.681 | 1.00 | 0.00 | xxxx | 2287 |
| ATOM | 2288 | CG1 | ILE | A | 297 | 62.442 | 67.139 | 158.205 | 1.00 | 0.00 | xxxx | 2288 |
| ATOM | 2289 | CD1 | ILE | A | 297 | 63.572 | 66.805 | 159.187 | 1.00 | 0.00 | xxxx | 2289 |
| ATOM | 2290 | CG2 | ILE | A | 297 | 60.875 | 65.225 | 158.779 | 1.00 | 0.00 | xxxx | 2290 |
| ATOM | 2291 | C | ILE | A | 297 | 61.860 | 63.716 | 156.435 | 1.00 | 0.00 | xxxx | 2291 |
| ATOM | 2292 | O | ILE | A | 297 | 61.168 | 63.845 | 155.428 | 1.00 | 0.00 | xxxx | 2292 |
| ATOM | 2293 | N | PRO | A | 298 | 61.994 | 62.544 | 157.072 | 1.00 | 0.00 | xxxx | 2293 |
| ATOM | 2294 | CA | PRO | A | 298 | 61.335 | 61.350 | 156.526 | 1.00 | 0.00 | xxxx | 2294 |
| ATOM | 2295 | CB | PRO | A | 298 | 61.776 | 60.232 | 157.476 | 1.00 | 0.00 | xxxx | 2295 |
| ATOM | 2296 | CG | PRO | A | 298 | 63.030 | 60.727 | 158.091 | 1.00 | 0.00 | xxxx | 2296 |
| ATOM | 2297 | CD | PRO | A | 298 | 62.879 | 62.218 | 158.201 | 1.00 | 0.00 | xxxx | 2297 |
| ATOM | 2298 | C | PRO | A | 298 | 59.814 | 61.425 | 156.506 | 1.00 | 0.00 | xxxx | 2298 |
| ATOM | 2299 | O | PRO | A | 298 | 59.187 | 62.048 | 157.366 | 1.00 | 0.00 | xxxx | 2299 |
| ATOM | 2300 | N | TYR | A | 299 | 59.248 | 60.763 | 155.507 | 1.00 | 0.00 | xxxx | 2300 |
| ATOM | 2301 | CA | TYR | A | 299 | 57.828 | 60.450 | 155.457 | 1.00 | 0.00 | xxxx | 2301 |
| ATOM | 2302 | CB | TYR | A | 299 | 57.354 | 60.373 | 154.019 | 1.00 | 0.00 | xxxx | 2302 |
| ATOM | 2303 | CG | TYR | A | 299 | 57.128 | 61.683 | 153.320 | 1.00 | 0.00 | xxxx | 2303 |
| ATOM | 2304 | CD1 | TYR | A | 299 | 56.016 | 62.464 | 153.623 | 1.00 | 0.00 | xxxx | 2304 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 2305 | CE1 | TYR | A | 299 | 55.781 | 63.651 | 152.964 | 1.00 | 0.00 | xxxx | 2305 |
| ATOM | 2306 | CZ | TYR | A | 299 | 56.642 | 64.066 | 151.973 | 1.00 | 0.00 | xxxx | 2306 |
| ATOM | 2307 | OH | TYR | A | 299 | 56.379 | 65.254 | 151.326 | 1.00 | 0.00 | xxxx | 2307 |
| ATOM | 2308 | CE2 | TYR | A | 299 | 57.753 | 63.298 | 151.630 | 1.00 | 0.00 | xxxx | 2308 |
| ATOM | 2309 | CD2 | TYR | A | 299 | 57.987 | 62.117 | 152.310 | 1.00 | 0.00 | xxxx | 2309 |
| ATOM | 2310 | C | TYR | A | 299 | 57.579 | 59.107 | 156.120 | 1.00 | 0.00 | xxxx | 2310 |
| ATOM | 2311 | O | TYR | A | 299 | 58.478 | 58.275 | 156.169 | 1.00 | 0.00 | xxxx | 2311 |
| ATOM | 2312 | N | LYS | A | 300 | 56.348 | 58.873 | 156.572 | 1.00 | 0.00 | xxxx | 2312 |
| ATOM | 2313 | CA | LYS | A | 300 | 55.993 | 57.607 | 157.212 | 1.00 | 0.00 | xxxx | 2313 |
| ATOM | 2314 | CB | LYS | A | 300 | 56.044 | 57.758 | 158.737 | 1.00 | 0.00 | xxxx | 2314 |
| ATOM | 2315 | CG | LYS | A | 300 | 55.632 | 56.512 | 159.500 | 1.00 | 0.00 | xxxx | 2315 |
| ATOM | 2316 | CD | LYS | A | 300 | 55.948 | 56.652 | 160.981 | 1.00 | 0.00 | xxxx | 2316 |
| ATOM | 2317 | CE | LYS | A | 300 | 55.732 | 55.342 | 161.715 | 1.00 | 0.00 | xxxx | 2317 |
| ATOM | 2318 | NZ | LYS | A | 300 | 56.541 | 54.228 | 161.143 | 1.00 | 0.00 | xxxx | 2318 |
| ATOM | 2319 | C | LYS | A | 300 | 54.601 | 57.129 | 156.772 | 1.00 | 0.00 | xxxx | 2319 |
| ATOM | 2320 | O | LYS | A | 300 | 53.637 | 57.899 | 156.808 | 1.00 | 0.00 | xxxx | 2320 |
| ATOM | 2321 | N | LYS | A | 301 | 54.493 | 55.862 | 156.376 | 1.00 | 0.00 | xxxx | 2321 |
| ATOM | 2322 | CA | LYS | A | 301 | 53.200 | 55.299 | 155.946 | 1.00 | 0.00 | xxxx | 2322 |
| ATOM | 2323 | CB | LYS | A | 301 | 53.409 | 53.910 | 155.323 | 1.00 | 0.00 | xxxx | 2323 |
| ATOM | 2324 | CG | LYS | A | 301 | 52.154 | 53.289 | 154.718 | 1.00 | 0.00 | xxxx | 2324 |
| ATOM | 2325 | CD | LYS | A | 301 | 52.372 | 51.812 | 154.360 | 1.00 | 0.00 | xxxx | 2325 |
| ATOM | 2326 | CE | LYS | A | 301 | 53.431 | 51.658 | 153.267 | 1.00 | 0.00 | xxxx | 2326 |
| ATOM | 2327 | NZ | LYS | A | 301 | 53.686 | 50.216 | 152.948 | 1.00 | 0.00 | xxxx | 2327 |
| ATOM | 2328 | C | LYS | A | 301 | 52.212 | 55.213 | 157.116 | 1.00 | 0.00 | xxxx | 2328 |
| ATOM | 2329 | O | LYS | A | 301 | 52.585 | 54.798 | 158.215 | 1.00 | 0.00 | xxxx | 2329 |
| ATOM | 2330 | N | ILE | A | 302 | 50.959 | 55.605 | 156.873 | 1.00 | 0.00 | xxxx | 2330 |
| ATOM | 2331 | CA | ILE | A | 302 | 49.900 | 55.566 | 157.892 | 1.00 | 0.00 | xxxx | 2331 |
| ATOM | 2332 | CB | ILE | A | 302 | 49.534 | 56.984 | 158.400 | 1.00 | 0.00 | xxxx | 2332 |
| ATOM | 2333 | CG1 | ILE | A | 302 | 50.755 | 57.717 | 158.975 | 1.00 | 0.00 | xxxx | 2333 |
| ATOM | 2334 | CD1 | ILE | A | 302 | 51.290 | 57.107 | 160.271 | 1.00 | 0.00 | xxxx | 2334 |
| ATOM | 2335 | CG2 | ILE | A | 302 | 48.379 | 56.906 | 159.406 | 1.00 | 0.00 | xxxx | 2335 |
| ATOM | 2336 | C | ILE | A | 302 | 48.642 | 54.893 | 157.348 | 1.00 | 0.00 | xxxx | 2336 |
| ATOM | 2337 | O | ILE | A | 302 | 48.058 | 55.349 | 156.350 | 1.00 | 0.00 | xxxx | 2337 |
| ATOM | 2338 | N | THR | A | 303 | 48.217 | 53.815 | 158.003 | 1.00 | 0.00 | xxxx | 2338 |
| ATOM | 2339 | CA | THR | A | 303 | 46.919 | 53.208 | 157.730 | 1.00 | 0.00 | xxxx | 2339 |
| ATOM | 2340 | CB | THR | A | 303 | 47.028 | 51.873 | 156.955 | 1.00 | 0.00 | xxxx | 2340 |
| ATOM | 2341 | OG1 | THR | A | 303 | 47.652 | 50.881 | 157.783 | 1.00 | 0.00 | xxxx | 2341 |
| ATOM | 2342 | CG2 | THR | A | 303 | 47.839 | 52.044 | 155.668 | 1.00 | 0.00 | xxxx | 2342 |
| ATOM | 2343 | C | THR | A | 303 | 46.224 | 52.959 | 159.061 | 1.00 | 0.00 | xxxx | 2343 |
| ATOM | 2344 | O | THR | A | 303 | 46.742 | 53.339 | 160.115 | 1.00 | 0.00 | xxxx | 2344 |
| ATOM | 2345 | N | LYS | A | 304 | 45.062 | 52.310 | 159.031 | 1.00 | 0.00 | xxxx | 2345 |
| ATOM | 2346 | CA | LYS | A | 304 | 44.365 | 52.034 | 160.284 | 1.00 | 0.00 | xxxx | 2346 |
| ATOM | 2347 | CB | LYS | A | 304 | 43.014 | 51.356 | 160.027 | 1.00 | 0.00 | xxxx | 2347 |
| ATOM | 2348 | CG | LYS | A | 304 | 43.113 | 49.981 | 159.388 | 1.00 | 0.00 | xxxx | 2348 |
| ATOM | 2349 | CD | LYS | A | 304 | 41.728 | 49.408 | 159.091 | 1.00 | 0.00 | xxxx | 2349 |
| ATOM | 2350 | CE | LYS | A | 304 | 41.817 | 48.045 | 158.422 | 1.00 | 0.00 | xxxx | 2350 |
| ATOM | 2351 | NZ | LYS | A | 304 | 40.513 | 47.632 | 157.829 | 1.00 | 0.00 | xxxx | 2351 |
| ATOM | 2352 | C | LYS | A | 304 | 45.224 | 51.168 | 161.207 | 1.00 | 0.00 | xxxx | 2352 |
| ATOM | 2353 | O | LYS | A | 304 | 45.055 | 51.198 | 162.423 | 1.00 | 0.00 | xxxx | 2353 |
| ATOM | 2354 | N | ASP | A | 305 | 46.162 | 50.421 | 160.626 | 1.00 | 0.00 | xxxx | 2354 |
| ATOM | 2355 | CA | ASP | A | 305 | 47.010 | 49.503 | 161.393 | 1.00 | 0.00 | xxxx | 2355 |
| ATOM | 2356 | CB | ASP | A | 305 | 47.778 | 48.575 | 160.446 | 1.00 | 0.00 | xxxx | 2356 |
| ATOM | 2357 | CG | ASP | A | 305 | 46.869 | 47.611 | 159.704 | 1.00 | 0.00 | xxxx | 2357 |
| ATOM | 2358 | OD1 | ASP | A | 305 | 45.789 | 47.276 | 160.236 | 1.00 | 0.00 | xxxx | 2358 |
| ATOM | 2359 | OD2 | ASP | A | 305 | 47.240 | 47.187 | 158.588 | 1.00 | 0.00 | xxxx | 2359 |
| ATOM | 2360 | C | ASP | A | 305 | 48.002 | 50.209 | 162.316 | 1.00 | 0.00 | xxxx | 2360 |
| ATOM | 2361 | O | ASP | A | 305 | 48.483 | 49.618 | 163.280 | 1.00 | 0.00 | xxxx | 2361 |
| ATOM | 2362 | N | ASN | A | 306 | 48.314 | 51.466 | 162.026 | 1.00 | 0.00 | xxxx | 2362 |
| ATOM | 2363 | CA | ASN | A | 306 | 49.287 | 52.189 | 162.835 | 1.00 | 0.00 | xxxx | 2363 |
| ATOM | 2364 | CB | ASN | A | 306 | 50.698 | 52.038 | 162.248 | 1.00 | 0.00 | xxxx | 2364 |
| ATOM | 2365 | CG | ASN | A | 306 | 50.854 | 52.713 | 160.891 | 1.00 | 0.00 | xxxx | 2365 |
| ATOM | 2366 | OD1 | ASN | A | 306 | 49.928 | 52.732 | 160.082 | 1.00 | 0.00 | xxxx | 2366 |
| ATOM | 2367 | ND2 | ASN | A | 306 | 52.037 | 53.261 | 160.637 | 1.00 | 0.00 | xxxx | 2367 |
| ATOM | 2368 | C | ASN | A | 306 | 48.918 | 53.660 | 162.969 | 1.00 | 0.00 | xxxx | 2368 |
| ATOM | 2369 | O | ASN | A | 306 | 49.786 | 54.536 | 162.985 | 1.00 | 0.00 | xxxx | 2369 |
| ATOM | 2370 | N | ILE | A | 307 | 47.618 | 53.920 | 163.088 | 1.00 | 0.00 | xxxx | 2370 |
| ATOM | 2371 | CA | ILE | A | 307 | 47.113 | 55.284 | 163.115 | 1.00 | 0.00 | xxxx | 2371 |
| ATOM | 2372 | CB | ILE | A | 307 | 45.566 | 55.285 | 163.204 | 1.00 | 0.00 | xxxx | 2372 |
| ATOM | 2373 | CG1 | ILE | A | 307 | 45.008 | 56.676 | 162.905 | 1.00 | 0.00 | xxxx | 2373 |
| ATOM | 2374 | CD1 | ILE | A | 307 | 45.401 | 57.215 | 161.543 | 1.00 | 0.00 | xxxx | 2374 |
| ATOM | 2375 | CG2 | ILE | A | 307 | 45.101 | 54.783 | 164.565 | 1.00 | 0.00 | xxxx | 2375 |
| ATOM | 2376 | C | ILE | A | 307 | 47.740 | 56.099 | 164.252 | 1.00 | 0.00 | xxxx | 2376 |
| ATOM | 2377 | O | ILE | A | 307 | 47.861 | 57.320 | 164.148 | 1.00 | 0.00 | xxxx | 2377 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| ATOM | 2378 | N | SER | A | 308 | 48.172 | 55.431 | 165.320 | 1.00 | 0.00 | xxxx | 2378 |
| ATOM | 2379 | CA | SER | A | 308 | 48.767 | 56.141 | 166.452 | 1.00 | 0.00 | xxxx | 2379 |
| ATOM | 2380 | CB | SER | A | 308 | 48.875 | 55.219 | 167.673 | 1.00 | 0.00 | xxxx | 2380 |
| ATOM | 2381 | OG | SER | A | 308 | 49.886 | 54.245 | 167.496 | 1.00 | 0.00 | xxxx | 2381 |
| ATOM | 2382 | C | SER | A | 308 | 50.141 | 56.731 | 166.124 | 1.00 | 0.00 | xxxx | 2382 |
| ATOM | 2383 | O | SER | A | 308 | 50.586 | 57.664 | 166.790 | 1.00 | 0.00 | xxxx | 2383 |
| ATOM | 2384 | N | ASP | A | 309 | 50.805 | 56.205 | 165.095 | 1.00 | 0.00 | xxxx | 2384 |
| ATOM | 2385 | CA | ASP | A | 309 | 52.090 | 56.752 | 164.660 | 1.00 | 0.00 | xxxx | 2385 |
| ATOM | 2386 | CB | ASP | A | 309 | 52.726 | 55.882 | 163.569 | 1.00 | 0.00 | xxxx | 2386 |
| ATOM | 2387 | CG | ASP | A | 309 | 53.171 | 54.518 | 164.078 | 1.00 | 0.00 | xxxx | 2387 |
| ATOM | 2388 | OD1 | ASP | A | 309 | 53.127 | 54.286 | 165.307 | 1.00 | 0.00 | xxxx | 2388 |
| ATOM | 2389 | OD2 | ASP | A | 309 | 53.576 | 53.678 | 163.241 | 1.00 | 0.00 | xxxx | 2389 |
| ATOM | 2390 | C | ASP | A | 309 | 51.934 | 58.179 | 164.141 | 1.00 | 0.00 | xxxx | 2390 |
| ATOM | 2391 | O | ASP | A | 309 | 52.904 | 58.931 | 164.058 | 1.00 | 0.00 | xxxx | 2391 |
| ATOM | 2392 | N | ALA | A | 310 | 50.708 | 58.547 | 163.779 | 1.00 | 0.00 | xxxx | 2392 |
| ATOM | 2393 | CA | ALA | A | 310 | 50.434 | 59.898 | 163.299 | 1.00 | 0.00 | xxxx | 2393 |
| ATOM | 2394 | CB | ALA | A | 310 | 49.382 | 59.865 | 162.204 | 1.00 | 0.00 | xxxx | 2394 |
| ATOM | 2395 | C | ALA | A | 310 | 49.984 | 60.816 | 164.433 | 1.00 | 0.00 | xxxx | 2395 |
| ATOM | 2396 | O | ALA | A | 310 | 49.930 | 62.035 | 164.267 | 1.00 | 0.00 | xxxx | 2396 |
| ATOM | 2397 | N | GLU | A | 311 | 49.659 | 60.222 | 165.578 | 1.00 | 0.00 | xxxx | 2397 |
| ATOM | 2398 | CA | GLU | A | 311 | 49.189 | 60.972 | 166.740 | 1.00 | 0.00 | xxxx | 2398 |
| ATOM | 2399 | CB | GLU | A | 311 | 47.813 | 60.467 | 167.181 | 1.00 | 0.00 | xxxx | 2399 |
| ATOM | 2400 | CG | GLU | A | 311 | 46.695 | 60.765 | 166.192 | 1.00 | 0.00 | xxxx | 2400 |
| ATOM | 2401 | CD | GLU | A | 311 | 45.341 | 60.264 | 166.667 | 1.00 | 0.00 | xxxx | 2401 |
| ATOM | 2402 | OE1 | GLU | A | 311 | 45.230 | 59.066 | 167.007 | 1.00 | 0.00 | xxxx | 2402 |
| ATOM | 2403 | OE2 | GLU | A | 311 | 44.389 | 61.074 | 166.706 | 1.00 | 0.00 | xxxx | 2403 |
| ATOM | 2404 | C | GLU | A | 311 | 50.176 | 60.877 | 167.901 | 1.00 | 0.00 | xxxx | 2404 |
| ATOM | 2405 | O | GLU | A | 311 | 51.196 | 61.567 | 167.922 | 1.00 | 0.00 | xxxx | 2405 |
| HETATM | 2406 | CA | CA | B | 1 | 39.371 | 47.012 | 136.545 | 1.00 | 0.00 | xxxx | 2406 |
| HETATM | 2407 | C1 | GLC | D | 1 | 52.565 | 69.686 | 150.506 | 1.00 | 0.00 | xxxx | 2407 |
| HETATM | 2408 | O1 | GLC | D | 1 | 53.728 | 69.129 | 150.956 | 1.00 | 0.00 | xxxx | 2408 |
| HETATM | 2409 | C2 | GLC | D | 1 | 51.391 | 69.237 | 151.365 | 1.00 | 0.00 | xxxx | 2409 |
| HETATM | 2410 | O2 | GLC | D | 1 | 51.234 | 67.810 | 151.200 | 1.00 | 0.00 | xxxx | 2410 |
| HETATM | 2411 | C3 | GLC | D | 1 | 50.148 | 69.960 | 150.972 | 1.00 | 0.00 | xxxx | 2411 |
| HETATM | 2412 | O3 | GLC | D | 1 | 49.046 | 69.627 | 151.871 | 1.00 | 0.00 | xxxx | 2412 |
| HETATM | 2413 | C4 | GLC | D | 1 | 50.326 | 71.452 | 150.956 | 1.00 | 0.00 | xxxx | 2413 |
| HETATM | 2414 | O4 | GLC | D | 1 | 49.123 | 72.037 | 150.423 | 1.00 | 0.00 | xxxx | 2414 |
| HETATM | 2415 | C5 | GLC | D | 1 | 51.531 | 71.878 | 150.110 | 1.00 | 0.00 | xxxx | 2415 |
| HETATM | 2416 | O5 | GLC | D | 1 | 52.725 | 71.167 | 150.570 | 1.00 | 0.00 | xxxx | 2416 |
| HETATM | 2417 | C6 | GLC | D | 1 | 51.798 | 73.355 | 150.257 | 1.00 | 0.00 | xxxx | 2417 |
| HETATM | 2418 | O6 | GLC | D | 1 | 53.018 | 73.737 | 149.650 | 1.00 | 0.00 | xxxx | 2418 |
| HETATM | 2419 | K | K | E | 1 | 31.330 | 50.918 | 152.438 | 1.00 | 0.00 | xxxx | 2419 |
| HETATM | 2420 | O15 | BAD | H | 1 | 51.518 | 67.880 | 156.090 | 1.00 | 0.00 | xxxx | 2420 |
| HETATM | 2421 | C14 | BAD | H | 1 | 51.466 | 68.651 | 156.987 | 1.00 | 0.00 | xxxx | 2421 |
| HETATM | 2422 | C16 | BAD | H | 1 | 52.094 | 70.021 | 156.829 | 1.00 | 0.00 | xxxx | 2422 |
| HETATM | 2423 | C11 | BAD | H | 1 | 50.739 | 68.277 | 158.271 | 1.00 | 0.00 | xxxx | 2423 |
| HETATM | 2424 | C12 | BAD | H | 1 | 50.660 | 66.933 | 158.631 | 1.00 | 0.00 | xxxx | 2424 |
| HETATM | 2425 | C13 | BAD | H | 1 | 49.986 | 66.561 | 159.786 | 1.00 | 0.00 | xxxx | 2425 |
| HETATM | 2426 | CO6 | BAD | H | 1 | 49.377 | 67.558 | 160.602 | 1.00 | 0.00 | xxxx | 2426 |
| HETATM | 2427 | CO5 | BAD | H | 1 | 48.690 | 67.166 | 161.789 | 1.00 | 0.00 | xxxx | 2427 |
| HETATM | 2428 | CIO | BAD | H | 1 | 50.147 | 69.261 | 159.061 | 1.00 | 0.00 | xxxx | 2428 |
| HETATM | 2429 | CO7 | BAD | H | 1 | 49.452 | 68.876 | 160.251 | 1.00 | 0.00 | xxxx | 2429 |
| HETATM | 2430 | CO8 | BAD | H | 1 | 48.834 | 69.859 | 161.081 | 1.00 | 0.00 | xxxx | 2430 |
| HETATM | 2431 | CO9 | BAD | H | 1 | 48.162 | 69.475 | 162.242 | 1.00 | 0.00 | xxxx | 2431 |
| HETATM | 2432 | CO4 | BAD | H | 1 | 48.091 | 68.125 | 162.599 | 1.00 | 0.00 | xxxx | 2432 |
| HETATM | 2433 | NO2 | BAD | H | 1 | 47.388 | 67.716 | 163.803 | 1.00 | 0.00 | xxxx | 2433 |
| HETATM | 2434 | CO3 | BAD | H | 1 | 47.290 | 66.305 | 164.145 | 1.00 | 0.00 | xxxx | 2434 |
| HETATM | 2435 | CO1 | BAD | H | 1 | 46.768 | 68.713 | 164.659 | 1.00 | 0.00 | xxxx | 2435 |
| HETATM | 2436 | O | HOH | S | 1 | 46.201 | 68.225 | 153.472 | 1.00 | 0.00 | xxxx | 2436 |
| HETATM | 2437 | O | HOH | S | 2 | 57.279 | 69.627 | 150.623 | 1.00 | 0.00 | xxxx | 2437 |
| HETATM | 2438 | O | HOH | S | 3 | 58.043 | 66.399 | 149.833 | 1.00 | 0.00 | xxxx | 2438 |
| HETATM | 2439 | O | HOH | S | 4 | 66.517 | 72.086 | 144.915 | 1.00 | 0.00 | xxxx | 2439 |
| HETATM | 2440 | O | HOH | S | 5 | 57.929 | 64.558 | 156.347 | 1.00 | 0.00 | xxxx | 2440 |
| HETATM | 2441 | O | HOH | S | 6 | 37.622 | 49.306 | 143.693 | 1.00 | 0.00 | xxxx | 2441 |
| HETATM | 2442 | O | HOH | S | 7 | 56.704 | 54.067 | 156.413 | 1.00 | 0.00 | xxxx | 2442 |
| HETATM | 2443 | O | HOH | S | 8 | 46.778 | 48.831 | 152.298 | 1.00 | 0.00 | xxxx | 2443 |
| HETATM | 2444 | O | HOH | S | 9 | 30.024 | 63.081 | 131.116 | 1.00 | 0.00 | xxxx | 2444 |
| HETATM | 2445 | O | HOH | S | 10 | 36.187 | 49.751 | 136.009 | 1.00 | 0.00 | xxxx | 2445 |
| HETATM | 2446 | O | HOH | S | 11 | 48.055 | 42.688 | 150.299 | 1.00 | 0.00 | xxxx | 2446 |
| HETATM | 2447 | O | HOH | S | 12 | 51.905 | 91.444 | 154.694 | 1.00 | 0.00 | xxxx | 2447 |
| HETATM | 2448 | O | HOH | S | 13 | 74.040 | 77.495 | 151.343 | 1.00 | 0.00 | xxxx | 2448 |
| HETATM | 2449 | O | HOH | S | 14 | 47.118 | 71.039 | 153.130 | 1.00 | 0.00 | xxxx | 2449 |
| HETATM | 2450 | O | HOH | S | 15 | 49.393 | 92.404 | 147.572 | 1.00 | 0.00 | xxxx | 2450 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| HETATM | 2451 | O | HOH | S | 16 | 51.139 | 49.072 | 152.311 | 1.00 | 0.00 | xxxx | 2451 |
| HETATM | 2452 | O | HOH | S | 17 | 49.392 | 60.954 | 144.600 | 1.00 | 0.00 | xxxx | 2452 |
| HETATM | 2453 | O | HOH | S | 18 | 57.680 | 96.227 | 150.341 | 1.00 | 0.00 | xxxx | 2453 |
| HETATM | 2454 | O | HOH | S | 19 | 29.378 | 63.519 | 143.831 | 1.00 | 0.00 | xxxx | 2454 |
| HETATM | 2455 | O | HOH | S | 20 | 64.108 | 78.535 | 142.366 | 1.00 | 0.00 | xxxx | 2455 |
| HETATM | 2456 | O | HOH | S | 21 | 43.239 | 51.830 | 156.655 | 1.00 | 0.00 | xxxx | 2456 |
| HETATM | 2457 | O | HOH | S | 22 | 39.137 | 53.223 | 153.258 | 1.00 | 0.00 | xxxx | 2457 |
| HETATM | 2458 | O | HOH | S | 23 | 40.641 | 53.517 | 156.840 | 1.00 | 0.00 | xxxx | 2458 |
| HETATM | 2459 | O | HOH | S | 24 | 75.860 | 67.970 | 153.435 | 1.00 | 0.00 | xxxx | 2459 |
| HETATM | 2460 | O | HOH | S | 25 | 60.885 | 68.326 | 148.044 | 1.00 | 0.00 | xxxx | 2460 |
| HETATM | 2461 | O | HOH | S | 26 | 56.455 | 69.597 | 153.366 | 1.00 | 0.00 | xxxx | 2461 |
| HETATM | 2462 | O | HOH | S | 27 | 49.093 | 78.034 | 156.339 | 1.00 | 0.00 | xxxx | 2462 |
| HETATM | 2463 | O | HOH | S | 28 | 51.534 | 84.253 | 141.942 | 1.00 | 0.00 | xxxx | 2463 |
| HETATM | 2464 | O | HOH | S | 29 | 41.409 | 72.967 | 151.410 | 1.00 | 0.00 | xxxx | 2464 |
| HETATM | 2465 | O | HOH | S | 30 | 52.391 | 92.584 | 150.793 | 1.00 | 0.00 | xxxx | 2465 |
| HETATM | 2466 | O | HOH | S | 31 | 49.882 | 88.636 | 156.756 | 1.00 | 0.00 | xxxx | 2466 |
| HETATM | 2467 | O | HOH | S | 32 | 49.907 | 49.386 | 133.465 | 1.00 | 0.00 | xxxx | 2467 |
| HETATM | 2468 | O | HOH | S | 33 | 51.656 | 93.752 | 148.385 | 1.00 | 0.00 | xxxx | 2468 |
| HETATM | 2469 | O | HOH | S | 34 | 46.499 | 77.583 | 143.348 | 1.00 | 0.00 | xxxx | 2469 |
| HETATM | 2470 | O | HOH | S | 35 | 47.019 | 43.680 | 137.225 | 1.00 | 0.00 | xxxx | 2470 |
| HETATM | 2471 | O | HOH | S | 36 | 62.183 | 62.671 | 153.207 | 1.00 | 0.00 | xxxx | 2471 |
| HETATM | 2472 | O | HOH | S | 37 | 54.270 | 92.901 | 154.716 | 1.00 | 0.00 | xxxx | 2472 |
| HETATM | 2473 | O | HOH | S | 38 | 54.221 | 63.904 | 137.446 | 1.00 | 0.00 | xxxx | 2473 |
| HETATM | 2474 | O | HOH | S | 39 | 41.749 | 75.482 | 143.484 | 1.00 | 0.00 | xxxx | 2474 |
| HETATM | 2475 | O | HOH | S | 40 | 38.789 | 74.147 | 149.924 | 1.00 | 0.00 | xxxx | 2475 |
| HETATM | 2476 | O | HOH | S | 41 | 57.442 | 50.553 | 153.136 | 1.00 | 0.00 | xxxx | 2476 |
| HETATM | 2477 | O | HOH | S | 42 | 45.951 | 75.220 | 138.761 | 1.00 | 0.00 | xxxx | 2477 |
| HETATM | 2478 | O | HOH | S | 43 | 38.706 | 67.514 | 135.380 | 1.00 | 0.00 | xxxx | 2478 |
| HETATM | 2479 | O | HOH | S | 44 | 68.866 | 91.816 | 177.553 | 1.00 | 0.00 | xxxx | 2479 |
| HETATM | 2480 | O | HOH | S | 45 | 50.702 | 42.893 | 149.907 | 1.00 | 0.00 | xxxx | 2480 |
| HETATM | 2481 | O | HOH | S | 46 | 74.261 | 65.933 | 144.734 | 1.00 | 0.00 | xxxx | 2481 |
| HETATM | 2482 | O | HOH | S | 47 | 55.766 | 48.358 | 144.532 | 1.00 | 0.00 | xxxx | 2482 |
| HETATM | 2483 | O | HOH | S | 48 | 54.068 | 47.601 | 151.452 | 1.00 | 0.00 | xxxx | 2483 |
| HETATM | 2484 | O | HOH | S | 49 | 36.924 | 48.495 | 146.281 | 1.00 | 0.00 | xxxx | 2484 |
| HETATM | 2485 | O | HOH | S | 50 | 28.577 | 63.305 | 141.186 | 1.00 | 0.00 | xxxx | 2485 |
| HETATM | 2486 | O | HOH | S | 51 | 56.380 | 51.624 | 155.427 | 1.00 | 0.00 | xxxx | 2486 |
| HETATM | 2487 | O | HOH | S | 52 | 46.843 | 76.105 | 147.173 | 1.00 | 0.00 | xxxx | 2487 |
| HETATM | 2488 | O | HOH | S | 53 | 54.201 | 94.196 | 152.355 | 1.00 | 0.00 | xxxx | 2488 |
| HETATM | 2489 | O | HOH | S | 54 | 36.411 | 66.940 | 136.708 | 1.00 | 0.00 | xxxx | 2489 |
| HETATM | 2490 | O | HOH | S | 55 | 34.508 | 64.230 | 133.579 | 1.00 | 0.00 | xxxx | 2490 |
| HETATM | 2491 | O | HOH | S | 56 | 37.469 | 75.613 | 143.245 | 1.00 | 0.00 | xxxx | 2491 |
| HETATM | 2492 | O | HOH | S | 57 | 41.259 | 63.933 | 132.633 | 1.00 | 0.00 | xxxx | 2492 |
| HETATM | 2493 | O | HOH | S | 58 | 56.874 | 61.551 | 158.772 | 1.00 | 0.00 | xxxx | 2493 |
| HETATM | 2494 | O | HOH | S | 59 | 56.894 | 82.352 | 168.913 | 1.00 | 0.00 | xxxx | 2494 |
| HETATM | 2495 | O | HOH | S | 60 | 52.215 | 45.595 | 146.666 | 1.00 | 0.00 | xxxx | 2495 |
| HETATM | 2496 | O | HOH | S | 61 | 69.476 | 66.394 | 148.256 | 1.00 | 0.00 | xxxx | 2496 |
| HETATM | 2497 | O | HOH | S | 62 | 44.078 | 67.855 | 155.344 | 1.00 | 0.00 | xxxx | 2497 |
| HETATM | 2498 | O | HOH | S | 63 | 37.822 | 64.070 | 158.296 | 1.00 | 0.00 | xxxx | 2498 |
| HETATM | 2499 | O | HOH | S | 64 | 31.238 | 72.940 | 145.995 | 1.00 | 0.00 | xxxx | 2499 |
| HETATM | 2500 | O | HOH | S | 65 | 58.159 | 86.918 | 140.884 | 1.00 | 0.00 | xxxx | 2500 |
| HETATM | 2501 | O | HOH | S | 66 | 31.369 | 69.344 | 139.912 | 1.00 | 0.00 | xxxx | 2501 |
| HETATM | 2502 | O | HOH | S | 67 | 75.699 | 79.234 | 155.569 | 1.00 | 0.00 | xxxx | 2502 |
| HETATM | 2503 | O | HOH | S | 68 | 74.962 | 66.801 | 158.209 | 1.00 | 0.00 | xxxx | 2503 |
| HETATM | 2504 | O | HOH | S | 69 | 61.668 | 65.708 | 146.688 | 1.00 | 0.00 | xxxx | 2504 |
| HETATM | 2505 | O | HOH | S | 70 | 47.651 | 39.922 | 149.628 | 1.00 | 0.00 | xxxx | 2505 |
| HETATM | 2506 | O | HOH | S | 71 | 50.222 | 79.601 | 143.279 | 1.00 | 0.00 | xxxx | 2506 |
| HETATM | 2507 | O | HOH | S | 72 | 36.280 | 50.638 | 133.281 | 1.00 | 0.00 | xxxx | 2507 |
| HETATM | 2508 | O | HOH | S | 73 | 56.688 | 91.754 | 155.167 | 1.00 | 0.00 | xxxx | 2508 |
| HETATM | 2509 | O | HOH | S | 74 | 56.515 | 91.297 | 141.991 | 1.00 | 0.00 | xxxx | 2509 |
| HETATM | 2510 | O | HOH | S | 75 | 60.126 | 97.716 | 151.243 | 1.00 | 0.00 | xxxx | 2510 |
| HETATM | 2511 | O | HOH | S | 76 | 59.113 | 72.275 | 155.191 | 1.00 | 0.00 | xxxx | 2511 |
| HETATM | 2512 | O | HOH | S | 77 | 39.286 | 65.407 | 133.676 | 1.00 | 0.00 | xxxx | 2512 |
| HETATM | 2513 | O | HOH | S | 78 | 51.850 | 77.610 | 168.352 | 1.00 | 0.00 | xxxx | 2513 |
| HETATM | 2514 | O | HOH | S | 79 | 63.904 | 96.103 | 150.019 | 1.00 | 0.00 | xxxx | 2514 |
| HETATM | 2515 | O | HOH | S | 80 | 30.586 | 65.593 | 134.386 | 1.00 | 0.00 | xxxx | 2515 |
| HETATM | 2516 | O | HOH | S | 81 | 42.210 | 63.701 | 164.172 | 1.00 | 0.00 | xxxx | 2516 |
| HETATM | 2517 | O | HOH | S | 82 | 58.490 | 52.146 | 143.356 | 1.00 | 0.00 | xxxx | 2517 |
| HETATM | 2518 | O | HOH | S | 83 | 35.827 | 64.052 | 153.949 | 1.00 | 0.00 | xxxx | 2518 |
| HETATM | 2519 | O | HOH | S | 84 | 51.916 | 66.901 | 138.432 | 1.00 | 0.00 | xxxx | 2519 |
| HETATM | 2520 | O | HOH | S | 85 | 45.093 | 72.744 | 152.280 | 1.00 | 0.00 | xxxx | 2520 |
| HETATM | 2521 | O | HOH | S | 86 | 55.336 | 96.534 | 151.494 | 1.00 | 0.00 | xxxx | 2521 |
| HETATM | 2522 | O | HOH | S | 87 | 54.897 | 53.328 | 158.820 | 1.00 | 0.00 | xxxx | 2522 |
| HETATM | 2523 | O | HOH | S | 88 | 51.214 | 76.347 | 140.158 | 1.00 | 0.00 | xxxx | 2523 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| HETATM | 2524 | O | HOH | S | 89 | 76.016 | 74.651 | 156.563 | 1.00 | 0.00 | xxxx | 2524 |
| HETATM | 2525 | O | HOH | S | 90 | 76.998 | 77.686 | 147.743 | 1.00 | 0.00 | xxxx | 2525 |
| HETATM | 2526 | O | HOH | S | 91 | 45.905 | 86.694 | 146.512 | 1.00 | 0.00 | xxxx | 2526 |
| HETATM | 2527 | O | HOH | S | 92 | 49.430 | 92.090 | 144.568 | 1.00 | 0.00 | xxxx | 2527 |
| HETATM | 2528 | O | HOH | S | 93 | 39.674 | 61.796 | 131.497 | 1.00 | 0.00 | xxxx | 2528 |
| HETATM | 2529 | O | HOH | S | 94 | 55.245 | 99.007 | 153.139 | 1.00 | 0.00 | xxxx | 2529 |
| HETATM | 2530 | O | HOH | S | 95 | 69.244 | 63.350 | 148.315 | 1.00 | 0.00 | xxxx | 2530 |
| HETATM | 2531 | O | HOH | S | 96 | 62.369 | 67.500 | 144.662 | 1.00 | 0.00 | xxxx | 2531 |
| HETATM | 2532 | O | HOH | S | 97 | 51.637 | 42.869 | 152.661 | 1.00 | 0.00 | xxxx | 2532 |
| HETATM | 2533 | O | HOH | S | 98 | 53.212 | 61.591 | 136.064 | 1.00 | 0.00 | xxxx | 2533 |
| HETATM | 2534 | O | HOH | S | 99 | 66.212 | 62.210 | 156.589 | 1.00 | 0.00 | xxxx | 2534 |
| HETATM | 2535 | O | HOH | S | 100 | 35.206 | 69.485 | 136.668 | 1.00 | 0.00 | xxxx | 2535 |
| HETATM | 2536 | O | HOH | S | 101 | 67.877 | 74.242 | 138.545 | 1.00 | 0.00 | xxxx | 2536 |
| HETATM | 2537 | O | HOH | S | 102 | 47.256 | 88.958 | 147.564 | 1.00 | 0.00 | xxxx | 2537 |
| HETATM | 2538 | O | HOH | S | 103 | 48.802 | 89.549 | 152.888 | 1.00 | 0.00 | xxxx | 2538 |
| HETATM | 2539 | O | HOH | S | 104 | 55.533 | 47.093 | 149.026 | 1.00 | 0.00 | xxxx | 2539 |
| HETATM | 2540 | O | HOH | S | 105 | 58.683 | 84.568 | 172.531 | 1.00 | 0.00 | xxxx | 2540 |
| HETATM | 2541 | O | HOH | S | 106 | 46.755 | 54.806 | 131.997 | 1.00 | 0.00 | xxxx | 2541 |
| HETATM | 2542 | O | HOH | S | 107 | 79.055 | 76.628 | 162.628 | 1.00 | 0.00 | xxxx | 2542 |
| HETATM | 2543 | O | HOH | S | 108 | 35.822 | 74.142 | 141.537 | 1.00 | 0.00 | xxxx | 2543 |
| HETATM | 2544 | O | HOH | S | 109 | 50.310 | 81.760 | 142.022 | 1.00 | 0.00 | xxxx | 2544 |
| HETATM | 2545 | O | HOH | S | 110 | 63.805 | 83.471 | 140.207 | 1.00 | 0.00 | xxxx | 2545 |
| HETATM | 2546 | O | HOH | S | 111 | 27.119 | 60.930 | 140.514 | 1.00 | 0.00 | xxxx | 2546 |
| HETATM | 2547 | O | HOH | S | 112 | 57.702 | 49.618 | 146.404 | 1.00 | 0.00 | xxxx | 2547 |
| HETATM | 2548 | O | HOH | S | 113 | 53.156 | 41.009 | 142.253 | 1.00 | 0.00 | xxxx | 2548 |
| HETATM | 2549 | O | HOH | S | 114 | 60.853 | 82.005 | 137.338 | 1.00 | 0.00 | xxxx | 2549 |
| HETATM | 2550 | O | HOH | S | 115 | 65.759 | 67.945 | 145.250 | 1.00 | 0.00 | xxxx | 2550 |
| HETATM | 2551 | O | HOH | S | 116 | 79.693 | 79.535 | 162.418 | 1.00 | 0.00 | xxxx | 2551 |
| HETATM | 2552 | O | HOH | S | 117 | 42.135 | 47.615 | 154.138 | 1.00 | 0.00 | xxxx | 2552 |
| HETATM | 2553 | O | HOH | S | 118 | 57.040 | 63.514 | 136.108 | 1.00 | 0.00 | xxxx | 2553 |
| HETATM | 2554 | O | HOH | S | 119 | 31.769 | 48.527 | 146.542 | 1.00 | 0.00 | xxxx | 2554 |
| HETATM | 2555 | O | HOH | S | 120 | 57.039 | 84.513 | 139.915 | 1.00 | 0.00 | xxxx | 2555 |
| HETATM | 2556 | O | HOH | S | 121 | 46.159 | 42.652 | 139.578 | 1.00 | 0.00 | xxxx | 2556 |
| HETATM | 2557 | O | HOH | S | 122 | 53.925 | 44.527 | 149.407 | 1.00 | 0.00 | xxxx | 2557 |
| HETATM | 2558 | O | HOH | S | 123 | 66.892 | 67.604 | 166.801 | 1.00 | 0.00 | xxxx | 2558 |
| HETATM | 2559 | O | HOH | S | 124 | 35.159 | 66.646 | 134.153 | 1.00 | 0.00 | xxxx | 2559 |
| HETATM | 2560 | O | HOH | S | 125 | 78.744 | 72.675 | 165.106 | 1.00 | 0.00 | xxxx | 2560 |
| HETATM | 2561 | O | HOH | S | 126 | 76.832 | 75.603 | 145.788 | 1.00 | 0.00 | xxxx | 2561 |
| HETATM | 2562 | O | HOH | S | 127 | 54.214 | 57.362 | 136.743 | 1.00 | 0.00 | xxxx | 2562 |
| HETATM | 2563 | O | HOH | S | 128 | 53.898 | 47.656 | 146.752 | 1.00 | 0.00 | xxxx | 2563 |
| HETATM | 2564 | O | HOH | S | 129 | 49.728 | 63.948 | 162.353 | 1.00 | 0.00 | xxxx | 2564 |
| HETATM | 2565 | O | HOH | S | 130 | 57.315 | 85.289 | 167.511 | 1.00 | 0.00 | xxxx | 2565 |
| HETATM | 2566 | O | HOH | S | 131 | 72.797 | 63.380 | 153.609 | 1.00 | 0.00 | xxxx | 2566 |
| HETATM | 2567 | O | HOH | S | 132 | 55.428 | 92.803 | 143.759 | 1.00 | 0.00 | xxxx | 2567 |
| HETATM | 2568 | O | HOH | S | 133 | 68.279 | 93.604 | 148.640 | 1.00 | 0.00 | xxxx | 2568 |
| HETATM | 2569 | O | HOH | S | 134 | 76.091 | 89.391 | 150.922 | 1.00 | 0.00 | xxxx | 2569 |
| HETATM | 2570 | O | HOH | S | 135 | 45.377 | 74.405 | 150.380 | 1.00 | 0.00 | xxxx | 2570 |
| HETATM | 2571 | O | HOH | S | 136 | 44.404 | 77.789 | 145.325 | 1.00 | 0.00 | xxxx | 2571 |
| HETATM | 2572 | O | HOH | S | 137 | 45.325 | 74.050 | 136.311 | 1.00 | 0.00 | xxxx | 2572 |
| HETATM | 2573 | O | HOH | S | 138 | 73.690 | 79.101 | 140.386 | 1.00 | 0.00 | xxxx | 2573 |
| HETATM | 2574 | O | HOH | S | 139 | 52.155 | 93.059 | 144.447 | 1.00 | 0.00 | xxxx | 2574 |
| HETATM | 2575 | O | HOH | S | 140 | 40.016 | 69.933 | 155.465 | 1.00 | 0.00 | xxxx | 2575 |
| HETATM | 2576 | O | HOH | S | 141 | 50.687 | 90.990 | 157.036 | 1.00 | 0.00 | xxxx | 2576 |
| HETATM | 2577 | O | HOH | S | 142 | 32.692 | 60.138 | 157.561 | 1.00 | 0.00 | xxxx | 2577 |
| HETATM | 2578 | O | HOH | S | 143 | 37.136 | 46.283 | 149.886 | 1.00 | 0.00 | xxxx | 2578 |
| HETATM | 2579 | O | HOH | S | 144 | 64.760 | 94.189 | 148.540 | 1.00 | 0.00 | xxxx | 2579 |
| HETATM | 2580 | O | HOH | S | 145 | 44.949 | 83.318 | 153.400 | 1.00 | 0.00 | xxxx | 2580 |
| HETATM | 2581 | O | HOH | S | 146 | 49.102 | 45.603 | 154.088 | 1.00 | 0.00 | xxxx | 2581 |
| HETATM | 2582 | O | HOH | S | 147 | 50.741 | 82.205 | 161.982 | 1.00 | 0.00 | xxxx | 2582 |
| HETATM | 2583 | O | HOH | S | 148 | 45.534 | 91.850 | 151.024 | 1.00 | 0.00 | xxxx | 2583 |
| HETATM | 2584 | O | HOH | S | 149 | 26.998 | 57.738 | 151.095 | 1.00 | 0.00 | xxxx | 2584 |
| HETATM | 2585 | O | HOH | S | 150 | 57.998 | 96.596 | 147.563 | 1.00 | 0.00 | xxxx | 2585 |
| HETATM | 2586 | O | HOH | S | 151 | 54.046 | 55.078 | 135.707 | 1.00 | 0.00 | xxxx | 2586 |
| HETATM | 2587 | O | HOH | S | 152 | 36.107 | 62.034 | 158.248 | 1.00 | 0.00 | xxxx | 2587 |
| HETATM | 2588 | O | HOH | S | 153 | 69.880 | 93.089 | 164.909 | 1.00 | 0.00 | xxxx | 2588 |
| HETATM | 2589 | O | HOH | S | 154 | 44.962 | 55.765 | 130.418 | 1.00 | 0.00 | xxxx | 2589 |
| HETATM | 2590 | O | HOH | S | 155 | 69.382 | 76.162 | 166.572 | 1.00 | 0.00 | xxxx | 2590 |
| HETATM | 2591 | O | HOH | S | 156 | 48.993 | 48.521 | 153.991 | 1.00 | 0.00 | xxxx | 2591 |
| HETATM | 2592 | O | HOH | S | 157 | 42.538 | 75.186 | 150.705 | 1.00 | 0.00 | xxxx | 2592 |
| HETATM | 2593 | O | HOH | S | 158 | 34.529 | 47.526 | 131.504 | 1.00 | 0.00 | xxxx | 2593 |
| HETATM | 2594 | O | HOH | S | 159 | 68.597 | 95.583 | 154.648 | 1.00 | 0.00 | xxxx | 2594 |
| HETATM | 2595 | O | HOH | S | 160 | 47.611 | 89.569 | 155.230 | 1.00 | 0.00 | xxxx | 2595 |
| HETATM | 2596 | O | HOH | S | 161 | 41.586 | 43.733 | 142.934 | 1.00 | 0.00 | xxxx | 2596 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| HETATM | 2597 | O | HOH | S | 162 | 67.759 | 84.003 | 171.737 | 1.00 | 0.00 | xxxx | 2597 |
| HETATM | 2598 | O | HOH | S | 163 | 34.711 | 71.043 | 138.594 | 1.00 | 0.00 | xxxx | 2598 |
| HETATM | 2599 | O | HOH | S | 164 | 32.185 | 67.192 | 133.433 | 1.00 | 0.00 | xxxx | 2599 |
| HETATM | 2600 | O | HOH | S | 165 | 64.999 | 65.696 | 145.876 | 1.00 | 0.00 | xxxx | 2600 |
| HETATM | 2601 | O | HOH | S | 166 | 56.782 | 64.948 | 164.863 | 1.00 | 0.00 | xxxx | 2601 |
| HETATM | 2602 | O | HOH | S | 167 | 72.553 | 89.540 | 144.762 | 1.00 | 0.00 | xxxx | 2602 |
| HETATM | 2603 | O | HOH | S | 168 | 53.053 | 66.089 | 136.571 | 1.00 | 0.00 | xxxx | 2603 |
| HETATM | 2604 | O | HOH | S | 169 | 52.271 | 72.917 | 167.041 | 1.00 | 0.00 | xxxx | 2604 |
| HETATM | 2605 | O | HOH | S | 170 | 70.989 | 61.973 | 155.873 | 1.00 | 0.00 | xxxx | 2605 |
| HETATM | 2606 | O | HOH | S | 171 | 48.753 | 73.251 | 164.610 | 1.00 | 0.00 | xxxx | 2606 |
| HETATM | 2607 | O | HOH | S | 172 | 51.477 | 45.150 | 153.501 | 1.00 | 0.00 | xxxx | 2607 |
| HETATM | 2608 | O | HOH | S | 173 | 70.613 | 93.728 | 160.943 | 1.00 | 0.00 | xxxx | 2608 |
| HETATM | 2609 | O | HOH | S | 174 | 51.891 | 92.250 | 158.877 | 1.00 | 0.00 | xxxx | 2609 |
| HETATM | 2610 | O | HOH | S | 175 | 48.940 | 42.197 | 136.314 | 1.00 | 0.00 | xxxx | 2610 |
| HETATM | 2611 | O | HOH | S | 176 | 68.735 | 63.111 | 155.715 | 1.00 | 0.00 | xxxx | 2611 |
| HETATM | 2612 | O | HOH | S | 177 | 60.769 | 62.992 | 166.104 | 1.00 | 0.00 | xxxx | 2612 |
| HETATM | 2613 | O | HOH | S | 178 | 50.187 | 93.478 | 153.677 | 1.00 | 0.00 | xxxx | 2613 |
| HETATM | 2614 | O | HOH | S | 179 | 51.213 | 80.674 | 164.196 | 1.00 | 0.00 | xxxx | 2614 |
| HETATM | 2615 | O | HOH | S | 180 | 49.537 | 49.269 | 156.623 | 1.00 | 0.00 | xxxx | 2615 |
| HETATM | 2616 | O | HOH | S | 181 | 77.139 | 80.622 | 157.215 | 1.00 | 0.00 | xxxx | 2616 |
| HETATM | 2617 | O | HOH | S | 182 | 71.895 | 90.577 | 158.371 | 1.00 | 0.00 | xxxx | 2617 |
| HETATM | 2618 | O | HOH | S | 183 | 49.979 | 79.111 | 167.457 | 1.00 | 0.00 | xxxx | 2618 |
| HETATM | 2619 | O | HOH | S | 184 | 39.460 | 72.232 | 154.081 | 1.00 | 0.00 | xxxx | 2619 |
| HETATM | 2620 | O | HOH | S | 185 | 57.704 | 47.790 | 153.481 | 1.00 | 0.00 | xxxx | 2620 |
| HETATM | 2621 | O | HOH | S | 186 | 36.677 | 72.491 | 139.643 | 1.00 | 0.00 | xxxx | 2621 |
| HETATM | 2622 | O | HOH | S | 187 | 71.999 | 61.960 | 151.927 | 1.00 | 0.00 | xxxx | 2622 |
| HETATM | 2623 | O | HOH | S | 188 | 47.075 | 72.908 | 162.806 | 1.00 | 0.00 | xxxx | 2623 |
| HETATM | 2624 | O | HOH | S | 189 | 35.414 | 76.807 | 144.818 | 1.00 | 0.00 | xxxx | 2624 |
| HETATM | 2625 | O | HOH | S | 190 | 78.789 | 76.672 | 149.395 | 1.00 | 0.00 | xxxx | 2625 |
| HETATM | 2626 | O | HOH | S | 191 | 60.444 | 53.912 | 142.416 | 1.00 | 0.00 | xxxx | 2626 |
| HETATM | 2627 | O | HOH | S | 192 | 42.137 | 43.424 | 130.368 | 1.00 | 0.00 | xxxx | 2627 |
| HETATM | 2628 | O | HOH | S | 193 | 40.114 | 41.774 | 129.906 | 1.00 | 0.00 | xxxx | 2628 |
| HETATM | 2629 | O | HOH | S | 194 | 60.042 | 77.391 | 172.458 | 1.00 | 0.00 | xxxx | 2629 |
| HETATM | 2630 | O | HOH | S | 195 | 58.805 | 47.855 | 156.024 | 1.00 | 0.00 | xxxx | 2630 |
| HETATM | 2631 | O | HOH | S | 196 | 60.005 | 50.731 | 150.338 | 1.00 | 0.00 | xxxx | 2631 |
| HETATM | 2632 | O | HOH | S | 197 | 59.841 | 61.910 | 160.341 | 1.00 | 0.00 | xxxx | 2632 |
| HETATM | 2633 | O | HOH | S | 198 | 77.400 | 74.129 | 149.989 | 1.00 | 0.00 | xxxx | 2633 |
| HETATM | 2634 | O | HOH | S | 199 | 53.896 | 98.937 | 155.309 | 1.00 | 0.00 | xxxx | 2634 |
| HETATM | 2635 | O | HOH | S | 200 | 59.636 | 83.798 | 138.796 | 1.00 | 0.00 | xxxx | 2635 |
| HETATM | 2636 | O | HOH | S | 201 | 32.247 | 43.843 | 140.408 | 1.00 | 0.00 | xxxx | 2636 |
| HETATM | 2637 | O | HOH | S | 202 | 29.486 | 64.466 | 155.083 | 1.00 | 0.00 | xxxx | 2637 |
| HETATM | 2638 | O | HOH | S | 203 | 42.716 | 72.150 | 135.089 | 1.00 | 0.00 | xxxx | 2638 |
| HETATM | 2639 | O | HOH | S | 204 | 71.987 | 88.136 | 159.671 | 1.00 | 0.00 | xxxx | 2639 |
| HETATM | 2640 | O | HOH | S | 205 | 33.381 | 49.010 | 136.893 | 1.00 | 0.00 | xxxx | 2640 |
| HETATM | 2641 | O | HOH | S | 206 | 69.194 | 95.620 | 149.891 | 1.00 | 0.00 | xxxx | 2641 |
| HETATM | 2642 | O | HOH | S | 207 | 29.387 | 55.844 | 141.016 | 1.00 | 0.00 | xxxx | 2642 |
| HETATM | 2643 | O | HOH | S | 208 | 45.490 | 92.898 | 153.531 | 1.00 | 0.00 | xxxx | 2643 |
| HETATM | 2644 | O | HOH | S | 209 | 78.479 | 75.596 | 143.871 | 1.00 | 0.00 | xxxx | 2644 |
| HETATM | 2645 | O | HOH | S | 210 | 54.709 | 51.509 | 162.804 | 1.00 | 0.00 | xxxx | 2645 |
| HETATM | 2646 | O | HOH | S | 211 | 48.561 | 89.863 | 144.071 | 1.00 | 0.00 | xxxx | 2646 |
| HETATM | 2647 | O | HOH | S | 212 | 39.863 | 48.853 | 153.284 | 1.00 | 0.00 | xxxx | 2647 |
| HETATM | 2648 | O | HOH | S | 213 | 80.062 | 74.843 | 164.569 | 1.00 | 0.00 | xxxx | 2648 |
| HETATM | 2649 | O | HOH | S | 214 | 38.835 | 54.728 | 150.936 | 1.00 | 0.00 | xxxx | 2649 |
| HETATM | 2650 | O | HOH | S | 215 | 68.967 | 65.864 | 155.242 | 1.00 | 0.00 | xxxx | 2650 |
| HETATM | 2651 | O | HOH | S | 216 | 68.172 | 67.122 | 145.858 | 1.00 | 0.00 | xxxx | 2651 |
| HETATM | 2652 | O | HOH | S | 217 | 68.298 | 64.720 | 144.670 | 1.00 | 0.00 | xxxx | 2652 |
| HETATM | 2653 | O | HOH | S | 218 | 71.593 | 72.342 | 144.610 | 1.00 | 0.00 | xxxx | 2653 |
| HETATM | 2654 | O | HOH | S | 219 | 64.396 | 61.473 | 153.855 | 1.00 | 0.00 | xxxx | 2654 |
| HETATM | 2655 | O | HOH | S | 220 | 55.312 | 96.339 | 144.330 | 1.00 | 0.00 | xxxx | 2655 |
| HETATM | 2656 | O | HOH | S | 221 | 54.183 | 48.804 | 155.351 | 1.00 | 0.00 | xxxx | 2656 |
| HETATM | 2657 | O | HOH | S | 222 | 74.731 | 90.692 | 145.593 | 1.00 | 0.00 | xxxx | 2657 |
| HETATM | 2658 | O | HOH | S | 223 | 37.467 | 65.926 | 160.398 | 1.00 | 0.00 | xxxx | 2658 |
| HETATM | 2659 | O | HOH | S | 224 | 27.727 | 58.401 | 140.473 | 1.00 | 0.00 | xxxx | 2659 |
| HETATM | 2660 | O | HOH | S | 225 | 43.576 | 85.936 | 150.480 | 1.00 | 0.00 | xxxx | 2660 |
| HETATM | 2661 | O | HOH | S | 226 | 45.728 | 86.581 | 156.293 | 1.00 | 0.00 | xxxx | 2661 |
| HETATM | 2662 | O | HOH | S | 227 | 49.995 | 92.055 | 151.996 | 1.00 | 0.00 | xxxx | 2662 |
| HETATM | 2663 | O | HOH | S | 228 | 37.499 | 47.113 | 152.538 | 1.00 | 0.00 | xxxx | 2663 |
| HETATM | 2664 | O | HOH | S | 229 | 44.424 | 61.222 | 132.009 | 1.00 | 0.00 | xxxx | 2664 |
| HETATM | 2665 | O | HOH | S | 230 | 76.652 | 68.937 | 159.384 | 1.00 | 0.00 | xxxx | 2665 |
| HETATM | 2666 | O | HOH | S | 231 | 40.922 | 61.562 | 164.902 | 1.00 | 0.00 | xxxx | 2666 |
| HETATM | 2667 | O | HOH | S | 232 | 64.719 | 94.729 | 167.844 | 1.00 | 0.00 | xxxx | 2667 |
| HETATM | 2668 | O | HOH | S | 233 | 43.542 | 59.604 | 131.071 | 1.00 | 0.00 | xxxx | 2668 |
| HETATM | 2669 | O | HOH | S | 234 | 51.200 | 63.892 | 135.249 | 1.00 | 0.00 | xxxx | 2669 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| HETATM | 2670 | O | HOH | S | 235 | 55.405 | 91.022 | 139.852 | 1.00 | 0.00 | xxxx | 2670 |
| HETATM | 2671 | O | HOH | S | 236 | 40.342 | 65.511 | 164.886 | 1.00 | 0.00 | xxxx | 2671 |
| HETATM | 2672 | O | HOH | S | 237 | 66.483 | 99.541 | 155.727 | 1.00 | 0.00 | xxxx | 2672 |
| HETATM | 2673 | O | HOH | S | 238 | 69.457 | 86.310 | 171.372 | 1.00 | 0.00 | xxxx | 2673 |
| HETATM | 2674 | O | HOH | S | 239 | 44.207 | 49.050 | 155.766 | 1.00 | 0.00 | xxxx | 2674 |
| HETATM | 2675 | O | HOH | S | 240 | 77.984 | 88.107 | 149.281 | 1.00 | 0.00 | xxxx | 2675 |
| HETATM | 2676 | O | HOH | S | 241 | 63.936 | 65.431 | 143.959 | 1.00 | 0.00 | xxxx | 2676 |
| HETATM | 2677 | O | HOH | S | 242 | 59.342 | 56.830 | 138.270 | 1.00 | 0.00 | xxxx | 2677 |
| HETATM | 2678 | O | HOH | S | 243 | 57.960 | 56.896 | 136.242 | 1.00 | 0.00 | xxxx | 2678 |
| HETATM | 2679 | O | HOH | S | 244 | 58.013 | 47.012 | 148.836 | 1.00 | 0.00 | xxxx | 2679 |
| HETATM | 2680 | O | HOH | S | 245 | 75.427 | 69.810 | 142.388 | 1.00 | 0.00 | xxxx | 2680 |
| HETATM | 2681 | O | HOH | S | 246 | 73.826 | 68.223 | 143.334 | 1.00 | 0.00 | xxxx | 2681 |
| HETATM | 2682 | O | HOH | S | 247 | 42.971 | 82.759 | 155.019 | 1.00 | 0.00 | xxxx | 2682 |
| HETATM | 2683 | O | HOH | S | 248 | 52.571 | 85.235 | 164.090 | 1.00 | 0.00 | xxxx | 2683 |
| HETATM | 2684 | O | HOH | S | 249 | 45.214 | 46.605 | 152.420 | 1.00 | 0.00 | xxxx | 2684 |
| HETATM | 2685 | O | HOH | S | 250 | 29.343 | 67.140 | 135.830 | 1.00 | 0.00 | xxxx | 2685 |
| HETATM | 2686 | O | HOH | S | 251 | 32.366 | 55.742 | 159.321 | 1.00 | 0.00 | xxxx | 2686 |
| HETATM | 2687 | O | HOH | S | 252 | 24.677 | 53.488 | 148.443 | 1.00 | 0.00 | xxxx | 2687 |
| HETATM | 2688 | O | HOH | S | 253 | 53.247 | 94.555 | 156.841 | 1.00 | 0.00 | xxxx | 2688 |
| HETATM | 2689 | O | HOH | S | 254 | 74.994 | 84.859 | 143.239 | 1.00 | 0.00 | xxxx | 2689 |
| HETATM | 2690 | O | HOH | S | 255 | 42.936 | 91.602 | 150.830 | 1.00 | 0.00 | xxxx | 2690 |
| HETATM | 2691 | O | HOH | S | 256 | 58.422 | 83.991 | 169.629 | 1.00 | 0.00 | xxxx | 2691 |
| HETATM | 2692 | O | HOH | S | 257 | 69.838 | 92.467 | 158.698 | 1.00 | 0.00 | xxxx | 2692 |
| HETATM | 2693 | O | HOH | S | 258 | 68.045 | 85.333 | 139.314 | 1.00 | 0.00 | xxxx | 2693 |
| HETATM | 2694 | O | HOH | S | 259 | 60.263 | 52.077 | 139.361 | 1.00 | 0.00 | xxxx | 2694 |
| HETATM | 2695 | O | HOH | S | 260 | 27.165 | 65.538 | 140.881 | 1.00 | 0.00 | xxxx | 2695 |
| HETATM | 2696 | O | HOH | S | 261 | 64.093 | 93.917 | 162.579 | 1.00 | 0.00 | xxxx | 2696 |
| HETATM | 2697 | O | HOH | S | 262 | 58.261 | 93.702 | 145.184 | 1.00 | 0.00 | xxxx | 2697 |
| HETATM | 2698 | O | HOH | S | 263 | 43.274 | 41.321 | 143.716 | 1.00 | 0.00 | xxxx | 2698 |
| HETATM | 2699 | O | HOH | S | 264 | 44.457 | 63.916 | 165.291 | 1.00 | 0.00 | xxxx | 2699 |
| HETATM | 2700 | O | HOH | S | 265 | 42.371 | 41.840 | 141.713 | 1.00 | 0.00 | xxxx | 2700 |
| HETATM | 2701 | O | HOH | S | 266 | 32.912 | 69.796 | 134.996 | 1.00 | 0.00 | xxxx | 2701 |
| HETATM | 2702 | O | HOH | S | 267 | 38.574 | 62.379 | 129.054 | 1.00 | 0.00 | xxxx | 2702 |
| HETATM | 2703 | O | HOH | S | 268 | 52.919 | 55.185 | 167.684 | 1.00 | 0.00 | xxxx | 2703 |
| HETATM | 2704 | O | HOH | S | 269 | 42.297 | 73.045 | 138.008 | 1.00 | 0.00 | xxxx | 2704 |
| HETATM | 2705 | O | HOH | S | 270 | 55.678 | 97.395 | 147.147 | 1.00 | 0.00 | xxxx | 2705 |
| HETATM | 2706 | O | HOH | S | 271 | 52.073 | 77.661 | 142.443 | 1.00 | 0.00 | xxxx | 2706 |
| HETATM | 2707 | O | HOH | S | 272 | 53.656 | 79.318 | 140.562 | 1.00 | 0.00 | xxxx | 2707 |
| HETATM | 2708 | O | HOH | S | 273 | 46.237 | 72.352 | 160.290 | 1.00 | 0.00 | xxxx | 2708 |
| HETATM | 2709 | O | HOH | S | 274 | 46.994 | 92.936 | 143.057 | 1.00 | 0.00 | xxxx | 2709 |
| HETATM | 2710 | O | HOH | S | 275 | 44.477 | 81.823 | 145.212 | 1.00 | 0.00 | xxxx | 2710 |
| HETATM | 2711 | O | HOH | S | 276 | 54.031 | 87.747 | 163.437 | 1.00 | 0.00 | xxxx | 2711 |
| HETATM | 2712 | O | HOH | S | 277 | 47.434 | 52.681 | 166.283 | 1.00 | 0.00 | xxxx | 2712 |
| HETATM | 2713 | O | HOH | S | 278 | 59.600 | 57.004 | 158.284 | 1.00 | 0.00 | xxxx | 2713 |
| HETATM | 2714 | O | HOH | S | 279 | 60.963 | 54.848 | 139.584 | 1.00 | 0.00 | xxxx | 2714 |
| HETATM | 2715 | O | HOH | S | 280 | 37.148 | 63.959 | 132.391 | 1.00 | 0.00 | xxxx | 2715 |
| HETATM | 2716 | O | HOH | S | 281 | 28.986 | 71.953 | 146.829 | 1.00 | 0.00 | xxxx | 2716 |
| HETATM | 2717 | O | HOH | S | 282 | 68.512 | 94.290 | 162.575 | 1.00 | 0.00 | xxxx | 2717 |
| HETATM | 2718 | O | HOH | S | 283 | 52.234 | 40.696 | 137.518 | 1.00 | 0.00 | xxxx | 2718 |
| HETATM | 2719 | O | HOH | S | 284 | 66.206 | 85.004 | 174.135 | 1.00 | 0.00 | xxxx | 2719 |
| HETATM | 2720 | O | HOH | S | 285 | 75.905 | 76.142 | 152.137 | 1.00 | 0.00 | xxxx | 2720 |
| HETATM | 2721 | O | HOH | S | 286 | 50.731 | 54.152 | 132.775 | 1.00 | 0.00 | xxxx | 2721 |
| HETATM | 2722 | O | HOH | S | 287 | 54.504 | 71.995 | 168.294 | 1.00 | 0.00 | xxxx | 2722 |
| HETATM | 2723 | O | HOH | S | 288 | 56.248 | 96.171 | 141.897 | 1.00 | 0.00 | xxxx | 2723 |
| HETATM | 2724 | O | HOH | S | 289 | 69.486 | 62.152 | 150.746 | 1.00 | 0.00 | xxxx | 2724 |
| HETATM | 2725 | O | HOH | S | 290 | 40.024 | 40.276 | 140.882 | 1.00 | 0.00 | xxxx | 2725 |
| HETATM | 2726 | O | HOH | S | 291 | 44.385 | 41.941 | 132.405 | 1.00 | 0.00 | xxxx | 2726 |
| HETATM | 2727 | O | HOH | S | 292 | 71.883 | 78.785 | 169.503 | 1.00 | 0.00 | xxxx | 2727 |
| HETATM | 2728 | O | HOH | S | 293 | 56.087 | 94.966 | 139.562 | 1.00 | 0.00 | xxxx | 2728 |
| HETATM | 2729 | O | HOH | S | 294 | 50.604 | 86.542 | 161.142 | 1.00 | 0.00 | xxxx | 2729 |
| HETATM | 2730 | O | HOH | S | 295 | 49.091 | 55.663 | 133.859 | 1.00 | 0.00 | xxxx | 2730 |
| HETATM | 2731 | O | HOH | S | 296 | 62.140 | 68.428 | 142.203 | 1.00 | 0.00 | xxxx | 2731 |
| HETATM | 2732 | O | HOH | S | 297 | 58.188 | 60.998 | 161.107 | 1.00 | 0.00 | xxxx | 2732 |
| HETATM | 2733 | O | HOH | S | 298 | 34.634 | 46.282 | 149.220 | 1.00 | 0.00 | xxxx | 2733 |
| HETATM | 2734 | O | HOH | S | 299 | 53.105 | 97.360 | 156.777 | 1.00 | 0.00 | xxxx | 2734 |
| HETATM | 2735 | O | HOH | S | 300 | 23.462 | 59.601 | 146.117 | 1.00 | 0.00 | xxxx | 2735 |
| HETATM | 2736 | O | HOH | S | 301 | 55.964 | 92.355 | 162.949 | 1.00 | 0.00 | xxxx | 2736 |
| HETATM | 2737 | O | HOH | S | 302 | 27.393 | 66.398 | 134.317 | 1.00 | 0.00 | xxxx | 2737 |
| HETATM | 2738 | O | HOH | S | 303 | 61.386 | 88.815 | 145.169 | 1.00 | 0.00 | xxxx | 2738 |
| HETATM | 2739 | O | HOH | S | 304 | 51.190 | 51.469 | 157.598 | 1.00 | 0.00 | xxxx | 2739 |
| HETATM | 2740 | O | HOH | S | 305 | 25.996 | 59.783 | 135.372 | 1.00 | 0.00 | xxxx | 2740 |
| HETATM | 2741 | O | HOH | S | 306 | 33.722 | 43.191 | 142.370 | 1.00 | 0.00 | xxxx | 2741 |
| HETATM | 2742 | O | HOH | S | 307 | 42.824 | 79.527 | 144.482 | 1.00 | 0.00 | xxxx | 2742 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| HETATM | 2743 | O | HOH | S | 308 | 46.683 | 73.714 | 134.659 | 1.00 | 0.00 | xxxx | 2743 |
| HETATM | 2744 | O | HOH | S | 309 | 39.500 | 50.446 | 155.833 | 1.00 | 0.00 | xxxx | 2744 |
| HETATM | 2745 | O | HOH | S | 310 | 55.858 | 87.737 | 140.514 | 1.00 | 0.00 | xxxx | 2745 |
| HETATM | 2746 | O | HOH | S | 311 | 51.193 | 56.462 | 133.700 | 1.00 | 0.00 | xxxx | 2746 |
| HETATM | 2747 | O | HOH | S | 312 | 59.165 | 45.441 | 139.785 | 1.00 | 0.00 | xxxx | 2747 |
| HETATM | 2748 | O | HOH | S | 313 | 53.333 | 78.458 | 170.965 | 1.00 | 0.00 | xxxx | 2748 |
| HETATM | 2749 | O | HOH | S | 314 | 49.285 | 85.987 | 141.326 | 1.00 | 0.00 | xxxx | 2749 |
| HETATM | 2750 | O | HOH | S | 315 | 35.185 | 60.851 | 156.183 | 1.00 | 0.00 | xxxx | 2750 |
| HETATM | 2751 | O | HOH | S | 316 | 75.105 | 83.783 | 158.857 | 1.00 | 0.00 | xxxx | 2751 |
| HETATM | 2752 | O | HOH | S | 317 | 64.272 | 59.277 | 147.662 | 1.00 | 0.00 | xxxx | 2752 |
| HETATM | 2753 | O | HOH | S | 318 | 77.413 | 76.276 | 140.638 | 1.00 | 0.00 | xxxx | 2753 |
| HETATM | 2754 | O | HOH | S | 319 | 76.605 | 82.256 | 158.647 | 1.00 | 0.00 | xxxx | 2754 |
| HETATM | 2755 | O | HOH | S | 320 | 29.536 | 56.236 | 132.756 | 1.00 | 0.00 | xxxx | 2755 |
| HETATM | 2756 | O | HOH | S | 321 | 78.091 | 77.379 | 142.155 | 1.00 | 0.00 | xxxx | 2756 |
| HETATM | 2757 | O | HOH | S | 322 | 59.988 | 69.316 | 150.305 | 1.00 | 0.00 | xxxx | 2757 |
| HETATM | 2758 | O | HOH | S | 323 | 52.661 | 46.359 | 135.892 | 1.00 | 0.00 | xxxx | 2758 |
| HETATM | 2759 | O | HOH | S | 324 | 34.321 | 47.279 | 146.428 | 1.00 | 0.00 | xxxx | 2759 |
| HETATM | 2760 | O | HOH | S | 325 | 75.579 | 93.207 | 168.490 | 1.00 | 0.00 | xxxx | 2760 |
| HETATM | 2761 | O | HOH | S | 326 | 43.288 | 63.060 | 132.086 | 1.00 | 0.00 | xxxx | 2761 |
| HETATM | 2762 | O | HOH | S | 327 | 66.171 | 97.517 | 150.411 | 1.00 | 0.00 | xxxx | 2762 |
| HETATM | 2763 | O | HOH | S | 328 | 31.253 | 56.201 | 131.353 | 1.00 | 0.00 | xxxx | 2763 |
| HETATM | 2764 | O | HOH | S | 329 | 45.863 | 41.542 | 134.212 | 1.00 | 0.00 | xxxx | 2764 |
| HETATM | 2765 | O | HOH | S | 330 | 51.530 | 72.106 | 164.595 | 1.00 | 0.00 | xxxx | 2765 |
| HETATM | 2766 | O | HOH | S | 331 | 57.118 | 92.826 | 158.098 | 1.00 | 0.00 | xxxx | 2766 |
| HETATM | 2767 | O | HOH | S | 332 | 60.186 | 54.769 | 150.237 | 1.00 | 0.00 | xxxx | 2767 |
| HETATM | 2768 | O | HOH | S | 333 | 77.624 | 72.381 | 139.249 | 1.00 | 0.00 | xxxx | 2768 |
| HETATM | 2769 | O | HOH | S | 334 | 45.538 | 77.271 | 164.125 | 1.00 | 0.00 | xxxx | 2769 |
| HETATM | 2770 | O | HOH | S | 335 | 25.140 | 65.377 | 135.730 | 1.00 | 0.00 | xxxx | 2770 |
| HETATM | 2771 | O | HOH | S | 336 | 74.824 | 77.536 | 168.183 | 1.00 | 0.00 | xxxx | 2771 |
| HETATM | 2772 | O | HOH | S | 337 | 78.522 | 85.266 | 151.265 | 1.00 | 0.00 | xxxx | 2772 |
| HETATM | 2773 | O | HOH | S | 338 | 57.875 | 71.649 | 166.102 | 1.00 | 0.00 | xxxx | 2773 |
| HETATM | 2774 | O | HOH | S | 339 | 39.030 | 37.543 | 149.135 | 1.00 | 0.00 | xxxx | 2774 |
| HETATM | 2775 | O | HOH | S | 340 | 41.320 | 40.877 | 138.844 | 1.00 | 0.00 | xxxx | 2775 |
| HETATM | 2776 | O | HOH | S | 341 | 65.399 | 60.174 | 155.252 | 1.00 | 0.00 | xxxx | 2776 |
| HETATM | 2777 | O | HOH | S | 342 | 72.011 | 89.306 | 162.040 | 1.00 | 0.00 | xxxx | 2777 |
| HETATM | 2778 | O | HOH | S | 343 | 47.174 | 48.497 | 131.385 | 1.00 | 0.00 | xxxx | 2778 |
| HETATM | 2779 | O | HOH | S | 344 | 75.680 | 73.049 | 169.298 | 1.00 | 0.00 | xxxx | 2779 |
| HETATM | 2780 | O | HOH | S | 345 | 40.786 | 70.442 | 133.027 | 1.00 | 0.00 | xxxx | 2780 |
| HETATM | 2781 | O | HOH | S | 346 | 37.925 | 40.317 | 149.883 | 1.00 | 0.00 | xxxx | 2781 |
| HETATM | 2782 | O | HOH | S | 347 | 76.697 | 72.821 | 154.946 | 1.00 | 0.00 | xxxx | 2782 |
| HETATM | 2783 | O | HOH | S | 348 | 63.421 | 65.807 | 141.012 | 1.00 | 0.00 | xxxx | 2783 |
| HETATM | 2784 | O | HOH | S | 349 | 51.122 | 59.252 | 136.857 | 1.00 | 0.00 | xxxx | 2784 |
| HETATM | 2785 | O | HOH | S | 350 | 70.369 | 94.016 | 156.050 | 1.00 | 0.00 | xxxx | 2785 |
| HETATM | 2786 | O | HOH | S | 351 | 49.992 | 60.017 | 134.717 | 1.00 | 0.00 | xxxx | 2786 |
| HETATM | 2787 | O | HOH | S | 352 | 75.350 | 86.671 | 157.529 | 1.00 | 0.00 | xxxx | 2787 |
| HETATM | 2788 | O | HOH | S | 353 | 77.823 | 75.935 | 166.556 | 1.00 | 0.00 | xxxx | 2788 |
| HETATM | 2789 | O | HOH | S | 354 | 55.100 | 90.751 | 160.307 | 1.00 | 0.00 | xxxx | 2789 |
| HETATM | 2790 | O | HOH | S | 355 | 27.904 | 71.090 | 145.335 | 1.00 | 0.00 | xxxx | 2790 |
| HETATM | 2791 | O | HOH | S | 356 | 43.946 | 74.064 | 159.815 | 1.00 | 0.00 | xxxx | 2791 |
| HETATM | 2792 | O | HOH | S | 357 | 53.394 | 90.181 | 160.815 | 1.00 | 0.00 | xxxx | 2792 |
| HETATM | 2793 | O | HOH | S | 358 | 64.402 | 87.495 | 170.323 | 1.00 | 0.00 | xxxx | 2793 |
| HETATM | 2794 | O | HOH | S | 359 | 73.875 | 86.615 | 159.747 | 1.00 | 0.00 | xxxx | 2794 |
| HETATM | 2795 | O | HOH | S | 360 | 39.522 | 67.049 | 162.161 | 1.00 | 0.00 | xxxx | 2795 |
| HETATM | 2796 | O | HOH | S | 361 | 44.455 | 81.429 | 142.143 | 1.00 | 0.00 | xxxx | 2796 |
| HETATM | 2797 | O | HOH | S | 362 | 25.454 | 62.332 | 138.307 | 1.00 | 0.00 | xxxx | 2797 |
| HETATM | 2798 | O | HOH | S | 363 | 55.641 | 89.241 | 165.418 | 1.00 | 0.00 | xxxx | 2798 |
| HETATM | 2799 | O | HOH | S | 364 | 44.808 | 82.801 | 150.463 | 1.00 | 0.00 | xxxx | 2799 |
| HETATM | 2800 | O | HOH | S | 365 | 72.236 | 81.203 | 173.001 | 1.00 | 0.00 | xxxx | 2800 |
| HETATM | 2801 | O | HOH | S | 366 | 68.892 | 66.917 | 168.696 | 1.00 | 0.00 | xxxx | 2801 |
| HETATM | 2802 | O | HOH | S | 367 | 56.464 | 50.291 | 134.278 | 1.00 | 0.00 | xxxx | 2802 |
| HETATM | 2803 | O | HOH | S | 368 | 62.491 | 61.198 | 139.575 | 1.00 | 0.00 | xxxx | 2803 |
| HETATM | 2804 | O | HOH | S | 369 | 60.971 | 62.929 | 137.733 | 1.00 | 0.00 | xxxx | 2804 |
| HETATM | 2805 | O | HOH | S | 370 | 61.950 | 98.032 | 148.878 | 1.00 | 0.00 | xxxx | 2805 |
| HETATM | 2806 | O | HOH | S | 371 | 30.702 | 69.382 | 135.319 | 1.00 | 0.00 | xxxx | 2806 |
| HETATM | 2807 | O | HOH | S | 372 | 72.835 | 83.672 | 172.687 | 1.00 | 0.00 | xxxx | 2807 |
| HETATM | 2808 | O | HOH | S | 373 | 30.631 | 53.789 | 158.886 | 1.00 | 0.00 | xxxx | 2808 |
| HETATM | 2809 | O | HOH | S | 374 | 58.769 | 92.752 | 159.679 | 1.00 | 0.00 | xxxx | 2809 |
| HETATM | 2810 | O | HOH | S | 375 | 55.480 | 50.180 | 157.300 | 1.00 | 0.00 | xxxx | 2810 |
| HETATM | 2811 | O | HOH | S | 376 | 39.942 | 68.852 | 162.294 | 1.00 | 0.00 | xxxx | 2811 |
| HETATM | 2812 | O | HOH | S | 377 | 63.692 | 63.207 | 141.734 | 1.00 | 0.00 | xxxx | 2812 |
| HETATM | 2813 | O | HOH | S | 378 | 56.000 | 76.808 | 172.839 | 1.00 | 0.00 | xxxx | 2813 |
| HETATM | 2814 | O | HOH | S | 379 | 74.372 | 83.991 | 169.863 | 1.00 | 0.00 | xxxx | 2814 |
| HETATM | 2815 | O | HOH | S | 380 | 22.549 | 63.907 | 135.222 | 1.00 | 0.00 | xxxx | 2815 |

-continued

CA, calcium
HOH, water
BAD, Badan
K, potassium
EDO, ethylene glycol

| | | | | | | | | | | | | |
|---|---|---|---|---|---|---|---|---|---|---|---|---|
| HETATM | 2816 | O | HOH | S | 381 | 23.412 | 65.534 | 135.198 | 1.00 | 0.00 | xxxx | 2816 |
| HETATM | 2817 | O | HOH | S | 382 | 60.263 | 67.901 | 140.518 | 1.00 | 0.00 | xxxx | 2817 |
| HETATM | 2818 | O | HOH | S | 383 | 45.221 | 69.427 | 160.951 | 1.00 | 0.00 | xxxx | 2818 |
| HETATM | 2819 | O | HOH | S | 384 | 66.498 | 92.424 | 164.876 | 1.00 | 0.00 | xxxx | 2819 |
| HETATM | 2820 | O | HOH | S | 385 | 37.032 | 71.203 | 135.720 | 1.00 | 0.00 | xxxx | 2820 |
| HETATM | 2821 | O | HOH | S | 386 | 77.411 | 79.795 | 146.037 | 1.00 | 0.00 | xxxx | 2821 |
| HETATM | 2822 | O | HOH | S | 387 | 47.947 | 41.913 | 141.390 | 1.00 | 0.00 | xxxx | 2822 |
| HETATM | 2823 | O | HOH | S | 388 | 60.964 | 60.212 | 161.343 | 1.00 | 0.00 | xxxx | 2823 |
| HETATM | 2824 | O | HOH | S | 389 | 45.817 | 86.091 | 143.837 | 1.00 | 0.00 | xxxx | 2824 |
| HETATM | 2825 | O | HOH | S | 390 | 76.619 | 77.018 | 167.654 | 1.00 | 0.00 | xxxx | 2825 |
| HETATM | 2826 | O | HOH | S | 391 | 42.858 | 79.646 | 148.541 | 1.00 | 0.00 | xxxx | 2826 |
| HETATM | 2827 | O | HOH | S | 392 | 54.410 | 83.651 | 164.891 | 1.00 | 0.00 | xxxx | 2827 |
| HETATM | 2828 | O | HOH | S | 393 | 70.894 | 63.870 | 144.402 | 1.00 | 0.00 | xxxx | 2828 |
| HETATM | 2829 | O | HOH | S | 394 | 36.961 | 58.639 | 165.920 | 1.00 | 0.00 | xxxx | 2829 |
| HETATM | 2830 | O | HOH | S | 395 | 58.708 | 92.155 | 141.294 | 1.00 | 0.00 | xxxx | 2830 |
| HETATM | 2831 | O | HOH | S | 396 | 78.814 | 78.170 | 154.417 | 1.00 | 0.00 | xxxx | 2831 |
| HETATM | 2832 | O | HOH | S | 397 | 42.611 | 75.099 | 155.809 | 1.00 | 0.00 | xxxx | 2832 |
| HETATM | 2833 | O | HOH | S | 398 | 72.716 | 86.788 | 143.422 | 1.00 | 0.00 | xxxx | 2833 |
| HETATM | 2834 | O | HOH | S | 399 | 43.847 | 80.375 | 147.143 | 1.00 | 0.00 | xxxx | 2834 |
| HETATM | 2835 | O | HOH | S | 400 | 44.815 | 39.074 | 135.864 | 1.00 | 0.00 | xxxx | 2835 |
| HETATM | 2836 | O | HOH | S | 401 | 62.460 | 74.450 | 172.476 | 1.00 | 0.00 | xxxx | 2836 |
| HETATM | 2837 | O | HOH | S | 402 | 79.224 | 81.985 | 160.103 | 1.00 | 0.00 | xxxx | 2837 |
| HETATM | 2838 | O | HOH | S | 403 | 79.319 | 80.456 | 154.759 | 1.00 | 0.00 | xxxx | 2838 |

Example 12. Crystal Structure Coordinates for a *T. thermosaccharolyticum* Glucose-Galactose Binding Protein: ttHGBP182C.Acrylodan (Acrylodan Attached to W182C Mutant+R91K,Q18E Double Mutant)

Naming is standard three-letter amino acid code. For hetero atom (HETATM) records:

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1 | O | MET | A | 1 | 45.210 | 37.591 | 106.914 | 1.00 | 0.00 | xxxx | 1 |
| ATOM | 2 | N | MET | A | 1 | 45.762 | 36.296 | 109.277 | 1.00 | 0.00 | xxxx | 2 |
| ATOM | 3 | CA | MET | A | 1 | 46.329 | 35.790 | 108.035 | 1.00 | 0.00 | xxxx | 3 |
| ATOM | 4 | C | MET | A | 1 | 46.138 | 36.788 | 106.900 | 1.00 | 0.00 | xxxx | 4 |
| ATOM | 5 | CB | MET | A | 1 | 45.670 | 34.462 | 107.649 | 1.00 | 0.00 | xxxx | 5 |
| ATOM | 6 | CG | MET | A | 1 | 45.720 | 33.401 | 108.732 | 1.00 | 0.00 | xxxx | 6 |
| ATOM | 7 | SD | MET | A | 1 | 47.393 | 32.806 | 109.049 | 1.00 | 0.00 | xxxx | 7 |
| ATOM | 8 | CE | MET | A | 1 | 47.362 | 32.657 | 110.834 | 1.00 | 0.00 | xxxx | 8 |
| ATOM | 9 | N | LYS | A | 2 | 47.025 | 36.728 | 105.914 | 1.00 | 0.00 | xxxx | 9 |
| ATOM | 10 | CA | LYS | A | 2 | 46.833 | 37.493 | 104.692 | 1.00 | 0.00 | xxxx | 10 |
| ATOM | 11 | C | LYS | A | 2 | 45.651 | 36.919 | 103.923 | 1.00 | 0.00 | xxxx | 11 |
| ATOM | 12 | O | LYS | A | 2 | 45.477 | 35.699 | 103.844 | 1.00 | 0.00 | xxxx | 12 |
| ATOM | 13 | CB | LYS | A | 2 | 48.101 | 37.412 | 103.835 | 1.00 | 0.00 | xxxx | 13 |
| ATOM | 14 | CG | LYS | A | 2 | 48.098 | 38.337 | 102.634 | 1.00 | 0.00 | xxxx | 14 |
| ATOM | 15 | CD | LYS | A | 2 | 49.485 | 38.473 | 102.012 | 1.00 | 0.00 | xxxx | 15 |
| ATOM | 16 | CE | LYS | A | 2 | 49.883 | 37.224 | 101.251 | 1.00 | 0.00 | xxxx | 16 |
| ATOM | 17 | NZ | LYS | A | 2 | 51.165 | 37.424 | 100.517 | 1.00 | 0.00 | xxxx | 17 |
| ATOM | 18 | N | GLN | A | 3 | 44.819 | 37.797 | 103.364 | 1.00 | 0.00 | xxxx | 18 |
| ATOM | 19 | CA | GLN | A | 3 | 43.674 | 37.341 | 102.583 | 1.00 | 0.00 | xxxx | 19 |
| ATOM | 20 | C | GLN | A | 3 | 44.115 | 37.047 | 101.155 | 1.00 | 0.00 | xxxx | 20 |
| ATOM | 21 | O | GLN | A | 3 | 44.627 | 37.928 | 100.458 | 1.00 | 0.00 | xxxx | 21 |
| ATOM | 22 | CB | GLN | A | 3 | 42.546 | 38.370 | 102.593 | 1.00 | 0.00 | xxxx | 22 |
| ATOM | 23 | CG | GLN | A | 3 | 41.288 | 37.854 | 101.877 | 1.00 | 0.00 | xxxx | 23 |
| ATOM | 24 | CD | GLN | A | 3 | 40.152 | 38.869 | 101.821 | 1.00 | 0.00 | xxxx | 24 |
| ATOM | 25 | OE1 | GLN | A | 3 | 40.188 | 39.812 | 101.033 | 1.00 | 0.00 | xxxx | 25 |
| ATOM | 26 | NE2 | GLN | A | 3 | 39.133 | 38.666 | 102.650 | 1.00 | 0.00 | xxxx | 26 |
| ATOM | 27 | N | LEU | A | 4 | 43.922 | 35.808 | 100.729 | 1.00 | 0.00 | xxxx | 27 |
| ATOM | 28 | CA | LEU | A | 4 | 44.155 | 35.405 | 99.356 | 1.00 | 0.00 | xxxx | 28 |
| ATOM | 29 | C | LEU | A | 4 | 42.819 | 35.406 | 98.634 | 1.00 | 0.00 | xxxx | 29 |
| ATOM | 30 | O | LEU | A | 4 | 41.807 | 34.955 | 99.179 | 1.00 | 0.00 | xxxx | 30 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 31 | CB | LEU | A | 4 | 44.758 | 33.999 | 99.317 | 1.00 | 0.00 | xxxx | 31 |
| ATOM | 32 | CG | LEU | A | 4 | 46.128 | 33.906 | 99.989 | 1.00 | 0.00 | xxxx | 32 |
| ATOM | 33 | CD1 | LEU | A | 4 | 46.603 | 32.466 | 100.045 | 1.00 | 0.00 | xxxx | 33 |
| ATOM | 34 | CD2 | LEU | A | 4 | 47.122 | 34.771 | 99.240 | 1.00 | 0.00 | xxxx | 34 |
| ATOM | 35 | N | ASN | A | 5 | 42.816 | 35.928 | 97.417 | 1.00 | 0.00 | xxxx | 35 |
| ATOM | 36 | CA | ASN | A | 5 | 41.601 | 36.070 | 96.627 | 1.00 | 0.00 | xxxx | 36 |
| ATOM | 37 | C | ASN | A | 5 | 41.719 | 35.224 | 95.378 | 1.00 | 0.00 | xxxx | 37 |
| ATOM | 38 | O | ASN | A | 5 | 42.670 | 35.378 | 94.602 | 1.00 | 0.00 | xxxx | 38 |
| ATOM | 39 | CB | ASN | A | 5 | 41.379 | 37.526 | 96.236 | 1.00 | 0.00 | xxxx | 39 |
| ATOM | 40 | CG | ASN | A | 5 | 40.748 | 38.312 | 97.342 | 1.00 | 0.00 | xxxx | 40 |
| ATOM | 41 | OD1 | ASN | A | 5 | 39.555 | 38.182 | 97.600 | 1.00 | 0.00 | xxxx | 41 |
| ATOM | 42 | ND2 | ASN | A | 5 | 41.547 | 39.128 | 98.019 | 1.00 | 0.00 | xxxx | 42 |
| ATOM | 43 | N | ILE | A | 6 | 40.751 | 34.341 | 95.183 | 1.00 | 0.00 | xxxx | 43 |
| ATOM | 44 | CA | ILE | A | 6 | 40.687 | 33.487 | 94.005 | 1.00 | 0.00 | xxxx | 44 |
| ATOM | 45 | C | ILE | A | 6 | 39.419 | 33.829 | 93.242 | 1.00 | 0.00 | xxxx | 45 |
| ATOM | 46 | O | ILE | A | 6 | 38.324 | 33.826 | 93.814 | 1.00 | 0.00 | xxxx | 46 |
| ATOM | 47 | CB | ILE | A | 6 | 40.716 | 31.997 | 94.388 | 1.00 | 0.00 | xxxx | 47 |
| ATOM | 48 | CG1 | ILE | A | 6 | 42.005 | 31.679 | 95.151 | 1.00 | 0.00 | xxxx | 48 |
| ATOM | 49 | CG2 | ILE | A | 6 | 40.600 | 31.126 | 93.145 | 1.00 | 0.00 | xxxx | 49 |
| ATOM | 50 | CD1 | ILE | A | 6 | 41.999 | 30.321 | 95.825 | 1.00 | 0.00 | xxxx | 50 |
| ATOM | 51 | N | GLY | A | 7 | 39.570 | 34.145 | 91.963 | 1.00 | 0.00 | xxxx | 51 |
| ATOM | 52 | CA | GLY | A | 7 | 38.413 | 34.396 | 91.134 | 1.00 | 0.00 | xxxx | 52 |
| ATOM | 53 | C | GLY | A | 7 | 37.924 | 33.090 | 90.543 | 1.00 | 0.00 | xxxx | 53 |
| ATOM | 54 | O | GLY | A | 7 | 38.686 | 32.412 | 89.855 | 1.00 | 0.00 | xxxx | 54 |
| ATOM | 55 | N | VAL | A | 8 | 36.679 | 32.708 | 90.822 | 1.00 | 0.00 | xxxx | 55 |
| ATOM | 56 | CA | VAL | A | 8 | 36.120 | 31.439 | 90.353 | 1.00 | 0.00 | xxxx | 56 |
| ATOM | 57 | C | VAL | A | 8 | 34.927 | 31.749 | 89.466 | 1.00 | 0.00 | xxxx | 57 |
| ATOM | 58 | O | VAL | A | 8 | 33.987 | 32.428 | 89.901 | 1.00 | 0.00 | xxxx | 58 |
| ATOM | 59 | CB | VAL | A | 8 | 35.678 | 30.544 | 91.522 | 1.00 | 0.00 | xxxx | 59 |
| ATOM | 60 | CG1 | VAL | A | 8 | 35.179 | 29.191 | 90.997 | 1.00 | 0.00 | xxxx | 60 |
| ATOM | 61 | CG2 | VAL | A | 8 | 36.802 | 30.361 | 92.528 | 1.00 | 0.00 | xxxx | 61 |
| ATOM | 62 | N | ALA | A | 9 | 34.956 | 31.258 | 88.235 | 1.00 | 0.00 | xxxx | 62 |
| ATOM | 63 | CA | ALA | A | 9 | 33.838 | 31.406 | 87.312 | 1.00 | 0.00 | xxxx | 63 |
| ATOM | 64 | C | ALA | A | 9 | 33.262 | 30.028 | 87.040 | 1.00 | 0.00 | xxxx | 64 |
| ATOM | 65 | O | ALA | A | 9 | 33.993 | 29.131 | 86.602 | 1.00 | 0.00 | xxxx | 65 |
| ATOM | 66 | CB | ALA | A | 9 | 34.284 | 32.061 | 86.002 | 1.00 | 0.00 | xxxx | 66 |
| ATOM | 67 | N | ILE | A | 10 | 31.967 | 29.858 | 87.321 | 1.00 | 0.00 | xxxx | 67 |
| ATOM | 68 | CA | ILE | A | 10 | 31.236 | 28.619 | 87.049 | 1.00 | 0.00 | xxxx | 68 |
| ATOM | 69 | C | ILE | A | 10 | 30.422 | 28.837 | 85.784 | 1.00 | 0.00 | xxxx | 69 |
| ATOM | 70 | O | ILE | A | 10 | 29.765 | 29.873 | 85.640 | 1.00 | 0.00 | xxxx | 70 |
| ATOM | 71 | CB | ILE | A | 10 | 30.325 | 28.257 | 88.238 | 1.00 | 0.00 | xxxx | 71 |
| ATOM | 72 | CG1 | ILE | A | 10 | 31.138 | 28.181 | 89.538 | 1.00 | 0.00 | xxxx | 72 |
| ATOM | 73 | CG2 | ILE | A | 10 | 29.577 | 26.954 | 87.986 | 1.00 | 0.00 | xxxx | 73 |
| ATOM | 74 | CD1 | ILE | A | 10 | 32.132 | 27.050 | 89.563 | 1.00 | 0.00 | xxxx | 74 |
| ATOM | 75 | N | TYR | A | 11 | 30.445 | 27.866 | 84.863 | 1.00 | 0.00 | xxxx | 75 |
| ATOM | 76 | CA | TYR | A | 11 | 29.862 | 28.130 | 83.545 | 1.00 | 0.00 | xxxx | 76 |
| ATOM | 77 | C | TYR | A | 11 | 28.373 | 28.468 | 83.643 | 1.00 | 0.00 | xxxx | 77 |
| ATOM | 78 | O | TYR | A | 11 | 27.889 | 29.339 | 82.916 | 1.00 | 0.00 | xxxx | 78 |
| ATOM | 79 | CB | TYR | A | 11 | 30.170 | 27.001 | 82.546 | 1.00 | 0.00 | xxxx | 79 |
| ATOM | 80 | CG | TYR | A | 11 | 29.092 | 25.948 | 82.396 | 1.00 | 0.00 | xxxx | 80 |
| ATOM | 81 | CD1 | TYR | A | 11 | 28.144 | 26.043 | 81.384 | 1.00 | 0.00 | xxxx | 81 |
| ATOM | 82 | CD2 | TYR | A | 11 | 29.034 | 24.856 | 83.261 | 1.00 | 0.00 | xxxx | 82 |
| ATOM | 83 | CE1 | TYR | A | 11 | 27.158 | 25.080 | 81.241 | 1.00 | 0.00 | xxxx | 83 |
| ATOM | 84 | CE2 | TYR | A | 11 | 28.045 | 23.892 | 83.125 | 1.00 | 0.00 | xxxx | 84 |
| ATOM | 85 | CZ | TYR | A | 11 | 27.118 | 24.018 | 82.115 | 1.00 | 0.00 | xxxx | 85 |
| ATOM | 86 | OH | TYR | A | 11 | 26.134 | 23.080 | 81.984 | 1.00 | 0.00 | xxxx | 86 |
| ATOM | 87 | N | LYS | A | 12 | 27.630 | 27.782 | 84.516 | 1.00 | 0.00 | xxxx | 87 |
| ATOM | 88 | CA | LYS | A | 12 | 26.283 | 28.208 | 84.866 | 1.00 | 0.00 | xxxx | 88 |
| ATOM | 89 | C | LYS | A | 12 | 25.909 | 27.598 | 86.210 | 1.00 | 0.00 | xxxx | 89 |
| ATOM | 90 | O | LYS | A | 12 | 26.226 | 26.436 | 86.496 | 1.00 | 0.00 | xxxx | 90 |
| ATOM | 91 | CB | LYS | A | 12 | 25.243 | 27.891 | 83.780 | 1.00 | 0.00 | xxxx | 91 |
| ATOM | 92 | CG | LYS | A | 12 | 24.862 | 26.446 | 83.644 | 1.00 | 0.00 | xxxx | 92 |
| ATOM | 93 | CD | LYS | A | 12 | 23.817 | 26.256 | 82.538 | 1.00 | 0.00 | xxxx | 93 |
| ATOM | 94 | CE | LYS | A | 12 | 23.394 | 24.805 | 82.448 | 1.00 | 0.00 | xxxx | 94 |
| ATOM | 95 | NZ | LYS | A | 12 | 22.368 | 24.593 | 81.393 | 1.00 | 0.00 | xxxx | 95 |
| ATOM | 96 | N | PHE | A | 13 | 25.249 | 28.403 | 87.036 | 1.00 | 0.00 | xxxx | 96 |
| ATOM | 97 | CA | PHE | A | 13 | 24.853 | 27.945 | 88.361 | 1.00 | 0.00 | xxxx | 97 |
| ATOM | 98 | C | PHE | A | 13 | 23.757 | 26.882 | 88.320 | 1.00 | 0.00 | xxxx | 98 |
| ATOM | 99 | O | PHE | A | 13 | 23.655 | 26.093 | 89.267 | 1.00 | 0.00 | xxxx | 99 |
| ATOM | 100 | CB | PHE | A | 13 | 24.403 | 29.131 | 89.226 | 1.00 | 0.00 | xxxx | 100 |
| ATOM | 101 | CG | PHE | A | 13 | 25.524 | 29.827 | 89.958 | 1.00 | 0.00 | xxxx | 101 |
| ATOM | 102 | CD1 | PHE | A | 13 | 26.849 | 29.623 | 89.627 | 1.00 | 0.00 | xxxx | 102 |
| ATOM | 103 | CD2 | PHE | A | 13 | 25.234 | 30.700 | 90.997 | 1.00 | 0.00 | xxxx | 103 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 104 | CE1 | PHE | A | 13 | 27.871 | 30.277 | 90.315 | 1.00 | 0.00 | xxxx | 104 |
| ATOM | 105 | CE2 | PHE | A | 13 | 26.245 | 31.352 | 91.691 | 1.00 | 0.00 | xxxx | 105 |
| ATOM | 106 | CZ | PHE | A | 13 | 27.567 | 31.139 | 91.351 | 1.00 | 0.00 | xxxx | 106 |
| ATOM | 107 | N | ASP | A | 14 | 22.962 | 26.805 | 87.251 | 1.00 | 0.00 | xxxx | 107 |
| ATOM | 108 | CA | ASP | A | 14 | 21.868 | 25.834 | 87.224 | 1.00 | 0.00 | xxxx | 108 |
| ATOM | 109 | C | ASP | A | 14 | 22.293 | 24.430 | 86.781 | 1.00 | 0.00 | xxxx | 109 |
| ATOM | 110 | O | ASP | A | 14 | 21.433 | 23.546 | 86.663 | 1.00 | 0.00 | xxxx | 110 |
| ATOM | 111 | CB | ASP | A | 14 | 20.671 | 26.348 | 86.413 | 1.00 | 0.00 | xxxx | 111 |
| ATOM | 112 | CG | ASP | A | 14 | 21.055 | 26.809 | 85.025 | 1.00 | 0.00 | xxxx | 112 |
| ATOM | 113 | OD1 | ASP | A | 14 | 22.089 | 27.496 | 84.889 | 1.00 | 0.00 | xxxx | 113 |
| ATOM | 114 | OD2 | ASP | A | 14 | 20.313 | 26.493 | 84.071 | 1.00 | 0.00 | xxxx | 114 |
| ATOM | 115 | N | ASP | A | 15 | 23.582 | 24.188 | 86.573 | 1.00 | 0.00 | xxxx | 115 |
| ATOM | 116 | CA | ASP | A | 15 | 24.059 | 22.858 | 86.222 | 1.00 | 0.00 | xxxx | 116 |
| ATOM | 117 | C | ASP | A | 15 | 24.132 | 22.010 | 87.491 | 1.00 | 0.00 | xxxx | 117 |
| ATOM | 118 | O | ASP | A | 15 | 24.761 | 22.414 | 88.478 | 1.00 | 0.00 | xxxx | 118 |
| ATOM | 119 | CB | ASP | A | 15 | 25.435 | 22.975 | 85.574 | 1.00 | 0.00 | xxxx | 119 |
| ATOM | 120 | CG | ASP | A | 15 | 25.957 | 21.651 | 85.075 | 1.00 | 0.00 | xxxx | 120 |
| ATOM | 121 | OD1 | ASP | A | 15 | 25.794 | 21.363 | 83.873 | 1.00 | 0.00 | xxxx | 121 |
| ATOM | 122 | OD2 | ASP | A | 15 | 26.530 | 20.893 | 85.881 | 1.00 | 0.00 | xxxx | 122 |
| ATOM | 123 | N | THR | A | 16 | 23.478 | 20.843 | 87.476 | 1.00 | 0.00 | xxxx | 123 |
| ATOM | 124 | CA | THR | A | 16 | 23.363 | 20.037 | 88.690 | 1.00 | 0.00 | xxxx | 124 |
| ATOM | 125 | C | THR | A | 16 | 24.724 | 19.543 | 89.166 | 1.00 | 0.00 | xxxx | 125 |
| ATOM | 126 | O | THR | A | 16 | 25.055 | 19.655 | 90.355 | 1.00 | 0.00 | xxxx | 126 |
| ATOM | 127 | CB | THR | A | 16 | 22.423 | 18.855 | 88.463 | 1.00 | 0.00 | xxxx | 127 |
| ATOM | 128 | OG1 | THR | A | 16 | 21.163 | 19.330 | 87.960 | 1.00 | 0.00 | xxxx | 128 |
| ATOM | 129 | CG2 | THR | A | 16 | 22.184 | 18.113 | 89.776 | 1.00 | 0.00 | xxxx | 129 |
| ATOM | 130 | N | PHE | A | 17 | 25.529 | 18.990 | 88.255 | 1.00 | 0.00 | xxxx | 130 |
| ATOM | 131 | CA | PHE | A | 17 | 26.844 | 18.493 | 88.656 | 1.00 | 0.00 | xxxx | 131 |
| ATOM | 132 | C | PHE | A | 17 | 27.726 | 19.624 | 89.167 | 1.00 | 0.00 | xxxx | 132 |
| ATOM | 133 | O | PHE | A | 17 | 28.395 | 19.494 | 90.206 | 1.00 | 0.00 | xxxx | 133 |
| ATOM | 134 | CB | PHE | A | 17 | 27.522 | 17.737 | 87.506 | 1.00 | 0.00 | xxxx | 134 |
| ATOM | 135 | CG | PHE | A | 17 | 28.944 | 17.377 | 87.815 | 1.00 | 0.00 | xxxx | 135 |
| ATOM | 136 | CD1 | PHE | A | 17 | 29.221 | 16.313 | 88.658 | 1.00 | 0.00 | xxxx | 136 |
| ATOM | 137 | CD2 | PHE | A | 17 | 29.992 | 18.137 | 87.324 | 1.00 | 0.00 | xxxx | 137 |
| ATOM | 138 | CE1 | PHE | A | 17 | 30.527 | 15.998 | 89.000 | 1.00 | 0.00 | xxxx | 138 |
| ATOM | 139 | CE2 | PHE | A | 17 | 31.315 | 17.815 | 87.651 | 1.00 | 0.00 | xxxx | 139 |
| ATOM | 140 | CZ | PHE | A | 17 | 31.572 | 16.752 | 88.491 | 1.00 | 0.00 | xxxx | 140 |
| ATOM | 141 | N | MET | A | 18 | 27.749 | 20.745 | 88.449 | 1.00 | 0.00 | xxxx | 141 |
| ATOM | 142 | CA | MET | A | 18 | 28.609 | 21.840 | 88.859 | 1.00 | 0.00 | xxxx | 142 |
| ATOM | 143 | C | MET | A | 18 | 28.149 | 22.496 | 90.158 | 1.00 | 0.00 | xxxx | 143 |
| ATOM | 144 | O | MET | A | 18 | 28.966 | 23.127 | 90.832 | 1.00 | 0.00 | xxxx | 144 |
| ATOM | 145 | CB | MET | A | 18 | 28.780 | 22.851 | 87.723 | 1.00 | 0.00 | xxxx | 145 |
| ATOM | 146 | CG | MET | A | 18 | 29.638 | 22.310 | 86.563 | 1.00 | 0.00 | xxxx | 146 |
| ATOM | 147 | SD | MET | A | 18 | 31.269 | 21.698 | 87.068 | 1.00 | 0.00 | xxxx | 147 |
| ATOM | 148 | CE | MET | A | 18 | 31.997 | 23.172 | 87.760 | 1.00 | 0.00 | xxxx | 148 |
| ATOM | 149 | N | THR | A | 19 | 26.872 | 22.368 | 90.531 | 1.00 | 0.00 | xxxx | 149 |
| ATOM | 150 | CA | THR | A | 19 | 26.451 | 22.829 | 91.850 | 1.00 | 0.00 | xxxx | 150 |
| ATOM | 151 | C | THR | A | 19 | 27.156 | 22.040 | 92.945 | 1.00 | 0.00 | xxxx | 151 |
| ATOM | 152 | O | THR | A | 19 | 27.605 | 22.608 | 93.946 | 1.00 | 0.00 | xxxx | 152 |
| ATOM | 153 | CB | THR | A | 19 | 24.937 | 22.719 | 91.970 | 1.00 | 0.00 | xxxx | 153 |
| ATOM | 154 | OG1 | THR | A | 19 | 24.344 | 23.589 | 90.996 | 1.00 | 0.00 | xxxx | 154 |
| ATOM | 155 | CG2 | THR | A | 19 | 24.485 | 23.130 | 93.358 | 1.00 | 0.00 | xxxx | 155 |
| ATOM | 156 | N | GLY | A | 20 | 27.297 | 20.729 | 92.755 | 1.00 | 0.00 | xxxx | 156 |
| ATOM | 157 | CA | GLY | A | 20 | 28.061 | 19.945 | 93.709 | 1.00 | 0.00 | xxxx | 157 |
| ATOM | 158 | C | GLY | A | 20 | 29.516 | 20.366 | 93.780 | 1.00 | 0.00 | xxxx | 158 |
| ATOM | 159 | O | GLY | A | 20 | 30.103 | 20.412 | 94.866 | 1.00 | 0.00 | xxxx | 159 |
| ATOM | 160 | N | VAL | A | 21 | 30.118 | 20.682 | 92.628 | 1.00 | 0.00 | xxxx | 160 |
| ATOM | 161 | CA | VAL | A | 21 | 31.509 | 21.135 | 92.614 | 1.00 | 0.00 | xxxx | 161 |
| ATOM | 162 | C | VAL | A | 21 | 31.650 | 22.459 | 93.348 | 1.00 | 0.00 | xxxx | 162 |
| ATOM | 163 | O | VAL | A | 21 | 32.525 | 22.622 | 94.203 | 1.00 | 0.00 | xxxx | 163 |
| ATOM | 164 | CB | VAL | A | 21 | 32.041 | 21.238 | 91.175 | 1.00 | 0.00 | xxxx | 164 |
| ATOM | 165 | CG1 | VAL | A | 21 | 33.437 | 21.844 | 91.180 | 1.00 | 0.00 | xxxx | 165 |
| ATOM | 166 | CG2 | VAL | A | 21 | 32.058 | 19.874 | 90.497 | 1.00 | 0.00 | xxxx | 166 |
| ATOM | 167 | N | ARG | A | 22 | 30.810 | 23.440 | 93.015 | 1.00 | 0.00 | xxxx | 167 |
| ATOM | 168 | CA | ARG | A | 22 | 31.006 | 24.739 | 93.649 | 1.00 | 0.00 | xxxx | 168 |
| ATOM | 169 | C | ARG | A | 22 | 30.718 | 24.699 | 95.149 | 1.00 | 0.00 | xxxx | 169 |
| ATOM | 170 | O | ARG | A | 22 | 31.406 | 25.379 | 95.918 | 1.00 | 0.00 | xxxx | 170 |
| ATOM | 171 | CB | ARG | A | 22 | 30.269 | 25.848 | 92.897 | 1.00 | 0.00 | xxxx | 171 |
| ATOM | 172 | CG | ARG | A | 22 | 28.782 | 25.708 | 92.836 | 1.00 | 0.00 | xxxx | 172 |
| ATOM | 173 | CD | ARG | A | 22 | 28.239 | 26.768 | 91.886 | 1.00 | 0.00 | xxxx | 173 |
| ATOM | 174 | NE | ARG | A | 22 | 26.839 | 26.539 | 91.568 | 1.00 | 0.00 | xxxx | 174 |
| ATOM | 175 | CZ | ARG | A | 22 | 25.837 | 26.992 | 92.305 | 1.00 | 0.00 | xxxx | 175 |
| ATOM | 176 | NH1 | ARG | A | 22 | 26.091 | 27.690 | 93.407 | 1.00 | 0.00 | xxxx | 176 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 177 | NH2 | ARG | A | 22 | 24.585 | 26.746 | 91.952 | 1.00 | 0.00 | xxxx | 177 |
| ATOM | 178 | N | ASN | A | 23 | 29.746 | 23.897 | 95.592 | 1.00 | 0.00 | xxxx | 178 |
| ATOM | 179 | CA | ASN | A | 23 | 29.515 | 23.756 | 97.027 | 1.00 | 0.00 | xxxx | 179 |
| ATOM | 180 | C | ASN | A | 23 | 30.709 | 23.111 | 97.717 | 1.00 | 0.00 | xxxx | 180 |
| ATOM | 181 | O | ASN | A | 23 | 31.083 | 23.507 | 98.825 | 1.00 | 0.00 | xxxx | 181 |
| ATOM | 182 | CB | ASN | A | 23 | 28.260 | 22.929 | 97.291 | 1.00 | 0.00 | xxxx | 182 |
| ATOM | 183 | CG | ASN | A | 23 | 26.988 | 23.666 | 96.932 | 1.00 | 0.00 | xxxx | 183 |
| ATOM | 184 | OD1 | ASN | A | 23 | 26.978 | 24.886 | 96.797 | 1.00 | 0.00 | xxxx | 184 |
| ATOM | 185 | ND2 | ASN | A | 23 | 25.905 | 22.922 | 96.777 | 1.00 | 0.00 | xxxx | 185 |
| ATOM | 186 | N | ALA | A | 24 | 31.328 | 22.119 | 97.076 | 1.00 | 0.00 | xxxx | 186 |
| ATOM | 187 | CA | ALA | A | 24 | 32.500 | 21.497 | 97.682 | 1.00 | 0.00 | xxxx | 187 |
| ATOM | 188 | C | ALA | A | 24 | 33.708 | 22.429 | 97.666 | 1.00 | 0.00 | xxxx | 188 |
| ATOM | 189 | O | ALA | A | 24 | 34.502 | 22.416 | 98.615 | 1.00 | 0.00 | xxxx | 189 |
| ATOM | 190 | CB | ALA | A | 24 | 32.809 | 20.168 | 96.998 | 1.00 | 0.00 | xxxx | 190 |
| ATOM | 191 | N | MET | A | 25 | 33.850 | 23.259 | 96.627 | 1.00 | 0.00 | xxxx | 191 |
| ATOM | 192 | CA | MET | A | 25 | 34.940 | 24.231 | 96.613 | 1.00 | 0.00 | xxxx | 192 |
| ATOM | 193 | C | MET | A | 25 | 34.787 | 25.222 | 97.753 | 1.00 | 0.00 | xxxx | 193 |
| ATOM | 194 | O | MET | A | 25 | 35.764 | 25.546 | 98.437 | 1.00 | 0.00 | xxxx | 194 |
| ATOM | 195 | CB | MET | A | 25 | 34.981 | 24.968 | 95.270 | 1.00 | 0.00 | xxxx | 195 |
| ATOM | 196 | CG | MET | A | 25 | 35.449 | 24.116 | 94.095 | 1.00 | 0.00 | xxxx | 196 |
| ATOM | 197 | SD | MET | A | 25 | 35.613 | 25.003 | 92.534 | 1.00 | 0.00 | xxxx | 197 |
| ATOM | 198 | CE | MET | A | 25 | 36.694 | 26.323 | 93.078 | 1.00 | 0.00 | xxxx | 198 |
| ATOM | 199 | N | THR | A | 26 | 33.564 | 25.721 | 97.964 | 1.00 | 0.00 | xxxx | 199 |
| ATOM | 200 | CA | THR | A | 26 | 33.301 | 26.646 | 99.061 | 1.00 | 0.00 | xxxx | 200 |
| ATOM | 201 | C | THR | A | 26 | 33.669 | 26.015 | 100.393 | 1.00 | 0.00 | xxxx | 201 |
| ATOM | 202 | O | THR | A | 26 | 34.274 | 26.667 | 101.256 | 1.00 | 0.00 | xxxx | 202 |
| ATOM | 203 | CB | THR | A | 26 | 31.825 | 27.039 | 99.033 | 1.00 | 0.00 | xxxx | 203 |
| ATOM | 204 | OG1 | THR | A | 26 | 31.547 | 27.723 | 97.806 | 1.00 | 0.00 | xxxx | 204 |
| ATOM | 205 | CG2 | THR | A | 26 | 31.469 | 27.953 | 100.202 | 1.00 | 0.00 | xxxx | 205 |
| ATOM | 206 | N | ALA | A | 27 | 33.338 | 24.735 | 100.573 | 1.00 | 0.00 | xxxx | 206 |
| ATOM | 207 | CA | ALA | A | 27 | 33.658 | 24.071 | 101.828 | 1.00 | 0.00 | xxxx | 207 |
| ATOM | 208 | C | ALA | A | 27 | 35.165 | 23.922 | 102.008 | 1.00 | 0.00 | xxxx | 208 |
| ATOM | 209 | O | ALA | A | 27 | 35.680 | 24.097 | 103.116 | 1.00 | 0.00 | xxxx | 209 |
| ATOM | 210 | CB | ALA | A | 27 | 32.957 | 22.717 | 101.889 | 1.00 | 0.00 | xxxx | 210 |
| ATOM | 211 | N | GLU | A | 28 | 35.892 | 23.621 | 100.930 | 1.00 | 0.00 | xxxx | 211 |
| ATOM | 212 | CA | GLU | A | 28 | 37.337 | 23.457 | 101.064 | 1.00 | 0.00 | xxxx | 212 |
| ATOM | 213 | C | GLU | A | 28 | 38.032 | 24.785 | 101.340 | 1.00 | 0.00 | xxxx | 213 |
| ATOM | 214 | O | GLU | A | 28 | 39.046 | 24.814 | 102.045 | 1.00 | 0.00 | xxxx | 214 |
| ATOM | 215 | CB | GLU | A | 28 | 37.917 | 22.797 | 99.812 | 1.00 | 0.00 | xxxx | 215 |
| ATOM | 216 | CG | GLU | A | 28 | 39.357 | 22.325 | 99.980 | 1.00 | 0.00 | xxxx | 216 |
| ATOM | 217 | CD | GLU | A | 28 | 39.498 | 21.215 | 101.005 | 1.00 | 0.00 | xxxx | 217 |
| ATOM | 218 | OE1 | GLU | A | 28 | 38.534 | 20.443 | 101.189 | 1.00 | 0.00 | xxxx | 218 |
| ATOM | 219 | OE2 | GLU | A | 28 | 40.576 | 21.116 | 101.631 | 1.00 | 0.00 | xxxx | 219 |
| ATOM | 220 | N | ALA | A | 29 | 37.501 | 25.884 | 100.801 | 1.00 | 0.00 | xxxx | 220 |
| ATOM | 221 | CA | ALA | A | 29 | 38.119 | 27.195 | 100.943 | 1.00 | 0.00 | xxxx | 221 |
| ATOM | 222 | C | ALA | A | 29 | 37.903 | 27.814 | 102.314 | 1.00 | 0.00 | xxxx | 222 |
| ATOM | 223 | O | ALA | A | 29 | 38.651 | 28.725 | 102.677 | 1.00 | 0.00 | xxxx | 223 |
| ATOM | 224 | CB | ALA | A | 29 | 37.566 | 28.156 | 99.889 | 1.00 | 0.00 | xxxx | 224 |
| ATOM | 225 | N | GLN | A | 30 | 36.902 | 27.355 | 103.065 | 1.00 | 0.00 | xxxx | 225 |
| ATOM | 226 | CA | GLN | A | 30 | 36.545 | 27.956 | 104.346 | 1.00 | 0.00 | xxxx | 226 |
| ATOM | 227 | C | GLN | A | 30 | 37.751 | 28.033 | 105.270 | 1.00 | 0.00 | xxxx | 227 |
| ATOM | 228 | O | GLN | A | 30 | 38.410 | 27.024 | 105.533 | 1.00 | 0.00 | xxxx | 228 |
| ATOM | 229 | CB | GLN | A | 30 | 35.435 | 27.124 | 104.995 | 1.00 | 0.00 | xxxx | 229 |
| ATOM | 230 | CG | GLN | A | 30 | 34.875 | 27.717 | 106.281 | 1.00 | 0.00 | xxxx | 230 |
| ATOM | 231 | CD | GLN | A | 30 | 33.897 | 26.782 | 106.972 | 1.00 | 0.00 | xxxx | 231 |
| ATOM | 232 | OE1 | GLN | A | 30 | 34.295 | 25.762 | 107.534 | 1.00 | 0.00 | xxxx | 232 |
| ATOM | 233 | NE2 | GLN | A | 30 | 32.610 | 27.120 | 106.922 | 1.00 | 0.00 | xxxx | 233 |
| ATOM | 234 | N | GLY | A | 31 | 38.042 | 29.243 | 105.757 | 1.00 | 0.00 | xxxx | 234 |
| ATOM | 235 | CA | GLY | A | 31 | 39.175 | 29.474 | 106.631 | 1.00 | 0.00 | xxxx | 235 |
| ATOM | 236 | C | GLY | A | 31 | 40.523 | 29.560 | 105.946 | 1.00 | 0.00 | xxxx | 236 |
| ATOM | 237 | O | GLY | A | 31 | 41.533 | 29.751 | 106.633 | 1.00 | 0.00 | xxxx | 237 |
| ATOM | 238 | N | LYS | A | 32 | 40.578 | 29.446 | 104.618 | 1.00 | 0.00 | xxxx | 238 |
| ATOM | 239 | CA | LYS | A | 32 | 41.841 | 29.380 | 103.886 | 1.00 | 0.00 | xxxx | 239 |
| ATOM | 240 | C | LYS | A | 32 | 42.007 | 30.507 | 102.883 | 1.00 | 0.00 | xxxx | 240 |
| ATOM | 241 | O | LYS | A | 32 | 43.072 | 31.130 | 102.829 | 1.00 | 0.00 | xxxx | 241 |
| ATOM | 242 | CB | LYS | A | 32 | 41.971 | 28.034 | 103.156 | 1.00 | 0.00 | xxxx | 242 |
| ATOM | 243 | CG | LYS | A | 32 | 42.024 | 26.831 | 104.078 | 1.00 | 0.00 | xxxx | 243 |
| ATOM | 244 | CD | LYS | A | 32 | 42.100 | 25.541 | 103.276 | 1.00 | 0.00 | xxxx | 244 |
| ATOM | 245 | CE | LYS | A | 32 | 41.788 | 24.341 | 104.156 | 1.00 | 0.00 | xxxx | 245 |
| ATOM | 246 | NZ | LYS | A | 32 | 41.472 | 23.132 | 103.346 | 1.00 | 0.00 | xxxx | 246 |
| ATOM | 247 | N | ALA | A | 33 | 40.990 | 30.782 | 102.079 | 1.00 | 0.00 | xxxx | 247 |
| ATOM | 248 | CA | ALA | A | 33 | 41.101 | 31.780 | 101.029 | 1.00 | 0.00 | xxxx | 248 |
| ATOM | 249 | C | ALA | A | 33 | 39.702 | 32.228 | 100.659 | 1.00 | 0.00 | xxxx | 249 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 250 | O | ALA | A | 33 | 38.728 | 31.492 | 100.837 | 1.00 | 0.00 | xxxx | 250 |
| ATOM | 251 | CB | ALA | A | 33 | 41.816 | 31.214 | 99.799 | 1.00 | 0.00 | xxxx | 251 |
| ATOM | 252 | N | LYS | A | 34 | 39.615 | 33.438 | 100.121 | 1.00 | 0.00 | xxxx | 252 |
| ATOM | 253 | CA | LYS | A | 34 | 38.337 | 34.001 | 99.709 | 1.00 | 0.00 | xxxx | 253 |
| ATOM | 254 | C | LYS | A | 34 | 38.080 | 33.631 | 98.255 | 1.00 | 0.00 | xxxx | 254 |
| ATOM | 255 | O | LYS | A | 34 | 38.876 | 33.970 | 97.373 | 1.00 | 0.00 | xxxx | 255 |
| ATOM | 256 | CB | LYS | A | 34 | 38.348 | 35.519 | 99.870 | 1.00 | 0.00 | xxxx | 256 |
| ATOM | 257 | CG | LYS | A | 34 | 37.036 | 36.178 | 99.475 | 1.00 | 0.00 | xxxx | 257 |
| ATOM | 258 | CD | LYS | A | 34 | 37.045 | 37.663 | 99.792 | 1.00 | 0.00 | xxxx | 258 |
| ATOM | 259 | CE | LYS | A | 34 | 35.786 | 38.332 | 99.252 | 1.00 | 0.00 | xxxx | 259 |
| ATOM | 260 | NZ | LYS | A | 34 | 35.790 | 39.805 | 99.460 | 1.00 | 0.00 | xxxx | 260 |
| ATOM | 261 | N | LEU | A | 35 | 36.987 | 32.912 | 98.007 | 1.00 | 0.00 | xxxx | 261 |
| ATOM | 262 | CA | LEU | A | 35 | 36.547 | 32.647 | 96.645 | 1.00 | 0.00 | xxxx | 262 |
| ATOM | 263 | C | LEU | A | 35 | 35.617 | 33.769 | 96.220 | 1.00 | 0.00 | xxxx | 263 |
| ATOM | 264 | O | LEU | A | 35 | 34.622 | 34.052 | 96.898 | 1.00 | 0.00 | xxxx | 264 |
| ATOM | 265 | CB | LEU | A | 35 | 35.817 | 31.311 | 96.533 | 1.00 | 0.00 | xxxx | 265 |
| ATOM | 266 | CG | LEU | A | 35 | 36.570 | 30.079 | 97.011 | 1.00 | 0.00 | xxxx | 266 |
| ATOM | 267 | CD1 | LEU | A | 35 | 35.771 | 28.820 | 96.682 | 1.00 | 0.00 | xxxx | 267 |
| ATOM | 268 | CD2 | LEU | A | 35 | 37.962 | 30.024 | 96.405 | 1.00 | 0.00 | xxxx | 268 |
| ATOM | 269 | N | ASN | A | 36 | 35.946 | 34.414 | 95.113 | 1.00 | 0.00 | xxxx | 269 |
| ATOM | 270 | CA | ASN | A | 36 | 35.060 | 35.395 | 94.494 | 1.00 | 0.00 | xxxx | 270 |
| ATOM | 271 | C | ASN | A | 36 | 34.382 | 34.638 | 93.360 | 1.00 | 0.00 | xxxx | 271 |
| ATOM | 272 | O | ASN | A | 36 | 34.899 | 34.555 | 92.243 | 1.00 | 0.00 | xxxx | 272 |
| ATOM | 273 | CB | ASN | A | 36 | 35.870 | 36.593 | 94.027 | 1.00 | 0.00 | xxxx | 273 |
| ATOM | 274 | CG | ASN | A | 36 | 36.557 | 37.289 | 95.182 | 1.00 | 0.00 | xxxx | 274 |
| ATOM | 275 | OD1 | ASN | A | 36 | 35.957 | 38.126 | 95.846 | 1.00 | 0.00 | xxxx | 275 |
| ATOM | 276 | ND2 | ASN | A | 36 | 37.793 | 36.897 | 95.469 | 1.00 | 0.00 | xxxx | 276 |
| ATOM | 277 | N | MET | A | 37 | 33.217 | 34.063 | 93.641 | 1.00 | 0.00 | xxxx | 277 |
| ATOM | 278 | CA | MET | A | 37 | 32.609 | 33.085 | 92.743 | 1.00 | 0.00 | xxxx | 278 |
| ATOM | 279 | C | MET | A | 37 | 31.433 | 33.697 | 91.990 | 1.00 | 0.00 | xxxx | 279 |
| ATOM | 280 | O | MET | A | 37 | 30.486 | 34.207 | 92.603 | 1.00 | 0.00 | xxxx | 280 |
| ATOM | 281 | CB | MET | A | 37 | 32.180 | 31.831 | 93.499 | 1.00 | 0.00 | xxxx | 281 |
| ATOM | 282 | CG | MET | A | 37 | 31.663 | 30.735 | 92.582 | 1.00 | 0.00 | xxxx | 282 |
| ATOM | 283 | SD | MET | A | 37 | 31.040 | 29.361 | 93.555 | 1.00 | 0.00 | xxxx | 283 |
| ATOM | 284 | CE | MET | A | 37 | 32.585 | 28.543 | 93.944 | 1.00 | 0.00 | xxxx | 284 |
| ATOM | 285 | N | VAL | A | 38 | 31.493 | 33.622 | 90.662 | 1.00 | 0.00 | xxxx | 285 |
| ATOM | 286 | CA | VAL | A | 38 | 30.527 | 34.240 | 89.764 | 1.00 | 0.00 | xxxx | 286 |
| ATOM | 287 | C | VAL | A | 38 | 29.901 | 33.185 | 88.859 | 1.00 | 0.00 | xxxx | 287 |
| ATOM | 288 | O | VAL | A | 38 | 30.500 | 32.143 | 88.569 | 1.00 | 0.00 | xxxx | 288 |
| ATOM | 289 | CB | VAL | A | 38 | 31.133 | 35.399 | 88.929 | 1.00 | 0.00 | xxxx | 289 |
| ATOM | 290 | CG1 | VAL | A | 38 | 31.703 | 36.485 | 89.833 | 1.00 | 0.00 | xxxx | 290 |
| ATOM | 291 | CG2 | VAL | A | 38 | 32.187 | 34.886 | 87.965 | 1.00 | 0.00 | xxxx | 291 |
| ATOM | 292 | N | ASP | A | 39 | 28.679 | 33.478 | 88.428 | 1.00 | 0.00 | xxxx | 292 |
| ATOM | 293 | CA | ASP | A | 39 | 27.868 | 32.649 | 87.543 | 1.00 | 0.00 | xxxx | 293 |
| ATOM | 294 | C | ASP | A | 39 | 27.994 | 33.221 | 86.135 | 1.00 | 0.00 | xxxx | 294 |
| ATOM | 295 | O | ASP | A | 39 | 27.584 | 34.359 | 85.879 | 1.00 | 0.00 | xxxx | 295 |
| ATOM | 296 | CB | ASP | A | 39 | 26.413 | 32.740 | 88.030 | 1.00 | 0.00 | xxxx | 296 |
| ATOM | 297 | CG | ASP | A | 39 | 25.435 | 31.916 | 87.197 | 1.00 | 0.00 | xxxx | 297 |
| ATOM | 298 | OD1 | ASP | A | 39 | 25.864 | 31.210 | 86.273 | 1.00 | 0.00 | xxxx | 298 |
| ATOM | 299 | OD2 | ASP | A | 39 | 24.217 | 31.984 | 87.482 | 1.00 | 0.00 | xxxx | 299 |
| ATOM | 300 | N | SER | A | 40 | 28.582 | 32.448 | 85.224 | 1.00 | 0.00 | xxxx | 300 |
| ATOM | 301 | CA | SER | A | 40 | 28.718 | 32.933 | 83.852 | 1.00 | 0.00 | xxxx | 301 |
| ATOM | 302 | C | SER | A | 40 | 27.437 | 32.805 | 83.040 | 1.00 | 0.00 | xxxx | 302 |
| ATOM | 303 | O | SER | A | 40 | 27.412 | 33.251 | 81.888 | 1.00 | 0.00 | xxxx | 303 |
| ATOM | 304 | CB | SER | A | 40 | 29.876 | 32.232 | 83.136 | 1.00 | 0.00 | xxxx | 304 |
| ATOM | 305 | OG | SER | A | 40 | 31.102 | 32.449 | 83.831 | 1.00 | 0.00 | xxxx | 305 |
| ATOM | 306 | N | GLN | A | 41 | 26.383 | 32.212 | 83.608 | 1.00 | 0.00 | xxxx | 306 |
| ATOM | 307 | CA | GLN | A | 41 | 25.049 | 32.190 | 83.005 | 1.00 | 0.00 | xxxx | 307 |
| ATOM | 308 | C | GLN | A | 41 | 25.053 | 31.588 | 81.602 | 1.00 | 0.00 | xxxx | 308 |
| ATOM | 309 | O | GLN | A | 41 | 24.299 | 32.010 | 80.720 | 1.00 | 0.00 | xxxx | 309 |
| ATOM | 310 | CB | GLN | A | 41 | 24.394 | 33.572 | 83.017 | 1.00 | 0.00 | xxxx | 310 |
| ATOM | 311 | CG | GLN | A | 41 | 24.215 | 34.163 | 84.415 | 1.00 | 0.00 | xxxx | 311 |
| ATOM | 312 | CD | GLN | A | 41 | 23.401 | 35.430 | 84.386 | 1.00 | 0.00 | xxxx | 312 |
| ATOM | 313 | OE1 | GLN | A | 41 | 23.931 | 36.521 | 84.568 | 1.00 | 0.00 | xxxx | 313 |
| ATOM | 314 | NE2 | GLN | A | 41 | 22.103 | 35.294 | 84.144 | 1.00 | 0.00 | xxxx | 314 |
| ATOM | 315 | N | ASN | A | 42 | 25.921 | 30.598 | 81.388 | 1.00 | 0.00 | xxxx | 315 |
| ATOM | 316 | CA | ASN | A | 42 | 25.990 | 29.866 | 80.122 | 1.00 | 0.00 | xxxx | 316 |
| ATOM | 317 | C | ASN | A | 42 | 26.345 | 30.772 | 78.942 | 1.00 | 0.00 | xxxx | 317 |
| ATOM | 318 | O | ASN | A | 42 | 25.944 | 30.504 | 77.809 | 1.00 | 0.00 | xxxx | 318 |
| ATOM | 319 | CB | ASN | A | 42 | 24.694 | 29.085 | 79.850 | 1.00 | 0.00 | xxxx | 319 |
| ATOM | 320 | CG | ASN | A | 42 | 24.907 | 27.888 | 78.954 | 1.00 | 0.00 | xxxx | 320 |
| ATOM | 321 | OD1 | ASN | A | 42 | 23.973 | 27.408 | 78.298 | 1.00 | 0.00 | xxxx | 321 |
| ATOM | 322 | ND2 | ASN | A | 42 | 26.124 | 27.401 | 78.908 | 1.00 | 0.00 | xxxx | 322 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 323 | N | SER | A | 43 | 27.103 | 31.840 | 79.204 | 1.00 | 0.00 | xxxx | 323 |
| ATOM | 324 | CA | SER | A | 43 | 27.490 | 32.810 | 78.185 | 1.00 | 0.00 | xxxx | 324 |
| ATOM | 325 | C | SER | A | 43 | 28.996 | 33.028 | 78.247 | 1.00 | 0.00 | xxxx | 325 |
| ATOM | 326 | O | SER | A | 43 | 29.512 | 33.541 | 79.245 | 1.00 | 0.00 | xxxx | 326 |
| ATOM | 327 | CB | SER | A | 43 | 26.766 | 34.134 | 78.438 | 1.00 | 0.00 | xxxx | 327 |
| ATOM | 328 | OG | SER | A | 43 | 27.295 | 35.177 | 77.627 | 1.00 | 0.00 | xxxx | 328 |
| ATOM | 329 | N | GLN | A | 44 | 29.707 | 32.653 | 77.183 | 1.00 | 0.00 | xxxx | 329 |
| ATOM | 330 | CA | GLN | A | 44 | 31.145 | 32.903 | 77.183 | 1.00 | 0.00 | xxxx | 330 |
| ATOM | 331 | C | GLN | A | 44 | 31.464 | 34.397 | 77.155 | 1.00 | 0.00 | xxxx | 331 |
| ATOM | 332 | O | GLN | A | 44 | 32.416 | 34.810 | 77.829 | 1.00 | 0.00 | xxxx | 332 |
| ATOM | 333 | CB | GLN | A | 44 | 31.877 | 32.158 | 76.060 | 1.00 | 0.00 | xxxx | 333 |
| ATOM | 334 | CG | GLN | A | 44 | 33.404 | 32.203 | 76.217 | 1.00 | 0.00 | xxxx | 334 |
| ATOM | 335 | CD | GLN | A | 44 | 33.891 | 31.519 | 77.490 | 1.00 | 0.00 | xxxx | 335 |
| ATOM | 336 | OE1 | GLN | A | 44 | 33.482 | 30.407 | 77.804 | 1.00 | 0.00 | xxxx | 336 |
| ATOM | 337 | NE2 | GLN | A | 44 | 34.769 | 32.193 | 78.233 | 1.00 | 0.00 | xxxx | 337 |
| ATOM | 338 | N | PRO | A | 45 | 30.726 | 35.240 | 76.409 | 1.00 | 0.00 | xxxx | 338 |
| ATOM | 339 | CA | PRO | A | 45 | 30.953 | 36.693 | 76.549 | 1.00 | 0.00 | xxxx | 339 |
| ATOM | 340 | C | PRO | A | 45 | 30.815 | 37.191 | 77.980 | 1.00 | 0.00 | xxxx | 340 |
| ATOM | 341 | O | PRO | A | 45 | 31.629 | 38.014 | 78.421 | 1.00 | 0.00 | xxxx | 341 |
| ATOM | 342 | CB | PRO | A | 45 | 29.924 | 37.307 | 75.589 | 1.00 | 0.00 | xxxx | 342 |
| ATOM | 343 | CG | PRO | A | 45 | 29.751 | 36.260 | 74.530 | 1.00 | 0.00 | xxxx | 343 |
| ATOM | 344 | CD | PRO | A | 45 | 29.797 | 34.957 | 75.292 | 1.00 | 0.00 | xxxx | 344 |
| ATOM | 345 | N | THR | A | 46 | 29.825 | 36.701 | 78.730 | 1.00 | 0.00 | xxxx | 345 |
| ATOM | 346 | CA | THR | A | 46 | 29.725 | 37.065 | 80.142 | 1.00 | 0.00 | xxxx | 346 |
| ATOM | 347 | C | THR | A | 46 | 30.965 | 36.622 | 80.903 | 1.00 | 0.00 | xxxx | 347 |
| ATOM | 348 | O | THR | A | 46 | 31.536 | 37.383 | 81.693 | 1.00 | 0.00 | xxxx | 348 |
| ATOM | 349 | CB | THR | A | 46 | 28.468 | 36.445 | 80.753 | 1.00 | 0.00 | xxxx | 349 |
| ATOM | 350 | OG1 | THR | A | 46 | 27.309 | 36.962 | 80.093 | 1.00 | 0.00 | xxxx | 350 |
| ATOM | 351 | CG2 | THR | A | 46 | 28.374 | 36.765 | 82.240 | 1.00 | 0.00 | xxxx | 351 |
| ATOM | 352 | N | GLN | A | 47 | 31.397 | 35.377 | 80.687 | 1.00 | 0.00 | xxxx | 352 |
| ATOM | 353 | CA | GLN | A | 47 | 32.586 | 34.892 | 81.372 | 1.00 | 0.00 | xxxx | 353 |
| ATOM | 354 | C | GLN | A | 47 | 33.819 | 35.708 | 81.003 | 1.00 | 0.00 | xxxx | 354 |
| ATOM | 355 | O | GLN | A | 47 | 34.664 | 35.984 | 81.863 | 1.00 | 0.00 | xxxx | 355 |
| ATOM | 356 | CB | GLN | A | 47 | 32.806 | 33.415 | 81.067 | 1.00 | 0.00 | xxxx | 356 |
| ATOM | 357 | CG | GLN | A | 47 | 33.924 | 32.840 | 81.894 | 1.00 | 0.00 | xxxx | 357 |
| ATOM | 358 | CD | GLN | A | 47 | 34.000 | 31.341 | 81.767 | 1.00 | 0.00 | xxxx | 358 |
| ATOM | 359 | OE1 | GLN | A | 47 | 34.729 | 30.823 | 80.926 | 1.00 | 0.00 | xxxx | 359 |
| ATOM | 360 | NE2 | GLN | A | 47 | 33.239 | 30.638 | 82.593 | 1.00 | 0.00 | xxxx | 360 |
| ATOM | 361 | N | ASN | A | 48 | 33.944 | 36.101 | 79.733 | 1.00 | 0.00 | xxxx | 361 |
| ATOM | 362 | CA | ASN | A | 48 | 35.106 | 36.886 | 79.329 | 1.00 | 0.00 | xxxx | 362 |
| ATOM | 363 | C | ASN | A | 48 | 35.147 | 38.210 | 80.081 | 1.00 | 0.00 | xxxx | 363 |
| ATOM | 364 | O | ASN | A | 48 | 36.215 | 38.640 | 80.526 | 1.00 | 0.00 | xxxx | 364 |
| ATOM | 365 | CB | ASN | A | 48 | 35.093 | 37.119 | 77.818 | 1.00 | 0.00 | xxxx | 365 |
| ATOM | 366 | CG | ASN | A | 48 | 35.338 | 35.844 | 77.022 | 1.00 | 0.00 | xxxx | 366 |
| ATOM | 367 | OD1 | ASN | A | 48 | 35.813 | 34.837 | 77.560 | 1.00 | 0.00 | xxxx | 367 |
| ATOM | 368 | ND2 | ASN | A | 48 | 35.005 | 35.879 | 75.742 | 1.00 | 0.00 | xxxx | 368 |
| ATOM | 369 | N | ASP | A | 49 | 33.984 | 38.847 | 80.264 | 1.00 | 0.00 | xxxx | 369 |
| ATOM | 370 | CA | ASP | A | 49 | 33.916 | 40.074 | 81.054 | 1.00 | 0.00 | xxxx | 370 |
| ATOM | 371 | C | ASP | A | 49 | 34.280 | 39.820 | 82.512 | 1.00 | 0.00 | xxxx | 371 |
| ATOM | 372 | O | ASP | A | 49 | 34.934 | 40.660 | 83.147 | 1.00 | 0.00 | xxxx | 372 |
| ATOM | 373 | CB | ASP | A | 49 | 32.508 | 40.675 | 80.986 | 1.00 | 0.00 | xxxx | 373 |
| ATOM | 374 | CG | ASP | A | 49 | 32.154 | 41.215 | 79.609 | 1.00 | 0.00 | xxxx | 374 |
| ATOM | 375 | OD1 | ASP | A | 49 | 33.076 | 41.514 | 78.817 | 1.00 | 0.00 | xxxx | 375 |
| ATOM | 376 | OD2 | ASP | A | 49 | 30.936 | 41.359 | 79.327 | 1.00 | 0.00 | xxxx | 376 |
| ATOM | 377 | N | GLN | A | 50 | 33.840 | 38.683 | 83.065 | 1.00 | 0.00 | xxxx | 377 |
| ATOM | 378 | CA | GLN | A | 50 | 34.152 | 38.357 | 84.456 | 1.00 | 0.00 | xxxx | 378 |
| ATOM | 379 | C | GLN | A | 50 | 35.644 | 38.123 | 84.643 | 1.00 | 0.00 | xxxx | 379 |
| ATOM | 380 | O | GLN | A | 50 | 36.229 | 38.561 | 85.640 | 1.00 | 0.00 | xxxx | 380 |
| ATOM | 381 | CB | GLN | A | 50 | 33.346 | 37.126 | 84.890 | 1.00 | 0.00 | xxxx | 381 |
| ATOM | 382 | CG | GLN | A | 50 | 31.866 | 37.420 | 85.041 | 1.00 | 0.00 | xxxx | 382 |
| ATOM | 383 | CD | GLN | A | 50 | 30.984 | 36.172 | 85.027 | 1.00 | 0.00 | xxxx | 383 |
| ATOM | 384 | OE1 | GLN | A | 50 | 31.348 | 35.136 | 84.463 | 1.00 | 0.00 | xxxx | 384 |
| ATOM | 385 | NE2 | GLN | A | 50 | 29.819 | 36.278 | 85.644 | 1.00 | 0.00 | xxxx | 385 |
| ATOM | 386 | N | VAL | A | 51 | 36.277 | 37.439 | 83.691 | 1.00 | 0.00 | xxxx | 386 |
| ATOM | 387 | CA | VAL | A | 51 | 37.723 | 37.252 | 83.744 | 1.00 | 0.00 | xxxx | 387 |
| ATOM | 388 | C | VAL | A | 51 | 38.437 | 38.594 | 83.676 | 1.00 | 0.00 | xxxx | 388 |
| ATOM | 389 | O | VAL | A | 51 | 39.393 | 38.843 | 84.424 | 1.00 | 0.00 | xxxx | 389 |
| ATOM | 390 | CB | VAL | A | 51 | 38.168 | 36.313 | 82.613 | 1.00 | 0.00 | xxxx | 390 |
| ATOM | 391 | CG1 | VAL | A | 51 | 39.692 | 36.311 | 82.501 | 1.00 | 0.00 | xxxx | 391 |
| ATOM | 392 | CG2 | VAL | A | 51 | 37.640 | 34.914 | 82.858 | 1.00 | 0.00 | xxxx | 392 |
| ATOM | 393 | N | ASP | A | 52 | 37.987 | 39.480 | 82.783 | 1.00 | 0.00 | xxxx | 393 |
| ATOM | 394 | CA | ASP | A | 52 | 38.587 | 40.807 | 82.716 | 1.00 | 0.00 | xxxx | 394 |
| ATOM | 395 | C | ASP | A | 52 | 38.515 | 41.507 | 84.069 | 1.00 | 0.00 | xxxx | 395 |

-continued

| | | | | | | | | | | | | |
|---|---|---|---|---|---|---|---|---|---|---|---|---|
| CA, calcium<br>HOH, water<br>ACR, Acrylodan<br>K, potassium<br>EDO, ethylene glycol | | | | | | | | | | | | |
| ATOM | 396 | O | ASP | A | 52 | 39.484 | 42.144 | 84.500 | 1.00 | 0.00 | xxxx | 396 |
| ATOM | 397 | CB | ASP | A | 52 | 37.899 | 41.657 | 81.645 | 1.00 | 0.00 | xxxx | 397 |
| ATOM | 398 | CG | ASP | A | 52 | 38.259 | 41.239 | 80.228 | 1.00 | 0.00 | xxxx | 398 |
| ATOM | 399 | OD1 | ASP | A | 52 | 39.185 | 40.416 | 80.046 | 1.00 | 0.00 | xxxx | 399 |
| ATOM | 400 | OD2 | ASP | A | 52 | 37.614 | 41.754 | 79.288 | 1.00 | 0.00 | xxxx | 400 |
| ATOM | 401 | N | LEU | A | 53 | 37.374 | 41.403 | 84.754 | 1.00 | 0.00 | xxxx | 401 |
| ATOM | 402 | CA | LEU | A | 53 | 37.227 | 42.087 | 86.038 | 1.00 | 0.00 | xxxx | 402 |
| ATOM | 403 | C | LEU | A | 53 | 38.088 | 41.440 | 87.121 | 1.00 | 0.00 | xxxx | 403 |
| ATOM | 404 | O | LEU | A | 53 | 38.674 | 42.141 | 87.954 | 1.00 | 0.00 | xxxx | 404 |
| ATOM | 405 | CB | LEU | A | 53 | 35.758 | 42.117 | 86.454 | 1.00 | 0.00 | xxxx | 405 |
| ATOM | 406 | CG | LEU | A | 53 | 35.448 | 42.973 | 87.687 | 1.00 | 0.00 | xxxx | 406 |
| ATOM | 407 | CD1 | LEU | A | 53 | 35.863 | 44.424 | 87.464 | 1.00 | 0.00 | xxxx | 407 |
| ATOM | 408 | CD2 | LEU | A | 53 | 33.967 | 42.886 | 88.029 | 1.00 | 0.00 | xxxx | 408 |
| ATOM | 409 | N | PHE | A | 54 | 38.176 | 40.109 | 87.135 | 1.00 | 0.00 | xxxx | 409 |
| ATOM | 410 | CA | PHE | A | 54 | 39.078 | 39.445 | 88.071 | 1.00 | 0.00 | xxxx | 410 |
| ATOM | 411 | C | PHE | A | 54 | 40.501 | 39.957 | 87.905 | 1.00 | 0.00 | xxxx | 411 |
| ATOM | 412 | O | PHE | A | 54 | 41.227 | 40.139 | 88.889 | 1.00 | 0.00 | xxxx | 412 |
| ATOM | 413 | CB | PHE | A | 54 | 39.098 | 37.940 | 87.795 | 1.00 | 0.00 | xxxx | 413 |
| ATOM | 414 | CG | PHE | A | 54 | 37.895 | 37.183 | 88.296 | 1.00 | 0.00 | xxxx | 414 |
| ATOM | 415 | CD1 | PHE | A | 54 | 37.168 | 37.619 | 89.387 | 1.00 | 0.00 | xxxx | 415 |
| ATOM | 416 | CD2 | PHE | A | 54 | 37.503 | 36.017 | 87.661 | 1.00 | 0.00 | xxxx | 416 |
| ATOM | 417 | CE1 | PHE | A | 54 | 36.072 | 36.896 | 89.840 | 1.00 | 0.00 | xxxx | 417 |
| ATOM | 418 | CE2 | PHE | A | 54 | 36.407 | 35.290 | 88.111 | 1.00 | 0.00 | xxxx | 418 |
| ATOM | 419 | CZ | PHE | A | 54 | 35.692 | 35.739 | 89.193 | 1.00 | 0.00 | xxxx | 419 |
| ATOM | 420 | N | ILE | A | 55 | 40.929 | 40.159 | 86.657 | 1.00 | 0.00 | xxxx | 420 |
| ATOM | 421 | CA | ILE | A | 55 | 42.280 | 40.634 | 86.395 | 1.00 | 0.00 | xxxx | 421 |
| ATOM | 422 | C | ILE | A | 55 | 42.449 | 42.073 | 86.874 | 1.00 | 0.00 | xxxx | 422 |
| ATOM | 423 | O | ILE | A | 55 | 43.450 | 42.413 | 87.519 | 1.00 | 0.00 | xxxx | 423 |
| ATOM | 424 | CB | ILE | A | 55 | 42.612 | 40.457 | 84.901 | 1.00 | 0.00 | xxxx | 424 |
| ATOM | 425 | CG1 | ILE | A | 55 | 42.783 | 38.969 | 84.590 | 1.00 | 0.00 | xxxx | 425 |
| ATOM | 426 | CG2 | ILE | A | 55 | 43.853 | 41.263 | 84.512 | 1.00 | 0.00 | xxxx | 426 |
| ATOM | 427 | CD1 | ILE | A | 55 | 42.900 | 38.654 | 83.114 | 1.00 | 0.00 | xxxx | 427 |
| ATOM | 428 | N | THR | A | 56 | 41.470 | 42.941 | 86.588 | 1.00 | 0.00 | xxxx | 428 |
| ATOM | 429 | CA | THR | A | 56 | 41.569 | 44.323 | 87.048 | 1.00 | 0.00 | xxxx | 429 |
| ATOM | 430 | C | THR | A | 56 | 41.538 | 44.409 | 88.569 | 1.00 | 0.00 | xxxx | 430 |
| ATOM | 431 | O | THR | A | 56 | 42.149 | 45.310 | 89.155 | 1.00 | 0.00 | xxxx | 431 |
| ATOM | 432 | CB | THR | A | 56 | 40.458 | 45.172 | 86.432 | 1.00 | 0.00 | xxxx | 432 |
| ATOM | 433 | OG1 | THR | A | 56 | 39.187 | 44.752 | 86.937 | 1.00 | 0.00 | xxxx | 433 |
| ATOM | 434 | CG2 | THR | A | 56 | 40.467 | 45.040 | 84.930 | 1.00 | 0.00 | xxxx | 434 |
| ATOM | 435 | N | LYS | A | 57 | 40.841 | 43.486 | 89.223 | 1.00 | 0.00 | xxxx | 435 |
| ATOM | 436 | CA | LYS | A | 57 | 40.787 | 43.451 | 90.680 | 1.00 | 0.00 | xxxx | 436 |
| ATOM | 437 | C | LYS | A | 57 | 41.975 | 42.728 | 91.294 | 1.00 | 0.00 | xxxx | 437 |
| ATOM | 438 | O | LYS | A | 57 | 42.015 | 42.567 | 92.519 | 1.00 | 0.00 | xxxx | 438 |
| ATOM | 439 | CB | LYS | A | 57 | 39.490 | 42.779 | 91.139 | 1.00 | 0.00 | xxxx | 439 |
| ATOM | 440 | CG | LYS | A | 57 | 38.236 | 43.606 | 90.893 | 1.00 | 0.00 | xxxx | 440 |
| ATOM | 441 | CD | LYS | A | 57 | 36.997 | 42.845 | 91.342 | 1.00 | 0.00 | xxxx | 441 |
| ATOM | 442 | CE | LYS | A | 57 | 35.754 | 43.721 | 91.300 | 1.00 | 0.00 | xxxx | 442 |
| ATOM | 443 | NZ | LYS | A | 57 | 34.543 | 42.975 | 91.742 | 1.00 | 0.00 | xxxx | 443 |
| ATOM | 444 | N | LYS | A | 58 | 42.920 | 42.268 | 90.474 | 1.00 | 0.00 | xxxx | 444 |
| ATOM | 445 | CA | LYS | A | 58 | 44.163 | 41.654 | 90.948 | 1.00 | 0.00 | xxxx | 445 |
| ATOM | 446 | C | LYS | A | 58 | 43.915 | 40.432 | 91.838 | 1.00 | 0.00 | xxxx | 446 |
| ATOM | 447 | O | LYS | A | 58 | 44.473 | 40.308 | 92.930 | 1.00 | 0.00 | xxxx | 447 |
| ATOM | 448 | CB | LYS | A | 58 | 45.084 | 42.677 | 91.621 | 1.00 | 0.00 | xxxx | 448 |
| ATOM | 449 | CG | LYS | A | 58 | 45.491 | 43.832 | 90.708 | 1.00 | 0.00 | xxxx | 449 |
| ATOM | 450 | CD | LYS | A | 58 | 46.466 | 44.767 | 91.415 | 1.00 | 0.00 | xxxx | 450 |
| ATOM | 451 | CE | LYS | A | 58 | 46.876 | 45.934 | 90.528 | 1.00 | 0.00 | xxxx | 451 |
| ATOM | 452 | NZ | LYS | A | 58 | 47.689 | 45.497 | 89.360 | 1.00 | 0.00 | xxxx | 452 |
| ATOM | 453 | N | MET | A | 59 | 43.076 | 39.515 | 91.355 | 1.00 | 0.00 | xxxx | 453 |
| ATOM | 454 | CA | MET | A | 59 | 42.977 | 38.209 | 91.994 | 1.00 | 0.00 | xxxx | 454 |
| ATOM | 455 | C | MET | A | 59 | 44.359 | 37.567 | 92.043 | 1.00 | 0.00 | xxxx | 455 |
| ATOM | 456 | O | MET | A | 59 | 45.208 | 37.809 | 91.177 | 1.00 | 0.00 | xxxx | 456 |
| ATOM | 457 | CB | MET | A | 59 | 42.041 | 37.296 | 91.195 | 1.00 | 0.00 | xxxx | 457 |
| ATOM | 458 | CG | MET | A | 59 | 40.570 | 37.704 | 91.162 | 1.00 | 0.00 | xxxx | 458 |
| ATOM | 459 | SD | MET | A | 59 | 39.731 | 37.646 | 92.761 | 1.00 | 0.00 | xxxx | 459 |
| ATOM | 460 | CE | MET | A | 59 | 39.788 | 39.371 | 93.232 | 1.00 | 0.00 | xxxx | 460 |
| ATOM | 461 | N | ASN | A | 60 | 44.589 | 36.749 | 93.080 | 1.00 | 0.00 | xxxx | 461 |
| ATOM | 462 | CA | ASN | A | 60 | 45.864 | 36.048 | 93.213 | 1.00 | 0.00 | xxxx | 462 |
| ATOM | 463 | C | ASN | A | 60 | 45.940 | 34.809 | 92.329 | 1.00 | 0.00 | xxxx | 463 |
| ATOM | 464 | O | ASN | A | 60 | 47.045 | 34.367 | 91.978 | 1.00 | 0.00 | xxxx | 464 |
| ATOM | 465 | CB | ASN | A | 60 | 46.117 | 35.663 | 94.677 | 1.00 | 0.00 | xxxx | 465 |
| ATOM | 466 | CG | ASN | A | 60 | 46.186 | 36.866 | 95.592 | 1.00 | 0.00 | xxxx | 466 |
| ATOM | 467 | OD1 | ASN | A | 60 | 45.232 | 37.173 | 96.299 | 1.00 | 0.00 | xxxx | 467 |
| ATOM | 468 | ND2 | ASN | A | 60 | 47.323 | 37.552 | 95.584 | 1.00 | 0.00 | xxxx | 468 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 469 | N | ALA | A | 61 | 44.793 | 34.248 | 91.968 | 1.00 | 0.00 | xxxx | 469 |
| ATOM | 470 | CA | ALA | A | 61 | 44.730 | 33.123 | 91.049 | 1.00 | 0.00 | xxxx | 470 |
| ATOM | 471 | C | ALA | A | 61 | 43.314 | 33.070 | 90.501 | 1.00 | 0.00 | xxxx | 471 |
| ATOM | 472 | O | ALA | A | 61 | 42.387 | 33.651 | 91.072 | 1.00 | 0.00 | xxxx | 472 |
| ATOM | 473 | CB | ALA | A | 61 | 45.102 | 31.798 | 91.738 | 1.00 | 0.00 | xxxx | 473 |
| ATOM | 474 | N | LEU | A | 62 | 43.161 | 32.376 | 89.375 | 1.00 | 0.00 | xxxx | 474 |
| ATOM | 475 | CA | LEU | A | 62 | 41.862 | 32.166 | 88.747 | 1.00 | 0.00 | xxxx | 475 |
| ATOM | 476 | C | LEU | A | 62 | 41.563 | 30.678 | 88.674 | 1.00 | 0.00 | xxxx | 476 |
| ATOM | 477 | O | LEU | A | 62 | 42.460 | 29.874 | 88.422 | 1.00 | 0.00 | xxxx | 477 |
| ATOM | 478 | CB | LEU | A | 62 | 41.854 | 32.700 | 87.318 | 1.00 | 0.00 | xxxx | 478 |
| ATOM | 479 | CG | LEU | A | 62 | 42.259 | 34.157 | 87.163 | 1.00 | 0.00 | xxxx | 479 |
| ATOM | 480 | CD1 | LEU | A | 62 | 42.234 | 34.565 | 85.685 | 1.00 | 0.00 | xxxx | 480 |
| ATOM | 481 | CD2 | LEU | A | 62 | 41.333 | 35.015 | 87.996 | 1.00 | 0.00 | xxxx | 481 |
| ATOM | 482 | N | ALA | A | 63 | 40.294 | 30.331 | 88.884 | 1.00 | 0.00 | xxxx | 482 |
| ATOM | 483 | CA | ALA | A | 63 | 39.776 | 28.979 | 88.669 | 1.00 | 0.00 | xxxx | 483 |
| ATOM | 484 | C | ALA | A | 63 | 38.579 | 29.137 | 87.743 | 1.00 | 0.00 | xxxx | 484 |
| ATOM | 485 | O | ALA | A | 63 | 37.558 | 29.721 | 88.136 | 1.00 | 0.00 | xxxx | 485 |
| ATOM | 486 | CB | ALA | A | 63 | 39.374 | 28.307 | 89.990 | 1.00 | 0.00 | xxxx | 486 |
| ATOM | 487 | N | ILE | A | 64 | 38.705 | 28.644 | 86.509 | 1.00 | 0.00 | xxxx | 487 |
| ATOM | 488 | CA | ILE | A | 64 | 37.737 | 28.928 | 85.451 | 1.00 | 0.00 | xxxx | 488 |
| ATOM | 489 | C | ILE | A | 64 | 37.144 | 27.627 | 84.929 | 1.00 | 0.00 | xxxx | 489 |
| ATOM | 490 | O | ILE | A | 64 | 37.870 | 26.740 | 84.477 | 1.00 | 0.00 | xxxx | 490 |
| ATOM | 491 | CB | ILE | A | 64 | 38.361 | 29.719 | 84.285 | 1.00 | 0.00 | xxxx | 491 |
| ATOM | 492 | CG1 | ILE | A | 64 | 39.018 | 31.018 | 84.786 | 1.00 | 0.00 | xxxx | 492 |
| ATOM | 493 | CD1 | ILE | A | 64 | 38.075 | 31.990 | 85.470 | 1.00 | 0.00 | xxxx | 493 |
| ATOM | 494 | CG2 | ILE | A | 64 | 37.297 | 29.986 | 83.205 | 1.00 | 0.00 | xxxx | 494 |
| ATOM | 495 | N | ASN | A | 65 | 35.821 | 27.545 | 84.951 | 1.00 | 0.00 | xxxx | 495 |
| ATOM | 496 | CA | ASN | A | 65 | 35.047 | 26.466 | 84.354 | 1.00 | 0.00 | xxxx | 496 |
| ATOM | 497 | C | ASN | A | 65 | 34.469 | 27.053 | 83.070 | 1.00 | 0.00 | xxxx | 497 |
| ATOM | 498 | O | ASN | A | 65 | 33.449 | 27.756 | 83.123 | 1.00 | 0.00 | xxxx | 498 |
| ATOM | 499 | CB | ASN | A | 65 | 33.940 | 26.087 | 85.351 | 1.00 | 0.00 | xxxx | 499 |
| ATOM | 500 | CG | ASN | A | 65 | 32.918 | 25.098 | 84.818 | 1.00 | 0.00 | xxxx | 500 |
| ATOM | 501 | OD1 | ASN | A | 65 | 31.715 | 25.263 | 85.062 | 1.00 | 0.00 | xxxx | 501 |
| ATOM | 502 | ND2 | ASN | A | 65 | 33.364 | 24.068 | 84.105 | 1.00 | 0.00 | xxxx | 502 |
| ATOM | 503 | N | PRO | A | 66 | 35.101 | 26.838 | 81.906 | 1.00 | 0.00 | xxxx | 503 |
| ATOM | 504 | CA | PRO | A | 66 | 34.677 | 27.548 | 80.684 | 1.00 | 0.00 | xxxx | 504 |
| ATOM | 505 | C | PRO | A | 66 | 33.239 | 27.261 | 80.289 | 1.00 | 0.00 | xxxx | 505 |
| ATOM | 506 | O | PRO | A | 66 | 32.722 | 26.159 | 80.478 | 1.00 | 0.00 | xxxx | 506 |
| ATOM | 507 | CB | PRO | A | 66 | 35.636 | 27.022 | 79.610 | 1.00 | 0.00 | xxxx | 507 |
| ATOM | 508 | CG | PRO | A | 66 | 36.833 | 26.497 | 80.362 | 1.00 | 0.00 | xxxx | 508 |
| ATOM | 509 | CD | PRO | A | 66 | 36.293 | 25.996 | 81.686 | 1.00 | 0.00 | xxxx | 509 |
| ATOM | 510 | N | VAL | A | 67 | 32.607 | 28.264 | 79.673 | 1.00 | 0.00 | xxxx | 510 |
| ATOM | 511 | CA | VAL | A | 67 | 31.380 | 27.994 | 78.935 | 1.00 | 0.00 | xxxx | 511 |
| ATOM | 512 | C | VAL | A | 67 | 31.706 | 27.288 | 77.625 | 1.00 | 0.00 | xxxx | 512 |
| ATOM | 513 | O | VAL | A | 67 | 31.181 | 26.207 | 77.331 | 1.00 | 0.00 | xxxx | 513 |
| ATOM | 514 | CB | VAL | A | 67 | 30.587 | 29.294 | 78.713 | 1.00 | 0.00 | xxxx | 514 |
| ATOM | 515 | CG1 | VAL | A | 67 | 29.312 | 29.005 | 77.929 | 1.00 | 0.00 | xxxx | 515 |
| ATOM | 516 | CG2 | VAL | A | 67 | 30.270 | 29.937 | 80.054 | 1.00 | 0.00 | xxxx | 516 |
| ATOM | 517 | N | ASP | A | 68 | 32.586 | 27.896 | 76.825 | 1.00 | 0.00 | xxxx | 517 |
| ATOM | 518 | CA | ASP | A | 68 | 33.089 | 27.344 | 75.570 | 1.00 | 0.00 | xxxx | 518 |
| ATOM | 519 | C | ASP | A | 68 | 34.566 | 27.052 | 75.820 | 1.00 | 0.00 | xxxx | 519 |
| ATOM | 520 | O | ASP | A | 68 | 35.363 | 27.978 | 75.992 | 1.00 | 0.00 | xxxx | 520 |
| ATOM | 521 | CB | ASP | A | 68 | 32.902 | 28.403 | 74.483 | 1.00 | 0.00 | xxxx | 521 |
| ATOM | 522 | CG | ASP | A | 68 | 33.509 | 28.022 | 73.150 | 1.00 | 0.00 | xxxx | 522 |
| ATOM | 523 | OD1 | ASP | A | 68 | 34.190 | 26.984 | 73.041 | 1.00 | 0.00 | xxxx | 523 |
| ATOM | 524 | OD2 | ASP | A | 68 | 33.299 | 28.793 | 72.184 | 1.00 | 0.00 | xxxx | 524 |
| ATOM | 525 | N | ARG | A | 69 | 34.938 | 25.771 | 75.870 | 1.00 | 0.00 | xxxx | 525 |
| ATOM | 526 | CA | ARG | A | 69 | 36.314 | 25.449 | 76.240 | 1.00 | 0.00 | xxxx | 526 |
| ATOM | 527 | C | ARG | A | 69 | 37.342 | 25.935 | 75.220 | 1.00 | 0.00 | xxxx | 527 |
| ATOM | 528 | O | ARG | A | 69 | 38.520 | 26.068 | 75.573 | 1.00 | 0.00 | xxxx | 528 |
| ATOM | 529 | CB | ARG | A | 69 | 36.478 | 23.954 | 76.527 | 1.00 | 0.00 | xxxx | 529 |
| ATOM | 530 | CG | ARG | A | 69 | 36.394 | 23.077 | 75.307 | 1.00 | 0.00 | xxxx | 530 |
| ATOM | 531 | CD | ARG | A | 69 | 36.008 | 21.656 | 75.723 | 1.00 | 0.00 | xxxx | 531 |
| ATOM | 532 | NE | ARG | A | 69 | 35.941 | 20.732 | 74.600 | 1.00 | 0.00 | xxxx | 532 |
| ATOM | 533 | CZ | ARG | A | 69 | 36.959 | 19.992 | 74.168 | 1.00 | 0.00 | xxxx | 533 |
| ATOM | 534 | NH1 | ARG | A | 69 | 38.142 | 20.069 | 74.758 | 1.00 | 0.00 | xxxx | 534 |
| ATOM | 535 | NH2 | ARG | A | 69 | 36.789 | 19.184 | 73.138 | 1.00 | 0.00 | xxxx | 535 |
| ATOM | 536 | N | THR | A | 70 | 36.934 | 26.219 | 73.984 | 1.00 | 0.00 | xxxx | 536 |
| ATOM | 537 | CA | THR | A | 70 | 37.874 | 26.788 | 73.025 | 1.00 | 0.00 | xxxx | 537 |
| ATOM | 538 | C | THR | A | 70 | 38.253 | 28.221 | 73.383 | 1.00 | 0.00 | xxxx | 538 |
| ATOM | 539 | O | THR | A | 70 | 39.257 | 28.731 | 72.874 | 1.00 | 0.00 | xxxx | 539 |
| ATOM | 540 | CB | THR | A | 70 | 37.344 | 26.680 | 71.590 | 1.00 | 0.00 | xxxx | 540 |
| ATOM | 541 | OG1 | THR | A | 70 | 36.207 | 27.530 | 71.423 | 1.00 | 0.00 | xxxx | 541 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 542 | CG2 | THR | A | 70 | 36.956 | 25.244 | 71.267 | 1.00 | 0.00 | xxxx | 542 |
| ATOM | 543 | N | ALA | A | 71 | 37.482 | 28.876 | 74.253 | 1.00 | 0.00 | xxxx | 543 |
| ATOM | 544 | CA | ALA | A | 71 | 37.821 | 30.216 | 74.719 | 1.00 | 0.00 | xxxx | 544 |
| ATOM | 545 | C | ALA | A | 71 | 38.947 | 30.224 | 75.737 | 1.00 | 0.00 | xxxx | 545 |
| ATOM | 546 | O | ALA | A | 71 | 39.421 | 31.308 | 76.104 | 1.00 | 0.00 | xxxx | 546 |
| ATOM | 547 | CB | ALA | A | 71 | 36.596 | 30.899 | 75.331 | 1.00 | 0.00 | xxxx | 547 |
| ATOM | 548 | N | ALA | A | 72 | 39.407 | 29.056 | 76.180 | 1.00 | 0.00 | xxxx | 548 |
| ATOM | 549 | CA | ALA | A | 72 | 40.478 | 29.019 | 77.168 | 1.00 | 0.00 | xxxx | 549 |
| ATOM | 550 | C | ALA | A | 72 | 41.765 | 29.642 | 76.638 | 1.00 | 0.00 | xxxx | 550 |
| ATOM | 551 | O | ALA | A | 72 | 42.545 | 30.201 | 77.417 | 1.00 | 0.00 | xxxx | 551 |
| ATOM | 552 | CB | ALA | A | 72 | 40.710 | 27.581 | 77.640 | 1.00 | 0.00 | xxxx | 552 |
| ATOM | 553 | N | GLY | A | 73 | 41.988 | 29.591 | 75.324 | 1.00 | 0.00 | xxxx | 553 |
| ATOM | 554 | CA | GLY | A | 73 | 43.196 | 30.180 | 74.765 | 1.00 | 0.00 | xxxx | 554 |
| ATOM | 555 | C | GLY | A | 73 | 43.308 | 31.668 | 75.049 | 1.00 | 0.00 | xxxx | 555 |
| ATOM | 556 | O | GLY | A | 73 | 44.358 | 32.156 | 75.469 | 1.00 | 0.00 | xxxx | 556 |
| ATOM | 557 | N | THR | A | 74 | 42.218 | 32.404 | 74.826 | 1.00 | 0.00 | xxxx | 557 |
| ATOM | 558 | CA | THR | A | 74 | 42.237 | 33.842 | 75.074 | 1.00 | 0.00 | xxxx | 558 |
| ATOM | 559 | C | THR | A | 74 | 42.330 | 34.142 | 76.565 | 1.00 | 0.00 | xxxx | 559 |
| ATOM | 560 | O | THR | A | 74 | 43.006 | 35.094 | 76.973 | 1.00 | 0.00 | xxxx | 560 |
| ATOM | 561 | CB | THR | A | 74 | 40.990 | 34.484 | 74.469 | 1.00 | 0.00 | xxxx | 561 |
| ATOM | 562 | OG1 | THR | A | 74 | 40.899 | 34.126 | 73.085 | 1.00 | 0.00 | xxxx | 562 |
| ATOM | 563 | CG2 | THR | A | 74 | 41.061 | 35.997 | 74.587 | 1.00 | 0.00 | xxxx | 563 |
| ATOM | 564 | N | ILE | A | 75 | 41.662 | 33.340 | 77.393 | 1.00 | 0.00 | xxxx | 564 |
| ATOM | 565 | CA | ILE | A | 75 | 41.765 | 33.525 | 78.838 | 1.00 | 0.00 | xxxx | 565 |
| ATOM | 566 | C | ILE | A | 75 | 43.202 | 33.322 | 79.304 | 1.00 | 0.00 | xxxx | 566 |
| ATOM | 567 | O | ILE | A | 75 | 43.710 | 34.083 | 80.138 | 1.00 | 0.00 | xxxx | 567 |
| ATOM | 568 | CB | ILE | A | 75 | 40.771 | 32.605 | 79.565 | 1.00 | 0.00 | xxxx | 568 |
| ATOM | 569 | CG1 | ILE | A | 75 | 39.344 | 33.021 | 79.219 | 1.00 | 0.00 | xxxx | 569 |
| ATOM | 570 | CG2 | ILE | A | 75 | 40.994 | 32.655 | 81.070 | 1.00 | 0.00 | xxxx | 570 |
| ATOM | 571 | CD1 | ILE | A | 75 | 38.305 | 32.030 | 79.674 | 1.00 | 0.00 | xxxx | 571 |
| ATOM | 572 | N | ILE | A | 76 | 43.887 | 32.309 | 78.757 | 1.00 | 0.00 | xxxx | 572 |
| ATOM | 573 | CA | ILE | A | 76 | 45.294 | 32.094 | 79.085 | 1.00 | 0.00 | xxxx | 573 |
| ATOM | 574 | C | ILE | A | 76 | 46.139 | 33.290 | 78.665 | 1.00 | 0.00 | xxxx | 574 |
| ATOM | 575 | O | ILE | A | 76 | 47.021 | 33.729 | 79.412 | 1.00 | 0.00 | xxxx | 575 |
| ATOM | 576 | CB | ILE | A | 76 | 45.804 | 30.775 | 78.476 | 1.00 | 0.00 | xxxx | 576 |
| ATOM | 577 | CG1 | ILE | A | 76 | 45.122 | 29.589 | 79.156 | 1.00 | 0.00 | xxxx | 577 |
| ATOM | 578 | CG2 | ILE | A | 76 | 47.316 | 30.664 | 78.638 | 1.00 | 0.00 | xxxx | 578 |
| ATOM | 579 | CD1 | ILE | A | 76 | 45.268 | 28.282 | 78.392 | 1.00 | 0.00 | xxxx | 579 |
| ATOM | 580 | N | ASP | A | 77 | 45.887 | 33.840 | 77.467 | 1.00 | 0.00 | xxxx | 580 |
| ATOM | 581 | CA | ASP | A | 77 | 46.636 | 35.016 | 77.025 | 1.00 | 0.00 | xxxx | 581 |
| ATOM | 582 | C | ASP | A | 77 | 46.484 | 36.159 | 78.020 | 1.00 | 0.00 | xxxx | 582 |
| ATOM | 583 | O | ASP | A | 77 | 47.464 | 36.818 | 78.387 | 1.00 | 0.00 | xxxx | 583 |
| ATOM | 584 | CB | ASP | A | 77 | 46.158 | 35.467 | 75.644 | 1.00 | 0.00 | xxxx | 584 |
| ATOM | 585 | CG | ASP | A | 77 | 46.590 | 34.533 | 74.533 | 1.00 | 0.00 | xxxx | 585 |
| ATOM | 586 | OD1 | ASP | A | 77 | 47.614 | 33.841 | 74.696 | 1.00 | 0.00 | xxxx | 586 |
| ATOM | 587 | OD2 | ASP | A | 77 | 45.904 | 34.500 | 73.489 | 1.00 | 0.00 | xxxx | 587 |
| ATOM | 588 | N | LYS | A | 78 | 45.253 | 36.401 | 78.471 | 1.00 | 0.00 | xxxx | 588 |
| ATOM | 589 | CA | LYS | A | 78 | 45.010 | 37.504 | 79.394 | 1.00 | 0.00 | xxxx | 589 |
| ATOM | 590 | C | LYS | A | 78 | 45.652 | 37.237 | 80.747 | 1.00 | 0.00 | xxxx | 590 |
| ATOM | 591 | O | LYS | A | 78 | 46.258 | 38.138 | 81.339 | 1.00 | 0.00 | xxxx | 591 |
| ATOM | 592 | CB | LYS | A | 78 | 43.507 | 37.715 | 79.564 | 1.00 | 0.00 | xxxx | 592 |
| ATOM | 593 | CG | LYS | A | 78 | 42.806 | 38.240 | 78.327 | 1.00 | 0.00 | xxxx | 593 |
| ATOM | 594 | CD | LYS | A | 78 | 41.302 | 38.175 | 78.521 | 1.00 | 0.00 | xxxx | 594 |
| ATOM | 595 | CE | LYS | A | 78 | 40.571 | 38.956 | 77.442 | 1.00 | 0.00 | xxxx | 595 |
| ATOM | 596 | NZ | LYS | A | 78 | 39.097 | 38.909 | 77.649 | 1.00 | 0.00 | xxxx | 596 |
| ATOM | 597 | N | ALA | A | 79 | 45.525 | 36.008 | 81.251 | 1.00 | 0.00 | xxxx | 597 |
| ATOM | 598 | CA | ALA | A | 79 | 46.115 | 35.671 | 82.541 | 1.00 | 0.00 | xxxx | 598 |
| ATOM | 599 | C | ALA | A | 79 | 47.635 | 35.750 | 82.490 | 1.00 | 0.00 | xxxx | 599 |
| ATOM | 600 | O | ALA | A | 79 | 48.268 | 36.274 | 83.414 | 1.00 | 0.00 | xxxx | 600 |
| ATOM | 601 | CB | ALA | A | 79 | 45.666 | 34.273 | 82.964 | 1.00 | 0.00 | xxxx | 601 |
| ATOM | 602 | N | LYS | A | 80 | 48.238 | 35.242 | 81.412 | 1.00 | 0.00 | xxxx | 602 |
| ATOM | 603 | CA | LYS | A | 80 | 49.691 | 35.320 | 81.266 | 1.00 | 0.00 | xxxx | 603 |
| ATOM | 604 | C | LYS | A | 80 | 50.169 | 36.768 | 81.250 | 1.00 | 0.00 | xxxx | 604 |
| ATOM | 605 | O | LYS | A | 80 | 51.180 | 37.105 | 81.878 | 1.00 | 0.00 | xxxx | 605 |
| ATOM | 606 | CB | LYS | A | 80 | 50.113 | 34.607 | 79.981 | 1.00 | 0.00 | xxxx | 606 |
| ATOM | 607 | CG | LYS | A | 80 | 51.616 | 34.566 | 79.750 | 1.00 | 0.00 | xxxx | 607 |
| ATOM | 608 | CD | LYS | A | 80 | 51.944 | 33.783 | 78.485 | 1.00 | 0.00 | xxxx | 608 |
| ATOM | 609 | CE | LYS | A | 80 | 53.444 | 33.672 | 78.273 | 1.00 | 0.00 | xxxx | 609 |
| ATOM | 610 | NZ | LYS | A | 80 | 53.760 | 32.800 | 77.108 | 1.00 | 0.00 | xxxx | 610 |
| ATOM | 611 | N | GLN | A | 81 | 49.453 | 37.640 | 80.537 | 1.00 | 0.00 | xxxx | 611 |
| ATOM | 612 | CA | GLN | A | 81 | 49.845 | 39.044 | 80.476 | 1.00 | 0.00 | xxxx | 612 |
| ATOM | 613 | C | GLN | A | 81 | 49.766 | 39.701 | 81.849 | 1.00 | 0.00 | xxxx | 613 |
| ATOM | 614 | O | GLN | A | 81 | 50.602 | 40.547 | 82.187 | 1.00 | 0.00 | xxxx | 614 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 615 | CB | GLN | A | 81 | 48.974 | 39.782 | 79.461 | 1.00 | 0.00 | xxxx | 615 |
| ATOM | 616 | CG | GLN | A | 81 | 49.389 | 41.224 | 79.220 | 1.00 | 0.00 | xxxx | 616 |
| ATOM | 617 | CD | GLN | A | 81 | 50.816 | 41.343 | 78.709 | 1.00 | 0.00 | xxxx | 617 |
| ATOM | 618 | OE1 | GLN | A | 81 | 51.242 | 40.586 | 77.835 | 1.00 | 0.00 | xxxx | 618 |
| ATOM | 619 | NE2 | GLN | A | 81 | 51.566 | 42.293 | 79.262 | 1.00 | 0.00 | xxxx | 619 |
| ATOM | 620 | N | ALA | A | 82 | 48.780 | 39.312 | 82.660 | 1.00 | 0.00 | xxxx | 620 |
| ATOM | 621 | CA | ALA | A | 82 | 48.623 | 39.844 | 84.008 | 1.00 | 0.00 | xxxx | 621 |
| ATOM | 622 | C | ALA | A | 82 | 49.461 | 39.096 | 85.034 | 1.00 | 0.00 | xxxx | 622 |
| ATOM | 623 | O | ALA | A | 82 | 49.497 | 39.505 | 86.201 | 1.00 | 0.00 | xxxx | 623 |
| ATOM | 624 | CB | ALA | A | 82 | 47.153 | 39.754 | 84.433 | 1.00 | 0.00 | xxxx | 624 |
| ATOM | 625 | N | ASN | A | 83 | 50.124 | 38.015 | 84.625 | 1.00 | 0.00 | xxxx | 625 |
| ATOM | 626 | CA | ASN | A | 83 | 50.869 | 37.141 | 85.534 | 1.00 | 0.00 | xxxx | 626 |
| ATOM | 627 | C | ASN | A | 83 | 49.992 | 36.622 | 86.673 | 1.00 | 0.00 | xxxx | 627 |
| ATOM | 628 | O | ASN | A | 83 | 50.401 | 36.599 | 87.834 | 1.00 | 0.00 | xxxx | 628 |
| ATOM | 629 | CB | ASN | A | 83 | 52.149 | 37.799 | 86.058 | 1.00 | 0.00 | xxxx | 629 |
| ATOM | 630 | CG | ASN | A | 83 | 53.128 | 36.794 | 86.629 | 1.00 | 0.00 | xxxx | 630 |
| ATOM | 631 | OD1 | ASN | A | 83 | 53.159 | 35.632 | 86.215 | 1.00 | 0.00 | xxxx | 631 |
| ATOM | 632 | ND2 | ASN | A | 83 | 53.924 | 37.229 | 87.597 | 1.00 | 0.00 | xxxx | 632 |
| ATOM | 633 | N | ILE | A | 84 | 48.776 | 36.201 | 86.341 | 1.00 | 0.00 | xxxx | 633 |
| ATOM | 634 | CA | ILE | A | 84 | 47.852 | 35.601 | 87.298 | 1.00 | 0.00 | xxxx | 634 |
| ATOM | 635 | C | ILE | A | 84 | 47.658 | 34.144 | 86.894 | 1.00 | 0.00 | xxxx | 635 |
| ATOM | 636 | O | ILE | A | 84 | 47.107 | 33.871 | 85.815 | 1.00 | 0.00 | xxxx | 636 |
| ATOM | 637 | CB | ILE | A | 84 | 46.518 | 36.361 | 87.359 | 1.00 | 0.00 | xxxx | 637 |
| ATOM | 638 | CG1 | ILE | A | 84 | 46.762 | 37.810 | 87.791 | 1.00 | 0.00 | xxxx | 638 |
| ATOM | 639 | CG2 | ILE | A | 84 | 45.558 | 35.670 | 88.330 | 1.00 | 0.00 | xxxx | 639 |
| ATOM | 640 | CD1 | ILE | A | 84 | 45.500 | 38.666 | 87.830 | 1.00 | 0.00 | xxxx | 640 |
| ATOM | 641 | N | PRO | A | 85 | 48.091 | 33.178 | 87.706 | 1.00 | 0.00 | xxxx | 641 |
| ATOM | 642 | CA | PRO | A | 85 | 47.973 | 31.764 | 87.327 | 1.00 | 0.00 | xxxx | 642 |
| ATOM | 643 | C | PRO | A | 85 | 46.520 | 31.335 | 87.238 | 1.00 | 0.00 | xxxx | 643 |
| ATOM | 644 | O | PRO | A | 85 | 45.632 | 31.916 | 87.868 | 1.00 | 0.00 | xxxx | 644 |
| ATOM | 645 | CB | PRO | A | 85 | 48.674 | 31.022 | 88.473 | 1.00 | 0.00 | xxxx | 645 |
| ATOM | 646 | CG | PRO | A | 85 | 49.463 | 32.051 | 89.196 | 1.00 | 0.00 | xxxx | 646 |
| ATOM | 647 | CD | PRO | A | 85 | 48.742 | 33.353 | 89.015 | 1.00 | 0.00 | xxxx | 647 |
| ATOM | 648 | N | VAL | A | 86 | 46.274 | 30.286 | 86.454 | 1.00 | 0.00 | xxxx | 648 |
| ATOM | 649 | CA | VAL | A | 86 | 44.901 | 29.859 | 86.196 | 1.00 | 0.00 | xxxx | 649 |
| ATOM | 650 | C | VAL | A | 86 | 44.797 | 28.340 | 86.202 | 1.00 | 0.00 | xxxx | 650 |
| ATOM | 651 | O | VAL | A | 86 | 45.611 | 27.646 | 85.583 | 1.00 | 0.00 | xxxx | 651 |
| ATOM | 652 | CB | VAL | A | 86 | 44.352 | 30.464 | 84.890 | 1.00 | 0.00 | xxxx | 652 |
| ATOM | 653 | CG1 | VAL | A | 86 | 45.289 | 30.182 | 83.719 | 1.00 | 0.00 | xxxx | 653 |
| ATOM | 654 | CG2 | VAL | A | 86 | 42.942 | 29.968 | 84.607 | 1.00 | 0.00 | xxxx | 654 |
| ATOM | 655 | N | VAL | A | 87 | 43.791 | 27.823 | 86.898 | 1.00 | 0.00 | xxxx | 655 |
| ATOM | 656 | CA | VAL | A | 87 | 43.403 | 26.420 | 86.794 | 1.00 | 0.00 | xxxx | 656 |
| ATOM | 657 | C | VAL | A | 87 | 42.027 | 26.354 | 86.148 | 1.00 | 0.00 | xxxx | 657 |
| ATOM | 658 | O | VAL | A | 87 | 41.089 | 27.044 | 86.577 | 1.00 | 0.00 | xxxx | 658 |
| ATOM | 659 | CB | VAL | A | 87 | 43.467 | 25.691 | 88.150 | 1.00 | 0.00 | xxxx | 659 |
| ATOM | 660 | CG1 | VAL | A | 87 | 42.648 | 26.394 | 89.236 | 1.00 | 0.00 | xxxx | 660 |
| ATOM | 661 | CG2 | VAL | A | 87 | 43.054 | 24.220 | 87.999 | 1.00 | 0.00 | xxxx | 661 |
| ATOM | 662 | N | PHE | A | 88 | 41.928 | 25.582 | 85.072 | 1.00 | 0.00 | xxxx | 662 |
| ATOM | 663 | CA | PHE | A | 88 | 40.648 | 25.303 | 84.448 | 1.00 | 0.00 | xxxx | 663 |
| ATOM | 664 | C | PHE | A | 88 | 40.078 | 24.014 | 85.014 | 1.00 | 0.00 | xxxx | 664 |
| ATOM | 665 | O | PHE | A | 88 | 40.818 | 23.151 | 85.499 | 1.00 | 0.00 | xxxx | 665 |
| ATOM | 666 | CB | PHE | A | 88 | 40.792 | 25.194 | 82.930 | 1.00 | 0.00 | xxxx | 666 |
| ATOM | 667 | CG | PHE | A | 88 | 41.186 | 26.487 | 82.271 | 1.00 | 0.00 | xxxx | 667 |
| ATOM | 668 | CD1 | PHE | A | 88 | 42.515 | 26.781 | 82.032 | 1.00 | 0.00 | xxxx | 668 |
| ATOM | 669 | CD2 | PHE | A | 88 | 40.219 | 27.411 | 81.928 | 1.00 | 0.00 | xxxx | 669 |
| ATOM | 670 | CE1 | PHE | A | 88 | 42.878 | 27.966 | 81.428 | 1.00 | 0.00 | xxxx | 670 |
| ATOM | 671 | CE2 | PHE | A | 88 | 40.578 | 28.605 | 81.324 | 1.00 | 0.00 | xxxx | 671 |
| ATOM | 672 | CZ | PHE | A | 88 | 41.913 | 28.873 | 81.079 | 1.00 | 0.00 | xxxx | 672 |
| ATOM | 673 | N | PHE | A | 89 | 38.754 | 23.890 | 84.964 | 1.00 | 0.00 | xxxx | 673 |
| ATOM | 674 | CA | PHE | A | 89 | 38.138 | 22.676 | 85.482 | 1.00 | 0.00 | xxxx | 674 |
| ATOM | 675 | C | PHE | A | 89 | 36.867 | 22.330 | 84.727 | 1.00 | 0.00 | xxxx | 675 |
| ATOM | 676 | O | PHE | A | 89 | 36.149 | 23.222 | 84.267 | 1.00 | 0.00 | xxxx | 676 |
| ATOM | 677 | CB | PHE | A | 89 | 37.961 | 22.673 | 87.012 | 1.00 | 0.00 | xxxx | 677 |
| ATOM | 678 | CG | PHE | A | 89 | 37.089 | 23.782 | 87.578 | 1.00 | 0.00 | xxxx | 678 |
| ATOM | 679 | CD1 | PHE | A | 89 | 35.896 | 23.470 | 88.214 | 1.00 | 0.00 | xxxx | 679 |
| ATOM | 680 | CD2 | PHE | A | 89 | 37.503 | 25.112 | 87.565 | 1.00 | 0.00 | xxxx | 680 |
| ATOM | 681 | CE1 | PHE | A | 89 | 35.109 | 24.467 | 88.797 | 1.00 | 0.00 | xxxx | 681 |
| ATOM | 682 | CE2 | PHE | A | 89 | 36.706 | 26.122 | 88.140 | 1.00 | 0.00 | xxxx | 682 |
| ATOM | 683 | CZ | PHE | A | 89 | 35.519 | 25.786 | 88.760 | 1.00 | 0.00 | xxxx | 683 |
| ATOM | 684 | N | ASN | A | 90 | 36.640 | 21.017 | 84.573 | 1.00 | 0.00 | xxxx | 684 |
| ATOM | 685 | CA | ASN | A | 90 | 35.397 | 20.414 | 84.098 | 1.00 | 0.00 | xxxx | 685 |
| ATOM | 686 | C | ASN | A | 90 | 35.146 | 20.491 | 82.586 | 1.00 | 0.00 | xxxx | 686 |
| ATOM | 687 | O | ASN | A | 90 | 34.669 | 19.517 | 81.999 | 1.00 | 0.00 | xxxx | 687 |

-continued

| | | | | | | | | | | | | |
|---|---|---|---|---|---|---|---|---|---|---|---|---|
| CA, calcium<br>HOH, water<br>ACR, Acrylodan<br>K, potassium<br>EDO, ethylene glycol | | | | | | | | | | | | |
| ATOM | 688 | CB | ASN | A | 90 | 34.186 | 20.871 | 84.920 | 1.00 | 0.00 | xxxx | 688 |
| ATOM | 689 | CG | ASN | A | 90 | 32.872 | 20.498 | 84.265 | 1.00 | 0.00 | xxxx | 689 |
| ATOM | 690 | OD1 | ASN | A | 90 | 32.284 | 21.310 | 83.565 | 1.00 | 0.00 | xxxx | 690 |
| ATOM | 691 | ND2 | ASN | A | 90 | 32.415 | 19.264 | 84.478 | 1.00 | 0.00 | xxxx | 691 |
| ATOM | 692 | N | LYS | A | 91 | 35.426 | 21.627 | 81.945 | 1.00 | 0.00 | xxxx | 692 |
| ATOM | 693 | CA | LYS | A | 91 | 35.463 | 21.697 | 80.485 | 1.00 | 0.00 | xxxx | 693 |
| ATOM | 694 | C | LYS | A | 91 | 36.912 | 21.923 | 80.081 | 1.00 | 0.00 | xxxx | 694 |
| ATOM | 695 | O | LYS | A | 91 | 37.547 | 22.880 | 80.539 | 1.00 | 0.00 | xxxx | 695 |
| ATOM | 696 | CB | LYS | A | 91 | 34.549 | 22.803 | 79.949 | 1.00 | 0.00 | xxxx | 696 |
| ATOM | 697 | CG | LYS | A | 91 | 33.064 | 22.644 | 80.345 | 1.00 | 0.00 | xxxx | 697 |
| ATOM | 698 | CD | LYS | A | 91 | 32.142 | 23.327 | 79.326 | 1.00 | 0.00 | xxxx | 698 |
| ATOM | 699 | CE | LYS | A | 91 | 30.781 | 23.654 | 79.916 | 1.00 | 0.00 | xxxx | 699 |
| ATOM | 700 | NZ | LYS | A | 91 | 29.882 | 24.261 | 78.901 | 1.00 | 0.00 | xxxx | 700 |
| ATOM | 701 | N | GLU | A | 92 | 37.437 | 21.027 | 79.254 | 1.00 | 0.00 | xxxx | 701 |
| ATOM | 702 | CA | GLU | A | 92 | 38.879 | 20.872 | 79.104 | 1.00 | 0.00 | xxxx | 702 |
| ATOM | 703 | C | GLU | A | 92 | 39.423 | 21.794 | 78.015 | 1.00 | 0.00 | xxxx | 703 |
| ATOM | 704 | O | GLU | A | 92 | 39.003 | 21.685 | 76.856 | 1.00 | 0.00 | xxxx | 704 |
| ATOM | 705 | CB | GLU | A | 92 | 39.200 | 19.429 | 78.753 | 1.00 | 0.00 | xxxx | 705 |
| ATOM | 706 | CG | GLU | A | 92 | 40.684 | 19.125 | 78.709 | 1.00 | 0.00 | xxxx | 706 |
| ATOM | 707 | CD | GLU | A | 92 | 40.980 | 17.677 | 78.380 | 1.00 | 0.00 | xxxx | 707 |
| ATOM | 708 | OE1 | GLU | A | 92 | 40.090 | 16.814 | 78.537 | 1.00 | 0.00 | xxxx | 708 |
| ATOM | 709 | OE2 | GLU | A | 92 | 42.114 | 17.396 | 77.934 | 1.00 | 0.00 | xxxx | 709 |
| ATOM | 710 | N | PRO | A | 93 | 40.368 | 22.684 | 78.324 | 1.00 | 0.00 | xxxx | 710 |
| ATOM | 711 | CA | PRO | A | 93 | 41.034 | 23.444 | 77.259 | 1.00 | 0.00 | xxxx | 711 |
| ATOM | 712 | C | PRO | A | 93 | 41.689 | 22.509 | 76.256 | 1.00 | 0.00 | xxxx | 712 |
| ATOM | 713 | O | PRO | A | 93 | 42.107 | 21.392 | 76.583 | 1.00 | 0.00 | xxxx | 713 |
| ATOM | 714 | CB | PRO | A | 93 | 42.093 | 24.257 | 78.012 | 1.00 | 0.00 | xxxx | 714 |
| ATOM | 715 | CG | PRO | A | 93 | 41.509 | 24.413 | 79.383 | 1.00 | 0.00 | xxxx | 715 |
| ATOM | 716 | CD | PRO | A | 93 | 40.824 | 23.096 | 79.663 | 1.00 | 0.00 | xxxx | 716 |
| ATOM | 717 | N | LEU | A | 94 | 41.800 | 22.993 | 75.024 | 1.00 | 0.00 | xxxx | 717 |
| ATOM | 718 | CA | LEU | A | 94 | 42.433 | 22.213 | 73.972 | 1.00 | 0.00 | xxxx | 718 |
| ATOM | 719 | C | LEU | A | 94 | 43.893 | 21.933 | 74.330 | 1.00 | 0.00 | xxxx | 719 |
| ATOM | 720 | O | LEU | A | 94 | 44.551 | 22.767 | 74.965 | 1.00 | 0.00 | xxxx | 720 |
| ATOM | 721 | CB | LEU | A | 94 | 42.347 | 22.978 | 72.650 | 1.00 | 0.00 | xxxx | 721 |
| ATOM | 722 | CG | LEU | A | 94 | 40.914 | 23.234 | 72.166 | 1.00 | 0.00 | xxxx | 722 |
| ATOM | 723 | CD1 | LEU | A | 94 | 40.921 | 24.250 | 71.041 | 1.00 | 0.00 | xxxx | 723 |
| ATOM | 724 | CD2 | LEU | A | 94 | 40.254 | 21.938 | 71.720 | 1.00 | 0.00 | xxxx | 724 |
| ATOM | 725 | N | PRO | A | 95 | 44.429 | 20.766 | 73.960 | 1.00 | 0.00 | xxxx | 725 |
| ATOM | 726 | CA | PRO | A | 95 | 45.799 | 20.416 | 74.381 | 1.00 | 0.00 | xxxx | 726 |
| ATOM | 727 | C | PRO | A | 95 | 46.854 | 21.452 | 74.020 | 1.00 | 0.00 | xxxx | 727 |
| ATOM | 728 | O | PRO | A | 95 | 47.771 | 21.701 | 74.817 | 1.00 | 0.00 | xxxx | 728 |
| ATOM | 729 | CB | PRO | A | 95 | 46.057 | 19.076 | 73.674 | 1.00 | 0.00 | xxxx | 729 |
| ATOM | 730 | CG | PRO | A | 95 | 44.717 | 18.514 | 73.408 | 1.00 | 0.00 | xxxx | 730 |
| ATOM | 731 | CD | PRO | A | 95 | 43.761 | 19.661 | 73.254 | 1.00 | 0.00 | xxxx | 731 |
| ATOM | 732 | N | GLU | A | 96 | 46.771 | 22.046 | 72.830 | 1.00 | 0.00 | xxxx | 732 |
| ATOM | 733 | CA | GLU | A | 96 | 47.793 | 23.013 | 72.448 | 1.00 | 0.00 | xxxx | 733 |
| ATOM | 734 | C | GLU | A | 96 | 47.633 | 24.324 | 73.203 | 1.00 | 0.00 | xxxx | 734 |
| ATOM | 735 | O | GLU | A | 96 | 48.621 | 25.037 | 73.416 | 1.00 | 0.00 | xxxx | 735 |
| ATOM | 736 | CB | GLU | A | 96 | 47.803 | 23.232 | 70.934 | 1.00 | 0.00 | xxxx | 736 |
| ATOM | 737 | CG | GLU | A | 96 | 48.235 | 22.015 | 70.147 | 1.00 | 0.00 | xxxx | 737 |
| ATOM | 738 | CD | GLU | A | 96 | 49.629 | 21.547 | 70.513 | 1.00 | 0.00 | xxxx | 738 |
| ATOM | 739 | OE1 | GLU | A | 96 | 50.534 | 22.401 | 70.614 | 1.00 | 0.00 | xxxx | 739 |
| ATOM | 740 | OE2 | GLU | A | 96 | 49.815 | 20.327 | 70.706 | 1.00 | 0.00 | xxxx | 740 |
| ATOM | 741 | N | ASP | A | 97 | 46.412 | 24.657 | 73.623 | 1.00 | 0.00 | xxxx | 741 |
| ATOM | 742 | CA | ASP | A | 97 | 46.227 | 25.848 | 74.446 | 1.00 | 0.00 | xxxx | 742 |
| ATOM | 743 | C | ASP | A | 97 | 46.855 | 25.669 | 75.824 | 1.00 | 0.00 | xxxx | 743 |
| ATOM | 744 | O | ASP | A | 97 | 47.407 | 26.621 | 76.384 | 1.00 | 0.00 | xxxx | 744 |
| ATOM | 745 | CB | ASP | A | 97 | 44.739 | 26.187 | 74.565 | 1.00 | 0.00 | xxxx | 745 |
| ATOM | 746 | CG | ASP | A | 97 | 44.180 | 26.845 | 73.303 | 1.00 | 0.00 | xxxx | 746 |
| ATOM | 747 | OD1 | ASP | A | 97 | 44.968 | 27.227 | 72.401 | 1.00 | 0.00 | xxxx | 747 |
| ATOM | 748 | OD2 | ASP | A | 97 | 42.939 | 27.003 | 73.227 | 1.00 | 0.00 | xxxx | 748 |
| ATOM | 749 | N | MET | A | 98 | 46.809 | 24.450 | 76.372 | 1.00 | 0.00 | xxxx | 749 |
| ATOM | 750 | CA | MET | A | 98 | 47.442 | 24.187 | 77.662 | 1.00 | 0.00 | xxxx | 750 |
| ATOM | 751 | C | MET | A | 98 | 48.953 | 24.408 | 77.626 | 1.00 | 0.00 | xxxx | 751 |
| ATOM | 752 | O | MET | A | 98 | 49.562 | 24.632 | 78.679 | 1.00 | 0.00 | xxxx | 752 |
| ATOM | 753 | CB | MET | A | 98 | 47.125 | 22.758 | 78.114 | 1.00 | 0.00 | xxxx | 753 |
| ATOM | 754 | CG | MET | A | 98 | 45.647 | 22.489 | 78.418 | 1.00 | 0.00 | xxxx | 754 |
| ATOM | 755 | SD | MET | A | 98 | 45.085 | 23.366 | 79.897 | 1.00 | 0.00 | xxxx | 755 |
| ATOM | 756 | CE | MET | A | 98 | 46.117 | 22.612 | 81.168 | 1.00 | 0.00 | xxxx | 756 |
| ATOM | 757 | N | LYS | A | 99 | 49.570 | 24.361 | 76.449 | 1.00 | 0.00 | xxxx | 757 |
| ATOM | 758 | CA | LYS | A | 99 | 51.007 | 24.541 | 76.305 | 1.00 | 0.00 | xxxx | 758 |
| ATOM | 759 | C | LYS | A | 99 | 51.424 | 26.004 | 76.175 | 1.00 | 0.00 | xxxx | 759 |
| ATOM | 760 | O | LYS | A | 99 | 52.622 | 26.282 | 76.069 | 1.00 | 0.00 | xxxx | 760 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 761 | CB | LYS | A | 99 | 51.500 | 23.752 | 75.092 | 1.00 | 0.00 | xxxx | 761 |
| ATOM | 762 | CG | LYS | A | 99 | 51.309 | 22.254 | 75.227 | 1.00 | 0.00 | xxxx | 762 |
| ATOM | 763 | CD | LYS | A | 99 | 51.695 | 21.541 | 73.938 | 1.00 | 0.00 | xxxx | 763 |
| ATOM | 764 | CE | LYS | A | 99 | 51.555 | 20.033 | 74.071 | 1.00 | 0.00 | xxxx | 764 |
| ATOM | 765 | NZ | LYS | A | 99 | 52.567 | 19.465 | 75.004 | 1.00 | 0.00 | xxxx | 765 |
| ATOM | 766 | N | LYS | A | 100 | 50.472 | 26.942 | 76.211 | 1.00 | 0.00 | xxxx | 766 |
| ATOM | 767 | CA | LYS | A | 100 | 50.794 | 28.352 | 76.012 | 1.00 | 0.00 | xxxx | 767 |
| ATOM | 768 | C | LYS | A | 100 | 51.533 | 28.962 | 77.197 | 1.00 | 0.00 | xxxx | 768 |
| ATOM | 769 | O | LYS | A | 100 | 52.212 | 29.977 | 77.025 | 1.00 | 0.00 | xxxx | 769 |
| ATOM | 770 | CB | LYS | A | 100 | 49.513 | 29.152 | 75.759 | 1.00 | 0.00 | xxxx | 770 |
| ATOM | 771 | CG | LYS | A | 100 | 48.831 | 28.827 | 74.448 | 1.00 | 0.00 | xxxx | 771 |
| ATOM | 772 | CD | LYS | A | 100 | 47.377 | 29.291 | 74.441 | 1.00 | 0.00 | xxxx | 772 |
| ATOM | 773 | CE | LYS | A | 100 | 47.258 | 30.796 | 74.398 | 1.00 | 0.00 | xxxx | 773 |
| ATOM | 774 | NZ | LYS | A | 100 | 47.635 | 31.353 | 73.062 | 1.00 | 0.00 | xxxx | 774 |
| ATOM | 775 | N | TRP | A | 101 | 51.406 | 28.382 | 78.391 | 1.00 | 0.00 | xxxx | 775 |
| ATOM | 776 | CA | TRP | A | 101 | 52.010 | 28.966 | 79.579 | 1.00 | 0.00 | xxxx | 776 |
| ATOM | 777 | C | TRP | A | 101 | 52.277 | 27.853 | 80.580 | 1.00 | 0.00 | xxxx | 777 |
| ATOM | 778 | O | TRP | A | 101 | 51.626 | 26.806 | 80.555 | 1.00 | 0.00 | xxxx | 778 |
| ATOM | 779 | CB | TRP | A | 101 | 51.056 | 29.999 | 80.188 | 1.00 | 0.00 | xxxx | 779 |
| ATOM | 780 | CG | TRP | A | 101 | 51.640 | 30.945 | 81.199 | 1.00 | 0.00 | xxxx | 780 |
| ATOM | 781 | CD1 | TRP | A | 101 | 52.949 | 31.320 | 81.335 | 1.00 | 0.00 | xxxx | 781 |
| ATOM | 782 | CD2 | TRP | A | 101 | 50.912 | 31.647 | 82.215 | 1.00 | 0.00 | xxxx | 782 |
| ATOM | 783 | NE1 | TRP | A | 101 | 53.078 | 32.218 | 82.377 | 1.00 | 0.00 | xxxx | 783 |
| ATOM | 784 | CE2 | TRP | A | 101 | 51.842 | 32.434 | 82.930 | 1.00 | 0.00 | xxxx | 784 |
| ATOM | 785 | CE3 | TRP | A | 101 | 49.561 | 31.694 | 82.582 | 1.00 | 0.00 | xxxx | 785 |
| ATOM | 786 | CZ2 | TRP | A | 101 | 51.464 | 33.257 | 83.995 | 1.00 | 0.00 | xxxx | 786 |
| ATOM | 787 | CZ3 | TRP | A | 101 | 49.188 | 32.507 | 83.645 | 1.00 | 0.00 | xxxx | 787 |
| ATOM | 788 | CH2 | TRP | A | 101 | 50.136 | 33.277 | 84.336 | 1.00 | 0.00 | xxxx | 788 |
| ATOM | 789 | N | ASP | A | 102 | 53.224 | 28.102 | 81.483 | 1.00 | 0.00 | xxxx | 789 |
| ATOM | 790 | CA | ASP | A | 102 | 53.626 | 27.126 | 82.488 | 1.00 | 0.00 | xxxx | 790 |
| ATOM | 791 | C | ASP | A | 102 | 52.973 | 27.364 | 83.847 | 1.00 | 0.00 | xxxx | 791 |
| ATOM | 792 | O | ASP | A | 102 | 53.411 | 26.777 | 84.842 | 1.00 | 0.00 | xxxx | 792 |
| ATOM | 793 | CB | ASP | A | 102 | 55.155 | 27.039 | 82.598 | 1.00 | 0.00 | xxxx | 793 |
| ATOM | 794 | CG | ASP | A | 102 | 55.797 | 28.340 | 83.059 | 1.00 | 0.00 | xxxx | 794 |
| ATOM | 795 | OD1 | ASP | A | 102 | 55.124 | 29.388 | 83.125 | 1.00 | 0.00 | xxxx | 795 |
| ATOM | 796 | OD2 | ASP | A | 102 | 57.013 | 28.310 | 83.351 | 1.00 | 0.00 | xxxx | 796 |
| ATOM | 797 | N | LYS | A | 103 | 51.950 | 28.211 | 83.912 | 1.00 | 0.00 | xxxx | 797 |
| ATOM | 798 | CA | LYS | A | 103 | 51.156 | 28.402 | 85.119 | 1.00 | 0.00 | xxxx | 798 |
| ATOM | 799 | C | LYS | A | 103 | 49.689 | 28.099 | 84.858 | 1.00 | 0.00 | xxxx | 799 |
| ATOM | 800 | O | LYS | A | 103 | 48.798 | 28.736 | 85.427 | 1.00 | 0.00 | xxxx | 800 |
| ATOM | 801 | CB | LYS | A | 103 | 51.366 | 29.804 | 85.695 | 1.00 | 0.00 | xxxx | 801 |
| ATOM | 802 | CG | LYS | A | 103 | 52.824 | 30.084 | 86.062 | 1.00 | 0.00 | xxxx | 802 |
| ATOM | 803 | CD | LYS | A | 103 | 52.960 | 31.395 | 86.808 | 1.00 | 0.00 | xxxx | 803 |
| ATOM | 804 | CE | LYS | A | 103 | 54.412 | 31.709 | 87.110 | 1.00 | 0.00 | xxxx | 804 |
| ATOM | 805 | NZ | LYS | A | 103 | 54.516 | 32.987 | 87.861 | 1.00 | 0.00 | xxxx | 805 |
| ATOM | 806 | N | VAL | A | 104 | 49.422 | 27.112 | 83.996 | 1.00 | 0.00 | xxxx | 806 |
| ATOM | 807 | CA | VAL | A | 104 | 48.073 | 26.720 | 83.609 | 1.00 | 0.00 | xxxx | 807 |
| ATOM | 808 | C | VAL | A | 104 | 47.869 | 25.249 | 83.945 | 1.00 | 0.00 | xxxx | 808 |
| ATOM | 809 | O | VAL | A | 104 | 48.705 | 24.411 | 83.596 | 1.00 | 0.00 | xxxx | 809 |
| ATOM | 810 | CB | VAL | A | 104 | 47.826 | 26.956 | 82.111 | 1.00 | 0.00 | xxxx | 810 |
| ATOM | 811 | CG1 | VAL | A | 104 | 46.404 | 26.572 | 81.757 | 1.00 | 0.00 | xxxx | 811 |
| ATOM | 812 | CG2 | VAL | A | 104 | 48.111 | 28.418 | 81.741 | 1.00 | 0.00 | xxxx | 812 |
| ATOM | 813 | N | TYR | A | 105 | 46.758 | 24.943 | 84.611 | 1.00 | 0.00 | xxxx | 813 |
| ATOM | 814 | CA | TYR | A | 105 | 46.428 | 23.587 | 85.034 | 1.00 | 0.00 | xxxx | 814 |
| ATOM | 815 | C | TYR | A | 105 | 45.001 | 23.257 | 84.625 | 1.00 | 0.00 | xxxx | 815 |
| ATOM | 816 | O | TYR | A | 105 | 44.203 | 24.138 | 84.306 | 1.00 | 0.00 | xxxx | 816 |
| ATOM | 817 | CB | TYR | A | 105 | 46.590 | 23.433 | 86.558 | 1.00 | 0.00 | xxxx | 817 |
| ATOM | 818 | CG | TYR | A | 105 | 48.029 | 23.536 | 86.975 | 1.00 | 0.00 | xxxx | 818 |
| ATOM | 819 | CD1 | TYR | A | 105 | 48.641 | 24.778 | 87.146 | 1.00 | 0.00 | xxxx | 819 |
| ATOM | 820 | CD2 | TYR | A | 105 | 48.805 | 22.395 | 87.140 | 1.00 | 0.00 | xxxx | 820 |
| ATOM | 821 | CE1 | TYR | A | 105 | 49.989 | 24.873 | 87.485 | 1.00 | 0.00 | xxxx | 821 |
| ATOM | 822 | CE2 | TYR | A | 105 | 50.146 | 22.478 | 87.485 | 1.00 | 0.00 | xxxx | 822 |
| ATOM | 823 | CZ | TYR | A | 105 | 50.737 | 23.719 | 87.661 | 1.00 | 0.00 | xxxx | 823 |
| ATOM | 824 | OH | TYR | A | 105 | 52.074 | 23.794 | 87.999 | 1.00 | 0.00 | xxxx | 824 |
| ATOM | 825 | N | TYR | A | 106 | 44.671 | 21.959 | 84.666 | 1.00 | 0.00 | xxxx | 825 |
| ATOM | 826 | CA | TYR | A | 106 | 43.319 | 21.482 | 84.412 | 1.00 | 0.00 | xxxx | 826 |
| ATOM | 827 | C | TYR | A | 106 | 42.980 | 20.374 | 85.400 | 1.00 | 0.00 | xxxx | 827 |
| ATOM | 828 | O | TYR | A | 106 | 43.782 | 19.459 | 85.601 | 1.00 | 0.00 | xxxx | 828 |
| ATOM | 829 | CB | TYR | A | 106 | 43.141 | 20.937 | 82.973 | 1.00 | 0.00 | xxxx | 829 |
| ATOM | 830 | CG | TYR | A | 106 | 41.739 | 20.422 | 82.780 | 1.00 | 0.00 | xxxx | 830 |
| ATOM | 831 | CD1 | TYR | A | 106 | 40.675 | 21.304 | 82.676 | 1.00 | 0.00 | xxxx | 831 |
| ATOM | 832 | CD2 | TYR | A | 106 | 41.455 | 19.050 | 82.778 | 1.00 | 0.00 | xxxx | 832 |
| ATOM | 833 | CE1 | TYR | A | 106 | 39.369 | 20.857 | 82.542 | 1.00 | 0.00 | xxxx | 833 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 834 | CE2 | TYR | A | 106 | 40.142 | 18.593 | 82.648 | 1.00 | 0.00 | xxxx | 834 |
| ATOM | 835 | CZ | TYR | A | 106 | 39.107 | 19.497 | 82.522 | 1.00 | 0.00 | xxxx | 835 |
| ATOM | 836 | OH | TYR | A | 106 | 37.803 | 19.075 | 82.396 | 1.00 | 0.00 | xxxx | 836 |
| ATOM | 837 | N | VAL | A | 107 | 41.773 | 20.428 | 85.968 | 1.00 | 0.00 | xxxx | 837 |
| ATOM | 838 | CA | VAL | A | 107 | 41.248 | 19.379 | 86.842 | 1.00 | 0.00 | xxxx | 838 |
| ATOM | 839 | C | VAL | A | 107 | 39.975 | 18.819 | 86.226 | 1.00 | 0.00 | xxxx | 839 |
| ATOM | 840 | O | VAL | A | 107 | 39.050 | 19.574 | 85.900 | 1.00 | 0.00 | xxxx | 840 |
| ATOM | 841 | CB | VAL | A | 107 | 40.951 | 19.903 | 88.259 | 1.00 | 0.00 | xxxx | 841 |
| ATOM | 842 | CG1 | VAL | A | 107 | 40.361 | 18.800 | 89.114 | 1.00 | 0.00 | xxxx | 842 |
| ATOM | 843 | CG2 | VAL | A | 107 | 42.213 | 20.446 | 88.908 | 1.00 | 0.00 | xxxx | 843 |
| ATOM | 844 | N | GLY | A | 108 | 39.915 | 17.493 | 86.100 | 1.00 | 0.00 | xxxx | 844 |
| ATOM | 845 | CA | GLY | A | 108 | 38.702 | 16.866 | 85.622 | 1.00 | 0.00 | xxxx | 845 |
| ATOM | 846 | C | GLY | A | 108 | 38.800 | 15.365 | 85.755 | 1.00 | 0.00 | xxxx | 846 |
| ATOM | 847 | O | GLY | A | 108 | 39.295 | 14.851 | 86.763 | 1.00 | 0.00 | xxxx | 847 |
| ATOM | 848 | N | ALA | A | 109 | 38.332 | 14.650 | 84.743 | 1.00 | 0.00 | xxxx | 848 |
| ATOM | 849 | CA | ALA | A | 109 | 38.287 | 13.200 | 84.787 | 1.00 | 0.00 | xxxx | 849 |
| ATOM | 850 | C | ALA | A | 109 | 38.364 | 12.689 | 83.362 | 1.00 | 0.00 | xxxx | 850 |
| ATOM | 851 | O | ALA | A | 109 | 38.064 | 13.415 | 82.414 | 1.00 | 0.00 | xxxx | 851 |
| ATOM | 852 | CB | ALA | A | 109 | 37.007 | 12.726 | 85.481 | 1.00 | 0.00 | xxxx | 852 |
| ATOM | 853 | N | LYS | A | 110 | 38.779 | 11.435 | 83.217 | 1.00 | 0.00 | xxxx | 853 |
| ATOM | 854 | CA | LYS | A | 110 | 38.965 | 10.850 | 81.892 | 1.00 | 0.00 | xxxx | 854 |
| ATOM | 855 | C | LYS | A | 110 | 37.616 | 10.372 | 81.379 | 1.00 | 0.00 | xxxx | 855 |
| ATOM | 856 | O | LYS | A | 110 | 37.135 | 9.308 | 81.764 | 1.00 | 0.00 | xxxx | 856 |
| ATOM | 857 | CB | LYS | A | 110 | 39.942 | 9.684 | 81.966 | 1.00 | 0.00 | xxxx | 857 |
| ATOM | 858 | CG | LYS | A | 110 | 41.382 | 10.111 | 82.235 | 1.00 | 0.00 | xxxx | 858 |
| ATOM | 859 | CD | LYS | A | 110 | 41.886 | 11.014 | 81.116 | 1.00 | 0.00 | xxxx | 859 |
| ATOM | 860 | CE | LYS | A | 110 | 43.406 | 11.034 | 81.063 | 1.00 | 0.00 | xxxx | 860 |
| ATOM | 861 | NZ | LYS | A | 110 | 43.975 | 9.730 | 80.625 | 1.00 | 0.00 | xxxx | 861 |
| ATOM | 862 | N | ALA | A | 111 | 37.021 | 11.140 | 80.467 | 1.00 | 0.00 | xxxx | 862 |
| ATOM | 863 | CA | ALA | A | 111 | 35.667 | 10.836 | 80.021 | 1.00 | 0.00 | xxxx | 863 |
| ATOM | 864 | C | ALA | A | 111 | 35.566 | 9.462 | 79.362 | 1.00 | 0.00 | xxxx | 864 |
| ATOM | 865 | O | ALA | A | 111 | 34.507 | 8.820 | 79.423 | 1.00 | 0.00 | xxxx | 865 |
| ATOM | 866 | CB | ALA | A | 111 | 35.170 | 11.933 | 79.076 | 1.00 | 0.00 | xxxx | 866 |
| ATOM | 867 | N | GLU | A | 112 | 36.657 | 9.000 | 78.744 | 1.00 | 0.00 | xxxx | 867 |
| ATOM | 868 | CA | GLU | A | 112 | 36.709 | 7.645 | 78.202 | 1.00 | 0.00 | xxxx | 868 |
| ATOM | 869 | C | GLU | A | 112 | 36.330 | 6.615 | 79.255 | 1.00 | 0.00 | xxxx | 869 |
| ATOM | 870 | O | GLU | A | 112 | 35.572 | 5.675 | 78.978 | 1.00 | 0.00 | xxxx | 870 |
| ATOM | 871 | CB | GLU | A | 112 | 38.121 | 7.355 | 77.686 | 1.00 | 0.00 | xxxx | 871 |
| ATOM | 872 | CG | GLU | A | 112 | 38.618 | 8.313 | 76.606 | 1.00 | 0.00 | xxxx | 872 |
| ATOM | 873 | CD | GLU | A | 112 | 39.455 | 9.466 | 77.141 | 1.00 | 0.00 | xxxx | 873 |
| ATOM | 874 | OE1 | GLU | A | 112 | 39.153 | 10.008 | 78.232 | 1.00 | 0.00 | xxxx | 874 |
| ATOM | 875 | OE2 | GLU | A | 112 | 40.432 | 9.841 | 76.453 | 1.00 | 0.00 | xxxx | 875 |
| ATOM | 876 | N | GLN | A | 113 | 36.855 | 6.776 | 80.473 | 1.00 | 0.00 | xxxx | 876 |
| ATOM | 877 | CA | GLN | A | 113 | 36.564 | 5.823 | 81.540 | 1.00 | 0.00 | xxxx | 877 |
| ATOM | 878 | C | GLN | A | 113 | 35.081 | 5.814 | 81.880 | 1.00 | 0.00 | xxxx | 878 |
| ATOM | 879 | O | GLN | A | 113 | 34.488 | 4.748 | 82.097 | 1.00 | 0.00 | xxxx | 879 |
| ATOM | 880 | CB | GLN | A | 113 | 37.402 | 6.166 | 82.776 | 1.00 | 0.00 | xxxx | 880 |
| ATOM | 881 | CG | GLN | A | 113 | 37.058 | 5.368 | 84.034 | 1.00 | 0.00 | xxxx | 881 |
| ATOM | 882 | CD | GLN | A | 113 | 37.890 | 5.767 | 85.260 | 1.00 | 0.00 | xxxx | 882 |
| ATOM | 883 | OE1 | GLN | A | 113 | 38.035 | 6.954 | 85.590 | 1.00 | 0.00 | xxxx | 883 |
| ATOM | 884 | NE2 | GLN | A | 113 | 38.439 | 4.765 | 85.941 | 1.00 | 0.00 | xxxx | 884 |
| ATOM | 885 | N | SER | A | 114 | 34.455 | 6.990 | 81.911 | 1.00 | 0.00 | xxxx | 885 |
| ATOM | 886 | CA | SER | A | 114 | 33.031 | 7.032 | 82.216 | 1.00 | 0.00 | xxxx | 886 |
| ATOM | 887 | C | SER | A | 114 | 32.215 | 6.359 | 81.116 | 1.00 | 0.00 | xxxx | 887 |
| ATOM | 888 | O | SER | A | 114 | 31.241 | 5.660 | 81.410 | 1.00 | 0.00 | xxxx | 888 |
| ATOM | 889 | CB | SER | A | 114 | 32.564 | 8.459 | 82.527 | 1.00 | 0.00 | xxxx | 889 |
| ATOM | 890 | OG | SER | A | 114 | 32.609 | 9.317 | 81.402 | 1.00 | 0.00 | xxxx | 890 |
| ATOM | 891 | N | GLY | A | 115 | 32.617 | 6.521 | 79.848 | 1.00 | 0.00 | xxxx | 891 |
| ATOM | 892 | CA | GLY | A | 115 | 31.920 | 5.842 | 78.762 | 1.00 | 0.00 | xxxx | 892 |
| ATOM | 893 | C | GLY | A | 115 | 32.049 | 4.333 | 78.862 | 1.00 | 0.00 | xxxx | 893 |
| ATOM | 894 | O | GLY | A | 115 | 31.061 | 3.602 | 78.700 | 1.00 | 0.00 | xxxx | 894 |
| ATOM | 895 | N | ILE | A | 116 | 33.252 | 3.848 | 79.163 | 1.00 | 0.00 | xxxx | 895 |
| ATOM | 896 | CA | ILE | A | 116 | 33.454 | 2.405 | 79.314 | 1.00 | 0.00 | xxxx | 896 |
| ATOM | 897 | C | ILE | A | 116 | 32.591 | 1.865 | 80.443 | 1.00 | 0.00 | xxxx | 897 |
| ATOM | 898 | O | ILE | A | 116 | 31.934 | 0.825 | 80.301 | 1.00 | 0.00 | xxxx | 898 |
| ATOM | 899 | CB | ILE | A | 116 | 34.940 | 2.081 | 79.537 | 1.00 | 0.00 | xxxx | 899 |
| ATOM | 900 | CG1 | ILE | A | 116 | 35.755 | 2.410 | 78.283 | 1.00 | 0.00 | xxxx | 900 |
| ATOM | 901 | CG2 | ILE | A | 116 | 35.112 | 0.620 | 79.957 | 1.00 | 0.00 | xxxx | 901 |
| ATOM | 902 | CD1 | ILE | A | 116 | 37.259 | 2.474 | 78.545 | 1.00 | 0.00 | xxxx | 902 |
| ATOM | 903 | N | LEU | A | 117 | 32.590 | 2.549 | 81.588 | 1.00 | 0.00 | xxxx | 903 |
| ATOM | 904 | CA | LEU | A | 117 | 31.816 | 2.045 | 82.721 | 1.00 | 0.00 | xxxx | 904 |
| ATOM | 905 | C | LEU | A | 117 | 30.326 | 2.034 | 82.407 | 1.00 | 0.00 | xxxx | 905 |
| ATOM | 906 | O | LEU | A | 117 | 29.605 | 1.110 | 82.800 | 1.00 | 0.00 | xxxx | 906 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 907 | CB | LEU | A | 117 | 32.116 | 2.869 | 83.974 | 1.00 | 0.00 | xxxx | 907 |
| ATOM | 908 | CG | LEU | A | 117 | 33.569 | 2.740 | 84.443 | 1.00 | 0.00 | xxxx | 908 |
| ATOM | 909 | CD1 | LEU | A | 117 | 33.871 | 3.740 | 85.536 | 1.00 | 0.00 | xxxx | 909 |
| ATOM | 910 | CD2 | LEU | A | 117 | 33.858 | 1.322 | 84.933 | 1.00 | 0.00 | xxxx | 910 |
| ATOM | 911 | N | GLN | A | 118 | 29.852 | 3.033 | 81.669 | 1.00 | 0.00 | xxxx | 911 |
| ATOM | 912 | CA | GLN | A | 118 | 28.444 | 3.055 | 81.301 | 1.00 | 0.00 | xxxx | 912 |
| ATOM | 913 | C | GLN | A | 118 | 28.099 | 1.925 | 80.332 | 1.00 | 0.00 | xxxx | 913 |
| ATOM | 914 | O | GLN | A | 118 | 27.021 | 1.323 | 80.431 | 1.00 | 0.00 | xxxx | 914 |
| ATOM | 915 | CB | GLN | A | 118 | 28.100 | 4.415 | 80.706 | 1.00 | 0.00 | xxxx | 915 |
| ATOM | 916 | CG | GLN | A | 118 | 26.672 | 4.525 | 80.317 | 1.00 | 0.00 | xxxx | 916 |
| ATOM | 917 | CD | GLN | A | 118 | 26.359 | 5.813 | 79.604 | 1.00 | 0.00 | xxxx | 917 |
| ATOM | 918 | OE1 | GLN | A | 118 | 26.587 | 5.942 | 78.406 | 1.00 | 0.00 | xxxx | 918 |
| ATOM | 919 | NE2 | GLN | A | 118 | 25.821 | 6.774 | 80.339 | 1.00 | 0.00 | xxxx | 919 |
| ATOM | 920 | N | GLY | A | 119 | 28.997 | 1.622 | 79.391 | 1.00 | 0.00 | xxxx | 920 |
| ATOM | 921 | CA | GLY | A | 119 | 28.759 | 0.516 | 78.490 | 1.00 | 0.00 | xxxx | 921 |
| ATOM | 922 | C | GLY | A | 119 | 28.777 | −0.821 | 79.199 | 1.00 | 0.00 | xxxx | 922 |
| ATOM | 923 | O | GLY | A | 119 | 28.010 | −1.722 | 78.851 | 1.00 | 0.00 | xxxx | 923 |
| ATOM | 924 | N | GLN | A | 120 | 29.643 | −0.969 | 80.210 | 1.00 | 0.00 | xxxx | 924 |
| ATOM | 925 | CA | GLN | A | 120 | 29.658 | −2.210 | 80.978 | 1.00 | 0.00 | xxxx | 925 |
| ATOM | 926 | C | GLN | A | 120 | 28.335 | −2.435 | 81.700 | 1.00 | 0.00 | xxxx | 926 |
| ATOM | 927 | O | GLN | A | 120 | 27.832 | −3.566 | 81.743 | 1.00 | 0.00 | xxxx | 927 |
| ATOM | 928 | CB | GLN | A | 120 | 30.821 | −2.219 | 81.964 | 1.00 | 0.00 | xxxx | 928 |
| ATOM | 929 | CG | GLN | A | 120 | 32.178 | −2.283 | 81.299 | 1.00 | 0.00 | xxxx | 929 |
| ATOM | 930 | CD | GLN | A | 120 | 33.308 | −2.245 | 82.300 | 1.00 | 0.00 | xxxx | 930 |
| ATOM | 931 | OE1 | GLN | A | 120 | 33.092 | −2.012 | 83.493 | 1.00 | 0.00 | xxxx | 931 |
| ATOM | 932 | NE2 | GLN | A | 120 | 34.526 | −2.486 | 81.827 | 1.00 | 0.00 | xxxx | 932 |
| ATOM | 933 | N | ILE | A | 121 | 27.765 | −1.384 | 82.289 | 1.00 | 0.00 | xxxx | 933 |
| ATOM | 934 | CA | ILE | A | 121 | 26.481 | −1.522 | 82.973 | 1.00 | 0.00 | xxxx | 934 |
| ATOM | 935 | C | ILE | A | 121 | 25.433 | −2.060 | 82.012 | 1.00 | 0.00 | xxxx | 935 |
| ATOM | 936 | O | ILE | A | 121 | 24.703 | −3.015 | 82.318 | 1.00 | 0.00 | xxxx | 936 |
| ATOM | 937 | CB | ILE | A | 121 | 26.044 | −0.170 | 83.567 | 1.00 | 0.00 | xxxx | 937 |
| ATOM | 938 | CG1 | ILE | A | 121 | 26.980 | 0.263 | 84.696 | 1.00 | 0.00 | xxxx | 938 |
| ATOM | 939 | CG2 | ILE | A | 121 | 24.601 | −0.259 | 84.071 | 1.00 | 0.00 | xxxx | 939 |
| ATOM | 940 | CD1 | ILE | A | 121 | 26.783 | 1.722 | 85.103 | 1.00 | 0.00 | xxxx | 940 |
| ATOM | 941 | N | MET | A | 122 | 25.338 | −1.450 | 80.831 | 1.00 | 0.00 | xxxx | 941 |
| ATOM | 942 | CA | MET | A | 122 | 24.306 | −1.857 | 79.886 | 1.00 | 0.00 | xxxx | 942 |
| ATOM | 943 | C | MET | A | 122 | 24.573 | −3.252 | 79.344 | 1.00 | 0.00 | xxxx | 943 |
| ATOM | 944 | O | MET | A | 122 | 23.640 | −4.049 | 79.180 | 1.00 | 0.00 | xxxx | 944 |
| ATOM | 945 | CB | MET | A | 122 | 24.209 | −0.852 | 78.742 | 1.00 | 0.00 | xxxx | 945 |
| ATOM | 946 | CG | MET | A | 122 | 23.000 | −1.108 | 77.851 | 1.00 | 0.00 | xxxx | 946 |
| ATOM | 947 | SD | MET | A | 122 | 21.435 | −0.672 | 78.643 | 1.00 | 0.00 | xxxx | 947 |
| ATOM | 948 | CE | MET | A | 122 | 21.453 | 1.110 | 78.453 | 1.00 | 0.00 | xxxx | 948 |
| ATOM | 949 | N | ALA | A | 123 | 25.839 | −3.564 | 79.049 | 1.00 | 0.00 | xxxx | 949 |
| ATOM | 950 | CA | ALA | A | 123 | 26.157 | −4.867 | 78.473 | 1.00 | 0.00 | xxxx | 950 |
| ATOM | 951 | C | ALA | A | 123 | 25.888 | −5.980 | 79.471 | 1.00 | 0.00 | xxxx | 951 |
| ATOM | 952 | O | ALA | A | 123 | 25.370 | −7.043 | 79.104 | 1.00 | 0.00 | xxxx | 952 |
| ATOM | 953 | CB | ALA | A | 123 | 27.618 | −4.898 | 78.014 | 1.00 | 0.00 | xxxx | 953 |
| ATOM | 954 | N | ASP | A | 124 | 26.216 | −5.746 | 80.744 | 1.00 | 0.00 | xxxx | 954 |
| ATOM | 955 | CA | ASP | A | 124 | 25.959 | −6.760 | 81.759 | 1.00 | 0.00 | xxxx | 955 |
| ATOM | 956 | C | ASP | A | 124 | 24.465 | −6.967 | 81.961 | 1.00 | 0.00 | xxxx | 956 |
| ATOM | 957 | O | ASP | A | 124 | 24.005 | −8.103 | 82.152 | 1.00 | 0.00 | xxxx | 957 |
| ATOM | 958 | CB | ASP | A | 124 | 26.654 | −6.386 | 83.067 | 1.00 | 0.00 | xxxx | 958 |
| ATOM | 959 | CG | ASP | A | 124 | 28.160 | −6.575 | 82.996 | 1.00 | 0.00 | xxxx | 959 |
| ATOM | 960 | OD1 | ASP | A | 124 | 28.633 | −7.287 | 82.084 | 1.00 | 0.00 | xxxx | 960 |
| ATOM | 961 | OD2 | ASP | A | 124 | 28.877 | −6.021 | 83.851 | 1.00 | 0.00 | xxxx | 961 |
| ATOM | 962 | N | TYR | A | 125 | 23.681 | −5.890 | 81.898 | 1.00 | 0.00 | xxxx | 962 |
| ATOM | 963 | CA | TYR | A | 125 | 22.236 | −6.059 | 81.995 | 1.00 | 0.00 | xxxx | 963 |
| ATOM | 964 | C | TYR | A | 125 | 21.709 | −6.872 | 80.819 | 1.00 | 0.00 | xxxx | 964 |
| ATOM | 965 | O | TYR | A | 125 | 20.909 | −7.803 | 80.994 | 1.00 | 0.00 | xxxx | 965 |
| ATOM | 966 | CB | TYR | A | 125 | 21.544 | −4.692 | 82.073 | 1.00 | 0.00 | xxxx | 966 |
| ATOM | 967 | CG | TYR | A | 125 | 20.049 | −4.820 | 81.878 | 1.00 | 0.00 | xxxx | 967 |
| ATOM | 968 | CD1 | TYR | A | 125 | 19.209 | −5.126 | 82.944 | 1.00 | 0.00 | xxxx | 968 |
| ATOM | 969 | CD2 | TYR | A | 125 | 19.487 | −4.695 | 80.614 | 1.00 | 0.00 | xxxx | 969 |
| ATOM | 970 | CE1 | TYR | A | 125 | 17.838 | −5.281 | 82.746 | 1.00 | 0.00 | xxxx | 970 |
| ATOM | 971 | CE2 | TYR | A | 125 | 18.132 | −4.858 | 80.411 | 1.00 | 0.00 | xxxx | 971 |
| ATOM | 972 | CZ | TYR | A | 125 | 17.323 | −5.140 | 81.472 | 1.00 | 0.00 | xxxx | 972 |
| ATOM | 973 | OH | TYR | A | 125 | 15.974 | −5.294 | 81.249 | 1.00 | 0.00 | xxxx | 973 |
| ATOM | 974 | N | TRP | A | 126 | 22.144 | −6.522 | 79.607 | 1.00 | 0.00 | xxxx | 974 |
| ATOM | 975 | CA | TRP | A | 126 | 21.697 | −7.212 | 78.402 | 1.00 | 0.00 | xxxx | 975 |
| ATOM | 976 | C | TRP | A | 126 | 21.984 | −8.704 | 78.489 | 1.00 | 0.00 | xxxx | 976 |
| ATOM | 977 | O | TRP | A | 126 | 21.119 | −9.535 | 78.184 | 1.00 | 0.00 | xxxx | 977 |
| ATOM | 978 | CB | TRP | A | 126 | 22.395 | −6.598 | 77.184 | 1.00 | 0.00 | xxxx | 978 |
| ATOM | 979 | CG | TRP | A | 126 | 22.086 | −7.259 | 75.841 | 1.00 | 0.00 | xxxx | 979 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 980 | CD1 | TRP | A | 126 | 22.802 | −8.247 | 75.234 | 1.00 | 0.00 | xxxx | 980 |
| ATOM | 981 | CD2 | TRP | A | 126 | 21.009 | −6.938 | 74.949 | 1.00 | 0.00 | xxxx | 981 |
| ATOM | 982 | NE1 | TRP | A | 126 | 22.229 | −8.578 | 74.023 | 1.00 | 0.00 | xxxx | 982 |
| ATOM | 983 | CE2 | TRP | A | 126 | 21.131 | −7.782 | 73.827 | 1.00 | 0.00 | xxxx | 983 |
| ATOM | 984 | CE3 | TRP | A | 126 | 19.953 | −6.027 | 74.995 | 1.00 | 0.00 | xxxx | 984 |
| ATOM | 985 | CZ2 | TRP | A | 126 | 20.231 | −7.746 | 72.762 | 1.00 | 0.00 | xxxx | 985 |
| ATOM | 986 | CZ3 | TRP | A | 126 | 19.054 | −5.988 | 73.925 | 1.00 | 0.00 | xxxx | 986 |
| ATOM | 987 | CH2 | TRP | A | 126 | 19.206 | −6.841 | 72.832 | 1.00 | 0.00 | xxxx | 987 |
| ATOM | 988 | N | LYS | A | 127 | 23.197 | −9.063 | 78.918 | 1.00 | 0.00 | xxxx | 988 |
| ATOM | 989 | CA | LYS | A | 127 | 23.576 | −10.473 | 78.961 | 1.00 | 0.00 | xxxx | 989 |
| ATOM | 990 | C | LYS | A | 127 | 22.768 | −11.247 | 79.995 | 1.00 | 0.00 | xxxx | 990 |
| ATOM | 991 | O | LYS | A | 127 | 22.540 | −12.453 | 79.826 | 1.00 | 0.00 | xxxx | 991 |
| ATOM | 992 | CB | LYS | A | 127 | 25.073 | −10.596 | 79.250 | 1.00 | 0.00 | xxxx | 992 |
| ATOM | 993 | CG | LYS | A | 127 | 25.956 | −10.147 | 78.103 | 1.00 | 0.00 | xxxx | 993 |
| ATOM | 994 | CD | LYS | A | 127 | 27.414 | −10.102 | 78.521 | 1.00 | 0.00 | xxxx | 994 |
| ATOM | 995 | CE | LYS | A | 127 | 28.307 | −9.804 | 77.331 | 1.00 | 0.00 | xxxx | 995 |
| ATOM | 996 | NZ | LYS | A | 127 | 29.742 | −9.750 | 77.743 | 1.00 | 0.00 | xxxx | 996 |
| ATOM | 997 | N | ALA | A | 128 | 22.332 | −10.583 | 81.067 | 1.00 | 0.00 | xxxx | 997 |
| ATOM | 998 | CA | ALA | A | 128 | 21.615 | −11.253 | 82.147 | 1.00 | 0.00 | xxxx | 998 |
| ATOM | 999 | C | ALA | A | 128 | 20.110 | −11.293 | 81.937 | 1.00 | 0.00 | xxxx | 999 |
| ATOM | 1000 | O | ALA | A | 128 | 19.420 | −12.022 | 82.657 | 1.00 | 0.00 | xxxx | 1000 |
| ATOM | 1001 | CB | ALA | A | 128 | 21.898 | −10.540 | 83.473 | 1.00 | 0.00 | xxxx | 1001 |
| ATOM | 1002 | N | HIS | A | 129 | 19.583 | −10.530 | 80.984 | 1.00 | 0.00 | xxxx | 1002 |
| ATOM | 1003 | CA | HIS | A | 129 | 18.139 | −10.395 | 80.799 | 1.00 | 0.00 | xxxx | 1003 |
| ATOM | 1004 | C | HIS | A | 129 | 17.763 | −10.624 | 79.343 | 1.00 | 0.00 | xxxx | 1004 |
| ATOM | 1005 | O | HIS | A | 129 | 17.662 | −9.671 | 78.558 | 1.00 | 0.00 | xxxx | 1005 |
| ATOM | 1006 | CB | HIS | A | 129 | 17.662 | −9.033 | 81.295 | 1.00 | 0.00 | xxxx | 1006 |
| ATOM | 1007 | CG | HIS | A | 129 | 17.943 | −8.800 | 82.743 | 1.00 | 0.00 | xxxx | 1007 |
| ATOM | 1008 | ND1 | HIS | A | 129 | 17.015 | −9.057 | 83.730 | 1.00 | 0.00 | xxxx | 1008 |
| ATOM | 1009 | CD2 | HIS | A | 129 | 19.060 | −8.370 | 83.377 | 1.00 | 0.00 | xxxx | 1009 |
| ATOM | 1010 | CE1 | HIS | A | 129 | 17.544 | −8.781 | 84.909 | 1.00 | 0.00 | xxxx | 1010 |
| ATOM | 1011 | NE2 | HIS | A | 129 | 18.782 | −8.363 | 84.723 | 1.00 | 0.00 | xxxx | 1011 |
| ATOM | 1012 | N | PRO | A | 130 | 17.512 | −11.875 | 78.955 | 1.00 | 0.00 | xxxx | 1012 |
| ATOM | 1013 | CA | PRO | A | 130 | 17.138 | −12.147 | 77.556 | 1.00 | 0.00 | xxxx | 1013 |
| ATOM | 1014 | C | PRO | A | 130 | 15.891 | −11.409 | 77.117 | 1.00 | 0.00 | xxxx | 1014 |
| ATOM | 1015 | O | PRO | A | 130 | 15.751 | −11.087 | 75.930 | 1.00 | 0.00 | xxxx | 1015 |
| ATOM | 1016 | CB | PRO | A | 130 | 16.922 | −13.667 | 77.532 | 1.00 | 0.00 | xxxx | 1016 |
| ATOM | 1017 | CG | PRO | A | 130 | 17.575 | −14.187 | 78.772 | 1.00 | 0.00 | xxxx | 1017 |
| ATOM | 1018 | CD | PRO | A | 130 | 17.522 | −13.090 | 79.785 | 1.00 | 0.00 | xxxx | 1018 |
| ATOM | 1019 | N | GLU | A | 131 | 14.981 | −11.120 | 78.046 | 1.00 | 0.00 | xxxx | 1019 |
| ATOM | 1020 | CA | GLU | A | 131 | 13.760 | −10.409 | 77.702 | 1.00 | 0.00 | xxxx | 1020 |
| ATOM | 1021 | C | GLU | A | 131 | 14.022 | −8.977 | 77.257 | 1.00 | 0.00 | xxxx | 1021 |
| ATOM | 1022 | O | GLU | A | 131 | 13.108 | −8.337 | 76.722 | 1.00 | 0.00 | xxxx | 1022 |
| ATOM | 1023 | CB | GLU | A | 131 | 12.791 | −10.429 | 78.885 | 1.00 | 0.00 | xxxx | 1023 |
| ATOM | 1024 | CG | GLU | A | 131 | 13.175 | −9.489 | 80.025 | 1.00 | 0.00 | xxxx | 1024 |
| ATOM | 1025 | CD | GLU | A | 131 | 14.111 | −10.120 | 81.050 | 1.00 | 0.00 | xxxx | 1025 |
| ATOM | 1026 | OE1 | GLU | A | 131 | 14.789 | −11.127 | 80.739 | 1.00 | 0.00 | xxxx | 1026 |
| ATOM | 1027 | OE2 | GLU | A | 131 | 14.164 | −9.598 | 82.186 | 1.00 | 0.00 | xxxx | 1027 |
| ATOM | 1028 | N | ALA | A | 132 | 15.240 | −8.470 | 77.452 | 1.00 | 0.00 | xxxx | 1028 |
| ATOM | 1029 | CA | ALA | A | 132 | 15.558 | −7.112 | 77.019 | 1.00 | 0.00 | xxxx | 1029 |
| ATOM | 1030 | C | ALA | A | 132 | 15.533 | −6.981 | 75.502 | 1.00 | 0.00 | xxxx | 1030 |
| ATOM | 1031 | O | ALA | A | 132 | 15.259 | −5.893 | 74.977 | 1.00 | 0.00 | xxxx | 1031 |
| ATOM | 1032 | CB | ALA | A | 132 | 16.920 | −6.693 | 77.571 | 1.00 | 0.00 | xxxx | 1032 |
| ATOM | 1033 | N | ASP | A | 133 | 15.820 | −8.070 | 74.788 | 1.00 | 0.00 | xxxx | 1033 |
| ATOM | 1034 | CA | ASP | A | 133 | 15.782 | −8.100 | 73.326 | 1.00 | 0.00 | xxxx | 1034 |
| ATOM | 1035 | C | ASP | A | 133 | 14.326 | −8.311 | 72.915 | 1.00 | 0.00 | xxxx | 1035 |
| ATOM | 1036 | O | ASP | A | 133 | 13.884 | −9.410 | 72.571 | 1.00 | 0.00 | xxxx | 1036 |
| ATOM | 1037 | CB | ASP | A | 133 | 16.710 | −9.194 | 72.816 | 1.00 | 0.00 | xxxx | 1037 |
| ATOM | 1038 | CG | ASP | A | 133 | 16.793 | −9.243 | 71.311 | 1.00 | 0.00 | xxxx | 1038 |
| ATOM | 1039 | OD1 | ASP | A | 133 | 16.448 | −8.238 | 70.665 | 1.00 | 0.00 | xxxx | 1039 |
| ATOM | 1040 | OD2 | ASP | A | 133 | 17.207 | −10.292 | 70.769 | 1.00 | 0.00 | xxxx | 1040 |
| ATOM | 1041 | N | LYS | A | 134 | 13.564 | −7.217 | 72.960 | 1.00 | 0.00 | xxxx | 1041 |
| ATOM | 1042 | CA | LYS | A | 134 | 12.112 | −7.327 | 72.850 | 1.00 | 0.00 | xxxx | 1042 |
| ATOM | 1043 | C | LYS | A | 134 | 11.679 | −7.919 | 71.514 | 1.00 | 0.00 | xxxx | 1043 |
| ATOM | 1044 | O | LYS | A | 134 | 10.719 | −8.697 | 71.460 | 1.00 | 0.00 | xxxx | 1044 |
| ATOM | 1045 | CB | LYS | A | 134 | 11.446 | −5.975 | 73.106 | 1.00 | 0.00 | xxxx | 1045 |
| ATOM | 1046 | CG | LYS | A | 134 | 11.290 | −5.645 | 74.582 | 1.00 | 0.00 | xxxx | 1046 |
| ATOM | 1047 | CD | LYS | A | 134 | 10.626 | −4.292 | 74.777 | 1.00 | 0.00 | xxxx | 1047 |
| ATOM | 1048 | CE | LYS | A | 134 | 11.499 | −3.172 | 74.246 | 1.00 | 0.00 | xxxx | 1048 |
| ATOM | 1049 | NZ | LYS | A | 134 | 10.924 | −1.840 | 74.594 | 1.00 | 0.00 | xxxx | 1049 |
| ATOM | 1050 | N | ASN | A | 135 | 12.370 | −7.572 | 70.428 | 1.00 | 0.00 | xxxx | 1050 |
| ATOM | 1051 | CA | ASN | A | 135 | 11.992 | −8.084 | 69.112 | 1.00 | 0.00 | xxxx | 1051 |
| ATOM | 1052 | C | ASN | A | 135 | 12.741 | −9.357 | 68.735 | 1.00 | 0.00 | xxxx | 1052 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1053 | O | ASN | A | 135 | 12.604 | −9.833 | 67.603 | 1.00 | 0.00 | xxxx | 1053 |
| ATOM | 1054 | CB | ASN | A | 135 | 12.122 | −7.014 | 68.020 | 1.00 | 0.00 | xxxx | 1054 |
| ATOM | 1055 | CG | ASN | A | 135 | 13.561 | −6.704 | 67.666 | 1.00 | 0.00 | xxxx | 1055 |
| ATOM | 1056 | OD1 | ASN | A | 135 | 14.467 | −6.947 | 68.452 | 1.00 | 0.00 | xxxx | 1056 |
| ATOM | 1057 | ND2 | ASN | A | 135 | 13.774 | −6.149 | 66.479 | 1.00 | 0.00 | xxxx | 1057 |
| ATOM | 1058 | N | HIS | A | 136 | 13.522 | −9.917 | 69.662 | 1.00 | 0.00 | xxxx | 1058 |
| ATOM | 1059 | CA | HIS | A | 136 | 14.134 | −11.237 | 69.512 | 1.00 | 0.00 | xxxx | 1059 |
| ATOM | 1060 | C | HIS | A | 136 | 15.038 | −11.338 | 68.285 | 1.00 | 0.00 | xxxx | 1060 |
| ATOM | 1061 | O | HIS | A | 136 | 15.151 | −12.405 | 67.677 | 1.00 | 0.00 | xxxx | 1061 |
| ATOM | 1062 | CB | HIS | A | 136 | 13.080 | −12.350 | 69.509 | 1.00 | 0.00 | xxxx | 1062 |
| ATOM | 1063 | CG | HIS | A | 136 | 12.084 | −12.240 | 70.621 | 1.00 | 0.00 | xxxx | 1063 |
| ATOM | 1064 | ND1 | HIS | A | 136 | 12.436 | −12.352 | 71.949 | 1.00 | 0.00 | xxxx | 1064 |
| ATOM | 1065 | CD2 | HIS | A | 136 | 10.746 | −12.032 | 70.602 | 1.00 | 0.00 | xxxx | 1065 |
| ATOM | 1066 | CE1 | HIS | A | 136 | 11.358 | −12.214 | 72.701 | 1.00 | 0.00 | xxxx | 1066 |
| ATOM | 1067 | NE2 | HIS | A | 136 | 10.319 | −12.020 | 71.908 | 1.00 | 0.00 | xxxx | 1067 |
| ATOM | 1068 | N | ASP | A | 137 | 15.700 | −10.243 | 67.908 | 1.00 | 0.00 | xxxx | 1068 |
| ATOM | 1069 | CA | ASP | A | 137 | 16.562 | −10.248 | 66.733 | 1.00 | 0.00 | xxxx | 1069 |
| ATOM | 1070 | C | ASP | A | 137 | 18.042 | −10.399 | 67.064 | 1.00 | 0.00 | xxxx | 1070 |
| ATOM | 1071 | O | ASP | A | 137 | 18.867 | −10.406 | 66.145 | 1.00 | 0.00 | xxxx | 1071 |
| ATOM | 1072 | CB | ASP | A | 137 | 16.307 | −9.015 | 65.842 | 1.00 | 0.00 | xxxx | 1072 |
| ATOM | 1073 | CG | ASP | A | 137 | 16.759 | −7.702 | 66.476 | 1.00 | 0.00 | xxxx | 1073 |
| ATOM | 1074 | OD1 | ASP | A | 137 | 17.124 | −7.680 | 67.671 | 1.00 | 0.00 | xxxx | 1074 |
| ATOM | 1075 | OD2 | ASP | A | 137 | 16.738 | −6.676 | 65.760 | 1.00 | 0.00 | xxxx | 1075 |
| ATOM | 1076 | N | GLY | A | 138 | 18.398 | −10.520 | 68.345 | 1.00 | 0.00 | xxxx | 1076 |
| ATOM | 1077 | CA | GLY | A | 138 | 19.792 | −10.644 | 68.720 | 1.00 | 0.00 | xxxx | 1077 |
| ATOM | 1078 | C | GLY | A | 138 | 20.591 | −9.366 | 68.624 | 1.00 | 0.00 | xxxx | 1078 |
| ATOM | 1079 | O | GLY | A | 138 | 21.826 | −9.417 | 68.631 | 1.00 | 0.00 | xxxx | 1079 |
| ATOM | 1080 | N | VAL | A | 139 | 19.923 | −8.221 | 68.520 | 1.00 | 0.00 | xxxx | 1080 |
| ATOM | 1081 | CA | VAL | A | 139 | 20.562 | −6.922 | 68.351 | 1.00 | 0.00 | xxxx | 1081 |
| ATOM | 1082 | C | VAL | A | 139 | 19.945 | −5.964 | 69.360 | 1.00 | 0.00 | xxxx | 1082 |
| ATOM | 1083 | O | VAL | A | 139 | 18.726 | −5.970 | 69.560 | 1.00 | 0.00 | xxxx | 1083 |
| ATOM | 1084 | CB | VAL | A | 139 | 20.342 | −6.386 | 66.917 | 1.00 | 0.00 | xxxx | 1084 |
| ATOM | 1085 | CG1 | VAL | A | 139 | 20.987 | −5.023 | 66.742 | 1.00 | 0.00 | xxxx | 1085 |
| ATOM | 1086 | CG2 | VAL | A | 139 | 20.877 | −7.353 | 65.882 | 1.00 | 0.00 | xxxx | 1086 |
| ATOM | 1087 | N | MET | A | 140 | 20.775 | −5.124 | 69.979 | 1.00 | 0.00 | xxxx | 1087 |
| ATOM | 1088 | CA | MET | A | 140 | 20.291 | −4.122 | 70.927 | 1.00 | 0.00 | xxxx | 1088 |
| ATOM | 1089 | C | MET | A | 140 | 19.945 | −2.835 | 70.175 | 1.00 | 0.00 | xxxx | 1089 |
| ATOM | 1090 | O | MET | A | 140 | 20.842 | −2.119 | 69.723 | 1.00 | 0.00 | xxxx | 1090 |
| ATOM | 1091 | CB | MET | A | 140 | 21.358 | −3.856 | 71.989 | 1.00 | 0.00 | xxxx | 1091 |
| ATOM | 1092 | CG | MET | A | 140 | 21.000 | −2.732 | 72.964 | 1.00 | 0.00 | xxxx | 1092 |
| ATOM | 1093 | SD | MET | A | 140 | 22.400 | −2.094 | 73.929 | 1.00 | 0.00 | xxxx | 1093 |
| ATOM | 1094 | CE | MET | A | 140 | 22.726 | −3.488 | 74.998 | 1.00 | 0.00 | xxxx | 1094 |
| ATOM | 1095 | N | GLN | A | 141 | 18.650 | −2.525 | 70.064 | 1.00 | 0.00 | xxxx | 1095 |
| ATOM | 1096 | CA | GLN | A | 141 | 18.204 | −1.251 | 69.491 | 1.00 | 0.00 | xxxx | 1096 |
| ATOM | 1097 | C | GLN | A | 141 | 18.274 | −0.171 | 70.563 | 1.00 | 0.00 | xxxx | 1097 |
| ATOM | 1098 | O | GLN | A | 141 | 17.623 | −0.295 | 71.606 | 1.00 | 0.00 | xxxx | 1098 |
| ATOM | 1099 | CB | GLN | A | 141 | 16.764 | −1.368 | 68.989 | 1.00 | 0.00 | xxxx | 1099 |
| ATOM | 1100 | CG | GLN | A | 141 | 16.604 | −1.910 | 67.573 | 1.00 | 0.00 | xxxx | 1100 |
| ATOM | 1101 | CD | GLN | A | 141 | 16.779 | −3.409 | 67.477 | 1.00 | 0.00 | xxxx | 1101 |
| ATOM | 1102 | OE1 | GLN | A | 141 | 16.319 | −4.156 | 68.337 | 1.00 | 0.00 | xxxx | 1102 |
| ATOM | 1103 | NE2 | GLN | A | 141 | 17.405 | −3.866 | 66.395 | 1.00 | 0.00 | xxxx | 1103 |
| ATOM | 1104 | N | TYR | A | 142 | 19.048 | 0.886 | 70.324 | 1.00 | 0.00 | xxxx | 1104 |
| ATOM | 1105 | CA | TYR | A | 142 | 19.253 | 1.886 | 71.361 | 1.00 | 0.00 | xxxx | 1105 |
| ATOM | 1106 | C | TYR | A | 142 | 19.068 | 3.293 | 70.811 | 1.00 | 0.00 | xxxx | 1106 |
| ATOM | 1107 | O | TYR | A | 142 | 19.085 | 3.532 | 69.599 | 1.00 | 0.00 | xxxx | 1107 |
| ATOM | 1108 | CB | TYR | A | 142 | 20.644 | 1.775 | 71.996 | 1.00 | 0.00 | xxxx | 1108 |
| ATOM | 1109 | CG | TYR | A | 142 | 21.784 | 2.201 | 71.095 | 1.00 | 0.00 | xxxx | 1109 |
| ATOM | 1110 | CD1 | TYR | A | 142 | 22.257 | 3.508 | 71.115 | 1.00 | 0.00 | xxxx | 1110 |
| ATOM | 1111 | CD2 | TYR | A | 142 | 22.402 | 1.298 | 70.239 | 1.00 | 0.00 | xxxx | 1111 |
| ATOM | 1112 | CE1 | TYR | A | 142 | 23.303 | 3.906 | 70.304 | 1.00 | 0.00 | xxxx | 1112 |
| ATOM | 1113 | CE2 | TYR | A | 142 | 23.450 | 1.681 | 69.428 | 1.00 | 0.00 | xxxx | 1113 |
| ATOM | 1114 | CZ | TYR | A | 142 | 23.894 | 2.990 | 69.456 | 1.00 | 0.00 | xxxx | 1114 |
| ATOM | 1115 | OH | TYR | A | 142 | 24.936 | 3.386 | 68.661 | 1.00 | 0.00 | xxxx | 1115 |
| ATOM | 1116 | N | VAL | A | 143 | 18.883 | 4.230 | 71.738 | 1.00 | 0.00 | xxxx | 1116 |
| ATOM | 1117 | CA | VAL | A | 143 | 18.962 | 5.652 | 71.435 | 1.00 | 0.00 | xxxx | 1117 |
| ATOM | 1118 | C | VAL | A | 143 | 20.031 | 6.273 | 72.337 | 1.00 | 0.00 | xxxx | 1118 |
| ATOM | 1119 | O | VAL | A | 143 | 20.359 | 5.757 | 73.414 | 1.00 | 0.00 | xxxx | 1119 |
| ATOM | 1120 | CB | VAL | A | 143 | 17.605 | 6.379 | 71.563 | 1.00 | 0.00 | xxxx | 1120 |
| ATOM | 1121 | CG1 | VAL | A | 143 | 16.575 | 5.795 | 70.582 | 1.00 | 0.00 | xxxx | 1121 |
| ATOM | 1122 | CG2 | VAL | A | 143 | 17.088 | 6.309 | 73.005 | 1.00 | 0.00 | xxxx | 1122 |
| ATOM | 1123 | N | MET | A | 144 | 20.561 | 7.412 | 71.891 | 1.00 | 0.00 | xxxx | 1123 |
| ATOM | 1124 | CA | MET | A | 144 | 21.693 | 8.058 | 72.540 | 1.00 | 0.00 | xxxx | 1124 |
| ATOM | 1125 | C | MET | A | 144 | 21.416 | 9.548 | 72.683 | 1.00 | 0.00 | xxxx | 1125 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1126 | O | MET | A | 144 | 21.234 | 10.247 | 71.675 | 1.00 | 0.00 | xxxx | 1126 |
| ATOM | 1127 | CB | MET | A | 144 | 22.955 | 7.829 | 71.701 | 1.00 | 0.00 | xxxx | 1127 |
| ATOM | 1128 | CG | MET | A | 144 | 24.158 | 8.670 | 72.136 | 1.00 | 0.00 | xxxx | 1128 |
| ATOM | 1129 | SD | MET | A | 144 | 24.866 | 8.211 | 73.720 | 1.00 | 0.00 | xxxx | 1129 |
| ATOM | 1130 | CE | MET | A | 144 | 25.631 | 6.652 | 73.300 | 1.00 | 0.00 | xxxx | 1130 |
| ATOM | 1131 | N | LEU | A | 145 | 21.407 | 10.030 | 73.924 | 1.00 | 0.00 | xxxx | 1131 |
| ATOM | 1132 | CA | LEU | A | 145 | 21.252 | 11.456 | 74.226 | 1.00 | 0.00 | xxxx | 1132 |
| ATOM | 1133 | C | LEU | A | 145 | 22.628 | 12.034 | 74.512 | 1.00 | 0.00 | xxxx | 1133 |
| ATOM | 1134 | O | LEU | A | 145 | 23.225 | 11.765 | 75.565 | 1.00 | 0.00 | xxxx | 1134 |
| ATOM | 1135 | CB | LEU | A | 145 | 20.324 | 11.660 | 75.424 | 1.00 | 0.00 | xxxx | 1135 |
| ATOM | 1136 | CG | LEU | A | 145 | 18.866 | 11.314 | 75.142 | 1.00 | 0.00 | xxxx | 1136 |
| ATOM | 1137 | CD1 | LEU | A | 145 | 18.133 | 10.928 | 76.428 | 1.00 | 0.00 | xxxx | 1137 |
| ATOM | 1138 | CD2 | LEU | A | 145 | 18.168 | 12.496 | 74.475 | 1.00 | 0.00 | xxxx | 1138 |
| ATOM | 1139 | N | MET | A | 146 | 23.136 | 12.811 | 73.570 | 1.00 | 0.00 | xxxx | 1139 |
| ATOM | 1140 | CA | MET | A | 146 | 24.437 | 13.437 | 73.707 | 1.00 | 0.00 | xxxx | 1140 |
| ATOM | 1141 | C | MET | A | 146 | 24.308 | 14.773 | 74.425 | 1.00 | 0.00 | xxxx | 1141 |
| ATOM | 1142 | O | MET | A | 146 | 23.244 | 15.412 | 74.435 | 1.00 | 0.00 | xxxx | 1142 |
| ATOM | 1143 | CB | MET | A | 146 | 25.059 | 13.655 | 72.327 | 1.00 | 0.00 | xxxx | 1143 |
| ATOM | 1144 | CG | MET | A | 146 | 25.250 | 12.362 | 71.514 | 1.00 | 0.00 | xxxx | 1144 |
| ATOM | 1145 | SD | MET | A | 146 | 26.103 | 12.630 | 69.952 | 1.00 | 0.00 | xxxx | 1145 |
| ATOM | 1146 | CE | MET | A | 146 | 24.844 | 13.565 | 69.077 | 1.00 | 0.00 | xxxx | 1146 |
| ATOM | 1147 | O | GLY | A | 147 | 24.826 | 17.862 | 73.869 | 1.00 | 0.00 | xxxx | 1147 |
| ATOM | 1148 | N | GLY | A | 147 | 25.415 | 15.202 | 75.022 | 1.00 | 0.00 | xxxx | 1148 |
| ATOM | 1149 | CA | GLY | A | 147 | 25.436 | 16.476 | 75.723 | 1.00 | 0.00 | xxxx | 1149 |
| ATOM | 1150 | C | GLY | A | 147 | 25.590 | 17.683 | 74.822 | 1.00 | 0.00 | xxxx | 1150 |
| ATOM | 1151 | N | GLU | A | 148 | 26.569 | 18.521 | 75.124 | 1.00 | 0.00 | xxxx | 1151 |
| ATOM | 1152 | CA | GLU | A | 148 | 26.830 | 19.738 | 74.364 | 1.00 | 0.00 | xxxx | 1152 |
| ATOM | 1153 | C | GLU | A | 148 | 27.800 | 19.435 | 73.230 | 1.00 | 0.00 | xxxx | 1153 |
| ATOM | 1154 | O | GLU | A | 148 | 28.843 | 18.813 | 73.472 | 1.00 | 0.00 | xxxx | 1154 |
| ATOM | 1155 | CB | GLU | A | 148 | 27.474 | 20.786 | 75.259 | 1.00 | 0.00 | xxxx | 1155 |
| ATOM | 1156 | CG | GLU | A | 148 | 26.577 | 21.408 | 76.319 | 1.00 | 0.00 | xxxx | 1156 |
| ATOM | 1157 | CD | GLU | A | 148 | 27.303 | 22.486 | 77.115 | 1.00 | 0.00 | xxxx | 1157 |
| ATOM | 1158 | OE1 | GLU | A | 148 | 28.551 | 22.430 | 77.195 | 1.00 | 0.00 | xxxx | 1158 |
| ATOM | 1159 | OE2 | GLU | A | 148 | 26.631 | 23.394 | 77.651 | 1.00 | 0.00 | xxxx | 1159 |
| ATOM | 1160 | N | PRO | A | 149 | 27.507 | 19.872 | 72.005 | 1.00 | 0.00 | xxxx | 1160 |
| ATOM | 1161 | CA | PRO | A | 149 | 28.435 | 19.633 | 70.884 | 1.00 | 0.00 | xxxx | 1161 |
| ATOM | 1162 | C | PRO | A | 149 | 29.837 | 20.134 | 71.206 | 1.00 | 0.00 | xxxx | 1162 |
| ATOM | 1163 | O | PRO | A | 149 | 30.029 | 21.262 | 71.667 | 1.00 | 0.00 | xxxx | 1163 |
| ATOM | 1164 | CB | PRO | A | 149 | 27.817 | 20.432 | 69.728 | 1.00 | 0.00 | xxxx | 1164 |
| ATOM | 1165 | CG | PRO | A | 149 | 26.358 | 20.518 | 70.061 | 1.00 | 0.00 | xxxx | 1165 |
| ATOM | 1166 | CD | PRO | A | 149 | 26.263 | 20.535 | 71.571 | 1.00 | 0.00 | xxxx | 1166 |
| ATOM | 1167 | N | GLY | A | 150 | 30.819 | 19.267 | 71.005 | 1.00 | 0.00 | xxxx | 1167 |
| ATOM | 1168 | CA | GLY | A | 150 | 32.191 | 19.679 | 71.219 | 1.00 | 0.00 | xxxx | 1168 |
| ATOM | 1169 | C | GLY | A | 150 | 32.672 | 19.657 | 72.657 | 1.00 | 0.00 | xxxx | 1169 |
| ATOM | 1170 | O | GLY | A | 150 | 33.853 | 19.917 | 72.892 | 1.00 | 0.00 | xxxx | 1170 |
| ATOM | 1171 | N | HIS | A | 151 | 31.811 | 19.374 | 73.627 | 1.00 | 0.00 | xxxx | 1171 |
| ATOM | 1172 | CA | HIS | A | 151 | 32.271 | 19.161 | 74.993 | 1.00 | 0.00 | xxxx | 1172 |
| ATOM | 1173 | C | HIS | A | 151 | 33.023 | 17.836 | 75.007 | 1.00 | 0.00 | xxxx | 1173 |
| ATOM | 1174 | O | HIS | A | 151 | 32.548 | 16.854 | 74.436 | 1.00 | 0.00 | xxxx | 1174 |
| ATOM | 1175 | CB | HIS | A | 151 | 31.026 | 19.066 | 75.879 | 1.00 | 0.00 | xxxx | 1175 |
| ATOM | 1176 | CG | HIS | A | 151 | 31.279 | 19.122 | 77.355 | 1.00 | 0.00 | xxxx | 1176 |
| ATOM | 1177 | ND1 | HIS | A | 151 | 32.075 | 18.215 | 78.024 | 1.00 | 0.00 | xxxx | 1177 |
| ATOM | 1178 | CD2 | HIS | A | 151 | 30.743 | 19.927 | 78.305 | 1.00 | 0.00 | xxxx | 1178 |
| ATOM | 1179 | CE1 | HIS | A | 151 | 32.060 | 18.497 | 79.320 | 1.00 | 0.00 | xxxx | 1179 |
| ATOM | 1180 | NE2 | HIS | A | 151 | 31.259 | 19.530 | 79.516 | 1.00 | 0.00 | xxxx | 1180 |
| ATOM | 1181 | N | GLN | A | 152 | 34.205 | 17.798 | 75.636 | 1.00 | 0.00 | xxxx | 1181 |
| ATOM | 1182 | CA | GLN | A | 152 | 34.984 | 16.565 | 75.564 | 1.00 | 0.00 | xxxx | 1182 |
| ATOM | 1183 | C | GLN | A | 152 | 34.239 | 15.390 | 76.189 | 1.00 | 0.00 | xxxx | 1183 |
| ATOM | 1184 | O | GLN | A | 152 | 34.395 | 14.242 | 75.743 | 1.00 | 0.00 | xxxx | 1184 |
| ATOM | 1185 | CB | GLN | A | 152 | 36.365 | 16.753 | 76.199 | 1.00 | 0.00 | xxxx | 1185 |
| ATOM | 1186 | CG | GLN | A | 152 | 36.399 | 16.645 | 77.736 | 1.00 | 0.00 | xxxx | 1186 |
| ATOM | 1187 | CD | GLN | A | 152 | 35.868 | 17.885 | 78.446 | 1.00 | 0.00 | xxxx | 1187 |
| ATOM | 1188 | OE1 | GLN | A | 152 | 35.823 | 18.983 | 77.878 | 1.00 | 0.00 | xxxx | 1188 |
| ATOM | 1189 | NE2 | GLN | A | 152 | 35.489 | 17.713 | 79.712 | 1.00 | 0.00 | xxxx | 1189 |
| ATOM | 1190 | N | ASP | A | 153 | 33.406 | 15.643 | 77.203 | 1.00 | 0.00 | xxxx | 1190 |
| ATOM | 1191 | CA | ASP | A | 153 | 32.689 | 14.532 | 77.822 | 1.00 | 0.00 | xxxx | 1191 |
| ATOM | 1192 | C | ASP | A | 153 | 31.615 | 13.986 | 76.890 | 1.00 | 0.00 | xxxx | 1192 |
| ATOM | 1193 | O | ASP | A | 153 | 31.383 | 12.771 | 76.853 | 1.00 | 0.00 | xxxx | 1193 |
| ATOM | 1194 | CB | ASP | A | 153 | 32.064 | 14.961 | 79.148 | 1.00 | 0.00 | xxxx | 1194 |
| ATOM | 1195 | CG | ASP | A | 153 | 33.095 | 15.277 | 80.215 | 1.00 | 0.00 | xxxx | 1195 |
| ATOM | 1196 | OD1 | ASP | A | 153 | 34.296 | 14.931 | 80.061 | 1.00 | 0.00 | xxxx | 1196 |
| ATOM | 1197 | OD2 | ASP | A | 153 | 32.701 | 15.876 | 81.232 | 1.00 | 0.00 | xxxx | 1197 |
| ATOM | 1198 | N | ALA | A | 154 | 30.964 | 14.862 | 76.115 | 1.00 | 0.00 | xxxx | 1198 |

-continued

| | | | | | | | | | | | | |
|---|---|---|---|---|---|---|---|---|---|---|---|---|
| CA, calcium<br>HOH, water<br>ACR, Acrylodan<br>K, potassium<br>EDO, ethylene glycol | | | | | | | | | | | | |
| ATOM | 1199 | CA | ALA | A | 154 | 29.979 | 14.370 | 75.161 | 1.00 | 0.00 | xxxx | 1199 |
| ATOM | 1200 | C | ALA | A | 154 | 30.644 | 13.545 | 74.074 | 1.00 | 0.00 | xxxx | 1200 |
| ATOM | 1201 | O | ALA | A | 154 | 30.166 | 12.455 | 73.733 | 1.00 | 0.00 | xxxx | 1201 |
| ATOM | 1202 | CB | ALA | A | 154 | 29.177 | 15.525 | 74.558 | 1.00 | 0.00 | xxxx | 1202 |
| ATOM | 1203 | N | ILE | A | 155 | 31.762 | 14.032 | 73.542 | 1.00 | 0.00 | xxxx | 1203 |
| ATOM | 1204 | CA | ILE | A | 155 | 32.466 | 13.305 | 72.491 | 1.00 | 0.00 | xxxx | 1204 |
| ATOM | 1205 | C | ILE | A | 155 | 32.849 | 11.911 | 72.974 | 1.00 | 0.00 | xxxx | 1205 |
| ATOM | 1206 | O | ILE | A | 155 | 32.526 | 10.898 | 72.339 | 1.00 | 0.00 | xxxx | 1206 |
| ATOM | 1207 | CB | ILE | A | 155 | 33.694 | 14.109 | 72.028 | 1.00 | 0.00 | xxxx | 1207 |
| ATOM | 1208 | CG1 | ILE | A | 155 | 33.273 | 15.433 | 71.375 | 1.00 | 0.00 | xxxx | 1208 |
| ATOM | 1209 | CG2 | ILE | A | 155 | 34.527 | 13.289 | 71.054 | 1.00 | 0.00 | xxxx | 1209 |
| ATOM | 1210 | CD1 | ILE | A | 155 | 34.421 | 16.397 | 71.165 | 1.00 | 0.00 | xxxx | 1210 |
| ATOM | 1211 | N | LEU | A | 156 | 33.498 | 11.835 | 74.134 | 1.00 | 0.00 | xxxx | 1211 |
| ATOM | 1212 | CA | LEU | A | 156 | 34.123 | 10.585 | 74.552 | 1.00 | 0.00 | xxxx | 1212 |
| ATOM | 1213 | C | LEU | A | 156 | 33.131 | 9.618 | 75.197 | 1.00 | 0.00 | xxxx | 1213 |
| ATOM | 1214 | O | LEU | A | 156 | 33.229 | 8.403 | 74.991 | 1.00 | 0.00 | xxxx | 1214 |
| ATOM | 1215 | CB | LEU | A | 156 | 35.308 | 10.892 | 75.465 | 1.00 | 0.00 | xxxx | 1215 |
| ATOM | 1216 | CG | LEU | A | 156 | 36.440 | 11.611 | 74.728 | 1.00 | 0.00 | xxxx | 1216 |
| ATOM | 1217 | CD1 | LEU | A | 156 | 37.439 | 12.150 | 75.743 | 1.00 | 0.00 | xxxx | 1217 |
| ATOM | 1218 | CD2 | LEU | A | 156 | 37.134 | 10.715 | 73.700 | 1.00 | 0.00 | xxxx | 1218 |
| ATOM | 1219 | N | ARG | A | 157 | 32.159 | 10.119 | 75.961 | 1.00 | 0.00 | xxxx | 1219 |
| ATOM | 1220 | CA | ARG | A | 157 | 31.169 | 9.206 | 76.539 | 1.00 | 0.00 | xxxx | 1220 |
| ATOM | 1221 | C | ARG | A | 157 | 30.329 | 8.554 | 75.453 | 1.00 | 0.00 | xxxx | 1221 |
| ATOM | 1222 | O | ARG | A | 157 | 29.998 | 7.367 | 75.547 | 1.00 | 0.00 | xxxx | 1222 |
| ATOM | 1223 | CB | ARG | A | 157 | 30.271 | 9.934 | 77.538 | 1.00 | 0.00 | xxxx | 1223 |
| ATOM | 1224 | CG | ARG | A | 157 | 30.988 | 10.314 | 78.814 | 1.00 | 0.00 | xxxx | 1224 |
| ATOM | 1225 | CD | ARG | A | 157 | 30.118 | 11.204 | 79.671 | 1.00 | 0.00 | xxxx | 1225 |
| ATOM | 1226 | NE | ARG | A | 157 | 30.846 | 11.651 | 80.851 | 1.00 | 0.00 | xxxx | 1226 |
| ATOM | 1227 | CZ | ARG | A | 157 | 30.435 | 12.638 | 81.635 | 1.00 | 0.00 | xxxx | 1227 |
| ATOM | 1228 | NH1 | ARG | A | 157 | 29.287 | 13.248 | 81.365 | 1.00 | 0.00 | xxxx | 1228 |
| ATOM | 1229 | NH2 | ARG | A | 157 | 31.153 | 13.017 | 82.682 | 1.00 | 0.00 | xxxx | 1229 |
| ATOM | 1230 | N | THR | A | 158 | 29.976 | 9.320 | 74.421 | 1.00 | 0.00 | xxxx | 1230 |
| ATOM | 1231 | CA | THR | A | 158 | 29.191 | 8.785 | 73.315 | 1.00 | 0.00 | xxxx | 1231 |
| ATOM | 1232 | C | THR | A | 158 | 29.959 | 7.686 | 72.595 | 1.00 | 0.00 | xxxx | 1232 |
| ATOM | 1233 | O | THR | A | 158 | 29.416 | 6.605 | 72.330 | 1.00 | 0.00 | xxxx | 1233 |
| ATOM | 1234 | CB | THR | A | 158 | 28.833 | 9.930 | 72.372 | 1.00 | 0.00 | xxxx | 1234 |
| ATOM | 1235 | OG1 | THR | A | 158 | 28.018 | 10.882 | 73.082 | 1.00 | 0.00 | xxxx | 1235 |
| ATOM | 1236 | CG2 | THR | A | 158 | 28.062 | 9.415 | 71.167 | 1.00 | 0.00 | xxxx | 1236 |
| ATOM | 1237 | N | GLN | A | 159 | 31.233 | 7.940 | 72.272 | 1.00 | 0.00 | xxxx | 1237 |
| ATOM | 1238 | CA | GLN | A | 159 | 32.036 | 6.955 | 71.558 | 1.00 | 0.00 | xxxx | 1238 |
| ATOM | 1239 | C | GLN | A | 159 | 32.249 | 5.703 | 72.401 | 1.00 | 0.00 | xxxx | 1239 |
| ATOM | 1240 | O | GLN | A | 159 | 31.998 | 4.580 | 71.945 | 1.00 | 0.00 | xxxx | 1240 |
| ATOM | 1241 | CB | GLN | A | 159 | 33.383 | 7.574 | 71.176 | 1.00 | 0.00 | xxxx | 1241 |
| ATOM | 1242 | CG | GLN | A | 159 | 34.323 | 6.608 | 70.470 | 1.00 | 0.00 | xxxx | 1242 |
| ATOM | 1243 | CD | GLN | A | 159 | 35.726 | 7.162 | 70.282 | 1.00 | 0.00 | xxxx | 1243 |
| ATOM | 1244 | OE1 | GLN | A | 159 | 36.606 | 6.481 | 69.755 | 1.00 | 0.00 | xxxx | 1244 |
| ATOM | 1245 | NE2 | GLN | A | 159 | 35.940 | 8.397 | 70.714 | 1.00 | 0.00 | xxxx | 1245 |
| ATOM | 1246 | N | TYR | A | 160 | 32.726 | 5.877 | 73.632 | 1.00 | 0.00 | xxxx | 1246 |
| ATOM | 1247 | CA | TYR | A | 160 | 33.216 | 4.739 | 74.401 | 1.00 | 0.00 | xxxx | 1247 |
| ATOM | 1248 | C | TYR | A | 160 | 32.105 | 3.875 | 74.979 | 1.00 | 0.00 | xxxx | 1248 |
| ATOM | 1249 | O | TYR | A | 160 | 32.308 | 2.669 | 75.158 | 1.00 | 0.00 | xxxx | 1249 |
| ATOM | 1250 | CB | TYR | A | 160 | 34.204 | 5.198 | 75.472 | 1.00 | 0.00 | xxxx | 1250 |
| ATOM | 1251 | CG | TYR | A | 160 | 35.601 | 5.391 | 74.914 | 1.00 | 0.00 | xxxx | 1251 |
| ATOM | 1252 | CD1 | TYR | A | 160 | 35.946 | 6.552 | 74.224 | 1.00 | 0.00 | xxxx | 1252 |
| ATOM | 1253 | CD2 | TYR | A | 160 | 36.569 | 4.399 | 75.043 | 1.00 | 0.00 | xxxx | 1253 |
| ATOM | 1254 | CE1 | TYR | A | 160 | 37.221 | 6.732 | 73.701 | 1.00 | 0.00 | xxxx | 1254 |
| ATOM | 1255 | CE2 | TYR | A | 160 | 37.844 | 4.572 | 74.517 | 1.00 | 0.00 | xxxx | 1255 |
| ATOM | 1256 | CZ | TYR | A | 160 | 38.156 | 5.739 | 73.849 | 1.00 | 0.00 | xxxx | 1256 |
| ATOM | 1257 | OH | TYR | A | 160 | 39.427 | 5.902 | 73.335 | 1.00 | 0.00 | xxxx | 1257 |
| ATOM | 1258 | N | SER | A | 161 | 30.942 | 4.453 | 75.289 | 1.00 | 0.00 | xxxx | 1258 |
| ATOM | 1259 | CA | SER | A | 161 | 29.842 | 3.626 | 75.783 | 1.00 | 0.00 | xxxx | 1259 |
| ATOM | 1260 | C | SER | A | 161 | 29.450 | 2.579 | 74.750 | 1.00 | 0.00 | xxxx | 1260 |
| ATOM | 1261 | O | SER | A | 161 | 29.409 | 1.380 | 75.045 | 1.00 | 0.00 | xxxx | 1261 |
| ATOM | 1262 | CB | SER | A | 161 | 28.635 | 4.486 | 76.172 | 1.00 | 0.00 | xxxx | 1262 |
| ATOM | 1263 | OG | SER | A | 161 | 28.180 | 5.293 | 75.088 | 1.00 | 0.00 | xxxx | 1263 |
| ATOM | 1264 | N | ILE | A | 162 | 29.211 | 3.013 | 73.512 | 1.00 | 0.00 | xxxx | 1264 |
| ATOM | 1265 | CA | ILE | A | 162 | 28.751 | 2.089 | 72.486 | 1.00 | 0.00 | xxxx | 1265 |
| ATOM | 1266 | C | ILE | A | 162 | 29.858 | 1.119 | 72.084 | 1.00 | 0.00 | xxxx | 1266 |
| ATOM | 1267 | O | ILE | A | 162 | 29.612 | −0.081 | 71.896 | 1.00 | 0.00 | xxxx | 1267 |
| ATOM | 1268 | CB | ILE | A | 162 | 28.164 | 2.856 | 71.291 | 1.00 | 0.00 | xxxx | 1268 |
| ATOM | 1269 | CG1 | ILE | A | 162 | 26.955 | 3.692 | 71.732 | 1.00 | 0.00 | xxxx | 1269 |
| ATOM | 1270 | CG2 | ILE | A | 162 | 27.772 | 1.878 | 70.193 | 1.00 | 0.00 | xxxx | 1270 |
| ATOM | 1271 | CD1 | ILE | A | 162 | 25.902 | 2.898 | 72.512 | 1.00 | 0.00 | xxxx | 1271 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1272 | N | GLN | A | 163 | 31.097 | 1.609 | 71.946 | 1.00 | 0.00 | xxxx | 1272 |
| ATOM | 1273 | CA | GLN | A | 163 | 32.182 | 0.701 | 71.592 | 1.00 | 0.00 | xxxx | 1273 |
| ATOM | 1274 | C | GLN | A | 163 | 32.360 | −0.382 | 72.651 | 1.00 | 0.00 | xxxx | 1274 |
| ATOM | 1275 | O | GLN | A | 163 | 32.675 | −1.531 | 72.318 | 1.00 | 0.00 | xxxx | 1275 |
| ATOM | 1276 | CB | GLN | A | 163 | 33.485 | 1.469 | 71.379 | 1.00 | 0.00 | xxxx | 1276 |
| ATOM | 1277 | CG | GLN | A | 163 | 34.589 | 0.592 | 70.798 | 1.00 | 0.00 | xxxx | 1277 |
| ATOM | 1278 | CD | GLN | A | 163 | 34.210 | 0.021 | 69.443 | 1.00 | 0.00 | xxxx | 1278 |
| ATOM | 1279 | OE1 | GLN | A | 163 | 33.819 | 0.760 | 68.534 | 1.00 | 0.00 | xxxx | 1279 |
| ATOM | 1280 | NE2 | GLN | A | 163 | 34.325 | −1.297 | 69.299 | 1.00 | 0.00 | xxxx | 1280 |
| ATOM | 1281 | N | THR | A | 164 | 32.138 | −0.042 | 73.924 | 1.00 | 0.00 | xxxx | 1281 |
| ATOM | 1282 | CA | THR | A | 164 | 32.266 | −1.035 | 74.989 | 1.00 | 0.00 | xxxx | 1282 |
| ATOM | 1283 | C | THR | A | 164 | 31.188 | −2.114 | 74.887 | 1.00 | 0.00 | xxxx | 1283 |
| ATOM | 1284 | O | THR | A | 164 | 31.462 | −3.298 | 75.115 | 1.00 | 0.00 | xxxx | 1284 |
| ATOM | 1285 | CB | THR | A | 164 | 32.231 | −0.326 | 76.339 | 1.00 | 0.00 | xxxx | 1285 |
| ATOM | 1286 | OG1 | THR | A | 164 | 33.385 | 0.516 | 76.443 | 1.00 | 0.00 | xxxx | 1286 |
| ATOM | 1287 | CG2 | THR | A | 164 | 32.192 | −1.322 | 77.498 | 1.00 | 0.00 | xxxx | 1287 |
| ATOM | 1288 | N | VAL | A | 165 | 29.962 | −1.726 | 74.523 | 1.00 | 0.00 | xxxx | 1288 |
| ATOM | 1289 | CA | VAL | A | 165 | 28.908 | −2.715 | 74.291 | 1.00 | 0.00 | xxxx | 1289 |
| ATOM | 1290 | C | VAL | A | 165 | 29.292 | −3.652 | 73.148 | 1.00 | 0.00 | xxxx | 1290 |
| ATOM | 1291 | O | VAL | A | 165 | 29.170 | −4.881 | 73.256 | 1.00 | 0.00 | xxxx | 1291 |
| ATOM | 1292 | CB | VAL | A | 165 | 27.558 | −2.016 | 74.045 | 1.00 | 0.00 | xxxx | 1292 |
| ATOM | 1293 | CG1 | VAL | A | 165 | 26.507 | −3.043 | 73.702 | 1.00 | 0.00 | xxxx | 1293 |
| ATOM | 1294 | CG2 | VAL | A | 165 | 27.136 | −1.217 | 75.278 | 1.00 | 0.00 | xxxx | 1294 |
| ATOM | 1295 | N | LYS | A | 166 | 29.769 | −3.081 | 72.031 | 1.00 | 0.00 | xxxx | 1295 |
| ATOM | 1296 | CA | LYS | A | 166 | 30.209 | −3.908 | 70.910 | 1.00 | 0.00 | xxxx | 1296 |
| ATOM | 1297 | C | LYS | A | 166 | 31.347 | −4.835 | 71.321 | 1.00 | 0.00 | xxxx | 1297 |
| ATOM | 1298 | O | LYS | A | 166 | 31.358 | −6.019 | 70.956 | 1.00 | 0.00 | xxxx | 1298 |
| ATOM | 1299 | CB | LYS | A | 166 | 30.642 | −3.042 | 69.724 | 1.00 | 0.00 | xxxx | 1299 |
| ATOM | 1300 | CG | LYS | A | 166 | 29.518 | −2.242 | 69.057 | 1.00 | 0.00 | xxxx | 1300 |
| ATOM | 1301 | CD | LYS | A | 166 | 30.103 | −1.408 | 67.921 | 1.00 | 0.00 | xxxx | 1301 |
| ATOM | 1302 | CE | LYS | A | 166 | 29.086 | −0.449 | 67.330 | 1.00 | 0.00 | xxxx | 1302 |
| ATOM | 1303 | NZ | LYS | A | 166 | 29.719 | 0.434 | 66.305 | 1.00 | 0.00 | xxxx | 1303 |
| ATOM | 1304 | N | ASP | A | 167 | 32.314 | −4.317 | 72.091 | 1.00 | 0.00 | xxxx | 1304 |
| ATOM | 1305 | CA | ASP | A | 167 | 33.450 | −5.133 | 72.516 | 1.00 | 0.00 | xxxx | 1305 |
| ATOM | 1306 | C | ASP | A | 167 | 33.025 | −6.249 | 73.457 | 1.00 | 0.00 | xxxx | 1306 |
| ATOM | 1307 | O | ASP | A | 167 | 33.751 | −7.243 | 73.593 | 1.00 | 0.00 | xxxx | 1307 |
| ATOM | 1308 | CB | ASP | A | 167 | 34.501 | −4.266 | 73.205 | 1.00 | 0.00 | xxxx | 1308 |
| ATOM | 1309 | CG | ASP | A | 167 | 35.185 | −3.296 | 72.251 | 1.00 | 0.00 | xxxx | 1309 |
| ATOM | 1310 | OD1 | ASP | A | 167 | 35.057 | −3.472 | 71.021 | 1.00 | 0.00 | xxxx | 1310 |
| ATOM | 1311 | OD2 | ASP | A | 167 | 35.853 | −2.359 | 72.741 | 1.00 | 0.00 | xxxx | 1311 |
| ATOM | 1312 | N | ALA | A | 168 | 31.877 | −6.097 | 74.113 | 1.00 | 0.00 | xxxx | 1312 |
| ATOM | 1313 | CA | ALA | A | 168 | 31.300 | −7.137 | 74.956 | 1.00 | 0.00 | xxxx | 1313 |
| ATOM | 1314 | C | ALA | A | 168 | 30.633 | −8.245 | 74.151 | 1.00 | 0.00 | xxxx | 1314 |
| ATOM | 1315 | O | ALA | A | 168 | 30.095 | −9.183 | 74.748 | 1.00 | 0.00 | xxxx | 1315 |
| ATOM | 1316 | CB | ALA | A | 168 | 30.296 | −6.524 | 75.940 | 1.00 | 0.00 | xxxx | 1316 |
| ATOM | 1317 | N | GLY | A | 169 | 30.670 | −8.168 | 72.823 | 1.00 | 0.00 | xxxx | 1317 |
| ATOM | 1318 | CA | GLY | A | 169 | 30.091 | −9.188 | 71.970 | 1.00 | 0.00 | xxxx | 1318 |
| ATOM | 1319 | C | GLY | A | 169 | 28.645 | −8.970 | 71.596 | 1.00 | 0.00 | xxxx | 1319 |
| ATOM | 1320 | O | GLY | A | 169 | 28.017 | −9.884 | 71.050 | 1.00 | 0.00 | xxxx | 1320 |
| ATOM | 1321 | N | ILE | A | 170 | 28.099 | −7.792 | 71.854 | 1.00 | 0.00 | xxxx | 1321 |
| ATOM | 1322 | CA | ILE | A | 170 | 26.694 | −7.506 | 71.609 | 1.00 | 0.00 | xxxx | 1322 |
| ATOM | 1323 | C | ILE | A | 170 | 26.583 | −6.703 | 70.322 | 1.00 | 0.00 | xxxx | 1323 |
| ATOM | 1324 | O | ILE | A | 170 | 27.296 | −5.707 | 70.139 | 1.00 | 0.00 | xxxx | 1324 |
| ATOM | 1325 | CB | ILE | A | 170 | 26.093 | −6.735 | 72.795 | 1.00 | 0.00 | xxxx | 1325 |
| ATOM | 1326 | CG1 | ILE | A | 170 | 26.183 | −7.579 | 74.066 | 1.00 | 0.00 | xxxx | 1326 |
| ATOM | 1327 | CG2 | ILE | A | 170 | 24.659 | −6.295 | 72.475 | 1.00 | 0.00 | xxxx | 1327 |
| ATOM | 1328 | CD1 | ILE | A | 170 | 26.067 | −6.777 | 75.344 | 1.00 | 0.00 | xxxx | 1328 |
| ATOM | 1329 | N | LYS | A | 171 | 25.697 | −7.136 | 69.425 | 1.00 | 0.00 | xxxx | 1329 |
| ATOM | 1330 | CA | LYS | A | 171 | 25.391 | −6.374 | 68.220 | 1.00 | 0.00 | xxxx | 1330 |
| ATOM | 1331 | C | LYS | A | 171 | 24.407 | −5.264 | 68.570 | 1.00 | 0.00 | xxxx | 1331 |
| ATOM | 1332 | O | LYS | A | 171 | 23.503 | −5.464 | 69.384 | 1.00 | 0.00 | xxxx | 1332 |
| ATOM | 1333 | CB | LYS | A | 171 | 24.764 | −7.289 | 67.167 | 1.00 | 0.00 | xxxx | 1333 |
| ATOM | 1334 | CG | LYS | A | 171 | 25.686 | −8.416 | 66.699 | 1.00 | 0.00 | xxxx | 1334 |
| ATOM | 1335 | CD | LYS | A | 171 | 24.971 | −9.366 | 65.729 | 1.00 | 0.00 | xxxx | 1335 |
| ATOM | 1336 | CE | LYS | A | 171 | 25.825 | −10.588 | 65.435 | 1.00 | 0.00 | xxxx | 1336 |
| ATOM | 1337 | NZ | LYS | A | 171 | 25.031 | −11.698 | 64.837 | 1.00 | 0.00 | xxxx | 1337 |
| ATOM | 1338 | N | VAL | A | 172 | 24.593 | −4.083 | 67.966 | 1.00 | 0.00 | xxxx | 1338 |
| ATOM | 1339 | CA | VAL | A | 172 | 23.787 | −2.912 | 68.297 | 1.00 | 0.00 | xxxx | 1339 |
| ATOM | 1340 | C | VAL | A | 172 | 23.218 | −2.271 | 67.036 | 1.00 | 0.00 | xxxx | 1340 |
| ATOM | 1341 | O | VAL | A | 172 | 23.733 | −2.440 | 65.927 | 1.00 | 0.00 | xxxx | 1341 |
| ATOM | 1342 | CB | VAL | A | 172 | 24.574 | −1.866 | 69.114 | 1.00 | 0.00 | xxxx | 1342 |
| ATOM | 1343 | CG1 | VAL | A | 172 | 25.130 | −2.494 | 70.391 | 1.00 | 0.00 | xxxx | 1343 |
| ATOM | 1344 | CG2 | VAL | A | 172 | 25.686 | −1.255 | 68.279 | 1.00 | 0.00 | xxxx | 1344 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1345 | N | GLN | A | 173 | 22.145 | −1.498 | 67.226 | 1.00 | 0.00 | xxxx | 1345 |
| ATOM | 1346 | CA | GLN | A | 173 | 21.547 | −0.710 | 66.155 | 1.00 | 0.00 | xxxx | 1346 |
| ATOM | 1347 | C | GLN | A | 173 | 21.113 | 0.620 | 66.741 | 1.00 | 0.00 | xxxx | 1347 |
| ATOM | 1348 | O | GLN | A | 173 | 20.268 | 0.654 | 67.635 | 1.00 | 0.00 | xxxx | 1348 |
| ATOM | 1349 | CB | GLN | A | 173 | 20.343 | −1.417 | 65.536 | 1.00 | 0.00 | xxxx | 1349 |
| ATOM | 1350 | CG | GLN | A | 173 | 19.716 | −0.603 | 64.411 | 1.00 | 0.00 | xxxx | 1350 |
| ATOM | 1351 | CD | GLN | A | 173 | 18.550 | −1.322 | 63.755 | 1.00 | 0.00 | xxxx | 1351 |
| ATOM | 1352 | OE1 | GLN | A | 173 | 17.694 | −1.888 | 64.437 | 1.00 | 0.00 | xxxx | 1352 |
| ATOM | 1353 | NE2 | GLN | A | 173 | 18.504 | −1.298 | 62.422 | 1.00 | 0.00 | xxxx | 1353 |
| ATOM | 1354 | N | GLU | A | 174 | 21.667 | 1.708 | 66.216 | 1.00 | 0.00 | xxxx | 1354 |
| ATOM | 1355 | CA | GLU | A | 174 | 21.374 | 3.052 | 66.698 | 1.00 | 0.00 | xxxx | 1355 |
| ATOM | 1356 | C | GLU | A | 174 | 20.115 | 3.563 | 66.003 | 1.00 | 0.00 | xxxx | 1356 |
| ATOM | 1357 | O | GLU | A | 174 | 20.152 | 3.932 | 64.825 | 1.00 | 0.00 | xxxx | 1357 |
| ATOM | 1358 | CB | GLU | A | 174 | 22.555 | 3.952 | 66.369 | 1.00 | 0.00 | xxxx | 1358 |
| ATOM | 1359 | CG | GLU | A | 174 | 22.459 | 5.336 | 66.957 | 1.00 | 0.00 | xxxx | 1359 |
| ATOM | 1360 | CD | GLU | A | 174 | 23.746 | 6.107 | 66.755 | 1.00 | 0.00 | xxxx | 1360 |
| ATOM | 1361 | OE1 | GLU | A | 174 | 23.782 | 6.964 | 65.861 | 1.00 | 0.00 | xxxx | 1361 |
| ATOM | 1362 | OE2 | GLU | A | 174 | 24.724 | 5.832 | 67.487 | 1.00 | 0.00 | xxxx | 1362 |
| ATOM | 1363 | N | LEU | A | 175 | 19.000 | 3.589 | 66.736 | 1.00 | 0.00 | xxxx | 1363 |
| ATOM | 1364 | CA | LEU | A | 175 | 17.750 | 4.086 | 66.168 | 1.00 | 0.00 | xxxx | 1364 |
| ATOM | 1365 | C | LEU | A | 175 | 17.743 | 5.599 | 66.073 | 1.00 | 0.00 | xxxx | 1365 |
| ATOM | 1366 | O | LEU | A | 175 | 17.143 | 6.155 | 65.145 | 1.00 | 0.00 | xxxx | 1366 |
| ATOM | 1367 | CB | LEU | A | 175 | 16.565 | 3.645 | 67.029 | 1.00 | 0.00 | xxxx | 1367 |
| ATOM | 1368 | CG | LEU | A | 175 | 16.264 | 2.145 | 67.095 | 1.00 | 0.00 | xxxx | 1368 |
| ATOM | 1369 | CD1 | LEU | A | 175 | 15.106 | 1.900 | 68.076 | 1.00 | 0.00 | xxxx | 1369 |
| ATOM | 1370 | CD2 | LEU | A | 175 | 15.921 | 1.605 | 65.723 | 1.00 | 0.00 | xxxx | 1370 |
| ATOM | 1371 | N | ALA | A | 176 | 18.385 | 6.272 | 67.022 | 1.00 | 0.00 | xxxx | 1371 |
| ATOM | 1372 | CA | ALA | A | 176 | 18.405 | 7.726 | 67.039 | 1.00 | 0.00 | xxxx | 1372 |
| ATOM | 1373 | C | ALA | A | 176 | 19.520 | 8.206 | 67.955 | 1.00 | 0.00 | xxxx | 1373 |
| ATOM | 1374 | O | ALA | A | 176 | 19.854 | 7.567 | 68.956 | 1.00 | 0.00 | xxxx | 1374 |
| ATOM | 1375 | CB | ALA | A | 176 | 17.061 | 8.289 | 67.522 | 1.00 | 0.00 | xxxx | 1375 |
| ATOM | 1376 | N | LYS | A | 177 | 20.073 | 9.361 | 67.610 | 1.00 | 0.00 | xxxx | 1376 |
| ATOM | 1377 | CA | LYS | A | 177 | 21.068 | 10.012 | 68.447 | 1.00 | 0.00 | xxxx | 1377 |
| ATOM | 1378 | C | LYS | A | 177 | 20.969 | 11.508 | 68.191 | 1.00 | 0.00 | xxxx | 1378 |
| ATOM | 1379 | O | LYS | A | 177 | 20.868 | 11.934 | 67.036 | 1.00 | 0.00 | xxxx | 1379 |
| ATOM | 1380 | CB | LYS | A | 177 | 22.451 | 9.486 | 68.063 | 1.00 | 0.00 | xxxx | 1380 |
| ATOM | 1381 | CG | LYS | A | 177 | 23.620 | 10.280 | 68.569 | 1.00 | 0.00 | xxxx | 1381 |
| ATOM | 1382 | CD | LYS | A | 177 | 24.936 | 9.671 | 68.080 | 1.00 | 0.00 | xxxx | 1382 |
| ATOM | 1383 | CE | LYS | A | 177 | 25.116 | 9.859 | 66.580 | 1.00 | 0.00 | xxxx | 1383 |
| ATOM | 1384 | NZ | LYS | A | 177 | 26.421 | 9.325 | 66.103 | 1.00 | 0.00 | xxxx | 1384 |
| ATOM | 1385 | N | ASP | A | 178 | 20.972 | 12.305 | 69.256 | 1.00 | 0.00 | xxxx | 1385 |
| ATOM | 1386 | CA | ASP | A | 178 | 20.891 | 13.751 | 69.083 | 1.00 | 0.00 | xxxx | 1386 |
| ATOM | 1387 | C | ASP | A | 178 | 21.464 | 14.426 | 70.321 | 1.00 | 0.00 | xxxx | 1387 |
| ATOM | 1388 | O | ASP | A | 178 | 21.598 | 13.806 | 71.386 | 1.00 | 0.00 | xxxx | 1388 |
| ATOM | 1389 | CB | ASP | A | 178 | 19.438 | 14.192 | 68.859 | 1.00 | 0.00 | xxxx | 1389 |
| ATOM | 1390 | CG | ASP | A | 178 | 19.325 | 15.526 | 68.130 | 1.00 | 0.00 | xxxx | 1390 |
| ATOM | 1391 | OD1 | ASP | A | 178 | 20.358 | 16.190 | 67.860 | 1.00 | 0.00 | xxxx | 1391 |
| ATOM | 1392 | OD2 | ASP | A | 178 | 18.171 | 15.921 | 67.840 | 1.00 | 0.00 | xxxx | 1392 |
| ATOM | 1393 | N | TYR | A | 179 | 21.795 | 15.709 | 70.170 | 1.00 | 0.00 | xxxx | 1393 |
| ATOM | 1394 | CA | TYR | A | 179 | 22.231 | 16.525 | 71.294 | 1.00 | 0.00 | xxxx | 1394 |
| ATOM | 1395 | C | TYR | A | 179 | 21.036 | 17.016 | 72.102 | 1.00 | 0.00 | xxxx | 1395 |
| ATOM | 1396 | O | TYR | A | 179 | 20.065 | 17.544 | 71.543 | 1.00 | 0.00 | xxxx | 1396 |
| ATOM | 1397 | CB | TYR | A | 179 | 22.997 | 17.731 | 70.768 | 1.00 | 0.00 | xxxx | 1397 |
| ATOM | 1398 | CG | TYR | A | 179 | 24.266 | 17.368 | 70.052 | 1.00 | 0.00 | xxxx | 1398 |
| ATOM | 1399 | CD1 | TYR | A | 179 | 25.388 | 16.951 | 70.763 | 1.00 | 0.00 | xxxx | 1399 |
| ATOM | 1400 | CD2 | TYR | A | 179 | 24.364 | 17.476 | 68.668 | 1.00 | 0.00 | xxxx | 1400 |
| ATOM | 1401 | CE1 | TYR | A | 179 | 26.562 | 16.628 | 70.123 | 1.00 | 0.00 | xxxx | 1401 |
| ATOM | 1402 | CE2 | TYR | A | 179 | 25.540 | 17.153 | 68.015 | 1.00 | 0.00 | xxxx | 1402 |
| ATOM | 1403 | CZ | TYR | A | 179 | 26.634 | 16.732 | 68.753 | 1.00 | 0.00 | xxxx | 1403 |
| ATOM | 1404 | OH | TYR | A | 179 | 27.818 | 16.416 | 68.129 | 1.00 | 0.00 | xxxx | 1404 |
| ATOM | 1405 | N | ALA | A | 180 | 21.129 | 16.886 | 73.425 | 1.00 | 0.00 | xxxx | 1405 |
| ATOM | 1406 | CA | ALA | A | 180 | 20.161 | 17.491 | 74.341 | 1.00 | 0.00 | xxxx | 1406 |
| ATOM | 1407 | C | ALA | A | 180 | 20.827 | 18.427 | 75.349 | 1.00 | 0.00 | xxxx | 1407 |
| ATOM | 1408 | O | ALA | A | 180 | 20.185 | 18.846 | 76.324 | 1.00 | 0.00 | xxxx | 1408 |
| ATOM | 1409 | CB | ALA | A | 180 | 19.282 | 16.432 | 75.019 | 1.00 | 0.00 | xxxx | 1409 |
| ATOM | 1410 | N | ASN | A | 181 | 22.103 | 18.760 | 75.148 | 1.00 | 0.00 | xxxx | 1410 |
| ATOM | 1411 | CA | ASN | A | 181 | 22.741 | 19.891 | 75.828 | 1.00 | 0.00 | xxxx | 1411 |
| ATOM | 1412 | C | ASN | A | 181 | 22.737 | 19.750 | 77.348 | 1.00 | 0.00 | xxxx | 1412 |
| ATOM | 1413 | O | ASN | A | 181 | 22.585 | 20.733 | 78.075 | 1.00 | 0.00 | xxxx | 1413 |
| ATOM | 1414 | CB | ASN | A | 181 | 22.109 | 21.218 | 75.410 | 1.00 | 0.00 | xxxx | 1414 |
| ATOM | 1415 | CG | ASN | A | 181 | 22.101 | 21.407 | 73.914 | 1.00 | 0.00 | xxxx | 1415 |
| ATOM | 1416 | OD1 | ASN | A | 181 | 23.098 | 21.152 | 73.242 | 1.00 | 0.00 | xxxx | 1416 |
| ATOM | 1417 | ND2 | ASN | A | 181 | 20.967 | 21.841 | 73.379 | 1.00 | 0.00 | xxxx | 1417 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1418 | N | CYS | A | 182 | 22.892 | 18.522 | 77.836 | 1.00 | 0.00 | xxxx | 1418 |
| ATOM | 1419 | CA | CYS | A | 182 | 23.033 | 18.226 | 79.262 | 1.00 | 0.00 | xxxx | 1419 |
| ATOM | 1420 | C | CYS | A | 182 | 21.808 | 18.592 | 80.072 | 1.00 | 0.00 | xxxx | 1420 |
| ATOM | 1421 | O | CYS | A | 182 | 21.891 | 18.631 | 81.308 | 1.00 | 0.00 | xxxx | 1421 |
| ATOM | 1422 | CB | CYS | A | 182 | 24.251 | 18.909 | 79.885 | 1.00 | 0.00 | xxxx | 1422 |
| ATOM | 1423 | SG | CYS | A | 182 | 25.697 | 18.733 | 78.864 | 1.00 | 0.00 | xxxx | 1423 |
| ATOM | 1424 | N | ASP | A | 183 | 20.679 | 18.850 | 79.417 | 1.00 | 0.00 | xxxx | 1424 |
| ATOM | 1425 | CA | ASP | A | 183 | 19.525 | 19.500 | 80.025 | 1.00 | 0.00 | xxxx | 1425 |
| ATOM | 1426 | C | ASP | A | 183 | 18.357 | 18.525 | 80.123 | 1.00 | 0.00 | xxxx | 1426 |
| ATOM | 1427 | O | ASP | A | 183 | 18.018 | 17.854 | 79.145 | 1.00 | 0.00 | xxxx | 1427 |
| ATOM | 1428 | CB | ASP | A | 183 | 19.134 | 20.721 | 79.186 | 1.00 | 0.00 | xxxx | 1428 |
| ATOM | 1429 | CG | ASP | A | 183 | 17.898 | 21.418 | 79.700 | 1.00 | 0.00 | xxxx | 1429 |
| ATOM | 1430 | OD1 | ASP | A | 183 | 17.964 | 22.029 | 80.787 | 1.00 | 0.00 | xxxx | 1430 |
| ATOM | 1431 | OD2 | ASP | A | 183 | 16.865 | 21.371 | 79.002 | 1.00 | 0.00 | xxxx | 1431 |
| ATOM | 1432 | N | ARG | A | 184 | 17.722 | 18.489 | 81.299 | 1.00 | 0.00 | xxxx | 1432 |
| ATOM | 1433 | CA | ARG | A | 184 | 16.621 | 17.559 | 81.545 | 1.00 | 0.00 | xxxx | 1433 |
| ATOM | 1434 | C | ARG | A | 184 | 15.435 | 17.809 | 80.611 | 1.00 | 0.00 | xxxx | 1434 |
| ATOM | 1435 | O | ARG | A | 184 | 14.903 | 16.872 | 80.007 | 1.00 | 0.00 | xxxx | 1435 |
| ATOM | 1436 | CB | ARG | A | 184 | 16.204 | 17.645 | 83.015 | 1.00 | 0.00 | xxxx | 1436 |
| ATOM | 1437 | CG | ARG | A | 184 | 15.048 | 16.728 | 83.405 | 1.00 | 0.00 | xxxx | 1437 |
| ATOM | 1438 | CD | ARG | A | 184 | 14.741 | 16.814 | 84.892 | 1.00 | 0.00 | xxxx | 1438 |
| ATOM | 1439 | NE | ARG | A | 184 | 14.478 | 18.190 | 85.306 | 1.00 | 0.00 | xxxx | 1439 |
| ATOM | 1440 | CZ | ARG | A | 184 | 13.315 | 18.812 | 85.142 | 1.00 | 0.00 | xxxx | 1440 |
| ATOM | 1441 | NH1 | ARG | A | 184 | 12.298 | 18.184 | 84.566 | 1.00 | 0.00 | xxxx | 1441 |
| ATOM | 1442 | NH2 | ARG | A | 184 | 13.168 | 20.067 | 85.551 | 1.00 | 0.00 | xxxx | 1442 |
| ATOM | 1443 | N | VAL | A | 185 | 15.000 | 19.066 | 80.470 | 1.00 | 0.00 | xxxx | 1443 |
| ATOM | 1444 | CA | VAL | A | 185 | 13.800 | 19.336 | 79.668 | 1.00 | 0.00 | xxxx | 1444 |
| ATOM | 1445 | C | VAL | A | 185 | 14.028 | 19.039 | 78.183 | 1.00 | 0.00 | xxxx | 1445 |
| ATOM | 1446 | O | VAL | A | 185 | 13.175 | 18.443 | 77.516 | 1.00 | 0.00 | xxxx | 1446 |
| ATOM | 1447 | CB | VAL | A | 185 | 13.286 | 20.764 | 79.905 | 1.00 | 0.00 | xxxx | 1447 |
| ATOM | 1448 | CG1 | VAL | A | 185 | 12.201 | 21.110 | 78.884 | 1.00 | 0.00 | xxxx | 1448 |
| ATOM | 1449 | CG2 | VAL | A | 185 | 12.752 | 20.892 | 81.327 | 1.00 | 0.00 | xxxx | 1449 |
| ATOM | 1450 | N | THR | A | 186 | 15.168 | 19.461 | 77.633 | 1.00 | 0.00 | xxxx | 1450 |
| ATOM | 1451 | CA | THR | A | 186 | 15.460 | 19.147 | 76.237 | 1.00 | 0.00 | xxxx | 1451 |
| ATOM | 1452 | C | THR | A | 186 | 15.495 | 17.640 | 76.014 | 1.00 | 0.00 | xxxx | 1452 |
| ATOM | 1453 | O | THR | A | 186 | 14.978 | 17.136 | 75.006 | 1.00 | 0.00 | xxxx | 1453 |
| ATOM | 1454 | CB | THR | A | 186 | 16.810 | 19.741 | 75.852 | 1.00 | 0.00 | xxxx | 1454 |
| ATOM | 1455 | OG1 | THR | A | 186 | 16.814 | 21.143 | 76.153 | 1.00 | 0.00 | xxxx | 1455 |
| ATOM | 1456 | CG2 | THR | A | 186 | 17.068 | 19.526 | 74.365 | 1.00 | 0.00 | xxxx | 1456 |
| ATOM | 1457 | N | ALA | A | 187 | 16.116 | 16.907 | 76.937 | 1.00 | 0.00 | xxxx | 1457 |
| ATOM | 1458 | CA | ALA | A | 187 | 16.173 | 15.456 | 76.812 | 1.00 | 0.00 | xxxx | 1458 |
| ATOM | 1459 | C | ALA | A | 187 | 14.783 | 14.846 | 76.878 | 1.00 | 0.00 | xxxx | 1459 |
| ATOM | 1460 | O | ALA | A | 187 | 14.469 | 13.918 | 76.122 | 1.00 | 0.00 | xxxx | 1460 |
| ATOM | 1461 | CB | ALA | A | 187 | 17.059 | 14.868 | 77.909 | 1.00 | 0.00 | xxxx | 1461 |
| ATOM | 1462 | N | HIS | A | 188 | 13.941 | 15.351 | 77.785 | 1.00 | 0.00 | xxxx | 1462 |
| ATOM | 1463 | CA | HIS | A | 188 | 12.551 | 14.900 | 77.834 | 1.00 | 0.00 | xxxx | 1463 |
| ATOM | 1464 | C | HIS | A | 188 | 11.883 | 15.050 | 76.474 | 1.00 | 0.00 | xxxx | 1464 |
| ATOM | 1465 | O | HIS | A | 188 | 11.220 | 14.127 | 75.989 | 1.00 | 0.00 | xxxx | 1465 |
| ATOM | 1466 | CB | HIS | A | 188 | 11.780 | 15.697 | 78.885 | 1.00 | 0.00 | xxxx | 1466 |
| ATOM | 1467 | CG | HIS | A | 188 | 10.299 | 15.513 | 78.787 | 1.00 | 0.00 | xxxx | 1467 |
| ATOM | 1468 | ND1 | HIS | A | 188 | 9.512 | 16.277 | 77.951 | 1.00 | 0.00 | xxxx | 1468 |
| ATOM | 1469 | CD2 | HIS | A | 188 | 9.467 | 14.632 | 79.390 | 1.00 | 0.00 | xxxx | 1469 |
| ATOM | 1470 | CE1 | HIS | A | 188 | 8.252 | 15.887 | 78.063 | 1.00 | 0.00 | xxxx | 1470 |
| ATOM | 1471 | NE2 | HIS | A | 188 | 8.199 | 14.889 | 78.926 | 1.00 | 0.00 | xxxx | 1471 |
| ATOM | 1472 | N | ASP | A | 189 | 12.049 | 16.221 | 75.846 | 1.00 | 0.00 | xxxx | 1472 |
| ATOM | 1473 | CA | ASP | A | 189 | 11.368 | 16.487 | 74.584 | 1.00 | 0.00 | xxxx | 1473 |
| ATOM | 1474 | C | ASP | A | 189 | 11.903 | 15.599 | 73.467 | 1.00 | 0.00 | xxxx | 1474 |
| ATOM | 1475 | O | ASP | A | 189 | 11.126 | 15.099 | 72.645 | 1.00 | 0.00 | xxxx | 1475 |
| ATOM | 1476 | CB | ASP | A | 189 | 11.479 | 17.973 | 74.226 | 1.00 | 0.00 | xxxx | 1476 |
| ATOM | 1477 | CG | ASP | A | 189 | 10.710 | 18.880 | 75.188 | 1.00 | 0.00 | xxxx | 1477 |
| ATOM | 1478 | OD1 | ASP | A | 189 | 9.954 | 18.372 | 76.049 | 1.00 | 0.00 | xxxx | 1478 |
| ATOM | 1479 | OD2 | ASP | A | 189 | 10.857 | 20.117 | 75.077 | 1.00 | 0.00 | xxxx | 1479 |
| ATOM | 1480 | N | LYS | A | 190 | 13.223 | 15.368 | 73.429 | 1.00 | 0.00 | xxxx | 1480 |
| ATOM | 1481 | CA | LYS | A | 190 | 13.777 | 14.496 | 72.396 | 1.00 | 0.00 | xxxx | 1481 |
| ATOM | 1482 | C | LYS | A | 190 | 13.285 | 13.068 | 72.579 | 1.00 | 0.00 | xxxx | 1482 |
| ATOM | 1483 | O | LYS | A | 190 | 12.891 | 12.408 | 71.606 | 1.00 | 0.00 | xxxx | 1483 |
| ATOM | 1484 | CB | LYS | A | 190 | 15.308 | 14.513 | 72.449 | 1.00 | 0.00 | xxxx | 1484 |
| ATOM | 1485 | CG | LYS | A | 190 | 15.945 | 15.863 | 72.248 | 1.00 | 0.00 | xxxx | 1485 |
| ATOM | 1486 | CD | LYS | A | 190 | 15.977 | 16.260 | 70.788 | 1.00 | 0.00 | xxxx | 1486 |
| ATOM | 1487 | CE | LYS | A | 190 | 16.701 | 17.585 | 70.608 | 1.00 | 0.00 | xxxx | 1487 |
| ATOM | 1488 | NZ | LYS | A | 190 | 16.722 | 17.978 | 69.176 | 1.00 | 0.00 | xxxx | 1488 |
| ATOM | 1489 | N | MET | A | 191 | 13.301 | 12.577 | 73.824 | 1.00 | 0.00 | xxxx | 1489 |
| ATOM | 1490 | CA | MET | A | 191 | 12.870 | 11.208 | 74.093 | 1.00 | 0.00 | xxxx | 1490 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1491 | C | MET | A | 191 | 11.392 | 11.025 | 73.776 | 1.00 | 0.00 | xxxx | 1491 |
| ATOM | 1492 | O | MET | A | 191 | 10.990 | 9.992 | 73.224 | 1.00 | 0.00 | xxxx | 1492 |
| ATOM | 1493 | CB | MET | A | 191 | 13.165 | 10.842 | 75.548 | 1.00 | 0.00 | xxxx | 1493 |
| ATOM | 1494 | CG | MET | A | 191 | 12.888 | 9.385 | 75.898 | 1.00 | 0.00 | xxxx | 1494 |
| ATOM | 1495 | SD | MET | A | 191 | 14.209 | 8.341 | 75.237 | 1.00 | 0.00 | xxxx | 1495 |
| ATOM | 1496 | CE | MET | A | 191 | 13.275 | 6.864 | 74.858 | 1.00 | 0.00 | xxxx | 1496 |
| ATOM | 1497 | N | ALA | A | 192 | 10.562 | 12.018 | 74.119 | 1.00 | 0.00 | xxxx | 1497 |
| ATOM | 1498 | CA | ALA | A | 192 | 9.135 | 11.911 | 73.822 | 1.00 | 0.00 | xxxx | 1498 |
| ATOM | 1499 | C | ALA | A | 192 | 8.894 | 11.783 | 72.320 | 1.00 | 0.00 | xxxx | 1499 |
| ATOM | 1500 | O | ALA | A | 192 | 8.039 | 11.002 | 71.882 | 1.00 | 0.00 | xxxx | 1500 |
| ATOM | 1501 | CB | ALA | A | 192 | 8.394 | 13.125 | 74.388 | 1.00 | 0.00 | xxxx | 1501 |
| ATOM | 1502 | N | ALA | A | 193 | 9.640 | 12.543 | 71.517 | 1.00 | 0.00 | xxxx | 1502 |
| ATOM | 1503 | CA | ALA | A | 193 | 9.506 | 12.450 | 70.066 | 1.00 | 0.00 | xxxx | 1503 |
| ATOM | 1504 | C | ALA | A | 193 | 9.962 | 11.087 | 69.559 | 1.00 | 0.00 | xxxx | 1504 |
| ATOM | 1505 | O | ALA | A | 193 | 9.311 | 10.487 | 68.692 | 1.00 | 0.00 | xxxx | 1505 |
| ATOM | 1506 | CB | ALA | A | 193 | 10.276 | 13.595 | 69.410 | 1.00 | 0.00 | xxxx | 1506 |
| ATOM | 1507 | N | TRP | A | 194 | 11.061 | 10.565 | 70.105 | 1.00 | 0.00 | xxxx | 1507 |
| ATOM | 1508 | CA | TRP | A | 194 | 11.526 | 9.246 | 69.692 | 1.00 | 0.00 | xxxx | 1508 |
| ATOM | 1509 | C | TRP | A | 194 | 10.520 | 8.165 | 70.052 | 1.00 | 0.00 | xxxx | 1509 |
| ATOM | 1510 | O | TRP | A | 194 | 10.333 | 7.207 | 69.293 | 1.00 | 0.00 | xxxx | 1510 |
| ATOM | 1511 | CB | TRP | A | 194 | 12.867 | 8.939 | 70.347 | 1.00 | 0.00 | xxxx | 1511 |
| ATOM | 1512 | CG | TRP | A | 194 | 14.000 | 9.749 | 69.833 | 1.00 | 0.00 | xxxx | 1512 |
| ATOM | 1513 | CD1 | TRP | A | 194 | 14.080 | 10.407 | 68.635 | 1.00 | 0.00 | xxxx | 1513 |
| ATOM | 1514 | CD2 | TRP | A | 194 | 15.233 | 9.977 | 70.505 | 1.00 | 0.00 | xxxx | 1514 |
| ATOM | 1515 | NE1 | TRP | A | 194 | 15.297 | 11.041 | 68.533 | 1.00 | 0.00 | xxxx | 1515 |
| ATOM | 1516 | CE2 | TRP | A | 194 | 16.022 | 10.787 | 69.671 | 1.00 | 0.00 | xxxx | 1516 |
| ATOM | 1517 | CE3 | TRP | A | 194 | 15.748 | 9.571 | 71.743 | 1.00 | 0.00 | xxxx | 1517 |
| ATOM | 1518 | CZ2 | TRP | A | 194 | 17.316 | 11.195 | 70.033 | 1.00 | 0.00 | xxxx | 1518 |
| ATOM | 1519 | CZ3 | TRP | A | 194 | 17.023 | 9.974 | 72.104 | 1.00 | 0.00 | xxxx | 1519 |
| ATOM | 1520 | CH2 | TRP | A | 194 | 17.791 | 10.779 | 71.250 | 1.00 | 0.00 | xxxx | 1520 |
| ATOM | 1521 | N | LEU | A | 195 | 9.876 | 8.283 | 71.217 | 1.00 | 0.00 | xxxx | 1521 |
| ATOM | 1522 | CA | LEU | A | 195 | 8.870 | 7.294 | 71.602 | 1.00 | 0.00 | xxxx | 1522 |
| ATOM | 1523 | C | LEU | A | 195 | 7.678 | 7.327 | 70.656 | 1.00 | 0.00 | xxxx | 1523 |
| ATOM | 1524 | O | LEU | A | 195 | 7.104 | 6.280 | 70.327 | 1.00 | 0.00 | xxxx | 1524 |
| ATOM | 1525 | CB | LEU | A | 195 | 8.423 | 7.516 | 73.047 | 1.00 | 0.00 | xxxx | 1525 |
| ATOM | 1526 | CG | LEU | A | 195 | 9.482 | 7.078 | 74.060 | 1.00 | 0.00 | xxxx | 1526 |
| ATOM | 1527 | CD1 | LEU | A | 195 | 9.204 | 7.715 | 75.422 | 1.00 | 0.00 | xxxx | 1527 |
| ATOM | 1528 | CD2 | LEU | A | 195 | 9.505 | 5.553 | 74.169 | 1.00 | 0.00 | xxxx | 1528 |
| ATOM | 1529 | N | SER | A | 196 | 7.294 | 8.521 | 70.208 | 1.00 | 0.00 | xxxx | 1529 |
| ATOM | 1530 | CA | SER | A | 196 | 6.212 | 8.625 | 69.237 | 1.00 | 0.00 | xxxx | 1530 |
| ATOM | 1531 | C | SER | A | 196 | 6.607 | 7.996 | 67.904 | 1.00 | 0.00 | xxxx | 1531 |
| ATOM | 1532 | O | SER | A | 196 | 5.787 | 7.331 | 67.256 | 1.00 | 0.00 | xxxx | 1532 |
| ATOM | 1533 | CB | SER | A | 196 | 5.842 | 10.096 | 69.058 | 1.00 | 0.00 | xxxx | 1533 |
| ATOM | 1534 | OG | SER | A | 196 | 4.793 | 10.240 | 68.117 | 1.00 | 0.00 | xxxx | 1534 |
| ATOM | 1535 | N | SER | A | 197 | 7.867 | 8.170 | 67.498 | 1.00 | 0.00 | xxxx | 1535 |
| ATOM | 1536 | CA | SER | A | 197 | 8.327 | 7.660 | 66.209 | 1.00 | 0.00 | xxxx | 1536 |
| ATOM | 1537 | C | SER | A | 197 | 8.543 | 6.155 | 66.227 | 1.00 | 0.00 | xxxx | 1537 |
| ATOM | 1538 | O | SER | A | 197 | 8.182 | 5.467 | 65.265 | 1.00 | 0.00 | xxxx | 1538 |
| ATOM | 1539 | CB | SER | A | 197 | 9.638 | 8.333 | 65.817 | 1.00 | 0.00 | xxxx | 1539 |
| ATOM | 1540 | OG | SER | A | 197 | 9.428 | 9.672 | 65.436 | 1.00 | 0.00 | xxxx | 1540 |
| ATOM | 1541 | N | PHE | A | 198 | 9.146 | 5.631 | 67.296 | 1.00 | 0.00 | xxxx | 1541 |
| ATOM | 1542 | CA | PHE | A | 198 | 9.667 | 4.272 | 67.310 | 1.00 | 0.00 | xxxx | 1542 |
| ATOM | 1543 | C | PHE | A | 198 | 9.012 | 3.374 | 68.341 | 1.00 | 0.00 | xxxx | 1543 |
| ATOM | 1544 | O | PHE | A | 198 | 9.050 | 2.147 | 68.178 | 1.00 | 0.00 | xxxx | 1544 |
| ATOM | 1545 | CB | PHE | A | 198 | 11.186 | 4.271 | 67.567 | 1.00 | 0.00 | xxxx | 1545 |
| ATOM | 1546 | CG | PHE | A | 198 | 11.980 | 5.046 | 66.550 | 1.00 | 0.00 | xxxx | 1546 |
| ATOM | 1547 | CD1 | PHE | A | 198 | 12.121 | 4.570 | 65.254 | 1.00 | 0.00 | xxxx | 1547 |
| ATOM | 1548 | CD2 | PHE | A | 198 | 12.595 | 6.237 | 66.891 | 1.00 | 0.00 | xxxx | 1548 |
| ATOM | 1549 | CE1 | PHE | A | 198 | 12.854 | 5.280 | 64.315 | 1.00 | 0.00 | xxxx | 1549 |
| ATOM | 1550 | CE2 | PHE | A | 198 | 13.327 | 6.954 | 65.959 | 1.00 | 0.00 | xxxx | 1550 |
| ATOM | 1551 | CZ | PHE | A | 198 | 13.459 | 6.474 | 64.672 | 1.00 | 0.00 | xxxx | 1551 |
| ATOM | 1552 | N | GLY | A | 199 | 8.436 | 3.938 | 69.396 | 1.00 | 0.00 | xxxx | 1552 |
| ATOM | 1553 | CA | GLY | A | 199 | 7.622 | 3.144 | 70.303 | 1.00 | 0.00 | xxxx | 1553 |
| ATOM | 1554 | C | GLY | A | 199 | 8.407 | 2.021 | 70.947 | 1.00 | 0.00 | xxxx | 1554 |
| ATOM | 1555 | O | GLY | A | 199 | 9.526 | 2.204 | 71.447 | 1.00 | 0.00 | xxxx | 1555 |
| ATOM | 1556 | N | ASP | A | 200 | 7.823 | 0.827 | 70.915 | 1.00 | 0.00 | xxxx | 1556 |
| ATOM | 1557 | CA | ASP | A | 200 | 8.417 | −0.299 | 71.617 | 1.00 | 0.00 | xxxx | 1557 |
| ATOM | 1558 | C | ASP | A | 200 | 9.670 | −0.829 | 70.935 | 1.00 | 0.00 | xxxx | 1558 |
| ATOM | 1559 | O | ASP | A | 200 | 10.269 | −1.778 | 71.448 | 1.00 | 0.00 | xxxx | 1559 |
| ATOM | 1560 | CB | ASP | A | 200 | 7.385 | −1.416 | 71.804 | 1.00 | 0.00 | xxxx | 1560 |
| ATOM | 1561 | CG | ASP | A | 200 | 7.738 | −2.355 | 72.951 | 1.00 | 0.00 | xxxx | 1561 |
| ATOM | 1562 | OD1 | ASP | A | 200 | 8.129 | −1.859 | 74.030 | 1.00 | 0.00 | xxxx | 1562 |
| ATOM | 1563 | OD2 | ASP | A | 200 | 7.629 | −3.588 | 72.771 | 1.00 | 0.00 | xxxx | 1563 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1564 | N | LYS | A | 201 | 10.100 | −0.242 | 69.813 | 1.00 | 0.00 | xxxx | 1564 |
| ATOM | 1565 | CA | LYS | A | 201 | 11.350 | −0.688 | 69.204 | 1.00 | 0.00 | xxxx | 1565 |
| ATOM | 1566 | C | LYS | A | 201 | 12.558 | −0.358 | 70.073 | 1.00 | 0.00 | xxxx | 1566 |
| ATOM | 1567 | O | LYS | A | 201 | 13.589 | −1.034 | 69.975 | 1.00 | 0.00 | xxxx | 1567 |
| ATOM | 1568 | CB | LYS | A | 201 | 11.546 | −0.053 | 67.826 | 1.00 | 0.00 | xxxx | 1568 |
| ATOM | 1569 | CG | LYS | A | 201 | 10.675 | −0.615 | 66.715 | 1.00 | 0.00 | xxxx | 1569 |
| ATOM | 1570 | CD | LYS | A | 201 | 10.986 | 0.110 | 65.409 | 1.00 | 0.00 | xxxx | 1570 |
| ATOM | 1571 | CE | LYS | A | 201 | 10.412 | −0.603 | 64.198 | 1.00 | 0.00 | xxxx | 1571 |
| ATOM | 1572 | NZ | LYS | A | 201 | 11.042 | −1.941 | 64.005 | 1.00 | 0.00 | xxxx | 1572 |
| ATOM | 1573 | N | ILE | A | 202 | 12.474 | 0.683 | 70.904 | 1.00 | 0.00 | xxxx | 1573 |
| ATOM | 1574 | CA | ILE | A | 202 | 13.634 | 1.098 | 71.688 | 1.00 | 0.00 | xxxx | 1574 |
| ATOM | 1575 | C | ILE | A | 202 | 13.860 | 0.108 | 72.824 | 1.00 | 0.00 | xxxx | 1575 |
| ATOM | 1576 | O | ILE | A | 202 | 12.953 | −0.158 | 73.623 | 1.00 | 0.00 | xxxx | 1576 |
| ATOM | 1577 | CB | ILE | A | 202 | 13.439 | 2.518 | 72.238 | 1.00 | 0.00 | xxxx | 1577 |
| ATOM | 1578 | CG1 | ILE | A | 202 | 13.178 | 3.517 | 71.109 | 1.00 | 0.00 | xxxx | 1578 |
| ATOM | 1579 | CG2 | ILE | A | 202 | 14.660 | 2.953 | 73.069 | 1.00 | 0.00 | xxxx | 1579 |
| ATOM | 1580 | CD1 | ILE | A | 202 | 12.815 | 4.917 | 71.597 | 1.00 | 0.00 | xxxx | 1580 |
| ATOM | 1581 | N | GLU | A | 203 | 15.077 | −0.424 | 72.911 | 1.00 | 0.00 | xxxx | 1581 |
| ATOM | 1582 | CA | GLU | A | 203 | 15.426 | −1.422 | 73.910 | 1.00 | 0.00 | xxxx | 1582 |
| ATOM | 1583 | C | GLU | A | 203 | 16.410 | −0.926 | 74.962 | 1.00 | 0.00 | xxxx | 1583 |
| ATOM | 1584 | O | GLU | A | 203 | 16.580 | −1.596 | 75.992 | 1.00 | 0.00 | xxxx | 1584 |
| ATOM | 1585 | CB | GLU | A | 203 | 15.978 | −2.673 | 73.209 | 1.00 | 0.00 | xxxx | 1585 |
| ATOM | 1586 | CG | GLU | A | 203 | 14.941 | −3.342 | 72.310 | 1.00 | 0.00 | xxxx | 1586 |
| ATOM | 1587 | CD | GLU | A | 203 | 15.505 | −4.464 | 71.460 | 1.00 | 0.00 | xxxx | 1587 |
| ATOM | 1588 | OE1 | GLU | A | 203 | 16.743 | −4.593 | 71.349 | 1.00 | 0.00 | xxxx | 1588 |
| ATOM | 1589 | OE2 | GLU | A | 203 | 14.699 | −5.228 | 70.893 | 1.00 | 0.00 | xxxx | 1589 |
| ATOM | 1590 | N | ALA | A | 204 | 17.064 | 0.210 | 74.739 | 1.00 | 0.00 | xxxx | 1590 |
| ATOM | 1591 | CA | ALA | A | 204 | 18.049 | 0.717 | 75.685 | 1.00 | 0.00 | xxxx | 1591 |
| ATOM | 1592 | C | ALA | A | 204 | 18.211 | 2.210 | 75.445 | 1.00 | 0.00 | xxxx | 1592 |
| ATOM | 1593 | O | ALA | A | 204 | 18.120 | 2.675 | 74.308 | 1.00 | 0.00 | xxxx | 1593 |
| ATOM | 1594 | CB | ALA | A | 204 | 19.400 | 0.028 | 75.483 | 1.00 | 0.00 | xxxx | 1594 |
| ATOM | 1595 | N | VAL | A | 205 | 18.470 | 2.955 | 76.520 | 1.00 | 0.00 | xxxx | 1595 |
| ATOM | 1596 | CA | VAL | A | 205 | 18.690 | 4.399 | 76.447 | 1.00 | 0.00 | xxxx | 1596 |
| ATOM | 1597 | C | VAL | A | 205 | 20.029 | 4.721 | 77.097 | 1.00 | 0.00 | xxxx | 1597 |
| ATOM | 1598 | O | VAL | A | 205 | 20.225 | 4.455 | 78.288 | 1.00 | 0.00 | xxxx | 1598 |
| ATOM | 1599 | CB | VAL | A | 205 | 17.566 | 5.182 | 77.147 | 1.00 | 0.00 | xxxx | 1599 |
| ATOM | 1600 | CG1 | VAL | A | 205 | 17.870 | 6.677 | 77.115 | 1.00 | 0.00 | xxxx | 1600 |
| ATOM | 1601 | CG2 | VAL | A | 205 | 16.203 | 4.854 | 76.517 | 1.00 | 0.00 | xxxx | 1601 |
| ATOM | 1602 | N | PHE | A | 206 | 20.919 | 5.354 | 76.337 | 1.00 | 0.00 | xxxx | 1602 |
| ATOM | 1603 | CA | PHE | A | 206 | 22.159 | 5.899 | 76.870 | 1.00 | 0.00 | xxxx | 1603 |
| ATOM | 1604 | C | PHE | A | 206 | 22.051 | 7.414 | 76.907 | 1.00 | 0.00 | xxxx | 1604 |
| ATOM | 1605 | O | PHE | A | 206 | 21.570 | 8.028 | 75.954 | 1.00 | 0.00 | xxxx | 1605 |
| ATOM | 1606 | CB | PHE | A | 206 | 23.337 | 5.550 | 75.956 | 1.00 | 0.00 | xxxx | 1606 |
| ATOM | 1607 | CG | PHE | A | 206 | 23.627 | 4.061 | 75.837 | 1.00 | 0.00 | xxxx | 1607 |
| ATOM | 1608 | CD1 | PHE | A | 206 | 24.652 | 3.482 | 76.557 | 1.00 | 0.00 | xxxx | 1608 |
| ATOM | 1609 | CD2 | PHE | A | 206 | 22.889 | 3.258 | 74.969 | 1.00 | 0.00 | xxxx | 1609 |
| ATOM | 1610 | CE1 | PHE | A | 206 | 24.937 | 2.113 | 76.419 | 1.00 | 0.00 | xxxx | 1610 |
| ATOM | 1611 | CE2 | PHE | A | 206 | 23.158 | 1.899 | 74.835 | 1.00 | 0.00 | xxxx | 1611 |
| ATOM | 1612 | CZ | PHE | A | 206 | 24.180 | 1.336 | 75.555 | 1.00 | 0.00 | xxxx | 1612 |
| ATOM | 1613 | N | ALA | A | 207 | 22.503 | 8.018 | 78.005 | 1.00 | 0.00 | xxxx | 1613 |
| ATOM | 1614 | CA | ALA | A | 207 | 22.572 | 9.470 | 78.099 | 1.00 | 0.00 | xxxx | 1614 |
| ATOM | 1615 | C | ALA | A | 207 | 23.937 | 9.866 | 78.637 | 1.00 | 0.00 | xxxx | 1615 |
| ATOM | 1616 | O | ALA | A | 207 | 24.471 | 9.208 | 79.539 | 1.00 | 0.00 | xxxx | 1616 |
| ATOM | 1617 | CB | ALA | A | 207 | 21.467 | 10.027 | 79.005 | 1.00 | 0.00 | xxxx | 1617 |
| ATOM | 1618 | N | ASN | A | 208 | 24.498 | 10.944 | 78.082 | 1.00 | 0.00 | xxxx | 1618 |
| ATOM | 1619 | CA | ASN | A | 208 | 25.825 | 11.375 | 78.507 | 1.00 | 0.00 | xxxx | 1619 |
| ATOM | 1620 | C | ASN | A | 208 | 25.850 | 11.893 | 79.944 | 1.00 | 0.00 | xxxx | 1620 |
| ATOM | 1621 | O | ASN | A | 208 | 26.935 | 11.977 | 80.516 | 1.00 | 0.00 | xxxx | 1621 |
| ATOM | 1622 | CB | ASN | A | 208 | 26.378 | 12.499 | 77.614 | 1.00 | 0.00 | xxxx | 1622 |
| ATOM | 1623 | CG | ASN | A | 208 | 26.794 | 12.066 | 76.190 | 1.00 | 0.00 | xxxx | 1623 |
| ATOM | 1624 | OD1 | ASN | A | 208 | 27.122 | 12.946 | 75.398 | 1.00 | 0.00 | xxxx | 1624 |
| ATOM | 1625 | ND2 | ASN | A | 208 | 26.799 | 10.770 | 75.868 | 1.00 | 0.00 | xxxx | 1625 |
| ATOM | 1626 | N | ASN | A | 209 | 24.720 | 12.312 | 80.515 | 1.00 | 0.00 | xxxx | 1626 |
| ATOM | 1627 | CA | ASN | A | 209 | 24.716 | 12.706 | 81.922 | 1.00 | 0.00 | xxxx | 1627 |
| ATOM | 1628 | C | ASN | A | 209 | 23.396 | 12.327 | 82.587 | 1.00 | 0.00 | xxxx | 1628 |
| ATOM | 1629 | O | ASN | A | 209 | 22.425 | 11.927 | 81.931 | 1.00 | 0.00 | xxxx | 1629 |
| ATOM | 1630 | CB | ASN | A | 209 | 25.102 | 14.184 | 82.128 | 1.00 | 0.00 | xxxx | 1630 |
| ATOM | 1631 | CG | ASN | A | 209 | 23.948 | 15.150 | 81.859 | 1.00 | 0.00 | xxxx | 1631 |
| ATOM | 1632 | OD1 | ASN | A | 209 | 22.944 | 14.798 | 81.229 | 1.00 | 0.00 | xxxx | 1632 |
| ATOM | 1633 | ND2 | ASN | A | 209 | 24.091 | 16.374 | 82.348 | 1.00 | 0.00 | xxxx | 1633 |
| ATOM | 1634 | N | ASP | A | 210 | 23.383 | 12.465 | 83.917 | 1.00 | 0.00 | xxxx | 1634 |
| ATOM | 1635 | CA | ASP | A | 210 | 22.205 | 12.098 | 84.697 | 1.00 | 0.00 | xxxx | 1635 |
| ATOM | 1636 | C | ASP | A | 210 | 21.016 | 12.992 | 84.382 | 1.00 | 0.00 | xxxx | 1636 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1637 | O | ASP | A | 210 | 19.892 | 12.496 | 84.280 | 1.00 | 0.00 | xxxx | 1637 |
| ATOM | 1638 | CB | ASP | A | 210 | 22.499 | 12.120 | 86.200 | 1.00 | 0.00 | xxxx | 1638 |
| ATOM | 1639 | CG | ASP | A | 210 | 23.228 | 10.885 | 86.679 | 1.00 | 0.00 | xxxx | 1639 |
| ATOM | 1640 | OD1 | ASP | A | 210 | 23.451 | 9.951 | 85.873 | 1.00 | 0.00 | xxxx | 1640 |
| ATOM | 1641 | OD2 | ASP | A | 210 | 23.550 | 10.846 | 87.885 | 1.00 | 0.00 | xxxx | 1641 |
| ATOM | 1642 | N | ASP | A | 211 | 21.228 | 14.304 | 84.218 | 1.00 | 0.00 | xxxx | 1642 |
| ATOM | 1643 | CA | ASP | A | 211 | 20.071 | 15.166 | 83.960 | 1.00 | 0.00 | xxxx | 1643 |
| ATOM | 1644 | C | ASP | A | 211 | 19.346 | 14.769 | 82.678 | 1.00 | 0.00 | xxxx | 1644 |
| ATOM | 1645 | O | ASP | A | 211 | 18.109 | 14.733 | 82.643 | 1.00 | 0.00 | xxxx | 1645 |
| ATOM | 1646 | CB | ASP | A | 211 | 20.456 | 16.641 | 83.956 | 1.00 | 0.00 | xxxx | 1646 |
| ATOM | 1647 | CG | ASP | A | 211 | 20.279 | 17.293 | 85.323 | 1.00 | 0.00 | xxxx | 1647 |
| ATOM | 1648 | OD1 | ASP | A | 211 | 19.754 | 16.629 | 86.253 | 1.00 | 0.00 | xxxx | 1648 |
| ATOM | 1649 | OD2 | ASP | A | 211 | 20.643 | 18.479 | 85.456 | 1.00 | 0.00 | xxxx | 1649 |
| ATOM | 1650 | N | MET | A | 212 | 20.089 | 14.423 | 81.627 | 1.00 | 0.00 | xxxx | 1650 |
| ATOM | 1651 | CA | MET | A | 212 | 19.418 | 13.970 | 80.413 | 1.00 | 0.00 | xxxx | 1651 |
| ATOM | 1652 | C | MET | A | 212 | 18.766 | 12.608 | 80.614 | 1.00 | 0.00 | xxxx | 1652 |
| ATOM | 1653 | O | MET | A | 212 | 17.664 | 12.359 | 80.105 | 1.00 | 0.00 | xxxx | 1653 |
| ATOM | 1654 | CB | MET | A | 212 | 20.388 | 13.937 | 79.232 | 1.00 | 0.00 | xxxx | 1654 |
| ATOM | 1655 | CG | MET | A | 212 | 20.811 | 15.334 | 78.819 | 1.00 | 0.00 | xxxx | 1655 |
| ATOM | 1656 | SD | MET | A | 212 | 21.785 | 15.350 | 77.315 | 1.00 | 0.00 | xxxx | 1656 |
| ATOM | 1657 | CE | MET | A | 212 | 23.183 | 14.347 | 77.803 | 1.00 | 0.00 | xxxx | 1657 |
| ATOM | 1658 | N | ALA | A | 213 | 19.418 | 11.707 | 81.356 | 1.00 | 0.00 | xxxx | 1658 |
| ATOM | 1659 | CA | ALA | A | 213 | 18.786 | 10.419 | 81.642 | 1.00 | 0.00 | xxxx | 1659 |
| ATOM | 1660 | C | ALA | A | 213 | 17.469 | 10.612 | 82.378 | 1.00 | 0.00 | xxxx | 1660 |
| ATOM | 1661 | O | ALA | A | 213 | 16.484 | 9.916 | 82.096 | 1.00 | 0.00 | xxxx | 1661 |
| ATOM | 1662 | CB | ALA | A | 213 | 19.728 | 9.536 | 82.462 | 1.00 | 0.00 | xxxx | 1662 |
| ATOM | 1663 | N | LEU | A | 214 | 17.433 | 11.567 | 83.311 | 1.00 | 0.00 | xxxx | 1663 |
| ATOM | 1664 | CA | LEU | A | 214 | 16.230 | 11.827 | 84.099 | 1.00 | 0.00 | xxxx | 1664 |
| ATOM | 1665 | C | LEU | A | 214 | 15.123 | 12.421 | 83.242 | 1.00 | 0.00 | xxxx | 1665 |
| ATOM | 1666 | O | LEU | A | 214 | 13.948 | 12.090 | 83.429 | 1.00 | 0.00 | xxxx | 1666 |
| ATOM | 1667 | CB | LEU | A | 214 | 16.562 | 12.751 | 85.271 | 1.00 | 0.00 | xxxx | 1667 |
| ATOM | 1668 | CG | LEU | A | 214 | 17.503 | 12.139 | 86.310 | 1.00 | 0.00 | xxxx | 1668 |
| ATOM | 1669 | CD1 | LEU | A | 214 | 18.009 | 13.201 | 87.272 | 1.00 | 0.00 | xxxx | 1669 |
| ATOM | 1670 | CD2 | LEU | A | 214 | 16.789 | 11.031 | 87.065 | 1.00 | 0.00 | xxxx | 1670 |
| ATOM | 1671 | N | GLY | A | 215 | 15.471 | 13.308 | 82.309 | 1.00 | 0.00 | xxxx | 1671 |
| ATOM | 1672 | CA | GLY | A | 215 | 14.475 | 13.776 | 81.359 | 1.00 | 0.00 | xxxx | 1672 |
| ATOM | 1673 | C | GLY | A | 215 | 13.929 | 12.650 | 80.503 | 1.00 | 0.00 | xxxx | 1673 |
| ATOM | 1674 | O | GLY | A | 215 | 12.723 | 12.584 | 80.244 | 1.00 | 0.00 | xxxx | 1674 |
| ATOM | 1675 | N | ALA | A | 216 | 14.806 | 11.757 | 80.039 | 1.00 | 0.00 | xxxx | 1675 |
| ATOM | 1676 | CA | ALA | A | 216 | 14.338 | 10.602 | 79.279 | 1.00 | 0.00 | xxxx | 1676 |
| ATOM | 1677 | C | ALA | A | 216 | 13.396 | 9.751 | 80.110 | 1.00 | 0.00 | xxxx | 1677 |
| ATOM | 1678 | O | ALA | A | 216 | 12.360 | 9.292 | 79.612 | 1.00 | 0.00 | xxxx | 1678 |
| ATOM | 1679 | CB | ALA | A | 216 | 15.529 | 9.769 | 78.802 | 1.00 | 0.00 | xxxx | 1679 |
| ATOM | 1680 | N | ILE | A | 217 | 13.738 | 9.538 | 81.385 | 1.00 | 0.00 | xxxx | 1680 |
| ATOM | 1681 | CA | ILE | A | 217 | 12.897 | 8.739 | 82.277 | 1.00 | 0.00 | xxxx | 1681 |
| ATOM | 1682 | C | ILE | A | 217 | 11.510 | 9.355 | 82.420 | 1.00 | 0.00 | xxxx | 1682 |
| ATOM | 1683 | O | ILE | A | 217 | 10.499 | 8.646 | 82.418 | 1.00 | 0.00 | xxxx | 1683 |
| ATOM | 1684 | CB | ILE | A | 217 | 13.605 | 8.537 | 83.627 | 1.00 | 0.00 | xxxx | 1684 |
| ATOM | 1685 | CG1 | ILE | A | 217 | 14.716 | 7.494 | 83.461 | 1.00 | 0.00 | xxxx | 1685 |
| ATOM | 1686 | CG2 | ILE | A | 217 | 12.598 | 8.125 | 84.691 | 1.00 | 0.00 | xxxx | 1686 |
| ATOM | 1687 | CD1 | ILE | A | 217 | 15.733 | 7.486 | 84.585 | 1.00 | 0.00 | xxxx | 1687 |
| ATOM | 1688 | N | GLU | A | 218 | 11.430 | 10.685 | 82.521 | 1.00 | 0.00 | xxxx | 1688 |
| ATOM | 1689 | CA | GLU | A | 218 | 10.119 | 11.329 | 82.600 | 1.00 | 0.00 | xxxx | 1689 |
| ATOM | 1690 | C | GLU | A | 218 | 9.289 | 11.080 | 81.342 | 1.00 | 0.00 | xxxx | 1690 |
| ATOM | 1691 | O | GLU | A | 218 | 8.080 | 10.843 | 81.427 | 1.00 | 0.00 | xxxx | 1691 |
| ATOM | 1692 | CB | GLU | A | 218 | 10.273 | 12.826 | 82.880 | 1.00 | 0.00 | xxxx | 1692 |
| ATOM | 1693 | CG | GLU | A | 218 | 10.768 | 13.106 | 84.295 | 1.00 | 0.00 | xxxx | 1693 |
| ATOM | 1694 | CD | GLU | A | 218 | 9.954 | 12.360 | 85.351 | 1.00 | 0.00 | xxxx | 1694 |
| ATOM | 1695 | OE1 | GLU | A | 218 | 8.711 | 12.546 | 85.409 | 1.00 | 0.00 | xxxx | 1695 |
| ATOM | 1696 | OE2 | GLU | A | 218 | 10.550 | 11.574 | 86.125 | 1.00 | 0.00 | xxxx | 1696 |
| ATOM | 1697 | N | ALA | A | 219 | 9.917 | 11.127 | 80.162 | 1.00 | 0.00 | xxxx | 1697 |
| ATOM | 1698 | CA | ALA | A | 219 | 9.177 | 10.831 | 78.937 | 1.00 | 0.00 | xxxx | 1698 |
| ATOM | 1699 | C | ALA | A | 219 | 8.754 | 9.368 | 78.887 | 1.00 | 0.00 | xxxx | 1699 |
| ATOM | 1700 | O | ALA | A | 219 | 7.645 | 9.048 | 78.448 | 1.00 | 0.00 | xxxx | 1700 |
| ATOM | 1701 | CB | ALA | A | 219 | 10.025 | 11.184 | 77.715 | 1.00 | 0.00 | xxxx | 1701 |
| ATOM | 1702 | N | LEU | A | 220 | 9.623 | 8.468 | 79.358 | 1.00 | 0.00 | xxxx | 1702 |
| ATOM | 1703 | CA | LEU | A | 220 | 9.266 | 7.051 | 79.431 | 1.00 | 0.00 | xxxx | 1703 |
| ATOM | 1704 | C | LEU | A | 220 | 8.105 | 6.809 | 80.392 | 1.00 | 0.00 | xxxx | 1704 |
| ATOM | 1705 | O | LEU | A | 220 | 7.181 | 6.049 | 80.078 | 1.00 | 0.00 | xxxx | 1705 |
| ATOM | 1706 | CB | LEU | A | 220 | 10.492 | 6.229 | 79.828 | 1.00 | 0.00 | xxxx | 1706 |
| ATOM | 1707 | CG | LEU | A | 220 | 11.577 | 6.146 | 78.748 | 1.00 | 0.00 | xxxx | 1707 |
| ATOM | 1708 | CD1 | LEU | A | 220 | 12.935 | 5.811 | 79.350 | 1.00 | 0.00 | xxxx | 1708 |
| ATOM | 1709 | CD2 | LEU | A | 220 | 11.184 | 5.099 | 77.725 | 1.00 | 0.00 | xxxx | 1709 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1710 | N | LYS | A | 221 | 8.129 | 7.452 | 81.566 | 1.00 | 0.00 | xxxx | 1710 |
| ATOM | 1711 | CA | LYS | A | 221 | 7.009 | 7.320 | 82.497 | 1.00 | 0.00 | xxxx | 1711 |
| ATOM | 1712 | C | LYS | A | 221 | 5.709 | 7.782 | 81.858 | 1.00 | 0.00 | xxxx | 1712 |
| ATOM | 1713 | O | LYS | A | 221 | 4.675 | 7.119 | 81.991 | 1.00 | 0.00 | xxxx | 1713 |
| ATOM | 1714 | CB | LYS | A | 221 | 7.284 | 8.142 | 83.756 | 1.00 | 0.00 | xxxx | 1714 |
| ATOM | 1715 | CG | LYS | A | 221 | 8.319 | 7.544 | 84.684 | 1.00 | 0.00 | xxxx | 1715 |
| ATOM | 1716 | CD | LYS | A | 221 | 8.604 | 8.504 | 85.825 | 1.00 | 0.00 | xxxx | 1716 |
| ATOM | 1717 | CE | LYS | A | 221 | 9.505 | 7.891 | 86.871 | 1.00 | 0.00 | xxxx | 1717 |
| ATOM | 1718 | NZ | LYS | A | 221 | 9.758 | 8.870 | 87.968 | 1.00 | 0.00 | xxxx | 1718 |
| ATOM | 1719 | N | SER | A | 222 | 5.750 | 8.912 | 81.144 | 1.00 | 0.00 | xxxx | 1719 |
| ATOM | 1720 | CA | SER | A | 222 | 4.546 | 9.442 | 80.517 | 1.00 | 0.00 | xxxx | 1720 |
| ATOM | 1721 | C | SER | A | 222 | 3.975 | 8.470 | 79.493 | 1.00 | 0.00 | xxxx | 1721 |
| ATOM | 1722 | O | SER | A | 222 | 2.756 | 8.427 | 79.292 | 1.00 | 0.00 | xxxx | 1722 |
| ATOM | 1723 | CB | SER | A | 222 | 4.887 | 10.783 | 79.868 | 1.00 | 0.00 | xxxx | 1723 |
| ATOM | 1724 | OG | SER | A | 222 | 3.742 | 11.388 | 79.291 | 1.00 | 0.00 | xxxx | 1724 |
| ATOM | 1725 | N | ALA | A | 223 | 4.835 | 7.670 | 78.859 | 1.00 | 0.00 | xxxx | 1725 |
| ATOM | 1726 | CA | ALA | A | 223 | 4.440 | 6.652 | 77.894 | 1.00 | 0.00 | xxxx | 1726 |
| ATOM | 1727 | C | ALA | A | 223 | 4.151 | 5.298 | 78.533 | 1.00 | 0.00 | xxxx | 1727 |
| ATOM | 1728 | O | ALA | A | 223 | 3.934 | 4.323 | 77.806 | 1.00 | 0.00 | xxxx | 1728 |
| ATOM | 1729 | CB | ALA | A | 223 | 5.525 | 6.498 | 76.820 | 1.00 | 0.00 | xxxx | 1729 |
| ATOM | 1730 | N | GLY | A | 224 | 4.168 | 5.203 | 79.857 | 1.00 | 0.00 | xxxx | 1730 |
| ATOM | 1731 | CA | GLY | A | 224 | 3.714 | 4.007 | 80.540 | 1.00 | 0.00 | xxxx | 1731 |
| ATOM | 1732 | C | GLY | A | 224 | 4.788 | 3.065 | 81.044 | 1.00 | 0.00 | xxxx | 1732 |
| ATOM | 1733 | O | GLY | A | 224 | 4.453 | 1.960 | 81.485 | 1.00 | 0.00 | xxxx | 1733 |
| ATOM | 1734 | N | TYR | A | 225 | 6.059 | 3.453 | 80.996 | 1.00 | 0.00 | xxxx | 1734 |
| ATOM | 1735 | CA | TYR | A | 225 | 7.105 | 2.588 | 81.524 | 1.00 | 0.00 | xxxx | 1735 |
| ATOM | 1736 | C | TYR | A | 225 | 7.240 | 2.767 | 83.030 | 1.00 | 0.00 | xxxx | 1736 |
| ATOM | 1737 | O | TYR | A | 225 | 6.821 | 3.775 | 83.605 | 1.00 | 0.00 | xxxx | 1737 |
| ATOM | 1738 | CB | TYR | A | 225 | 8.454 | 2.918 | 80.882 | 1.00 | 0.00 | xxxx | 1738 |
| ATOM | 1739 | CG | TYR | A | 225 | 8.570 | 2.480 | 79.443 | 1.00 | 0.00 | xxxx | 1739 |
| ATOM | 1740 | CD1 | TYR | A | 225 | 8.000 | 3.229 | 78.424 | 1.00 | 0.00 | xxxx | 1740 |
| ATOM | 1741 | CD2 | TYR | A | 225 | 9.239 | 1.309 | 79.106 | 1.00 | 0.00 | xxxx | 1741 |
| ATOM | 1742 | CE1 | TYR | A | 225 | 8.099 | 2.830 | 77.102 | 1.00 | 0.00 | xxxx | 1742 |
| ATOM | 1743 | CE2 | TYR | A | 225 | 9.345 | 0.901 | 77.786 | 1.00 | 0.00 | xxxx | 1743 |
| ATOM | 1744 | CZ | TYR | A | 225 | 8.774 | 1.667 | 76.790 | 1.00 | 0.00 | xxxx | 1744 |
| ATOM | 1745 | OH | TYR | A | 225 | 8.868 | 1.275 | 75.474 | 1.00 | 0.00 | xxxx | 1745 |
| ATOM | 1746 | N | PHE | A | 226 | 7.838 | 1.757 | 83.665 | 1.00 | 0.00 | xxxx | 1746 |
| ATOM | 1747 | CA | PHE | A | 226 | 8.172 | 1.755 | 85.089 | 1.00 | 0.00 | xxxx | 1747 |
| ATOM | 1748 | C | PHE | A | 226 | 6.955 | 1.612 | 85.993 | 1.00 | 0.00 | xxxx | 1748 |
| ATOM | 1749 | O | PHE | A | 226 | 7.021 | 1.935 | 87.183 | 1.00 | 0.00 | xxxx | 1749 |
| ATOM | 1750 | CB | PHE | A | 226 | 9.049 | 2.945 | 85.479 | 1.00 | 0.00 | xxxx | 1750 |
| ATOM | 1751 | CG | PHE | A | 226 | 10.263 | 3.081 | 84.613 | 1.00 | 0.00 | xxxx | 1751 |
| ATOM | 1752 | CD1 | PHE | A | 226 | 11.193 | 2.054 | 84.551 | 1.00 | 0.00 | xxxx | 1752 |
| ATOM | 1753 | CD2 | PHE | A | 226 | 10.472 | 4.221 | 83.846 | 1.00 | 0.00 | xxxx | 1753 |
| ATOM | 1754 | CE1 | PHE | A | 226 | 12.318 | 2.161 | 83.746 | 1.00 | 0.00 | xxxx | 1754 |
| ATOM | 1755 | CE2 | PHE | A | 226 | 11.592 | 4.336 | 83.036 | 1.00 | 0.00 | xxxx | 1755 |
| ATOM | 1756 | CZ | PHE | A | 226 | 12.521 | 3.300 | 82.988 | 1.00 | 0.00 | xxxx | 1756 |
| ATOM | 1757 | N | THR | A | 227 | 5.843 | 1.150 | 85.430 | 1.00 | 0.00 | xxxx | 1757 |
| ATOM | 1758 | CA | THR | A | 227 | 4.682 | 0.684 | 86.169 | 1.00 | 0.00 | xxxx | 1758 |
| ATOM | 1759 | C | THR | A | 227 | 4.250 | −0.624 | 85.528 | 1.00 | 0.00 | xxxx | 1759 |
| ATOM | 1760 | O | THR | A | 227 | 4.433 | −0.828 | 84.324 | 1.00 | 0.00 | xxxx | 1760 |
| ATOM | 1761 | CB | THR | A | 227 | 3.523 | 1.686 | 86.088 | 1.00 | 0.00 | xxxx | 1761 |
| ATOM | 1762 | OG1 | THR | A | 227 | 3.120 | 1.844 | 84.721 | 1.00 | 0.00 | xxxx | 1762 |
| ATOM | 1763 | CG2 | THR | A | 227 | 3.933 | 3.041 | 86.656 | 1.00 | 0.00 | xxxx | 1763 |
| ATOM | 1764 | N | GLY | A | 228 | 3.678 | −1.510 | 86.331 | 1.00 | 0.00 | xxxx | 1764 |
| ATOM | 1765 | CA | GLY | A | 228 | 3.389 | −2.839 | 85.817 | 1.00 | 0.00 | xxxx | 1765 |
| ATOM | 1766 | C | GLY | A | 228 | 4.687 | −3.566 | 85.519 | 1.00 | 0.00 | xxxx | 1766 |
| ATOM | 1767 | O | GLY | A | 228 | 5.616 | −3.577 | 86.333 | 1.00 | 0.00 | xxxx | 1767 |
| ATOM | 1768 | N | ASN | A | 229 | 4.770 | −4.170 | 84.336 | 1.00 | 0.00 | xxxx | 1768 |
| ATOM | 1769 | CA | ASN | A | 229 | 5.949 | −4.930 | 83.939 | 1.00 | 0.00 | xxxx | 1769 |
| ATOM | 1770 | C | ASN | A | 229 | 6.702 | −4.298 | 82.773 | 1.00 | 0.00 | xxxx | 1770 |
| ATOM | 1771 | O | ASN | A | 229 | 7.568 | −4.953 | 82.181 | 1.00 | 0.00 | xxxx | 1771 |
| ATOM | 1772 | CB | ASN | A | 229 | 5.568 | −6.377 | 83.610 | 1.00 | 0.00 | xxxx | 1772 |
| ATOM | 1773 | CG | ASN | A | 229 | 4.838 | −7.063 | 84.752 | 1.00 | 0.00 | xxxx | 1773 |
| ATOM | 1774 | OD1 | ASN | A | 229 | 3.804 | −7.703 | 84.550 | 1.00 | 0.00 | xxxx | 1774 |
| ATOM | 1775 | ND2 | ASN | A | 229 | 5.372 | −6.928 | 85.962 | 1.00 | 0.00 | xxxx | 1775 |
| ATOM | 1776 | N | LYS | A | 230 | 6.405 | −3.042 | 82.438 | 1.00 | 0.00 | xxxx | 1776 |
| ATOM | 1777 | CA | LYS | A | 230 | 6.967 | −2.385 | 81.260 | 1.00 | 0.00 | xxxx | 1777 |
| ATOM | 1778 | C | LYS | A | 230 | 8.247 | −1.659 | 81.660 | 1.00 | 0.00 | xxxx | 1778 |
| ATOM | 1779 | O | LYS | A | 230 | 8.196 | −0.602 | 82.292 | 1.00 | 0.00 | xxxx | 1779 |
| ATOM | 1780 | CB | LYS | A | 230 | 5.952 | −1.404 | 80.685 | 1.00 | 0.00 | xxxx | 1780 |
| ATOM | 1781 | CG | LYS | A | 230 | 6.277 | −0.908 | 79.292 | 1.00 | 0.00 | xxxx | 1781 |
| ATOM | 1782 | CD | LYS | A | 230 | 5.185 | 0.026 | 78.796 | 1.00 | 0.00 | xxxx | 1782 |

-continued

| | | | | | | | | | | | |
|---|---|---|---|---|---|---|---|---|---|---|---|
| CA, calcium<br>HOH, water<br>ACR, Acrylodan<br>K, potassium<br>EDO, ethylene glycol | | | | | | | | | | | |
| ATOM | 1783 | CE | LYS | A | 230 | 5.326 | 0.329 | 77.315 | 1.00 | 0.00 xxxx | 1783 |
| ATOM | 1784 | NZ | LYS | A | 230 | 4.308 | 1.323 | 76.869 | 1.00 | 0.00 xxxx | 1784 |
| ATOM | 1785 | N | TYR | A | 231 | 9.391 | −2.211 | 81.264 | 1.00 | 0.00 xxxx | 1785 |
| ATOM | 1786 | CA | TYR | A | 231 | 10.690 | −1.754 | 81.735 | 1.00 | 0.00 xxxx | 1786 |
| ATOM | 1787 | C | TYR | A | 231 | 11.625 | −1.492 | 80.561 | 1.00 | 0.00 xxxx | 1787 |
| ATOM | 1788 | O | TYR | A | 231 | 11.531 | −2.142 | 79.519 | 1.00 | 0.00 xxxx | 1788 |
| ATOM | 1789 | CB | TYR | A | 231 | 11.305 | −2.813 | 82.651 | 1.00 | 0.00 xxxx | 1789 |
| ATOM | 1790 | CG | TYR | A | 231 | 12.673 | −2.447 | 83.152 | 1.00 | 0.00 xxxx | 1790 |
| ATOM | 1791 | CD1 | TYR | A | 231 | 12.824 | −1.635 | 84.264 | 1.00 | 0.00 xxxx | 1791 |
| ATOM | 1792 | CD2 | TYR | A | 231 | 13.814 | −2.906 | 82.508 | 1.00 | 0.00 xxxx | 1792 |
| ATOM | 1793 | CE1 | TYR | A | 231 | 14.077 | −1.293 | 84.726 | 1.00 | 0.00 xxxx | 1793 |
| ATOM | 1794 | CE2 | TYR | A | 231 | 15.065 | −2.574 | 82.960 | 1.00 | 0.00 xxxx | 1794 |
| ATOM | 1795 | CZ | TYR | A | 231 | 15.197 | −1.764 | 84.060 | 1.00 | 0.00 xxxx | 1795 |
| ATOM | 1796 | OH | TYR | A | 231 | 16.452 | −1.437 | 84.506 | 1.00 | 0.00 xxxx | 1796 |
| ATOM | 1797 | N | ILE | A | 232 | 12.542 | −0.539 | 80.740 | 1.00 | 0.00 xxxx | 1797 |
| ATOM | 1798 | CA | ILE | A | 232 | 13.594 | −0.267 | 79.760 | 1.00 | 0.00 xxxx | 1798 |
| ATOM | 1799 | C | ILE | A | 232 | 14.838 | 0.172 | 80.524 | 1.00 | 0.00 xxxx | 1799 |
| ATOM | 1800 | O | ILE | A | 232 | 14.719 | 0.936 | 81.494 | 1.00 | 0.00 xxxx | 1800 |
| ATOM | 1801 | CB | ILE | A | 232 | 13.147 | 0.780 | 78.728 | 1.00 | 0.00 xxxx | 1801 |
| ATOM | 1802 | CG1 | ILE | A | 232 | 14.186 | 0.924 | 77.622 | 1.00 | 0.00 xxxx | 1802 |
| ATOM | 1803 | CG2 | ILE | A | 232 | 12.864 | 2.122 | 79.397 | 1.00 | 0.00 xxxx | 1803 |
| ATOM | 1804 | CD1 | ILE | A | 232 | 13.684 | 1.726 | 76.428 | 1.00 | 0.00 xxxx | 1804 |
| ATOM | 1805 | N | PRO | A | 233 | 16.035 | −0.298 | 80.160 | 1.00 | 0.00 xxxx | 1805 |
| ATOM | 1806 | CA | PRO | A | 233 | 17.246 | 0.122 | 80.880 | 1.00 | 0.00 xxxx | 1806 |
| ATOM | 1807 | C | PRO | A | 233 | 17.726 | 1.475 | 80.372 | 1.00 | 0.00 xxxx | 1807 |
| ATOM | 1808 | O | PRO | A | 233 | 17.838 | 1.700 | 79.163 | 1.00 | 0.00 xxxx | 1808 |
| ATOM | 1809 | CB | PRO | A | 233 | 18.260 | −0.975 | 80.535 | 1.00 | 0.00 xxxx | 1809 |
| ATOM | 1810 | CG | PRO | A | 233 | 17.816 | −1.455 | 79.173 | 1.00 | 0.00 xxxx | 1810 |
| ATOM | 1811 | CD | PRO | A | 233 | 16.306 | −1.417 | 79.237 | 1.00 | 0.00 xxxx | 1811 |
| ATOM | 1812 | N | VAL | A | 234 | 18.000 | 2.378 | 81.311 | 1.00 | 0.00 xxxx | 1812 |
| ATOM | 1813 | CA | VAL | A | 234 | 18.495 | 3.726 | 81.046 | 1.00 | 0.00 xxxx | 1813 |
| ATOM | 1814 | C | VAL | A | 234 | 19.765 | 3.893 | 81.869 | 1.00 | 0.00 xxxx | 1814 |
| ATOM | 1815 | O | VAL | A | 234 | 19.782 | 3.535 | 83.053 | 1.00 | 0.00 xxxx | 1815 |
| ATOM | 1816 | CB | VAL | A | 234 | 17.460 | 4.778 | 81.487 | 1.00 | 0.00 xxxx | 1816 |
| ATOM | 1817 | CG1 | VAL | A | 234 | 17.978 | 6.191 | 81.195 | 1.00 | 0.00 xxxx | 1817 |
| ATOM | 1818 | CG2 | VAL | A | 234 | 16.112 | 4.530 | 80.804 | 1.00 | 0.00 xxxx | 1818 |
| ATOM | 1819 | N | VAL | A | 235 | 20.823 | 4.394 | 81.240 | 1.00 | 0.00 xxxx | 1819 |
| ATOM | 1820 | CA | VAL | A | 235 | 22.057 | 4.675 | 81.959 | 1.00 | 0.00 xxxx | 1820 |
| ATOM | 1821 | C | VAL | A | 235 | 22.430 | 6.139 | 81.791 | 1.00 | 0.00 xxxx | 1821 |
| ATOM | 1822 | O | VAL | A | 235 | 22.133 | 6.778 | 80.774 | 1.00 | 0.00 xxxx | 1822 |
| ATOM | 1823 | CB | VAL | A | 235 | 23.217 | 3.756 | 81.523 | 1.00 | 0.00 xxxx | 1823 |
| ATOM | 1824 | CG1 | VAL | A | 235 | 22.953 | 2.340 | 81.988 | 1.00 | 0.00 xxxx | 1824 |
| ATOM | 1825 | CG2 | VAL | A | 235 | 23.378 | 3.811 | 80.029 | 1.00 | 0.00 xxxx | 1825 |
| ATOM | 1826 | N | GLY | A | 236 | 23.088 | 6.666 | 82.819 | 1.00 | 0.00 xxxx | 1826 |
| ATOM | 1827 | CA | GLY | A | 236 | 23.609 | 8.026 | 82.778 | 1.00 | 0.00 xxxx | 1827 |
| ATOM | 1828 | C | GLY | A | 236 | 25.040 | 8.151 | 83.282 | 1.00 | 0.00 xxxx | 1828 |
| ATOM | 1829 | O | GLY | A | 236 | 25.756 | 7.147 | 83.372 | 1.00 | 0.00 xxxx | 1829 |
| ATOM | 1830 | N | VAL | A | 237 | 25.485 | 9.375 | 83.586 | 1.00 | 0.00 xxxx | 1830 |
| ATOM | 1831 | CA | VAL | A | 237 | 26.766 | 9.634 | 84.252 | 1.00 | 0.00 xxxx | 1831 |
| ATOM | 1832 | C | VAL | A | 237 | 26.558 | 10.798 | 85.209 | 1.00 | 0.00 xxxx | 1832 |
| ATOM | 1833 | O | VAL | A | 237 | 25.967 | 11.808 | 84.815 | 1.00 | 0.00 xxxx | 1833 |
| ATOM | 1834 | CB | VAL | A | 237 | 27.894 | 10.024 | 83.266 | 1.00 | 0.00 xxxx | 1834 |
| ATOM | 1835 | CG1 | VAL | A | 237 | 29.137 | 10.427 | 84.038 | 1.00 | 0.00 xxxx | 1835 |
| ATOM | 1836 | CG2 | VAL | A | 237 | 28.220 | 8.897 | 82.312 | 1.00 | 0.00 xxxx | 1836 |
| ATOM | 1837 | N | ASP | A | 238 | 27.024 | 10.642 | 86.462 | 1.00 | 0.00 xxxx | 1837 |
| ATOM | 1838 | CA | ASP | A | 238 | 27.345 | 11.681 | 87.450 | 1.00 | 0.00 xxxx | 1838 |
| ATOM | 1839 | C | ASP | A | 238 | 27.114 | 11.178 | 88.868 | 1.00 | 0.00 xxxx | 1839 |
| ATOM | 1840 | O | ASP | A | 238 | 27.899 | 11.481 | 89.767 | 1.00 | 0.00 xxxx | 1840 |
| ATOM | 1841 | CB | ASP | A | 238 | 26.536 | 12.973 | 87.299 | 1.00 | 0.00 xxxx | 1841 |
| ATOM | 1842 | CG | ASP | A | 238 | 27.067 | 13.885 | 86.218 | 1.00 | 0.00 xxxx | 1842 |
| ATOM | 1843 | OD1 | ASP | A | 238 | 28.247 | 13.776 | 85.824 | 1.00 | 0.00 xxxx | 1843 |
| ATOM | 1844 | OD2 | ASP | A | 238 | 26.279 | 14.734 | 85.762 | 1.00 | 0.00 xxxx | 1844 |
| ATOM | 1845 | N | ALA | A | 239 | 26.025 | 10.432 | 89.073 | 1.00 | 0.00 xxxx | 1845 |
| ATOM | 1846 | CA | ALA | A | 239 | 25.549 | 10.070 | 90.408 | 1.00 | 0.00 xxxx | 1846 |
| ATOM | 1847 | C | ALA | A | 239 | 25.271 | 11.317 | 91.243 | 1.00 | 0.00 xxxx | 1847 |
| ATOM | 1848 | O | ALA | A | 239 | 25.662 | 11.417 | 92.406 | 1.00 | 0.00 xxxx | 1848 |
| ATOM | 1849 | CB | ALA | A | 239 | 26.493 | 9.092 | 91.121 | 1.00 | 0.00 xxxx | 1849 |
| ATOM | 1850 | N | THR | A | 240 | 24.590 | 12.283 | 90.626 | 1.00 | 0.00 xxxx | 1850 |
| ATOM | 1851 | CA | THR | A | 240 | 24.058 | 13.399 | 91.396 | 1.00 | 0.00 xxxx | 1851 |
| ATOM | 1852 | C | THR | A | 240 | 22.968 | 12.895 | 92.340 | 1.00 | 0.00 xxxx | 1852 |
| ATOM | 1853 | O | THR | A | 240 | 22.496 | 11.758 | 92.239 | 1.00 | 0.00 xxxx | 1853 |
| ATOM | 1854 | CB | THR | A | 240 | 23.417 | 14.440 | 90.476 | 1.00 | 0.00 xxxx | 1854 |
| ATOM | 1855 | OG1 | THR | A | 240 | 22.331 | 13.837 | 89.764 | 1.00 | 0.00 xxxx | 1855 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1856 | CG2 | THR | A | 240 | 24.422 | 15.016 | 89.473 | 1.00 | 0.00 | xxxx | 1856 |
| ATOM | 1857 | N | ALA | A | 241 | 22.542 | 13.762 | 93.258 | 1.00 | 0.00 | xxxx | 1857 |
| ATOM | 1858 | CA | ALA | A | 241 | 21.444 | 13.384 | 94.147 | 1.00 | 0.00 | xxxx | 1858 |
| ATOM | 1859 | C | ALA | A | 241 | 20.197 | 12.922 | 93.397 | 1.00 | 0.00 | xxxx | 1859 |
| ATOM | 1860 | O | ALA | A | 241 | 19.662 | 11.858 | 93.744 | 1.00 | 0.00 | xxxx | 1860 |
| ATOM | 1861 | CB | ALA | A | 241 | 21.143 | 14.492 | 95.165 | 1.00 | 0.00 | xxxx | 1861 |
| ATOM | 1862 | N | PRO | A | 242 | 19.696 | 13.626 | 92.375 | 1.00 | 0.00 | xxxx | 1862 |
| ATOM | 1863 | CA | PRO | A | 242 | 18.529 | 13.084 | 91.664 | 1.00 | 0.00 | xxxx | 1863 |
| ATOM | 1864 | C | PRO | A | 242 | 18.840 | 11.821 | 90.880 | 1.00 | 0.00 | xxxx | 1864 |
| ATOM | 1865 | O | PRO | A | 242 | 17.951 | 10.979 | 90.725 | 1.00 | 0.00 | xxxx | 1865 |
| ATOM | 1866 | CB | PRO | A | 242 | 18.056 | 14.241 | 90.771 | 1.00 | 0.00 | xxxx | 1866 |
| ATOM | 1867 | CG | PRO | A | 242 | 19.187 | 15.185 | 90.708 | 1.00 | 0.00 | xxxx | 1867 |
| ATOM | 1868 | CD | PRO | A | 242 | 20.012 | 15.003 | 91.949 | 1.00 | 0.00 | xxxx | 1868 |
| ATOM | 1869 | N | GLY | A | 243 | 20.072 | 11.652 | 90.396 | 1.00 | 0.00 | xxxx | 1869 |
| ATOM | 1870 | CA | GLY | A | 243 | 20.421 | 10.405 | 89.729 | 1.00 | 0.00 | xxxx | 1870 |
| ATOM | 1871 | C | GLY | A | 243 | 20.411 | 9.234 | 90.694 | 1.00 | 0.00 | xxxx | 1871 |
| ATOM | 1872 | O | GLY | A | 243 | 19.869 | 8.164 | 90.392 | 1.00 | 0.00 | xxxx | 1872 |
| ATOM | 1873 | N | ILE | A | 244 | 20.995 | 9.423 | 91.880 | 1.00 | 0.00 | xxxx | 1873 |
| ATOM | 1874 | CA | ILE | A | 244 | 20.952 | 8.389 | 92.913 | 1.00 | 0.00 | xxxx | 1874 |
| ATOM | 1875 | C | ILE | A | 244 | 19.513 | 8.030 | 93.257 | 1.00 | 0.00 | xxxx | 1875 |
| ATOM | 1876 | O | ILE | A | 244 | 19.168 | 6.850 | 93.408 | 1.00 | 0.00 | xxxx | 1876 |
| ATOM | 1877 | CB | ILE | A | 244 | 21.745 | 8.848 | 94.148 | 1.00 | 0.00 | xxxx | 1877 |
| ATOM | 1878 | CG1 | ILE | A | 244 | 23.233 | 8.926 | 93.802 | 1.00 | 0.00 | xxxx | 1878 |
| ATOM | 1879 | CG2 | ILE | A | 244 | 21.491 | 7.935 | 95.335 | 1.00 | 0.00 | xxxx | 1879 |
| ATOM | 1880 | CD1 | ILE | A | 244 | 24.048 | 9.638 | 94.852 | 1.00 | 0.00 | xxxx | 1880 |
| ATOM | 1881 | N | GLN | A | 245 | 18.644 | 9.036 | 93.363 | 1.00 | 0.00 | xxxx | 1881 |
| ATOM | 1882 | CA | GLN | A | 245 | 17.257 | 8.751 | 93.706 | 1.00 | 0.00 | xxxx | 1882 |
| ATOM | 1883 | C | GLN | A | 245 | 16.587 | 7.904 | 92.626 | 1.00 | 0.00 | xxxx | 1883 |
| ATOM | 1884 | O | GLN | A | 245 | 15.791 | 7.013 | 92.938 | 1.00 | 0.00 | xxxx | 1884 |
| ATOM | 1885 | CB | GLN | A | 245 | 16.496 | 10.053 | 93.937 | 1.00 | 0.00 | xxxx | 1885 |
| ATOM | 1886 | CG | GLN | A | 245 | 15.085 | 9.835 | 94.443 | 1.00 | 0.00 | xxxx | 1886 |
| ATOM | 1887 | CD | GLN | A | 245 | 15.060 | 9.092 | 95.773 | 1.00 | 0.00 | xxxx | 1887 |
| ATOM | 1888 | OE1 | GLN | A | 245 | 15.750 | 9.467 | 96.722 | 1.00 | 0.00 | xxxx | 1888 |
| ATOM | 1889 | NE2 | GLN | A | 245 | 14.295 | 8.014 | 95.832 | 1.00 | 0.00 | xxxx | 1889 |
| ATOM | 1890 | N | ALA | A | 246 | 16.919 | 8.145 | 91.353 | 1.00 | 0.00 | xxxx | 1890 |
| ATOM | 1891 | CA | ALA | A | 246 | 16.345 | 7.341 | 90.279 | 1.00 | 0.00 | xxxx | 1891 |
| ATOM | 1892 | C | ALA | A | 246 | 16.863 | 5.904 | 90.301 | 1.00 | 0.00 | xxxx | 1892 |
| ATOM | 1893 | O | ALA | A | 246 | 16.121 | 4.980 | 89.942 | 1.00 | 0.00 | xxxx | 1893 |
| ATOM | 1894 | CB | ALA | A | 246 | 16.582 | 8.001 | 88.924 | 1.00 | 0.00 | xxxx | 1894 |
| ATOM | 1895 | N | ILE | A | 247 | 18.113 | 5.690 | 90.717 | 1.00 | 0.00 | xxxx | 1895 |
| ATOM | 1896 | CA | ILE | A | 247 | 18.587 | 4.325 | 90.955 | 1.00 | 0.00 | xxxx | 1896 |
| ATOM | 1897 | C | ILE | A | 247 | 17.725 | 3.647 | 92.016 | 1.00 | 0.00 | xxxx | 1897 |
| ATOM | 1898 | O | ILE | A | 247 | 17.258 | 2.514 | 91.840 | 1.00 | 0.00 | xxxx | 1898 |
| ATOM | 1899 | CB | ILE | A | 247 | 20.070 | 4.327 | 91.361 | 1.00 | 0.00 | xxxx | 1899 |
| ATOM | 1900 | CG1 | ILE | A | 247 | 20.940 | 4.927 | 90.259 | 1.00 | 0.00 | xxxx | 1900 |
| ATOM | 1901 | CG2 | ILE | A | 247 | 20.533 | 2.903 | 91.692 | 1.00 | 0.00 | xxxx | 1901 |
| ATOM | 1902 | CD1 | ILE | A | 247 | 21.292 | 3.964 | 89.184 | 1.00 | 0.00 | xxxx | 1902 |
| ATOM | 1903 | N | LYS | A | 248 | 17.490 | 4.342 | 93.134 | 1.00 | 0.00 | xxxx | 1903 |
| ATOM | 1904 | CA | LYS | A | 248 | 16.681 | 3.779 | 94.214 | 1.00 | 0.00 | xxxx | 1904 |
| ATOM | 1905 | C | LYS | A | 248 | 15.234 | 3.559 | 93.784 | 1.00 | 0.00 | xxxx | 1905 |
| ATOM | 1906 | O | LYS | A | 248 | 14.592 | 2.608 | 94.245 | 1.00 | 0.00 | xxxx | 1906 |
| ATOM | 1907 | CB | LYS | A | 248 | 16.728 | 4.699 | 95.431 | 1.00 | 0.00 | xxxx | 1907 |
| ATOM | 1908 | CG | LYS | A | 248 | 18.108 | 4.863 | 96.041 | 1.00 | 0.00 | xxxx | 1908 |
| ATOM | 1909 | CD | LYS | A | 248 | 18.059 | 5.846 | 97.200 | 1.00 | 0.00 | xxxx | 1909 |
| ATOM | 1910 | CE | LYS | A | 248 | 19.406 | 5.968 | 97.881 | 1.00 | 0.00 | xxxx | 1910 |
| ATOM | 1911 | NZ | LYS | A | 248 | 19.339 | 6.962 | 98.994 | 1.00 | 0.00 | xxxx | 1911 |
| ATOM | 1912 | N | ASP | A | 249 | 14.709 | 4.416 | 92.901 | 1.00 | 0.00 | xxxx | 1912 |
| ATOM | 1913 | CA | ASP | A | 249 | 13.350 | 4.285 | 92.385 | 1.00 | 0.00 | xxxx | 1913 |
| ATOM | 1914 | C | ASP | A | 249 | 13.212 | 3.147 | 91.379 | 1.00 | 0.00 | xxxx | 1914 |
| ATOM | 1915 | O | ASP | A | 249 | 12.078 | 2.765 | 91.056 | 1.00 | 0.00 | xxxx | 1915 |
| ATOM | 1916 | CB | ASP | A | 249 | 12.911 | 5.580 | 91.688 | 1.00 | 0.00 | xxxx | 1916 |
| ATOM | 1917 | CG | ASP | A | 249 | 12.763 | 6.758 | 92.637 | 1.00 | 0.00 | xxxx | 1917 |
| ATOM | 1918 | OD1 | ASP | A | 249 | 12.696 | 6.548 | 93.866 | 1.00 | 0.00 | xxxx | 1918 |
| ATOM | 1919 | OD2 | ASP | A | 249 | 12.697 | 7.906 | 92.134 | 1.00 | 0.00 | xxxx | 1919 |
| ATOM | 1920 | N | GLY | A | 250 | 14.319 | 2.612 | 90.869 | 1.00 | 0.00 | xxxx | 1920 |
| ATOM | 1921 | CA | GLY | A | 250 | 14.265 | 1.554 | 89.881 | 1.00 | 0.00 | xxxx | 1921 |
| ATOM | 1922 | C | GLY | A | 250 | 14.164 | 2.022 | 88.441 | 1.00 | 0.00 | xxxx | 1922 |
| ATOM | 1923 | O | GLY | A | 250 | 14.071 | 1.180 | 87.540 | 1.00 | 0.00 | xxxx | 1923 |
| ATOM | 1924 | N | THR | A | 251 | 14.179 | 3.330 | 88.194 | 1.00 | 0.00 | xxxx | 1924 |
| ATOM | 1925 | CA | THR | A | 251 | 13.998 | 3.850 | 86.841 | 1.00 | 0.00 | xxxx | 1925 |
| ATOM | 1926 | C | THR | A | 251 | 15.314 | 4.102 | 86.118 | 1.00 | 0.00 | xxxx | 1926 |
| ATOM | 1927 | O | THR | A | 251 | 15.324 | 4.183 | 84.881 | 1.00 | 0.00 | xxxx | 1927 |
| ATOM | 1928 | CB | THR | A | 251 | 13.191 | 5.156 | 86.889 | 1.00 | 0.00 | xxxx | 1928 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 1929 | OG1 | THR | A | 251 | 13.881 | 6.094 | 87.723 | 1.00 | 0.00 | xxxx | 1929 |
| ATOM | 1930 | CG2 | THR | A | 251 | 11.778 | 4.916 | 87.433 | 1.00 | 0.00 | xxxx | 1930 |
| ATOM | 1931 | N | LEU | A | 252 | 16.412 | 4.249 | 86.843 | 1.00 | 0.00 | xxxx | 1931 |
| ATOM | 1932 | CA | LEU | A | 252 | 17.732 | 4.400 | 86.245 | 1.00 | 0.00 | xxxx | 1932 |
| ATOM | 1933 | C | LEU | A | 252 | 18.501 | 3.128 | 86.565 | 1.00 | 0.00 | xxxx | 1933 |
| ATOM | 1934 | O | LEU | A | 252 | 18.624 | 2.759 | 87.735 | 1.00 | 0.00 | xxxx | 1934 |
| ATOM | 1935 | CB | LEU | A | 252 | 18.432 | 5.630 | 86.828 | 1.00 | 0.00 | xxxx | 1935 |
| ATOM | 1936 | CG | LEU | A | 252 | 19.763 | 6.044 | 86.193 | 1.00 | 0.00 | xxxx | 1936 |
| ATOM | 1937 | CD1 | LEU | A | 252 | 19.584 | 6.416 | 84.720 | 1.00 | 0.00 | xxxx | 1937 |
| ATOM | 1938 | CD2 | LEU | A | 252 | 20.375 | 7.224 | 86.963 | 1.00 | 0.00 | xxxx | 1938 |
| ATOM | 1939 | N | LEU | A | 253 | 18.960 | 2.428 | 85.521 | 1.00 | 0.00 | xxxx | 1939 |
| ATOM | 1940 | CA | LEU | A | 253 | 19.663 | 1.166 | 85.737 | 1.00 | 0.00 | xxxx | 1940 |
| ATOM | 1941 | C | LEU | A | 253 | 21.013 | 1.394 | 86.390 | 1.00 | 0.00 | xxxx | 1941 |
| ATOM | 1942 | O | LEU | A | 253 | 21.428 | 0.632 | 87.277 | 1.00 | 0.00 | xxxx | 1942 |
| ATOM | 1943 | CB | LEU | A | 253 | 19.849 | 0.445 | 84.402 | 1.00 | 0.00 | xxxx | 1943 |
| ATOM | 1944 | CG | LEU | A | 253 | 20.806 | −0.752 | 84.408 | 1.00 | 0.00 | xxxx | 1944 |
| ATOM | 1945 | CD1 | LEU | A | 253 | 20.224 | −1.883 | 85.239 | 1.00 | 0.00 | xxxx | 1945 |
| ATOM | 1946 | CD2 | LEU | A | 253 | 21.120 | −1.217 | 82.996 | 1.00 | 0.00 | xxxx | 1946 |
| ATOM | 1947 | N | GLY | A | 254 | 21.721 | 2.421 | 85.957 | 1.00 | 0.00 | xxxx | 1947 |
| ATOM | 1948 | CA | GLY | A | 254 | 23.032 | 2.651 | 86.518 | 1.00 | 0.00 | xxxx | 1948 |
| ATOM | 1949 | C | GLY | A | 254 | 23.542 | 4.002 | 86.097 | 1.00 | 0.00 | xxxx | 1949 |
| ATOM | 1950 | O | GLY | A | 254 | 23.017 | 4.642 | 85.180 | 1.00 | 0.00 | xxxx | 1950 |
| ATOM | 1951 | N | THR | A | 255 | 24.595 | 4.416 | 86.787 | 1.00 | 0.00 | xxxx | 1951 |
| ATOM | 1952 | CA | THR | A | 255 | 25.286 | 5.638 | 86.447 | 1.00 | 0.00 | xxxx | 1952 |
| ATOM | 1953 | C | THR | A | 255 | 26.754 | 5.460 | 86.803 | 1.00 | 0.00 | xxxx | 1953 |
| ATOM | 1954 | O | THR | A | 255 | 27.211 | 4.363 | 87.144 | 1.00 | 0.00 | xxxx | 1954 |
| ATOM | 1955 | CB | THR | A | 255 | 24.607 | 6.845 | 87.111 | 1.00 | 0.00 | xxxx | 1955 |
| ATOM | 1956 | OG1 | THR | A | 255 | 25.209 | 8.054 | 86.631 | 1.00 | 0.00 | xxxx | 1956 |
| ATOM | 1957 | CG2 | THR | A | 255 | 24.713 | 6.788 | 88.627 | 1.00 | 0.00 | xxxx | 1957 |
| ATOM | 1958 | N | VAL | A | 256 | 27.504 | 6.539 | 86.670 | 1.00 | 0.00 | xxxx | 1958 |
| ATOM | 1959 | CA | VAL | A | 256 | 28.924 | 6.541 | 86.956 | 1.00 | 0.00 | xxxx | 1959 |
| ATOM | 1960 | C | VAL | A | 256 | 29.165 | 7.740 | 87.852 | 1.00 | 0.00 | xxxx | 1960 |
| ATOM | 1961 | O | VAL | A | 256 | 28.821 | 8.862 | 87.478 | 1.00 | 0.00 | xxxx | 1961 |
| ATOM | 1962 | CB | VAL | A | 256 | 29.741 | 6.649 | 85.658 | 1.00 | 0.00 | xxxx | 1962 |
| ATOM | 1963 | CG1 | VAL | A | 256 | 31.235 | 6.627 | 85.977 | 1.00 | 0.00 | xxxx | 1963 |
| ATOM | 1964 | CG2 | VAL | A | 256 | 29.356 | 5.528 | 84.679 | 1.00 | 0.00 | xxxx | 1964 |
| ATOM | 1965 | N | LEU | A | 257 | 29.711 | 7.504 | 89.040 | 1.00 | 0.00 | xxxx | 1965 |
| ATOM | 1966 | CA | LEU | A | 257 | 30.015 | 8.606 | 89.941 | 1.00 | 0.00 | xxxx | 1966 |
| ATOM | 1967 | C | LEU | A | 257 | 31.080 | 9.495 | 89.321 | 1.00 | 0.00 | xxxx | 1967 |
| ATOM | 1968 | O | LEU | A | 257 | 32.188 | 9.032 | 89.022 | 1.00 | 0.00 | xxxx | 1968 |
| ATOM | 1969 | CB | LEU | A | 257 | 30.487 | 8.069 | 91.291 | 1.00 | 0.00 | xxxx | 1969 |
| ATOM | 1970 | CG | LEU | A | 257 | 30.976 | 9.158 | 92.256 | 1.00 | 0.00 | xxxx | 1970 |
| ATOM | 1971 | CD1 | LEU | A | 257 | 29.845 | 10.097 | 92.657 | 1.00 | 0.00 | xxxx | 1971 |
| ATOM | 1972 | CD2 | LEU | A | 257 | 31.614 | 8.517 | 93.481 | 1.00 | 0.00 | xxxx | 1972 |
| ATOM | 1973 | N | ASN | A | 258 | 30.718 | 10.764 | 89.095 | 1.00 | 0.00 | xxxx | 1973 |
| ATOM | 1974 | CA | ASN | A | 258 | 31.640 | 11.815 | 88.691 | 1.00 | 0.00 | xxxx | 1974 |
| ATOM | 1975 | C | ASN | A | 258 | 31.941 | 12.557 | 89.986 | 1.00 | 0.00 | xxxx | 1975 |
| ATOM | 1976 | O | ASN | A | 258 | 31.043 | 13.144 | 90.596 | 1.00 | 0.00 | xxxx | 1976 |
| ATOM | 1977 | CB | ASN | A | 258 | 30.968 | 12.719 | 87.655 | 1.00 | 0.00 | xxxx | 1977 |
| ATOM | 1978 | CG | ASN | A | 258 | 31.938 | 13.653 | 86.968 | 1.00 | 0.00 | xxxx | 1978 |
| ATOM | 1979 | OD1 | ASN | A | 258 | 33.139 | 13.611 | 87.231 | 1.00 | 0.00 | xxxx | 1979 |
| ATOM | 1980 | ND2 | ASN | A | 258 | 31.428 | 14.497 | 86.073 | 1.00 | 0.00 | xxxx | 1980 |
| ATOM | 1981 | N | ASP | A | 259 | 33.184 | 12.460 | 90.442 | 1.00 | 0.00 | xxxx | 1981 |
| ATOM | 1982 | CA | ASP | A | 259 | 33.543 | 12.754 | 91.829 | 1.00 | 0.00 | xxxx | 1982 |
| ATOM | 1983 | C | ASP | A | 259 | 33.747 | 14.260 | 91.986 | 1.00 | 0.00 | xxxx | 1983 |
| ATOM | 1984 | O | ASP | A | 259 | 34.868 | 14.780 | 91.900 | 1.00 | 0.00 | xxxx | 1984 |
| ATOM | 1985 | CB | ASP | A | 259 | 34.781 | 11.940 | 92.193 | 1.00 | 0.00 | xxxx | 1985 |
| ATOM | 1986 | CG | ASP | A | 259 | 35.185 | 12.071 | 93.647 | 1.00 | 0.00 | xxxx | 1986 |
| ATOM | 1987 | OD1 | ASP | A | 259 | 34.667 | 12.950 | 94.362 | 1.00 | 0.00 | xxxx | 1987 |
| ATOM | 1988 | OD2 | ASP | A | 259 | 36.067 | 11.285 | 94.061 | 1.00 | 0.00 | xxxx | 1988 |
| ATOM | 1989 | N | ALA | A | 260 | 32.639 | 14.961 | 92.251 | 1.00 | 0.00 | xxxx | 1989 |
| ATOM | 1990 | CA | ALA | A | 260 | 32.671 | 16.414 | 92.388 | 1.00 | 0.00 | xxxx | 1990 |
| ATOM | 1991 | C | ALA | A | 260 | 33.505 | 16.846 | 93.584 | 1.00 | 0.00 | xxxx | 1991 |
| ATOM | 1992 | O | ALA | A | 260 | 34.188 | 17.878 | 93.531 | 1.00 | 0.00 | xxxx | 1992 |
| ATOM | 1993 | CB | ALA | A | 260 | 31.246 | 16.943 | 92.547 | 1.00 | 0.00 | xxxx | 1993 |
| ATOM | 1994 | N | LYS | A | 261 | 33.456 | 16.085 | 94.680 | 1.00 | 0.00 | xxxx | 1994 |
| ATOM | 1995 | CA | LYS | A | 261 | 34.170 | 16.493 | 95.885 | 1.00 | 0.00 | xxxx | 1995 |
| ATOM | 1996 | C | LYS | A | 261 | 35.681 | 16.499 | 95.667 | 1.00 | 0.00 | xxxx | 1996 |
| ATOM | 1997 | O | LYS | A | 261 | 36.364 | 17.463 | 96.037 | 1.00 | 0.00 | xxxx | 1997 |
| ATOM | 1998 | CB | LYS | A | 261 | 33.771 | 15.608 | 97.064 | 1.00 | 0.00 | xxxx | 1998 |
| ATOM | 1999 | CG | LYS | A | 261 | 32.314 | 15.783 | 97.477 | 1.00 | 0.00 | xxxx | 1999 |
| ATOM | 2000 | CD | LYS | A | 261 | 31.976 | 14.931 | 98.695 | 1.00 | 0.00 | xxxx | 2000 |
| ATOM | 2001 | CE | LYS | A | 261 | 30.512 | 15.071 | 99.081 | 1.00 | 0.00 | xxxx | 2001 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 2002 | NZ | LYS | A | 261 | 30.150 | 16.484 | 99.379 | 1.00 | 0.00 | xxxx | 2002 |
| ATOM | 2003 | N | ASN | A | 262 | 36.227 | 15.441 | 95.052 | 1.00 | 0.00 | xxxx | 2003 |
| ATOM | 2004 | CA | ASN | A | 262 | 37.666 | 15.428 | 94.815 | 1.00 | 0.00 | xxxx | 2004 |
| ATOM | 2005 | C | ASN | A | 262 | 38.082 | 16.350 | 93.674 | 1.00 | 0.00 | xxxx | 2005 |
| ATOM | 2006 | O | ASN | A | 262 | 39.187 | 16.901 | 93.721 | 1.00 | 0.00 | xxxx | 2006 |
| ATOM | 2007 | CB | ASN | A | 262 | 38.198 | 14.002 | 94.643 | 1.00 | 0.00 | xxxx | 2007 |
| ATOM | 2008 | CG | ASN | A | 262 | 38.342 | 13.280 | 95.971 | 1.00 | 0.00 | xxxx | 2008 |
| ATOM | 2009 | OD1 | ASN | A | 262 | 39.094 | 13.708 | 96.849 | 1.00 | 0.00 | xxxx | 2009 |
| ATOM | 2010 | ND2 | ASN | A | 262 | 37.614 | 12.190 | 96.125 | 1.00 | 0.00 | xxxx | 2010 |
| ATOM | 2011 | N | GLN | A | 263 | 37.226 | 16.564 | 92.668 | 1.00 | 0.00 | xxxx | 2011 |
| ATOM | 2012 | CA | GLN | A | 263 | 37.565 | 17.566 | 91.657 | 1.00 | 0.00 | xxxx | 2012 |
| ATOM | 2013 | C | GLN | A | 263 | 37.590 | 18.958 | 92.268 | 1.00 | 0.00 | xxxx | 2013 |
| ATOM | 2014 | O | GLN | A | 263 | 38.479 | 19.759 | 91.957 | 1.00 | 0.00 | xxxx | 2014 |
| ATOM | 2015 | CB | GLN | A | 263 | 36.608 | 17.491 | 90.463 | 1.00 | 0.00 | xxxx | 2015 |
| ATOM | 2016 | CG | GLN | A | 263 | 36.799 | 16.209 | 89.647 | 1.00 | 0.00 | xxxx | 2016 |
| ATOM | 2017 | CD | GLN | A | 263 | 35.778 | 16.030 | 88.551 | 1.00 | 0.00 | xxxx | 2017 |
| ATOM | 2018 | OE1 | GLN | A | 263 | 35.494 | 16.960 | 87.787 | 1.00 | 0.00 | xxxx | 2018 |
| ATOM | 2019 | NE2 | GLN | A | 263 | 35.240 | 14.823 | 88.445 | 1.00 | 0.00 | xxxx | 2019 |
| ATOM | 2020 | N | ALA | A | 264 | 36.644 | 19.248 | 93.163 | 1.00 | 0.00 | xxxx | 2020 |
| ATOM | 2021 | CA | ALA | A | 264 | 36.625 | 20.545 | 93.830 | 1.00 | 0.00 | xxxx | 2021 |
| ATOM | 2022 | C | ALA | A | 264 | 37.857 | 20.733 | 94.698 | 1.00 | 0.00 | xxxx | 2022 |
| ATOM | 2023 | O | ALA | A | 264 | 38.449 | 21.820 | 94.715 | 1.00 | 0.00 | xxxx | 2023 |
| ATOM | 2024 | CB | ALA | A | 264 | 35.364 | 20.685 | 94.682 | 1.00 | 0.00 | xxxx | 2024 |
| ATOM | 2025 | N | LYS | A | 265 | 38.251 | 19.688 | 95.441 | 1.00 | 0.00 | xxxx | 2025 |
| ATOM | 2026 | CA | LYS | A | 265 | 39.406 | 19.798 | 96.327 | 1.00 | 0.00 | xxxx | 2026 |
| ATOM | 2027 | C | LYS | A | 265 | 40.695 | 19.981 | 95.537 | 1.00 | 0.00 | xxxx | 2027 |
| ATOM | 2028 | O | LYS | A | 265 | 41.549 | 20.796 | 95.911 | 1.00 | 0.00 | xxxx | 2028 |
| ATOM | 2029 | CB | LYS | A | 265 | 39.493 | 18.569 | 97.235 | 1.00 | 0.00 | xxxx | 2029 |
| ATOM | 2030 | CG | LYS | A | 265 | 40.520 | 18.700 | 98.345 | 1.00 | 0.00 | xxxx | 2030 |
| ATOM | 2031 | CD | LYS | A | 265 | 40.489 | 17.514 | 99.304 | 1.00 | 0.00 | xxxx | 2031 |
| ATOM | 2032 | CE | LYS | A | 265 | 41.232 | 17.846 | 100.589 | 1.00 | 0.00 | xxxx | 2032 |
| ATOM | 2033 | NZ | LYS | A | 265 | 42.514 | 18.556 | 100.318 | 1.00 | 0.00 | xxxx | 2033 |
| ATOM | 2034 | N | ALA | A | 266 | 40.855 | 19.237 | 94.440 | 1.00 | 0.00 | xxxx | 2034 |
| ATOM | 2035 | CA | ALA | A | 266 | 42.049 | 19.392 | 93.619 | 1.00 | 0.00 | xxxx | 2035 |
| ATOM | 2036 | C | ALA | A | 266 | 42.104 | 20.779 | 92.984 | 1.00 | 0.00 | xxxx | 2036 |
| ATOM | 2037 | O | ALA | A | 266 | 43.165 | 21.411 | 92.952 | 1.00 | 0.00 | xxxx | 2037 |
| ATOM | 2038 | CB | ALA | A | 266 | 42.111 | 18.298 | 92.553 | 1.00 | 0.00 | xxxx | 2038 |
| ATOM | 2039 | N | THR | A | 267 | 40.959 | 21.279 | 92.503 | 1.00 | 0.00 | xxxx | 2039 |
| ATOM | 2040 | CA | THR | A | 267 | 40.914 | 22.606 | 91.884 | 1.00 | 0.00 | xxxx | 2040 |
| ATOM | 2041 | C | THR | A | 267 | 41.245 | 23.686 | 92.901 | 1.00 | 0.00 | xxxx | 2041 |
| ATOM | 2042 | O | THR | A | 267 | 42.079 | 24.570 | 92.647 | 1.00 | 0.00 | xxxx | 2042 |
| ATOM | 2043 | CB | THR | A | 267 | 39.529 | 22.864 | 91.293 | 1.00 | 0.00 | xxxx | 2043 |
| ATOM | 2044 | OG1 | THR | A | 267 | 39.235 | 21.873 | 90.304 | 1.00 | 0.00 | xxxx | 2044 |
| ATOM | 2045 | CG2 | THR | A | 267 | 39.483 | 24.234 | 90.627 | 1.00 | 0.00 | xxxx | 2045 |
| ATOM | 2046 | N | PHE | A | 268 | 40.600 | 23.633 | 94.067 | 1.00 | 0.00 | xxxx | 2046 |
| ATOM | 2047 | CA | PHE | A | 268 | 40.922 | 24.609 | 95.096 | 1.00 | 0.00 | xxxx | 2047 |
| ATOM | 2048 | C | PHE | A | 268 | 42.388 | 24.525 | 95.490 | 1.00 | 0.00 | xxxx | 2048 |
| ATOM | 2049 | O | PHE | A | 268 | 43.061 | 25.554 | 95.609 | 1.00 | 0.00 | xxxx | 2049 |
| ATOM | 2050 | CB | PHE | A | 268 | 40.052 | 24.460 | 96.344 | 1.00 | 0.00 | xxxx | 2050 |
| ATOM | 2051 | CG | PHE | A | 268 | 40.498 | 25.370 | 97.436 | 1.00 | 0.00 | xxxx | 2051 |
| ATOM | 2052 | CD1 | PHE | A | 268 | 40.176 | 26.712 | 97.382 | 1.00 | 0.00 | xxxx | 2052 |
| ATOM | 2053 | CD2 | PHE | A | 268 | 41.316 | 24.920 | 98.463 | 1.00 | 0.00 | xxxx | 2053 |
| ATOM | 2054 | CE1 | PHE | A | 268 | 40.627 | 27.585 | 98.350 | 1.00 | 0.00 | xxxx | 2054 |
| ATOM | 2055 | CE2 | PHE | A | 268 | 41.770 | 25.791 | 99.436 | 1.00 | 0.00 | xxxx | 2055 |
| ATOM | 2056 | CZ | PHE | A | 268 | 41.430 | 27.125 | 99.382 | 1.00 | 0.00 | xxxx | 2056 |
| ATOM | 2057 | N | ASN | A | 269 | 42.891 | 23.307 | 95.749 | 1.00 | 0.00 | xxxx | 2057 |
| ATOM | 2058 | CA | ASN | A | 269 | 44.260 | 23.169 | 96.239 | 1.00 | 0.00 | xxxx | 2058 |
| ATOM | 2059 | C | ASN | A | 269 | 45.260 | 23.728 | 95.236 | 1.00 | 0.00 | xxxx | 2059 |
| ATOM | 2060 | O | ASN | A | 269 | 46.225 | 24.396 | 95.627 | 1.00 | 0.00 | xxxx | 2060 |
| ATOM | 2061 | CB | ASN | A | 269 | 44.596 | 21.705 | 96.537 | 1.00 | 0.00 | xxxx | 2061 |
| ATOM | 2062 | CG | ASN | A | 269 | 43.939 | 21.179 | 97.797 | 1.00 | 0.00 | xxxx | 2062 |
| ATOM | 2063 | OD1 | ASN | A | 269 | 44.044 | 19.987 | 98.102 | 1.00 | 0.00 | xxxx | 2063 |
| ATOM | 2064 | ND2 | ASN | A | 269 | 43.253 | 22.045 | 98.526 | 1.00 | 0.00 | xxxx | 2064 |
| ATOM | 2065 | N | ILE | A | 270 | 45.040 | 23.483 | 93.939 | 1.00 | 0.00 | xxxx | 2065 |
| ATOM | 2066 | CA | ILE | A | 270 | 45.923 | 24.058 | 92.923 | 1.00 | 0.00 | xxxx | 2066 |
| ATOM | 2067 | C | ILE | A | 270 | 45.859 | 25.579 | 92.962 | 1.00 | 0.00 | xxxx | 2067 |
| ATOM | 2068 | O | ILE | A | 270 | 46.893 | 26.259 | 92.973 | 1.00 | 0.00 | xxxx | 2068 |
| ATOM | 2069 | CB | ILE | A | 270 | 45.571 | 23.517 | 91.527 | 1.00 | 0.00 | xxxx | 2069 |
| ATOM | 2070 | CG1 | ILE | A | 270 | 46.007 | 22.072 | 91.408 | 1.00 | 0.00 | xxxx | 2070 |
| ATOM | 2071 | CG2 | ILE | A | 270 | 46.236 | 24.370 | 90.425 | 1.00 | 0.00 | xxxx | 2071 |
| ATOM | 2072 | CD1 | ILE | A | 270 | 45.457 | 21.393 | 90.169 | 1.00 | 0.00 | xxxx | 2072 |
| ATOM | 2073 | N | ALA | A | 271 | 44.645 | 26.142 | 92.967 | 1.00 | 0.00 | xxxx | 2073 |
| ATOM | 2074 | CA | ALA | A | 271 | 44.510 | 27.599 | 92.969 | 1.00 | 0.00 | xxxx | 2074 |

-continued

| | | | | | | | | | | | |
|---|---|---|---|---|---|---|---|---|---|---|---|
| CA, calcium<br>HOH, water<br>ACR, Acrylodan<br>K, potassium<br>EDO, ethylene glycol | | | | | | | | | | | |
| ATOM | 2075 C | ALA | A | 271 | 45.108 | 28.206 | 94.229 | 1.00 | 0.00 | xxxx | 2075 |
| ATOM | 2076 O | ALA | A | 271 | 45.705 | 29.292 | 94.188 | 1.00 | 0.00 | xxxx | 2076 |
| ATOM | 2077 CB | ALA | A | 271 | 43.038 | 27.994 | 92.836 | 1.00 | 0.00 | xxxx | 2077 |
| ATOM | 2078 N | TYR | A | 272 | 44.980 | 27.506 | 95.354 | 1.00 | 0.00 | xxxx | 2078 |
| ATOM | 2079 CA | TYR | A | 272 | 45.485 | 28.004 | 96.629 | 1.00 | 0.00 | xxxx | 2079 |
| ATOM | 2080 C | TYR | A | 272 | 47.012 | 28.021 | 96.651 | 1.00 | 0.00 | xxxx | 2080 |
| ATOM | 2081 O | TYR | A | 272 | 47.624 | 28.977 | 97.147 | 1.00 | 0.00 | xxxx | 2081 |
| ATOM | 2082 CB | TYR | A | 272 | 44.909 | 27.125 | 97.741 | 1.00 | 0.00 | xxxx | 2082 |
| ATOM | 2083 CG | TYR | A | 272 | 45.268 | 27.495 | 99.162 | 1.00 | 0.00 | xxxx | 2083 |
| ATOM | 2084 CD1 | TYR | A | 272 | 44.912 | 28.721 | 99.698 | 1.00 | 0.00 | xxxx | 2084 |
| ATOM | 2085 CD2 | TYR | A | 272 | 45.916 | 26.584 | 99.983 | 1.00 | 0.00 | xxxx | 2085 |
| ATOM | 2086 CE1 | TYR | A | 272 | 45.223 | 29.047 | 101.014 | 1.00 | 0.00 | xxxx | 2086 |
| ATOM | 2087 CE2 | TYR | A | 272 | 46.228 | 26.900 | 101.296 | 1.00 | 0.00 | xxxx | 2087 |
| ATOM | 2088 CZ | TYR | A | 272 | 45.876 | 28.133 | 101.799 | 1.00 | 0.00 | xxxx | 2088 |
| ATOM | 2089 OH | TYR | A | 272 | 46.183 | 28.458 | 103.102 | 1.00 | 0.00 | xxxx | 2089 |
| ATOM | 2090 N | GLU | A | 273 | 47.651 | 26.968 | 96.126 | 1.00 | 0.00 | xxxx | 2090 |
| ATOM | 2091 CA | GLU | A | 273 | 49.107 | 26.974 | 96.051 | 1.00 | 0.00 | xxxx | 2091 |
| ATOM | 2092 C | GLU | A | 273 | 49.592 | 28.062 | 95.104 | 1.00 | 0.00 | xxxx | 2092 |
| ATOM | 2093 O | GLU | A | 273 | 50.506 | 28.826 | 95.437 | 1.00 | 0.00 | xxxx | 2093 |
| ATOM | 2094 CB | GLU | A | 273 | 49.621 | 25.598 | 95.622 | 1.00 | 0.00 | xxxx | 2094 |
| ATOM | 2095 CG | GLU | A | 273 | 49.298 | 24.482 | 96.611 | 1.00 | 0.00 | xxxx | 2095 |
| ATOM | 2096 CD | GLU | A | 273 | 49.896 | 24.718 | 97.992 | 1.00 | 0.00 | xxxx | 2096 |
| ATOM | 2097 OE1 | GLU | A | 273 | 51.089 | 25.073 | 98.078 | 1.00 | 0.00 | xxxx | 2097 |
| ATOM | 2098 OE2 | GLU | A | 273 | 49.168 | 24.555 | 98.993 | 1.00 | 0.00 | xxxx | 2098 |
| ATOM | 2099 N | LEU | A | 274 | 48.968 | 28.165 | 93.928 | 1.00 | 0.00 | xxxx | 2099 |
| ATOM | 2100 CA | LEU | A | 274 | 49.361 | 29.188 | 92.963 | 1.00 | 0.00 | xxxx | 2100 |
| ATOM | 2101 C | LEU | A | 274 | 49.151 | 30.589 | 93.519 | 1.00 | 0.00 | xxxx | 2101 |
| ATOM | 2102 O | LEU | A | 274 | 49.959 | 31.488 | 93.267 | 1.00 | 0.00 | xxxx | 2102 |
| ATOM | 2103 CB | LEU | A | 274 | 48.577 | 29.004 | 91.666 | 1.00 | 0.00 | xxxx | 2103 |
| ATOM | 2104 CG | LEU | A | 274 | 48.907 | 27.761 | 90.837 | 1.00 | 0.00 | xxxx | 2104 |
| ATOM | 2105 CD1 | LEU | A | 274 | 47.868 | 27.549 | 89.742 | 1.00 | 0.00 | xxxx | 2105 |
| ATOM | 2106 CD2 | LEU | A | 274 | 50.315 | 27.857 | 90.249 | 1.00 | 0.00 | xxxx | 2106 |
| ATOM | 2107 N | ALA | A | 275 | 48.073 | 30.794 | 94.281 | 1.00 | 0.00 | xxxx | 2107 |
| ATOM | 2108 CA | ALA | A | 275 | 47.819 | 32.092 | 94.897 | 1.00 | 0.00 | xxxx | 2108 |
| ATOM | 2109 C | ALA | A | 275 | 48.931 | 32.488 | 95.856 | 1.00 | 0.00 | xxxx | 2109 |
| ATOM | 2110 O | ALA | A | 275 | 49.166 | 33.683 | 96.076 | 1.00 | 0.00 | xxxx | 2110 |
| ATOM | 2111 CB | ALA | A | 275 | 46.482 | 32.054 | 95.636 | 1.00 | 0.00 | xxxx | 2111 |
| ATOM | 2112 N | GLN | A | 276 | 49.604 | 31.510 | 96.454 | 1.00 | 0.00 | xxxx | 2112 |
| ATOM | 2113 CA | GLN | A | 276 | 50.722 | 31.741 | 97.361 | 1.00 | 0.00 | xxxx | 2113 |
| ATOM | 2114 C | GLN | A | 276 | 52.057 | 31.817 | 96.634 | 1.00 | 0.00 | xxxx | 2114 |
| ATOM | 2115 O | GLN | A | 276 | 53.094 | 31.981 | 97.288 | 1.00 | 0.00 | xxxx | 2115 |
| ATOM | 2116 CB | GLN | A | 276 | 50.784 | 30.628 | 98.409 | 1.00 | 0.00 | xxxx | 2116 |
| ATOM | 2117 CG | GLN | A | 276 | 49.579 | 30.556 | 99.333 | 1.00 | 0.00 | xxxx | 2117 |
| ATOM | 2118 CD | GLN | A | 276 | 49.603 | 29.331 | 100.233 | 1.00 | 0.00 | xxxx | 2118 |
| ATOM | 2119 OE1 | GLN | A | 276 | 48.887 | 28.352 | 100.001 | 1.00 | 0.00 | xxxx | 2119 |
| ATOM | 2120 NE2 | GLN | A | 276 | 50.426 | 29.386 | 101.275 | 1.00 | 0.00 | xxxx | 2120 |
| ATOM | 2121 N | GLY | A | 277 | 52.056 | 31.705 | 95.308 | 1.00 | 0.00 | xxxx | 2121 |
| ATOM | 2122 CA | GLY | A | 277 | 53.294 | 31.680 | 94.550 | 1.00 | 0.00 | xxxx | 2122 |
| ATOM | 2123 C | GLY | A | 277 | 54.045 | 30.369 | 94.618 | 1.00 | 0.00 | xxxx | 2123 |
| ATOM | 2124 O | GLY | A | 277 | 55.264 | 30.349 | 94.415 | 1.00 | 0.00 | xxxx | 2124 |
| ATOM | 2125 N | ILE | A | 278 | 53.350 | 29.266 | 94.886 | 1.00 | 0.00 | xxxx | 2125 |
| ATOM | 2126 CA | ILE | A | 278 | 53.963 | 27.956 | 95.076 | 1.00 | 0.00 | xxxx | 2126 |
| ATOM | 2127 C | ILE | A | 278 | 53.561 | 27.072 | 93.905 | 1.00 | 0.00 | xxxx | 2127 |
| ATOM | 2128 O | ILE | A | 278 | 52.384 | 27.034 | 93.527 | 1.00 | 0.00 | xxxx | 2128 |
| ATOM | 2129 CB | ILE | A | 278 | 53.511 | 27.336 | 96.409 | 1.00 | 0.00 | xxxx | 2129 |
| ATOM | 2130 CG1 | ILE | A | 278 | 53.891 | 28.251 | 97.577 | 1.00 | 0.00 | xxxx | 2130 |
| ATOM | 2131 CG2 | ILE | A | 278 | 54.097 | 25.940 | 96.585 | 1.00 | 0.00 | xxxx | 2131 |
| ATOM | 2132 CD1 | ILE | A | 278 | 53.323 | 27.804 | 98.910 | 1.00 | 0.00 | xxxx | 2132 |
| ATOM | 2133 N | THR | A | 279 | 54.528 | 26.350 | 93.339 | 1.00 | 0.00 | xxxx | 2133 |
| ATOM | 2134 CA | THR | A | 279 | 54.222 | 25.468 | 92.210 | 1.00 | 0.00 | xxxx | 2134 |
| ATOM | 2135 C | THR | A | 279 | 53.522 | 24.206 | 92.708 | 1.00 | 0.00 | xxxx | 2135 |
| ATOM | 2136 O | THR | A | 279 | 54.030 | 23.542 | 93.616 | 1.00 | 0.00 | xxxx | 2136 |
| ATOM | 2137 CB | THR | A | 279 | 55.507 | 25.085 | 91.474 | 1.00 | 0.00 | xxxx | 2137 |
| ATOM | 2138 OG1 | THR | A | 279 | 56.136 | 26.266 | 90.970 | 1.00 | 0.00 | xxxx | 2138 |
| ATOM | 2139 CG2 | THR | A | 279 | 55.206 | 24.153 | 90.305 | 1.00 | 0.00 | xxxx | 2139 |
| ATOM | 2140 N | PRO | A | 280 | 52.372 | 23.844 | 92.141 | 1.00 | 0.00 | xxxx | 2140 |
| ATOM | 2141 CA | PRO | A | 280 | 51.693 | 22.611 | 92.562 | 1.00 | 0.00 | xxxx | 2141 |
| ATOM | 2142 C | PRO | A | 280 | 52.570 | 21.376 | 92.401 | 1.00 | 0.00 | xxxx | 2142 |
| ATOM | 2143 O | PRO | A | 280 | 53.312 | 21.237 | 91.426 | 1.00 | 0.00 | xxxx | 2143 |
| ATOM | 2144 CB | PRO | A | 280 | 50.483 | 22.551 | 91.626 | 1.00 | 0.00 | xxxx | 2144 |
| ATOM | 2145 CG | PRO | A | 280 | 50.192 | 23.983 | 91.318 | 1.00 | 0.00 | xxxx | 2145 |
| ATOM | 2146 CD | PRO | A | 280 | 51.543 | 24.644 | 91.222 | 1.00 | 0.00 | xxxx | 2146 |
| ATOM | 2147 N | THR | A | 281 | 52.488 | 20.487 | 93.396 | 1.00 | 0.00 | xxxx | 2147 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 2148 | CA | THR | A | 281 | 53.091 | 19.158 | 93.353 | 1.00 | 0.00 | xxxx | 2148 |
| ATOM | 2149 | C | THR | A | 281 | 52.078 | 18.181 | 93.927 | 1.00 | 0.00 | xxxx | 2149 |
| ATOM | 2150 | O | THR | A | 281 | 51.140 | 18.577 | 94.621 | 1.00 | 0.00 | xxxx | 2150 |
| ATOM | 2151 | CB | THR | A | 281 | 54.352 | 19.067 | 94.218 | 1.00 | 0.00 | xxxx | 2151 |
| ATOM | 2152 | OG1 | THR | A | 281 | 53.984 | 19.227 | 95.593 | 1.00 | 0.00 | xxxx | 2152 |
| ATOM | 2153 | CG2 | THR | A | 281 | 55.373 | 20.140 | 93.839 | 1.00 | 0.00 | xxxx | 2153 |
| ATOM | 2154 | N | LYS | A | 282 | 52.285 | 16.887 | 93.664 | 1.00 | 0.00 | xxxx | 2154 |
| ATOM | 2155 | CA | LYS | A | 282 | 51.404 | 15.889 | 94.267 | 1.00 | 0.00 | xxxx | 2155 |
| ATOM | 2156 | C | LYS | A | 282 | 51.395 | 16.013 | 95.786 | 1.00 | 0.00 | xxxx | 2156 |
| ATOM | 2157 | O | LYS | A | 282 | 50.346 | 15.855 | 96.420 | 1.00 | 0.00 | xxxx | 2157 |
| ATOM | 2158 | CB | LYS | A | 282 | 51.817 | 14.480 | 93.832 | 1.00 | 0.00 | xxxx | 2158 |
| ATOM | 2159 | CG | LYS | A | 282 | 51.023 | 13.369 | 94.510 | 1.00 | 0.00 | xxxx | 2159 |
| ATOM | 2160 | CD | LYS | A | 282 | 51.461 | 11.990 | 94.042 | 1.00 | 0.00 | xxxx | 2160 |
| ATOM | 2161 | CE | LYS | A | 282 | 50.575 | 10.900 | 94.638 | 1.00 | 0.00 | xxxx | 2161 |
| ATOM | 2162 | NZ | LYS | A | 282 | 50.903 | 9.547 | 94.098 | 1.00 | 0.00 | xxxx | 2162 |
| ATOM | 2163 | N | ASP | A | 283 | 52.544 | 16.331 | 96.386 | 1.00 | 0.00 | xxxx | 2163 |
| ATOM | 2164 | CA | ASP | A | 283 | 52.605 | 16.451 | 97.839 | 1.00 | 0.00 | xxxx | 2164 |
| ATOM | 2165 | C | ASP | A | 283 | 51.787 | 17.636 | 98.342 | 1.00 | 0.00 | xxxx | 2165 |
| ATOM | 2166 | O | ASP | A | 283 | 51.107 | 17.529 | 99.369 | 1.00 | 0.00 | xxxx | 2166 |
| ATOM | 2167 | CB | ASP | A | 283 | 54.055 | 16.583 | 98.304 | 1.00 | 0.00 | xxxx | 2167 |
| ATOM | 2168 | CG | ASP | A | 283 | 54.833 | 15.287 | 98.184 | 1.00 | 0.00 | xxxx | 2168 |
| ATOM | 2169 | OD1 | ASP | A | 283 | 54.208 | 14.208 | 98.131 | 1.00 | 0.00 | xxxx | 2169 |
| ATOM | 2170 | OD2 | ASP | A | 283 | 56.081 | 15.351 | 98.155 | 1.00 | 0.00 | xxxx | 2170 |
| ATOM | 2171 | N | ASN | A | 284 | 51.834 | 18.777 | 97.647 | 1.00 | 0.00 | xxxx | 2171 |
| ATOM | 2172 | CA | ASN | A | 284 | 51.185 | 19.963 | 98.195 | 1.00 | 0.00 | xxxx | 2172 |
| ATOM | 2173 | C | ASN | A | 284 | 49.744 | 20.169 | 97.733 | 1.00 | 0.00 | xxxx | 2173 |
| ATOM | 2174 | O | ASN | A | 284 | 49.050 | 21.012 | 98.313 | 1.00 | 0.00 | xxxx | 2174 |
| ATOM | 2175 | CB | ASN | A | 284 | 52.050 | 21.233 | 98.047 | 1.00 | 0.00 | xxxx | 2175 |
| ATOM | 2176 | CG | ASN | A | 284 | 52.213 | 21.691 | 96.609 | 1.00 | 0.00 | xxxx | 2176 |
| ATOM | 2177 | OD1 | ASN | A | 284 | 51.340 | 21.487 | 95.771 | 1.00 | 0.00 | xxxx | 2177 |
| ATOM | 2178 | ND2 | ASN | A | 284 | 53.339 | 22.348 | 96.327 | 1.00 | 0.00 | xxxx | 2178 |
| ATOM | 2179 | N | ILE | A | 285 | 49.265 | 19.429 | 96.732 | 1.00 | 0.00 | xxxx | 2179 |
| ATOM | 2180 | CA | ILE | A | 285 | 47.845 | 19.447 | 96.394 | 1.00 | 0.00 | xxxx | 2180 |
| ATOM | 2181 | C | ILE | A | 285 | 47.131 | 18.152 | 96.753 | 1.00 | 0.00 | xxxx | 2181 |
| ATOM | 2182 | O | ILE | A | 285 | 45.892 | 18.151 | 96.822 | 1.00 | 0.00 | xxxx | 2182 |
| ATOM | 2183 | CB | ILE | A | 285 | 47.552 | 19.846 | 94.929 | 1.00 | 0.00 | xxxx | 2183 |
| ATOM | 2184 | CG1 | ILE | A | 285 | 47.964 | 18.729 | 93.966 | 1.00 | 0.00 | xxxx | 2184 |
| ATOM | 2185 | CG2 | ILE | A | 285 | 48.214 | 21.176 | 94.591 | 1.00 | 0.00 | xxxx | 2185 |
| ATOM | 2186 | CD1 | ILE | A | 285 | 47.381 | 18.877 | 92.565 | 1.00 | 0.00 | xxxx | 2186 |
| ATOM | 2187 | N | GLY | A | 286 | 47.853 | 17.057 | 96.966 | 1.00 | 0.00 | xxxx | 2187 |
| ATOM | 2188 | CA | GLY | A | 286 | 47.239 | 15.817 | 97.401 | 1.00 | 0.00 | xxxx | 2188 |
| ATOM | 2189 | C | GLY | A | 286 | 46.744 | 14.889 | 96.311 | 1.00 | 0.00 | xxxx | 2189 |
| ATOM | 2190 | O | GLY | A | 286 | 45.989 | 13.958 | 96.620 | 1.00 | 0.00 | xxxx | 2190 |
| ATOM | 2191 | N | TYR | A | 287 | 47.117 | 15.123 | 95.049 | 1.00 | 0.00 | xxxx | 2191 |
| ATOM | 2192 | CA | TYR | A | 287 | 46.656 | 14.329 | 93.912 | 1.00 | 0.00 | xxxx | 2192 |
| ATOM | 2193 | C | TYR | A | 287 | 47.783 | 14.234 | 92.898 | 1.00 | 0.00 | xxxx | 2193 |
| ATOM | 2194 | O | TYR | A | 287 | 48.562 | 15.175 | 92.738 | 1.00 | 0.00 | xxxx | 2194 |
| ATOM | 2195 | CB | TYR | A | 287 | 45.445 | 14.977 | 93.206 | 1.00 | 0.00 | xxxx | 2195 |
| ATOM | 2196 | CG | TYR | A | 287 | 44.247 | 15.146 | 94.110 | 1.00 | 0.00 | xxxx | 2196 |
| ATOM | 2197 | CD1 | TYR | A | 287 | 44.120 | 16.268 | 94.922 | 1.00 | 0.00 | xxxx | 2197 |
| ATOM | 2198 | CD2 | TYR | A | 287 | 43.247 | 14.173 | 94.173 | 1.00 | 0.00 | xxxx | 2198 |
| ATOM | 2199 | CE1 | TYR | A | 287 | 43.045 | 16.414 | 95.778 | 1.00 | 0.00 | xxxx | 2199 |
| ATOM | 2200 | CE2 | TYR | A | 287 | 42.169 | 14.310 | 95.020 | 1.00 | 0.00 | xxxx | 2200 |
| ATOM | 2201 | CZ | TYR | A | 287 | 42.072 | 15.436 | 95.823 | 1.00 | 0.00 | xxxx | 2201 |
| ATOM | 2202 | OH | TYR | A | 287 | 41.016 | 15.600 | 96.685 | 1.00 | 0.00 | xxxx | 2202 |
| ATOM | 2203 | N | ASP | A | 288 | 47.849 | 13.100 | 92.198 | 1.00 | 0.00 | xxxx | 2203 |
| ATOM | 2204 | CA | ASP | A | 288 | 48.789 | 12.962 | 91.092 | 1.00 | 0.00 | xxxx | 2204 |
| ATOM | 2205 | C | ASP | A | 288 | 48.519 | 13.995 | 90.009 | 1.00 | 0.00 | xxxx | 2205 |
| ATOM | 2206 | O | ASP | A | 288 | 47.367 | 14.248 | 89.636 | 1.00 | 0.00 | xxxx | 2206 |
| ATOM | 2207 | CB | ASP | A | 288 | 48.654 | 11.590 | 90.440 | 1.00 | 0.00 | xxxx | 2207 |
| ATOM | 2208 | CG | ASP | A | 288 | 49.223 | 10.483 | 91.279 | 1.00 | 0.00 | xxxx | 2208 |
| ATOM | 2209 | OD1 | ASP | A | 288 | 50.454 | 10.475 | 91.494 | 1.00 | 0.00 | xxxx | 2209 |
| ATOM | 2210 | OD2 | ASP | A | 288 | 48.442 | 9.600 | 91.691 | 1.00 | 0.00 | xxxx | 2210 |
| ATOM | 2211 | N | ILE | A | 289 | 49.601 | 14.562 | 89.485 | 1.00 | 0.00 | xxxx | 2211 |
| ATOM | 2212 | CA | ILE | A | 289 | 49.578 | 15.483 | 88.353 | 1.00 | 0.00 | xxxx | 2212 |
| ATOM | 2213 | C | ILE | A | 289 | 50.142 | 14.742 | 87.150 | 1.00 | 0.00 | xxxx | 2213 |
| ATOM | 2214 | O | ILE | A | 289 | 51.215 | 14.129 | 87.235 | 1.00 | 0.00 | xxxx | 2214 |
| ATOM | 2215 | CB | ILE | A | 289 | 50.395 | 16.751 | 88.654 | 1.00 | 0.00 | xxxx | 2215 |
| ATOM | 2216 | CG1 | ILE | A | 289 | 49.854 | 17.448 | 89.904 | 1.00 | 0.00 | xxxx | 2216 |
| ATOM | 2217 | CG2 | ILE | A | 289 | 50.393 | 17.699 | 87.452 | 1.00 | 0.00 | xxxx | 2217 |
| ATOM | 2218 | CD1 | ILE | A | 289 | 50.751 | 18.579 | 90.397 | 1.00 | 0.00 | xxxx | 2218 |
| ATOM | 2219 | N | THR | A | 290 | 49.412 | 14.779 | 86.040 | 1.00 | 0.00 | xxxx | 2219 |
| ATOM | 2220 | CA | THR | A | 290 | 49.764 | 14.060 | 84.824 | 1.00 | 0.00 | xxxx | 2220 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 2221 | C | THR | A | 290 | 50.168 | 15.065 | 83.756 | 1.00 | 0.00 | xxxx | 2221 |
| ATOM | 2222 | O | THR | A | 290 | 49.539 | 16.124 | 83.623 | 1.00 | 0.00 | xxxx | 2222 |
| ATOM | 2223 | CB | THR | A | 290 | 48.550 | 13.264 | 84.336 | 1.00 | 0.00 | xxxx | 2223 |
| ATOM | 2224 | OG1 | THR | A | 290 | 48.119 | 12.361 | 85.365 | 1.00 | 0.00 | xxxx | 2224 |
| ATOM | 2225 | CG2 | THR | A | 290 | 48.887 | 12.467 | 83.098 | 1.00 | 0.00 | xxxx | 2225 |
| ATOM | 2226 | N | ASP | A | 291 | 51.224 | 14.740 | 83.002 | 1.00 | 0.00 | xxxx | 2226 |
| ATOM | 2227 | CA | ASP | A | 291 | 51.724 | 15.614 | 81.931 | 1.00 | 0.00 | xxxx | 2227 |
| ATOM | 2228 | C | ASP | A | 291 | 52.036 | 17.022 | 82.437 | 1.00 | 0.00 | xxxx | 2228 |
| ATOM | 2229 | O | ASP | A | 291 | 51.957 | 17.998 | 81.684 | 1.00 | 0.00 | xxxx | 2229 |
| ATOM | 2230 | CB | ASP | A | 291 | 50.750 | 15.669 | 80.746 | 1.00 | 0.00 | xxxx | 2230 |
| ATOM | 2231 | CG | ASP | A | 291 | 50.608 | 14.341 | 80.042 | 1.00 | 0.00 | xxxx | 2231 |
| ATOM | 2232 | OD1 | ASP | A | 291 | 51.635 | 13.723 | 79.686 | 1.00 | 0.00 | xxxx | 2232 |
| ATOM | 2233 | OD2 | ASP | A | 291 | 49.463 | 13.904 | 79.833 | 1.00 | 0.00 | xxxx | 2233 |
| ATOM | 2234 | N | GLY | A | 292 | 52.400 | 17.143 | 83.712 | 1.00 | 0.00 | xxxx | 2234 |
| ATOM | 2235 | CA | GLY | A | 292 | 52.765 | 18.411 | 84.313 | 1.00 | 0.00 | xxxx | 2235 |
| ATOM | 2236 | C | GLY | A | 292 | 51.636 | 19.388 | 84.564 | 1.00 | 0.00 | xxxx | 2236 |
| ATOM | 2237 | O | GLY | A | 292 | 51.868 | 20.414 | 85.213 | 1.00 | 0.00 | xxxx | 2237 |
| ATOM | 2238 | N | LYS | A | 293 | 50.420 | 19.117 | 84.082 | 1.00 | 0.00 | xxxx | 2238 |
| ATOM | 2239 | CA | LYS | A | 293 | 49.356 | 20.122 | 84.076 | 1.00 | 0.00 | xxxx | 2239 |
| ATOM | 2240 | C | LYS | A | 293 | 47.995 | 19.597 | 84.474 | 1.00 | 0.00 | xxxx | 2240 |
| ATOM | 2241 | O | LYS | A | 293 | 47.118 | 20.418 | 84.763 | 1.00 | 0.00 | xxxx | 2241 |
| ATOM | 2242 | CB | LYS | A | 293 | 49.212 | 20.750 | 82.682 | 1.00 | 0.00 | xxxx | 2242 |
| ATOM | 2243 | CG | LYS | A | 293 | 50.461 | 21.455 | 82.158 | 1.00 | 0.00 | xxxx | 2243 |
| ATOM | 2244 | CD | LYS | A | 293 | 50.271 | 21.857 | 80.705 | 1.00 | 0.00 | xxxx | 2244 |
| ATOM | 2245 | CE | LYS | A | 293 | 51.504 | 22.554 | 80.140 | 1.00 | 0.00 | xxxx | 2245 |
| ATOM | 2246 | NZ | LYS | A | 293 | 51.585 | 24.001 | 80.516 | 1.00 | 0.00 | xxxx | 2246 |
| ATOM | 2247 | N | TYR | A | 294 | 47.750 | 18.290 | 84.462 | 1.00 | 0.00 | xxxx | 2247 |
| ATOM | 2248 | CA | TYR | A | 294 | 46.396 | 17.766 | 84.562 | 1.00 | 0.00 | xxxx | 2248 |
| ATOM | 2249 | C | TYR | A | 294 | 46.234 | 16.963 | 85.842 | 1.00 | 0.00 | xxxx | 2249 |
| ATOM | 2250 | O | TYR | A | 294 | 47.120 | 16.196 | 86.223 | 1.00 | 0.00 | xxxx | 2250 |
| ATOM | 2251 | CB | TYR | A | 294 | 46.107 | 16.820 | 83.394 | 1.00 | 0.00 | xxxx | 2251 |
| ATOM | 2252 | CG | TYR | A | 294 | 46.133 | 17.445 | 82.024 | 1.00 | 0.00 | xxxx | 2252 |
| ATOM | 2253 | CD1 | TYR | A | 294 | 47.322 | 17.549 | 81.311 | 1.00 | 0.00 | xxxx | 2253 |
| ATOM | 2254 | CD2 | TYR | A | 294 | 44.970 | 17.922 | 81.426 | 1.00 | 0.00 | xxxx | 2254 |
| ATOM | 2255 | CE1 | TYR | A | 294 | 47.355 | 18.114 | 80.041 | 1.00 | 0.00 | xxxx | 2255 |
| ATOM | 2256 | CE2 | TYR | A | 294 | 44.989 | 18.493 | 80.157 | 1.00 | 0.00 | xxxx | 2256 |
| ATOM | 2257 | CZ | TYR | A | 294 | 46.178 | 18.580 | 79.466 | 1.00 | 0.00 | xxxx | 2257 |
| ATOM | 2258 | OH | TYR | A | 294 | 46.194 | 19.133 | 78.209 | 1.00 | 0.00 | xxxx | 2258 |
| ATOM | 2259 | N | VAL | A | 295 | 45.098 | 17.116 | 86.503 | 1.00 | 0.00 | xxxx | 2259 |
| ATOM | 2260 | CA | VAL | A | 295 | 44.716 | 16.234 | 87.600 | 1.00 | 0.00 | xxxx | 2260 |
| ATOM | 2261 | C | VAL | A | 295 | 43.472 | 15.475 | 87.175 | 1.00 | 0.00 | xxxx | 2261 |
| ATOM | 2262 | O | VAL | A | 295 | 42.414 | 16.086 | 86.951 | 1.00 | 0.00 | xxxx | 2262 |
| ATOM | 2263 | CB | VAL | A | 295 | 44.463 | 17.008 | 88.897 | 1.00 | 0.00 | xxxx | 2263 |
| ATOM | 2264 | CG1 | VAL | A | 295 | 43.877 | 16.067 | 89.959 | 1.00 | 0.00 | xxxx | 2264 |
| ATOM | 2265 | CG2 | VAL | A | 295 | 45.740 | 17.633 | 89.385 | 1.00 | 0.00 | xxxx | 2265 |
| ATOM | 2266 | N | TRP | A | 296 | 43.597 | 14.154 | 87.058 | 1.00 | 0.00 | xxxx | 2266 |
| ATOM | 2267 | CA | TRP | A | 296 | 42.499 | 13.286 | 86.651 | 1.00 | 0.00 | xxxx | 2267 |
| ATOM | 2268 | C | TRP | A | 296 | 41.963 | 12.562 | 87.875 | 1.00 | 0.00 | xxxx | 2268 |
| ATOM | 2269 | O | TRP | A | 296 | 42.720 | 11.879 | 88.579 | 1.00 | 0.00 | xxxx | 2269 |
| ATOM | 2270 | CB | TRP | A | 296 | 42.984 | 12.264 | 85.627 | 1.00 | 0.00 | xxxx | 2270 |
| ATOM | 2271 | CG | TRP | A | 296 | 43.564 | 12.875 | 84.394 | 1.00 | 0.00 | xxxx | 2271 |
| ATOM | 2272 | CD1 | TRP | A | 296 | 44.852 | 12.768 | 83.952 | 1.00 | 0.00 | xxxx | 2272 |
| ATOM | 2273 | CD2 | TRP | A | 296 | 42.868 | 13.664 | 83.428 | 1.00 | 0.00 | xxxx | 2273 |
| ATOM | 2274 | NE1 | TRP | A | 296 | 45.002 | 13.449 | 82.772 | 1.00 | 0.00 | xxxx | 2274 |
| ATOM | 2275 | CE2 | TRP | A | 296 | 43.799 | 14.014 | 82.430 | 1.00 | 0.00 | xxxx | 2275 |
| ATOM | 2276 | CE3 | TRP | A | 296 | 41.548 | 14.121 | 83.318 | 1.00 | 0.00 | xxxx | 2276 |
| ATOM | 2277 | CZ2 | TRP | A | 296 | 43.451 | 14.796 | 81.322 | 1.00 | 0.00 | xxxx | 2277 |
| ATOM | 2278 | CZ3 | TRP | A | 296 | 41.197 | 14.894 | 82.230 | 1.00 | 0.00 | xxxx | 2278 |
| ATOM | 2279 | CH2 | TRP | A | 296 | 42.143 | 15.230 | 81.242 | 1.00 | 0.00 | xxxx | 2279 |
| ATOM | 2280 | N | ILE | A | 297 | 40.669 | 12.705 | 88.116 | 1.00 | 0.00 | xxxx | 2280 |
| ATOM | 2281 | CA | ILE | A | 297 | 39.992 | 12.097 | 89.258 | 1.00 | 0.00 | xxxx | 2281 |
| ATOM | 2282 | C | ILE | A | 297 | 39.213 | 10.888 | 88.746 | 1.00 | 0.00 | xxxx | 2282 |
| ATOM | 2283 | O | ILE | A | 297 | 38.483 | 11.019 | 87.754 | 1.00 | 0.00 | xxxx | 2283 |
| ATOM | 2284 | CB | ILE | A | 297 | 39.048 | 13.123 | 89.911 | 1.00 | 0.00 | xxxx | 2284 |
| ATOM | 2285 | CG1 | ILE | A | 297 | 39.825 | 14.359 | 90.410 | 1.00 | 0.00 | xxxx | 2285 |
| ATOM | 2286 | CG2 | ILE | A | 297 | 38.234 | 12.494 | 91.020 | 1.00 | 0.00 | xxxx | 2286 |
| ATOM | 2287 | CD1 | ILE | A | 297 | 40.936 | 14.067 | 91.410 | 1.00 | 0.00 | xxxx | 2287 |
| ATOM | 2288 | N | PRO | A | 298 | 39.335 | 9.717 | 89.373 | 1.00 | 0.00 | xxxx | 2288 |
| ATOM | 2289 | CA | PRO | A | 298 | 38.673 | 8.511 | 88.848 | 1.00 | 0.00 | xxxx | 2289 |
| ATOM | 2290 | C | PRO | A | 298 | 37.153 | 8.600 | 88.852 | 1.00 | 0.00 | xxxx | 2290 |
| ATOM | 2291 | O | PRO | A | 298 | 36.541 | 9.254 | 89.701 | 1.00 | 0.00 | xxxx | 2291 |
| ATOM | 2292 | CB | PRO | A | 298 | 39.139 | 7.402 | 89.803 | 1.00 | 0.00 | xxxx | 2292 |
| ATOM | 2293 | CG | PRO | A | 298 | 40.414 | 7.921 | 90.386 | 1.00 | 0.00 | xxxx | 2293 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 2294 | CD | PRO | A | 298 | 40.239 | 9.409 | 90.493 | 1.00 | 0.00 | xxxx | 2294 |
| ATOM | 2295 | N | TYR | A | 299 | 36.553 | 7.896 | 87.896 | 1.00 | 0.00 | xxxx | 2295 |
| ATOM | 2296 | CA | TYR | A | 299 | 35.127 | 7.600 | 87.859 | 1.00 | 0.00 | xxxx | 2296 |
| ATOM | 2297 | C | TYR | A | 299 | 34.886 | 6.243 | 88.512 | 1.00 | 0.00 | xxxx | 2297 |
| ATOM | 2298 | O | TYR | A | 299 | 35.783 | 5.406 | 88.587 | 1.00 | 0.00 | xxxx | 2298 |
| ATOM | 2299 | CB | TYR | A | 299 | 34.673 | 7.509 | 86.405 | 1.00 | 0.00 | xxxx | 2299 |
| ATOM | 2300 | CG | TYR | A | 299 | 34.448 | 8.814 | 85.684 | 1.00 | 0.00 | xxxx | 2300 |
| ATOM | 2301 | CD1 | TYR | A | 299 | 33.321 | 9.584 | 85.936 | 1.00 | 0.00 | xxxx | 2301 |
| ATOM | 2302 | CD2 | TYR | A | 299 | 35.339 | 9.257 | 84.695 | 1.00 | 0.00 | xxxx | 2302 |
| ATOM | 2303 | CE1 | TYR | A | 299 | 33.088 | 10.760 | 85.251 | 1.00 | 0.00 | xxxx | 2303 |
| ATOM | 2304 | CE2 | TYR | A | 299 | 35.117 | 10.428 | 84.012 | 1.00 | 0.00 | xxxx | 2304 |
| ATOM | 2305 | CZ | TYR | A | 299 | 33.974 | 11.176 | 84.286 | 1.00 | 0.00 | xxxx | 2305 |
| ATOM | 2306 | OH | TYR | A | 299 | 33.700 | 12.363 | 83.634 | 1.00 | 0.00 | xxxx | 2306 |
| ATOM | 2307 | N | LYS | A | 300 | 33.647 | 6.018 | 88.962 | 1.00 | 0.00 | xxxx | 2307 |
| ATOM | 2308 | CA | LYS | A | 300 | 33.281 | 4.772 | 89.636 | 1.00 | 0.00 | xxxx | 2308 |
| ATOM | 2309 | C | LYS | A | 300 | 31.892 | 4.324 | 89.199 | 1.00 | 0.00 | xxxx | 2309 |
| ATOM | 2310 | O | LYS | A | 300 | 30.955 | 5.125 | 89.201 | 1.00 | 0.00 | xxxx | 2310 |
| ATOM | 2311 | CB | LYS | A | 300 | 33.304 | 4.942 | 91.163 | 1.00 | 0.00 | xxxx | 2311 |
| ATOM | 2312 | CG | LYS | A | 300 | 32.995 | 3.686 | 91.943 | 1.00 | 0.00 | xxxx | 2312 |
| ATOM | 2313 | CD | LYS | A | 300 | 33.317 | 3.875 | 93.417 | 1.00 | 0.00 | xxxx | 2313 |
| ATOM | 2314 | CE | LYS | A | 300 | 33.211 | 2.565 | 94.182 | 1.00 | 0.00 | xxxx | 2314 |
| ATOM | 2315 | NZ | LYS | A | 300 | 33.711 | 2.702 | 95.580 | 1.00 | 0.00 | xxxx | 2315 |
| ATOM | 2316 | N | LYS | A | 301 | 31.750 | 3.047 | 88.847 | 1.00 | 0.00 | xxxx | 2316 |
| ATOM | 2317 | CA | LYS | A | 301 | 30.456 | 2.506 | 88.445 | 1.00 | 0.00 | xxxx | 2317 |
| ATOM | 2318 | C | LYS | A | 301 | 29.495 | 2.456 | 89.631 | 1.00 | 0.00 | xxxx | 2318 |
| ATOM | 2319 | O | LYS | A | 301 | 29.872 | 2.039 | 90.729 | 1.00 | 0.00 | xxxx | 2319 |
| ATOM | 2320 | CB | LYS | A | 301 | 30.668 | 1.089 | 87.913 | 1.00 | 0.00 | xxxx | 2320 |
| ATOM | 2321 | CG | LYS | A | 301 | 29.452 | 0.450 | 87.283 | 1.00 | 0.00 | xxxx | 2321 |
| ATOM | 2322 | CD | LYS | A | 301 | 29.731 | −1.015 | 86.917 | 1.00 | 0.00 | xxxx | 2322 |
| ATOM | 2323 | CE | LYS | A | 301 | 30.833 | −1.162 | 85.862 | 1.00 | 0.00 | xxxx | 2323 |
| ATOM | 2324 | NZ | LYS | A | 301 | 31.026 | −2.605 | 85.495 | 1.00 | 0.00 | xxxx | 2324 |
| ATOM | 2325 | N | ILE | A | 302 | 28.237 | 2.850 | 89.401 | 1.00 | 0.00 | xxxx | 2325 |
| ATOM | 2326 | CA | ILE | A | 302 | 27.199 | 2.842 | 90.435 | 1.00 | 0.00 | xxxx | 2326 |
| ATOM | 2327 | C | ILE | A | 302 | 25.950 | 2.144 | 89.895 | 1.00 | 0.00 | xxxx | 2327 |
| ATOM | 2328 | O | ILE | A | 302 | 25.369 | 2.584 | 88.892 | 1.00 | 0.00 | xxxx | 2328 |
| ATOM | 2329 | CB | ILE | A | 302 | 26.836 | 4.266 | 90.901 | 1.00 | 0.00 | xxxx | 2329 |
| ATOM | 2330 | CG1 | ILE | A | 302 | 28.054 | 5.047 | 91.407 | 1.00 | 0.00 | xxxx | 2330 |
| ATOM | 2331 | CG2 | ILE | A | 302 | 25.714 | 4.217 | 91.934 | 1.00 | 0.00 | xxxx | 2331 |
| ATOM | 2332 | CD1 | ILE | A | 302 | 28.689 | 4.485 | 92.677 | 1.00 | 0.00 | xxxx | 2332 |
| ATOM | 2333 | N | THR | A | 303 | 25.510 | 1.093 | 90.584 | 1.00 | 0.00 | xxxx | 2333 |
| ATOM | 2334 | CA | THR | A | 303 | 24.195 | 0.508 | 90.335 | 1.00 | 0.00 | xxxx | 2334 |
| ATOM | 2335 | C | THR | A | 303 | 23.474 | 0.302 | 91.663 | 1.00 | 0.00 | xxxx | 2335 |
| ATOM | 2336 | O | THR | A | 303 | 23.969 | 0.724 | 92.713 | 1.00 | 0.00 | xxxx | 2336 |
| ATOM | 2337 | CB | THR | A | 303 | 24.281 | −0.832 | 89.591 | 1.00 | 0.00 | xxxx | 2337 |
| ATOM | 2338 | OG1 | THR | A | 303 | 24.863 | −1.821 | 90.450 | 1.00 | 0.00 | xxxx | 2338 |
| ATOM | 2339 | CG2 | THR | A | 303 | 25.111 | −0.723 | 88.315 | 1.00 | 0.00 | xxxx | 2339 |
| ATOM | 2340 | O | LYS | A | 304 | 22.265 | −1.400 | 95.049 | 1.00 | 0.00 | xxxx | 2340 |
| ATOM | 2341 | N | LYS | A | 304 | 22.310 | −0.349 | 91.637 | 1.00 | 0.00 | xxxx | 2341 |
| ATOM | 2342 | CA | LYS | A | 304 | 21.616 | −0.622 | 92.889 | 1.00 | 0.00 | xxxx | 2342 |
| ATOM | 2343 | C | LYS | A | 304 | 22.469 | −1.461 | 93.833 | 1.00 | 0.00 | xxxx | 2343 |
| ATOM | 2344 | CB | LYS | A | 304 | 20.262 | −1.290 | 92.628 | 1.00 | 0.00 | xxxx | 2344 |
| ATOM | 2345 | CG | LYS | A | 304 | 20.350 | −2.695 | 92.059 | 1.00 | 0.00 | xxxx | 2345 |
| ATOM | 2346 | CD | LYS | A | 304 | 18.954 | −3.279 | 91.841 | 1.00 | 0.00 | xxxx | 2346 |
| ATOM | 2347 | CE | LYS | A | 304 | 19.020 | −4.700 | 91.304 | 1.00 | 0.00 | xxxx | 2347 |
| ATOM | 2348 | NZ | LYS | A | 304 | 17.663 | −5.253 | 91.028 | 1.00 | 0.00 | xxxx | 2348 |
| ATOM | 2349 | O | ASP | A | 305 | 25.678 | −2.904 | 96.040 | 1.00 | 0.00 | xxxx | 2349 |
| ATOM | 2350 | N | ASP | A | 305 | 23.438 | −2.214 | 93.303 | 1.00 | 0.00 | xxxx | 2350 |
| ATOM | 2351 | CA | ASP | A | 305 | 24.251 | −3.096 | 94.137 | 1.00 | 0.00 | xxxx | 2351 |
| ATOM | 2352 | C | ASP | A | 305 | 25.233 | −2.346 | 95.030 | 1.00 | 0.00 | xxxx | 2352 |
| ATOM | 2353 | CB | ASP | A | 305 | 25.015 | −4.096 | 93.267 | 1.00 | 0.00 | xxxx | 2353 |
| ATOM | 2354 | CG | ASP | A | 305 | 24.095 | −5.040 | 92.517 | 1.00 | 0.00 | xxxx | 2354 |
| ATOM | 2355 | OD1 | ASP | A | 305 | 22.980 | −5.309 | 93.014 | 1.00 | 0.00 | xxxx | 2355 |
| ATOM | 2356 | OD2 | ASP | A | 305 | 24.492 | −5.517 | 91.432 | 1.00 | 0.00 | xxxx | 2356 |
| ATOM | 2357 | O | ASN | A | 306 | 27.103 | 1.971 | 95.532 | 1.00 | 0.00 | xxxx | 2357 |
| ATOM | 2358 | N | ASN | A | 306 | 25.591 | −1.108 | 94.693 | 1.00 | 0.00 | xxxx | 2358 |
| ATOM | 2359 | CA | ASN | A | 306 | 26.605 | −0.378 | 95.451 | 1.00 | 0.00 | xxxx | 2359 |
| ATOM | 2360 | C | ASN | A | 306 | 26.239 | 1.091 | 95.577 | 1.00 | 0.00 | xxxx | 2360 |
| ATOM | 2361 | CB | ASN | A | 306 | 28.002 | −0.550 | 94.848 | 1.00 | 0.00 | xxxx | 2361 |
| ATOM | 2362 | CG | ASN | A | 306 | 28.157 | 0.154 | 93.506 | 1.00 | 0.00 | xxxx | 2362 |
| ATOM | 2363 | OD1 | ASN | A | 306 | 27.213 | 0.251 | 92.728 | 1.00 | 0.00 | xxxx | 2363 |
| ATOM | 2364 | ND2 | ASN | A | 306 | 29.350 | 0.652 | 93.237 | 1.00 | 0.00 | xxxx | 2364 |
| ATOM | 2365 | N | ILE | A | 307 | 24.949 | 1.374 | 95.760 | 1.00 | 0.00 | xxxx | 2365 |
| ATOM | 2366 | CA | ILE | A | 307 | 24.491 | 2.758 | 95.743 | 1.00 | 0.00 | xxxx | 2366 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| ATOM | 2367 | C | ILE | A | 307 | 25.148 | 3.570 | 96.853 | 1.00 | 0.00 | xxxx | 2367 |
| ATOM | 2368 | O | ILE | A | 307 | 25.348 | 4.783 | 96.713 | 1.00 | 0.00 | xxxx | 2368 |
| ATOM | 2369 | CB | ILE | A | 307 | 22.947 | 2.803 | 95.773 | 1.00 | 0.00 | xxxx | 2369 |
| ATOM | 2370 | CG1 | ILE | A | 307 | 22.438 | 4.196 | 95.404 | 1.00 | 0.00 | xxxx | 2370 |
| ATOM | 2371 | CG2 | ILE | A | 307 | 22.418 | 2.342 | 97.124 | 1.00 | 0.00 | xxxx | 2371 |
| ATOM | 2372 | CD1 | ILE | A | 307 | 22.867 | 4.653 | 94.025 | 1.00 | 0.00 | xxxx | 2372 |
| ATOM | 2373 | O | SER | A | 308 | 28.067 | 5.083 | 99.317 | 1.00 | 0.00 | xxxx | 2373 |
| ATOM | 2374 | N | SER | A | 308 | 25.542 | 2.914 | 97.949 | 1.00 | 0.00 | xxxx | 2374 |
| ATOM | 2375 | CA | SER | A | 308 | 26.201 | 3.623 | 99.038 | 1.00 | 0.00 | xxxx | 2375 |
| ATOM | 2376 | C | SER | A | 308 | 27.576 | 4.164 | 98.655 | 1.00 | 0.00 | xxxx | 2376 |
| ATOM | 2377 | CB | SER | A | 308 | 26.294 | 2.732 | 100.281 | 1.00 | 0.00 | xxxx | 2377 |
| ATOM | 2378 | OG | SER | A | 308 | 27.025 | 1.548 | 100.014 | 1.00 | 0.00 | xxxx | 2378 |
| ATOM | 2379 | O | ASP | A | 309 | 30.354 | 6.303 | 96.505 | 1.00 | 0.00 | xxxx | 2379 |
| ATOM | 2380 | N | ASP | A | 309 | 28.208 | 3.628 | 97.602 | 1.00 | 0.00 | xxxx | 2380 |
| ATOM | 2381 | CA | ASP | A | 309 | 29.484 | 4.176 | 97.152 | 1.00 | 0.00 | xxxx | 2381 |
| ATOM | 2382 | C | ASP | A | 309 | 29.348 | 5.594 | 96.612 | 1.00 | 0.00 | xxxx | 2382 |
| ATOM | 2383 | CB | ASP | A | 309 | 30.119 | 3.293 | 96.076 | 1.00 | 0.00 | xxxx | 2383 |
| ATOM | 2384 | CG | ASP | A | 309 | 30.435 | 1.895 | 96.574 | 1.00 | 0.00 | xxxx | 2384 |
| ATOM | 2385 | OD1 | ASP | A | 309 | 30.291 | 1.646 | 97.790 | 1.00 | 0.00 | xxxx | 2385 |
| ATOM | 2386 | OD2 | ASP | A | 309 | 30.836 | 1.048 | 95.746 | 1.00 | 0.00 | xxxx | 2386 |
| ATOM | 2387 | O | ALA | A | 310 | 27.266 | 9.493 | 96.726 | 1.00 | 0.00 | xxxx | 2387 |
| ATOM | 2388 | N | ALA | A | 310 | 28.140 | 6.016 | 96.251 | 1.00 | 0.00 | xxxx | 2388 |
| ATOM | 2389 | CA | ALA | A | 310 | 27.910 | 7.386 | 95.816 | 1.00 | 0.00 | xxxx | 2389 |
| ATOM | 2390 | C | ALA | A | 310 | 27.485 | 8.298 | 96.957 | 1.00 | 0.00 | xxxx | 2390 |
| ATOM | 2391 | CB | ALA | A | 310 | 26.869 | 7.420 | 94.692 | 1.00 | 0.00 | xxxx | 2391 |
| ATOM | 2392 | O | ALA | A | 311 | 24.594 | 8.506 | 99.260 | 1.00 | 0.00 | xxxx | 2392 |
| ATOM | 2393 | N | ALA | A | 311 | 27.370 | 7.760 | 98.171 | 1.00 | 0.00 | xxxx | 2393 |
| ATOM | 2394 | CA | ALA | A | 311 | 26.990 | 8.515 | 99.366 | 1.00 | 0.00 | xxxx | 2394 |
| ATOM | 2395 | C | ALA | A | 311 | 25.625 | 9.178 | 99.219 | 1.00 | 0.00 | xxxx | 2395 |
| ATOM | 2396 | CB | ALA | A | 311 | 28.065 | 9.543 | 99.730 | 1.00 | 0.00 | xxxx | 2396 |
| HETATM | 2397 | CA | CA | B | 1 | 16.457 | −6.247 | 69.477 | 1.00 | 0.00 | xxxx | 2397 |
| HETATM | 2398 | K | K | C | 1 | 8.586 | −1.863 | 85.542 | 1.00 | 0.00 | xxxx | 2398 |
| HETATM | 2399 | C2 | GLC | D | 1 | 28.679 | 16.468 | 83.705 | 1.00 | 0.00 | xxxx | 2399 |
| HETATM | 2400 | C3 | GLC | D | 1 | 27.481 | 17.202 | 83.221 | 1.00 | 0.00 | xxxx | 2400 |
| HETATM | 2401 | C4 | GLC | D | 1 | 27.709 | 18.688 | 83.223 | 1.00 | 0.00 | xxxx | 2401 |
| HETATM | 2402 | C5 | GLC | D | 1 | 28.951 | 19.065 | 82.410 | 1.00 | 0.00 | xxxx | 2402 |
| HETATM | 2403 | C6 | GLC | D | 1 | 29.243 | 20.532 | 82.547 | 1.00 | 0.00 | xxxx | 2403 |
| HETATM | 2404 | C1 | GLC | D | 1 | 29.897 | 16.851 | 82.877 | 1.00 | 0.00 | xxxx | 2404 |
| HETATM | 2405 | O1 | GLC | D | 1 | 31.017 | 16.223 | 83.335 | 1.00 | 0.00 | xxxx | 2405 |
| HETATM | 2406 | O2 | GLC | D | 1 | 28.476 | 15.049 | 83.557 | 1.00 | 0.00 | xxxx | 2406 |
| HETATM | 2407 | O3 | GLC | D | 1 | 26.342 | 16.887 | 84.074 | 1.00 | 0.00 | xxxx | 2407 |
| HETATM | 2408 | O4 | GLC | D | 1 | 26.558 | 19.344 | 82.679 | 1.00 | 0.00 | xxxx | 2408 |
| HETATM | 2409 | O5 | GLC | D | 1 | 30.117 | 18.327 | 82.909 | 1.00 | 0.00 | xxxx | 2409 |
| HETATM | 2410 | O6 | GLC | D | 1 | 30.409 | 20.896 | 81.835 | 1.00 | 0.00 | xxxx | 2410 |
| HETATM | 2411 | C1 | EDO | E | 1 | 28.447 | 15.468 | 78.549 | 1.00 | 0.00 | xxxx | 2411 |
| HETATM | 2412 | O1 | EDO | E | 1 | 27.629 | 15.608 | 79.715 | 1.00 | 0.00 | xxxx | 2412 |
| HETATM | 2413 | C2 | EDO | E | 1 | 29.009 | 16.837 | 78.200 | 1.00 | 0.00 | xxxx | 2413 |
| HETATM | 2414 | O2 | EDO | E | 1 | 27.978 | 17.680 | 77.675 | 1.00 | 0.00 | xxxx | 2414 |
| HETATM | 2415 | C1 | EDO | E | 2 | 53.188 | 23.568 | 84.402 | 1.00 | 0.00 | xxxx | 2415 |
| HETATM | 2416 | O1 | EDO | E | 2 | 53.278 | 22.553 | 83.402 | 1.00 | 0.00 | xxxx | 2416 |
| HETATM | 2417 | C2 | EDO | E | 2 | 51.756 | 24.090 | 84.478 | 1.00 | 0.00 | xxxx | 2417 |
| HETATM | 2418 | O2 | EDO | E | 2 | 51.308 | 24.639 | 83.236 | 1.00 | 0.00 | xxxx | 2418 |
| HETATM | 2419 | C01 | ACR | H | 1 | 19.055 | 26.785 | 76.517 | 1.00 | 0.00 | xxxx | 2419 |
| HETATM | 2420 | N02 | ACR | H | 1 | 20.403 | 26.622 | 76.004 | 1.00 | 0.00 | xxxx | 2420 |
| HETATM | 2421 | C03 | ACR | H | 1 | 20.830 | 27.369 | 74.835 | 1.00 | 0.00 | xxxx | 2421 |
| HETATM | 2422 | C04 | ACR | H | 1 | 21.328 | 25.718 | 76.663 | 1.00 | 0.00 | xxxx | 2422 |
| HETATM | 2423 | C05 | ACR | H | 1 | 22.614 | 25.565 | 76.162 | 1.00 | 0.00 | xxxx | 2423 |
| HETATM | 2424 | C06 | ACR | H | 1 | 23.528 | 24.678 | 76.800 | 1.00 | 0.00 | xxxx | 2424 |
| HETATM | 2425 | C07 | ACR | H | 1 | 23.153 | 23.984 | 77.912 | 1.00 | 0.00 | xxxx | 2425 |
| HETATM | 2426 | C08 | ACR | H | 1 | 21.832 | 24.146 | 78.425 | 1.00 | 0.00 | xxxx | 2426 |
| HETATM | 2427 | C09 | ACR | H | 1 | 20.933 | 25.003 | 77.796 | 1.00 | 0.00 | xxxx | 2427 |
| HETATM | 2428 | C10 | ACR | H | 1 | 24.080 | 23.107 | 78.556 | 1.00 | 0.00 | xxxx | 2428 |
| HETATM | 2429 | C11 | ACR | H | 1 | 25.359 | 22.951 | 78.034 | 1.00 | 0.00 | xxxx | 2429 |
| HETATM | 2430 | C12 | ACR | H | 1 | 25.728 | 23.661 | 76.894 | 1.00 | 0.00 | xxxx | 2430 |
| HETATM | 2431 | C13 | ACR | H | 1 | 24.838 | 24.526 | 76.273 | 1.00 | 0.00 | xxxx | 2431 |
| HETATM | 2432 | C14 | ACR | H | 1 | 26.395 | 22.024 | 78.667 | 1.00 | 0.00 | xxxx | 2432 |
| HETATM | 2433 | O15 | ACR | H | 1 | 27.467 | 21.949 | 78.192 | 1.00 | 0.00 | xxxx | 2433 |
| HETATM | 2434 | C16 | ACR | H | 1 | 26.126 | 21.160 | 79.883 | 1.00 | 0.00 | xxxx | 2434 |
| HETATM | 2435 | C17 | ACR | H | 1 | 26.800 | 19.811 | 79.689 | 1.00 | 0.00 | xxxx | 2435 |
| HETATM | 2436 | O | HOH | S | 1 | 30.092 | 16.560 | 69.763 | 1.00 | 0.00 | xxxx | 2436 |
| HETATM | 2437 | O | HOH | S | 2 | 36.450 | 31.048 | 102.042 | 1.00 | 0.00 | xxxx | 2437 |
| HETATM | 2438 | O | HOH | S | 3 | 16.169 | 1.966 | 83.610 | 1.00 | 0.00 | xxxx | 2438 |
| HETATM | 2439 | O | HOH | S | 4 | 27.012 | −3.982 | 66.101 | 1.00 | 0.00 | xxxx | 2439 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| HETATM | 2440 | O | HOH | S | 5 | 27.395 | 35.750 | 89.728 | 1.00 | 0.00 | xxxx | 2440 |
| HETATM | 2441 | O | HOH | S | 6 | 35.304 | 11.725 | 88.646 | 1.00 | 0.00 | xxxx | 2441 |
| HETATM | 2442 | O | HOH | S | 7 | 34.716 | 3.959 | 68.498 | 1.00 | 0.00 | xxxx | 2442 |
| HETATM | 2443 | O | HOH | S | 8 | 16.439 | 12.089 | 65.942 | 1.00 | 0.00 | xxxx | 2443 |
| HETATM | 2444 | O | HOH | S | 9 | 6.696 | 12.145 | 83.586 | 1.00 | 0.00 | xxxx | 2444 |
| HETATM | 2445 | O | HOH | S | 10 | 14.814 | −3.632 | 76.616 | 1.00 | 0.00 | xxxx | 2445 |
| HETATM | 2446 | O | HOH | S | 11 | 23.616 | 15.519 | 85.687 | 1.00 | 0.00 | xxxx | 2446 |
| HETATM | 2447 | O | HOH | S | 12 | 46.338 | 12.955 | 87.369 | 1.00 | 0.00 | xxxx | 2447 |
| HETATM | 2448 | O | HOH | S | 13 | 26.279 | 2.184 | 66.534 | 1.00 | 0.00 | xxxx | 2448 |
| HETATM | 2449 | O | HOH | S | 14 | 34.001 | 1.213 | 88.945 | 1.00 | 0.00 | xxxx | 2449 |
| HETATM | 2450 | O | HOH | S | 15 | 34.606 | 16.880 | 82.868 | 1.00 | 0.00 | xxxx | 2450 |
| HETATM | 2451 | O | HOH | S | 16 | 12.461 | 8.169 | 88.923 | 1.00 | 0.00 | xxxx | 2451 |
| HETATM | 2452 | O | HOH | S | 17 | 37.297 | 16.495 | 82.586 | 1.00 | 0.00 | xxxx | 2452 |
| HETATM | 2453 | O | HOH | S | 18 | 43.859 | 19.311 | 77.028 | 1.00 | 0.00 | xxxx | 2453 |
| HETATM | 2454 | O | HOH | S | 19 | 28.529 | −3.638 | 85.001 | 1.00 | 0.00 | xxxx | 2454 |
| HETATM | 2455 | O | HOH | S | 20 | 33.875 | 38.445 | 74.722 | 1.00 | 0.00 | xxxx | 2455 |
| HETATM | 2456 | O | HOH | S | 21 | 17.882 | 0.880 | 89.534 | 1.00 | 0.00 | xxxx | 2456 |
| HETATM | 2457 | O | HOH | S | 22 | 11.808 | 11.066 | 65.996 | 1.00 | 0.00 | xxxx | 2457 |
| HETATM | 2458 | O | HOH | S | 23 | 24.159 | −9.493 | 70.074 | 1.00 | 0.00 | xxxx | 2458 |
| HETATM | 2459 | O | HOH | S | 24 | 20.576 | −0.886 | 89.292 | 1.00 | 0.00 | xxxx | 2459 |
| HETATM | 2460 | O | HOH | S | 25 | 29.190 | 18.985 | 97.045 | 1.00 | 0.00 | xxxx | 2460 |
| HETATM | 2461 | O | HOH | S | 26 | 26.788 | 39.605 | 80.411 | 1.00 | 0.00 | xxxx | 2461 |
| HETATM | 2462 | O | HOH | S | 27 | 24.557 | 18.202 | 85.565 | 1.00 | 0.00 | xxxx | 2462 |
| HETATM | 2463 | O | HOH | S | 28 | 35.400 | 13.582 | 82.109 | 1.00 | 0.00 | xxxx | 2463 |
| HETATM | 2464 | O | HOH | S | 29 | 44.791 | 21.375 | 70.688 | 1.00 | 0.00 | xxxx | 2464 |
| HETATM | 2465 | O | HOH | S | 30 | 6.697 | 10.506 | 76.242 | 1.00 | 0.00 | xxxx | 2465 |
| HETATM | 2466 | O | HOH | S | 31 | 51.672 | 12.982 | 77.051 | 1.00 | 0.00 | xxxx | 2466 |
| HETATM | 2467 | O | HOH | S | 32 | 56.034 | 19.661 | 97.314 | 1.00 | 0.00 | xxxx | 2467 |
| HETATM | 2468 | O | HOH | S | 33 | 29.447 | 38.703 | 87.461 | 1.00 | 0.00 | xxxx | 2468 |
| HETATM | 2469 | O | HOH | S | 34 | 31.834 | 40.107 | 87.450 | 1.00 | 0.00 | xxxx | 2469 |
| HETATM | 2470 | O | HOH | S | 35 | 26.756 | 8.061 | 76.968 | 1.00 | 0.00 | xxxx | 2470 |
| HETATM | 2471 | O | HOH | S | 36 | 24.158 | −3.872 | 85.032 | 1.00 | 0.00 | xxxx | 2471 |
| HETATM | 2472 | O | HOH | S | 37 | 28.052 | −9.997 | 82.594 | 1.00 | 0.00 | xxxx | 2472 |
| HETATM | 2473 | O | HOH | S | 38 | 34.765 | −2.208 | 85.587 | 1.00 | 0.00 | xxxx | 2473 |
| HETATM | 2474 | O | HOH | S | 39 | 44.975 | 12.459 | 90.427 | 1.00 | 0.00 | xxxx | 2474 |
| HETATM | 2475 | O | HOH | S | 40 | 15.133 | −2.935 | 64.022 | 1.00 | 0.00 | xxxx | 2475 |
| HETATM | 2476 | O | HOH | S | 41 | 8.577 | 16.115 | 72.053 | 1.00 | 0.00 | xxxx | 2476 |
| HETATM | 2477 | O | HOH | S | 42 | 7.570 | 15.181 | 85.619 | 1.00 | 0.00 | xxxx | 2477 |
| HETATM | 2478 | O | HOH | S | 43 | 26.618 | 25.114 | 89.009 | 1.00 | 0.00 | xxxx | 2478 |
| HETATM | 2479 | O | HOH | S | 44 | 15.306 | 11.677 | 90.607 | 1.00 | 0.00 | xxxx | 2479 |
| HETATM | 2480 | O | HOH | S | 45 | 31.455 | 11.143 | 69.784 | 1.00 | 0.00 | xxxx | 2480 |
| HETATM | 2481 | O | HOH | S | 46 | 14.230 | −4.380 | 79.195 | 1.00 | 0.00 | xxxx | 2481 |
| HETATM | 2482 | O | HOH | S | 47 | 28.436 | 31.409 | 74.855 | 1.00 | 0.00 | xxxx | 2482 |
| HETATM | 2483 | O | HOH | S | 48 | 13.398 | −3.445 | 68.777 | 1.00 | 0.00 | xxxx | 2483 |
| HETATM | 2484 | O | HOH | S | 49 | 46.833 | 13.403 | 80.483 | 1.00 | 0.00 | xxxx | 2484 |
| HETATM | 2485 | O | HOH | S | 50 | 39.393 | 9.798 | 85.489 | 1.00 | 0.00 | xxxx | 2485 |
| HETATM | 2486 | O | HOH | S | 51 | 53.217 | 26.247 | 87.539 | 1.00 | 0.00 | xxxx | 2486 |
| HETATM | 2487 | O | HOH | S | 52 | 52.319 | 13.823 | 90.231 | 1.00 | 0.00 | xxxx | 2487 |
| HETATM | 2488 | O | HOH | S | 53 | 25.425 | −10.186 | 83.126 | 1.00 | 0.00 | xxxx | 2488 |
| HETATM | 2489 | O | HOH | S | 54 | 33.599 | −1.151 | 87.935 | 1.00 | 0.00 | xxxx | 2489 |
| HETATM | 2490 | O | HOH | S | 55 | 35.829 | −0.809 | 75.826 | 1.00 | 0.00 | xxxx | 2490 |
| HETATM | 2491 | O | HOH | S | 56 | 44.377 | 39.555 | 97.245 | 1.00 | 0.00 | xxxx | 2491 |
| HETATM | 2492 | O | HOH | S | 57 | 41.203 | 25.747 | 74.709 | 1.00 | 0.00 | xxxx | 2492 |
| HETATM | 2493 | O | HOH | S | 58 | 29.032 | 40.994 | 81.246 | 1.00 | 0.00 | xxxx | 2493 |
| HETATM | 2494 | O | HOH | S | 59 | 29.561 | 24.457 | 100.956 | 1.00 | 0.00 | xxxx | 2494 |
| HETATM | 2495 | O | HOH | S | 60 | 35.032 | 43.355 | 82.796 | 1.00 | 0.00 | xxxx | 2495 |
| HETATM | 2496 | O | HOH | S | 61 | 32.631 | −9.718 | 77.045 | 1.00 | 0.00 | xxxx | 2496 |
| HETATM | 2497 | O | HOH | S | 62 | 13.214 | 11.510 | 86.158 | 1.00 | 0.00 | xxxx | 2497 |
| HETATM | 2498 | O | HOH | S | 63 | 56.614 | 23.565 | 94.666 | 1.00 | 0.00 | xxxx | 2498 |
| HETATM | 2499 | O | HOH | S | 64 | 33.119 | −4.569 | 76.962 | 1.00 | 0.00 | xxxx | 2499 |
| HETATM | 2500 | O | HOH | S | 65 | 12.974 | 21.174 | 73.803 | 1.00 | 0.00 | xxxx | 2500 |
| HETATM | 2501 | O | HOH | S | 66 | 22.604 | 19.997 | 84.777 | 1.00 | 0.00 | xxxx | 2501 |
| HETATM | 2502 | O | HOH | S | 67 | 46.034 | 10.343 | 87.911 | 1.00 | 0.00 | xxxx | 2502 |
| HETATM | 2503 | O | HOH | S | 68 | 23.211 | 33.726 | 89.295 | 1.00 | 0.00 | xxxx | 2503 |
| HETATM | 2504 | O | HOH | S | 69 | 28.425 | 14.026 | 91.190 | 1.00 | 0.00 | xxxx | 2504 |
| HETATM | 2505 | O | HOH | S | 70 | 12.304 | 13.485 | 66.471 | 1.00 | 0.00 | xxxx | 2505 |
| HETATM | 2506 | O | HOH | S | 71 | 19.625 | 11.334 | 96.551 | 1.00 | 0.00 | xxxx | 2506 |
| HETATM | 2507 | O | HOH | S | 72 | 31.429 | −5.274 | 84.049 | 1.00 | 0.00 | xxxx | 2507 |
| HETATM | 2508 | O | HOH | S | 73 | 57.230 | 26.290 | 94.575 | 1.00 | 0.00 | xxxx | 2508 |
| HETATM | 2509 | O | HOH | S | 74 | 30.402 | 8.799 | 68.454 | 1.00 | 0.00 | xxxx | 2509 |
| HETATM | 2510 | O | HOH | S | 75 | 42.305 | 41.421 | 80.757 | 1.00 | 0.00 | xxxx | 2510 |
| HETATM | 2511 | O | HOH | S | 76 | 31.668 | −4.011 | 87.949 | 1.00 | 0.00 | xxxx | 2511 |
| HETATM | 2512 | O | HOH | S | 77 | 31.815 | 41.234 | 84.994 | 1.00 | 0.00 | xxxx | 2512 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| HETATM | 2513 | O | HOH | S | 78 | 23.437 | 16.457 | 93.563 | 1.00 | 0.00 | xxxx | 2513 |
| HETATM | 2514 | O | HOH | S | 79 | 41.303 | 43.139 | 82.512 | 1.00 | 0.00 | xxxx | 2514 |
| HETATM | 2515 | O | HOH | S | 80 | 21.590 | 15.150 | 87.659 | 1.00 | 0.00 | xxxx | 2515 |
| HETATM | 2516 | O | HOH | S | 81 | 18.486 | 10.518 | 65.200 | 1.00 | 0.00 | xxxx | 2516 |
| HETATM | 2517 | O | HOH | S | 82 | 9.071 | −4.275 | 79.356 | 1.00 | 0.00 | xxxx | 2517 |
| HETATM | 2518 | O | HOH | S | 83 | 36.449 | 19.498 | 87.421 | 1.00 | 0.00 | xxxx | 2518 |
| HETATM | 2519 | O | HOH | S | 84 | 21.050 | −3.581 | 88.635 | 1.00 | 0.00 | xxxx | 2519 |
| HETATM | 2520 | O | HOH | S | 85 | 35.483 | 43.694 | 80.045 | 1.00 | 0.00 | xxxx | 2520 |
| HETATM | 2521 | O | HOH | S | 86 | 37.504 | 44.950 | 83.775 | 1.00 | 0.00 | xxxx | 2521 |
| HETATM | 2522 | O | HOH | S | 87 | 16.431 | 0.525 | 86.039 | 1.00 | 0.00 | xxxx | 2522 |
| HETATM | 2523 | O | HOH | S | 88 | 31.460 | 4.265 | 69.160 | 1.00 | 0.00 | xxxx | 2523 |
| HETATM | 2524 | O | HOH | S | 89 | 29.009 | −10.068 | 85.371 | 1.00 | 0.00 | xxxx | 2524 |
| HETATM | 2525 | O | HOH | S | 90 | 13.694 | 13.831 | 68.979 | 1.00 | 0.00 | xxxx | 2525 |
| HETATM | 2526 | O | HOH | S | 91 | 28.377 | 38.397 | 89.848 | 1.00 | 0.00 | xxxx | 2526 |
| HETATM | 2527 | O | HOH | S | 92 | 48.576 | 19.589 | 76.520 | 1.00 | 0.00 | xxxx | 2527 |
| HETATM | 2528 | O | HOH | S | 93 | 39.565 | 14.665 | 76.878 | 1.00 | 0.00 | xxxx | 2528 |
| HETATM | 2529 | O | HOH | S | 94 | 47.590 | 40.078 | 97.330 | 1.00 | 0.00 | xxxx | 2529 |
| HETATM | 2530 | O | HOH | S | 95 | 32.776 | 43.743 | 84.124 | 1.00 | 0.00 | xxxx | 2530 |
| HETATM | 2531 | O | HOH | S | 96 | 43.503 | 9.388 | 88.768 | 1.00 | 0.00 | xxxx | 2531 |
| HETATM | 2532 | O | HOH | S | 97 | 36.606 | 31.514 | 104.837 | 1.00 | 0.00 | xxxx | 2532 |
| HETATM | 2533 | O | HOH | S | 98 | 23.177 | 34.181 | 79.704 | 1.00 | 0.00 | xxxx | 2533 |
| HETATM | 2534 | O | HOH | S | 99 | 49.499 | 25.604 | 101.501 | 1.00 | 0.00 | xxxx | 2534 |
| HETATM | 2535 | O | HOH | S | 100 | 47.490 | 39.442 | 91.128 | 1.00 | 0.00 | xxxx | 2535 |
| HETATM | 2536 | O | HOH | S | 101 | 26.419 | −4.194 | 86.572 | 1.00 | 0.00 | xxxx | 2536 |
| HETATM | 2537 | O | HOH | S | 102 | 34.198 | 38.905 | 87.825 | 1.00 | 0.00 | xxxx | 2537 |
| HETATM | 2538 | O | HOH | S | 103 | 4.491 | 5.093 | 83.968 | 1.00 | 0.00 | xxxx | 2538 |
| HETATM | 2539 | O | HOH | S | 104 | 46.687 | 10.503 | 80.515 | 1.00 | 0.00 | xxxx | 2539 |
| HETATM | 2540 | O | HOH | S | 105 | 29.607 | −7.424 | 79.355 | 1.00 | 0.00 | xxxx | 2540 |
| HETATM | 2541 | O | HOH | S | 106 | 27.866 | 16.980 | 91.747 | 1.00 | 0.00 | xxxx | 2541 |
| HETATM | 2542 | O | HOH | S | 107 | 31.275 | 2.036 | 68.201 | 1.00 | 0.00 | xxxx | 2542 |
| HETATM | 2543 | O | HOH | S | 108 | 7.908 | 12.189 | 66.781 | 1.00 | 0.00 | xxxx | 2543 |
| HETATM | 2544 | O | HOH | S | 109 | 9.363 | −9.067 | 73.636 | 1.00 | 0.00 | xxxx | 2544 |
| HETATM | 2545 | O | HOH | S | 110 | 40.595 | 31.137 | 72.661 | 1.00 | 0.00 | xxxx | 2545 |
| HETATM | 2546 | O | HOH | S | 111 | 35.532 | 40.803 | 77.645 | 1.00 | 0.00 | xxxx | 2546 |
| HETATM | 2547 | O | HOH | S | 112 | 16.446 | 8.631 | 64.211 | 1.00 | 0.00 | xxxx | 2547 |
| HETATM | 2548 | O | HOH | S | 113 | 29.345 | 40.196 | 77.301 | 1.00 | 0.00 | xxxx | 2548 |
| HETATM | 2549 | O | HOH | S | 114 | 17.140 | −3.801 | 86.092 | 1.00 | 0.00 | xxxx | 2549 |
| HETATM | 2550 | O | HOH | S | 115 | 31.311 | −8.460 | 82.052 | 1.00 | 0.00 | xxxx | 2550 |
| HETATM | 2551 | O | HOH | S | 116 | 21.060 | −11.983 | 72.146 | 1.00 | 0.00 | xxxx | 2551 |
| HETATM | 2552 | O | HOH | S | 117 | 32.758 | 46.230 | 85.726 | 1.00 | 0.00 | xxxx | 2552 |
| HETATM | 2553 | O | HOH | S | 118 | 53.994 | 22.636 | 77.590 | 1.00 | 0.00 | xxxx | 2553 |
| HETATM | 2554 | O | HOH | S | 119 | 34.245 | 8.721 | 91.171 | 1.00 | 0.00 | xxxx | 2554 |
| HETATM | 2555 | O | HOH | S | 120 | 38.082 | 10.310 | 98.438 | 1.00 | 0.00 | xxxx | 2555 |
| HETATM | 2556 | O | HOH | S | 121 | 30.850 | 36.982 | 93.600 | 1.00 | 0.00 | xxxx | 2556 |
| HETATM | 2557 | O | HOH | S | 122 | 26.285 | 19.723 | 97.088 | 1.00 | 0.00 | xxxx | 2557 |
| HETATM | 2558 | O | HOH | S | 123 | 45.716 | 40.764 | 80.927 | 1.00 | 0.00 | xxxx | 2558 |
| HETATM | 2559 | O | HOH | S | 124 | 36.475 | 30.550 | 71.465 | 1.00 | 0.00 | xxxx | 2559 |
| HETATM | 2560 | O | HOH | S | 125 | 32.694 | 39.932 | 76.320 | 1.00 | 0.00 | xxxx | 2560 |
| HETATM | 2561 | O | HOH | S | 126 | 50.009 | 10.367 | 86.104 | 1.00 | 0.00 | xxxx | 2561 |
| HETATM | 2562 | O | HOH | S | 127 | 19.479 | −5.083 | 86.899 | 1.00 | 0.00 | xxxx | 2562 |
| HETATM | 2563 | O | HOH | S | 128 | 27.186 | 11.686 | 94.668 | 1.00 | 0.00 | xxxx | 2563 |
| HETATM | 2564 | O | HOH | S | 129 | 6.860 | 11.716 | 87.403 | 1.00 | 0.00 | xxxx | 2564 |
| HETATM | 2565 | O | HOH | S | 130 | 41.852 | 41.554 | 100.254 | 1.00 | 0.00 | xxxx | 2565 |
| HETATM | 2566 | O | HOH | S | 131 | 43.068 | 15.082 | 77.399 | 1.00 | 0.00 | xxxx | 2566 |
| HETATM | 2567 | O | HOH | S | 132 | 33.563 | −10.047 | 74.521 | 1.00 | 0.00 | xxxx | 2567 |
| HETATM | 2568 | O | HOH | S | 133 | 37.144 | 9.300 | 92.542 | 1.00 | 0.00 | xxxx | 2568 |
| HETATM | 2569 | O | HOH | S | 134 | 54.774 | 26.897 | 78.378 | 1.00 | 0.00 | xxxx | 2569 |
| HETATM | 2570 | O | HOH | S | 135 | 15.642 | 9.381 | 61.627 | 1.00 | 0.00 | xxxx | 2570 |
| HETATM | 2571 | O | HOH | S | 136 | 34.168 | 11.752 | 97.033 | 1.00 | 0.00 | xxxx | 2571 |
| HETATM | 2572 | O | HOH | S | 137 | 19.053 | −9.754 | 63.423 | 1.00 | 0.00 | xxxx | 2572 |
| HETATM | 2573 | O | HOH | S | 138 | 18.427 | 9.458 | 97.304 | 1.00 | 0.00 | xxxx | 2573 |
| HETATM | 2574 | O | HOH | S | 139 | 32.375 | 30.044 | 102.996 | 1.00 | 0.00 | xxxx | 2574 |
| HETATM | 2575 | O | HOH | S | 140 | 30.318 | −12.055 | 74.888 | 1.00 | 0.00 | xxxx | 2575 |
| HETATM | 2576 | O | HOH | S | 141 | 25.415 | 17.615 | 92.333 | 1.00 | 0.00 | xxxx | 2576 |
| HETATM | 2577 | O | HOH | S | 142 | 40.031 | 8.276 | 72.106 | 1.00 | 0.00 | xxxx | 2577 |
| HETATM | 2578 | O | HOH | S | 143 | 31.155 | −5.135 | 79.278 | 1.00 | 0.00 | xxxx | 2578 |
| HETATM | 2579 | O | HOH | S | 144 | 20.293 | −13.572 | 84.517 | 1.00 | 0.00 | xxxx | 2579 |
| HETATM | 2580 | O | HOH | S | 145 | 47.032 | 42.857 | 82.340 | 1.00 | 0.00 | xxxx | 2580 |
| HETATM | 2581 | O | HOH | S | 146 | 30.539 | 27.905 | 103.630 | 1.00 | 0.00 | xxxx | 2581 |
| HETATM | 2582 | O | HOH | S | 147 | 26.102 | −11.385 | 69.050 | 1.00 | 0.00 | xxxx | 2582 |
| HETATM | 2583 | O | HOH | S | 148 | 32.306 | 18.813 | 100.642 | 1.00 | 0.00 | xxxx | 2583 |
| HETATM | 2584 | O | HOH | S | 149 | 34.316 | 23.340 | 105.452 | 1.00 | 0.00 | xxxx | 2584 |
| HETATM | 2585 | O | HOH | S | 150 | 48.231 | 40.600 | 93.204 | 1.00 | 0.00 | xxxx | 2585 |

-continued

| CA, calcium<br>HOH, water<br>ACR, Acrylodan<br>K, potassium<br>EDO, ethylene glycol | | | | | | | | | | | | |
|---|---|---|---|---|---|---|---|---|---|---|---|---|
| HETATM | 2586 | O | HOH | S | 151 | 26.105 | 32.866 | 74.276 | 1.00 | 0.00 | xxxx | 2586 |
| HETATM | 2587 | O | HOH | S | 152 | 26.276 | −7.076 | 87.052 | 1.00 | 0.00 | xxxx | 2587 |
| HETATM | 2588 | O | HOH | S | 153 | 28.787 | 27.403 | 97.004 | 1.00 | 0.00 | xxxx | 2588 |
| HETATM | 2589 | O | HOH | S | 154 | 17.129 | −12.891 | 74.110 | 1.00 | 0.00 | xxxx | 2589 |
| HETATM | 2590 | O | HOH | S | 155 | 9.512 | 14.016 | 65.802 | 1.00 | 0.00 | xxxx | 2590 |
| HETATM | 2591 | O | HOH | S | 156 | 21.215 | 17.960 | 93.737 | 1.00 | 0.00 | xxxx | 2591 |
| HETATM | 2592 | O | HOH | S | 157 | 41.716 | 8.612 | 86.096 | 1.00 | 0.00 | xxxx | 2592 |
| HETATM | 2593 | O | HOH | S | 158 | 29.408 | −12.119 | 70.047 | 1.00 | 0.00 | xxxx | 2593 |
| HETATM | 2594 | O | HOH | S | 159 | 25.011 | −12.819 | 82.517 | 1.00 | 0.00 | xxxx | 2594 |
| HETATM | 2595 | O | HOH | S | 160 | 32.663 | −5.811 | 81.679 | 1.00 | 0.00 | xxxx | 2595 |
| HETATM | 2596 | O | HOH | S | 161 | 24.880 | 19.576 | 95.065 | 1.00 | 0.00 | xxxx | 2596 |
| HETATM | 2597 | O | HOH | S | 162 | 44.355 | 29.891 | 71.184 | 1.00 | 0.00 | xxxx | 2597 |
| HETATM | 2598 | O | HOH | S | 163 | 34.518 | 29.416 | 101.548 | 1.00 | 0.00 | xxxx | 2598 |
| HETATM | 2599 | O | HOH | S | 164 | 35.180 | 32.267 | 100.121 | 1.00 | 0.00 | xxxx | 2599 |
| HETATM | 2600 | O | HOH | S | 165 | 23.399 | −10.513 | 72.364 | 1.00 | 0.00 | xxxx | 2600 |
| HETATM | 2601 | O | HOH | S | 166 | 16.052 | 14.146 | 67.637 | 1.00 | 0.00 | xxxx | 2601 |
| HETATM | 2602 | O | HOH | S | 167 | 14.427 | −6.559 | 82.883 | 1.00 | 0.00 | xxxx | 2602 |
| HETATM | 2603 | O | HOH | S | 168 | 13.244 | −2.741 | 65.936 | 1.00 | 0.00 | xxxx | 2603 |
| HETATM | 2604 | O | HOH | S | 169 | 7.373 | 2.815 | 64.826 | 1.00 | 0.00 | xxxx | 2604 |
| HETATM | 2605 | O | HOH | S | 170 | 19.049 | −9.891 | 75.701 | 1.00 | 0.00 | xxxx | 2605 |
| HETATM | 2606 | O | HOH | S | 171 | 45.770 | 25.436 | 70.089 | 1.00 | 0.00 | xxxx | 2606 |
| HETATM | 2607 | O | HOH | S | 172 | 14.520 | 22.711 | 75.198 | 1.00 | 0.00 | xxxx | 2607 |
| HETATM | 2608 | O | HOH | S | 173 | 11.837 | −6.376 | 82.392 | 1.00 | 0.00 | xxxx | 2608 |
| HETATM | 2609 | O | HOH | S | 174 | 42.682 | 22.064 | 101.116 | 1.00 | 0.00 | xxxx | 2609 |
| HETATM | 2610 | O | HOH | S | 175 | 11.747 | −5.386 | 79.675 | 1.00 | 0.00 | xxxx | 2610 |
| HETATM | 2611 | O | HOH | S | 176 | 51.980 | 18.978 | 79.010 | 1.00 | 0.00 | xxxx | 2611 |
| HETATM | 2612 | O | HOH | S | 177 | 28.850 | −7.885 | 86.063 | 1.00 | 0.00 | xxxx | 2612 |
| HETATM | 2613 | O | HOH | S | 178 | 15.864 | −12.993 | 83.108 | 1.00 | 0.00 | xxxx | 2613 |
| HETATM | 2614 | O | HOH | S | 179 | 12.312 | −0.800 | 87.994 | 1.00 | 0.00 | xxxx | 2614 |
| HETATM | 2615 | O | HOH | S | 180 | 22.300 | 7.722 | 64.043 | 1.00 | 0.00 | xxxx | 2615 |
| HETATM | 2616 | O | HOH | S | 181 | 15.971 | 21.384 | 82.137 | 1.00 | 0.00 | xxxx | 2616 |
| HETATM | 2617 | O | HOH | S | 182 | 30.811 | 25.553 | 103.189 | 1.00 | 0.00 | xxxx | 2617 |
| HETATM | 2618 | O | HOH | S | 183 | 29.318 | 13.972 | 70.591 | 1.00 | 0.00 | xxxx | 2618 |
| HETATM | 2619 | O | HOH | S | 184 | 27.674 | 25.600 | 77.740 | 1.00 | 0.00 | xxxx | 2619 |
| HETATM | 2620 | O | HOH | S | 185 | 32.834 | 23.568 | 75.565 | 1.00 | 0.00 | xxxx | 2620 |
| HETATM | 2621 | O | HOH | S | 186 | 15.402 | −10.518 | 83.634 | 1.00 | 0.00 | xxxx | 2621 |
| HETATM | 2622 | O | HOH | S | 187 | 29.808 | 39.756 | 83.574 | 1.00 | 0.00 | xxxx | 2622 |
| HETATM | 2623 | O | HOH | S | 188 | 33.887 | 31.270 | 104.772 | 1.00 | 0.00 | xxxx | 2623 |
| HETATM | 2624 | O | HOH | S | 189 | 20.488 | −11.771 | 76.677 | 1.00 | 0.00 | xxxx | 2624 |
| HETATM | 2625 | O | HOH | S | 190 | 12.518 | 16.212 | 68.881 | 1.00 | 0.00 | xxxx | 2625 |
| HETATM | 2626 | O | HOH | S | 191 | 54.565 | 27.676 | 89.397 | 1.00 | 0.00 | xxxx | 2626 |
| HETATM | 2627 | O | HOH | S | 192 | 53.012 | 16.808 | 74.423 | 1.00 | 0.00 | xxxx | 2627 |
| HETATM | 2628 | O | HOH | S | 193 | 49.804 | 36.751 | 76.677 | 1.00 | 0.00 | xxxx | 2628 |
| HETATM | 2629 | O | HOH | S | 194 | 49.635 | 35.394 | 91.979 | 1.00 | 0.00 | xxxx | 2629 |
| HETATM | 2630 | O | HOH | S | 195 | 13.533 | 9.420 | 90.707 | 1.00 | 0.00 | xxxx | 2630 |
| HETATM | 2631 | O | HOH | S | 196 | 36.374 | −7.847 | 71.968 | 1.00 | 0.00 | xxxx | 2631 |
| HETATM | 2632 | O | HOH | S | 197 | 53.604 | 36.390 | 82.878 | 1.00 | 0.00 | xxxx | 2632 |
| HETATM | 2633 | O | HOH | S | 198 | 51.181 | 15.057 | 75.617 | 1.00 | 0.00 | xxxx | 2633 |
| HETATM | 2634 | O | HOH | S | 199 | 28.232 | 28.892 | 94.774 | 1.00 | 0.00 | xxxx | 2634 |
| HETATM | 2635 | O | HOH | S | 200 | 31.413 | 23.690 | 105.190 | 1.00 | 0.00 | xxxx | 2635 |
| HETATM | 2636 | O | HOH | S | 201 | 35.263 | −5.032 | 85.936 | 1.00 | 0.00 | xxxx | 2636 |
| HETATM | 2637 | O | HOH | S | 202 | 30.282 | 32.380 | 96.955 | 1.00 | 0.00 | xxxx | 2637 |
| HETATM | 2638 | O | HOH | S | 203 | 28.203 | 31.685 | 95.320 | 1.00 | 0.00 | xxxx | 2638 |
| HETATM | 2639 | O | HOH | S | 204 | 49.772 | 37.811 | 90.376 | 1.00 | 0.00 | xxxx | 2639 |
| HETATM | 2640 | O | HOH | S | 205 | 42.346 | 31.385 | 70.795 | 1.00 | 0.00 | xxxx | 2640 |
| HETATM | 2641 | O | HOH | S | 206 | 31.448 | 13.764 | 94.887 | 1.00 | 0.00 | xxxx | 2641 |
| HETATM | 2642 | O | HOH | S | 207 | 45.518 | 14.293 | 78.127 | 1.00 | 0.00 | xxxx | 2642 |
| HETATM | 2643 | O | HOH | S | 208 | 28.442 | 5.875 | 69.185 | 1.00 | 0.00 | xxxx | 2643 |
| HETATM | 2644 | O | HOH | S | 209 | 49.554 | 35.069 | 106.432 | 1.00 | 0.00 | xxxx | 2644 |
| HETATM | 2645 | O | HOH | S | 210 | 27.200 | 6.622 | 67.192 | 1.00 | 0.00 | xxxx | 2645 |
| HETATM | 2646 | O | HOH | S | 211 | 31.168 | 33.125 | 101.975 | 1.00 | 0.00 | xxxx | 2646 |
| HETATM | 2647 | O | HOH | S | 212 | 26.450 | 36.711 | 86.006 | 1.00 | 0.00 | xxxx | 2647 |
| HETATM | 2648 | O | HOH | S | 213 | 55.824 | 32.193 | 83.580 | 1.00 | 0.00 | xxxx | 2648 |
| HETATM | 2649 | O | HOH | S | 214 | 13.304 | 10.253 | 88.335 | 1.00 | 0.00 | xxxx | 2649 |
| HETATM | 2650 | O | HOH | S | 215 | 29.506 | 13.799 | 93.673 | 1.00 | 0.00 | xxxx | 2650 |
| HETATM | 2651 | O | HOH | S | 216 | 20.507 | 9.464 | 64.402 | 1.00 | 0.00 | xxxx | 2651 |
| HETATM | 2652 | O | HOH | S | 217 | 14.748 | 13.431 | 92.671 | 1.00 | 0.00 | xxxx | 2652 |
| HETATM | 2653 | O | HOH | S | 218 | 26.847 | 39.185 | 77.674 | 1.00 | 0.00 | xxxx | 2653 |
| HETATM | 2654 | O | HOH | S | 219 | 10.406 | 16.438 | 66.823 | 1.00 | 0.00 | xxxx | 2654 |
| HETATM | 2655 | O | HOH | S | 220 | 2.716 | 4.132 | 75.046 | 1.00 | 0.00 | xxxx | 2655 |
| HETATM | 2656 | O | HOH | S | 221 | 32.567 | −2.540 | 89.806 | 1.00 | 0.00 | xxxx | 2656 |
| HETATM | 2657 | O | HOH | S | 222 | 48.057 | 8.630 | 88.418 | 1.00 | 0.00 | xxxx | 2657 |
| HETATM | 2658 | O | HOH | S | 223 | 38.623 | 36.281 | 77.233 | 1.00 | 0.00 | xxxx | 2658 |

-continued

CA, calcium
HOH, water
ACR, Acrylodan
K, potassium
EDO, ethylene glycol

| | | | | | | | | | | | | | |
|---|---|---|---|---|---|---|---|---|---|---|---|---|---|
| HETATM | 2659 | O | HOH | S | 224 | 5.367 | 0.438 | 69.681 | 1.00 | 0.00 | xxxx | 2659 |
| HETATM | 2660 | O | HOH | S | 225 | 55.509 | 29.545 | 79.721 | 1.00 | 0.00 | xxxx | 2660 |
| HETATM | 2661 | O | HOH | S | 226 | 45.784 | 11.649 | 77.043 | 1.00 | 0.00 | xxxx | 2661 |
| HETATM | 2662 | O | HOH | S | 227 | 46.921 | 22.993 | 98.717 | 1.00 | 0.00 | xxxx | 2662 |
| HETATM | 2663 | O | HOH | S | 228 | 14.908 | −6.015 | 85.254 | 1.00 | 0.00 | xxxx | 2663 |
| HETATM | 2664 | O | HOH | S | 229 | 41.066 | 29.306 | 109.579 | 1.00 | 0.00 | xxxx | 2664 |
| HETATM | 2665 | O | HOH | S | 230 | 22.133 | 30.392 | 83.355 | 1.00 | 0.00 | xxxx | 2665 |
| HETATM | 2666 | O | HOH | S | 231 | 41.120 | 9.979 | 74.044 | 1.00 | 0.00 | xxxx | 2666 |
| HETATM | 2667 | O | HOH | S | 232 | 51.131 | 37.451 | 106.185 | 1.00 | 0.00 | xxxx | 2667 |
| HETATM | 2668 | O | HOH | S | 233 | 55.796 | 23.522 | 81.726 | 1.00 | 0.00 | xxxx | 2668 |
| HETATM | 2669 | O | HOH | S | 234 | 30.767 | 13.535 | 69.149 | 1.00 | 0.00 | xxxx | 2669 |
| HETATM | 2670 | O | HOH | S | 235 | 30.378 | −13.413 | 72.516 | 1.00 | 0.00 | xxxx | 2670 |
| HETATM | 2671 | O | HOH | S | 236 | 32.947 | 5.925 | 96.446 | 1.00 | 0.00 | xxxx | 2671 |
| HETATM | 2672 | O | HOH | S | 237 | 25.500 | 16.096 | 79.243 | 1.00 | 0.00 | xxxx | 2672 |
| HETATM | 2673 | O | HOH | S | 238 | 26.802 | 29.069 | 75.273 | 1.00 | 0.00 | xxxx | 2673 |
| HETATM | 2674 | O | HOH | S | 239 | 14.192 | 17.963 | 67.834 | 1.00 | 0.00 | xxxx | 2674 |
| HETATM | 2675 | O | HOH | S | 240 | 5.905 | 10.203 | 73.585 | 1.00 | 0.00 | xxxx | 2675 |
| HETATM | 2676 | O | HOH | S | 241 | 4.513 | 7.800 | 73.072 | 1.00 | 0.00 | xxxx | 2676 |
| HETATM | 2677 | O | HOH | S | 242 | 43.660 | 44.657 | 83.268 | 1.00 | 0.00 | xxxx | 2677 |
| HETATM | 2678 | O | HOH | S | 243 | 22.969 | 21.825 | 70.556 | 1.00 | 0.00 | xxxx | 2678 |
| HETATM | 2679 | O | HOH | S | 244 | 22.901 | −13.995 | 84.304 | 1.00 | 0.00 | xxxx | 2679 |
| HETATM | 2680 | O | HOH | S | 245 | 14.508 | 14.371 | 65.000 | 1.00 | 0.00 | xxxx | 2680 |
| HETATM | 2681 | O | HOH | S | 246 | 9.488 | 16.688 | 86.964 | 1.00 | 0.00 | xxxx | 2681 |
| HETATM | 2682 | O | HOH | S | 247 | 54.267 | 24.642 | 79.573 | 1.00 | 0.00 | xxxx | 2682 |
| HETATM | 2683 | O | HOH | S | 248 | 38.086 | 13.849 | 99.533 | 1.00 | 0.00 | xxxx | 2683 |
| HETATM | 2684 | O | HOH | S | 249 | 30.344 | 25.159 | 107.966 | 1.00 | 0.00 | xxxx | 2684 |
| HETATM | 2685 | O | HOH | S | 250 | 27.639 | −1.869 | 64.685 | 1.00 | 0.00 | xxxx | 2685 |
| HETATM | 2686 | O | HOH | S | 251 | 37.885 | 24.209 | 105.067 | 1.00 | 0.00 | xxxx | 2686 |
| HETATM | 2687 | O | HOH | S | 252 | 24.776 | −0.007 | 98.826 | 1.00 | 0.00 | xxxx | 2687 |
| HETATM | 2688 | O | HOH | S | 253 | 30.015 | 19.826 | 99.611 | 1.00 | 0.00 | xxxx | 2688 |
| HETATM | 2689 | O | HOH | S | 254 | 23.631 | −4.295 | 63.805 | 1.00 | 0.00 | xxxx | 2689 |
| HETATM | 2690 | O | HOH | S | 255 | 18.259 | −12.433 | 71.943 | 1.00 | 0.00 | xxxx | 2690 |
| HETATM | 2691 | O | HOH | S | 256 | 14.315 | 10.556 | 64.808 | 1.00 | 0.00 | xxxx | 2691 |
| HETATM | 2692 | O | HOH | S | 257 | 41.561 | 5.948 | 79.800 | 1.00 | 0.00 | xxxx | 2692 |
| HETATM | 2693 | O | HOH | S | 258 | 54.871 | 21.422 | 81.888 | 1.00 | 0.00 | xxxx | 2693 |
| HETATM | 2694 | O | HOH | S | 259 | 10.817 | −9.778 | 75.712 | 1.00 | 0.00 | xxxx | 2694 |
| HETATM | 2695 | O | HOH | S | 260 | 47.176 | 25.537 | 68.505 | 1.00 | 0.00 | xxxx | 2695 |
| HETATM | 2696 | O | HOH | S | 261 | 25.754 | −0.489 | 64.311 | 1.00 | 0.00 | xxxx | 2696 |
| HETATM | 2697 | O | HOH | S | 262 | 20.717 | 32.971 | 83.280 | 1.00 | 0.00 | xxxx | 2697 |
| HETATM | 2698 | O | HOH | S | 263 | 21.527 | 20.805 | 93.076 | 1.00 | 0.00 | xxxx | 2698 |
| HETATM | 2699 | O | HOH | S | 264 | 35.227 | 33.913 | 73.496 | 1.00 | 0.00 | xxxx | 2699 |
| HETATM | 2700 | O | HOH | S | 265 | 9.419 | 3.884 | 91.548 | 1.00 | 0.00 | xxxx | 2700 |
| HETATM | 2701 | O | HOH | S | 266 | 30.772 | 42.236 | 89.132 | 1.00 | 0.00 | xxxx | 2701 |
| HETATM | 2702 | O | HOH | S | 267 | 14.889 | 11.697 | 60.585 | 1.00 | 0.00 | xxxx | 2702 |
| HETATM | 2703 | O | HOH | S | 268 | 16.782 | −10.334 | 62.350 | 1.00 | 0.00 | xxxx | 2703 |
| HETATM | 2704 | O | HOH | S | 269 | 10.923 | −4.229 | 70.024 | 1.00 | 0.00 | xxxx | 2704 |
| HETATM | 2705 | O | HOH | S | 270 | 18.813 | 20.066 | 83.551 | 1.00 | 0.00 | xxxx | 2705 |
| HETATM | 2706 | O | HOH | S | 271 | 30.048 | 2.118 | 100.339 | 1.00 | 0.00 | xxxx | 2706 |
| HETATM | 2707 | O | HOH | S | 272 | 8.909 | −5.707 | 70.349 | 1.00 | 0.00 | xxxx | 2707 |
| HETATM | 2708 | O | HOH | S | 273 | 38.277 | 9.852 | 70.341 | 1.00 | 0.00 | xxxx | 2708 |
| HETATM | 2709 | O | HOH | S | 274 | 17.404 | 17.026 | 87.678 | 1.00 | 0.00 | xxxx | 2709 |
| HETATM | 2710 | O | HOH | S | 275 | 2.083 | 0.874 | 81.599 | 1.00 | 0.00 | xxxx | 2710 |
| HETATM | 2711 | O | HOH | S | 276 | 40.573 | 25.786 | 107.080 | 1.00 | 0.00 | xxxx | 2711 |
| HETATM | 2712 | O | HOH | S | 277 | 47.238 | 18.686 | 100.507 | 1.00 | 0.00 | xxxx | 2712 |
| HETATM | 2713 | O | HOH | S | 278 | 45.356 | 30.895 | 104.313 | 1.00 | 0.00 | xxxx | 2713 |
| HETATM | 2714 | O | HOH | S | 279 | 37.886 | 0.890 | 74.951 | 1.00 | 0.00 | xxxx | 2714 |
| HETATM | 2715 | O | HOH | S | 280 | 44.882 | 32.449 | 71.587 | 1.00 | 0.00 | xxxx | 2715 |
| HETATM | 2716 | O | HOH | S | 281 | 45.071 | 19.230 | 101.060 | 1.00 | 0.00 | xxxx | 2716 |
| HETATM | 2717 | O | HOH | S | 282 | 53.338 | 21.767 | 88.706 | 1.00 | 0.00 | xxxx | 2717 |
| HETATM | 2718 | O | HOH | S | 283 | 38.872 | 12.899 | 78.989 | 1.00 | 0.00 | xxxx | 2718 |
| HETATM | 2719 | O | HOH | S | 284 | 50.214 | 34.572 | 75.391 | 1.00 | 0.00 | xxxx | 2719 |
| HETATM | 2720 | O | HOH | S | 285 | 9.787 | 22.391 | 75.366 | 1.00 | 0.00 | xxxx | 2720 |
| HETATM | 2721 | O | HOH | S | 286 | 25.330 | 34.970 | 91.174 | 1.00 | 0.00 | xxxx | 2721 |
| HETATM | 2722 | O | HOH | S | 287 | 19.025 | 22.704 | 75.489 | 1.00 | 0.00 | xxxx | 2722 |
| HETATM | 2723 | O | HOH | S | 288 | 6.732 | 14.329 | 70.989 | 1.00 | 0.00 | xxxx | 2723 |
| HETATM | 2724 | O | HOH | S | 289 | 28.593 | 23.713 | 71.566 | 1.00 | 0.00 | xxxx | 2724 |
| HETATM | 2725 | O | HOH | S | 290 | 48.417 | 10.687 | 76.682 | 1.00 | 0.00 | xxxx | 2725 |
| HETATM | 2726 | O | HOH | S | 291 | 9.233 | 23.335 | 72.944 | 1.00 | 0.00 | xxxx | 2726 |
| HETATM | 2727 | O | HOH | S | 292 | 19.769 | −1.136 | 96.415 | 1.00 | 0.00 | xxxx | 2727 |
| HETATM | 2728 | O | HOH | S | 293 | 15.597 | 23.489 | 79.366 | 1.00 | 0.00 | xxxx | 2728 |
| HETATM | 2729 | O | HOH | S | 294 | 48.418 | 12.805 | 75.957 | 1.00 | 0.00 | xxxx | 2729 |
| HETATM | 2730 | O | HOH | S | 295 | 24.690 | 36.388 | 80.735 | 1.00 | 0.00 | xxxx | 2730 |
| HETATM | 2731 | O | HOH | S | 296 | 3.277 | 6.734 | 67.960 | 1.00 | 0.00 | xxxx | 2731 |

-continued

CA, calcium
HOH, water
ACR, Acrylodan
K, potassium
EDO, ethylene glycol

| | | | | | | | | | | | | |
|---|---|---|---|---|---|---|---|---|---|---|---|---|
| HETATM | 2732 | O | HOH | S | 297 | 33.665 | 24.109 | 72.624 | 1.00 | 0.00 | xxxx | 2732 |
| HETATM | 2733 | O | HOH | S | 298 | 22.977 | 21.117 | 82.694 | 1.00 | 0.00 | xxxx | 2733 |
| HETATM | 2734 | O | HOH | S | 299 | 29.752 | −7.071 | 68.645 | 1.00 | 0.00 | xxxx | 2734 |
| HETATM | 2735 | O | HOH | S | 300 | 6.795 | 14.005 | 67.913 | 1.00 | 0.00 | xxxx | 2735 |
| HETATM | 2736 | O | HOH | S | 301 | 28.876 | 7.221 | 65.323 | 1.00 | 0.00 | xxxx | 2736 |
| HETATM | 2737 | O | HOH | S | 302 | 54.121 | 19.945 | 78.093 | 1.00 | 0.00 | xxxx | 2737 |
| HETATM | 2738 | O | HOH | S | 303 | 28.461 | −1.344 | 90.238 | 1.00 | 0.00 | xxxx | 2738 |
| HETATM | 2739 | O | HOH | S | 304 | 32.077 | 0.296 | 91.320 | 1.00 | 0.00 | xxxx | 2739 |
| HETATM | 2740 | O | HOH | S | 305 | 52.762 | 33.840 | 89.496 | 1.00 | 0.00 | xxxx | 2740 |
| HETATM | 2741 | O | HOH | S | 306 | 33.055 | 24.497 | 109.572 | 1.00 | 0.00 | xxxx | 2741 |
| HETATM | 2742 | O | HOH | S | 307 | 17.403 | 7.927 | 60.363 | 1.00 | 0.00 | xxxx | 2742 |
| HETATM | 2743 | O | HOH | S | 308 | 43.466 | 33.878 | 102.677 | 1.00 | 0.00 | xxxx | 2743 |
| HETATM | 2744 | O | HOH | S | 309 | 12.277 | 17.804 | 70.661 | 1.00 | 0.00 | xxxx | 2744 |
| HETATM | 2745 | O | HOH | S | 310 | 11.041 | 11.796 | 89.974 | 1.00 | 0.00 | xxxx | 2745 |
| HETATM | 2746 | O | HOH | S | 311 | 23.651 | 14.294 | 65.562 | 1.00 | 0.00 | xxxx | 2746 |
| HETATM | 2747 | O | HOH | S | 312 | 42.026 | 45.298 | 94.042 | 1.00 | 0.00 | xxxx | 2747 |
| HETATM | 2748 | O | HOH | S | 313 | 22.517 | 16.293 | 65.454 | 1.00 | 0.00 | xxxx | 2748 |
| HETATM | 2749 | O | HOH | S | 314 | 22.627 | 12.480 | 64.518 | 1.00 | 0.00 | xxxx | 2749 |
| HETATM | 2750 | O | HOH | S | 315 | 2.884 | 8.870 | 71.069 | 1.00 | 0.00 | xxxx | 2750 |
| HETATM | 2751 | O | HOH | S | 316 | 33.745 | 16.834 | 85.547 | 1.00 | 0.00 | xxxx | 2751 |
| HETATM | 2752 | O | HOH | S | 317 | 22.276 | −5.729 | 85.346 | 1.00 | 0.00 | xxxx | 2752 |
| HETATM | 2753 | O | HOH | S | 318 | 17.902 | 8.547 | 58.415 | 1.00 | 0.00 | xxxx | 2753 |
| HETATM | 2754 | O | HOH | S | 319 | 37.913 | 34.004 | 75.956 | 1.00 | 0.00 | xxxx | 2754 |
| HETATM | 2755 | O | HOH | S | 320 | 4.531 | 12.700 | 72.802 | 1.00 | 0.00 | xxxx | 2755 |
| HETATM | 2756 | O | HOH | S | 321 | 24.012 | −0.883 | 62.835 | 1.00 | 0.00 | xxxx | 2756 |
| HETATM | 2757 | O | HOH | S | 322 | 25.236 | −11.299 | 74.409 | 1.00 | 0.00 | xxxx | 2757 |
| HETATM | 2758 | O | HOH | S | 323 | 16.111 | −2.210 | 88.800 | 1.00 | 0.00 | xxxx | 2758 |
| HETATM | 2759 | O | HOH | S | 324 | 37.659 | −1.206 | 71.051 | 1.00 | 0.00 | xxxx | 2759 |
| HETATM | 2760 | O | HOH | S | 325 | 37.666 | −6.192 | 71.121 | 1.00 | 0.00 | xxxx | 2760 |
| HETATM | 2761 | O | HOH | S | 326 | 28.307 | 3.226 | 66.321 | 1.00 | 0.00 | xxxx | 2761 |
| HETATM | 2762 | O | HOH | S | 327 | 18.264 | 17.811 | 65.553 | 1.00 | 0.00 | xxxx | 2762 |
| HETATM | 2763 | O | HOH | S | 328 | 32.832 | 36.516 | 97.649 | 1.00 | 0.00 | xxxx | 2763 |
| HETATM | 2764 | O | HOH | S | 329 | 37.812 | 34.108 | 72.992 | 1.00 | 0.00 | xxxx | 2764 |
| HETATM | 2765 | O | HOH | S | 330 | 31.618 | −1.175 | 95.798 | 1.00 | 0.00 | xxxx | 2765 |
| HETATM | 2766 | O | HOH | S | 331 | 34.949 | −3.372 | 78.898 | 1.00 | 0.00 | xxxx | 2766 |
| HETATM | 2767 | O | HOH | S | 332 | 23.906 | −12.954 | 76.241 | 1.00 | 0.00 | xxxx | 2767 |
| HETATM | 2768 | O | HOH | S | 333 | 36.425 | 4.098 | 70.822 | 1.00 | 0.00 | xxxx | 2768 |
| HETATM | 2769 | O | HOH | S | 334 | 39.250 | 45.244 | 81.350 | 1.00 | 0.00 | xxxx | 2769 |
| HETATM | 2770 | O | HOH | S | 335 | 4.762 | 13.877 | 66.822 | 1.00 | 0.00 | xxxx | 2770 |
| HETATM | 2771 | O | HOH | S | 336 | 28.360 | 33.885 | 93.919 | 1.00 | 0.00 | xxxx | 2771 |
| HETATM | 2772 | O | HOH | S | 337 | 37.026 | −2.278 | 82.988 | 1.00 | 0.00 | xxxx | 2772 |
| HETATM | 2773 | O | HOH | S | 339 | 52.387 | 24.552 | 100.326 | 1.00 | 0.00 | xxxx | 2773 |
| HETATM | 2774 | O | HOH | S | 340 | 23.731 | 19.281 | 92.922 | 1.00 | 0.00 | xxxx | 2774 |
| HETATM | 2775 | O | HOH | S | 341 | 22.622 | 29.993 | 86.246 | 1.00 | 0.00 | xxxx | 2775 |
| HETATM | 2776 | O | HOH | S | 342 | 47.903 | 18.185 | 70.488 | 1.00 | 0.00 | xxxx | 2776 |
| HETATM | 2777 | O | HOH | S | 343 | 41.398 | 34.777 | 102.884 | 1.00 | 0.00 | xxxx | 2777 |
| HETATM | 2778 | O | HOH | S | 344 | 48.646 | 39.218 | 75.315 | 1.00 | 0.00 | xxxx | 2778 |
| HETATM | 2779 | O | HOH | S | 345 | 38.330 | 15.569 | 80.280 | 1.00 | 0.00 | xxxx | 2779 |
| HETATM | 2780 | O | HOH | S | 346 | 31.644 | 34.806 | 96.101 | 1.00 | 0.00 | xxxx | 2780 |
| HETATM | 2781 | O | HOH | S | 347 | 47.364 | 33.541 | 103.953 | 1.00 | 0.00 | xxxx | 2781 |
| HETATM | 2782 | O | HOH | S | 348 | 44.632 | 14.267 | 99.126 | 1.00 | 0.00 | xxxx | 2782 |
| HETATM | 2783 | O | HOH | S | 349 | 49.644 | 35.980 | 94.514 | 1.00 | 0.00 | xxxx | 2783 |
| HETATM | 2784 | O | HOH | S | 350 | 21.713 | 24.372 | 91.316 | 1.00 | 0.00 | xxxx | 2784 |
| HETATM | 2785 | O | HOH | S | 351 | 52.309 | 31.191 | 91.054 | 1.00 | 0.00 | xxxx | 2785 |
| HETATM | 2786 | O | HOH | S | 352 | 22.952 | 34.465 | 76.990 | 1.00 | 0.00 | xxxx | 2786 |
| HETATM | 2787 | O | HOH | S | 353 | 1.535 | 7.911 | 68.662 | 1.00 | 0.00 | xxxx | 2787 |
| HETATM | 2788 | O | HOH | S | 354 | 42.120 | 12.888 | 78.426 | 1.00 | 0.00 | xxxx | 2788 |
| HETATM | 2789 | O | HOH | S | 355 | 23.184 | −11.886 | 67.081 | 1.00 | 0.00 | xxxx | 2789 |
| HETATM | 2790 | O | HOH | S | 356 | 28.553 | 29.065 | 101.938 | 1.00 | 0.00 | xxxx | 2790 |
| HETATM | 2791 | O | HOH | S | 357 | 41.272 | 12.381 | 76.436 | 1.00 | 0.00 | xxxx | 2791 |
| HETATM | 2792 | O | HOH | S | 358 | 19.489 | 19.564 | 69.735 | 1.00 | 0.00 | xxxx | 2792 |
| HETATM | 2793 | O | HOH | S | 359 | 46.136 | 39.282 | 76.126 | 1.00 | 0.00 | xxxx | 2793 |
| HETATM | 2794 | O | HOH | S | 360 | 15.145 | 9.336 | 99.422 | 1.00 | 0.00 | xxxx | 2794 |
| HETATM | 2795 | O | HOH | S | 361 | 22.838 | 23.616 | 97.095 | 1.00 | 0.00 | xxxx | 2795 |
| HETATM | 2796 | O | HOH | S | 362 | 9.603 | 13.336 | 89.036 | 1.00 | 0.00 | xxxx | 2796 |
| HETATM | 2797 | O | HOH | S | 363 | 26.386 | −2.108 | 62.392 | 1.00 | 0.00 | xxxx | 2797 |
| HETATM | 2798 | O | HOH | S | 364 | 52.011 | 37.819 | 77.771 | 1.00 | 0.00 | xxxx | 2798 |
| HETATM | 2799 | O | HOH | S | 365 | 28.168 | 8.938 | 63.919 | 1.00 | 0.00 | xxxx | 2799 |
| HETATM | 2800 | O | HOH | S | 366 | 27.589 | 39.294 | 85.068 | 1.00 | 0.00 | xxxx | 2800 |
| HETATM | 2801 | O | HOH | S | 367 | 27.687 | −12.163 | 86.695 | 1.00 | 0.00 | xxxx | 2801 |
| HETATM | 2802 | O | HOH | S | 368 | 44.266 | 8.368 | 83.648 | 1.00 | 0.00 | xxxx | 2802 |
| HETATM | 2803 | O | HOH | S | 369 | 46.173 | 42.782 | 86.952 | 1.00 | 0.00 | xxxx | 2803 |
| HETATM | 2804 | O | HOH | S | 370 | 14.140 | 12.958 | 88.666 | 1.00 | 0.00 | xxxx | 2804 |

-continued

| CA, calcium<br>HOH, water<br>ACR, Acrylodan<br>K, potassium<br>EDO, ethylene glycol | | | | | | | | | | | | |
|---|---|---|---|---|---|---|---|---|---|---|---|---|
| HETATM | 2805 | O | HOH | S | 371 | 34.823 | 19.732 | 100.091 | 1.00 | 0.00 | xxxx | 2805 |
| HETATM | 2806 | O | HOH | S | 372 | 46.908 | 9.147 | 83.618 | 1.00 | 0.00 | xxxx | 2806 |
| HETATM | 2807 | O | HOH | S | 373 | 24.142 | 29.305 | 94.702 | 1.00 | 0.00 | xxxx | 2807 |
| HETATM | 2808 | O | HOH | S | 374 | 18.119 | −1.328 | 89.006 | 1.00 | 0.00 | xxxx | 2808 |
| HETATM | 2809 | O | HOH | S | 375 | 33.026 | 38.391 | 92.683 | 1.00 | 0.00 | xxxx | 2809 |
| HETATM | 2810 | O | HOH | S | 376 | 58.201 | 22.385 | 92.378 | 1.00 | 0.00 | xxxx | 2810 |
| HETATM | 2811 | O | HOH | S | 377 | 54.105 | 29.892 | 90.670 | 1.00 | 0.00 | xxxx | 2811 |
| HETATM | 2812 | O | HOH | S | 378 | 34.565 | 8.799 | 95.893 | 1.00 | 0.00 | xxxx | 2812 |
| HETATM | 2813 | O | HOH | S | 379 | 27.908 | 0.262 | 61.279 | 1.00 | 0.00 | xxxx | 2813 |
| HETATM | 2814 | O | HOH | S | 380 | 19.941 | 22.488 | 82.984 | 1.00 | 0.00 | xxxx | 2814 |
| HETATM | 2815 | O | HOH | S | 381 | 29.525 | −1.794 | 97.959 | 1.00 | 0.00 | xxxx | 2815 |
| HETATM | 2816 | O | HOH | S | 382 | 49.648 | 29.585 | 104.557 | 1.00 | 0.00 | xxxx | 2816 |
| HETATM | 2817 | O | HOH | S | 383 | 35.408 | 8.346 | 93.778 | 1.00 | 0.00 | xxxx | 2817 |
| HETATM | 2818 | O | HOH | S | 384 | 52.470 | 22.521 | 101.253 | 1.00 | 0.00 | xxxx | 2818 |
| HETATM | 2819 | O | HOH | S | 385 | 26.897 | −3.606 | 89.300 | 1.00 | 0.00 | xxxx | 2819 |
| HETATM | 2820 | O | HOH | S | 386 | 47.051 | 43.266 | 84.658 | 1.00 | 0.00 | xxxx | 2820 |
| HETATM | 2821 | O | HOH | S | 387 | 27.492 | −1.155 | 98.711 | 1.00 | 0.00 | xxxx | 2821 |
| HETATM | 2822 | O | HOH | S | 388 | 50.334 | 39.736 | 96.998 | 1.00 | 0.00 | xxxx | 2822 |
| HETATM | 2823 | O | HOH | S | 389 | 53.977 | 16.042 | 91.468 | 1.00 | 0.00 | xxxx | 2823 |
| HETATM | 2824 | O | HOH | S | 390 | 55.332 | 22.862 | 98.469 | 1.00 | 0.00 | xxxx | 2824 |
| HETATM | 2825 | O | HOH | S | 391 | 55.356 | 15.678 | 95.126 | 1.00 | 0.00 | xxxx | 2825 |
| HETATM | 2826 | O | HOH | S | 392 | 29.452 | 26.421 | 74.947 | 1.00 | 0.00 | xxxx | 2826 |

Example 13. Robust, Thermostable, Reagentless, Fluorescently Responsive Glucose Biosensors We report the construction of a robust, thermostable, reagentless, fluorescently responsive glucose biosensor and its variants derived from *T. thermosaccharolyticum* (ttGGBP). These proteins are useful for high-precision chemometric measurements that span the entire clinical and industrial glucose concentration range, using fluorescence ratiometry measured with straightforward, inexpensive instrumentation.

Thermostable homologs of the *E. coli* Glucose-galactose binding protein (ecGGBP) were identified using a bioinformatics search strategy that applied a structure-based sequence filter to identify the subset of sequences that retain the original function within the larger collection of aligned sequence homologs. The homologs of interest appeared at sequence identities below 60% of the ecGGBP probe an unusual and surprising discovery. At this level, overall identities are weak predictors of biological function, application of the structure-based filter therefore was essential for accurate identification. The glucose-binding properties of the predicted hits were tested experimentally by constructing synthetic genes optimized for heterologous protein expression in *E. coli* and determining the glucose-binding properties of the expressed proteins. This search resulted in the identification of a homolog from *Thermoanaerobacter thermosaccharolyticum* (ttGGBP) as a suitable candidate for glucose sensor engineering.

Endosterically placed Acrylodan and Badan fluorescent conjugates were found to be highly effective ratiometric glucose sensors. A series of additional mutations were introduced to manipulate glucose affinities. Variants spanning four orders of magnitude (0.1-100 mM) were identified. Within these, a subset of mutants covers the entire pathophysiological glucose concentration range with responses that remain within 90% of the maximally achievable precision.

The ttGGBP-based FRSs can be immobilized site-specifically on magnetic beads or other solid or semi-solid substrates without affecting protein stability, fluorescence responses, or glucose affinities. They can be dried, and aged aggressively (incubation at 50° C. for 7 days or more, e g mimicking and/or exceeding environmental conditions in the field, storage or shipping) without adversely affecting sensing performance.

Reagentless, fluorescently responsive sensors present a number of advantages over enzyme-based biosensors, including self-calibration, elimination of chemical transformations and multiple substrates, which together lead to simple sample-handling fluidic circuitry and rapid response times. FRSs can be used for one-time, episodic, and continuous monitoring measurements. Additionally, the use of robust engineered glucose sensors based on thermophilic proteins is likely to simplify manufacturing and distribution processes. Combination of mutant glucose sensors reported here into multiplexed arrays or composites determine glucose concentrations from hypoglycemic to the hyperosmolar hyperglycemic state samples with high precision in one measurement. Such systems have significant potential for the development of next-generation high-accuracy, wide dynamic range sensing applications in continuous monitoring, point-of-care, or wearable systems.

The following materials and methods were used to generate the data described herein.

Bioinformatic Searches.

Annotated genomic and plasmid sequences of 4592 prokaryotes were downloaded from the National Center of Biotechnology Information (ftp://ftp.ncbi.nih.gov/genomes/Bacteria/all.gbk.tar.gz), together with annotations recording prokaryotic lifestyles (../ProkaryotesOrganismInfo.txt). We developed the 'ProteinHunter' program to provide an interface and methods for organizing, querying, and analyzing these genomic sequences as well as protein structures. ProteinHunter comprises a graphical user interface, set of computer scripts, and a parallel computing environment. Together these set up the calculations, manage the flow of information and execution in each of the calculation phases, control other programs that carry out specific calculations such as BLAST and ClustalW, and visualize the results. The protein sequence for the *E. coli* glucose-galactose binding protein (ecGGBP) was extracted from the protein structure file 2gbp (Vyas et al. 1988 *Science,* 242, 1290-5), and used as the seed sequence for a uni-directional BLAST search of the downloaded prokaryotes. Pairwise BLAST alignment were selected in ProteinHunter as hits if these contained 25% or identical residues, and if the alignment covered at least 70% of the probe and target sequences. The BLAST hits identified in ProteinHunter were aligned using ClustalW (Chenna et al. 2003 *Nucleic Acids Res,* 31, 3497-500). A structure-based sequence filter was used to accurately distinguish glucose-binding protein from other functions within the hits. A 10-residue, non-contiguous sequence comprising the primary complementary surface (PCS) between the protein and the bound glucose in the 2gbp structure (FIG. 1A-C) was identified using ProteinHunter. PCS residues were selected as members of the PCS if the calculated distance between any of their atoms and any glucose atom was less than 5 Å, and the distances between their backbone $C_{\alpha}$ and any atom in glucose was greater than that of their $C_{\beta}$ atom and any atom in glucose. Secondary shell residues that do not form hydrogen bonds or van der Waals contacts were removed by inspection from the resulting set. Using the overall ClustalW alignments, the subset of PCS residues were identified within each homolog and aligned. For each homolog, the number of PCS mutations relative to the ecGGBP PCS (Hamming distance, $H_{PCS}$) was counted. A $H_{PCS}$=0 value means that the PCS sequence is identical to that of eCGGBP; homologs with this $H_{PCS}$ value were inferred to be glucose-binding proteins. The PCS sequences were displayed sorted by their $H_{PCS}$ values, and within each $H_{PCS}$ value sorted by their fraction identical residues, indicating the replicon within which they reside (chromosome or plasmid), whether this replicon contains paralogs, and the temperature tolerance (hyperthermophile, thermophile, mesophile, psychrophile, unknown), their Gram stain classification (if known), and the percentage genomic AT content. Duplicate hits were removed automatically from this list if the organism name (genus and species), fractional identity and paralogs were the same. From this list unique hyper(thermophilic) ecGGBP homologs with $H_{PCS}$=0 were readily identified by inspection.

Gene Synthesis and Mutagenesis.

The amino acid sequences for the GGBP homologs identified in the bioinformatic search (see above) were extracted from the ClustalW alignment file and edited further to construct a mature polypeptide with a single cysteine that replaces the equivalent of W183 in ecGGBP for site-specific labeling with Acrylodan, using AaEditor, an in-house program developed to manipulate protein sequences. The putative leader peptide that mediates anchoring of the periplasmic-binding protein on the outside of the membrane (Gram positive bacteria) or directs secretion into the periplasm (Gram negative bacteria) was deleted by examining the multiple sequence alignment and removing the sequences N-terminal to the start of the mature ecGGBP amino acid sequence. The residue equivalent to W183 in the ecGGBP sequence was mutated to cysteine; all other cysteines were changed to alanine. A hexahistidine tag was placed behind a GGS linker at the C-terminus of the mature protein to enable metal-mediated affinity purification (Hengen 1995 *Methods Enzymol,* 210, 129-192). The final amino acid sequence was back-translated into a DNA sequence encoding the open reading frame (ORF), which was placed in a construct behind an efficient Shine-Dalgarno ribosome-binding site, and flanked by a T7 promoter and terminator at the 5' and 3' ends respectively, using the GeneFab program (Cox et al. 2007 *Protein Sci,* 16, 379-90). The resulting ORF sequence was optimized in context by OrfOpt or OrfMorph programs designed to predict highly expressed mRNA sequences in *E. coli.* The resulting DNA sequences were synthesized by oligonucleotide assembly and cloned into pUC57 by GeneWiz, Inc. (South Plainfield, N.J.). Subsequent single and multiple point mutations were constructed by preparing mutant sequences of the synthetic ORF sequences using GfMutagenesis, an in-house program that introduces point mutations into an ORF using the most prevalent codon in *E. coli* for an amino acid, followed by total gene synthesis.

Synthetic Gene Optimization.

The OrfOpt and OrfMorph programs use stochastic optimization algorithms that alter choose different codons within an ORF without altering the amino acid sequence to optimize a target function designed to identify mRNA sequences that express proteins at high levels in *E. coli.* The OrfOpt simultaneously imposes AU-rich nucleotide composition at the 5' and 3' ends of the ORF, low RNA secondary structure content and favorable codon usage (Allert et al. 2010 *J Mol Biol,* 402, 905-18). The OrfMorph program reproduces the pattern of codon usage and RNA secondary observed in the parent genome of a protein, but using *E. coli* codon preferences and nucleotide composition.

Codon usage is calculated using the codon adaptation index (CAI), as described for OrfOpt, using codon frequency tables calculated for the genome under examination. The mean CAI value for a genome, $\mu_c$, and its standard deviation, $\sigma_c$, are calculated over all the codons in a genome. A codon usage score, c, is calculated for each codon in an open reading frame (ORF) by averaging the CAI over a 9-codon window, centered on the codon for which this score is calculated. A normalized codon usage score, $z_c$, is calculated for each codon as the Z-score: $z_c=(c-\mu_c)/\sigma_c$. A plot of $z_c$ along an ORF establishes the codon usage pattern of that ORF. Rare codons ($z_c<0$) are hypothesized to slow down the elongation rate of ribosome translation, introducing "pause" sites at extremes. Such pause sites are hypothesized to direct the kinetics of co-translational protein folding, allowing a newly synthesized segment to fold before more protein is made. An RNA secondary structure score, s, is determined for each nucleotide by summing its participation in all possible hairpins that can form in its vicinity (settings: minimum stem duplex length, 4 basepairs; maximum loop length, 30 bases; vicinity length, 100 bases), as described for OrfOpt. The average secondary structure energy, $\mu_s$, and its standard deviation, $\sigma_s$, are calculated over all the nucleotides in a genome. A normalized secondary structure energy score, $z_s$, is calculated for each codon as the Z-score: $z_s=(s-\mu_s)/\sigma_s$. A plot of $z_s$ along an ORF establishes the secondary structure pattern of that ORF. Regions of above-average secondary structure ($z_s>0$) are hypothesized to slow down the elongation rate of ribosome translation, introducing "pause" sites at extremes. As with CAI-mediated pause sites, secondary structure-driven pause sites are hypothesized to direct the kinetics of co-translational protein folding. To imitate these patterns for heterologous expression of an ORF in *E. coli,* first the $z_c$ and $z_s$ scores are calculated using the parent organism codon table, $\mu_c$, $\sigma_c$, and $\sigma_s$ values. Second, a stochastic search algorithm is used that randomly chooses between degenerate codons to construct trial mRNA nucleotide sequences, calculating $z_c$ and $z_s$ scores for each trial sequence, but using the *E. coli* codon table, and *E. coli* $\mu_c$, $\sigma_c$, $\mu_s$, and $\sigma_s$ values. For each trial sequence, the absolute differences between the *E. coli* trial scores, and the wild-type scores are summed over the entire ORF. The OrfMorph program searches for a minimum of these differences. The stochastic search algorithm operates by first choosing a codon position, second choosing a degenerate codon within the allowed codons at that position. If the choice results in an improved score, the sequence is kept, otherwise it is rejected. After a position has been selected, it is removed from the pool of allowed positions, and the next is chosen from the remained. A "sweep" is completed, when all the codons in the sequence have been examined. The algorithm terminates, when two successive sweeps do not yield further improvements in the score. The resulting RNA nucleotide sequence then has codon usage patterns and secondary structure patterns that closely match those of the wild-type mRNA sequence in its parental genomic context. The hypothesis is that such matching improves production of soluble protein by mimicking co-translation folding contributions that minimize mis-folded protein intermediate aggregation.

Protein Expression, Purification, and Fluorescent Conjugate Preparation.

Plasmids carrying the expression constructs (see above) were transformed into KRX competent cells (Promega), and grown overnight at 37° C. on LB agar plates (100 mg/mL ampicillin). A single colony was picked and grown overnight at 37° C. in Terrific Broth (TB; Research Products International). The overnight cultures were diluted 1:20 in 500 mL TB (100 mg/mL ampicillin, 1 mM $CaCl_2$), grown to an optical density of $A_{600}$=0.5 at 37° C. in vigorously aerated shaker flasks, induced by the addition of 2.5 mL rhamnose (20% w/v), and grown for a further 3-4 hrs. The cells were harvested by centrifugation (5,000 rpm, 10 mM). After decanting the supernatant, the cell pellets were stored −80° C. The cell pellets were thawed, resuspended in 8 mL binding buffer (10 mM imadozole, 20 mM MOPS, 500 mM NaCl, 1 mM $CaCl_2$, pH 7.8). Following resuspension, 3 mL of BugBuster HT (EMD Millipore) was added. After incubation (20 mins, 25° C.), the cells were lysed on ice by sonication (2 minutes of one-second on/off pulses, 20-30% power). A clarified lysate was prepared by centrifugation (15,000 rpm, 20 mM, 4° C.) from which recombinant protein was purified by batch immobilized metal affinity chromatography (IMAC). Resuspended IMAC agarose beads (5 mL; Sigma-Aldrich, P6611) were added to the lysate. After incubation at 4° C. in a Mini LabRoller (Labnet International) for 1 hr, the beads were washed at least five times with binding buffer. The immobilized protein beads were resuspended in labeling buffer (20 mM MOPS, 100 mM NaCl, 1 mM $CaCl_2$, pH 6.9) and labeled overnight (4° C., rotating end-over-end) with a thiol-reactive fluorophore (5-fold stoichiometric excess over protein). Following two rinses with labeling buffer to remove unincorporated label, the proteins were eluted from the beads. To elute labeled protein from the IMAC beads, 6 mL of elution buffer (400 mM imidazole, 500 mM NaCl, 1 mM $CaCl_2$, 20 mM MOPS, pH 7.8) was added, incubated for 30 min (4° C., rotating end-over-end), and the beads removed by centrifugation. Following dialysis of the eluate against three changes of assay buffer (20 mM MOPS, 20 mM KCl, 1 mM $CaCl_2$, pH 7.4), using 10 kDa semi-permeable membrane (Snakeskin tubing, Thermo Scientific), the fluorescent conjugates were concentrated in a 10 kDa cutoff spin concentrator (Vivaspin, GE Healthcare). Protein purity was assessed by SDS/PAGE. Protein concentrations were determined by (Nanodrop1000) at 280 nm (using extinction coefficients calculated from their sequence (Gill and von Hippel 1989 *Anal Biochem,* 182, 319-26; Artimo et al. 2012 *Nucleic Acids Res,* 40, W597-603), or at the fluorophore absorbance peak (Acrylodan, 391 nm and Badan, 387 nm).

Determination of Temperature- and Ligand-Dependent Fluorescence Landscapes.

12-, 24-, or 48-point logarithmic titration series were prepared on a Tecan Freedom liquid-handling robot, using an in-house program, 'TitrationPlate', that compiles an abstract description of a multi-component titration series into machine instructions for operating the robot. Glucose concentrations were varied from 0-1.7 M in 20 mM KCl, 20 mM MOPS (pH 7.4) supplemented with either 1 mM EGTA or 1 mM $CaCl_2$. Temperature-dependent fluorescence emission intensities of 20 μL aliquots, each containing 10 μM protein, were measured in 384-well microtiter plates in a LightCycler 480 II (Roche) using excitation and emission wavelengths available for this instrument that most closely matched the optical characteristics of the fluorescent conjugate. Temperatures were advanced in 1K steps. At each temperature, data was collected at 1-second intervals for 60 seconds at which point the signal had relaxed to a steady value associated with the new temperature. Under these experimental photobleaching was not observed. The in-house program 'TitrationMeltPlate' was used to convert these observations into time-independent datasets that record fluorescence as a function of temperature for each well and associate wells with their concentration of titrant and additive. Management tools were developed to maintain a database of titrations and their analyses.

Determination of Emission Intensity Spectra.

Ligand- and wavelength-dependent emission intensities were recorded on a Nanodrop3300 (Thermo Scientific) at room temperature. Using the LED closest to the optimal excitation wavelength of the fluorophore (UV, 365 nm; blue, 470 nm; 'white', 460-550 nm).

Ratiometric Analysis of Glucose Binding.

Isothermal glucose titrations were extracted from the fluorescent landscape or emission spectra datasets obtained as described above. Monochromatic emission intensities $I_\lambda$ (these intensities correspond to a bandpass intensity, recorded either with a physical filter in the case of the Roche LightCycler, or by integrating in the interval λ−δ, λ+δ in the case of an emission spectrum), were fit to $$I\lambda={}^{apo}\beta_\lambda(1-\bar{y}_{true})+{}^{sat}\beta_\lambda\bar{y}_{true} \qquad 1$$

where ${}^{apo}\beta_\lambda$ and ${}^{sat}\beta_\lambda$ are the fluorescence baselines associated with the ligand-free and ligand-bound states of the protein, respectively, and $\bar{y}_{true}$ the fractional saturation of the protein. (Layton and Hellinga 2010 *Biochemistry,* 49, 10831-41.) Baseline functions can be constant, linear, or a second-order polynomial. For the ligand- and temperature-dependent fluorescence landscapes, we use a constant value for ${}^{apo}\beta_x$, ${}^{sat}\beta_x$ is described by a linear dependence on glucose concentration, [L]:

$${}^{sat}\beta_x=a_x+b_x[L] \qquad 2$$

For a single glucose-binding site, the fractional saturation is given by $$\bar{y}=\frac{[L]}{[L]+K_d} \qquad 3$$

where [L] is the ligand (glucose) concentration and $K_d$ the dissociation constant, ${}^{true}K_d$ for $\bar{y}_{true}$.

A dichromatic, ratiometric signal is defined as the ratio of the intensities at two independent wavelengths, $\lambda_1$ and $\lambda_2$ $$R_{1,2}=I_{\lambda 1}/I_{\lambda 2} \qquad 4$$

This signal removes wavelength-independent emission intensity attenuation effects due to variations in conjugate concentration, photobleaching, fluctuations in excitation source intensities, and detection efficiency. (Demchenko 2010 *J Fluoresc,* 20, 1099-128; Demchenko 2014 *Journal of Molecular Structure,* 1077, 51-67) It is a key aspect for high-precision sensing using the reagentless fluorescently-responsive sensors described here. The ratiometric signal also can be fit to a binding isotherm:

$$R_{1,2}={}^{apo}\beta_R(1-\bar{y}_R)+{}^{sat}\beta_R\bar{y}_R \quad (5)$$

where ${}^{apo}\beta_R$ and ${}^{sat}\beta_R$ are the baselines, and $\bar{y}_R$ the apparent fractional saturation of the protein (with ${}^{app}K_d$). In general, ${}^{true}K_d \neq {}^{app}K_d$; if both baselines are constant, a simple relationship can be derived relating ${}^{app}K_d$ to ${}^{true}K_d$: (Grimley et al. 2013 *J Neurosci,* 33, 16297-309)

$$ {}^{app}K_d = {}^{true}K_d \frac{{}^{apo}I_{\lambda 2}}{{}^{sat}I_{\lambda 2}} \quad (6)$$

where ${}^{apo}I_{\lambda 2}$ and ${}^{sat}I_{\lambda 2}$ are the emission intensities of the monochromatic signal at wavelength $\lambda_2$ of the ligand-free and ligand-bound protein, respectively.

The fractional error in the chemometric concentration measurement, depends on the first derivative of the binding isotherm as follows (Marvin et al. 1997 *Proc Natl Acad Sci USA,* 94, 4366-71):

$$\frac{\partial S}{S} = \frac{\varepsilon_{1,2}}{S} \times \left(\frac{dyR_{1,2}}{dS}\right)^{-1} \quad (7)$$

Where $R_{1,2}$ is the ratiometric signal (equation 5), $\varepsilon_{1,2}$ its experimental error, and $\delta S$ is the resulting chemometric error in the concentration. We can then define a relative precision function $$P(S) = \frac{S}{\delta S} \times \frac{1}{P_{max}} \quad (8)$$

where P(S) is the relative precision at concentration S, which reaches a maximum value (i.e. lowest error), $P_{max}$, at the $K_d$.

For a given isothermal titration, values for ${}^{app}K_d$ and ${}^{true}K_d$ were obtained using a non-linear fitting algorithm in which these two parameters were simultaneously fit to the three experimental binding isotherms using equations 1 and 5, with the two monochromatic isotherms sharing the same ${}^{true}K_d$ value. Three separate pairs of ${}^{apo}\beta$ and ${}^{sat}\beta$ were fit in this procedure. Programs 'Nanodrop3300' and 'TitrationMeltAnalysis' were developed to analyze wavelength- or temperature-dependent ligand-binding datasets respectively.

Analysis of Temperature- and Ligand-Dependent Fluorescent Landscapes.

To obtain the temperature dependence of the binding reaction, the $K_d$ values of all the individually determined isotherms were fit the Gibbs-Hemholtz equation (Layton and Hellinga 2010 *Biochemistry,* 49, 10831-41):

$$\Delta G_b^*(T) = \Delta^{ref}H_b^* + \Delta C_{p,b}(T - T_{ref}) - T\left(\Delta^{ref}S_b^* + \Delta C_{p,b}\ln\frac{T}{T_{ref}}\right) \quad (9)$$

where $\Delta G_b^*(T)$ is the standard free energy of binding at 1 M ligand at temperature T, $$\Delta G_b^*(T) = -RT\ln\left(1 + \frac{1}{K_d(T)}\right) \quad (10)$$

$\Delta^{ref}H_b^*$ and $\Delta^{ref}S_b^*$ the molar enthalpy and entropy of binding, respectively, at the reference temperature, $T_{ref}$, and $\Delta C_{p,b}$ the heat capacity of the binding reaction. This data analysis was carried out using 'TitrationMeltAnalysis'.

Analysis of Emission Spectra Components.

Wavelength-dependent, I(λ), emission intensities at were converted to wavenumber-dependent intensities (Valeur 2012 *Principles and Applications.* Weinheim: Wiley; Lakowicz 2006 *Principles of fluorescence spectroscopy.* Springer, New York), I(ν):

$$I(\nu)=\lambda^2 I(\lambda) \quad (11)$$

Singular value decomposition was used for model-free identification of regions in the emission spectra that vary with respect to glucose concentration (Henry 1992 *Methods Enzymol,* 210, 129-192). An $A_{mn}$ data matrix was constructed by recording I(ν) values of m frequencies in columns for n titration points in rows. This matrix was decomposed as $$A_{mn}=U_{mn}S_{nn}V_{nn}^T \quad (12)$$

where $U_{mn}$ records n spectral components at m frequencies ranked by the weight of their contribution to the reconstruction of the experimental data, $V_{nn}$ records the contribution of the nth component to the $n^{th}$ titration point, $S_{nn}$ records the weight of the $n^{th}$ component. Decomposition was carried using the in-house Nanodrop3300 program, written in Python. The linalg.svd method in the open-source Python scipy package (www.scipy.org, version 0.7.2) was used to solve the decomposition. The relative weight of the $n^{th}$ component in $U_{mn}$, $f_n$, was calculated from $S_{nn}$, by normalizing the values in S with its trace:

$$f_n = \frac{S_{nn}(n, n)}{tr(S_{nn})} \quad (13)$$

The fractional states of n individual electronic transitions in a spectrum were determined by fitting n Gaussians (Valeur 2012 Principles and Applications. Weinheim: Wiley; Lakowicz 2006 Principles of fluorescence spectroscopy. Springer, New York) to the emission intensities of the corrected spectra (equation 5) transformed into the frequency domain (equation 6):

$$ {}^{calc}I_i(\nu) = \sum_{i=1}^{i=n} \frac{A_i}{\sqrt{2\pi}} e^{-\frac{1}{2}\left(\frac{\nu-\mu_i}{\sigma}\right)^2} \quad (14)$$

where $\mu_i$ is the wavenumber corresponding to the peak intensity of the $i^{th}$ transition, $A_i$ the area contributed to the total spectrum by this transition, and σ the spectral width of all transitions. The fraction, $f_i$, of the $i^{th}$ transition is given by:

$$f_i = \frac{A_i}{\sum_{j=1}^{j=n} A_j} \quad 15$$

Wavelength dependent residuals are given by:

$$\Delta(v) = {}^{obs}I(v) - {}^{calc}I(v) \quad 16$$

Fits were carried out by minimizing the least squares difference between observed and calculated spectra, using simplex and conjugate gradient methods implemented in Nanodrop3300 (scipy package methods optimize.fmin and optimize.leastsq, respectively). For titration series with N spectra, collected as a function of titrant concentration, global fits were used in which, as a first approximation, μi values were kept identical in the apo-protein and saturated glucose complex, and σ was universal for all transitions in all spectra. $A_{i,k}$ values were allowed to vary in each $k^{th}$ spectrum. The variation of the fraction for each transition, $f_{i,k}$, was then fit to a binding isotherm (equation 1), constraining the fit ${}^{app}K_d$ value to be common to all transitions.

Structure Determination by X-Ray Crystallography.

Glucose-binding protein fluorescent conjugates were mixed with 2 mM D-glucose, and 1 mM $CaCl_2$. Sitting-drop vapor-diffusion Crystallization trials were carried out at 17° C. using sparse-matrix screening conditions. The ecGGBP183C•Acrylodan, ttGGBP182C•Acrylodan and ttGGBP.17C•Badan conjugates crystallized in 20% PEG 3350 and 0.2 M potassium thiocyanate as clusters of needles. Single crystals were isolated mechanically (Micro-Tools, Hampton Research), transferred stepwise into mother liquor containing 30% ethylene glycol, and flash-frozen in liquid nitrogen. Diffraction data was collected remotely at the Advanced Photon Source, SER-CAT beamline 22-ID; 0.5° oscillation angle frames were collected and processed using XDS program (Kabsch 2010 Acta Cryst., D66, 125-132). The data was phased by molecular replacement using PHASER (MCCoy 2007 *J. Appl. Cryst., D*66, 125-312) with a poly-alanine of the *E. coli* glucose-galactose-binding protein (2gbp (Vyas et al. 1988 *Science,* 242, 1290-5)) as the search model. Initial models were built after 10 cycles of rigid-body refinement in PHENIX, AutoBuild (Adams 2010 *Acta Crystallogr D Biol Crystallogr,* 66, 213-331). Multiple rounds of positional, individual B-factor and occupancy refinement and subsequent model building were performed in PHENIX and COOT, respectively. Solvent molecules were added both automatically as implemented in phenix.refine and by manual inspection. The structures were validated using PHENIX tools. The final refined models has crystallographic $R_{factor}$ and $R_{free}$ values that were within the range of average values refined at these resolutions (Kleywegt 1996 *Structure,* 4, 897-904).

Example 14. FRS Uses

The glucose sensors can be incorporated into point-of-care clinical devices to measure glucose concentrations accurately, and rapidly at the patient bedside. In such a device, a small blood sample (<10 μL) is obtained by means of a finger stick using a lancet. This sample droplet is then placed on the aperture of a disposable cartridge containing desiccated, immobilized glucose sensors inside a small measurement chamber. The sample enters the chamber by virtue of passive capillary action, wetting the sensors upon contact. As soon as the sensors have been wetted, they bind glucose, and report on its concentration by virtue of the engineered fluorescent sensor mechanism. The cartridge is placed inside a small reader (handheld or on a desktop), and their fluorescence signal is measured by the (inexpensive) optoelectronic components of the reader. Excitation light is provided by a light-emitting diode (LED. In the case of Acrylodan or Badan, a commercially available 400 nm blue LED is used, and the emitted light is measured through two bandpass filters. Cartridges can contain multiple sensors, spanning the entire clinical range of possible glucose concentrations. Each sensor is immobilized at a particular, known location inside the cartridge, providing "spatial addressability". The intensity at a particular wavelength is then recorded by imagining these sensors using an inexpensive camera, such as a Complementary metal-oxide semiconductor (CMOS) device commonly found in consumer electronics such as cell phones. Each pixel in the camera records the emitted light on a gray scale. Integration of that signal imaged through the two signals, is analyzed by an on-board computer to calculate the ratiometric signal for each immobilized sensor. Pre-recorded hyperbolic binding curves are then used to calculate the glucose concentration in the sample. Recording through multiple sensors, tuned for accurate detection at different glucose concentrations provides a high-accuracy reading. This process is completed in less than a minute.

Similar instrumentation can be used for any type of episodic measurements, for instance, using other bodily fluids, or samples obtained from animals, or non-biological samples such as foods and beverages.

The FRS glucose sensors also can be used to monitor glucose levels continuously. For instance, sensors can be immobilized at the tip of a thin optical fiber to construct a glucose-responsive optode. Such an optode can be introduced into the body subcutaneously, using a small needle. Excitation and emission light are passed to and from the immobilized sensor, respectively. The sensor is in continuous contact with the sample. Fluctuations in the glucose sample alter the dynamic equilibrium between the open and closed states of the glucose-binding protein, which is transduced into fluctuations of the fluorescent emission signal, by virtue of the sensing mechanism of the conjugated fluorophore. The emitted light intensities are read through filters by a reader connected to the optode. This reader continuously displays the change in signal, and the corresponding calculated glucose concentrations. Continuous glucose monitoring accomplished using a device containing the immobilized glucose biosensor(s), e.g., a fiber optic biosensor, introduced into the subject intradermally or subcutaneously (Judge et al., 2011, Diabetes Technology & Therapeutics 13 (3):309-317; Weidemaier et al., 2011, Biosensors and Bioelectronics 26:4117-4123; hereby incorporated by reference). For example, subcutaneously placed sensors can be used to monitor the glucose levels in a patient, guiding automated delivery of insulin in an artificial pancreas.

Similar instrumentation can be used to monitor glucose levels in a fermentor or bioreactor, coupled to automated injection of glucose for growth optimization of bacteria, fungi, and eukaryotic cells.

As was discussed above, the features that distinguish the described constructs, devices, and methods from earlier glucose assay systems include:

Self-calibration

Rapid response time

- Simple sample-handling fluidic circuitry
- No additional components/substrates ("reagentless")
- No incubation time to develop signal. Reading is near-instantaneous and continuous
- Stability (simplifies manufacturing, distribution, storage)
- Small sample volume (<10 μL).
- Capable of precise measurements over extended glucose concentration range (from the hypoglycemic to the hyperglycemic-hyperosmotic range)
- Multiple sensors also provides redundancy, lowering error
- Large scope of uses: episodic, continuous, ex vivo, in vivo, optodes, implants.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A biosensor for a ligand, comprising a ligand-binding protein and a reporter group attached to said ligand-binding protein, wherein binding of said ligand to a ligand-binding domain of said ligand-binding protein causes a change in signaling by said reporter group, wherein said ligand comprises glucose or galactose, wherein said ligand-binding protein is or is a mutant of a *Thermoanaerobacter* sp. glucose-galactose binding protein (GGBP), and wherein said ligand-binding protein comprises an amino acid sequence having at least 90% identity to the amino acid sequence of SEQ ID NO: 298, 92, 98, 102, or 66-68.

2. The biosensor of claim 1, wherein said ligand-binding protein comprises a mutation compared to a naturally occurring protein, and wherein at least one amino acid of the ligand-binding protein has been substituted with a cysteine.

3. The biosensor of claim 1, wherein said ligand-binding protein comprises a mutation compared to a naturally occurring protein, and wherein said ligand-binding protein has no deletions or insertions compared to the naturally occurring protein.

4. The biosensor of claim 1, wherein said ligand-binding protein comprises a mutation compared to a naturally occurring protein, and wherein said ligand-binding protein comprises (i) less than about 5, 4, 3, 2, or 1 inserted amino acids, and/or (ii) less than about 5, 4, 3, 2, or 1 deleted amino acids compared to the naturally occurring protein.

5. The biosensor of claim 1, wherein said ligand-binding protein comprises a mutant of a microbial glucose-galactose binding protein, and wherein said mutant comprises a mutation that alters the mutant's affinity and/or specificity for glucose and/or galactose compared to the microbial glucose-galactose binding protein.

6. The biosensor of claim 1, wherein said ligand-binding protein is or is a mutant of: a *Thermoanaerobacter thermosaccharolyticum* GGBP (ttGGBP).

7. The biosensor of claim 1, wherein said glucose-galactose binding protein comprises an amino acid sequence that is between 10% and 100% identical to the amino acid sequence of ttGGBP (SEQ ID NO: 2 or 18).

8. The biosensor of claim 1, wherein said ligand-binding protein comprises (a) a stretch of at least 5 amino acids having at least about 50% identity to a stretch of consecutive amino acids including position 10 of ecGGBP;

(b) a stretch of at least 5 amino acids having at least about 50% identity to a stretch of consecutive amino acids including position 14 of ecGGBP;

(c) a stretch of at least 5 amino acids having at least about 50%, 55%, 60%, 65%, 75%, 80%, 85%, 90%, or 95% identity to a stretch of consecutive amino acids including position 91 of ecGGBP;

(d) a stretch of at least 5 amino acids having at least about 50% identity to a stretch of consecutive amino acids including position 149 of ecGGBP;

(e) a stretch of at least 5 amino acids having at least about 50% identity to a stretch of consecutive amino acids including position 150 of ecGGBP;

(f) a stretch of at least 5 amino acids having at least about 50% identity to a stretch of consecutive amino acids including position 155 of ecGGBP;

(g) a stretch of at least 5 amino acids having at least about 50% identity to a stretch of consecutive amino acids including position 160 of ecGGBP;

(h) a stretch of at least 5 amino acids having at least about 50% identity to a stretch of consecutive amino acids including position 183 of ecGGBP;

(i) a stretch of at least 5 amino acids having at least about 50% identity to a stretch of consecutive amino acids including position 210 of ecGGBP;

(j) a stretch of at least 5 amino acids having at least about 50% identity to a stretch of consecutive amino acids including position 235 of ecGGBP;

(k) a stretch of at least 5 amino acids having at least about 50% identity to a stretch of consecutive amino acids including position 240 of ecGGBP;

(l) a stretch of at least 5 amino acids having at least about 50% identity to a stretch of consecutive amino acids including position 255 of ecGGBP; or (m) a stretch of at least 5 amino acids having at least about 50% identity to a stretch of consecutive amino acids including position 260 of ecGGBP, wherein each ecGGBP amino acid position is numbered as in SEQ ID NO: 17.

9. The biosensor of claim 1, wherein when said ligand-binding protein shares a primary complementary surface (PCS) with ecGGBP, wherein the PCS of ecGGBP comprises positions 14, 16, 91, 152, 154, 158, 183, 211, 236, and 256, wherein each position is counted as in SEQ ID NO: 17, and wherein when the amino acid sequence of said ligand-binding protein is aligned with ecGGBP (SEQ ID NO: 17), then said amino acid sequence comprises (i) D or N at the position that aligns with position 14 of ecGGBP;

(ii) F, Y, or W at the position that aligns with position 16 of ecGGBP;

(iii) N or D at the position that aligns with position 91 of ecGGBP;

(iv) H, N, or Q at the position that aligns with position 152 of ecGGBP;

(v) D or N at the position that aligns with position 154 of ecGGBP;

(vi) R at the position that aligns with position 158 of ecGGBP;

(vii) W, F, or Y at the position that aligns with position 183 of ecGGBP;

(viii) N or D at the position that aligns with position 211 of ecGGBP;

(ix) D or N at the position that aligns with position 236 of ecGGBP; and (x) N or D at the position that aligns with position 256 of ecGGBP.

10. The biosensor of claim 1, wherein the $C_\alpha$ root-mean-square deviation (RMSD) between the backbone of the ligand-binding polypeptide and ttGGBP is between about 0.1-3, 0.5-1, 0.5-1.5, or 0.5-2, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å.

11. The biosensor of claim 1, wherein said reporter group is covalently attached to said ligand-binding protein.

12. The biosensor of claim 1, wherein said reporter group is conjugated to a cysteine of the ligand-binding protein.

13. The biosensor of claim 1, wherein said reporter group comprises a fluorophore, and wherein said signal comprises a fluorescent signal.

14. The biosensor of claim 13, wherein an emission spectrum of said fluorophore exhibits hypsochromicity or bathochromicity upon ligand binding to the ligand-binding domain of said ligand-binding protein.

15. The biosensor of claim 13, wherein said fluorophore comprises 5-iodoacetamidofluorescein (5IAF) or 6-iodoacetamidofluorescein (6IAF), rhodamine, Oregon Green, eosin, Texas Red, indocarbocyanine, oxacarbocyanine, thiacarbocyanine, merocyanine, Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD), N-((2-(iodoacetoxy)ethyl)-N-methy-1) amino-7-nitrobenz-2-oxa-1,3-diazole (NBDE), JPW4039, JPW4042, JPW4045, Oregon Green, Pacific Blue, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507, Alexa488, Alexa532, Alexa546, Cy5, or 1-(2-maleimidylethyl)-4-(5-(4-methoxyphenyl)oxazol-2-yl) pyridinium methanesulfonate (PyMPO maleimide) (PyMPO).

16. The biosensor of claim 13, comprising Acrylodan (6-acryloyl-2-dimethylaminonaphthalene) or Badan (6-bromo-acetyl-2-dimethylamino-naphthalene) or a derivative thereof.

17. The biosensor of claim 16, wherein said derivative comprises a replacement of the two-ring naphthalene of Acrylodan or Badan with a three-ring anthracene, a fluorene, or a styrene.

18. The biosensor of claim 1, wherein said ligand-binding protein is a mutant of ttGGBP comprising one or more of the following substitutions: Y11X, D15X, T16X, F17X, G20X, N42X, V67X, R69X, R91X, E92X, A111X, Q148X, H151X, Q152X, A154X, N181X, W182X, D183X, D211X, T237X, T240X, L257X, N258X, D259X, A260X, and K300X where X is any amino acid, an amino acid that results in a conservative substitution, or a cysteine, and where each position is counted in ttGGBP without including the signal peptide (SEQ ID NO: 18).

19. The biosensor of claim 18, wherein said ligand-binding protein is a mutant of ttGGBP comprising a W182C substitution and/or a F17C substitution to SEQ ID NO: 18.

20. The biosensor of claim 1, wherein said ligand-binding protein comprises the amino acid sequence of SEQ ID NO: 298, 92, 98, 102, or 66-68.

21. The biosensor of claim 1, wherein said ligand-binding protein comprises the amino acid sequence of SEQ ID NO: 298.

22. The biosensor of claim 1, wherein said ligand-binding protein consists of the amino acid sequence of SEQ ID NO: 298.

23. The biosensor of claim 1, wherein said ligand-binding protein consists of the amino acid sequence of SEQ ID NO: 298, and wherein said reporter group consists of Acrylodan.

24. A method of detecting the presence of a ligand in a sample, the method comprising:

(a) contacting the biosensor of claim 1 with the sample;

(b) measuring a signal from the biosensor; and (c) comparing the signal to a ligand-free control, wherein a difference in signal indicates the presence of ligand in the sample, and wherein the ligand comprises glucose, galactose, or combination thereof.

25. A method for monitoring the level of a ligand in a subject, comprising (a) administering a biosensor according to claim 1 or a device comprising a biosensor according to claim 1 to said subject, wherein after administration the biosensor is in contact with a bodily fluid or surface of said subject, and (b) detecting (i) a signal produced by a reporter group of said biosensor continuously or repeatedly at intervals less than about 30 minutes apart, and/or (ii) whether a signal is produced by a reporter group of said biosensor continuously or repeatedly at intervals less than about 30 minutes apart.

* * * * *

SEQUENCE LISTING

```
<160> NUMBER OF SEQ ID NOS: 298

<210> SEQ ID NO 1
<211> LENGTH: 332
<212> TYPE: PRT
<213> ORGANISM: Escherichia coli

<400> SEQUENCE: 1

Met Asn Lys Lys Val Leu Thr Leu Ser Ala Ile Met Ala Ser Met Leu
1               5                   10                  15

Phe Gly Ala Ala Ala His Ala Ala Asp Thr Arg Ile Gly Val Thr Ile
            20                  25                  30

Tyr Lys Tyr Asp Asp Asn Phe Met Ser Val Val Arg Lys Ala Ile Glu
        35                  40                  45

Gln Asp Ala Lys Ala Ala Pro Asp Val Gln Leu Leu Met Asn Asp Ser
    50                  55                  60

Gln Asn Asp Gln Ser Lys Gln Asn Asp Gln Ile Asp Val Leu Leu Ala
65                  70                  75                  80

Lys Gly Val Lys Ala Leu Ala Ile Asn Leu Val Asp Pro Ala Ala Ala
                85                  90                  95

Gly Thr Val Ile Glu Lys Ala Arg Gly Gln Asn Val Pro Val Val Phe
            100                 105                 110

Phe Asn Lys Glu Pro Ser Arg Lys Ala Leu Asp Ser Tyr Asp Lys Ala
        115                 120                 125

Tyr Tyr Val Gly Thr Asp Ser Lys Glu Ser Gly Ile Ile Gln Gly Asp
    130                 135                 140

Leu Ile Ala Lys His Trp Ala Ala Asn Gln Gly Trp Asp Leu Asn Lys
145                 150                 155                 160

Asp Gly Gln Ile Gln Phe Val Leu Leu Lys Gly Glu Pro Gly His Pro
                165                 170                 175

Asp Ala Glu Ala Arg Thr Thr Tyr Val Ile Lys Glu Leu Asn Asp Lys
            180                 185                 190

Gly Ile Lys Thr Glu Gln Leu Gln Leu Asp Thr Ala Met Trp Asp Thr
        195                 200                 205

Ala Gln Ala Lys Asp Lys Met Asp Ala Trp Leu Ser Gly Pro Asn Ala
    210                 215                 220

Asn Lys Ile Glu Val Val Ile Ala Asn Asn Asp Ala Met Ala Met Gly
225                 230                 235                 240
```

```
Ala Val Glu Ala Leu Lys Ala His Asn Lys Ser Ser Ile Pro Val Phe
                245                 250                 255

Gly Val Asp Ala Leu Pro Glu Ala Leu Ala Leu Val Lys Ser Gly Ala
            260                 265                 270

Leu Ala Gly Thr Val Leu Asn Asp Ala Asn Asn Gln Ala Lys Ala Thr
        275                 280                 285

Phe Asp Leu Ala Lys Asn Leu Ala Asp Gly Lys Gly Ala Ala Asp Gly
    290                 295                 300

Thr Asn Trp Lys Ile Asp Asn Lys Val Val Arg Val Pro Tyr Val Gly
305                 310                 315                 320

Val Asp Lys Asp Asn Leu Ala Glu Phe Ser Lys Lys
                325                 330


<210> SEQ ID NO 2
<211> LENGTH: 360
<212> TYPE: PRT
<213> ORGANISM: Thermoanaerobacterium thermosaccharolyticum

<400> SEQUENCE: 2

Met Lys Lys Ile Leu Thr Tyr Leu Val Leu Val Val Leu Val Leu Ser
1               5                   10                  15

Ala Leu Leu Thr Gly Cys Gly Asn Ser Asn Thr Thr Ser Ser Asn Ser
            20                  25                  30

Ser Ser Ser Ser Ser Gln Gln Ser Asp Lys Thr Ala Ser Ser Asp Ser
        35                  40                  45

Gly Lys Gln Leu Asn Ile Gly Val Ala Ile Tyr Lys Phe Asp Asp Thr
    50                  55                  60

Phe Met Thr Gly Val Arg Asn Ala Met Thr Ala Glu Ala Gln Gly Lys
65                  70                  75                  80

Ala Lys Leu Asn Met Val Asp Ser Gln Asn Ser Gln Pro Thr Gln Asn
                85                  90                  95

Asp Gln Val Asp Leu Phe Ile Thr Lys Lys Met Asn Ala Leu Ala Ile
            100                 105                 110

Asn Pro Val Asp Arg Thr Ala Ala Gly Thr Ile Ile Asp Lys Ala Lys
        115                 120                 125

Gln Ala Asn Ile Pro Val Val Phe Phe Asn Arg Glu Pro Leu Pro Glu
    130                 135                 140

Asp Met Lys Lys Trp Asp Lys Val Tyr Tyr Val Gly Ala Lys Ala Glu
145                 150                 155                 160

Gln Ser Gly Ile Leu Gln Gly Gln Ile Met Ala Asp Tyr Trp Lys Ala
                165                 170                 175

His Pro Glu Ala Asp Lys Asn His Asp Gly Val Met Gln Tyr Val Met
            180                 185                 190

Leu Met Gly Gln Pro Gly His Gln Asp Ala Ile Leu Arg Thr Gln Tyr
        195                 200                 205

Ser Ile Gln Thr Val Lys Asp Ala Gly Ile Lys Val Gln Glu Leu Ala
    210                 215                 220

Lys Asp Tyr Ala Asn Trp Asp Arg Val Thr Ala His Asp Lys Met Ala
225                 230                 235                 240

Ala Trp Leu Ser Ser Phe Gly Asp Lys Ile Glu Ala Val Phe Cys Asn
                245                 250                 255

Asn Asp Asp Met Ala Leu Gly Ala Ile Glu Ala Leu Lys Ser Ala Gly
            260                 265                 270

Tyr Phe Thr Gly Asn Lys Tyr Ile Pro Val Val Gly Val Asp Ala Thr
```

275 280 285

Ala Pro Gly Ile Gln Ala Ile Lys Asp Gly Thr Leu Leu Gly Thr Val
290 295 300

Leu Asn Asp Ala Lys Asn Gln Ala Lys Ala Thr Phe Asn Ile Ala Tyr
305 310 315 320

Glu Leu Ala Gln Gly Ile Thr Pro Thr Lys Asp Asn Ile Gly Tyr Asp
325 330 335

Ile Thr Asp Gly Lys Tyr Val Trp Ile Pro Tyr Lys Lys Ile Thr Lys
340 345 350

Asp Asn Ile Ser Asp Ala Glu Gln
355 360

<210> SEQ ID NO 3
<211> LENGTH: 332
<212> TYPE: PRT
<213> ORGANISM: Salmonella enterica

<400> SEQUENCE: 3

Met Asn Lys Lys Val Leu Thr Leu Ser Ala Val Met Ala Ser Leu Leu
1 5 10 15

Phe Gly Ala His Ala His Ala Ala Asp Thr Arg Ile Gly Val Thr Ile
20 25 30

Tyr Lys Tyr Asp Asp Asn Phe Met Ser Val Val Arg Lys Ala Ile Glu
35 40 45

Lys Asp Gly Lys Ser Ala Pro Asp Val Gln Leu Leu Met Asn Asp Ser
50 55 60

Gln Asn Asp Gln Ser Lys Gln Asn Asp Gln Ile Asp Val Leu Leu Ala
65 70 75 80

Lys Gly Val Lys Ala Leu Ala Ile Asn Leu Val Asp Pro Ala Ala Ala
85 90 95

Gly Thr Val Ile Glu Lys Ala Arg Gly Gln Asn Val Pro Val Val Phe
100 105 110

Phe Asn Lys Glu Pro Ser Arg Lys Ala Leu Asp Ser Tyr Asp Lys Ala
115 120 125

Tyr Tyr Val Gly Thr Asp Ser Lys Glu Ser Gly Val Ile Gln Gly Asp
130 135 140

Leu Ile Ala Lys His Trp Gln Ala Asn Gln Gly Trp Asp Leu Asn Lys
145 150 155 160

Asp Gly Lys Ile Gln Tyr Val Leu Leu Lys Gly Glu Pro Gly His Pro
165 170 175

Asp Ala Glu Ala Arg Thr Thr Tyr Val Val Lys Glu Leu Asn Asp Lys
180 185 190

Gly Ile Gln Thr Glu Gln Leu Ala Leu Asp Thr Ala Met Trp Asp Thr
195 200 205

Ala Gln Ala Lys Asp Lys Met Asp Ala Trp Leu Ser Gly Pro Asn Ala
210 215 220

Asn Lys Ile Glu Val Val Ile Ala Asn Asn Asp Ala Met Ala Met Gly
225 230 235 240

Ala Val Glu Ala Leu Lys Ala His Asn Lys Ser Ser Ile Pro Val Phe
245 250 255

Gly Val Asp Ala Leu Pro Glu Ala Leu Ala Leu Val Lys Ser Gly Ala
260 265 270

Met Ala Gly Thr Val Leu Asn Asp Ala Asn Asn Gln Ala Lys Ala Thr
275 280 285

```
Phe Asp Leu Ala Lys Asn Leu Ala Glu Gly Lys Gly Ala Ala Asp Gly
    290                 295                 300

Thr Ser Trp Lys Ile Glu Asn Lys Ile Val Arg Val Pro Tyr Val Gly
305                 310                 315                 320

Val Asp Lys Asp Asn Leu Ser Glu Phe Thr Gln Lys
                325                 330


<210> SEQ ID NO 4
<211> LENGTH: 356
<212> TYPE: PRT
<213> ORGANISM: Caldicellulosiruptor hydrothermalis

<400> SEQUENCE: 4

Met Phe Asn Lys Lys Lys Phe Trp Val Val Leu Val Ser Met Val Leu
1               5                   10                  15

Ile Ile Ser Leu Val Leu Val Gly Cys Gly Lys Lys Ser Thr Asn Asp
            20                  25                  30

Ser Ser Asn Gly Thr Ser Glu Glu Asn Lys Pro Tyr Ile Gly Val Ala
        35                  40                  45

Ile Tyr Lys Phe Asp Asp Thr Phe Met Thr Gly Val Arg Asn Ala Ile
    50                  55                  60

Ala Lys Glu Gly Glu Gly Lys Ala Lys Leu Asp Phe Val Asp Cys Gln
65                  70                  75                  80

Asn Ser Gln Ser Thr Gln Asn Asp Lys Ile Asp Leu Phe Ile Thr Lys
                85                  90                  95

Lys Val Asp Ala Leu Ala Ile Asn Pro Val Asp Arg Thr Ala Ala Gly
            100                 105                 110

Val Leu Ile Asp Lys Ala Lys Gln Ala Asn Ile Pro Val Val Phe Phe
        115                 120                 125

Asn Arg Glu Pro Leu Pro Glu Asp Met Lys Lys Trp Asp Lys Val Tyr
    130                 135                 140

Tyr Val Gly Ala Lys Ala Glu Gln Ser Gly Thr Leu Gln Gly Glu Ile
145                 150                 155                 160

Met Ala Glu Tyr Trp Lys Ser His Pro Glu Ala Asp Lys Asn His Asn
                165                 170                 175

Gly Ile Met Glu Tyr Val Met Ile Thr Gly Glu Pro Gly His Gln Asp
            180                 185                 190

Ala Ile Leu Arg Thr Glu Tyr Ser Ile Lys Ala Val Glu Ala Ala Gly
        195                 200                 205

Ile Lys Thr Lys Ala Leu Ala Gln Asp Thr Ala Met Trp Asp Arg Val
    210                 215                 220

Lys Gly Gln Glu Lys Met Gln Ala Phe Leu Ala Ser Phe Gly Asp Arg
225                 230                 235                 240

Ile Glu Ala Val Phe Cys Asn Asn Asp Asp Met Ala Leu Gly Ala Ile
                245                 250                 255

Glu Ala Leu Lys Ala Ala Gly Tyr Phe Lys Asn Gly Lys Tyr Ile Pro
            260                 265                 270

Val Val Gly Val Asp Ala Thr Thr Pro Gly Leu Gln Ala Leu Glu Glu
        275                 280                 285

Gly Thr Leu Leu Gly Thr Val Leu Asn Asp Ala Lys Ala Gln Gly Lys
    290                 295                 300

Ala Thr Phe Asn Leu Ala Tyr Val Leu Ala Lys Gly Glu Lys Pro Thr
305                 310                 315                 320

Lys Glu Asn Val Gly Phe Asp Ile Thr Asp Gly Lys Tyr Ile Trp Val
                325                 330                 335
```

Pro Tyr Gln Lys Val Thr Lys Asp Asn Leu Glu Glu Met Lys Lys Tyr
340 345 350

Val Asn Glu Gln
355

<210> SEQ ID NO 5
<211> LENGTH: 356
<212> TYPE: PRT
<213> ORGANISM: Caldicellulosiruptor obsidiansis

<400> SEQUENCE: 5

Met Leu Asn Lys Lys Lys Phe Trp Val Val Leu Val Ser Ile Val Leu
1 5 10 15

Ala Ile Ser Leu Val Leu Val Gly Cys Gly Lys Lys Ser Thr Asn Glu
20 25 30

Asn Ser Gly Gly Thr Ser Glu Asp Asn Lys Pro Tyr Ile Gly Val Ala
35 40 45

Ile Tyr Lys Phe Asp Asp Thr Phe Met Thr Gly Val Arg Asn Ala Ile
50 55 60

Ala Lys Glu Gly Glu Gly Lys Ala Lys Leu Asp Phe Val Asp Cys Gln
65 70 75 80

Asn Ser Gln Ser Thr Gln Asn Asp Lys Ile Asp Leu Phe Ile Thr Lys
85 90 95

Lys Val Asp Ala Leu Ala Ile Asn Pro Val Asp Arg Thr Ala Ala Gly
100 105 110

Val Leu Ile Asp Lys Ala Lys Gln Ala Asn Ile Pro Val Val Phe Phe
115 120 125

Asn Arg Glu Pro Leu Pro Glu Asp Met Lys Lys Trp Asp Lys Val Tyr
130 135 140

Tyr Val Gly Ala Lys Ala Glu Gln Ser Gly Thr Leu Gln Gly Glu Ile
145 150 155 160

Met Ala Glu Tyr Trp Lys Ser His Pro Glu Ala Asp Lys Asn His Asp
165 170 175

Gly Ile Met Gln Tyr Val Met Ile Thr Gly Glu Pro Gly His Gln Asp
180 185 190

Ala Ile Leu Arg Thr Glu Tyr Ser Ile Lys Ala Val Glu Ala Ala Gly
195 200 205

Ile Arg Val Lys Cys Leu Ala Gln Asp Thr Ala Met Trp Asp Arg Val
210 215 220

Lys Gly Gln Glu Lys Met Gln Ala Phe Leu Ala Ser Phe Gly Asp Lys
225 230 235 240

Ile Glu Ala Val Phe Cys Asn Asn Asp Asp Met Ala Leu Gly Ala Ile
245 250 255

Glu Ala Leu Lys Ala Ala Gly Tyr Phe Lys Asp Gly Lys Tyr Val Pro
260 265 270

Val Val Gly Val Asp Ala Thr Thr Pro Gly Leu Gln Ala Leu Glu Glu
275 280 285

Gly Thr Leu Leu Gly Thr Val Leu Asn Asp Ala Lys Ala Gln Gly Lys
290 295 300

Ala Thr Phe Asn Leu Ala Tyr Val Leu Ala Lys Gly Glu Lys Pro Thr
305 310 315 320

Lys Glu Asn Val Gly Phe Glu Ile Thr Asp Gly Lys Tyr Ile Trp Val
325 330 335

Pro Tyr Gln Lys Val Thr Lys Asp Asn Leu Glu Glu Met Lys Lys Tyr

```
            340                 345                 350

Val Asn Glu Gln
        355


<210> SEQ ID NO 6
<211> LENGTH: 350
<212> TYPE: PRT
<213> ORGANISM: Paenibacillus sp

<400> SEQUENCE: 6

Met Lys Lys Lys Trp Leu Phe Val Leu Met Ala Gly Met Met Leu Thr
1               5                   10                  15

Thr Ala Ala Cys Asn Asn Gly Gly Ser Ser Ser Thr Gly Ser Asp Ser
            20                  25                  30

Thr Gly Gly Asp Ala Val Gly Gly Ser Thr Pro Gln Val Gly Val Ala
        35                  40                  45

Ile Tyr Lys Phe Asp Asp Thr Phe Met Thr Gly Val Arg Asn Ala Met
    50                  55                  60

Ser Asp Ala Ala Asn Gly Val Ala Lys Leu Asp Ile Val Asp Ser Gln
65                  70                  75                  80

Asn Ala Gln Pro Thr Gln Asn Glu Lys Ile Asp Leu Phe Ile Ser Lys
                85                  90                  95

Lys Tyr Ser Ser Met Ile Ile Asn Pro Val Asp Arg Thr Ala Ala Gly
            100                 105                 110

Val Ile Ile Asp Lys Ala Lys Thr Ala Asn Thr Pro Val Val Phe Leu
        115                 120                 125

Asn Arg Glu Pro Ile Ala Glu Asp Met Asn Lys Trp Asp Lys Val Tyr
    130                 135                 140

Tyr Val Gly Ala Lys Ala Glu Glu Ser Gly Thr Ile Ser Gly Gln Leu
145                 150                 155                 160

Ile Val Asp Tyr Trp Lys Ala Asn Pro Lys Ala Asp Lys Asn Gly Asp
                165                 170                 175

Gly Lys Leu Gln Tyr Val Leu Leu Gln Gly Glu Pro Gly His Gln Asp
            180                 185                 190

Ala Glu Leu Arg Thr Lys Phe Ser Val Gln Ala Ile Gln Asp Ala Gly
        195                 200                 205

Ile Glu Val Glu Ala Leu Ala Val Asp Thr Ala Met Trp Asp Arg Val
    210                 215                 220

Lys Gly Gln Glu Lys Met Gln Thr Phe Leu Ala Ser His Gly Asp Lys
225                 230                 235                 240

Ile Glu Ala Val Leu Ala Asn Asn Asp Asp Met Ala Leu Gly Ala Ile
                245                 250                 255

Glu Ala Leu Lys Ala Ala Gly Tyr Phe Ser Gly Asp Lys Tyr Met Pro
            260                 265                 270

Val Val Gly Val Asp Ala Thr Ala Pro Ala Val Gln Ala Leu Glu Asp
        275                 280                 285

Gly Thr Leu Leu Gly Thr Val Leu Asn Asp Ala Lys Ser Gln Gly Lys
    290                 295                 300

Ala Ser Val Ala Ile Ala Ala Ala Leu Ser Lys Gly Glu Ala Pro Asn
305                 310                 315                 320

Lys Glu Asn Thr Gly Phe Asp Ile Thr Asp Gly Lys Tyr Val Trp Ile
                325                 330                 335

Ala Tyr Lys Lys Ile Thr Lys Asp Asn Ile Ala Asp Ala Lys
            340                 345                 350
```

<210> SEQ ID NO 7
<211> LENGTH: 354
<212> TYPE: PRT
<213> ORGANISM: Clostridium saccharolyticum

<400> SEQUENCE: 7

Met Lys Arg Leu Arg Lys Gly Ile Phe Leu Phe Phe Phe Ile Val Trp
1 5 10 15

Thr Ala Phe Pro Leu Tyr Gly Cys Ala Pro Met Glu Gln Lys Lys Asp
20 25 30

Val Gly Glu Ser Ala Thr Ser Glu Ala Gly Thr Glu Gly Val Pro Glu
35 40 45

Glu Thr Gly Pro Lys Ile Gly Val Ser Ile Tyr Arg Tyr Asp Asp Thr
50 55 60

Phe Met Lys Leu Tyr Arg Gln Glu Leu Lys Gln Tyr Leu Glu Glu Thr
65 70 75 80

Tyr His Ala Glu Val Ile Met Arg Asn Ala Gly Gly Asp Gln Lys Glu
85 90 95

Gln Asp Lys Gln Val Asn Gln Phe Ile Ser Asp Gly Cys Asp Gly Ile
100 105 110

Ile Val Asn Pro Val Glu Ile Pro Ala Ala Gln Glu Leu Ala Asp Ala
115 120 125

Cys Ser Arg Ala Gly Ile Pro Leu Val Phe Ile Asn Arg Glu Pro Lys
130 135 140

Glu Glu Glu Gln Lys Arg Trp Arg Glu Lys Gln Met Ala Val Ser Cys
145 150 155 160

Val Gly Thr Asp Ser Arg Gln Ala Gly Thr Tyr Gln Gly Glu Ile Ile
165 170 175

Leu Glu Thr Leu Asn Lys Gly Asp Phe Asn Gly Asp Gly Val Val Ser
180 185 190

Tyr Val Met Leu Met Gly Glu Lys Gly Asn Glu Asp Ser Gln Tyr Arg
195 200 205

Thr Glu Tyr Ser Ile Lys Ala Leu Glu Glu Gly Gly Met Lys Thr Glu
210 215 220

Glu Leu Phe Ser Gly Asn Gly Asn Trp Asn Lys Asp Glu Gly Lys Lys
225 230 235 240

Leu Ala Lys Gln Ala Leu Ala Ser Trp Gly Asn Arg Ile Glu Val Phe
245 250 255

Phe Cys Asn Asn Asp Ser Met Ala Asn Gly Ala Leu Glu Ala Val Glu
260 265 270

Glu Ala Gly Arg Ile Pro Gly Lys Asp Ile Tyr Leu Val Gly Val Asp
275 280 285

Ala Leu Gln Asp Thr Val Thr Tyr Ile Lys Glu Gly Arg Met Thr Gly
290 295 300

Thr Val Leu Asn Asp His Glu Gly Gln Ser Gln Met Ala Ala Asp Thr
305 310 315 320

Leu Lys Lys Met Ile Asp Gly Glu Ser Val Glu Thr Arg Tyr Gln Val
325 330 335

Asp Tyr Ile Lys Val Thr Ala Ile Ser Thr Phe Gln Thr Leu Lys Gly
340 345 350

Glu Asp

<210> SEQ ID NO 8
<211> LENGTH: 354

```
<212> TYPE: PRT
<213> ORGANISM: Butyrivibrio proteoclasticus

<400> SEQUENCE: 8

Met Lys Lys Lys Met Ile Cys Tyr Met Ile Ile Ala Ala Leu Ala Leu
1               5                   10                  15

Ser Leu Met Ala Gly Cys Ser Asn Thr Gln Glu Ser Glu Pro Val Gln
            20                  25                  30

Glu Ser Val Ala Tyr Ser Ser Tyr Ser Asp Ala Lys Val Gly Val Cys
        35                  40                  45

Ile Tyr Gln Lys Ser Asp Asn Phe Met Ser Leu Phe Ser Ser Glu Leu
    50                  55                  60

Val Lys Tyr Leu Val Ser Arg Gly Phe Ser Lys Asp Asn Ile Ile Leu
65                  70                  75                  80

Tyr Asp Ser Asn Asn Asp Glu Asn Val Gln Leu Ser Gln Val Glu Glu
                85                  90                  95

Leu Ile Ala Ser Gly Ile Asn Ala Leu Ile Ile Asn Pro Val Asn Ser
            100                 105                 110

Ser Val Ala His Ser Ile Thr Asp Met Ala Ser Ala Ser Asn Ile Pro
        115                 120                 125

Leu Val Tyr Ile Asn Arg Glu Pro Ser Gly Asp Glu Glu Asn Arg Trp
    130                 135                 140

Glu Met Tyr Gln Leu Asn Val Cys Tyr Val Gly Cys Asp Ala Arg Gln
145                 150                 155                 160

Ser Gly Ile Tyr Gln Gly Glu Ile Leu Leu Ser Leu Gly Lys Asn Lys
                165                 170                 175

Leu Asp His Asn Gly Asp Gly Lys Ile Gln Tyr Phe Met Ile Glu Gly
            180                 185                 190

Ala Pro Glu Asn Ile Asp Ala Gly Tyr Arg Thr Leu Tyr Ser Val Ser
        195                 200                 205

Ala Leu Gln Asn Ser Glu Met Glu Met Asp Cys Leu Leu Asp Glu Val
    210                 215                 220

Gly Asn Trp Asp Glu Thr Thr Ala Ser Leu Leu Val Ser Lys Gly Ile
225                 230                 235                 240

Gln Asn Gly Leu Lys Pro Glu Val Ile Ile Cys Asn Asn Asp Ala Met
                245                 250                 255

Ala Leu Gly Ala Ile Lys Ala Ala Glu Lys Ser Gly Leu Val Pro Gly
            260                 265                 270

Glu Asp Val Tyr Ile Val Gly Val Asp Ala Leu Pro Glu Ala Ile Glu
        275                 280                 285

Met Ile Lys Ala Gly Lys Leu Ala Gly Thr Val Tyr Asn Asp Tyr Val
    290                 295                 300

Leu Gln Ser His Lys Ser Ala Asp Ala Val Ile Asn Tyr Leu Lys Gly
305                 310                 315                 320

Ile Asp Asn Glu His Tyr Ile Gly Cys Asp Tyr Val Lys Val Asp Ile
                325                 330                 335

Asp Asn Ala Glu Ser Ile Ala Gly Leu Thr Asn Thr Asp Glu Glu Asp
            340                 345                 350

Ile Asp


<210> SEQ ID NO 9
<211> LENGTH: 383
<212> TYPE: PRT
<213> ORGANISM: Roseburia intestinalis
```

<400> SEQUENCE: 9

Met Lys Arg Lys Val Val Ser Val Ile Leu Ala Thr Ala Met Val Ala
1 5 10 15

Ser Met Val Ala Gly Cys Gly Gly Ser Asn Asn Ala Ser Thr Asn Asn
20 25 30

Ala Gly Thr Thr Thr Asp Ala Ala Ala Ser Asp Ala Ser Ser Asp Thr
35 40 45

Ser Asn Asp Ala Ala Ala Thr Glu Ala Ala Asp Ala Gly Asp Ala Ala
50 55 60

Ala Asp Ala Ala Thr Asp Ala Asp Ala Ser Leu Ala Asp Lys Lys Val
65 70 75 80

Gly Val Cys Ile Tyr Gln Phe Ser Asp Asn Phe Met Thr Leu Phe Arg
85 90 95

Thr Glu Leu Glu Asn Tyr Leu Val Glu Lys Gly Phe Ser Lys Asp Asn
100 105 110

Ile Thr Ile Val Asp Gly Ala Asn Asp Gln Ala Thr Gln Thr Gly Gln
115 120 125

Ile Asp Asn Phe Ile Thr Glu Gly Val Asp Val Leu Ile Ile Asn Pro
130 135 140

Val Asn Ser Ser Ser Ala Ala Thr Ile Thr Asp Lys Val Val Ala Ala
145 150 155 160

Gly Ile Pro Leu Val Tyr Ile Asn Arg Glu Pro Asp Glu Glu Glu Gln
165 170 175

Lys Arg Trp Ser Asp Asn Asn Trp Asp Val Thr Tyr Val Gly Cys Asp
180 185 190

Ala Arg Gln Ser Gly Thr Phe Gln Gly Glu Met Ile Ser Asp Leu Gly
195 200 205

Leu Asp Thr Val Asp Leu Asn Gly Asn Gly Lys Ile Asp Tyr Val Met
210 215 220

Val Glu Gly Asp Pro Glu Asn Val Asp Ala Gln Tyr Arg Thr Glu Tyr
225 230 235 240

Ser Val Lys Ala Leu Glu Asp Ala Gly Leu Glu Val Asn Cys Leu Ser
245 250 255

Asp Gln Val Gly Asn Trp Gln Gln Asp Gln Ala Gln Gln Ile Val Ala
260 265 270

Asn Ala Leu Gly Gln Tyr Gly Asn Asp Val Glu Val Val Phe Cys Asn
275 280 285

Asn Asp Ala Met Ala Leu Gly Ala Leu Gln Ala Ile Gln Ser Ala Gly
290 295 300

Arg Thr Val Gly Thr Asp Ile Tyr Leu Val Gly Val Asp Ala Leu Ser
305 310 315 320

Glu Ala Leu Glu Asp Val Leu Ala Gly Thr Met Thr Gly Thr Val Phe
325 330 335

Asn Asp His Phe Ser Gln Ser His Ser Ala Ala Asp Ala Ala Ile Asn
340 345 350

Tyr Ile Thr Gly Ala Gly Asn Asp His Tyr Ile Gly Cys Asp Tyr Val
355 360 365

Lys Val Thr Lys Asp Asn Ala Gln Asp Val Leu Asp Met Val Lys
370 375 380

<210> SEQ ID NO 10
<211> LENGTH: 350
<212> TYPE: PRT
<213> ORGANISM: Faecalibacterium prausnitzii

<400> SEQUENCE: 10

```
Met Lys Met Ile Ser Arg Arg Asp Phe Leu Lys Ala Ser Ala Val Val
1               5                   10                  15

Gly Ala Thr Ala Ala Met Thr Ala Cys Gly Gly Ser Ser Ser Thr Ser
            20                  25                  30

Thr Ala Ala Ser Ser Val Ala Ser Ser Thr Ala Ala Ser Ala Ala Ala
        35                  40                  45

Thr Asn Gly Ser Ala Asn Ile Gly Val Cys Ile Tyr Gln Phe Ala Asp
    50                  55                  60

Asn Phe Met Thr Leu Tyr Arg Ala Asp Leu Glu Gly Tyr Leu Lys Asp
65                  70                  75                  80

Met Gly Tyr Ser Val Thr Ile Met Asp Gly Lys Asn Asp Gln Asn Thr
                85                  90                  95

Gln Thr Glu Gln Ile Asn Thr Phe Leu Gln Gln Gly Val Asp Val Leu
            100                 105                 110

Val Ile Asn Pro Val Gln Thr Thr Ser Ala Gln Thr Ile Val Asp Thr
        115                 120                 125

Val Ser Pro Ser Gly Thr Pro Ile Val Phe Ile Asn Arg Glu Pro Glu
    130                 135                 140

Glu Ser Val Leu Asp Ser Tyr Lys Gly Lys Cys Cys Tyr Val Gly Ala
145                 150                 155                 160

Asp Ala Arg Gln Ser Gly Thr Tyr Gln Gly Glu Leu Ile Leu Ala Thr
                165                 170                 175

Asp Thr Gln Gly Asp Ile Asn Gly Asp Gly Lys Ile Thr Tyr Ile Met
            180                 185                 190

Cys Lys Gly Asp Pro Glu Asn Ile Asp Ala Gln Tyr Arg Thr Glu Tyr
        195                 200                 205

Ser Ile Lys Ala Leu Thr Asp Ala Gly Lys Glu Val Glu Cys Leu Tyr
    210                 215                 220

Glu Tyr Leu Asp Asn Trp Asp Gln Thr Thr Ala Gln Gln Asp Val Ala
225                 230                 235                 240

Asn Ala Leu Ser Gln Tyr Gly Glu Lys Ile Glu Val Val Phe Cys Asn
                245                 250                 255

Asn Asp Ala Met Ala Leu Gly Ala Leu Gln Ser Ile Gln Gln Ala Gly
            260                 265                 270

Arg Thr Val Gly Lys Asp Val Tyr Leu Val Gly Val Asp Ala Leu Val
        275                 280                 285

Glu Ala Val Gln Asn Val Val Asp Gly Asn Met Thr Gly Thr Val Leu
    290                 295                 300

Asn Asp Asp Val Gly Gln Ala Thr Lys Ala Ala Glu Ala Thr Lys Leu
305                 310                 315                 320

Phe Val Glu Gly Lys Asp Val Glu Lys Tyr Tyr Trp Val Asp Tyr Val
                325                 330                 335

Lys Val Thr Lys Asp Asn Ala Ser Gln Tyr Leu Lys Glu Asp
            340                 345                 350
```

<210> SEQ ID NO 11
<211> LENGTH: 338
<212> TYPE: PRT
<213> ORGANISM: Clostridium ljungdahlii

<400> SEQUENCE: 11

```
Met Ile Val Lys Lys Cys Met Lys Ser Ile Ala Val Thr Gly Leu Leu
1               5                   10                  15
```

Thr Ile Ile Leu Gly Thr Gly Cys Ser Asn Ser Leu Ser Ser Asn Lys
20 25 30

Asn Glu Pro Val Ile Gly Phe Val Ala Tyr Glu Phe Asn Asn Thr Trp
35 40 45

Ile Thr Glu Leu Lys Asn Glu Ile Tyr Lys Val Ser Ser Gly Lys Ala
50 55 60

Arg Val Asp Ile Trp Asn Gly Asp Asn Ile Gln Thr Val Glu Asn Asp
65 70 75 80

Lys Ile Asn Leu Phe Ile Asn Arg Lys Val Asn Val Leu Asp Ile Asn
85 90 95

Pro Val Asp Val Asn Ala Ala Gly Gln Ile Ile Glu Lys Cys Lys Lys
100 105 110

Ala Asn Ile Pro Thr Val Phe Val Asn Arg Gln Pro Lys Lys Glu Asp
115 120 125

Met Glu Lys Trp Asn Lys Val Tyr Tyr Val Gly Ala Lys Ala Glu Gln
130 135 140

Ser Gly Thr Ile Gln Gly Gln Met Leu Val Asn Tyr Phe Lys Gly His
145 150 155 160

Pro Thr Gln Asp Gly Thr Ile Arg Tyr Ile Met Leu Lys Gly Glu Thr
165 170 175

Arg Asn Gln Asp Ala Glu Lys Arg Thr Gln Tyr Ser Ile Lys Ala Leu
180 185 190

Lys Asp Ser Gly Phe Lys Val Gln Lys Val Ala Glu Asp Thr Ala Met
195 200 205

Trp Asp Arg Thr Lys Ala Gln Glu Lys Met Thr Ser Phe Ile Ser Ser
210 215 220

Tyr Gly Pro Asn Phe Asp Cys Val Ile Ala Asn Asn Asp Asp Met Ala
225 230 235 240

Leu Gly Ala Val Asp Ala Leu Lys Ala Ala Gly Tyr Phe Asn Gly Gly
245 250 255

Lys Tyr Val Pro Val Val Gly Val Asp Ala Thr Ala Pro Ala Val Lys
260 265 270

Ala Val Glu Asp Gly Thr Leu Phe Gly Thr Val Leu Asn Asp Ala Ala
275 280 285

Lys Gln Gly Asp Ala Ala Phe Asp Leu Ser Tyr Ile Leu Ser Lys Gly
290 295 300

Lys Ile Pro Asp Glu Ser Asn Phe Lys Tyr Lys Val Thr Asp Gly Lys
305 310 315 320

Tyr Ile Trp Ile Asp Tyr Lys Met Ile Thr Lys Glu Asn Val Gln Asp
325 330 335

Ala Lys

<210> SEQ ID NO 12
<211> LENGTH: 336
<212> TYPE: PRT
<213> ORGANISM: Clostridium autoethanogenum

<400> SEQUENCE: 12

Met Lys Lys Cys Met Lys Ser Ile Ala Val Thr Gly Leu Leu Thr Ile
1 5 10 15

Ile Leu Gly Thr Gly Cys Ser Asn Ser Leu Ser Ser Asn Lys Asn Glu
20 25 30

Pro Val Ile Gly Phe Val Ala Tyr Glu Phe Asn Asn Thr Trp Ile Thr
35 40 45

```
Glu Leu Lys Asn Glu Met Tyr Lys Val Ser Asn Gly Lys Ala Arg Val
    50                  55                  60

Asp Ile Trp Asn Gly Asn Asn Ile Gln Thr Val Glu Asn Asp Lys Ile
65                  70                  75                  80

Ser Leu Phe Ile Asn Arg Lys Val Asp Val Leu Asp Ile Asn Pro Val
                85                  90                  95

Asp Val Asn Ala Ala Gly Gln Ile Ile Glu Lys Cys Lys Lys Ala Asn
            100                 105                 110

Ile Pro Thr Val Phe Val Asn Arg Gln Pro Lys Lys Glu Asp Val Glu
        115                 120                 125

Lys Trp Asn Lys Val Tyr Tyr Val Gly Ala Lys Ala Glu Gln Ser Gly
    130                 135                 140

Thr Ile Gln Gly Gln Met Leu Val Asn Tyr Phe Lys Gly His Pro Thr
145                 150                 155                 160

Gln Asp Gly Thr Ile Arg Tyr Ile Met Leu Lys Gly Glu Met Arg Asn
                165                 170                 175

Gln Asp Ala Glu Lys Arg Thr Gln Tyr Ser Ile Lys Ala Leu Glu Asp
            180                 185                 190

Ser Gly Phe Lys Val Gln Lys Val Ala Glu Asp Thr Ala Met Trp Asp
        195                 200                 205

Arg Thr Lys Ala Gln Glu Lys Met Thr Ser Phe Ile Ser Ser Tyr Gly
    210                 215                 220

Pro Asn Phe Asp Cys Val Ile Ala Asn Asn Asp Asp Met Ala Leu Gly
225                 230                 235                 240

Ala Val Asp Ala Leu Lys Ala Ala Gly Tyr Phe Asn Gly Gly Lys Tyr
                245                 250                 255

Val Pro Val Val Gly Val Asp Ala Thr Ala Pro Ala Val Lys Ala Val
            260                 265                 270

Glu Asp Gly Thr Leu Phe Gly Thr Val Leu Asn Asp Ala Ala Lys Gln
        275                 280                 285

Gly Asp Ala Ala Phe Asp Leu Ser Tyr Ile Leu Ser Lys Gly Lys Ile
    290                 295                 300

Pro Asp Glu Ser Asn Phe Lys Tyr Lys Ile Thr Asp Gly Lys Tyr Ile
305                 310                 315                 320

Trp Ile Asp Tyr Lys Met Ile Thr Lys Glu Asn Val Gln Asp Ala Lys
                325                 330                 335
```

<210> SEQ ID NO 13
<211> LENGTH: 367
<212> TYPE: PRT
<213> ORGANISM: Roseburia intestinalis

<400> SEQUENCE: 13

```
Met Cys Gly Ala Glu Lys Val Arg His Met Leu Met Gly Glu Gln Val
1               5                   10                  15

Leu Lys Lys Trp Lys Lys Ser Lys Lys Met Thr Val Ala Phe Gly Gly
            20                  25                  30

Ile Leu Val Met Ser Val Val Ile Gly Gly Cys Gly Gly Arg Glu Asp
        35                  40                  45

Ala Lys Lys Ser Ile Lys Ile Gly Ile Ser Val Tyr Asp Gln Tyr Asp
    50                  55                  60

Thr Phe Val Ser Glu Met Met Lys Asp Phe Asn Asp Tyr Ala Thr Lys
65                  70                  75                  80

Lys Glu Glu Glu Thr Gly Val Ala Ile Asn Ile Asp Thr Tyr Asn Ala
```

```
                85                  90                  95

Ser Ala Ser Gln Ser Thr Gln Asn Ser Gln Val Glu Asn Met Ile Thr
            100                 105                 110

Glu Gly Cys Asp Val Ile Cys Val Asn Leu Val Asp Arg Thr Asp Pro
        115                 120                 125

Thr Ala Ile Ile Asp Leu Ala Glu Lys Asn Asn Ile Pro Val Ile Phe
    130                 135                 140

Phe Asn Arg Glu Leu Val Glu Glu Asp Leu Glu Arg Trp Thr Arg Leu
145                 150                 155                 160

Tyr Tyr Val Gly Ala Gln Ala Phe Glu Ser Gly Ile Met Gln Gly Glu
                165                 170                 175

Leu Ala Ala Glu Ala Phe Leu Thr Asp Gln Ser Leu Asp Lys Asn Gly
            180                 185                 190

Asp Gly Ile Phe Gln Tyr Val Val Leu Glu Gly Glu Ala Gly His Gln
        195                 200                 205

Asp Ala Ile Val Arg Thr Glu Tyr Ser Val Ser Thr Met Ile Asp Ser
    210                 215                 220

Gly Val Glu Val Glu Lys Leu Gly Tyr Ala Ile Ala Asn Trp Asn Arg
225                 230                 235                 240

Ala Gln Ala Gln Thr Lys Met Ala Gln Leu Met Ser Gln Phe Gly Asp
                245                 250                 255

Ser Ile Glu Leu Val Ile Ala Asn Asn Asp Asp Met Ala Leu Gly Ala
            260                 265                 270

Ile Asp Ala Leu Lys Ala Ser Gly Leu Thr Lys Asp Glu Trp Pro Ala
        275                 280                 285

Val Ile Gly Ile Asp Gly Thr Asp Val Gly Leu Glu Ala Val Lys Asn
    290                 295                 300

Lys Glu Met Ile Gly Thr Val Tyr Asn Asp Lys Glu Gly Gln Ala Asp
305                 310                 315                 320

Ala Met Leu Asn Leu Ala Tyr Glu Leu Ser Thr Gly Ser Asp Leu Ser
                325                 330                 335

Asp Leu Asn Leu Ile Asp Gly Lys Tyr Ile Arg Leu Pro Tyr Ala Arg
            340                 345                 350

Val Thr Cys Asp Asp Val Asp Ser Tyr Met Glu Gly Asp Thr Glu
        355                 360                 365


<210> SEQ ID NO 14
<211> LENGTH: 360
<212> TYPE: PRT
<213> ORGANISM: Erysipelothrix rhusiopathiae

<400> SEQUENCE: 14

Met Lys Lys Leu Ser Lys Leu Ile Leu Val Ser Leu Leu Ala Leu Thr
1               5                   10                  15

Leu Phe Gly Cys Ser Ser Lys Gly Gly Ala Glu Gly Asn Ala Asn Glu
            20                  25                  30

Gly Gly Lys Thr Tyr Asn Ile Gly Val Ala Ile Tyr Lys Phe Asp Asp
        35                  40                  45

Asn Phe Met Thr Leu Tyr Arg Glu Glu Leu Ala Ser Tyr Phe Lys Glu
    50                  55                  60

Val Gly Glu Lys Asp Gly Asn Thr Tyr Lys Leu Asp Ile Gln Asp Gly
65                  70                  75                  80

Lys Gln Asp Gln Ala Asn Gln Thr Glu Gln Ile Asn Asn Phe Ile Ala
                85                  90                  95
```

Gln Gly Lys Asp Leu Ile Ile Ala Asn Met Val Asp Pro Thr Ala Ala
            100                 105                 110

Gly Ser Ile Ile Asn Ser Ala Lys Ala Lys Glu Ile Pro Val Val Phe
        115                 120                 125

Ile Asn Arg Glu Pro Glu Thr Gln Glu Leu Glu Ile Trp Pro Gly Lys
    130                 135                 140

Thr Thr Tyr Val Gly Ala Asp Ala Thr Gln Ser Gly Thr Ile Gln Gly
145                 150                 155                 160

Tyr Met Ile Ala Asn Leu Glu Asn Lys Gly Asp Ile Asp Gly Asp Gly
                165                 170                 175

Ser Val Ser Tyr Ile Thr Leu Met Gly Asp Pro Ala Asn Val Asp Ala
            180                 185                 190

Lys Gln Arg Thr Glu Tyr Ser Val Lys Gly Leu Glu Glu Lys Gly Val
        195                 200                 205

Lys Thr Asn Ala Leu Ala Gln Pro Tyr Gln Ala Asn Trp Asp Thr Ala
    210                 215                 220

Lys Gly Gln Glu Phe Thr Ala Asn Ala Leu Glu Gln Phe Gly Asn Lys
225                 230                 235                 240

Leu Glu Val Val Phe Ala Asn Asn Asp Gly Met Ala Val Gly Ala Val
                245                 250                 255

Thr Ala Ile Glu Ala Ala Gly Arg Lys Val Gly Glu Asp Ile Phe Val
            260                 265                 270

Val Gly Val Asp Ala Ile Pro Asp Ala Ile Glu Leu Leu Lys Gly Gly
        275                 280                 285

Lys Leu Thr Gly Thr Val Leu Asn Asp His Phe Asn Gln Ser His Thr
    290                 295                 300

Ala Val Asp Val Ala Leu Glu Leu Leu Gln Gly Lys Asp Val Ser Ala
305                 310                 315                 320

Tyr Tyr Trp His Asp Tyr Val Gly Val Thr Lys Pro Glu Glu Ala Glu
                325                 330                 335

Leu Lys Arg Ala Glu Ala Arg Lys Glu Thr Val Glu Glu Ala Val Lys
            340                 345                 350

Arg Tyr Ala Glu Arg Asp Ala Gln
        355                 360

<210> SEQ ID NO 15
<211> LENGTH: 338
<212> TYPE: PRT
<213> ORGANISM: Eubacterium rectale

<400> SEQUENCE: 15

Met Met Ile Leu Cys Phe Ala Leu Ile Leu Ser Phe Val Ser Cys Ser
1               5                   10                  15

Asn Thr Arg Val Asp Glu Lys Lys Gln Ile Tyr Ile Gly Val Thr Cys
            20                  25                  30

Tyr Asp Gln Lys Asp Thr Phe Ile Gly Glu Leu Ile Glu Thr Phe Lys
        35                  40                  45

Lys Glu Cys Ala Ser Leu Asp Thr Asp Lys Tyr Asp Ile Ser Met Thr
    50                  55                  60

Ile Met Asp Ala Ala Gly Ser Gln Arg Ala Gln Asp Asp Gln Val Gln
65                  70                  75                  80

Glu Met Ile Glu Asp Gly Cys Asn Val Leu Cys Ile Asn Leu Ala Asp
                85                  90                  95

Arg Thr Asp Leu Ser His Ile Ile Asn Ala Ala Met Glu Lys Asp Ile
            100                 105                 110

Pro Ile Ile Phe Phe Asn Arg Glu Pro Val Asp Glu Asp Leu Asn Arg
115 120 125

Trp Asp Lys Leu Tyr Tyr Val Gly Ala Lys Ala Lys Gln Ser Gly Gln
130 135 140

Met Gln Gly Glu Leu Ile Ala Asp Tyr Ile Lys Asn Asn Pro Gly Val
145 150 155 160

Asp Lys Asn Gly Asp Gly Arg Ile Gln Tyr Val Ile Leu Glu Gly Glu
165 170 175

Met Gly His Gln Asp Ala Ile Val Arg Thr Glu Ser Val Thr Glu Ser
180 185 190

Met Lys Asn Asn Gly Leu Gln Ile Glu Lys Leu Ser Cys Gln Ile Ala
195 200 205

Asn Trp Asn Arg Ala Gln Ala Gln Asn Arg Met Thr Gln Leu Ile Gly
210 215 220

Gln Tyr Lys Asn Ser Ile Glu Leu Val Ile Ala Asn Asn Asp Ala Met
225 230 235 240

Ala Leu Gly Ala Ile Asp Ala Tyr Glu Lys Leu Gly Val Thr Glu Ser
245 250 255

Asn Val Pro Ala Phe Phe Gly Val Asp Gly Thr Asp Asp Gly Leu Glu
260 265 270

Ala Val Gln Gln Ser Lys Leu Ala Ala Thr Val Tyr Asn Asp Lys Glu
275 280 285

Gly Gln Ala Met Ala Met Ala Gln Leu Ala Tyr Leu Ala Ala Thr Gly
290 295 300

Gly Ser Met Lys Asn Ile Lys Phe Glu Asp Lys Lys Tyr Val Tyr Leu
305 310 315 320

Pro Tyr Glu Lys Val Thr Pro Asp Asn Val Asn Glu Phe Val Lys Asp
325 330 335

Glu Gln

<210> SEQ ID NO 16
<211> LENGTH: 310
<212> TYPE: PRT
<213> ORGANISM: Artificial Sequence
<220> FEATURE:
<223> OTHER INFORMATION: ecGGBP (with signal peptide replaced with M)

<400> SEQUENCE: 16

Met Ala Asp Thr Arg Ile Gly Val Thr Ile Tyr Lys Tyr Asp Asp Asn
1 5 10 15

Phe Met Ser Val Val Arg Lys Ala Ile Glu Gln Asp Ala Lys Ala Ala
20 25 30

Pro Asp Val Gln Leu Leu Met Asn Asp Ser Gln Asn Asp Gln Ser Lys
35 40 45

Gln Asn Asp Gln Ile Asp Val Leu Leu Ala Lys Gly Val Lys Ala Leu
50 55 60

Ala Ile Asn Leu Val Asp Pro Ala Ala Ala Gly Thr Val Ile Glu Lys
65 70 75 80

Ala Arg Gly Gln Asn Val Pro Val Val Phe Phe Asn Lys Glu Pro Ser
85 90 95

Arg Lys Ala Leu Asp Ser Tyr Asp Lys Ala Tyr Tyr Val Gly Thr Asp
100 105 110

Ser Lys Glu Ser Gly Ile Ile Gln Gly Asp Leu Ile Ala Lys His Trp
115 120 125

```
Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Trp Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Gln Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe Ser Lys Lys
305                 310


<210> SEQ ID NO 17
<211> LENGTH: 309
<212> TYPE: PRT
<213> ORGANISM: Artificial Sequence
<220> FEATURE:
<223> OTHER INFORMATION: ecGGBP (with signal sequence removed)

<400> SEQUENCE: 17

Ala Asp Thr Arg Ile Gly Val Thr Ile Tyr Lys Tyr Asp Asp Asn Phe
1               5                   10                  15

Met Ser Val Val Arg Lys Ala Ile Glu Gln Asp Ala Lys Ala Ala Pro
            20                  25                  30

Asp Val Gln Leu Leu Met Asn Asp Ser Gln Asn Asp Gln Ser Lys Gln
        35                  40                  45

Asn Asp Gln Ile Asp Val Leu Leu Ala Lys Gly Val Lys Ala Leu Ala
    50                  55                  60

Ile Asn Leu Val Asp Pro Ala Ala Ala Gly Thr Val Ile Glu Lys Ala
65                  70                  75                  80

Arg Gly Gln Asn Val Pro Val Val Phe Phe Asn Lys Glu Pro Ser Arg
                85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
        115                 120                 125

Ala Asn Gln Gly Trp Asp Leu Asn Lys Asp Gly Gln Ile Gln Phe Val
    130                 135                 140

Leu Leu Lys Gly Glu Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175
```

Gln Leu Asp Thr Ala Met Trp Asp Thr Ala Gln Ala Lys Asp Lys Met
180 185 190

Asp Ala Trp Leu Ser Gly Pro Asn Ala Asn Lys Ile Glu Val Val Ile
195 200 205

Ala Asn Asn Asp Ala Met Ala Met Gly Ala Val Glu Ala Leu Lys Ala
210 215 220

His Asn Lys Ser Ser Ile Pro Val Phe Gly Val Asp Ala Leu Pro Glu
225 230 235 240

Ala Leu Ala Leu Val Lys Ser Gly Ala Leu Ala Gly Thr Val Leu Asn
245 250 255

Asp Ala Asn Asn Gln Ala Lys Ala Thr Phe Asp Leu Ala Lys Asn Gln
260 265 270

Ala Asp Gly Lys Gly Ala Ala Asp Gly Thr Asn Trp Lys Ile Asp Asn
275 280 285

Lys Val Val Arg Val Pro Tyr Val Gly Val Asp Lys Asp Asn Leu Ala
290 295 300

Glu Phe Ser Lys Lys
305

<210> SEQ ID NO 18
<211> LENGTH: 312
<212> TYPE: PRT
<213> ORGANISM: Artificial Sequence
<220> FEATURE:
<223> OTHER INFORMATION: ttGGBP (with signal peptide replaced with M)

<400> SEQUENCE: 18

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Cys Asn
195 200 205

Asn Asp Asp Met Ala Leu Gly Ala Ile Glu Ala Leu Lys Ser Ala Gly
210 215 220

```
Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln
305                 310


<210> SEQ ID NO 19
<211> LENGTH: 310
<212> TYPE: PRT
<213> ORGANISM: Artificial Sequence
<220> FEATURE:
<223> OTHER INFORMATION: stGGBP (with signal peptide replaced with M)

<400> SEQUENCE: 19

Met Ala Asp Thr Arg Ile Gly Val Thr Ile Tyr Lys Tyr Asp Asp Asn
1               5                   10                  15

Phe Met Ser Val Val Arg Lys Ala Ile Glu Lys Asp Gly Lys Ser Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Val Ile Gln Gly Asp Leu Ile Ala Lys His Trp
        115                 120                 125

Gln Ala Asn Gln Gly Trp Asp Leu Asn Lys Asp Gly Lys Ile Gln Tyr
    130                 135                 140

Val Leu Leu Lys Gly Glu Pro Gly His Pro Asp Ala Glu Ala Arg Thr
145                 150                 155                 160

Thr Tyr Val Val Lys Glu Leu Asn Asp Lys Gly Ile Gln Thr Glu Gln
                165                 170                 175

Leu Ala Leu Asp Thr Ala Met Trp Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Met Ala Gly Thr Val Leu
                245                 250                 255

Asn Asp Ala Asn Asn Gln Ala Lys Ala Thr Phe Asp Leu Ala Lys Asn
            260                 265                 270
```

```
Leu Ala Glu Gly Lys Gly Ala Ala Asp Gly Thr Ser Trp Lys Ile Glu
        275                 280                 285

Asn Lys Ile Val Arg Val Pro Tyr Val Gly Val Asp Lys Asp Asn Leu
    290                 295                 300

Ser Glu Phe Thr Gln Lys
305                 310


<210> SEQ ID NO 20
<211> LENGTH: 316
<212> TYPE: PRT
<213> ORGANISM: Artificial Sequence
<220> FEATURE:
<223> OTHER INFORMATION: chyGGBP (with signal peptide replaced with M)

<400> SEQUENCE: 20

Met Lys Pro Tyr Ile Gly Val Ala Ile Tyr Lys Phe Asp Asp Thr Phe
1               5                   10                  15

Met Thr Gly Val Arg Asn Ala Ile Ala Lys Glu Gly Glu Gly Lys Ala
            20                  25                  30

Lys Leu Asp Phe Val Asp Cys Gln Asn Ser Gln Ser Thr Gln Asn Asp
        35                  40                  45

Lys Ile Asp Leu Phe Ile Thr Lys Lys Val Asp Ala Leu Ala Ile Asn
    50                  55                  60

Pro Val Asp Arg Thr Ala Ala Gly Val Leu Ile Asp Lys Ala Lys Gln
65                  70                  75                  80

Ala Asn Ile Pro Val Val Phe Phe Asn Arg Glu Pro Leu Pro Glu Asp
                85                  90                  95

Met Lys Lys Trp Asp Lys Val Tyr Tyr Val Gly Ala Lys Ala Glu Gln
            100                 105                 110

Ser Gly Thr Leu Gln Gly Glu Ile Met Ala Glu Tyr Trp Lys Ser His
        115                 120                 125

Pro Glu Ala Asp Lys Asn His Asn Gly Ile Met Glu Tyr Val Met Ile
    130                 135                 140

Thr Gly Glu Pro Gly His Gln Asp Ala Ile Leu Arg Thr Glu Tyr Ser
145                 150                 155                 160

Ile Lys Ala Val Glu Ala Ala Gly Ile Lys Thr Lys Ala Leu Ala Gln
                165                 170                 175

Asp Thr Ala Met Trp Asp Arg Val Lys Gly Gln Glu Lys Met Gln Ala
            180                 185                 190

Phe Leu Ala Ser Phe Gly Asp Arg Ile Glu Ala Val Phe Cys Asn Asn
        195                 200                 205

Asp Asp Met Ala Leu Gly Ala Ile Glu Ala Leu Lys Ala Ala Gly Tyr
    210                 215                 220

Phe Lys Asn Gly Lys Tyr Ile Pro Val Val Gly Val Asp Ala Thr Thr
225                 230                 235                 240

Pro Gly Leu Gln Ala Leu Glu Glu Gly Thr Leu Leu Gly Thr Val Leu
                245                 250                 255

Asn Asp Ala Lys Ala Gln Gly Lys Ala Thr Phe Asn Leu Ala Tyr Val
            260                 265                 270

Leu Ala Lys Gly Glu Lys Pro Thr Lys Glu Asn Val Gly Phe Asp Ile
        275                 280                 285

Thr Asp Gly Lys Tyr Ile Trp Val Pro Tyr Gln Lys Val Thr Lys Asp
    290                 295                 300

Asn Leu Glu Glu Met Lys Lys Tyr Val Asn Glu Gln
305                 310                 315
```

<210> SEQ ID NO 21
<211> LENGTH: 316
<212> TYPE: PRT
<213> ORGANISM: Artificial Sequence
<220> FEATURE:
<223> OTHER INFORMATION: cobGGBP (with signal peptide replaced with M)

<400> SEQUENCE: 21

```
Met Lys Pro Tyr Ile Gly Val Ala Ile Tyr Lys Phe Asp Asp Thr Phe
1               5                   10                  15

Met Thr Gly Val Arg Asn Ala Ile Ala Lys Glu Gly Glu Gly Lys Ala
            20                  25                  30

Lys Leu Asp Phe Val Asp Cys Gln Asn Ser Gln Ser Thr Gln Asn Asp
        35                  40                  45

Lys Ile Asp Leu Phe Ile Thr Lys Lys Val Asp Ala Leu Ala Ile Asn
    50                  55                  60

Pro Val Asp Arg Thr Ala Ala Gly Val Leu Ile Asp Lys Ala Lys Gln
65                  70                  75                  80

Ala Asn Ile Pro Val Val Phe Phe Asn Arg Glu Pro Leu Pro Glu Asp
                85                  90                  95

Met Lys Lys Trp Asp Lys Val Tyr Tyr Val Gly Ala Lys Ala Glu Gln
            100                 105                 110

Ser Gly Thr Leu Gln Gly Glu Ile Met Ala Glu Tyr Trp Lys Ser His
        115                 120                 125

Pro Glu Ala Asp Lys Asn His Asp Gly Ile Met Gln Tyr Val Met Ile
    130                 135                 140

Thr Gly Glu Pro Gly His Gln Asp Ala Ile Leu Arg Thr Glu Tyr Ser
145                 150                 155                 160

Ile Lys Ala Val Glu Ala Ala Gly Ile Arg Val Lys Cys Leu Ala Gln
                165                 170                 175

Asp Thr Ala Met Trp Asp Arg Val Lys Gly Gln Glu Lys Met Gln Ala
            180                 185                 190

Phe Leu Ala Ser Phe Gly Asp Lys Ile Glu Ala Val Phe Cys Asn Asn
        195                 200                 205

Asp Asp Met Ala Leu Gly Ala Ile Glu Ala Leu Lys Ala Ala Gly Tyr
    210                 215                 220

Phe Lys Asp Gly Lys Tyr Val Pro Val Val Gly Val Asp Ala Thr Thr
225                 230                 235                 240

Pro Gly Leu Gln Ala Leu Glu Glu Gly Thr Leu Leu Gly Thr Val Leu
                245                 250                 255

Asn Asp Ala Lys Ala Gln Gly Lys Ala Thr Phe Asn Leu Ala Tyr Val
            260                 265                 270

Leu Ala Lys Gly Glu Lys Pro Thr Lys Glu Asn Val Gly Phe Glu Ile
        275                 280                 285

Thr Asp Gly Lys Tyr Ile Trp Val Pro Tyr Gln Lys Val Thr Lys Asp
    290                 295                 300

Asn Leu Glu Glu Met Lys Lys Tyr Val Asn Glu Gln
305                 310                 315
```

<210> SEQ ID NO 22
<211> LENGTH: 307
<212> TYPE: PRT
<213> ORGANISM: Artificial Sequence
<220> FEATURE:
<223> OTHER INFORMATION: pspGGBP (with signal peptide replaced with M)

<400> SEQUENCE: 22

Met Val Gly Val Ala Ile Tyr Lys Phe Asp Asp Thr Phe Met Thr Gly
1 5 10 15

Val Arg Asn Ala Met Ser Asp Ala Ala Asn Gly Val Ala Lys Leu Asp
20 25 30

Ile Val Asp Ser Gln Asn Ala Gln Pro Thr Gln Asn Glu Lys Ile Asp
35 40 45

Leu Phe Ile Ser Lys Lys Tyr Ser Ser Met Ile Ile Asn Pro Val Asp
50 55 60

Arg Thr Ala Ala Gly Val Ile Ile Asp Lys Ala Lys Thr Ala Asn Thr
65 70 75 80

Pro Val Val Phe Leu Asn Arg Glu Pro Ile Ala Glu Asp Met Asn Lys
85 90 95

Trp Asp Lys Val Tyr Tyr Val Gly Ala Lys Ala Glu Glu Ser Gly Thr
100 105 110

Ile Ser Gly Gln Leu Ile Val Asp Tyr Trp Lys Ala Asn Pro Lys Ala
115 120 125

Asp Lys Asn Gly Asp Gly Lys Leu Gln Tyr Val Leu Leu Gln Gly Glu
130 135 140

Pro Gly His Gln Asp Ala Glu Leu Arg Thr Lys Phe Ser Val Gln Ala
145 150 155 160

Ile Gln Asp Ala Gly Ile Glu Val Glu Ala Leu Ala Val Asp Thr Ala
165 170 175

Met Trp Asp Arg Val Lys Gly Gln Glu Lys Met Gln Thr Phe Leu Ala
180 185 190

Ser His Gly Asp Lys Ile Glu Ala Val Leu Ala Asn Asn Asp Asp Met
195 200 205

Ala Leu Gly Ala Ile Glu Ala Leu Lys Ala Ala Gly Tyr Phe Ser Gly
210 215 220

Asp Lys Tyr Met Pro Val Val Gly Val Asp Ala Thr Ala Pro Ala Val
225 230 235 240

Gln Ala Leu Glu Asp Gly Thr Leu Leu Gly Thr Val Leu Asn Asp Ala
245 250 255

Lys Ser Gln Gly Lys Ala Ser Val Ala Ile Ala Ala Ala Leu Ser Lys
260 265 270

Gly Glu Ala Pro Asn Lys Glu Asn Thr Gly Phe Asp Ile Thr Asp Gly
275 280 285

Lys Tyr Val Trp Ile Ala Tyr Lys Lys Ile Thr Lys Asp Asn Ile Ala
290 295 300

Asp Ala Lys
305

<210> SEQ ID NO 23
<211> LENGTH: 307
<212> TYPE: PRT
<213> ORGANISM: Artificial Sequence
<220> FEATURE:
<223> OTHER INFORMATION: csaGGBP (with signal peptide replaced with M)

<400> SEQUENCE: 23

Met Glu Thr Gly Pro Lys Ile Gly Val Ser Ile Tyr Arg Tyr Asp Asp
1 5 10 15

Thr Phe Met Lys Leu Tyr Arg Gln Glu Leu Lys Gln Tyr Leu Glu Glu
20 25 30

Thr Tyr His Ala Glu Val Ile Met Arg Asn Ala Gly Gly Asp Gln Lys
35 40 45

Glu Gln Asp Lys Gln Val Asn Gln Phe Ile Ser Asp Gly Cys Asp Gly
50 55 60

Ile Ile Val Asn Pro Val Glu Ile Pro Ala Ala Gln Glu Leu Ala Asp
65 70 75 80

Ala Cys Ser Arg Ala Gly Ile Pro Leu Val Phe Ile Asn Arg Glu Pro
85 90 95

Lys Glu Glu Glu Gln Lys Arg Trp Arg Glu Lys Gln Met Ala Val Ser
100 105 110

Cys Val Gly Thr Asp Ser Arg Gln Ala Gly Thr Tyr Gln Gly Glu Ile
115 120 125

Ile Leu Glu Thr Leu Asn Lys Gly Asp Phe Asn Gly Asp Gly Val Val
130 135 140

Ser Tyr Val Met Leu Met Gly Glu Lys Gly Asn Glu Asp Ser Gln Tyr
145 150 155 160

Arg Thr Glu Tyr Ser Ile Lys Ala Leu Glu Glu Gly Gly Met Lys Thr
165 170 175

Glu Glu Leu Phe Ser Gly Asn Gly Asn Trp Asn Lys Asp Glu Gly Lys
180 185 190

Lys Leu Ala Lys Gln Ala Leu Ala Ser Trp Gly Asn Arg Ile Glu Val
195 200 205

Phe Phe Cys Asn Asn Asp Ser Met Ala Asn Gly Ala Leu Glu Ala Val
210 215 220

Glu Glu Ala Gly Arg Ile Pro Gly Lys Asp Ile Tyr Leu Val Gly Val
225 230 235 240

Asp Ala Leu Gln Asp Thr Val Thr Tyr Ile Lys Glu Gly Arg Met Thr
245 250 255

Gly Thr Val Leu Asn Asp His Glu Gly Gln Ser Gln Met Ala Ala Asp
260 265 270

Thr Leu Lys Lys Met Ile Asp Gly Glu Ser Val Glu Thr Arg Tyr Gln
275 280 285

Val Asp Tyr Ile Lys Val Thr Ala Ile Ser Thr Phe Gln Thr Leu Lys
290 295 300

Gly Glu Asp
305

<210> SEQ ID NO 24
<211> LENGTH: 314
<212> TYPE: PRT
<213> ORGANISM: Artificial Sequence
<220> FEATURE:
<223> OTHER INFORMATION: bprGGBP (with signal peptide replaced with M)

<400> SEQUENCE: 24

Met Asp Ala Lys Val Gly Val Cys Ile Tyr Gln Lys Ser Asp Asn Phe
1 5 10 15

Met Ser Leu Phe Ser Ser Glu Leu Val Lys Tyr Leu Val Ser Arg Gly
20 25 30

Phe Ser Lys Asp Asn Ile Ile Leu Tyr Asp Ser Asn Asn Asp Glu Asn
35 40 45

Val Gln Leu Ser Gln Val Glu Glu Leu Ile Ala Ser Gly Ile Asn Ala
50 55 60

Leu Ile Ile Asn Pro Val Asn Ser Ser Val Ala His Ser Ile Thr Asp
65 70 75 80

Met Ala Ser Ala Ser Asn Ile Pro Leu Val Tyr Ile Asn Arg Glu Pro
85 90 95

Ser Gly Asp Glu Glu Asn Arg Trp Glu Met Tyr Gln Leu Asn Val Cys
100 105 110

Tyr Val Gly Cys Asp Ala Arg Gln Ser Gly Ile Tyr Gln Gly Glu Ile
115 120 125

Leu Leu Ser Leu Gly Lys Asn Lys Leu Asp His Asn Gly Asp Gly Lys
130 135 140

Ile Gln Tyr Phe Met Ile Glu Gly Ala Pro Glu Asn Ile Asp Ala Gly
145 150 155 160

Tyr Arg Thr Leu Tyr Ser Val Ser Ala Leu Gln Asn Ser Glu Met Glu
165 170 175

Met Asp Cys Leu Leu Asp Glu Val Gly Asn Trp Asp Glu Thr Thr Ala
180 185 190

Ser Leu Leu Val Ser Lys Gly Ile Gln Asn Gly Leu Lys Pro Glu Val
195 200 205

Ile Ile Cys Asn Asn Asp Ala Met Ala Leu Gly Ala Ile Lys Ala Ala
210 215 220

Glu Lys Ser Gly Leu Val Pro Gly Glu Asp Val Tyr Ile Val Gly Val
225 230 235 240

Asp Ala Leu Pro Glu Ala Ile Glu Met Ile Lys Ala Gly Lys Leu Ala
245 250 255

Gly Thr Val Tyr Asn Asp Tyr Val Leu Gln Ser His Lys Ser Ala Asp
260 265 270

Ala Val Ile Asn Tyr Leu Lys Gly Ile Asp Asn Glu His Tyr Ile Gly
275 280 285

Cys Asp Tyr Val Lys Val Asp Ile Asp Asn Ala Glu Ser Ile Ala Gly
290 295 300

Leu Thr Asn Thr Asp Glu Glu Asp Ile Asp
305 310

<210> SEQ ID NO 25
<211> LENGTH: 306
<212> TYPE: PRT
<213> ORGANISM: Artificial Sequence
<220> FEATURE:
<223> OTHER INFORMATION: rinGGBP_A (with signal peptide replaced with M)

<400> SEQUENCE: 25

Met Lys Val Gly Val Cys Ile Tyr Gln Phe Ser Asp Asn Phe Met Thr
1 5 10 15

Leu Phe Arg Thr Glu Leu Glu Asn Tyr Leu Val Glu Lys Gly Phe Ser
20 25 30

Lys Asp Asn Ile Thr Ile Val Asp Gly Ala Asn Asp Gln Ala Thr Gln
35 40 45

Thr Gly Gln Ile Asp Asn Phe Ile Thr Glu Gly Val Asp Val Leu Ile
50 55 60

Ile Asn Pro Val Asn Ser Ser Ser Ala Ala Thr Ile Thr Asp Lys Val
65 70 75 80

Val Ala Ala Gly Ile Pro Leu Val Tyr Ile Asn Arg Glu Pro Asp Glu
85 90 95

Glu Glu Gln Lys Arg Trp Ser Asp Asn Asn Trp Asp Val Thr Tyr Val
100 105 110

Gly Cys Asp Ala Arg Gln Ser Gly Thr Phe Gln Gly Glu Met Ile Ser
115 120 125

Asp Leu Gly Leu Asp Thr Val Asp Leu Asn Gly Asn Gly Lys Ile Asp

```
    130                 135                 140

Tyr Val Met Val Glu Gly Asp Pro Glu Asn Val Asp Ala Gln Tyr Arg
145                 150                 155                 160

Thr Glu Tyr Ser Val Lys Ala Leu Glu Asp Ala Gly Leu Glu Val Asn
                165                 170                 175

Cys Leu Ser Asp Gln Val Gly Asn Trp Gln Gln Asp Gln Ala Gln Gln
            180                 185                 190

Ile Val Ala Asn Ala Leu Gly Gln Tyr Gly Asn Asp Val Glu Val Val
        195                 200                 205

Phe Cys Asn Asn Asp Ala Met Ala Leu Gly Ala Leu Gln Ala Ile Gln
    210                 215                 220

Ser Ala Gly Arg Thr Val Gly Thr Asp Ile Tyr Leu Val Gly Val Asp
225                 230                 235                 240

Ala Leu Ser Glu Ala Leu Glu Asp Val Leu Ala Gly Thr Met Thr Gly
                245                 250                 255

Thr Val Phe Asn Asp His Phe Ser Gln Ser His Ser Ala Ala Asp Ala
            260                 265                 270

Ala Ile Asn Tyr Ile Thr Gly Ala Gly Asn Asp His Tyr Ile Gly Cys
        275                 280                 285

Asp Tyr Val Lys Val Thr Lys Asp Asn Ala Gln Asp Val Leu Asp Met
    290                 295                 300

Val Lys
305


<210> SEQ ID NO 26
<211> LENGTH: 300
<212> TYPE: PRT
<213> ORGANISM: Artificial Sequence
<220> FEATURE:
<223> OTHER INFORMATION: fprGGBP  (with signal peptide replaced with M)

<400> SEQUENCE: 26

Met Ser Ala Asn Ile Gly Val Cys Ile Tyr Gln Phe Ala Asp Asn Phe
1               5                   10                  15

Met Thr Leu Tyr Arg Ala Asp Leu Glu Gly Tyr Leu Lys Asp Met Gly
            20                  25                  30

Tyr Ser Val Thr Ile Met Asp Gly Lys Asn Asp Gln Asn Thr Gln Thr
        35                  40                  45

Glu Gln Ile Asn Thr Phe Leu Gln Gln Gly Val Asp Val Leu Val Ile
    50                  55                  60

Asn Pro Val Gln Thr Thr Ser Ala Gln Thr Ile Val Asp Thr Val Ser
65                  70                  75                  80

Pro Ser Gly Thr Pro Ile Val Phe Ile Asn Arg Glu Pro Glu Glu Ser
                85                  90                  95

Val Leu Asp Ser Tyr Lys Gly Lys Cys Cys Tyr Val Gly Ala Asp Ala
            100                 105                 110

Arg Gln Ser Gly Thr Tyr Gln Gly Glu Leu Ile Leu Ala Thr Asp Thr
        115                 120                 125

Gln Gly Asp Ile Asn Gly Asp Gly Lys Ile Thr Tyr Ile Met Cys Lys
    130                 135                 140

Gly Asp Pro Glu Asn Ile Asp Ala Gln Tyr Arg Thr Glu Tyr Ser Ile
145                 150                 155                 160

Lys Ala Leu Thr Asp Ala Gly Lys Glu Val Glu Cys Leu Tyr Glu Tyr
                165                 170                 175

Leu Asp Asn Trp Asp Gln Thr Thr Ala Gln Gln Asp Val Ala Asn Ala
```

```
            180                 185                 190

Leu Ser Gln Tyr Gly Glu Lys Ile Glu Val Val Phe Cys Asn Asn Asp
        195                 200                 205

Ala Met Ala Leu Gly Ala Leu Gln Ser Ile Gln Gln Ala Gly Arg Thr
    210                 215                 220

Val Gly Lys Asp Val Tyr Leu Val Gly Val Asp Ala Leu Val Glu Ala
225                 230                 235                 240

Val Gln Asn Val Val Asp Gly Asn Met Thr Gly Thr Val Leu Asn Asp
                245                 250                 255

Asp Val Gly Gln Ala Thr Lys Ala Ala Glu Ala Thr Lys Leu Phe Val
            260                 265                 270

Glu Gly Lys Asp Val Glu Lys Tyr Tyr Trp Val Asp Tyr Val Lys Val
        275                 280                 285

Thr Lys Asp Asn Ala Ser Gln Tyr Leu Lys Glu Asp
    290                 295                 300


<210> SEQ ID NO 27
<211> LENGTH: 305
<212> TYPE: PRT
<213> ORGANISM: Artificial Sequence
<220> FEATURE:
<223> OTHER INFORMATION: cljGGBP  (with signal peptide replaced with M)

<400> SEQUENCE: 27

Met Pro Val Ile Gly Phe Val Ala Tyr Glu Phe Asn Asn Thr Trp Ile
1               5                   10                  15

Thr Glu Leu Lys Asn Glu Ile Tyr Lys Val Ser Ser Gly Lys Ala Arg
            20                  25                  30

Val Asp Ile Trp Asn Gly Asp Asn Ile Gln Thr Val Glu Asn Asp Lys
        35                  40                  45

Ile Asn Leu Phe Ile Asn Arg Lys Val Asn Val Leu Asp Ile Asn Pro
    50                  55                  60

Val Asp Val Asn Ala Ala Gly Gln Ile Ile Glu Lys Cys Lys Lys Ala
65                  70                  75                  80

Asn Ile Pro Thr Val Phe Val Asn Arg Gln Pro Lys Lys Glu Asp Met
                85                  90                  95

Glu Lys Trp Asn Lys Val Tyr Tyr Val Gly Ala Lys Ala Glu Gln Ser
            100                 105                 110

Gly Thr Ile Gln Gly Gln Met Leu Val Asn Tyr Phe Lys Gly His Pro
        115                 120                 125

Thr Gln Asp Gly Thr Ile Arg Tyr Ile Met Leu Lys Gly Glu Thr Arg
    130                 135                 140

Asn Gln Asp Ala Glu Lys Arg Thr Gln Tyr Ser Ile Lys Ala Leu Lys
145                 150                 155                 160

Asp Ser Gly Phe Lys Val Gln Lys Val Ala Glu Asp Thr Ala Met Trp
                165                 170                 175

Asp Arg Thr Lys Ala Gln Glu Lys Met Thr Ser Phe Ile Ser Ser Tyr
            180                 185                 190

Gly Pro Asn Phe Asp Cys Val Ile Ala Asn Asn Asp Asp Met Ala Leu
        195                 200                 205

Gly Ala Val Asp Ala Leu Lys Ala Ala Gly Tyr Phe Asn Gly Gly Lys
    210                 215                 220

Tyr Val Pro Val Val Gly Val Asp Ala Thr Ala Pro Ala Val Lys Ala
225                 230                 235                 240

Val Glu Asp Gly Thr Leu Phe Gly Thr Val Leu Asn Asp Ala Ala Lys
```

```
                245                 250                 255

Gln Gly Asp Ala Ala Phe Asp Leu Ser Tyr Ile Leu Ser Lys Gly Lys
            260                 265                 270

Ile Pro Asp Glu Ser Asn Phe Lys Tyr Lys Val Thr Asp Gly Lys Tyr
        275                 280                 285

Ile Trp Ile Asp Tyr Lys Met Ile Thr Lys Glu Asn Val Gln Asp Ala
    290                 295                 300

Lys
305


<210> SEQ ID NO 28
<211> LENGTH: 306
<212> TYPE: PRT
<213> ORGANISM: Artificial Sequence
<220> FEATURE:
<223> OTHER INFORMATION: cauGGBP  (with signal peptide replaced with M)

<400> SEQUENCE: 28

Met Glu Pro Val Ile Gly Phe Val Ala Tyr Glu Phe Asn Asn Thr Trp
1               5                   10                  15

Ile Thr Glu Leu Lys Asn Glu Met Tyr Lys Val Ser Asn Gly Lys Ala
            20                  25                  30

Arg Val Asp Ile Trp Asn Gly Asn Asn Ile Gln Thr Val Glu Asn Asp
        35                  40                  45

Lys Ile Ser Leu Phe Ile Asn Arg Lys Val Asp Val Leu Asp Ile Asn
    50                  55                  60

Pro Val Asp Val Asn Ala Ala Gly Gln Ile Ile Glu Lys Cys Lys Lys
65                  70                  75                  80

Ala Asn Ile Pro Thr Val Phe Val Asn Arg Gln Pro Lys Lys Glu Asp
                85                  90                  95

Val Glu Lys Trp Asn Lys Val Tyr Tyr Val Gly Ala Lys Ala Glu Gln
            100                 105                 110

Ser Gly Thr Ile Gln Gly Gln Met Leu Val Asn Tyr Phe Lys Gly His
        115                 120                 125

Pro Thr Gln Asp Gly Thr Ile Arg Tyr Ile Met Leu Lys Gly Glu Met
    130                 135                 140

Arg Asn Gln Asp Ala Glu Lys Arg Thr Gln Tyr Ser Ile Lys Ala Leu
145                 150                 155                 160

Glu Asp Ser Gly Phe Lys Val Gln Lys Val Ala Glu Asp Thr Ala Met
                165                 170                 175

Trp Asp Arg Thr Lys Ala Gln Glu Lys Met Thr Ser Phe Ile Ser Ser
            180                 185                 190

Tyr Gly Pro Asn Phe Asp Cys Val Ile Ala Asn Asn Asp Asp Met Ala
        195                 200                 205

Leu Gly Ala Val Asp Ala Leu Lys Ala Ala Gly Tyr Phe Asn Gly Gly
    210                 215                 220

Lys Tyr Val Pro Val Val Gly Val Asp Ala Thr Ala Pro Ala Val Lys
225                 230                 235                 240

Ala Val Glu Asp Gly Thr Leu Phe Gly Thr Val Leu Asn Asp Ala Ala
                245                 250                 255

Lys Gln Gly Asp Ala Ala Phe Asp Leu Ser Tyr Ile Leu Ser Lys Gly
            260                 265                 270

Lys Ile Pro Asp Glu Ser Asn Phe Lys Tyr Lys Ile Thr Asp Gly Lys
        275                 280                 285

Tyr Ile Trp Ile Asp Tyr Lys Met Ile Thr Lys Glu Asn Val Gln Asp
```

290 295 300

Ala Lys
305

<210> SEQ ID NO 29
<211> LENGTH: 318
<212> TYPE: PRT
<213> ORGANISM: Artificial Sequence
<220> FEATURE:
<223> OTHER INFORMATION: rinGGBP_B (with signal peptide replaced with M)

<400> SEQUENCE: 29

Met Lys Ser Ile Lys Ile Gly Ile Ser Val Tyr Asp Gln Tyr Asp Thr
1 5 10 15

Phe Val Ser Glu Met Met Lys Asp Phe Asn Asp Tyr Ala Thr Lys Lys
20 25 30

Glu Glu Glu Thr Gly Val Ala Ile Asn Ile Asp Thr Tyr Asn Ala Ser
35 40 45

Ala Ser Gln Ser Thr Gln Asn Ser Gln Val Glu Asn Met Ile Thr Glu
50 55 60

Gly Cys Asp Val Ile Cys Val Asn Leu Val Asp Arg Thr Asp Pro Thr
65 70 75 80

Ala Ile Ile Asp Leu Ala Glu Lys Asn Asn Ile Pro Val Ile Phe Phe
85 90 95

Asn Arg Glu Leu Val Glu Glu Asp Leu Glu Arg Trp Thr Arg Leu Tyr
100 105 110

Tyr Val Gly Ala Gln Ala Phe Glu Ser Gly Ile Met Gln Gly Glu Leu
115 120 125

Ala Ala Glu Ala Phe Leu Thr Asp Gln Ser Leu Asp Lys Asn Gly Asp
130 135 140

Gly Ile Phe Gln Tyr Val Val Leu Glu Gly Glu Ala Gly His Gln Asp
145 150 155 160

Ala Ile Val Arg Thr Glu Tyr Ser Val Ser Thr Met Ile Asp Ser Gly
165 170 175

Val Glu Val Glu Lys Leu Gly Tyr Ala Ile Ala Asn Trp Asn Arg Ala
180 185 190

Gln Ala Gln Thr Lys Met Ala Gln Leu Met Ser Gln Phe Gly Asp Ser
195 200 205

Ile Glu Leu Val Ile Ala Asn Asn Asp Asp Met Ala Leu Gly Ala Ile
210 215 220

Asp Ala Leu Lys Ala Ser Gly Leu Thr Lys Asp Glu Trp Pro Ala Val
225 230 235 240

Ile Gly Ile Asp Gly Thr Asp Val Gly Leu Glu Ala Val Lys Asn Lys
245 250 255

Glu Met Ile Gly Thr Val Tyr Asn Asp Lys Glu Gly Gln Ala Asp Ala
260 265 270

Met Leu Asn Leu Ala Tyr Glu Leu Ser Thr Gly Ser Asp Leu Ser Asp
275 280 285

Leu Asn Leu Ile Asp Gly Lys Tyr Ile Arg Leu Pro Tyr Ala Arg Val
290 295 300

Thr Cys Asp Asp Val Asp Ser Tyr Met Glu Gly Asp Thr Glu
305 310 315

<210> SEQ ID NO 30
<211> LENGTH: 327

<212> TYPE: PRT
<213> ORGANISM: Artificial Sequence
<220> FEATURE:
<223> OTHER INFORMATION: erhGGBP (with signal peptide replaced with M)

<400> SEQUENCE: 30

Met Lys Thr Tyr Asn Ile Gly Val Ala Ile Tyr Lys Phe Asp Asp Asn
1               5                   10                  15

Phe Met Thr Leu Tyr Arg Glu Glu Leu Ala Ser Tyr Phe Lys Glu Val
            20                  25                  30

Gly Glu Lys Asp Gly Asn Thr Tyr Lys Leu Asp Ile Gln Asp Gly Lys
        35                  40                  45

Gln Asp Gln Ala Asn Gln Thr Glu Gln Ile Asn Asn Phe Ile Ala Gln
    50                  55                  60

Gly Lys Asp Leu Ile Ile Ala Asn Met Val Asp Pro Thr Ala Ala Gly
65                  70                  75                  80

Ser Ile Ile Asn Ser Ala Lys Ala Lys Glu Ile Pro Val Val Phe Ile
                85                  90                  95

Asn Arg Glu Pro Glu Thr Gln Glu Leu Glu Ile Trp Pro Gly Lys Thr
            100                 105                 110

Thr Tyr Val Gly Ala Asp Ala Thr Gln Ser Gly Thr Ile Gln Gly Tyr
        115                 120                 125

Met Ile Ala Asn Leu Glu Asn Lys Gly Asp Ile Asp Gly Asp Gly Ser
    130                 135                 140

Val Ser Tyr Ile Thr Leu Met Gly Asp Pro Ala Asn Val Asp Ala Lys
145                 150                 155                 160

Gln Arg Thr Glu Tyr Ser Val Lys Gly Leu Glu Glu Lys Gly Val Lys
                165                 170                 175

Thr Asn Ala Leu Ala Gln Pro Tyr Gln Ala Asn Trp Asp Thr Ala Lys
            180                 185                 190

Gly Gln Glu Phe Thr Ala Asn Ala Leu Glu Gln Phe Gly Asn Lys Leu
        195                 200                 205

Glu Val Val Phe Ala Asn Asn Asp Gly Met Ala Val Gly Ala Val Thr
    210                 215                 220

Ala Ile Glu Ala Ala Gly Arg Lys Val Gly Glu Asp Ile Phe Val Val
225                 230                 235                 240

Gly Val Asp Ala Ile Pro Asp Ala Ile Glu Leu Leu Lys Gly Gly Lys
                245                 250                 255

Leu Thr Gly Thr Val Leu Asn Asp His Phe Asn Gln Ser His Thr Ala
            260                 265                 270

Val Asp Val Ala Leu Glu Leu Leu Gln Gly Lys Asp Val Ser Ala Tyr
        275                 280                 285

Tyr Trp His Asp Tyr Val Gly Val Thr Lys Pro Glu Glu Ala Glu Leu
    290                 295                 300

Lys Arg Ala Glu Ala Arg Lys Glu Thr Val Glu Glu Ala Val Lys Arg
305                 310                 315                 320

Tyr Ala Glu Arg Asp Ala Gln
                325

<210> SEQ ID NO 31
<211> LENGTH: 316
<212> TYPE: PRT
<213> ORGANISM: Artificial Sequence
<220> FEATURE:
<223> OTHER INFORMATION: ereGGBP (with signal peptide replaced with M)

<400> SEQUENCE: 31

-continued

```
Met Lys Gln Ile Tyr Ile Gly Val Thr Cys Tyr Asp Gln Lys Asp Thr
1               5                   10                  15

Phe Ile Gly Glu Leu Ile Glu Thr Phe Lys Lys Glu Cys Ala Ser Leu
            20                  25                  30

Asp Thr Asp Lys Tyr Asp Ile Ser Met Thr Ile Met Asp Ala Ala Gly
        35                  40                  45

Ser Gln Arg Ala Gln Asp Asp Gln Val Gln Glu Met Ile Glu Asp Gly
    50                  55                  60

Cys Asn Val Leu Cys Ile Asn Leu Ala Asp Arg Thr Asp Leu Ser His
65                  70                  75                  80

Ile Ile Asn Ala Ala Met Glu Lys Asp Ile Pro Ile Ile Phe Phe Asn
                85                  90                  95

Arg Glu Pro Val Asp Glu Asp Leu Asn Arg Trp Asp Lys Leu Tyr Tyr
            100                 105                 110

Val Gly Ala Lys Ala Lys Gln Ser Gly Gln Met Gln Gly Glu Leu Ile
        115                 120                 125

Ala Asp Tyr Ile Lys Asn Asn Pro Gly Val Asp Lys Asn Gly Asp Gly
    130                 135                 140

Arg Ile Gln Tyr Val Ile Leu Glu Gly Glu Met Gly His Gln Asp Ala
145                 150                 155                 160

Ile Val Arg Thr Glu Ser Val Thr Glu Ser Met Lys Asn Asn Gly Leu
                165                 170                 175

Gln Ile Glu Lys Leu Ser Cys Gln Ile Ala Asn Trp Asn Arg Ala Gln
            180                 185                 190

Ala Gln Asn Arg Met Thr Gln Leu Ile Gly Gln Tyr Lys Asn Ser Ile
        195                 200                 205

Glu Leu Val Ile Ala Asn Asn Asp Ala Met Ala Leu Gly Ala Ile Asp
    210                 215                 220

Ala Tyr Glu Lys Leu Gly Val Thr Glu Ser Asn Val Pro Ala Phe Phe
225                 230                 235                 240

Gly Val Asp Gly Thr Asp Asp Gly Leu Glu Ala Val Gln Gln Ser Lys
                245                 250                 255

Leu Ala Ala Thr Val Tyr Asn Asp Lys Glu Gly Gln Ala Met Ala Met
            260                 265                 270

Ala Gln Leu Ala Tyr Leu Ala Ala Thr Gly Gly Ser Met Lys Asn Ile
        275                 280                 285

Lys Phe Glu Asp Lys Lys Tyr Val Tyr Leu Pro Tyr Glu Lys Val Thr
    290                 295                 300

Pro Asp Asn Val Asn Glu Phe Val Lys Asp Glu Gln
305                 310                 315
```

<210> SEQ ID NO 32
<211> LENGTH: 319
<212> TYPE: PRT
<213> ORGANISM: Artificial Sequence
<220> FEATURE:
<223> OTHER INFORMATION: ecGGBPW183C (with signal peptide replaced with M; a W183C mutation; and a GGSHHHHHH at C-terminus)

<400> SEQUENCE: 32

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
```

35 40 45

Gln Asn Asp Gln Ile Asp Val Leu Leu Ala Lys Gly Val Lys Ala Leu
50 55 60

Ala Ile Asn Leu Val Asp Pro Ala Ala Ala Gly Thr Val Ile Glu Lys
65 70 75 80

Ala Arg Gly Gln Asn Val Pro Val Val Phe Phe Asn Lys Glu Pro Ser
85 90 95

Arg Lys Ala Leu Asp Ser Tyr Asp Lys Ala Tyr Tyr Val Gly Thr Asp
100 105 110

Ser Lys Glu Ser Gly Ile Ile Gln Gly Asp Leu Ile Ala Lys His Trp
115 120 125

Ala Ala Asn Gln Gly Trp Asp Leu Asn Lys Asp Gly Gln Ile Gln Phe
130 135 140

Val Leu Leu Lys Gly Glu Pro Gly His Pro Asp Ala Glu Ala Arg Thr
145 150 155 160

Thr Tyr Val Ile Lys Glu Leu Asn Asp Lys Gly Ile Lys Thr Glu Gln
165 170 175

Leu Gln Leu Asp Thr Ala Met Cys Asp Thr Ala Gln Ala Lys Asp Lys
180 185 190

Met Asp Ala Trp Leu Ser Gly Pro Asn Ala Asn Lys Ile Glu Val Val
195 200 205

Ile Ala Asn Asn Asp Ala Met Ala Met Gly Ala Val Glu Ala Leu Lys
210 215 220

Ala His Asn Lys Ser Ser Ile Pro Val Phe Gly Val Asp Ala Leu Pro
225 230 235 240

Glu Ala Leu Ala Leu Val Lys Ser Gly Ala Leu Ala Gly Thr Val Leu
245 250 255

Asn Asp Ala Asn Asn Gln Ala Lys Ala Thr Phe Asp Leu Ala Lys Asn
260 265 270

Leu Ala Asp Gly Lys Gly Ala Ala Asp Gly Thr Asn Trp Lys Ile Asp
275 280 285

Asn Lys Val Val Arg Val Pro Tyr Val Gly Val Asp Lys Asp Asn Leu
290 295 300

Ala Glu Phe Ser Lys Lys Gly Gly Ser His His His His His His
305 310 315

<210> SEQ ID NO 33
<211> LENGTH: 319
<212> TYPE: PRT
<213> ORGANISM: Artificial Sequence
<220> FEATURE:
<223> OTHER INFORMATION: ecGGBP (with signal peptide replaced with M and a GGSHHHHHH at C-terminus)

<400> SEQUENCE: 33

Met Ala Asp Thr Arg Ile Gly Val Thr Ile Tyr Lys Tyr Asp Asp Asn
1 5 10 15

Phe Met Ser Val Val Arg Lys Ala Ile Glu Gln Asp Ala Lys Ala Ala
20 25 30

Pro Asp Val Gln Leu Leu Met Asn Asp Ser Gln Asn Asp Gln Ser Lys
35 40 45

Gln Asn Asp Gln Ile Asp Val Leu Leu Ala Lys Gly Val Lys Ala Leu
50 55 60

Ala Ile Asn Leu Val Asp Pro Ala Ala Ala Gly Thr Val Ile Glu Lys
65 70 75 80

```
Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Trp Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Gln Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe Ser Lys Lys Gly Gly Ser His His His His His His
305                 310                 315
```

<210> SEQ ID NO 34
<211> LENGTH: 316
<212> TYPE: PRT
<213> ORGANISM: Artificial Sequence
<220> FEATURE:
<223> OTHER INFORMATION: csaGGBP (with signal peptide replaced with M
      and a GGSHHHHHH at C-terminus)

<400> SEQUENCE: 34

```
Met Glu Thr Gly Pro Lys Ile Gly Val Ser Ile Tyr Arg Tyr Asp Asp
1               5                   10                  15

Thr Phe Met Lys Leu Tyr Arg Gln Glu Leu Lys Gln Tyr Leu Glu Glu
            20                  25                  30

Thr Tyr His Ala Glu Val Ile Met Arg Asn Ala Gly Gly Asp Gln Lys
        35                  40                  45

Glu Gln Asp Lys Gln Val Asn Gln Phe Ile Ser Asp Gly Cys Asp Gly
    50                  55                  60

Ile Ile Val Asn Pro Val Glu Ile Pro Ala Ala Gln Glu Leu Ala Asp
65                  70                  75                  80

Ala Cys Ser Arg Ala Gly Ile Pro Leu Val Phe Ile Asn Arg Glu Pro
                85                  90                  95

Lys Glu Glu Glu Gln Lys Arg Trp Arg Glu Lys Gln Met Ala Val Ser
            100                 105                 110

Cys Val Gly Thr Asp Ser Arg Gln Ala Gly Thr Tyr Gln Gly Glu Ile
        115                 120                 125
```

```
Ile Leu Glu Thr Leu Asn Lys Gly Asp Phe Asn Gly Asp Gly Val Val
    130                 135                 140

Ser Tyr Val Met Leu Met Gly Glu Lys Gly Asn Glu Asp Ser Gln Tyr
145                 150                 155                 160

Arg Thr Glu Tyr Ser Ile Lys Ala Leu Glu Glu Gly Gly Met Lys Thr
                165                 170                 175

Glu Glu Leu Phe Ser Gly Asn Gly Asn Trp Asn Lys Asp Glu Gly Lys
            180                 185                 190

Lys Leu Ala Lys Gln Ala Leu Ala Ser Trp Gly Asn Arg Ile Glu Val
        195                 200                 205

Phe Phe Cys Asn Asn Asp Ser Met Ala Asn Gly Ala Leu Glu Ala Val
    210                 215                 220

Glu Glu Ala Gly Arg Ile Pro Gly Lys Asp Ile Tyr Leu Val Gly Val
225                 230                 235                 240

Asp Ala Leu Gln Asp Thr Val Thr Tyr Ile Lys Glu Gly Arg Met Thr
                245                 250                 255

Gly Thr Val Leu Asn Asp His Glu Gly Gln Ser Gln Met Ala Ala Asp
            260                 265                 270

Thr Leu Lys Lys Met Ile Asp Gly Glu Ser Val Glu Thr Arg Tyr Gln
        275                 280                 285

Val Asp Tyr Ile Lys Val Thr Ala Ile Ser Thr Phe Gln Thr Leu Lys
    290                 295                 300

Gly Glu Asp Gly Gly Ser His His His His His His
305                 310                 315
```

<210> SEQ ID NO 35
<211> LENGTH: 323
<212> TYPE: PRT
<213> ORGANISM: Artificial Sequence
<220> FEATURE:
<223> OTHER INFORMATION: bprGGBP (with signal peptide replaced with M and a GGSHHHHHH at C-terminus)

<400> SEQUENCE: 35

```
Met Asp Ala Lys Val Gly Val Cys Ile Tyr Gln Lys Ser Asp Asn Phe
1               5                   10                  15

Met Ser Leu Phe Ser Ser Glu Leu Val Lys Tyr Leu Val Ser Arg Gly
            20                  25                  30

Phe Ser Lys Asp Asn Ile Ile Leu Tyr Asp Ser Asn Asn Asp Glu Asn
        35                  40                  45

Val Gln Leu Ser Gln Val Glu Glu Leu Ile Ala Ser Gly Ile Asn Ala
    50                  55                  60

Leu Ile Ile Asn Pro Val Asn Ser Ser Val Ala His Ser Ile Thr Asp
65                  70                  75                  80

Met Ala Ser Ala Ser Asn Ile Pro Leu Val Tyr Ile Asn Arg Glu Pro
                85                  90                  95

Ser Gly Asp Glu Glu Asn Arg Trp Glu Met Tyr Gln Leu Asn Val Cys
            100                 105                 110

Tyr Val Gly Cys Asp Ala Arg Gln Ser Gly Ile Tyr Gln Gly Glu Ile
        115                 120                 125

Leu Leu Ser Leu Gly Lys Asn Lys Leu Asp His Asn Gly Asp Gly Lys
    130                 135                 140

Ile Gln Tyr Phe Met Ile Glu Gly Ala Pro Glu Asn Ile Asp Ala Gly
145                 150                 155                 160

Tyr Arg Thr Leu Tyr Ser Val Ser Ala Leu Gln Asn Ser Glu Met Glu
```

165 170 175

Met Asp Cys Leu Leu Asp Glu Val Gly Asn Trp Asp Glu Thr Thr Ala
180 185 190

Ser Leu Leu Val Ser Lys Gly Ile Gln Asn Gly Leu Lys Pro Glu Val
195 200 205

Ile Ile Cys Asn Asn Asp Ala Met Ala Leu Gly Ala Ile Lys Ala Ala
210 215 220

Glu Lys Ser Gly Leu Val Pro Gly Glu Asp Val Tyr Ile Val Gly Val
225 230 235 240

Asp Ala Leu Pro Glu Ala Ile Glu Met Ile Lys Ala Gly Lys Leu Ala
245 250 255

Gly Thr Val Tyr Asn Asp Tyr Val Leu Gln Ser His Lys Ser Ala Asp
260 265 270

Ala Val Ile Asn Tyr Leu Lys Gly Ile Asp Asn Glu His Tyr Ile Gly
275 280 285

Cys Asp Tyr Val Lys Val Asp Ile Asp Asn Ala Glu Ser Ile Ala Gly
290 295 300

Leu Thr Asn Thr Asp Glu Glu Asp Ile Asp Gly Gly Ser His His His
305 310 315 320

His His His

<210> SEQ ID NO 36
<211> LENGTH: 315
<212> TYPE: PRT
<213> ORGANISM: Artificial Sequence
<220> FEATURE:
<223> OTHER INFORMATION: rinGGBP_A (with signal peptide replaced with M and a GGSHHHHHH at C-terminus)

<400> SEQUENCE: 36

Met Lys Val Gly Val Cys Ile Tyr Gln Phe Ser Asp Asn Phe Met Thr
1 5 10 15

Leu Phe Arg Thr Glu Leu Glu Asn Tyr Leu Val Glu Lys Gly Phe Ser
20 25 30

Lys Asp Asn Ile Thr Ile Val Asp Gly Ala Asn Asp Gln Ala Thr Gln
35 40 45

Thr Gly Gln Ile Asp Asn Phe Ile Thr Glu Gly Val Asp Val Leu Ile
50 55 60

Ile Asn Pro Val Asn Ser Ser Ser Ala Ala Thr Ile Thr Asp Lys Val
65 70 75 80

Val Ala Ala Gly Ile Pro Leu Val Tyr Ile Asn Arg Glu Pro Asp Glu
85 90 95

Glu Glu Gln Lys Arg Trp Ser Asp Asn Asn Trp Asp Val Thr Tyr Val
100 105 110

Gly Cys Asp Ala Arg Gln Ser Gly Thr Phe Gln Gly Glu Met Ile Ser
115 120 125

Asp Leu Gly Leu Asp Thr Val Asp Leu Asn Gly Asn Gly Lys Ile Asp
130 135 140

Tyr Val Met Val Glu Gly Asp Pro Glu Asn Val Asp Ala Gln Tyr Arg
145 150 155 160

Thr Glu Tyr Ser Val Lys Ala Leu Glu Asp Ala Gly Leu Glu Val Asn
165 170 175

Cys Leu Ser Asp Gln Val Gly Asn Trp Gln Gln Asp Gln Ala Gln Gln
180 185 190

Ile Val Ala Asn Ala Leu Gly Gln Tyr Gly Asn Asp Val Glu Val Val

```
        195                 200                 205

Phe Cys Asn Asn Asp Ala Met Ala Leu Gly Ala Leu Gln Ala Ile Gln
    210                 215                 220

Ser Ala Gly Arg Thr Val Gly Thr Asp Ile Tyr Leu Val Gly Val Asp
225                 230                 235                 240

Ala Leu Ser Glu Ala Leu Glu Asp Val Leu Ala Gly Thr Met Thr Gly
                245                 250                 255

Thr Val Phe Asn Asp His Phe Ser Gln Ser His Ser Ala Ala Asp Ala
            260                 265                 270

Ala Ile Asn Tyr Ile Thr Gly Ala Gly Asn Asp His Tyr Ile Gly Cys
        275                 280                 285

Asp Tyr Val Lys Val Thr Lys Asp Asn Ala Gln Asp Val Leu Asp Met
    290                 295                 300

Val Lys Gly Gly Ser His His His His His His
305                 310                 315


<210> SEQ ID NO 37
<211> LENGTH: 309
<212> TYPE: PRT
<213> ORGANISM: Artificial Sequence
<220> FEATURE:
<223> OTHER INFORMATION: fprGGBP (with signal peptide replaced with M
      and a GGSHHHHHH at C-terminus)

<400> SEQUENCE: 37

Met Ser Ala Asn Ile Gly Val Cys Ile Tyr Gln Phe Ala Asp Asn Phe
1               5                   10                  15

Met Thr Leu Tyr Arg Ala Asp Leu Glu Gly Tyr Leu Lys Asp Met Gly
            20                  25                  30

Tyr Ser Val Thr Ile Met Asp Gly Lys Asn Asp Gln Asn Thr Gln Thr
        35                  40                  45

Glu Gln Ile Asn Thr Phe Leu Gln Gln Gly Val Asp Val Leu Val Ile
    50                  55                  60

Asn Pro Val Gln Thr Thr Ser Ala Gln Thr Ile Val Asp Thr Val Ser
65                  70                  75                  80

Pro Ser Gly Thr Pro Ile Val Phe Ile Asn Arg Glu Pro Glu Glu Ser
                85                  90                  95

Val Leu Asp Ser Tyr Lys Gly Lys Cys Cys Tyr Val Gly Ala Asp Ala
            100                 105                 110

Arg Gln Ser Gly Thr Tyr Gln Gly Glu Leu Ile Leu Ala Thr Asp Thr
        115                 120                 125

Gln Gly Asp Ile Asn Gly Asp Gly Lys Ile Thr Tyr Ile Met Cys Lys
    130                 135                 140

Gly Asp Pro Glu Asn Ile Asp Ala Gln Tyr Arg Thr Glu Tyr Ser Ile
145                 150                 155                 160

Lys Ala Leu Thr Asp Ala Gly Lys Glu Val Glu Cys Leu Tyr Glu Tyr
                165                 170                 175

Leu Asp Asn Trp Asp Gln Thr Thr Ala Gln Gln Asp Val Ala Asn Ala
            180                 185                 190

Leu Ser Gln Tyr Gly Glu Lys Ile Glu Val Val Phe Cys Asn Asn Asp
        195                 200                 205

Ala Met Ala Leu Gly Ala Leu Gln Ser Ile Gln Gln Ala Gly Arg Thr
    210                 215                 220

Val Gly Lys Asp Val Tyr Leu Val Gly Val Asp Ala Leu Val Glu Ala
225                 230                 235                 240
```

-continued

```
Val Gln Asn Val Val Asp Gly Asn Met Thr Gly Thr Val Leu Asn Asp
                245                 250                 255

Asp Val Gly Gln Ala Thr Lys Ala Ala Glu Ala Thr Lys Leu Phe Val
            260                 265                 270

Glu Gly Lys Asp Val Glu Lys Tyr Tyr Trp Val Asp Tyr Val Lys Val
        275                 280                 285

Thr Lys Asp Asn Ala Ser Gln Tyr Leu Lys Glu Asp Gly Gly Ser His
    290                 295                 300

His His His His His
305
```

<210> SEQ ID NO 38
<211> LENGTH: 314
<212> TYPE: PRT
<213> ORGANISM: Artificial Sequence
<220> FEATURE:
<223> OTHER INFORMATION: cljGGBP (with signal peptide replaced with M and a GGSHHHHHH at C-terminus)

<400> SEQUENCE: 38

```
Met Pro Val Ile Gly Phe Val Ala Tyr Glu Phe Asn Asn Thr Trp Ile
1               5                   10                  15

Thr Glu Leu Lys Asn Glu Ile Tyr Lys Val Ser Ser Gly Lys Ala Arg
            20                  25                  30

Val Asp Ile Trp Asn Gly Asp Asn Ile Gln Thr Val Glu Asn Asp Lys
        35                  40                  45

Ile Asn Leu Phe Ile Asn Arg Lys Val Asn Val Leu Asp Ile Asn Pro
    50                  55                  60

Val Asp Val Asn Ala Ala Gly Gln Ile Ile Glu Lys Cys Lys Lys Ala
65                  70                  75                  80

Asn Ile Pro Thr Val Phe Val Asn Arg Gln Pro Lys Lys Glu Asp Met
                85                  90                  95

Glu Lys Trp Asn Lys Val Tyr Tyr Val Gly Ala Lys Ala Glu Gln Ser
            100                 105                 110

Gly Thr Ile Gln Gly Gln Met Leu Val Asn Tyr Phe Lys Gly His Pro
        115                 120                 125

Thr Gln Asp Gly Thr Ile Arg Tyr Ile Met Leu Lys Gly Glu Thr Arg
    130                 135                 140

Asn Gln Asp Ala Glu Lys Arg Thr Gln Tyr Ser Ile Lys Ala Leu Lys
145                 150                 155                 160

Asp Ser Gly Phe Lys Val Gln Lys Val Ala Glu Asp Thr Ala Met Trp
                165                 170                 175

Asp Arg Thr Lys Ala Gln Glu Lys Met Thr Ser Phe Ile Ser Ser Tyr
            180                 185                 190

Gly Pro Asn Phe Asp Cys Val Ile Ala Asn Asn Asp Asp Met Ala Leu
        195                 200                 205

Gly Ala Val Asp Ala Leu Lys Ala Ala Gly Tyr Phe Asn Gly Gly Lys
    210                 215                 220

Tyr Val Pro Val Val Gly Val Asp Ala Thr Ala Pro Ala Val Lys Ala
225                 230                 235                 240

Val Glu Asp Gly Thr Leu Phe Gly Thr Val Leu Asn Asp Ala Ala Lys
                245                 250                 255

Gln Gly Asp Ala Ala Phe Asp Leu Ser Tyr Ile Leu Ser Lys Gly Lys
            260                 265                 270

Ile Pro Asp Glu Ser Asn Phe Lys Tyr Lys Val Thr Asp Gly Lys Tyr
        275                 280                 285
```

Ile Trp Ile Asp Tyr Lys Met Ile Thr Lys Glu Asn Val Gln Asp Ala
    290                 295                 300

Lys Gly Gly Ser His His His His His His
305                 310

<210> SEQ ID NO 39
<211> LENGTH: 315
<212> TYPE: PRT
<213> ORGANISM: Artificial Sequence
<220> FEATURE:
<223> OTHER INFORMATION: cauGGBP (with signal peptide replaced with M
      and a GGSHHHHHH at C-terminus)

<400> SEQUENCE: 39

Met Glu Pro Val Ile Gly Phe Val Ala Tyr Glu Phe Asn Asn Thr Trp
1               5                   10                  15

Ile Thr Glu Leu Lys Asn Glu Met Tyr Lys Val Ser Asn Gly Lys Ala
            20                  25                  30

Arg Val Asp Ile Trp Asn Gly Asn Asn Ile Gln Thr Val Glu Asn Asp
        35                  40                  45

Lys Ile Ser Leu Phe Ile Asn Arg Lys Val Asp Val Leu Asp Ile Asn
    50                  55                  60

Pro Val Asp Val Asn Ala Ala Gly Gln Ile Ile Glu Lys Cys Lys Lys
65                  70                  75                  80

Ala Asn Ile Pro Thr Val Phe Val Asn Arg Gln Pro Lys Lys Glu Asp
                85                  90                  95

Val Glu Lys Trp Asn Lys Val Tyr Tyr Val Gly Ala Lys Ala Glu Gln
            100                 105                 110

Ser Gly Thr Ile Gln Gly Gln Met Leu Val Asn Tyr Phe Lys Gly His
        115                 120                 125

Pro Thr Gln Asp Gly Thr Ile Arg Tyr Ile Met Leu Lys Gly Glu Met
    130                 135                 140

Arg Asn Gln Asp Ala Glu Lys Arg Thr Gln Tyr Ser Ile Lys Ala Leu
145                 150                 155                 160

Glu Asp Ser Gly Phe Lys Val Gln Lys Val Ala Glu Asp Thr Ala Met
                165                 170                 175

Trp Asp Arg Thr Lys Ala Gln Glu Lys Met Thr Ser Phe Ile Ser Ser
            180                 185                 190

Tyr Gly Pro Asn Phe Asp Cys Val Ile Ala Asn Asn Asp Asp Met Ala
        195                 200                 205

Leu Gly Ala Val Asp Ala Leu Lys Ala Ala Gly Tyr Phe Asn Gly Gly
    210                 215                 220

Lys Tyr Val Pro Val Val Gly Val Asp Ala Thr Ala Pro Ala Val Lys
225                 230                 235                 240

Ala Val Glu Asp Gly Thr Leu Phe Gly Thr Val Leu Asn Asp Ala Ala
                245                 250                 255

Lys Gln Gly Asp Ala Ala Phe Asp Leu Ser Tyr Ile Leu Ser Lys Gly
            260                 265                 270

Lys Ile Pro Asp Glu Ser Asn Phe Lys Tyr Lys Ile Thr Asp Gly Lys
        275                 280                 285

Tyr Ile Trp Ile Asp Tyr Lys Met Ile Thr Lys Glu Asn Val Gln Asp
    290                 295                 300

Ala Lys Gly Gly Ser His His His His His His
305                 310                 315

```
<210> SEQ ID NO 40
<211> LENGTH: 327
<212> TYPE: PRT
<213> ORGANISM: Artificial Sequence
<220> FEATURE:
<223> OTHER INFORMATION: rinGGBP_B (with signal peptide replaced with M
      and a GGSHHHHHH at C-terminus)

<400> SEQUENCE: 40

Met Lys Ser Ile Lys Ile Gly Ile Ser Val Tyr Asp Gln Tyr Asp Thr
1               5                   10                  15

Phe Val Ser Glu Met Met Lys Asp Phe Asn Asp Tyr Ala Thr Lys Lys
            20                  25                  30

Glu Glu Glu Thr Gly Val Ala Ile Asn Ile Asp Thr Tyr Asn Ala Ser
        35                  40                  45

Ala Ser Gln Ser Thr Gln Asn Ser Gln Val Glu Asn Met Ile Thr Glu
    50                  55                  60

Gly Cys Asp Val Ile Cys Val Asn Leu Val Asp Arg Thr Asp Pro Thr
65                  70                  75                  80

Ala Ile Ile Asp Leu Ala Glu Lys Asn Asn Ile Pro Val Ile Phe Phe
                85                  90                  95

Asn Arg Glu Leu Val Glu Glu Asp Leu Glu Arg Trp Thr Arg Leu Tyr
            100                 105                 110

Tyr Val Gly Ala Gln Ala Phe Glu Ser Gly Ile Met Gln Gly Glu Leu
        115                 120                 125

Ala Ala Glu Ala Phe Leu Thr Asp Gln Ser Leu Asp Lys Asn Gly Asp
    130                 135                 140

Gly Ile Phe Gln Tyr Val Val Leu Glu Gly Glu Ala Gly His Gln Asp
145                 150                 155                 160

Ala Ile Val Arg Thr Glu Tyr Ser Val Ser Thr Met Ile Asp Ser Gly
                165                 170                 175

Val Glu Val Glu Lys Leu Gly Tyr Ala Ile Ala Asn Trp Asn Arg Ala
            180                 185                 190

Gln Ala Gln Thr Lys Met Ala Gln Leu Met Ser Gln Phe Gly Asp Ser
        195                 200                 205

Ile Glu Leu Val Ile Ala Asn Asn Asp Asp Met Ala Leu Gly Ala Ile
    210                 215                 220

Asp Ala Leu Lys Ala Ser Gly Leu Thr Lys Asp Glu Trp Pro Ala Val
225                 230                 235                 240

Ile Gly Ile Asp Gly Thr Asp Val Gly Leu Glu Ala Val Lys Asn Lys
                245                 250                 255

Glu Met Ile Gly Thr Val Tyr Asn Asp Lys Glu Gly Gln Ala Asp Ala
            260                 265                 270

Met Leu Asn Leu Ala Tyr Glu Leu Ser Thr Gly Ser Asp Leu Ser Asp
        275                 280                 285

Leu Asn Leu Ile Asp Gly Lys Tyr Ile Arg Leu Pro Tyr Ala Arg Val
    290                 295                 300

Thr Cys Asp Asp Val Asp Ser Tyr Met Glu Gly Asp Thr Glu Gly Gly
305                 310                 315                 320

Ser His His His His His His
                325


<210> SEQ ID NO 41
<211> LENGTH: 336
<212> TYPE: PRT
<213> ORGANISM: Artificial Sequence
<220> FEATURE:
```

<223> OTHER INFORMATION: erhGGBP (with signal peptide replaced with M
and a GGSHHHHHH at C-terminus)

<400> SEQUENCE: 41

Met Lys Thr Tyr Asn Ile Gly Val Ala Ile Tyr Lys Phe Asp Asp Asn
1 5 10 15

Phe Met Thr Leu Tyr Arg Glu Glu Leu Ala Ser Tyr Phe Lys Glu Val
20 25 30

Gly Glu Lys Asp Gly Asn Thr Tyr Lys Leu Asp Ile Gln Asp Gly Lys
35 40 45

Gln Asp Gln Ala Asn Gln Thr Glu Gln Ile Asn Asn Phe Ile Ala Gln
50 55 60

Gly Lys Asp Leu Ile Ile Ala Asn Met Val Asp Pro Thr Ala Ala Gly
65 70 75 80

Ser Ile Ile Asn Ser Ala Lys Ala Lys Glu Ile Pro Val Val Phe Ile
85 90 95

Asn Arg Glu Pro Glu Thr Gln Glu Leu Glu Ile Trp Pro Gly Lys Thr
100 105 110

Thr Tyr Val Gly Ala Asp Ala Thr Gln Ser Gly Thr Ile Gln Gly Tyr
115 120 125

Met Ile Ala Asn Leu Glu Asn Lys Gly Asp Ile Asp Gly Asp Gly Ser
130 135 140

Val Ser Tyr Ile Thr Leu Met Gly Asp Pro Ala Asn Val Asp Ala Lys
145 150 155 160

Gln Arg Thr Glu Tyr Ser Val Lys Gly Leu Glu Glu Lys Gly Val Lys
165 170 175

Thr Asn Ala Leu Ala Gln Pro Tyr Gln Ala Asn Trp Asp Thr Ala Lys
180 185 190

Gly Gln Glu Phe Thr Ala Asn Ala Leu Glu Gln Phe Gly Asn Lys Leu
195 200 205

Glu Val Val Phe Ala Asn Asn Asp Gly Met Ala Val Gly Ala Val Thr
210 215 220

Ala Ile Glu Ala Ala Gly Arg Lys Val Gly Glu Asp Ile Phe Val Val
225 230 235 240

Gly Val Asp Ala Ile Pro Asp Ala Ile Glu Leu Leu Lys Gly Gly Lys
245 250 255

Leu Thr Gly Thr Val Leu Asn Asp His Phe Asn Gln Ser His Thr Ala
260 265 270

Val Asp Val Ala Leu Glu Leu Leu Gln Gly Lys Asp Val Ser Ala Tyr
275 280 285

Tyr Trp His Asp Tyr Val Gly Val Thr Lys Pro Glu Glu Ala Glu Leu
290 295 300

Lys Arg Ala Glu Ala Arg Lys Glu Thr Val Glu Glu Ala Val Lys Arg
305 310 315 320

Tyr Ala Glu Arg Asp Ala Gln Gly Gly Ser His His His His His His
325 330 335

<210> SEQ ID NO 42
<211> LENGTH: 325
<212> TYPE: PRT
<213> ORGANISM: Artificial Sequence
<220> FEATURE:
<223> OTHER INFORMATION: ereGGBP (with signal peptide replaced with M
and a GGSHHHHHH at C-terminus)

<400> SEQUENCE: 42

-continued

```
Met Lys Gln Ile Tyr Ile Gly Val Thr Cys Tyr Asp Gln Lys Asp Thr
1               5                   10                  15

Phe Ile Gly Glu Leu Ile Glu Thr Phe Lys Lys Glu Cys Ala Ser Leu
            20                  25                  30

Asp Thr Asp Lys Tyr Asp Ile Ser Met Thr Ile Met Asp Ala Ala Gly
        35                  40                  45

Ser Gln Arg Ala Gln Asp Asp Gln Val Gln Glu Met Ile Glu Asp Gly
    50                  55                  60

Cys Asn Val Leu Cys Ile Asn Leu Ala Asp Arg Thr Asp Leu Ser His
65                  70                  75                  80

Ile Ile Asn Ala Ala Met Glu Lys Asp Ile Pro Ile Ile Phe Phe Asn
                85                  90                  95

Arg Glu Pro Val Asp Glu Asp Leu Asn Arg Trp Asp Lys Leu Tyr Tyr
            100                 105                 110

Val Gly Ala Lys Ala Lys Gln Ser Gly Gln Met Gln Gly Glu Leu Ile
        115                 120                 125

Ala Asp Tyr Ile Lys Asn Asn Pro Gly Val Asp Lys Asn Gly Asp Gly
    130                 135                 140

Arg Ile Gln Tyr Val Ile Leu Glu Gly Glu Met Gly His Gln Asp Ala
145                 150                 155                 160

Ile Val Arg Thr Glu Ser Val Thr Glu Ser Met Lys Asn Asn Gly Leu
                165                 170                 175

Gln Ile Glu Lys Leu Ser Cys Gln Ile Ala Asn Trp Asn Arg Ala Gln
            180                 185                 190

Ala Gln Asn Arg Met Thr Gln Leu Ile Gly Gln Tyr Lys Asn Ser Ile
        195                 200                 205

Glu Leu Val Ile Ala Asn Asn Asp Ala Met Ala Leu Gly Ala Ile Asp
    210                 215                 220

Ala Tyr Glu Lys Leu Gly Val Thr Glu Ser Asn Val Pro Ala Phe Phe
225                 230                 235                 240

Gly Val Asp Gly Thr Asp Asp Gly Leu Glu Ala Val Gln Gln Ser Lys
                245                 250                 255

Leu Ala Ala Thr Val Tyr Asn Asp Lys Glu Gly Gln Ala Met Ala Met
            260                 265                 270

Ala Gln Leu Ala Tyr Leu Ala Ala Thr Gly Gly Ser Met Lys Asn Ile
        275                 280                 285

Lys Phe Glu Asp Lys Lys Tyr Val Tyr Leu Pro Tyr Glu Lys Val Thr
    290                 295                 300

Pro Asp Asn Val Asn Glu Phe Val Lys Asp Glu Gln Gly Gly Ser His
305                 310                 315                 320

His His His His His
                325


<210> SEQ ID NO 43
<211> LENGTH: 321
<212> TYPE: PRT
<213> ORGANISM: Artificial Sequence
<220> FEATURE:
<223> OTHER INFORMATION: ttGGBP (with signal peptide replaced with M and
      a GGSHHHHHH at C-terminus)

<400> SEQUENCE: 43

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30
```

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Cys Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 44
<211> LENGTH: 325
<212> TYPE: PRT
<213> ORGANISM: Artificial Sequence
<220> FEATURE:
<223> OTHER INFORMATION: cobGGBP (with signal peptide replaced with M and a GGSHHHHHH at C-terminus)

<400> SEQUENCE: 44

Met Lys Pro Tyr Ile Gly Val Ala Ile Tyr Lys Phe Asp Asp Thr Phe
1 5 10 15

Met Thr Gly Val Arg Asn Ala Ile Ala Lys Glu Gly Glu Gly Lys Ala
20 25 30

Lys Leu Asp Phe Val Asp Cys Gln Asn Ser Gln Ser Thr Gln Asn Asp
35 40 45

Lys Ile Asp Leu Phe Ile Thr Lys Lys Val Asp Ala Leu Ala Ile Asn
50 55 60

```
Pro Val Asp Arg Thr Ala Ala Gly Val Leu Ile Asp Lys Ala Lys Gln
65                  70                  75                  80

Ala Asn Ile Pro Val Val Phe Phe Asn Arg Glu Pro Leu Pro Glu Asp
                85                  90                  95

Met Lys Lys Trp Asp Lys Val Tyr Tyr Val Gly Ala Lys Ala Glu Gln
            100                 105                 110

Ser Gly Thr Leu Gln Gly Glu Ile Met Ala Glu Tyr Trp Lys Ser His
        115                 120                 125

Pro Glu Ala Asp Lys Asn His Asp Gly Ile Met Gln Tyr Val Met Ile
    130                 135                 140

Thr Gly Glu Pro Gly His Gln Asp Ala Ile Leu Arg Thr Glu Tyr Ser
145                 150                 155                 160

Ile Lys Ala Val Glu Ala Ala Gly Ile Arg Val Lys Cys Leu Ala Gln
                165                 170                 175

Asp Thr Ala Met Trp Asp Arg Val Lys Gly Gln Glu Lys Met Gln Ala
            180                 185                 190

Phe Leu Ala Ser Phe Gly Asp Lys Ile Glu Ala Val Phe Cys Asn Asn
        195                 200                 205

Asp Asp Met Ala Leu Gly Ala Ile Glu Ala Leu Lys Ala Ala Gly Tyr
    210                 215                 220

Phe Lys Asp Gly Lys Tyr Val Pro Val Val Gly Val Asp Ala Thr Thr
225                 230                 235                 240

Pro Gly Leu Gln Ala Leu Glu Glu Gly Thr Leu Leu Gly Thr Val Leu
                245                 250                 255

Asn Asp Ala Lys Ala Gln Gly Lys Ala Thr Phe Asn Leu Ala Tyr Val
            260                 265                 270

Leu Ala Lys Gly Glu Lys Pro Thr Lys Glu Asn Val Gly Phe Glu Ile
        275                 280                 285

Thr Asp Gly Lys Tyr Ile Trp Val Pro Tyr Gln Lys Val Thr Lys Asp
    290                 295                 300

Asn Leu Glu Glu Met Lys Lys Tyr Val Asn Glu Gln Gly Gly Ser His
305                 310                 315                 320

His His His His His
                325


<210> SEQ ID NO 45
<211> LENGTH: 325
<212> TYPE: PRT
<213> ORGANISM: Artificial Sequence
<220> FEATURE:
<223> OTHER INFORMATION: chyGGBP (with signal peptide replaced with M
      and a GGSHHHHHH at C-terminus)

<400> SEQUENCE: 45

Met Lys Pro Tyr Ile Gly Val Ala Ile Tyr Lys Phe Asp Asp Thr Phe
1               5                   10                  15

Met Thr Gly Val Arg Asn Ala Ile Ala Lys Glu Gly Glu Gly Lys Ala
            20                  25                  30

Lys Leu Asp Phe Val Asp Cys Gln Asn Ser Gln Ser Thr Gln Asn Asp
        35                  40                  45

Lys Ile Asp Leu Phe Ile Thr Lys Lys Val Asp Ala Leu Ala Ile Asn
    50                  55                  60

Pro Val Asp Arg Thr Ala Ala Gly Val Leu Ile Asp Lys Ala Lys Gln
65                  70                  75                  80

Ala Asn Ile Pro Val Val Phe Phe Asn Arg Glu Pro Leu Pro Glu Asp
```

```
                85                  90                  95

Met Lys Lys Trp Asp Lys Val Tyr Tyr Val Gly Ala Lys Ala Glu Gln
            100                 105                 110

Ser Gly Thr Leu Gln Gly Glu Ile Met Ala Glu Tyr Trp Lys Ser His
        115                 120                 125

Pro Glu Ala Asp Lys Asn His Asn Gly Ile Met Glu Tyr Val Met Ile
    130                 135                 140

Thr Gly Glu Pro Gly His Gln Asp Ala Ile Leu Arg Thr Glu Tyr Ser
145                 150                 155                 160

Ile Lys Ala Val Glu Ala Ala Gly Ile Lys Thr Lys Ala Leu Ala Gln
                165                 170                 175

Asp Thr Ala Met Trp Asp Arg Val Lys Gly Gln Glu Lys Met Gln Ala
            180                 185                 190

Phe Leu Ala Ser Phe Gly Asp Arg Ile Glu Ala Val Phe Cys Asn Asn
        195                 200                 205

Asp Asp Met Ala Leu Gly Ala Ile Glu Ala Leu Lys Ala Ala Gly Tyr
    210                 215                 220

Phe Lys Asn Gly Lys Tyr Ile Pro Val Val Gly Val Asp Ala Thr Thr
225                 230                 235                 240

Pro Gly Leu Gln Ala Leu Glu Glu Gly Thr Leu Leu Gly Thr Val Leu
                245                 250                 255

Asn Asp Ala Lys Ala Gln Gly Lys Ala Thr Phe Asn Leu Ala Tyr Val
            260                 265                 270

Leu Ala Lys Gly Glu Lys Pro Thr Lys Glu Asn Val Gly Phe Asp Ile
        275                 280                 285

Thr Asp Gly Lys Tyr Ile Trp Val Pro Tyr Gln Lys Val Thr Lys Asp
    290                 295                 300

Asn Leu Glu Glu Met Lys Lys Tyr Val Asn Glu Gln Gly Gly Ser His
305                 310                 315                 320

His His His His His
                325


<210> SEQ ID NO 46
<211> LENGTH: 316
<212> TYPE: PRT
<213> ORGANISM: Artificial Sequence
<220> FEATURE:
<223> OTHER INFORMATION: pspGGBP (with signal peptide replaced with M
      and a GGSHHHHHH at C-terminus)

<400> SEQUENCE: 46

Met Val Gly Val Ala Ile Tyr Lys Phe Asp Asp Thr Phe Met Thr Gly
1               5                   10                  15

Val Arg Asn Ala Met Ser Asp Ala Ala Asn Gly Val Ala Lys Leu Asp
            20                  25                  30

Ile Val Asp Ser Gln Asn Ala Gln Pro Thr Gln Asn Glu Lys Ile Asp
        35                  40                  45

Leu Phe Ile Ser Lys Lys Tyr Ser Ser Met Ile Ile Asn Pro Val Asp
    50                  55                  60

Arg Thr Ala Ala Gly Val Ile Ile Asp Lys Ala Lys Thr Ala Asn Thr
65                  70                  75                  80

Pro Val Val Phe Leu Asn Arg Glu Pro Ile Ala Glu Asp Met Asn Lys
                85                  90                  95

Trp Asp Lys Val Tyr Tyr Val Gly Ala Lys Ala Glu Glu Ser Gly Thr
            100                 105                 110
```

```
Ile Ser Gly Gln Leu Ile Val Asp Tyr Trp Lys Ala Asn Pro Lys Ala
        115                 120                 125

Asp Lys Asn Gly Asp Gly Lys Leu Gln Tyr Val Leu Leu Gln Gly Glu
    130                 135                 140

Pro Gly His Gln Asp Ala Glu Leu Arg Thr Lys Phe Ser Val Gln Ala
145                 150                 155                 160

Ile Gln Asp Ala Gly Ile Glu Val Glu Ala Leu Ala Val Asp Thr Ala
                165                 170                 175

Met Trp Asp Arg Val Lys Gly Gln Glu Lys Met Gln Thr Phe Leu Ala
            180                 185                 190

Ser His Gly Asp Lys Ile Glu Ala Val Leu Ala Asn Asn Asp Asp Met
        195                 200                 205

Ala Leu Gly Ala Ile Glu Ala Leu Lys Ala Ala Gly Tyr Phe Ser Gly
    210                 215                 220

Asp Lys Tyr Met Pro Val Val Gly Val Asp Ala Thr Ala Pro Ala Val
225                 230                 235                 240

Gln Ala Leu Glu Asp Gly Thr Leu Leu Gly Thr Val Leu Asn Asp Ala
                245                 250                 255

Lys Ser Gln Gly Lys Ala Ser Val Ala Ile Ala Ala Ala Leu Ser Lys
            260                 265                 270

Gly Glu Ala Pro Asn Lys Glu Asn Thr Gly Phe Asp Ile Thr Asp Gly
        275                 280                 285

Lys Tyr Val Trp Ile Ala Tyr Lys Lys Ile Thr Lys Asp Asn Ile Ala
    290                 295                 300

Asp Ala Lys Gly Gly Ser His His His His His His
305                 310                 315


<210> SEQ ID NO 47
<211> LENGTH: 325
<212> TYPE: PRT
<213> ORGANISM: Artificial Sequence
<220> FEATURE:
<223> OTHER INFORMATION: cobGGBP.W181C (Signaling cys mutant of cobGGBP
      with signal peptide replaced with M and GGSHHHHHH at C-terminus)

<400> SEQUENCE: 47

Met Lys Pro Tyr Ile Gly Val Ala Ile Tyr Lys Phe Asp Asp Thr Phe
1               5                   10                  15

Met Thr Gly Val Arg Asn Ala Ile Ala Lys Glu Gly Glu Gly Lys Ala
            20                  25                  30

Lys Leu Asp Phe Val Asp Ala Gln Asn Ser Gln Ser Thr Gln Asn Asp
        35                  40                  45

Lys Ile Asp Leu Phe Ile Thr Lys Lys Val Asp Ala Leu Ala Ile Asn
    50                  55                  60

Pro Val Asp Arg Thr Ala Ala Gly Val Leu Ile Asp Lys Ala Lys Gln
65                  70                  75                  80

Ala Asn Ile Pro Val Val Phe Phe Asn Arg Glu Pro Leu Pro Glu Asp
                85                  90                  95

Met Lys Lys Trp Asp Lys Val Tyr Tyr Val Gly Ala Lys Ala Glu Gln
            100                 105                 110

Ser Gly Thr Leu Gln Gly Glu Ile Met Ala Glu Tyr Trp Lys Ser His
        115                 120                 125

Pro Glu Ala Asp Lys Asn His Asp Gly Ile Met Gln Tyr Val Met Ile
    130                 135                 140

Thr Gly Glu Pro Gly His Gln Asp Ala Ile Leu Arg Thr Glu Tyr Ser
145                 150                 155                 160
```

```
Ile Lys Ala Val Glu Ala Ala Gly Ile Arg Val Lys Ser Leu Ala Gln
                165                 170                 175

Asp Thr Ala Met Cys Asp Arg Val Lys Gly Gln Glu Lys Met Gln Ala
            180                 185                 190

Phe Leu Ala Ser Phe Gly Asp Lys Ile Glu Ala Val Phe Ala Asn Asn
        195                 200                 205

Asp Asp Met Ala Leu Gly Ala Ile Glu Ala Leu Lys Ala Ala Gly Tyr
    210                 215                 220

Phe Lys Asp Gly Lys Tyr Val Pro Val Val Gly Val Asp Ala Thr Thr
225                 230                 235                 240

Pro Gly Leu Gln Ala Leu Glu Glu Gly Thr Leu Leu Gly Thr Val Leu
                245                 250                 255

Asn Asp Ala Lys Ala Gln Gly Lys Ala Thr Phe Asn Leu Ala Tyr Val
            260                 265                 270

Leu Ala Lys Gly Glu Lys Pro Thr Lys Glu Asn Val Gly Phe Glu Ile
        275                 280                 285

Thr Asp Gly Lys Tyr Ile Trp Val Pro Tyr Gln Lys Val Thr Lys Asp
    290                 295                 300

Asn Leu Glu Glu Met Lys Lys Tyr Val Asn Glu Gln Gly Gly Ser His
305                 310                 315                 320

His His His His His
                325
```

```
<210> SEQ ID NO 48
<211> LENGTH: 325
<212> TYPE: PRT
<213> ORGANISM: Artificial Sequence
<220> FEATURE:
<223> OTHER INFORMATION: chyGGBP.W181C (Signaling cys mutants of chyGGBP
      with signal peptide replaced with M and GGSHHHHHH at C-terminus)

<400> SEQUENCE: 48

Met Lys Pro Tyr Ile Gly Val Ala Ile Tyr Lys Phe Asp Asp Thr Phe
1               5                   10                  15

Met Thr Gly Val Arg Asn Ala Ile Ala Lys Glu Gly Glu Gly Lys Ala
            20                  25                  30

Lys Leu Asp Phe Val Asp Ala Gln Asn Ser Gln Ser Thr Gln Asn Asp
        35                  40                  45

Lys Ile Asp Leu Phe Ile Thr Lys Lys Val Asp Ala Leu Ala Ile Asn
    50                  55                  60

Pro Val Asp Arg Thr Ala Ala Gly Val Leu Ile Asp Lys Ala Lys Gln
65                  70                  75                  80

Ala Asn Ile Pro Val Val Phe Phe Asn Arg Glu Pro Leu Pro Glu Asp
                85                  90                  95

Met Lys Lys Trp Asp Lys Val Tyr Tyr Val Gly Ala Lys Ala Glu Gln
            100                 105                 110

Ser Gly Thr Leu Gln Gly Glu Ile Met Ala Glu Tyr Trp Lys Ser His
        115                 120                 125

Pro Glu Ala Asp Lys Asn His Asn Gly Ile Met Glu Tyr Val Met Ile
    130                 135                 140

Thr Gly Glu Pro Gly His Gln Asp Ala Ile Leu Arg Thr Glu Tyr Ser
145                 150                 155                 160

Ile Lys Ala Val Glu Ala Ala Gly Ile Lys Thr Lys Ala Leu Ala Gln
                165                 170                 175

Asp Thr Ala Met Cys Asp Arg Val Lys Gly Gln Glu Lys Met Gln Ala
```

180 185 190

Phe Leu Ala Ser Phe Gly Asp Arg Ile Glu Ala Val Phe Ala Asn Asn
195 200 205

Asp Asp Met Ala Leu Gly Ala Ile Glu Ala Leu Lys Ala Ala Gly Tyr
210 215 220

Phe Lys Asn Gly Lys Tyr Ile Pro Val Val Gly Val Asp Ala Thr Thr
225 230 235 240

Pro Gly Leu Gln Ala Leu Glu Glu Gly Thr Leu Leu Gly Thr Val Leu
245 250 255

Asn Asp Ala Lys Ala Gln Gly Lys Ala Thr Phe Asn Leu Ala Tyr Val
260 265 270

Leu Ala Lys Gly Glu Lys Pro Thr Lys Glu Asn Val Gly Phe Asp Ile
275 280 285

Thr Asp Gly Lys Tyr Ile Trp Val Pro Tyr Gln Lys Val Thr Lys Asp
290 295 300

Asn Leu Glu Glu Met Lys Lys Tyr Val Asn Glu Gln Gly Gly Ser His
305 310 315 320

His His His His His
325

<210> SEQ ID NO 49
<211> LENGTH: 321
<212> TYPE: PRT
<213> ORGANISM: Artificial Sequence
<220> FEATURE:
<223> OTHER INFORMATION: ttGGBP11C (ttGGBP cys mutant with signal peptide replaced with M and GGSHHHHHH at C-terminus)

<400> SEQUENCE: 49

Met Lys Gln Leu Asn Ile Gly Val Ala Ile Cys Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

```
Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 50
<211> LENGTH: 321
<212> TYPE: PRT
<213> ORGANISM: Artificial Sequence
<220> FEATURE:
<223> OTHER INFORMATION: ttGGBP16C (ttGGBP cys mutant with signal
      peptide replaced with M and GGSHHHHHH at C-terminus)

<400> SEQUENCE: 50

Met Lys Gln Leu Asn Ile Gly Val Ala Ile Tyr Lys Phe Asp Asp Cys
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240
```

```
Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 51
<211> LENGTH: 321
<212> TYPE: PRT
<213> ORGANISM: Artificial Sequence
<220> FEATURE:
<223> OTHER INFORMATION: ttGGBP17C (ttGGBP cys mutant with signal
      peptide replaced with M and GGSHHHHHH at C-terminus)

<400> SEQUENCE: 51

Met Lys Gln Leu Asn Ile Gly Val Ala Ile Tyr Lys Phe Asp Asp Thr
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270
```

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 52
<211> LENGTH: 321
<212> TYPE: PRT
<213> ORGANISM: Artificial Sequence
<220> FEATURE:
<223> OTHER INFORMATION: ttGGBP42C (ttGGBP cys mutant with signal peptide replaced with M and GGSHHHHHH at C-terminus)

<400> SEQUENCE: 52

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Cys Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

```
Asp Asn Ile Ser Asp Ala Glu Gln Gly Gly Ser His His His His His
305                 310                 315                 320

His


<210> SEQ ID NO 53
<211> LENGTH: 321
<212> TYPE: PRT
<213> ORGANISM: Artificial Sequence
<220> FEATURE:
<223> OTHER INFORMATION: ttGGBP67C (ttGGBP cys mutant with signal
      peptide replaced with M and GGSHHHHHH at C-terminus)

<400> SEQUENCE: 53

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Cys Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His
```

-continued

<210> SEQ ID NO 54
<211> LENGTH: 321
<212> TYPE: PRT
<213> ORGANISM: Artificial Sequence
<220> FEATURE:
<223> OTHER INFORMATION: ttGGBP91C (ttGGBP cys mutant with signal peptide replaced with M and GGSHHHHHH at C-terminus)

<400> SEQUENCE: 54

```
Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Cys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His
```

<210> SEQ ID NO 55
<211> LENGTH: 321
<212> TYPE: PRT
<213> ORGANISM: Artificial Sequence
<220> FEATURE:
<223> OTHER INFORMATION: ttGGBP92C (ttGGBP cys mutant with signal peptide replaced with M and GGSHHHHHH at C-terminus)

<400> SEQUENCE: 55

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Cys Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 56
<211> LENGTH: 321
<212> TYPE: PRT
<213> ORGANISM: Artificial Sequence
<220> FEATURE:
<223> OTHER INFORMATION: ttGGBP111C (ttGGBP cys mutant with signal
peptide replaced with M and GGSHHHHHH at C-terminus)

<400> SEQUENCE: 56

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Cys Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 57
<211> LENGTH: 321
<212> TYPE: PRT
<213> ORGANISM: Artificial Sequence
<220> FEATURE:
<223> OTHER INFORMATION: ttGGBP148C (ttGGBP cys mutant with signal peptide replaced with M and GGSHHHHHH at C-terminus)

<400> SEQUENCE: 57

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Cys Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His

<210> SEQ ID NO 58
<211> LENGTH: 321
<212> TYPE: PRT
<213> ORGANISM: Artificial Sequence
<220> FEATURE:
<223> OTHER INFORMATION: ttGGBP151C (ttGGBP cys mutant with signal
      peptide replaced with M and GGSHHHHHH at C-terminus)

<400> SEQUENCE: 58

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly Cys Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 59
<211> LENGTH: 321
<212> TYPE: PRT
<213> ORGANISM: Artificial Sequence
<220> FEATURE:
<223> OTHER INFORMATION: ttGGBP152C (ttGGBP cys mutant with signal peptide replaced with M and GGSHHHHHH at C-terminus)

<400> SEQUENCE: 59

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Cys Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His

<210> SEQ ID NO 60
<211> LENGTH: 321
<212> TYPE: PRT
<213> ORGANISM: Artificial Sequence
<220> FEATURE:
<223> OTHER INFORMATION: ttGGBP181C (ttGGBP cys mutant with signal
      peptide replaced with M and GGSHHHHHH at C-terminus)

<400> SEQUENCE: 60

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Cys Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 61
<211> LENGTH: 321
<212> TYPE: PRT
<213> ORGANISM: Artificial Sequence
<220> FEATURE:
<223> OTHER INFORMATION: ttGGBP182C (ttGGBP cys mutant with signal
peptide replaced with M and GGSHHHHHH at C-terminus)

<400> SEQUENCE: 61

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 62
<211> LENGTH: 321
<212> TYPE: PRT
<213> ORGANISM: Artificial Sequence
<220> FEATURE:
<223> OTHER INFORMATION: ttGGBP183C (ttGGBP cys mutant with signal
peptide replaced with M and GGSHHHHHH at C-terminus)

<400> SEQUENCE: 62

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Cys Arg Val Thr Ala His Asp Lys Met Ala
180 185 190

Ala Trp Leu Ser Ser Phe Gly Asp Lys Ile Glu Ala Val Phe Ala Asn
195 200 205

```
Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 63
<211> LENGTH: 321
<212> TYPE: PRT
<213> ORGANISM: Artificial Sequence
<220> FEATURE:
<223> OTHER INFORMATION: ttGGBP257C (ttGGBP cys mutant with signal
      peptide replaced with M and GGSHHHHHH at C-terminus)

<400> SEQUENCE: 63

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240
```

```
Ala Pro Gly Ile Gln Ala Ile Lys Asp Gly Thr Leu Leu Gly Thr Val
                245                 250                 255

Cys Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 64
<211> LENGTH: 321
<212> TYPE: PRT
<213> ORGANISM: Artificial Sequence
<220> FEATURE:
<223> OTHER INFORMATION: ttGGBP259C (ttGGBP cys mutant with signal
      peptide replaced with M and GGSHHHHHH at C-terminus)

<400> SEQUENCE: 64

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Cys Ala Lys Asn Gln Ala Lys Ala Thr Phe Asn Ile Ala Tyr
            260                 265                 270
```

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 65
<211> LENGTH: 321
<212> TYPE: PRT
<213> ORGANISM: Artificial Sequence
<220> FEATURE:
<223> OTHER INFORMATION: ttGGBP300C (ttGGBP cys mutant with signal peptide replaced with M and GGSHHHHHH at C-terminus)

<400> SEQUENCE: 65

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Cys Lys Ile Thr Lys
290 295 300

Asp Asn Ile Ser Asp Ala Glu Gln Gly Gly Ser His His His His His
305 310 315 320

His

<210> SEQ ID NO 66
<211> LENGTH: 321
<212> TYPE: PRT
<213> ORGANISM: Artificial Sequence
<220> FEATURE:
<223> OTHER INFORMATION: ttGGBP17C.1 (affinity-tuning mutant, 17C background (Table 6) with signal peptide replaced with M and GGSHHHHHH at C-terminus)

<400> SEQUENCE: 66

Met Lys Gln Leu Asn Ile Gly Val Ala Ile Tyr Lys Phe Asp Asp Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Glu Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 67
<211> LENGTH: 321
<212> TYPE: PRT
<213> ORGANISM: Artificial Sequence
<220> FEATURE:
<223> OTHER INFORMATION: ttGGBP17C.2 (affinity-tuning mutant, 17C background (Table 6) with signal peptide replaced with M and GGSHHHHHH at C-terminus)

<400> SEQUENCE: 67

```
Met Lys Gln Leu Asn Ile Gly Val Ala Ile Tyr Lys Phe Asp Asp Thr
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Pro Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Pro Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His
```

<210> SEQ ID NO 68
<211> LENGTH: 321
<212> TYPE: PRT

<213> ORGANISM: Artificial Sequence
<220> FEATURE:
<223> OTHER INFORMATION: ttGGBP17C.3 (affinity-tuning mutant, 17C background (Table 6) with signal peptide replaced with M and GGSHHHHHH at C-terminus)

<400> SEQUENCE: 68

```
Met Lys Gln Leu Asn Ile Gly Val Ala Ile Tyr Lys Phe Asp Asp Asn
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Ala Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His
```

<210> SEQ ID NO 69
<211> LENGTH: 321
<212> TYPE: PRT
<213> ORGANISM: Artificial Sequence
<220> FEATURE:
<223> OTHER INFORMATION: ttGGBP17C.4 (affinity-tuning mutant, 17C background (Table 6) with signal peptide replaced with M and GGSHHHHHH at C-terminus)

<400> SEQUENCE: 69

Met Lys Gln Leu Asn Ile Gly Val Ala Ile Tyr Lys Phe Asp Asp Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly Gln Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 70
<211> LENGTH: 321
<212> TYPE: PRT
<213> ORGANISM: Artificial Sequence
<220> FEATURE:
<223> OTHER INFORMATION: ttGGBP17C.5 (affinity-tuning mutant, 17C background (Table 6) with signal peptide replaced with M and GGSHHHHHH at C-terminus)

<400> SEQUENCE: 70

Met Lys Gln Leu Asn Ile Gly Val Ala Ile Tyr Lys Phe Asp Ala Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 71
<211> LENGTH: 321
<212> TYPE: PRT
<213> ORGANISM: Artificial Sequence
<220> FEATURE:
<223> OTHER INFORMATION: ttGGBP17C.6 (affinity-tuning mutant, 17C background (Table 6) with signal peptide replaced with M and GGSHHHHHH at C-terminus)

<400> SEQUENCE: 71

Met Lys Gln Leu Asn Ile Gly Val Ala Ile Tyr Lys Phe Asp Glu Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn

```
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 72
<211> LENGTH: 321
<212> TYPE: PRT
<213> ORGANISM: Artificial Sequence
<220> FEATURE:
<223> OTHER INFORMATION: ttGGBP17C.7 (affinity-tuning mutant, 17C
      background (Table 6) with signal peptide replaced with M and
      GGSHHHHHH at C-terminus)

<400> SEQUENCE: 72

Met Lys Gln Leu Asn Ile Gly Val Ala Ile Tyr Lys Phe Asp Asn Thr
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60
```

-continued

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 73
<211> LENGTH: 321
<212> TYPE: PRT
<213> ORGANISM: Artificial Sequence
<220> FEATURE:
<223> OTHER INFORMATION: ttGGBP17C.8 (affinity-tuning mutant, 17C background (Table 6) with signal peptide replaced with M and GGSHHHHHH at C-terminus)

<400> SEQUENCE: 73

Met Lys Gln Leu Asn Ile Gly Val Ala Ile Tyr Lys Phe Asp Asp Asn
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

```
Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 74
<211> LENGTH: 321
<212> TYPE: PRT
<213> ORGANISM: Artificial Sequence
<220> FEATURE:
<223> OTHER INFORMATION: ttGGBP17C.9 (affinity-tuning mutant, 17C
      background (Table 6) with signal peptide replaced with M and
      GGSHHHHHH at C-terminus)

<400> SEQUENCE: 74

Met Lys Gln Leu Asn Ile Gly Val Ala Ile Tyr Lys Phe Asp Asp Ser
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
```

```
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 75
<211> LENGTH: 321
<212> TYPE: PRT
<213> ORGANISM: Artificial Sequence
<220> FEATURE:
<223> OTHER INFORMATION: ttGGBP17C.10 (affinity-tuning mutant, 17C
      background (Table 6) with signal peptide replaced with M and
      GGSHHHHHH at C-terminus)

<400> SEQUENCE: 75

Met Lys Gln Leu Asn Ile Gly Val Ala Ile Tyr Lys Phe Asp Asp Thr
1               5                   10                  15

Cys Met Thr Ala Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140
```

-continued

```
Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 76
<211> LENGTH: 321
<212> TYPE: PRT
<213> ORGANISM: Artificial Sequence
<220> FEATURE:
<223> OTHER INFORMATION: ttGGBP17C.11 (affinity-tuning mutant, 17C
      background (Table 6) with signal peptide replaced with M and
      GGSHHHHHH at C-terminus)

<400> SEQUENCE: 76

Met Lys Gln Leu Asn Ile Gly Val Ala Ile Tyr Lys Phe Asp Asp Thr
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175
```

```
Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Ala
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 77
<211> LENGTH: 321
<212> TYPE: PRT
<213> ORGANISM: Artificial Sequence
<220> FEATURE:
<223> OTHER INFORMATION: ttGGBP17C.19 (affinity-tuning mutant, 17C
      background (Table 6) with signal peptide replaced with M and
      GGSHHHHHH at C-terminus)

<400> SEQUENCE: 77

Met Lys Gln Leu Asn Ile Gly Val Ala Ile Tyr Lys Phe Asp Asp Thr
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
```

195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asp Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 78
<211> LENGTH: 321
<212> TYPE: PRT
<213> ORGANISM: Artificial Sequence
<220> FEATURE:
<223> OTHER INFORMATION: ttGGBP17C.20 (affinity-tuning mutant, 17C background (Table 6) with signal peptide replaced with M and GGSHHHHHH at C-terminus)

<400> SEQUENCE: 78

Met Lys Gln Leu Asn Ile Gly Val Ala Ile Tyr Lys Phe Asp Asp Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

```
Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Ser Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 79
<211> LENGTH: 321
<212> TYPE: PRT
<213> ORGANISM: Artificial Sequence
<220> FEATURE:
<223> OTHER INFORMATION: ttGGBP17C.21 (affinity-tuning mutant, 17C
      background (Table 6) with signal peptide replaced with M and
      GGSHHHHHH at C-terminus)

<400> SEQUENCE: 79

Met Lys Gln Leu Asn Ile Gly Val Ala Ile Tyr Lys Phe Asp Asp Thr
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255
```

Leu Ala Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 80
<211> LENGTH: 321
<212> TYPE: PRT
<213> ORGANISM: Artificial Sequence
<220> FEATURE:
<223> OTHER INFORMATION: ttGGBP17C.22 (affinity-tuning mutant, 17C background (Table 6) with signal peptide replaced with M and GGSHHHHHH at C-terminus)

<400> SEQUENCE: 80

Met Lys Gln Leu Asn Ile Gly Val Ala Ile Tyr Lys Phe Asp Asp Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Asn Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp 275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 81
<211> LENGTH: 321
<212> TYPE: PRT
<213> ORGANISM: Artificial Sequence
<220> FEATURE:
<223> OTHER INFORMATION: ttGGBP17C.23 (affinity-tuning mutant, 17C background (Table 6) with signal peptide replaced with M and GGSHHHHHH at C-terminus)

<400> SEQUENCE: 81

Met Lys Gln Leu Asn Ile Gly Val Ala Ile Tyr Lys Phe Asp Asp Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Gln Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 82
<211> LENGTH: 321
<212> TYPE: PRT
<213> ORGANISM: Artificial Sequence
<220> FEATURE:
<223> OTHER INFORMATION: ttGGBP17C.24 (affinity-tuning mutant, 17C background (Table 6) with signal peptide replaced with M and GGSHHHHHH at C-terminus)

<400> SEQUENCE: 82

Met Lys Gln Leu Asn Ile Gly Val Ala Ile Tyr Lys Phe Asp Asp Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Arg Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 83
<211> LENGTH: 321
<212> TYPE: PRT
<213> ORGANISM: Artificial Sequence
<220> FEATURE:
<223> OTHER INFORMATION: ttGGBP17C.25 (affinity-tuning mutant, 17C background (Table 6) with signal peptide replaced with M and GGSHHHHHH at C-terminus)

<400> SEQUENCE: 83

```
Met Lys Gln Leu Asn Ile Gly Val Ala Ile Tyr Lys Phe Asp Asp Thr
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Lys Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His
```

<210> SEQ ID NO 84
<211> LENGTH: 321
<212> TYPE: PRT
<213> ORGANISM: Artificial Sequence
<220> FEATURE:
<223> OTHER INFORMATION: ttGGBP17C.26 (affinity-tuning mutant, 17C background (Table 6) with signal peptide replaced with M and GGSHHHHHH at C-terminus)

<400> SEQUENCE: 84

Met Lys Gln Leu Asn Ile Gly Val Ala Ile Tyr Lys Phe Asp Asp Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Trp Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 85
<211> LENGTH: 321
<212> TYPE: PRT
<213> ORGANISM: Artificial Sequence
<220> FEATURE:
<223> OTHER INFORMATION: ttGGBP17C.27 (affinity-tuning mutant, 17C background (Table 6) with signal peptide replaced with M and GGSHHHHHH at C-terminus)

<400> SEQUENCE: 85

Met Lys Gln Leu Asn Ile Gly Val Ala Ile Tyr Lys Phe Asp Asp Thr
1               5                   10                  15

Cys Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Phe Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His

<210> SEQ ID NO 86
<211> LENGTH: 321
<212> TYPE: PRT
<213> ORGANISM: Artificial Sequence
<220> FEATURE:
<223> OTHER INFORMATION: ttGGBP17C.28 (affinity-tuning mutant, 17C background (Table 6) with signal peptide replaced with M and GGSHHHHHH at C-terminus)

<400> SEQUENCE: 86

Met Lys Gln Leu Asn Ile Gly Val Ala Ile Tyr Lys Phe Asp Asp Thr
1               5                   10                  15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Trp Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Tyr Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 87
<211> LENGTH: 321
<212> TYPE: PRT
<213> ORGANISM: Artificial Sequence
<220> FEATURE:
<223> OTHER INFORMATION: ttGGBP17C.29 (affinity-tuning mutant, 17C background (Table 6) with signal peptide replaced with M and GGSHHHHHH at C-terminus)

<400> SEQUENCE: 87

Met Lys Gln Leu Asn Ile Gly Val Ala Ile Tyr Lys Phe Asp Asp Thr
1 5 10 15

Cys Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Trp Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ser Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His

<210> SEQ ID NO 88
<211> LENGTH: 321
<212> TYPE: PRT
<213> ORGANISM: Artificial Sequence
<220> FEATURE:
<223> OTHER INFORMATION: ttGGBP182C.2.0 (affinity-tuning mutant, 182C background (Table 6) with signal peptide replaced with M and GGSHHHHHH at C-terminus)

<400> SEQUENCE: 88

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys 65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Glu Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 89
<211> LENGTH: 321
<212> TYPE: PRT
<213> ORGANISM: Artificial Sequence
<220> FEATURE:
<223> OTHER INFORMATION: ttGGBP182C.2.1 (affinity-tuning mutant, 182C background (Table 6) with signal peptide replaced with M and GGSHHHHHH at C-terminus)

<400> SEQUENCE: 89

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Glu Pro Gly His Gln Asp Ser Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 90
<211> LENGTH: 321
<212> TYPE: PRT
<213> ORGANISM: Artificial Sequence
<220> FEATURE:
<223> OTHER INFORMATION: ttGGBP182C.2.3 (affinity-tuning mutant, 182C background (Table 6) with signal peptide replaced with M and GGSHHHHHH at C-terminus)

<400> SEQUENCE: 90

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Glu Pro Gly His Gln Asp Asn Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 91
<211> LENGTH: 321
<212> TYPE: PRT
<213> ORGANISM: Artificial Sequence
<220> FEATURE:
<223> OTHER INFORMATION: ttGGBP182C.2.4 (affinity-tuning mutant, 182C background (Table 6) with signal peptide replaced with M and GGSHHHHHH at C-terminus)

<400> SEQUENCE: 91

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Glu Pro Gly His Gln Asp Met Ile Leu Arg Thr Gln Tyr 145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 92
<211> LENGTH: 321
<212> TYPE: PRT
<213> ORGANISM: Artificial Sequence
<220> FEATURE:
<223> OTHER INFORMATION: ttGGBP182C.2.5 (affinity-tuning mutant, 182C background (Table 6) with signal peptide replaced with M and GGSHHHHHH at C-terminus)

<400> SEQUENCE: 92

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Glu Pro Gly Gln Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

-continued

```
Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 93
<211> LENGTH: 321
<212> TYPE: PRT
<213> ORGANISM: Artificial Sequence
<220> FEATURE:
<223> OTHER INFORMATION: ttGGBP182C.2.6 (affinity-tuning mutant, 182C
      background (Table 6) with signal peptide replaced with M and
      GGSHHHHHH at C-terminus)

<400> SEQUENCE: 93

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Lys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Glu Pro Gly Asn Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205
```

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 94
<211> LENGTH: 321
<212> TYPE: PRT
<213> ORGANISM: Artificial Sequence
<220> FEATURE:
<223> OTHER INFORMATION: ttGGBP182C.2.7 (affinity-tuning mutant, 182C background (Table 6) with signal peptide replaced with M and GGSHHHHHH at C-terminus)

<400> SEQUENCE: 94

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Glu Pro Gly Phe Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr

```
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 95
<211> LENGTH: 321
<212> TYPE: PRT
<213> ORGANISM: Artificial Sequence
<220> FEATURE:
<223> OTHER INFORMATION: ttGGBP182C.2.8 (affinity-tuning mutant, 182C
      background (Table 6) with signal peptide replaced with M and
      GGSHHHHHH at C-terminus)

<400> SEQUENCE: 95

Met Lys Gln Leu Asn Ile Gly Val Ala Ile Tyr Lys Phe Asp Asn Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Lys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Glu Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255
```

```
Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 96
<211> LENGTH: 321
<212> TYPE: PRT
<213> ORGANISM: Artificial Sequence
<220> FEATURE:
<223> OTHER INFORMATION: ttGGBP182C.2.9 (affinity-tuning mutant, 182C
      background (Table 6) with signal peptide replaced with M and
      GGSHHHHHH at C-terminus)

<400> SEQUENCE: 96

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Lys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Glu Pro Gly His Gln Asp Phe Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285
```

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 97
<211> LENGTH: 321
<212> TYPE: PRT
<213> ORGANISM: Artificial Sequence
<220> FEATURE:
<223> OTHER INFORMATION: ttGGBP182C.3 (affinity-tuning mutant, 182C background (Table 6) with signal peptide replaced with M and GGSHHHHHH at C-terminus)

<400> SEQUENCE: 97

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His 305 310 315 320

His

<210> SEQ ID NO 98
<211> LENGTH: 321
<212> TYPE: PRT
<213> ORGANISM: Artificial Sequence
<220> FEATURE:
<223> OTHER INFORMATION: ttGGBP182C.4 (affinity-tuning mutant, 182C background (Table 6) with signal peptide replaced with M and GGSHHHHHH at C-terminus)

<400> SEQUENCE: 98

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Glu Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 99
<211> LENGTH: 321
<212> TYPE: PRT
<213> ORGANISM: Artificial Sequence
<220> FEATURE:
<223> OTHER INFORMATION: ttGGBP182C.5 (affinity-tuning mutant, 182C background (Table 6) with signal peptide replaced with M and GGSHHHHHH at C-terminus)

<400> SEQUENCE: 99

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Pro Thr Ala Ala Gly Thr Ile Ile Asp Lys Ala Lys
65 70 75 80

Gln Ala Asn Ile Pro Val Val Phe Phe Asn Arg Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Gln Pro Gly His Pro Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 100
<211> LENGTH: 321
<212> TYPE: PRT
<213> ORGANISM: Artificial Sequence
<220> FEATURE:

<223> OTHER INFORMATION: ttGGBP182C.6 (affinity-tuning mutant, 182C background (Table 6) with signal peptide replaced with M and GGSHHHHHH at C-terminus)

<400> SEQUENCE: 100

```
Met Lys Gln Leu Asn Ile Gly Val Ala Ile Tyr Lys Phe Asp Asp Asn
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Ala Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His
```

<210> SEQ ID NO 101
<211> LENGTH: 321
<212> TYPE: PRT
<213> ORGANISM: Artificial Sequence
<220> FEATURE:
<223> OTHER INFORMATION: ttGGBP182C.7 (affinity-tuning mutant, 182C background (Table 6) with signal peptide replaced with M and GGSHHHHHH at C-terminus)

<400> SEQUENCE: 101

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys
20 25 30

Ala Lys Leu Asn Met Val Asp Ser Gln Asn Ser Gln Pro Thr Gln Asn
35 40 45

Asp Gln Val Asp Leu Phe Ile Thr Lys Lys Met Asn Ala Leu Ala Ile
50 55 60

Asn Pro Val Asp Arg Thr Ala Ala Gly Thr Ile Ile Asp Lys Ala Lys
65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Ser Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser His His His His His
305 310 315 320

His

<210> SEQ ID NO 102
<211> LENGTH: 321
<212> TYPE: PRT
<213> ORGANISM: Artificial Sequence
<220> FEATURE:
<223> OTHER INFORMATION: ttGGBP182C.8 (affinity-tuning mutant, 182C background (Table 6) with signal peptide replaced with M and GGSHHHHHH at C-terminus)

<400> SEQUENCE: 102

Met Lys Gln Leu Asn Ile Gly Val Ala Ile Tyr Lys Phe Asp Asp Thr
1 5 10 15

Phe Met Thr Gly Val Arg Asn Ala Met Thr Ala Glu Ala Gln Gly Lys

```
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Lys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Lys Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His
```

<210> SEQ ID NO 103
<211> LENGTH: 321
<212> TYPE: PRT
<213> ORGANISM: Artificial Sequence
<220> FEATURE:
<223> OTHER INFORMATION: ttGGBP182C.9 (affinity-tuning mutant, 182C background (Table 6) with signal peptide replaced with M and GGSHHHHHH at C-terminus)

<400> SEQUENCE: 103

```
Met Lys Gln Leu Asn Ile Gly Val Ala Ile Tyr Lys Phe Asp Asn Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45
```

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Arg Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Gln Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His

<210> SEQ ID NO 104
<211> LENGTH: 9
<212> TYPE: PRT
<213> ORGANISM: Artificial Sequence
<220> FEATURE:
<223> OTHER INFORMATION: GGSHHHHHH Tag Sequence

<400> SEQUENCE: 104

Gly Gly Ser His His His His His His
1               5

<210> SEQ ID NO 105
<211> LENGTH: 1328
<212> TYPE: DNA
<213> ORGANISM: Artificial Sequence
<220> FEATURE:
<223> OTHER INFORMATION: csaGGBP Exemplary Expression Construct (Table
      2)

<400> SEQUENCE: 105
cggtcacgct tgggactgcc ataggctggc ccggtgatgc cggccacgat gcgtccggcg      60

```
tagaggatcg agatctcgat cccgcgaaat taatacgact cactataggg agaccacaac    120

ggtttccctc tagaaataat tttgtttaac tttaagaagg agatatacca tggaaacagg    180

tccaaaaatt ggtgtaagta tatacaggta cgacgacacc ttcatgaagc tgtatcgcca    240

ggaactgaag cagtacctgg aagaaaccta ccatgcggaa gtgatcatgc gcaatgctgg    300

tggtgaccag aaagagcagg acaaacaggt gaaccagttc atctcagacg gatgtgacgg    360

gatcatagtg aatccggtgg aaattccggc agctcaggag cttgcggatg cgtgcagtcg    420

tgcgggaatc cccccttgtgt tcataaaccg tgaacccaag gaagaagaac agaaacgttg    480

gcgcgaaaag cagatggcag tttcgtgtgt aggcaccgat agccgtcagg cgggtaccta    540

tcagggcgaa atcatcctgg aaaccctgaa caaaggcgac ttcaacggtg atggtgtcgt    600

gtcctacgtg atgctcatgg gtgagaaggg caatgaggac tcgcaatacc ggacggaata    660

cagcatcaaa gcgctggaag aaggcggcat gaaaaccgaa gagctgtttt cgggcaacgg    720

caactggaac aaagacgaag gcaagaaact ggcgaaacag gcgcttgcct cttggggtaa    780

ccgcatagag gtgttcttct gcaacaacga ttcgatggcg aatggtgcgt tggaagcagt    840

ggaggaggca ggtaggatcc caggcaaaga catctacctg gttggtgtgg atgcgttgca    900

ggatacggtg acctacatca aagaaggccg tatgaccgga acagtcctga acgaccacga    960

aggtcagagc cagatggcag ctgatacgct gaagaaaatg atcgatggag agtcagtgga   1020

gactcggtat caggtggact acatcaaagt gactgccatc tctacgtttc aaactttaaa   1080

aggtgaagat ggaggaagcc atcatcatca tcatcattaa taatgaaagg gcgatatcca   1140

gcacactggc ggccgttact agtggatccg gctgctaaca aagcccgaaa ggaagctgag   1200

ttggctgctg ccaccgctga gcaataacta gcataacccc ttggggcctc taaacgggtc   1260

ttgaggggtt ttttgctgaa aggaggaact atatccggag cgactcccac ggcacgttgg   1320

caagctcg                                                            1328
```

<210> SEQ ID NO 106
<211> LENGTH: 1349
<212> TYPE: DNA
<213> ORGANISM: Artificial Sequence
<220> FEATURE:
<223> OTHER INFORMATION: bprGGBP Exemplary Expression Construct (Table 2)

<400> SEQUENCE: 106

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggatgcaaa    180

agttggtgta tgtatatatc aaaaatcgga caacttcatg tcgctcttct ccagcgaact    240

ggtgaagtac ctggtgagtc gtgggttcag caaggacaac atcatcctgt acgactccaa    300

caacgacgag aacgtgcagt tgtcgcaggt ggaagagctc attgcgtctg ggatcaatgc    360

gctcatcatc aacccagtga actcgagtgt tgctcactcg atcacggaca tggcatctgc    420

ctcgaacatc ccgttagtct acatcaaccg tgaaccgtct ggtgacgaag agaaccgttg    480

ggagatgtat cagctgaacg tgtgctatgt cggctgtgat gcacgccaat ctggcatcta    540

ccagggggaa atcctcctgt ctctgggcaa aaacaagctg gatcacaacg gagatggcaa    600

gatccagtac ttcatgatcg aaggtgcacc ggagaacatc gatgcaggct atcgtacgct    660

gtactccgtt tctgctctgc agaacagcga aatggagatg gattgcctgc tggatgaagt    720
```

-continued gggcaactgg gatgaaacca ctgccagtct gctggtctcc aagggcatcc agaatgggct 780
caaaccggag gtcatcatct gcaacaacga cgcgatggca ctgggtgcca tcaaagcggc 840
ggaaaaatcg ggtctggttc cgggtgaaga cgtctacatc gtgggtgttg acgccttgcc 900
tgaagcgatc gaaatgatca aagcagggaa gctcgcaggt accgtgtaca acgactacgt 960
gctgcagtcc cacaaaagcg cagatgcggt catcaactac ctgaaaggga tcgacaacga 1020
gcactacatc ggttgcgatt acgtgaaagt ggatatcgac aacgcggaaa gcattgcggg 1080
gttgacaaat acagatgaag aagatattga tggaggaagc catcatcatc atcatcatta 1140
gtaataaaag ggcgatatcc agcacactgg cggccgttac tagtggatcc ggctgctaac 1200
aaagcccgaa aggaagctga gttggctgct gccaccgctg agcaataact agcataaccc 1260
cttggggcct ctaaacgggt cttgaggggt tttttgctga aaggaggaac tatatccgga 1320
gcgactccca cggcacgttg gcaagctcg 1349

<210> SEQ ID NO 107
<211> LENGTH: 1325
<212> TYPE: DNA
<213> ORGANISM: Artificial Sequence
<220> FEATURE:
<223> OTHER INFORMATION: rinGGBP_A Exemplary Expression Construct (Table 2)

<400> SEQUENCE: 107
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaagttgg 180
tgtatgtatt taccaattta gtgacaactt catgacgctc ttccgtaccg aactggaaaa 240
ctacctggtg gaaaaaggct ttagcaagga caacatcacc atcgttgatg gcgctaacga 300
tcaggctacg cagactggcc agatcgacaa cttcatcacc gaaggggtgg atgtcctcat 360
catcaatccg gtcaacagca gcagtgcagc gacgattacc gataaagtgg tggcagcagg 420
cattccgctg gtctacatca accgagaacc ggatgaagaa gagcagaaac gctggagtga 480
caacaactgg gacgtgacgt acgtgggttg cgatgcgcgt cagtctggga cattccaggg 540
tgagatgatc agcgatcttg gcctggatac ggtcgatctg aacggaaacg ggaaaatcga 600
ctacgtcatg gtggaaggtg atccagagaa cgtggatgcc cagtatcgca cggaatactc 660
cgtgaaagca ctggaagatg cgggtctcga agtgaactgc ttgagcgatc aggttgggaa 720
ctggcagcag gatcaggcac agcagattgt ggcgaatgct ctcggtcagt atggcaacga 780
cgtagaggtt gtgttctgca acaacgacgc tatggcgtta ggtgccttac aggcgattca 840
gagcgcaggt cgtaccgttg gtactgacat ctacctggtt ggtgtggatg cgttgagcga 900
agcactggag gatgtgctgg ctggtaccat gaccggaact gtgttcaacg accacttcag 960
tcagtcccat agtgcggcag atgcggctat caactacatc acaggagctg gaaacgacca 1020
ctacatcggc tgcgattacg tgaaagtgac caaagacaac gcacaagatg tgttagatat 1080
ggttaaagga ggaagccatc atcatcatca tcattaatga taaaagggcg atatccagca 1140
cactggcggc cgttactagt ggatccggct gctaacaaag cccgaaagga agctgagttg 1200
gctgctgcca ccgctgagca ataactagca taaccccttg gggcctctaa acgggtcttg 1260
aggggttttt tgctgaaagg aggaactata tccggagcga ctcccacggc acgttggcaa 1320
gctcg 1325

<210> SEQ ID NO 108
<211> LENGTH: 1307
<212> TYPE: DNA
<213> ORGANISM: Artificial Sequence
<220> FEATURE:
<223> OTHER INFORMATION: fprGGBP Exemplary Expression Construct (Table 2)

<400> SEQUENCE: 108
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgtctgctaa 180
tattggagtt tgtatttatc aatttgccga caacttcatg accctctatc gtgctgacct 240
ggaaggctac ctgaaggaca tgggctattc cgtcaccatc atggacggga aaaacgacca 300
gaacacccaa accgagcaga tcaacacctt cctgcagcaa ggcgttgacg tgctggtcat 360
caacccagtt cagaccacta gtgcacagac catcgtagac accgtttctc cgtctggtac 420
cccaatcgtg ttcatcaacc gtgaacctga ggaaagcgtc ctggatagct acaagggcaa 480
gtgctgctac gtgggagctg atgctcggca gagtggtacg taccagggtg agctgatcct 540
ggcaaccgat acgcaaggcg acatcaacgg tgatggcaag atcacctaca tcatgtgcaa 600
aggcgatccg gagaacatcg acgcacagta ccgtaccgag tacagcatca aggcactgac 660
cgatgcaggc aaggaagtgg agtgcctgta cgagtacctg gacaactggg atcagaccac 720
tgcacagcaa gacgtggcta acgcactgtc ccagtatggc gagaagatcg aagtcgtctt 780
ctgcaacaac gacgctatgg cactgggcgc attgcagagc atccagcaag ctggtcgtac 840
cgttggcaaa gacgtctacc tggttggagt cgatgcgctg gtagaggctg tccagaacgt 900
tgtcgacggt aacatgaccg gaaccgtgct caacgacgac gttggtcagg caacgaaagc 960
tgcagaagcg accaagctgt tcgtggaggg caaagacgtg gagaagtact actgggtgga 1020
ctacgtcaaa gtcaccaagg ataatgcaag tcaatatctg aaagaagatg gaggaagcca 1080
tcatcatcat catcattagt aataaaaggg cgatatccag cacactggcg gccgttacta 1140
gtggatccgg ctgctaacaa agcccgaaag gaagctgagt tggctgctgc caccgctgag 1200
caataactag cataacccct tggggcctct aaacgggtct tgaggggttt tttgctgaaa 1260
ggaggaacta tatccggagc gactcccacg gcacgttggc aagctcg 1307

<210> SEQ ID NO 109
<211> LENGTH: 1322
<212> TYPE: DNA
<213> ORGANISM: Artificial Sequence
<220> FEATURE:
<223> OTHER INFORMATION: cljGGBP Exemplary Expression Construct (Table 2)

<400> SEQUENCE: 109
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgccagttat 180
tggatttgtt gcttatgaat ttaacaacac gtggatcacc gaactgaaga acgagatcta 240
caaggtgtct agcggcaaag cgcgtgtgga catctggaac ggcgataaca tccagaccgt 300
tgagaacgac aagatcaacc tcttcatcaa ccgcaaagtg aacgtgctcg acatcaaccc 360
ggttgatgtc aacgcagctg gacagatcat cgaaaagtgc aaaaaagcga acattccgac 420

```
cgtgttcgtg aatcgccaac cgaaaaaaga ggatatggag aaatggaaca aagtgtacta    480

cgttggtgcc aaagccgaac agtcgggtac catccaaggg cagatgctcg tgaactactt    540

caaaggccat ccgactcagg atggcactat ccgctacatc atgctcaagg gtgaaacgcg    600

aaaccaggat gcggagaaac gcacccagta cagcatcaaa gcgctgaaag acagcggttt    660

caaggtgcag aaggttgcgg aagacaccgc aatgtgggat cgtacgaagg cacaggagaa    720

gatgacttcg ttcatatcct cctacggacc caacttcgac tgtgtgatag cgaacaacga    780

cgacatggcc ttaggagccg ttgatgccct caaagcggca ggctacttca acggcggcaa    840

atatgtgccg gtggttggtg tggatgccac tgctccggct gtcaaagcag tggaagacgg    900

aacgttgttc ggaactgtgc tgaacgatgc tgcgaaacag ggtgatgcgg cctttgatct    960

gtcgtacatc ctttccaaag ggaagatccc ggatgaaagc aacttcaagt acaaggtgac   1020

ggatggcaag tacatttgga tcgactacaa gatgatcact aaagaaaatg ttcaagatgc   1080

aaaaggagga agccatcatc atcatcatca ttagtgataa aagggcgata tccagcacac   1140

tggcggccgt tactagtgga tccggctgct aacaaagccc gaaaggaagc tgagttggct   1200

gctgccaccg ctgagcaata actagcataa ccccttgggg cctctaaacg ggtcttgagg   1260

ggtttttgc tgaaaggagg aactatatcc ggagcgactc ccacggcacg ttggcaagct    1320

cg                                                                  1322
```

<210> SEQ ID NO 110
<211> LENGTH: 1325
<212> TYPE: DNA
<213> ORGANISM: Artificial Sequence
<220> FEATURE:
<223> OTHER INFORMATION: cauGGBP Exemplary Expression Construct (Table 2)

<400> SEQUENCE: 110

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggaaccagt    180

aattggtttt gttgcttatg agttcaacaa cacgtggatt accgaactga agaacgagat    240

gtacaaggtg tctaacggca aagcgcgtgt ggacatctgg aacggcaaca acatccagac    300

ggtcgagaac gacaagatct ccctgttcat caaccgcaaa gtcgacgttc tggacatcaa    360

cccggttgac gtgaacgcag ctggacagat catcgagaaa tgcaaaaaag cgaacattcc    420

gacggtgttc gtgaaccgtc aaccgaaaaa ggaagatgtg gaaaagtgga acaaagtcta    480

ctacgttggt gcgaaagccg aacagtctgg caccatacag ggacagatgc tggtgaacta    540

cttcaaaggg catccgaccc aggatggaac catccgctac atcatgctca aaggggaaat    600

gcgcaaccag gatgcggaga aacgcaccca gtacagcatc aaagccctgg aagattctgg    660

gttcaaggtc cagaaggtgg cagaagacac cgctatgtgg gatcgtacca aggctcagga    720

gaagatgact tcgttcatct cctcatacgg accgaacttc gactgtgtga tcgccaacaa    780

cgacgacatg gccttaggag ctgttgatgc cctgaaagct gcaggctact tcaacggcgg    840

caaatatgtg ccggtggttg gtgtggatgc tactgctccg gcagtgaaag ctgtcgagga    900

tgggacactg ttcggaactg tcctgaacga tgcagcgaaa cagggtgatg cggcctttga    960

tctgtcgtac atcctttcca aggggaagat tccggatgaa agcaacttca agtacaagat   1020

cacggatggc aagtacattt ggatcgacta caagatgatt actaaagaaa atgttcaaga   1080
```

tgctaaagga ggaagccatc atcatcatca tcattagtaa taaaagggcg atatccagca 1140
cactggcggc cgttactagt ggatccggct gctaacaaag cccgaaagga agctgagttg 1200
gctgctgcca ccgctgagca ataactagca taaccccttg gggcctctaa acgggtcttg 1260
aggggttttt tgctgaaagg aggaactata tccggagcga ctcccacggc acgttggcaa 1320
gctcg 1325

<210> SEQ ID NO 111
<211> LENGTH: 1361
<212> TYPE: DNA
<213> ORGANISM: Artificial Sequence
<220> FEATURE:
<223> OTHER INFORMATION: rinGGBP_B Exemplary Expression Construct (Table 2)

<400> SEQUENCE: 111
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaatcaat 180
aaaaattggt ataagtgttt atgatcagta tgacaccttt gtgagcgaaa tgatgaaaga 240
cttcaacgat tatgcgacca agaaagaaga agagactggt gttgccatca acatcgacac 300
atacaacgct agtgcaagcc agtctacgca gaacagtcag gtcgagaaca tgatcacgga 360
aggctgcgat gtgatctgtg tcaacctggt tgacaggacg gatccaactg cgatcatcga 420
tcttgcggag aaaaacaaca tccccgtgat ttttttcaac cgtgaactgg tggaggaaga 480
cctggaacgt tggacaaggc tgtactacgt tggtgcacag gcgttcgaaa gcggcatcat 540
gcagggtgaa ctggctgcag aagcctttct gaccgatcag agcctggaca agaacggaga 600
tgggatcttc cagtacgtgg tgcttgaagg tgaggctgga caccaggatg ccatcgtgcg 660
tacggagtac tcggttagca ccatgatcga tagcggagtg gaagtggaga aactgggcta 720
cgcaatcgcc aactggaatc gtgcacaggc tcagacgaaa atggcgcagc tgatgtccca 780
gtttggtgac agcatagagc tggtcatcgc caacaacgac gacatggctc taggagccat 840
agatgcgctc aaggcgtctg gtctgaccaa ggacgaatgg ccggcagtca ttgggatcga 900
tggaacggat gtgggcttag aggcggtcaa gaacaaagag atgatcggta ccgtgtacaa 960
cgataaggaa ggccaagcgg atgcgatgct gaacctggcg tacgaactga gtaccggtag 1020
cgatctgtcg gatctgaacc tgatcgatgg caaatacatc cgtctgcctt atgcgcgagt 1080
gacgtgtgat gatgtggata gttatatgga aggtgatacc gaaggaggaa gccatcatca 1140
tcatcatcat taataatgaa agggcgatat ccagcacact ggcggccgtt actagtggat 1200
ccggctgcta acaaagcccg aaaggaagct gagttggctg ctgccaccgc tgagcaataa 1260
ctagcataac cccttggggc ctctaaacgg gtcttgaggg gttttttgct gaaaggagga 1320
actatatccg gagcgactcc cacggcacgt tggcaagctc g 1361

<210> SEQ ID NO 112
<211> LENGTH: 1388
<212> TYPE: DNA
<213> ORGANISM: Artificial Sequence
<220> FEATURE:
<223> OTHER INFORMATION: erhGGBP Exemplary Expression Construct (Table 2)

<400> SEQUENCE: 112

-continued

```
cggtcacgct tgggactgcc ataggctggc ccggtgatgc cggccacgat gcgtccggcg      60

tagaggatcg agatctcgat cccgcgaaat taatacgact cactataggg agaccacaac     120

ggtttccctc tagaaataat tttgtttaac tttaagaagg agatatacca tgaaaactta     180

taatattggt gttgcaattt ataagttcga tgacaacttc atgacgctgt atcgtgaaga     240

actggcgagc tacttcaaag aagtgggtga gaaagacggc aacacgtaca aactggacat     300

ccaggatggc aagcaggacc aagctaacca gaccgaacag atcaacaact ttatcgcaca     360

gggtaaagac ctgatcatcg cgaacatggt cgatccgacc gcagcgggta gcatcatcaa     420

cagcgcgaaa gcgaaagaaa tcccggtggt cttcatcaac cgagaaccgg aaacccagga     480

actggaaatc tggccgggca aaaccaccta cgttggtgcg gatgcgaccc agtcaggcac     540

cattcagggc tacatgatcg cgaacttgga gaacaaaggc gacatcgacg gtgatgggag     600

tgtcagctac atcacgctga tgggagatcc tgcgaacgtg gatgcgaaac agcgtaccga     660

atacagcgtg aaaggcctgg aagagaaagg cgtgaaaacc aacgcgcttg cgcagccgta     720

ccaagcgaac tgggataccg cgaaaggcca ggaattcacc gcaaacgcgc tggaacagtt     780

tggcaacaaa ctggaagtgg tgttcgcgaa caacgatggc atggcggttg gtgcggtgac     840

cgcgattgaa gctgcgggac gcaaagtcgg agaggacatc ttcgtggttg gtgtcgatgc     900

cattccggat gccatcgagc tcctgaaagg cggtaaactg accggtactg tcctcaacga     960

ccacttcaac cagagccata ccgcggtgga tgtggcactg gaactgctgc agggcaaaga    1020

tgtgagcgcc tactactggc atgactacgt tggcgtgacc aaaccggaag aagcggaact    1080

gaaacgtgca gaagcacgca aagagaccgt ggaagaagcg gttaaacgtt atgcagaacg    1140

tgatgctcaa ggaggaagcc atcatcatca tcatcattaa taatgaaagg gcgatatcca    1200

gcacactggc ggccgttact agtggatccg gctgctaaca aagcccgaaa ggaagctgag    1260

ttggctgctg ccaccgctga gcaataacta gcataacccc ttggggcctc taaacgggtc    1320

ttgaggggtt ttttgctgaa aggaggaact atatccggag cgactcccac ggcacgttgg    1380

caagctcg                                                             1388
```

```
<210> SEQ ID NO 113
<211> LENGTH: 1355
<212> TYPE: DNA
<213> ORGANISM: Artificial Sequence
<220> FEATURE:
<223> OTHER INFORMATION: ereGGBP Exemplary Expression Construct (Table
      2)

<400> SEQUENCE: 113
```

```
cggtcacgct tgggactgcc ataggctggc ccggtgatgc cggccacgat gcgtccggcg      60

tagaggatcg agatctcgat cccgcgaaat taatacgact cactataggg agaccacaac     120

ggtttccctc tagaaataat tttgtttaac tttaagaagg agatatacca tgaaacagat     180

ttatattggt gtaacttgtt atgatcagaa ggataccttc attggagagc tgatcgagac     240

cttcaagaag gaatgcgcgt ctctggatac cgacaagtac gacatcagca tgaccatcat     300

ggatgctgca ggtagccagc gtgcacagga tgatcaggtg caggagatga tcgaagacgg     360

ttgcaacgta ctgtgcatca acctggcaga tcgtaccgac ttgtcgcaca tcatcaacgc     420

ggcgatggag aaggatatcc cgatcatctt cttcaaccga gaaccggtgg atgaggatct     480

caaccgttgg gacaagctgt actacgtagg agcaaaggcg aaacagagcg gtcagatgca     540

aggagagctc attgcggact acatcaaaaa caacccgggt gtggacaaga acggtgatgg     600
```

-continued

```
gaggatccag tacgtcatcc tggaagggga aatgggtcat caggatgcca tcgtacggac     660

tgaaagcgtg accgaatcga tgaagaacaa cggtctgcag atcgagaagc tgagctgcca     720

gatcgcgaac tggaatcgag ctcaagctca gaaccggatg acgcagctga ttggccagta     780

caagaactcg atcgagctgg tgatcgccaa caacgatgcc atggctctag gtgcgatcga     840

tgcctacgag aaactcggtg taacggaaag caacgttcca gcgtttttcg gtgtggatgg     900

tacagacgat ggactggaag cagtgcagca gagcaagctt gcggcaacgg tgtacaacga     960

caaggaaggt caggcgatgg cgatggctca gttggcctat ctcgctgcaa ctggtggaag    1020

catgaagaac atcaaattcg aagacaaaaa gtatgtgtat ctgccgtatg agaaggtgac    1080

accggataac gttaatgaat ttgttaaaga tgaacaagga ggaagccatc atcatcatca    1140

tcattgataa taaaagggcg atatccagca cactggcggc cgttactagt ggatccggct    1200

gctaacaaag cccgaaagga agctgagttg gctgctgcca ccgctgagca ataactagca    1260

taaccccttg gggcctctaa acgggtcttg aggggttttt tgctgaaagg aggaactata    1320

tccggagcga ctcccacggc acgttggcaa gctcg                               1355
```

<210> SEQ ID NO 114
<211> LENGTH: 1343
<212> TYPE: DNA
<213> ORGANISM: Artificial Sequence
<220> FEATURE:
<223> OTHER INFORMATION: ttGGBP  Exemplary Expression Construct (Table
      2)

<400> SEQUENCE: 114

```
cggtcacgct tgggactgcc ataggctggc ccggtgatgc cggccacgat gcgtccggcg      60

tagaggatcg agatctcgat cccgcgaaat taatacgact cactataggg agaccacaac     120

ggtttccctc tagaaataat tttgtttaac tttaagaagg agatatacca tgaaacaatt     180

aaatattggt gttgcgattt ataaattcga tgacaccttc atgaccggtg ttcggaatgc     240

gatgactgcg gaagcgcaag gcaaggcgaa gctcaacatg gttgacagcc agaacagcca     300

accaacccag aacgatcagg ttgacctgtt catcacgaag aagatgaacg cacttgcgat     360

caacccggtg gatcgcactg cagcaggcac catcatcgac aaagccaaac aggccaacat     420

tccggtggtc ttcttcaacc gtgaaccgct gccggaagac atgaagaaat gggataaagt     480

gtactatgtg ggtgcgaaag cggaacagag tggcattttg cagggtcaga tcatggctga     540

ctactggaaa gcccatcctg aagcggacaa gaaccatgat ggcgtgatgc agtacgtcat     600

gctgatgggt cagccaggtc atcaggatgc gatactgcgt acacagtaca gcatccaaac     660

ggtgaaagat gcaggcatca aagtgcagga actggccaaa gactacgcaa actgggatcg     720

cgttaccgcg catgacaaaa tggcagcgtg gttgtcgagc tttggcgaca agatcgaagc     780

cgtcttctgc aacaacgacg acatggcgtt gggtgccatc gaagcgctga agtctgcagg     840

ctacttcacc ggcaacaaat acatcccggt tgtgggcgtg gatgcgaccg caccgggcat     900

tcaggcgatc aaggatggta ccctgttggg aaccgtgttg aacgatgcga agaaccaggc     960

gaaagccacc ttcaacatcg cctacgaact ggctcagggc attaccccga cgaaggacaa    1020

catagggtac gacatcacag acgggaagta cgtgtggatt ccgtacaaaa agatcacgaa    1080

agacaatata tcagatgctg aacaaggagg aagccatcat catcatcatc attagtaata    1140

aaagggcgat atccagcaca ctggcggccg ttactagtgg atccggctgc taacaaagcc    1200

cgaaaggaag ctgagttggc tgctgccacc gctgagcaat aactagcata accccttggg    1260
```

```
gcctctaaac gggtcttgag gggttttttg ctgaaaggag gaactatatc cggagcgact   1320

cccacggcac gttggcaagc tcg                                            1343


<210> SEQ ID NO 115
<211> LENGTH: 1355
<212> TYPE: DNA
<213> ORGANISM: Artificial Sequence
<220> FEATURE:
<223> OTHER INFORMATION: cobGGBP  Exemplary Expression Construct (Table
      2)

<400> SEQUENCE: 115

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacctta    180

tataggtgtt gctatatata agtttgacga caccttcatg accggtgtgc gtaacgcgat    240

tgcgaaagaa ggcgaaggca aagcgaaact ggatttcgtc gattgccaga acagccagtc    300

gacccagaac gacaagatcg acctgttcat caccaagaag gtcgatgcac tggcgatcaa    360

cccagttgat cgcacagcag caggtgtgct catcgacaag gcgaaacagg cgaacatccc    420

tgttgtcttc ttcaaccgtg aaccgcttcc ggaagacatg aagaaatggg ataaggtgta    480

ctacgtgggt gcgaaagcgg aacagagtgg cactctgcaa ggcgaaatca tggcggagta    540

ctggaaaagc catccggaag cggacaaaaa ccatgatggc attatgcagt atgtcatgat    600

cactggtgaa cctggacacc aggatgccat actccggact gagtactcca taaaggcggt    660

ggaagcggct ggtatccgcg tgaaatgcct ggcgcaggat accgcgatgt gggatcgagt    720

gaaaggccag gaaaagatgc aggcattcct tgcgagcttt ggcgacaaaa tcgaagccgt    780

gttctgcaac aacgacgaca tggcactggg tgcgattgaa gcgctgaaag cggctggcta    840

cttcaaggat ggcaagtatg tgccggttgt gggcgtggat gcgaccaccc cgggtctgca    900

ggcgctggaa gaaggtaccc tgcttggtac cgtgttgaac gatgcgaaag cgcaaggtaa    960

ggctactttc aacctcgctt acgtgctggc gaaaggcgaa aaaccgacca aagaaaacgt   1020

gggtttcgaa atcaccgatg gcaaatacat ctgggttccg taccagaaag tgaccaaaga   1080

caacctggaa gaaatgaaaa aatatgtgaa tgaacaggga ggaagccatc atcatcatca   1140

tcattaataa tgaaagggcg atatccagca cactggcggc cgttactagt ggatccggct   1200

gctaacaaag cccgaaagga agctgagttg gctgctgcca ccgctgagca ataactagca   1260

taaccccttg gggcctctaa acgggtcttg aggggttttt tgctgaaagg aggaactata   1320

tccggagcga ctcccacggc acgttggcaa gctcg                              1355


<210> SEQ ID NO 116
<211> LENGTH: 1355
<212> TYPE: DNA
<213> ORGANISM: Artificial Sequence
<220> FEATURE:
<223> OTHER INFORMATION: chyGGBP Exemplary Expression Construct (Table
      2)

<400> SEQUENCE: 116

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacctta    180

tattggtgtt gcaatatata agtttgacga cacattcatg accggtgttc gcaacgcgat    240
```

```
tgcgaaagaa ggcgaaggca aagcgaaact ggactttgtc gattgccaga acagccagtc    300
gacccagaac gacaagatcg acctcttcat aaccaagaaa gtggacgctt tggcgatcaa    360
tccggttgat cgtaccgcgg caggtgtgtt gatcgacaag gcgaaacagg cgaacatccc    420
agtcgtcttc ttcaaccgag agccgttacc ggaagatatg aagaaatggg ataaggtgta    480
ctacgttggt gccaaagctg aacagtcagg cactctgcag gggaaatca tggcagagta     540
ctggaaaagc catccggaag ccgacaagaa ccacaacggc atcatggaat acgtgatgat    600
caccggtgaa ccgggtcatc aggatgcgat cttgcgtacc gagtactcga tcaaagcggt    660
tgaggctgcg ggtatcaaga ccaaagcgct tgctcaggat acagccatgt gggatagggt    720
gaaaggtcag gagaagatgc aggcgttcct tgcgagcttt ggcgatcgga ttgaggctgt    780
attctgcaac aacgacgata tggcactggg tgccattgaa gcgctcaaag cagcagggta    840
cttcaagaac ggcaaataca tccctgttgt gggtgtggat gcgaccactc cgggtctgca    900
ggcgctggaa gaaggtaccc tgctgggtac cgtcttgaac gacgccaaag ctcagggtaa    960
ggctacgttc aacttggcgt atgtgctggc gaaaggcgaa aaaccgacca aagagaatgt   1020
cggcttcgac atcacggatg gcaagtacat ttgggtgccg taccagaaag tgaccaagga   1080
caacttggaa gagatgaaaa aatacgtaaa tgaacaagga ggaagccatc atcatcatca   1140
tcattaataa tgaaagggcg atatccagca cactggcggc cgttactagt ggatccggct   1200
gctaacaaag cccgaaagga agctgagttg gctgctgcca ccgctgagca ataactagca   1260
taaccccttg gggcctctaa acgggtcttg aggggttttt tgctgaaagg aggaactata   1320
tccggagcga ctcccacggc acgttggcaa gctcg                              1355
```

<210> SEQ ID NO 117
<211> LENGTH: 1328
<212> TYPE: DNA
<213> ORGANISM: Artificial Sequence
<220> FEATURE:
<223> OTHER INFORMATION: pspGGBP23 Exemplary Expression Construct (Table 2)

<400> SEQUENCE: 117

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tggttggtgt    180
agcaatttat aagtttgatg ataccttcat gacaggcgtt cgaaacgcga tgagcgatgc    240
agcgaacggt gtagcgaaac tggacatcgt ggattcgcaa aacgcccaac cgacccagaa    300
cgagaaaatc gacctgttca tcagcaaaaa gtacagcagc atgatcatca accccgttga    360
tcgtaccgca gctggcgtca tcatcgacaa agccaaaacc gccaataccc cggtggtttt    420
cctgaatcgc gaaccgattg cggaagacat gaacaaatgg gacaaggtgt actatgtcgg    480
tgccaaagcg gaggaaagcg gtaccatcag cggtcagctg atcgtggact actggaaagc    540
gaacccgaaa gccgacaaga acggagatgg caaactgcag tacgtgctgt tgcagggtga    600
accgggtcat caggatgccg aactgcgtac caagttcagc gttcaggcta tccaggatgc    660
aggcatcgag gtggaagcgt tagcggtgga taccgctatg tgggatcgtg tgaaagggca    720
ggaaaagatg cagaccttcc ttgcgtctca tggcgacaaa atcgaagcgg ttctggcgaa    780
caacgacgat atggcgttag gagcgattga ggccttgaaa gctgcaggct acttcagtgg    840
cgataagtac atgccggtgg ttggtgtgga tgcaaccgct ccagccgttc aggcgctgga    900
```

agatggcaca ttgctcggaa ccgtgctcaa cgacgcgaaa agccagggca aagcgagtgt 960
tgcgatagca gcggcgcttt cgaagggtga agcgccgaac aaagagaaca ccggtttcga 1020
catcaccgat gggaagtacg tgtggattgc gtacaagaag atcaccaaag ataatattgc 1080
agatgctaaa ggcggcagcc atcatcatca tcatcattaa tgataaaagg gcgatatcca 1140
gcacactggc ggccgttact agtggatccg gctgctaaca aagcccgaaa ggaagctgag 1200
ttggctgctg ccaccgctga gcaataacta gcataacccc ttggggcctc taaacgggtc 1260
ttgaggggtt ttttgctgaa aggaggaact atatccggag cgactcccac ggcacgttgg 1320
caagctcg 1328

<210> SEQ ID NO 118
<211> LENGTH: 1340
<212> TYPE: DNA
<213> ORGANISM: Artificial Sequence
<220> FEATURE:
<223> OTHER INFORMATION: ttGGBP11C Exemplary Cysteine Scan Mutant Expression Construct (Table 3)

<400> SEQUENCE: 118
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt gcaaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgggatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 119
<211> LENGTH: 1340
<212> TYPE: DNA
<213> ORGANISM: Artificial Sequence
<220> FEATURE:
<223> OTHER INFORMATION: ttGGBP16C Exemplary Cysteine Scan Mutant
Expression Construct (Table 3)

<400> SEQUENCE: 119

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgactgcttc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc cagccggggc accaagacgc aatcttacgt acgcaatact cgatccaaac    660
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccaccg ccccagggat    900
ccaggcgatc aaagacggta cattactggg gacagtcctg aacgacgcca aaaaccaggc    960
gaaagccact ttcaacattg catacgaact tgcacaaggg atcacgccaa ccaaagataa   1020
catcggttac gacatcaccg acggcaaata cgtttggatt ccatataaaa aaattacaaa   1080
agacaacatt tcggatgcag agcaaggtgg ttcacatcat catcatcatc attaatgaaa   1140
gggcgatatc cagcacactg gcggccgtta ctagtggatc cggctgctaa caaagcccga   1200
aaggaagctg agttggctgc tgccaccgct gagcaataac tagcataacc ccttggggcc   1260
tctaaacggg tcttgagggg ttttttgctg aaaggaggaa ctatatccgg agcgactccc   1320
acggcacgtt ggcaagctcg                                               1340
```

<210> SEQ ID NO 120
<211> LENGTH: 1340
<212> TYPE: DNA
<213> ORGANISM: Artificial Sequence
<220> FEATURE:
<223> OTHER INFORMATION: ttGGBP17C Exemplary Cysteine Scan Mutant
Expression Construct (Table 3)

<400> SEQUENCE: 120

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgacacatgc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
```

```
atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                                1340
```

```
<210> SEQ ID NO 121
<211> LENGTH: 1340
<212> TYPE: DNA
<213> ORGANISM: Artificial Sequence
<220> FEATURE:
<223> OTHER INFORMATION: ttGGBP42C Exemplary Cysteine Scan Mutant
      Expression Construct (Table 3)

<400> SEQUENCE: 121
```

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacattc atgactgggg tccggaatgc    240

tatgaccgca gaagcccaag gcaaggccaa gttaaacatg gtagacagtc agtgctcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140
```

-continued

```
gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                                1340
```

```
<210> SEQ ID NO 122
<211> LENGTH: 1340
<212> TYPE: DNA
<213> ORGANISM: Artificial Sequence
<220> FEATURE:
<223> OTHER INFORMATION: ttGGBP67C Exemplary Cysteine Scan Mutant
      Expression Construct (Table 3)

<400> SEQUENCE: 122

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacattc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caacccttgc gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                                1340
```

```
<210> SEQ ID NO 123
<211> LENGTH: 1340
<212> TYPE: DNA
<213> ORGANISM: Artificial Sequence
<220> FEATURE:
<223> OTHER INFORMATION: ttGGBP91C Exemplary Cysteine Scan Mutant
      Expression Construct (Table 3)

<400> SEQUENCE: 123

cggtcacgct tgggactgcc ataggctggc ccggtgatgc cggccacgat gcgtccggcg     60

tagaggatcg agatctcgat cccgcgaaat taatacgact cactataggg agaccacaac    120
```

```
ggtttccctc tagaaataat tttgtttaac tttaagaagg agatatacca tgaaacaact    180

caatatcggt gtagctattt ataaattcga cgacacattc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaact gcgaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 124
<211> LENGTH: 1340
<212> TYPE: DNA
<213> ORGANISM: Artificial Sequence
<220> FEATURE:
<223> OTHER INFORMATION: ttGGBP92C Exemplary Cysteine Scan Mutant Expression Construct (Table 3)

<400> SEQUENCE: 124

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacattc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc ggtgcccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780
```

```
cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340


<210> SEQ ID NO 125
<211> LENGTH: 1340
<212> TYPE: DNA
<213> ORGANISM: Artificial Sequence
<220> FEATURE:
<223> OTHER INFORMATION: ttGGBP111C Exemplary Cysteine Scan Mutant
      Expression Construct (Table 3)

<400> SEQUENCE: 125

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacattc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagt gcgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 126
<211> LENGTH: 1340
<212> TYPE: DNA
<213> ORGANISM: Artificial Sequence
<220> FEATURE:
<223> OTHER INFORMATION: ttGGBP148C Exemplary Cysteine Scan Mutant
Expression Construct (Table 3)

<400> SEQUENCE: 126

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgacacattc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc tgcccggggc accaagacgc aatcttacgt acgcaatact cgatccaaac    660
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccaccg ccccagggat    900
ccaggcgatc aaagacggta cattactggg gacagtcctg aacgacgcca aaaaccaggc    960
gaaagccact ttcaacattg catacgaact tgcacaaggg atcacgccaa ccaaagataa   1020
catcggttac gacatcaccg acggcaaata cgtttggatt ccatataaaa aaattacaaa   1080
agacaacatt tcggatgcag agcaaggtgg ttcacatcat catcatcatc attaatgaaa   1140
gggcgatatc cagcacactg gcggccgtta ctagtggatc cggctgctaa caaagcccga   1200
aaggaagctg agttggctgc tgccaccgct gagcaataac tagcataacc ccttggggcc   1260
tctaaacggg tcttgagggg ttttttgctg aaaggaggaa ctatatccgg agcgactccc   1320
acggcacgtt ggcaagctcg                                                1340
```

<210> SEQ ID NO 127
<211> LENGTH: 1340
<212> TYPE: DNA
<213> ORGANISM: Artificial Sequence
<220> FEATURE:
<223> OTHER INFORMATION: ttGGBP151C Exemplary Cysteine Scan Mutant
Expression Construct (Table 3)

<400> SEQUENCE: 127

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgacacattc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
```

-continued

```
caaccctgta gatcgcaccg cagctgggac tatcatcgac aaggcaaagc aagcaaatat     420

ccctgtagtg ttcttcaacc gggaaccttt accagaagac atgaaaaaat gggataaggt     480

atattacgta ggcgcaaagg ccgaacagag tggcattctc caaggtcaaa tcatggctga     540

ttattggaaa gctcatccgg aagcggacaa gaaccacgac ggggttatgc aatatgtcat     600

gttaatgggc cagccggggt gccaagacgc aatcttacgt acgcaatact cgatccaaac     660

cgtgaaagat gcaggcatca aggtccagga gctggctaaa gactacgcca attgggatcg     720

tgtcaccgct catgacaaaa tggctgcttg gctctcgtcc tttggcgaca agattgaagc     780

cgtttttgca aataacgacg atatggccct gggtgccatt gaagccctca agtctgctgg     840

ctatttcacg ggcaacaagt acatcccagt tgtaggcgtc gacgccaccg ccccagggat     900

ccaggcgatc aaagacggta cattactggg gacagtcctg aacgacgcca aaaaccaggc     960

gaaagccact ttcaacattg catacgaact tgcacaaggg atcacgccaa ccaaagataa    1020

catcggttac gacatcaccg acggcaaata cgtttggatt ccatataaaa aaattacaaa    1080

agacaacatt tcggatgcag agcaaggtgg ttcacatcat catcatcatc attaatgaaa    1140

gggcgatatc cagcacactg gcggccgtta ctagtggatc cggctgctaa caaagcccga    1200

aaggaagctg agttggctgc tgccaccgct gagcaataac tagcataacc ccttggggcc    1260

tctaaacggg tcttgagggg ttttttgctg aaaggaggaa ctatatccgg agcgactccc    1320

acggcacgtt ggcaagctcg                                                1340
```

<210> SEQ ID NO 128
<211> LENGTH: 1340
<212> TYPE: DNA
<213> ORGANISM: Artificial Sequence
<220> FEATURE:
<223> OTHER INFORMATION: ttGGBP152C Exemplary Cysteine Scan Mutant
      Expression Construct (Table 3)

<400> SEQUENCE: 128

```
cggtcacgct tgggactgcc ataggctggc ccggtgatgc cggccacgat gcgtccggcg      60

tagaggatcg agatctcgat cccgcgaaat taatacgact cactataggg agaccacaac     120

ggtttccctc tagaaataat tttgtttaac tttaagaagg agatatacca tgaaacaact     180

caatatcggt gtagctattt ataaattcga cgacacattc atgactgggg tccggaatgc     240

tatgaccgca gaagcccaag gcaaggccaa gttaaacatg gtagacagtc agaactcaca     300

acctacacaa aatgatcagg tcgacctctt catcacgaaa aaaatgaatg cgttggcaat     360

caaccctgta gatcgcaccg cagctgggac tatcatcgac aaggcaaagc aagcaaatat     420

ccctgtagtg ttcttcaacc gggaaccttt accagaagac atgaaaaaat gggataaggt     480

atattacgta ggcgcaaagg ccgaacagag tggcattctc caaggtcaaa tcatggctga     540

ttattggaaa gctcatccgg aagcggacaa gaaccacgac ggggttatgc aatatgtcat     600

gttaatgggc cagccggggc actgcgacgc aatcttacgt acgcaatact cgatccaaac     660

cgtgaaagat gcaggcatca aggtccagga gctggctaaa gactacgcca attgggatcg     720

tgtcaccgct catgacaaaa tggctgcttg gctctcgtcc tttggcgaca agattgaagc     780

cgtttttgca aataacgacg atatggccct gggtgccatt gaagccctca agtctgctgg     840

ctatttcacg ggcaacaagt acatcccagt tgtaggcgtc gacgccaccg ccccagggat     900

ccaggcgatc aaagacggta cattactggg gacagtcctg aacgacgcca aaaaccaggc     960

gaaagccact ttcaacattg catacgaact tgcacaaggg atcacgccaa ccaaagataa    1020
```

-continued catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 129
<211> LENGTH: 1340
<212> TYPE: DNA
<213> ORGANISM: Artificial Sequence
<220> FEATURE:
<223> OTHER INFORMATION: ttGGBP181C Exemplary Cysteine Scan Mutant
Expression Construct (Table 3)

<400> SEQUENCE: 129
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcct gctgggatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 130
<211> LENGTH: 1340
<212> TYPE: DNA
<213> ORGANISM: Artificial Sequence
<220> FEATURE:
<223> OTHER INFORMATION: ttGGBP182C Exemplary Cysteine Scan Mutant
Expression Construct (Table 3)

<400> SEQUENCE: 130

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgacacattc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc cagccggggc accaagacgc aatcttacgt acgcaatact cgatccaaac    660
cgtgaaagat gcaggcatca aggtccagga gctggctaaa gactacgcca attgcgatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccaccg ccccagggat    900
ccaggcgatc aaagacggta cattactggg gacagtcctg aacgacgcca aaaaccaggc    960
gaaagccact ttcaacattg catacgaact tgcacaaggg atcacgccaa ccaaagataa   1020
catcggttac gacatcaccg acggcaaata cgtttggatt ccatataaaa aaattacaaa   1080
agacaacatt tcggatgcag agcaaggtgg ttcacatcat catcatcatc attaatgaaa   1140
gggcgatatc cagcacactg gcggccgtta ctagtggatc cggctgctaa caaagcccga   1200
aaggaagctg agttggctgc tgccaccgct gagcaataac tagcataacc ccttggggcc   1260
tctaaacggg tcttgagggg ttttttgctg aaaggaggaa ctatatccgg agcgactccc   1320
acggcacgtt ggcaagctcg                                                1340
```

<210> SEQ ID NO 131
<211> LENGTH: 1340
<212> TYPE: DNA
<213> ORGANISM: Artificial Sequence
<220> FEATURE:
<223> OTHER INFORMATION: ttGGBP183C Exemplary Cysteine Scan Mutant
      Expression Construct (Table 3)

<400> SEQUENCE: 131

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgacacattc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc cagccggggc accaagacgc aatcttacgt acgcaatact cgatccaaac    660
```

```
cgtgaaagat gcaggcatca aggtccagga gctggctaaa gactacgcca attggtgccg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 132
<211> LENGTH: 1340
<212> TYPE: DNA
<213> ORGANISM: Artificial Sequence
<220> FEATURE:
<223> OTHER INFORMATION: ttGGBP257C Exemplary Cysteine Scan Mutant Expression Construct (Table 3)

<400> SEQUENCE: 132

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacattc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtctgc aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320
```

acggcacgtt ggcaagctcg 1340

<210> SEQ ID NO 133
<211> LENGTH: 1340
<212> TYPE: DNA
<213> ORGANISM: Artificial Sequence
<220> FEATURE:
<223> OTHER INFORMATION: ttGGBP259C Exemplary Cysteine Scan Mutant
Expression Construct (Table 3)

<400> SEQUENCE: 133
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgggatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aactgcgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 134
<211> LENGTH: 1340
<212> TYPE: DNA
<213> ORGANISM: Artificial Sequence
<220> FEATURE:
<223> OTHER INFORMATION: ttGGBP300C Exemplary Cysteine Scan Mutant
Expression Construct (Table 3)

<400> SEQUENCE: 134
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240

-continued

```
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc cagccggggc accaagacgc aatcttacgt acgcaatact cgatccaaac    660
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccaccg ccccagggat    900
ccaggcgatc aaagacggta cattactggg gacagtcctg aacgacgcca aaaaccaggc    960
gaaagccact ttcaacattg catacgaact tgcacaaggg atcacgccaa ccaaagataa   1020
catcggttac gacatcaccg acggcaaata cgtttggatt ccatattgca aaattacaaa   1080
agacaacatt tcggatgcag agcaaggtgg ttcacatcat catcatcatc attaatgaaa   1140
gggcgatatc cagcacactg gcggccgtta ctagtggatc cggctgctaa caaagcccga   1200
aaggaagctg agttggctgc tgccaccgct gagcaataac tagcataacc ccttggggcc   1260
tctaaacggg tcttgagggg ttttttgctg aaaggaggaa ctatatccgg agcgactccc   1320
acggcacgtt ggcaagctcg                                               1340
```

```
<210> SEQ ID NO 135
<211> LENGTH: 1340
<212> TYPE: DNA
<213> ORGANISM: Artificial Sequence
<220> FEATURE:
<223> OTHER INFORMATION: ttGGBP17C.1 Exemplary Affinity-Tuning mutant
      (17C Background) Expression Construct (Table 6)

<400> SEQUENCE: 135
```

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgacacatgc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaaca aagaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc gaaccggggc accaagacgc aatcttacgt acgcaatact cgatccaaac    660
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccaccg ccccagggat    900
```

-continued

```
ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 136
<211> LENGTH: 1340
<212> TYPE: DNA
<213> ORGANISM: Artificial Sequence
<220> FEATURE:
<223> OTHER INFORMATION: ttGGBP17C.2 Exemplary Affinity-Tuning mutant (17C Background) Expression Construct (Table 6)

<400> SEQUENCE: 136

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacatgc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatccgaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc acccggacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 137
<211> LENGTH: 1340
<212> TYPE: DNA
<213> ORGANISM: Artificial Sequence
<220> FEATURE:

<223> OTHER INFORMATION: ttGGBP17C.3 Exemplary Affinity-Tuning mutant (17C Background) Expression Construct (Table 6)

<400> SEQUENCE: 137
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacaactgc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgggatcg 720
tgtcaccgct catgacaaaa tggctgcttg gctctcgtcc tttggcgaca agattgaagc 780
cgtttttgca aataacgacg cgatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 138
<211> LENGTH: 1340
<212> TYPE: DNA
<213> ORGANISM: Artificial Sequence
<220> FEATURE:
<223> OTHER INFORMATION: ttGGBP17C.4 Exemplary Affinity-Tuning mutant (17C Background) Expression Construct (Table 6)

<400> SEQUENCE: 138
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacatgc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540

```
ttattggaaa gctcatccgg aagcggacaa gaaccacgac ggggttatgc aatatgtcat    600

gttaatgggc cagccggggc agcaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 139
<211> LENGTH: 1340
<212> TYPE: DNA
<213> ORGANISM: Artificial Sequence
<220> FEATURE:
<223> OTHER INFORMATION: ttGGBP17C.5 Exemplary Affinity-Tuning mutant
(17C Background) Expression Construct (Table 6)

<400> SEQUENCE: 139

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgcgacatgc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200
```

aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 140
<211> LENGTH: 1340
<212> TYPE: DNA
<213> ORGANISM: Artificial Sequence
<220> FEATURE:
<223> OTHER INFORMATION: ttGGBP17C.6 Exemplary Affinity-Tuning mutant
(17C Background) Expression Construct (Table 6)

<400> SEQUENCE: 140
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgaaacatgc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgggatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 141
<211> LENGTH: 1340
<212> TYPE: DNA
<213> ORGANISM: Artificial Sequence
<220> FEATURE:
<223> OTHER INFORMATION: ttGGBP17C.7 Exemplary Affinity-Tuning mutant
(17C Background) Expression Construct (Table 6)

<400> SEQUENCE: 141
cggtcacgct tgggactgcc ataggctggc ccggtgatgc cggccacgat gcgtccggcg 60
tagaggatcg agatctcgat cccgcgaaat taatacgact cactataggg agaccacaac 120

```
ggtttccctc tagaaataat tttgtttaac tttaagaagg agatatacca tgaaacaact    180
caatatcggt gtagctattt ataaattcga caacacatgc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc cagccggggc accaagacgc aatcttacgt acgcaatact cgatccaaac    660
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccaccg ccccagggat    900
ccaggcgatc aaagacggta cattactggg gacagtcctg aacgacgcca aaaaccaggc    960
gaaagccact ttcaacattg catacgaact tgcacaaggg atcacgccaa ccaaagataa   1020
catcggttac gacatcaccg acggcaaata cgtttggatt ccatataaaa aaattacaaa   1080
agacaacatt tcggatgcag agcaaggtgg ttcacatcat catcatcatc attaatgaaa   1140
gggcgatatc cagcacactg gcggccgtta ctagtggatc cggctgctaa caaagcccga   1200
aaggaagctg agttggctgc tgccaccgct gagcaataac tagcataacc ccttggggcc   1260
tctaaacggg tcttgagggg ttttttgctg aaaggaggaa ctatatccgg agcgactccc   1320
acggcacgtt ggcaagctcg                                               1340
```

```
<210> SEQ ID NO 142
<211> LENGTH: 1340
<212> TYPE: DNA
<213> ORGANISM: Artificial Sequence
<220> FEATURE:
<223> OTHER INFORMATION: ttGGBP17C.8 Exemplary Affinity-Tuning mutant
      (17C Background) Expression Construct (Table 6)

<400> SEQUENCE: 142
```

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgacaactgc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc cagccggggc accaagacgc aatcttacgt acgcaatact cgatccaaac    660
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
```

cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 143
<211> LENGTH: 1340
<212> TYPE: DNA
<213> ORGANISM: Artificial Sequence
<220> FEATURE:
<223> OTHER INFORMATION: ttGGBP17C.9 Exemplary Affinity-Tuning mutant
(17C Background) Expression Construct (Table 6)

<400> SEQUENCE: 143
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacagctgc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgggatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 144

<211> LENGTH: 1340
<212> TYPE: DNA
<213> ORGANISM: Artificial Sequence
<220> FEATURE:
<223> OTHER INFORMATION: ttGGBP17C.10 Exemplary Affinity-Tuning mutant
(17C Background) Expression Construct (Table 6)

<400> SEQUENCE: 144

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacatgc atgactgcgg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 145
<211> LENGTH: 1340
<212> TYPE: DNA
<213> ORGANISM: Artificial Sequence
<220> FEATURE:
<223> OTHER INFORMATION: ttGGBP17C.11 Exemplary Affinity-Tuning mutant
(17C Background) Expression Construct (Table 6)

<400> SEQUENCE: 145

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacatgc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420
```

-continued

```
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc cagccggggc accaagacgc aatcttacgt acgcaatact cgatccaaac    660
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccgcgg ccccagggat    900
ccaggcgatc aaagacggta cattactggg gacagtcctg aacgacgcca aaaaccaggc    960
gaaagccact ttcaacattg catacgaact tgcacaaggg atcacgccaa ccaaagataa   1020
catcggttac gacatcaccg acggcaaata cgtttggatt ccatataaaa aaattacaaa   1080
agacaacatt tcggatgcag agcaaggtgg ttcacatcat catcatcatc attaatgaaa   1140
gggcgatatc cagcacactg gcggccgtta ctagtggatc cggctgctaa caaagcccga   1200
aaggaagctg agttggctgc tgccaccgct gagcaataac tagcataacc ccttggggcc   1260
tctaaacggg tcttgagggg ttttttgctg aaaggaggaa ctatatccgg agcgactccc   1320
acggcacgtt ggcaagctcg                                                1340
```

<210> SEQ ID NO 146
<211> LENGTH: 1340
<212> TYPE: DNA
<213> ORGANISM: Artificial Sequence
<220> FEATURE:
<223> OTHER INFORMATION: ttGGBP17C.19 Exemplary Affinity-Tuning mutant (17C Background) Expression Construct (Table 6)

<400> SEQUENCE: 146

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgacacatgc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc cagccggggc accaagacgc aatcttacgt acgcaatact cgatccaaac    660
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccaccg ccccagggat    900
ccaggcgatc aaagacggta cattactggg gacagtcctg gatgacgcca aaaaccaggc    960
gaaagccact ttcaacattg catacgaact tgcacaaggg atcacgccaa ccaaagataa   1020
catcggttac gacatcaccg acggcaaata cgtttggatt ccatataaaa aaattacaaa   1080
```

agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 147
<211> LENGTH: 1340
<212> TYPE: DNA
<213> ORGANISM: Artificial Sequence
<220> FEATURE:
<223> OTHER INFORMATION: ttGGBP17C.20 Exemplary Affinity-Tuning mutant (17C Background) Expression Construct (Table 6)

<400> SEQUENCE: 147
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacatgc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgggatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg agcgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 148
<211> LENGTH: 1340
<212> TYPE: DNA
<213> ORGANISM: Artificial Sequence
<220> FEATURE:
<223> OTHER INFORMATION: ttGGBP17C.21 Exemplary Affinity-Tuning mutant (17C Background) Expression Construct (Table 6)

<400> SEQUENCE: 148

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacatgc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg gcggacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                                1340
```

<210> SEQ ID NO 149
<211> LENGTH: 1340
<212> TYPE: DNA
<213> ORGANISM: Artificial Sequence
<220> FEATURE:
<223> OTHER INFORMATION: ttGGBP17C.22 Exemplary Affinity-Tuning mutant (17C Background) Expression Construct (Table 6)

<400> SEQUENCE: 149

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacatgc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660
```

```
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccaccg ccccagggat    900
ccaggcgatc aaagacggta cattactggg gacagtcctg aacgacaaca aaaaccaggc    960
gaaagccact ttcaacattg catacgaact tgcacaaggg atcacgccaa ccaaagataa   1020
catcggttac gacatcaccg acggcaaata cgtttggatt ccatataaaa aaattacaaa   1080
agacaacatt tcggatgcag agcaaggtgg ttcacatcat catcatcatc attaatgaaa   1140
gggcgatatc cagcacactg gcggccgtta ctagtggatc cggctgctaa caaagcccga   1200
aaggaagctg agttggctgc tgccaccgct gagcaataac tagcataacc ccttggggcc   1260
tctaaacggg tcttgagggg ttttttgctg aaaggaggaa ctatatccgg agcgactccc   1320
acggcacgtt ggcaagctcg                                               1340
```

<210> SEQ ID NO 150
<211> LENGTH: 1340
<212> TYPE: DNA
<213> ORGANISM: Artificial Sequence
<220> FEATURE:
<223> OTHER INFORMATION: ttGGBP17C.23 Exemplary Affinity-Tuning mutant (17C Background) Expression Construct (Table 6)

<400> SEQUENCE: 150

```
cggtcacgct tgggactgcc ataggctggc ccggtgatgc cggccacgat gcgtccggcg     60
tagaggatcg agatctcgat cccgcgaaat taatacgact cactataggg agaccacaac    120
ggtttccctc tagaaataat tttgtttaac tttaagaagg agatatacca tgaaacaact    180
caatatcggt gtagctattt ataaattcga cgacacatgc atgactgggg tccggaatgc    240
tatgaccgca gaagcccaag gcaaggccaa gttaaacatg gtagacagtc agaactcaca    300
acctacacaa aatgatcagg tcgacctctt catcacgaaa aaaatgaatg cgttggcaat    360
caaccctgta gatcgcaccg cagctgggac tatcatcgac aaggcaaagc aagcaaatat    420
ccctgtagtg ttcttcaacc gggaaccttt accagaagac atgaaaaaat gggataaggt    480
atattacgta ggcgcaaagg ccgaacagag tggcattctc caaggtcaaa tcatggctga    540
ttattggaaa gctcatccgg aagcggacaa gaaccacgac ggggttatgc aatatgtcat    600
gttaatgggc cagccggggc accaagacgc aatcttacgt acgcaatact cgatccaaac    660
cgtgaaagat gcaggcatca aggtccagga gctggctaaa gactacgcca attgggatcg    720
tgtcaccgct catgacaaaa tggctgcttg gctctcgtcc tttggcgaca agattgaagc    780
cgtttttgca aataacgacg atatggccct gggtgccatt gaagccctca agtctgctgg    840
ctatttcacg ggcaacaagt acatcccagt tgtaggcgtc gacgccaccg ccccagggat    900
ccaggcgatc aaagacggta cattactggg gacagtcctg aacgaccaga aaaaccaggc    960
gaaagccact ttcaacattg catacgaact tgcacaaggg atcacgccaa ccaaagataa   1020
catcggttac gacatcaccg acggcaaata cgtttggatt ccatataaaa aaattacaaa   1080
agacaacatt tcggatgcag agcaaggtgg ttcacatcat catcatcatc attaatgaaa   1140
gggcgatatc cagcacactg gcggccgtta ctagtggatc cggctgctaa caaagcccga   1200
aaggaagctg agttggctgc tgccaccgct gagcaataac tagcataacc ccttggggcc   1260
tctaaacggg tcttgagggg ttttttgctg aaaggaggaa ctatatccgg agcgactccc   1320
```

```
acggcacgtt ggcaagctcg                                         1340


<210> SEQ ID NO 151
<211> LENGTH: 1340
<212> TYPE: DNA
<213> ORGANISM: Artificial Sequence
<220> FEATURE:
<223> OTHER INFORMATION: ttGGBP17C.24 Exemplary Affinity-Tuning mutant
      (17C Background) Expression Construct (Table 6)

<400> SEQUENCE: 151

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacatgc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgaccgca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340


<210> SEQ ID NO 152
<211> LENGTH: 1340
<212> TYPE: DNA
<213> ORGANISM: Artificial Sequence
<220> FEATURE:
<223> OTHER INFORMATION: ttGGBP17C.25 Exemplary Affinity-Tuning mutant
      (17C Background) Expression Construct (Table 6)

<400> SEQUENCE: 152

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacatgc atgactgggg tccggaatgc    240

tatgaccgca gaagcccaag gcaaggccaa gttaaacatg gtagacagtc agaactcaca    300
```

```
acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacaaaa aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 153
<211> LENGTH: 1340
<212> TYPE: DNA
<213> ORGANISM: Artificial Sequence
<220> FEATURE:
<223> OTHER INFORMATION: ttGGBP17C.26 Exemplary Affinity-Tuning mutant
(17C Background) Expression Construct (Table 6)

<400> SEQUENCE: 153

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacatgc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaacc gggaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgactgga aaaaccaggc    960
```

gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 154
<211> LENGTH: 1340
<212> TYPE: DNA
<213> ORGANISM: Artificial Sequence
<220> FEATURE:
<223> OTHER INFORMATION: ttGGBP17C.27 Exemplary Affinity-Tuning mutant (17C Background) Expression Construct (Table 6)

<400> SEQUENCE: 154
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacatgc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgggatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacttta aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 155
<211> LENGTH: 1340
<212> TYPE: DNA
<213> ORGANISM: Artificial Sequence
<220> FEATURE:
<223> OTHER INFORMATION: ttGGBP17C.28 Exemplary Affinity-Tuning mutant (17C Background) Expression Construct (Table 6)

<400> SEQUENCE: 155
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacatgc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgggatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgactata aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 156
<211> LENGTH: 1340
<212> TYPE: DNA
<213> ORGANISM: Artificial Sequence
<220> FEATURE:
<223> OTHER INFORMATION: ttGGBP17C.29 Exemplary Affinity-Tuning mutant
(17C Background) Expression Construct (Table 6)

<400> SEQUENCE: 156
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacatgc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540

-continued

```
ttattggaaa gctcatccgg aagcggacaa gaaccacgac ggggttatgc aatatgtcat    600

gttaatgggc cagccggggc accaagacgc aatcttacgt acgcaatact cgatccaaac    660

cgtgaaagat gcaggcatca aggtccagga gctggctaaa gactacgcca attgggatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacagca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                                1340


<210> SEQ ID NO 157
<211> LENGTH: 1340
<212> TYPE: DNA
<213> ORGANISM: Artificial Sequence
<220> FEATURE:
<223> OTHER INFORMATION: ttGGBP182C.2.0 Exemplary Affinity-Tuning mutant
      (182C Background) Expression Construct (Table 6)

<400> SEQUENCE: 157

cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacattc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaaca aagaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc gaaccggggc accaagacgc aatcttacgt acgcaatact cgatccaaac    660

cgtgaaagat gcaggcatca aggtccagga gctggctaaa gactacgcca attgcgatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200
```

aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 158
<211> LENGTH: 1340
<212> TYPE: DNA
<213> ORGANISM: Artificial Sequence
<220> FEATURE:
<223> OTHER INFORMATION: ttGGBP182C.2.1 Exemplary Affinity-Tuning mutant (182C Background) Expression Construct (Table 6)

<400> SEQUENCE: 158
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaaca aagaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc gaaccggggc accaagacag catcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 159
<211> LENGTH: 1340
<212> TYPE: DNA
<213> ORGANISM: Artificial Sequence
<220> FEATURE:
<223> OTHER INFORMATION: ttGGBP182C.2.3 Exemplary Affinity-Tuning mutant (182C Background) Expression Construct (Table 6)

<400> SEQUENCE: 159
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaaca aagaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc gaaccggggc accaagacaa catcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 160
<211> LENGTH: 1340
<212> TYPE: DNA
<213> ORGANISM: Artificial Sequence
<220> FEATURE:
<223> OTHER INFORMATION: ttGGBP182C.2.4 Exemplary Affinity-Tuning mutant (182C Background) Expression Construct (Table 6)

<400> SEQUENCE: 160
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaaca aagaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc gaaccggggc accaagacat gatcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840

-continued ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 161
<211> LENGTH: 1340
<212> TYPE: DNA
<213> ORGANISM: Artificial Sequence
<220> FEATURE:
<223> OTHER INFORMATION: ttGGBP182C.2.5 Exemplary Affinity-Tuning mutant (182C Background) Expression Construct (Table 6)

<400> SEQUENCE: 161
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaaca aagaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc gaaccggggc agcaagacgc aatcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 162
<211> LENGTH: 1340

<212> TYPE: DNA
<213> ORGANISM: Artificial Sequence
<220> FEATURE:
<223> OTHER INFORMATION: ttGGBP182C.2.6 Exemplary Affinity-Tuning mutant (182C Background) Expression Construct (Table 6)

<400> SEQUENCE: 162
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaaca aagaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc gaaccgggga accaagacgc aatcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 163
<211> LENGTH: 1340
<212> TYPE: DNA
<213> ORGANISM: Artificial Sequence
<220> FEATURE:
<223> OTHER INFORMATION: ttGGBP182C.2.7 Exemplary Affinity-Tuning mutant (182C Background) Expression Construct (Table 6)

<400> SEQUENCE: 163
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420

```
ccctgtagtg ttcttcaaca aagaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc gaaccggggt ttcaagacgc aatcttacgt acgcaatact cgatccaaac    660

cgtgaaagat gcaggcatca aggtccagga gctggctaaa gactacgcca attgcgatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 164
<211> LENGTH: 1340
<212> TYPE: DNA
<213> ORGANISM: Artificial Sequence
<220> FEATURE:
<223> OTHER INFORMATION: ttGGBP182C.2.8 Exemplary Affinity-Tuning mutant (182C Background) Expression Construct (Table 6)

<400> SEQUENCE: 164

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga caacacattc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaaca aagaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc gaaccggggc accaagacgc aatcttacgt acgcaatact cgatccaaac    660

cgtgaaagat gcaggcatca aggtccagga gctggctaaa gactacgcca attgcgatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080
```

-continued

```
agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 165
<211> LENGTH: 1340
<212> TYPE: DNA
<213> ORGANISM: Artificial Sequence
<220> FEATURE:
<223> OTHER INFORMATION: ttGGBP182C.2.9 Exemplary Affinity-Tuning mutant (182C Background) Expression Construct (Table 6)

<400> SEQUENCE: 165

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacattc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaaca aagaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc gaaccggggc accaagactt tatcttacgt acgcaatact cgatccaaac    660

cgtgaaagat gcaggcatca aggtccagga gctggctaaa gactacgcca attgcgatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                               1340
```

<210> SEQ ID NO 166
<211> LENGTH: 1340
<212> TYPE: DNA
<213> ORGANISM: Artificial Sequence
<220> FEATURE:
<223> OTHER INFORMATION: ttGGBP182C.3 Exemplary Affinity-Tuning mutant (182C Background) Expression Construct (Table 6)

<400> SEQUENCE: 166

```
cggtcacgct tgggactgcc ataggctggc ccggtgatgc cggccacgat gcgtccggcg     60
```

tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaaca aagaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 167
<211> LENGTH: 1340
<212> TYPE: DNA
<213> ORGANISM: Artificial Sequence
<220> FEATURE:
<223> OTHER INFORMATION: ttGGBP182C.4 Exemplary Affinity-Tuning mutant
(182C Background) Expression Construct (Table 6)

<400> SEQUENCE: 167
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc gaaccggggc accaagacgc aatcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 168
<211> LENGTH: 1340
<212> TYPE: DNA
<213> ORGANISM: Artificial Sequence
<220> FEATURE:
<223> OTHER INFORMATION: ttGGBP182C.5 Exemplary Affinity-Tuning mutant (182C Background) Expression Construct (Table 6)

<400> SEQUENCE: 168
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatccgaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc acccggacgc aatcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 169
<211> LENGTH: 1340
<212> TYPE: DNA
<213> ORGANISM: Artificial Sequence
<220> FEATURE:
<223> OTHER INFORMATION: ttGGBP182C.6 Exemplary Affinity-Tuning mutant
(182C Background) Expression Construct (Table 6)

<400> SEQUENCE: 169
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacaacttc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg cgatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 170
<211> LENGTH: 1340
<212> TYPE: DNA
<213> ORGANISM: Artificial Sequence
<220> FEATURE:
<223> OTHER INFORMATION: ttGGBP182C.7 Exemplary Affinity-Tuning mutant
(182C Background) Expression Construct (Table 6)

<400> SEQUENCE: 170
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga cgacacattc atgactgggg tccggaatgc 240
tatgaccgca gaagcccaag gcaaggccaa gttaaacatg gtagacagtc agaactcaca 300

-continued

```
acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaaca aagaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc agcccggggc accaagacgc aatcttacgt acgcaatact cgatccaaac    660

cgtgaaagat gcaggcatca aggtccagga gctggctaaa gactacgcca attgcgatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960

gaaagccact ttcaacattg catacgaact tgcacaaggg atcacgccaa ccaaagataa   1020

catcggttac gacatcaccg acggcaaata cgtttggatt ccatataaaa aaattacaaa   1080

agacaacatt tcggatgcag agcaaggtgg ttcacatcat catcatcatc attaatgaaa   1140

gggcgatatc cagcacactg gcggccgtta ctagtggatc cggctgctaa caaagcccga   1200

aaggaagctg agttggctgc tgccaccgct gagcaataac tagcataacc ccttggggcc   1260

tctaaacggg tcttgagggg ttttttgctg aaaggaggaa ctatatccgg agcgactccc   1320

acggcacgtt ggcaagctcg                                                1340
```

<210> SEQ ID NO 171
<211> LENGTH: 1340
<212> TYPE: DNA
<213> ORGANISM: Artificial Sequence
<220> FEATURE:
<223> OTHER INFORMATION: ttGGBP182C.8 Exemplary Affinity-Tuning mutant
      (182C Background) Expression Construct (Table 6)

<400> SEQUENCE: 171

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaaacaact    180

caatatcggt gtagctattt ataaattcga cgacacattc atgactgggg tccggaatgc    240

tatgaccgca gaagcccaag gcaaggccaa gttaaacatg gtagacagtc agaactcaca    300

acctacacaa aatgatcagg tcgacctctt catcacgaaa aaaatgaatg cgttggcaat    360

caaccctgta gatcgcaccg cagctgggac tatcatcgac aaggcaaagc aagcaaatat    420

ccctgtagtg ttcttcaaca aagaaccttt accagaagac atgaaaaaat gggataaggt    480

atattacgta ggcgcaaagg ccgaacagag tggcattctc caaggtcaaa tcatggctga    540

ttattggaaa gctcatccgg aagcggacaa gaaccacgac ggggttatgc aatatgtcat    600

gttaatgggc aaaccggggc accaagacgc aatcttacgt acgcaatact cgatccaaac    660

cgtgaaagat gcaggcatca aggtccagga gctggctaaa gactacgcca attgcgatcg    720

tgtcaccgct catgacaaaa tggctgcttg gctctcgtcc tttggcgaca agattgaagc    780

cgtttttgca aataacgacg atatggccct gggtgccatt gaagccctca agtctgctgg    840

ctatttcacg ggcaacaagt acatcccagt tgtaggcgtc gacgccaccg ccccagggat    900

ccaggcgatc aaagacggta cattactggg gacagtcctg aacgacgcca aaaaccaggc    960
```

gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 172
<211> LENGTH: 1340
<212> TYPE: DNA
<213> ORGANISM: Artificial Sequence
<220> FEATURE:
<223> OTHER INFORMATION: ttGGBP182C.9 Exemplary Affinity-Tuning mutant
(182C Background) Expression Construct (Table 6)

<400> SEQUENCE: 172
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaacaact 180
caatatcggt gtagctattt ataaattcga caacacattc atgactgggg tccggaatgc 240
tatgaccgca gaagcccaag gcaaggccaa gttaaacatg gtagacagtc agaactcaca 300
acctacacaa aatgatcagg tcgacctctt catcacgaaa aaaatgaatg cgttggcaat 360
caaccctgta gatcgcaccg cagctgggac tatcatcgac aaggcaaagc aagcaaatat 420
ccctgtagtg ttcttcaacc gggaaccttt accagaagac atgaaaaaat gggataaggt 480
atattacgta ggcgcaaagg ccgaacagag tggcattctc caaggtcaaa tcatggctga 540
ttattggaaa gctcatccgg aagcggacaa gaaccacgac ggggttatgc aatatgtcat 600
gttaatgggc cagccggggc accaagacgc aatcttacgt acgcaatact cgatccaaac 660
cgtgaaagat gcaggcatca aggtccagga gctggctaaa gactacgcca attgcgatcg 720
tgtcaccgct catgacaaaa tggctgcttg gctctcgtcc tttggcgaca agattgaagc 780
cgtttttgca aataacgacg atatggccct gggtgccatt gaagccctca agtctgctgg 840
ctatttcacg ggcaacaagt acatcccagt tgtaggcgtc gacgccaccg ccccagggat 900
ccaggcgatc aaagacggta cattactggg gacagtcctg aacgacgcca aaaaccaggc 960
gaaagccact ttcaacattg catacgaact tgcacaaggg atcacgccaa ccaaagataa 1020
catcggttac gacatcaccg acggcaaata cgtttggatt ccatataaaa aaattacaaa 1080
agacaacatt tcggatgcag agcaaggtgg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 173
<211> LENGTH: 321
<212> TYPE: PRT
<213> ORGANISM: Artificial Sequence
<220> FEATURE:
<223> OTHER INFORMATION: ttGGBP182C.2.0_Imm0

<400> SEQUENCE: 173

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Lys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Glu Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His

<210> SEQ ID NO 174
<211> LENGTH: 321
<212> TYPE: PRT
<213> ORGANISM: Artificial Sequence
<220> FEATURE:
<223> OTHER INFORMATION: ttGBP,R91K,Q148E

<400> SEQUENCE: 174

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

```
Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Lys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Glu Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser His His His His His
305                 310                 315                 320

His


<210> SEQ ID NO 175
<211> LENGTH: 333
<212> TYPE: PRT
<213> ORGANISM: Artificial Sequence
<220> FEATURE:
<223> OTHER INFORMATION: ttGGBP182C.2.0_Imm1

<400> SEQUENCE: 175

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60
```

-continued

Asn Pro Val Asp Arg Thr Ala Ala Gly Thr Ile Ile Asp Lys Ala Lys
65 70 75 80

Gln Ala Asn Ile Pro Val Val Phe Phe Asn Lys Glu Pro Leu Pro Glu
85 90 95

Asp Met Lys Lys Trp Asp Lys Val Tyr Tyr Val Gly Ala Lys Ala Glu
100 105 110

Gln Ser Gly Ile Leu Gln Gly Gln Ile Met Ala Asp Tyr Trp Lys Ala
115 120 125

His Pro Glu Ala Asp Lys Asn His Asp Gly Val Met Gln Tyr Val Met
130 135 140

Leu Met Gly Glu Pro Gly His Gln Asp Ala Ile Leu Arg Thr Gln Tyr
145 150 155 160

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser Gly Gly Ser Lys Lys
305 310 315 320

Lys Lys Lys Lys Gly Gly Ser His His His His His His
325 330

<210> SEQ ID NO 176
<211> LENGTH: 333
<212> TYPE: PRT
<213> ORGANISM: Artificial Sequence
<220> FEATURE:
<223> OTHER INFORMATION: ttGGBP182C.2.0_Imm2

<400> SEQUENCE: 176

Met His His His His His His Gly Gly Ser Lys Gln Leu Asn Ile Gly
1 5 10 15

Val Ala Ile Tyr Lys Phe Asp Asp Thr Phe Met Thr Gly Val Arg Asn
20 25 30

Ala Met Thr Ala Glu Ala Gln Gly Lys Ala Lys Leu Asn Met Val Asp
35 40 45

Ser Gln Asn Ser Gln Pro Thr Gln Asn Asp Gln Val Asp Leu Phe Ile
50 55 60

Thr Lys Lys Met Asn Ala Leu Ala Ile Asn Pro Val Asp Arg Thr Ala
65 70 75 80

Ala Gly Thr Ile Ile Asp Lys Ala Lys Gln Ala Asn Ile Pro Val Val
85 90 95

-continued

Phe Phe Asn Lys Glu Pro Leu Pro Glu Asp Met Lys Lys Trp Asp Lys
100 105 110

Val Tyr Tyr Val Gly Ala Lys Ala Glu Gln Ser Gly Ile Leu Gln Gly
115 120 125

Gln Ile Met Ala Asp Tyr Trp Lys Ala His Pro Glu Ala Asp Lys Asn
130 135 140

His Asp Gly Val Met Gln Tyr Val Met Leu Met Gly Glu Pro Gly His
145 150 155 160

Gln Asp Ala Ile Leu Arg Thr Gln Tyr Ser Ile Gln Thr Val Lys Asp
165 170 175

Ala Gly Ile Lys Val Gln Glu Leu Ala Lys Asp Tyr Ala Asn Cys Asp
180 185 190

Arg Val Thr Ala His Asp Lys Met Ala Ala Trp Leu Ser Ser Phe Gly
195 200 205

Asp Lys Ile Glu Ala Val Phe Ala Asn Asn Asp Asp Met Ala Leu Gly
210 215 220

Ala Ile Glu Ala Leu Lys Ser Ala Gly Tyr Phe Thr Gly Asn Lys Tyr
225 230 235 240

Ile Pro Val Val Gly Val Asp Ala Thr Ala Pro Gly Ile Gln Ala Ile
245 250 255

Lys Asp Gly Thr Leu Leu Gly Thr Val Leu Asn Asp Ala Lys Asn Gln
260 265 270

Ala Lys Ala Thr Phe Asn Ile Ala Tyr Glu Leu Ala Gln Gly Ile Thr
275 280 285

Pro Thr Lys Asp Asn Ile Gly Tyr Asp Ile Thr Asp Gly Lys Tyr Val
290 295 300

Trp Ile Pro Tyr Lys Lys Ile Thr Lys Asp Asn Ile Ser Asp Ala Glu
305 310 315 320

Gln Gly Gly Ser Gly Gly Ser Lys Lys Lys Lys Lys Lys
325 330

<210> SEQ ID NO 177
<211> LENGTH: 333
<212> TYPE: PRT
<213> ORGANISM: Artificial Sequence
<220> FEATURE:
<223> OTHER INFORMATION: ttGGBP182C.2.0_Imm3

<400> SEQUENCE: 177

Met Lys Lys Lys Lys Lys Lys Gly Gly Ser Gly Gly Ser Lys Gln Leu
1 5 10 15

Asn Ile Gly Val Ala Ile Tyr Lys Phe Asp Asp Thr Phe Met Thr Gly
20 25 30

Val Arg Asn Ala Met Thr Ala Glu Ala Gln Gly Lys Ala Lys Leu Asn
35 40 45

Met Val Asp Ser Gln Asn Ser Gln Pro Thr Gln Asn Asp Gln Val Asp
50 55 60

Leu Phe Ile Thr Lys Lys Met Asn Ala Leu Ala Ile Asn Pro Val Asp
65 70 75 80

Arg Thr Ala Ala Gly Thr Ile Ile Asp Lys Ala Lys Gln Ala Asn Ile
85 90 95

Pro Val Val Phe Phe Asn Lys Glu Pro Leu Pro Glu Asp Met Lys Lys
100 105 110

Trp Asp Lys Val Tyr Tyr Val Gly Ala Lys Ala Glu Gln Ser Gly Ile
115 120 125

-continued

Leu Gln Gly Gln Ile Met Ala Asp Tyr Trp Lys Ala His Pro Glu Ala
    130                 135                 140

Asp Lys Asn His Asp Gly Val Met Gln Tyr Val Met Leu Met Gly Glu
145                 150                 155                 160

Pro Gly His Gln Asp Ala Ile Leu Arg Thr Gln Tyr Ser Ile Gln Thr
                165                 170                 175

Val Lys Asp Ala Gly Ile Lys Val Gln Glu Leu Ala Lys Asp Tyr Ala
            180                 185                 190

Asn Cys Asp Arg Val Thr Ala His Asp Lys Met Ala Ala Trp Leu Ser
        195                 200                 205

Ser Phe Gly Asp Lys Ile Glu Ala Val Phe Ala Asn Asn Asp Asp Met
    210                 215                 220

Ala Leu Gly Ala Ile Glu Ala Leu Lys Ser Ala Gly Tyr Phe Thr Gly
225                 230                 235                 240

Asn Lys Tyr Ile Pro Val Val Gly Val Asp Ala Thr Ala Pro Gly Ile
                245                 250                 255

Gln Ala Ile Lys Asp Gly Thr Leu Leu Gly Thr Val Leu Asn Asp Ala
            260                 265                 270

Lys Asn Gln Ala Lys Ala Thr Phe Asn Ile Ala Tyr Glu Leu Ala Gln
        275                 280                 285

Gly Ile Thr Pro Thr Lys Asp Asn Ile Gly Tyr Asp Ile Thr Asp Gly
    290                 295                 300

Lys Tyr Val Trp Ile Pro Tyr Lys Lys Ile Thr Lys Asp Asn Ile Ser
305                 310                 315                 320

Asp Ala Glu Gln Gly Gly Ser His His His His His His
                325                 330

<210> SEQ ID NO 178
<211> LENGTH: 359
<212> TYPE: PRT
<213> ORGANISM: Artificial Sequence
<220> FEATURE:
<223> OTHER INFORMATION: ttGGBP182C.2.0_Imm4

<400> SEQUENCE: 178

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Lys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Glu Pro Gly His Gln Asp Ala Ile Leu Arg Thr Gln Tyr
145                 150                 155                 160

-continued

```
Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270

Glu Leu Ala Gln Gly Ile Thr Pro Thr Lys Asp Asn Ile Gly Tyr Asp
        275                 280                 285

Ile Thr Asp Gly Lys Tyr Val Trp Ile Pro Tyr Lys Lys Ile Thr Lys
    290                 295                 300

Asp Asn Ile Ser Asp Ala Glu Gln Gly Gly Ser Gly Gly Ser Thr Gly
305                 310                 315                 320

Glu Lys Pro Tyr Lys Cys Pro Glu Cys Gly Lys Ser Phe Ser Arg Ser
                325                 330                 335

Asp His Leu Ser Arg His Gln Arg Thr His Gln Asn Lys Lys Gly Gly
            340                 345                 350

Ser His His His His His His
        355


<210> SEQ ID NO 179
<211> LENGTH: 359
<212> TYPE: PRT
<213> ORGANISM: Artificial Sequence
<220> FEATURE:
<223> OTHER INFORMATION: ttGGBP182C.2.0_Imm5

<400> SEQUENCE: 179

Met Thr Gly Glu Lys Pro Tyr Lys Cys Pro Glu Cys Gly Lys Ser Phe
1               5                   10                  15

Ser Arg Ser Asp His Leu Ser Arg His Gln Arg Thr His Gln Asn Lys
            20                  25                  30

Lys Gly Gly Ser Gly Gly Ser Lys Gln Leu Asn Ile Gly Val Ala Ile
        35                  40                  45

Tyr Lys Phe Asp Asp Thr Phe Met Thr Gly Val Arg Asn Ala Met Thr
    50                  55                  60

Ala Glu Ala Gln Gly Lys Ala Lys Leu Asn Met Val Asp Ser Gln Asn
65                  70                  75                  80

Ser Gln Pro Thr Gln Asn Asp Gln Val Asp Leu Phe Ile Thr Lys Lys
                85                  90                  95

Met Asn Ala Leu Ala Ile Asn Pro Val Asp Arg Thr Ala Ala Gly Thr
            100                 105                 110

Ile Ile Asp Lys Ala Lys Gln Ala Asn Ile Pro Val Val Phe Phe Asn
        115                 120                 125

Lys Glu Pro Leu Pro Glu Asp Met Lys Lys Trp Asp Lys Val Tyr Tyr
    130                 135                 140

Val Gly Ala Lys Ala Glu Gln Ser Gly Ile Leu Gln Gly Gln Ile Met
145                 150                 155                 160
```

```
Ala Asp Tyr Trp Lys Ala His Pro Glu Ala Asp Lys Asn His Asp Gly
                165                 170                 175

Val Met Gln Tyr Val Met Leu Met Gly Glu Pro Gly His Gln Asp Ala
            180                 185                 190

Ile Leu Arg Thr Gln Tyr Ser Ile Gln Thr Val Lys Asp Ala Gly Ile
        195                 200                 205

Lys Val Gln Glu Leu Ala Lys Asp Tyr Ala Asn Cys Asp Arg Val Thr
    210                 215                 220

Ala His Asp Lys Met Ala Ala Trp Leu Ser Ser Phe Gly Asp Lys Ile
225                 230                 235                 240

Glu Ala Val Phe Ala Asn Asn Asp Asp Met Ala Leu Gly Ala Ile Glu
                245                 250                 255

Ala Leu Lys Ser Ala Gly Tyr Phe Thr Gly Asn Lys Tyr Ile Pro Val
            260                 265                 270

Val Gly Val Asp Ala Thr Ala Pro Gly Ile Gln Ala Ile Lys Asp Gly
        275                 280                 285

Thr Leu Leu Gly Thr Val Leu Asn Asp Ala Lys Asn Gln Ala Lys Ala
    290                 295                 300

Thr Phe Asn Ile Ala Tyr Glu Leu Ala Gln Gly Ile Thr Pro Thr Lys
305                 310                 315                 320

Asp Asn Ile Gly Tyr Asp Ile Thr Asp Gly Lys Tyr Val Trp Ile Pro
                325                 330                 335

Tyr Lys Lys Ile Thr Lys Asp Asn Ile Ser Asp Ala Glu Gln Gly Gly
            340                 345                 350

Ser His His His His His His
        355


<210> SEQ ID NO 180
<211> LENGTH: 345
<212> TYPE: PRT
<213> ORGANISM: Artificial Sequence
<220> FEATURE:
<223> OTHER INFORMATION: ttGGBP182C.2.0_Imm6

<400> SEQUENCE: 180

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Lys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Glu Pro Gly His Gln Asp Ala Ile Leu Arg Thr Gln Tyr
145                 150                 155                 160
```

Ser Ile Gln Thr Val Lys Asp Ala Gly Ile Lys Val Gln Glu Leu Ala
165 170 175

Lys Asp Tyr Ala Asn Cys Asp Arg Val Thr Ala His Asp Lys Met Ala
180 185 190

Ala Trp Leu Ser Ser Phe Gly Asp Lys Ile Glu Ala Val Phe Ala Asn
195 200 205

Asn Asp Asp Met Ala Leu Gly Ala Ile Glu Ala Leu Lys Ser Ala Gly
210 215 220

Tyr Phe Thr Gly Asn Lys Tyr Ile Pro Val Val Gly Val Asp Ala Thr
225 230 235 240

Ala Pro Gly Ile Gln Ala Ile Lys Asp Gly Thr Leu Leu Gly Thr Val
245 250 255

Leu Asn Asp Ala Lys Asn Gln Ala Lys Ala Thr Phe Asn Ile Ala Tyr
260 265 270

Glu Leu Ala Gln Gly Ile Thr Pro Thr Lys Asp Asn Ile Gly Tyr Asp
275 280 285

Ile Thr Asp Gly Lys Tyr Val Trp Ile Pro Tyr Lys Lys Ile Thr Lys
290 295 300

Asp Asn Ile Ser Asp Ala Glu Gln Gly Gly Ser Gly Gly Ser Thr Gly
305 310 315 320

Glu Lys Pro Tyr Lys Cys Pro Glu Cys Gly Lys Ser Phe Ser Arg Ser
325 330 335

Gly Gly Ser His His His His His His
340 345

<210> SEQ ID NO 181
<211> LENGTH: 345
<212> TYPE: PRT
<213> ORGANISM: Artificial Sequence
<220> FEATURE:
<223> OTHER INFORMATION: ttGGBP182C.2.0_Imm7

<400> SEQUENCE: 181

Met Thr Gly Glu Lys Pro Tyr Lys Cys Pro Glu Cys Gly Lys Ser Phe
1 5 10 15

Ser Arg Ser Gly Gly Ser Gly Gly Ser Lys Gln Leu Asn Ile Gly Val
20 25 30

Ala Ile Tyr Lys Phe Asp Asp Thr Phe Met Thr Gly Val Arg Asn Ala
35 40 45

Met Thr Ala Glu Ala Gln Gly Lys Ala Lys Leu Asn Met Val Asp Ser
50 55 60

Gln Asn Ser Gln Pro Thr Gln Asn Asp Gln Val Asp Leu Phe Ile Thr
65 70 75 80

Lys Lys Met Asn Ala Leu Ala Ile Asn Pro Val Asp Arg Thr Ala Ala
85 90 95

Gly Thr Ile Ile Asp Lys Ala Lys Gln Ala Asn Ile Pro Val Val Phe
100 105 110

Phe Asn Lys Glu Pro Leu Pro Glu Asp Met Lys Lys Trp Asp Lys Val
115 120 125

Tyr Tyr Val Gly Ala Lys Ala Glu Gln Ser Gly Ile Leu Gln Gly Gln
130 135 140

Ile Met Ala Asp Tyr Trp Lys Ala His Pro Glu Ala Asp Lys Asn His
145 150 155 160

Asp Gly Val Met Gln Tyr Val Met Leu Met Gly Glu Pro Gly His Gln
165 170 175

```
Asp Ala Ile Leu Arg Thr Gln Tyr Ser Ile Gln Thr Val Lys Asp Ala
            180                 185                 190

Gly Ile Lys Val Gln Glu Leu Ala Lys Asp Tyr Ala Asn Cys Asp Arg
        195                 200                 205

Val Thr Ala His Asp Lys Met Ala Ala Trp Leu Ser Ser Phe Gly Asp
    210                 215                 220

Lys Ile Glu Ala Val Phe Ala Asn Asn Asp Asp Met Ala Leu Gly Ala
225                 230                 235                 240

Ile Glu Ala Leu Lys Ser Ala Gly Tyr Phe Thr Gly Asn Lys Tyr Ile
                245                 250                 255

Pro Val Val Gly Val Asp Ala Thr Ala Pro Gly Ile Gln Ala Ile Lys
            260                 265                 270

Asp Gly Thr Leu Leu Gly Thr Val Leu Asn Asp Ala Lys Asn Gln Ala
        275                 280                 285

Lys Ala Thr Phe Asn Ile Ala Tyr Glu Leu Ala Gln Gly Ile Thr Pro
    290                 295                 300

Thr Lys Asp Asn Ile Gly Tyr Asp Ile Thr Asp Gly Lys Tyr Val Trp
305                 310                 315                 320

Ile Pro Tyr Lys Lys Ile Thr Lys Asp Asn Ile Ser Asp Ala Glu Gln
                325                 330                 335

Gly Gly Ser His His His His His His
            340                 345


<210> SEQ ID NO 182
<211> LENGTH: 9
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 182

Ile Tyr Lys Xaa Asp Asp Xaa Phe Met
1               5


<210> SEQ ID NO 183
<211> LENGTH: 8
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 183

Tyr Lys Xaa Asp Asp Xaa Phe Met
1               5


<210> SEQ ID NO 184
<211> LENGTH: 7
<212> TYPE: PRT
```

<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 184

Tyr Lys Xaa Asp Asp Xaa Phe
1               5

<210> SEQ ID NO 185
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 185

Lys Xaa Asp Asp Xaa Phe
1               5

<210> SEQ ID NO 186
<211> LENGTH: 5
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 186

Tyr Lys Xaa Asp Asp
1               5

<210> SEQ ID NO 187
<211> LENGTH: 4
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 187

Lys Xaa Asp Asp
1

<210> SEQ ID NO 188
<211> LENGTH: 4
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 188

Asp Asp Xaa Phe
1

<210> SEQ ID NO 189
<211> LENGTH: 8
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 189

Asp Xaa Phe Met Xaa Xaa Val Arg
1               5

<210> SEQ ID NO 190
<211> LENGTH: 7
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 190

Asp Xaa Phe Met Xaa Xaa Val
1               5

<210> SEQ ID NO 191
<211> LENGTH: 4
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 191

Asp Xaa Phe Met
1

<210> SEQ ID NO 192
<211> LENGTH: 9
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)

<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 192

Ile Tyr Lys Xaa Asp Asn Xaa Phe Met
1               5

<210> SEQ ID NO 193
<211> LENGTH: 8
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 193

Tyr Lys Xaa Asp Asn Xaa Phe Met
1               5

<210> SEQ ID NO 194
<211> LENGTH: 7
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 194

Tyr Lys Xaa Asp Asn Xaa Phe
1               5

<210> SEQ ID NO 195
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 195

Lys Xaa Asp Asn Xaa Phe
1               5

<210> SEQ ID NO 196
<211> LENGTH: 5
<212> TYPE: PRT
<213> ORGANISM: Artificial Sequence -continued
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 196

Tyr Lys Xaa Asp Asn
1               5

<210> SEQ ID NO 197
<211> LENGTH: 4
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 197

Lys Xaa Asp Asn
1

<210> SEQ ID NO 198
<211> LENGTH: 4
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 198

Asp Asn Xaa Phe
1

<210> SEQ ID NO 199
<211> LENGTH: 8
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 199

Asn Xaa Phe Met Xaa Xaa Val Arg
1               5

<210> SEQ ID NO 200
<211> LENGTH: 7
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:

<221> NAME/KEY: misc_feature
<222> LOCATION: (5)..(6)
<223> OTHER INFORMATION: Xaa can be any naturally occurring amino acid

<400> SEQUENCE: 200

Asn Xaa Phe Met Xaa Xaa Val
1 5

<210> SEQ ID NO 201
<211> LENGTH: 4
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 201

Asn Xaa Phe Met
1

<210> SEQ ID NO 202
<211> LENGTH: 9
<212> TYPE: PRT
<213> ORGANISM: Artificial Sequence
<220> FEATURE:
<223> OTHER INFORMATION: Conserved GGBP Sequence

<400> SEQUENCE: 202

Pro Val Val Phe Phe Asn Lys Glu Pro
1 5

<210> SEQ ID NO 203
<211> LENGTH: 9
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 203

Pro Val Val Phe Xaa Asn Lys Glu Pro
1 5

<210> SEQ ID NO 204
<211> LENGTH: 9
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 204

Pro Val Val Phe Phe Asn Xaa Glu Pro
1 5

<210> SEQ ID NO 205
<211> LENGTH: 9
<212> TYPE: PRT
<213> ORGANISM: Artificial Sequence
<220> FEATURE:

<223> OTHER INFORMATION: Conserved GGBP Sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 205

Pro Val Val Phe Xaa Asn Xaa Glu Pro
1               5

<210> SEQ ID NO 206
<211> LENGTH: 8
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 206

Val Val Phe Xaa Asn Xaa Glu Pro
1               5

<210> SEQ ID NO 207
<211> LENGTH: 7
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 207

Val Phe Xaa Asn Xaa Glu Pro
1               5

<210> SEQ ID NO 208
<211> LENGTH: 8
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 208

Pro Val Val Phe Xaa Asn Xaa Glu
1               5

<210> SEQ ID NO 209
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 209

Pro Val Val Phe Xaa Asn
1               5

<210> SEQ ID NO 210
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 210

Pro Xaa Val Phe Xaa Asn
1               5

<210> SEQ ID NO 211
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 211

Pro Val Xaa Phe Xaa Asn
1               5

<210> SEQ ID NO 212
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 212

Phe Xaa Asn Xaa Glu Pro
1               5

<210> SEQ ID NO 213
<211> LENGTH: 5
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 213

Phe Xaa Asn Xaa Glu
1 5

<210> SEQ ID NO 214
<211> LENGTH: 10
<212> TYPE: PRT
<213> ORGANISM: Artificial Sequence
<220> FEATURE:
<223> OTHER INFORMATION: Conserved GGBP Sequence

<400> SEQUENCE: 214

Pro Gly His Pro Asp Ala Glu Ala Arg Thr
1 5 10

<210> SEQ ID NO 215
<211> LENGTH: 10
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 215

Pro Gly His Xaa Asp Ala Xaa Xaa Arg Thr
1 5 10

<210> SEQ ID NO 216
<211> LENGTH: 9
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 216

Gly His Xaa Asp Ala Xaa Xaa Arg Thr
1 5

<210> SEQ ID NO 217
<211> LENGTH: 8

<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 217

His Xaa Asp Ala Xaa Xaa Arg Thr
1               5

<210> SEQ ID NO 218
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(4)
<223> OTHER INFORMATION: Xaa can be any naturally occurring amino acid

<400> SEQUENCE: 218

Asp Ala Xaa Xaa Arg Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 219

Pro Gly His Xaa Asp Ala Xaa Xaa Arg
1               5

<210> SEQ ID NO 220
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 220

Pro Gly His Xaa Asp Ala
1               5

<210> SEQ ID NO 221
<211> LENGTH: 5
<212> TYPE: PRT
<213> ORGANISM: Artificial Sequence
<220> FEATURE:

<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 221

Pro Gly His Xaa Asp
1               5

<210> SEQ ID NO 222
<211> LENGTH: 10
<212> TYPE: PRT
<213> ORGANISM: Artificial Sequence
<220> FEATURE:
<223> OTHER INFORMATION: Conserved GGBP Sequence

<400> SEQUENCE: 222

Pro Gly Asn Pro Asp Ala Glu Ala Arg Thr
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 223

Pro Gly Asn Xaa Asp Ala Xaa Xaa Arg Thr
1               5                   10

<210> SEQ ID NO 224
<211> LENGTH: 9
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 224

Gly Asn Xaa Asp Ala Xaa Xaa Arg Thr
1               5

<210> SEQ ID NO 225
<211> LENGTH: 8
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 225

Asn Xaa Asp Ala Xaa Xaa Arg Thr
1 5

<210> SEQ ID NO 226
<211> LENGTH: 9
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 226

Pro Gly Asn Xaa Asp Ala Xaa Xaa Arg
1 5

<210> SEQ ID NO 227
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 227

Pro Gly Asn Xaa Asp Ala
1 5

<210> SEQ ID NO 228
<211> LENGTH: 5
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 228

Pro Gly Asn Xaa Asp
1 5

<210> SEQ ID NO 229
<211> LENGTH: 6
<212> TYPE: PRT
<213> ORGANISM: Artificial Sequence
<220> FEATURE:
<223> OTHER INFORMATION: Conserved GGBP Sequence

<400> SEQUENCE: 229

Asp Thr Ala Met Trp Asp
1 5

<210> SEQ ID NO 230
<211> LENGTH: 6

<212> TYPE: PRT
<213> ORGANISM: Artificial Sequence
<220> FEATURE:
<223> OTHER INFORMATION: DTAMCD (Conserved Sequence)

<400> SEQUENCE: 230

Asp Thr Ala Met Cys Asp
1               5

<210> SEQ ID NO 231
<211> LENGTH: 5
<212> TYPE: PRT
<213> ORGANISM: Artificial Sequence
<220> FEATURE:
<223> OTHER INFORMATION: Conserved GGBP Sequence

<400> SEQUENCE: 231

Asp Thr Ala Met Trp
1               5

<210> SEQ ID NO 232
<211> LENGTH: 5
<212> TYPE: PRT
<213> ORGANISM: Artificial Sequence
<220> FEATURE:
<223> OTHER INFORMATION: Conserved GGBP Sequence

<400> SEQUENCE: 232

Asp Thr Ala Met Cys
1               5

<210> SEQ ID NO 233
<211> LENGTH: 5
<212> TYPE: PRT
<213> ORGANISM: Artificial Sequence
<220> FEATURE:
<223> OTHER INFORMATION: Conserved GGBP Sequence

<400> SEQUENCE: 233

Thr Ala Met Trp Asp
1               5

<210> SEQ ID NO 234
<211> LENGTH: 5
<212> TYPE: PRT
<213> ORGANISM: Artificial Sequence
<220> FEATURE:
<223> OTHER INFORMATION: Conserved GGBP Sequence

<400> SEQUENCE: 234

Thr Ala Met Cys Asp
1               5

<210> SEQ ID NO 235
<211> LENGTH: 5
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 235

Ala Xaa Trp Xaa Xaa
1 5

<210> SEQ ID NO 236
<211> LENGTH: 5
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 236

Ala Xaa Cys Xaa Xaa
1 5

<210> SEQ ID NO 237
<211> LENGTH: 9
<212> TYPE: PRT
<213> ORGANISM: Artificial Sequence
<220> FEATURE:
<223> OTHER INFORMATION: Conserved GGBP Sequence

<400> SEQUENCE: 237

Ile Glu Val Val Ile Ala Asn Asn Asp
1 5

<210> SEQ ID NO 238
<211> LENGTH: 8
<212> TYPE: PRT
<213> ORGANISM: Artificial Sequence
<220> FEATURE:
<223> OTHER INFORMATION: Conserved GGBP Sequence

<400> SEQUENCE: 238

Glu Val Val Ile Ala Asn Asn Asp
1 5

<210> SEQ ID NO 239
<211> LENGTH: 8
<212> TYPE: PRT
<213> ORGANISM: Artificial Sequence
<220> FEATURE:
<223> OTHER INFORMATION: Conserved GGBP Sequence

<400> SEQUENCE: 239

Ile Glu Val Val Ile Ala Asn Asn
1 5

<210> SEQ ID NO 240
<211> LENGTH: 7
<212> TYPE: PRT
<213> ORGANISM: Artificial Sequence
<220> FEATURE:
<223> OTHER INFORMATION: Conserved GGBP Sequence

<400> SEQUENCE: 240

Glu Val Val Ile Ala Asn Asn
1 5

<210> SEQ ID NO 241

<211> LENGTH: 9
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 241

Ile Glu Xaa Val Xaa Xaa Asn Asn Asp
1               5

<210> SEQ ID NO 242
<211> LENGTH: 8
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 242

Ile Glu Xaa Val Xaa Xaa Asn Asn
1               5

<210> SEQ ID NO 243
<211> LENGTH: 8
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 243

Glu Xaa Val Xaa Xaa Asn Asn Asp
1               5

<210> SEQ ID NO 244
<211> LENGTH: 7
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 244

Glu Xaa Val Xaa Xaa Asn Asn
1 5

<210> SEQ ID NO 245
<211> LENGTH: 7
<212> TYPE: PRT
<213> ORGANISM: Artificial Sequence
<220> FEATURE:
<223> OTHER INFORMATION: Conserved GGBP Sequence

<400> SEQUENCE: 245

Pro Val Phe Gly Val Asp Ala
1 5

<210> SEQ ID NO 246
<211> LENGTH: 6
<212> TYPE: PRT
<213> ORGANISM: Artificial Sequence
<220> FEATURE:
<223> OTHER INFORMATION: Conserved GGBP Sequence

<400> SEQUENCE: 246

Val Phe Gly Val Asp Ala
1 5

<210> SEQ ID NO 247
<211> LENGTH: 6
<212> TYPE: PRT
<213> ORGANISM: Artificial Sequence
<220> FEATURE:
<223> OTHER INFORMATION: Conserved GGBP Sequence

<400> SEQUENCE: 247

Pro Val Phe Gly Val Asp
1 5

<210> SEQ ID NO 248
<211> LENGTH: 5
<212> TYPE: PRT
<213> ORGANISM: Artificial Sequence
<220> FEATURE:
<223> OTHER INFORMATION: Conserved GGBP Sequence

<400> SEQUENCE: 248

Phe Gly Val Asp Ala
1 5

<210> SEQ ID NO 249
<211> LENGTH: 7
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 249

Pro Val Xaa Gly Val Asp Ala
1 5

<210> SEQ ID NO 250
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 250

Val Xaa Gly Val Asp Ala
1               5

<210> SEQ ID NO 251
<211> LENGTH: 6
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 251

Pro Val Xaa Gly Val Asp
1               5

<210> SEQ ID NO 252
<211> LENGTH: 5
<212> TYPE: PRT
<213> ORGANISM: Artificial Sequence
<220> FEATURE:
<223> OTHER INFORMATION: Conserved GGBP Sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 252

Val Xaa Gly Val Asp
1               5

<210> SEQ ID NO 253
<211> LENGTH: 7
<212> TYPE: PRT
<213> ORGANISM: Artificial Sequence
<220> FEATURE:
<223> OTHER INFORMATION: Conserved GGBP Sequence

<400> SEQUENCE: 253

Gly Thr Val Leu Asn Asp Ala
1               5

<210> SEQ ID NO 254
<211> LENGTH: 6
<212> TYPE: PRT
<213> ORGANISM: Artificial Sequence
<220> FEATURE:
<223> OTHER INFORMATION: Conserved GGBP Sequence

<400> SEQUENCE: 254

Gly Thr Val Leu Asn Asp
1               5

<210> SEQ ID NO 255
<211> LENGTH: 5
<212> TYPE: PRT
<213> ORGANISM: Artificial Sequence
<220> FEATURE:
<223> OTHER INFORMATION: Conserved GGBP Sequence

<400> SEQUENCE: 255

Gly Thr Val Leu Asn
1 5

<210> SEQ ID NO 256
<211> LENGTH: 5
<212> TYPE: PRT
<213> ORGANISM: Artificial Sequence
<220> FEATURE:
<223> OTHER INFORMATION: Conserved GGBP Sequence

<400> SEQUENCE: 256

Thr Val Leu Asn Asp
1 5

<210> SEQ ID NO 257
<211> LENGTH: 325
<212> TYPE: PRT
<213> ORGANISM: Artificial Sequence
<220> FEATURE:
<223> OTHER INFORMATION: chyGGBP_F12C (chGGBP with signal sequence replaced with M; F12C, C39A, and C206A mutations; and GGSHHHHHH at C-terminus)

<400> SEQUENCE: 257

Met Lys Pro Tyr Ile Gly Val Ala Ile Tyr Lys Cys Asp Asp Thr Phe
1 5 10 15

Met Thr Gly Val Arg Asn Ala Ile Ala Lys Glu Gly Glu Gly Lys Ala
20 25 30

Lys Leu Asp Phe Val Asp Ala Gln Asn Ser Gln Ser Thr Gln Asn Asp
35 40 45

Lys Ile Asp Leu Phe Ile Thr Lys Lys Val Asp Ala Leu Ala Ile Asn
50 55 60

Pro Val Asp Arg Thr Ala Ala Gly Val Leu Ile Asp Lys Ala Lys Gln
65 70 75 80

Ala Asn Ile Pro Val Val Phe Phe Asn Arg Glu Pro Leu Pro Glu Asp
85 90 95

Met Lys Lys Trp Asp Lys Val Tyr Tyr Val Gly Ala Lys Ala Glu Gln
100 105 110

Ser Gly Thr Leu Gln Gly Glu Ile Met Ala Glu Tyr Trp Lys Ser His
115 120 125

Pro Glu Ala Asp Lys Asn His Asn Gly Ile Met Glu Tyr Val Met Ile
130 135 140

Thr Gly Glu Pro Gly His Gln Asp Ala Ile Leu Arg Thr Glu Tyr Ser
145 150 155 160

Ile Lys Ala Val Glu Ala Ala Gly Ile Lys Thr Lys Ala Leu Ala Gln
165 170 175

Asp Thr Ala Met Trp Asp Arg Val Lys Gly Gln Glu Lys Met Gln Ala
180 185 190

Phe Leu Ala Ser Phe Gly Asp Arg Ile Glu Ala Val Phe Ala Asn Asn
195 200 205

Asp Asp Met Ala Leu Gly Ala Ile Glu Ala Leu Lys Ala Ala Gly Tyr
210 215 220

Phe Lys Asn Gly Lys Tyr Ile Pro Val Val Gly Val Asp Ala Thr Thr
225 230 235 240

Pro Gly Leu Gln Ala Leu Glu Glu Gly Thr Leu Leu Gly Thr Val Leu
245 250 255

Asn Asp Ala Lys Ala Gln Gly Lys Ala Thr Phe Asn Leu Ala Tyr Val
260 265 270

Leu Ala Lys Gly Glu Lys Pro Thr Lys Glu Asn Val Gly Phe Asp Ile
275 280 285

Thr Asp Gly Lys Tyr Ile Trp Val Pro Tyr Gln Lys Val Thr Lys Asp
290 295 300

Asn Leu Glu Glu Met Lys Lys Tyr Val Asn Glu Gln Gly Gly Ser His
305 310 315 320

His His His His His
325

<210> SEQ ID NO 258
<211> LENGTH: 325
<212> TYPE: PRT
<213> ORGANISM: Artificial Sequence
<220> FEATURE:
<223> OTHER INFORMATION: chyGGBP_F16C (chGGBP with signal sequence replaced with M; F16C, C39A, and C206A mutations; and GGSHHHHHH at C-terminus)

<400> SEQUENCE: 258

Met Lys Pro Tyr Ile Gly Val Ala Ile Tyr Lys Phe Asp Asp Thr Cys
1 5 10 15

Met Thr Gly Val Arg Asn Ala Ile Ala Lys Glu Gly Glu Gly Lys Ala
20 25 30

Lys Leu Asp Phe Val Asp Ala Gln Asn Ser Gln Ser Thr Gln Asn Asp
35 40 45

Lys Ile Asp Leu Phe Ile Thr Lys Lys Val Asp Ala Leu Ala Ile Asn
50 55 60

Pro Val Asp Arg Thr Ala Ala Gly Val Leu Ile Asp Lys Ala Lys Gln
65 70 75 80

Ala Asn Ile Pro Val Val Phe Phe Asn Arg Glu Pro Leu Pro Glu Asp
85 90 95

Met Lys Lys Trp Asp Lys Val Tyr Tyr Val Gly Ala Lys Ala Glu Gln
100 105 110

Ser Gly Thr Leu Gln Gly Glu Ile Met Ala Glu Tyr Trp Lys Ser His
115 120 125

Pro Glu Ala Asp Lys Asn His Asn Gly Ile Met Glu Tyr Val Met Ile
130 135 140

Thr Gly Glu Pro Gly His Gln Asp Ala Ile Leu Arg Thr Glu Tyr Ser
145 150 155 160

Ile Lys Ala Val Glu Ala Ala Gly Ile Lys Thr Lys Ala Leu Ala Gln
165 170 175

Asp Thr Ala Met Trp Asp Arg Val Lys Gly Gln Glu Lys Met Gln Ala
180 185 190

Phe Leu Ala Ser Phe Gly Asp Arg Ile Glu Ala Val Phe Ala Asn Asn
195 200 205

Asp Asp Met Ala Leu Gly Ala Ile Glu Ala Leu Lys Ala Ala Gly Tyr
210 215 220

Phe Lys Asn Gly Lys Tyr Ile Pro Val Val Gly Val Asp Ala Thr Thr
225 230 235 240

Pro Gly Leu Gln Ala Leu Glu Glu Gly Thr Leu Leu Gly Thr Val Leu
245 250 255

Asn Asp Ala Lys Ala Gln Gly Lys Ala Thr Phe Asn Leu Ala Tyr Val
260 265 270

Leu Ala Lys Gly Glu Lys Pro Thr Lys Glu Asn Val Gly Phe Asp Ile
275 280 285

-continued

```
Thr Asp Gly Lys Tyr Ile Trp Val Pro Tyr Gln Lys Val Thr Lys Asp
    290                 295                 300

Asn Leu Glu Glu Met Lys Lys Tyr Val Asn Glu Gln Gly Gly Ser His
305                 310                 315                 320

His His His His His
                325


<210> SEQ ID NO 259
<211> LENGTH: 325
<212> TYPE: PRT
<213> ORGANISM: Artificial Sequence
<220> FEATURE:
<223> OTHER INFORMATION: chyGGBP_W181C (chGGBP with signal sequence
      replaced with M; W181C, C39A, and C206A mutations; and GGSHHHHHH
      at C-terminus)

<400> SEQUENCE: 259

Met Lys Pro Tyr Ile Gly Val Ala Ile Tyr Lys Phe Asp Asp Thr Phe
1               5                   10                  15

Met Thr Gly Val Arg Asn Ala Ile Ala Lys Glu Gly Glu Gly Lys Ala
            20                  25                  30

Lys Leu Asp Phe Val Asp Ala Gln Asn Ser Gln Ser Thr Gln Asn Asp
        35                  40                  45

Lys Ile Asp Leu Phe Ile Thr Lys Lys Val Asp Ala Leu Ala Ile Asn
    50                  55                  60

Pro Val Asp Arg Thr Ala Ala Gly Val Leu Ile Asp Lys Ala Lys Gln
65                  70                  75                  80

Ala Asn Ile Pro Val Val Phe Phe Asn Arg Glu Pro Leu Pro Glu Asp
                85                  90                  95

Met Lys Lys Trp Asp Lys Val Tyr Tyr Val Gly Ala Lys Ala Glu Gln
            100                 105                 110

Ser Gly Thr Leu Gln Gly Glu Ile Met Ala Glu Tyr Trp Lys Ser His
        115                 120                 125

Pro Glu Ala Asp Lys Asn His Asn Gly Ile Met Glu Tyr Val Met Ile
    130                 135                 140

Thr Gly Glu Pro Gly His Gln Asp Ala Ile Leu Arg Thr Glu Tyr Ser
145                 150                 155                 160

Ile Lys Ala Val Glu Ala Ala Gly Ile Lys Thr Lys Ala Leu Ala Gln
                165                 170                 175

Asp Thr Ala Met Cys Asp Arg Val Lys Gly Gln Glu Lys Met Gln Ala
            180                 185                 190

Phe Leu Ala Ser Phe Gly Asp Arg Ile Glu Ala Val Phe Ala Asn Asn
        195                 200                 205

Asp Asp Met Ala Leu Gly Ala Ile Glu Ala Leu Lys Ala Ala Gly Tyr
    210                 215                 220

Phe Lys Asn Gly Lys Tyr Ile Pro Val Val Gly Val Asp Ala Thr Thr
225                 230                 235                 240

Pro Gly Leu Gln Ala Leu Glu Glu Gly Thr Leu Leu Gly Thr Val Leu
                245                 250                 255

Asn Asp Ala Lys Ala Gln Gly Lys Ala Thr Phe Asn Leu Ala Tyr Val
            260                 265                 270

Leu Ala Lys Gly Glu Lys Pro Thr Lys Glu Asn Val Gly Phe Asp Ile
        275                 280                 285

Thr Asp Gly Lys Tyr Ile Trp Val Pro Tyr Gln Lys Val Thr Lys Asp
    290                 295                 300

Asn Leu Glu Glu Met Lys Lys Tyr Val Asn Glu Gln Gly Gly Ser His
```

305 310 315 320

His His His His His
325

<210> SEQ ID NO 260
<211> LENGTH: 325
<212> TYPE: PRT
<213> ORGANISM: Artificial Sequence
<220> FEATURE:
<223> OTHER INFORMATION: cobGGBP_F12C (cobGGBP with signal sequence replaced with M; F12C, C39A, C173A, and C206A mutations; and GGSHHHHHH at C-terminus)

<400> SEQUENCE: 260

Met Lys Pro Tyr Ile Gly Val Ala Ile Tyr Lys Cys Asp Asp Thr Phe
1 5 10 15

Met Thr Gly Val Arg Asn Ala Ile Ala Lys Glu Gly Glu Gly Lys Ala
20 25 30

Lys Leu Asp Phe Val Asp Ala Gln Asn Ser Gln Ser Thr Gln Asn Asp
35 40 45

Lys Ile Asp Leu Phe Ile Thr Lys Lys Val Asp Ala Leu Ala Ile Asn
50 55 60

Pro Val Asp Arg Thr Ala Ala Gly Val Leu Ile Asp Lys Ala Lys Gln
65 70 75 80

Ala Asn Ile Pro Val Val Phe Phe Asn Arg Glu Pro Leu Pro Glu Asp
85 90 95

Met Lys Lys Trp Asp Lys Val Tyr Tyr Val Gly Ala Lys Ala Glu Gln
100 105 110

Ser Gly Thr Leu Gln Gly Glu Ile Met Ala Glu Tyr Trp Lys Ser His
115 120 125

Pro Glu Ala Asp Lys Asn His Asp Gly Ile Met Gln Tyr Val Met Ile
130 135 140

Thr Gly Glu Pro Gly His Gln Asp Ala Ile Leu Arg Thr Glu Tyr Ser
145 150 155 160

Ile Lys Ala Val Glu Ala Ala Gly Ile Arg Val Lys Ala Leu Ala Gln
165 170 175

Asp Thr Ala Met Trp Asp Arg Val Lys Gly Gln Glu Lys Met Gln Ala
180 185 190

Phe Leu Ala Ser Phe Gly Asp Lys Ile Glu Ala Val Phe Ala Asn Asn
195 200 205

Asp Asp Met Ala Leu Gly Ala Ile Glu Ala Leu Lys Ala Ala Gly Tyr
210 215 220

Phe Lys Asp Gly Lys Tyr Val Pro Val Val Gly Val Asp Ala Thr Thr
225 230 235 240

Pro Gly Leu Gln Ala Leu Glu Glu Gly Thr Leu Leu Gly Thr Val Leu
245 250 255

Asn Asp Ala Lys Ala Gln Gly Lys Ala Thr Phe Asn Leu Ala Tyr Val
260 265 270

Leu Ala Lys Gly Glu Lys Pro Thr Lys Glu Asn Val Gly Phe Glu Ile
275 280 285

Thr Asp Gly Lys Tyr Ile Trp Val Pro Tyr Gln Lys Val Thr Lys Asp
290 295 300

Asn Leu Glu Glu Met Lys Lys Tyr Val Asn Glu Gln Gly Gly Ser His
305 310 315 320

His His His His His
325

<210> SEQ ID NO 261
<211> LENGTH: 325
<212> TYPE: PRT
<213> ORGANISM: Artificial Sequence
<220> FEATURE:
<223> OTHER INFORMATION: cobGGBP_F16C (cobGGBP with signal sequence replaced with M; F16C, C39A, C173A, and C206A mutations; and GGSHHHHHH at C-terminus)

<400> SEQUENCE: 261

```
Met Lys Pro Tyr Ile Gly Val Ala Ile Tyr Lys Phe Asp Asp Thr Cys
1               5                   10                  15

Met Thr Gly Val Arg Asn Ala Ile Ala Lys Glu Gly Glu Gly Lys Ala
            20                  25                  30

Lys Leu Asp Phe Val Asp Ala Gln Asn Ser Gln Ser Thr Gln Asn Asp
        35                  40                  45

Lys Ile Asp Leu Phe Ile Thr Lys Lys Val Asp Ala Leu Ala Ile Asn
    50                  55                  60

Pro Val Asp Arg Thr Ala Ala Gly Val Leu Ile Asp Lys Ala Lys Gln
65                  70                  75                  80

Ala Asn Ile Pro Val Val Phe Phe Asn Arg Glu Pro Leu Pro Glu Asp
                85                  90                  95

Met Lys Lys Trp Asp Lys Val Tyr Tyr Val Gly Ala Lys Ala Glu Gln
            100                 105                 110

Ser Gly Thr Leu Gln Gly Glu Ile Met Ala Glu Tyr Trp Lys Ser His
        115                 120                 125

Pro Glu Ala Asp Lys Asn His Asp Gly Ile Met Gln Tyr Val Met Ile
    130                 135                 140

Thr Gly Glu Pro Gly His Gln Asp Ala Ile Leu Arg Thr Glu Tyr Ser
145                 150                 155                 160

Ile Lys Ala Val Glu Ala Ala Gly Ile Arg Val Lys Ala Leu Ala Gln
                165                 170                 175

Asp Thr Ala Met Trp Asp Arg Val Lys Gly Gln Glu Lys Met Gln Ala
            180                 185                 190

Phe Leu Ala Ser Phe Gly Asp Lys Ile Glu Ala Val Phe Ala Asn Asn
        195                 200                 205

Asp Asp Met Ala Leu Gly Ala Ile Glu Ala Leu Lys Ala Ala Gly Tyr
    210                 215                 220

Phe Lys Asp Gly Lys Tyr Val Pro Val Val Gly Val Asp Ala Thr Thr
225                 230                 235                 240

Pro Gly Leu Gln Ala Leu Glu Glu Gly Thr Leu Leu Gly Thr Val Leu
                245                 250                 255

Asn Asp Ala Lys Ala Gln Gly Lys Ala Thr Phe Asn Leu Ala Tyr Val
            260                 265                 270

Leu Ala Lys Gly Glu Lys Pro Thr Lys Glu Asn Val Gly Phe Glu Ile
        275                 280                 285

Thr Asp Gly Lys Tyr Ile Trp Val Pro Tyr Gln Lys Val Thr Lys Asp
    290                 295                 300

Asn Leu Glu Glu Met Lys Lys Tyr Val Asn Glu Gln Gly Gly Ser His
305                 310                 315                 320

His His His His His
                325
```

<210> SEQ ID NO 262
<211> LENGTH: 325

<212> TYPE: PRT
<213> ORGANISM: Artificial Sequence
<220> FEATURE:
<223> OTHER INFORMATION: cobGGBP_W181C (cobGGBP with signal sequence replaced with M, W181C, C39A, C173A, and C206A mutations; and GGSHHHHHH at C-terminus)

<400> SEQUENCE: 262

```
Met Lys Pro Tyr Ile Gly Val Ala Ile Tyr Lys Phe Asp Asp Thr Phe
1               5                   10                  15

Met Thr Gly Val Arg Asn Ala Ile Ala Lys Glu Gly Glu Gly Lys Ala
            20                  25                  30

Lys Leu Asp Phe Val Asp Ala Gln Asn Ser Gln Ser Thr Gln Asn Asp
        35                  40                  45

Lys Ile Asp Leu Phe Ile Thr Lys Lys Val Asp Ala Leu Ala Ile Asn
    50                  55                  60

Pro Val Asp Arg Thr Ala Ala Gly Val Leu Ile Asp Lys Ala Lys Gln
65                  70                  75                  80

Ala Asn Ile Pro Val Val Phe Phe Asn Arg Glu Pro Leu Pro Glu Asp
                85                  90                  95

Met Lys Lys Trp Asp Lys Val Tyr Tyr Val Gly Ala Lys Ala Glu Gln
            100                 105                 110

Ser Gly Thr Leu Gln Gly Glu Ile Met Ala Glu Tyr Trp Lys Ser His
        115                 120                 125

Pro Glu Ala Asp Lys Asn His Asp Gly Ile Met Gln Tyr Val Met Ile
    130                 135                 140

Thr Gly Glu Pro Gly His Gln Asp Ala Ile Leu Arg Thr Glu Tyr Ser
145                 150                 155                 160

Ile Lys Ala Val Glu Ala Ala Gly Ile Arg Val Lys Ala Leu Ala Gln
                165                 170                 175

Asp Thr Ala Met Cys Asp Arg Val Lys Gly Gln Glu Lys Met Gln Ala
            180                 185                 190

Phe Leu Ala Ser Phe Gly Asp Lys Ile Glu Ala Val Phe Ala Asn Asn
        195                 200                 205

Asp Asp Met Ala Leu Gly Ala Ile Glu Ala Leu Lys Ala Ala Gly Tyr
    210                 215                 220

Phe Lys Asp Gly Lys Tyr Val Pro Val Val Gly Val Asp Ala Thr Thr
225                 230                 235                 240

Pro Gly Leu Gln Ala Leu Glu Glu Gly Thr Leu Leu Gly Thr Val Leu
                245                 250                 255

Asn Asp Ala Lys Ala Gln Gly Lys Ala Thr Phe Asn Leu Ala Tyr Val
            260                 265                 270

Leu Ala Lys Gly Glu Lys Pro Thr Lys Glu Asn Val Gly Phe Glu Ile
        275                 280                 285

Thr Asp Gly Lys Tyr Ile Trp Val Pro Tyr Gln Lys Val Thr Lys Asp
    290                 295                 300

Asn Leu Glu Glu Met Lys Lys Tyr Val Asn Glu Gln Gly Gly Ser His
305                 310                 315                 320

His His His His His
                325
```

<210> SEQ ID NO 263
<211> LENGTH: 316
<212> TYPE: PRT
<213> ORGANISM: Artificial Sequence
<220> FEATURE:
<223> OTHER INFORMATION: pspGGPB_F13C (pspGGBP with signal sequence replaced with M; F13C mutation; and GGSHHHHHH at C-terminus)

<400> SEQUENCE: 263

Met Val Gly Val Ala Ile Tyr Lys Phe Asp Asp Thr Cys Met Thr Gly
1               5                   10                  15

Val Arg Asn Ala Met Ser Asp Ala Ala Asn Gly Val Ala Lys Leu Asp
            20                  25                  30

Ile Val Asp Ser Gln Asn Ala Gln Pro Thr Gln Asn Glu Lys Ile Asp
        35                  40                  45

Leu Phe Ile Ser Lys Lys Tyr Ser Ser Met Ile Ile Asn Pro Val Asp
    50                  55                  60

Arg Thr Ala Ala Gly Val Ile Ile Asp Lys Ala Lys Thr Ala Asn Thr
65                  70                  75                  80

Pro Val Val Phe Leu Asn Arg Glu Pro Ile Ala Glu Asp Met Asn Lys
                85                  90                  95

Trp Asp Lys Val Tyr Tyr Val Gly Ala Lys Ala Glu Glu Ser Gly Thr
            100                 105                 110

Ile Ser Gly Gln Leu Ile Val Asp Tyr Trp Lys Ala Asn Pro Lys Ala
        115                 120                 125

Asp Lys Asn Gly Asp Gly Lys Leu Gln Tyr Val Leu Leu Gln Gly Glu
    130                 135                 140

Pro Gly His Gln Asp Ala Glu Leu Arg Thr Lys Phe Ser Val Gln Ala
145                 150                 155                 160

Ile Gln Asp Ala Gly Ile Glu Val Glu Ala Leu Ala Val Asp Thr Ala
                165                 170                 175

Met Trp Asp Arg Val Lys Gly Gln Glu Lys Met Gln Thr Phe Leu Ala
            180                 185                 190

Ser His Gly Asp Lys Ile Glu Ala Val Leu Ala Asn Asn Asp Asp Met
        195                 200                 205

Ala Leu Gly Ala Ile Glu Ala Leu Lys Ala Ala Gly Tyr Phe Ser Gly
    210                 215                 220

Asp Lys Tyr Met Pro Val Val Gly Val Asp Ala Thr Ala Pro Ala Val
225                 230                 235                 240

Gln Ala Leu Glu Asp Gly Thr Leu Leu Gly Thr Val Leu Asn Asp Ala
                245                 250                 255

Lys Ser Gln Gly Lys Ala Ser Val Ala Ile Ala Ala Ala Leu Ser Lys
            260                 265                 270

Gly Glu Ala Pro Asn Lys Glu Asn Thr Gly Phe Asp Ile Thr Asp Gly
        275                 280                 285

Lys Tyr Val Trp Ile Ala Tyr Lys Lys Ile Thr Lys Asp Asn Ile Ala
    290                 295                 300

Asp Ala Lys Gly Gly Ser His His His His His His
305                 310                 315

<210> SEQ ID NO 264
<211> LENGTH: 316
<212> TYPE: PRT
<213> ORGANISM: Artificial Sequence
<220> FEATURE:
<223> OTHER INFORMATION: pspGGPB_F9C (pspGGBP with signal sequence
replaced with M; F9C mutation; and GGSHHHHHH at C-terminus)

<400> SEQUENCE: 264

Met Val Gly Val Ala Ile Tyr Lys Cys Asp Asp Thr Phe Met Thr Gly
1               5                   10                  15

Val Arg Asn Ala Met Ser Asp Ala Ala Asn Gly Val Ala Lys Leu Asp

```
            20                  25                  30

Ile Val Asp Ser Gln Asn Ala Gln Pro Thr Gln Asn Glu Lys Ile Asp
        35                  40                  45

Leu Phe Ile Ser Lys Lys Tyr Ser Ser Met Ile Ile Asn Pro Val Asp
    50                  55                  60

Arg Thr Ala Ala Gly Val Ile Ile Asp Lys Ala Lys Thr Ala Asn Thr
65                  70                  75                  80

Pro Val Val Phe Leu Asn Arg Glu Pro Ile Ala Glu Asp Met Asn Lys
                85                  90                  95

Trp Asp Lys Val Tyr Tyr Val Gly Ala Lys Ala Glu Glu Ser Gly Thr
            100                 105                 110

Ile Ser Gly Gln Leu Ile Val Asp Tyr Trp Lys Ala Asn Pro Lys Ala
        115                 120                 125

Asp Lys Asn Gly Asp Gly Lys Leu Gln Tyr Val Leu Leu Gln Gly Glu
    130                 135                 140

Pro Gly His Gln Asp Ala Glu Leu Arg Thr Lys Phe Ser Val Gln Ala
145                 150                 155                 160

Ile Gln Asp Ala Gly Ile Glu Val Glu Ala Leu Ala Val Asp Thr Ala
                165                 170                 175

Met Trp Asp Arg Val Lys Gly Gln Glu Lys Met Gln Thr Phe Leu Ala
            180                 185                 190

Ser His Gly Asp Lys Ile Glu Ala Val Leu Ala Asn Asn Asp Asp Met
        195                 200                 205

Ala Leu Gly Ala Ile Glu Ala Leu Lys Ala Ala Gly Tyr Phe Ser Gly
    210                 215                 220

Asp Lys Tyr Met Pro Val Val Gly Val Asp Ala Thr Ala Pro Ala Val
225                 230                 235                 240

Gln Ala Leu Glu Asp Gly Thr Leu Leu Gly Thr Val Leu Asn Asp Ala
                245                 250                 255

Lys Ser Gln Gly Lys Ala Ser Val Ala Ile Ala Ala Ala Leu Ser Lys
            260                 265                 270

Gly Glu Ala Pro Asn Lys Glu Asn Thr Gly Phe Asp Ile Thr Asp Gly
        275                 280                 285

Lys Tyr Val Trp Ile Ala Tyr Lys Lys Ile Thr Lys Asp Asn Ile Ala
    290                 295                 300

Asp Ala Lys Gly Gly Ser His His His His His His
305                 310                 315


<210> SEQ ID NO 265
<211> LENGTH: 316
<212> TYPE: PRT
<213> ORGANISM: Artificial Sequence
<220> FEATURE:
<223> OTHER INFORMATION: pspGGPB_W178C (pspGGBP with signal sequence
      replaced with M; W178C mutation; and GGSHHHHHH at C-terminus)

<400> SEQUENCE: 265

Met Val Gly Val Ala Ile Tyr Lys Phe Asp Asp Thr Phe Met Thr Gly
1               5                   10                  15

Val Arg Asn Ala Met Ser Asp Ala Ala Asn Gly Val Ala Lys Leu Asp
            20                  25                  30

Ile Val Asp Ser Gln Asn Ala Gln Pro Thr Gln Asn Glu Lys Ile Asp
        35                  40                  45

Leu Phe Ile Ser Lys Lys Tyr Ser Ser Met Ile Ile Asn Pro Val Asp
    50                  55                  60
```

```
Arg Thr Ala Ala Gly Val Ile Ile Asp Lys Ala Lys Thr Ala Asn Thr
65                  70                  75                  80

Pro Val Val Phe Leu Asn Arg Glu Pro Ile Ala Glu Asp Met Asn Lys
                85                  90                  95

Trp Asp Lys Val Tyr Tyr Val Gly Ala Lys Ala Glu Glu Ser Gly Thr
            100                 105                 110

Ile Ser Gly Gln Leu Ile Val Asp Tyr Trp Lys Ala Asn Pro Lys Ala
        115                 120                 125

Asp Lys Asn Gly Asp Gly Lys Leu Gln Tyr Val Leu Leu Gln Gly Glu
    130                 135                 140

Pro Gly His Gln Asp Ala Glu Leu Arg Thr Lys Phe Ser Val Gln Ala
145                 150                 155                 160

Ile Gln Asp Ala Gly Ile Glu Val Glu Ala Leu Ala Val Asp Thr Ala
                165                 170                 175

Met Cys Asp Arg Val Lys Gly Gln Glu Lys Met Gln Thr Phe Leu Ala
            180                 185                 190

Ser His Gly Asp Lys Ile Glu Ala Val Leu Ala Asn Asn Asp Asp Met
        195                 200                 205

Ala Leu Gly Ala Ile Glu Ala Leu Lys Ala Ala Gly Tyr Phe Ser Gly
    210                 215                 220

Asp Lys Tyr Met Pro Val Val Gly Val Asp Ala Thr Ala Pro Ala Val
225                 230                 235                 240

Gln Ala Leu Glu Asp Gly Thr Leu Leu Gly Thr Val Leu Asn Asp Ala
                245                 250                 255

Lys Ser Gln Gly Lys Ala Ser Val Ala Ile Ala Ala Ala Leu Ser Lys
            260                 265                 270

Gly Glu Ala Pro Asn Lys Glu Asn Thr Gly Phe Asp Ile Thr Asp Gly
        275                 280                 285

Lys Tyr Val Trp Ile Ala Tyr Lys Lys Ile Thr Lys Asp Asn Ile Ala
    290                 295                 300

Asp Ala Lys Gly Gly Ser His His His His His His
305                 310                 315


<210> SEQ ID NO 266
<211> LENGTH: 316
<212> TYPE: PRT
<213> ORGANISM: Artificial Sequence
<220> FEATURE:
<223> OTHER INFORMATION: csaGGBP_F18C  (csaGGBP with signal sequence
      replaced with M; F18C, C62A,C82A,C113A, and C211A mutations; and
      GGSHHHHHH at C-terminus)

<400> SEQUENCE: 266

Met Glu Thr Gly Pro Lys Ile Gly Val Ser Ile Tyr Arg Tyr Asp Asp
1               5                   10                  15

Thr Cys Met Lys Leu Tyr Arg Gln Glu Leu Lys Gln Tyr Leu Glu Glu
            20                  25                  30

Thr Tyr His Ala Glu Val Ile Met Arg Asn Ala Gly Gly Asp Gln Lys
        35                  40                  45

Glu Gln Asp Lys Gln Val Asn Gln Phe Ile Ser Asp Gly Ala Asp Gly
    50                  55                  60

Ile Ile Val Asn Pro Val Glu Ile Pro Ala Ala Gln Glu Leu Ala Asp
65                  70                  75                  80

Ala Ala Ser Arg Ala Gly Ile Pro Leu Val Phe Ile Asn Arg Glu Pro
                85                  90                  95

Lys Glu Glu Glu Gln Lys Arg Trp Arg Glu Lys Gln Met Ala Val Ser
```

```
            100                 105                 110

Ala Val Gly Thr Asp Ser Arg Gln Ala Gly Thr Tyr Gln Gly Glu Ile
        115                 120                 125

Ile Leu Glu Thr Leu Asn Lys Gly Asp Phe Asn Gly Asp Gly Val Val
    130                 135                 140

Ser Tyr Val Met Leu Met Gly Glu Lys Gly Asn Glu Asp Ser Gln Tyr
145                 150                 155                 160

Arg Thr Glu Tyr Ser Ile Lys Ala Leu Glu Glu Gly Gly Met Lys Thr
                165                 170                 175

Glu Glu Leu Phe Ser Gly Asn Gly Asn Trp Asn Lys Asp Glu Gly Lys
            180                 185                 190

Lys Leu Ala Lys Gln Ala Leu Ala Ser Trp Gly Asn Arg Ile Glu Val
        195                 200                 205

Phe Phe Ala Asn Asn Asp Ser Met Ala Asn Gly Ala Leu Glu Ala Val
    210                 215                 220

Glu Glu Ala Gly Arg Ile Pro Gly Lys Asp Ile Tyr Leu Val Gly Val
225                 230                 235                 240

Asp Ala Leu Gln Asp Thr Val Thr Tyr Ile Lys Glu Gly Arg Met Thr
                245                 250                 255

Gly Thr Val Leu Asn Asp His Glu Gly Gln Ser Gln Met Ala Ala Asp
            260                 265                 270

Thr Leu Lys Lys Met Ile Asp Gly Glu Ser Val Glu Thr Arg Tyr Gln
        275                 280                 285

Val Asp Tyr Ile Lys Val Thr Ala Ile Ser Thr Phe Gln Thr Leu Lys
    290                 295                 300

Gly Glu Asp Gly Gly Ser His His His His His His
305                 310                 315


<210> SEQ ID NO 267
<211> LENGTH: 316
<212> TYPE: PRT
<213> ORGANISM: Artificial Sequence
<220> FEATURE:
<223> OTHER INFORMATION: csaGGBP_W186C  (csaGGBP with signal sequence
      replaced with M; W186C, C62A,C82A,C113A, and C211A mutations; and
      GGSHHHHHH at C-terminus)

<400> SEQUENCE: 267

Met Glu Thr Gly Pro Lys Ile Gly Val Ser Ile Tyr Arg Tyr Asp Asp
1               5                   10                  15

Thr Phe Met Lys Leu Tyr Arg Gln Glu Leu Lys Gln Tyr Leu Glu Glu
            20                  25                  30

Thr Tyr His Ala Glu Val Ile Met Arg Asn Ala Gly Gly Asp Gln Lys
        35                  40                  45

Glu Gln Asp Lys Gln Val Asn Gln Phe Ile Ser Asp Gly Ala Asp Gly
    50                  55                  60

Ile Ile Val Asn Pro Val Glu Ile Pro Ala Ala Gln Glu Leu Ala Asp
65                  70                  75                  80

Ala Ala Ser Arg Ala Gly Ile Pro Leu Val Phe Ile Asn Arg Glu Pro
                85                  90                  95

Lys Glu Glu Glu Gln Lys Arg Trp Arg Glu Lys Gln Met Ala Val Ser
            100                 105                 110

Ala Val Gly Thr Asp Ser Arg Gln Ala Gly Thr Tyr Gln Gly Glu Ile
        115                 120                 125

Ile Leu Glu Thr Leu Asn Lys Gly Asp Phe Asn Gly Asp Gly Val Val
    130                 135                 140
```

Ser Tyr Val Met Leu Met Gly Glu Lys Gly Asn Glu Asp Ser Gln Tyr
145 150 155 160

Arg Thr Glu Tyr Ser Ile Lys Ala Leu Glu Glu Gly Gly Met Lys Thr
165 170 175

Glu Glu Leu Phe Ser Gly Asn Gly Asn Cys Asn Lys Asp Glu Gly Lys
180 185 190

Lys Leu Ala Lys Gln Ala Leu Ala Ser Trp Gly Asn Arg Ile Glu Val
195 200 205

Phe Phe Ala Asn Asn Asp Ser Met Ala Asn Gly Ala Leu Glu Ala Val
210 215 220

Glu Glu Ala Gly Arg Ile Pro Gly Lys Asp Ile Tyr Leu Val Gly Val
225 230 235 240

Asp Ala Leu Gln Asp Thr Val Thr Tyr Ile Lys Glu Gly Arg Met Thr
245 250 255

Gly Thr Val Leu Asn Asp His Glu Gly Gln Ser Gln Met Ala Ala Asp
260 265 270

Thr Leu Lys Lys Met Ile Asp Gly Glu Ser Val Glu Thr Arg Tyr Gln
275 280 285

Val Asp Tyr Ile Lys Val Thr Ala Ile Ser Thr Phe Gln Thr Leu Lys
290 295 300

Gly Glu Asp Gly Gly Ser His His His His His His
305 310 315

<210> SEQ ID NO 268
<211> LENGTH: 316
<212> TYPE: PRT
<213> ORGANISM: Artificial Sequence
<220> FEATURE:
<223> OTHER INFORMATION: csaGGBP_Y14C (csaGGBP with signal sequence replaced with M; Y14C, C62A,C82A,C113A, and C211A mutations; and GGSHHHHHH at C-terminus)

<400> SEQUENCE: 268

Met Glu Thr Gly Pro Lys Ile Gly Val Ser Ile Tyr Arg Cys Asp Asp
1 5 10 15

Thr Phe Met Lys Leu Tyr Arg Gln Glu Leu Lys Gln Tyr Leu Glu Glu
20 25 30

Thr Tyr His Ala Glu Val Ile Met Arg Asn Ala Gly Gly Asp Gln Lys
35 40 45

Glu Gln Asp Lys Gln Val Asn Gln Phe Ile Ser Asp Gly Ala Asp Gly
50 55 60

Ile Ile Val Asn Pro Val Glu Ile Pro Ala Ala Gln Glu Leu Ala Asp
65 70 75 80

Ala Ala Ser Arg Ala Gly Ile Pro Leu Val Phe Ile Asn Arg Glu Pro
85 90 95

Lys Glu Glu Glu Gln Lys Arg Trp Arg Glu Lys Gln Met Ala Val Ser
100 105 110

Ala Val Gly Thr Asp Ser Arg Gln Ala Gly Thr Tyr Gln Gly Glu Ile
115 120 125

Ile Leu Glu Thr Leu Asn Lys Gly Asp Phe Asn Gly Asp Gly Val Val
130 135 140

Ser Tyr Val Met Leu Met Gly Glu Lys Gly Asn Glu Asp Ser Gln Tyr
145 150 155 160

Arg Thr Glu Tyr Ser Ile Lys Ala Leu Glu Glu Gly Gly Met Lys Thr
165 170 175

```
Glu Glu Leu Phe Ser Gly Asn Gly Asn Trp Asn Lys Asp Glu Gly Lys
            180                 185                 190

Lys Leu Ala Lys Gln Ala Leu Ala Ser Trp Gly Asn Arg Ile Glu Val
        195                 200                 205

Phe Phe Ala Asn Asn Asp Ser Met Ala Asn Gly Ala Leu Glu Ala Val
    210                 215                 220

Glu Glu Ala Gly Arg Ile Pro Gly Lys Asp Ile Tyr Leu Val Gly Val
225                 230                 235                 240

Asp Ala Leu Gln Asp Thr Val Thr Tyr Ile Lys Glu Gly Arg Met Thr
                245                 250                 255

Gly Thr Val Leu Asn Asp His Glu Gly Gln Ser Gln Met Ala Ala Asp
            260                 265                 270

Thr Leu Lys Lys Met Ile Asp Gly Glu Ser Val Glu Thr Arg Tyr Gln
        275                 280                 285

Val Asp Tyr Ile Lys Val Thr Ala Ile Ser Thr Phe Gln Thr Leu Lys
    290                 295                 300

Gly Glu Asp Gly Gly Ser His His His His His His
305                 310                 315


<210> SEQ ID NO 269
<211> LENGTH: 323
<212> TYPE: PRT
<213> ORGANISM: Artificial Sequence
<220> FEATURE:
<223> OTHER INFORMATION: bprGGBP_F16C  (bprGGBP with signal sequence
      replaced with M; F16C, C8A, C112A, C116A, C179A, C211A, and C289A
      mutations; and GGSHHHHHH at C-terminus)

<400> SEQUENCE: 269

Met Asp Ala Lys Val Gly Val Ala Ile Tyr Gln Lys Ser Asp Asn Cys
1               5                   10                  15

Met Ser Leu Phe Ser Ser Glu Leu Val Lys Tyr Leu Val Ser Arg Gly
            20                  25                  30

Phe Ser Lys Asp Asn Ile Ile Leu Tyr Asp Ser Asn Asn Asp Glu Asn
        35                  40                  45

Val Gln Leu Ser Gln Val Glu Glu Leu Ile Ala Ser Gly Ile Asn Ala
    50                  55                  60

Leu Ile Ile Asn Pro Val Asn Ser Ser Val Ala His Ser Ile Thr Asp
65                  70                  75                  80

Met Ala Ser Ala Ser Asn Ile Pro Leu Val Tyr Ile Asn Arg Glu Pro
                85                  90                  95

Ser Gly Asp Glu Glu Asn Arg Trp Glu Met Tyr Gln Leu Asn Val Ala
            100                 105                 110

Tyr Val Gly Ala Asp Ala Arg Gln Ser Gly Ile Tyr Gln Gly Glu Ile
        115                 120                 125

Leu Leu Ser Leu Gly Lys Asn Lys Leu Asp His Asn Gly Asp Gly Lys
    130                 135                 140

Ile Gln Tyr Phe Met Ile Glu Gly Ala Pro Glu Asn Ile Asp Ala Gly
145                 150                 155                 160

Tyr Arg Thr Leu Tyr Ser Val Ser Ala Leu Gln Asn Ser Glu Met Glu
                165                 170                 175

Met Asp Ala Leu Leu Asp Glu Val Gly Asn Trp Asp Glu Thr Thr Ala
            180                 185                 190

Ser Leu Leu Val Ser Lys Gly Ile Gln Asn Gly Leu Lys Pro Glu Val
        195                 200                 205

Ile Ile Ala Asn Asn Asp Ala Met Ala Leu Gly Ala Ile Lys Ala Ala
```

```
    210                 215                 220

Glu Lys Ser Gly Leu Val Pro Gly Glu Asp Val Tyr Ile Val Gly Val
225                 230                 235                 240

Asp Ala Leu Pro Glu Ala Ile Glu Met Ile Lys Ala Gly Lys Leu Ala
                245                 250                 255

Gly Thr Val Tyr Asn Asp Tyr Val Leu Gln Ser His Lys Ser Ala Asp
            260                 265                 270

Ala Val Ile Asn Tyr Leu Lys Gly Ile Asp Asn Glu His Tyr Ile Gly
        275                 280                 285

Ala Asp Tyr Val Lys Val Asp Ile Asp Asn Ala Glu Ser Ile Ala Gly
    290                 295                 300

Leu Thr Asn Thr Asp Glu Glu Asp Ile Asp Gly Gly Ser His His His
305                 310                 315                 320

His His His


<210> SEQ ID NO 270
<211> LENGTH: 323
<212> TYPE: PRT
<213> ORGANISM: Artificial Sequence
<220> FEATURE:
<223> OTHER INFORMATION: bprGGBP_K12C  (bprGGBP with signal sequence
      replaced with M; K12C, C8A, C112A, C116A, C179A, C211A, and C289A
      mutations; and GGSHHHHHH at C-terminus)

<400> SEQUENCE: 270

Met Asp Ala Lys Val Gly Val Ala Ile Tyr Gln Cys Ser Asp Asn Phe
1               5                   10                  15

Met Ser Leu Phe Ser Ser Glu Leu Val Lys Tyr Leu Val Ser Arg Gly
            20                  25                  30

Phe Ser Lys Asp Asn Ile Ile Leu Tyr Asp Ser Asn Asn Asp Glu Asn
        35                  40                  45

Val Gln Leu Ser Gln Val Glu Glu Leu Ile Ala Ser Gly Ile Asn Ala
    50                  55                  60

Leu Ile Ile Asn Pro Val Asn Ser Ser Val Ala His Ser Ile Thr Asp
65                  70                  75                  80

Met Ala Ser Ala Ser Asn Ile Pro Leu Val Tyr Ile Asn Arg Glu Pro
                85                  90                  95

Ser Gly Asp Glu Glu Asn Arg Trp Glu Met Tyr Gln Leu Asn Val Ala
            100                 105                 110

Tyr Val Gly Ala Asp Ala Arg Gln Ser Gly Ile Tyr Gln Gly Glu Ile
        115                 120                 125

Leu Leu Ser Leu Gly Lys Asn Lys Leu Asp His Asn Gly Asp Gly Lys
    130                 135                 140

Ile Gln Tyr Phe Met Ile Glu Gly Ala Pro Glu Asn Ile Asp Ala Gly
145                 150                 155                 160

Tyr Arg Thr Leu Tyr Ser Val Ser Ala Leu Gln Asn Ser Glu Met Glu
                165                 170                 175

Met Asp Ala Leu Leu Asp Glu Val Gly Asn Trp Asp Glu Thr Thr Ala
            180                 185                 190

Ser Leu Leu Val Ser Lys Gly Ile Gln Asn Gly Leu Lys Pro Glu Val
        195                 200                 205

Ile Ile Ala Asn Asn Asp Ala Met Ala Leu Gly Ala Ile Lys Ala Ala
    210                 215                 220

Glu Lys Ser Gly Leu Val Pro Gly Glu Asp Val Tyr Ile Val Gly Val
225                 230                 235                 240
```

-continued

```
Asp Ala Leu Pro Glu Ala Ile Glu Met Ile Lys Ala Gly Lys Leu Ala
                245                 250                 255

Gly Thr Val Tyr Asn Asp Tyr Val Leu Gln Ser His Lys Ser Ala Asp
            260                 265                 270

Ala Val Ile Asn Tyr Leu Lys Gly Ile Asp Asn Glu His Tyr Ile Gly
        275                 280                 285

Ala Asp Tyr Val Lys Val Asp Ile Asp Asn Ala Glu Ser Ile Ala Gly
    290                 295                 300

Leu Thr Asn Thr Asp Glu Glu Asp Ile Asp Gly Gly Ser His His His
305                 310                 315                 320

His His His


<210> SEQ ID NO 271
<211> LENGTH: 323
<212> TYPE: PRT
<213> ORGANISM: Artificial Sequence
<220> FEATURE:
<223> OTHER INFORMATION: bprGGBP_W187C  (bprGGBP with signal sequence
      replaced with M; W187C, C8A, C112A, C116A, C179A, C211A, and C289A
      mutations; and GGSHHHHHH at C-terminus)

<400> SEQUENCE: 271

Met Asp Ala Lys Val Gly Val Ala Ile Tyr Gln Lys Ser Asp Asn Phe
1               5                   10                  15

Met Ser Leu Phe Ser Ser Glu Leu Val Lys Tyr Leu Val Ser Arg Gly
            20                  25                  30

Phe Ser Lys Asp Asn Ile Ile Leu Tyr Asp Ser Asn Asn Asp Glu Asn
        35                  40                  45

Val Gln Leu Ser Gln Val Glu Glu Leu Ile Ala Ser Gly Ile Asn Ala
    50                  55                  60

Leu Ile Ile Asn Pro Val Asn Ser Ser Val Ala His Ser Ile Thr Asp
65                  70                  75                  80

Met Ala Ser Ala Ser Asn Ile Pro Leu Val Tyr Ile Asn Arg Glu Pro
                85                  90                  95

Ser Gly Asp Glu Glu Asn Arg Trp Glu Met Tyr Gln Leu Asn Val Ala
            100                 105                 110

Tyr Val Gly Ala Asp Ala Arg Gln Ser Gly Ile Tyr Gln Gly Glu Ile
        115                 120                 125

Leu Leu Ser Leu Gly Lys Asn Lys Leu Asp His Asn Gly Asp Gly Lys
    130                 135                 140

Ile Gln Tyr Phe Met Ile Glu Gly Ala Pro Glu Asn Ile Asp Ala Gly
145                 150                 155                 160

Tyr Arg Thr Leu Tyr Ser Val Ser Ala Leu Gln Asn Ser Glu Met Glu
                165                 170                 175

Met Asp Ala Leu Leu Asp Glu Val Gly Asn Cys Asp Glu Thr Thr Ala
            180                 185                 190

Ser Leu Leu Val Ser Lys Gly Ile Gln Asn Gly Leu Lys Pro Glu Val
        195                 200                 205

Ile Ile Ala Asn Asn Asp Ala Met Ala Leu Gly Ala Ile Lys Ala Ala
    210                 215                 220

Glu Lys Ser Gly Leu Val Pro Gly Glu Asp Val Tyr Ile Val Gly Val
225                 230                 235                 240

Asp Ala Leu Pro Glu Ala Ile Glu Met Ile Lys Ala Gly Lys Leu Ala
                245                 250                 255

Gly Thr Val Tyr Asn Asp Tyr Val Leu Gln Ser His Lys Ser Ala Asp
            260                 265                 270
```

Ala Val Ile Asn Tyr Leu Lys Gly Ile Asp Asn Glu His Tyr Ile Gly
275 280 285

Ala Asp Tyr Val Lys Val Asp Ile Asp Asn Ala Glu Ser Ile Ala Gly
290 295 300

Leu Thr Asn Thr Asp Glu Glu Asp Ile Asp Gly Gly Ser His His His
305 310 315 320

His His His

<210> SEQ ID NO 272
<211> LENGTH: 315
<212> TYPE: PRT
<213> ORGANISM: Artificial Sequence
<220> FEATURE:
<223> OTHER INFORMATION: rinGGBP_A_F10C (rinGGBP_A with signal sequence replaced with M; F10C, C6A, C114A, C177A, C210A, and C288A mutations; and GGSHHHHHH at C-terminus)

<400> SEQUENCE: 272

Met Lys Val Gly Val Ala Ile Tyr Gln Cys Ser Asp Asn Phe Met Thr
1 5 10 15

Leu Phe Arg Thr Glu Leu Glu Asn Tyr Leu Val Glu Lys Gly Phe Ser
20 25 30

Lys Asp Asn Ile Thr Ile Val Asp Gly Ala Asn Asp Gln Ala Thr Gln
35 40 45

Thr Gly Gln Ile Asp Asn Phe Ile Thr Glu Gly Val Asp Val Leu Ile
50 55 60

Ile Asn Pro Val Asn Ser Ser Ser Ala Ala Thr Ile Thr Asp Lys Val
65 70 75 80

Val Ala Ala Gly Ile Pro Leu Val Tyr Ile Asn Arg Glu Pro Asp Glu
85 90 95

Glu Glu Gln Lys Arg Trp Ser Asp Asn Asn Trp Asp Val Thr Tyr Val
100 105 110

Gly Ala Asp Ala Arg Gln Ser Gly Thr Phe Gln Gly Glu Met Ile Ser
115 120 125

Asp Leu Gly Leu Asp Thr Val Asp Leu Asn Gly Asn Gly Lys Ile Asp
130 135 140

Tyr Val Met Val Glu Gly Asp Pro Glu Asn Val Asp Ala Gln Tyr Arg
145 150 155 160

Thr Glu Tyr Ser Val Lys Ala Leu Glu Asp Ala Gly Leu Glu Val Asn
165 170 175

Ala Leu Ser Asp Gln Val Gly Asn Trp Gln Gln Asp Gln Ala Gln Gln
180 185 190

Ile Val Ala Asn Ala Leu Gly Gln Tyr Gly Asn Asp Val Glu Val Val
195 200 205

Phe Ala Asn Asn Asp Ala Met Ala Leu Gly Ala Leu Gln Ala Ile Gln
210 215 220

Ser Ala Gly Arg Thr Val Gly Thr Asp Ile Tyr Leu Val Gly Val Asp
225 230 235 240

Ala Leu Ser Glu Ala Leu Glu Asp Val Leu Ala Gly Thr Met Thr Gly
245 250 255

Thr Val Phe Asn Asp His Phe Ser Gln Ser His Ser Ala Ala Asp Ala
260 265 270

Ala Ile Asn Tyr Ile Thr Gly Ala Gly Asn Asp His Tyr Ile Gly Ala
275 280 285

Asp Tyr Val Lys Val Thr Lys Asp Asn Ala Gln Asp Val Leu Asp Met 290 295 300

Val Lys Gly Gly Ser His His His His His His
305 310 315

<210> SEQ ID NO 273
<211> LENGTH: 315
<212> TYPE: PRT
<213> ORGANISM: Artificial Sequence
<220> FEATURE:
<223> OTHER INFORMATION: rinGGBP_A_F14C (rinGGBP_A with signal sequence replaced with M; F14C, C6A, C114A, C177A, C210A, and C288A mutations; and GGSHHHHHH at C-terminus)

<400> SEQUENCE: 273

Met Lys Val Gly Val Ala Ile Tyr Gln Phe Ser Asp Asn Cys Met Thr
1 5 10 15

Leu Phe Arg Thr Glu Leu Glu Asn Tyr Leu Val Glu Lys Gly Phe Ser
20 25 30

Lys Asp Asn Ile Thr Ile Val Asp Gly Ala Asn Asp Gln Ala Thr Gln
35 40 45

Thr Gly Gln Ile Asp Asn Phe Ile Thr Glu Gly Val Asp Val Leu Ile
50 55 60

Ile Asn Pro Val Asn Ser Ser Ser Ala Ala Thr Ile Thr Asp Lys Val
65 70 75 80

Val Ala Ala Gly Ile Pro Leu Val Tyr Ile Asn Arg Glu Pro Asp Glu
85 90 95

Glu Glu Gln Lys Arg Trp Ser Asp Asn Asn Trp Asp Val Thr Tyr Val
100 105 110

Gly Ala Asp Ala Arg Gln Ser Gly Thr Phe Gln Gly Glu Met Ile Ser
115 120 125

Asp Leu Gly Leu Asp Thr Val Asp Leu Asn Gly Asn Gly Lys Ile Asp
130 135 140

Tyr Val Met Val Glu Gly Asp Pro Glu Asn Val Asp Ala Gln Tyr Arg
145 150 155 160

Thr Glu Tyr Ser Val Lys Ala Leu Glu Asp Ala Gly Leu Glu Val Asn
165 170 175

Ala Leu Ser Asp Gln Val Gly Asn Trp Gln Gln Asp Gln Ala Gln Gln
180 185 190

Ile Val Ala Asn Ala Leu Gly Gln Tyr Gly Asn Asp Val Glu Val Val
195 200 205

Phe Ala Asn Asn Asp Ala Met Ala Leu Gly Ala Leu Gln Ala Ile Gln
210 215 220

Ser Ala Gly Arg Thr Val Gly Thr Asp Ile Tyr Leu Val Gly Val Asp
225 230 235 240

Ala Leu Ser Glu Ala Leu Glu Asp Val Leu Ala Gly Thr Met Thr Gly
245 250 255

Thr Val Phe Asn Asp His Phe Ser Gln Ser His Ser Ala Ala Asp Ala
260 265 270

Ala Ile Asn Tyr Ile Thr Gly Ala Gly Asn Asp His Tyr Ile Gly Ala
275 280 285

Asp Tyr Val Lys Val Thr Lys Asp Asn Ala Gln Asp Val Leu Asp Met
290 295 300

Val Lys Gly Gly Ser His His His His His His
305 310 315

<210> SEQ ID NO 274

<211> LENGTH: 315
<212> TYPE: PRT
<213> ORGANISM: Artificial Sequence
<220> FEATURE:
<223> OTHER INFORMATION: rinGGBP_A_W185C (rinGGBP_A with signal sequence replaced with M; W185C, C6A, C114A, C177A, C210A, and C288A mutations; and GGSHHHHHH at C-terminus)

<400> SEQUENCE: 274

Met Lys Val Gly Val Ala Ile Tyr Gln Phe Ser Asp Asn Phe Met Thr
1               5                   10                  15

Leu Phe Arg Thr Glu Leu Glu Asn Tyr Leu Val Glu Lys Gly Phe Ser
            20                  25                  30

Lys Asp Asn Ile Thr Ile Val Asp Gly Ala Asn Asp Gln Ala Thr Gln
        35                  40                  45

Thr Gly Gln Ile Asp Asn Phe Ile Thr Glu Gly Val Asp Val Leu Ile
    50                  55                  60

Ile Asn Pro Val Asn Ser Ser Ser Ala Ala Thr Ile Thr Asp Lys Val
65                  70                  75                  80

Val Ala Ala Gly Ile Pro Leu Val Tyr Ile Asn Arg Glu Pro Asp Glu
                85                  90                  95

Glu Glu Gln Lys Arg Trp Ser Asp Asn Asn Trp Asp Val Thr Tyr Val
            100                 105                 110

Gly Ala Asp Ala Arg Gln Ser Gly Thr Phe Gln Gly Glu Met Ile Ser
        115                 120                 125

Asp Leu Gly Leu Asp Thr Val Asp Leu Asn Gly Asn Gly Lys Ile Asp
    130                 135                 140

Tyr Val Met Val Glu Gly Asp Pro Glu Asn Val Asp Ala Gln Tyr Arg
145                 150                 155                 160

Thr Glu Tyr Ser Val Lys Ala Leu Glu Asp Ala Gly Leu Glu Val Asn
                165                 170                 175

Ala Leu Ser Asp Gln Val Gly Asn Cys Gln Gln Asp Gln Ala Gln Gln
            180                 185                 190

Ile Val Ala Asn Ala Leu Gly Gln Tyr Gly Asn Asp Val Glu Val Val
        195                 200                 205

Phe Ala Asn Asn Asp Ala Met Ala Leu Gly Ala Leu Gln Ala Ile Gln
    210                 215                 220

Ser Ala Gly Arg Thr Val Gly Thr Asp Ile Tyr Leu Val Gly Val Asp
225                 230                 235                 240

Ala Leu Ser Glu Ala Leu Glu Asp Val Leu Ala Gly Thr Met Thr Gly
                245                 250                 255

Thr Val Phe Asn Asp His Phe Ser Gln Ser His Ser Ala Ala Asp Ala
            260                 265                 270

Ala Ile Asn Tyr Ile Thr Gly Ala Gly Asn Asp His Tyr Ile Gly Ala
        275                 280                 285

Asp Tyr Val Lys Val Thr Lys Asp Asn Ala Gln Asp Val Leu Asp Met
    290                 295                 300

Val Lys Gly Gly Ser His His His His His His
305                 310                 315

<210> SEQ ID NO 275
<211> LENGTH: 327
<212> TYPE: PRT
<213> ORGANISM: Artificial Sequence
<220> FEATURE:
<223> OTHER INFORMATION: rinGGBP_B_F17C (rinGGBP_B with signal sequence replaced with M; F17C, C66A, C70A, and C306A; and GGSHHHHHH at C-terminus)

-continued

<400> SEQUENCE: 275

Met Lys Ser Ile Lys Ile Gly Ile Ser Val Tyr Asp Gln Tyr Asp Thr
1 5 10 15

Cys Val Ser Glu Met Met Lys Asp Phe Asn Asp Tyr Ala Thr Lys Lys
20 25 30

Glu Glu Glu Thr Gly Val Ala Ile Asn Ile Asp Thr Tyr Asn Ala Ser
35 40 45

Ala Ser Gln Ser Thr Gln Asn Ser Gln Val Glu Asn Met Ile Thr Glu
50 55 60

Gly Ala Asp Val Ile Ala Val Asn Leu Val Asp Arg Thr Asp Pro Thr
65 70 75 80

Ala Ile Ile Asp Leu Ala Glu Lys Asn Asn Ile Pro Val Ile Phe Phe
85 90 95

Asn Arg Glu Leu Val Glu Glu Asp Leu Glu Arg Trp Thr Arg Leu Tyr
100 105 110

Tyr Val Gly Ala Gln Ala Phe Glu Ser Gly Ile Met Gln Gly Glu Leu
115 120 125

Ala Ala Glu Ala Phe Leu Thr Asp Gln Ser Leu Asp Lys Asn Gly Asp
130 135 140

Gly Ile Phe Gln Tyr Val Val Leu Glu Gly Glu Ala Gly His Gln Asp
145 150 155 160

Ala Ile Val Arg Thr Glu Tyr Ser Val Ser Thr Met Ile Asp Ser Gly
165 170 175

Val Glu Val Glu Lys Leu Gly Tyr Ala Ile Ala Asn Trp Asn Arg Ala
180 185 190

Gln Ala Gln Thr Lys Met Ala Gln Leu Met Ser Gln Phe Gly Asp Ser
195 200 205

Ile Glu Leu Val Ile Ala Asn Asn Asp Asp Met Ala Leu Gly Ala Ile
210 215 220

Asp Ala Leu Lys Ala Ser Gly Leu Thr Lys Asp Glu Trp Pro Ala Val
225 230 235 240

Ile Gly Ile Asp Gly Thr Asp Val Gly Leu Glu Ala Val Lys Asn Lys
245 250 255

Glu Met Ile Gly Thr Val Tyr Asn Asp Lys Glu Gly Gln Ala Asp Ala
260 265 270

Met Leu Asn Leu Ala Tyr Glu Leu Ser Thr Gly Ser Asp Leu Ser Asp
275 280 285

Leu Asn Leu Ile Asp Gly Lys Tyr Ile Arg Leu Pro Tyr Ala Arg Val
290 295 300

Thr Ala Asp Asp Val Asp Ser Tyr Met Glu Gly Asp Thr Glu Gly Gly
305 310 315 320

Ser His His His His His His
325

<210> SEQ ID NO 276
<211> LENGTH: 327
<212> TYPE: PRT
<213> ORGANISM: Artificial Sequence
<220> FEATURE:
<223> OTHER INFORMATION: rinGGBP_B_Q13C (rinGGBP_B with signal sequence replaced with M; Q13C, C66A, C70A, and C306A mutations; and GGSHHHHHH at C-terminus)

<400> SEQUENCE: 276

Met Lys Ser Ile Lys Ile Gly Ile Ser Val Tyr Asp Cys Tyr Asp Thr

```
1               5                   10                  15

Phe Val Ser Glu Met Met Lys Asp Phe Asn Asp Tyr Ala Thr Lys Lys
            20                  25                  30

Glu Glu Glu Thr Gly Val Ala Ile Asn Ile Asp Thr Tyr Asn Ala Ser
        35                  40                  45

Ala Ser Gln Ser Thr Gln Asn Ser Gln Val Glu Asn Met Ile Thr Glu
    50                  55                  60

Gly Ala Asp Val Ile Ala Val Asn Leu Val Asp Arg Thr Asp Pro Thr
65                  70                  75                  80

Ala Ile Ile Asp Leu Ala Glu Lys Asn Asn Ile Pro Val Ile Phe Phe
                85                  90                  95

Asn Arg Glu Leu Val Glu Glu Asp Leu Glu Arg Trp Thr Arg Leu Tyr
            100                 105                 110

Tyr Val Gly Ala Gln Ala Phe Glu Ser Gly Ile Met Gln Gly Glu Leu
        115                 120                 125

Ala Ala Glu Ala Phe Leu Thr Asp Gln Ser Leu Asp Lys Asn Gly Asp
    130                 135                 140

Gly Ile Phe Gln Tyr Val Val Leu Glu Gly Glu Ala Gly His Gln Asp
145                 150                 155                 160

Ala Ile Val Arg Thr Glu Tyr Ser Val Ser Thr Met Ile Asp Ser Gly
                165                 170                 175

Val Glu Val Glu Lys Leu Gly Tyr Ala Ile Ala Asn Trp Asn Arg Ala
            180                 185                 190

Gln Ala Gln Thr Lys Met Ala Gln Leu Met Ser Gln Phe Gly Asp Ser
        195                 200                 205

Ile Glu Leu Val Ile Ala Asn Asn Asp Asp Met Ala Leu Gly Ala Ile
    210                 215                 220

Asp Ala Leu Lys Ala Ser Gly Leu Thr Lys Asp Glu Trp Pro Ala Val
225                 230                 235                 240

Ile Gly Ile Asp Gly Thr Asp Val Gly Leu Glu Ala Val Lys Asn Lys
                245                 250                 255

Glu Met Ile Gly Thr Val Tyr Asn Asp Lys Glu Gly Gln Ala Asp Ala
            260                 265                 270

Met Leu Asn Leu Ala Tyr Glu Leu Ser Thr Gly Ser Asp Leu Ser Asp
        275                 280                 285

Leu Asn Leu Ile Asp Gly Lys Tyr Ile Arg Leu Pro Tyr Ala Arg Val
    290                 295                 300

Thr Ala Asp Asp Val Asp Ser Tyr Met Glu Gly Asp Thr Glu Gly Gly
305                 310                 315                 320

Ser His His His His His His
                325
```

<210> SEQ ID NO 277
<211> LENGTH: 327
<212> TYPE: PRT
<213> ORGANISM: Artificial Sequence
<220> FEATURE:
<223> OTHER INFORMATION: rinGGBP_B_W189C (rinGGBP_B with signal sequence replaced with M; W189C, C66A, C70A, and C306A mutations; and GGSHHHHHH at C-terminus)

<400> SEQUENCE: 277

```
Met Lys Ser Ile Lys Ile Gly Ile Ser Val Tyr Asp Gln Tyr Asp Thr
1               5                   10                  15

Phe Val Ser Glu Met Met Lys Asp Phe Asn Asp Tyr Ala Thr Lys Lys
            20                  25                  30
```

```
Glu Glu Glu Thr Gly Val Ala Ile Asn Ile Asp Thr Tyr Asn Ala Ser
        35                  40                  45

Ala Ser Gln Ser Thr Gln Asn Ser Gln Val Glu Asn Met Ile Thr Glu
    50                  55                  60

Gly Ala Asp Val Ile Ala Val Asn Leu Val Asp Arg Thr Asp Pro Thr
65                  70                  75                  80

Ala Ile Ile Asp Leu Ala Glu Lys Asn Asn Ile Pro Val Ile Phe Phe
                85                  90                  95

Asn Arg Glu Leu Val Glu Glu Asp Leu Glu Arg Trp Thr Arg Leu Tyr
            100                 105                 110

Tyr Val Gly Ala Gln Ala Phe Glu Ser Gly Ile Met Gln Gly Glu Leu
        115                 120                 125

Ala Ala Glu Ala Phe Leu Thr Asp Gln Ser Leu Asp Lys Asn Gly Asp
    130                 135                 140

Gly Ile Phe Gln Tyr Val Val Leu Glu Gly Glu Ala Gly His Gln Asp
145                 150                 155                 160

Ala Ile Val Arg Thr Glu Tyr Ser Val Ser Thr Met Ile Asp Ser Gly
                165                 170                 175

Val Glu Val Glu Lys Leu Gly Tyr Ala Ile Ala Asn Cys Asn Arg Ala
            180                 185                 190

Gln Ala Gln Thr Lys Met Ala Gln Leu Met Ser Gln Phe Gly Asp Ser
        195                 200                 205

Ile Glu Leu Val Ile Ala Asn Asn Asp Asp Met Ala Leu Gly Ala Ile
    210                 215                 220

Asp Ala Leu Lys Ala Ser Gly Leu Thr Lys Asp Glu Trp Pro Ala Val
225                 230                 235                 240

Ile Gly Ile Asp Gly Thr Asp Val Gly Leu Glu Ala Val Lys Asn Lys
                245                 250                 255

Glu Met Ile Gly Thr Val Tyr Asn Asp Lys Glu Gly Gln Ala Asp Ala
            260                 265                 270

Met Leu Asn Leu Ala Tyr Glu Leu Ser Thr Gly Ser Asp Leu Ser Asp
        275                 280                 285

Leu Asn Leu Ile Asp Gly Lys Tyr Ile Arg Leu Pro Tyr Ala Arg Val
    290                 295                 300

Thr Ala Asp Asp Val Asp Ser Tyr Met Glu Gly Asp Thr Glu Gly Gly
305                 310                 315                 320

Ser His His His His His His
                325
```

<210> SEQ ID NO 278
<211> LENGTH: 309
<212> TYPE: PRT
<213> ORGANISM: Artificial Sequence
<220> FEATURE:
<223> OTHER INFORMATION: fprGGBP_F12C (fprGGBP with signal sequence replaced with M; F12C, C8A, C105A, C106A, C143A, and C205A mutations; and GGSHHHHHH at C-terminus)

<400> SEQUENCE: 278

```
Met Ser Ala Asn Ile Gly Val Ala Ile Tyr Gln Cys Ala Asp Asn Phe
1               5                   10                  15

Met Thr Leu Tyr Arg Ala Asp Leu Glu Gly Tyr Leu Lys Asp Met Gly
            20                  25                  30

Tyr Ser Val Thr Ile Met Asp Gly Lys Asn Asp Gln Asn Thr Gln Thr
        35                  40                  45
```

Glu Gln Ile Asn Thr Phe Leu Gln Gln Gly Val Asp Val Leu Val Ile
50 55 60

Asn Pro Val Gln Thr Thr Ser Ala Gln Thr Ile Val Asp Thr Val Ser
65 70 75 80

Pro Ser Gly Thr Pro Ile Val Phe Ile Asn Arg Glu Pro Glu Glu Ser
85 90 95

Val Leu Asp Ser Tyr Lys Gly Lys Ala Ala Tyr Val Gly Ala Asp Ala
100 105 110

Arg Gln Ser Gly Thr Tyr Gln Gly Glu Leu Ile Leu Ala Thr Asp Thr
115 120 125

Gln Gly Asp Ile Asn Gly Asp Gly Lys Ile Thr Tyr Ile Met Ala Lys
130 135 140

Gly Asp Pro Glu Asn Ile Asp Ala Gln Tyr Arg Thr Glu Tyr Ser Ile
145 150 155 160

Lys Ala Leu Thr Asp Ala Gly Lys Glu Val Glu Cys Leu Tyr Glu Tyr
165 170 175

Leu Asp Asn Trp Asp Gln Thr Thr Ala Gln Gln Asp Val Ala Asn Ala
180 185 190

Leu Ser Gln Tyr Gly Glu Lys Ile Glu Val Val Phe Ala Asn Asn Asp
195 200 205

Ala Met Ala Leu Gly Ala Leu Gln Ser Ile Gln Gln Ala Gly Arg Thr
210 215 220

Val Gly Lys Asp Val Tyr Leu Val Gly Val Asp Ala Leu Val Glu Ala
225 230 235 240

Val Gln Asn Val Val Asp Gly Asn Met Thr Gly Thr Val Leu Asn Asp
245 250 255

Asp Val Gly Gln Ala Thr Lys Ala Ala Glu Ala Thr Lys Leu Phe Val
260 265 270

Glu Gly Lys Asp Val Glu Lys Tyr Tyr Trp Val Asp Tyr Val Lys Val
275 280 285

Thr Lys Asp Asn Ala Ser Gln Tyr Leu Lys Glu Asp Gly Gly Ser His
290 295 300

His His His His His
305

<210> SEQ ID NO 279
<211> LENGTH: 309
<212> TYPE: PRT
<213> ORGANISM: Artificial Sequence
<220> FEATURE:
<223> OTHER INFORMATION: fprGGBP_F16C (fprGGBP with signal sequence replaced with M; F16C, C8A, C105A, C106A, C143A, and C205A mutations; and GGSHHHHHH at C-terminus)

<400> SEQUENCE: 279

Met Ser Ala Asn Ile Gly Val Ala Ile Tyr Gln Phe Ala Asp Asn Cys
1 5 10 15

Met Thr Leu Tyr Arg Ala Asp Leu Glu Gly Tyr Leu Lys Asp Met Gly
20 25 30

Tyr Ser Val Thr Ile Met Asp Gly Lys Asn Asp Gln Asn Thr Gln Thr
35 40 45

Glu Gln Ile Asn Thr Phe Leu Gln Gln Gly Val Asp Val Leu Val Ile
50 55 60

Asn Pro Val Gln Thr Thr Ser Ala Gln Thr Ile Val Asp Thr Val Ser
65 70 75 80

Pro Ser Gly Thr Pro Ile Val Phe Ile Asn Arg Glu Pro Glu Glu Ser

```
                85                  90                  95

Val Leu Asp Ser Tyr Lys Gly Lys Ala Ala Tyr Val Gly Ala Asp Ala
            100                 105                 110

Arg Gln Ser Gly Thr Tyr Gln Gly Glu Leu Ile Leu Ala Thr Asp Thr
        115                 120                 125

Gln Gly Asp Ile Asn Gly Asp Gly Lys Ile Thr Tyr Ile Met Ala Lys
    130                 135                 140

Gly Asp Pro Glu Asn Ile Asp Ala Gln Tyr Arg Thr Glu Tyr Ser Ile
145                 150                 155                 160

Lys Ala Leu Thr Asp Ala Gly Lys Glu Val Glu Cys Leu Tyr Glu Tyr
                165                 170                 175

Leu Asp Asn Trp Asp Gln Thr Thr Ala Gln Gln Asp Val Ala Asn Ala
            180                 185                 190

Leu Ser Gln Tyr Gly Glu Lys Ile Glu Val Val Phe Ala Asn Asn Asp
        195                 200                 205

Ala Met Ala Leu Gly Ala Leu Gln Ser Ile Gln Gln Ala Gly Arg Thr
    210                 215                 220

Val Gly Lys Asp Val Tyr Leu Val Gly Val Asp Ala Leu Val Glu Ala
225                 230                 235                 240

Val Gln Asn Val Val Asp Gly Asn Met Thr Gly Thr Val Leu Asn Asp
                245                 250                 255

Asp Val Gly Gln Ala Thr Lys Ala Ala Glu Ala Thr Lys Leu Phe Val
            260                 265                 270

Glu Gly Lys Asp Val Glu Lys Tyr Tyr Trp Val Asp Tyr Val Lys Val
        275                 280                 285

Thr Lys Asp Asn Ala Ser Gln Tyr Leu Lys Glu Asp Gly Gly Ser His
    290                 295                 300

His His His His His
305
```

<210> SEQ ID NO 280
<211> LENGTH: 309
<212> TYPE: PRT
<213> ORGANISM: Artificial Sequence
<220> FEATURE:
<223> OTHER INFORMATION: fprGGBP_W180C (fprGGBP with signal sequence replaced with M; W180C, C8A, C105A, C106A, C143A, and C205A mutations; and GGSHHHHHH at C-terminus)

<400> SEQUENCE: 280

```
Met Ser Ala Asn Ile Gly Val Ala Ile Tyr Gln Phe Ala Asp Asn Phe
1               5                   10                  15

Met Thr Leu Tyr Arg Ala Asp Leu Glu Gly Tyr Leu Lys Asp Met Gly
            20                  25                  30

Tyr Ser Val Thr Ile Met Asp Gly Lys Asn Asp Gln Asn Thr Gln Thr
        35                  40                  45

Glu Gln Ile Asn Thr Phe Leu Gln Gln Gly Val Asp Val Leu Val Ile
    50                  55                  60

Asn Pro Val Gln Thr Thr Ser Ala Gln Thr Ile Val Asp Thr Val Ser
65                  70                  75                  80

Pro Ser Gly Thr Pro Ile Val Phe Ile Asn Arg Glu Pro Glu Glu Ser
                85                  90                  95

Val Leu Asp Ser Tyr Lys Gly Lys Ala Ala Tyr Val Gly Ala Asp Ala
            100                 105                 110

Arg Gln Ser Gly Thr Tyr Gln Gly Glu Leu Ile Leu Ala Thr Asp Thr
        115                 120                 125
```

Gln Gly Asp Ile Asn Gly Asp Gly Lys Ile Thr Tyr Ile Met Ala Lys
    130                 135                 140

Gly Asp Pro Glu Asn Ile Asp Ala Gln Tyr Arg Thr Glu Tyr Ser Ile
145                 150                 155                 160

Lys Ala Leu Thr Asp Ala Gly Lys Glu Val Glu Cys Leu Tyr Glu Tyr
                165                 170                 175

Leu Asp Asn Cys Asp Gln Thr Thr Ala Gln Gln Asp Val Ala Asn Ala
            180                 185                 190

Leu Ser Gln Tyr Gly Glu Lys Ile Glu Val Val Phe Ala Asn Asn Asp
        195                 200                 205

Ala Met Ala Leu Gly Ala Leu Gln Ser Ile Gln Gln Ala Gly Arg Thr
    210                 215                 220

Val Gly Lys Asp Val Tyr Leu Val Gly Val Asp Ala Leu Val Glu Ala
225                 230                 235                 240

Val Gln Asn Val Val Asp Gly Asn Met Thr Gly Thr Val Leu Asn Asp
                245                 250                 255

Asp Val Gly Gln Ala Thr Lys Ala Ala Glu Ala Thr Lys Leu Phe Val
            260                 265                 270

Glu Gly Lys Asp Val Glu Lys Tyr Tyr Trp Val Asp Tyr Val Lys Val
        275                 280                 285

Thr Lys Asp Asn Ala Ser Gln Tyr Leu Lys Glu Asp Gly Gly Ser His
    290                 295                 300

His His His His His
305

<210> SEQ ID NO 281
<211> LENGTH: 314
<212> TYPE: PRT
<213> ORGANISM: Artificial Sequence
<220> FEATURE:
<223> OTHER INFORMATION: cljGGBP_F11C (cljGGBP with signal sequence replaced with M; F11C, C77A, and C198A mutations; and GGSHHHHHH at C-terminus)

<400> SEQUENCE: 281

Met Pro Val Ile Gly Phe Val Ala Tyr Glu Cys Asn Asn Thr Trp Ile
1               5                   10                  15

Thr Glu Leu Lys Asn Glu Ile Tyr Lys Val Ser Ser Gly Lys Ala Arg
            20                  25                  30

Val Asp Ile Trp Asn Gly Asp Asn Ile Gln Thr Val Glu Asn Asp Lys
        35                  40                  45

Ile Asn Leu Phe Ile Asn Arg Lys Val Asn Val Leu Asp Ile Asn Pro
    50                  55                  60

Val Asp Val Asn Ala Ala Gly Gln Ile Ile Glu Lys Ala Lys Lys Ala
65                  70                  75                  80

Asn Ile Pro Thr Val Phe Val Asn Arg Gln Pro Lys Lys Glu Asp Met
                85                  90                  95

Glu Lys Trp Asn Lys Val Tyr Tyr Val Gly Ala Lys Ala Glu Gln Ser
            100                 105                 110

Gly Thr Ile Gln Gly Gln Met Leu Val Asn Tyr Phe Lys Gly His Pro
        115                 120                 125

Thr Gln Asp Gly Thr Ile Arg Tyr Ile Met Leu Lys Gly Glu Thr Arg
    130                 135                 140

Asn Gln Asp Ala Glu Lys Arg Thr Gln Tyr Ser Ile Lys Ala Leu Lys
145                 150                 155                 160

```
Asp Ser Gly Phe Lys Val Gln Lys Val Ala Glu Asp Thr Ala Met Trp
                165                 170                 175

Asp Arg Thr Lys Ala Gln Glu Lys Met Thr Ser Phe Ile Ser Ser Tyr
            180                 185                 190

Gly Pro Asn Phe Asp Ala Val Ile Ala Asn Asn Asp Asp Met Ala Leu
        195                 200                 205

Gly Ala Val Asp Ala Leu Lys Ala Ala Gly Tyr Phe Asn Gly Gly Lys
    210                 215                 220

Tyr Val Pro Val Val Gly Val Asp Ala Thr Ala Pro Ala Val Lys Ala
225                 230                 235                 240

Val Glu Asp Gly Thr Leu Phe Gly Thr Val Leu Asn Asp Ala Ala Lys
                245                 250                 255

Gln Gly Asp Ala Ala Phe Asp Leu Ser Tyr Ile Leu Ser Lys Gly Lys
            260                 265                 270

Ile Pro Asp Glu Ser Asn Phe Lys Tyr Lys Val Thr Asp Gly Lys Tyr
        275                 280                 285

Ile Trp Ile Asp Tyr Lys Met Ile Thr Lys Glu Asn Val Gln Asp Ala
    290                 295                 300

Lys Gly Gly Ser His His His His His His
305                 310


<210> SEQ ID NO 282
<211> LENGTH: 314
<212> TYPE: PRT
<213> ORGANISM: Artificial Sequence
<220> FEATURE:
<223> OTHER INFORMATION: cljGGBP_W15C  (cljGGBP with signal sequence
      replaced with M; W15C, C77A, and C198A mutations; and GGSHHHHHH at
      C-terminus)

<400> SEQUENCE: 282

Met Pro Val Ile Gly Phe Val Ala Tyr Glu Phe Asn Asn Thr Cys Ile
1               5                   10                  15

Thr Glu Leu Lys Asn Glu Ile Tyr Lys Val Ser Ser Gly Lys Ala Arg
            20                  25                  30

Val Asp Ile Trp Asn Gly Asp Asn Ile Gln Thr Val Glu Asn Asp Lys
        35                  40                  45

Ile Asn Leu Phe Ile Asn Arg Lys Val Asn Val Leu Asp Ile Asn Pro
    50                  55                  60

Val Asp Val Asn Ala Ala Gly Gln Ile Ile Glu Lys Ala Lys Lys Ala
65                  70                  75                  80

Asn Ile Pro Thr Val Phe Val Asn Arg Gln Pro Lys Lys Glu Asp Met
                85                  90                  95

Glu Lys Trp Asn Lys Val Tyr Tyr Val Gly Ala Lys Ala Glu Gln Ser
            100                 105                 110

Gly Thr Ile Gln Gly Gln Met Leu Val Asn Tyr Phe Lys Gly His Pro
        115                 120                 125

Thr Gln Asp Gly Thr Ile Arg Tyr Ile Met Leu Lys Gly Glu Thr Arg
    130                 135                 140

Asn Gln Asp Ala Glu Lys Arg Thr Gln Tyr Ser Ile Lys Ala Leu Lys
145                 150                 155                 160

Asp Ser Gly Phe Lys Val Gln Lys Val Ala Glu Asp Thr Ala Met Trp
                165                 170                 175

Asp Arg Thr Lys Ala Gln Glu Lys Met Thr Ser Phe Ile Ser Ser Tyr
            180                 185                 190

Gly Pro Asn Phe Asp Ala Val Ile Ala Asn Asn Asp Asp Met Ala Leu
```

```
        195                 200                 205

Gly Ala Val Asp Ala Leu Lys Ala Ala Gly Tyr Phe Asn Gly Gly Lys
    210                 215                 220

Tyr Val Pro Val Val Gly Val Asp Ala Thr Ala Pro Ala Val Lys Ala
225                 230                 235                 240

Val Glu Asp Gly Thr Leu Phe Gly Thr Val Leu Asn Asp Ala Ala Lys
                245                 250                 255

Gln Gly Asp Ala Ala Phe Asp Leu Ser Tyr Ile Leu Ser Lys Gly Lys
            260                 265                 270

Ile Pro Asp Glu Ser Asn Phe Lys Tyr Lys Val Thr Asp Gly Lys Tyr
        275                 280                 285

Ile Trp Ile Asp Tyr Lys Met Ile Thr Lys Glu Asn Val Gln Asp Ala
    290                 295                 300

Lys Gly Gly Ser His His His His His His
305                 310
```

<210> SEQ ID NO 283
<211> LENGTH: 314
<212> TYPE: PRT
<213> ORGANISM: Artificial Sequence
<220> FEATURE:
<223> OTHER INFORMATION: cljGGBP_W176C (cljGGBP with signal sequence replaced with M; W176C, C77A, and C198A mutations; and GGSHHHHHH at C-terminus)

<400> SEQUENCE: 283

```
Met Pro Val Ile Gly Phe Val Ala Tyr Glu Phe Asn Asn Thr Trp Ile
1               5                   10                  15

Thr Glu Leu Lys Asn Glu Ile Tyr Lys Val Ser Ser Gly Lys Ala Arg
            20                  25                  30

Val Asp Ile Trp Asn Gly Asp Asn Ile Gln Thr Val Glu Asn Asp Lys
        35                  40                  45

Ile Asn Leu Phe Ile Asn Arg Lys Val Asn Val Leu Asp Ile Asn Pro
    50                  55                  60

Val Asp Val Asn Ala Ala Gly Gln Ile Ile Glu Lys Ala Lys Lys Ala
65                  70                  75                  80

Asn Ile Pro Thr Val Phe Val Asn Arg Gln Pro Lys Lys Glu Asp Met
                85                  90                  95

Glu Lys Trp Asn Lys Val Tyr Tyr Val Gly Ala Lys Ala Glu Gln Ser
            100                 105                 110

Gly Thr Ile Gln Gly Gln Met Leu Val Asn Tyr Phe Lys Gly His Pro
        115                 120                 125

Thr Gln Asp Gly Thr Ile Arg Tyr Ile Met Leu Lys Gly Glu Thr Arg
    130                 135                 140

Asn Gln Asp Ala Glu Lys Arg Thr Gln Tyr Ser Ile Lys Ala Leu Lys
145                 150                 155                 160

Asp Ser Gly Phe Lys Val Gln Lys Val Ala Glu Asp Thr Ala Met Cys
                165                 170                 175

Asp Arg Thr Lys Ala Gln Glu Lys Met Thr Ser Phe Ile Ser Ser Tyr
            180                 185                 190

Gly Pro Asn Phe Asp Ala Val Ile Ala Asn Asn Asp Asp Met Ala Leu
        195                 200                 205

Gly Ala Val Asp Ala Leu Lys Ala Ala Gly Tyr Phe Asn Gly Gly Lys
    210                 215                 220

Tyr Val Pro Val Val Gly Val Asp Ala Thr Ala Pro Ala Val Lys Ala
225                 230                 235                 240
```

Val Glu Asp Gly Thr Leu Phe Gly Thr Val Leu Asn Asp Ala Ala Lys
245 250 255

Gln Gly Asp Ala Ala Phe Asp Leu Ser Tyr Ile Leu Ser Lys Gly Lys
260 265 270

Ile Pro Asp Glu Ser Asn Phe Lys Tyr Lys Val Thr Asp Gly Lys Tyr
275 280 285

Ile Trp Ile Asp Tyr Lys Met Ile Thr Lys Glu Asn Val Gln Asp Ala
290 295 300

Lys Gly Gly Ser His His His His His His
305 310

<210> SEQ ID NO 284
<211> LENGTH: 315
<212> TYPE: PRT
<213> ORGANISM: Artificial Sequence
<220> FEATURE:
<223> OTHER INFORMATION: cauGGBP_F12C (cauGGBP with signal sequence replaced with M; F12C, C78A, and C199A mutations; and GGSHHHHHH at C-terminus)

<400> SEQUENCE: 284

Met Glu Pro Val Ile Gly Phe Val Ala Tyr Glu Cys Asn Asn Thr Trp
1 5 10 15

Ile Thr Glu Leu Lys Asn Glu Met Tyr Lys Val Ser Asn Gly Lys Ala
20 25 30

Arg Val Asp Ile Trp Asn Gly Asn Asn Ile Gln Thr Val Glu Asn Asp
35 40 45

Lys Ile Ser Leu Phe Ile Asn Arg Lys Val Asp Val Leu Asp Ile Asn
50 55 60

Pro Val Asp Val Asn Ala Ala Gly Gln Ile Ile Glu Lys Ala Lys Lys
65 70 75 80

Ala Asn Ile Pro Thr Val Phe Val Asn Arg Gln Pro Lys Lys Glu Asp
85 90 95

Val Glu Lys Trp Asn Lys Val Tyr Tyr Val Gly Ala Lys Ala Glu Gln
100 105 110

Ser Gly Thr Ile Gln Gly Gln Met Leu Val Asn Tyr Phe Lys Gly His
115 120 125

Pro Thr Gln Asp Gly Thr Ile Arg Tyr Ile Met Leu Lys Gly Glu Met
130 135 140

Arg Asn Gln Asp Ala Glu Lys Arg Thr Gln Tyr Ser Ile Lys Ala Leu
145 150 155 160

Glu Asp Ser Gly Phe Lys Val Gln Lys Val Ala Glu Asp Thr Ala Met
165 170 175

Trp Asp Arg Thr Lys Ala Gln Glu Lys Met Thr Ser Phe Ile Ser Ser
180 185 190

Tyr Gly Pro Asn Phe Asp Ala Val Ile Ala Asn Asn Asp Asp Met Ala
195 200 205

Leu Gly Ala Val Asp Ala Leu Lys Ala Ala Gly Tyr Phe Asn Gly Gly
210 215 220

Lys Tyr Val Pro Val Val Gly Val Asp Ala Thr Ala Pro Ala Val Lys
225 230 235 240

Ala Val Glu Asp Gly Thr Leu Phe Gly Thr Val Leu Asn Asp Ala Ala
245 250 255

Lys Gln Gly Asp Ala Ala Phe Asp Leu Ser Tyr Ile Leu Ser Lys Gly
260 265 270

```
Lys Ile Pro Asp Glu Ser Asn Phe Lys Tyr Lys Ile Thr Asp Gly Lys
        275                 280                 285

Tyr Ile Trp Ile Asp Tyr Lys Met Ile Thr Lys Glu Asn Val Gln Asp
    290                 295                 300

Ala Lys Gly Gly Ser His His His His His His
305                 310                 315


<210> SEQ ID NO 285
<211> LENGTH: 315
<212> TYPE: PRT
<213> ORGANISM: Artificial Sequence
<220> FEATURE:
<223> OTHER INFORMATION: cauGGBP_W16C (cauGGBP with signal sequence
      replaced with M; W16C, C78A, and C199A mutations; and GGSHHHHHH at
      C-terminus)

<400> SEQUENCE: 285

Met Glu Pro Val Ile Gly Phe Val Ala Tyr Glu Phe Asn Asn Thr Cys
1               5                   10                  15

Ile Thr Glu Leu Lys Asn Glu Met Tyr Lys Val Ser Asn Gly Lys Ala
            20                  25                  30

Arg Val Asp Ile Trp Asn Gly Asn Asn Ile Gln Thr Val Glu Asn Asp
        35                  40                  45

Lys Ile Ser Leu Phe Ile Asn Arg Lys Val Asp Val Leu Asp Ile Asn
    50                  55                  60

Pro Val Asp Val Asn Ala Ala Gly Gln Ile Ile Glu Lys Ala Lys Lys
65                  70                  75                  80

Ala Asn Ile Pro Thr Val Phe Val Asn Arg Gln Pro Lys Lys Glu Asp
                85                  90                  95

Val Glu Lys Trp Asn Lys Val Tyr Tyr Val Gly Ala Lys Ala Glu Gln
            100                 105                 110

Ser Gly Thr Ile Gln Gly Gln Met Leu Val Asn Tyr Phe Lys Gly His
        115                 120                 125

Pro Thr Gln Asp Gly Thr Ile Arg Tyr Ile Met Leu Lys Gly Glu Met
    130                 135                 140

Arg Asn Gln Asp Ala Glu Lys Arg Thr Gln Tyr Ser Ile Lys Ala Leu
145                 150                 155                 160

Glu Asp Ser Gly Phe Lys Val Gln Lys Val Ala Glu Asp Thr Ala Met
                165                 170                 175

Trp Asp Arg Thr Lys Ala Gln Glu Lys Met Thr Ser Phe Ile Ser Ser
            180                 185                 190

Tyr Gly Pro Asn Phe Asp Ala Val Ile Ala Asn Asn Asp Asp Met Ala
        195                 200                 205

Leu Gly Ala Val Asp Ala Leu Lys Ala Ala Gly Tyr Phe Asn Gly Gly
    210                 215                 220

Lys Tyr Val Pro Val Val Gly Val Asp Ala Thr Ala Pro Ala Val Lys
225                 230                 235                 240

Ala Val Glu Asp Gly Thr Leu Phe Gly Thr Val Leu Asn Asp Ala Ala
                245                 250                 255

Lys Gln Gly Asp Ala Ala Phe Asp Leu Ser Tyr Ile Leu Ser Lys Gly
            260                 265                 270

Lys Ile Pro Asp Glu Ser Asn Phe Lys Tyr Lys Ile Thr Asp Gly Lys
        275                 280                 285

Tyr Ile Trp Ile Asp Tyr Lys Met Ile Thr Lys Glu Asn Val Gln Asp
    290                 295                 300

Ala Lys Gly Gly Ser His His His His His His
```

305 310 315

<210> SEQ ID NO 286
<211> LENGTH: 315
<212> TYPE: PRT
<213> ORGANISM: Artificial Sequence
<220> FEATURE:
<223> OTHER INFORMATION: cauGGBP_W177C (cauGGBP with signal sequence replaced with M; W177C, C78A, and C199A mutations; and GGSHHHHHH at C-terminus)

<400> SEQUENCE: 286

Met Glu Pro Val Ile Gly Phe Val Ala Tyr Glu Phe Asn Asn Thr Trp
1 5 10 15

Ile Thr Glu Leu Lys Asn Glu Met Tyr Lys Val Ser Asn Gly Lys Ala
20 25 30

Arg Val Asp Ile Trp Asn Gly Asn Asn Ile Gln Thr Val Glu Asn Asp
35 40 45

Lys Ile Ser Leu Phe Ile Asn Arg Lys Val Asp Val Leu Asp Ile Asn
50 55 60

Pro Val Asp Val Asn Ala Ala Gly Gln Ile Ile Glu Lys Ala Lys Lys
65 70 75 80

Ala Asn Ile Pro Thr Val Phe Val Asn Arg Gln Pro Lys Lys Glu Asp
85 90 95

Val Glu Lys Trp Asn Lys Val Tyr Tyr Val Gly Ala Lys Ala Glu Gln
100 105 110

Ser Gly Thr Ile Gln Gly Gln Met Leu Val Asn Tyr Phe Lys Gly His
115 120 125

Pro Thr Gln Asp Gly Thr Ile Arg Tyr Ile Met Leu Lys Gly Glu Met
130 135 140

Arg Asn Gln Asp Ala Glu Lys Arg Thr Gln Tyr Ser Ile Lys Ala Leu
145 150 155 160

Glu Asp Ser Gly Phe Lys Val Gln Lys Val Ala Glu Asp Thr Ala Met
165 170 175

Cys Asp Arg Thr Lys Ala Gln Glu Lys Met Thr Ser Phe Ile Ser Ser
180 185 190

Tyr Gly Pro Asn Phe Asp Ala Val Ile Ala Asn Asn Asp Asp Met Ala
195 200 205

Leu Gly Ala Val Asp Ala Leu Lys Ala Ala Gly Tyr Phe Asn Gly Gly
210 215 220

Lys Tyr Val Pro Val Val Gly Val Asp Ala Thr Ala Pro Ala Val Lys
225 230 235 240

Ala Val Glu Asp Gly Thr Leu Phe Gly Thr Val Leu Asn Asp Ala Ala
245 250 255

Lys Gln Gly Asp Ala Ala Phe Asp Leu Ser Tyr Ile Leu Ser Lys Gly
260 265 270

Lys Ile Pro Asp Glu Ser Asn Phe Lys Tyr Lys Ile Thr Asp Gly Lys
275 280 285

Tyr Ile Trp Ile Asp Tyr Lys Met Ile Thr Lys Glu Asn Val Gln Asp
290 295 300

Ala Lys Gly Gly Ser His His His His His His
305 310 315

<210> SEQ ID NO 287
<211> LENGTH: 336
<212> TYPE: PRT
<213> ORGANISM: Artificial Sequence

```
<220> FEATURE:
<223> OTHER INFORMATION: erhGGBP_F13C  (erhGGBP with signal sequence
      replaced with M; F13C mutation; and GGSHHHHHH at C-terminus)

<400> SEQUENCE: 287

Met Lys Thr Tyr Asn Ile Gly Val Ala Ile Tyr Lys Cys Asp Asp Asn
1               5                   10                  15

Phe Met Thr Leu Tyr Arg Glu Glu Leu Ala Ser Tyr Phe Lys Glu Val
            20                  25                  30

Gly Glu Lys Asp Gly Asn Thr Tyr Lys Leu Asp Ile Gln Asp Gly Lys
        35                  40                  45

Gln Asp Gln Ala Asn Gln Thr Glu Gln Ile Asn Asn Phe Ile Ala Gln
    50                  55                  60

Gly Lys Asp Leu Ile Ile Ala Asn Met Val Asp Pro Thr Ala Ala Gly
65                  70                  75                  80

Ser Ile Ile Asn Ser Ala Lys Ala Lys Glu Ile Pro Val Val Phe Ile
                85                  90                  95

Asn Arg Glu Pro Glu Thr Gln Glu Leu Glu Ile Trp Pro Gly Lys Thr
            100                 105                 110

Thr Tyr Val Gly Ala Asp Ala Thr Gln Ser Gly Thr Ile Gln Gly Tyr
        115                 120                 125

Met Ile Ala Asn Leu Glu Asn Lys Gly Asp Ile Asp Gly Asp Gly Ser
    130                 135                 140

Val Ser Tyr Ile Thr Leu Met Gly Asp Pro Ala Asn Val Asp Ala Lys
145                 150                 155                 160

Gln Arg Thr Glu Tyr Ser Val Lys Gly Leu Glu Glu Lys Gly Val Lys
                165                 170                 175

Thr Asn Ala Leu Ala Gln Pro Tyr Gln Ala Asn Trp Asp Thr Ala Lys
            180                 185                 190

Gly Gln Glu Phe Thr Ala Asn Ala Leu Glu Gln Phe Gly Asn Lys Leu
        195                 200                 205

Glu Val Val Phe Ala Asn Asn Asp Gly Met Ala Val Gly Ala Val Thr
    210                 215                 220

Ala Ile Glu Ala Ala Gly Arg Lys Val Gly Glu Asp Ile Phe Val Val
225                 230                 235                 240

Gly Val Asp Ala Ile Pro Asp Ala Ile Glu Leu Leu Lys Gly Gly Lys
                245                 250                 255

Leu Thr Gly Thr Val Leu Asn Asp His Phe Asn Gln Ser His Thr Ala
            260                 265                 270

Val Asp Val Ala Leu Glu Leu Leu Gln Gly Lys Asp Val Ser Ala Tyr
        275                 280                 285

Tyr Trp His Asp Tyr Val Gly Val Thr Lys Pro Glu Glu Ala Glu Leu
    290                 295                 300

Lys Arg Ala Glu Ala Arg Lys Glu Thr Val Glu Glu Ala Val Lys Arg
305                 310                 315                 320

Tyr Ala Glu Arg Asp Ala Gln Gly Gly Ser His His His His His His
                325                 330                 335


<210> SEQ ID NO 288
<211> LENGTH: 336
<212> TYPE: PRT
<213> ORGANISM: Artificial Sequence
<220> FEATURE:
<223> OTHER INFORMATION: erhGGBP_F17C  (erhGGBP with signal sequence
      replaced with M; F17C mutation; and GGSHHHHHH at C-terminus)

<400> SEQUENCE: 288
```

-continued

Met Lys Thr Tyr Asn Ile Gly Val Ala Ile Tyr Lys Phe Asp Asp Asn
1 5 10 15

Cys Met Thr Leu Tyr Arg Glu Glu Leu Ala Ser Tyr Phe Lys Glu Val
20 25 30

Gly Glu Lys Asp Gly Asn Thr Tyr Lys Leu Asp Ile Gln Asp Gly Lys
35 40 45

Gln Asp Gln Ala Asn Gln Thr Glu Gln Ile Asn Asn Phe Ile Ala Gln
50 55 60

Gly Lys Asp Leu Ile Ile Ala Asn Met Val Asp Pro Thr Ala Ala Gly
65 70 75 80

Ser Ile Ile Asn Ser Ala Lys Ala Lys Glu Ile Pro Val Val Phe Ile
85 90 95

Asn Arg Glu Pro Glu Thr Gln Glu Leu Glu Ile Trp Pro Gly Lys Thr
100 105 110

Thr Tyr Val Gly Ala Asp Ala Thr Gln Ser Gly Thr Ile Gln Gly Tyr
115 120 125

Met Ile Ala Asn Leu Glu Asn Lys Gly Asp Ile Asp Gly Asp Gly Ser
130 135 140

Val Ser Tyr Ile Thr Leu Met Gly Asp Pro Ala Asn Val Asp Ala Lys
145 150 155 160

Gln Arg Thr Glu Tyr Ser Val Lys Gly Leu Glu Glu Lys Gly Val Lys
165 170 175

Thr Asn Ala Leu Ala Gln Pro Tyr Gln Ala Asn Trp Asp Thr Ala Lys
180 185 190

Gly Gln Glu Phe Thr Ala Asn Ala Leu Glu Gln Phe Gly Asn Lys Leu
195 200 205

Glu Val Val Phe Ala Asn Asn Asp Gly Met Ala Val Gly Ala Val Thr
210 215 220

Ala Ile Glu Ala Ala Gly Arg Lys Val Gly Glu Asp Ile Phe Val Val
225 230 235 240

Gly Val Asp Ala Ile Pro Asp Ala Ile Glu Leu Leu Lys Gly Gly Lys
245 250 255

Leu Thr Gly Thr Val Leu Asn Asp His Phe Asn Gln Ser His Thr Ala
260 265 270

Val Asp Val Ala Leu Glu Leu Leu Gln Gly Lys Asp Val Ser Ala Tyr
275 280 285

Tyr Trp His Asp Tyr Val Gly Val Thr Lys Pro Glu Glu Ala Glu Leu
290 295 300

Lys Arg Ala Glu Ala Arg Lys Glu Thr Val Glu Glu Ala Val Lys Arg
305 310 315 320

Tyr Ala Glu Arg Asp Ala Gln Gly Gly Ser His His His His His His
325 330 335

<210> SEQ ID NO 289
<211> LENGTH: 336
<212> TYPE: PRT
<213> ORGANISM: Artificial Sequence
<220> FEATURE:
<223> OTHER INFORMATION: erhGGBP_W188C (erhGGBP with signal sequence replaced with M; W188C mutation; and GGSHHHHHH at C-terminus)

<400> SEQUENCE: 289

Met Lys Thr Tyr Asn Ile Gly Val Ala Ile Tyr Lys Phe Asp Asp Asn
1 5 10 15

Phe Met Thr Leu Tyr Arg Glu Glu Leu Ala Ser Tyr Phe Lys Glu Val

```
            20                  25                  30

Gly Glu Lys Asp Gly Asn Thr Tyr Lys Leu Asp Ile Gln Asp Gly Lys
        35                  40                  45

Gln Asp Gln Ala Asn Gln Thr Glu Gln Ile Asn Asn Phe Ile Ala Gln
    50                  55                  60

Gly Lys Asp Leu Ile Ile Ala Asn Met Val Asp Pro Thr Ala Ala Gly
65                  70                  75                  80

Ser Ile Ile Asn Ser Ala Lys Ala Lys Glu Ile Pro Val Val Phe Ile
                85                  90                  95

Asn Arg Glu Pro Glu Thr Gln Glu Leu Glu Ile Trp Pro Gly Lys Thr
            100                 105                 110

Thr Tyr Val Gly Ala Asp Ala Thr Gln Ser Gly Thr Ile Gln Gly Tyr
        115                 120                 125

Met Ile Ala Asn Leu Glu Asn Lys Gly Asp Ile Asp Gly Asp Gly Ser
    130                 135                 140

Val Ser Tyr Ile Thr Leu Met Gly Asp Pro Ala Asn Val Asp Ala Lys
145                 150                 155                 160

Gln Arg Thr Glu Tyr Ser Val Lys Gly Leu Glu Glu Lys Gly Val Lys
                165                 170                 175

Thr Asn Ala Leu Ala Gln Pro Tyr Gln Ala Asn Cys Asp Thr Ala Lys
            180                 185                 190

Gly Gln Glu Phe Thr Ala Asn Ala Leu Glu Gln Phe Gly Asn Lys Leu
        195                 200                 205

Glu Val Val Phe Ala Asn Asn Asp Gly Met Ala Val Gly Ala Val Thr
    210                 215                 220

Ala Ile Glu Ala Ala Gly Arg Lys Val Gly Glu Asp Ile Phe Val Val
225                 230                 235                 240

Gly Val Asp Ala Ile Pro Asp Ala Ile Glu Leu Leu Lys Gly Gly Lys
                245                 250                 255

Leu Thr Gly Thr Val Leu Asn Asp His Phe Asn Gln Ser His Thr Ala
            260                 265                 270

Val Asp Val Ala Leu Glu Leu Leu Gln Gly Lys Asp Val Ser Ala Tyr
        275                 280                 285

Tyr Trp His Asp Tyr Val Gly Val Thr Lys Pro Glu Glu Ala Glu Leu
    290                 295                 300

Lys Arg Ala Glu Ala Arg Lys Glu Thr Val Glu Glu Ala Val Lys Arg
305                 310                 315                 320

Tyr Ala Glu Arg Asp Ala Gln Gly Gly Ser His His His His His His
                325                 330                 335
```

<210> SEQ ID NO 290
<211> LENGTH: 325
<212> TYPE: PRT
<213> ORGANISM: Artificial Sequence
<220> FEATURE:
<223> OTHER INFORMATION: ereGGBP_F17C (ereGGBP with signal sequence replaced with M; F17C, C10A, C29A, C65A, C69A, and C183A mutations; and GGSHHHHHH at C-terminus)

<400> SEQUENCE: 290

```
Met Lys Gln Ile Tyr Ile Gly Val Thr Ala Tyr Asp Gln Lys Asp Thr
1               5                   10                  15

Cys Ile Gly Glu Leu Ile Glu Thr Phe Lys Lys Glu Ala Ala Ser Leu
            20                  25                  30

Asp Thr Asp Lys Tyr Asp Ile Ser Met Thr Ile Met Asp Ala Ala Gly
        35                  40                  45
```

Ser Gln Arg Ala Gln Asp Asp Gln Val Gln Glu Met Ile Glu Asp Gly
    50                  55                  60

Ala Asn Val Leu Ala Ile Asn Leu Ala Asp Arg Thr Asp Leu Ser His
65                  70                  75                  80

Ile Ile Asn Ala Ala Met Glu Lys Asp Ile Pro Ile Ile Phe Phe Asn
                85                  90                  95

Arg Glu Pro Val Asp Glu Asp Leu Asn Arg Trp Asp Lys Leu Tyr Tyr
            100                 105                 110

Val Gly Ala Lys Ala Lys Gln Ser Gly Gln Met Gln Gly Glu Leu Ile
        115                 120                 125

Ala Asp Tyr Ile Lys Asn Asn Pro Gly Val Asp Lys Asn Gly Asp Gly
    130                 135                 140

Arg Ile Gln Tyr Val Ile Leu Glu Gly Glu Met Gly His Gln Asp Ala
145                 150                 155                 160

Ile Val Arg Thr Glu Ser Val Thr Glu Ser Met Lys Asn Asn Gly Leu
                165                 170                 175

Gln Ile Glu Lys Leu Ser Ala Gln Ile Ala Asn Trp Asn Arg Ala Gln
            180                 185                 190

Ala Gln Asn Arg Met Thr Gln Leu Ile Gly Gln Tyr Lys Asn Ser Ile
        195                 200                 205

Glu Leu Val Ile Ala Asn Asn Asp Ala Met Ala Leu Gly Ala Ile Asp
    210                 215                 220

Ala Tyr Glu Lys Leu Gly Val Thr Glu Ser Asn Val Pro Ala Phe Phe
225                 230                 235                 240

Gly Val Asp Gly Thr Asp Asp Gly Leu Glu Ala Val Gln Gln Ser Lys
                245                 250                 255

Leu Ala Ala Thr Val Tyr Asn Asp Lys Glu Gly Gln Ala Met Ala Met
            260                 265                 270

Ala Gln Leu Ala Tyr Leu Ala Ala Thr Gly Gly Ser Met Lys Asn Ile
        275                 280                 285

Lys Phe Glu Asp Lys Lys Tyr Val Tyr Leu Pro Tyr Glu Lys Val Thr
    290                 295                 300

Pro Asp Asn Val Asn Glu Phe Val Lys Asp Glu Gln Gly Gly Ser His
305                 310                 315                 320

His His His His His
                325

<210> SEQ ID NO 291
<211> LENGTH: 325
<212> TYPE: PRT
<213> ORGANISM: Artificial Sequence
<220> FEATURE:
<223> OTHER INFORMATION: ereGGBP_Q13C (ereGGBP with signal sequence replaced with M; Q13C, C10A, C29A, C65A, C69A, and C183A mutations; and GGSHHHHHH at C-terminus)

<400> SEQUENCE: 291

Met Lys Gln Ile Tyr Ile Gly Val Thr Ala Tyr Asp Cys Lys Asp Thr
1               5                   10                  15

Phe Ile Gly Glu Leu Ile Glu Thr Phe Lys Lys Glu Ala Ala Ser Leu
            20                  25                  30

Asp Thr Asp Lys Tyr Asp Ile Ser Met Thr Ile Met Asp Ala Ala Gly
        35                  40                  45

Ser Gln Arg Ala Gln Asp Asp Gln Val Gln Glu Met Ile Glu Asp Gly
    50                  55                  60

Ala Asn Val Leu Ala Ile Asn Leu Ala Asp Arg Thr Asp Leu Ser His
65 70 75 80

Ile Ile Asn Ala Ala Met Glu Lys Asp Ile Pro Ile Ile Phe Phe Asn
85 90 95

Arg Glu Pro Val Asp Glu Asp Leu Asn Arg Trp Asp Lys Leu Tyr Tyr
100 105 110

Val Gly Ala Lys Ala Lys Gln Ser Gly Gln Met Gln Gly Glu Leu Ile
115 120 125

Ala Asp Tyr Ile Lys Asn Asn Pro Gly Val Asp Lys Asn Gly Asp Gly
130 135 140

Arg Ile Gln Tyr Val Ile Leu Glu Gly Glu Met Gly His Gln Asp Ala
145 150 155 160

Ile Val Arg Thr Glu Ser Val Thr Glu Ser Met Lys Asn Asn Gly Leu
165 170 175

Gln Ile Glu Lys Leu Ser Ala Gln Ile Ala Asn Trp Asn Arg Ala Gln
180 185 190

Ala Gln Asn Arg Met Thr Gln Leu Ile Gly Gln Tyr Lys Asn Ser Ile
195 200 205

Glu Leu Val Ile Ala Asn Asn Asp Ala Met Ala Leu Gly Ala Ile Asp
210 215 220

Ala Tyr Glu Lys Leu Gly Val Thr Glu Ser Asn Val Pro Ala Phe Phe
225 230 235 240

Gly Val Asp Gly Thr Asp Asp Gly Leu Glu Ala Val Gln Gln Ser Lys
245 250 255

Leu Ala Ala Thr Val Tyr Asn Asp Lys Glu Gly Gln Ala Met Ala Met
260 265 270

Ala Gln Leu Ala Tyr Leu Ala Ala Thr Gly Gly Ser Met Lys Asn Ile
275 280 285

Lys Phe Glu Asp Lys Lys Tyr Val Tyr Leu Pro Tyr Glu Lys Val Thr
290 295 300

Pro Asp Asn Val Asn Glu Phe Val Lys Asp Glu Gln Gly Gly Ser His
305 310 315 320

His His His His His
325

<210> SEQ ID NO 292
<211> LENGTH: 325
<212> TYPE: PRT
<213> ORGANISM: Artificial Sequence
<220> FEATURE:
<223> OTHER INFORMATION: ereGGBP_W188C (ereGGBP with signal sequence replaced with M; W188C, C10A, C29A, C65A, C69A, and C183A mutations; and GGSHHHHHH at C-terminus)

<400> SEQUENCE: 292

Met Lys Gln Ile Tyr Ile Gly Val Thr Ala Tyr Asp Gln Lys Asp Thr
1 5 10 15

Phe Ile Gly Glu Leu Ile Glu Thr Phe Lys Lys Glu Ala Ala Ser Leu
20 25 30

Asp Thr Asp Lys Tyr Asp Ile Ser Met Thr Ile Met Asp Ala Ala Gly
35 40 45

Ser Gln Arg Ala Gln Asp Asp Gln Val Gln Glu Met Ile Glu Asp Gly
50 55 60

Ala Asn Val Leu Ala Ile Asn Leu Ala Asp Arg Thr Asp Leu Ser His
65 70 75 80

Ile Ile Asn Ala Ala Met Glu Lys Asp Ile Pro Ile Ile Phe Phe Asn

```
                85                  90                  95

Arg Glu Pro Val Asp Glu Asp Leu Asn Arg Trp Asp Lys Leu Tyr Tyr
            100                 105                 110

Val Gly Ala Lys Ala Lys Gln Ser Gly Gln Met Gln Gly Glu Leu Ile
        115                 120                 125

Ala Asp Tyr Ile Lys Asn Asn Pro Gly Val Asp Lys Asn Gly Asp Gly
    130                 135                 140

Arg Ile Gln Tyr Val Ile Leu Glu Gly Glu Met Gly His Gln Asp Ala
145                 150                 155                 160

Ile Val Arg Thr Glu Ser Val Thr Glu Ser Met Lys Asn Asn Gly Leu
                165                 170                 175

Gln Ile Glu Lys Leu Ser Ala Gln Ile Ala Asn Cys Asn Arg Ala Gln
            180                 185                 190

Ala Gln Asn Arg Met Thr Gln Leu Ile Gly Gln Tyr Lys Asn Ser Ile
        195                 200                 205

Glu Leu Val Ile Ala Asn Asn Asp Ala Met Ala Leu Gly Ala Ile Asp
    210                 215                 220

Ala Tyr Glu Lys Leu Gly Val Thr Glu Ser Asn Val Pro Ala Phe Phe
225                 230                 235                 240

Gly Val Asp Gly Thr Asp Asp Gly Leu Glu Ala Val Gln Gln Ser Lys
                245                 250                 255

Leu Ala Ala Thr Val Tyr Asn Asp Lys Glu Gly Gln Ala Met Ala Met
            260                 265                 270

Ala Gln Leu Ala Tyr Leu Ala Ala Thr Gly Gly Ser Met Lys Asn Ile
        275                 280                 285

Lys Phe Glu Asp Lys Lys Tyr Val Tyr Leu Pro Tyr Glu Lys Val Thr
    290                 295                 300

Pro Asp Asn Val Asn Glu Phe Val Lys Asp Glu Gln Gly Gly Ser His
305                 310                 315                 320

His His His His His
                325


<210> SEQ ID NO 293
<211> LENGTH: 18
<212> TYPE: PRT
<213> ORGANISM: Artificial Sequence
<220> FEATURE:
<223> OTHER INFORMATION: bZif Sequence

<400> SEQUENCE: 293

Thr Gly Glu Lys Pro Tyr Lys Cys Pro Glu Cys Gly Lys Ser Phe Ser
1               5                   10                  15

Arg Ser


<210> SEQ ID NO 294
<211> LENGTH: 32
<212> TYPE: PRT
<213> ORGANISM: Artificial Sequence
<220> FEATURE:
<223> OTHER INFORMATION: ZF-QNK

<400> SEQUENCE: 294

Thr Gly Glu Lys Pro Tyr Lys Cys Pro Glu Cys Gly Lys Ser Phe Ser
1               5                   10                  15

Arg Ser Asp His Leu Ser Arg His Gln Arg Thr His Gln Asn Lys Lys
            20                  25                  30
```

<210> SEQ ID NO 295
<211> LENGTH: 6
<212> TYPE: PRT
<213> ORGANISM: Artificial Sequence
<220> FEATURE:
<223> OTHER INFORMATION: Hexahistidine Tag

<400> SEQUENCE: 295

His His His His His His
1               5

<210> SEQ ID NO 296
<211> LENGTH: 6
<212> TYPE: PRT
<213> ORGANISM: Artificial Sequence
<220> FEATURE:
<223> OTHER INFORMATION: Hexalysine Tag

<400> SEQUENCE: 296

Lys Lys Lys Lys Lys Lys
1               5

<210> SEQ ID NO 297
<211> LENGTH: 319
<212> TYPE: PRT
<213> ORGANISM: Artificial Sequence
<220> FEATURE:
<223> OTHER INFORMATION: ecGGBP.F16C (with signal peptide replaced with
      M; a F16C mutation; and a GGSHHHHHH at C-terminus)

<400> SEQUENCE: 297

Met Ala Asp Thr Arg Ile Gly Val Thr Ile Tyr Lys Tyr Asp Asp Asn
1               5                   10                  15

Cys Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Trp Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro

```
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe Ser Lys Lys Gly Gly Ser His His His His His His
305                 310                 315


<210> SEQ ID NO 298
<211> LENGTH: 312
<212> TYPE: PRT
<213> ORGANISM: Artificial Sequence
<220> FEATURE:
<223> OTHER INFORMATION: ttGGBP182C.2.0 (affinity-tuning mutant, 182C
      background (Table 6) with signal peptide replaced with M)

<400> SEQUENCE: 298

Met Lys Gln Leu Asn Ile Gly Val Ala Ile Tyr Lys Phe Asp Asp Thr
1               5                   10                  15

Phe Met Thr Gly Val Arg Asn Ala Met Thr Ala Glu Ala Gln Gly Lys
            20                  25                  30

Ala Lys Leu Asn Met Val Asp Ser Gln Asn Ser Gln Pro Thr Gln Asn
        35                  40                  45

Asp Gln Val Asp Leu Phe Ile Thr Lys Lys Met Asn Ala Leu Ala Ile
    50                  55                  60

Asn Pro Val Asp Arg Thr Ala Ala Gly Thr Ile Ile Asp Lys Ala Lys
65                  70                  75                  80

Gln Ala Asn Ile Pro Val Val Phe Phe Asn Lys Glu Pro Leu Pro Glu
                85                  90                  95

Asp Met Lys Lys Trp Asp Lys Val Tyr Tyr Val Gly Ala Lys Ala Glu
            100                 105                 110

Gln Ser Gly Ile Leu Gln Gly Gln Ile Met Ala Asp Tyr Trp Lys Ala
        115                 120                 125

His Pro Glu Ala Asp Lys Asn His Asp Gly Val Met Gln Tyr Val Met
    130                 135                 140

Leu Met Gly Glu Pro Gly His Gln Asp Ala Ile Leu Arg Thr Gln Tyr
145                 150                 155                 160

Ser Ile Gln Thr Val Lys Asp Ala Gly Ile Lys Val Gln Glu Leu Ala
                165                 170                 175

Lys Asp Tyr Ala Asn Cys Asp Arg Val Thr Ala His Asp Lys Met Ala
            180                 185                 190

Ala Trp Leu Ser Ser Phe Gly Asp Lys Ile Glu Ala Val Phe Ala Asn
        195                 200                 205

Asn Asp Asp Met Ala Leu Gly Ala Ile Glu Ala Leu Lys Ser Ala Gly
    210                 215                 220

Tyr Phe Thr Gly Asn Lys Tyr Ile Pro Val Val Gly Val Asp Ala Thr
225                 230                 235                 240

Ala Pro Gly Ile Gln Ala Ile Lys Asp Gly Thr Leu Leu Gly Thr Val
                245                 250                 255

Leu Asn Asp Ala Lys Asn Gln Ala Lys Ala Thr Phe Asn Ile Ala Tyr
            260                 265                 270
```

-continued

| | | | | | | | | | | | | | | | |
|---|---|---|---|---|---|---|---|---|---|---|---|---|---|---|---|
| Glu | Leu | Ala | Gln | Gly | Ile | Thr | Pro | Thr | Lys | Asp | Asn | Ile | Gly | Tyr | Asp |
| | | 275 | | | | | 280 | | | | | 285 | | | |
| Ile | Thr | Asp | Gly | Lys | Tyr | Val | Trp | Ile | Pro | Tyr | Lys | Lys | Ile | Thr | Lys |
| | 290 | | | | | 295 | | | | | 300 | | | | |
| Asp | Asn | Ile | Ser | Asp | Ala | Glu | Gln | | | | | | | | |
| 305 | | | | | 310 | | | | | | | | | | |